US006889145B1

(12) United States Patent
Jardetzky et al.

(10) Patent No.: US 6,889,145 B1
(45) Date of Patent: May 3, 2005

(54) THREE-DIMENSIONAL MODEL OF A FC REGION OF AN IGE ANTIBODY AND USES THEREOF

(75) Inventors: Theodore S. Jardetzky, Evanston, IL (US); Beth A. Wurzburg, Evanston, IL (US)

(73) Assignee: Northwestern University, Evanston, IL (US)

( * ) Notice: Subject to any disclaimer, the term of this patent is extended or adjusted under 35 U.S.C. 154(b) by 301 days.

(21) Appl. No.: 10/211,948

(22) Filed: Aug. 1, 2002

Related U.S. Application Data

(63) Continuation-in-part of application No. 09/809,746, filed on Mar. 15, 2001, now abandoned.
(60) Provisional application No. 60/234,877, filed on Sep. 22, 2000, and provisional application No. 60/189,403, filed on Mar. 15, 2000.

(51) Int. Cl.$^7$ ............................ G01N 33/48; G06G 7/60
(52) U.S. Cl. ............................................. 702/27; 703/11
(58) Field of Search ............................... 702/27; 703/11

(56) References Cited

U.S. PATENT DOCUMENTS

| 4,962,035 A | 10/1990 | Leder et al. |
|---|---|---|
| 5,180,805 A | 1/1993 | Gould et al. |
| 5,639,660 A | 6/1997 | Kinet et al. |
| 5,693,758 A | 12/1997 | Gould et al. |
| 5,978,740 A | 11/1999 | Armistead et al. |

FOREIGN PATENT DOCUMENTS

| DE | 38 20 556 A1 | 12/1989 |
|---|---|---|
| EP | 0 404 186 A2 | 12/1990 |
| JP | 5113443 | 5/1993 |
| JP | 8-101194 | 4/1996 |
| WO | WO 89/01520 | 2/1989 |
| WO | WO 89/05352 | 6/1989 |
| WO | WO 91/06570 | 5/1991 |
| WO | WO 93/04173 | 3/1993 |
| WO | WO 95/14779 | 6/1995 |
| WO | WO 95/16203 | 6/1995 |
| WO | WO 95/35367 | 12/1995 |
| WO | WO 96/01643 | 1/1996 |
| WO | WO 97/20859 | 6/1997 |
| WO | WO 97/40033 | 10/1997 |
| WO | WO 98/23964 | 6/1998 |
| WO | WO 98/27208 | 6/1998 |
| WO | WO 98/45707 | 10/1998 |
| WO | WO 99/38974 | 8/1999 |
| WO | WO 99/40117 | 8/1999 |
| WO | WO 01 68861 A2 | 9/2001 |

OTHER PUBLICATIONS

Beavil et al., 1993, *Biochemical Society Transactions*, vol. 21, pp. 968–972.
Blank et al., 1991, *J. Biol. Chem.*, vol. 266, No. 4, pp. 2639–2646.
Cook et al., 1997, *Biochemistry*, vol. 36, pp. 15579–15588.
Dombrowicz et al., 1993, *Cell*, vol. 75, pp. 969–976.
Dombrowicz et al., 1997, *J. Clin. Invest.*, vol. 99, No. 5, pp. 915–925.
Garman et al., 1998, *Cell*, vol. 95, pp. 951–961.
Gounni et al., 1994, *Nature*, vol. 367, pp. 183–186.
Greer, Jonathan, 1990, *Proteins: Structure, Function, and Genetics*, vol. 7, pp. 317–334.
Havel et al., 1991, *J. Mol. Biol.*, vol. 217, pp. 1–7.
Hayashi, et al., GenBank Accession No. D16413, submitted Jun. 8, 1993.
Helm et al., 1988, *Nature*, vol. 331, pp. 180–183.
Heusser et al., 1997, *Curr. Opin. Immunol.*, vol. 9, pp. 805–813.
Hill et al., 1996, *Human Molecular Genetics*, vol. 5, No. 7, pp. 959–962.
Hulett et al., 1994, *J. Biol. Chem.*, vol. 269, No. 21, pp. 15287–15293.
Hulett et al., 1995, *J. Biol. Chem.*, vol. 270, No. 36, pp. 21188–21194.
Joseph et al., 1997, *Eur. J. Immunol.*, vol. 27, pp. 2212–2218.
Keown et al., 1997, *Eur Biophys J*, vol. 25, pp. 471–476.
Keown et al., 1998, *Biochemistry*, vol. 37, pp. 8863–8869.
Kinet, Jean–Pierre, 1999, *Annu. Rev. Immunol.*, vol. 17, pp. 931–972.
Kochan et al., *Immunobiology of Proteins and Peptides VII*, Edited by M.Z. Atassi, Plenum Press, NY, 1994, pp. 31–38.
Kochan et al., 1988, *Nucleic Acids Res.*, vol. 16, No. 8, p. 3584.
Kuster et al., 1990, *J. Biol. Chem.* 265, 6448–6452.
Kuster et al., 1992, *J. Biol. Chem.* 267, 12782–12787.
LaCroix et al., 1993, *Mol. Immunol.*, vol. 30, pp. 321–330.
Letourneur et al., *J. Biol. Chem.*, vol. 270, No. 14, pp. 8249–8256.
Mallamaci et al., 1993, *J. Biol. Chem.*, vol. 268, No. 29, pp. 22076–22083

(Continued)

Primary Examiner—John S. Brusca
(74) Attorney, Agent, or Firm—Heska Corporation

(57) ABSTRACT

The present invention includes three-dimensional models of antibodies, such as Fc-Cϵ/Cϵ4 regions of IgE antibodies, as well as methods to produce such models. The present invention also includes muteins having increased stability and/or antibody receptor binding activity, as well as methods to produce such muteins, preferably using information derived from three-dimensional models of the present invention. Also included are nucleic acid sequences encoding muteins of the present invention and use of those sequences to produce such muteins. Also included is the use of the model to identify compounds that inhibit the binding of an antibody receptor protein to an antibody. The present invention also includes uses of such muteins and inhibitory compounds, for example, in methods to diagnose and protect animals from allergy and other abnormal immune responses.

11 Claims, No Drawings

OTHER PUBLICATIONS

Mao et al., 1998, *Clin. Genet.*, vol. 53, pp. 54–56.

Maurer et al., 1998, *J. Immunol.*, vol. 161, pp. 2731–2739.

McDonnell et al., 1996, *Nat. Struc. Biol.*, vol. 3, No. 5, pp. 419–426.

McDonnell et al., 1997, *Biochem. Soc. Trans.*, vol. 25, pp. 387–392.

Murgolo et al., 1993, *Proteins: Structure, Function and Genetics*, vol. 17, pp. 62–74.

Nakamura et al., *Handbook of Experimental Immunology in Four Volumes*, vol. 1: Immunochemistry, Ed. D.M. Weir, Chapter 27, pp. 27.1–27.20, 1987.

Oettgen et al., 1994, *Nature*, vol. 370, pp. 367–370.

Padlan et al., 1992 Summer, *Receptor*, 2(2), pp. 129–44, XP000892125.

Padlan et al., 1993 Nov., *Biochemical Society Transactions*, 21(4), pp. 963–7, Ref: 19, XP000892109.

Padlan et al., 1993, *Receptor*, vol. 3, pp. 325–341.

Pang et al., 1993, *J. Immunol.* 151, 6166–6174.

Patent Abstract of Japan, vol. 095, No. 006, Jul. 31, 1995 and JP 07 072150A (Tonen Corp.; Others: 01) Mar. 7, 1995.

Patent Abstract of Japan, vol. 095, No. 007, Aug. 31, 1995 and JP 07 092167A (Kinki Univ..; Others: 01) Apr. 7, 1995.

Ravetch et al., 1998, *Annu Rev Immunolo 16*, 421–432.

Robertson, Michael W., 1993, *J. Biol. Chem.*, vol. 268, No. 17, pp. 12736–12743.

Samoilovich et al., *ACI News*, 4, pp. 21–25, 1992.

Sánchez–Madrid, et al., 1984, *Journal of Immunological Methods*, vol. 73, pp. 367–378.

Scarselli et al., 1996, *FEBS*, vol. 329, No. 1,2, pp. 223–226.

Schiffer et al., 1990, *Proteins: Structure, Function, and Genetics*, vol. 8, pp. 30–43.

Seto et al., 1995, *Protein Science*, vol. 4, pp. 655–670.

Schimizu et al., 1988, *Proc. Natl. Acad Sci. USA 85*, 1907–1911.

Shirakawa et al., 1994, *Nature Genetics*, vol. 7, pp. 125–130.

Stämpfli et al., *Journal of Immunology*, 155, pp. 2948–2954, 1995.

Suto et al., *Jpn J Dermatol*, 106, pp. 1377–1384, 1996.

Vercelli et al., 1989, *Nature*, vol. 338, pp. 649–651.

Garman, et al., 2000, *Nature*, vol. 406, pp. 259–266.

Malissard, et al., 1996, *Eur. J. Biochem.*, vol. 239, pp. 340–348.

US 6,889,145 B1

SEQUENCE LISTING

<160> NUMBER OF SEQ ID NOS: 9

<210> SEQ ID NO 1
<211> LENGTH: 669
<212> TYPE: DNA
<213> ORGANISM: Homo sapiens
<220> FEATURE:
<221> NAME/KEY: CDS
<222> LOCATION: (1)..(666)
<223> OTHER INFORMATION:

<400> SEQUENCE: 1

```
gcg gat ccc tgt gat tcc aac ccg aga ggg gtg agc gcc tac cta agc      48
Ala Asp Pro Cys Asp Ser Asn Pro Arg Gly Val Ser Ala Tyr Leu Ser
1               5                   10                  15 cgg ccc agc ccg ttc gac ctg ttc atc cgc aag tcg ccc acg atc acc      96
Arg Pro Ser Pro Phe Asp Leu Phe Ile Arg Lys Ser Pro Thr Ile Thr
            20                  25                  30 tgt ctg gtg gtg gac ctg gca ccc agc aag ggg acc gtg aac ctg acc     144
Cys Leu Val Val Asp Leu Ala Pro Ser Lys Gly Thr Val Asn Leu Thr
```

```
                35                  40                  45
tgg tcc cgg gcc agt ggg aag cct gtg aac cac tcc acc aga aag gag    192
Trp Ser Arg Ala Ser Gly Lys Pro Val Asn His Ser Thr Arg Lys Glu
     50                  55                  60 gag aag cag cgc aat ggc acg tta acc gtc acg tcc acc ctg ccg gtg    240
Glu Lys Gln Arg Asn Gly Thr Leu Thr Val Thr Ser Thr Leu Pro Val
 65                  70                  75                  80 ggc acc cga gac tgg atc gag ggg gag acc tac cag tgc agg gtg acc    288
Gly Thr Arg Asp Trp Ile Glu Gly Glu Thr Tyr Gln Cys Arg Val Thr
                 85                  90                  95 cac ccc cac ctg ccc agg gcc ctc atg cgg tcc acg acc aag acc agc    336
His Pro His Leu Pro Arg Ala Leu Met Arg Ser Thr Thr Lys Thr Ser
            100                 105                 110 ggc ccg cgt gct gcc ccg gaa gtc tat gcg ttt gcg acg ccg gag tgg    384
Gly Pro Arg Ala Ala Pro Glu Val Tyr Ala Phe Ala Thr Pro Glu Trp
        115                 120                 125 ccg ggg agc cgg gac aag cgc acc ctc gcc tgc ctg atc cag aac ttc    432
Pro Gly Ser Arg Asp Lys Arg Thr Leu Ala Cys Leu Ile Gln Asn Phe
    130                 135                 140 atg cct gag gac atc tcg gtg cag tgg ctg cac aac gag gtg cag ctc    480
Met Pro Glu Asp Ile Ser Val Gln Trp Leu His Asn Glu Val Gln Leu
145                 150                 155                 160 ccg gac gcc cgg cac agc acg acg cag ccc cgc aag acc aag ggc tcc    528
Pro Asp Ala Arg His Ser Thr Thr Gln Pro Arg Lys Thr Lys Gly Ser
                165                 170                 175 ggc ttc ttc gtc ttc agc cgc ctg gag gtg acc agg gcc gaa tgg gag    576
Gly Phe Phe Val Phe Ser Arg Leu Glu Val Thr Arg Ala Glu Trp Glu
            180                 185                 190 cag aaa gat gag ttc atc tgc cgt gca gtc cat gag gca gcg agc ccc    624
Gln Lys Asp Glu Phe Ile Cys Arg Ala Val His Glu Ala Ala Ser Pro
        195                 200                 205 tca cag acc gtc cag cga gcg gtg tct gta aat ccc ggt aaa tga        669
Ser Gln Thr Val Gln Arg Ala Val Ser Val Asn Pro Gly Lys
    210                 215                 220

<210> SEQ ID NO 2
<211> LENGTH: 222
<212> TYPE: PRT
<213> ORGANISM: Homo sapiens

<400> SEQUENCE: 2

Ala Asp Pro Cys Asp Ser Asn Pro Arg Gly Val Ser Ala Tyr Leu Ser
 1               5                  10                  15

Arg Pro Ser Pro Phe Asp Leu Phe Ile Arg Lys Ser Pro Thr Ile Thr
            20                  25                  30

Cys Leu Val Val Asp Leu Ala Pro Ser Lys Gly Thr Val Asn Leu Thr
        35                  40                  45

Trp Ser Arg Ala Ser Gly Lys Pro Val Asn His Ser Thr Arg Lys Glu
    50                  55                  60

Glu Lys Gln Arg Asn Gly Thr Leu Thr Val Thr Ser Thr Leu Pro Val
 65                  70                  75                  80

Gly Thr Arg Asp Trp Ile Glu Gly Glu Thr Tyr Gln Cys Arg Val Thr
                 85                  90                  95

His Pro His Leu Pro Arg Ala Leu Met Arg Ser Thr Thr Lys Thr Ser
            100                 105                 110

Gly Pro Arg Ala Ala Pro Glu Val Tyr Ala Phe Ala Thr Pro Glu Trp
        115                 120                 125

Pro Gly Ser Arg Asp Lys Arg Thr Leu Ala Cys Leu Ile Gln Asn Phe
```

```
            130                 135                 140
Met Pro Glu Asp Ile Ser Val Gln Trp Leu His Asn Glu Val Gln Leu
145                 150                 155                 160

Pro Asp Ala Arg His Ser Thr Thr Gln Pro Arg Lys Thr Lys Gly Ser
                165                 170                 175

Gly Phe Phe Val Phe Ser Arg Leu Glu Val Thr Arg Ala Glu Trp Glu
            180                 185                 190

Gln Lys Asp Glu Phe Ile Cys Arg Ala Val His Glu Ala Ala Ser Pro
        195                 200                 205

Ser Gln Thr Val Gln Arg Ala Val Ser Val Asn Pro Gly Lys
    210                 215                 220

<210> SEQ ID NO 3
<211> LENGTH: 29
<212> TYPE: DNA
<213> ORGANISM: Artificial sequence
<220> FEATURE:
<223> OTHER INFORMATION: Synthetic Primer

<400> SEQUENCE: 3
tagggctacg tagattccaa cccgagagg                                   29

<210> SEQ ID NO 4
<211> LENGTH: 43
<212> TYPE: DNA
<213> ORGANISM: Artificial sequence
<220> FEATURE:
<223> OTHER INFORMATION: Synthetic Primer

<400> SEQUENCE: 4
actggctcga gaccaggtca gctgcacggt cccttgctg ggt                    43

<210> SEQ ID NO 5
<211> LENGTH: 53
<212> TYPE: DNA
<213> ORGANISM: Artificial sequence
<220> FEATURE:
<223> OTHER INFORMATION: Synthetic Primer

<400> SEQUENCE: 5
cctggtctcg agccagtggg aagcctgtgc aacactccac cagaaaggag gag        53

<210> SEQ ID NO 6
<211> LENGTH: 39
<212> TYPE: DNA
<213> ORGANISM: Artificial sequence
<220> FEATURE:
<223> OTHER INFORMATION: Synthetic Primer

<400> SEQUENCE: 6
tctaggcagc ggccgcttat catttaccgg gatttacag                        39

<210> SEQ ID NO 7
<211> LENGTH: 669
<212> TYPE: DNA
<213> ORGANISM: Homo sapiens
<220> FEATURE:
<221> NAME/KEY: CDS
<222> LOCATION: (1)..(666)
<223> OTHER INFORMATION:

<400> SEQUENCE: 7 gcg gat ccc tgt gat tcc aac ccg aga ggg gtg agc gcc tac cta agc   48
Ala Asp Pro Cys Asp Ser Asn Pro Arg Gly Val Ser Ala Tyr Leu Ser
```

```
1               5                   10                  15
cgg ccc agc ccg ttc gac ctg ttc atc cgc aag tcg ccc acg atc acc    96
Arg Pro Ser Pro Phe Asp Leu Phe Ile Arg Lys Ser Pro Thr Ile Thr
            20                  25                  30 tgt ctg gtg gtg gac ctg gca ccc agc aag ggg acc gtg cag ctg acc    144
Cys Leu Val Val Asp Leu Ala Pro Ser Lys Gly Thr Val Gln Leu Thr
        35                  40                  45 tgg tcc cgg gcc agt ggg aag cct gtg caa cac tcc acc aga aag gag    192
Trp Ser Arg Ala Ser Gly Lys Pro Val Gln His Ser Thr Arg Lys Glu
    50                  55                  60 gag aag cag cgc aat ggc acg tta acc gtc acg tcc acc ctg ccg gtg    240
Glu Lys Gln Arg Asn Gly Thr Leu Thr Val Thr Ser Thr Leu Pro Val
65                  70                  75                  80 ggc acc cga gac tgg atc gag ggg gag acc tac cag tgc agg gtg acc    288
Gly Thr Arg Asp Trp Ile Glu Gly Glu Thr Tyr Gln Cys Arg Val Thr
                85                  90                  95 cac ccc cac ctg ccc agg gcc ctc atg cgg tcc acg acc aag acc agc    336
His Pro His Leu Pro Arg Ala Leu Met Arg Ser Thr Thr Lys Thr Ser
            100                 105                 110 ggc ccg cgt gct gcc ccg gaa gtc tat gcg ttt gcg acg ccg gag tgg    384
Gly Pro Arg Ala Ala Pro Glu Val Tyr Ala Phe Ala Thr Pro Glu Trp
        115                 120                 125 ccg ggg agc cgg gac aag cgc acc ctc gcc tgc ctg atc cag aac ttc    432
Pro Gly Ser Arg Asp Lys Arg Thr Leu Ala Cys Leu Ile Gln Asn Phe
    130                 135                 140 atg cct gag gac atc tcg gtg cag tgg ctg cac aac gag gtg cag ctc    480
Met Pro Glu Asp Ile Ser Val Gln Trp Leu His Asn Glu Val Gln Leu
145                 150                 155                 160 ccg gac gcc cgg cac agc acg acg cag ccc cgc aag acc aag ggc tcc    528
Pro Asp Ala Arg His Ser Thr Thr Gln Pro Arg Lys Thr Lys Gly Ser
                165                 170                 175 ggc ttc ttc gtc ttc agc cgc ctg gag gtg acc agg gcc gaa tgg gag    576
Gly Phe Phe Val Phe Ser Arg Leu Glu Val Thr Arg Ala Glu Trp Glu
            180                 185                 190 cag aaa gat gag ttc atc tgc cgt gca gtc cat gag gca gcg agc ccc    624
Gln Lys Asp Glu Phe Ile Cys Arg Ala Val His Glu Ala Ala Ser Pro
        195                 200                 205 tca cag acc gtc cag cga gcg gtg tct gta aat ccc ggt aaa tga        669
Ser Gln Thr Val Gln Arg Ala Val Ser Val Asn Pro Gly Lys
    210                 215                 220

<210> SEQ ID NO 8
<211> LENGTH: 222
<212> TYPE: PRT
<213> ORGANISM: Homo sapiens

<400> SEQUENCE: 8

Ala Asp Pro Cys Asp Ser Asn Pro Arg Gly Val Ser Ala Tyr Leu Ser
1               5                   10                  15

Arg Pro Ser Pro Phe Asp Leu Phe Ile Arg Lys Ser Pro Thr Ile Thr
            20                  25                  30

Cys Leu Val Val Asp Leu Ala Pro Ser Lys Gly Thr Val Gln Leu Thr
        35                  40                  45

Trp Ser Arg Ala Ser Gly Lys Pro Val Gln His Ser Thr Arg Lys Glu
    50                  55                  60

Glu Lys Gln Arg Asn Gly Thr Leu Thr Val Thr Ser Thr Leu Pro Val
65                  70                  75                  80

Gly Thr Arg Asp Trp Ile Glu Gly Glu Thr Tyr Gln Cys Arg Val Thr
                85                  90                  95
```

-continued

```
His Pro His Leu Pro Arg Ala Leu Met Arg Ser Thr Thr Lys Thr Ser
            100                 105                 110

Gly Pro Arg Ala Ala Pro Glu Val Tyr Ala Phe Ala Thr Pro Glu Trp
        115                 120                 125

Pro Gly Ser Arg Asp Lys Arg Thr Leu Ala Cys Leu Ile Gln Asn Phe
        130                 135                 140

Met Pro Glu Asp Ile Ser Val Gln Trp Leu His Asn Glu Val Gln Leu
145                 150                 155                 160

Pro Asp Ala Arg His Ser Thr Thr Gln Pro Arg Lys Thr Lys Gly Ser
                165                 170                 175

Gly Phe Phe Val Phe Ser Arg Leu Glu Val Thr Arg Ala Glu Trp Glu
            180                 185                 190

Gln Lys Asp Glu Phe Ile Cys Arg Ala Val His Glu Ala Ala Ser Pro
        195                 200                 205

Ser Gln Thr Val Gln Arg Ala Val Ser Val Asn Pro Gly Lys
        210                 215                 220

<210> SEQ ID NO 9
<211> LENGTH: 44
<212> TYPE: DNA
<213> ORGANISM: Artificial sequence
<220> FEATURE:
<223> OTHER INFORMATION: Synthetic Primer

<400> SEQUENCE: 9
tagggcggat ccctgtgcag attcgaaccc gagagggtg agcg                44
```

THREE-DIMENSIONAL MODEL OF A FC REGION OF AN IGE ANTIBODY AND USES THEREOF

CROSS-REFERENCE TO RELATED APPLICATIONS

This application is a continuation in part to U.S. patent application Ser. No. 09/809,746, filed Mar. 15, 2001 now abandoned, entitled "THREE-DIMENSIONAL MODEL OF A Fc REGION OF AN IgE ANTIBODY AND USES THEREOF"; which claims priority to U.S. Provisional Patent Application Ser. No. 60/234,877, filed Sep. 22, 2000, entitled "STRUCTURE OF THE HUMAN IgE-Fc Ce3-Ce4 Reveals Conformational Flexibility In The Antibody Effector Domains"; which claims priority to U.S. Provisional Patent Application Ser. No. 60/189,403, filed Mar. 15, 2000, entitled "THREE-DIMENSIONAL MODEL OF A Fc REGION OF AN IgE ANTIBODY AND USES THEREOF"; all of which are incorporated by reference herein.

This invention was made at least in part with government support under NIH Grant No. RO1 AI38972, awarded by the National Institutes of Health to Northwestern University. The government has certain rights in this invention.

FIELD OF THE INVENTION

The present invention relates to a crystal and a three-dimensional (3-D) model of a constant region of an IgE antibody that includes the C$\epsilon$3 and C$\epsilon$4 domains (Fc-C$\epsilon$3/C$\epsilon$4, or Fc-C$\epsilon$3/C$\epsilon$4, region). The present invention also relates to the use of that model to produce muteins and inhibitors useful in the diagnosis and treatment of allergy and the regulation of other immune responses in an animal.

BACKGROUND OF THE INVENTION

Antibody Fc-receptors (FcRs) play an important role in the immune response by coupling the specificity of secreted antibodies to a variety of cells of the immune system. A number of cell types, including macrophages, mast cells, eosinophils, and basophils, express membrane-bound FcRs at their surfaces. The binding of antibodies to FcRs provides antigen-specificity to these cells, which upon activation release further cell-specific mediators of the immune response, such as interleukins, initiators of inflammation, leukotrienes, prostaglandins, histamines, or cytotoxic proteins. The adoptive specificity of the FcRs allows a combinatorial approach to pathogen elimination, by coupling the diversity of antibody antigen-recognition sites to the variety of cell-types expressing these receptors.

FcR-initiated mechanisms are important in normal immunity to infectious disease as well as in allergies, antibody-mediated tumor recognition, autoimmune diseases, and other diseases in which immune responses are abnormal (i.e., not regulated). Recent experiments with transgenic mice have demonstrated that the FcRs control key steps in the immune response, including antibody-directed cellular cytotoxicity and inflammatory cascades associated with the formation of immune complexes; see, for example, Ravetch et al., 1998, Annu Rev Immunolo 16, 421–432. Receptors that bind IgG (FcgRI, FcgRII, and FcgRIII, known collectively as FcgRs) mediate a variety of inflammatory reactions, regulate B-cell activation, and also trigger hypersensitivity reactions. The high affinity Fc epsilon receptor (also known as the IgE receptor or FceRI) is associated with the activation of mast cells and the triggering of allergic reactions and anaphylactic shock. Knockout mice for the FceRI alpha chain (FceRI$\alpha$) are unable to mount IgE-mediated anaphylaxis (see for example, Dombrowicz et al., 1993, Cell 75, 969–976), although FcgRs are still able to activate mast cells (see, for example, Dombrowicz et al., 1997, J. Clin. Invest. 99, 915–925; Oettgen et al., 1994, Nature 370, 367–370). FceRI has also been shown to trigger anti-parasitic reactions from platelets and eosinophils as well as deliver antigen into the MHC class II presentation pathway for the activation of T cells; see, for example, Gounni et al., 1994, Nature 367, 183–186; Joseph et al., 1997, Eur. J. Immunol. 27, 2212–2218; Maurer et al., 1998, J. Immunol. 161, 2731–2739. The beta subunit of FceRI has been associated with asthma in genetic studies; see, for example, Hill et al., 1996, Hum. Mol. Genet. 5, 959–962; Hill et al., 1995, Bmj 311, 776–779; Kim et al., 1998, Curr. Opin. Pulm. Med. 4, 4648; Mao et al., 1998, Clin. Genet. 53, 54–56; Shirakawa et al., 1994, Nat. Genet. 7, 125–129. A significant fraction of the population (~20%) may be affected by allergies, and this century has seen a substantial increase in asthma. Since IgE binding to FceRI is a requisite event in the reaction to different-allergens, therapeutic strategies aimed at inhibiting FceRI could provide a useful treatment for these diseases. For example, monoclonal antibodies that target IgE and block receptor binding have shown therapeutic potential; see, for example, Heusser et al., 1997, Curr. Opin. Immunol. 9, 805–813.

FceRI is found as a tetrameric (abg$_2$) or trimeric (ag$_2$) membrane bound receptor on the surface of mast cells, basophils, eosinophils, langerhans cells and platelets. The alpha chain, also referred to as FceRI$\alpha$, of FceRI binds IgE molecules with high affinity (K$_D$ of about $10^{-9}$ to $10^{-10}$ moles/liter (M)), and can be secreted as a 172-amino acid soluble, IgE-binding fragment by the introduction of a stop codon before the single C-terminal transmembrane anchor; see, for example, Blank et al., 1991, E. J. Biol. Chem. 266, 2639–2646, which describes the secretion of a soluble IgE-binding fragment of 172 amino acids. The extracellular domains of the human FceRI$\alpha$ protein belong to the immunoglobulin (Ig) superfamily and contain seven N-linked glycosylation sites. Glycosylation of FceRI$\alpha$ affects the secretion and stability of the receptor, but is not required for IgE-binding; see, for example, LaCroix et al., 1993, Mol. Immunol. 30, 321–330; Letourneur et al., 1995, J. Biol. Chem. 270, 8249–8256; Robertson, 1993, J. Biol. Chem. 268, 12736–12743; Scarselli et al., 1993, FEBS Lett 329, 223–226. The beta and gamma chains of FceRI are signal transduction modules.

Prior investigators have disclosed the nucleic acid sequence for human FceRI$\alpha$; see, for example, U.S. Pat. No. 4,962,035, by Leder, issued Oct. 9, 1990; U.S. Pat. No. 5,639,660, by Kinet et al., issued Jun. 17, 1997; Kochan et al., 1988, Nucleic Acids Res. 16, 3584; Shimizu et al., 1988, Proc. Natl. Acad. Sci. USA 85, 1907–1911; and Pang et al., 1993, J. Immunol. 151, 6166–6174. Nucleic acid sequences have also been reported for the human FceRI beta and gamma chains; see, respectively, Kuster et al., 1992, J. Biol. Chem. 267, 12782–12787; Kuster et al., 1990, J. Biol. Chem 265, 6448-6452. Nucleic acid sequences have also been reported for nucleic acid molecules encoding canine FceRI$\alpha$, murine FceRI$\alpha$, rat FceRI$\alpha$, feline FceRI$\alpha$ and equine FceRI$\alpha$ proteins; see, respectively, GenBank™ accession number D16413; Swiss-Prot accession number P20489 (represents encoded protein sequence); GenBank accession number J03606; PCT Publication No. WO 98/27208, by Frank et al., published Jun. 25, 1998, referred to herein as WO 98/27208; and PCT Publication No. WO 99/38974, by Weber et al., published Aug. 5, 1999, referred to herein as WO 99/38974. In addition, methods to detect IgE antibodies using a FcεRIα protein have been reported in PCT Publication No. WO 98/23964, by Frank et al., published Jun. 4, 1998, referred to herein as WO 98/23964; WO 98/27208, ibid.; PCT Publication No. WO 98/45707, by Frank et al., published Oct. 15, 1998, referred to herein as WO 98/45707; and WO 99/38974, ibid. WO 98/23964, WO 98/27208, WO 98/45707 and WO 99/38974 are each incorporated by reference herein in its entirety.

There have been several reports of the use of mutagenesis and swapping techniques to attempt to identify amino acids of either FcεRIα or IgE involved in the binding of (i.e., interaction between) those respective proteins, reports attempting to model FcεRIα proteins based on homology to other Ig-superfamily members, and reports that identify compounds that apparently inhibit such binding; see, for example, Cook et al., 1997, *Biochemistry* 36, 15579–15588; Hulett et al., 1994, *J. Biol. Chem.* 269, 15287-15293; Hulett et al., 1995, *J. Biol. Chem* 270, 21188–21194; Mallamaci et al., 1993, J. Biol. Chem. 268, 22076–22083; Robertson, 1993, ibid.; Scarselli et al., 1993, ibid. McDonnell et al., 1997, Biochem. Soc. Trans. 25, 387–392; McDonnell et al., 1996, *Nat. Struc. Biol.* 3, 419–426; PCT Publication No. WO 97/40033, by Cheng et al., published Oct. 30, 1997; U.S. Pat. No. 5,180,805, by Gould et al, issued Jan. 19, 1993; U.S. Pat. No. 5,693,758, by Gould et al., issued Dec. 2, 1997; PCT Publication No. WO 96/01643, by Gould et al., published Jan. 25, 1996; PCT Publication No. WO 95/14779, by Gould et al., published Jun. 1, 1995. None of these references, however, describe isolated crystals of FcεRIα proteins or 3-D models derived from crystals.

Despite what is known about FcRs and their interaction with antibodies, there remains a need for FcRs and antibodies with improved characteristics, such as enhanced affinity for their ligands, altered substrate specificity, increased stability, and increased solubility for use in diagnosis, treatment and prevention of allergy and other abnormal immune responses. Also needed for safe and efficacious compounds to prevent or treat allergy and to regulate other immune responses in an animal.

SUMMARY OF THE INVENTION

The present invention includes an isolated crystal of a constant region (Fc region) of an antibody, a three-dimensional (3-D) model of such a crystal and a modification of such a model. The present invention also includes compounds that inhibit the ability of FcRs to bind to antibodies as well as antibody muteins and other modified antibodies.

Also included in the present invention are methods to produce and use such crystals, models, inhibitory compounds, muteins, and other modified proteins. As such, the present invention includes antibodies with improved functions such as increased stability, increased affinity for an Ig binding domain of a FcR, altered substrate specificity, and increased solubility, including but not limited to reduced aggregation. Such proteins, also referred to as muteins, are useful to detect allergy and other immune response abnormalities as well as to protect an animal from such abnormalities. The present invention also provides safe and efficacious inhibitory compounds to protect (e.g., prevent, treat, reduce the consequences of) an animal from allergy and to regulate other immune responses in an animal. Accordingly, the present invention builds on the work of U.S. patent application Ser. No. 09/809,746, which is incorporated herein by reference in its entirety.

The present invention includes a 3-D model of a human IgE Fc region comprising Cε3 and Cε4 domains, wherein the model substantially represents the atomic coordinates specified in Table 1, Table 2 or Table 3 of Publication No. US-2001-0039479-A or the atomic coordinates specified in Table I, Table II or Table III. The present invention also includes a 3-D model comprising a modification of a model substantially representing the atomic coordinates specified in Table 1, Table 2 or Table 3 of U.S. Patent Publication No. US-2001-0039479-A1 or the atomic coordinates specified in Table I, Table II or Table III. Also included in the present invention are methods to produce such models.

The present invention also includes an isolated crystal of a human IgE Fc region comprising Cε3 and Cε4 domains.

The present invention includes a method to identify a compound that inhibits the binding between an IgE antibody and a FcεRIα protein. The method includes the step of using a 3-D model of the present invention, and particularly one substantially represented by the atomic coordinates specified in Table 1, Table 2 or Table 3 of U.S. Patent Publication No. US-2001-0039479-A1 or the atomic coordinates specified in Table I, Table II or Table III. Also included in the present invention are inhibitory compounds identified using such a method. Also included are therapeutic compositions that include such inhibitory compounds and methods to use such therapeutic compositions to protect an animal from allergy or to regulate other immune responses (e.g., protect an animal from other abnormal immune responses).

The present invention also includes a mutein that binds to a Fc binding domain of a FcR. Such a mutein has an improved function compared to a protein that includes SEQ ID NO:2. Examples of such an improved function include increased stability, increased affinity for an Fc domain of an antibody, altered substrate specificity, decreased aggregation, and increased solubility. Such a mutein is produced by a method that includes the following steps: (a) analyzing a 3-D model substantially representing the atomic coordinates specified in Table 1, Table 2, or Table 3 of U.S. Patent Publication No. US-2001-0039479-A1 or the atomic coordinates specified in Table I, Table II or Table III to identify at least one amino acid of the protein represented by the model which if replaced by a specified amino acid would effect an improved function of the protein; and (b) replacing the identified amino acid(s) to produce the mutein having such an improved function. The present invention also includes a mutein having an improved function compared to an unmodified IgE Fc region.

Also included are muteins that are chemically modified IgE Fc regions. Also included are nucleic acid molecules that encode muteins of the present invention, recombinant molecules and recombinant cells including such nucleic acid molecules and methods to produce such muteins. Also included are diagnostic reagents and diagnostic kits including such muteins, therapeutic compositions including such muteins, and methods to detect or protect an animal from allergy or other abnormal immune responses.

The present invention also includes a method to improve a function of a IgE Fc region which includes the steps of: (a) analyzing a 3-D model substantially representing the atomic coordinates specified in Table 1, Table 2 or Table 3 of U.S. Patent Publication No. US-2001-0039479-A1 or the atomic coordinates specified in Table I, Table II or Table III to identify at least one amino acid of the protein which if replaced by a specified amino acid improves at least one of the functions of the protein; and (b) replacing the identified amino acid(s) to produce a mutein having at least one of the improved functions.

DETAILED DESCRIPTION OF THE INVENTION

The present invention includes isolated crystals of Fc regions of antibodies, 3-D models of such crystals and modifications of such models. The present invention also includes compounds that inhibit the ability of FcRs to bind to antibodies as well as muteins and other modified antibodies. Also included in the present invention are methods to produce and use such crystals, models, inhibitory compounds, muteins, and other modified proteins.

The present invention includes an isolated crystal of a Fc region comprising the Cε3 and Cε4 domains of an IgE antibody (Fc-Cε3/Cε4), a 3-D model of such a crystal and a modification of such a model. As used herein, the term "a" entity or "an" entity refers to one or more of that entity; for example, a crystal or a model refers to one or more crystals or models, respectively. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures, or combinations, of two or more of the compounds.

As used herein, an extracellular domain of a FcεRIα protein is the portion of the FceRI alpha chain that is exposed to the environment outside the cell and that binds to the Fc domain of an IgE antibody. Such an extracellular domain can be (a) a complete extracellular domain which is a domain that extends from the first amino acid of a mature FceRI alpha chain through the last amino acid prior to the start of the transmembrane region or a domain that is functionally equivalent, in that such a domain includes a D1 and D2 domain, displays a similar affinity for the IgE antibody to which such an FcεRIα protein naturally binds, and produces crystals having sufficient quality to enable structure determination, or (b) a fragment of any of the extracellular domains of (a), wherein the fragment retains its ability to bind to the Fc domain of an antibody. As used herein, the terms binding to an antibody and binding to the Fc domain (i.e., constant region) of an antibody can be used interchangeably since it is recognized that a FcR binds to the Fc domain of an antibody. A FcR (i.e., a protein that can bind to an antibody), such as a FcεRIα protein, can be a full-length FcR (e.g., a full-length FceRI alpha chain), or any fragment thereof, wherein the fragment binds to an antibody. Similarly an antibody, or an Fc region thereof, can be a full-length antibody, or full-length Fc region thereof, or any fragment thereof that binds to a FcR. In one embodiment an Fc region comprises Cε3 and Cε4 domains. Preferably a FcR binds to an antibody with an affinity ($K_A$) of at least about $10^8$ liters/mole ($M^{-1}$), more preferably of at least about $10^9 M^{-1}$, and even more preferably of at least about $10^{10} M^{-1}$.

The present invention is surprising in several aspects. For example, this is the first report of an isolated crystal of a Fc-Cε3/Cε4 region of an IgE antibody, and in particular of an isolated crystal of sufficient quality that a crystal structure, i.e., a 3-D model, could be derived therefrom. Generation of such a crystal was very difficult and non-obvious and has been attempted by others without success. The inventors tried many approaches before discovering a preferred Fc-Cε3/Cε4 region from which to make a useful crystal. The first such region to be used successfully is referred to herein as PhFc-Cε3/Cε4$_{1-222}$ which is composed of the four amino acids alanine, aspartic acid, proline and cysteine at the amino terminus followed by amino acids 330 through 547 of the human IgE Fc constant region, using the numbering system of Dorrington et al, 1978, *Immunol Rev* 41, 3–25. PhFc-Cε3/Cε4$_{1-222}$ is represented herein by SEQ ID NO:2. An example of a nucleic acid molecule encoding PhFc-Cε3/Cε4$_{1-222}$ is referred to herein as nhFc-Cε3/Cε4$_{1-666}$, the nucleic acid sequence of which is referred to herein as SEQ ID NO: 1. It was also discovered that better crystals are generated when PhFc-Cε3/Cε4$_{1-222}$ is produced in insect cells, using a method such as that described in Examples 1 and 2 of U.S. Patent Publication No. US-2001-0039479-A1. Solution of the crystal structure was also very difficult, as described in more detail in Examples 1 and 2 of U.S. Patent Publication No. US-2001-0039479-A1. For example, as part of the effort, approximately 12,000 models were generated and used in complete Molecular Replacement searches with the program Amore, taking about 10 days on 5 Silicon Graphics computers.

Determination of the crystal structure of PhFc-Cε3/Cε4$_{1-222}$, and mutants thereof, produced in *Trichoplusia ni* (Hi-5) cells resulted in a 3-D model that substantially represents the atomic coordinates specified in Table 1, Table 2 or Table 3 of U.S. Patent Publication No. US-2001-0039479-A1 or in Table I, Table II or Table III. Amino acids are represented herein by their standard three or one letter codes; see, for example, Sambrook et al., *Molecular Cloning: A Laboratory Manual*, Cold Spring Harbor Labs Press, 1989, which is incorporated herein by reference in its entirety.

The 3-D model of PhFc-Cε3/Cε4$_{1-222}$ is also very surprising in view of what is known about the crystal structure of the Fc region of IgG. The Fc region of IgE exists in a novel conformation that is more compact than that of IgG. The Cε3 domains are also much closer to each other in IgE compared to IgG (about 13 angstroms compared to about 22 angstroms), leading to the descriptor of "closed conformation" for the IgE Fc structure. This closed conformation is also surprising in view of the crystal structures of FcεRIα alone, which is disclosed in U.S. patent application Ser. No. 09/434,193, filed Nov. 4, 1999, by Jardetzky et al., an in PCT Publication No. WO 00/26246, published May 11, 2000, by Jardetzky et al., and of the complex between FcεRIα and Fcε3/Cε4 alone, which is disclosed in U.S. Patent Application Ser. No. 60/189,853. U.S. Ser. No. 09/434,193, ibid., WO 00/26246, ibid. and Ser. No. 60/189,853, ibid., are incorporated by reference herein in their entireties. The structure of Fc-Cε3/Cε4 in the complex is an open conformation, also referred to as a receptor-bound conformation. The distance between the two Cε3 domains in the receptor-bound conformation is about 23 angstroms. Comparison of these structural similarities and differences are described in greater detail in the Examples and in Ser. No. 60/189,853, ibid. Analysis of the model which substantially represents the atomic coordinates specified in Table 1, Table 2 or Table 3 of U.S. Patent Publication No. US-2001-0039479-A1 or the atomic coordinates specified in Table I, Table II or Table III indicates the necessity of such a model for proper interpretation and refinement of mutagenesis studies that have been reported. Such a model permits differentiation between amino acids directly or indirectly influencing binding of FcεRIα to IgE and demonstrates where amino acids and amino acid segments identified in mutagenesis studies are positioned on the protein. By using a model of the present invention one can identify the interactions of FcεRIα and IgE, thereby identifying amino acids to target for mutein production or regions to target for the development of compounds to inhibit binding of IgE to its receptor. Such a model also leads to the ability to design inhibitory compounds that stabilize the closed conformation of IgE, thereby reducing its ability to bind to a FcR. Such a model can be used alone or in conjunction with a model of FcεRIα alone (U.S. Ser. No. 09/434,193, ibid. and WO 00/26246, ibid.) or of the complex between FcεRIα and Fc-Cε3/Cε4 alone (Ser. No. 60/189,853, ibid.).

One embodiment of the present invention is an isolated crystal of a Fc-Cε3/Cε4 region of an IgE antibody. As used herein, an isolated crystal is a crystal of a protein that has been produced in a laboratory; that is, an isolated crystal is produced by an individual and is not an object found in situ in nature. It is appreciated by those skilled in the art that there are a variety of techniques to produce crystals including, but not limited to, vapor diffusion using a hanging or sitting drop methodology, vapor diffusion under oil, and batch methods; see, for example, Ducruix et al., eds., 1991, *Crystallization of nucleic acids and proteins; A practical approach*, Oxford University Press, and Wyckoff et al., eds., 1985, *Methods in Enzymology* 11, 49–185; each reference is incorporated by reference herein in its entirety. It is also to be appreciated that crystallization conditions can be adjusted depending on a protein's inherent characteristics as well as on a protein's concentration in a solution and that a variety of precipitants can be added to a protein solution in order to effect crystallization; such precipitants are known to those skilled in the art. In a preferred embodiment, a crystal of a Fc-Cε3/Cε4 region is produced in a solution by adding a precipitant such as polyethylene glycol (PEG) or PEG monomethylether. It is also to be noted that a Fc-Cε3/CCε4 region used to produce a crystal can be produced by a variety of methods, including purification of a native protein, chemical synthesis of a protein, or recombinant production of a protein. Although a number of cell types can be used to recombinantly produce such a protein, insect cells, such as, but not limited to *Trichoplusia ni* and *Spodoptera frugiperda*, are preferred, with *Trichoplusia ni* cells being more preferred. Additional methods to produce proteins are disclosed below.

Isolated crystals of the present invention can include heavy atom derivatives, such as, but not limited to, gold, platinum, mercury, selenium, copper, and lead. Such heavy atoms can be introduced randomly or introduced in a manner based on knowledge of 3-D models of the present invention. Additional crystals of the present invention are not derivatized. In one embodiment, an isolated crystal of the present invention is a co-crystal of a FcεRIα protein bound to a Fc domain of an IgE antibody in the presence of a compound that inhibits the binding of a FcεRIα protein to a Fc domain of an IgE antibody. Additional crystals of the present invention include crystals produced from proteins that are muteins of the present invention or other proteins that are represented by a 3-D model of the present invention.

An isolated crystal of the present invention can be the crystal of any suitable Fc region that binds to FεRIα, such as a Fc comprising Cε3 domains or a Fc comprising Cε3 and Cε4 domains. Suitable Fc-Cε3/Cε4 regions include mammalian Fc-Cε3/Cε4 regions, with human, canine, feline, equine, rat and murine Fc-Cε3/Cε4 regions being preferred, and human Fc-Cε3/Cε4 regions being even more preferred. A preferred crystal of the present invention diffracts X-rays to a resolution of about 4.5 angstroms or higher (i.e., lower number meaning higher resolution), with resolutions of about 4.0 angstroms or higher, about 3.5 angstroms or higher, about 3.25 angstroms or higher, about 3 angstroms or higher, about 2.5 angstroms or higher, about 2.3 angstroms or higher, about 2 angstroms or higher, about 1.5 angstroms or higher, and about 1 angstrom or higher being increasingly more preferred. It is appreciated, however, that additional crystals of lower resolutions can have utility in discerning overall topology of the structures, e.g., location of a binding site or where a molecule binds to a receptor or to an antibody. A particularly preferred isolated crystal of the present invention has amino acid sequence SEQ ID NO:2 or SEQ ID NO:8, or a sequence essentially equivalent that represents another mammalian Fc-Cε3/Cε4 region. Preferred are crystals that belong to spacegroup P42$_1$2, C2, or P2$_1$. A particularly preferred crystal includes a crystal belonging to spacegroup P42$_1$2 that has cell dimensions of about 105.6 angstroms x about 105.6 angstroms x about 47.1 angstroms, alpha=beta=gamma=90 degrees and that contains one Cε3/Cε4 chain per asymmetric unit of the crystal. A particularly preferred crystal includes a crystal belonging to spacegroup C2 that has cell dimensions of about 158 angstroms x about 108 angstroms x about 102 angstroms, and that contains 1.5 Cε3/Cε4 chains per asymmetric unit of the crystal. A particularly preferred crystal includes a crystal belonging to spacegroup P2$_1$, that has cell dimensions of about 66 angstroms x about 99 angstroms x about 77 angstroms, and that contains two Cε3/Cε4 chains per asymmetric unit of the crystal. A particularly preferred crystal includes a crystal belonging to spacegroup P2$_1$, that has cell dimensions of about 48 angstroms x about 104 angstroms x about 150 angstroms, and that contains three Cε3/Cε4 chains per asymmetric unit of the crystal. Such preferred crystals preferably diffracts X-rays to a resolution of about 2.3 angstroms.

The present invention includes a 3-D model of a Fc-Cε3/Cε4 region that substantially represents the atomic coordinates specified in Table 1, Table 2 or Table 3 of U.S. Patent Publication No. US-2001-0039479-A1 or the atomic coordinates specified in Table I, Table II or Table III. The present invention also includes 3-D models that comprise modifications of the model substantially represented by the atomic coordinates specified in Table 1, Table 2 or Table 3 of U.S. Patent Publication No. US-2001-0039479-A1 or the atomic coordinates specified in Table I, Table II or Table III. Each such modification represents an antibody Fc region that binds to a Fc receptor protein. A 3-D model of a Fc-Cε3/Cε4 region is a representation, or image, that predicts the actual structure of the corresponding region. As such, a 3-D model is a tool that can be used to probe the relationship between the region's structure and function at the atomic level and to design muteins (i.e., genetically and/or chemically altered antibodies) having an improved function, such as, but not limited to: increased (i.e., enhanced) stability; increased FcR binding activity, for example, by, increasing the affinity for an FcR by, for example, increasing the association rate and/or decreasing the dissociation rate between a FcR and an antibody or by altering substrate specificity (e.g., enhancing the ability of an Fc region of a certain species and class to bind to an antibody binding site from another species and/or another antibody class); and/or increased solubility (e.g., reduced aggregation). It is well known to those skilled in the art, however, that a 3-D model of a protein derived by analysis of protein crystals is not identical to the inherent structure of the protein. See, for example, Branden et al., *Introduction to Protein Structure*, Garland Publishing Inc., New York and London, 1991, especially on page 277, which states "not surprisingly the model never corresponds precisely to the actual crystal." Furthermore, the model can be subjected to further refinements to more closely correspond to the actual structure of a Fc region of an antibody. Such a refined model, which is an example of a modification of the present invention, is a better predictor of the actual structure and mechanism of action of the protein that the model represents. A refinement of a 3-D model of the present invention refers to an improved model of a Fc-Cε3/Cε4 region that can be obtained in a variety of ways known to those skilled in the art. Refinements can include models determined to more preferred degrees of resolution, preferably to about 4.5 angstroms, more preferably to about 4 angstroms, more preferably to about 3.5 angstroms, more preferably to about 3.25 angstroms, more preferably to about 3 angstroms, more preferably to about 2.5 angstroms, more preferably to about 2.3 angstroms, more preferably to about 2 angstroms, more preferably to about 1.5 angstroms, and even more preferably to about 1 angstrom. Preferred refinements are obtained using the 3-D model as a basis for such improvements.

One embodiment of the present invention is a 3-D model of a Fc-Cε3/Cε4 region that substantially represents the atomic coordinates specified (i.e., listed) in Table 1, Table 2 or Table 3 of U.S. Patent Publication No. US-2001-0039479-A1.

Another embodiment of the present invention is a 3-D model of a Fc-Cε3/Cε4 region that substantially represents the atomic coordinates specified (i.e., listed) in Table I.

TABLE I

Atomic coordinates of Crystal 1

| ATOM # | ATOM TYPE | RES | CHN | # | X | Y | Z | OCC | B |
|---|---|---|---|---|---|---|---|---|---|
| 1 | CB | VAL | A | 336 | 0.000 | 57.361 | 68.916 | 1.00 | 104.06 |
| 2 | CG1 | VAL | A | 336 | 0.939 | 57.582 | 67.743 | 1.00 | 100.47 |
| 3 | CG2 | VAL | A | 336 | −1.439 | 57.266 | 68.439 | 1.00 | 100.95 |
| 4 | C | VAL | A | 336 | 1.824 | 56.226 | 70.177 | 1.00 | 105.63 |
| 5 | O | VAL | A | 336 | 2.088 | 56.988 | 71.110 | 1.00 | 108.45 |
| 6 | N | VAL | A | 336 | −0.551 | 55.803 | 70.796 | 1.00 | 107.78 |
| 7 | CA | VAL | A | 336 | 0.391 | 56.074 | 69.671 | 1.00 | 104.13 |
| 8 | N | SER | A | 337 | 2.745 | 55.495 | 69.554 | 1.00 | 105.70 |
| 9 | CA | SER | A | 337 | 4.157 | 55.544 | 69.928 | 1.00 | 101.17 |
| 10 | CB | SER | A | 337 | 4.469 | 54.442 | 70.944 | 1.00 | 104.17 |
| 11 | OG | SER | A | 337 | 4.064 | 53.174 | 70.460 | 1.00 | 107.93 |
| 12 | C | SER | A | 337 | 5.047 | 55.388 | 68.695 | 1.00 | 94.73 |
| 13 | O | SER | A | 337 | 4.684 | 54.693 | 67.745 | 1.00 | 95.46 |
| 14 | N | ALA | A | 338 | 6.209 | 56.039 | 68.712 | 1.00 | 89.09 |
| 15 | CA | ALA | A | 338 | 7.136 | 55.971 | 67.584 | 1.00 | 81.46 |
| 16 | CB | ALA | A | 338 | 7.086 | 57.275 | 66.791 | 1.00 | 79.77 |
| 17 | C | ALA | A | 338 | 8.568 | 55.681 | 68.023 | 1.00 | 77.63 |
| 18 | O | ALA | A | 338 | 9.003 | 56.136 | 69.082 | 1.00 | 75.50 |
| 19 | N | TYR | A | 339 | 9.293 | 54.926 | 67.196 | 1.00 | 73.75 |
| 20 | CA | TYR | A | 339 | 10.680 | 54.558 | 67.476 | 1.00 | 71.29 |
| 21 | CB | TYR | A | 339 | 10.761 | 53.085 | 67.893 | 1.00 | 76.73 |
| 22 | CG | TYR | A | 339 | 9.608 | 52.639 | 68.763 | 1.00 | 82.05 |
| 23 | CD1 | TYR | A | 339 | 8.376 | 52.304 | 68.201 | 1.00 | 85.08 |
| 24 | CE1 | TYR | A | 339 | 7.292 | 51.937 | 69.003 | 1.00 | 88.51 |
| 25 | CD2 | TYR | A | 339 | 9.734 | 52.595 | 70.151 | 1.00 | 85.02 |
| 26 | CE2 | TYR | A | 339 | 8.658 | 52.231 | 70.962 | 1.00 | 88.15 |
| 27 | CZ | TYR | A | 339 | 7.440 | 51.905 | 70.381 | 1.00 | 89.19 |
| 28 | OH | TYR | A | 339 | 6.372 | 51.553 | 71.176 | 1.00 | 90.60 |
| 29 | C | TYR | A | 339 | 11.565 | 54.795 | 66.250 | 1.00 | 67.27 |
| 30 | O | TYR | A | 339 | 11.099 | 54.732 | 65.110 | 1.00 | 65.48 |
| 31 | N | LEU | A | 340 | 12.845 | 55.061 | 66.492 | 1.00 | 62.65 |
| 32 | CA | LEU | A | 340 | 13.797 | 55.323 | 65.416 | 1.00 | 58.34 |
| 33 | CB | LEU | A | 340 | 13.986 | 56.836 | 65.256 | 1.00 | 56.92 |
| 34 | CG | LEU | A | 340 | 14.901 | 57.348 | 64.143 | 1.00 | 54.29 |
| 35 | CD1 | LEU | A | 340 | 14.312 | 56.998 | 62.774 | 1.00 | 52.41 |
| 36 | CD2 | LEU | A | 340 | 15.061 | 58.855 | 64.296 | 1.00 | 52.78 |
| 37 | C | LEU | A | 340 | 15.127 | 54.662 | 65.753 | 1.00 | 55.96 |
| 38 | O | LEU | A | 340 | 15.737 | 54.987 | 66.773 | 1.00 | 56.22 |
| 39 | N | SER | A | 341 | 15.585 | 53.758 | 64.888 | 1.00 | 53.74 |
| 40 | CA | SER | A | 341 | 16.830 | 53.026 | 65.134 | 1.00 | 51.54 |
| 41 | CB | SER | A | 341 | 16.593 | 51.527 | 64.911 | 1.00 | 53.44 |
| 42 | OG | SER | A | 341 | 16.138 | 51.273 | 63.592 | 1.00 | 56.74 |
| 43 | C | SER | A | 341 | 18.072 | 53.457 | 64.349 | 1.00 | 48.19 |
| 44 | O | SER | A | 341 | 18.008 | 54.314 | 63.471 | 1.00 | 48.75 |
| 45 | N | ARG | A | 342 | 19.203 | 52.842 | 64.688 | 1.00 | 43.52 |
| 46 | CA | ARG | A | 342 | 20.492 | 53.117 | 64.045 | 1.00 | 41.30 |
| 47 | CB | ARG | A | 342 | 21.594 | 53.232 | 65.114 | 1.00 | 37.04 |
| 48 | CG | ARG | A | 342 | 21.298 | 54.283 | 66.209 | 1.00 | 37.13 |
| 49 | CD | ARG | A | 342 | 22.417 | 54.380 | 67.265 | 1.00 | 37.05 |
| 50 | NE | ARG | A | 342 | 22.432 | 53.205 | 68.140 | 1.00 | 42.66 |
| 51 | CZ | ARG | A | 342 | 21.724 | 53.086 | 69.264 | 1.00 | 44.38 |
| 52 | NH1 | ARG | A | 342 | 20.938 | 54.075 | 69.676 | 1.00 | 44.22 |
| 53 | NH2 | ARG | A | 342 | 21.787 | 51.965 | 69.972 | 1.00 | 44.68 |
| 54 | C | ARG | A | 342 | 20.817 | 51.977 | 63.057 | 1.00 | 39.38 |
| 55 | O | ARG | A | 342 | 20.214 | 50.904 | 63.118 | 1.00 | 37.50 |
| 56 | N | PRO | A | 343 | 21.767 | 52.202 | 62.132 | 1.00 | 38.43 |
| 57 | CD | PRO | A | 343 | 22.548 | 53.434 | 61.918 | 1.00 | 39.15 |
| 58 | CA | PRO | A | 343 | 22.129 | 51.165 | 61.154 | 1.00 | 38.25 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 59 | CB | PRO | A | 343 | 23.113 | 51.878 | 60.220 | 1.00 | 37.40 |
| 60 | CG | PRO | A | 343 | 22.845 | 53.367 | 60.455 | 1.00 | 40.48 |
| 61 | C | PRO | A | 343 | 22.790 | 49.949 | 61.810 | 1.00 | 36.64 |
| 62 | O | PRO | A | 343 | 23.403 | 50.068 | 62.875 | 1.00 | 33.99 |
| 63 | N | SER | A | 344 | 22.672 | 48.787 | 61.170 | 1.00 | 34.16 |
| 64 | CA | SER | A | 344 | 23.306 | 47.583 | 61.693 | 1.00 | 34.69 |
| 65 | CB | SER | A | 344 | 22.689 | 46.328 | 61.078 | 1.00 | 35.68 |
| 66 | OG | SER | A | 344 | 23.333 | 46.005 | 59.850 | 1.00 | 35.40 |
| 67 | C | SER | A | 344 | 24.761 | 47.661 | 61.245 | 1.00 | 34.74 |
| 68 | O | SER | A | 344 | 25.048 | 48.178 | 60.152 | 1.00 | 34.95 |
| 69 | N | PRO | A | 345 | 25.697 | 47.164 | 62.079 | 1.00 | 33.59 |
| 70 | CD | PRO | A | 345 | 25.470 | 46.819 | 63.496 | 1.00 | 33.16 |
| 71 | CA | PRO | A | 345 | 27.133 | 47.165 | 61.771 | 1.00 | 34.50 |
| 72 | CB | PRO | A | 345 | 27.759 | 46.559 | 63.030 | 1.00 | 32.68 |
| 73 | CG | PRO | A | 345 | 26.848 | 47.053 | 64.111 | 1.00 | 33.43 |
| 74 | C | PRO | A | 345 | 27.477 | 46.357 | 60.509 | 1.00 | 35.51 |
| 75 | O | PRO | A | 345 | 28.525 | 46.560 | 59.894 | 1.00 | 35.61 |
| 76 | N | PHE | A | 346 | 26.604 | 45.427 | 60.137 | 1.00 | 37.85 |
| 77 | CA | PHE | A | 346 | 26.831 | 44.624 | 58.943 | 1.00 | 39.17 |
| 78 | CB | PHE | A | 346 | 25.926 | 43.386 | 58.966 | 1.00 | 41.13 |
| 79 | CG | PHE | A | 346 | 25.902 | 42.624 | 57.664 | 1.00 | 45.05 |
| 80 | CD1 | PHE | A | 346 | 27.088 | 42.207 | 57.060 | 1.00 | 45.79 |
| 81 | CD2 | PHE | A | 346 | 24.692 | 42.343 | 57.031 | 1.00 | 45.55 |
| 82 | CE1 | PHE | A | 346 | 27.071 | 41.526 | 55.841 | 1.00 | 47.70 |
| 83 | CE2 | PHE | A | 346 | 24.662 | 41.662 | 55.812 | 1.00 | 45.55 |
| 84 | CZ | PHE | A | 346 | 25.854 | 41.254 | 55.216 | 1.00 | 46.20 |
| 85 | C | PHE | A | 346 | 26.551 | 45.482 | 57.696 | 1.00 | 39.19 |
| 86 | O | PHE | A | 346 | 27.328 | 45.483 | 56.734 | 1.00 | 36.31 |
| 87 | N | ASP | A | 347 | 25.437 | 46.207 | 57.720 | 1.00 | 40.01 |
| 88 | CA | ASP | A | 347 | 25.073 | 47.096 | 56.614 | 1.00 | 42.31 |
| 89 | CB | ASP | A | 347 | 23.701 | 47.733 | 56.861 | 1.00 | 43.13 |
| 90 | CG | ASP | A | 347 | 22.549 | 46.803 | 56.531 | 1.00 | 45.70 |
| 91 | OD1 | ASP | A | 347 | 21.378 | 47.182 | 56.773 | 1.00 | 48.25 |
| 92 | OD2 | ASP | A | 347 | 22.809 | 45.697 | 56.021 | 1.00 | 47.26 |
| 93 | C | ASP | A | 347 | 26.100 | 48.222 | 56.463 | 1.00 | 41.39 |
| 94 | O | ASP | A | 347 | 26.561 | 48.522 | 55.359 | 1.00 | 41.54 |
| 95 | N | LEU | A | 348 | 26.454 | 48.837 | 57.585 | 1.00 | 41.41 |
| 96 | CA | LEU | A | 348 | 27.386 | 49.959 | 57.596 | 1.00 | 43.11 |
| 97 | CB | LEU | A | 348 | 27.425 | 50.585 | 59.004 | 1.00 | 42.07 |
| 98 | CG | LEU | A | 348 | 28.343 | 51.789 | 59.303 | 1.00 | 44.92 |
| 99 | CD1 | LEU | A | 348 | 27.776 | 53.072 | 58.685 | 1.00 | 41.62 |
| 100 | CD2 | LEU | A | 348 | 28.471 | 51.969 | 60.817 | 1.00 | 42.64 |
| 101 | C | LEU | A | 348 | 28.808 | 49.632 | 57.149 | 1.00 | 45.09 |
| 102 | O | LEU | A | 348 | 29.396 | 50.380 | 56.362 | 1.00 | 44.24 |
| 103 | N | PHE | A | 349 | 29.351 | 48.516 | 57.636 | 1.00 | 47.12 |
| 104 | CA | PHE | A | 349 | 30.729 | 48.134 | 57.330 | 1.00 | 50.16 |
| 105 | CB | PHE | A | 349 | 31.428 | 47.649 | 58.604 | 1.00 | 50.23 |
| 106 | CG | PHE | A | 349 | 31.420 | 48.647 | 59.726 | 1.00 | 48.57 |
| 107 | CD1 | PHE | A | 349 | 30.617 | 48.448 | 60.846 | 1.00 | 47.65 |
| 108 | CD2 | PHE | A | 349 | 32.224 | 49.780 | 59.670 | 1.00 | 47.71 |
| 109 | CE1 | PHE | A | 349 | 30.617 | 49.364 | 61.895 | 1.00 | 47.17 |
| 110 | CE2 | PHE | A | 349 | 32.230 | 50.702 | 60.715 | 1.00 | 46.32 |
| 111 | CZ | PHE | A | 349 | 31.426 | 50.492 | 61.829 | 1.00 | 45.76 |
| 112 | C | PHE | A | 349 | 31.010 | 47.117 | 56.228 | 1.00 | 52.31 |
| 113 | O | PHE | A | 349 | 32.022 | 47.231 | 55.548 | 1.00 | 53.83 |
| 114 | N | ILE | A | 350 | 30.158 | 46.112 | 56.053 | 1.00 | 55.68 |
| 115 | CA | ILE | A | 350 | 30.410 | 45.113 | 55.011 | 1.00 | 59.20 |
| 116 | CB | ILE | A | 350 | 29.993 | 43.697 | 55.474 | 1.00 | 59.22 |
| 117 | CG2 | ILE | A | 350 | 30.534 | 42.657 | 54.502 | 1.00 | 57.64 |
| 118 | CG1 | ILE | A | 350 | 30.545 | 43.416 | 56.879 | 1.00 | 58.89 |
| 119 | CD1 | ILE | A | 350 | 32.053 | 43.509 | 56.993 | 1.00 | 59.28 |
| 120 | C | ILE | A | 350 | 29.708 | 45.444 | 53.685 | 1.00 | 61.93 |
| 121 | O | ILE | A | 350 | 30.362 | 45.575 | 52.649 | 1.00 | 61.54 |
| 122 | N | ARG | A | 351 | 28.383 | 45.564 | 53.711 | 1.00 | 65.31 |
| 123 | CA | ARG | A | 351 | 27.639 | 45.913 | 52.507 | 1.00 | 69.63 |
| 124 | CB | ARG | A | 351 | 26.139 | 45.823 | 52.750 | 1.00 | 73.51 |
| 125 | CG | ARG | A | 351 | 25.547 | 44.450 | 52.600 | 1.00 | 80.96 |
| 126 | CD | ARG | A | 351 | 24.043 | 44.580 | 52.511 | 1.00 | 87.70 |
| 127 | NE | ARG | A | 351 | 23.382 | 43.305 | 52.268 | 1.00 | 94.46 |
| 128 | CZ | ARG | A | 351 | 22.071 | 43.172 | 52.097 | 1.00 | 97.33 |
| 129 | NH1 | ARG | A | 351 | 21.286 | 44.241 | 52.142 | 1.00 | 98.99 |
| 130 | NH2 | ARG | A | 351 | 21.543 | 41.972 | 51.890 | 1.00 | 98.89 |
| 131 | C | ARG | A | 351 | 27.977 | 47.345 | 52.104 | 1.00 | 69.92 |
| 132 | O | ARG | A | 351 | 27.964 | 47.689 | 50.925 | 1.00 | 68.97 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 133 | N | LYS | A | 352 | 28.268 | 48.172 | 53.105 | 1.00 | 69.13 |
| 134 | CA | LYS | A | 352 | 28.609 | 49.573 | 52.904 | 1.00 | 68.80 |
| 135 | CB | LYS | A | 352 | 29.796 | 49.708 | 51.948 | 1.00 | 75.97 |
| 136 | CG | LYS | A | 352 | 31.139 | 49.352 | 52.564 | 1.00 | 84.57 |
| 137 | CD | LYS | A | 352 | 32.279 | 49.770 | 51.646 | 1.00 | 92.06 |
| 138 | CE | LYS | A | 352 | 33.634 | 49.599 | 52.311 | 1.00 | 96.52 |
| 139 | NZ | LYS | A | 352 | 34.732 | 50.108 | 51.444 | 1.00 | 100.31 |
| 140 | C | LYS | A | 352 | 27.451 | 50.425 | 52.398 | 1.00 | 63.52 |
| 141 | O | LYS | A | 352 | 27.642 | 51.297 | 51.561 | 1.00 | 64.35 |
| 142 | N | SER | A | 353 | 26.250 | 50.165 | 52.903 | 1.00 | 58.83 |
| 143 | CA | SER | A | 353 | 25.077 | 50.942 | 52.524 | 1.00 | 51.90 |
| 144 | CB | SER | A | 353 | 24.469 | 50.423 | 51.214 | 1.00 | 51.89 |
| 145 | OG | SER | A | 353 | 24.432 | 49.011 | 51.164 | 1.00 | 53.69 |
| 146 | C | SER | A | 353 | 24.058 | 50.931 | 53.662 | 1.00 | 47.46 |
| 147 | O | SER | A | 353 | 23.078 | 50.183 | 53.654 | 1.00 | 45.58 |
| 148 | N | PRO | A | 354 | 24.288 | 51.789 | 54.665 | 1.00 | 43.97 |
| 149 | CD | PRO | A | 354 | 25.405 | 52.741 | 54.627 | 1.00 | 41.02 |
| 150 | CA | PRO | A | 354 | 23.490 | 51.990 | 55.880 | 1.00 | 40.75 |
| 151 | CB | PRO | A | 354 | 24.310 | 53.005 | 56.671 | 1.00 | 42.87 |
| 152 | CG | PRO | A | 354 | 25.674 | 52.927 | 56.071 | 1.00 | 43.56 |
| 153 | C | PRO | A | 354 | 22.088 | 52.526 | 55.630 | 1.00 | 38.72 |
| 154 | O | PRO | A | 354 | 21.832 | 53.158 | 54.609 | 1.00 | 38.14 |
| 155 | N | THR | A | 355 | 21.195 | 52.288 | 56.587 | 1.00 | 36.15 |
| 156 | CA | THR | A | 355 | 19.817 | 52.769 | 56.517 | 1.00 | 35.50 |
| 157 | CB | THR | A | 355 | 18.877 | 51.810 | 55.735 | 1.00 | 35.97 |
| 158 | OG1 | THR | A | 355 | 18.864 | 50.526 | 56.372 | 1.00 | 35.90 |
| 159 | CG2 | THR | A | 355 | 19.320 | 51.668 | 54.282 | 1.00 | 34.64 |
| 160 | C | THR | A | 355 | 19.264 | 52.870 | 57.931 | 1.00 | 36.82 |
| 161 | O | THR | A | 355 | 19.794 | 52.233 | 58.854 | 1.00 | 36.51 |
| 162 | N | ILE | A | 356 | 18.214 | 53.680 | 58.098 | 1.00 | 35.09 |
| 163 | CA | ILE | A | 356 | 17.551 | 53.836 | 59.386 | 1.00 | 36.31 |
| 164 | CB | ILE | A | 356 | 17.935 | 55.171 | 60.093 | 1.00 | 35.45 |
| 165 | CG2 | ILE | A | 356 | 19.434 | 55.160 | 60.414 | 1.00 | 33.84 |
| 166 | CG1 | ILE | A | 356 | 17.579 | 56.377 | 59.224 | 1.00 | 37.61 |
| 167 | CD1 | ILE | A | 356 | 17.927 | 57.715 | 59.871 | 1.00 | 37.21 |
| 168 | C | ILE | A | 356 | 16.048 | 53.747 | 59.156 | 1.00 | 37.70 |
| 169 | O | ILE | A | 356 | 15.578 | 53.963 | 58.040 | 1.00 | 39.33 |
| 170 | N | THR | A | 357 | 15.298 | 53.414 | 60.203 | 1.00 | 40.22 |
| 171 | CA | THR | A | 357 | 13.851 | 53.243 | 60.083 | 1.00 | 43.07 |
| 172 | CB | THR | A | 357 | 13.465 | 51.725 | 60.133 | 1.00 | 44.03 |
| 173 | OG1 | THR | A | 357 | 14.248 | 50.990 | 59.185 | 1.00 | 43.21 |
| 174 | CG2 | THR | A | 357 | 11.988 | 51.530 | 59.835 | 1.00 | 41.88 |
| 175 | C | THR | A | 357 | 13.044 | 53.937 | 61.178 | 1.00 | 45.79 |
| 176 | O | THR | A | 357 | 13.340 | 53.787 | 62.366 | 1.00 | 42.42 |
| 177 | N | CYS | A | 358 | 12.028 | 54.694 | 60.763 | 1.00 | 48.83 |
| 178 | CA | CYS | A | 358 | 11.129 | 55.368 | 61.693 | 1.00 | 53.66 |
| 179 | C | CYS | A | 358 | 9.898 | 54.467 | 61.756 | 1.00 | 59.13 |
| 180 | O | CYS | A | 358 | 9.310 | 54.133 | 60.722 | 1.00 | 57.49 |
| 181 | CB | CYS | A | 358 | 10.723 | 56.757 | 61.180 | 1.00 | 54.24 |
| 182 | SG | CYS | A | 358 | 9.787 | 57.758 | 62.392 | 1.00 | 54.74 |
| 183 | N | LEU | A | 359 | 9.518 | 54.068 | 62.965 | 1.00 | 64.88 |
| 184 | CA | LEU | A | 359 | 8.375 | 53.184 | 63.159 | 1.00 | 70.87 |
| 185 | CB | LEU | A | 359 | 8.863 | 51.828 | 63.676 | 1.00 | 77.13 |
| 186 | CG | LEU | A | 359 | 7.815 | 50.862 | 64.236 | 1.00 | 81.88 |
| 187 | CD1 | LEU | A | 359 | 6.840 | 50.456 | 63.146 | 1.00 | 84.81 |
| 188 | CD2 | LEU | A | 359 | 8.517 | 49.643 | 64.810 | 1.00 | 85.45 |
| 189 | C | LEU | A | 359 | 7.348 | 53.748 | 64.130 | 1.00 | 72.38 |
| 190 | O | LEU | A | 359 | 7.701 | 54.214 | 65.211 | 1.00 | 73.65 |
| 191 | N | VAL | A | 360 | 6.076 | 53.693 | 63.746 | 1.00 | 78.19 |
| 192 | CA | VAL | A | 360 | 5.004 | 54.190 | 64.603 | 1.00 | 83.33 |
| 193 | CB | VAL | A | 360 | 4.459 | 55.549 | 64.083 | 1.00 | 78.64 |
| 194 | CG1 | VAL | A | 360 | 4.065 | 55.436 | 62.626 | 1.00 | 77.28 |
| 195 | CG2 | VAL | A | 360 | 3.278 | 55.995 | 64.925 | 1.00 | 76.95 |
| 196 | C | VAL | A | 360 | 3.860 | 53.177 | 64.730 | 1.00 | 92.26 |
| 197 | O | VAL | A | 360 | 3.277 | 52.747 | 63.732 | 1.00 | 87.65 |
| 198 | N | VAL | A | 361 | 3.561 | 52.797 | 65.971 | 1.00 | 99.42 |
| 199 | CA | VAL | A | 361 | 2.503 | 51.831 | 66.273 | 1.00 | 113.92 |
| 200 | CB | VAL | A | 361 | 2.940 | 50.849 | 67.388 | 1.00 | 112.90 |
| 201 | CG1 | VAL | A | 361 | 1.845 | 49.823 | 67.640 | 1.00 | 111.27 |
| 202 | CG2 | VAL | A | 361 | 4.234 | 50.160 | 66.997 | 1.00 | 111.01 |
| 203 | C | VAL | A | 361 | 1.225 | 52.530 | 66.728 | 1.00 | 123.35 |
| 204 | O | VAL | A | 361 | 1.195 | 53.171 | 67.780 | 1.00 | 126.04 |
| 205 | N | ASP | A | 362 | 0.169 | 52.394 | 65.932 | 1.00 | 136.18 |
| 206 | CA | ASP | A | 362 | −1.111 | 53.018 | 66.242 | 1.00 | 146.85 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 207 | CB | ASP | A | 362 | −1.629 | 53.771 | 65.014 | 1.00 | 148.02 |
| 208 | CG | ASP | A | 362 | −2.962 | 54.445 | 65.263 | 1.00 | 150.54 |
| 209 | OD1 | ASP | A | 362 | −3.965 | 53.726 | 65.444 | 1.00 | 151.61 |
| 210 | OD2 | ASP | A | 362 | −3.006 | 55.692 | 65.283 | 1.00 | 151.29 |
| 211 | C | ASP | A | 362 | −2.141 | 51.989 | 66.696 | 1.00 | 151.14 |
| 212 | O | ASP | A | 362 | −2.586 | 51.155 | 65.907 | 1.00 | 153.60 |
| 213 | N | GLY | A | 363 | −2.518 | 52.062 | 67.970 | 1.00 | 154.63 |
| 214 | CA | GLY | A | 363 | −3.493 | 51.135 | 68.522 | 1.00 | 157.96 |
| 215 | C | GLY | A | 363 | −4.789 | 51.023 | 67.733 | 1.00 | 158.58 |
| 216 | O | GLY | A | 363 | −4.991 | 50.051 | 67.002 | 1.00 | 160.20 |
| 217 | N | ALA | A | 364 | −5.669 | 52.012 | 67.884 | 1.00 | 155.34 |
| 218 | CA | ALA | A | 364 | −6.955 | 52.023 | 67.184 | 1.00 | 149.90 |
| 219 | CB | ALA | A | 364 | −8.068 | 52.429 | 68.149 | 1.00 | 152.03 |
| 220 | C | ALA | A | 364 | −6.935 | 52.967 | 65.978 | 1.00 | 145.03 |
| 221 | O | ALA | A | 364 | −7.096 | 54.180 | 66.121 | 1.00 | 145.13 |
| 222 | N | PRO | A | 365 | −6.742 | 52.413 | 64.769 | 1.00 | 138.72 |
| 223 | CD | PRO | A | 365 | −6.496 | 50.984 | 64.507 | 1.00 | 137.09 |
| 224 | CA | PRO | A | 365 | −6.693 | 53.179 | 63.520 | 1.00 | 138.26 |
| 225 | CB | PRO | A | 365 | −6.604 | 52.089 | 62.456 | 1.00 | 135.27 |
| 226 | CG | PRO | A | 365 | −5.832 | 51.020 | 63.151 | 1.00 | 134.41 |
| 227 | C | PRO | A | 365 | −7.883 | 54.109 | 63.293 | 1.00 | 138.58 |
| 228 | O | PRO | A | 365 | −8.929 | 53.974 | 63.928 | 1.00 | 137.38 |
| 229 | N | SER | A | 366 | −7.702 | 55.050 | 62.372 | 1.00 | 139.37 |
| 230 | CA | SER | A | 366 | −8.726 | 56.026 | 62.017 | 1.00 | 142.78 |
| 231 | CB | SER | A | 366 | −8.815 | 57.118 | 63.084 | 1.00 | 139.65 |
| 232 | OG | SER | A | 366 | −9.679 | 58.160 | 62.670 | 1.00 | 135.85 |
| 233 | C | SER | A | 366 | −8.347 | 56.652 | 60.682 | 1.00 | 146.17 |
| 234 | O | SER | A | 366 | −7.245 | 56.428 | 60.182 | 1.00 | 146.26 |
| 235 | N | LYS | A | 367 | −9.256 | 57.431 | 60.105 | 1.00 | 147.16 |
| 236 | CA | LYS | A | 367 | −8.982 | 58.086 | 58.831 | 1.00 | 149.47 |
| 237 | CB | LYS | A | 367 | −10.221 | 58.841 | 58.339 | 1.00 | 142.71 |
| 238 | CG | LYS | A | 367 | −10.094 | 59.408 | 56.929 | 1.00 | 130.61 |
| 239 | CD | LYS | A | 367 | −10.038 | 58.303 | 55.881 | 1.00 | 120.16 |
| 240 | CE | LYS | A | 367 | −10.020 | 58.875 | 54.469 | 1.00 | 113.56 |
| 241 | NZ | LYS | A | 367 | −10.093 | 57.811 | 53.425 | 1.00 | 109.32 |
| 242 | C | LYS | A | 367 | −7.834 | 59.066 | 59.044 | 1.00 | 154.50 |
| 243 | O | LYS | A | 367 | −8.055 | 60.258 | 59.260 | 1.00 | 158.25 |
| 244 | N | GLY | A | 368 | −6.608 | 58.555 | 58.992 | 1.00 | 158.03 |
| 245 | CA | GLY | A | 368 | −5.451 | 59.405 | 59.194 | 1.00 | 157.11 |
| 246 | C | GLY | A | 368 | −4.319 | 59.151 | 58.222 | 1.00 | 153.09 |
| 247 | O | GLY | A | 368 | −3.624 | 58.138 | 58.311 | 1.00 | 157.69 |
| 248 | N | THR | A | 369 | −4.134 | 60.076 | 57.287 | 1.00 | 149.27 |
| 249 | CA | THR | A | 369 | −3.068 | 59.958 | 56.304 | 1.00 | 141.52 |
| 250 | CB | THR | A | 369 | −3.332 | 60.867 | 55.083 | 1.00 | 139.43 |
| 251 | OG1 | THR | A | 369 | −4.683 | 60.694 | 54.642 | 1.00 | 138.01 |
| 252 | CG2 | THR | A | 369 | −2.392 | 60.511 | 53.937 | 1.00 | 137.94 |
| 253 | C | THR | A | 369 | −1.776 | 60.395 | 56.992 | 1.00 | 135.66 |
| 254 | O | THR | A | 369 | −1.075 | 61.289 | 56.514 | 1.00 | 135.20 |
| 255 | N | VAL | A | 370 | −1.480 | 59.761 | 58.126 | 1.00 | 126.78 |
| 256 | CA | VAL | A | 370 | −0.286 | 60.063 | 58.911 | 1.00 | 119.50 |
| 257 | CB | VAL | A | 370 | 0.044 | 58.921 | 59.888 | 1.00 | 114.83 |
| 258 | CG1 | VAL | A | 370 | 1.308 | 59.249 | 60.661 | 1.00 | 108.60 |
| 259 | CG2 | VAL | A | 370 | −1.115 | 58.706 | 60.838 | 1.00 | 108.26 |
| 260 | C | VAL | A | 370 | 0.923 | 60.299 | 58.019 | 1.00 | 117.32 |
| 261 | O | VAL | A | 370 | 1.193 | 59.520 | 57.106 | 1.00 | 119.66 |
| 262 | N | GLN | A | 371 | 1.653 | 61.373 | 58.297 | 1.00 | 116.06 |
| 263 | CA | GLN | A | 371 | 2.825 | 61.719 | 57.508 | 1.00 | 112.26 |
| 264 | CB | GLN | A | 371 | 2.622 | 63.091 | 56.861 | 1.00 | 115.51 |
| 265 | CG | GLN | A | 371 | 3.836 | 63.619 | 56.121 | 1.00 | 120.20 |
| 266 | CD | GLN | A | 371 | 3.612 | 65.008 | 55.560 | 1.00 | 122.67 |
| 267 | OE1 | GLN | A | 371 | 3.289 | 65.942 | 56.296 | 1.00 | 123.89 |
| 268 | NE2 | GLN | A | 371 | 3.783 | 65.153 | 54.250 | 1.00 | 123.80 |
| 269 | C | GLN | A | 371 | 4.110 | 61.731 | 58.330 | 1.00 | 104.60 |
| 270 | O | GLN | A | 371 | 4.152 | 62.291 | 59.426 | 1.00 | 105.97 |
| 271 | N | LEU | A | 372 | 5.152 | 61.101 | 57.794 | 1.00 | 94.82 |
| 272 | CA | LEU | A | 372 | 6.456 | 61.058 | 58.449 | 1.00 | 82.83 |
| 273 | CB | LEU | A | 372 | 7.014 | 59.625 | 58.473 | 1.00 | 77.58 |
| 274 | CG | LEU | A | 372 | 6.138 | 58.506 | 59.057 | 1.00 | 71.87 |
| 275 | CD1 | LEU | A | 372 | 6.970 | 57.244 | 59.215 | 1.00 | 68.07 |
| 276 | CD2 | LEU | A | 372 | 5.567 | 58.919 | 60.403 | 1.00 | 68.54 |
| 277 | C | LEU | A | 372 | 7.374 | 61.963 | 57.630 | 1.00 | 77.97 |
| 278 | O | LEU | A | 372 | 7.464 | 61.817 | 56.413 | 1.00 | 78.19 |
| 279 | N | THR | A | 373 | 8.044 | 62.900 | 58.293 | 1.00 | 72.62 |
| 280 | CA | THR | A | 373 | 8.933 | 63.828 | 57.601 | 1.00 | 65.65 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 281 | CB | THR | A | 373 | 8.496 | 65.291 | 57.861 | 1.00 | 66.67 |
| 282 | OG1 | THR | A | 373 | 7.091 | 65.421 | 57.612 | 1.00 | 68.45 |
| 283 | CG2 | THR | A | 373 | 9.242 | 66.247 | 56.946 | 1.00 | 67.92 |
| 284 | C | THR | A | 373 | 10.378 | 63.647 | 58.066 | 1.00 | 59.92 |
| 285 | O | THR | A | 373 | 10.630 | 63.483 | 59.256 | 1.00 | 59.17 |
| 286 | N | TRP | A | 374 | 11.316 | 63.675 | 57.122 | 1.00 | 54.24 |
| 287 | CA | TRP | A | 374 | 12.742 | 63.517 | 57.422 | 1.00 | 49.23 |
| 288 | CB | TRP | A | 374 | 13.384 | 62.461 | 56.501 | 1.00 | 48.26 |
| 289 | CG | TRP | A | 374 | 12.965 | 61.020 | 56.737 | 1.00 | 49.73 |
| 290 | CD2 | TRP | A | 374 | 13.452 | 60.131 | 57.759 | 1.00 | 49.10 |
| 291 | CE2 | TRP | A | 374 | 12.773 | 58.902 | 57.601 | 1.00 | 49.51 |
| 292 | CE3 | TRP | A | 374 | 14.392 | 60.258 | 58.792 | 1.00 | 47.52 |
| 293 | CD1 | TRP | A | 374 | 12.043 | 60.309 | 56.025 | 1.00 | 50.00 |
| 294 | NE1 | TRP | A | 374 | 11.923 | 59.037 | 56.536 | 1.00 | 49.99 |
| 295 | CZ2 | TRP | A | 374 | 13.003 | 57.804 | 58.439 | 1.00 | 48.41 |
| 296 | CZ3 | TRP | A | 374 | 14.621 | 59.170 | 59.624 | 1.00 | 46.95 |
| 297 | CH2 | TRP | A | 374 | 13.927 | 57.957 | 59.442 | 1.00 | 48.46 |
| 298 | C | TRP | A | 374 | 13.527 | 64.831 | 57.263 | 1.00 | 46.69 |
| 299 | O | TRP | A | 374 | 13.150 | 65.692 | 56.461 | 1.00 | 45.27 |
| 300 | N | SER | A | 375 | 14.608 | 64.980 | 58.034 | 1.00 | 41.44 |
| 301 | CA | SER | A | 375 | 15.482 | 66.154 | 57.949 | 1.00 | 38.36 |
| 302 | CB | SER | A | 375 | 14.760 | 67.435 | 58.402 | 1.00 | 37.02 |
| 303 | OG | SER | A | 375 | 14.270 | 67.347 | 59.725 | 1.00 | 38.55 |
| 304 | C | SER | A | 375 | 16.773 | 65.966 | 58.748 | 1.00 | 36.95 |
| 305 | O | SER | A | 375 | 16.863 | 65.074 | 59.600 | 1.00 | 37.91 |
| 306 | N | ARG | A | 376 | 17.775 | 66.789 | 58.445 | 1.00 | 33.92 |
| 307 | CA | ARG | A | 376 | 19.067 | 66.733 | 59.122 | 1.00 | 30.80 |
| 308 | CB | ARG | A | 376 | 20.202 | 66.702 | 58.107 | 1.00 | 28.45 |
| 309 | CG | ARG | A | 376 | 20.337 | 65.438 | 57.274 | 1.00 | 31.06 |
| 310 | CD | ARG | A | 376 | 21.810 | 65.310 | 56.865 | 1.00 | 32.28 |
| 311 | NE | ARG | A | 376 | 21.986 | 65.032 | 55.453 | 1.00 | 31.12 |
| 312 | CZ | ARG | A | 376 | 23.160 | 65.009 | 54.829 | 1.00 | 33.76 |
| 313 | NH1 | ARG | A | 376 | 24.296 | 65.246 | 55.487 | 1.00 | 29.77 |
| 314 | NH2 | ARG | A | 376 | 23.191 | 64.756 | 53.526 | 1.00 | 33.89 |
| 315 | C | ARG | A | 376 | 19.286 | 67.947 | 60.023 | 1.00 | 30.22 |
| 316 | O | ARG | A | 376 | 18.887 | 69.058 | 59.682 | 1.00 | 29.31 |
| 317 | N | ALA | A | 377 | 19.955 | 67.743 | 61.155 | 1.00 | 31.18 |
| 318 | CA | ALA | A | 377 | 20.225 | 68.836 | 62.089 | 1.00 | 30.68 |
| 319 | CB | ALA | A | 377 | 20.972 | 68.311 | 63.321 | 1.00 | 31.59 |
| 320 | C | ALA | A | 377 | 21.058 | 69.902 | 61.397 | 1.00 | 30.28 |
| 321 | O | ALA | A | 377 | 20.957 | 71.080 | 61.711 | 1.00 | 30.54 |
| 322 | N | SER | A | 378 | 21.880 | 69.476 | 60.447 | 1.00 | 30.07 |
| 323 | CA | SER | A | 378 | 22.730 | 70.398 | 59.704 | 1.00 | 33.91 |
| 324 | CB | SER | A | 378 | 23.904 | 69.631 | 59.082 | 1.00 | 30.74 |
| 325 | OG | SER | A | 378 | 23.484 | 68.951 | 57.906 | 1.00 | 28.95 |
| 326 | C | SER | A | 378 | 22.012 | 71.180 | 58.587 | 1.00 | 36.15 |
| 327 | O | SER | A | 378 | 22.587 | 72.104 | 58.022 | 1.00 | 37.34 |
| 328 | N | GLY | A | 379 | 20.776 | 70.807 | 58.261 | 1.00 | 38.58 |
| 329 | CA | GLY | A | 379 | 20.066 | 71.484 | 57.187 | 1.00 | 42.61 |
| 330 | C | GLY | A | 379 | 20.322 | 70.882 | 55.802 | 1.00 | 45.44 |
| 331 | O | GLY | A | 379 | 19.533 | 71.098 | 54.884 | 1.00 | 46.89 |
| 332 | N | LYS | A | 380 | 21.412 | 70.131 | 55.636 | 1.00 | 47.14 |
| 333 | CA | LYS | A | 380 | 21.735 | 69.503 | 54.344 | 1.00 | 47.19 |
| 334 | CB | LYS | A | 380 | 23.072 | 68.764 | 54.427 | 1.00 | 49.01 |
| 335 | CG | LYS | A | 380 | 24.264 | 69.686 | 54.622 | 1.00 | 52.20 |
| 336 | CD | LYS | A | 380 | 25.553 | 68.898 | 54.818 | 1.00 | 53.66 |
| 337 | CE | LYS | A | 380 | 26.750 | 69.826 | 54.914 | 1.00 | 56.18 |
| 338 | NZ | LYS | A | 380 | 28.004 | 69.074 | 55.204 | 1.00 | 58.19 |
| 339 | C | LYS | A | 380 | 20.634 | 68.543 | 53.879 | 1.00 | 48.36 |
| 340 | O | LYS | A | 380 | 19.939 | 67.947 | 54.698 | 1.00 | 45.32 |
| 341 | N | PRO | A | 381 | 20.472 | 68.382 | 52.550 | 1.00 | 43.99 |
| 342 | CD | PRO | A | 381 | 21.338 | 68.987 | 51.521 | 1.00 | 46.44 |
| 343 | CA | PRO | A | 381 | 19.459 | 67.514 | 51.928 | 1.00 | 43.77 |
| 344 | CB | PRO | A | 381 | 19.630 | 67.798 | 50.432 | 1.00 | 45.82 |
| 345 | CG | PRO | A | 381 | 21.095 | 68.089 | 50.325 | 1.00 | 48.82 |
| 346 | C | PRO | A | 381 | 19.492 | 66.015 | 52.247 | 1.00 | 43.92 |
| 347 | O | PRO | A | 381 | 20.550 | 65.437 | 52.485 | 1.00 | 39.85 |
| 348 | N | VAL | A | 382 | 18.304 | 65.414 | 52.253 | 1.00 | 38.55 |
| 349 | CA | VAL | A | 382 | 18.118 | 63.995 | 52.528 | 1.00 | 39.11 |
| 350 | CB | VAL | A | 382 | 17.031 | 63.773 | 53.587 | 1.00 | 40.72 |
| 351 | CG1 | VAL | A | 382 | 17.458 | 64.375 | 54.918 | 1.00 | 39.77 |
| 352 | CG2 | VAL | A | 382 | 15.719 | 64.389 | 53.107 | 1.00 | 37.97 |
| 353 | C | VAL | A | 382 | 17.673 | 63.256 | 51.263 | 1.00 | 40.51 |
| 354 | O | VAL | A | 382 | 16.994 | 63.837 | 50.410 | 1.00 | 40.14 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 355 | N | GLN | A | 383 | 18.034 | 61.975 | 51.158 | 1.00 | 41.70 |
| 356 | CA | GLN | A | 383 | 17.677 | 61.158 | 49.998 | 1.00 | 42.82 |
| 357 | CB | GLN | A | 383 | 18.549 | 59.898 | 49.948 | 1.00 | 46.07 |
| 358 | CG | GLN | A | 383 | 20.043 | 60.155 | 49.739 | 1.00 | 53.12 |
| 359 | CD | GLN | A | 383 | 20.861 | 58.861 | 49.645 | 1.00 | 58.75 |
| 360 | OE1 | GLN | A | 383 | 20.574 | 57.983 | 48.818 | 1.00 | 60.78 |
| 361 | NE2 | GLN | A | 383 | 21.889 | 58.747 | 50.487 | 1.00 | 59.32 |
| 362 | C | GLN | A | 383 | 16.204 | 60.756 | 50.029 | 1.00 | 44.03 |
| 363 | O | GLN | A | 383 | 15.508 | 60.978 | 51.024 | 1.00 | 37.68 |
| 364 | N | HIS | A | 384 | 15.735 | 60.152 | 48.936 | 1.00 | 47.97 |
| 365 | CA | HIS | A | 384 | 14.345 | 59.703 | 48.831 | 1.00 | 54.11 |
| 366 | CB | HIS | A | 384 | 14.015 | 59.358 | 47.372 | 1.00 | 64.00 |
| 367 | CG | HIS | A | 384 | 12.608 | 58.886 | 47.160 | 1.00 | 74.55 |
| 368 | CD2 | HIS | A | 384 | 12.119 | 57.678 | 46.793 | 1.00 | 79.32 |
| 369 | ND1 | HIS | A | 384 | 11.512 | 59.704 | 47.342 | 1.00 | 79.27 |
| 370 | CE1 | HIS | A | 384 | 10.409 | 59.019 | 47.096 | 1.00 | 83.06 |
| 371 | NE2 | HIS | A | 384 | 10.749 | 57.788 | 46.761 | 1.00 | 83.59 |
| 372 | C | HIS | A | 384 | 14.130 | 58.473 | 49.714 | 1.00 | 52.33 |
| 373 | O | HIS | A | 384 | 14.932 | 57.540 | 49.680 | 1.00 | 52.41 |
| 374 | N | SER | A | 385 | 13.048 | 58.466 | 50.488 | 1.00 | 50.77 |
| 375 | CA | SER | A | 385 | 12.753 | 57.346 | 51.380 | 1.00 | 51.02 |
| 376 | CB | SER | A | 385 | 12.450 | 57.860 | 52.791 | 1.00 | 49.37 |
| 377 | OG | SER | A | 385 | 11.281 | 58.658 | 52.807 | 1.00 | 46.00 |
| 378 | C | SER | A | 385 | 11.601 | 56.447 | 50.911 | 1.00 | 54.45 |
| 379 | O | SER | A | 385 | 10.924 | 56.742 | 49.918 | 1.00 | 53.12 |
| 380 | N | THR | A | 386 | 11.383 | 55.354 | 51.643 | 1.00 | 57.83 |
| 381 | CA | THR | A | 386 | 10.340 | 54.382 | 51.311 | 1.00 | 62.39 |
| 382 | CB | THR | A | 386 | 10.960 | 52.997 | 51.012 | 1.00 | 66.04 |
| 383 | OG1 | THR | A | 386 | 11.768 | 53.077 | 49.830 | 1.00 | 70.54 |
| 384 | CG2 | THR | A | 386 | 9.871 | 51.949 | 50.817 | 1.00 | 69.70 |
| 385 | C | THR | A | 386 | 9.293 | 54.191 | 52.406 | 1.00 | 64.12 |
| 386 | O | THR | A | 386 | 9.629 | 53.873 | 53.548 | 1.00 | 61.03 |
| 387 | N | ARG | A | 387 | 8.023 | 54.364 | 52.049 | 1.00 | 66.97 |
| 388 | CA | ARG | A | 387 | 6.931 | 54.190 | 53.009 | 1.00 | 71.02 |
| 389 | CB | ARG | A | 387 | 5.797 | 55.185 | 52.718 | 1.00 | 72.96 |
| 390 | CG | ARG | A | 387 | 4.643 | 55.152 | 53.729 | 1.00 | 76.95 |
| 391 | CD | ARG | A | 387 | 3.517 | 56.111 | 53.328 | 1.00 | 81.46 |
| 392 | NE | ARG | A | 387 | 2.297 | 55.927 | 54.120 | 1.00 | 85.96 |
| 393 | CZ | ARG | A | 387 | 2.163 | 56.272 | 55.399 | 1.00 | 87.86 |
| 394 | NH1 | ARG | A | 387 | 3.174 | 56.828 | 56.049 | 1.00 | 89.59 |
| 395 | NH2 | ARG | A | 387 | 1.014 | 56.060 | 56.030 | 1.00 | 87.90 |
| 396 | C | ARG | A | 387 | 6.400 | 52.752 | 52.951 | 1.00 | 75.33 |
| 397 | O | ARG | A | 387 | 6.377 | 52.131 | 51.887 | 1.00 | 72.85 |
| 398 | N | LYS | A | 388 | 5.979 | 52.230 | 54.100 | 1.00 | 81.39 |
| 399 | CA | LYS | A | 388 | 5.457 | 50.866 | 54.191 | 1.00 | 90.63 |
| 400 | CB | LYS | A | 388 | 6.594 | 49.893 | 54.523 | 1.00 | 97.57 |
| 401 | CG | LYS | A | 388 | 6.135 | 48.486 | 54.893 | 1.00 | 110.17 |
| 402 | CD | LYS | A | 388 | 7.263 | 47.678 | 55.525 | 1.00 | 120.96 |
| 403 | CE | LYS | A | 388 | 6.759 | 46.346 | 56.066 | 1.00 | 127.88 |
| 404 | NZ | LYS | A | 388 | 7.805 | 45.615 | 56.838 | 1.00 | 132.65 |
| 405 | C | LYS | A | 388 | 4.377 | 50.762 | 55.267 | 1.00 | 92.29 |
| 406 | O | LYS | A | 388 | 4.618 | 51.090 | 56.428 | 1.00 | 91.44 |
| 407 | N | GLU | A | 389 | 3.191 | 50.301 | 54.886 | 1.00 | 95.05 |
| 408 | CA | GLU | A | 389 | 2.105 | 50.155 | 55.847 | 1.00 | 100.81 |
| 409 | CB | GLU | A | 389 | 0.980 | 51.140 | 55.529 | 1.00 | 105.17 |
| 410 | CG | GLU | A | 389 | 0.612 | 51.220 | 54.066 | 1.00 | 114.62 |
| 411 | CD | GLU | A | 389 | −0.393 | 52.319 | 53.795 | 1.00 | 119.95 |
| 412 | OE1 | GLU | A | 389 | −0.114 | 53.483 | 54.154 | 1.00 | 123.14 |
| 413 | OE2 | GLU | A | 389 | −1.461 | 52.020 | 53.225 | 1.00 | 123.96 |
| 414 | C | GLU | A | 389 | 1.566 | 48.730 | 55.900 | 1.00 | 101.21 |
| 415 | O | GLU | A | 389 | 1.504 | 48.037 | 54.884 | 1.00 | 99.84 |
| 416 | N | GLU | A | 390 | 1.177 | 48.303 | 57.098 | 1.00 | 102.80 |
| 417 | CA | GLU | A | 390 | 0.664 | 46.957 | 57.320 | 1.00 | 104.21 |
| 418 | CB | GLU | A | 390 | 1.798 | 46.070 | 57.845 | 1.00 | 109.94 |
| 419 | CG | GLU | A | 390 | 1.349 | 44.896 | 58.693 | 1.00 | 118.37 |
| 420 | CD | GLU | A | 390 | 2.005 | 43.597 | 58.279 | 1.00 | 123.49 |
| 421 | OE1 | GLU | A | 390 | 3.253 | 43.551 | 58.218 | 1.00 | 126.59 |
| 422 | OE2 | GLU | A | 390 | 1.268 | 42.622 | 58.017 | 1.00 | 127.01 |
| 423 | C | GLU | A | 390 | −0.524 | 46.905 | 58.283 | 1.00 | 102.24 |
| 424 | O | GLU | A | 390 | −0.735 | 47.818 | 59.081 | 1.00 | 102.80 |
| 425 | N | ALA | A | 391 | −1.301 | 45.830 | 58.190 | 1.00 | 104.49 |
| 426 | CA | ALA | A | 391 | −2.456 | 45.624 | 59.058 | 1.00 | 106.71 |
| 427 | CB | ALA | A | 391 | −3.709 | 45.392 | 58.221 | 1.00 | 102.38 |
| 428 | C | ALA | A | 391 | −2.169 | 44.403 | 59.933 | 1.00 | 110.26 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 429 | O | ALA | A | 391 | −1.912 | 43.312 | 59.419 | 1.00 | 108.07 |
| 430 | N | GLN | A | 392 | −2.213 | 44.590 | 61.252 | 1.00 | 113.99 |
| 431 | CA | GLN | A | 392 | −1.933 | 43.507 | 62.196 | 1.00 | 121.32 |
| 432 | CB | GLN | A | 392 | −1.082 | 44.043 | 63.350 | 1.00 | 119.17 |
| 433 | CG | GLN | A | 392 | 0.274 | 44.587 | 62.908 | 1.00 | 114.57 |
| 434 | CD | GLN | A | 392 | 1.159 | 43.527 | 62.267 | 1.00 | 112.24 |
| 435 | OE1 | GLN | A | 392 | 0.776 | 42.892 | 61.286 | 1.00 | 110.70 |
| 436 | NE2 | GLN | A | 392 | 2.350 | 43.335 | 62.821 | 1.00 | 109.96 |
| 437 | C | GLN | A | 392 | −3.172 | 42.796 | 62.746 | 1.00 | 127.08 |
| 438 | O | GLN | A | 392 | −4.214 | 43.413 | 62.970 | 1.00 | 128.89 |
| 439 | N | ALA | A | 393 | −3.025 | 41.489 | 62.965 | 1.00 | 133.17 |
| 440 | CA | ALA | A | 393 | −4.085 | 40.612 | 63.467 | 1.00 | 135.47 |
| 441 | CB | ALA | A | 393 | −3.472 | 39.330 | 64.008 | 1.00 | 137.08 |
| 442 | C | ALA | A | 393 | −5.002 | 41.220 | 64.521 | 1.00 | 136.49 |
| 443 | O | ALA | A | 393 | −6.222 | 41.177 | 64.381 | 1.00 | 138.60 |
| 444 | N | ASN | A | 394 | −4.414 | 41.775 | 65.575 | 1.00 | 139.42 |
| 445 | CA | ASN | A | 394 | −5.183 | 42.375 | 66.658 | 1.00 | 140.02 |
| 446 | CB | ASN | A | 394 | −4.258 | 42.698 | 67.834 | 1.00 | 138.98 |
| 447 | CG | ASN | A | 394 | −3.057 | 43.542 | 67.427 | 1.00 | 134.01 |
| 448 | OD1 | ASN | A | 394 | −2.881 | 43.876 | 66.256 | 1.00 | 139.16 |
| 449 | ND2 | ASN | A | 394 | −2.224 | 43.881 | 68.406 | 1.00 | 121.11 |
| 450 | C | ASN | A | 394 | −5.966 | 43.627 | 66.267 | 1.00 | 141.93 |
| 451 | O | ASN | A | 394 | −6.504 | 44.325 | 67.129 | 1.00 | 140.17 |
| 452 | N | GLY | A | 395 | −6.027 | 43.914 | 64.970 | 1.00 | 142.39 |
| 453 | CA | GLY | A | 395 | −6.759 | 45.080 | 64.506 | 1.00 | 145.89 |
| 454 | C | GLY | A | 395 | −6.017 | 46.378 | 64.754 | 1.00 | 147.08 |
| 455 | O | GLY | A | 395 | −6.618 | 47.385 | 65.127 | 1.00 | 147.98 |
| 456 | N | THR | A | 396 | −4.706 | 46.354 | 64.531 | 1.00 | 148.15 |
| 457 | CA | THR | A | 396 | −3.862 | 47.527 | 64.742 | 1.00 | 150.12 |
| 458 | CB | THR | A | 396 | −2.833 | 47.264 | 65.872 | 1.00 | 150.16 |
| 459 | OG1 | THR | A | 396 | −3.525 | 47.080 | 67.113 | 1.00 | 152.01 |
| 460 | CG2 | THR | A | 396 | −1.857 | 48.425 | 66.007 | 1.00 | 152.01 |
| 461 | C | THR | A | 396 | −3.110 | 47.905 | 63.469 | 1.00 | 147.77 |
| 462 | O | THR | A | 396 | −2.731 | 47.036 | 62.684 | 1.00 | 147.99 |
| 463 | N | LEU | A | 397 | −2.897 | 49.203 | 63.271 | 1.00 | 139.43 |
| 464 | CA | LEU | A | 397 | −2.184 | 49.693 | 62.094 | 1.00 | 130.57 |
| 465 | CB | LEU | A | 397 | −2.807 | 51.002 | 61.594 | 1.00 | 131.01 |
| 466 | CG | LEU | A | 397 | −2.104 | 51.698 | 60.422 | 1.00 | 126.51 |
| 467 | CD1 | LEU | A | 397 | −1.995 | 50.750 | 59.234 | 1.00 | 123.20 |
| 468 | CD2 | LEU | A | 397 | −2.876 | 52.952 | 60.044 | 1.00 | 123.36 |
| 469 | C | LEU | A | 397 | −0.706 | 49.915 | 62.395 | 1.00 | 122.42 |
| 470 | O | LEU | A | 397 | −0.343 | 50.390 | 63.472 | 1.00 | 128.00 |
| 471 | N | THR | A | 398 | 0.140 | 49.567 | 61.431 | 1.00 | 115.38 |
| 472 | CA | THR | A | 398 | 1.581 | 49.718 | 61.571 | 1.00 | 98.48 |
| 473 | CB | THR | A | 398 | 2.257 | 48.354 | 61.819 | 1.00 | 94.19 |
| 474 | OG1 | THR | A | 398 | 1.913 | 47.884 | 63.127 | 1.00 | 90.17 |
| 475 | CG2 | THR | A | 398 | 3.767 | 48.471 | 61.710 | 1.00 | 89.54 |
| 476 | C | THR | A | 398 | 2.173 | 50.343 | 60.313 | 1.00 | 91.99 |
| 477 | O | THR | A | 398 | 1.990 | 49.831 | 59.209 | 1.00 | 90.99 |
| 478 | N | VAL | A | 399 | 2.883 | 51.452 | 60.488 | 1.00 | 84.29 |
| 479 | CA | VAL | A | 399 | 3.503 | 52.137 | 59.362 | 1.00 | 76.60 |
| 480 | CB | VAL | A | 399 | 2.711 | 53.432 | 59.006 | 1.00 | 77.64 |
| 481 | CG1 | VAL | A | 399 | 2.402 | 54.219 | 60.262 | 1.00 | 77.31 |
| 482 | CG2 | VAL | A | 399 | 3.495 | 54.277 | 58.013 | 1.00 | 77.44 |
| 483 | C | VAL | A | 399 | 4.982 | 52.451 | 59.631 | 1.00 | 71.75 |
| 484 | O | VAL | A | 399 | 5.357 | 52.871 | 60.727 | 1.00 | 68.99 |
| 485 | N | THR | A | 400 | 5.814 | 52.224 | 58.618 | 1.00 | 65.86 |
| 486 | CA | THR | A | 400 | 7.251 | 52.457 | 58.721 | 1.00 | 61.52 |
| 487 | CB | THR | A | 400 | 8.031 | 51.108 | 58.795 | 1.00 | 60.95 |
| 488 | OG1 | THR | A | 400 | 8.161 | 50.543 | 57.481 | 1.00 | 59.59 |
| 489 | CG2 | THR | A | 400 | 7.284 | 50.109 | 59.674 | 1.00 | 59.72 |
| 490 | C | THR | A | 400 | 7.774 | 53.241 | 57.513 | 1.00 | 59.74 |
| 491 | O | THR | A | 400 | 7.136 | 53.266 | 56.456 | 1.00 | 58.86 |
| 492 | N | SER | A | 401 | 8.930 | 53.884 | 57.686 | 1.00 | 56.88 |
| 493 | CA | SER | A | 401 | 9.586 | 54.643 | 56.620 | 1.00 | 54.28 |
| 494 | CB | SER | A | 401 | 9.267 | 56.141 | 56.723 | 1.00 | 53.59 |
| 495 | OG | SER | A | 401 | 9.714 | 56.842 | 55.565 | 1.00 | 50.31 |
| 496 | C | SER | A | 401 | 11.088 | 54.407 | 56.779 | 1.00 | 53.78 |
| 497 | O | SER | A | 401 | 11.620 | 54.509 | 57.887 | 1.00 | 54.70 |
| 498 | N | THR | A | 402 | 11.762 | 54.081 | 55.676 | 1.00 | 52.25 |
| 499 | CA | THR | A | 402 | 13.198 | 53.791 | 55.693 | 1.00 | 49.98 |
| 500 | CB | THR | A | 402 | 13.457 | 52.354 | 55.189 | 1.00 | 51.79 |
| 501 | OG1 | THR | A | 402 | 12.735 | 51.433 | 56.012 | 1.00 | 50.71 |
| 502 | CG2 | THR | A | 402 | 14.953 | 52.014 | 55.244 | 1.00 | 53.62 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 503 | C | THR | A | 402 | 14.019 | 54.766 | 54.854 | 1.00 | 47.11 |
| 504 | O | THR | A | 402 | 13.679 | 55.059 | 53.704 | 1.00 | 46.73 |
| 505 | N | LEU | A | 403 | 15.119 | 55.244 | 55.428 | 1.00 | 43.26 |
| 506 | CA | LEU | A | 403 | 15.978 | 56.210 | 54.750 | 1.00 | 39.98 |
| 507 | CB | LEU | A | 403 | 15.918 | 57.559 | 55.494 | 1.00 | 36.57 |
| 508 | CG | LEU | A | 403 | 16.723 | 58.742 | 54.930 | 1.00 | 36.76 |
| 509 | CD1 | LEU | A | 403 | 16.043 | 59.244 | 53.644 | 1.00 | 33.55 |
| 510 | CD2 | LEU | A | 403 | 16.810 | 59.886 | 55.970 | 1.00 | 35.49 |
| 511 | C | LEU | A | 403 | 17.449 | 55.793 | 54.601 | 1.00 | 38.68 |
| 512 | O | LEU | A | 403 | 18.133 | 55.514 | 55.589 | 1.00 | 38.64 |
| 513 | N | PRO | A | 404 | 17.954 | 55.754 | 53.358 | 1.00 | 34.83 |
| 514 | CD | PRO | A | 404 | 17.185 | 55.883 | 52.107 | 1.00 | 35.21 |
| 515 | CA | PRO | A | 404 | 19.348 | 55.386 | 53.085 | 1.00 | 34.58 |
| 516 | CB | PRO | A | 404 | 19.391 | 55.274 | 51.561 | 1.00 | 35.11 |
| 517 | CG | PRO | A | 404 | 17.964 | 55.000 | 51.175 | 1.00 | 34.29 |
| 518 | C | PRO | A | 404 | 20.225 | 56.546 | 53.560 | 1.00 | 36.27 |
| 519 | O | PRO | A | 404 | 19.881 | 57.703 | 53.330 | 1.00 | 34.21 |
| 520 | N | VAL | A | 405 | 21.343 | 56.255 | 54.213 | 1.00 | 35.67 |
| 521 | CA | VAL | A | 405 | 22.223 | 57.324 | 54.674 | 1.00 | 38.54 |
| 522 | CB | VAL | A | 405 | 22.283 | 57.417 | 56.236 | 1.00 | 38.93 |
| 523 | CG1 | VAL | A | 405 | 20.887 | 57.645 | 56.793 | 1.00 | 38.14 |
| 524 | CG2 | VAL | A | 405 | 22.900 | 56.151 | 56.829 | 1.00 | 38.25 |
| 525 | C | VAL | A | 405 | 23.638 | 57.142 | 54.144 | 1.00 | 42.27 |
| 526 | O | VAL | A | 405 | 24.018 | 56.057 | 53.683 | 1.00 | 41.35 |
| 527 | N | GLY | A | 406 | 24.409 | 58.221 | 54.192 | 1.00 | 43.33 |
| 528 | CA | CLY | A | 406 | 25.778 | 58.166 | 53.719 | 1.00 | 47.67 |
| 529 | C | GLY | A | 406 | 26.613 | 57.452 | 54.757 | 1.00 | 48.45 |
| 530 | O | GLY | A | 406 | 26.325 | 57.543 | 55.953 | 1.00 | 50.09 |
| 531 | N | THR | A | 407 | 27.636 | 56.734 | 54.313 | 1.00 | 48.31 |
| 532 | CA | THR | A | 407 | 28.496 | 56.014 | 55.240 | 1.00 | 47.97 |
| 533 | CB | THR | A | 407 | 29.399 | 55.009 | 54.488 | 1.00 | 47.59 |
| 534 | OG1 | THR | A | 407 | 28.574 | 54.083 | 53.769 | 1.00 | 45.39 |
| 535 | CG2 | THR | A | 407 | 30.287 | 54.235 | 55.473 | 1.00 | 46.45 |
| 536 | C | THR | A | 407 | 29.371 | 57.012 | 56.001 | 1.00 | 49.40 |
| 537 | O | THR | A | 407 | 29.462 | 56.982 | 57.238 | 1.00 | 45.86 |
| 538 | N | ARG | A | 408 | 29.999 | 57.903 | 55.241 | 1.00 | 50.73 |
| 539 | CA | ARG | A | 408 | 30.875 | 58.918 | 55.795 | 1.00 | 52.69 |
| 540 | CB | ARG | A | 408 | 31.607 | 59.631 | 54.654 | 1.00 | 59.82 |
| 541 | CG | ARG | A | 408 | 32.960 | 60.180 | 55.051 | 1.00 | 70.46 |
| 542 | CD | ARG | A | 408 | 33.797 | 59.100 | 55.723 | 1.00 | 78.80 |
| 543 | NE | ARG | A | 408 | 34.997 | 59.652 | 56.345 | 1.00 | 85.62 |
| 544 | CZ | ARG | A | 408 | 35.786 | 58.984 | 57.181 | 1.00 | 87.83 |
| 545 | NH1 | ARG | A | 408 | 35.505 | 57.726 | 57.503 | 1.00 | 88.30 |
| 546 | NH2 | ARG | A | 408 | 36.855 | 59.577 | 57.698 | 1.00 | 89.52 |
| 547 | C | ARG | A | 408 | 30.086 | 59.913 | 56.649 | 1.00 | 49.59 |
| 548 | O | ARG | A | 408 | 30.572 | 60.377 | 57.678 | 1.00 | 45.53 |
| 549 | N | ASP | A | 409 | 28.863 | 60.228 | 56.234 | 1.00 | 47.48 |
| 550 | CA | ASP | A | 409 | 28.037 | 61.155 | 56.996 | 1.00 | 45.96 |
| 551 | CB | ASP | A | 409 | 26.711 | 61.437 | 56.271 | 1.00 | 52.07 |
| 552 | CG | ASP | A | 409 | 26.887 | 62.312 | 55.036 | 1.00 | 55.32 |
| 553 | OD1 | ASP | A | 409 | 27.718 | 63.243 | 55.078 | 1.00 | 56.39 |
| 554 | OD2 | ASP | A | 409 | 26.179 | 62.078 | 54.030 | 1.00 | 59.17 |
| 555 | C | ASP | A | 409 | 27.745 | 60.585 | 58.385 | 1.00 | 43.79 |
| 556 | O | ASP | A | 409 | 27.873 | 61.285 | 59.395 | 1.00 | 40.91 |
| 557 | N | TRP | A | 410 | 27.347 | 59.314 | 58.437 | 1.00 | 41.00 |
| 558 | CA | TRP | A | 410 | 27.042 | 58.681 | 59.717 | 1.00 | 39.07 |
| 559 | CB | TRP | A | 410 | 26.488 | 57.260 | 59.510 | 1.00 | 37.50 |
| 560 | CG | TRP | A | 410 | 26.053 | 56.634 | 60.800 | 1.00 | 33.25 |
| 561 | CD2 | TRP | A | 410 | 24.797 | 56.839 | 61.470 | 1.00 | 31.51 |
| 562 | CE2 | TRP | A | 410 | 24.882 | 56.193 | 62.731 | 1.00 | 31.31 |
| 563 | CE3 | TRP | A | 410 | 23.612 | 57.510 | 61.131 | 1.00 | 30.30 |
| 564 | CD1 | TRP | A | 410 | 26.824 | 55.881 | 61.651 | 1.00 | 32.15 |
| 565 | NE1 | TRP | A | 410 | 26.125 | 55.618 | 62.813 | 1.00 | 33.70 |
| 566 | CZ2 | TRP | A | 410 | 23.827 | 56.201 | 63.655 | 1.00 | 29.59 |
| 567 | CZ3 | TRP | A | 410 | 22.552 | 57.516 | 62.059 | 1.00 | 29.07 |
| 568 | CH2 | TRP | A | 410 | 22.674 | 56.865 | 63.303 | 1.00 | 30.38 |
| 569 | C | TRP | A | 410 | 28.281 | 58.624 | 60.608 | 1.00 | 40.01 |
| 570 | O | TRP | A | 410 | 28.253 | 59.067 | 61.768 | 1.00 | 38.01 |
| 571 | N | ILE | A | 411 | 29.368 | 58.092 | 60.052 | 1.00 | 42.65 |
| 572 | CA | ILE | A | 411 | 30.627 | 57.957 | 60.777 | 1.00 | 46.51 |
| 573 | CB | ILE | A | 411 | 31.728 | 57.384 | 59.854 | 1.00 | 48.37 |
| 574 | CG2 | ILE | A | 411 | 33.047 | 57.286 | 60.599 | 1.00 | 49.73 |
| 575 | CG1 | ILE | A | 411 | 31.307 | 56.008 | 59.335 | 1.00 | 51.00 |
| 576 | CD1 | ILE | A | 411 | 30.965 | 55.028 | 60.422 | 1.00 | 54.66 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 577 | C | ILE | A | 411 | 31.117 | 59.278 | 61.377 | 1.00 | 48.81 |
| 578 | O | ILE | A | 411 | 31.580 | 59.316 | 62.517 | 1.00 | 47.21 |
| 579 | N | GLU | A | 412 | 30.998 | 60.363 | 60.619 | 1.00 | 51.61 |
| 580 | CA | GLU | A | 412 | 31.455 | 61.656 | 61.095 | 1.00 | 55.51 |
| 581 | CB | GLU | A | 412 | 31.762 | 62.558 | 59.903 | 1.00 | 64.52 |
| 582 | CG | GLU | A | 412 | 33.194 | 62.375 | 59.409 | 1.00 | 78.25 |
| 583 | CD | GLU | A | 412 | 33.405 | 62.826 | 57.980 | 1.00 | 85.50 |
| 584 | OE1 | GLU | A | 412 | 32.850 | 63.874 | 57.593 | 1.00 | 91.23 |
| 585 | OE2 | GLU | A | 412 | 34.141 | 62.134 | 57.245 | 1.00 | 90.21 |
| 586 | C | GLU | A | 412 | 30.582 | 62.378 | 62.120 | 1.00 | 53.17 |
| 587 | O | GLU | A | 412 | 31.018 | 63.372 | 62.695 | 1.00 | 52.91 |
| 588 | N | GLY | A | 413 | 29.358 | 61.903 | 62.348 | 1.00 | 49.97 |
| 589 | CA | GLY | A | 413 | 28.531 | 62.520 | 63.376 | 1.00 | 43.84 |
| 590 | C | GLY | A | 413 | 27.173 | 63.152 | 63.124 | 1.00 | 40.54 |
| 591 | O | GLY | A | 413 | 26.593 | 63.709 | 64.058 | 1.00 | 40.90 |
| 592 | N | GLU | A | 414 | 26.637 | 63.068 | 61.911 | 1.00 | 37.91 |
| 593 | CA | GLU | A | 414 | 25.342 | 63.700 | 61.630 | 1.00 | 35.93 |
| 594 | CB | GLU | A | 414 | 24.987 | 63.536 | 60.137 | 1.00 | 33.18 |
| 595 | CG | GLU | A | 414 | 23.672 | 64.195 | 59.684 | 1.00 | 29.51 |
| 596 | CD | GLU | A | 414 | 23.733 | 65.741 | 59.629 | 1.00 | 33.11 |
| 597 | OE1 | GLU | A | 414 | 23.572 | 66.403 | 60.678 | 1.00 | 32.05 |
| 598 | OE2 | GLU | A | 414 | 23.943 | 66.291 | 58.528 | 1.00 | 29.22 |
| 599 | C | GLU | A | 414 | 24.207 | 63.160 | 62.506 | 1.00 | 36.10 |
| 600 | O | GLU | A | 414 | 24.298 | 62.065 | 63.048 | 1.00 | 34.81 |
| 601 | N | THR | A | 415 | 23.151 | 63.948 | 62.673 | 1.00 | 37.34 |
| 602 | CA | THR | A | 415 | 21.993 | 63.493 | 63.440 | 1.00 | 39.64 |
| 603 | CB | THR | A | 415 | 21.831 | 64.278 | 64.767 | 1.00 | 40.50 |
| 604 | OG1 | THR | A | 415 | 20.458 | 64.247 | 65.181 | 1.00 | 44.26 |
| 605 | CG2 | THR | A | 415 | 22.290 | 65.691 | 64.611 | 1.00 | 45.66 |
| 606 | C | THR | A | 415 | 20.749 | 63.628 | 62.561 | 1.00 | 38.89 |
| 607 | O | THR | A | 415 | 20.559 | 64.650 | 61.893 | 1.00 | 41.24 |
| 608 | N | TYR | A | 416 | 19.911 | 62.593 | 62.552 | 1.00 | 37.47 |
| 609 | CA | TYR | A | 416 | 18.705 | 62.561 | 61.719 | 1.00 | 36.62 |
| 610 | CB | TYR | A | 416 | 18.706 | 61.270 | 60.873 | 1.00 | 32.69 |
| 611 | CG | TYR | A | 416 | 19.958 | 61.099 | 60.030 | 1.00 | 29.98 |
| 612 | CD1 | TYR | A | 416 | 21.200 | 60.829 | 60.620 | 1.00 | 27.94 |
| 613 | CE1 | TYR | A | 416 | 22.364 | 60.745 | 59.848 | 1.00 | 27.72 |
| 614 | CD2 | TYR | A | 416 | 19.917 | 61.273 | 58.654 | 1.00 | 26.72 |
| 615 | CE2 | TYR | A | 416 | 21.072 | 61.194 | 57.878 | 1.00 | 28.48 |
| 616 | CZ | TYR | A | 416 | 22.291 | 60.933 | 58.472 | 1.00 | 27.41 |
| 617 | OH | TYR | A | 416 | 23.432 | 60.872 | 57.679 | 1.00 | 30.86 |
| 618 | C | TYR | A | 416 | 17.427 | 62.648 | 62.552 | 1.00 | 40.91 |
| 619 | O | TYR | A | 416 | 17.410 | 62.223 | 63.704 | 1.00 | 41.32 |
| 620 | N | GLN | A | 417 | 16.351 | 63.181 | 61.978 | 1.00 | 46.40 |
| 621 | CA | GLN | A | 417 | 15.114 | 63.314 | 62.737 | 1.00 | 55.98 |
| 622 | CB | GLN | A | 417 | 15.015 | 64.733 | 63.301 | 1.00 | 66.91 |
| 623 | CG | GLN | A | 417 | 15.146 | 65.829 | 62.257 | 1.00 | 88.21 |
| 624 | CD | GLN | A | 417 | 15.478 | 67.184 | 62.861 | 1.00 | 99.20 |
| 625 | OE1 | GLN | A | 417 | 16.561 | 67.381 | 63.416 | 1.00 | 106.33 |
| 626 | NE2 | GLN | A | 417 | 14.546 | 68.125 | 62.756 | 1.00 | 106.86 |
| 627 | C | GLN | A | 417 | 13.834 | 62.967 | 61.988 | 1.00 | 56.11 |
| 628 | O | GLN | A | 417 | 13.679 | 63.290 | 60.813 | 1.00 | 54.11 |
| 629 | N | CYS | A | 418 | 12.921 | 62.308 | 62.698 | 1.00 | 57.23 |
| 630 | CA | CYS | A | 418 | 11.630 | 61.878 | 62.163 | 1.00 | 59.38 |
| 631 | C | CYS | A | 418 | 10.495 | 62.642 | 62.840 | 1.00 | 64.39 |
| 632 | O | CYS | A | 418 | 10.379 | 62.625 | 64.063 | 1.00 | 62.81 |
| 633 | CB | CYS | A | 418 | 11.437 | 60.367 | 62.402 | 1.00 | 58.71 |
| 634 | SG | CYS | A | 418 | 9.910 | 59.662 | 61.678 | 1.00 | 59.30 |
| 635 | N | ARG | A | 419 | 9.659 | 63.307 | 62.047 | 1.00 | 73.56 |
| 636 | CA | ARG | A | 419 | 8.530 | 64.057 | 62.593 | 1.00 | 84.82 |
| 637 | CB | ARG | A | 419 | 8.590 | 65.516 | 62.134 | 1.00 | 95.95 |
| 638 | CG | ARG | A | 419 | 7.643 | 66.434 | 62.889 | 1.00 | 116.30 |
| 639 | CD | ARG | A | 419 | 7.891 | 67.903 | 62.571 | 1.00 | 133.00 |
| 640 | NE | ARG | A | 419 | 6.987 | 68.773 | 63.319 | 1.00 | 145.68 |
| 641 | CZ | ARG | A | 419 | 6.990 | 70.101 | 63.248 | 1.00 | 151.66 |
| 642 | NH1 | ARG | A | 419 | 7.855 | 70.724 | 62.461 | 1.00 | 154.68 |
| 643 | NH2 | ARG | A | 419 | 6.123 | 70.807 | 63.963 | 1.00 | 154.67 |
| 644 | C | ARG | A | 419 | 7.223 | 63.412 | 62.138 | 1.00 | 85.05 |
| 645 | O | ARG | A | 419 | 7.030 | 63.164 | 60.950 | 1.00 | 82.32 |
| 646 | N | VAL | A | 420 | 6.328 | 63.138 | 63.085 | 1.00 | 86.26 |
| 647 | CA | VAL | A | 420 | 5.053 | 62.498 | 62.769 | 1.00 | 90.82 |
| 648 | CB | VAL | A | 420 | 4.795 | 61.290 | 63.693 | 1.00 | 88.05 |
| 649 | CG1 | VAL | A | 420 | 3.459 | 60.657 | 63.353 | 1.00 | 84.66 |
| 650 | CG2 | VAL | A | 420 | 5.914 | 60.272 | 63.543 | 1.00 | 84.36 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 651 | C | VAL | A | 420 | 3.837 | 63.419 | 62.844 | 1.00 | 98.80 |
| 652 | O | VAL | A | 420 | 3.618 | 64.105 | 63.841 | 1.00 | 97.75 |
| 653 | N | THR | A | 421 | 3.041 | 63.404 | 61.780 | 1.00 | 109.23 |
| 654 | CA | THR | A | 421 | 1.837 | 64.222 | 61.686 | 1.00 | 121.13 |
| 655 | CB | THR | A | 421 | 1.845 | 65.068 | 60.397 | 1.00 | 122.13 |
| 656 | OG1 | THR | A | 421 | 2.985 | 65.934 | 60.398 | 1.00 | 124.54 |
| 657 | CG2 | THR | A | 421 | 0.580 | 65.903 | 60.297 | 1.00 | 125.09 |
| 658 | C | THR | A | 421 | 0.597 | 63.331 | 61.665 | 1.00 | 127.80 |
| 659 | O | THR | A | 421 | 0.376 | 62.587 | 60.709 | 1.00 | 128.43 |
| 660 | N | HIS | A | 422 | −0.211 | 63.410 | 62.720 | 1.00 | 133.25 |
| 661 | CA | HIS | A | 422 | −1.429 | 62.609 | 62.814 | 1.00 | 139.77 |
| 662 | CB | HIS | A | 422 | −1.360 | 61.680 | 64.032 | 1.00 | 155.32 |
| 663 | CG | HIS | A | 422 | −2.476 | 60.681 | 64.097 | 1.00 | 171.34 |
| 664 | CD2 | HIS | A | 422 | −2.463 | 59.327 | 64.061 | 1.00 | 178.32 |
| 665 | ND1 | HIS | A | 422 | −3.800 | 61.048 | 64.206 | 1.00 | 178.39 |
| 666 | CE1 | HIS | A | 422 | −4.555 | 59.963 | 64.233 | 1.00 | 182.85 |
| 667 | NE2 | HIS | A | 422 | −3.768 | 58.906 | 64.147 | 1.00 | 182.83 |
| 668 | C | HIS | A | 422 | −2.657 | 63.512 | 62.924 | 1.00 | 134.43 |
| 669 | O | HIS | A | 422 | −2.637 | 64.516 | 63.639 | 1.00 | 134.00 |
| 670 | N | PRO | A | 423 | −3.746 | 63.162 | 62.217 | 1.00 | 127.06 |
| 671 | CD | PRO | A | 423 | −3.903 | 61.975 | 61.359 | 1.00 | 123.35 |
| 672 | CA | PRO | A | 423 | −4.984 | 63.947 | 62.239 | 1.00 | 125.39 |
| 673 | CB | PRO | A | 423 | −5.894 | 63.177 | 61.280 | 1.00 | 121.89 |
| 674 | CG | PRO | A | 423 | −5.392 | 61.771 | 61.388 | 1.00 | 120.16 |
| 675 | C | PRO | A | 423 | −5.612 | 64.140 | 63.623 | 1.00 | 127.58 |
| 676 | O | PRO | A | 423 | −5.965 | 65.259 | 63.997 | 1.00 | 124.81 |
| 677 | N | HIS | A | 424 | −5.747 | 63.053 | 64.379 | 1.00 | 131.78 |
| 678 | CA | HIS | A | 424 | −6.339 | 63.115 | 65.714 | 1.00 | 140.11 |
| 679 | CB | HIS | A | 424 | −6.597 | 61.701 | 66.245 | 1.00 | 146.49 |
| 680 | CG | HIS | A | 424 | −7.762 | 61.015 | 65.603 | 1.00 | 156.23 |
| 681 | CD2 | HIS | A | 424 | −7.846 | 59.854 | 64.912 | 1.00 | 160.32 |
| 682 | ND1 | HIS | A | 424 | −9.042 | 61.525 | 65.650 | 1.00 | 160.45 |
| 683 | CE1 | HIS | A | 424 | −9.863 | 60.707 | 65.017 | 1.00 | 163.44 |
| 684 | NE2 | HIS | A | 424 | −9.162 | 59.685 | 64.560 | 1.00 | 163.22 |
| 685 | C | HIS | A | 424 | −5.503 | 63.886 | 66.736 | 1.00 | 141.75 |
| 686 | O | HIS | A | 424 | −6.022 | 64.750 | 67.442 | 1.00 | 139.80 |
| 687 | N | LEU | A | 425 | −4.214 | 63.572 | 66.814 | 1.00 | 140.68 |
| 688 | CA | LEU | A | 425 | −3.316 | 64.222 | 67.763 | 1.00 | 142.28 |
| 689 | CB | LEU | A | 425 | −1.998 | 63.446 | 67.835 | 1.00 | 142.48 |
| 690 | CG | LEU | A | 425 | −2.145 | 61.967 | 68.204 | 1.00 | 140.93 |
| 691 | CD1 | LEU | A | 425 | −0.776 | 61.313 | 68.235 | 1.00 | 140.05 |
| 692 | CD2 | LEU | A | 425 | −2.835 | 61.832 | 69.555 | 1.00 | 140.16 |
| 693 | C | LEU | A | 425 | −3.042 | 65.690 | 67.429 | 1.00 | 142.83 |
| 694 | O | LEU | A | 425 | −3.316 | 66.142 | 66.316 | 1.00 | 145.00 |
| 695 | N | PRO | A | 426 | −2.499 | 66.452 | 68.398 | 1.00 | 146.06 |
| 696 | CD | PRO | A | 426 | −2.230 | 66.020 | 69.782 | 1.00 | 145.03 |
| 697 | CA | PRO | A | 426 | −2.178 | 67.876 | 68.237 | 1.00 | 147.57 |
| 698 | CB | PRO | A | 426 | −1.480 | 68.217 | 69.550 | 1.00 | 145.22 |
| 699 | CG | PRO | A | 426 | −2.175 | 67.335 | 70.525 | 1.00 | 144.99 |
| 700 | C | PRO | A | 426 | −1.301 | 68.186 | 67.026 | 1.00 | 148.03 |
| 701 | O | PRO | A | 426 | −0.926 | 69.339 | 66.802 | 1.00 | 147.61 |
| 702 | N | ARG | A | 427 | −0.977 | 67.154 | 66.253 | 1.00 | 145.04 |
| 703 | CA | ARG | A | 427 | −0.145 | 67.305 | 65.065 | 1.00 | 143.64 |
| 704 | CB | ARG | A | 427 | −0.739 | 68.369 | 64.129 | 1.00 | 143.94 |
| 705 | CG | ARG | A | 427 | −0.940 | 67.914 | 62.685 | 1.00 | 140.13 |
| 706 | CD | ARG | A | 427 | −2.353 | 67.398 | 62.435 | 1.00 | 135.84 |
| 707 | NE | ARG | A | 427 | −2.512 | 66.870 | 61.081 | 1.00 | 132.18 |
| 708 | CZ | ARG | A | 427 | −3.679 | 66.540 | 60.537 | 1.00 | 130.46 |
| 709 | NH1 | ARG | A | 427 | −4.801 | 66.686 | 61.230 | 1.00 | 129.59 |
| 710 | NH2 | ARG | A | 427 | −3.723 | 66.055 | 59.303 | 1.00 | 129.69 |
| 711 | C | ARG | A | 427 | 1.274 | 67.710 | 65.471 | 1.00 | 140.63 |
| 712 | O | ARG | A | 427 | 1.751 | 68.786 | 65.104 | 1.00 | 143.76 |
| 713 | N | ALA | A | 428 | 1.941 | 66.845 | 66.234 | 1.00 | 136.36 |
| 714 | CA | ALA | A | 428 | 3.304 | 67.108 | 66.690 | 1.00 | 125.63 |
| 715 | CB | ALA | A | 428 | 3.320 | 68.344 | 67.586 | 1.00 | 127.18 |
| 716 | C | ALA | A | 428 | 3.904 | 65.912 | 67.435 | 1.00 | 118.41 |
| 717 | O | ALA | A | 428 | 3.282 | 65.359 | 68.340 | 1.00 | 119.20 |
| 718 | N | LEU | A | 429 | 5.116 | 65.522 | 67.044 | 1.00 | 111.26 |
| 719 | CA | LEU | A29 | 5.831 | 64.400 | 67.657 | 1.00 | 100.59 |
| 720 | CB | LEU | A | 429 | 5.005 | 63.113 | 67.554 | 1.00 | 102.46 |
| 721 | CG | LEU | A | 429 | 4.782 | 62.353 | 68.864 | 1.00 | 103.66 |
| 722 | CD1 | LEU | A | 429 | 4.029 | 61.065 | 68.585 | 1.00 | 104.40 |
| 723 | CD2 | LEU | A | 429 | 6.118 | 62.051 | 69.522 | 1.00 | 105.10 |
| 724 | C | LEU | A | 429 | 7.163 | 64.216 | 66.927 | 1.00 | 94.00 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 725 | O | LEU | A | 429 | 7.188 | 64.090 | 65.702 | 1.00 | 92.45 |
| 726 | N | MET | A | 430 | 8.267 | 64.192 | 67.669 | 1.00 | 87.59 |
| 727 | CA | MET | A | 430 | 9.579 | 64.056 | 67.042 | 1.00 | 81.03 |
| 728 | CB | MET | A | 430 | 10.239 | 65.436 | 66.975 | 1.00 | 89.51 |
| 729 | CG | MET | A | 430 | 9.401 | 66.444 | 66.188 | 1.00 | 103.03 |
| 730 | SD | MET | A | 430 | 10.019 | 68.135 | 66.179 | 1.00 | 113.06 |
| 731 | CE | MET | A | 430 | 9.013 | 68.877 | 67.471 | 1.00 | 121.73 |
| 732 | C | MET | A | 430 | 10.527 | 63.046 | 67.691 | 1.00 | 73.11 |
| 733 | O | MET | A | 430 | 10.482 | 62.822 | 68.896 | 1.00 | 69.28 |
| 734 | N | ARG | A | 431 | 11.379 | 62.437 | 66.870 | 1.00 | 65.61 |
| 735 | CA | ARG | A | 431 | 12.359 | 61.449 | 67.325 | 1.00 | 60.21 |
| 736 | CB | ARG | A | 431 | 11.830 | 60.025 | 67.101 | 1.00 | 70.12 |
| 737 | CG | ARG | A | 431 | 10.409 | 59.757 | 67.593 | 1.00 | 85.13 |
| 738 | CD | ARG | A | 431 | 10.268 | 59.860 | 69.104 | 1.00 | 99.23 |
| 739 | NE | ARG | A | 431 | 8.886 | 59.642 | 69.522 | 1.00 | 111.13 |
| 740 | CZ | ARG | A | 431 | 8.454 | 59.737 | 70.775 | 1.00 | 116.98 |
| 741 | NH1 | ARG | A | 431 | 9.296 | 60.048 | 71.748 | 1.00 | 120.59 |
| 742 | NH2 | ARG | A | 431 | 7.177 | 59.520 | 71.055 | 1.00 | 120.57 |
| 743 | C | ARG | A | 431 | 13.647 | 61.631 | 66.515 | 1.00 | 52.51 |
| 744 | O | ARG | A | 431 | 13.587 | 61.953 | 65.329 | 1.00 | 46.94 |
| 745 | N | SER | A | 432 | 14.809 | 61.430 | 67.135 | 1.00 | 43.74 |
| 746 | CA | SER | A | 432 | 16.060 | 61.581 | 66.391 | 1.00 | 39.88 |
| 747 | CB | SER | A | 432 | 16.632 | 62.988 | 66.584 | 1.00 | 41.42 |
| 748 | OG | SER | A | 432 | 16.783 | 63.302 | 67.950 | 1.00 | 43.69 |
| 749 | C | SER | A | 432 | 17.119 | 60.540 | 66.722 | 1.00 | 37.72 |
| 750 | O | SER | A | 432 | 17.014 | 59.853 | 67.734 | 1.00 | 36.21 |
| 751 | N | THR | A | 433 | 18.141 | 60.430 | 65.870 | 1.00 | 35.10 |
| 752 | CA | THR | A | 433 | 19.201 | 59.437 | 66.074 | 1.00 | 34.86 |
| 753 | CB | THR | A | 433 | 18.821 | 58.092 | 65.365 | 1.00 | 36.46 |
| 754 | OG1 | THR | A | 433 | 19.809 | 57.098 | 65.649 | 1.00 | 37.61 |
| 755 | CG2 | THR | A | 433 | 18.721 | 58.280 | 63.848 | 1.00 | 35.45 |
| 756 | C | THR | A | 433 | 20.585 | 59.901 | 65.583 | 1.00 | 34.48 |
| 757 | O | THR | A | 433 | 20.690 | 60.789 | 64.726 | 1.00 | 36.96 |
| 758 | N | THR | A | 434 | 21.642 | 59.305 | 66.133 | 1.00 | 32.59 |
| 759 | CA | THR | A | 434 | 23.022 | 59.649 | 65.768 | 1.00 | 33.04 |
| 760 | CB | THR | A | 434 | 23.413 | 61.067 | 66.330 | 1.00 | 30.94 |
| 761 | OG1 | THR | A | 434 | 24.788 | 61.355 | 66.050 | 1.00 | 27.88 |
| 762 | CG2 | THR | A | 434 | 23.205 | 61.123 | 67.816 | 1.00 | 29.39 |
| 763 | C | THR | A | 434 | 23.948 | 58.583 | 66.357 | 1.00 | 34.46 |
| 764 | O | THR | A | 434 | 23.567 | 57.898 | 67.303 | 1.00 | 34.13 |
| 765 | N | LYS | A | 435 | 25.155 | 58.448 | 65.807 | 1.00 | 37.93 |
| 766 | CA | LYS | A | 435 | 26.121 | 57.454 | 66.280 | 1.00 | 44.00 |
| 767 | CB | LYS | A | 435 | 27.448 | 57.598 | 65.525 | 1.00 | 43.02 |
| 768 | CG | LYS | A | 435 | 28.204 | 58.865 | 65.881 | 1.00 | 45.53 |
| 769 | CD | LYS | A | 435 | 29.501 | 59.046 | 65.097 | 1.00 | 46.71 |
| 770 | CE | LYS | A | 435 | 30.724 | 58.583 | 65.873 | 1.00 | 45.95 |
| 771 | NZ | LYS | A | 435 | 30.768 | 57.105 | 66.027 | 1.00 | 48.21 |
| 772 | C | LYS | A | 435 | 26.375 | 57.590 | 67.785 | 1.00 | 48.24 |
| 773 | O | LYS | A | 435 | 26.355 | 58.700 | 68.326 | 1.00 | 49.48 |
| 774 | N | THR | A | 436 | 26.627 | 56.469 | 68.462 | 1.00 | 52.44 |
| 775 | CA | THR | A | 436 | 26.868 | 56.506 | 69.907 | 1.00 | 55.68 |
| 776 | CB | THR | A | 436 | 26.698 | 55.111 | 70.551 | 1.00 | 55.99 |
| 777 | OG1 | THR | A | 436 | 25.356 | 54.656 | 70.350 | 1.00 | 58.79 |
| 778 | CG2 | THR | A | 436 | 26.974 | 55.174 | 72.050 | 1.00 | 55.84 |
| 779 | C | THR | A | 436 | 28.255 | 57.033 | 70.252 | 1.00 | 58.02 |
| 780 | O | THR | A | 436 | 29.215 | 56.814 | 69.517 | 1.00 | 57.54 |
| 781 | N | SER | A | 437 | 28.347 | 57.732 | 71.377 | 1.00 | 61.19 |
| 782 | CA | SER | A | 437 | 29.611 | 58.298 | 71.825 | 1.00 | 65.76 |
| 783 | CB | SER | A | 437 | 29.406 | 59.751 | 72.259 | 1.00 | 70.35 |
| 784 | OG | SER | A | 437 | 28.387 | 59.848 | 73.244 | 1.00 | 78.24 |
| 785 | C | SER | A | 437 | 30.174 | 57.494 | 72.987 | 1.00 | 64.22 |
| 786 | O | SER | A | 437 | 29.431 | 56.822 | 73.704 | 1.00 | 65.19 |
| 787 | N | GLY | A | 438 | 31.489 | 57.562 | 73.170 | 1.00 | 60.74 |
| 788 | CA | GLY | A | 438 | 32.113 | 56.840 | 74.262 | 1.00 | 55.77 |
| 789 | C | GLY | A | 438 | 33.338 | 56.050 | 73.851 | 1.00 | 52.23 |
| 790 | O | GLY | A | 438 | 33.750 | 56.092 | 72.695 | 1.00 | 51.74 |
| 791 | N | PRO | A | 439 | 33.970 | 55.342 | 74.798 | 1.00 | 49.78 |
| 792 | CD | PRO | A | 439 | 33.778 | 55.507 | 76.250 | 1.00 | 45.99 |
| 793 | CA | PRO | A | 439 | 35.164 | 54.534 | 74.515 | 1.00 | 48.31 |
| 794 | CB | PRO | A | 439 | 35.570 | 54.030 | 75.902 | 1.00 | 46.96 |
| 795 | CG | PRO | A | 439 | 35.150 | 55.163 | 76.792 | 1.00 | 46.88 |
| 796 | C | PRO | A | 439 | 34.850 | 53.387 | 73.547 | 1.00 | 48.11 |
| 797 | O | PRO | A | 439 | 33.687 | 53.132 | 73.230 | 1.00 | 45.10 |
| 798 | N | ARG | A | 440 | 35.891 | 52.702 | 73.084 | 1.00 | 48.02 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 799 | CA | ARG | A | 440 | 35.729 | 51.594 | 72.149 | 1.00 | 51.46 |
| 800 | CB | ARG | A | 440 | 36.172 | 52.036 | 70.751 | 1.00 | 53.76 |
| 801 | CG | ARG | A | 440 | 35.598 | 53.383 | 70.309 | 1.00 | 60.38 |
| 802 | CD | ARG | A | 440 | 34.162 | 53.295 | 69.795 | 1.00 | 63.77 |
| 803 | NE | ARG | A | 440 | 33.377 | 54.463 | 70.195 | 1.00 | 68.00 |
| 804 | CZ | ARG | A | 440 | 32.206 | 54.814 | 69.667 | 1.00 | 70.91 |
| 805 | NH1 | ARG | A | 440 | 31.657 | 54.098 | 68.693 | 1.00 | 71.66 |
| 806 | NH2 | ARG | A | 440 | 31.568 | 55.879 | 70.130 | 1.00 | 73.31 |
| 807 | C | ARG | A | 440 | 36.544 | 50.361 | 72.579 | 1.00 | 52.34 |
| 808 | O | ARG | A | 440 | 37.697 | 50.491 | 73.018 | 1.00 | 51.87 |
| 809 | N | ALA | A | 441 | 35.943 | 49.174 | 72.447 | 1.00 | 50.86 |
| 810 | CA | ALA | A | 441 | 36.605 | 47.906 | 72.803 | 1.00 | 50.24 |
| 811 | CB | ALA | A | 441 | 36.334 | 47.565 | 74.263 | 1.00 | 47.33 |
| 812 | C | ALA | A | 441 | 36.128 | 46.757 | 71.902 | 1.00 | 50.02 |
| 813 | O | ALA | A | 441 | 34.924 | 46.599 | 71.679 | 1.00 | 49.53 |
| 814 | N | ALA | A | 442 | 37.072 | 45.965 | 71.391 | 1.00 | 49.04 |
| 815 | CA | ALA | A | 442 | 36.766 | 44.826 | 70.513 | 1.00 | 49.11 |
| 816 | CB | ALA | A | 442 | 38.032 | 44.372 | 69.784 | 1.00 | 50.63 |
| 817 | C | ALA | A | 442 | 36.143 | 43.635 | 71.263 | 1.00 | 47.39 |
| 818 | O | ALA | A | 442 | 36.332 | 43.484 | 72.471 | 1.00 | 47.88 |
| 819 | N | PRO | A | 443 | 35.399 | 42.770 | 70.546 | 1.00 | 43.23 |
| 820 | CD | PRO | A | 443 | 34.899 | 42.990 | 69.180 | 1.00 | 42.39 |
| 821 | CA | PRO | A | 443 | 34.741 | 41.596 | 71.138 | 1.00 | 41.34 |
| 822 | CB | PRO | A | 443 | 33.531 | 41.372 | 70.224 | 1.00 | 41.48 |
| 823 | CG | PRO | A | 443 | 33.478 | 42.588 | 69.326 | 1.00 | 41.46 |
| 824 | C | PRO | A | 443 | 35.568 | 40.310 | 71.244 | 1.00 | 40.24 |
| 825 | O | PRO | A | 443 | 36.450 | 40.053 | 70.428 | 1.00 | 36.98 |
| 826 | N | GLU | A | 444 | 35.251 | 39.505 | 72.256 | 1.00 | 38.87 |
| 827 | CA | GLU | A | 444 | 35.883 | 38.202 | 72.466 | 1.00 | 36.63 |
| 828 | CB | GLU | A | 444 | 36.108 | 37.939 | 73.952 | 1.00 | 39.15 |
| 829 | CG | GLU | A | 444 | 37.146 | 38.802 | 74.643 | 1.00 | 42.86 |
| 830 | CD | GLU | A | 444 | 37.117 | 38.612 | 76.155 | 1.00 | 44.44 |
| 831 | OE1 | GLU | A | 444 | 36.976 | 37.458 | 76.611 | 1.00 | 43.91 |
| 832 | OE2 | GLU | A | 444 | 37.240 | 39.612 | 76.892 | 1.00 | 46.93 |
| 833 | C | GLU | A | 444 | 34.839 | 37.204 | 71.963 | 1.00 | 34.84 |
| 834 | O | GLU | A | 444 | 33.639 | 37.402 | 72.182 | 1.00 | 32.71 |
| 835 | N | VAL | A | 445 | 35.274 | 36.131 | 71.311 | 1.00 | 33.59 |
| 836 | CA | VAL | A | 445 | 34.324 | 35.142 | 70.805 | 1.00 | 32.62 |
| 837 | CB | VAL | A | 445 | 34.247 | 35.199 | 69.274 | 1.00 | 33.92 |
| 838 | CG1 | VAL | A | 445 | 33.138 | 34.285 | 68.778 | 1.00 | 31.47 |
| 839 | CG2 | VAL | A | 445 | 34.044 | 36.632 | 68.809 | 1.00 | 34.42 |
| 840 | C | VAL | A | 445 | 34.647 | 33.691 | 71.191 | 1.00 | 33.12 |
| 841 | O | VAL | A | 445 | 35.781 | 33.243 | 71.029 | 1.00 | 32.76 |
| 842 | N | TYR | A | 446 | 33.641 | 32.967 | 71.688 | 1.00 | 31.34 |
| 843 | CA | TYR | A | 446 | 33.781 | 31.557 | 72.070 | 1.00 | 31.71 |
| 844 | CB | TYR | A | 446 | 33.826 | 31.393 | 73.599 | 1.00 | 30.19 |
| 845 | CG | TYR | A | 446 | 34.789 | 32.308 | 74.300 | 1.00 | 31.61 |
| 846 | CD1 | TYR | A | 446 | 34.360 | 33.527 | 74.814 | 1.00 | 32.88 |
| 847 | CE1 | TYR | A | 446 | 35.250 | 34.403 | 75.442 | 1.00 | 34.03 |
| 848 | CD2 | TYR | A | 446 | 36.147 | 31.973 | 74.429 | 1.00 | 33.52 |
| 849 | CE2 | TYR | A | 446 | 37.047 | 32.841 | 75.053 | 1.00 | 31.78 |
| 850 | CZ | TYR | A | 446 | 36.590 | 34.058 | 75.557 | 1.00 | 34.67 |
| 851 | OH | TYR | A | 446 | 37.459 | 34.953 | 76.161 | 1.00 | 34.45 |
| 852 | C | TYR | A | 446 | 32.598 | 30.740 | 71.524 | 1.00 | 31.02 |
| 853 | O | TYR | A | 446 | 31.451 | 31.198 | 71.548 | 1.00 | 31.08 |
| 854 | N | ALA | A | 447 | 32.879 | 29.527 | 71.058 | 1.00 | 29.50 |
| 855 | CA | ALA | A | 447 | 31.850 | 28.651 | 70.497 | 1.00 | 29.44 |
| 856 | CB | ALA | A | 447 | 32.012 | 28.591 | 68.972 | 1.00 | 30.35 |
| 857 | C | ALA | A | 447 | 31.900 | 27.227 | 71.084 | 1.00 | 30.27 |
| 858 | O | ALA | A | 447 | 32.985 | 26.677 | 71.280 | 1.00 | 25.97 |
| 859 | N | PHE | A | 448 | 30.722 | 26.644 | 71.340 | 1.00 | 29.40 |
| 860 | CA | PHE | A | 448 | 30.595 | 25.292 | 71.899 | 1.00 | 30.81 |
| 861 | CB | PHE | A | 448 | 30.237 | 25.346 | 73.395 | 1.00 | 34.02 |
| 862 | CG | PHE | A | 448 | 31.006 | 26.366 | 74.188 | 1.00 | 41.43 |
| 863 | CD1 | PHE | A | 448 | 30.547 | 27.676 | 74.290 | 1.00 | 41.87 |
| 864 | CD2 | PHE | A | 448 | 32.175 | 26.009 | 74.860 | 1.00 | 44.21 |
| 865 | CE1 | PHE | A | 448 | 31.238 | 28.622 | 75.052 | 1.00 | 45.64 |
| 866 | CE2 | PHE | A | 448 | 32.876 | 26.944 | 75.625 | 1.00 | 45.91 |
| 867 | CZ | PHE | A | 448 | 32.404 | 28.257 | 75.721 | 1.00 | 46.82 |
| 868 | C | PHE | A | 448 | 29.520 | 24.401 | 71.214 | 1.00 | 31.88 |
| 869 | O | PHE | A | 448 | 28.594 | 24.900 | 70.568 | 1.00 | 28.30 |
| 870 | N | ALA | A | 449 | 29.632 | 23.086 | 71.432 | 1.00 | 29.47 |
| 871 | CA | ALA | A | 449 | 28.710 | 22.066 | 70.907 | 1.00 | 28.35 |
| 872 | CB | ALA | A | 449 | 29.408 | 21.245 | 69.865 | 1.00 | 29.03 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 873 | C | ALA | A | 449 | 28.214 | 21.129 | 72.036 | 1.00 | 30.69 |
| 874 | O | ALA | A | 449 | 29.009 | 20.684 | 72.879 | 1.00 | 26.16 |
| 875 | N | THR | A | 450 | 26.914 | 20.824 | 72.046 | 1.00 | 25.64 |
| 876 | CA | THR | A | 450 | 26.353 | 19.944 | 73.063 | 1.00 | 27.70 |
| 877 | CB | THR | A | 450 | 24.812 | 20.147 | 73.256 | 1.00 | 30.44 |
| 878 | OG1 | THR | A | 450 | 24.125 | 19.850 | 72.024 | 1.00 | 27.92 |
| 879 | CG2 | THR | A | 450 | 24.495 | 21.583 | 73.700 | 1.00 | 29.90 |
| 880 | C | THR | A | 450 | 26.539 | 18.466 | 72.712 | 1.00 | 32.47 |
| 881 | O | THR | A | 450 | 26.715 | 18.105 | 71.546 | 1.00 | 29.26 |
| 882 | N | PRO | A | 451 | 26.536 | 17.598 | 73.733 | 1.00 | 28.85 |
| 883 | CD | PRO | A | 451 | 26.691 | 17.948 | 75.160 | 1.00 | 28.70 |
| 884 | CA | PRO | A | 451 | 26.683 | 16.150 | 73.536 | 1.00 | 31.11 |
| 885 | CB | PRO | A | 451 | 27.253 | 15.675 | 74.872 | 1.00 | 30.78 |
| 886 | CG | PRO | A | 451 | 26.565 | 16.571 | 75.845 | 1.00 | 32.08 |
| 887 | C | PRO | A | 451 | 25.283 | 15.593 | 73.287 | 1.00 | 34.67 |
| 888 | O | PRO | A | 451 | 24.294 | 16.295 | 73.489 | 1.00 | 29.91 |
| 889 | N | GLU | A | 452 | 25.201 | 14.331 | 72.878 | 1.00 | 39.60 |
| 890 | CA | GLU | A | 452 | 23.924 | 13.680 | 72.589 | 1.00 | 46.79 |
| 891 | CB | GLU | A | 452 | 24.182 | 12.292 | 71.995 | 1.00 | 49.02 |
| 892 | CG | GLU | A | 452 | 23.006 | 11.705 | 71.236 | 1.00 | 54.73 |
| 893 | CD | GLU | A | 452 | 23.284 | 10.295 | 70.744 | 1.00 | 57.72 |
| 894 | OE1 | GLU | A | 452 | 23.132 | 9.353 | 71.549 | 1.00 | 60.03 |
| 895 | OE2 | GLU | A | 452 | 23.669 | 10.129 | 69.562 | 1.00 | 58.58 |
| 896 | C | GLU | A | 452 | 22.997 | 13.539 | 73.802 | 1.00 | 51.14 |
| 897 | O | GLU | A | 452 | 23.454 | 13.290 | 74.912 | 1.00 | 48.65 |
| 898 | N | TRP | A | 453 | 21.696 | 13.706 | 73.570 | 1.00 | 57.63 |
| 899 | CA | TRP | A | 453 | 20.671 | 13.576 | 74.608 | 1.00 | 66.64 |
| 900 | CB | TRP | A | 453 | 19.946 | 14.923 | 74.816 | 1.00 | 61.45 |
| 901 | CG | TRP | A | 453 | 18.923 | 14.976 | 75.959 | 1.00 | 56.02 |
| 902 | CD2 | TRP | A | 453 | 19.137 | 15.460 | 77.304 | 1.00 | 53.09 |
| 903 | CE2 | TRP | A | 453 | 17.917 | 15.304 | 78.005 | 1.00 | 52.60 |
| 904 | CE3 | TRP | A | 453 | 20.239 | 16.010 | 77.980 | 1.00 | 51.68 |
| 905 | CD1 | TRP | A | 453 | 17.620 | 14.564 | 75.912 | 1.00 | 54.97 |
| 906 | NE1 | TRP | A | 453 | 17.011 | 14.757 | 77.134 | 1.00 | 54.00 |
| 907 | CZ2 | TRP | A | 453 | 17.767 | 15.676 | 79.352 | 1.00 | 50.87 |
| 908 | CZ3 | TRP | A | 453 | 20.092 | 16.381 | 79.320 | 1.00 | 50.92 |
| 909 | CH2 | TRP | A | 453 | 18.861 | 16.210 | 79.990 | 1.00 | 51.03 |
| 910 | C | TRP | A | 453 | 19.710 | 12.496 | 74.094 | 1.00 | 76.57 |
| 911 | O | TRP | A | 453 | 19.291 | 12.531 | 72.938 | 1.00 | 78.21 |
| 912 | N | PRO | A | 454 | 19.358 | 11.517 | 74.945 | 1.00 | 90.74 |
| 913 | CD | PRO | A | 454 | 19.554 | 11.556 | 76.404 | 1.00 | 93.22 |
| 914 | CA | PRO | A | 454 | 18.453 | 10.417 | 74.582 | 1.00 | 96.67 |
| 915 | CB | PRO | A | 454 | 18.127 | 9.777 | 75.932 | 1.00 | 97.65 |
| 916 | CG | PRO | A | 454 | 18.286 | 10.910 | 76.899 | 1.00 | 97.29 |
| 917 | C | PRO | A | 454 | 17.197 | 10.808 | 73.806 | 1.00 | 101.83 |
| 918 | O | PRO | A | 454 | 16.471 | 11.725 | 74.193 | 1.00 | 104.17 |
| 919 | N | GLY | A | 455 | 16.952 | 10.095 | 72.710 | 1.00 | 103.70 |
| 920 | CA | GLY | A | 455 | 15.790 | 10.364 | 71.883 | 1.00 | 103.02 |
| 921 | C | GLY | A | 455 | 16.083 | 11.381 | 70.798 | 1.00 | 98.34 |
| 922 | O | GLY | A | 455 | 15.206 | 11.724 | 70.004 | 1.00 | 103.10 |
| 923 | N | SER | A | 456 | 17.323 | 11.858 | 70.761 | 1.00 | 95.80 |
| 924 | CA | SER | A | 456 | 17.729 | 12.850 | 69.776 | 1.00 | 84.05 |
| 925 | CB | SER | A | 456 | 17.710 | 14.236 | 70.411 | 1.00 | 85.44 |
| 926 | OG | SER | A | 456 | 16.451 | 14.485 | 71.009 | 1.00 | 85.18 |
| 927 | C | SER | A | 456 | 19.116 | 12.548 | 69.222 | 1.00 | 77.91 |
| 928 | O | SER | A | 456 | 20.028 | 13.371 | 69.301 | 1.00 | 76.00 |
| 929 | N | ARG | A | 457 | 19.261 | 11.358 | 68.653 | 1.00 | 73.29 |
| 930 | CA | ARG | A | 457 | 20.526 | 10.918 | 68.082 | 1.00 | 69.56 |
| 931 | CB | ARG | A | 457 | 20.442 | 9.443 | 67.696 | 1.00 | 79.50 |
| 932 | CG | ARG | A | 457 | 21.294 | 8.523 | 68.529 | 1.00 | 94.83 |
| 933 | CD | ARG | A | 457 | 21.421 | 7.178 | 67.848 | 1.00 | 108.21 |
| 934 | NE | ARG | A | 457 | 22.215 | 6.242 | 68.633 | 1.00 | 118.28 |
| 935 | CZ | ARG | A | 457 | 22.650 | 5.073 | 68.176 | 1.00 | 123.09 |
| 936 | NH1 | ARG | A | 457 | 22.367 | 4.699 | 66.935 | 1.00 | 125.36 |
| 937 | NH2 | ARG | A | 457 | 23.365 | 4.276 | 68.960 | 1.00 | 124.96 |
| 938 | C | ARG | A | 457 | 20.951 | 11.703 | 66.851 | 1.00 | 62.85 |
| 939 | O | ARG | A | 457 | 22.141 | 11.849 | 66.591 | 1.00 | 56.67 |
| 940 | N | ASP | A | 458 | 19.987 | 12.208 | 66.092 | 1.00 | 55.82 |
| 941 | CA | ASP | A | 458 | 20.310 | 12.933 | 64.868 | 1.00 | 55.22 |
| 942 | CB | ASP | A | 458 | 19.413 | 12.434 | 63.735 | 1.00 | 59.63 |
| 943 | CG | ASP | A | 458 | 19.671 | 10.979 | 63.382 | 1.00 | 63.16 |
| 944 | OD1 | ASP | A | 458 | 19.550 | 10.101 | 64.265 | 1.00 | 65.68 |
| 945 | OD2 | ASP | A | 458 | 19.997 | 10.714 | 62.210 | 1.00 | 68.45 |
| 946 | C | ASP | A | 458 | 20.288 | 14.468 | 64.893 | 1.00 | 55.10 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 947 | O | ASP | A | 458 | 19.922 | 15.098 | 63.897 | 1.00 | 54.51 |
| 948 | N | LYS | A | 459 | 20.688 | 15.069 | 66.013 | 1.00 | 53.61 |
| 949 | CA | LYS | A | 459 | 20.737 | 16.529 | 66.120 | 1.00 | 53.48 |
| 950 | CB | LYS | A | 459 | 19.318 | 17.113 | 66.143 | 1.00 | 61.56 |
| 951 | CG | LYS | A | 459 | 18.418 | 16.584 | 67.248 | 1.00 | 75.53 |
| 952 | CD | LYS | A | 459 | 17.040 | 17.235 | 67.179 | 1.00 | 86.31 |
| 953 | CE | LYS | A | 459 | 16.153 | 16.788 | 68.331 | 1.00 | 94.24 |
| 954 | NZ | LYS | A | 459 | 14.825 | 17.460 | 68.313 | 1.00 | 99.81 |
| 955 | C | LYS | A | 459 | 21.526 | 17.032 | 67.337 | 1.00 | 48.10 |
| 956 | O | LYS | A | 459 | 21.617 | 16.347 | 68.361 | 1.00 | 42.91 |
| 957 | N | ARG | A | 460 | 22.105 | 18.226 | 67.208 | 1.00 | 42.67 |
| 958 | CA | ARG | A | 460 | 22.870 | 18.844 | 68.293 | 1.00 | 39.67 |
| 959 | CB | ARG | A | 460 | 24.380 | 18.639 | 68.082 | 1.00 | 43.30 |
| 960 | CG | ARG | A | 460 | 24.804 | 17.197 | 67.869 | 1.00 | 50.66 |
| 961 | CD | ARG | A | 460 | 24.625 | 16.348 | 69.118 | 1.00 | 56.67 |
| 962 | NE | ARG | A | 460 | 24.225 | 14.992 | 68.767 | 1.00 | 64.46 |
| 963 | CZ | ARG | A | 460 | 24.971 | 13.912 | 68.963 | 1.00 | 68.23 |
| 964 | NH1 | ARG | A | 460 | 26.168 | 14.024 | 69.518 | 1.00 | 72.33 |
| 965 | NH2 | ARG | A | 460 | 24.520 | 12.722 | 68.592 | 1.00 | 69.27 |
| 966 | C | ARG | A | 460 | 22.565 | 20.341 | 68.291 | 1.00 | 35.66 |
| 967 | O | ARG | A | 460 | 21.975 | 20.856 | 67.332 | 1.00 | 33.46 |
| 968 | N | THR | A | 461 | 22.958 | 21.034 | 69.362 | 1.00 | 31.05 |
| 969 | CA | THR | A | 461 | 22.742 | 22.479 | 69.461 | 1.00 | 28.67 |
| 970 | CB | THR | A | 461 | 21.863 | 22.849 | 70.669 | 1.00 | 24.62 |
| 971 | OG1 | THR | A | 461 | 20.657 | 22.082 | 70.634 | 1.00 | 26.68 |
| 972 | CG2 | THR | A | 461 | 21.497 | 24.324 | 70.638 | 1.00 | 23.92 |
| 973 | C | THR | A | 461 | 24.095 | 23.157 | 69.622 | 1.00 | 27.35 |
| 974 | O | THR | A | 461 | 24.918 | 22.731 | 70.435 | 1.00 | 28.86 |
| 975 | N | LEU | A | 462 | 24.343 | 24.194 | 68.835 | 1.00 | 26.68 |
| 976 | CA | LEU | A | 462 | 25.611 | 24.906 | 68.934 | 1.00 | 28.37 |
| 977 | CB | LEU | A | 462 | 26.233 | 25.083 | 67.542 | 1.00 | 28.11 |
| 978 | CG | LEU | A | 462 | 26.576 | 23.771 | 66.809 | 1.00 | 31.18 |
| 979 | CD1 | LEU | A | 462 | 27.140 | 24.065 | 65.413 | 1.00 | 29.73 |
| 980 | CD2 | LEU | A | 462 | 27.591 | 22.991 | 67.612 | 1.00 | 28.50 |
| 981 | C | LEU | A | 462 | 25.360 | 26.256 | 69.597 | 1.00 | 25.64 |
| 982 | O | LEU | A | 462 | 24.311 | 26.872 | 69.374 | 1.00 | 27.27 |
| 983 | N | ALA | A | 463 | 26.305 | 26.715 | 70.416 | 1.00 | 25.94 |
| 984 | CA | ALA | A | 463 | 26.147 | 27.999 | 71.117 | 1.00 | 23.77 |
| 985 | CB | ALA | A | 463 | 25.755 | 27.741 | 72.564 | 1.00 | 22.78 |
| 986 | C | ALA | A | 463 | 27.409 | 28.857 | 71.066 | 1.00 | 25.42 |
| 987 | O | ALA | A | 463 | 28.529 | 28.325 | 71.168 | 1.00 | 25.79 |
| 988 | N | CYS | A | 464 | 27.213 | 30.179 | 70.944 | 1.00 | 24.86 |
| 989 | CA | CYS | A | 464 | 28.295 | 31.169 | 70.860 | 1.00 | 27.26 |
| 990 | C | CYS | A | 464 | 28.132 | 32.298 | 71.903 | 1.00 | 27.47 |
| 991 | O | CYS | A | 464 | 27.027 | 32.823 | 72.091 | 1.00 | 28.39 |
| 992 | CB | CYS | A | 464 | 28.320 | 31.780 | 69.447 | 1.00 | 26.55 |
| 993 | SG | CYS | A | 464 | 29.830 | 32.711 | 68.981 | 1.00 | 30.90 |
| 994 | N | LEU | A | 465 | 29.230 | 32.649 | 72.579 | 1.00 | 26.79 |
| 995 | CA | LEU | A | 465 | 29.263 | 33.722 | 73.594 | 1.00 | 28.83 |
| 996 | CB | LEU | A | 465 | 29.809 | 33.199 | 74.951 | 1.00 | 28.76 |
| 997 | CG | LEU | A | 465 | 30.227 | 34.268 | 75.998 | 1.00 | 27.83 |
| 998 | CD1 | LEU | A | 465 | 29.047 | 35.140 | 76.354 | 1.00 | 23.09 |
| 999 | CD2 | LEU | A | 465 | 30.775 | 33.628 | 77.265 | 1.00 | 29.42 |
| 1000 | C | LEU | A | 465 | 30.188 | 34.833 | 73.080 | 1.00 | 27.46 |
| 1001 | O | LEU | A | 465 | 31.350 | 34.577 | 72.778 | 1.00 | 28.31 |
| 1002 | N | ILE | A | 466 | 29.667 | 36.050 | 72.959 | 1.00 | 28.99 |
| 1003 | CA | ILE | A | 466 | 30.446 | 37.200 | 72.487 | 1.00 | 28.21 |
| 1004 | CB | ILE | A | 466 | 29.795 | 37.856 | 71.241 | 1.00 | 32.28 |
| 1005 | CG2 | ILE | A | 466 | 30.837 | 38.678 | 70.478 | 1.00 | 30.44 |
| 1006 | CG1 | ILE | A | 466 | 29.203 | 36.790 | 70.312 | 1.00 | 35.82 |
| 1007 | CD1 | ILE | A | 466 | 30.216 | 35.894 | 69.667 | 1.00 | 41.41 |
| 1008 | C | ILE | A | 466 | 30.409 | 38.207 | 73.645 | 1.00 | 26.22 |
| 1009 | O | ILE | A | 466 | 29.337 | 38.563 | 74.105 | 1.00 | 24.55 |
| 1010 | N | GLN | A | 467 | 31.559 | 38.684 | 74.110 | 1.00 | 25.69 |
| 1011 | CA | GLN | A | 467 | 31.544 | 39.602 | 75.248 | 1.00 | 29.38 |
| 1012 | CB | GLN | A | 467 | 31.497 | 38.785 | 76.545 | 1.00 | 24.90 |
| 1013 | CG | GLN | A | 467 | 32.492 | 37.624 | 76.582 | 1.00 | 27.39 |
| 1014 | CD | GLN | A | 467 | 32.590 | 36.972 | 77.963 | 1.00 | 28.47 |
| 1015 | OE1 | GLN | A | 467 | 31.570 | 36.702 | 78.614 | 1.00 | 25.32 |
| 1016 | NE2 | GLN | A | 467 | 33.820 | 36.716 | 78.413 | 1.00 | 24.87 |
| 1017 | C | GLN | A | 467 | 32.647 | 40.666 | 75.386 | 1.00 | 30.38 |
| 1018 | O | GLN | A | 467 | 33.661 | 40.645 | 74.686 | 1.00 | 30.81 |
| 1019 | N | ASN | A | 468 | 32.404 | 41.584 | 76.323 | 1.00 | 32.06 |
| 1020 | CA | ASN | A | 468 | 33.294 | 42.695 | 76.674 | 1.00 | 37.67 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1021 | CB | ASN | A | 468 | 34.643 | 42.150 | 77.187 | 1.00 | 38.18 |
| 1022 | CG | ASN | A | 468 | 34.508 | 41.409 | 78.528 | 1.00 | 40.31 |
| 1023 | OD1 | ASN | A | 468 | 33.721 | 41.797 | 79.398 | 1.00 | 39.02 |
| 1024 | ND2 | ASN | A | 468 | 35.287 | 40.351 | 78.698 | 1.00 | 41.43 |
| 1025 | C | ASN | A | 468 | 33.541 | 43.769 | 75.605 | 1.00 | 38.87 |
| 1026 | O | ASN | A | 468 | 34.601 | 44.410 | 75.599 | 1.00 | 39.51 |
| 1027 | N | PHE | A | 469 | 32.571 | 43.976 | 74.714 | 1.00 | 38.81 |
| 1028 | CA | PHE | A | 469 | 32.705 | 44.981 | 73.655 | 1.00 | 38.16 |
| 1029 | CB | PHE | A | 469 | 32.228 | 44.396 | 72.311 | 1.00 | 36.53 |
| 1030 | CG | PHE | A | 469 | 30.797 | 43.902 | 72.326 | 1.00 | 34.97 |
| 1031 | CD1 | PHE | A | 469 | 29.733 | 44.794 | 72.219 | 1.00 | 32.92 |
| 1032 | CD2 | PHE | A | 469 | 30.517 | 42.540 | 72.494 | 1.00 | 35.85 |
| 1033 | CE1 | PHE | A | 469 | 28.394 | 44.342 | 72.283 | 1.00 | 35.91 |
| 1034 | CE2 | PHE | A | 469 | 29.177 | 42.068 | 72.561 | 1.00 | 34.64 |
| 1035 | CZ | PHE | A | 469 | 28.119 | 42.965 | 72.456 | 1.00 | 35.06 |
| 1036 | C | PHE | A | 469 | 31.924 | 46.256 | 73.978 | 1.00 | 37.90 |
| 1037 | O | PHE | A | 469 | 31.091 | 46.261 | 74.880 | 1.00 | 37.54 |
| 1038 | N | MET | A | 470 | 32.215 | 47.339 | 73.259 | 1.00 | 40.24 |
| 1039 | CA | MET | A | 470 | 31.496 | 48.608 | 73.444 | 1.00 | 44.58 |
| 1040 | CB | MET | A | 470 | 31.769 | 49.211 | 74.841 | 1.00 | 48.00 |
| 1041 | CG | NET | A | 470 | 33.174 | 49.710 | 75.116 | 1.00 | 53.55 |
| 1042 | SD | MET | A | 470 | 33.455 | 49.998 | 76.911 | 1.00 | 57.94 |
| 1043 | CE | MET | A | 470 | 32.441 | 51.455 | 77.221 | 1.00 | 61.01 |
| 1044 | C | MET | A | 470 | 31.830 | 49.611 | 72.340 | 1.00 | 43.77 |
| 1045 | O | MET | A | 470 | 32.974 | 49.681 | 71.893 | 1.00 | 43.04 |
| 1046 | N | CPR | A | 471 | 30.826 | 50.381 | 71.863 | 1.00 | 42.30 |
| 1047 | CD | CPR | A | 471 | 31.063 | 51.350 | 70.782 | 1.00 | 42.87 |
| 1048 | CA | CPR | A | 471 | 29.409 | 50.412 | 72.251 | 1.00 | 42.86 |
| 1049 | CB | CPR | A | 471 | 28.821 | 51.530 | 71.374 | 1.00 | 42.78 |
| 1050 | CG | CPR | A | 471 | 29.990 | 52.377 | 71.058 | 1.00 | 44.27 |
| 1051 | C | CPR | A | 471 | 28.680 | 49.086 | 72.040 | 1.00 | 42.25 |
| 1052 | O | CPR | A | 471 | 29.274 | 48.100 | 71.605 | 1.00 | 41.05 |
| 1053 | N | GLU | A | 472 | 27.379 | 49.097 | 72.310 | 1.00 | 41.40 |
| 1054 | CA | GLU | A | 472 | 26.544 | 47.907 | 72.231 | 1.00 | 44.53 |
| 1055 | CB | GLU | A | 472 | 25.336 | 48.115 | 73.141 | 1.00 | 48.45 |
| 1056 | CG | GLU | A | 472 | 24.416 | 49.204 | 72.638 | 1.00 | 57.84 |
| 1057 | CD | GLU | A | 472 | 23.428 | 49.668 | 73.680 | 1.00 | 63.30 |
| 1058 | OE1 | GLU | A | 472 | 23.770 | 50.588 | 74.461 | 1.00 | 66.76 |
| 1059 | OE2 | GLU | A | 472 | 22.313 | 49.104 | 73.719 | 1.00 | 66.24 |
| 1060 | C | GLU | A | 472 | 26.062 | 47.399 | 70.860 | 1.00 | 43.88 |
| 1061 | O | GLU | A | 472 | 25.602 | 46.253 | 70.758 | 1.00 | 41.58 |
| 1062 | N | ASP | A | 473 | 26.149 | 48.221 | 69.814 | 1.00 | 43.14 |
| 1063 | CA | ASP | A | 473 | 25.698 | 47.782 | 68.486 | 1.00 | 41.21 |
| 1064 | CB | ASP | A | 473 | 25.710 | 48.958 | 67.500 | 1.00 | 46.55 |
| 1065 | CG | ASP | A | 473 | 24.562 | 49.932 | 67.732 | 1.00 | 51.86 |
| 1066 | OD1 | ASP | A | 473 | 23.615 | 49.578 | 68.471 | 1.00 | 55.29 |
| 1067 | OD2 | ASP | A | 473 | 24.599 | 51.045 | 67.164 | 1.00 | 54.62 |
| 1068 | C | ASP | A | 473 | 26.542 | 46.630 | 67.931 | 1.00 | 38.79 |
| 1069 | O | ASP | A | 473 | 27.775 | 46.694 | 67.954 | 1.00 | 39.62 |
| 1070 | N | ILE | A | 474 | 25.885 | 45.584 | 67.423 | 1.00 | 34.52 |
| 1071 | CA | ILE | A | 474 | 26.609 | 44.424 | 66.885 | 1.00 | 31.09 |
| 1072 | CB | ILE | A | 474 | 27.245 | 43.611 | 68.046 | 1.00 | 33.63 |
| 1073 | CG2 | ILE | A | 474 | 26.181 | 42.794 | 68.762 | 1.00 | 31.98 |
| 1074 | CG1 | ILE | A | 474 | 28.332 | 42.676 | 67.515 | 1.00 | 36.52 |
| 1075 | CD1 | ILE | A | 474 | 29.078 | 41.960 | 68.609 | 1.00 | 38.99 |
| 1076 | C | ILE | A | 474 | 25.791 | 43.463 | 66.001 | 1.00 | 29.76 |
| 1077 | O | ILE | A | 474 | 24.577 | 43.276 | 66.206 | 1.00 | 24.01 |
| 1078 | N | SER | A | 475 | 26.447 | 42.873 | 65.001 | 1.00 | 27.71 |
| 1079 | CA | SER | A | 475 | 25.774 | 41.893 | 64.123 | 1.00 | 28.79 |
| 1080 | CB | SER | A | 475 | 25.895 | 42.291 | 62.646 | 1.00 | 29.21 |
| 1081 | OG | SER | A | 475 | 25.312 | 43.564 | 62.403 | 1.00 | 35.16 |
| 1082 | C | SER | A | 475 | 26.398 | 40.506 | 64.320 | 1.00 | 27.94 |
| 1083 | O | SER | A | 475 | 27.607 | 40.399 | 64.489 | 1.00 | 29.76 |
| 1084 | N | VAL | A | 476 | 25.581 | 39.453 | 64.287 | 1.00 | 28.51 |
| 1085 | CA | VAL | A | 476 | 26.072 | 38.068 | 64.476 | 1.00 | 28.35 |
| 1086 | CB | VAL | A | 476 | 25.564 | 37.469 | 65.825 | 1.00 | 26.37 |
| 1087 | CG1 | VAL | A | 475 | 25.944 | 35.976 | 65.915 | 1.00 | 22.98 |
| 1088 | CG2 | VAL | A | 476 | 26.141 | 38.237 | 66.986 | 1.00 | 20.92 |
| 1089 | C | VAL | A | 476 | 25.640 | 37.088 | 63.377 | 1.00 | 28.79 |
| 1090 | O | VAL | A | 476 | 24.454 | 37.010 | 63.060 | 1.00 | 29.18 |
| 1091 | N | GLN | A | 477 | 26.572 | 36.327 | 62.805 | 1.00 | 30.58 |
| 1092 | CA | GLN | A | 477 | 26.176 | 35.353 | 61.779 | 1.00 | 34.44 |
| 1093 | CB | GLN | A | 477 | 26.379 | 35.954 | 60.379 | 1.00 | 40.93 |
| 1094 | CG | GLN | A | 477 | 27.815 | 36.318 | 60.025 | 1.00 | 54.01 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1095 | CD | GLN | A | 477 | 27.895 | 37.522 | 59.085 | 1.00 | 60.02 |
| 1096 | OE1 | GLN | A | 477 | 28.968 | 37.872 | 58.583 | 1.00 | 62.28 |
| 1097 | NE2 | GLN | A | 477 | 26.753 | 38.165 | 58.854 | 1.00 | 63.99 |
| 1098 | C | GLN | A | 477 | 26.858 | 33.975 | 61.890 | 1.00 | 32.88 |
| 1099 | O | GLN | A | 477 | 27.868 | 33.837 | 62.573 | 1.00 | 29.07 |
| 1100 | N | TRP | A | 478 | 26.279 | 32.957 | 61.240 | 1.00 | 32.51 |
| 1101 | CA | TRP | A | 478 | 26.838 | 31.594 | 61.253 | 1.00 | 34.89 |
| 1102 | CB | TRP | A | 478 | 25.890 | 30.580 | 61.932 | 1.00 | 32.45 |
| 1103 | CG | TRP | A | 478 | 25.651 | 30.738 | 63.458 | 1.00 | 32.89 |
| 1104 | CD2 | TRP | A | 478 | 26.302 | 30.008 | 64.524 | 1.00 | 30.58 |
| 1105 | CE2 | TRP | A | 478 | 25.747 | 30.462 | 65.743 | 1.00 | 31.28 |
| 1106 | CE3 | TRP | A | 478 | 27.297 | 29.017 | 64.563 | 1.00 | 30.30 |
| 1107 | CD1 | TRP | A | 478 | 24.761 | 31.575 | 64.066 | 1.00 | 28.75 |
| 1108 | NE1 | TRP | A | 478 | 24.812 | 31.415 | 65.437 | 1.00 | 30.17 |
| 1109 | CZ2 | TRP | A | 478 | 26.155 | 29.958 | 66.996 | 1.00 | 31.26 |
| 1110 | CZ3 | TRP | A | 478 | 27.709 | 28.512 | 65.811 | 1.00 | 27.57 |
| 1111 | CR2 | TRP | A | 478 | 27.134 | 28.987 | 67.006 | 1.00 | 32.46 |
| 1112 | C | TRP | A | 478 | 27.154 | 31.096 | 59.824 | 1.00 | 36.62 |
| 1113 | O | TRP | A | 478 | 26.439 | 31.415 | 58.863 | 1.00 | 35.64 |
| 1114 | N | LEU | A | 479 | 28.225 | 30.309 | 59.693 | 1.00 | 38.80 |
| 1115 | CA | LEU | A | 479 | 28.634 | 29.782 | 58.389 | 1.00 | 42.23 |
| 1116 | CB | LEU | A | 479 | 29.803 | 30.603 | 57.849 | 1.00 | 41.10 |
| 1117 | CG | LEU | A | 479 | 29.539 | 32.097 | 57.687 | 1.00 | 42.47 |
| 1118 | CD1 | LEU | A | 479 | 30.260 | 32.870 | 58.776 | 1.00 | 42.65 |
| 1119 | CD2 | LEU | A | 479 | 30.031 | 32.540 | 56.327 | 1.00 | 45.05 |
| 1120 | C | LEU | A | 479 | 29.019 | 28.300 | 58.373 | 1.00 | 42.38 |
| 1121 | O | LEU | A | 479 | 29.552 | 27.776 | 59.356 | 1.00 | 43.78 |
| 1122 | N | HIS | A | 480 | 28.743 | 27.640 | 57.245 | 1.00 | 44.51 |
| 1123 | CA | HIS | A | 480 | 29.065 | 26.220 | 57.035 | 1.00 | 47.56 |
| 1124 | CB | HIS | A | 480 | 27.819 | 25.342 | 57.205 | 1.00 | 41.97 |
| 1125 | CG | HIS | A | 480 | 28.110 | 23.870 | 57.204 | 1.00 | 38.79 |
| 1126 | CD2 | HIS | A | 480 | 29.182 | 23.171 | 57.648 | 1.00 | 37.09 |
| 1127 | ND1 | HIS | A | 480 | 27.218 | 22.934 | 56.720 | 1.00 | 38.44 |
| 1128 | CE1 | HIS | A | 480 | 27.729 | 21.724 | 56.865 | 1.00 | 35.60 |
| 1129 | NE2 | HIS | A | 480 | 28.919 | 21.839 | 57.426 | 1.00 | 36.96 |
| 1130 | C | HIS | A | 480 | 29.627 | 26.026 | 55.614 | 1.00 | 52.26 |
| 1131 | O | HIS | A | 480 | 29.002 | 26.421 | 54.623 | 1.00 | 51.92 |
| 1132 | N | ASN | A | 481 | 30.799 | 25.401 | 55.530 | 1.00 | 56.31 |
| 1133 | CA | ASN | A | 481 | 31.496 | 25.160 | 54.265 | 1.00 | 61.14 |
| 1134 | CB | ASN | A | 481 | 30.539 | 24.641 | 53.184 | 1.00 | 60.44 |
| 1135 | CG | ASN | A | 481 | 30.368 | 23.131 | 53.235 | 1.00 | 58.56 |
| 1136 | OD1 | ASN | A | 481 | 31.297 | 22.379 | 52.933 | 1.00 | 56.41 |
| 1137 | ND2 | ASN | A | 481 | 29.182 | 22.681 | 53.625 | 1.00 | 56.35 |
| 1138 | C | ASN | A | 481 | 32.162 | 26.446 | 53.806 | 1.00 | 63.39 |
| 1139 | O | ASN | A | 481 | 33.388 | 26.576 | 53.837 | 1.00 | 69.38 |
| 1140 | N | ALA | A | 482 | 31.353 | 27.401 | 53.387 | 1.00 | 65.80 |
| 1141 | CA | ALA | A | 482 | 31.874 | 28.676 | 52.942 | 1.00 | 64.50 |
| 1142 | CB | ALA | A | 482 | 32.617 | 28.504 | 51.622 | 1.00 | 68.60 |
| 1143 | C | ALA | A | 482 | 30.684 | 29.598 | 52.769 | 1.00 | 61.79 |
| 1144 | O | ALA | A | 482 | 30.840 | 30.800 | 52.535 | 1.00 | 61.58 |
| 1145 | N | VAL | A | 483 | 29.493 | 29.018 | 52.907 | 1.00 | 55.76 |
| 1146 | CA | VAL | A | 483 | 28.246 | 29.757 | 52.754 | 1.00 | 49.99 |
| 1147 | CB | VAL | A | 483 | 27.248 | 28.973 | 51.868 | 1.00 | 50.21 |
| 1148 | CG1 | VAL | A | 483 | 27.871 | 28.735 | 50.497 | 1.00 | 51.24 |
| 1149 | CG2 | VAL | A | 483 | 26.882 | 27.648 | 52.514 | 1.00 | 48.45 |
| 1150 | C | VAL | A | 483 | 27.554 | 30.138 | 54.067 | 1.00 | 47.88 |
| 1151 | O | VAL | A | 483 | 27.424 | 29.329 | 54.994 | 1.00 | 42.37 |
| 1152 | N | GLN | A | 484 | 27.121 | 31.390 | 54.127 | 1.00 | 44.00 |
| 1153 | CA | GLN | A | 484 | 26.427 | 31.906 | 55.286 | 1.00 | 43.89 |
| 1154 | CB | GLN | A | 484 | 26.385 | 33.434 | 55.214 | 1.00 | 48.57 |
| 1155 | CG | GLN | A | 484 | 25.644 | 34.084 | 56.362 | 1.00 | 56.47 |
| 1156 | CD | GLN | A | 484 | 25.813 | 35.588 | 56.376 | 1.00 | 61.62 |
| 1157 | OE1 | GLN | A | 484 | 24.900 | 36.323 | 56.755 | 1.00 | 63.15 |
| 1158 | NE2 | GLN | A | 484 | 26.991 | 36.055 | 55.973 | 1.00 | 63.81 |
| 1159 | C | GLN | A | 484 | 25.011 | 31.333 | 55.333 | 1.00 | 39.96 |
| 1160 | O | GLN | A | 484 | 24.328 | 31.278 | 54.313 | 1.00 | 39.03 |
| 1161 | N | LEU | A | 485 | 24.583 | 30.912 | 56.523 | 1.00 | 36.45 |
| 1162 | CA | LEU | A | 485 | 23.261 | 30.328 | 56.728 | 1.00 | 33.34 |
| 1163 | CB | LEU | A | 485 | 23.265 | 29.451 | 57.975 | 1.00 | 32.66 |
| 1164 | CG | LEU | A | 485 | 24.283 | 28.305 | 58.007 | 1.00 | 33.34 |
| 1165 | CD1 | LEU | A | 485 | 24.307 | 27.699 | 59.407 | 1.00 | 33.21 |
| 1166 | CD2 | LEU | A | 485 | 23.918 | 27.251 | 56.968 | 1.00 | 30.67 |
| 1167 | C | LEU | A | 485 | 22.164 | 31.365 | 56.871 | 1.00 | 31.28 |
| 1168 | O | LEU | A | 485 | 22.402 | 32.471 | 57.349 | 1.00 | 30.60 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1169 | N | PRO | A | 486 | 20.933 | 31.013 | 56.467 | 1.00 | 33.48 |
| 1170 | CD | PRO | A | 486 | 20.504 | 29.670 | 56.037 | 1.00 | 30.98 |
| 1171 | CA | PRO | A | 486 | 19.782 | 31.929 | 56.559 | 1.00 | 36.84 |
| 1172 | CB | PRO | A | 486 | 18.591 | 31.043 | 56.189 | 1.00 | 33.00 |
| 1173 | CG | PRO | A | 486 | 19.185 | 29.972 | 55.362 | 1.00 | 32.99 |
| 1174 | C | PRO | A | 486 | 19.671 | 32.424 | 58.002 | 1.00 | 42.49 |
| 1175 | O | PRO | A | 486 | 19.868 | 31.640 | 58.934 | 1.00 | 41.99 |
| 1176 | N | ASP | A | 487 | 19.353 | 33.705 | 58.182 | 1.00 | 49.15 |
| 1177 | CA | ASP | A | 487 | 19.237 | 34.299 | 59.514 | 1.00 | 56.17 |
| 1178 | CB | ASP | A | 487 | 18.963 | 35.809 | 59.413 | 1.00 | 67.71 |
| 1179 | CG | ASP | A | 487 | 20.178 | 36.607 | 58.951 | 1.00 | 77.98 |
| 1180 | OD1 | ASP | A | 487 | 21.256 | 36.489 | 59.578 | 1.00 | 84.67 |
| 1181 | OD2 | ASP | A | 487 | 20.051 | 37.365 | 57.965 | 1.00 | 84.56 |
| 1182 | C | ASP | A | 487 | 18.139 | 33.658 | 60.367 | 1.00 | 54.87 |
| 1183 | O | ASP | A | 487 | 18.198 | 33.694 | 61.603 | 1.00 | 56.46 |
| 1184 | N | ALA | A | 488 | 17.146 | 33.067 | 59.707 | 1.00 | 51.12 |
| 1185 | CA | ALA | A | 488 | 16.026 | 32.450 | 60.402 | 1.00 | 47.88 |
| 1186 | CB | ALA | A | 488 | 14.898 | 32.182 | 59.412 | 1.00 | 46.31 |
| 1187 | C | ALA | A | 488 | 16.387 | 31.164 | 61.146 | 1.00 | 45.88 |
| 1188 | O | ALA | A | 488 | 15.649 | 30.717 | 62.028 | 1.00 | 42.09 |
| 1189 | N | ARG | A | 489 | 17.522 | 30.575 | 60.793 | 1.00 | 42.41 |
| 1190 | CA | ARG | A | 489 | 17.965 | 29.338 | 61.421 | 1.00 | 41.05 |
| 1191 | CB | ARG | A | 489 | 19.029 | 28.678 | 60.549 | 1.00 | 43.11 |
| 1192 | CG | ARG | A | 489 | 18.476 | 27.604 | 59.640 | 1.00 | 42.37 |
| 1193 | CD | ARG | A | 489 | 18.881 | 26.261 | 60.158 | 1.00 | 43.57 |
| 1194 | NE | ARG | A | 489 | 19.716 | 25.620 | 59.161 | 1.00 | 49.11 |
| 1195 | CZ | ARG | A | 489 | 20.659 | 24.730 | 59.414 | 1.00 | 47.83 |
| 1196 | NH1 | ARG | A | 489 | 20.908 | 24.356 | 60.659 | 1.00 | 49.12 |
| 1197 | NH2 | ARG | A | 489 | 21.354 | 24.219 | 58.406 | 1.00 | 49.45 |
| 1198 | C | ARG | A | 489 | 18.504 | 29.469 | 62.847 | 1.00 | 41.09 |
| 1199 | O | ARG | A | 489 | 18.715 | 28.456 | 63.518 | 1.00 | 38.93 |
| 1200 | N | HIS | A | 490 | 18.714 | 30.702 | 63.309 | 1.00 | 38.92 |
| 1201 | CA | HIS | A | 490 | 19.252 | 30.933 | 64.652 | 1.00 | 38.70 |
| 1202 | CB | HIS | A | 490 | 20.773 | 31.189 | 64.567 | 1.00 | 38.24 |
| 1203 | CG | HIS | A | 490 | 21.131 | 32.515 | 63.963 | 1.00 | 40.24 |
| 1204 | CD2 | HIS | A | 490 | 21.530 | 32.848 | 62.710 | 1.00 | 42.89 |
| 1205 | ND1 | HIS | A | 490 | 21.055 | 33.700 | 64.666 | 1.00 | 41.53 |
| 1206 | CE1 | HIS | A | 490 | 21.390 | 34.703 | 63.874 | 1.00 | 41.06 |
| 1207 | NE2 | HIS | A | 490 | 21.682 | 34.214 | 62.681 | 1.00 | 41.76 |
| 1208 | C | HIS | A | 490 | 18.580 | 32.127 | 65.334 | 1.00 | 37.74 |
| 1209 | O | HIS | A | 490 | 17.792 | 32.841 | 64.719 | 1.00 | 34.09 |
| 1210 | N | SER | A | 491 | 18.900 | 32.332 | 66.607 | 1.00 | 37.28 |
| 1211 | CA | SER | A | 491 | 18.359 | 33.459 | 67.366 | 1.00 | 38.52 |
| 1212 | CB | SER | A | 491 | 17.101 | 33.061 | 68.156 | 1.00 | 41.46 |
| 1213 | OG | SER | A | 491 | 17.395 | 32.175 | 69.207 | 1.00 | 46.69 |
| 1214 | C | SER | A | 491 | 19.442 | 33.975 | 68.300 | 1.00 | 37.00 |
| 1215 | O | SER | A | 491 | 20.231 | 33.197 | 68.834 | 1.00 | 37.61 |
| 1216 | N | THR | A | 492 | 19.473 | 35.292 | 68.472 | 1.00 | 32.89 |
| 1217 | CA | THR | A | 492 | 20.461 | 35.970 | 69.295 | 1.00 | 31.85 |
| 1218 | CB | THR | A | 492 | 21.352 | 36.854 | 68.391 | 1.00 | 33.83 |
| 1219 | OG1 | THR | A | 492 | 21.903 | 36.053 | 67.331 | 1.00 | 31.03 |
| 1220 | CG2 | THR | A | 492 | 22.490 | 37.494 | 69.196 | 1.00 | 31.98 |
| 1221 | C | THR | A | 492 | 19.795 | 36.851 | 70.388 | 1.00 | 33.37 |
| 1222 | O | THR | A | 492 | 18.839 | 37.572 | 70.107 | 1.00 | 31.86 |
| 1223 | N | THR | A | 493 | 20.299 | 36.785 | 71.623 | 1.00 | 29.93 |
| 1224 | CA | THR | A | 493 | 19.744 | 37.565 | 72.745 | 1.00 | 31.75 |
| 1225 | CB | THR | A | 493 | 20.252 | 37.016 | 74.118 | 1.00 | 29.06 |
| 1226 | OG1 | THR | A | 493 | 21.688 | 37.084 | 74.172 | 1.00 | 23.92 |
| 1227 | CG2 | THR | A | 493 | 19.818 | 35.561 | 74.309 | 1.00 | 26.70 |
| 1228 | C | THR | A | 493 | 20.084 | 39.075 | 72.648 | 1.00 | 34.43 |
| 1229 | O | THR | A | 493 | 20.959 | 39.469 | 71.882 | 1.00 | 32.44 |
| 1230 | N | GLN | A | 494 | 19.386 | 39.916 | 73.407 | 1.00 | 37.86 |
| 1231 | CA | GLN | A | 494 | 19.656 | 41.364 | 73.368 | 1.00 | 42.46 |
| 1232 | CB | GLN | A | 494 | 18.416 | 42.147 | 73.824 | 1.00 | 48.75 |
| 1233 | CG | GLN | A | 494 | 17.205 | 41.991 | 72.894 | 1.00 | 60.70 |
| 1234 | CD | GLN | A | 494 | 17.427 | 42.602 | 71.513 | 1.00 | 65.23 |
| 1235 | OE1 | GLN | A | 494 | 17.562 | 43.819 | 71.377 | 1.00 | 69.46 |
| 1236 | NE2 | GLN | A | 494 | 17.465 | 41.756 | 70.484 | 1.00 | 69.60 |
| 1237 | C | GLN | A | 494 | 20.864 | 41.741 | 74.236 | 1.00 | 40.24 |
| 1238 | O | GLN | A | 494 | 21.159 | 41.064 | 75.220 | 1.00 | 40.25 |
| 1239 | N | PRO | A | 495 | 21.570 | 42.835 | 73.887 | 1.00 | 40.38 |
| 1240 | CD | PRO | A | 495 | 21.358 | 43.695 | 72.710 | 1.00 | 39.31 |
| 1241 | CA | PRO | A | 495 | 22.749 | 43.287 | 74.640 | 1.00 | 41.50 |
| 1242 | CB | PRO | A | 495 | 23.180 | 44.544 | 73.887 | 1.00 | 40.66 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1243 | CG | PRO | A | 495 | 22.746 | 44.248 | 72.475 | 1.00 | 37.94 |
| 1244 | C | PRO | A | 495 | 22.482 | 43.564 | 76.115 | 1.00 | 45.36 |
| 1245 | O | PRO | A | 495 | 21.482 | 44.188 | 76.473 | 1.00 | 43.49 |
| 1246 | N | ARG | A | 496 | 23.383 | 43.077 | 76.963 | 1.00 | 48.52 |
| 1247 | CA | ARG | A | 496 | 23.282 | 43.263 | 78.404 | 1.00 | 53.03 |
| 1248 | CB | ARG | A | 496 | 22.823 | 41.966 | 79.087 | 1.00 | 59.67 |
| 1249 | CG | ARG | A | 496 | 21.474 | 41.466 | 78.629 | 1.00 | 69.10 |
| 1250 | CD | ARG | A | 496 | 20.399 | 42.511 | 78.878 | 1.00 | 78.11 |
| 1251 | NE | ARG | A | 496 | 19.260 | 42.344 | 77.978 | 1.00 | 85.57 |
| 1252 | CZ | ARG | A | 496 | 18.232 | 43.185 | 77.905 | 1.00 | 88.36 |
| 1253 | NH1 | ARG | A | 496 | 18.195 | 44.257 | 78.686 | 1.00 | 90.24 |
| 1254 | NH2 | ARG | A | 496 | 17.252 | 42.964 | 77.036 | 1.00 | 90.50 |
| 1255 | C | ARG | A | 496 | 24.662 | 43.650 | 78.921 | 1.00 | 53.32 |
| 1256 | O | ARG | A | 496 | 25.681 | 43.262 | 78.340 | 1.00 | 50.88 |
| 1257 | N | LYS | A | 497 | 24.697 | 44.416 | 80.008 | 1.00 | 54.79 |
| 1258 | CA | LYS | A | 497 | 25.965 | 44.835 | 80.588 | 1.00 | 56.68 |
| 1259 | CB | LYS | A | 497 | 25.773 | 46.056 | 81.494 | 1.00 | 66.41 |
| 1260 | CG | LYS | A | 497 | 25.869 | 47.392 | 80.778 | 1.00 | 80.29 |
| 1261 | CD | LYS | A | 497 | 25.856 | 48.553 | 81.763 | 1.00 | 92.25 |
| 1262 | CE | LYS | A | 497 | 26.059 | 49.881 | 81.045 | 1.00 | 100.15 |
| 1263 | NZ | LYS | A | 497 | 26.026 | 51.042 | 81.977 | 1.00 | 106.34 |
| 1264 | C | LYS | A | 497 | 26.627 | 43.728 | 81.395 | 1.00 | 53.27 |
| 1265 | O | LYS | A | 497 | 25.954 | 43.002 | 82.131 | 1.00 | 50.50 |
| 1266 | N | THR | A | 498 | 27.945 | 43.598 | 81.237 | 1.00 | 51.44 |
| 1267 | CA | THR | A | 498 | 28.730 | 42.619 | 81.985 | 1.00 | 51.70 |
| 1268 | CB | THR | A | 498 | 30.173 | 42.455 | 81.413 | 1.00 | 48.34 |
| 1269 | OG1 | THR | A | 498 | 30.860 | 43.714 | 81.468 | 1.00 | 47.74 |
| 1270 | CG2 | THR | A | 498 | 30.144 | 41.968 | 79.978 | 1.00 | 43.06 |
| 1271 | C | THR | A | 498 | 28.843 | 43.235 | 83.377 | 1.00 | 57.40 |
| 1272 | O | THR | A | 498 | 28.120 | 44.177 | 83.701 | 1.00 | 54.47 |
| 1273 | N | LYS | A | 499 | 29.741 | 42.723 | 84.205 | 1.00 | 64.34 |
| 1274 | CA | LYS | A | 499 | 29.890 | 43.298 | 85.530 | 1.00 | 75.16 |
| 1275 | CB | LYS | A | 499 | 30.351 | 42.243 | 86.529 | 1.00 | 75.89 |
| 1276 | CG | LYS | A | 499 | 29.203 | 41.420 | 87.048 | 1.00 | 79.52 |
| 1277 | CD | LYS | A | 499 | 29.616 | 40.546 | 88.196 | 1.00 | 82.66 |
| 1278 | CE | LYS | A | 499 | 28.395 | 39.934 | 88.848 | 1.00 | 85.49 |
| 1279 | NZ | LYS | A | 499 | 28.777 | 38.957 | 89.905 | 1.00 | 88.63 |
| 1280 | C | LYS | A | 499 | 30.854 | 44.472 | 85.500 | 1.00 | 81.40 |
| 1281 | O | LYS | A | 499 | 31.085 | 45.123 | 86.514 | 1.00 | 81.74 |
| 1282 | N | GLY | A | 500 | 31.405 | 44.740 | 84.322 | 1.00 | 88.46 |
| 1283 | CA | GLY | A | 500 | 32.322 | 45.851 | 84.167 | 1.00 | 100.83 |
| 1284 | C | GLY | A | 500 | 31.793 | 46.796 | 83.109 | 1.00 | 110.53 |
| 1285 | O | GLY | A | 500 | 30.598 | 47.094 | 83.074 | 1.00 | 108.68 |
| 1286 | N | SER | A | 501 | 32.680 | 47.277 | 82.248 | 1.00 | 111.10 |
| 1287 | CA | SER | A | 501 | 32.283 | 48.171 | 81.171 | 1.00 | 114.59 |
| 1288 | CB | SER | A | 501 | 33.212 | 49.385 | 81.101 | 1.00 | 124.30 |
| 1289 | OG | SER | A | 501 | 33.042 | 50.224 | 82.229 | 1.00 | 133.35 |
| 1290 | C | SER | A | 501 | 32.352 | 47.383 | 79.872 | 1.00 | 106.94 |
| 1291 | O | SER | A | 501 | 33.428 | 47.182 | 79.306 | 1.00 | 114.66 |
| 1292 | N | GLY | A | 502 | 31.196 | 46.923 | 79.415 | 1.00 | 99.79 |
| 1293 | CA | GLY | A | 502 | 31.134 | 46.148 | 78.191 | 1.00 | 77.94 |
| 1294 | C | GLY | A | 502 | 29.849 | 45.352 | 78.183 | 1.00 | 63.81 |
| 1295 | O | GLY | A | 502 | 29.239 | 45.157 | 79.229 | 1.00 | 61.81 |
| 1296 | N | PHE | A | 503 | 29.426 | 44.895 | 77.012 | 1.00 | 52.19 |
| 1297 | CA | PHE | A | 503 | 28.191 | 44.124 | 76.924 | 1.00 | 41.77 |
| 1298 | CB | PHE | A | 503 | 27.235 | 44.796 | 75.932 | 1.00 | 37.21 |
| 1299 | CG | PHE | A | 503 | 26.952 | 46.244 | 76.250 | 1.00 | 34.82 |
| 1300 | CD1 | PHE | A | 503 | 27.816 | 47.247 | 75.818 | 1.00 | 33.45 |
| 1301 | CD2 | PHE | A | 503 | 25.846 | 46.598 | 77.023 | 1.00 | 31.93 |
| 1302 | CE1 | PHE | A | 503 | 27.584 | 48.591 | 76.157 | 1.00 | 35.88 |
| 1303 | CE2 | PHE | A | 503 | 25.605 | 47.934 | 77.369 | 1.00 | 33.66 |
| 1304 | CZ | PHE | A | 503 | 26.471 | 48.931 | 76.938 | 1.00 | 32.67 |
| 1305 | C | PHE | A | 503 | 28.457 | 42.673 | 76.501 | 1.00 | 36.13 |
| 1306 | O | PHE | A | 503 | 29.609 | 42.285 | 76.266 | 1.00 | 31.75 |
| 1307 | N | PHE | A | 504 | 27.396 | 41.871 | 76.426 | 1.00 | 31.49 |
| 1308 | CA | PHE | A | 504 | 27.516 | 40.486 | 75.985 | 1.00 | 28.86 |
| 1309 | CB | PHE | A | 504 | 27.900 | 39.550 | 77.157 | 1.00 | 26.43 |
| 1310 | CG | PHE | A | 504 | 26.742 | 39.194 | 78.069 | 1.00 | 27.56 |
| 1311 | CD1 | PHE | A | 504 | 25.811 | 38.212 | 77.696 | 1.00 | 24.86 |
| 1312 | CD2 | PHE | A | 504 | 26.565 | 39.860 | 79.286 | 1.00 | 26.83 |
| 1313 | CE1 | PHE | A | 504 | 24.713 | 37.902 | 78.524 | 1.00 | 23.89 |
| 1314 | CE2 | PHE | A | 504 | 25.471 | 39.559 | 80.123 | 1.00 | 29.27 |
| 1315 | CZ | PHE | A | 504 | 24.543 | 38.574 | 79.733 | 1.00 | 28.47 |
| 1316 | C | PHE | A | 504 | 26.206 | 40.012 | 75.363 | 1.00 | 28.55 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1317 | O | PHE | A | 504 | 25.133 | 40.525 | 75.679 | 1.00 | 25.71 |
| 1318 | N | VAL | A | 505 | 26.315 | 39.009 | 74.491 | 1.00 | 29.59 |
| 1319 | CA | VAL | A | 505 | 25.159 | 38.413 | 73.850 | 1.00 | 30.51 |
| 1320 | CB | VAL | A | 505 | 24.849 | 39.151 | 72.516 | 1.00 | 32.58 |
| 1321 | CG1 | VAL | A | 505 | 25.993 | 38.984 | 71.531 | 1.00 | 27.97 |
| 1322 | CG2 | VAL | A | 505 | 23.593 | 38.626 | 71.942 | 1.00 | 35.31 |
| 1323 | C | VAL | A | 505 | 25.423 | 36.912 | 73.591 | 1.00 | 29.31 |
| 1324 | O | VAL | A | 505 | 26.584 | 36.495 | 73.494 | 1.00 | 29.90 |
| 1325 | N | PHE | A | 506 | 24.354 | 36.117 | 73.502 | 1.00 | 28.63 |
| 1326 | CA | PHE | A | 506 | 24.444 | 34.671 | 73.221 | 1.00 | 29.37 |
| 1327 | CB | PHE | A | 506 | 23.747 | 33.830 | 74.294 | 1.00 | 31.36 |
| 1328 | CG | PHE | A | 506 | 24.518 | 33.681 | 75.566 | 1.00 | 34.45 |
| 1329 | CD1 | PHE | A | 506 | 24.285 | 34.533 | 76.640 | 1.00 | 35.04 |
| 1330 | CD2 | PHE | A | 506 | 25.446 | 32.656 | 75.712 | 1.00 | 35.34 |
| 1331 | CE1 | PHE | A | 506 | 24.967 | 34.357 | 77.851 | 1.00 | 37.12 |
| 1332 | CE2 | PHE | A | 506 | 26.132 | 32.475 | 76.916 | 1.00 | 35.05 |
| 1333 | CZ | PHE | A | 506 | 25.888 | 33.326 | 77.984 | 1.00 | 33.99 |
| 1334 | C | PHE | A | 506 | 23.724 | 34.362 | 71.918 | 1.00 | 28.17 |
| 1335 | O | PHE | A | 506 | 22.735 | 35.008 | 71.606 | 1.00 | 28.08 |
| 1336 | N | SER | A | 507 | 24.191 | 33.365 | 71.170 | 1.00 | 27.70 |
| 1337 | CA | SER | A | 507 | 23.508 | 32.982 | 69.922 | 1.00 | 28.38 |
| 1338 | CB | SER | A | 507 | 24.306 | 33.461 | 68.701 | 1.00 | 25.16 |
| 1339 | OG | SER | A | 507 | 23.540 | 33.333 | 67.513 | 1.00 | 24.35 |
| 1340 | C | SER | A | 507 | 23.301 | 31.456 | 69.866 | 1.00 | 26.99 |
| 1341 | O | SER | A | 507 | 24.224 | 30.690 | 70.124 | 1.00 | 29.76 |
| 1342 | N | ARG | A | 508 | 22.092 | 31.026 | 69.506 | 1.00 | 27.28 |
| 1343 | CA | ARG | A | 508 | 21.737 | 29.598 | 69.457 | 1.00 | 28.51 |
| 1344 | CB | ARG | A | 508 | 20.510 | 29.383 | 70.361 | 1.00 | 24.23 |
| 1345 | CG | ARG | A | 508 | 20.051 | 27.949 | 70.518 | 1.00 | 26.64 |
| 1346 | CD | ARG | A | 508 | 18.937 | 27.828 | 71.584 | 1.00 | 27.56 |
| 1347 | NE | ARG | A | 508 | 18.462 | 26.453 | 71.701 | 1.00 | 28.07 |
| 1348 | CZ | ARG | A | 508 | 17.588 | 25.902 | 70.865 | 1.00 | 34.41 |
| 1349 | NH1 | ARG | A | 508 | 17.087 | 26.634 | 69.865 | 1.00 | 33.05 |
| 1350 | NH2 | ARG | A | 508 | 17.261 | 24.612 | 70.984 | 1.00 | 27.94 |
| 1351 | C | ARG | A | 508 | 21.459 | 29.063 | 68.028 | 1.00 | 28.72 |
| 1352 | O | ARG | A | 508 | 20.758 | 29.707 | 67.254 | 1.00 | 28.60 |
| 1353 | N | LEU | A | 509 | 22.008 | 27.891 | 67.692 | 1.00 | 28.40 |
| 1354 | CA | LEU | A | 509 | 21.822 | 27.284 | 66.365 | 1.00 | 30.90 |
| 1355 | CB | LEU | A | 509 | 22.988 | 27.653 | 65.426 | 1.00 | 29.85 |
| 1356 | CG | LEU | A | 509 | 22.925 | 26.918 | 64.069 | 1.00 | 31.54 |
| 1357 | CD1 | LEU | A | 509 | 21.943 | 27.654 | 63.178 | 1.00 | 31.32 |
| 1358 | CD2 | LEU | A | 509 | 24.294 | 26.823 | 63.378 | 1.00 | 30.58 |
| 1359 | C | LEU | A | 509 | 21.721 | 25.747 | 66.384 | 1.00 | 31.81 |
| 1360 | O | LEU | A | 509 | 22.663 | 25.069 | 66.785 | 1.00 | 30.70 |
| 1361 | N | GLU | A | 510 | 20.598 | 25.197 | 65.934 | 1.00 | 31.31 |
| 1362 | CA | GLU | A | 510 | 20.459 | 23.740 | 65.878 | 1.00 | 36.28 |
| 1363 | CB | GLU | A | 510 | 19.002 | 23.303 | 66.094 | 1.00 | 44.72 |
| 1364 | CG | GLU | A | 510 | 18.373 | 23.782 | 67.404 | 1.00 | 56.42 |
| 1365 | CD | GLU | A | 510 | 17.405 | 24.946 | 67.214 | 1.00 | 64.31 |
| 1366 | OE1 | GLU | A | 510 | 17.806 | 25.965 | 66.587 | 1.00 | 67.62 |
| 1367 | OE2 | GLU | A | 510 | 16.249 | 24.839 | 67.700 | 1.00 | 66.63 |
| 1368 | C | GLU | A | 510 | 20.923 | 23.279 | 64.495 | 1.00 | 35.58 |
| 1369 | O | GLU | A | 510 | 20.708 | 23.983 | 63.499 | 1.00 | 33.90 |
| 1370 | N | VAL | A | 511 | 21.564 | 22.112 | 64.446 | 1.00 | 30.80 |
| 1371 | CA | VAL | A | 511 | 22.073 | 21.542 | 63.206 | 1.00 | 29.96 |
| 1372 | CB | VAL | A | 511 | 23.603 | 21.760 | 63.075 | 1.00 | 27.05 |
| 1373 | CG1 | VAL | A | 511 | 23.938 | 23.234 | 63.329 | 1.00 | 25.45 |
| 1374 | CG2 | VAL | A | 511 | 24.349 | 20.848 | 64.027 | 1.00 | 26.66 |
| 1375 | C | VAL | A | 511 | 21.742 | 20.037 | 63.103 | 1.00 | 33.31 |
| 1376 | O | VAL | A | 511 | 21.377 | 19.413 | 64.093 | 1.00 | 33.17 |
| 1377 | N | THR | A | 512 | 21.868 | 19.469 | 61.905 | 1.00 | 34.27 |
| 1378 | CA | THR | A | 512 | 21.536 | 18.055 | 61.679 | 1.00 | 36.50 |
| 1379 | CB | THR | A | 512 | 20.555 | 17.902 | 60.506 | 1.00 | 37.06 |
| 1380 | OG1 | THR | A | 512 | 21.167 | 18.422 | 59.315 | 1.00 | 33.99 |
| 1381 | CG2 | THR | A | 512 | 19.246 | 18.649 | 60.792 | 1.00 | 35.25 |
| 1382 | C | THR | A | 512 | 22.717 | 17.148 | 61.371 | 1.00 | 37.54 |
| 1383 | O | THR | A | 512 | 23.778 | 17.602 | 60.939 | 1.00 | 37.95 |
| 1384 | N | ARG | A | 513 | 22.509 | 15.853 | 61.574 | 1.00 | 40.33 |
| 1385 | CA | ARG | A | 513 | 23.537 | 14.851 | 61.311 | 1.00 | 44.00 |
| 1386 | CB | ARG | A | 513 | 22.981 | 13.456 | 61.614 | 1.00 | 46.23 |
| 1387 | CG | ARG | A | 513 | 23.833 | 12.303 | 61.103 | 1.00 | 52.56 |
| 1388 | CD | ARG | A | 513 | 23.413 | 11.006 | 61.770 | 1.00 | 56.12 |
| 1389 | NE | ARG | A | 513 | 24.025 | 10.885 | 63.089 | 1.00 | 62.66 |
| 1390 | CZ | ARG | A | 513 | 23.488 | 10.226 | 64.109 | 1.00 | 65.71 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1391 | NH1 | ARG | A | 513 | 22.313 | 9.620 | 63.965 | 1.00 | 67.45 |
| 1392 | NH2 | ARG | A | 513 | 24.124 | 10.178 | 65.274 | 1.00 | 67.18 |
| 1393 | C | ARG | A | 513 | 24.045 | 14.920 | 59.868 | 1.00 | 44.45 |
| 1394 | O | ARG | A | 513 | 25.247 | 14.804 | 59.609 | 1.00 | 44.28 |
| 1395 | N | ALA | A | 514 | 23.130 | 15.122 | 58.930 | 1.00 | 43.34 |
| 1396 | CA | ALA | A | 514 | 23.514 | 15.205 | 57.530 | 1.00 | 44.56 |
| 1397 | CB | ALA | A | 514 | 22.274 | 15.414 | 56.660 | 1.00 | 44.62 |
| 1398 | C | ALA | A | 514 | 24.523 | 16.332 | 57.301 | 1.00 | 44.93 |
| 1399 | O | ALA | A | 514 | 25.427 | 16.209 | 56.469 | 1.00 | 44.61 |
| 1400 | N | GLU | A | 515 | 24.381 | 17.424 | 58.048 | 1.00 | 45.93 |
| 1401 | CA | GLU | A | 515 | 25.286 | 18.559 | 57.897 | 1.00 | 45.47 |
| 1402 | CB | GLU | A | 515 | 24.697 | 19.812 | 58.555 | 1.00 | 48.34 |
| 1403 | CG | GLU | A | 515 | 23.272 | 20.120 | 58.142 | 1.00 | 55.51 |
| 1404 | CD | GLU | A | 515 | 22.741 | 21.403 | 58.761 | 1.00 | 58.51 |
| 1405 | OE1 | GLU | A | 515 | 23.100 | 22.488 | 58.268 | 1.00 | 59.47 |
| 1406 | OE2 | GLU | A | 515 | 21.974 | 21.325 | 59.745 | 1.00 | 61.29 |
| 1407 | C | GLU | A | 515 | 26.674 | 18.310 | 58.470 | 1.00 | 44.55 |
| 1408 | O | GLU | A | 515 | 27.680 | 18.614 | 57.822 | 1.00 | 44.79 |
| 1409 | N | TRP | A | 516 | 26.745 | 17.760 | 59.680 | 1.00 | 44.42 |
| 1410 | CA | TRP | A | 516 | 28.050 | 17.546 | 60.284 | 1.00 | 47.38 |
| 1411 | CB | TRP | A | 516 | 27.938 | 17.453 | 61.822 | 1.00 | 45.19 |
| 1412 | CG | TRP | A | 516 | 27.483 | 16.148 | 62.423 | 1.00 | 45.02 |
| 1413 | CD2 | TRP | A | 516 | 26.304 | 15.928 | 63.214 | 1.00 | 44.37 |
| 1414 | CE2 | TRP | A | 516 | 26.334 | 14.581 | 63.641 | 1.00 | 45.44 |
| 1415 | CE3 | TRP | A | 516 | 25.230 | 16.739 | 63.606 | 1.00 | 43.15 |
| 1416 | CD1 | TRP | A | 516 | 28.152 | 14.960 | 62.402 | 1.00 | 44.29 |
| 1417 | NE1 | TRP | A | 516 | 27.473 | 14.017 | 63.131 | 1.00 | 43.93 |
| 1418 | CZ2 | TRP | A | 516 | 25.325 | 14.021 | 64.442 | 1.00 | 44.86 |
| 1419 | CZ3 | TRP | A | 516 | 24.230 | 16.192 | 64.399 | 1.00 | 43.13 |
| 1420 | CH2 | TRP | A | 516 | 24.284 | 14.840 | 64.812 | 1.00 | 46.59 |
| 1421 | C | TRP | A | 516 | 28.810 | 16.369 | 59.678 | 1.00 | 49.64 |
| 1422 | O | TRP | A | 516 | 30.038 | 16.336 | 59.733 | 1.00 | 48.19 |
| 1423 | N | GLU | A | 517 | 28.096 | 15.423 | 59.071 | 1.00 | 51.96 |
| 1424 | CA | GLU | A | 517 | 28.772 | 14.297 | 58.427 | 1.00 | 56.09 |
| 1425 | CB | GLU | A | 517 | 27.821 | 13.106 | 58.247 | 1.00 | 60.71 |
| 1426 | CG | GLU | A | 517 | 27.463 | 12.425 | 59.564 | 1.00 | 68.11 |
| 1427 | CD | GLU | A | 517 | 26.802 | 11.068 | 59.392 | 1.00 | 71.68 |
| 1428 | OE1 | GLU | A | 517 | 25.751 | 10.980 | 58.724 | 1.00 | 74.56 |
| 1429 | OE2 | GLU | A | 517 | 27.335 | 10.082 | 59.938 | 1.00 | 74.22 |
| 1430 | C | GLU | A | 517 | 29.374 | 14.717 | 57.076 | 1.00 | 54.59 |
| 1431 | O | GLU | A | 517 | 30.323 | 14.096 | 56.606 | 1.00 | 55.82 |
| 1432 | N | ALA | A | 518 | 28.836 | 15.776 | 56.465 | 1.00 | 53.96 |
| 1433 | CA | ALA | A | 518 | 29.353 | 16.280 | 55.186 | 1.00 | 51.03 |
| 1434 | CB | ALA | A | 518 | 28.301 | 17.151 | 54.485 | 1.00 | 48.51 |
| 1435 | C | ALA | A | 518 | 30.630 | 17.096 | 55.419 | 1.00 | 51.30 |
| 1436 | O | ALA | A | 518 | 31.558 | 17.063 | 54.613 | 1.00 | 50.18 |
| 1437 | N | LYS | A | 519 | 30.664 | 17.824 | 56.533 | 1.00 | 51.14 |
| 1438 | CA | LYS | A | 519 | 31.804 | 18.662 | 56.909 | 1.00 | 50.77 |
| 1439 | CB | LYS | A | 519 | 31.854 | 19.906 | 56.022 | 1.00 | 54.90 |
| 1440 | CG | LYS | A | 519 | 32.838 | 20.975 | 56.471 | 1.00 | 60.84 |
| 1441 | CD | LYS | A | 519 | 34.276 | 20.593 | 56.200 | 1.00 | 67.36 |
| 1442 | CE | LYS | A | 519 | 35.185 | 21.806 | 56.359 | 1.00 | 72.28 |
| 1443 | NZ | LYS | A | 519 | 36.618 | 21.484 | 56.119 | 1.00 | 76.17 |
| 1444 | C | LYS | A | 519 | 31.590 | 19.070 | 58.363 | 1.00 | 48.16 |
| 1445 | O | LYS | A | 519 | 30.754 | 19.917 | 58.666 | 1.00 | 45.48 |
| 1446 | N | ASP | A | 520 | 32.349 | 18.463 | 59.263 | 1.00 | 46.57 |
| 1447 | CA | ASP | A | 520 | 32.203 | 18.744 | 60.682 | 1.00 | 45.91 |
| 1448 | CB | ASP | A | 520 | 32.542 | 17.483 | 61.479 | 1.00 | 47.43 |
| 1449 | CG | ASP | A | 520 | 32.343 | 17.669 | 62.965 | 1.00 | 49.42 |
| 1450 | OD1 | ASP | A | 520 | 31.590 | 18.588 | 63.346 | 1.00 | 50.03 |
| 1451 | OD2 | ASP | A | 520 | 32.933 | 16.893 | 63.745 | 1.00 | 49.50 |
| 1452 | C | ASP | A | 520 | 32.994 | 19.945 | 61.219 | 1.00 | 45.09 |
| 1453 | O | ASP | A | 520 | 33.987 | 19.787 | 61.933 | 1.00 | 42.35 |
| 1454 | N | GLU | A | 521 | 32.530 | 21.143 | 60.863 | 1.00 | 43.33 |
| 1455 | CA | GLU | A | 521 | 33.128 | 22.400 | 61.302 | 1.00 | 43.82 |
| 1456 | CB | GLU | A | 521 | 34.452 | 22.684 | 60.575 | 1.00 | 46.45 |
| 1457 | CG | GLU | A | 521 | 35.003 | 24.079 | 60.870 | 1.00 | 52.60 |
| 1458 | CD | GLU | A | 521 | 36.316 | 24.381 | 60.166 | 1.00 | 58.26 |
| 1459 | OE1 | GLU | A | 521 | 36.345 | 24.396 | 58.916 | 1.00 | 61.01 |
| 1460 | OE2 | GLU | A | 521 | 37.326 | 24.615 | 60.866 | 1.00 | 60.71 |
| 1461 | C | GLU | A | 521 | 32.140 | 23.520 | 60.999 | 1.00 | 40.20 |
| 1462 | O | GLU | A | 521 | 31.644 | 23.620 | 59.879 | 1.00 | 41.23 |
| 1463 | N | PHE | A | 522 | 31.853 | 24.347 | 62.000 | 1.00 | 36.95 |
| 1464 | CA | PHE | A | 522 | 30.922 | 25.461 | 61.852 | 1.00 | 35.37 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1465 | CB | PHE | A | 522 | 29.607 | 25.163 | 62.594 | 1.00 | 32.70 |
| 1466 | CG | PHE | A | 522 | 28.970 | 23.851 | 62.207 | 1.00 | 32.73 |
| 1467 | CD1 | PHE | A | 522 | 29.535 | 22.639 | 62.605 | 1.00 | 31.34 |
| 1468 | CD2 | PHE | A | 522 | 27.793 | 23.830 | 61.455 | 1.00 | 32.41 |
| 1469 | CE1 | PHE | A | 522 | 28.942 | 21.426 | 62.265 | 1.00 | 32.94 |
| 1470 | CE2 | PHE | A | 522 | 27.185 | 22.628 | 61.106 | 1.00 | 30.81 |
| 1471 | CZ | PHE | A | 522 | 27.757 | 21.416 | 61.509 | 1.00 | 32.68 |
| 1472 | C | PHE | A | 522 | 31.567 | 26.733 | 62.408 | 1.00 | 34.91 |
| 1473 | O | PHE | A | 522 | 32.378 | 26.668 | 63.327 | 1.00 | 36.18 |
| 1474 | N | ILE | A | 523 | 31.180 | 27.888 | 61.877 | 1.00 | 34.96 |
| 1475 | CA | ILE | A | 523 | 31.777 | 29.150 | 62.285 | 1.00 | 34.43 |
| 1476 | CB | ILE | A | 523 | 32.596 | 29.720 | 61.099 | 1.00 | 37.86 |
| 1477 | CG2 | ILE | A | 523 | 33.040 | 31.146 | 61.388 | 1.00 | 37.60 |
| 1478 | CG1 | ILE | A | 523 | 33.780 | 28.792 | 60.810 | 1.00 | 39.52 |
| 1479 | CD1 | ILE | A | 523 | 34.627 | 29.195 | 59.620 | 1.00 | 44.49 |
| 1480 | C | ILE | A | 523 | 30.821 | 30.235 | 62.796 | 1.00 | 35.88 |
| 1481 | O | ILE | A | 523 | 29.813 | 30.550 | 62.148 | 1.00 | 37.28 |
| 1482 | N | CYS | A | 524 | 31.147 | 30.791 | 63.965 | 1.00 | 32.80 |
| 1483 | CA | CYS | A | 524 | 30.385 | 31.876 | 64.581 | 1.00 | 31.72 |
| 1484 | C | CYS | A | 524 | 31.173 | 33.150 | 64.264 | 1.00 | 32.90 |
| 1485 | O | CYS | A | 524 | 32.373 | 33.215 | 64.531 | 1.00 | 33.82 |
| 1486 | CB | CYS | A | 524 | 30.298 | 31.708 | 66.110 | 1.00 | 31.81 |
| 1487 | SG | CYS | A | 524 | 29.590 | 33.148 | 66.996 | 1.00 | 30.98 |
| 1488 | N | ARG | A | 525 | 30.513 | 34.160 | 63.706 | 1.00 | 32.44 |
| 1489 | CA | ARG | A | 525 | 31.215 | 35.385 | 63.352 | 1.00 | 34.40 |
| 1490 | CB | ARG | A | 525 | 31.440 | 35.418 | 61.839 | 1.00 | 34.65 |
| 1491 | CG | ARG | A | 525 | 31.924 | 36.755 | 61.303 | 1.00 | 42.18 |
| 1492 | CD | ARG | A | 525 | 32.767 | 36.589 | 60.037 | 1.00 | 45.65 |
| 1493 | NE | ARG | A | 525 | 32.017 | 36.097 | 58.888 | 1.00 | 51.10 |
| 1494 | CZ | ARG | A | 525 | 32.586 | 35.604 | 57.786 | 1.00 | 56.14 |
| 1495 | NH1 | ARG | A | 525 | 33.909 | 35.529 | 57.688 | 1.00 | 56.03 |
| 1496 | NH2 | ARG | A | 525 | 31.836 | 35.199 | 56.768 | 1.00 | 58.32 |
| 1497 | C | ARG | A | 525 | 30.524 | 36.666 | 63.812 | 1.00 | 34.51 |
| 1498 | O | ARG | A | 525 | 29.302 | 36.813 | 63.674 | 1.00 | 35.39 |
| 1499 | N | ALA | A | 526 | 31.313 | 37.593 | 64.352 | 1.00 | 34.35 |
| 1500 | CA | ALA | A | 526 | 30.781 | 38.871 | 64.833 | 1.00 | 35.97 |
| 1501 | CB | ALA | A | 526 | 31.067 | 39.006 | 66.330 | 1.00 | 35.59 |
| 1502 | C | ALA | A | 526 | 31.328 | 40.104 | 64.087 | 1.00 | 36.06 |
| 1503 | O | ALA | A | 526 | 32.541 | 40.214 | 63.836 | 1.00 | 36.40 |
| 1504 | N | VAL | A | 527 | 30.438 | 41.028 | 63.721 | 1.00 | 36.70 |
| 1505 | CA | VAL | A | 527 | 30.863 | 42.256 | 63.039 | 1.00 | 35.94 |
| 1506 | CB | VAL | A | 527 | 30.047 | 42.531 | 61.760 | 1.00 | 35.40 |
| 1507 | CG1 | VAL | A | 527 | 30.436 | 43.899 | 61.179 | 1.00 | 33.40 |
| 1508 | CG2 | VAL | A | 527 | 30.326 | 41.469 | 60.733 | 1.00 | 33.50 |
| 1509 | C | VAL | A | 527 | 30.679 | 43.418 | 64.009 | 1.00 | 37.02 |
| 1510 | O | VAL | A | 527 | 29.563 | 43.687 | 64.458 | 1.00 | 36.71 |
| 1511 | N | HIS | A | 528 | 31.774 | 44.095 | 64.344 | 1.00 | 38.00 |
| 1512 | CA | HIS | A | 528 | 31.716 | 45.206 | 65.293 | 1.00 | 41.04 |
| 1513 | CB | HIS | A | 528 | 32.021 | 44.687 | 66.715 | 1.00 | 37.00 |
| 1514 | CG | HIS | A | 528 | 31.792 | 45.696 | 67.806 | 1.00 | 36.77 |
| 1515 | CD2 | HIS | A | 528 | 30.763 | 45.851 | 68.676 | 1.00 | 34.04 |
| 1516 | ND1 | HIS | A | 528 | 32.704 | 46.684 | 68.120 | 1.00 | 38.46 |
| 1517 | CE1 | HIS | A | 528 | 32.251 | 47.399 | 69.136 | 1.00 | 35.92 |
| 1518 | NE2 | HIS | A | 528 | 31.074 | 46.914 | 69.492 | 1.00 | 37.22 |
| 1519 | C | HIS | A | 528 | 32.685 | 46.331 | 64.913 | 1.00 | 43.66 |
| 1520 | O | HIS | A | 528 | 33.802 | 46.089 | 64.455 | 1.00 | 43.77 |
| 1521 | N | GLU | A | 529 | 32.247 | 47.563 | 65.121 | 1.00 | 48.12 |
| 1522 | CA | GLU | A | 529 | 33.045 | 48.743 | 64.806 | 1.00 | 51.92 |
| 1523 | CB | GLU | A | 529 | 32.336 | 49.984 | 65.352 | 1.00 | 55.42 |
| 1524 | CG | GLU | A | 529 | 33.232 | 50.942 | 66.102 | 1.00 | 63.10 |
| 1525 | CD | GLU | A | 529 | 32.478 | 52.140 | 66.637 | 1.00 | 66.05 |
| 1526 | OE1 | GLU | A | 529 | 31.413 | 51.938 | 67.260 | 1.00 | 68.44 |
| 1527 | OE2 | GLU | A | 529 | 32.958 | 53.277 | 66.443 | 1.00 | 68.74 |
| 1528 | C | GLU | A | 529 | 34.494 | 48.715 | 65.303 | 1.00 | 52.94 |
| 1529 | O | GLU | A | 529 | 35.398 | 49.187 | 64.609 | 1.00 | 53.08 |
| 1530 | N | ALA | A | 530 | 34.719 | 48.164 | 66.495 | 1.00 | 54.03 |
| 1531 | CA | ALA | A | 530 | 36.063 | 48.120 | 67.075 | 1.00 | 54.67 |
| 1532 | CB | ALA | A | 530 | 35.975 | 48.339 | 68.571 | 1.00 | 52.03 |
| 1533 | C | ALA | A | 530 | 36.879 | 46.856 | 66.785 | 1.00 | 57.82 |
| 1534 | O | ALA | A | 530 | 38.023 | 46.741 | 67.222 | 1.00 | 56.97 |
| 1535 | N | ALA | A | 531 | 36.299 | 45.914 | 66.048 | 1.00 | 63.20 |
| 1536 | CA | ALA | A | 531 | 36.989 | 44.675 | 65.715 | 1.00 | 70.87 |
| 1537 | CB | ALA | A | 531 | 35.979 | 43.633 | 65.230 | 1.00 | 65.81 |
| 1538 | C | ALA | A | 531 | 38.076 | 44.890 | 64.657 | 1.00 | 78.61 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1539 | O | ALA | A | 531 | 38.231 | 45.989 | 64.121 | 1.00 | 78.39 |
| 1540 | N | SER | A | 532 | 38.825 | 43.829 | 64.368 | 1.00 | 87.28 |
| 1541 | CA | SER | A | 532 | 39.899 | 43.865 | 63.379 | 1.00 | 98.78 |
| 1542 | CB | SER | A | 532 | 40.943 | 44.913 | 63.757 | 1.00 | 100.42 |
| 1543 | OG | SER | A | 532 | 41.543 | 44.592 | 64.998 | 1.00 | 104.31 |
| 1544 | C | SER | A | 532 | 40.563 | 42.494 | 63.322 | 1.00 | 102.56 |
| 1545 | O | SER | A | 532 | 40.586 | 41.766 | 64.314 | 1.00 | 105.63 |
| 1546 | N | CPR | A | 533 | 41.122 | 42.127 | 62.159 | 1.00 | 104.83 |
| 1547 | CD | CPR | A | 533 | 41.964 | 40.932 | 62.014 | 1.00 | 108.70 |
| 1548 | CA | CPR | A | 533 | 41.155 | 42.924 | 60.929 | 1.00 | 104.79 |
| 1549 | CB | CPR | A | 533 | 42.197 | 42.201 | 60.073 | 1.00 | 108.48 |
| 1550 | CG | CPR | A | 533 | 43.013 | 41.425 | 61.070 | 1.00 | 109.63 |
| 1551 | C | CPR | A | 533 | 39.798 | 42.961 | 60.234 | 1.00 | 100.65 |
| 1552 | O | CPR | A | 533 | 39.043 | 41.990 | 60.284 | 1.00 | 103.72 |
| 1553 | N | SER | A | 534 | 39.498 | 44.087 | 59.592 | 1.00 | 97.66 |
| 1554 | CA | SER | A | 534 | 38.249 | 44.260 | 58.853 | 1.00 | 89.94 |
| 1555 | CB | SER | A | 534 | 38.119 | 43.149 | 57.805 | 1.00 | 92.44 |
| 1556 | OG | SER | A | 534 | 39.309 | 43.032 | 57.041 | 1.00 | 97.38 |
| 1557 | C | SER | A | 534 | 36.988 | 44.297 | 59.723 | 1.00 | 83.11 |
| 1558 | O | SER | A | 534 | 35.906 | 43.911 | 59.281 | 1.00 | 79.71 |
| 1559 | N | GLN | A | 535 | 37.130 | 44.769 | 60.956 | 1.00 | 76.73 |
| 1560 | CA | GLN | A | 535 | 36.004 | 44.857 | 61.878 | 1.00 | 72.72 |
| 1561 | CB | GLN | A | 535 | 35.066 | 45.992 | 61.447 | 1.00 | 77.57 |
| 1562 | CG | GLN | A | 535 | 35.567 | 47.390 | 61.814 | 1.00 | 87.32 |
| 1563 | CD | GLN | A | 535 | 35.798 | 48.278 | 60.606 | 1.00 | 92.56 |
| 1564 | OE1 | GLN | A | 535 | 34.916 | 48.445 | 59.766 | 1.00 | 97.19 |
| 1565 | NE2 | GLN | A | 535 | 36.987 | 48.860 | 60.518 | 1.00 | 97.07 |
| 1566 | C | GLN | A | 535 | 35.205 | 43.557 | 62.066 | 1.00 | 67.74 |
| 1567 | O | GLN | A | 535 | 33.985 | 43.586 | 62.214 | 1.00 | 62.75 |
| 1568 | N | THR | A | 536 | 35.892 | 42.418 | 62.056 | 1.00 | 62.84 |
| 1569 | CA | THR | A | 536 | 35.225 | 41.137 | 62.274 | 1.00 | 60.42 |
| 1570 | CB | THR | A | 536 | 34.844 | 40.428 | 60.951 | 1.00 | 61.50 |
| 1571 | OG1 | THR | A | 536 | 36.002 | 39.812 | 60.388 | 1.00 | 65.27 |
| 1572 | CG2 | THR | A | 536 | 34.267 | 41.412 | 59.955 | 1.00 | 63.45 |
| 1573 | C | THR | A | 536 | 36.103 | 40.188 | 63.088 | 1.00 | 58.11 |
| 1574 | O | THR | A | 536 | 37.334 | 40.246 | 63.024 | 1.00 | 58.00 |
| 1575 | N | VAL | A | 537 | 35.453 | 39.329 | 63.868 | 1.00 | 54.81 |
| 1576 | CA | VAL | A | 537 | 36.133 | 38.336 | 64.699 | 1.00 | 49.60 |
| 1577 | CB | VAL | A | 537 | 36.218 | 38.801 | 66.173 | 1.00 | 50.62 |
| 1578 | CG1 | VAL | A | 537 | 36.885 | 37.729 | 67.023 | 1.00 | 54.37 |
| 1579 | CG2 | VAL | A | 537 | 37.008 | 40.086 | 66.263 | 1.00 | 52.60 |
| 1580 | C | VAL | A | 537 | 35.321 | 37.038 | 64.612 | 1.00 | 46.37 |
| 1581 | O | VAL | A | 537 | 34.087 | 37.075 | 64.613 | 1.00 | 42.47 |
| 1582 | N | GLN | A | 538 | 36.002 | 35.897 | 64.527 | 1.00 | 42.84 |
| 1583 | CA | GLN | A | 538 | 35.302 | 34.624 | 64.417 | 1.00 | 41.36 |
| 1584 | CB | GLN | A | 538 | 35.075 | 34.293 | 62.941 | 1.00 | 42.25 |
| 1585 | CG | GLN | A | 538 | 36.354 | 34.135 | 62.118 | 1.00 | 41.56 |
| 1586 | CD | GLN | A | 538 | 36.067 | 33.723 | 60.686 | 1.00 | 44.09 |
| 1587 | OE1 | GLN | A | 538 | 35.325 | 34.400 | 59.971 | 1.00 | 44.01 |
| 1588 | NE2 | GLN | A | 538 | 36.651 | 32.605 | 60.259 | 1.00 | 45.87 |
| 1589 | C | GLN | A | 538 | 35.992 | 33.448 | 65.097 | 1.00 | 43.05 |
| 1590 | O | GLN | A | 538 | 37.212 | 33.439 | 65.259 | 1.00 | 42.54 |
| 1591 | N | ARG | A | 539 | 35.196 | 32.450 | 65.476 | 1.00 | 44.84 |
| 1592 | CA | ARG | A | 539 | 35.690 | 31.238 | 66.134 | 1.00 | 49.34 |
| 1593 | CB | ARG | A | 539 | 35.365 | 31.298 | 67.628 | 1.00 | 63.30 |
| 1594 | CG | ARG | A | 539 | 36.335 | 30.555 | 68.525 | 1.00 | 84.06 |
| 1595 | CD | ARG | A | 539 | 37.664 | 31.287 | 68.609 | 1.00 | 102.03 |
| 1596 | NE | ARG | A | 539 | 38.542 | 30.701 | 69.616 | 1.00 | 117.69 |
| 1597 | CZ | ARG | A | 539 | 38.292 | 30.701 | 70.921 | 1.00 | 125.31 |
| 1598 | NH1 | ARG | A | 539 | 37.186 | 31.260 | 71.390 | 1.00 | 129.68 |
| 1599 | NH2 | ARG | A | 539 | 39.144 | 30.132 | 71.760 | 1.00 | 130.18 |
| 1600 | C | ARG | A | 539 | 35.031 | 29.991 | 65.511 | 1.00 | 44.56 |
| 1601 | O | ARG | A | 539 | 33.826 | 29.986 | 65.216 | 1.00 | 42.02 |
| 1602 | N | ALA | A | 540 | 35.807 | 28.929 | 65.327 | 1.00 | 37.57 |
| 1603 | CA | ALA | A | 540 | 35.279 | 27.698 | 64.717 | 1.00 | 35.76 |
| 1604 | CB | ALA | A | 540 | 36.221 | 27.219 | 63.616 | 1.00 | 36.62 |
| 1605 | C | ALA | A | 540 | 35.079 | 26.574 | 65.718 | 1.00 | 33.09 |
| 1606 | O | ALA | A | 540 | 35.892 | 26.416 | 66.617 | 1.00 | 31.01 |
| 1607 | N | VAL | A | 541 | 34.002 | 25.800 | 65.559 | 1.00 | 30.74 |
| 1608 | CA | VAL | A | 541 | 33.728 | 24.671 | 66.445 | 1.00 | 29.69 |
| 1609 | CB | VAL | A | 541 | 32.686 | 25.041 | 67.539 | 1.00 | 29.85 |
| 1610 | CG1 | VAL | A | 541 | 31.321 | 25.280 | 66.927 | 1.00 | 29.41 |
| 1611 | CG2 | VAL | A | 541 | 32.626 | 23.935 | 68.572 | 1.00 | 31.03 |
| 1612 | C | VAL | A | 541 | 33.261 | 23.415 | 65.700 | 1.00 | 31.84 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1613 | O | VAL | A | 541 | 32.678 | 23.497 | 64.611 | 1.00 | 31.19 |
| 1614 | N | SER | A | 542 | 33.518 | 22.253 | 66.294 | 1.00 | 33.20 |
| 1615 | CA | SER | A | 542 | 33.147 | 20.969 | 65.692 | 1.00 | 39.52 |
| 1616 | CB | SER | A | 542 | 34.409 | 20.186 | 65.281 | 1.00 | 38.56 |
| 1617 | OG | SER | A | 542 | 35.264 | 20.941 | 64.430 | 1.00 | 41.29 |
| 1618 | C | SER | A | 542 | 32.315 | 20.059 | 66.607 | 1.00 | 43.60 |
| 1619 | O | SER | A | 542 | 32.370 | 20.159 | 67.832 | 1.00 | 40.04 |
| 1620 | N | VAL | A | 543 | 31.539 | 19.174 | 65.996 | 1.00 | 48.49 |
| 1621 | CA | VAL | A | 543 | 30.747 | 18.201 | 66.745 | 1.00 | 58.05 |
| 1622 | CB | VAL | A | 543 | 29.413 | 17.881 | 66.036 | 1.00 | 58.40 |
| 1623 | CG1 | VAL | A | 543 | 28.592 | 16.925 | 66.885 | 1.00 | 60.83 |
| 1624 | CG2 | VAL | A | 543 | 28.646 | 19.157 | 65.758 | 1.00 | 60.94 |
| 1625 | C | VAL | A | 543 | 31.605 | 16.939 | 66.706 | 1.00 | 61.65 |
| 1626 | O | VAL | A | 543 | 31.824 | 16.383 | 65.636 | 1.00 | 64.87 |
| 1627 | N | ASN | A | 544 | 32.113 | 16.474 | 67.835 | 1.00 | 66.93 |
| 1628 | CA | ASN | A | 544 | 32.939 | 15.274 | 67.773 | 1.00 | 71.35 |
| 1629 | CB | ASN | A | 544 | 33.952 | 15.262 | 68.920 | 1.00 | 75.61 |
| 1630 | CG | ASN | A | 544 | 34.952 | 16.398 | 68.813 | 1.00 | 79.01 |
| 1631 | OD1 | ASN | A | 544 | 35.473 | 16.680 | 67.732 | 1.00 | 80.72 |
| 1632 | ND2 | ASN | A | 544 | 35.231 | 17.052 | 69.933 | 1.00 | 81.40 |
| 1633 | C | ASN | A | 544 | 32.116 | 13.983 | 67.753 | 1.00 | 72.19 |
| 1634 | O | ASN | A | 544 | 31.840 | 13.429 | 68.840 | 1.00 | 73.70 |
| 1635 | OXT | ASN | A | 544 | 31.737 | 13.554 | 66.638 | 1.00 | 71.06 |
| 1636 | CB | VAL | B | 336 | 3.622 | 51.609 | 34.127 | 1.00 | 77.92 |
| 1637 | CG1 | VAL | B | 336 | 3.596 | 50.616 | 35.277 | 1.00 | 77.49 |
| 1638 | CG2 | VAL | B | 336 | 3.509 | 53.023 | 34.657 | 1.00 | 79.06 |
| 1639 | C | VAL | B | 336 | 5.102 | 49.979 | 32.964 | 1.00 | 73.93 |
| 1640 | O | VAL | B | 336 | 4.238 | 49.375 | 32.326 | 1.00 | 75.08 |
| 1641 | N | VAL | B | 336 | 4.928 | 52.333 | 32.111 | 1.00 | 77.93 |
| 1642 | CA | VAL | B | 336 | 4.930 | 51.454 | 33.319 | 1.00 | 76.03 |
| 1643 | N | SER | B | 337 | 6.224 | 49.409 | 33.391 | 1.00 | 70.81 |
| 1644 | CA | SER | B | 337 | 6.530 | 48.006 | 33.145 | 1.00 | 65.26 |
| 1645 | CB | SER | B | 337 | 7.852 | 47.879 | 32.380 | 1.00 | 65.27 |
| 1646 | OG | SER | B | 337 | 7.742 | 48.410 | 31.072 | 1.00 | 64.61 |
| 1647 | C | SER | B | 337 | 6.635 | 47.269 | 34.481 | 1.00 | 61.33 |
| 1648 | O | SER | B | 337 | 6.676 | 47.899 | 35.534 | 1.00 | 60.42 |
| 1649 | N | ALA | B | 338 | 6.673 | 45.938 | 34.427 | 1.00 | 57.46 |
| 1650 | CA | ALA | B | 338 | 6.786 | 45.100 | 35.623 | 1.00 | 53.53 |
| 1651 | CB | ALA | B | 338 | 5.414 | 44.929 | 36.284 | 1.00 | 50.34 |
| 1652 | C | ALA | B | 338 | 7.365 | 43.737 | 35.250 | 1.00 | 51.90 |
| 1653 | O | ALA | B | 338 | 6.956 | 43.128 | 34.257 | 1.00 | 50.11 |
| 1654 | N | TYR | B | 339 | 8.319 | 43.268 | 36.051 | 1.00 | 52.16 |
| 1655 | CA | TYR | B | 339 | 8.974 | 41.984 | 35.817 | 1.00 | 51.78 |
| 1656 | CB | TYR | B | 339 | 10.394 | 42.200 | 35.283 | 1.00 | 59.49 |
| 1657 | CG | TYR | B | 339 | 10.495 | 43.237 | 34.182 | 1.00 | 69.76 |
| 1658 | CD1 | TYR | B | 339 | 10.342 | 44.599 | 34.465 | 1.00 | 73.26 |
| 1659 | CE1 | TYR | B | 339 | 10.414 | 45.559 | 33.460 | 1.00 | 76.91 |
| 1660 | CD2 | TYR | B | 339 | 10.726 | 42.861 | 32.856 | 1.00 | 72.90 |
| 1661 | CE2 | TYR | B | 339 | 10.800 | 43.814 | 31.841 | 1.00 | 77.09 |
| 1662 | CZ | TYR | B | 339 | 10.643 | 45.162 | 32.153 | 1.00 | 78.41 |
| 1663 | OH | TYR | B | 339 | 10.709 | 46.116 | 31.165 | 1.00 | 79.10 |
| 1664 | C | TYR | B | 339 | 9.037 | 41.169 | 37.112 | 1.00 | 49.45 |
| 1665 | O | TYR | B | 339 | 9.145 | 41.725 | 38.208 | 1.00 | 45.09 |
| 1666 | N | LEU | B | 340 | 8.971 | 39.849 | 36.973 | 1.00 | 44.78 |
| 1667 | CA | LEU | B | 340 | 9.017 | 38.953 | 38.120 | 1.00 | 42.45 |
| 1668 | CB | LEU | B | 340 | 7.620 | 38.366 | 38.375 | 1.00 | 40.31 |
| 1669 | CG | LEU | B | 340 | 7.378 | 37.492 | 39.613 | 1.00 | 39.26 |
| 1670 | CD1 | LEU | B | 340 | 7.697 | 38.255 | 40.896 | 1.00 | 38.36 |
| 1671 | CD2 | LEU | B | 340 | 5.922 | 37.054 | 39.608 | 1.00 | 39.32 |
| 1672 | C | LEU | B | 340 | 10.015 | 37.845 | 37.813 | 1.00 | 41.07 |
| 1673 | O | LEU | B | 340 | 9.819 | 37.093 | 36.862 | 1.00 | 41.75 |
| 1674 | N | SER | B | 341 | 11.078 | 37.743 | 38.610 | 1.00 | 38.47 |
| 1675 | CA | SER | B | 341 | 12.097 | 36.725 | 38.381 | 1.00 | 39.14 |
| 1676 | CB | SER | B | 341 | 13.483 | 37.302 | 38.644 | 1.00 | 40.00 |
| 1677 | OG | SER | B | 341 | 13.764 | 37.256 | 40.031 | 1.00 | 44.25 |
| 1678 | C | SER | B | 341 | 11.928 | 35.463 | 39.240 | 1.00 | 38.83 |
| 1679 | O | SER | B | 341 | 11.118 | 35.421 | 40.169 | 1.00 | 41.96 |
| 1680 | N | ARG | B | 342 | 12.698 | 34.430 | 38.911 | 1.00 | 35.60 |
| 1681 | CA | ARG | B | 342 | 12.668 | 33.168 | 39.654 | 1.00 | 35.02 |
| 1682 | CB | ARG | B | 342 | 12.685 | 31.981 | 38.672 | 1.00 | 31.17 |
| 1683 | CG | ARG | B | 342 | 11.371 | 31.800 | 37.905 | 1.00 | 32.16 |
| 1684 | CD | ARG | B | 342 | 11.374 | 30.536 | 37.040 | 1.00 | 33.84 |
| 1685 | NE | ARG | B | 342 | 12.371 | 30.642 | 35.984 | 1.00 | 40.79 |
| 1686 | CZ | ARG | B | 342 | 12.159 | 31.197 | 34.791 | 1.00 | 42.42 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1687 | NH1 | ARG | B | 342 | 10.967 | 31.694 | 34.473 | 1.00 | 42.13 |
| 1688 | NH2 | ARG | B | 342 | 13.159 | 31.286 | 33.927 | 1.00 | 42.42 |
| 1689 | C | ARG | B | 342 | 13.900 | 33.155 | 40.580 | 1.00 | 32.73 |
| 1690 | O | ARG | B | 342 | 14.765 | 34.025 | 40.458 | 1.00 | 29.51 |
| 1691 | N | PRO | B | 343 | 14.005 | 32.170 | 41.501 | 1.00 | 32.04 |
| 1692 | CD | PRO | B | 343 | 13.028 | 31.121 | 41.838 | 1.00 | 31.92 |
| 1693 | CA | PRO | B | 343 | 15.163 | 32.121 | 42.418 | 1.00 | 32.19 |
| 1694 | CB | PRO | B | 343 | 14.712 | 31.152 | 43.513 | 1.00 | 30.80 |
| 1695 | CG | PRO | B | 343 | 13.205 | 31.017 | 43.322 | 1.00 | 34.01 |
| 1696 | C | PRO | B | 343 | 16.466 | 31.648 | 41.776 | 1.00 | 30.41 |
| 1697 | O | PRO | B | 343 | 16.438 | 30.856 | 40.833 | 1.00 | 32.92 |
| 1698 | N | SER | B | 344 | 17.609 | 32.112 | 42.281 | 1.00 | 29.11 |
| 1699 | CA | SER | B | 344 | 18.885 | 31.665 | 41.728 | 1.00 | 30.90 |
| 1700 | CB | SER | B | 344 | 20.050 | 32.481 | 42.300 | 1.00 | 29.55 |
| 1701 | OG | SER | B | 344 | 20.527 | 31.911 | 43.508 | 1.00 | 31.61 |
| 1702 | C | SER | B | 344 | 19.053 | 30.189 | 42.128 | 1.00 | 31.73 |
| 1703 | O | SER | B | 344 | 18.650 | 29.784 | 43.220 | 1.00 | 30.69 |
| 1704 | N | PRO | B | 345 | 19.629 | 29.363 | 41.245 | 1.00 | 32.55 |
| 1705 | CD | PRO | B | 345 | 19.930 | 29.589 | 39.818 | 1.00 | 34.19 |
| 1706 | CA | PRO | B | 345 | 19.795 | 27.949 | 41.614 | 1.00 | 33.78 |
| 1707 | CB | PRO | B | 345 | 20.374 | 27.319 | 40.343 | 1.00 | 32.64 |
| 1708 | CG | PRO | B | 345 | 19.814 | 28.188 | 39.232 | 1.00 | 34.71 |
| 1709 | C | PRO | B | 345 | 20.691 | 27.711 | 42.850 | 1.00 | 33.77 |
| 1710 | O | PRO | B | 345 | 20.488 | 26.750 | 43.589 | 1.00 | 34.41 |
| 1711 | N | PHE | B | 346 | 21.683 | 28.572 | 43.058 | 1.00 | 36.26 |
| 1712 | CA | PHE | B | 346 | 22.580 | 28.444 | 44.206 | 1.00 | 38.67 |
| 1713 | CB | PHE | B | 346 | 23.659 | 29.533 | 44.170 | 1.00 | 41.12 |
| 1714 | CG | PHE | B | 346 | 24.617 | 29.493 | 45.351 | 1.00 | 46.34 |
| 1715 | CD1 | PHE | B | 346 | 25.501 | 28.431 | 45.515 | 1.00 | 49.51 |
| 1716 | CD2 | PHE | B | 346 | 24.627 | 30.514 | 46.293 | 1.00 | 47.53 |
| 1717 | CE1 | PHE | B | 346 | 26.383 | 28.386 | 46.597 | 1.00 | 51.09 |
| 1718 | CE2 | PHE | B | 346 | 25.502 | 30.478 | 47.376 | 1.00 | 50.39 |
| 1719 | CZ | PHE | B | 346 | 26.381 | 29.411 | 47.528 | 1.00 | 51.36 |
| 1720 | C | PHE | B | 346 | 21.774 | 28.574 | 45.504 | 1.00 | 36.95 |
| 1721 | O | PHE | B | 346 | 21.941 | 27.785 | 46.432 | 1.00 | 35.49 |
| 1722 | N | ASP | B | 347 | 20.907 | 29.580 | 45.546 | 1.00 | 35.02 |
| 1723 | CA | ASP | B | 347 | 20.045 | 29.851 | 46.691 | 1.00 | 36.97 |
| 1724 | CB | ASP | B | 347 | 19.285 | 31.171 | 46.479 | 1.00 | 36.88 |
| 1725 | CG | ASP | B | 347 | 20.113 | 32.402 | 46.842 | 1.00 | 36.42 |
| 1726 | OD1 | ASP | B | 347 | 19.688 | 33.537 | 46.509 | 1.00 | 35.17 |
| 1727 | OD2 | ASP | B | 347 | 21.182 | 32.232 | 47.470 | 1.00 | 35.27 |
| 1728 | C | ASP | B | 347 | 19.035 | 28.735 | 46.936 | 1.00 | 36.21 |
| 1729 | O | ASP | B | 347 | 18.750 | 28.386 | 48.087 | 1.00 | 36.84 |
| 1730 | N | LEU | B | 348 | 18.505 | 28.168 | 45.855 | 1.00 | 34.82 |
| 1731 | CA | LEU | B | 348 | 17.500 | 27.120 | 45.960 | 1.00 | 34.84 |
| 1732 | CB | LEU | B | 348 | 16.744 | 27.002 | 44.630 | 1.00 | 32.25 |
| 1733 | CG | LEU | B | 348 | 15.610 | 25.982 | 44.446 | 1.00 | 33.85 |
| 1734 | CD1 | LEU | B | 348 | 14.492 | 26.227 | 45.455 | 1.00 | 28.70 |
| 1735 | CD2 | LEU | B | 348 | 15.051 | 26.104 | 43.003 | 1.00 | 32.39 |
| 1736 | C | LEU | B | 348 | 18.028 | 25.748 | 46.376 | 1.00 | 35.85 |
| 1737 | O | LEU | B | 348 | 17.437 | 25.091 | 47.243 | 1.00 | 33.57 |
| 1738 | N | PHE | B | 349 | 19.129 | 25.308 | 45.769 | 1.00 | 37.65 |
| 1739 | CA | PHE | B | 349 | 19.669 | 23.986 | 46.097 | 1.00 | 41.55 |
| 1740 | CB | PHE | B | 349 | 19.995 | 23.205 | 44.809 | 1.00 | 40.76 |
| 1741 | CG | PHE | B | 349 | 18.832 | 23.090 | 43.841 | 1.00 | 39.70 |
| 1742 | CD1 | PHE | B | 349 | 18.851 | 23.773 | 42.623 | 1.00 | 37.15 |
| 1743 | CD2 | PHE | B | 349 | 17.722 | 22.305 | 44.147 | 1.00 | 38.88 |
| 1744 | CE1 | PHE | B | 349 | 17.782 | 23.678 | 41.721 | 1.00 | 36.73 |
| 1745 | CE2 | PHE | B | 349 | 16.642 | 22.203 | 43.250 | 1.00 | 38.48 |
| 1746 | CZ | PHE | B | 349 | 16.676 | 22.893 | 42.034 | 1.00 | 36.79 |
| 1747 | C | PHE | B | 349 | 20.890 | 23.945 | 47.035 | 1.00 | 44.98 |
| 1748 | O | PHE | B | 349 | 21.216 | 22.891 | 47.565 | 1.00 | 43.98 |
| 1749 | N | ILE | B | 350 | 21.569 | 25.065 | 47.253 | 1.00 | 49.10 |
| 1750 | CA | ILE | B | 350 | 22.730 | 25.037 | 48.140 | 1.00 | 55.08 |
| 1751 | CB | ILE | B | 350 | 23.987 | 25.587 | 47.437 | 1.00 | 61.96 |
| 1752 | CG2 | ILE | B | 350 | 25.132 | 25.726 | 48.439 | 1.00 | 64.49 |
| 1753 | CG1 | ILE | B | 350 | 24.388 | 24.637 | 46.304 | 1.00 | 67.56 |
| 1754 | CD1 | ILE | B | 350 | 25.622 | 25.067 | 45.541 | 1.00 | 75.57 |
| 1755 | C | ILE | B | 350 | 22.522 | 25.760 | 49.467 | 1.00 | 54.07 |
| 1756 | O | ILE | B | 350 | 22.595 | 25.133 | 50.521 | 1.00 | 52.70 |
| 1757 | N | ARG | B | 351 | 22.273 | 27.069 | 49.421 | 1.00 | 54.37 |
| 1758 | CA | ARG | B | 351 | 22.034 | 27.842 | 50.638 | 1.00 | 53.15 |
| 1759 | CB | ARG | B | 351 | 22.068 | 29.338 | 50.356 | 1.00 | 55.88 |
| 1760 | CG | ARG | B | 351 | 23.432 | 29.946 | 50.184 | 1.00 | 59.22 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1761 | CD | ARG | B | 351 | 23.281 | 31.445 | 50.281 | 1.00 | 64.06 |
| 1762 | NE | ARG | B | 351 | 22.534 | 31.791 | 51.485 | 1.00 | 69.08 |
| 1763 | CZ | ARG | B | 351 | 21.995 | 32.983 | 51.718 | 1.00 | 72.37 |
| 1764 | NH1 | ARG | B | 351 | 22.119 | 33.953 | 50.821 | 1.00 | 74.58 |
| 1765 | NH2 | ARG | B | 351 | 21.335 | 33.204 | 52.849 | 1.00 | 73.23 |
| 1766 | C | ARG | B | 351 | 20.666 | 27.507 | 51.200 | 1.00 | 52.85 |
| 1767 | O | ARG | B | 351 | 20.437 | 27.582 | 52.400 | 1.00 | 53.20 |
| 1768 | N | LYS | B | 352 | 19.749 | 27.160 | 50.308 | 1.00 | 52.85 |
| 1769 | CA | LYS | B | 352 | 18.387 | 26.812 | 50.676 | 1.00 | 52.08 |
| 1770 | CB | LYS | B | 352 | 18.386 | 25.596 | 51.604 | 1.00 | 57.57 |
| 1771 | CG | LYS | B | 352 | 18.931 | 24.348 | 50.917 | 1.00 | 63.48 |
| 1772 | CD | LYS | B | 352 | 18.412 | 23.069 | 51.552 | 1.00 | 68.48 |
| 1773 | CE | LYS | B | 352 | 18.872 | 21.852 | 50.763 | 1.00 | 72.76 |
| 1774 | NZ | LYS | B | 352 | 18.301 | 20.575 | 51.284 | 1.00 | 76.35 |
| 1775 | C | LYS | B | 352 | 17.530 | 27.933 | 51.263 | 1.00 | 50.12 |
| 1776 | O | LYS | B | 352 | 16.674 | 27.683 | 52.114 | 1.00 | 49.80 |
| 1777 | N | SER | B | 353 | 17.764 | 29.165 | 50.811 | 1.00 | 46.59 |
| 1778 | CA | SER | B | 353 | 16.950 | 30.301 | 51.236 | 1.00 | 46.12 |
| 1779 | CB | SER | B | 353 | 17.680 | 31.190 | 52.262 | 1.00 | 45.30 |
| 1780 | OG | SER | B | 353 | 18.829 | 31.804 | 51.710 | 1.00 | 50.88 |
| 1781 | C | SER | B | 353 | 16.576 | 31.097 | 49.973 | 1.00 | 42.05 |
| 1782 | O | SER | B | 353 | 17.095 | 32.181 | 49.711 | 1.00 | 40.03 |
| 1783 | N | PRO | B | 354 | 15.650 | 30.545 | 49.177 | 1.00 | 40.94 |
| 1784 | CD | PRO | B | 354 | 15.002 | 29.264 | 49.510 | 1.00 | 41.65 |
| 1785 | CA | PRO | B | 354 | 15.120 | 31.086 | 47.916 | 1.00 | 38.05 |
| 1786 | CB | PRO | B | 354 | 14.180 | 29.984 | 47.428 | 1.00 | 38.80 |
| 1787 | CG | PRO | B | 354 | 14.620 | 28.750 | 48.171 | 1.00 | 41.73 |
| 1788 | C | PRO | B | 354 | 14.359 | 32.406 | 48.046 | 1.00 | 36.17 |
| 1789 | O | PRO | B | 354 | 13.672 | 32.642 | 49.038 | 1.00 | 35.96 |
| 1790 | N | THR | B | 355 | 14.469 | 33.251 | 47.031 | 1.00 | 33.39 |
| 1791 | CA | THR | B | 355 | 13.727 | 34.514 | 47.004 | 1.00 | 32.86 |
| 1792 | CB | THR | B | 355 | 14.573 | 35.713 | 47.533 | 1.00 | 33.45 |
| 1793 | OG1 | THR | B | 355 | 15.717 | 35.897 | 46.693 | 1.00 | 33.95 |
| 1794 | CG2 | THR | B | 355 | 15.046 | 35.468 | 48.968 | 1.00 | 36.38 |
| 1795 | C | THR | B | 355 | 13.298 | 34.844 | 45.569 | 1.00 | 32.90 |
| 1796 | O | THR | B | 355 | 13.937 | 34.416 | 44.618 | 1.00 | 32.52 |
| 1797 | N | ILE | B | 356 | 12.200 | 35.581 | 45.415 | 1.00 | 33.65 |
| 1798 | CA | ILE | B | 356 | 11.743 | 36.026 | 44.091 | 1.00 | 33.14 |
| 1799 | CB | ILE | B | 356 | 10.362 | 35.419 | 43.692 | 1.00 | 35.28 |
| 1800 | CG2 | ILE | B | 356 | 10.470 | 33.884 | 43.580 | 1.00 | 32.71 |
| 1801 | CG1 | ILE | B | 356 | 9.293 | 35.816 | 44.704 | 1.00 | 33.33 |
| 1802 | CD1 | ILE | B | 356 | 7.929 | 35.200 | 44.418 | 1.00 | 33.89 |
| 1803 | C | ILE | B | 356 | 11.657 | 37.559 | 44.185 | 1.00 | 34.86 |
| 1804 | O | ILE | B | 356 | 11.522 | 38.094 | 45.282 | 1.00 | 34.82 |
| 1805 | N | THR | B | 357 | 11.748 | 38.256 | 43.052 | 1.00 | 35.49 |
| 1806 | CA | THR | B | 357 | 11.715 | 39.722 | 43.041 | 1.00 | 39.05 |
| 1807 | CB | THR | B | 357 | 13.128 | 40.288 | 42.765 | 1.00 | 39.55 |
| 1808 | OG1 | THR | B | 357 | 14.052 | 39.780 | 43.734 | 1.00 | 41.32 |
| 1809 | CG2 | THR | B | 357 | 13.112 | 41.802 | 42.807 | 1.00 | 40.20 |
| 1810 | C | THR | B | 357 | 10.766 | 40.341 | 41.999 | 1.00 | 40.46 |
| 1811 | O | THR | B | 357 | 10.772 | 39.945 | 40.832 | 1.00 | 39.35 |
| 1812 | N | CYS | B | 358 | 9.981 | 41.330 | 42.425 | 1.00 | 41.16 |
| 1813 | CA | CYS | B | 358 | 9.034 | 42.032 | 41.549 | 1.00 | 44.33 |
| 1814 | C | CYS | B | 358 | 9.556 | 43.453 | 41.299 | 1.00 | 45.87 |
| 1815 | O | CYS | B | 358 | 9.741 | 44.222 | 42.244 | 1.00 | 46.87 |
| 1816 | CB | CYS | B | 358 | 7.647 | 42.092 | 42.216 | 1.00 | 45.18 |
| 1817 | SG | CYS | B | 358 | 6.293 | 42.744 | 41.178 | 1.00 | 43.45 |
| 1818 | N | LEU | B | 359 | 9.792 | 43.802 | 40.036 | 1.00 | 48.26 |
| 1819 | CA | LEU | B | 359 | 10.312 | 45.127 | 39.680 | 1.00 | 50.89 |
| 1820 | CB | LEU | B | 359 | 11.659 | 44.987 | 38.954 | 1.00 | 53.55 |
| 1821 | CG | LEU | B | 359 | 12.236 | 46.227 | 38.262 | 1.00 | 56.25 |
| 1822 | CD1 | LEU | B | 359 | 12.350 | 47.364 | 39.252 | 1.00 | 58.88 |
| 1823 | CD2 | LEU | B | 359 | 13.594 | 45.902 | 37.668 | 1.00 | 57.61 |
| 1824 | C | LEU | B | 359 | 9.377 | 45.997 | 38.835 | 1.00 | 52.07 |
| 1825 | O | LEU | B | 359 | 8.863 | 45.564 | 37.799 | 1.00 | 51.86 |
| 1826 | N | VAL | B | 360 | 9.183 | 47.236 | 39.282 | 1.00 | 54.35 |
| 1827 | CA | VAL | B | 360 | 8.322 | 48.189 | 38.590 | 1.00 | 56.14 |
| 1828 | CB | VAL | B | 360 | 7.182 | 48.684 | 39.515 | 1.00 | 55.60 |
| 1829 | CG1 | VAL | B | 360 | 6.338 | 49.714 | 38.788 | 1.00 | 55.55 |
| 1830 | CG2 | VAL | B | 360 | 6.313 | 47.511 | 39.953 | 1.00 | 55.20 |
| 1831 | C | VAL | B | 360 | 9.103 | 49.404 | 38.065 | 1.00 | 59.78 |
| 1832 | O | VAL | B | 360 | 9.871 | 50.032 | 38.800 | 1.00 | 56.02 |
| 1833 | N | VAL | B | 361 | 8.891 | 49.717 | 36.787 | 1.00 | 64.38 |
| 1834 | CA | VAL | B | 361 | 9.547 | 50.841 | 36.125 | 1.00 | 72.03 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1835 | CB | VAL | B | 361 | 10.424 | 50.356 | 34.955 | 1.00 | 69.57 |
| 1836 | CG1 | VAL | B | 361 | 11.061 | 51.542 | 34.255 | 1.00 | 67.79 |
| 1837 | CG2 | VAL | B | 361 | 11.492 | 49.409 | 35.471 | 1.00 | 68.23 |
| 1838 | C | VAL | B | 361 | 8.529 | 51.854 | 35.589 | 1.00 | 80.49 |
| 1839 | O | VAL | B | 361 | 7.749 | 51.556 | 34.683 | 1.00 | 79.40 |
| 1840 | N | ASP | B | 362 | 8.557 | 53.056 | 36.154 | 1.00 | 89.93 |
| 1841 | CA | ASP | B | 362 | 7.649 | 54.128 | 35.764 | 1.00 | 100.39 |
| 1842 | CB | ASP | B | 362 | 6.754 | 54.496 | 36.954 | 1.00 | 104.28 |
| 1843 | CG | ASP | B | 362 | 5.783 | 55.614 | 36.635 | 1.00 | 107.71 |
| 1844 | OD1 | ASP | B | 362 | 6.244 | 56.735 | 36.340 | 1.00 | 109.93 |
| 1845 | OD2 | ASP | B | 362 | 4.558 | 55.375 | 36.681 | 1.00 | 109.91 |
| 1846 | C | ASP | B | 362 | 8.445 | 55.348 | 35.310 | 1.00 | 104.59 |
| 1847 | O | ASP | B | 362 | 9.206 | 55.920 | 36.086 | 1.00 | 106.46 |
| 1848 | N | GLY | B | 363 | 8.260 | 55.743 | 34.054 | 1.00 | 109.42 |
| 1849 | CA | GLY | B | 363 | 8.977 | 56.889 | 33.517 | 1.00 | 114.49 |
| 1850 | C | GLY | B | 363 | 8.390 | 58.259 | 33.823 | 1.00 | 118.03 |
| 1851 | O | GLY | B | 363 | 9.097 | 59.266 | 33.741 | 1.00 | 117.95 |
| 1852 | N | ALA | B | 364 | 7.106 | 58.308 | 34.170 | 1.00 | 115.75 |
| 1853 | CA | ALA | B | 364 | 6.436 | 59.572 | 34.485 | 1.00 | 114.37 |
| 1854 | CB | ALA | B | 364 | 5.330 | 59.841 | 33.465 | 1.00 | 117.75 |
| 1855 | C | ALA | B | 364 | 5.850 | 59.574 | 35.903 | 1.00 | 111.05 |
| 1856 | O | ALA | B | 364 | 4.664 | 59.304 | 36.093 | 1.00 | 111.81 |
| 1857 | N | PRO | B | 365 | 6.681 | 59.885 | 36.917 | 1.00 | 105.42 |
| 1858 | CD | PRO | B | 365 | 8.143 | 60.022 | 36.791 | 1.00 | 103.04 |
| 1859 | CA | PRO | B | 365 | 6.283 | 59.930 | 38.330 | 1.00 | 105.73 |
| 1860 | CB | PRO | B | 365 | 7.602 | 60.215 | 39.048 | 1.00 | 101.25 |
| 1861 | CG | PRO | B | 365 | 8.617 | 59.584 | 38.151 | 1.00 | 100.06 |
| 1862 | C | PRO | B | 365 | 5.205 | 60.951 | 38.706 | 1.00 | 107.73 |
| 1863 | O | PRO | B | 365 | 5.519 | 62.026 | 39.220 | 1.00 | 104.62 |
| 1864 | N | SER | B | 366 | 3.939 | 60.616 | 38.460 | 1.00 | 110.96 |
| 1865 | CA | SER | B | 366 | 2.834 | 61.509 | 38.809 | 1.00 | 119.09 |
| 1866 | CB | SER | B | 366 | 1.591 | 61.205 | 37.966 | 1.00 | 113.69 |
| 1867 | OG | SER | B | 366 | 1.020 | 59.957 | 38.316 | 1.00 | 107.57 |
| 1868 | C | SER | B | 366 | 2.529 | 61.277 | 40.284 | 1.00 | 129.01 |
| 1869 | O | SER | B | 366 | 1.419 | 60.898 | 40.658 | 1.00 | 127.64 |
| 1870 | N | LYS | B | 367 | 3.548 | 61.507 | 41.104 | 1.00 | 138.15 |
| 1871 | CA | LYS | B | 367 | 3.487 | 61.328 | 42.547 | 1.00 | 151.84 |
| 1872 | CB | LYS | B | 367 | 4.006 | 62.590 | 43.240 | 1.00 | 154.11 |
| 1873 | CG | LYS | B | 367 | 5.490 | 62.821 | 42.982 | 1.00 | 156.68 |
| 1874 | CD | LYS | B | 367 | 6.286 | 61.563 | 43.317 | 1.00 | 157.36 |
| 1875 | CE | LYS | B | 367 | 7.721 | 61.644 | 42.837 | 1.00 | 157.14 |
| 1876 | NZ | LYS | B | 367 | 8.443 | 60.373 | 43.118 | 1.00 | 156.67 |
| 1877 | C | LYS | B | 367 | 2.158 | 60.896 | 43.155 | 1.00 | 157.02 |
| 1878 | O | LYS | B | 367 | 1.192 | 61.657 | 43.211 | 1.00 | 160.16 |
| 1879 | N | GLY | B | 368 | 2.143 | 59.646 | 43.604 | 1.00 | 158.16 |
| 1880 | CA | GLY | B | 368 | 0.978 | 59.054 | 44.232 | 1.00 | 156.25 |
| 1881 | C | GLY | B | 368 | 1.493 | 57.985 | 45.179 | 1.00 | 149.94 |
| 1882 | O | GLY | B | 368 | 2.171 | 58.297 | 46.158 | 1.00 | 155.97 |
| 1883 | N | THR | B | 369 | 1.189 | 56.725 | 44.886 | 1.00 | 142.10 |
| 1884 | CA | THR | B | 369 | 1.652 | 55.619 | 45.717 | 1.00 | 125.55 |
| 1885 | CB | THR | B | 369 | 0.907 | 55.558 | 47.072 | 1.00 | 127.08 |
| 1886 | OG1 | THR | B | 369 | 1.216 | 56.723 | 47.847 | 1.00 | 125.92 |
| 1887 | CG2 | THR | B | 369 | 1.325 | 54.314 | 47.855 | 1.00 | 125.81 |
| 1888 | C | THR | B | 369 | 1.481 | 54.278 | 45.019 | 1.00 | 114.18 |
| 1889 | O | THR | B | 369 | 0.396 | 53.698 | 45.015 | 1.00 | 113.94 |
| 1890 | N | VAL | B | 370 | 2.561 | 53.794 | 44.420 | 1.00 | 103.09 |
| 1891 | CA | VAL | B | 370 | 2.529 | 52.510 | 43.742 | 1.00 | 87.57 |
| 1892 | CB | VAL | B | 370 | 3.800 | 52.279 | 42.918 | 1.00 | 84.84 |
| 1893 | CG1 | VAL | B | 370 | 3.735 | 50.925 | 42.230 | 1.00 | 80.60 |
| 1894 | CG2 | VAL | B | 370 | 3.959 | 53.390 | 41.903 | 1.00 | 80.89 |
| 1895 | C | VAL | B | 370 | 2.457 | 51.439 | 44.812 | 1.00 | 84.68 |
| 1896 | O | VAL | B | 370 | 3.304 | 51.391 | 45.698 | 1.00 | 81.01 |
| 1897 | N | GLN | B | 371 | 1.442 | 50.587 | 44.735 | 1.00 | 81.73 |
| 1898 | CA | GLN | B | 371 | 1.277 | 49.519 | 45.710 | 1.00 | 81.84 |
| 1899 | CB | GLN | B | 371 | −0.130 | 49.556 | 46.299 | 1.00 | 92.04 |
| 1900 | CG | GLN | B | 371 | −0.379 | 50.733 | 47.212 | 1.00 | 110.27 |
| 1901 | CD | GLN | B | 371 | −1.756 | 50.694 | 47.833 | 1.00 | 120.57 |
| 1902 | OE1 | GLN | B | 371 | −2.079 | 51.504 | 48.699 | 1.00 | 127.98 |
| 1903 | NE2 | GLN | B | 371 | −2.581 | 49.750 | 47.390 | 1.00 | 127.32 |
| 1904 | C | GLN | B | 371 | 1.544 | 48.141 | 45.121 | 1.00 | 75.54 |
| 1905 | O | GLN | B | 371 | 1.163 | 47.857 | 43.985 | 1.00 | 72.16 |
| 1906 | N | LEU | B | 372 | 2.205 | 47.293 | 45.906 | 1.00 | 68.37 |
| 1907 | CA | LEU | B | 372 | 2.529 | 45.933 | 45.490 | 1.00 | 62.73 |
| 1908 | CB | LEU | B | 372 | 4.036 | 45.771 | 45.306 | 1.00 | 61.97 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1909 | CG | LEU | B | 372 | 4.642 | 46.497 | 44.114 | 1.00 | 61.06 |
| 1910 | CD1 | LEU | B | 372 | 6.107 | 46.127 | 43.989 | 1.00 | 61.39 |
| 1911 | CD2 | LEU | B | 372 | 3.890 | 46.107 | 42.855 | 1.00 | 62.26 |
| 1912 | C | LEU | B | 372 | 2.039 | 44.912 | 46.509 | 1.00 | 60.32 |
| 1913 | O | LEU | B | 372 | 2.360 | 45.002 | 47.694 | 1.00 | 60.26 |
| 1914 | N | THR | B | 373 | 1.276 | 43.933 | 46.032 | 1.00 | 57.56 |
| 1915 | CA | THR | B | 373 | 0.725 | 42.893 | 46.889 | 1.00 | 54.46 |
| 1916 | CB | THR | B | 373 | −0.822 | 42.930 | 46.869 | 1.00 | 55.66 |
| 1917 | OG1 | THR | B | 373 | −1.274 | 44.217 | 47.296 | 1.00 | 56.84 |
| 1918 | CG2 | THR | B | 373 | −1.404 | 41.855 | 47.786 | 1.00 | 55.72 |
| 1919 | C | THR | B | 373 | 1.163 | 41.501 | 46.444 | 1.00 | 51.58 |
| 1920 | O | THR | B | 373 | 1.192 | 41.207 | 45.251 | 1.00 | 50.28 |
| 1921 | N | TRP | B | 374 | 1.482 | 40.650 | 47.416 | 1.00 | 48.55 |
| 1922 | CA | TRP | B | 374 | 1.893 | 39.275 | 47.156 | 1.00 | 46.76 |
| 1923 | CB | TRP | B | 374 | 3.166 | 38.931 | 47.937 | 1.00 | 46.52 |
| 1924 | CG | TRP | B | 374 | 4.416 | 39.630 | 47.495 | 1.00 | 46.19 |
| 1925 | CD2 | TRP | B | 374 | 5.212 | 39.322 | 46.340 | 1.00 | 45.05 |
| 1926 | CE2 | TRP | B | 374 | 6.340 | 40.178 | 46.367 | 1.00 | 44.19 |
| 1927 | CE3 | TRP | B | 374 | 5.083 | 38.406 | 45.288 | 1.00 | 43.57 |
| 1928 | CD1 | TRP | B | 374 | 5.070 | 40.637 | 48.151 | 1.00 | 46.23 |
| 1929 | NE1 | TRP | B | 374 | 6.229 | 40.968 | 47.480 | 1.00 | 45.32 |
| 1930 | CZ2 | TRP | B | 374 | 7.334 | 40.142 | 45.382 | 1.00 | 44.18 |
| 1931 | CZ3 | TRP | B | 374 | 6.078 | 38.369 | 44.306 | 1.00 | 44.87 |
| 1932 | CH2 | TRP | B | 374 | 7.188 | 39.233 | 44.364 | 1.00 | 44.46 |
| 1933 | C | TRP | B | 374 | 0.787 | 38.300 | 47.592 | 1.00 | 46.41 |
| 1934 | O | TRP | B | 374 | 0.119 | 38.522 | 48.608 | 1.00 | 45.95 |
| 1935 | N | SER | B | 375 | 0.601 | 37.226 | 46.828 | 1.00 | 43.93 |
| 1936 | CA | SER | B | 375 | −0.400 | 36.212 | 47.152 | 1.00 | 42.84 |
| 1937 | CB | SER | B | 375 | −1.794 | 36.654 | 46.687 | 1.00 | 42.82 |
| 1938 | OG | SER | B | 375 | −1.886 | 36.733 | 45.272 | 1.00 | 43.06 |
| 1939 | C | SER | B | 375 | −0.049 | 34.856 | 46.526 | 1.00 | 42.26 |
| 1940 | O | SER | B | 375 | 0.684 | 34.786 | 45.535 | 1.00 | 41.83 |
| 1941 | N | ARG | B | 376 | −0.571 | 33.784 | 47.112 | 1.00 | 40.21 |
| 1942 | CA | ARG | B | 376 | −0.322 | 32.436 | 46.624 | 1.00 | 37.61 |
| 1943 | CB | ARG | B | 376 | 0.185 | 31.545 | 47.754 | 1.00 | 35.88 |
| 1944 | CG | ARG | B | 376 | 1.617 | 31.776 | 48.161 | 1.00 | 34.92 |
| 1945 | CD | ARG | B | 376 | 2.155 | 30.480 | 48.737 | 1.00 | 37.26 |
| 1946 | NE | ARG | B | 376 | 2.357 | 30.521 | 50.177 | 1.00 | 36.82 |
| 1947 | CZ | ARG | B | 376 | 2.697 | 29.461 | 50.908 | 1.00 | 39.50 |
| 1948 | NH1 | ARG | B | 376 | 2.858 | 28.275 | 50.335 | 1.00 | 36.61 |
| 1949 | NH2 | ARG | B | 376 | 2.906 | 29.592 | 52.215 | 1.00 | 39.12 |
| 1950 | C | ARG | B | 376 | −1.584 | 31.818 | 46.046 | 1.00 | 38.01 |
| 1951 | O | ARG | B | 376 | −2.674 | 32.010 | 46.578 | 1.00 | 38.95 |
| 1952 | N | ALA | B | 377 | −1.428 | 31.051 | 44.970 | 1.00 | 38.18 |
| 1953 | CA | ALA | B | 377 | −2.565 | 30.411 | 44.312 | 1.00 | 38.50 |
| 1954 | CB | ALA | B | 377 | −2.089 | 29.642 | 43.087 | 1.00 | 38.54 |
| 1955 | C | ALA | B | 377 | −3.323 | 29.475 | 45.239 | 1.00 | 36.86 |
| 1956 | O | ALA | B | 377 | −4.538 | 29.312 | 45.126 | 1.00 | 33.90 |
| 1957 | N | SER | B | 378 | −2.591 | 28.858 | 46.156 | 1.00 | 37.17 |
| 1958 | CA | SER | B | 378 | −3.172 | 27.916 | 47.096 | 1.00 | 38.97 |
| 1959 | CB | SER | B | 378 | −2.056 | 27.145 | 47.805 | 1.00 | 38.81 |
| 1960 | OG | SER | B | 378 | −1.292 | 28.027 | 48.622 | 1.00 | 37.36 |
| 1961 | C | SER | B | 378 | −4.051 | 28.582 | 48.153 | 1.00 | 40.09 |
| 1962 | O | SER | B | 378 | −4.912 | 27.940 | 48.739 | 1.00 | 39.37 |
| 1963 | N | GLY | B | 379 | −3.834 | 29.868 | 48.389 | 1.00 | 41.02 |
| 1964 | CA | GLY | B | 379 | −4.590 | 30.547 | 49.416 | 1.00 | 42.69 |
| 1965 | C | GLY | B | 379 | −3.758 | 30.672 | 50.694 | 1.00 | 45.65 |
| 1966 | O | GLY | B | 379 | −4.098 | 31.455 | 51.581 | 1.00 | 46.28 |
| 1967 | N | LYS | B | 380 | −2.671 | 29.908 | 50.803 | 1.00 | 45.33 |
| 1968 | CA | LYS | B | 380 | −1.818 | 29.984 | 51.996 | 1.00 | 46.22 |
| 1969 | CB | LYS | B | 380 | −0.729 | 28.910 | 51.946 | 1.00 | 45.46 |
| 1970 | CG | LYS | B | 380 | −1.278 | 27.499 | 51.926 | 1.00 | 47.21 |
| 1971 | CD | LYS | B | 380 | −0.164 | 26.485 | 51.758 | 1.00 | 47.01 |
| 1972 | CE | LYS | B | 380 | −0.718 | 25.088 | 51.570 | 1.00 | 48.06 |
| 1973 | NZ | LYS | B | 380 | 0.380 | 24.117 | 51.292 | 1.00 | 49.70 |
| 1974 | C | LYS | B | 380 | −1.186 | 31.376 | 52.128 | 1.00 | 47.32 |
| 1975 | O | LYS | B | 380 | −1.146 | 32.135 | 51.164 | 1.00 | 45.87 |
| 1976 | N | PRO | B | 381 | −0.687 | 31.722 | 53.331 | 1.00 | 46.03 |
| 1977 | CD | PRO | B | 381 | −0.758 | 30.901 | 54.550 | 1.00 | 48.89 |
| 1978 | CA | PRO | B | 381 | −0.057 | 33.017 | 53.630 | 1.00 | 46.98 |
| 1979 | CB | PRO | B | 381 | −0.033 | 33.059 | 55.164 | 1.00 | 47.80 |
| 1980 | CG | PRO | B | 381 | −0.968 | 31.947 | 55.593 | 1.00 | 51.16 |
| 1981 | C | PRO | B | 381 | 1.350 | 33.222 | 53.058 | 1.00 | 48.51 |
| 1982 | O | PRO | B | 381 | 2.104 | 32.267 | 52.851 | 1.00 | 44.49 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 1983 | N | VAL | B | 382 | 1.695 | 34.486 | 52.830 | 1.00 | 45.96 |
| 1984 | CA | VAL | B | 382 | 3.003 | 34.857 | 52.312 | 1.00 | 47.91 |
| 1985 | CB | VAL | B | 382 | 2.892 | 35.902 | 51.175 | 1.00 | 45.90 |
| 1986 | CG1 | VAL | B | 382 | 2.317 | 35.258 | 49.932 | 1.00 | 42.79 |
| 1987 | CG2 | VAL | B | 382 | 2.013 | 37.055 | 51.616 | 1.00 | 43.59 |
| 1988 | C | VAL | B | 382 | 3.823 | 35.464 | 53.441 | 1.00 | 54.19 |
| 1989 | O | VAL | B | 382 | 3.283 | 36.158 | 54.298 | 1.00 | 52.96 |
| 1990 | N | GLN | B | 383 | 5.123 | 35.192 | 53.440 | 1.00 | 61.55 |
| 1991 | CA | GLN | B | 383 | 6.034 | 35.720 | 54.448 | 1.00 | 71.44 |
| 1992 | CB | GLN | B | 383 | 7.405 | 35.080 | 54.260 | 1.00 | 83.50 |
| 1993 | CG | GLN | B | 383 | 8.241 | 34.980 | 55.511 | 1.00 | 106.44 |
| 1994 | CD | GLN | B | 383 | 9.460 | 34.104 | 55.300 | 1.00 | 118.91 |
| 1995 | OE1 | GLN | B | 383 | 9.342 | 32.947 | 54.890 | 1.00 | 127.43 |
| 1996 | NE2 | GLN | B | 383 | 10.640 | 34.648 | 55.578 | 1.00 | 127.64 |
| 1997 | C | GLN | B | 383 | 6.115 | 37.235 | 54.245 | 1.00 | 71.67 |
| 1998 | O | GLN | B | 383 | 5.487 | 37.767 | 53.335 | 1.00 | 69.76 |
| 1999 | N | HIS | B | 384 | 6.875 | 37.934 | 55.081 | 1.00 | 75.93 |
| 2000 | CA | HIS | B | 384 | 6.997 | 39.388 | 54.947 | 1.00 | 83.03 |
| 2001 | CB | HIS | B | 384 | 7.442 | 40.013 | 56.278 | 1.00 | 108.24 |
| 2002 | CG | HIS | B | 384 | 8.696 | 39.419 | 56.844 | 1.00 | 137.90 |
| 2003 | CD2 | HIS | B | 384 | 9.862 | 39.995 | 57.226 | 1.00 | 150.62 |
| 2004 | ND1 | HIS | B | 384 | 8.835 | 38.072 | 57.101 | 1.00 | 150.60 |
| 2005 | CE1 | HIS | B | 384 | 10.029 | 37.843 | 57.617 | 1.00 | 159.79 |
| 2006 | NE2 | HIS | B | 384 | 10.672 | 38.994 | 57.704 | 1.00 | 159.84 |
| 2007 | C | HIS | B | 384 | 7.974 | 39.763 | 53.833 | 1.00 | 73.69 |
| 2008 | O | HIS | B | 384 | 8.970 | 39.075 | 53.628 | 1.00 | 68.07 |
| 2009 | N | SER | B | 385 | 7.693 | 40.854 | 53.122 | 1.00 | 63.66 |
| 2010 | CA | SER | B | 385 | 8.550 | 41.283 | 52.012 | 1.00 | 57.21 |
| 2011 | CB | SER | B | 385 | 7.754 | 41.253 | 50.713 | 1.00 | 53.81 |
| 2012 | OG | SER | B | 385 | 6.805 | 42.302 | 50.701 | 1.00 | 48.73 |
| 2013 | C | SER | B | 385 | 9.200 | 42.668 | 52.144 | 1.00 | 56.55 |
| 2014 | O | SER | B | 385 | 8.726 | 43.532 | 52.883 | 1.00 | 54.72 |
| 2015 | N | THR | B | 386 | 10.278 | 42.868 | 51.387 | 1.00 | 56.21 |
| 2016 | CA | THR | B | 386 | 11.029 | 44.122 | 51.384 | 1.00 | 56.89 |
| 2017 | CB | THR | B | 386 | 12.523 | 43.867 | 51.094 | 1.00 | 57.57 |
| 2018 | OG1 | THR | B | 386 | 13.050 | 42.964 | 52.072 | 1.00 | 58.73 |
| 2019 | CG2 | THR | B | 386 | 13.315 | 45.165 | 51.148 | 1.00 | 59.34 |
| 2020 | C | THR | B | 386 | 10.505 | 45.091 | 50.330 | 1.00 | 55.99 |
| 2021 | O | THR | B | 386 | 9.705 | 44.724 | 49.473 | 1.00 | 56.70 |
| 2022 | N | ARG | B | 387 | 10.954 | 46.337 | 50.409 | 1.00 | 56.49 |
| 2023 | CA | ARG | B | 387 | 10.562 | 47.365 | 49.459 | 1.00 | 55.40 |
| 2024 | CB | ARG | B | 387 | 9.193 | 47.949 | 49.816 | 1.00 | 52.39 |
| 2025 | CG | ARG | B | 387 | 8.861 | 49.187 | 49.008 | 1.00 | 49.50 |
| 2026 | CD | ARG | B | 387 | 7.368 | 49.387 | 48.828 | 1.00 | 50.75 |
| 2027 | NE | ARG | B | 387 | 7.091 | 50.620 | 48.096 | 1.00 | 51.41 |
| 2028 | CZ | ARG | B | 387 | 5.958 | 50.875 | 47.455 | 1.00 | 52.27 |
| 2029 | NH1 | ARG | B | 387 | 4.982 | 49.978 | 47.445 | 1.00 | 52.79 |
| 2030 | NH2 | ARG | B | 387 | 5.799 | 52.032 | 46.827 | 1.00 | 53.84 |
| 2031 | C | ARG | B | 387 | 11.614 | 48.467 | 49.443 | 1.00 | 58.05 |
| 2032 | O | ARG | B | 387 | 12.206 | 48.778 | 50.474 | 1.00 | 57.64 |
| 2033 | N | LYS | B | 388 | 11.840 | 49.045 | 48.266 | 1.00 | 62.91 |
| 2034 | CA | LYS | B | 388 | 12.827 | 50.103 | 48.086 | 1.00 | 70.60 |
| 2035 | CB | LYS | B | 388 | 14.225 | 49.496 | 47.949 | 1.00 | 72.48 |
| 2036 | CG | LYS | B | 388 | 15.309 | 50.514 | 47.640 | 1.00 | 79.69 |
| 2037 | CD | LYS | B | 388 | 16.655 | 49.846 | 47.407 | 1.00 | 86.20 |
| 2038 | CE | LYS | B | 388 | 17.711 | 50.869 | 47.004 | 1.00 | 90.36 |
| 2039 | NZ | LYS | B | 388 | 19.024 | 50.239 | 46.682 | 1.00 | 93.61 |
| 2040 | C | LYS | B | 388 | 12.517 | 50.934 | 46.843 | 1.00 | 73.88 |
| 2041 | O | LYS | B | 388 | 12.273 | 50.384 | 45.770 | 1.00 | 71.34 |
| 2042 | N | GLU | B | 389 | 12.540 | 52.258 | 46.992 | 1.00 | 75.89 |
| 2043 | CA | GLU | B | 389 | 12.258 | 53.170 | 45.882 | 1.00 | 80.71 |
| 2044 | CB | GLU | B | 389 | 11.136 | 54.139 | 46.269 | 1.00 | 82.16 |
| 2045 | CG | GLU | B | 389 | 9.814 | 53.446 | 46.562 | 1.00 | 84.78 |
| 2046 | CD | GLU | B | 389 | 8.708 | 54.411 | 46.942 | 1.00 | 86.28 |
| 2047 | OE1 | GLU | B | 389 | 8.440 | 55.351 | 46.162 | 1.00 | 86.86 |
| 2048 | OE2 | GLU | B | 389 | 8.102 | 54.223 | 48.020 | 1.00 | 87.78 |
| 2049 | C | GLU | B | 389 | 13.494 | 53.958 | 45.463 | 1.00 | 83.00 |
| 2050 | O | GLU | B | 389 | 14.145 | 54.595 | 46.290 | 1.00 | 83.84 |
| 2051 | N | GLU | B | 390 | 13.813 | 53.908 | 44.173 | 1.00 | 89.57 |
| 2052 | CA | GLU | B | 390 | 14.970 | 54.617 | 43.640 | 1.00 | 92.74 |
| 2053 | CB | GLU | B | 390 | 16.056 | 53.627 | 43.212 | 1.00 | 99.32 |
| 2054 | CG | GLU | B | 390 | 17.060 | 53.277 | 44.296 | 1.00 | 112.16 |
| 2055 | CD | GLU | B | 390 | 18.229 | 52.466 | 43.762 | 1.00 | 119.07 |
| 2056 | OE1 | GLU | B | 390 | 18.005 | 51.325 | 43.307 | 1.00 | 124.51 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2057 | OE2 | GLU | B | 390 | 19.372 | 52.970 | 43.790 | 1.00 | 123.93 |
| 2058 | C | GLU | B | 390 | 14.638 | 55.515 | 42.454 | 1.00 | 93.70 |
| 2059 | O | GLU | B | 390 | 14.035 | 55.073 | 41.479 | 1.00 | 91.64 |
| 2060 | N | LYS | B | 391 | 15.041 | 56.778 | 42.547 | 1.00 | 97.27 |
| 2061 | CA | LYS | B | 391 | 14.821 | 57.739 | 41.474 | 1.00 | 105.19 |
| 2062 | CB | LYS | B | 391 | 14.463 | 59.112 | 42.050 | 1.00 | 103.79 |
| 2063 | CG | LYS | B | 391 | 13.142 | 59.138 | 42.811 | 1.00 | 106.41 |
| 2064 | CD | LYS | B | 391 | 12.828 | 60.530 | 43.341 | 1.00 | 109.88 |
| 2065 | CE | LYS | B | 391 | 11.525 | 60.547 | 44.129 | 1.00 | 112.67 |
| 2066 | NZ | LYS | B | 391 | 11.212 | 61.901 | 44.669 | 1.00 | 114.80 |
| 2067 | C | LYS | B | 391 | 16.112 | 57.820 | 40.662 | 1.00 | 109.65 |
| 2068 | O | LYS | B | 391 | 17.116 | 58.367 | 41.120 | 1.00 | 107.47 |
| 2069 | N | GLN | B | 392 | 16.076 | 57.262 | 39.457 | 1.00 | 115.23 |
| 2070 | CA | GLN | B | 392 | 17.240 | 57.233 | 38.581 | 1.00 | 124.10 |
| 2071 | CB | GLN | B | 392 | 16.977 | 56.294 | 37.405 | 1.00 | 123.06 |
| 2072 | CG | GLN | B | 392 | 16.442 | 54.930 | 37.813 | 1.00 | 119.81 |
| 2073 | CD | GLN | B | 392 | 17.346 | 54.217 | 38.796 | 1.00 | 117.46 |
| 2074 | OE1 | GLN | B | 392 | 18.519 | 53.978 | 38.514 | 1.00 | 115.94 |
| 2075 | NE2 | GLN | B | 392 | 16.803 | 53.869 | 39.959 | 1.00 | 115.38 |
| 2076 | C | GLN | B | 392 | 17.635 | 58.608 | 38.059 | 1.00 | 131.44 |
| 2077 | O | GLN | B | 392 | 16.823 | 59.533 | 38.031 | 1.00 | 132.98 |
| 2078 | N | ALA | B | 393 | 18.892 | 58.725 | 37.639 | 1.00 | 135.48 |
| 2079 | CA | ALA | B | 393 | 19.431 | 59.977 | 37.121 | 1.00 | 135.45 |
| 2080 | CB | ALA | B | 393 | 20.885 | 59.782 | 36.707 | 1.00 | 141.07 |
| 2081 | C | ALA | B | 393 | 18.626 | 60.527 | 35.949 | 1.00 | 132.33 |
| 2082 | O | ALA | B | 393 | 18.650 | 61.728 | 35.682 | 1.00 | 136.80 |
| 2083 | N | ASN | B | 394 | 17.912 | 59.652 | 35.250 | 1.00 | 130.43 |
| 2084 | CA | ASN | B | 394 | 17.113 | 60.080 | 34.112 | 1.00 | 119.00 |
| 2085 | CB | ASN | B | 394 | 17.025 | 58.953 | 33.069 | 1.00 | 117.90 |
| 2086 | CG | ASN | B | 394 | 16.436 | 57.667 | 33.626 | 1.00 | 113.25 |
| 2087 | OD1 | ASN | B | 394 | 16.411 | 57.455 | 34.838 | 1.00 | 122.29 |
| 2088 | ND2 | ASN | B | 394 | 15.974 | 56.805 | 32.723 | 1.00 | 100.50 |
| 2089 | C | ASN | B | 394 | 15.722 | 60.551 | 34.527 | 1.00 | 112.52 |
| 2090 | O | ASN | B | 394 | 14.794 | 60.564 | 33.722 | 1.00 | 110.67 |
| 2091 | N | GLY | B | 395 | 15.596 | 60.938 | 35.793 | 1.00 | 106.22 |
| 2092 | CA | GLY | B | 395 | 14.334 | 61.434 | 36.315 | 1.00 | 100.31 |
| 2093 | C | GLY | B | 395 | 13.161 | 60.471 | 36.371 | 1.00 | 98.65 |
| 2094 | O | GLY | B | 395 | 12.009 | 60.890 | 36.258 | 1.00 | 95.02 |
| 2095 | N | THR | B | 396 | 13.438 | 59.186 | 36.559 | 1.00 | 95.84 |
| 2096 | CA | THR | B | 396 | 12.382 | 58.181 | 36.623 | 1.00 | 97.05 |
| 2097 | CB | THR | B | 396 | 12.557 | 57.142 | 35.502 | 1.00 | 99.27 |
| 2098 | OG1 | THR | B | 396 | 11.486 | 56.195 | 35.549 | 1.00 | 102.24 |
| 2099 | CG2 | THR | B | 396 | 13.871 | 56.416 | 35.663 | 1.00 | 102.25 |
| 2100 | C | THR | B | 396 | 12.387 | 57.470 | 37.978 | 1.00 | 93.62 |
| 2101 | O | THR | B | 396 | 13.390 | 57.491 | 38.691 | 1.00 | 94.37 |
| 2102 | N | LEU | B | 397 | 11.266 | 56.841 | 38.330 | 1.00 | 89.58 |
| 2103 | CA | LEU | B | 397 | 11.152 | 56.138 | 39.609 | 1.00 | 84.24 |
| 2104 | CB | LEU | B | 397 | 9.878 | 56.585 | 40.339 | 1.00 | 81.53 |
| 2105 | CG | LEU | B | 397 | 9.629 | 56.030 | 41.749 | 1.00 | 79.25 |
| 2106 | CD1 | LEU | B | 397 | 10.837 | 56.276 | 42.640 | 1.00 | 77.27 |
| 2107 | CD2 | LEU | B | 397 | 8.392 | 56.685 | 42.343 | 1.00 | 76.17 |
| 2108 | C | LEU | B | 397 | 11.164 | 54.611 | 39.474 | 1.00 | 81.45 |
| 2109 | O | LEU | B | 397 | 10.563 | 54.056 | 38.555 | 1.00 | 82.48 |
| 2110 | N | THR | B | 398 | 11.848 | 53.945 | 40.403 | 1.00 | 78.89 |
| 2111 | CA | THR | B | 398 | 11.961 | 52.485 | 40.415 | 1.00 | 73.75 |
| 2112 | CB | THR | B | 398 | 13.407 | 52.038 | 40.124 | 1.00 | 74.29 |
| 2113 | OG1 | THR | B | 398 | 13.751 | 52.384 | 38.780 | 1.00 | 76.09 |
| 2114 | CG2 | THR | B | 398 | 13.556 | 50.537 | 40.311 | 1.00 | 75.66 |
| 2115 | C | THR | B | 398 | 11.553 | 51.900 | 41.765 | 1.00 | 70.41 |
| 2116 | O | THR | B | 398 | 11.937 | 52.417 | 42.814 | 1.00 | 70.26 |
| 2117 | N | VAL | B | 399 | 10.786 | 50.814 | 41.734 | 1.00 | 66.07 |
| 2118 | CA | VAL | B | 399 | 10.336 | 50.158 | 42.958 | 1.00 | 62.76 |
| 2119 | CB | VAL | B | 399 | 8.849 | 50.476 | 43.248 | 1.00 | 62.17 |
| 2120 | CG1 | VAL | B | 399 | 8.309 | 49.558 | 44.337 | 1.00 | 62.14 |
| 2121 | CG2 | VAL | B | 399 | 8.711 | 51.923 | 43.683 | 1.00 | 63.51 |
| 2122 | C | VAL | B | 399 | 10.504 | 48.648 | 42.887 | 1.00 | 60.81 |
| 2123 | O | VAL | B | 399 | 9.948 | 48.002 | 42.006 | 1.00 | 59.47 |
| 2124 | N | THR | B | 400 | 11.271 | 48.087 | 43.816 | 1.00 | 57.40 |
| 2125 | CA | THR | B | 400 | 11.482 | 46.642 | 43.852 | 1.00 | 56.38 |
| 2126 | CB | THR | B | 400 | 12.964 | 46.266 | 43.598 | 1.00 | 57.88 |
| 2127 | OG1 | THR | B | 400 | 13.772 | 46.749 | 44.672 | 1.00 | 59.20 |
| 2128 | CG2 | THR | B | 400 | 13.462 | 46.879 | 42.307 | 1.00 | 60.00 |
| 2129 | C | THR | B | 400 | 11.066 | 46.069 | 45.211 | 1.00 | 52.46 |
| 2130 | O | THR | B | 400 | 11.098 | 46.766 | 46.233 | 1.00 | 54.14 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2131 | N | SER | B | 401 | 10.672 | 44.800 | 45.211 | 1.00 | 48.42 |
| 2132 | CA | SER | B | 401 | 10.252 | 44.111 | 46.421 | 1.00 | 42.47 |
| 2133 | CB | SER | B | 401 | 8.730 | 44.189 | 46.571 | 1.00 | 40.90 |
| 2134 | OG | SER | B | 401 | 8.286 | 43.440 | 47.691 | 1.00 | 38.86 |
| 2135 | C | SER | B | 401 | 10.686 | 42.658 | 46.304 | 1.00 | 40.92 |
| 2136 | O | SER | B | 401 | 10.391 | 42.008 | 45.304 | 1.00 | 41.21 |
| 2137 | N | THR | B | 402 | 11.376 | 42.149 | 47.323 | 1.00 | 38.37 |
| 2138 | CA | THR | B | 402 | 11.868 | 40.775 | 47.316 | 1.00 | 37.62 |
| 2139 | CB | THR | B | 402 | 13.385 | 40.765 | 47.570 | 1.00 | 39.11 |
| 2140 | OG1 | THR | B | 402 | 14.013 | 41.661 | 46.643 | 1.00 | 38.03 |
| 2141 | CG2 | THR | B | 402 | 13.958 | 39.372 | 47.392 | 1.00 | 38.02 |
| 2142 | C | THR | B | 402 | 11.160 | 39.929 | 48.372 | 1.00 | 39.39 |
| 2143 | O | THR | B | 402 | 11.118 | 40.291 | 49.551 | 1.00 | 38.51 |
| 2144 | N | LEU | B | 403 | 10.608 | 38.797 | 47.950 | 1.00 | 37.81 |
| 2145 | CA | LEU | B | 403 | 9.878 | 37.935 | 48.866 | 1.00 | 37.60 |
| 2146 | CB | LEU | B | 403 | 8.450 | 37.711 | 48.345 | 1.00 | 37.65 |
| 2147 | CG | LEU | B | 403 | 7.593 | 36.701 | 49.127 | 1.00 | 37.14 |
| 2148 | CD1 | LEU | B | 403 | 7.029 | 37.352 | 50.384 | 1.00 | 35.41 |
| 2149 | CD2 | LEU | B | 403 | 6.458 | 36.210 | 48.259 | 1.00 | 37.90 |
| 2150 | C | LEU | B | 403 | 10.522 | 36.578 | 49.115 | 1.00 | 37.93 |
| 2151 | O | LEU | B | 403 | 10.784 | 35.829 | 48.173 | 1.00 | 36.18 |
| 2152 | N | PRO | B | 404 | 10.791 | 36.247 | 50.391 | 1.00 | 34.78 |
| 2153 | CD | PRO | B | 404 | 10.848 | 37.198 | 51.510 | 1.00 | 36.88 |
| 2154 | CA | PRO | B | 404 | 11.395 | 34.969 | 50.782 | 1.00 | 35.08 |
| 2155 | CB | PRO | B | 404 | 11.650 | 35.144 | 52.277 | 1.00 | 35.30 |
| 2156 | CG | PRO | B | 404 | 11.928 | 36.579 | 52.390 | 1.00 | 37.24 |
| 2157 | C | PRO | B | 404 | 10.370 | 33.878 | 50.514 | 1.00 | 35.55 |
| 2158 | O | PRO | B | 404 | 9.173 | 34.115 | 50.653 | 1.00 | 32.96 |
| 2159 | N | VAL | B | 405 | 10.834 | 32.684 | 50.161 | 1.00 | 34.85 |
| 2160 | CA | VAL | B | 405 | 9.930 | 31.586 | 49.848 | 1.00 | 34.76 |
| 2161 | CB | VAL | B | 405 | 9.723 | 31.526 | 48.294 | 1.00 | 38.91 |
| 2162 | CG1 | VAL | B | 405 | 9.108 | 30.207 | 47.871 | 1.00 | 41.09 |
| 2163 | CG2 | VAL | B | 405 | 8.833 | 32.670 | 47.857 | 1.00 | 38.31 |
| 2164 | C | VAL | B | 405 | 10.381 | 30.212 | 50.371 | 1.00 | 33.49 |
| 2165 | O | VAL | B | 405 | 11.574 | 29.938 | 50.507 | 1.00 | 31.98 |
| 2166 | N | GLY | B | 406 | 9.418 | 29.344 | 50.661 | 1.00 | 32.80 |
| 2167 | CA | GLY | B | 406 | 9.750 | 28.011 | 51.141 | 1.00 | 32.28 |
| 2168 | C | GLY | B | 406 | 10.404 | 27.134 | 50.077 | 1.00 | 35.10 |
| 2169 | O | GLY | B | 406 | 9.899 | 27.012 | 48.958 | 1.00 | 31.41 |
| 2170 | N | THR | B | 407 | 11.528 | 26.514 | 50.428 | 1.00 | 37.28 |
| 2171 | CA | THR | B | 407 | 12.256 | 25.642 | 49.513 | 1.00 | 40.04 |
| 2172 | CB | THR | B | 407 | 13.537 | 25.093 | 50.165 | 1.00 | 41.31 |
| 2173 | OG1 | THR | B | 407 | 14.165 | 26.118 | 50.941 | 1.00 | 42.62 |
| 2174 | CG2 | THR | B | 407 | 14.509 | 24.639 | 49.093 | 1.00 | 45.50 |
| 2175 | C | THR | B | 407 | 11.404 | 24.449 | 49.064 | 1.00 | 41.62 |
| 2176 | O | THR | B | 407 | 11.378 | 24.094 | 47.876 | 1.00 | 41.84 |
| 2177 | N | ARG | B | 408 | 10.705 | 23.825 | 50.007 | 1.00 | 41.75 |
| 2178 | CA | ARG | B | 408 | 9.874 | 22.681 | 49.662 | 1.00 | 43.39 |
| 2179 | CB | ARG | B | 408 | 9.456 | 21.925 | 50.919 | 1.00 | 47.02 |
| 2180 | CG | ARG | B | 408 | 8.879 | 20.549 | 50.624 | 1.00 | 56.32 |
| 2181 | CD | ARG | B | 408 | 8.243 | 19.949 | 51.864 | 1.00 | 63.99 |
| 2182 | NE | ARG | B | 408 | 7.788 | 18.582 | 51.646 | 1.00 | 70.99 |
| 2183 | CZ | ARG | B | 408 | 6.934 | 17.947 | 52.444 | 1.00 | 75.42 |
| 2184 | NH1 | ARG | B | 408 | 6.440 | 18.560 | 53.512 | 1.00 | 78.24 |
| 2185 | NH2 | ARG | B | 408 | 6.579 | 16.696 | 52.177 | 1.00 | 78.08 |
| 2186 | C | ARG | B | 408 | 8.635 | 23.140 | 48.888 | 1.00 | 41.55 |
| 2187 | O | ARG | B | 408 | 8.156 | 22.448 | 47.988 | 1.00 | 40.10 |
| 2188 | N | ASP | B | 409 | 8.122 | 24.314 | 49.230 | 1.00 | 39.85 |
| 2189 | CA | ASP | B | 409 | 6.960 | 24.847 | 48.539 | 1.00 | 38.90 |
| 2190 | CB | ASP | B | 409 | 6.489 | 26.139 | 49.218 | 1.00 | 41.66 |
| 2191 | CG | ASP | B | 409 | 6.037 | 25.911 | 50.666 | 1.00 | 44.67 |
| 2192 | OD1 | ASP | B | 409 | 5.772 | 24.745 | 51.032 | 1.00 | 45.71 |
| 2193 | OD2 | ASP | B | 409 | 5.935 | 26.893 | 51.435 | 1.00 | 45.00 |
| 2194 | C | ASP | B | 409 | 7.280 | 25.100 | 47.057 | 1.00 | 38.36 |
| 2195 | O | ASP | B | 409 | 6.490 | 24.745 | 46.173 | 1.00 | 38.22 |
| 2196 | N | TRP | B | 410 | 8.440 | 25.688 | 46.774 | 1.00 | 36.80 |
| 2197 | CA | TRP | B | 410 | 8.812 | 25.962 | 45.383 | 1.00 | 35.16 |
| 2198 | CB | TRP | B | 410 | 10.061 | 26.855 | 45.321 | 1.00 | 32.94 |
| 2199 | CG | TRP | B | 410 | 10.457 | 27.228 | 43.927 | 1.00 | 28.69 |
| 2200 | CD2 | TRP | B | 410 | 9.987 | 28.357 | 43.172 | 1.00 | 28.25 |
| 2201 | CE2 | TRP | B | 410 | 10.520 | 28.237 | 41.864 | 1.00 | 27.55 |
| 2202 | CE3 | TRP | B | 410 | 9.167 | 29.456 | 43.470 | 1.00 | 28.96 |
| 2203 | CD1 | TRP | B | 410 | 11.244 | 26.500 | 43.074 | 1.00 | 28.30 |
| 2204 | NE1 | TRP | B | 410 | 11.282 | 27.100 | 41.836 | 1.00 | 25.74 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2205 | CZ2 | TRP | B | 410 | 10.257 | 29.177 | 40.852 | 1.00 | 29.09 |
| 2206 | CZ3 | TRP | B | 410 | 8.905 | 30.400 | 42.461 | 1.00 | 30.52 |
| 2207 | CH2 | TRP | B | 410 | 9.452 | 30.249 | 41.167 | 1.00 | 29.99 |
| 2208 | C | TRP | B | 410 | 9.041 | 24.659 | 44.608 | 1.00 | 35.39 |
| 2209 | O | TRP | B | 410 | 8.485 | 24.460 | 43.523 | 1.00 | 31.79 |
| 2210 | N | ILE | B | 411 | 9.837 | 23.764 | 45.183 | 1.00 | 38.31 |
| 2211 | CA | ILE | B | 411 | 10.137 | 22.487 | 44.547 | 1.00 | 42.04 |
| 2212 | CB | ILE | B | 411 | 11.087 | 21.651 | 45.425 | 1.00 | 43.35 |
| 2213 | CG2 | ILE | B | 411 | 11.362 | 20.301 | 44.767 | 1.00 | 43.71 |
| 2214 | CG1 | ILE | B | 411 | 12.389 | 22.421 | 45.651 | 1.00 | 44.86 |
| 2215 | CD1 | ILE | B | 411 | 13.077 | 22.842 | 44.371 | 1.00 | 46.76 |
| 2216 | C | ILE | B | 411 | 8.893 | 21.656 | 44.224 | 1.00 | 42.85 |
| 2217 | O | ILE | B | 411 | 8.926 | 20.813 | 43.335 | 1.00 | 43.40 |
| 2218 | N | GLU | B | 412 | 7.797 | 21.886 | 44.941 | 1.00 | 46.52 |
| 2219 | CA | GLU | B | 412 | 6.565 | 21.136 | 44.691 | 1.00 | 48.27 |
| 2220 | CB | GLU | B | 412 | 5.979 | 20.637 | 46.019 | 1.00 | 52.70 |
| 2221 | CG | GLU | B | 412 | 6.684 | 19.380 | 46.542 | 1.00 | 58.95 |
| 2222 | CD | GLU | B | 412 | 6.320 | 19.024 | 47.979 | 1.00 | 61.95 |
| 2223 | OE1 | GLU | B | 412 | 5.173 | 19.282 | 48.389 | 1.00 | 63.04 |
| 2224 | OE2 | GLU | B | 412 | 7.183 | 18.466 | 48.695 | 1.00 | 64.65 |
| 2225 | C | GLU | B | 412 | 5.496 | 21.863 | 43.857 | 1.00 | 47.49 |
| 2226 | O | GLU | B | 412 | 4.324 | 21.482 | 43.870 | 1.00 | 49.31 |
| 2227 | N | GLY | B | 413 | 5.893 | 22.921 | 43.149 | 1.00 | 46.24 |
| 2228 | CA | GLY | B | 413 | 4.968 | 23.614 | 42.264 | 1.00 | 42.41 |
| 2229 | C | GLY | B | 413 | 4.073 | 24.778 | 42.665 | 1.00 | 41.17 |
| 2230 | O | GLY | B | 413 | 3.195 | 25.143 | 41.882 | 1.00 | 40.16 |
| 2231 | N | GLU | B | 414 | 4.260 | 25.371 | 43.841 | 1.00 | 37.45 |
| 2232 | CA | GLU | B | 414 | 3.411 | 26.502 | 44.221 | 1.00 | 34.92 |
| 2233 | CB | GLU | B | 414 | 3.758 | 27.020 | 45.629 | 1.00 | 34.62 |
| 2234 | CG | GLU | B | 414 | 3.029 | 28.316 | 46.022 | 1.00 | 32.60 |
| 2235 | CD | GLU | B | 414 | 1.523 | 28.113 | 46.321 | 1.00 | 37.39 |
| 2236 | OE1 | GLU | B | 414 | 0.695 | 28.069 | 45.379 | 1.00 | 36.34 |
| 2237 | OE2 | GLU | B | 414 | 1.167 | 27.985 | 47.513 | 1.00 | 34.90 |
| 2238 | C | GLU | B | 414 | 3.563 | 27.660 | 43.235 | 1.00 | 32.58 |
| 2239 | O | GLU | B | 414 | 4.638 | 27.868 | 42.682 | 1.00 | 28.17 |
| 2240 | N | THR | B | 415 | 2.479 | 28.408 | 43.036 | 1.00 | 31.56 |
| 2241 | CA | THR | B | 415 | 2.471 | 29.576 | 42.150 | 1.00 | 32.89 |
| 2242 | CB | THR | B | 415 | 1.268 | 29.542 | 41.173 | 1.00 | 35.97 |
| 2243 | OG1 | THR | B | 415 | 1.333 | 28.361 | 40.356 | 1.00 | 40.58 |
| 2244 | CG2 | THR | B | 415 | 1.271 | 30.782 | 40.302 | 1.00 | 36.62 |
| 2245 | C | THR | B | 415 | 2.361 | 30.870 | 42.968 | 1.00 | 32.31 |
| 2246 | O | THR | B | 415 | 1.484 | 30.987 | 43.833 | 1.00 | 31.06 |
| 2247 | N | TYR | B | 416 | 3.232 | 31.839 | 42.680 | 1.00 | 34.14 |
| 2248 | CA | TYR | B | 416 | 3.243 | 33.137 | 43.383 | 1.00 | 32.15 |
| 2249 | CB | TYR | B | 416 | 4.623 | 33.385 | 43.997 | 1.00 | 33.41 |
| 2250 | CG | TYR | B | 416 | 5.102 | 32.289 | 44.920 | 1.00 | 33.04 |
| 2251 | CD1 | TYR | B | 416 | 5.493 | 31.054 | 44.415 | 1.00 | 33.89 |
| 2252 | CE1 | TYR | B | 416 | 5.914 | 30.028 | 45.258 | 1.00 | 35.66 |
| 2253 | CD2 | TYR | B | 416 | 5.143 | 32.480 | 46.307 | 1.00 | 34.91 |
| 2254 | CE2 | TYR | B | 416 | 5.562 | 31.454 | 47.171 | 1.00 | 33.08 |
| 2255 | CZ | TYR | B | 416 | 5.941 | 30.235 | 46.637 | 1.00 | 34.19 |
| 2256 | OH | TYR | B | 416 | 6.329 | 29.204 | 47.454 | 1.00 | 31.77 |
| 2257 | C | TYR | B | 416 | 2.880 | 34.318 | 42.474 | 1.00 | 34.75 |
| 2258 | O | TYR | B | 416 | 3.217 | 34.312 | 41.289 | 1.00 | 35.26 |
| 2259 | N | GLN | B | 417 | 2.226 | 35.341 | 43.029 | 1.00 | 39.82 |
| 2260 | CA | GLN | B | 417 | 1.808 | 36.507 | 42.237 | 1.00 | 46.38 |
| 2261 | CB | GLN | B | 417 | 0.307 | 36.420 | 41.924 | 1.00 | 53.45 |
| 2262 | CG | GLN | B | 417 | −0.215 | 37.633 | 41.141 | 1.00 | 65.54 |
| 2263 | CD | GLN | B | 417 | −1.730 | 37.685 | 41.025 | 1.00 | 72.20 |
| 2264 | OE1 | GLN | B | 417 | −2.439 | 37.874 | 42.017 | 1.00 | 76.21 |
| 2265 | NE2 | GLN | B | 417 | −2.234 | 37.523 | 39.804 | 1.00 | 75.54 |
| 2266 | C | GLN | B | 417 | 2.077 | 37.903 | 42.816 | 1.00 | 47.32 |
| 2267 | O | GLN | B | 417 | 1.948 | 38.132 | 44.018 | 1.00 | 45.04 |
| 2268 | N | CYS | B | 418 | 2.419 | 38.836 | 41.926 | 1.00 | 48.94 |
| 2269 | CA | CYS | B | 418 | 2.678 | 40.232 | 42.281 | 1.00 | 51.86 |
| 2270 | C | CYS | B | 418 | 1.572 | 41.094 | 41.650 | 1.00 | 55.11 |
| 2271 | O | CYS | B | 418 | 1.418 | 41.118 | 40.424 | 1.00 | 54.35 |
| 2272 | CB | CYS | B | 418 | 4.055 | 40.680 | 41.741 | 1.00 | 50.61 |
| 2273 | SG | CYS | B | 418 | 4.586 | 42.368 | 42.231 | 1.00 | 51.86 |
| 2274 | N | ARG | B | 419 | 0.797 | 41.787 | 42.481 | 1.00 | 58.74 |
| 2275 | CA | ARG | B | 419 | −0.279 | 42.652 | 41.982 | 1.00 | 63.02 |
| 2276 | CB | ARG | B | 419 | −1.569 | 42.435 | 42.780 | 1.00 | 67.75 |
| 2277 | CG | ARG | B | 419 | −2.742 | 43.280 | 42.294 | 1.00 | 74.96 |
| 2278 | CD | ARG | B | 419 | −3.972 | 43.114 | 43.181 | 1.00 | 82.08 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2279 | NE | ARG | B | 419 | −5.131 | 43.846 | 42.668 | 1.00 | 87.00 |
| 2280 | CZ | ARG | B | 419 | −5.804 | 43.514 | 41.569 | 1.00 | 89.34 |
| 2281 | NH1 | ARG | B | 419 | −5.446 | 42.455 | 40.857 | 1.00 | 90.61 |
| 2282 | NH2 | ARG | B | 419 | −6.834 | 44.250 | 41.175 | 1.00 | 90.50 |
| 2283 | C | ARG | B | 419 | 0.143 | 44.111 | 42.103 | 1.00 | 62.28 |
| 2284 | O | ARG | B | 419 | 0.492 | 44.564 | 43.188 | 1.00 | 62.36 |
| 2285 | N | VAL | B | 420 | 0.109 | 44.841 | 40.993 | 1.00 | 63.48 |
| 2286 | CA | VAL | B | 420 | 0.503 | 46.247 | 40.986 | 1.00 | 64.99 |
| 2287 | CB | VAL | B | 420 | 1.472 | 46.541 | 39.839 | 1.00 | 63.32 |
| 2288 | CG1 | VAL | B | 420 | 1.941 | 47.981 | 39.921 | 1.00 | 61.93 |
| 2289 | CG2 | VAL | B | 420 | 2.646 | 45.585 | 39.896 | 1.00 | 62.65 |
| 2290 | C | VAL | B | 420 | −0.692 | 47.186 | 40.848 | 1.00 | 69.15 |
| 2291 | O | VAL | B | 420 | −1.636 | 46.899 | 40.112 | 1.00 | 67.47 |
| 2292 | N | THR | B | 421 | −0.634 | 48.320 | 41.545 | 1.00 | 74.54 |
| 2293 | CA | THR | B | 421 | −1.721 | 49.294 | 41.516 | 1.00 | 80.25 |
| 2294 | CB | THR | B | 421 | −2.789 | 48.953 | 42.585 | 1.00 | 80.64 |
| 2295 | OG1 | THR | B | 421 | −3.329 | 47.651 | 42.330 | 1.00 | 80.31 |
| 2296 | CG2 | THR | B | 421 | −3.911 | 49.978 | 42.570 | 1.00 | 80.42 |
| 2297 | C | THR | B | 421 | −1.268 | 50.737 | 41.759 | 1.00 | 87.07 |
| 2298 | O | THR | B | 421 | −0.387 | 50.994 | 42.580 | 1.00 | 86.94 |
| 2299 | N | HIS | B | 422 | −1.884 | 51.667 | 41.033 | 1.00 | 97.95 |
| 2300 | CA | HIS | B | 422 | −1.609 | 53.097 | 41.165 | 1.00 | 108.73 |
| 2301 | CB | HIS | B | 422 | −0.306 | 53.491 | 40.462 | 1.00 | 115.40 |
| 2302 | CG | HIS | B | 422 | 0.107 | 54.912 | 40.714 | 1.00 | 125.23 |
| 2303 | CD2 | HIS | B | 422 | 1.196 | 55.428 | 41.332 | 1.00 | 129.46 |
| 2304 | ND1 | HIS | B | 422 | −0.658 | 55.991 | 40.324 | 1.00 | 129.31 |
| 2305 | CE1 | HIS | B | 422 | −0.058 | 57.110 | 40.691 | 1.00 | 132.34 |
| 2306 | NE2 | HIS | B | 422 | 1.069 | 56.797 | 41.305 | 1.00 | 132.22 |
| 2307 | C | HIS | B | 422 | −2.770 | 53.878 | 40.557 | 1.00 | 110.74 |
| 2308 | O | HIS | B | 422 | −3.174 | 53.626 | 39.418 | 1.00 | 110.82 |
| 2309 | N | PRO | B | 423 | −3.320 | 54.843 | 41.313 | 1.00 | 117.12 |
| 2310 | CD | PRO | B | 423 | −2.836 | 55.271 | 42.640 | 1.00 | 116.42 |
| 2311 | CA | PRO | B | 423 | −4.442 | 55.682 | 40.885 | 1.00 | 119.09 |
| 2312 | CB | PRO | B | 423 | −4.400 | 56.835 | 41.882 | 1.00 | 119.76 |
| 2313 | CG | PRO | B | 423 | −3.963 | 56.156 | 43.131 | 1.00 | 116.84 |
| 2314 | C | PRO | B | 423 | −4.394 | 56.165 | 39.433 | 1.00 | 125.00 |
| 2315 | O | PRO | B | 423 | −5.341 | 55.947 | 38.677 | 1.00 | 128.30 |
| 2316 | N | HIS | B | 424 | −3.291 | 56.807 | 39.051 | 1.00 | 134.40 |
| 2317 | CA | HIS | B | 424 | −3.120 | 57.352 | 37.701 | 1.00 | 139.82 |
| 2318 | CB | HIS | B | 424 | −1.635 | 57.384 | 37.320 | 1.00 | 148.83 |
| 2319 | CG | HIS | B | 424 | −1.330 | 58.276 | 36.154 | 1.00 | 160.69 |
| 2320 | CD2 | HIS | B | 424 | −0.854 | 57.999 | 34.917 | 1.00 | 165.67 |
| 2321 | ND1 | HIS | B | 424 | −1.525 | 59.641 | 36.191 | 1.00 | 165.83 |
| 2322 | CE1 | HIS | B | 424 | −1.181 | 60.165 | 35.027 | 1.00 | 168.95 |
| 2323 | NE2 | HIS | B | 424 | −0.771 | 59.190 | 34.237 | 1.00 | 168.96 |
| 2324 | C | HIS | B | 424 | −3.911 | 56.623 | 36.612 | 1.00 | 135.91 |
| 2325 | O | HIS | B | 424 | −4.972 | 57.090 | 36.198 | 1.00 | 136.48 |
| 2326 | N | LEU | B | 425 | −3.400 | 55.487 | 36.145 | 1.00 | 130.82 |
| 2327 | CA | LEU | B | 425 | −4.084 | 54.730 | 35.098 | 1.00 | 125.47 |
| 2328 | CB | LEU | B | 425 | −3.127 | 54.447 | 33.933 | 1.00 | 123.33 |
| 2329 | CG | LEU | B | 425 | −3.714 | 53.829 | 32.656 | 1.00 | 120.20 |
| 2330 | CD1 | LEU | B | 425 | −4.701 | 54.799 | 32.017 | 1.00 | 118.27 |
| 2331 | CD2 | LEU | B | 425 | −2.592 | 53.509 | 31.676 | 1.00 | 118.26 |
| 2332 | C | LEU | B | 425 | −4.650 | 53.415 | 35.627 | 1.00 | 124.33 |
| 2333 | O | LEU | B | 425 | −3.986 | 52.697 | 36.376 | 1.00 | 123.75 |
| 2334 | N | PRO | B | 426 | −5.898 | 53.091 | 35.248 | 1.00 | 123.63 |
| 2335 | CD | PRO | B | 426 | −6.820 | 53.923 | 34.453 | 1.00 | 121.82 |
| 2336 | CA | PRO | B | 426 | −6.559 | 51.859 | 35.681 | 1.00 | 124.76 |
| 2337 | CB | PRO | B | 426 | −8.026 | 52.143 | 35.391 | 1.00 | 122.33 |
| 2338 | CG | PRO | B | 426 | −7.944 | 52.957 | 34.142 | 1.00 | 120.97 |
| 2339 | C | PRO | B | 426 | −6.039 | 50.664 | 34.897 | 1.00 | 127.24 |
| 2340 | O | PRO | B | 426 | −6.347 | 50.505 | 33.717 | 1.00 | 126.79 |
| 2341 | N | ALA | B | 427 | −5.245 | 49.831 | 35.556 | 1.00 | 127.76 |
| 2342 | CA | ALA | B | 427 | −4.679 | 48.655 | 34.912 | 1.00 | 129.66 |
| 2343 | CB | ALA | B | 427 | −3.699 | 49.080 | 33.822 | 1.00 | 134.49 |
| 2344 | C | ALA | B | 427 | −3.972 | 47.785 | 35.939 | 1.00 | 126.95 |
| 2345 | O | ALA | B | 427 | −2.743 | 47.771 | 36.013 | 1.00 | 129.40 |
| 2346 | N | ALA | B | 428 | −4.752 | 47.061 | 36.735 | 1.00 | 119.37 |
| 2347 | CA | ALA | B | 428 | −4.187 | 46.193 | 37.755 | 1.00 | 107.56 |
| 2348 | CB | ALA | B | 428 | −5.298 | 45.439 | 38.471 | 1.00 | 110.32 |
| 2349 | C | ALA | B | 428 | −3.205 | 45.212 | 37.128 | 1.00 | 98.80 |
| 2350 | O | ALA | B | 428 | −3.605 | 44.174 | 36.602 | 1.00 | 99.77 |
| 2351 | N | LEU | B | 429 | −1.921 | 45.554 | 37.171 | 1.00 | 91.04 |
| 2352 | CA | LEU | B | 429 | −0.885 | 44.688 | 36.622 | 1.00 | 79.58 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2353 | CB | LEU | B | 429 | 0.462 | 45.413 | 36.580 | 1.00 | 77.80 |
| 2354 | CG | LEU | B | 429 | 0.591 | 46.556 | 35.576 | 1.00 | 77.77 |
| 2355 | CD1 | LEU | B | 429 | 1.992 | 47.142 | 35.646 | 1.00 | 77.33 |
| 2356 | CD2 | LEU | B | 429 | 0.303 | 46.033 | 34.177 | 1.00 | 77.63 |
| 2357 | C | LEU | B | 429 | −0.760 | 43.443 | 37.488 | 1.00 | 74.25 |
| 2358 | O | LEU | B | 429 | −0.702 | 43.526 | 38.714 | 1.00 | 69.97 |
| 2359 | N | MET | B | 430 | −0.726 | 42.287 | 36.840 | 1.00 | 69.37 |
| 2360 | CA | MET | B | 430 | −0.608 | 41.025 | 37.546 | 1.00 | 67.15 |
| 2361 | CB | MET | B | 430 | −1.938 | 40.277 | 37.503 | 1.00 | 73.72 |
| 2362 | CG | MET | B | 430 | −3.093 | 41.051 | 38.112 | 1.00 | 84.31 |
| 2363 | SD | MET | B | 430 | −4.644 | 40.124 | 38.094 | 1.00 | 93.30 |
| 2364 | CE | MET | B | 430 | −5.314 | 40.590 | 36.470 | 1.00 | 97.77 |
| 2365 | C | MET | B | 430 | 0.481 | 40.190 | 36.896 | 1.00 | 62.10 |
| 2366 | O | MET | B | 430 | 0.560 | 40.107 | 35.671 | 1.00 | 60.18 |
| 2367 | N | ARG | B | 431 | 1.326 | 39.584 | 37.725 | 1.00 | 56.31 |
| 2368 | CA | ARG | B | 431 | 2.424 | 38.747 | 37.248 | 1.00 | 50.29 |
| 2369 | CB | ARG | B | 431 | 3.755 | 39.497 | 37.342 | 1.00 | 51.82 |
| 2370 | CG | ARG | B | 431 | 3.759 | 40.852 | 36.677 | 1.00 | 53.25 |
| 2371 | CD | ARG | B | 431 | 3.833 | 40.743 | 35.166 | 1.00 | 56.77 |
| 2372 | NE | ARG | B | 431 | 3.134 | 41.861 | 34.547 | 1.00 | 60.75 |
| 2373 | CZ | ARG | B | 431 | 3.280 | 42.228 | 33.285 | 1.00 | 62.79 |
| 2374 | NH1 | ARG | B | 431 | 4.113 | 41.563 | 32.497 | 1.00 | 66.12 |
| 2375 | NH2 | ARG | B | 431 | 2.591 | 43.258 | 32.816 | 1.00 | 64.40 |
| 2376 | C | ARG | B | 431 | 2.496 | 37.512 | 38.130 | 1.00 | 45.72 |
| 2377 | O | ARG | B | 431 | 2.219 | 37.585 | 39.322 | 1.00 | 45.83 |
| 2378 | N | SER | B | 432 | 2.866 | 36.382 | 37.544 | 1.00 | 42.50 |
| 2379 | CA | SER | B | 432 | 2.981 | 35.149 | 38.303 | 1.00 | 40.29 |
| 2380 | CB | SER | B | 432 | 1.701 | 34.315 | 38.169 | 1.00 | 40.95 |
| 2381 | OG | SER | B | 432 | 1.434 | 33.977 | 36.822 | 1.00 | 44.53 |
| 2382 | C | SER | B | 432 | 4.195 | 34.348 | 37.851 | 1.00 | 37.91 |
| 2383 | O | SER | B | 432 | 4.657 | 34.505 | 36.722 | 1.00 | 36.61 |
| 2384 | N | THR | B | 433 | 4.710 | 33.500 | 38.744 | 1.00 | 34.99 |
| 2385 | CA | THR | B | 433 | 5.886 | 32.673 | 38.464 | 1.00 | 30.97 |
| 2386 | CB | THR | B | 433 | 7.179 | 33.438 | 38.855 | 1.00 | 31.18 |
| 2387 | OG1 | THR | B | 433 | 8.322 | 32.609 | 38.622 | 1.00 | 34.23 |
| 2388 | CG2 | THR | B | 433 | 7.149 | 33.841 | 40.334 | 1.00 | 31.96 |
| 2389 | C | THR | B | 433 | 5.819 | 31.325 | 39.211 | 1.00 | 31.66 |
| 2390 | O | THR | B | 433 | 5.276 | 31.248 | 40.320 | 1.00 | 32.46 |
| 2391 | N | THR | B | 434 | 6.360 | 30.268 | 38.601 | 1.00 | 30.64 |
| 2392 | CA | THR | B | 434 | 6.350 | 28.910 | 39.180 | 1.00 | 29.29 |
| 2393 | CB | THR | B | 434 | 4.961 | 28.224 | 38.979 | 1.00 | 32.47 |
| 2394 | OG1 | THR | B | 434 | 4.945 | 26.948 | 39.636 | 1.00 | 30.56 |
| 2395 | CG2 | THR | B | 434 | 4.673 | 28.005 | 37.470 | 1.00 | 32.95 |
| 2396 | C | THR | B | 434 | 7.412 | 28.034 | 38.521 | 1.00 | 28.34 |
| 2397 | O | THR | B | 434 | 7.967 | 28.407 | 37.490 | 1.00 | 30.37 |
| 2398 | N | LYS | B | 435 | 7.692 | 26.870 | 39.098 | 1.00 | 26.85 |
| 2399 | CA | LYS | B | 435 | 8.702 | 25.964 | 38.533 | 1.00 | 29.41 |
| 2400 | CB | LYS | B | 435 | 8.941 | 24.790 | 39.485 | 1.00 | 31.14 |
| 2401 | CG | LYS | B | 435 | 10.274 | 24.088 | 39.283 | 1.00 | 31.68 |
| 2402 | CD | LYS | B | 435 | 10.436 | 22.957 | 40.306 | 1.00 | 38.69 |
| 2403 | CE | LYS | B | 435 | 11.769 | 22.234 | 40.157 | 1.00 | 43.14 |
| 2404 | NZ | LYS | B | 435 | 12.932 | 23.067 | 40.631 | 1.00 | 48.29 |
| 2405 | C | LYS | B | 435 | 8.215 | 25.431 | 37.172 | 1.00 | 31.57 |
| 2406 | O | LYS | B | 435 | 7.041 | 25.064 | 37.041 | 1.00 | 25.22 |
| 2407 | N | THR | B | 436 | 9.111 | 25.352 | 36.181 | 1.00 | 33.78 |
| 2408 | CA | THR | B | 436 | 8.730 | 24.913 | 34.833 | 1.00 | 38.76 |
| 2409 | CB | THR | B | 436 | 9.870 | 25.199 | 33.802 | 1.00 | 45.57 |
| 2410 | OG1 | THR | B | 436 | 10.986 | 24.327 | 34.046 | 1.00 | 51.78 |
| 2411 | CG2 | THR | B | 436 | 10.336 | 26.654 | 33.912 | 1.00 | 51.84 |
| 2412 | C | THR | B | 436 | 8.318 | 23.441 | 34.682 | 1.00 | 37.31 |
| 2413 | O | THR | B | 436 | 8.862 | 22.576 | 35.343 | 1.00 | 37.14 |
| 2414 | N | SER | B | 437 | 7.350 | 23.177 | 33.803 | 1.00 | 34.85 |
| 2415 | CA | SER | B | 437 | 6.884 | 21.818 | 33.526 | 1.00 | 32.26 |
| 2416 | CB | SER | B | 437 | 5.381 | 21.671 | 33.833 | 1.00 | 31.32 |
| 2417 | OG | SER | B | 437 | 4.613 | 22.761 | 33.354 | 1.00 | 26.09 |
| 2418 | C | SER | B | 437 | 7.167 | 21.399 | 32.074 | 1.00 | 33.16 |
| 2419 | O | SER | B | 437 | 6.607 | 20.408 | 31.571 | 1.00 | 30.64 |
| 2420 | N | GLY | B | 438 | 8.060 | 22.148 | 31.427 | 1.00 | 35.50 |
| 2421 | CA | GLY | B | 438 | 8.456 | 21.882 | 30.049 | 1.00 | 36.32 |
| 2422 | C | GLY | B | 438 | 9.774 | 21.124 | 29.922 | 1.00 | 36.63 |
| 2423 | O | GLY | B | 438 | 10.229 | 20.531 | 30.895 | 1.00 | 37.59 |
| 2424 | N | PRO | B | 439 | 10.423 | 21.139 | 28.740 | 1.00 | 36.53 |
| 2425 | CD | PRO | B | 439 | 9.943 | 21.897 | 27.572 | 1.00 | 36.22 |
| 2426 | CA | PRO | B | 439 | 11.699 | 20.459 | 28.436 | 1.00 | 35.51 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2427 | CB | PRO | B | 439 | 11.975 | 20.858 | 26.981 | 1.00 | 36.84 |
| 2428 | CG | PRO | B | 439 | 10.605 | 21.158 | 26.424 | 1.00 | 39.52 |
| 2429 | C | PRO | B | 439 | 12.889 | 20.813 | 29.336 | 1.00 | 35.92 |
| 2430 | O | PRO | B | 439 | 13.103 | 21.986 | 29.639 | 1.00 | 33.89 |
| 2431 | N | ARG | B | 440 | 13.669 | 19.797 | 29.728 | 1.00 | 36.27 |
| 2432 | CA | ARG | B | 440 | 14.865 | 19.972 | 30.584 | 1.00 | 37.67 |
| 2433 | CB | ARG | B | 440 | 14.662 | 19.363 | 31.975 | 1.00 | 45.66 |
| 2434 | CG | ARG | B | 440 | 13.400 | 19.685 | 32.721 | 1.00 | 59.44 |
| 2435 | CD | ARG | B | 440 | 13.262 | 18.669 | 33.855 | 1.00 | 70.06 |
| 2436 | NE | ARG | B | 440 | 12.110 | 18.924 | 34.713 | 1.00 | 80.41 |
| 2437 | CZ | ARG | B | 440 | 10.844 | 18.914 | 34.306 | 1.00 | 85.12 |
| 2438 | NH1 | ARG | B | 440 | 10.538 | 18.659 | 33.039 | 1.00 | 87.59 |
| 2439 | NH2 | ARG | B | 440 | 9.877 | 19.170 | 35.174 | 1.00 | 88.35 |
| 2440 | C | ARG | B | 440 | 16.103 | 19.250 | 30.012 | 1.00 | 33.66 |
| 2441 | O | ARG | B | 440 | 15.969 | 18.242 | 29.308 | 1.00 | 31.08 |
| 2442 | N | ALA | B | 441 | 17.296 | 19.734 | 30.372 | 1.00 | 27.01 |
| 2443 | CA | ALA | B | 441 | 18.556 | 19.114 | 29.953 | 1.00 | 24.69 |
| 2444 | CB | ALA | B | 441 | 18.830 | 19.399 | 28.471 | 1.00 | 18.86 |
| 2445 | C | ALA | B | 441 | 19.739 | 19.592 | 30.824 | 1.00 | 24.32 |
| 2446 | O | ALA | B | 441 | 19.928 | 20.803 | 31.035 | 1.00 | 25.55 |
| 2447 | N | ALA | B | 442 | 20.503 | 18.632 | 31.345 | 1.00 | 23.59 |
| 2448 | CA | ALA | B | 442 | 21.679 | 18.887 | 32.202 | 1.00 | 27.58 |
| 2449 | CB | ALA | B | 442 | 22.117 | 17.587 | 32.899 | 1.00 | 23.00 |
| 2450 | C | ALA | B | 442 | 22.873 | 19.484 | 31.440 | 1.00 | 28.37 |
| 2451 | O | ALA | B | 442 | 23.092 | 19.201 | 30.274 | 1.00 | 24.28 |
| 2452 | N | PRO | B | 443 | 23.670 | 20.323 | 32.111 | 1.00 | 29.30 |
| 2453 | CD | PRO | B | 443 | 23.388 | 20.978 | 33.404 | 1.00 | 30.32 |
| 2454 | CA | PRO | B | 443 | 24.829 | 20.938 | 31.446 | 1.00 | 28.08 |
| 2455 | CB | PRO | B | 443 | 25.112 | 22.166 | 32.308 | 1.00 | 31.14 |
| 2456 | CG | PRO | B | 443 | 24.717 | 21.697 | 33.695 | 1.00 | 30.16 |
| 2457 | C | PRO | B | 443 | 26.086 | 20.106 | 31.267 | 1.00 | 30.36 |
| 2458 | O | PRO | B | 443 | 26.383 | 19.221 | 32.074 | 1.00 | 28.83 |
| 2459 | N | GLU | B | 444 | 26.826 | 20.423 | 30.203 | 1.00 | 29.47 |
| 2460 | CA | GLU | B | 444 | 28.122 | 19.801 | 29.894 | 1.00 | 28.75 |
| 2461 | CB | GLU | B | 444 | 28.351 | 19.684 | 28.373 | 1.00 | 31.46 |
| 2462 | CG | GLU | B | 444 | 27.458 | 18.705 | 27.608 | 1.00 | 35.33 |
| 2463 | CD | GLU | B | 444 | 27.620 | 18.833 | 26.087 | 1.00 | 36.87 |
| 2464 | OE1 | GLU | B | 444 | 28.761 | 18.962 | 25.594 | 1.00 | 38.69 |
| 2465 | OE2 | GLU | B | 444 | 26.608 | 18.795 | 25.372 | 1.00 | 37.81 |
| 2466 | C | GLU | B | 444 | 29.136 | 20.812 | 30.446 | 1.00 | 28.88 |
| 2467 | O | GLU | B | 444 | 28.941 | 22.024 | 30.314 | 1.00 | 28.27 |
| 2468 | N | VAL | B | 445 | 30.229 | 20.330 | 31.019 | 1.00 | 26.65 |
| 2469 | CA | VAL | B | 445 | 31.230 | 21.224 | 31.601 | 1.00 | 23.30 |
| 2470 | CB | VAL | B | 445 | 31.155 | 21.147 | 33.152 | 1.00 | 24.69 |
| 2471 | CG1 | VAL | B | 445 | 32.218 | 22.020 | 33.775 | 1.00 | 17.05 |
| 2472 | CG2 | VAL | B | 445 | 29.729 | 21.517 | 33.635 | 1.00 | 20.29 |
| 2473 | C | VAL | B | 445 | 32.665 | 20.889 | 31.154 | 1.00 | 26.36 |
| 2474 | O | VAL | B | 445 | 33.058 | 19.721 | 31.160 | 1.00 | 27.17 |
| 2475 | N | TYR | B | 446 | 33.434 | 21.911 | 30.774 | 1.00 | 23.03 |
| 2476 | CA | TYR | B | 446 | 34.836 | 21.747 | 30.340 | 1.00 | 22.67 |
| 2477 | CB | TYR | B | 446 | 34.945 | 21.712 | 28.804 | 1.00 | 24.11 |
| 2478 | CG | TYR | B | 446 | 33.945 | 20.812 | 28.088 | 1.00 | 29.23 |
| 2479 | CD1 | TYR | B | 446 | 32.731 | 21.317 | 27.606 | 1.00 | 31.18 |
| 2480 | CE1 | TYR | B | 446 | 31.813 | 20.484 | 26.952 | 1.00 | 31.32 |
| 2481 | CD2 | TYR | B | 446 | 34.214 | 19.454 | 27.894 | 1.00 | 29.46 |
| 2482 | CE2 | TYR | B | 446 | 33.313 | 18.623 | 27.242 | 1.00 | 27.58 |
| 2483 | CZ | TYR | B | 446 | 32.121 | 19.136 | 26.781 | 1.00 | 30.16 |
| 2484 | OH | TYR | B | 446 | 31.225 | 18.295 | 26.177 | 1.00 | 31.91 |
| 2485 | C | TYR | B | 446 | 35.686 | 22.934 | 30.857 | 1.00 | 24.73 |
| 2486 | O | TYR | B | 446 | 35.286 | 24.103 | 30.738 | 1.00 | 24.49 |
| 2487 | N | ALA | B | 447 | 36.865 | 22.644 | 31.396 | 1.00 | 20.68 |
| 2488 | CA | ALA | B | 447 | 37.732 | 23.689 | 31.921 | 1.00 | 25.74 |
| 2489 | CB | ALA | B | 447 | 37.846 | 23.531 | 33.453 | 1.00 | 23.39 |
| 2490 | C | ALA | B | 447 | 39.124 | 23.652 | 31.267 | 1.00 | 25.17 |
| 2491 | O | ALA | B | 447 | 39.661 | 22.560 | 31.045 | 1.00 | 20.76 |
| 2492 | N | PHE | B | 448 | 39.678 | 24.835 | 30.949 | 1.00 | 22.06 |
| 2493 | CA | PHE | B | 448 | 41.007 | 24.967 | 30.317 | 1.00 | 23.67 |
| 2494 | CB | PHE | B | 448 | 40.876 | 25.423 | 28.852 | 1.00 | 27.73 |
| 2495 | CG | PHE | B | 448 | 39.855 | 24.667 | 28.041 | 1.00 | 27.94 |
| 2496 | CD1 | PHE | B | 448 | 38.568 | 25.170 | 27.879 | 1.00 | 29.01 |
| 2497 | CD2 | PHE | B | 448 | 40.191 | 23.465 | 27.415 | 1.00 | 30.43 |
| 2498 | CE1 | PHE | B | 448 | 37.616 | 24.487 | 27.096 | 1.00 | 32.13 |
| 2499 | CE2 | PHE | B | 448 | 39.251 | 22.772 | 26.631 | 1.00 | 32.13 |
| 2500 | CZ | PHE | B | 448 | 37.959 | 23.287 | 26.471 | 1.00 | 29.63 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2501 | C | PHE | B | 448 | 41.929 | 26.000 | 31.030 | 1.00 | 27.05 |
| 2502 | O | PHE | B | 448 | 41.475 | 26.779 | 31.867 | 1.00 | 23.90 |
| 2503 | N | ALA | B | 449 | 43.214 | 26.009 | 30.663 | 1.00 | 27.07 |
| 2504 | CA | ALA | B | 449 | 44.209 | 26.943 | 31.213 | 1.00 | 28.05 |
| 2505 | CB | ALA | B | 449 | 45.103 | 26.231 | 32.208 | 1.00 | 30.79 |
| 2506 | C | ALA | B | 449 | 45.065 | 27.521 | 30.077 | 1.00 | 28.93 |
| 2507 | O | ALA | B | 449 | 45.470 | 26.781 | 29.178 | 1.00 | 23.30 |
| 2508 | N | THR | B | 450 | 45.335 | 28.830 | 30.104 | 1.00 | 28.19 |
| 2509 | CA | THR | B | 450 | 46.141 | 29.428 | 29.042 | 1.00 | 29.71 |
| 2510 | CB | THR | B | 450 | 46.025 | 30.992 | 28.967 | 1.00 | 31.54 |
| 2511 | OG1 | THR | B | 450 | 46.612 | 31.590 | 30.139 | 1.00 | 31.48 |
| 2512 | CG2 | THR | B | 450 | 44.575 | 31.415 | 28.821 | 1.00 | 28.34 |
| 2513 | C | THR | B | 450 | 47.624 | 29.123 | 29.196 | 1.00 | 31.76 |
| 2514 | O | THR | B | 450 | 48.101 | 28.827 | 30.286 | 1.00 | 26.98 |
| 2515 | N | PRO | B | 451 | 48.364 | 29.170 | 28.082 | 1.00 | 37.78 |
| 2516 | CD | PRO | B | 451 | 47.828 | 29.223 | 26.712 | 1.00 | 35.03 |
| 2517 | CA | PRO | B | 451 | 49.810 | 28.917 | 28.075 | 1.00 | 38.76 |
| 2518 | CB | PRO | B | 451 | 50.117 | 28.626 | 26.603 | 1.00 | 37.51 |
| 2519 | CG | PRO | B | 451 | 48.767 | 28.317 | 25.990 | 1.00 | 37.88 |
| 2520 | C | PRO | B | 451 | 50.468 | 30.222 | 28.519 | 1.00 | 44.19 |
| 2521 | O | PRO | B | 451 | 49.775 | 31.215 | 28.781 | 1.00 | 46.04 |
| 2522 | N | ALA | B | 452 | 51.794 | 30.234 | 28.579 | 1.00 | 51.12 |
| 2523 | CA | ALA | B | 452 | 52.513 | 31.434 | 28.983 | 1.00 | 56.36 |
| 2524 | CB | ALA | B | 452 | 53.908 | 31.066 | 29.489 | 1.00 | 57.46 |
| 2525 | C | ALA | B | 452 | 52.625 | 32.414 | 27.817 | 1.00 | 58.32 |
| 2526 | O | ALA | B | 452 | 52.893 | 32.011 | 26.688 | 1.00 | 57.75 |
| 2527 | N | TRP | B | 453 | 52.405 | 33.696 | 28.096 | 1.00 | 60.40 |
| 2528 | CA | TRP | B | 453 | 52.519 | 34.740 | 27.077 | 1.00 | 64.53 |
| 2529 | CB | TRP | B | 453 | 51.306 | 35.671 | 27.118 | 1.00 | 60.33 |
| 2530 | CG | TRP | B | 453 | 51.216 | 36.627 | 25.958 | 1.00 | 57.32 |
| 2531 | CD2 | TRP | B | 453 | 50.636 | 36.366 | 24.666 | 1.00 | 56.15 |
| 2532 | CE2 | TRP | B | 453 | 50.761 | 37.551 | 23.902 | 1.00 | 55.78 |
| 2533 | CE3 | TRP | B | 453 | 50.023 | 35.246 | 24.080 | 1.00 | 54.53 |
| 2534 | CD1 | TRP | B | 453 | 51.658 | 37.922 | 25.922 | 1.00 | 56.85 |
| 2535 | NE1 | TRP | B | 453 | 51.386 | 38.484 | 24.691 | 1.00 | 55.58 |
| 2536 | CZ2 | TRP | B | 453 | 50.294 | 37.648 | 22.579 | 1.00 | 55.31 |
| 2537 | CZ3 | TRP | B | 453 | 49.558 | 35.341 | 22.765 | 1.00 | 53.66 |
| 2538 | CH2 | TRP | B | 453 | 49.698 | 36.536 | 22.031 | 1.00 | 54.84 |
| 2539 | C | TRP | B | 453 | 53.795 | 35.522 | 27.391 | 1.00 | 70.08 |
| 2540 | O | TRP | B | 453 | 54.028 | 35.907 | 28.539 | 1.00 | 69.83 |
| 2541 | N | PRO | B | 454 | 54.637 | 35.769 | 26.373 | 1.00 | 75.18 |
| 2542 | CD | PRO | B | 454 | 54.343 | 35.563 | 24.943 | 1.00 | 77.18 |
| 2543 | CA | PRO | B | 454 | 55.900 | 36.502 | 26.541 | 1.00 | 76.22 |
| 2544 | CB | PRO | B | 454 | 56.392 | 36.681 | 25.101 | 1.00 | 78.79 |
| 2545 | CG | PRO | B | 454 | 55.117 | 36.684 | 24.298 | 1.00 | 79.73 |
| 2546 | C | PRO | B | 454 | 55.800 | 37.825 | 27.299 | 1.00 | 74.44 |
| 2547 | O | PRO | B | 454 | 55.115 | 38.750 | 26.869 | 1.00 | 75.36 |
| 2548 | N | GLY | B | 455 | 56.486 | 37.900 | 28.435 | 1.00 | 74.15 |
| 2549 | CA | GLY | B | 455 | 56.465 | 39.115 | 29.224 | 1.00 | 72.72 |
| 2550 | C | GLY | B | 455 | 55.558 | 39.073 | 30.439 | 1.00 | 74.66 |
| 2551 | O | GLY | B | 455 | 55.297 | 40.107 | 31.054 | 1.00 | 72.02 |
| 2552 | N | SER | B | 456 | 55.068 | 37.891 | 30.795 | 1.00 | 75.21 |
| 2553 | CA | SER | B | 456 | 54.195 | 37.772 | 31.963 | 1.00 | 79.20 |
| 2554 | CB | SER | B | 456 | 52.799 | 38.315 | 31.642 | 1.00 | 83.88 |
| 2555 | OG | SER | B | 456 | 52.201 | 37.592 | 30.582 | 1.00 | 93.70 |
| 2556 | C | SER | B | 456 | 54.091 | 36.332 | 32.452 | 1.00 | 76.21 |
| 2557 | O | SER | B | 456 | 52.994 | 35.789 | 32.588 | 1.00 | 76.23 |
| 2558 | N | ARG | B | 457 | 55.242 | 35.727 | 32.731 | 1.00 | 72.82 |
| 2559 | CA | ARG | B | 457 | 55.293 | 34.350 | 33.197 | 1.00 | 67.54 |
| 2560 | CB | ARG | B | 457 | 56.716 | 33.798 | 33.059 | 1.00 | 70.74 |
| 2561 | CG | ARG | B | 457 | 57.819 | 34.734 | 33.545 | 1.00 | 74.97 |
| 2562 | CD | ARG | B | 457 | 59.107 | 33.967 | 33.803 | 1.00 | 77.91 |
| 2563 | NE | ARG | B | 457 | 59.117 | 33.370 | 35.137 | 1.00 | 80.09 |
| 2564 | CZ | ARG | B | 457 | 59.735 | 32.235 | 35.447 | 1.00 | 80.13 |
| 2565 | NH1 | ARG | B | 457 | 60.395 | 31.560 | 34.517 | 1.00 | 79.55 |
| 2566 | NN2 | ARG | B | 457 | 59.695 | 31.779 | 36.691 | 1.00 | 81.21 |
| 2567 | C | ARG | B | 457 | 54.794 | 34.132 | 34.626 | 1.00 | 63.19 |
| 2568 | O | ARG | B | 457 | 54.742 | 32.996 | 35.090 | 1.00 | 61.64 |
| 2569 | N | ASP | B | 458 | 54.415 | 35.200 | 35.323 | 1.00 | 60.01 |
| 2570 | CA | ASP | B | 458 | 53.924 | 35.043 | 36.690 | 1.00 | 56.62 |
| 2571 | CB | ASP | B | 458 | 54.594 | 36.060 | 37.617 | 1.00 | 58.21 |
| 2572 | CG | ASP | B | 458 | 56.091 | 35.821 | 37.759 | 1.00 | 59.85 |
| 2573 | OD1 | ASP | B | 458 | 56.491 | 34.696 | 38.135 | 1.00 | 58.67 |
| 2574 | OD2 | ASP | B | 458 | 56.866 | 36.762 | 37.495 | 1.00 | 62.08 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2575 | C | ASP | B | 458 | 52.403 | 35.146 | 36.818 | 1.00 | 55.95 |
| 2576 | O | ASP | B | 458 | 51.882 | 35.367 | 37.913 | 1.00 | 53.67 |
| 2577 | N | LYS | B | 459 | 51.697 | 34.971 | 35.701 | 1.00 | 56.52 |
| 2578 | CA | LYS | B | 459 | 50.232 | 35.024 | 35.681 | 1.00 | 57.72 |
| 2579 | CB | LYS | B | 459 | 49.751 | 36.473 | 35.565 | 1.00 | 65.07 |
| 2580 | CG | LYS | B | 459 | 49.940 | 37.275 | 36.844 | 1.00 | 79.03 |
| 2581 | CD | LYS | B | 459 | 49.356 | 38.677 | 36.737 | 1.00 | 90.91 |
| 2582 | CE | LYS | B | 459 | 49.470 | 39.426 | 38.067 | 1.00 | 98.40 |
| 2583 | NZ | LYS | B | 459 | 48.873 | 40.796 | 38.015 | 1.00 | 103.47 |
| 2584 | C | LYS | B | 459 | 49.625 | 34.191 | 34.553 | 1.00 | 54.10 |
| 2585 | O | LYS | B | 459 | 50.227 | 34.016 | 33.492 | 1.00 | 50.39 |
| 2586 | N | ARG | B | 460 | 48.422 | 33.678 | 34.791 | 1.00 | 50.40 |
| 2587 | CA | ARG | B | 460 | 47.727 | 32.857 | 33.804 | 1.00 | 47.33 |
| 2588 | CB | ARG | B | 460 | 48.075 | 31.384 | 34.031 | 1.00 | 52.39 |
| 2589 | CG | ARG | B | 460 | 49.553 | 31.076 | 33.897 | 1.00 | 58.51 |
| 2590 | CD | ARG | B | 460 | 49.813 | 30.190 | 32.704 | 1.00 | 63.61 |
| 2591 | NE | ARG | B | 460 | 51.233 | 29.946 | 32.494 | 1.00 | 68.85 |
| 2592 | CZ | ARG | B | 460 | 51.711 | 28.900 | 31.826 | 1.00 | 72.68 |
| 2593 | NH1 | ARG | B | 460 | 50.878 | 28.004 | 31.310 | 1.00 | 73.54 |
| 2594 | NH2 | ARG | B | 460 | 53.019 | 28.746 | 31.671 | 1.00 | 74.85 |
| 2595 | C | ARG | B | 460 | 46.217 | 33.047 | 33.915 | 1.00 | 42.60 |
| 2596 | O | ARG | B | 460 | 45.724 | 33.505 | 34.944 | 1.00 | 43.64 |
| 2597 | N | THR | B | 461 | 45.482 | 32.696 | 32.863 | 1.00 | 38.09 |
| 2598 | CA | THR | B | 461 | 44.025 | 32.831 | 32.885 | 1.00 | 32.37 |
| 2599 | CB | THR | B | 461 | 43.544 | 33.731 | 31.737 | 1.00 | 31.59 |
| 2600 | OG1 | THR | B | 461 | 44.355 | 34.910 | 31.683 | 1.00 | 32.13 |
| 2601 | CG2 | THR | B | 461 | 42.106 | 34.153 | 31.960 | 1.00 | 29.79 |
| 2602 | C | THR | B | 461 | 43.323 | 31.462 | 32.776 | 1.00 | 30.58 |
| 2603 | O | THR | B | 461 | 43.725 | 30.610 | 31.990 | 1.00 | 28.27 |
| 2604 | N | LEU | B | 462 | 42.295 | 31.252 | 33.592 | 1.00 | 28.28 |
| 2605 | CA | LEU | B | 462 | 41.541 | 29.999 | 33.565 | 1.00 | 28.66 |
| 2606 | CB | LEU | B | 462 | 41.362 | 29.445 | 34.986 | 1.00 | 29.15 |
| 2607 | CG | LEU | B | 462 | 42.644 | 29.198 | 35.790 | 1.00 | 27.04 |
| 2608 | CD1 | LEU | B | 462 | 42.284 | 28.422 | 37.047 | 1.00 | 29.72 |
| 2609 | CD2 | LEU | B | 462 | 43.647 | 28.416 | 34.971 | 1.00 | 26.72 |
| 2610 | C | LEU | B | 462 | 40.171 | 30.255 | 32.930 | 1.00 | 29.38 |
| 2611 | O | LEU | B | 462 | 39.538 | 31.281 | 33.202 | 1.00 | 27.86 |
| 2612 | N | ALA | B | 463 | 39.722 | 29.320 | 32.090 | 1.00 | 28.27 |
| 2613 | CA | ALA | B | 463 | 38.441 | 29.452 | 31.387 | 1.00 | 27.74 |
| 2614 | CB | ALA | B | 463 | 38.715 | 29.774 | 29.911 | 1.00 | 26.50 |
| 2615 | C | ALA | B | 463 | 37.554 | 28.207 | 31.489 | 1.00 | 26.62 |
| 2616 | O | ALA | B | 463 | 38.038 | 27.087 | 31.356 | 1.00 | 28.91 |
| 2617 | N | CYS | B | 464 | 36.255 | 28.414 | 31.700 | 1.00 | 23.55 |
| 2618 | CA | CYS | B | 464 | 35.287 | 27.319 | 31.820 | 1.00 | 25.62 |
| 2619 | C | CYS | B | 464 | 34.084 | 27.482 | 30.851 | 1.00 | 25.25 |
| 2620 | O | CYS | B | 464 | 33.426 | 28.529 | 30.873 | 1.00 | 21.55 |
| 2621 | CB | CYS | B | 464 | 34.757 | 27.273 | 33.261 | 1.00 | 23.82 |
| 2622 | SG | CYS | B | 464 | 33.715 | 25.846 | 33.714 | 1.00 | 27.28 |
| 2623 | N | LEU | B | 465 | 33.796 | 26.447 | 30.044 | 1.00 | 19.29 |
| 2624 | CA | LEU | B | 465 | 32.651 | 26.437 | 29.094 | 1.00 | 22.10 |
| 2625 | CB | LEU | B | 465 | 33.105 | 26.002 | 27.676 | 1.00 | 19.13 |
| 2626 | CG | LEU | B | 465 | 32.014 | 25.595 | 26.654 | 1.00 | 21.75 |
| 2627 | CD1 | LEU | B | 465 | 31.073 | 26.769 | 26.319 | 1.00 | 18.36 |
| 2628 | CD2 | LEU | B | 465 | 32.707 | 25.095 | 25.375 | 1.00 | 24.61 |
| 2629 | C | LEU | B | 465 | 31.550 | 25.489 | 29.610 | 1.00 | 20.01 |
| 2630 | O | LEU | B | 465 | 31.814 | 24.314 | 29.904 | 1.00 | 20.77 |
| 2631 | N | ILE | B | 466 | 30.331 | 26.006 | 29.712 | 1.00 | 19.04 |
| 2632 | CA | ILE | B | 466 | 29.162 | 25.272 | 30.229 | 1.00 | 22.33 |
| 2633 | CB | ILE | B | 466 | 28.705 | 25.916 | 31.559 | 1.00 | 23.56 |
| 2634 | CG2 | ILE | B | 466 | 27.507 | 25.167 | 32.153 | 1.00 | 24.73 |
| 2635 | CG1 | ILE | B | 466 | 29.898 | 25.935 | 32.532 | 1.00 | 28.73 |
| 2636 | CD1 | ILE | B | 466 | 29.726 | 26.836 | 33.734 | 1.00 | 30.06 |
| 2637 | C | ILE | B | 466 | 28.067 | 25.403 | 29.147 | 1.00 | 20.84 |
| 2638 | O | ILE | B | 466 | 27.655 | 26.536 | 28.807 | 1.00 | 17.14 |
| 2639 | N | GLN | B | 467 | 27.592 | 24.257 | 28.627 | 1.00 | 19.24 |
| 2640 | CA | GLN | B | 467 | 26.646 | 24.279 | 27.506 | 1.00 | 23.95 |
| 2641 | CB | GLN | B | 467 | 27.458 | 24.314 | 26.183 | 1.00 | 16.73 |
| 2642 | CG | GLN | B | 467 | 28.332 | 23.071 | 25.939 | 1.00 | 18.13 |
| 2643 | CD | GLN | B | 467 | 29.137 | 23.145 | 24.622 | 1.00 | 21.86 |
| 2644 | OE1 | GLN | B | 467 | 29.481 | 24.235 | 24.141 | 1.00 | 18.91 |
| 2645 | NE2 | GLN | B | 467 | 29.455 | 21.981 | 24.051 | 1.00 | 16.92 |
| 2646 | C | GLN | B | 467 | 25.567 | 23.190 | 27.382 | 1.00 | 22.83 |
| 2647 | O | GLN | B | 467 | 25.598 | 22.139 | 28.059 | 1.00 | 23.04 |
| 2648 | N | ASN | B | 468 | 24.615 | 23.473 | 26.486 | 1.00 | 21.66 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2649 | CA | ASN | B | 468 | 23.482 | 22.601 | 26.168 | 1.00 | 23.94 |
| 2650 | CB | ASN | B | 468 | 23.977 | 21.272 | 25.550 | 1.00 | 20.66 |
| 2651 | CG | ASN | B | 468 | 24.661 | 21.478 | 24.193 | 1.00 | 26.16 |
| 2652 | OD1 | ASN | B | 468 | 24.290 | 22.390 | 23.433 | 1.00 | 28.49 |
| 2653 | ND2 | ASN | B | 468 | 25.647 | 20.630 | 23.875 | 1.00 | 20.86 |
| 2654 | C | ASN | B | 468 | 22.504 | 22.316 | 27.310 | 1.00 | 25.14 |
| 2655 | O | ASN | B | 468 | 21.930 | 21.224 | 27.375 | 1.00 | 23.88 |
| 2656 | N | PHE | B | 469 | 22.300 | 23.292 | 28.194 | 1.00 | 21.40 |
| 2657 | CA | PHE | B | 469 | 21.370 | 23.118 | 29.309 | 1.00 | 21.23 |
| 2658 | CB | PHE | B | 469 | 22.010 | 23.576 | 30.634 | 1.00 | 19.79 |
| 2659 | CG | PHE | B | 469 | 22.511 | 25.007 | 30.605 | 1.00 | 20.00 |
| 2660 | CD1 | PHE | B | 469 | 21.668 | 26.066 | 30.915 | 1.00 | 19.90 |
| 2661 | CD2 | PHE | B | 469 | 23.829 | 25.293 | 30.211 | 1.00 | 21.43 |
| 2662 | CE1 | PHE | B | 469 | 22.124 | 27.393 | 30.840 | 1.00 | 19.33 |
| 2663 | CE2 | PHE | B | 469 | 24.296 | 26.620 | 30.127 | 1.00 | 19.82 |
| 2664 | CZ | PHE | B | 469 | 23.445 | 27.664 | 30.444 | 1.00 | 22.04 |
| 2665 | C | PHE | B | 469 | 20.087 | 23.913 | 29.094 | 1.00 | 22.12 |
| 2666 | O | PHE | B | 469 | 20.052 | 24.845 | 28.290 | 1.00 | 23.02 |
| 2667 | N | MET | B | 470 | 19.037 | 23.541 | 29.823 | 1.00 | 24.41 |
| 2668 | CA | MET | B | 470 | 17.767 | 24.251 | 29.764 | 1.00 | 25.12 |
| 2669 | CB | MET | B | 470 | 17.117 | 24.122 | 28.373 | 1.00 | 31.43 |
| 2670 | CG | MET | B | 470 | 16.344 | 22.853 | 28.086 | 1.00 | 35.62 |
| 2671 | SD | MET | B | 470 | 15.412 | 23.024 | 26.495 | 1.00 | 39.52 |
| 2672 | CE | MET | B | 470 | 14.320 | 24.376 | 26.904 | 1.00 | 44.35 |
| 2673 | C | MET | B | 470 | 16.809 | 23.772 | 30.855 | 1.00 | 23.51 |
| 2674 | O | MET | B | 470 | 16.756 | 22.588 | 31.163 | 1.00 | 22.28 |
| 2675 | N | CPR | B | 471 | 16.037 | 24.692 | 31.458 | 1.00 | 27.66 |
| 2676 | CD | CPR | B | 471 | 15.213 | 24.298 | 32.611 | 1.00 | 26.00 |
| 2677 | CA | CPR | B | 471 | 15.958 | 26.150 | 31.229 | 1.00 | 25.79 |
| 2678 | CB | CPR | B | 471 | 14.957 | 26.635 | 32.290 | 1.00 | 27.22 |
| 2679 | CG | CPR | B | 471 | 14.197 | 25.402 | 32.661 | 1.00 | 29.25 |
| 2680 | C | CPR | B | 471 | 17.290 | 26.889 | 31.358 | 1.00 | 26.52 |
| 2681 | O | CPR | B | 471 | 18.339 | 26.293 | 31.654 | 1.00 | 26.59 |
| 2682 | N | GLU | B | 472 | 17.228 | 28.202 | 31.167 | 1.00 | 27.87 |
| 2683 | CA | GLU | B | 472 | 18.409 | 29.044 | 31.216 | 1.00 | 31.39 |
| 2684 | CB | CLU | B | 472 | 18.183 | 30.309 | 30.372 | 1.00 | 37.82 |
| 2685 | CG | GLU | B | 472 | 17.209 | 31.331 | 30.956 | 1.00 | 51.16 |
| 2686 | CD | GLU | B | 472 | 15.732 | 31.007 | 30.710 | 1.00 | 58.98 |
| 2687 | OE1 | GLU | B | 472 | 14.896 | 31.910 | 30.944 | 1.00 | 64.18 |
| 2688 | OE2 | GLU | B | 472 | 15.398 | 29.872 | 30.292 | 1.00 | 62.37 |
| 2689 | C | GLU | B | 472 | 18.943 | 29.442 | 32.599 | 1.00 | 29.29 |
| 2690 | O | GLU | B | 472 | 20.099 | 29.825 | 32.698 | 1.00 | 24.55 |
| 2691 | N | ASP | B | 473 | 18.128 | 29.344 | 33.652 | 1.00 | 28.67 |
| 2692 | CA | ASP | B | 473 | 18.574 | 29.714 | 35.019 | 1.00 | 30.81 |
| 2693 | CB | ASP | B | 473 | 17.441 | 29.477 | 36.052 | 1.00 | 35.62 |
| 2694 | CG | ASP | B | 473 | 16.114 | 30.167 | 35.672 | 1.00 | 41.08 |
| 2695 | OD1 | ASP | B | 473 | 16.122 | 31.151 | 34.908 | 1.00 | 47.23 |
| 2696 | OD2 | ASP | B | 473 | 15.051 | 29.740 | 36.157 | 1.00 | 44.02 |
| 2697 | C | ASP | B | 473 | 19.805 | 28.886 | 35.448 | 1.00 | 27.65 |
| 2698 | O | ASP | B | 473 | 19.756 | 27.657 | 35.431 | 1.00 | 28.61 |
| 2699 | N | ILE | B | 474 | 20.902 | 29.541 | 35.827 | 1.00 | 25.37 |
| 2700 | CA | ILE | B | 474 | 22.099 | 28.809 | 36.256 | 1.00 | 24.79 |
| 2701 | CB | ILE | B | 474 | 22.879 | 28.295 | 35.022 | 1.00 | 29.86 |
| 2702 | CG2 | ILE | B | 474 | 23.500 | 29.466 | 34.262 | 1.00 | 25.59 |
| 2703 | CG1 | ILE | B | 474 | 23.936 | 27.275 | 35.450 | 1.00 | 30.83 |
| 2704 | CD1 | ILE | B | 474 | 24.496 | 26.485 | 34.312 | 1.00 | 32.01 |
| 2705 | C | ILE | B | 474 | 23.033 | 29.648 | 37.157 | 1.00 | 24.25 |
| 2706 | O | ILE | B | 474 | 22.995 | 30.896 | 37.102 | 1.00 | 21.10 |
| 2707 | N | SER | B | 475 | 23.835 | 28.975 | 38.001 | 1.00 | 22.01 |
| 2708 | CA | SER | B | 475 | 24.807 | 29.658 | 38.906 | 1.00 | 20.53 |
| 2709 | CB | SER | B | 475 | 24.404 | 29.573 | 40.399 | 1.00 | 18.76 |
| 2710 | OG | SER | B | 475 | 23.050 | 29.959 | 40.624 | 1.00 | 19.78 |
| 2711 | C | SER | B | 475 | 26.181 | 29.006 | 38.775 | 1.00 | 21.14 |
| 2712 | O | SER | B | 475 | 26.292 | 27.766 | 38.655 | 1.00 | 17.79 |
| 2713 | N | VAL | B | 476 | 27.225 | 29.832 | 38.850 | 1.00 | 19.51 |
| 2714 | CA | VAL | B | 476 | 28.609 | 29.352 | 38.716 | 1.00 | 22.96 |
| 2715 | CB | VAL | B | 476 | 29.266 | 29.893 | 37.420 | 1.00 | 19.95 |
| 2716 | CG1 | VAL | B | 476 | 30.708 | 29.403 | 37.317 | 1.00 | 19.25 |
| 2717 | CG2 | VAL | B | 476 | 28.480 | 29.459 | 36.209 | 1.00 | 21.13 |
| 2718 | C | VAL | B | 476 | 29.535 | 29.775 | 39.854 | 1.00 | 26.81 |
| 2719 | O | VAL | B | 476 | 29.470 | 30.933 | 40.313 | 1.00 | 24.97 |
| 2720 | N | GLN | B | 477 | 30.400 | 28.849 | 40.296 | 1.00 | 27.71 |
| 2721 | CA | GLN | B | 477 | 31.414 | 29.151 | 41.325 | 1.00 | 29.22 |
| 2722 | CB | GLN | B | 477 | 30.911 | 28.818 | 42.731 | 1.00 | 33.19 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2723 | CG | GLN | B | 477 | 30.478 | 27.405 | 42.927 | 1.00 | 43.97 |
| 2724 | CD | GLN | B | 477 | 29.034 | 27.337 | 43.351 | 1.00 | 48.43 |
| 2725 | OE1 | GLN | B | 477 | 28.456 | 26.255 | 43.483 | 1.00 | 48.91 |
| 2726 | NE2 | GLN | B | 477 | 28.436 | 28.503 | 43.571 | 1.00 | 49.60 |
| 2727 | C | GLN | B | 477 | 32.753 | 28.439 | 41.072 | 1.00 | 28.67 |
| 2728 | O | GLN | B | 477 | 32.807 | 27.433 | 40.339 | 1.00 | 26.87 |
| 2729 | N | TRP | B | 478 | 33.830 | 28.992 | 41.645 | 1.00 | 25.59 |
| 2730 | CA | TRP | B | 478 | 35.188 | 28.436 | 41.527 | 1.00 | 27.16 |
| 2731 | CB | TRP | B | 478 | 36.165 | 29.444 | 40.889 | 1.00 | 26.48 |
| 2732 | CG | TRP | B | 478 | 35.941 | 29.745 | 39.408 | 1.00 | 29.15 |
| 2733 | CD2 | TRP | B | 478 | 36.618 | 29.131 | 38.288 | 1.00 | 27.18 |
| 2734 | CE2 | TRP | B | 478 | 36.054 | 29.675 | 37.107 | 1.00 | 28.94 |
| 2735 | CE3 | TRP | B | 478 | 37.639 | 28.169 | 38.172 | 1.00 | 26.29 |
| 2736 | CD1 | TRP | B | 478 | 35.027 | 30.616 | 38.871 | 1.00 | 24.61 |
| 2737 | NE1 | TRP | B | 478 | 35.091 | 30.577 | 37.489 | 1.00 | 27.46 |
| 2738 | CZ2 | TRP | B | 478 | 36.478 | 29.284 | 35.815 | 1.00 | 27.84 |
| 2739 | CZ3 | TRP | B | 478 | 38.063 | 27.774 | 36.881 | 1.00 | 27.34 |
| 2740 | CH2 | TRP | B | 478 | 37.477 | 28.335 | 35.723 | 1.00 | 26.13 |
| 2741 | C | TRP | B | 478 | 35.740 | 28.051 | 42.912 | 1.00 | 28.79 |
| 2742 | O | TRP | B | 478 | 35.603 | 28.813 | 43.882 | 1.00 | 27.65 |
| 2743 | N | LEU | B | 479 | 36.369 | 26.877 | 43.006 | 1.00 | 28.27 |
| 2744 | CA | LEU | B | 479 | 36.958 | 26.429 | 44.269 | 1.00 | 30.99 |
| 2745 | CB | LEU | B | 479 | 36.236 | 25.186 | 44.775 | 1.00 | 32.10 |
| 2746 | CG | LEU | B | 479 | 34.771 | 25.390 | 45.164 | 1.00 | 33.39 |
| 2747 | CD1 | LEU | B | 479 | 33.885 | 24.780 | 44.124 | 1.00 | 34.29 |
| 2748 | CD2 | LEU | B | 479 | 34.515 | 24.741 | 46.505 | 1.00 | 38.58 |
| 2749 | C | LEU | B | 479 | 38.475 | 26.153 | 44.196 | 1.00 | 33.77 |
| 2750 | O | LEU | B | 479 | 39.012 | 25.805 | 43.141 | 1.00 | 29.80 |
| 2751 | N | HIS | B | 480 | 39.150 | 26.338 | 45.328 | 1.00 | 37.41 |
| 2752 | CA | HIS | B | 480 | 40.593 | 26.114 | 45.476 | 1.00 | 42.13 |
| 2753 | CB | HIS | B | 480 | 41.379 | 27.399 | 45.179 | 1.00 | 40.74 |
| 2754 | CG | HIS | B | 480 | 42.862 | 27.196 | 45.060 | 1.00 | 40.57 |
| 2755 | CD2 | HIS | B | 480 | 43.585 | 26.275 | 44.380 | 1.00 | 40.82 |
| 2756 | ND1 | HIS | B | 480 | 43.780 | 28.043 | 45.646 | 1.00 | 40.61 |
| 2757 | CE1 | HIS | B | 480 | 45.002 | 27.654 | 45.328 | 1.00 | 40.34 |
| 2758 | NE2 | HIS | B | 480 | 44.913 | 26.585 | 44.560 | 1.00 | 41.96 |
| 2759 | C | HIS | B | 480 | 40.778 | 25.709 | 46.950 | 1.00 | 46.72 |
| 2760 | O | HIS | B | 480 | 40.283 | 26.390 | 47.852 | 1.00 | 44.93 |
| 2761 | N | ASN | B | 481 | 41.480 | 24.603 | 47.190 | 1.00 | 53.82 |
| 2762 | CA | ASN | B | 481 | 41.674 | 24.103 | 48.548 | 1.00 | 60.44 |
| 2763 | CB | ASN | B | 481 | 42.381 | 25.145 | 49.413 | 1.00 | 64.35 |
| 2764 | CG | ASN | B | 481 | 43.791 | 25.427 | 48.945 | 1.00 | 68.56 |
| 2765 | OD1 | ASN | B | 481 | 44.652 | 24.552 | 48.982 | 1.00 | 71.10 |
| 2766 | ND2 | ASN | B | 481 | 44.034 | 26.653 | 48.498 | 1.00 | 71.41 |
| 2767 | C | ASN | B | 481 | 40.302 | 23.790 | 49.137 | 1.00 | 62.96 |
| 2768 | O | ASN | B | 481 | 40.060 | 24.002 | 50.321 | 1.00 | 63.56 |
| 2769 | N | GLU | B | 482 | 39.403 | 23.295 | 48.288 | 1.00 | 64.66 |
| 2770 | CA | GLU | B | 482 | 38.039 | 22.939 | 48.688 | 1.00 | 65.85 |
| 2771 | CB | GLU | B | 482 | 38.061 | 21.847 | 49.766 | 1.00 | 70.27 |
| 2772 | CG | GLU | B | 482 | 38.698 | 20.528 | 49.330 | 1.00 | 74.78 |
| 2773 | CD | GLU | B | 482 | 40.214 | 20.603 | 49.243 | 1.00 | 77.99 |
| 2774 | OE1 | GLU | B | 482 | 40.855 | 20.838 | 50.290 | 1.00 | 80.08 |
| 2775 | OE2 | GLU | B | 482 | 40.764 | 20.431 | 48.133 | 1.00 | 79.27 |
| 2776 | C | GLU | B | 482 | 37.198 | 24.118 | 49.184 | 1.00 | 64.83 |
| 2777 | O | GLU | B | 482 | 36.060 | 23.937 | 49.625 | 1.00 | 65.56 |
| 2778 | N | VAL | B | 483 | 37.753 | 25.323 | 49.108 | 1.00 | 63.31 |
| 2779 | CA | VAL | B | 483 | 37.037 | 26.512 | 49.546 | 1.00 | 59.58 |
| 2780 | CB | VAL | B | 483 | 37.927 | 27.384 | 50.441 | 1.00 | 61.65 |
| 2781 | CG1 | VAL | B | 483 | 37.142 | 28.589 | 50.947 | 1.00 | 64.87 |
| 2782 | CG2 | VAL | B | 483 | 38.446 | 26.562 | 51.590 | 1.00 | 65.59 |
| 2783 | C | VAL | B | 483 | 36.567 | 27.362 | 48.364 | 1.00 | 54.65 |
| 2784 | O | VAL | B | 483 | 37.303 | 27.561 | 47.401 | 1.00 | 50.56 |
| 2785 | N | GLN | B | 484 | 35.342 | 27.866 | 48.456 | 1.00 | 47.96 |
| 2786 | CA | GLN | B | 484 | 34.771 | 28.709 | 47.415 | 1.00 | 44.65 |
| 2787 | CB | GLN | B | 484 | 33.254 | 28.806 | 47.593 | 1.00 | 42.30 |
| 2788 | CG | GLN | B | 484 | 32.605 | 29.744 | 46.601 | 1.00 | 42.28 |
| 2789 | CD | GLN | B | 484 | 31.096 | 29.865 | 46.772 | 1.00 | 42.47 |
| 2790 | OE1 | GLN | B | 484 | 30.465 | 30.713 | 46.151 | 1.00 | 44.35 |
| 2791 | NE2 | GLN | B | 484 | 30.517 | 29.021 | 47.606 | 1.00 | 43.09 |
| 2792 | C | GLN | B | 484 | 35.365 | 30.126 | 47.413 | 1.00 | 43.74 |
| 2793 | O | GLN | B | 484 | 35.297 | 30.833 | 48.420 | 1.00 | 43.97 |
| 2794 | N | LEU | B | 485 | 35.929 | 30.542 | 46.279 | 1.00 | 41.67 |
| 2795 | CA | LEU | B | 485 | 36.518 | 31.872 | 46.153 | 1.00 | 38.96 |
| 2796 | CB | LEU | B | 485 | 37.383 | 31.958 | 44.896 | 1.00 | 37.66 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2797 | CG | LEU | B | 485 | 38.580 | 31.011 | 44.777 | 1.00 | 38.71 |
| 2798 | CD1 | LEU | B | 485 | 39.309 | 31.280 | 43.455 | 1.00 | 38.93 |
| 2799 | CD2 | LEU | B | 485 | 39.530 | 31.224 | 45.948 | 1.00 | 38.49 |
| 2800 | C | LEU | B | 485 | 35.432 | 32.943 | 46.090 | 1.00 | 38.74 |
| 2801 | O | LEU | B | 485 | 34.288 | 32.666 | 45.746 | 1.00 | 36.57 |
| 2802 | N | PRO | B | 486 | 35.780 | 34.193 | 46.433 | 1.00 | 37.55 |
| 2803 | CD | PRO | B | 486 | 37.070 | 34.624 | 46.998 | 1.00 | 38.36 |
| 2804 | CA | PRO | B | 486 | 34.825 | 35.305 | 46.416 | 1.00 | 38.37 |
| 2805 | CB | PRO | B | 486 | 35.665 | 36.487 | 46.912 | 1.00 | 37.16 |
| 2806 | CG | PRO | B | 486 | 36.669 | 35.840 | 47.782 | 1.00 | 37.40 |
| 2807 | C | PRO | B | 486 | 34.273 | 35.542 | 45.013 | 1.00 | 38.45 |
| 2808 | O | PRO | B | 486 | 35.026 | 35.494 | 44.044 | 1.00 | 35.55 |
| 2809 | N | ASP | B | 487 | 32.971 | 35.806 | 44.912 | 1.00 | 39.56 |
| 2810 | CA | ASP | B | 487 | 32.342 | 36.046 | 43.612 | 1.00 | 44.82 |
| 2811 | CB | ASP | B | 487 | 30.897 | 36.526 | 43.788 | 1.00 | 51.39 |
| 2812 | CG | ASP | B | 487 | 29.998 | 35.467 | 44.406 | 1.00 | 58.78 |
| 2813 | OD1 | ASP | B | 487 | 30.077 | 34.289 | 43.985 | 1.00 | 64.82 |
| 2814 | OD2 | ASP | B | 487 | 29.201 | 35.810 | 45.304 | 1.00 | 61.76 |
| 2815 | C | ASP | B | 487 | 33.105 | 37.053 | 42.747 | 1.00 | 43.71 |
| 2816 | O | ASP | B | 487 | 33.509 | 36.742 | 41.619 | 1.00 | 45.18 |
| 2817 | N | ALA | B | 488 | 33.302 | 38.249 | 43.292 | 1.00 | 41.18 |
| 2818 | CA | ALA | B | 488 | 34.002 | 39.345 | 42.622 | 1.00 | 38.59 |
| 2819 | CB | ALA | B | 488 | 34.303 | 40.453 | 43.645 | 1.00 | 38.99 |
| 2820 | C | ALA | B | 488 | 35.290 | 38.942 | 41.901 | 1.00 | 35.29 |
| 2821 | O | ALA | B | 488 | 35.797 | 39.679 | 41.060 | 1.00 | 32.37 |
| 2822 | N | ARG | B | 489 | 35.812 | 37.770 | 42.236 | 1.00 | 35.72 |
| 2823 | CA | ARG | B | 489 | 37.040 | 37.254 | 41.634 | 1.00 | 35.93 |
| 2824 | CB | ARG | B | 489 | 37.578 | 36.096 | 42.487 | 1.00 | 36.51 |
| 2825 | CG | ARG | B | 489 | 38.692 | 36.494 | 43.464 | 1.00 | 37.88 |
| 2826 | CD | ARG | B | 489 | 40.068 | 36.265 | 42.845 | 1.00 | 36.26 |
| 2827 | NE | ARG | B | 489 | 40.831 | 35.327 | 43.657 | 1.00 | 40.17 |
| 2828 | CZ | ARG | B | 489 | 41.871 | 34.618 | 43.231 | 1.00 | 37.91 |
| 2829 | NH1 | ARG | B | 489 | 42.294 | 34.715 | 41.983 | 1.00 | 36.14 |
| 2830 | NH2 | ARG | B | 489 | 42.502 | 33.823 | 44.077 | 1.00 | 39.92 |
| 2831 | C | ARG | B | 489 | 36.895 | 36.775 | 40.177 | 1.00 | 34.71 |
| 2832 | O | ARG | B | 489 | 37.889 | 36.751 | 39.423 | 1.00 | 29.98 |
| 2833 | N | HIS | B | 490 | 35.670 | 36.416 | 39.780 | 1.00 | 33.04 |
| 2834 | CA | HIS | B | 490 | 35.450 | 35.897 | 38.424 | 1.00 | 34.13 |
| 2835 | CB | HIS | B | 490 | 35.098 | 34.396 | 38.482 | 1.00 | 25.85 |
| 2836 | CG | HIS | B | 490 | 33.673 | 34.126 | 38.874 | 1.00 | 23.52 |
| 2837 | CD2 | HIS | B | 490 | 32.515 | 34.285 | 38.186 | 1.00 | 21.56 |
| 2838 | ND1 | HIS | B | 490 | 33.309 | 33.705 | 40.138 | 1.00 | 22.85 |
| 2839 | CE1 | HIS | B | 490 | 31.991 | 33.627 | 40.214 | 1.00 | 21.41 |
| 2840 | NE2 | HIS | B | 490 | 31.485 | 33.973 | 39.042 | 1.00 | 23.56 |
| 2841 | C | HIS | B | 490 | 34.339 | 36.619 | 37.669 | 1.00 | 35.01 |
| 2842 | O | HIS | B | 490 | 33.560 | 37.360 | 38.256 | 1.00 | 35.02 |
| 2843 | N | SER | B | 491 | 34.261 | 36.357 | 36.366 | 1.00 | 37.11 |
| 2844 | CA | SER | B | 491 | 33.234 | 36.944 | 35.500 | 1.00 | 40.05 |
| 2845 | CB | SER | B | 491 | 33.856 | 37.982 | 34.575 | 1.00 | 41.61 |
| 2846 | OG | SER | B | 491 | 32.837 | 38.713 | 33.924 | 1.00 | 46.07 |
| 2847 | C | SER | B | 491 | 32.544 | 35.869 | 34.648 | 1.00 | 38.86 |
| 2848 | O | SER | B | 491 | 33.189 | 34.932 | 34.191 | 1.00 | 41.45 |
| 2849 | N | THR | B | 492 | 31.238 | 36.006 | 34.445 | 1.00 | 37.10 |
| 2850 | CA | THR | B | 492 | 30.460 | 35.049 | 33.649 | 1.00 | 36.08 |
| 2851 | CB | THR | B | 492 | 29.505 | 34.214 | 34.555 | 1.00 | 34.64 |
| 2852 | OG1 | THR | B | 492 | 30.258 | 33.568 | 35.589 | 1.00 | 34.78 |
| 2853 | CG2 | THR | B | 492 | 28.787 | 33.153 | 33.740 | 1.00 | 34.77 |
| 2854 | C | THR | B | 492 | 29.601 | 35.770 | 32.588 | 1.00 | 35.88 |
| 2855 | O | THR | B | 492 | 28.871 | 36.704 | 32.926 | 1.00 | 31.12 |
| 2856 | N | THR | B | 493 | 29.675 | 35.334 | 31.325 | 1.00 | 34.83 |
| 2857 | CA | THR | B | 493 | 28.873 | 35.959 | 30.243 | 1.00 | 35.48 |
| 2858 | CB | THR | B | 493 | 29.246 | 35.439 | 28.829 | 1.00 | 35.04 |
| 2859 | OG1 | THR | B | 493 | 29.047 | 34.018 | 28.769 | 1.00 | 33.14 |
| 2860 | CG2 | THR | B | 493 | 30.681 | 35.773 | 28.490 | 1.00 | 33.55 |
| 2861 | C | THR | B | 493 | 27.393 | 35.643 | 30.429 | 1.00 | 40.33 |
| 2862 | O | THR | B | 493 | 27.033 | 34.791 | 31.239 | 1.00 | 39.09 |
| 2863 | N | GLN | B | 494 | 26.537 | 36.330 | 29.683 | 1.00 | 45.69 |
| 2864 | CA | GLN | B | 494 | 25.095 | 36.086 | 29.764 | 1.00 | 53.06 |
| 2865 | CB | GLN | B | 494 | 24.324 | 37.331 | 29.318 | 1.00 | 68.92 |
| 2866 | CG | GLN | B | 494 | 24.506 | 38.521 | 30.250 | 1.00 | 95.71 |
| 2867 | CD | GLN | B | 494 | 23.718 | 39.737 | 29.811 | 1.00 | 109.75 |
| 2868 | OE1 | GLN | B | 494 | 22.494 | 39.687 | 29.687 | 1.00 | 119.27 |
| 2869 | NE2 | GLN | B | 494 | 24.418 | 40.841 | 29.575 | 1.00 | 119.37 |
| 2870 | C | GLN | B | 494 | 24.703 | 34.875 | 28.900 | 1.00 | 46.64 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2871 | O | GLN | B | 494 | 25.295 | 34.630 | 27.849 | 1.00 | 41.60 |
| 2872 | N | PRO | B | 495 | 23.698 | 34.101 | 29.337 | 1.00 | 41.78 |
| 2873 | CD | PRO | B | 495 | 22.982 | 34.186 | 30.619 | 1.00 | 37.61 |
| 2874 | CA | PRO | B | 495 | 23.277 | 32.922 | 28.567 | 1.00 | 39.00 |
| 2875 | CB | PRO | B | 495 | 22.245 | 32.254 | 29.478 | 1.00 | 38.11 |
| 2876 | CG | PRO | B | 495 | 21.762 | 33.365 | 30.352 | 1.00 | 40.04 |
| 2877 | C | PRO | B | 495 | 22.770 | 33.179 | 27.147 | 1.00 | 38.64 |
| 2878 | O | PRO | B | 495 | 21.855 | 33.947 | 26.930 | 1.00 | 38.89 |
| 2879 | N | ARG | B | 496 | 23.409 | 32.529 | 26.185 | 1.00 | 42.27 |
| 2880 | CA | ARG | B | 496 | 23.059 | 32.662 | 24.782 | 1.00 | 46.25 |
| 2881 | CB | ARG | B | 496 | 24.260 | 33.175 | 23.993 | 1.00 | 53.29 |
| 2882 | CG | ARG | B | 496 | 24.656 | 34.609 | 24.254 | 1.00 | 64.82 |
| 2883 | CD | ARG | B | 496 | 25.698 | 35.009 | 23.220 | 1.00 | 76.33 |
| 2884 | NE | ARG | B | 496 | 25.886 | 36.451 | 23.130 | 1.00 | 85.31 |
| 2885 | CZ | ARG | B | 496 | 26.180 | 37.087 | 22.001 | 1.00 | 89.03 |
| 2886 | NH1 | ARG | B | 496 | 26.315 | 36.404 | 20.870 | 1.00 | 90.30 |
| 2887 | NH2 | ARG | B | 496 | 26.341 | 38.405 | 22.002 | 1.00 | 91.83 |
| 2888 | C | ARG | B | 496 | 22.640 | 31.303 | 24.221 | 1.00 | 45.60 |
| 2889 | O | ARG | B | 496 | 23.020 | 30.255 | 24.744 | 1.00 | 40.47 |
| 2890 | N | LYS | B | 497 | 21.879 | 31.315 | 23.135 | 1.00 | 46.49 |
| 2891 | CA | LYS | B | 497 | 21.421 | 30.060 | 22.553 | 1.00 | 49.32 |
| 2892 | CB | LYS | B | 497 | 20.122 | 30.293 | 21.773 | 1.00 | 54.86 |
| 2893 | CG | LYS | B | 497 | 18.981 | 30.737 | 22.673 | 1.00 | 64.86 |
| 2894 | CD | LYS | B | 497 | 17.690 | 31.009 | 21.924 | 1.00 | 73.54 |
| 2895 | CE | LYS | B | 497 | 16.634 | 31.547 | 22.890 | 1.00 | 79.41 |
| 2896 | NZ | LYS | B | 497 | 15.310 | 31.801 | 22.263 | 1.00 | 83.77 |
| 2897 | C | LYS | B | 497 | 22.454 | 29.381 | 21.671 | 1.00 | 48.53 |
| 2898 | O | LYS | B | 497 | 23.169 | 30.036 | 20.923 | 1.00 | 47.15 |
| 2899 | N | THR | B | 498 | 22.549 | 28.061 | 21.791 | 1.00 | 51.24 |
| 2900 | CA | THR | B | 498 | 23.471 | 27.286 | 20.971 | 1.00 | 56.18 |
| 2901 | CB | THR | B | 498 | 23.759 | 25.892 | 21.569 | 1.00 | 52.22 |
| 2902 | OG1 | THR | B | 498 | 22.570 | 25.100 | 21.509 | 1.00 | 49.21 |
| 2903 | CG2 | THR | B | 498 | 24.197 | 26.001 | 23.007 | 1.00 | 51.66 |
| 2904 | C | THR | B | 498 | 22.730 | 27.069 | 19.656 | 1.00 | 63.36 |
| 2905 | O | THR | B | 498 | 21.571 | 27.464 | 19.520 | 1.00 | 59.21 |
| 2906 | N | LYS | B | 499 | 23.393 | 26.427 | 18.701 | 1.00 | 68.78 |
| 2907 | CA | LYS | B | 499 | 22.789 | 26.147 | 17.401 | 1.00 | 76.76 |
| 2908 | CB | LYS | B | 499 | 23.807 | 25.467 | 16.485 | 1.00 | 87.74 |
| 2909 | CG | LYS | B | 499 | 25.127 | 26.199 | 16.363 | 1.00 | 100.27 |
| 2910 | CD | LYS | B | 499 | 24.970 | 27.518 | 15.640 | 1.00 | 109.16 |
| 2911 | CE | LYS | B | 499 | 26.296 | 28.236 | 15.560 | 1.00 | 114.54 |
| 2912 | NZ | LYS | B | 499 | 26.159 | 29.503 | 14.816 | 1.00 | 117.52 |
| 2913 | C | LYS | B | 499 | 21.582 | 25.227 | 17.582 | 1.00 | 73.57 |
| 2914 | O | LYS | B | 499 | 20.477 | 25.540 | 17.136 | 1.00 | 76.28 |
| 2915 | N | GLY | B | 500 | 21.807 | 24.089 | 18.234 | 1.00 | 71.12 |
| 2916 | CA | GLY | B | 500 | 20.734 | 23.143 | 18.470 | 1.00 | 62.53 |
| 2917 | C | GLY | B | 500 | 19.804 | 23.656 | 19.549 | 1.00 | 57.34 |
| 2918 | O | GLY | B | 500 | 19.251 | 24.749 | 19.432 | 1.00 | 57.25 |
| 2919 | N | SER | B | 501 | 19.629 | 22.867 | 20.602 | 1.00 | 53.13 |
| 2920 | CA | SER | B | 501 | 18.776 | 23.264 | 21.712 | 1.00 | 51.49 |
| 2921 | CB | SER | B | 501 | 17.840 | 22.118 | 22.072 | 1.00 | 52.51 |
| 2922 | OG | SER | B | 501 | 18.592 | 20.936 | 22.271 | 1.00 | 60.47 |
| 2923 | C | SER | B | 501 | 19.634 | 23.646 | 22.924 | 1.00 | 48.17 |
| 2924 | O | SER | B | 501 | 20.812 | 23.287 | 23.005 | 1.00 | 45.13 |
| 2925 | N | GLY | B | 502 | 19.046 | 24.391 | 23.853 | 1.00 | 42.09 |
| 2926 | CA | GLY | B | 502 | 19.780 | 24.792 | 25.043 | 1.00 | 38.78 |
| 2927 | C | GLY | B | 502 | 20.528 | 26.110 | 24.938 | 1.00 | 33.72 |
| 2928 | O | GLY | B | 502 | 20.396 | 26.824 | 23.936 | 1.00 | 31.52 |
| 2929 | N | PHE | B | 503 | 21.308 | 26.414 | 25.981 | 1.00 | 28.64 |
| 2930 | CA | PHE | B | 503 | 22.098 | 27.650 | 26.096 | 1.00 | 23.61 |
| 2931 | CB | PHE | B | 503 | 21.520 | 28.586 | 27.177 | 1.00 | 24.44 |
| 2932 | CG | PHE | B | 503 | 20.085 | 29.034 | 26.939 | 1.00 | 28.54 |
| 2933 | CD1 | PHE | B | 503 | 19.018 | 28.183 | 27.207 | 1.00 | 25.64 |
| 2934 | CD2 | PHE | B | 503 | 19.812 | 30.318 | 26.459 | 1.00 | 29.21 |
| 2935 | CE1 | PHE | B | 503 | 17.684 | 28.594 | 27.002 | 1.00 | 30.26 |
| 2936 | CE2 | PHE | B | 503 | 18.486 | 30.743 | 26.246 | 1.00 | 34.23 |
| 2937 | CZ | PHE | B | 503 | 17.414 | 29.880 | 26.516 | 1.00 | 29.67 |
| 2938 | C | PHE | B | 503 | 23.545 | 27.350 | 26.510 | 1.00 | 19.89 |
| 2939 | O | PHE | B | 503 | 23.898 | 26.202 | 26.822 | 1.00 | 14.90 |
| 2940 | N | PHE | B | 504 | 24.367 | 28.401 | 26.522 | 1.00 | 18.39 |
| 2941 | CA | PHE | B | 504 | 25.759 | 28.311 | 26.948 | 1.00 | 18.63 |
| 2942 | CB | PHE | B | 504 | 26.685 | 27.980 | 25.753 | 1.00 | 21.66 |
| 2943 | CG | PHE | B | 504 | 26.937 | 29.142 | 24.814 | 1.00 | 24.85 |
| 2944 | CD1 | PHE | B | 504 | 27.936 | 30.079 | 25.087 | 1.00 | 28.73 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 2945 | CD2 | PHE | B | 504 | 26.200 | 29.273 | 23.624 | 1.00 | 28.19 |
| 2946 | CE1 | PHE | B | 504 | 28.210 | 31.131 | 24.185 | 1.00 | 27.89 |
| 2947 | CE2 | PHE | B | 504 | 26.456 | 30.308 | 22.721 | 1.00 | 25.22 |
| 2948 | CZ | PHE | B | 504 | 27.467 | 31.242 | 23.001 | 1.00 | 28.79 |
| 2949 | C | PHE | B | 504 | 26.220 | 29.619 | 27.612 | 1.00 | 21.84 |
| 2950 | O | PHE | B | 504 | 25.667 | 30.695 | 27.340 | 1.00 | 18.93 |
| 2951 | N | VAL | B | 505 | 27.231 | 29.504 | 28.479 | 1.00 | 20.68 |
| 2952 | CA | VAL | B | 505 | 27.859 | 30.637 | 29.156 | 1.00 | 19.06 |
| 2953 | CB | VAL | B | 505 | 27.310 | 30.843 | 30.595 | 1.00 | 23.45 |
| 2954 | CG1 | VAL | B | 505 | 25.808 | 31.144 | 30.578 | 1.00 | 26.83 |
| 2955 | CG2 | VAL | B | 505 | 27.568 | 29.609 | 31.417 | 1.00 | 23.74 |
| 2956 | C | VAL | B | 505 | 29.377 | 30.333 | 29.274 | 1.00 | 21.27 |
| 2957 | O | VAL | B | 505 | 29.794 | 29.156 | 29.201 | 1.00 | 18.72 |
| 2958 | N | PHE | B | 506 | 30.186 | 31.384 | 29.434 | 1.00 | 21.88 |
| 2959 | CA | PHE | B | 506 | 31.640 | 31.257 | 29.648 | 1.00 | 22.75 |
| 2960 | CB | PHE | B | 506 | 32.474 | 31.964 | 28.557 | 1.00 | 22.78 |
| 2961 | CG | PHE | B | 506 | 32.687 | 31.168 | 27.289 | 1.00 | 24.39 |
| 2962 | CD1 | PHE | B | 506 | 31.897 | 31.398 | 26.163 | 1.00 | 21.96 |
| 2963 | CD2 | PHE | B | 506 | 33.735 | 30.256 | 27.189 | 1.00 | 24.47 |
| 2964 | CE1 | PHE | B | 506 | 32.161 | 30.742 | 24.953 | 1.00 | 26.37 |
| 2965 | CE2 | PHE | B | 506 | 34.010 | 29.585 | 25.985 | 1.00 | 26.67 |
| 2966 | CZ | PHE | B | 506 | 33.221 | 29.834 | 24.859 | 1.00 | 26.93 |
| 2967 | C | PHE | B | 506 | 31.957 | 31.973 | 30.984 | 1.00 | 23.49 |
| 2968 | O | PHE | B | 506 | 31.348 | 33.010 | 31.299 | 1.00 | 26.66 |
| 2969 | N | SER | B | 507 | 32.897 | 31.429 | 31.755 | 1.00 | 27.37 |
| 2970 | CA | SER | B | 507 | 33.340 | 32.035 | 33.021 | 1.00 | 27.85 |
| 2971 | CB | SER | B | 507 | 32.985 | 31.135 | 34.210 | 1.00 | 26.26 |
| 2972 | OG | SER | B | 507 | 33.224 | 31.790 | 35.452 | 1.00 | 29.31 |
| 2973 | C | SER | B | 507 | 34.873 | 32.229 | 32.926 | 1.00 | 27.88 |
| 2974 | O | SER | B | 507 | 35.580 | 31.360 | 32.400 | 1.00 | 30.62 |
| 2975 | N | ARG | B | 508 | 35.372 | 33.364 | 33.419 | 1.00 | 29.30 |
| 2976 | CA | ARG | B | 508 | 36.804 | 33.708 | 33.356 | 1.00 | 33.43 |
| 2977 | CB | ARG | B | 508 | 36.965 | 34.912 | 32.415 | 1.00 | 32.46 |
| 2978 | CG | ARG | B | 508 | 38.388 | 35.415 | 32.193 | 1.00 | 33.83 |
| 2979 | CD | ARG | B | 508 | 38.435 | 36.520 | 31.115 | 1.00 | 34.33 |
| 2980 | NE | ARG | B | 508 | 39.774 | 37.093 | 30.972 | 1.00 | 34.48 |
| 2981 | CZ | ARG | B | 508 | 40.292 | 37.980 | 31.823 | 1.00 | 35.77 |
| 2982 | NH1 | ARG | B | 508 | 39.577 | 38.400 | 32.864 | 1.00 | 33.78 |
| 2983 | NH2 | ARG | B | 508 | 41.538 | 38.413 | 31.665 | 1.00 | 32.86 |
| 2984 | C | ARG | B | 508 | 37.429 | 34.021 | 34.735 | 1.00 | 32.34 |
| 2985 | O | ARG | B | 508 | 36.907 | 34.850 | 35.466 | 1.00 | 34.40 |
| 2986 | N | LEU | B | 509 | 38.547 | 33.366 | 35.072 | 1.00 | 31.62 |
| 2987 | CA | LEU | B | 509 | 39.240 | 33.555 | 36.368 | 1.00 | 30.13 |
| 2988 | CB | LEU | B | 509 | 39.091 | 32.306 | 37.252 | 1.00 | 26.00 |
| 2989 | CG | LEU | B | 509 | 39.818 | 32.337 | 38.609 | 1.00 | 25.08 |
| 2990 | CD1 | LEU | B | 509 | 39.134 | 33.344 | 39.528 | 1.00 | 21.22 |
| 2991 | CD2 | LEU | B | 509 | 39.829 | 30.964 | 39.277 | 1.00 | 20.13 |
| 2992 | C | LEU | B | 509 | 40.734 | 33.824 | 36.226 | 1.00 | 31.13 |
| 2993 | O | LEU | B | 509 | 41.462 | 32.958 | 35.767 | 1.00 | 30.95 |
| 2994 | N | GLU | B | 510 | 41.194 | 35.008 | 36.631 | 1.00 | 29.72 |
| 2995 | CA | GLU | B | 510 | 42.622 | 35.347 | 36.571 | 1.00 | 32.72 |
| 2996 | CB | GLU | B | 510 | 42.813 | 36.885 | 36.521 | 1.00 | 40.38 |
| 2997 | CG | GLU | B | 510 | 42.372 | 37.563 | 35.207 | 1.00 | 46.63 |
| 2998 | CD | GLU | B | 510 | 42.476 | 39.095 | 35.239 | 1.00 | 51.64 |
| 2999 | OE1 | GLU | B | 510 | 43.564 | 39.620 | 35.565 | 1.00 | 53.42 |
| 3000 | OE2 | GLU | B | 510 | 41.473 | 39.779 | 34.925 | 1.00 | 51.77 |
| 3001 | C | GLU | B | 510 | 43.312 | 34.789 | 37.832 | 1.00 | 33.04 |
| 3002 | O | GLU | B | 510 | 42.751 | 34.848 | 38.928 | 1.00 | 28.41 |
| 3003 | N | VAL | B | 511 | 44.517 | 34.248 | 37.684 | 1.00 | 32.00 |
| 3004 | CA | VAL | B | 511 | 45.241 | 33.691 | 38.831 | 1.00 | 32.81 |
| 3005 | CB | VAL | B | 511 | 45.021 | 32.151 | 38.936 | 1.00 | 33.79 |
| 3006 | CG1 | VAL | B | 511 | 43.536 | 31.843 | 39.060 | 1.00 | 31.75 |
| 3007 | CG2 | VAL | B | 511 | 45.624 | 31.446 | 37.714 | 1.00 | 32.69 |
| 3008 | C | VAL | B | 511 | 46.755 | 33.960 | 38.776 | 1.00 | 37.15 |
| 3009 | O | VAL | B | 511 | 47.309 | 34.151 | 37.687 | 1.00 | 35.64 |
| 3010 | N | THR | B | 512 | 47.411 | 33.933 | 39.948 | 1.00 | 40.47 |
| 3011 | CA | THR | B | 512 | 48.866 | 34.177 | 40.086 | 1.00 | 42.76 |
| 3012 | CB | THR | B | 512 | 49.166 | 35.213 | 41.178 | 1.00 | 45.58 |
| 3013 | OG1 | THR | B | 512 | 48.657 | 34.732 | 42.429 | 1.00 | 48.30 |
| 3014 | CG2 | THR | B | 512 | 48.529 | 36.537 | 40.849 | 1.00 | 47.93 |
| 3015 | C | THR | B | 512 | 49.752 | 32.975 | 40.428 | 1.00 | 41.55 |
| 3016 | O | THR | B | 512 | 49.295 | 31.966 | 40.950 | 1.00 | 42.52 |
| 3017 | N | ARG | B | 513 | 51.043 | 33.132 | 40.165 | 1.00 | 43.24 |
| 3018 | CA | ARG | B | 513 | 52.034 | 32.095 | 40.416 | 1.00 | 44.40 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3019 | CB | ARG | B | 513 | 53.429 | 32.639 | 40.092 | 1.00 | 48.55 |
| 3020 | CG | ARG | B | 513 | 54.515 | 31.587 | 40.138 | 1.00 | 54.26 |
| 3021 | CD | ARG | B | 513 | 55.695 | 31.963 | 39.264 | 1.00 | 58.25 |
| 3022 | NE | ARG | B | 513 | 56.364 | 30.756 | 38.802 | 1.00 | 64.77 |
| 3023 | CZ | ARG | B | 513 | 56.681 | 30.508 | 37.536 | 1.00 | 67.45 |
| 3024 | NH1 | ARG | B | 513 | 56.399 | 31.388 | 36.586 | 1.00 | 68.15 |
| 3025 | NH2 | ARG | B | 513 | 57.263 | 29.362 | 37.216 | 1.00 | 69.93 |
| 3026 | C | ARG | B | 513 | 51.999 | 31.553 | 41.846 | 1.00 | 44.39 |
| 3027 | O | ARG | B | 513 | 52.135 | 30.350 | 42.072 | 1.00 | 43.14 |
| 3028 | N | ALA | B | 514 | 51.807 | 32.441 | 42.810 | 1.00 | 42.61 |
| 3029 | CA | ALA | B | 514 | 51.748 | 32.034 | 44.206 | 1.00 | 43.64 |
| 3030 | CB | ALA | B | 514 | 51.521 | 33.262 | 45.101 | 1.00 | 42.72 |
| 3031 | C | ALA | B | 514 | 50.637 | 31.006 | 44.446 | 1.00 | 44.32 |
| 3032 | O | ALA | B | 514 | 50.832 | 30.019 | 45.170 | 1.00 | 42.77 |
| 3033 | N | GLU | B | 515 | 49.473 | 31.236 | 43.837 | 1.00 | 43.89 |
| 3034 | CA | GLU | B | 515 | 48.351 | 30.334 | 44.024 | 1.00 | 42.94 |
| 3035 | CB | GLU | B | 515 | 47.072 | 30.938 | 43.446 | 1.00 | 46.70 |
| 3036 | CG | GLU | B | 515 | 46.685 | 32.286 | 44.032 | 1.00 | 53.73 |
| 3037 | CD | GLU | B | 515 | 45.248 | 32.662 | 43.711 | 1.00 | 56.33 |
| 3038 | OE1 | GLU | B | 515 | 44.347 | 32.261 | 44.481 | 1.00 | 58.71 |
| 3039 | OE2 | GLU | B | 515 | 45.021 | 33.340 | 42.684 | 1.00 | 56.28 |
| 3040 | C | GLU | B | 515 | 48.552 | 28.930 | 43.450 | 1.00 | 42.23 |
| 3041 | O | GLU | B | 515 | 48.294 | 27.947 | 44.144 | 1.00 | 40.79 |
| 3042 | N | TRP | B | 516 | 49.012 | 28.813 | 42.207 | 1.00 | 41.32 |
| 3043 | CA | TRP | B | 516 | 49.176 | 27.476 | 41.649 | 1.00 | 43.64 |
| 3044 | CB | TRP | B | 516 | 49.116 | 27.505 | 40.106 | 1.00 | 43.60 |
| 3045 | CG | TRP | B | 516 | 50.380 | 27.858 | 39.372 | 1.00 | 43.58 |
| 3046 | CD2 | TRP | B | 516 | 50.616 | 29.036 | 38.592 | 1.00 | 44.28 |
| 3047 | CE2 | TRP | B | 516 | 51.916 | 28.926 | 38.048 | 1.00 | 44.81 |
| 3048 | CE3 | TRP | B | 516 | 49.853 | 30.176 | 38.299 | 1.00 | 45.90 |
| 3049 | CD1 | TRP | B | 516 | 51.516 | 27.102 | 39.275 | 1.00 | 43.51 |
| 3050 | NE1 | TRP | B | 516 | 52.442 | 27.736 | 38.479 | 1.00 | 43.86 |
| 3051 | CZ2 | TRP | B | 516 | 52.474 | 29.914 | 37.227 | 1.00 | 46.25 |
| 3052 | CZ3 | TRP | B | 516 | 50.406 | 31.163 | 37.480 | 1.00 | 47.00 |
| 3053 | CH2 | TRP | B | 516 | 51.706 | 31.023 | 36.955 | 1.00 | 48.45 |
| 3054 | C | TRP | B | 516 | 50.415 | 26.722 | 42.143 | 1.00 | 45.75 |
| 3055 | O | TRP | B | 516 | 50.456 | 25.500 | 42.070 | 1.00 | 45.55 |
| 3056 | N | GLU | B | 517 | 51.421 | 27.424 | 42.652 | 1.00 | 49.53 |
| 3057 | CA | GLU | B | 517 | 52.589 | 26.712 | 43.170 | 1.00 | 54.86 |
| 3058 | CB | GLU | B | 517 | 53.801 | 27.647 | 43.312 | 1.00 | 56.50 |
| 3059 | CG | GLU | B | 517 | 54.321 | 28.164 | 41.970 | 1.00 | 64.76 |
| 3060 | CD | GLU | B | 517 | 55.776 | 28.629 | 42.001 | 1.00 | 67.36 |
| 3061 | OE1 | GLU | B | 517 | 56.126 | 29.467 | 42.859 | 1.00 | 70.39 |
| 3062 | OE2 | GLU | B | 517 | 56.567 | 28.162 | 41.153 | 1.00 | 67.65 |
| 3063 | C | GLU | B | 517 | 52.214 | 26.088 | 44.522 | 1.00 | 56.49 |
| 3064 | O | GLU | B | 517 | 52.759 | 25.054 | 44.911 | 1.00 | 54.63 |
| 3065 | N | GLN | B | 518 | 51.267 | 26.708 | 45.228 | 1.00 | 57.77 |
| 3066 | CA | GLN | B | 518 | 50.809 | 26.179 | 46.514 | 1.00 | 60.71 |
| 3067 | CB | GLN | B | 518 | 49.877 | 27.160 | 47.221 | 1.00 | 66.68 |
| 3068 | CG | GLN | B | 518 | 49.270 | 26.583 | 48.490 | 1.00 | 74.07 |
| 3069 | CD | GLN | B | 518 | 47.797 | 26.899 | 48.628 | 1.00 | 78.96 |
| 3070 | OE1 | GLN | B | 518 | 46.998 | 26.576 | 47.752 | 1.00 | 81.43 |
| 3071 | NE2 | GLN | B | 518 | 47.428 | 27.529 | 49.736 | 1.00 | 82.74 |
| 3072 | C | GLN | B | 518 | 50.046 | 24.890 | 46.245 | 1.00 | 59.87 |
| 3073 | O | GLN | B | 518 | 50.371 | 23.840 | 46.799 | 1.00 | 61.27 |
| 3074 | N | LYS | B | 519 | 49.014 | 24.991 | 45.409 | 1.00 | 58.17 |
| 3075 | CA | LYS | B | 519 | 48.201 | 23.845 | 45.014 | 1.00 | 57.04 |
| 3076 | CB | LYS | B | 519 | 47.000 | 23.661 | 45.942 | 1.00 | 60.20 |
| 3077 | CG | LYS | B | 519 | 46.218 | 22.396 | 45.605 | 1.00 | 68.28 |
| 3078 | CD | LYS | B | 519 | 45.308 | 21.953 | 46.729 | 1.00 | 75.41 |
| 3079 | CE | LYS | B | 519 | 44.710 | 20.591 | 46.417 | 1.00 | 80.21 |
| 3080 | NZ | LYS | B | 519 | 43.843 | 20.092 | 47.521 | 1.00 | 84.94 |
| 3081 | C | LYS | B | 519 | 47.719 | 24.043 | 43.580 | 1.00 | 52.58 |
| 3082 | O | LYS | B | 519 | 46.870 | 24.898 | 43.305 | 1.00 | 48.47 |
| 3083 | N | ASP | B | 520 | 48.269 | 23.241 | 42.674 | 1.00 | 48.57 |
| 3084 | CA | ASP | B | 520 | 47.945 | 23.327 | 41.259 | 1.00 | 47.58 |
| 3085 | CB | ASP | B | 520 | 49.150 | 22.869 | 40.434 | 1.00 | 48.06 |
| 3086 | CG | ASP | B | 520 | 49.072 | 23.322 | 38.993 | 1.00 | 50.17 |
| 3087 | OD1 | ASP | B | 520 | 48.159 | 24.113 | 38.678 | 1.00 | 51.20 |
| 3088 | OD2 | ASP | B | 520 | 49.923 | 22.900 | 38.177 | 1.00 | 48.25 |
| 3089 | C | ASP | B | 520 | 46.707 | 22.522 | 40.871 | 1.00 | 46.32 |
| 3090 | O | ASP | B | 520 | 46.807 | 21.516 | 40.163 | 1.00 | 45.92 |
| 3091 | N | GLU | B | 521 | 45.545 | 22.969 | 41.340 | 1.00 | 45.91 |
| 3092 | CA | GLU | B | 521 | 44.277 | 22.313 | 41.036 | 1.00 | 46.47 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3093 | CB | GLU | B | 521 | 44.150 | 21.010 | 41.835 | 1.00 | 52.61 |
| 3094 | CG | GLU | B | 521 | 42.896 | 20.198 | 41.519 | 1.00 | 63.84 |
| 3095 | CD | GLU | B | 521 | 42.828 | 18.885 | 42.293 | 1.00 | 70.79 |
| 3096 | OE1 | GLU | B | 521 | 43.034 | 18.909 | 43.526 | 1.00 | 74.94 |
| 3097 | OE2 | GLU | B | 521 | 42.561 | 17.831 | 41.675 | 1.00 | 74.29 |
| 3098 | C | GLU | B | 521 | 43.101 | 23.242 | 41.346 | 1.00 | 42.03 |
| 3099 | O | GLU | B | 521 | 42.865 | 23.573 | 42.511 | 1.00 | 41.14 |
| 3100 | N | PHE | B | 522 | 42.380 | 23.667 | 40.301 | 1.00 | 36.54 |
| 3101 | CA | PHE | B | 522 | 41.222 | 24.568 | 40.439 | 1.00 | 31.99 |
| 3102 | CB | PHE | B | 522 | 41.492 | 25.900 | 39.718 | 1.00 | 32.49 |
| 3103 | CG | PHE | B | 522 | 42.770 | 26.585 | 40.147 | 1.00 | 30.70 |
| 3104 | CD1 | PHE | B | 522 | 44.006 | 26.101 | 39.742 | 1.00 | 32.68 |
| 3105 | CD2 | PHE | B | 522 | 42.732 | 27.719 | 40.960 | 1.00 | 29.41 |
| 3106 | CE1 | PHE | B | 522 | 45.201 | 26.743 | 40.143 | 1.00 | 34.24 |
| 3107 | CE2 | PHE | B | 522 | 43.894 | 28.359 | 41.360 | 1.00 | 28.76 |
| 3108 | CZ | PHE | B | 522 | 45.138 | 27.877 | 40.957 | 1.00 | 30.58 |
| 3109 | C | PHE | B | 522 | 39.929 | 23.936 | 39.895 | 1.00 | 31.10 |
| 3110 | O | PHE | B | 522 | 39.954 | 23.201 | 38.912 | 1.00 | 32.10 |
| 3111 | N | ILE | B | 523 | 38.792 | 24.254 | 40.504 | 1.00 | 29.89 |
| 3112 | CA | ILE | B | 523 | 37.519 | 23.655 | 40.101 | 1.00 | 27.23 |
| 3113 | CB | ILE | B | 523 | 36.971 | 22.796 | 41.237 | 1.00 | 31.94 |
| 3114 | CG2 | ILE | B | 523 | 35.554 | 22.313 | 40.910 | 1.00 | 31.25 |
| 3115 | CG1 | ILE | B | 523 | 37.938 | 21.644 | 41.515 | 1.00 | 34.53 |
| 3116 | CD1 | ILE | B | 523 | 37.509 | 20.788 | 42.684 | 1.00 | 36.51 |
| 3117 | C | ILE | B | 523 | 36.386 | 24.580 | 39.695 | 1.00 | 24.99 |
| 3118 | O | ILE | B | 523 | 36.039 | 25.493 | 40.433 | 1.00 | 22.57 |
| 3119 | N | CYS | B | 524 | 35.800 | 24.316 | 38.527 | 1.00 | 21.93 |
| 3120 | CA | CYS | B | 524 | 34.653 | 25.070 | 38.034 | 1.00 | 21.61 |
| 3121 | C | CYS | B | 524 | 33.404 | 24.210 | 38.278 | 1.00 | 22.18 |
| 3122 | O | CYS | B | 524 | 33.327 | 23.074 | 37.791 | 1.00 | 25.73 |
| 3123 | CB | CYS | B | 524 | 34.795 | 25.353 | 36.523 | 1.00 | 24.95 |
| 3124 | SG | CYS | B | 524 | 33.339 | 26.126 | 35.708 | 1.00 | 27.67 |
| 3125 | N | ARG | B | 525 | 32.438 | 24.744 | 39.021 | 1.00 | 24.48 |
| 3126 | CA | ARG | B | 525 | 31.188 | 24.046 | 39.325 | 1.00 | 23.02 |
| 3127 | CB | ARG | B | 525 | 31.070 | 23.810 | 40.833 | 1.00 | 24.98 |
| 3128 | CG | ARG | B | 525 | 29.740 | 23.162 | 41.266 | 1.00 | 30.26 |
| 3129 | CD | ARG | B | 525 | 29.771 | 22.743 | 42.741 | 1.00 | 32.38 |
| 3130 | NE | ARG | B | 525 | 29.529 | 23.882 | 43.616 | 1.00 | 40.36 |
| 3131 | CZ | ARG | B | 525 | 29.879 | 23.947 | 44.901 | 1.00 | 43.86 |
| 3132 | NH1 | ARG | B | 525 | 30.501 | 22.927 | 45.485 | 1.00 | 44.63 |
| 3133 | NH2 | ARG | B | 525 | 29.612 | 25.045 | 45.601 | 1.00 | 44.65 |
| 3134 | C | ARG | B | 525 | 29.931 | 24.789 | 38.873 | 1.00 | 23.26 |
| 3135 | O | ARG | B | 525 | 29.794 | 26.000 | 39.113 | 1.00 | 22.50 |
| 3136 | N | ALA | B | 526 | 29.003 | 24.069 | 38.234 | 1.00 | 20.51 |
| 3137 | CA | ALA | B | 526 | 27.735 | 24.686 | 37.816 | 1.00 | 21.72 |
| 3138 | CB | ALA | B | 526 | 27.485 | 24.466 | 36.292 | 1.00 | 21.05 |
| 3139 | C | ALA | B | 526 | 26.588 | 24.087 | 38.620 | 1.00 | 22.87 |
| 3140 | O | ALA | B | 526 | 26.587 | 22.879 | 38.905 | 1.00 | 24.74 |
| 3141 | N | VAL | B | 527 | 25.610 | 24.916 | 38.982 | 1.00 | 21.77 |
| 3142 | CA | VAL | B | 527 | 24.420 | 24.465 | 39.727 | 1.00 | 19.86 |
| 3143 | CB | VAL | B | 527 | 24.240 | 25.287 | 41.023 | 1.00 | 21.97 |
| 3144 | CG1 | VAL | B | 527 | 23.068 | 24.754 | 41.819 | 1.00 | 16.34 |
| 3145 | CG2 | VAL | B | 527 | 25.527 | 25.223 | 41.867 | 1.00 | 21.42 |
| 3146 | C | VAL | B | 527 | 23.164 | 24.640 | 38.832 | 1.00 | 24.22 |
| 3147 | O | VAL | B | 527 | 22.823 | 25.744 | 38.466 | 1.00 | 20.14 |
| 3148 | N | HIS | B | 528 | 22.472 | 23.552 | 38.496 | 1.00 | 22.11 |
| 3149 | CA | HIS | B | 528 | 21.301 | 23.629 | 37.612 | 1.00 | 22.12 |
| 3150 | CB | HIS | B | 528 | 21.784 | 23.433 | 36.151 | 1.00 | 21.32 |
| 3151 | CG | HIS | B | 528 | 20.698 | 23.507 | 35.117 | 1.00 | 25.03 |
| 3152 | CD2 | HIS | B | 528 | 19.923 | 22.539 | 34.570 | 1.00 | 23.68 |
| 3153 | ND1 | HIS | B | 528 | 20.314 | 24.689 | 34.513 | 1.00 | 26.95 |
| 3154 | CE1 | HIS | B | 528 | 19.350 | 24.446 | 33.640 | 1.00 | 24.11 |
| 3155 | NE2 | HIS | B | 528 | 19.095 | 23.149 | 33.656 | 1.00 | 25.99 |
| 3156 | C | HIS | B | 528 | 20.243 | 22.575 | 38.005 | 1.00 | 23.47 |
| 3157 | O | HIS | B | 528 | 20.578 | 21.430 | 38.327 | 1.00 | 17.81 |
| 3158 | N | GLU | B | 529 | 18.967 | 22.952 | 37.941 | 1.00 | 22.58 |
| 3159 | CA | GLU | B | 529 | 17.873 | 22.058 | 38.329 | 1.00 | 26.09 |
| 3160 | CB | GLU | B | 529 | 16.527 | 22.797 | 38.232 | 1.00 | 29.61 |
| 3161 | CG | GLU | B | 529 | 15.937 | 22.915 | 36.815 | 1.00 | 38.27 |
| 3162 | CD | GLU | B | 529 | 14.959 | 24.077 | 36.675 | 1.00 | 41.61 |
| 3163 | OE1 | GLU | B | 529 | 15.424 | 25.223 | 36.545 | 1.00 | 46.32 |
| 3164 | OE2 | GLU | B | 529 | 13.727 | 23.862 | 36.705 | 1.00 | 44.53 |
| 3165 | C | GLU | B | 529 | 17.750 | 20.707 | 37.605 | 1.00 | 29.87 |
| 3166 | O | GLU | B | 529 | 17.141 | 19.793 | 38.147 | 1.00 | 26.84 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3167 | N | ALA | B | 530 | 18.310 | 20.568 | 36.402 | 1.00 | 29.43 |
| 3168 | CA | ALA | B | 530 | 18.187 | 19.298 | 35.675 | 1.00 | 33.98 |
| 3169 | CB | ALA | B | 530 | 17.969 | 19.553 | 34.147 | 1.00 | 30.62 |
| 3170 | C | ALA | B | 530 | 19.370 | 13.361 | 35.869 | 1.00 | 37.01 |
| 3171 | O | ALA | B | 530 | 19.348 | 17.231 | 35.401 | 1.00 | 35.13 |
| 3172 | N | ALA | B | 531 | 20.409 | 18.825 | 36.545 | 1.00 | 42.22 |
| 3173 | CA | ALA | B | 531 | 21.565 | 17.973 | 36.760 | 1.00 | 49.18 |
| 3174 | CB | ALA | B | 531 | 22.756 | 18.818 | 37.202 | 1.00 | 45.42 |
| 3175 | C | ALA | B | 531 | 21.234 | 16.891 | 37.804 | 1.00 | 57.47 |
| 3176 | O | ALA | B | 531 | 20.548 | 17.145 | 38.795 | 1.00 | 57.09 |
| 3177 | N | SER | B | 532 | 21.710 | 15.675 | 37.568 | 1.00 | 67.71 |
| 3178 | CA | SER | B | 532 | 21.445 | 14.575 | 38.484 | 1.00 | 79.33 |
| 3179 | CB | SER | B | 532 | 20.712 | 13.447 | 37.761 | 1.00 | 88.69 |
| 3180 | OG | SER | B | 532 | 21.537 | 12.871 | 36.765 | 1.00 | 107.24 |
| 3181 | C | SER | B | 532 | 22.723 | 14.027 | 39.104 | 1.00 | 75.76 |
| 3182 | O | SER | B | 532 | 23.787 | 14.051 | 38.490 | 1.00 | 77.74 |
| 3183 | N | CPR | B | 533 | 22.623 | 13.503 | 40.330 | 1.00 | 72.29 |
| 3184 | CD | CPR | B | 533 | 23.631 | 12.592 | 40.899 | 1.00 | 72.24 |
| 3185 | CA | CPR | B | 533 | 21.374 | 13.430 | 41.091 | 1.00 | 67.71 |
| 3186 | CB | CPR | B | 533 | 21.470 | 12.063 | 41.736 | 1.00 | 70.24 |
| 3187 | CG | CPR | B | 533 | 22.920 | 12.029 | 42.122 | 1.00 | 71.12 |
| 3188 | C | CPR | B | 533 | 21.194 | 14.534 | 42.138 | 1.00 | 63.47 |
| 3189 | O | CPR | B | 533 | 20.165 | 14.587 | 42.816 | 1.00 | 65.21 |
| 3190 | N | SER | B | 534 | 22.177 | 15.421 | 42.257 | 1.00 | 59.82 |
| 3191 | CA | SER | B | 534 | 22.118 | 16.483 | 43.260 | 1.00 | 53.82 |
| 3192 | CB | SER | B | 534 | 23.255 | 16.290 | 44.250 | 1.00 | 55.00 |
| 3193 | OG | SER | B | 534 | 24.483 | 16.273 | 43.549 | 1.00 | 59.60 |
| 3194 | C | SER | B | 534 | 22.164 | 17.915 | 42.735 | 1.00 | 47.48 |
| 3195 | O | SER | B | 534 | 22.558 | 18.825 | 43.455 | 1.00 | 44.16 |
| 3196 | N | GLN | B | 535 | 21.755 | 18.106 | 41.487 | 1.00 | 41.62 |
| 3197 | CA | GLN | B | 535 | 21.732 | 19.423 | 40.859 | 1.00 | 36.22 |
| 3198 | CB | GLN | B | 535 | 20.759 | 20.350 | 41.609 | 1.00 | 37.01 |
| 3199 | CG | GLN | B | 535 | 19.292 | 19.881 | 41.630 | 1.00 | 38.34 |
| 3200 | CD | GLN | B | 535 | 19.035 | 18.676 | 42.551 | 1.00 | 40.64 |
| 3201 | OE1 | GLN | B | 535 | 19.331 | 18.716 | 43.750 | 1.00 | 39.57 |
| 3202 | NE2 | GLN | B | 535 | 18.469 | 17.608 | 41.991 | 1.00 | 39.55 |
| 3203 | C | GLN | B | 535 | 23.091 | 20.131 | 40.654 | 1.00 | 33.30 |
| 3204 | O | GLN | B | 535 | 23.147 | 21.370 | 40.609 | 1.00 | 30.54 |
| 3205 | N | THR | B | 536 | 24.174 | 19.359 | 40.525 | 1.00 | 28.86 |
| 3206 | CA | THR | B | 536 | 25.506 | 19.941 | 40.255 | 1.00 | 28.54 |
| 3207 | CB | THR | B | 536 | 26.374 | 20.139 | 41.540 | 1.00 | 28.97 |
| 3208 | OG1 | THR | B | 536 | 26.702 | 18.856 | 42.107 | 1.00 | 27.26 |
| 3209 | CG2 | THR | B | 536 | 25.642 | 20.999 | 42.565 | 1.00 | 28.67 |
| 3210 | C | THR | B | 536 | 26.364 | 19.104 | 39.285 | 1.00 | 27.09 |
| 3211 | O | THR | B | 536 | 26.221 | 17.880 | 39.194 | 1.00 | 29.78 |
| 3212 | N | VAL | B | 537 | 27.255 | 19.787 | 38.570 | 1.00 | 25.49 |
| 3213 | CA | VAL | B | 537 | 28.198 | 19.166 | 37.640 | 1.00 | 24.15 |
| 3214 | CB | VAL | B | 537 | 27.716 | 19.256 | 36.153 | 1.00 | 23.84 |
| 3215 | CG1 | VAL | B | 537 | 28.682 | 18.505 | 35.269 | 1.00 | 22.92 |
| 3216 | CG2 | VAL | B | 537 | 26.301 | 18.673 | 35.985 | 1.00 | 22.22 |
| 3217 | C | VAL | B | 537 | 29.471 | 20.010 | 37.789 | 1.00 | 23.69 |
| 3218 | O | VAL | B | 537 | 29.393 | 21.250 | 37.751 | 1.00 | 25.35 |
| 3219 | N | GLN | B | 538 | 30.635 | 19.368 | 37.929 | 1.00 | 24.17 |
| 3220 | CA | GLN | B | 538 | 31.891 | 20.104 | 38.121 | 1.00 | 25.27 |
| 3221 | CB | GLN | B | 538 | 32.156 | 20.290 | 39.634 | 1.00 | 22.52 |
| 3222 | CG | GLN | B | 538 | 32.587 | 18.998 | 40.384 | 1.00 | 15.19 |
| 3223 | CD | GLN | B | 538 | 32.660 | 19.202 | 41.909 | 1.00 | 18.11 |
| 3224 | OE1 | GLN | B | 538 | 31.643 | 19.378 | 42.563 | 1.00 | 13.97 |
| 3225 | NE2 | GLN | B | 538 | 33.869 | 19.182 | 42.462 | 1.00 | 13.44 |
| 3226 | C | GLN | B | 538 | 33.106 | 19.432 | 37.474 | 1.00 | 27.22 |
| 3227 | O | GLN | B | 538 | 33.119 | 18.213 | 37.290 | 1.00 | 28.68 |
| 3228 | N | ARG | B | 539 | 34.137 | 20.231 | 37.177 | 1.00 | 31.36 |
| 3229 | CA | ARG | B | 539 | 35.376 | 19.758 | 36.533 | 1.00 | 33.47 |
| 3230 | CB | ARG | B | 539 | 35.235 | 19.909 | 35.013 | 1.00 | 38.73 |
| 3231 | CG | ARG | B | 539 | 35.946 | 18.832 | 34.206 | 1.00 | 53.73 |
| 3232 | CD | ARG | B | 539 | 34.960 | 17.853 | 33.543 | 1.00 | 61.86 |
| 3233 | NE | ARG | B | 539 | 33.951 | 17.337 | 34.466 | 1.00 | 70.31 |
| 3234 | CZ | ARG | B | 539 | 32.965 | 16.510 | 34.123 | 1.00 | 73.78 |
| 3235 | NH1 | ARG | B | 539 | 32.846 | 16.088 | 32.874 | 1.00 | 77.48 |
| 3236 | NH2 | ARG | B | 539 | 32.080 | 16.122 | 35.029 | 1.00 | 76.72 |
| 3237 | C | ARG | B | 539 | 36.633 | 20.538 | 37.009 | 1.00 | 32.58 |
| 3238 | O | ARG | B | 539 | 36.588 | 21.759 | 37.215 | 1.00 | 30.08 |
| 3239 | N | ALA | B | 540 | 37.751 | 19.841 | 37.177 | 1.00 | 30.15 |
| 3240 | CA | ALA | B | 540 | 38.995 | 20.489 | 37.612 | 1.00 | 30.85 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3241 | CB | ALA | B | 540 | 39.638 | 19.663 | 38.718 | 1.00 | 29.13 |
| 3242 | C | ALA | B | 540 | 40.001 | 20.665 | 36.465 | 1.00 | 30.10 |
| 3243 | O | ALA | B | 540 | 39.922 | 19.962 | 35.465 | 1.00 | 30.73 |
| 3244 | N | VAL | B | 541 | 40.939 | 21.602 | 36.622 | 1.00 | 31.45 |
| 3245 | CA | VAL | B | 541 | 42.003 | 21.862 | 35.640 | 1.00 | 31.92 |
| 3246 | CB | VAL | B | 541 | 41.622 | 23.011 | 34.643 | 1.00 | 32.22 |
| 3247 | CG1 | VAL | B | 541 | 41.439 | 24.327 | 35.387 | 1.00 | 27.88 |
| 3248 | CG2 | VAL | B | 541 | 42.717 | 23.152 | 33.551 | 1.00 | 28.97 |
| 3249 | C | VAL | B | 541 | 43.300 | 22.273 | 36.368 | 1.00 | 35.97 |
| 3250 | O | VAL | B | 541 | 43.240 | 22.808 | 37.478 | 1.00 | 35.70 |
| 3251 | N | SER | B | 542 | 44.456 | 22.026 | 35.744 | 1.00 | 38.64 |
| 3252 | CA | SER | B | 542 | 45.765 | 22.374 | 36.316 | 1.00 | 44.88 |
| 3253 | CB | SER | B | 542 | 46.567 | 21.118 | 36.668 | 1.00 | 42.77 |
| 3254 | OG | SER | B | 542 | 45.966 | 20.419 | 37.737 | 1.00 | 44.30 |
| 3255 | C | SER | B | 542 | 46.599 | 23.219 | 35.362 | 1.00 | 49.71 |
| 3256 | O | SER | B | 542 | 46.374 | 23.211 | 34.154 | 1.00 | 48.56 |
| 3257 | N | VAL | B | 543 | 47.573 | 23.935 | 35.917 | 1.00 | 55.58 |
| 3258 | CA | VAL | B | 543 | 48.453 | 24.795 | 35.130 | 1.00 | 63.38 |
| 3259 | CB | VAL | B | 543 | 49.083 | 25.895 | 36.024 | 1.00 | 63.70 |
| 3260 | CG1 | VAL | B | 543 | 50.130 | 26.665 | 35.255 | 1.00 | 64.65 |
| 3261 | CG2 | VAL | B | 543 | 48.000 | 26.846 | 36.507 | 1.00 | 63.11 |
| 3262 | C | VAL | B | 543 | 49.561 | 24.012 | 34.414 | 1.00 | 68.07 |
| 3263 | O | VAL | B | 543 | 50.078 | 24.464 | 33.394 | 1.00 | 66.86 |
| 3264 | N | ASN | B | 544 | 49.916 | 22.842 | 34.944 | 1.00 | 72.23 |
| 3265 | CA | ASN | B | 544 | 50.947 | 22.000 | 34.337 | 1.00 | 78.30 |
| 3266 | CB | ASN | B | 544 | 52.157 | 21.901 | 35.261 | 1.00 | 81.38 |
| 3267 | CG | ASN | B | 544 | 53.286 | 22.807 | 34.834 | 1.00 | 84.69 |
| 3268 | OD1 | ASN | B | 544 | 54.207 | 23.071 | 35.602 | 1.00 | 87.17 |
| 3269 | ND2 | ASN | B | 544 | 53.229 | 23.280 | 33.596 | 1.00 | 86.49 |
| 3270 | C | ASN | B | 544 | 50.451 | 20.593 | 34.005 | 1.00 | 80.12 |
| 3271 | O | ASN | B | 544 | 50.295 | 20.304 | 32.801 | 1.00 | 81.32 |
| 3272 | OXT | ASN | B | 544 | 50.225 | 19.793 | 34.941 | 1.00 | 81.10 |
| 3273 | CB | VAL | E | 336 | 65.211 | 33.512 | 65.110 | 1.00 | 72.28 |
| 3274 | CG1 | VAL | E | 336 | 64.364 | 33.929 | 63.923 | 1.00 | 71.85 |
| 3275 | CG2 | VAL | E | 336 | 66.465 | 32.796 | 64.632 | 1.00 | 72.42 |
| 3276 | C | VAL | E | 336 | 64.312 | 35.476 | 66.372 | 1.00 | 72.75 |
| 3277 | O | VAL | E | 336 | 63.540 | 34.964 | 67.181 | 1.00 | 73.78 |
| 3278 | N | VAL | E | 336 | 66.418 | 34.361 | 67.142 | 1.00 | 72.22 |
| 3279 | CA | VAL | E | 336 | 65.596 | 34.754 | 65.959 | 1.00 | 72.60 |
| 3280 | N | SER | E | 337 | 64.098 | 36.666 | 65.809 | 1.00 | 71.93 |
| 3281 | CA | SER | E | 337 | 62.911 | 37.477 | 66.086 | 1.00 | 70.62 |
| 3282 | CB | SER | E | 337 | 63.179 | 38.430 | 67.250 | 1.00 | 70.02 |
| 3283 | OG | SER | E | 337 | 64.305 | 39.239 | 66.976 | 1.00 | 69.06 |
| 3284 | C | SER | E | 337 | 62.524 | 38.276 | 64.833 | 1.00 | 70.17 |
| 3285 | O | SER | E | 337 | 63.375 | 38.559 | 63.982 | 1.00 | 69.32 |
| 3286 | N | ALA | E | 338 | 61.246 | 38.640 | 64.724 | 1.00 | 69.77 |
| 3287 | CA | ALA | E | 338 | 60.760 | 39.375 | 63.555 | 1.00 | 69.11 |
| 3288 | CB | ALA | E | 338 | 60.139 | 38.397 | 62.562 | 1.00 | 69.29 |
| 3289 | C | ALA | E | 338 | 59.763 | 40.491 | 63.862 | 1.00 | 68.19 |
| 3290 | O | ALA | E | 338 | 58.955 | 40.382 | 64.782 | 1.00 | 68.18 |
| 3291 | N | TYR | E | 339 | 59.823 | 41.561 | 63.070 | 1.00 | 67.19 |
| 3292 | CA | TYR | E | 339 | 58.925 | 42.701 | 63.233 | 1.00 | 64.99 |
| 3293 | CB | TYR | E | 339 | 59.657 | 43.886 | 63.877 | 1.00 | 69.04 |
| 3294 | CG | TYR | E | 339 | 60.673 | 43.505 | 64.930 | 1.00 | 73.47 |
| 3295 | CD1 | TYR | E | 339 | 61.928 | 43.015 | 64.567 | 1.00 | 75.15 |
| 3296 | CE1 | TYR | E | 339 | 62.869 | 42.658 | 65.529 | 1.00 | 77.81 |
| 3297 | CD2 | TYR | E | 339 | 60.380 | 43.627 | 66.290 | 1.00 | 75.13 |
| 3298 | CE2 | TYR | E | 339 | 61.312 | 43.272 | 67.262 | 1.00 | 77.52 |
| 3299 | CZ | TYR | E | 339 | 62.557 | 42.788 | 66.874 | 1.00 | 79.04 |
| 3300 | OH | TYR | E | 339 | 63.495 | 42.444 | 67.824 | 1.00 | 79.90 |
| 3301 | C | TYR | E | 339 | 58.363 | 43.142 | 61.882 | 1.00 | 61.93 |
| 3302 | O | TYR | E | 339 | 58.949 | 42.874 | 60.828 | 1.00 | 61.60 |
| 3303 | N | LEU | E | 340 | 57.221 | 43.818 | 61.928 | 1.00 | 58.82 |
| 3304 | CA | LEU | E | 340 | 56.566 | 44.325 | 60.732 | 1.00 | 57.73 |
| 3305 | CB | LEU | E | 340 | 55.356 | 43.458 | 60.374 | 1.00 | 53.52 |
| 3306 | CG | LEU | E | 340 | 54.634 | 43.864 | 59.087 | 1.00 | 52.28 |
| 3307 | CD1 | LEU | E | 340 | 55.631 | 43.931 | 57.940 | 1.00 | 50.19 |
| 3308 | CD2 | LEU | E | 340 | 53.537 | 42.873 | 58.781 | 1.00 | 49.72 |
| 3309 | C | LEU | E | 340 | 56.128 | 45.753 | 61.044 | 1.00 | 58.27 |
| 3310 | O | LEU | E | 340 | 55.600 | 46.018 | 62.125 | 1.00 | 57.55 |
| 3311 | N | SER | E | 341 | 56.341 | 46.665 | 60.100 | 1.00 | 56.51 |
| 3312 | CA | SER | E | 341 | 56.003 | 48.078 | 60.304 | 1.00 | 56.85 |
| 3313 | CB | SER | E | 341 | 57.252 | 48.932 | 60.083 | 1.00 | 56.36 |
| 3314 | OG | SER | E | 341 | 57.679 | 48.839 | 58.731 | 1.00 | 56.62 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3315 | C | SER | E | 341 | 54.880 | 48.643 | 59.427 | 1.00 | 56.03 |
| 3316 | O | SER | E | 341 | 54.327 | 47.950 | 58.568 | 1.00 | 58.55 |
| 3317 | N | ARG | E | 342 | 54.561 | 49.916 | 59.664 | 1.00 | 54.57 |
| 3318 | CA | ARG | E | 342 | 53.535 | 50.642 | 58.918 | 1.00 | 51.89 |
| 3319 | CB | ARG | E | 342 | 52.535 | 51.298 | 59.888 | 1.00 | 52.28 |
| 3320 | CG | ARG | E | 342 | 51.683 | 50.324 | 60.727 | 1.00 | 54.06 |
| 3321 | CD | ARG | E | 342 | 50.594 | 51.051 | 61.555 | 1.00 | 55.45 |
| 3322 | NE | ARG | E | 342 | 51.146 | 51.826 | 62.668 | 1.00 | 58.61 |
| 3323 | CZ | ARG | E | 342 | 51.534 | 51.309 | 63.834 | 1.00 | 60.81 |
| 3324 | NH1 | ARG | E | 342 | 51.425 | 50.008 | 64.061 | 1.00 | 62.43 |
| 3325 | NH2 | ARG | E | 342 | 52.058 | 52.089 | 64.771 | 1.00 | 60.98 |
| 3326 | C | ARG | E | 342 | 54.238 | 51.723 | 58.066 | 1.00 | 49.34 |
| 3327 | O | ARG | E | 342 | 55.442 | 51.952 | 58.207 | 1.00 | 49.48 |
| 3328 | N | PRO | E | 343 | 53.500 | 52.391 | 57.166 | 1.00 | 45.75 |
| 3329 | CD | PRO | E | 343 | 52.110 | 52.094 | 56.769 | 1.00 | 46.54 |
| 3330 | CA | PRO | E | 343 | 54.078 | 53.440 | 56.307 | 1.00 | 46.24 |
| 3331 | CB | PRO | E | 343 | 52.987 | 53.682 | 55.249 | 1.00 | 45.62 |
| 3332 | CG | PRO | E | 343 | 52.130 | 52.420 | 55.296 | 1.00 | 45.23 |
| 3333 | C | PRO | E | 343 | 54.405 | 54.742 | 57.055 | 1.00 | 45.17 |
| 3334 | O | PRO | E | 343 | 53.788 | 55.053 | 58.079 | 1.00 | 43.05 |
| 3335 | N | SER | E | 344 | 55.361 | 55.510 | 56.537 | 1.00 | 43.37 |
| 3336 | CA | SER | E | 344 | 55.712 | 56.783 | 57.163 | 1.00 | 42.09 |
| 3337 | CB | SER | E | 344 | 57.133 | 57.215 | 56.780 | 1.00 | 43.90 |
| 3338 | OG | SER | E | 344 | 57.143 | 57.980 | 55.586 | 1.00 | 46.07 |
| 3339 | C | SER | E | 344 | 54.709 | 57.796 | 56.625 | 1.00 | 39.70 |
| 3340 | O | SER | E | 344 | 54.292 | 57.688 | 55.474 | 1.00 | 37.85 |
| 3341 | N | PRO | E | 345 | 54.279 | 58.770 | 57.457 | 1.00 | 36.08 |
| 3342 | CD | PRO | E | 345 | 54.394 | 58.808 | 58.927 | 1.00 | 36.33 |
| 3343 | CA | PRO | E | 345 | 53.312 | 59.774 | 56.986 | 1.00 | 34.66 |
| 3344 | CB | PRO | E | 345 | 53.084 | 60.635 | 58.221 | 1.00 | 34.48 |
| 3345 | CG | PRO | E | 345 | 53.160 | 59.613 | 59.334 | 1.00 | 34.92 |
| 3346 | C | PRO | E | 345 | 53.844 | 60.567 | 55.800 | 1.00 | 33.62 |
| 3347 | O | PRO | E | 345 | 53.090 | 60.959 | 54.909 | 1.00 | 32.02 |
| 3348 | N | PHE | E | 346 | 55.151 | 60.799 | 55.793 | 1.00 | 33.72 |
| 3349 | CA | PHE | E | 346 | 55.785 | 61.523 | 54.698 | 1.00 | 35.85 |
| 3350 | CB | PHE | E | 346 | 57.293 | 61.623 | 54.932 | 1.00 | 34.00 |
| 3351 | CG | PHE | E | 346 | 58.034 | 62.339 | 53.832 | 1.00 | 34.53 |
| 3352 | CD1 | PHE | E | 346 | 57.682 | 63.637 | 53.466 | 1.00 | 36.94 |
| 3353 | CD2 | PHE | E | 346 | 59.089 | 61.723 | 53.171 | 1.00 | 32.58 |
| 3354 | CE1 | PHE | E | 346 | 58.372 | 64.309 | 52.456 | 1.00 | 36.42 |
| 3355 | CE2 | PHE | E | 346 | 59.786 | 62.379 | 52.166 | 1.00 | 34.30 |
| 3356 | CZ | PHE | E | 346 | 59.426 | 63.680 | 51.803 | 1.00 | 35.55 |
| 3357 | C | PHE | E | 346 | 55.508 | 60.771 | 53.396 | 1.00 | 34.27 |
| 3358 | O | PHE | E | 346 | 55.007 | 61.345 | 52.441 | 1.00 | 34.44 |
| 3359 | N | ASP | E | 347 | 55.826 | 59.481 | 53.382 | 1.00 | 35.34 |
| 3360 | CA | ASP | E | 347 | 55.617 | 58.632 | 52.210 | 1.00 | 37.45 |
| 3361 | CB | ASP | E | 347 | 56.147 | 57.226 | 52.490 | 1.00 | 35.86 |
| 3362 | CG | ASP | E | 347 | 57.644 | 57.140 | 52.343 | 1.00 | 35.95 |
| 3363 | OD1 | ASP | E | 347 | 58.247 | 56.189 | 52.879 | 1.00 | 35.33 |
| 3364 | OD2 | ASP | E | 347 | 58.216 | 58.032 | 51.684 | 1.00 | 37.11 |
| 3365 | C | ASP | E | 347 | 54.169 | 58.523 | 51.767 | 1.00 | 38.47 |
| 3366 | O | ASP | E | 347 | 53.878 | 58.573 | 50.570 | 1.00 | 36.88 |
| 3367 | N | LEU | E | 348 | 53.275 | 58.377 | 52.746 | 1.00 | 38.67 |
| 3368 | CA | LEU | E | 348 | 51.847 | 58.222 | 52.506 | 1.00 | 40.90 |
| 3369 | CB | LEU | E | 348 | 51.179 | 57.680 | 53.781 | 1.00 | 40.05 |
| 3370 | CG | LEU | E | 348 | 49.666 | 57.420 | 53.799 | 1.00 | 39.20 |
| 3371 | CD1 | LEU | E | 348 | 49.278 | 56.437 | 52.704 | 1.00 | 38.16 |
| 3372 | CD2 | LEU | E | 348 | 49.262 | 56.875 | 55.157 | 1.00 | 38.48 |
| 3373 | C | LEU | E | 348 | 51.108 | 59.476 | 52.031 | 1.00 | 43.05 |
| 3374 | O | LEU | E | 348 | 50.343 | 59.409 | 51.060 | 1.00 | 42.88 |
| 3375 | N | PHE | E | 349 | 51.333 | 60.614 | 52.693 | 1.00 | 44.56 |
| 3376 | CA | PHE | E | 349 | 50.632 | 61.851 | 52.326 | 1.00 | 46.90 |
| 3377 | CB | PHE | E | 349 | 50.193 | 62.615 | 53.589 | 1.00 | 44.58 |
| 3378 | CG | PHE | E | 349 | 49.321 | 61.817 | 54.510 | 1.00 | 41.61 |
| 3379 | CD1 | PHE | E | 349 | 49.846 | 61.251 | 55.667 | 1.00 | 40.76 |
| 3380 | CD2 | PHE | E | 349 | 47.984 | 61.597 | 54.203 | 1.00 | 40.57 |
| 3381 | CE1 | PHE | E | 349 | 49.051 | 60.472 | 56.510 | 1.00 | 41.06 |
| 3382 | CE2 | PHE | E | 349 | 47.174 | 60.819 | 55.035 | 1.00 | 41.07 |
| 3383 | CZ | PHE | E | 349 | 47.709 | 60.253 | 56.193 | 1.00 | 40.69 |
| 3384 | C | PHE | E | 349 | 51.345 | 62.835 | 51.397 | 1.00 | 48.70 |
| 3385 | O | PHE | E | 349 | 50.688 | 63.537 | 50.633 | 1.00 | 48.35 |
| 3386 | N | ILE | E | 350 | 52.671 | 62.917 | 51.469 | 1.00 | 52.14 |
| 3387 | CA | ILE | E | 350 | 53.399 | 63.855 | 50.617 | 1.00 | 55.17 |
| 3388 | CB | ILE | E | 350 | 54.612 | 64.469 | 51.360 | 1.00 | 58.81 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3389 | CG2 | ILE | E | 350 | 55.303 | 65.509 | 50.468 | 1.00 | 58.11 |
| 3390 | CG1 | ILE | E | 350 | 54.153 | 65.117 | 52.674 | 1.00 | 59.58 |
| 3391 | CD1 | ILE | E | 350 | 53.124 | 66.218 | 52.505 | 1.00 | 61.49 |
| 3392 | C | ILE | E | 350 | 53.876 | 63.227 | 49.303 | 1.00 | 55.84 |
| 3393 | O | ILE | E | 350 | 53.384 | 63.587 | 48.232 | 1.00 | 55.61 |
| 3394 | N | ARG | E | 351 | 54.834 | 62.305 | 49.374 | 1.00 | 55.87 |
| 3395 | CA | ARG | E | 351 | 55.328 | 61.657 | 48.162 | 1.00 | 56.48 |
| 3396 | CB | ARG | E | 351 | 56.550 | 60.797 | 48.470 | 1.00 | 56.29 |
| 3397 | CG | ARG | E | 351 | 57.788 | 61.593 | 48.808 | 1.00 | 58.24 |
| 3398 | CD | ARG | E | 351 | 58.957 | 60.677 | 49.116 | 1.00 | 60.06 |
| 3399 | NE | ARG | E | 351 | 59.380 | 59.919 | 47.944 | 1.00 | 63.74 |
| 3400 | CZ | ARG | E | 351 | 59.512 | 58.595 | 47.920 | 1.00 | 66.34 |
| 3401 | NH1 | ARG | E | 351 | 59.253 | 57.882 | 49.008 | 1.00 | 66.50 |
| 3402 | NH2 | ARG | E | 351 | 59.900 | 57.983 | 46.807 | 1.00 | 66.90 |
| 3403 | C | ARG | E | 351 | 54.247 | 60.793 | 47.520 | 1.00 | 56.76 |
| 3404 | O | ARG | E | 351 | 54.204 | 60.642 | 46.299 | 1.00 | 56.88 |
| 3405 | N | LYS | E | 352 | 53.380 | 60.230 | 48.353 | 1.00 | 56.69 |
| 3406 | CA | LYS | E | 352 | 52.284 | 59.385 | 47.885 | 1.00 | 57.60 |
| 3407 | CB | LYS | E | 352 | 51.421 | 60.164 | 46.885 | 1.00 | 61.27 |
| 3408 | CG | LYS | E | 352 | 50.515 | 61.194 | 47.541 | 1.00 | 66.34 |
| 3409 | CD | LYS | E | 352 | 49.748 | 62.015 | 46.516 | 1.00 | 70.99 |
| 3410 | CE | LYS | E | 352 | 48.623 | 62.822 | 47.169 | 1.00 | 73.55 |
| 3411 | NZ | LYS | E | 352 | 49.109 | 63.742 | 48.227 | 1.00 | 76.07 |
| 3412 | C | LYS | E | 352 | 52.705 | 58.035 | 47.286 | 1.00 | 55.04 |
| 3413 | O | LYS | E | 352 | 52.194 | 57.612 | 46.248 | 1.00 | 54.10 |
| 3414 | N | SER | E | 353 | 53.644 | 57.370 | 47.947 | 1.00 | 52.38 |
| 3415 | CA | SER | E | 353 | 54.111 | 56.062 | 47.521 | 1.00 | 48.76 |
| 3416 | CB | SER | E | 353 | 55.312 | 56.184 | 46.580 | 1.00 | 52.52 |
| 3417 | OG | SER | E | 353 | 56.405 | 56.811 | 47.212 | 1.00 | 60.61 |
| 3418 | C | SER | E | 353 | 54.487 | 55.306 | 48.786 | 1.00 | 42.94 |
| 3419 | O | SER | E | 353 | 55.666 | 55.177 | 49.127 | 1.00 | 41.55 |
| 3420 | N | PRO | E | 354 | 53.469 | 54.808 | 49.507 | 1.00 | 38.57 |
| 3421 | CD | PRO | E | 354 | 52.063 | 54.974 | 49.109 | 1.00 | 36.69 |
| 3422 | CA | PRO | E | 354 | 53.567 | 54.048 | 50.762 | 1.00 | 37.12 |
| 3423 | CB | PRO | E | 354 | 52.112 | 53.957 | 51.245 | 1.00 | 35.43 |
| 3424 | CG | PRO | E | 354 | 51.369 | 54.972 | 50.427 | 1.00 | 36.47 |
| 3425 | C | PRO | E | 354 | 54.170 | 52.652 | 50.625 | 1.00 | 37.92 |
| 3426 | O | PRO | E | 354 | 53.886 | 51.942 | 49.648 | 1.00 | 36.41 |
| 3427 | N | THR | E | 355 | 54.970 | 52.260 | 51.621 | 1.00 | 38.30 |
| 3428 | CA | THR | E | 355 | 55.595 | 50.933 | 51.671 | 1.00 | 39.38 |
| 3429 | CB | THR | E | 355 | 57.047 | 50.970 | 51.117 | 1.00 | 41.63 |
| 3430 | OG1 | THR | E | 355 | 57.895 | 51.699 | 52.018 | 1.00 | 40.05 |
| 3431 | CG2 | THR | E | 355 | 57.081 | 51.641 | 49.737 | 1.00 | 42.46 |
| 3432 | C | THR | E | 355 | 55.647 | 50.393 | 53.125 | 1.00 | 41.14 |
| 3433 | O | THR | E | 355 | 55.641 | 51.169 | 54.084 | 1.00 | 37.71 |
| 3434 | N | ILE | E | 356 | 55.685 | 49.070 | 53.287 | 1.00 | 41.45 |
| 3435 | CA | ILE | E | 356 | 55.773 | 48.470 | 54.617 | 1.00 | 43.87 |
| 3436 | CB | ILE | E | 356 | 54.482 | 47.694 | 55.010 | 1.00 | 45.42 |
| 3437 | CG2 | ILE | E | 356 | 53.303 | 48.651 | 55.066 | 1.00 | 43.14 |
| 3438 | CG1 | ILE | E | 356 | 54.205 | 46.562 | 54.017 | 1.00 | 48.32 |
| 3439 | CD1 | ILE | E | 356 | 52.962 | 45.760 | 54.351 | 1.00 | 52.82 |
| 3440 | C | ILE | E | 356 | 56.969 | 47.527 | 54.610 | 1.00 | 46.35 |
| 3441 | O | ILE | E | 356 | 57.357 | 47.042 | 53.543 | 1.00 | 45.49 |
| 3442 | N | THR | E | 357 | 57.541 | 47.254 | 55.786 | 1.00 | 48.30 |
| 3443 | CA | THR | E | 357 | 58.734 | 46.406 | 55.872 | 1.00 | 51.07 |
| 3444 | CB | THR | E | 357 | 59.989 | 47.294 | 56.077 | 1.00 | 52.69 |
| 3445 | OG1 | THR | E | 357 | 60.133 | 48.178 | 54.959 | 1.00 | 54.03 |
| 3446 | CG2 | THR | E | 357 | 61.242 | 46.445 | 56.208 | 1.00 | 54.18 |
| 3447 | C | THR | E | 357 | 58.762 | 45.293 | 56.933 | 1.00 | 51.75 |
| 3448 | O | THR | E | 357 | 58.415 | 45.514 | 58.099 | 1.00 | 53.83 |
| 3449 | N | CYS | E | 358 | 59.212 | 44.109 | 56.513 | 1.00 | 52.24 |
| 3450 | CA | CYS | E | 358 | 59.331 | 42.930 | 57.379 | 1.00 | 51.80 |
| 3451 | C | CYS | E | 358 | 60.820 | 42.681 | 57.713 | 1.00 | 50.31 |
| 3452 | O | CYS | E | 358 | 61.638 | 42.437 | 56.815 | 1.00 | 48.51 |
| 3453 | CB | CYS | E | 358 | 58.738 | 41.713 | 56.662 | 1.00 | 54.79 |
| 3454 | SG | CYS | E | 358 | 58.345 | 40.265 | 57.710 | 1.00 | 60.14 |
| 3455 | N | LEU | E | 359 | 61.161 | 42.735 | 59.002 | 1.00 | 48.14 |
| 3456 | CA | LEU | E | 359 | 62.546 | 42.559 | 59.458 | 1.00 | 47.62 |
| 3457 | CB | LEU | E | 359 | 62.958 | 43.766 | 60.314 | 1.00 | 45.06 |
| 3458 | CG | LEU | E | 359 | 64.257 | 43.686 | 61.137 | 1.00 | 45.08 |
| 3459 | CD1 | LEU | E | 359 | 65.457 | 43.493 | 60.204 | 1.00 | 43.67 |
| 3460 | CD2 | LEU | E | 359 | 64.420 | 44.961 | 61.982 | 1.00 | 42.64 |
| 3461 | C | LEU | E | 359 | 62.827 | 41.274 | 60.244 | 1.00 | 49.61 |
| 3462 | O | LEU | E | 359 | 62.124 | 40.960 | 61.206 | 1.00 | 51.15 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3463 | N | VAL | E | 360 | 63.875 | 40.552 | 59.851 | 1.00 | 52.90 |
| 3464 | CA | VAL | E | 360 | 64.257 | 39.303 | 60.516 | 1.00 | 56.13 |
| 3465 | CB | VAL | E | 360 | 64.121 | 38.102 | 59.540 | 1.00 | 55.32 |
| 3466 | CG1 | VAL | E | 360 | 64.695 | 36.843 | 60.169 | 1.00 | 56.35 |
| 3467 | CG2 | VAL | E | 360 | 62.654 | 37.883 | 59.178 | 1.00 | 53.87 |
| 3468 | C | VAL | E | 360 | 65.692 | 39.350 | 61.074 | 1.00 | 60.25 |
| 3469 | O | VAL | E | 360 | 66.664 | 39.428 | 60.314 | 1.00 | 58.43 |
| 3470 | N | VAL | E | 361 | 65.814 | 39.302 | 62.402 | 1.00 | 65.34 |
| 3471 | CA | VAL | E | 361 | 67.118 | 39.339 | 63.077 | 1.00 | 72.87 |
| 3472 | CB | VAL | E | 361 | 67.076 | 40.261 | 64.320 | 1.00 | 68.69 |
| 3473 | CG1 | VAL | E | 361 | 68.474 | 40.389 | 64.922 | 1.00 | 65.39 |
| 3474 | CG2 | VAL | E | 361 | 66.525 | 41.628 | 63.944 | 1.00 | 65.81 |
| 3475 | C | VAL | E | 361 | 67.556 | 37.938 | 63.535 | 1.00 | 80.85 |
| 3476 | O | VAL | E | 361 | 66.993 | 37.388 | 64.484 | 1.00 | 80.83 |
| 3477 | N | ASP | E | 362 | 68.566 | 37.375 | 62.873 | 1.00 | 87.65 |
| 3478 | CA | ASP | E | 362 | 69.055 | 36.036 | 63.207 | 1.00 | 96.39 |
| 3479 | CB | ASP | E | 362 | 69.205 | 35.202 | 61.930 | 1.00 | 94.07 |
| 3480 | CG | ASP | E | 362 | 69.649 | 33.775 | 62.207 | 1.00 | 91.19 |
| 3481 | OD1 | ASP | E | 362 | 69.061 | 33.130 | 63.098 | 1.00 | 89.07 |
| 3482 | OD2 | ASP | E | 362 | 70.577 | 33.292 | 61.526 | 1.00 | 87.68 |
| 3483 | C | ASP | E | 362 | 70.378 | 36.049 | 63.970 | 1.00 | 102.01 |
| 3484 | O | ASP | E | 362 | 71.413 | 36.445 | 63.432 | 1.00 | 105.89 |
| 3485 | N | GLY | E | 363 | 70.333 | 35.597 | 65.222 | 1.00 | 107.45 |
| 3486 | CA | GLY | E | 363 | 71.521 | 35.562 | 66.061 | 1.00 | 108.30 |
| 3487 | C | GLY | E | 363 | 72.744 | 34.886 | 65.459 | 1.00 | 106.23 |
| 3488 | O | GLY | E | 363 | 73.732 | 35.550 | 65.146 | 1.00 | 110.43 |
| 3489 | N | ALA | E | 364 | 72.691 | 33.567 | 65.302 | 1.00 | 104.78 |
| 3490 | CA | ALA | E | 364 | 73.814 | 32.818 | 64.742 | 1.00 | 97.93 |
| 3491 | CB | ALA | E | 364 | 74.299 | 31.785 | 65.746 | 1.00 | 98.43 |
| 3492 | C | ALA | E | 364 | 73.454 | 32.134 | 63.426 | 1.00 | 93.77 |
| 3493 | O | ALA | E | 364 | 72.929 | 31.020 | 63.412 | 1.00 | 92.64 |
| 3494 | N | PRO | E | 365 | 73.753 | 32.795 | 62.299 | 1.00 | 90.90 |
| 3495 | CD | PRO | E | 365 | 74.509 | 34.058 | 62.245 | 1.00 | 88.11 |
| 3496 | CA | PRO | E | 365 | 73.478 | 32.296 | 60.948 | 1.00 | 91.64 |
| 3497 | CB | PRO | E | 365 | 74.371 | 33.173 | 60.082 | 1.00 | 88.68 |
| 3498 | CG | PRO | E | 365 | 74.329 | 34.479 | 60.812 | 1.00 | 86.61 |
| 3499 | C | PRO | E | 365 | 73.757 | 30.804 | 60.752 | 1.00 | 95.73 |
| 3500 | O | PRO | E | 365 | 74.650 | 30.237 | 61.382 | 1.00 | 95.04 |
| 3501 | N | SER | E | 366 | 72.982 | 30.177 | 59.873 | 1.00 | 101.17 |
| 3502 | CA | SER | E | 366 | 73.132 | 28.755 | 59.578 | 1.00 | 108.73 |
| 3503 | CB | SER | E | 366 | 72.238 | 27.927 | 60.498 | 1.00 | 106.63 |
| 3504 | OG | SER | E | 366 | 72.245 | 26.566 | 60.106 | 1.00 | 104.83 |
| 3505 | C | SER | E | 366 | 72.751 | 28.479 | 58.132 | 1.00 | 114.32 |
| 3506 | O | SER | E | 366 | 71.767 | 29.026 | 57.636 | 1.00 | 114.98 |
| 3507 | N | LYS | E | 367 | 73.525 | 27.626 | 57.464 | 1.00 | 118.60 |
| 3508 | CA | LYS | E | 367 | 73.260 | 27.286 | 56.069 | 1.00 | 124.51 |
| 3509 | CB | LYS | E | 367 | 74.054 | 26.046 | 55.654 | 1.00 | 126.92 |
| 3510 | CG | LYS | E | 367 | 73.657 | 24.773 | 56.379 | 1.00 | 128.24 |
| 3511 | CD | LYS | E | 367 | 74.459 | 23.583 | 55.881 | 1.00 | 128.15 |
| 3512 | CE | LYS | E | 367 | 74.031 | 22.302 | 56.576 | 1.00 | 127.84 |
| 3513 | NZ | LYS | E | 367 | 74.832 | 21.132 | 56.121 | 1.00 | 127.53 |
| 3514 | C | LYS | E | 367 | 71.772 | 27.034 | 55.868 | 1.00 | 125.10 |
| 3515 | O | LYS | E | 367 | 71.147 | 26.298 | 56.631 | 1.00 | 128.42 |
| 3516 | N | GLY | E | 368 | 71.210 | 27.653 | 54.838 | 1.00 | 123.68 |
| 3517 | CA | GLY | E | 368 | 69.794 | 27.501 | 54.569 | 1.00 | 116.94 |
| 3518 | C | GLY | E | 368 | 69.182 | 28.875 | 54.410 | 1.00 | 109.88 |
| 3519 | O | GLY | E | 368 | 69.250 | 29.704 | 55.317 | 1.00 | 113.04 |
| 3520 | N | THR | E | 369 | 68.586 | 29.114 | 53.249 | 1.00 | 104.65 |
| 3521 | CA | THR | E | 369 | 67.973 | 30.398 | 52.949 | 1.00 | 94.12 |
| 3522 | CB | THR | E | 369 | 67.562 | 30.463 | 51.467 | 1.00 | 91.72 |
| 3523 | OG1 | THR | E | 369 | 68.682 | 30.110 | 50.648 | 1.00 | 89.10 |
| 3524 | CG2 | THR | E | 369 | 67.098 | 31.865 | 51.099 | 1.00 | 89.87 |
| 3525 | C | THR | E | 369 | 66.748 | 30.700 | 53.808 | 1.00 | 91.19 |
| 3526 | O | THR | E | 369 | 65.993 | 29.798 | 54.173 | 1.00 | 88.68 |
| 3527 | N | VAL | E | 370 | 66.568 | 31.981 | 54.127 | 1.00 | 86.24 |
| 3528 | CA | VAL | E | 370 | 65.434 | 32.449 | 54.923 | 1.00 | 82.27 |
| 3529 | CB | VAL | E | 370 | 65.855 | 33.575 | 55.884 | 1.00 | 83.30 |
| 3530 | CG1 | VAL | E | 370 | 64.686 | 33.962 | 56.769 | 1.00 | 83.54 |
| 3531 | CG2 | VAL | E | 370 | 67.042 | 33.128 | 56.720 | 1.00 | 83.58 |
| 3532 | C | VAL | E | 370 | 64.372 | 32.994 | 53.966 | 1.00 | 80.11 |
| 3533 | O | VAL | E | 370 | 64.659 | 33.868 | 53.148 | 1.00 | 79.36 |
| 3534 | N | GLN | E | 371 | 63.150 | 32.484 | 54.074 | 1.00 | 77.99 |
| 3535 | CA | GLN | E | 371 | 62.065 | 32.907 | 53.192 | 1.00 | 76.38 |
| 3536 | CB | GLN | E | 371 | 61.291 | 31.682 | 52.695 | 1.00 | 81.25 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3537 | CG | GLN | E | 371 | 62.104 | 30.725 | 51.834 | 1.00 | 90.30 |
| 3538 | CD | GLN | E | 371 | 62.618 | 31.373 | 50.559 | 1.00 | 94.69 |
| 3539 | OE1 | GLN | E | 371 | 61.848 | 31.944 | 49.785 | 1.00 | 98.10 |
| 3540 | NE2 | GLN | E | 371 | 63.923 | 31.282 | 50.333 | 1.00 | 97.91 |
| 3541 | C | GLN | E | 371 | 61.084 | 33.890 | 53.815 | 1.00 | 72.15 |
| 3542 | O | GLN | E | 371 | 60.770 | 33.805 | 54.997 | 1.00 | 69.93 |
| 3543 | N | LEU | E | 372 | 60.599 | 34.819 | 52.996 | 1.00 | 67.69 |
| 3544 | CA | LEU | E | 372 | 59.629 | 35.828 | 53.419 | 1.00 | 63.42 |
| 3545 | CB | LEU | E | 372 | 60.313 | 37.194 | 53.569 | 1.00 | 63.83 |
| 3546 | CG | LEU | E | 372 | 61.392 | 37.302 | 54.656 | 1.00 | 63.94 |
| 3547 | CD1 | LEU | E | 372 | 62.163 | 38.596 | 54.507 | 1.00 | 63.16 |
| 3548 | CD2 | LEU | E | 372 | 60.749 | 37.225 | 56.027 | 1.00 | 63.27 |
| 3549 | C | LEU | E | 372 | 58.541 | 35.894 | 52.347 | 1.00 | 61.67 |
| 3550 | O | LEU | E | 372 | 58.848 | 36.078 | 51.166 | 1.00 | 61.62 |
| 3551 | N | THR | E | 373 | 57.279 | 35.739 | 52.754 | 1.00 | 60.11 |
| 3552 | CA | THR | E | 373 | 56.149 | 35.760 | 51.814 | 1.00 | 58.63 |
| 3553 | CB | THR | E | 373 | 55.471 | 34.364 | 51.712 | 1.00 | 61.25 |
| 3554 | OG1 | THR | E | 373 | 56.468 | 33.348 | 51.536 | 1.00 | 61.06 |
| 3555 | CG2 | THR | E | 373 | 54.504 | 34.331 | 50.522 | 1.00 | 62.39 |
| 3556 | C | THR | E | 373 | 55.052 | 36.771 | 52.172 | 1.00 | 56.37 |
| 3557 | O | THR | E | 373 | 54.615 | 36.837 | 53.319 | 1.00 | 54.18 |
| 3558 | N | TRP | E | 374 | 54.596 | 37.532 | 51.179 | 1.00 | 54.68 |
| 3559 | CA | TRP | E | 374 | 53.557 | 38.542 | 51.392 | 1.00 | 54.36 |
| 3560 | CB | TRP | E | 374 | 53.921 | 39.855 | 50.679 | 1.00 | 51.81 |
| 3561 | CG | TRP | E | 374 | 55.123 | 40.565 | 51.233 | 1.00 | 49.03 |
| 3562 | CD2 | TRP | E | 374 | 55.149 | 41.455 | 52.354 | 1.00 | 47.72 |
| 3563 | CE2 | TRP | E | 374 | 56.491 | 41.857 | 52.538 | 1.00 | 47.75 |
| 3564 | CE3 | TRP | E | 374 | 54.169 | 41.950 | 53.225 | 1.00 | 46.81 |
| 3565 | CD1 | TRP | E | 374 | 56.411 | 40.467 | 50.793 | 1.00 | 48.59 |
| 3566 | NE1 | TRP | E | 374 | 57.241 | 41.241 | 51.571 | 1.00 | 46.31 |
| 3567 | CZ2 | TRP | E | 374 | 56.879 | 42.736 | 53.561 | 1.00 | 47.87 |
| 3568 | CZ3 | TRP | E | 374 | 54.554 | 42.820 | 54.241 | 1.00 | 46.75 |
| 3569 | CH2 | TRP | E | 374 | 55.899 | 43.205 | 54.400 | 1.00 | 47.58 |
| 3570 | C | TRP | E | 374 | 52.167 | 38.113 | 50.918 | 1.00 | 56.19 |
| 3571 | O | TRP | E | 374 | 52.029 | 37.427 | 49.909 | 1.00 | 55.02 |
| 3572 | N | SER | E | 375 | 51.138 | 38.544 | 51.645 | 1.00 | 57.15 |
| 3573 | CA | SER | E | 375 | 49.757 | 38.226 | 51.282 | 1.00 | 57.75 |
| 3574 | CB | SER | E | 375 | 49.404 | 36.789 | 51.686 | 1.00 | 58.02 |
| 3575 | OG | SER | E | 375 | 49.057 | 36.705 | 53.059 | 1.00 | 56.77 |
| 3576 | C | SER | E | 375 | 48.771 | 39.185 | 51.948 | 1.00 | 56.57 |
| 3577 | O | SER | E | 375 | 49.063 | 39.766 | 52.998 | 1.00 | 57.62 |
| 3578 | N | ARG | E | 376 | 47.611 | 39.346 | 51.317 | 1.00 | 56.56 |
| 3579 | CA | ARG | E | 376 | 46.546 | 40.204 | 51.829 | 1.00 | 55.72 |
| 3580 | CB | ARG | E | 376 | 45.903 | 41.008 | 50.702 | 1.00 | 52.48 |
| 3581 | CG | ARG | E | 376 | 46.654 | 42.227 | 50.227 | 1.00 | 48.95 |
| 3582 | CD | ARG | E | 376 | 45.642 | 43.192 | 49.615 | 1.00 | 44.19 |
| 3583 | NE | ARG | E | 376 | 46.044 | 43.662 | 48.303 | 1.00 | 41.98 |
| 3584 | CZ | ARG | E | 376 | 45.293 | 44.423 | 47.516 | 1.00 | 41.40 |
| 3585 | NH1 | ARG | E | 376 | 44.081 | 44.812 | 47.902 | 1.00 | 41.15 |
| 3586 | NH2 | ARG | E | 376 | 45.764 | 44.801 | 46.336 | 1.00 | 41.83 |
| 3587 | C | ARG | E | 376 | 45.457 | 39.332 | 52.462 | 1.00 | 57.18 |
| 3588 | O | ARG | E | 376 | 45.360 | 38.138 | 52.169 | 1.00 | 56.64 |
| 3589 | N | ALA | E | 377 | 44.637 | 39.923 | 53.325 | 1.00 | 57.28 |
| 3590 | CA | ALA | E | 377 | 43.557 | 39.166 | 53.947 | 1.00 | 58.69 |
| 3591 | CB | ALA | E | 377 | 43.207 | 39.745 | 55.306 | 1.00 | 58.67 |
| 3592 | C | ALA | E | 377 | 42.346 | 39.208 | 53.018 | 1.00 | 58.16 |
| 3593 | O | ALA | E | 377 | 41.461 | 38.364 | 53.103 | 1.00 | 59.87 |
| 3594 | N | SER | E | 378 | 42.320 | 40.192 | 52.123 | 1.00 | 57.35 |
| 3595 | CA | SER | E | 378 | 41.228 | 40.324 | 51.165 | 1.00 | 55.19 |
| 3596 | CB | SER | E | 378 | 41.288 | 41.678 | 50.468 | 1.00 | 55.64 |
| 3597 | OG | SER | E | 378 | 42.409 | 41.730 | 49.597 | 1.00 | 54.48 |
| 3598 | C | SER | E | 378 | 41.403 | 39.239 | 50.111 | 1.00 | 55.40 |
| 3599 | O | SER | E | 378 | 40.527 | 39.030 | 49.263 | 1.00 | 54.23 |
| 3600 | N | GLY | E | 379 | 42.552 | 38.566 | 50.162 | 1.00 | 54.52 |
| 3601 | CA | GLY | E | 379 | 42.849 | 37.515 | 49.206 | 1.00 | 52.79 |
| 3602 | C | GLY | E | 379 | 43.310 | 38.051 | 47.859 | 1.00 | 53.06 |
| 3603 | O | GLY | E | 379 | 43.650 | 37.272 | 46.964 | 1.00 | 51.61 |
| 3604 | N | LYS | E | 380 | 43.329 | 39.376 | 47.711 | 1.00 | 53.65 |
| 3605 | CA | LYS | E | 380 | 43.744 | 40.004 | 46.460 | 1.00 | 54.38 |
| 3606 | CB | LYS | E | 380 | 43.205 | 41.436 | 46.403 | 1.00 | 59.02 |
| 3607 | CG | LYS | E | 380 | 41.689 | 41.507 | 46.430 | 1.00 | 65.19 |
| 3608 | CD | LYS | E | 380 | 41.193 | 42.944 | 46.425 | 1.00 | 71.65 |
| 3609 | CE | LYS | E | 380 | 39.677 | 43.009 | 46.565 | 1.00 | 75.37 |
| 3610 | NZ | LYS | E | 380 | 39.175 | 44.409 | 46.667 | 1.00 | 77.50 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3611 | C | LYS | E | 380 | 45.269 | 39.982 | 46.267 | 1.00 | 55.06 |
| 3612 | O | LYS | E | 380 | 46.014 | 39.638 | 47.188 | 1.00 | 53.19 |
| 3613 | N | PRO | E | 381 | 45.747 | 40.340 | 45.058 | 1.00 | 53.73 |
| 3614 | CD | PRO | E | 381 | 44.919 | 40.618 | 43.873 | 1.00 | 54.51 |
| 3615 | CA | PRO | E | 381 | 47.172 | 40.369 | 44.693 | 1.00 | 54.26 |
| 3616 | CB | PRO | E | 381 | 47.145 | 40.556 | 43.172 | 1.00 | 54.06 |
| 3617 | CG | PRO | E | 381 | 45.783 | 40.086 | 42.770 | 1.00 | 55.10 |
| 3618 | C | PRO | E | 381 | 48.022 | 41.452 | 45.355 | 1.00 | 56.60 |
| 3619 | O | PRO | E | 381 | 47.554 | 42.566 | 45.609 | 1.00 | 55.07 |
| 3620 | N | VAL | E | 382 | 49.281 | 41.104 | 45.614 | 1.00 | 55.04 |
| 3621 | CA | VAL | E | 382 | 50.252 | 42.012 | 46.212 | 1.00 | 55.38 |
| 3622 | CB | VAL | E | 382 | 50.964 | 41.350 | 47.410 | 1.00 | 54.01 |
| 3623 | CG1 | VAL | E | 382 | 49.956 | 41.019 | 48.489 | 1.00 | 51.60 |
| 3624 | CG2 | VAL | E | 382 | 51.681 | 40.090 | 46.962 | 1.00 | 50.68 |
| 3625 | C | VAL | E | 382 | 51.282 | 42.332 | 45.122 | 1.00 | 57.03 |
| 3626 | O | VAL | E | 382 | 51.411 | 41.582 | 44.154 | 1.00 | 57.59 |
| 3627 | N | GLN | E | 383 | 52.009 | 43.436 | 45.270 | 1.00 | 59.78 |
| 3628 | CA | GLN | E | 383 | 53.006 | 43.815 | 44.274 | 1.00 | 60.87 |
| 3629 | CB | GLN | E | 383 | 53.179 | 45.336 | 44.265 | 1.00 | 62.89 |
| 3630 | CG | GLN | E | 383 | 51.926 | 46.092 | 43.857 | 1.00 | 67.60 |
| 3631 | CD | GLN | E | 383 | 52.080 | 47.599 | 43.986 | 1.00 | 70.99 |
| 3632 | OE1 | GLN | E | 383 | 52.980 | 48.198 | 43.394 | 1.00 | 72.89 |
| 3633 | NE2 | GLN | E | 383 | 51.195 | 48.221 | 44.759 | 1.00 | 71.71 |
| 3634 | C | GLN | E | 383 | 54.352 | 43.132 | 44.520 | 1.00 | 59.58 |
| 3635 | O | GLN | E | 383 | 54.514 | 42.404 | 45.498 | 1.00 | 59.61 |
| 3636 | N | HIS | E | 384 | 55.311 | 43.366 | 43.626 | 1.00 | 58.82 |
| 3637 | CA | HIS | E | 384 | 56.645 | 42.777 | 43.743 | 1.00 | 59.44 |
| 3638 | CB | HIS | E | 384 | 57.362 | 42.840 | 42.391 | 1.00 | 68.91 |
| 3639 | CG | HIS | E | 384 | 56.753 | 41.961 | 41.340 | 1.00 | 80.46 |
| 3640 | CD2 | HIS | E | 384 | 56.176 | 42.260 | 40.152 | 1.00 | 85.71 |
| 3641 | ND1 | HIS | E | 384 | 56.703 | 40.587 | 41.453 | 1.00 | 85.31 |
| 3642 | CE1 | HIS | E | 384 | 56.123 | 40.078 | 40.381 | 1.00 | 88.95 |
| 3643 | NE2 | HIS | E | 384 | 55.794 | 41.071 | 39.576 | 1.00 | 89.84 |
| 3644 | C | HIS | E | 384 | 57.486 | 43.481 | 44.812 | 1.00 | 54.79 |
| 3645 | O | HIS | E | 384 | 57.646 | 44.700 | 44.778 | 1.00 | 50.76 |
| 3646 | N | SER | E | 385 | 58.026 | 42.703 | 45.750 | 1.00 | 49.96 |
| 3647 | CA | SER | E | 385 | 58.830 | 43.245 | 46.851 | 1.00 | 47.38 |
| 3648 | CB | SER | E | 385 | 58.538 | 42.470 | 48.140 | 1.00 | 46.95 |
| 3649 | OG | SER | E | 385 | 58.863 | 41.095 | 48.002 | 1.00 | 47.80 |
| 3650 | C | SER | E | 385 | 60.338 | 43.248 | 46.594 | 1.00 | 46.19 |
| 3651 | O | SER | E | 385 | 60.806 | 42.672 | 45.612 | 1.00 | 45.26 |
| 3652 | N | THR | E | 386 | 61.082 | 43.907 | 47.491 | 1.00 | 46.93 |
| 3653 | CA | THR | E | 386 | 62.544 | 44.028 | 47.412 | 1.00 | 46.60 |
| 3654 | CB | THR | E | 386 | 62.984 | 45.520 | 47.333 | 1.00 | 47.46 |
| 3655 | OG1 | THR | E | 386 | 62.401 | 46.143 | 46.179 | 1.00 | 45.77 |
| 3656 | CG2 | THR | E | 386 | 64.514 | 45.628 | 47.251 | 1.00 | 47.04 |
| 3657 | C | THR | E | 386 | 63.222 | 43.413 | 48.642 | 1.00 | 48.62 |
| 3658 | O | THR | E | 386 | 62.908 | 43.779 | 49.776 | 1.00 | 47.64 |
| 3659 | N | ARG | E | 387 | 64.164 | 42.499 | 48.417 | 1.00 | 50.61 |
| 3660 | CA | ARG | E | 387 | 64.869 | 41.836 | 49.512 | 1.00 | 53.74 |
| 3661 | CB | ARG | E | 387 | 64.967 | 40.331 | 49.241 | 1.00 | 57.69 |
| 3662 | CG | ARG | E | 387 | 65.640 | 39.534 | 50.364 | 1.00 | 61.62 |
| 3663 | CD | ARG | E | 387 | 66.167 | 38.188 | 49.859 | 1.00 | 66.72 |
| 3664 | NE | ARG | E | 387 | 66.783 | 37.382 | 50.916 | 1.00 | 70.20 |
| 3665 | CZ | ARG | E | 387 | 66.123 | 36.523 | 51.689 | 1.00 | 72.71 |
| 3666 | NH1 | ARG | E | 387 | 64.820 | 36.347 | 51.525 | 1.00 | 73.60 |
| 3667 | NH2 | ARG | E | 387 | 66.763 | 35.840 | 52.632 | 1.00 | 73.83 |
| 3668 | C | ARG | E | 387 | 66.276 | 42.390 | 49.741 | 1.00 | 54.89 |
| 3669 | O | ARG | E | 387 | 66.992 | 42.704 | 48.791 | 1.00 | 54.69 |
| 3670 | N | LYS | E | 388 | 66.666 | 42.477 | 51.010 | 1.00 | 56.40 |
| 3671 | CA | LYS | E | 388 | 67.978 | 42.983 | 51.409 | 1.00 | 58.48 |
| 3672 | CB | LYS | E | 388 | 67.850 | 44.457 | 51.795 | 1.00 | 61.58 |
| 3673 | CG | LYS | E | 388 | 69.032 | 45.012 | 52.566 | 1.00 | 68.85 |
| 3674 | CD | LYS | E | 388 | 68.595 | 46.163 | 53.463 | 1.00 | 75.09 |
| 3675 | CE | LYS | E | 388 | 69.603 | 46.419 | 54.580 | 1.00 | 78.90 |
| 3676 | NZ | LYS | E | 388 | 69.056 | 47.337 | 55.624 | 1.00 | 81.49 |
| 3677 | C | LYS | E | 388 | 68.564 | 42.180 | 52.590 | 1.00 | 57.75 |
| 3678 | O | LYS | E | 388 | 67.855 | 41.886 | 53.552 | 1.00 | 55.66 |
| 3679 | N | GLU | E | 389 | 69.852 | 41.834 | 52.504 | 1.00 | 58.84 |
| 3680 | CA | GLU | E | 389 | 70.558 | 41.068 | 53.550 | 1.00 | 61.48 |
| 3681 | CB | GLU | E | 389 | 70.898 | 39.660 | 53.072 | 1.00 | 62.78 |
| 3682 | CG | GLU | E | 389 | 69.742 | 38.750 | 52.765 | 1.00 | 68.71 |
| 3683 | CD | GLU | E | 389 | 70.235 | 37.391 | 52.310 | 1.00 | 71.90 |
| 3684 | OE1 | GLU | E | 389 | 71.019 | 36.769 | 53.058 | 1.00 | 73.58 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3685 | OE2 | GLU | E | 389 | 69.848 | 36.947 | 51.209 | 1.00 | 74.55 |
| 3686 | C | GLU | E | 389 | 71.883 | 41.729 | 53.913 | 1.00 | 62.68 |
| 3687 | O | GLU | E | 389 | 72.609 | 42.195 | 53.031 | 1.00 | 60.51 |
| 3688 | N | GLU | E | 390 | 72.225 | 41.730 | 55.197 | 1.00 | 66.34 |
| 3689 | CA | GLU | E | 390 | 73.482 | 42.338 | 55.627 | 1.00 | 71.01 |
| 3690 | CB | GLU | E | 390 | 73.283 | 43.843 | 55.807 | 1.00 | 76.40 |
| 3691 | CG | GLU | E | 390 | 74.489 | 44.576 | 56.349 | 1.00 | 86.39 |
| 3692 | CD | GLU | E | 390 | 74.255 | 46.068 | 56.454 | 1.00 | 92.03 |
| 3693 | OE1 | GLU | E | 390 | 73.230 | 46.473 | 57.042 | 1.00 | 96.01 |
| 3694 | OE2 | GLU | E | 390 | 75.100 | 46.836 | 55.952 | 1.00 | 96.33 |
| 3695 | C | GLU | E | 390 | 74.064 | 41.733 | 56.906 | 1.00 | 72.79 |
| 3696 | O | GLU | E | 390 | 73.380 | 41.642 | 57.926 | 1.00 | 71.18 |
| 3697 | N | LYS | E | 391 | 75.329 | 41.320 | 56.843 | 1.00 | 78.80 |
| 3698 | CA | LYS | E | 391 | 76.007 | 40.737 | 58.000 | 1.00 | 87.68 |
| 3699 | CB | LYS | E | 391 | 77.052 | 39.704 | 57.553 | 1.00 | 84.56 |
| 3700 | CG | LYS | E | 391 | 77.948 | 40.113 | 56.383 | 1.00 | 86.53 |
| 3701 | CD | LYS | E | 391 | 78.702 | 38.886 | 55.851 | 1.00 | 88.77 |
| 3702 | CE | LYS | E | 391 | 79.435 | 39.143 | 54.534 | 1.00 | 89.88 |
| 3703 | NZ | LYS | E | 391 | 80.762 | 39.788 | 54.716 | 1.00 | 91.38 |
| 3704 | C | LYS | E | 391 | 76.658 | 41.810 | 58.868 | 1.00 | 95.29 |
| 3705 | O | LYS | E | 391 | 77.592 | 42.488 | 58.441 | 1.00 | 92.60 |
| 3706 | N | GLN | E | 392 | 76.152 | 41.957 | 60.089 | 1.00 | 103.46 |
| 3707 | CA | GLN | E | 392 | 76.652 | 42.955 | 61.029 | 1.00 | 118.17 |
| 3708 | CB | GLN | E | 392 | 75.697 | 43.079 | 62.216 | 1.00 | 119.72 |
| 3709 | CG | GLN | E | 392 | 74.264 | 43.375 | 61.830 | 1.00 | 121.74 |
| 3710 | CD | GLN | E | 392 | 74.136 | 44.639 | 61.019 | 1.00 | 122.61 |
| 3711 | OE1 | GLN | E | 392 | 74.611 | 45.697 | 61.425 | 1.00 | 123.16 |
| 3712 | NE2 | GLN | E | 392 | 73.488 | 44.540 | 59.865 | 1.00 | 122.96 |
| 3713 | C | GLN | E | 392 | 78.052 | 42.652 | 61.549 | 1.00 | 125.78 |
| 3714 | O | GLN | E | 392 | 78.656 | 41.642 | 61.190 | 1.00 | 128.11 |
| 3715 | N | ALA | E | 393 | 78.557 | 43.537 | 62.404 | 1.00 | 132.49 |
| 3716 | CA | ALA | E | 393 | 79.885 | 43.383 | 62.987 | 1.00 | 135.66 |
| 3717 | CB | ALA | E | 393 | 80.312 | 44.680 | 63.663 | 1.00 | 139.73 |
| 3718 | C | ALA | E | 393 | 79.902 | 42.240 | 63.994 | 1.00 | 135.04 |
| 3719 | O | ALA | E | 393 | 80.820 | 41.421 | 63.998 | 1.00 | 138.89 |
| 3720 | N | ASN | E | 394 | 78.882 | 42.189 | 64.845 | 1.00 | 133.16 |
| 3721 | CA | ASN | E | 394 | 78.783 | 41.142 | 65.856 | 1.00 | 125.58 |
| 3722 | CB | ASN | E | 394 | 77.775 | 41.544 | 66.935 | 1.00 | 121.45 |
| 3723 | CG | ASN | E | 394 | 76.407 | 41.824 | 66.364 | 1.00 | 113.26 |
| 3724 | OD1 | ASN | E | 394 | 76.084 | 41.330 | 65.287 | 1.00 | 116.70 |
| 3725 | ND2 | ASN | E | 394 | 75.593 | 42.599 | 67.076 | 1.00 | 100.85 |
| 3726 | C | ASN | E | 394 | 78.367 | 39.807 | 65.238 | 1.00 | 122.71 |
| 3727 | O | ASN | E | 394 | 77.642 | 39.024 | 65.853 | 1.00 | 124.57 |
| 3728 | N | GLY | E | 395 | 78.822 | 39.564 | 64.013 | 1.00 | 119.24 |
| 3729 | CA | GLY | E | 395 | 78.513 | 38.323 | 63.324 | 1.00 | 112.14 |
| 3730 | C | GLY | E | 395 | 77.050 | 37.921 | 63.240 | 1.00 | 107.79 |
| 3731 | O | GLY | E | 395 | 76.738 | 36.730 | 63.197 | 1.00 | 106.98 |
| 3732 | N | THR | E | 396 | 76.149 | 38.898 | 63.209 | 1.00 | 103.15 |
| 3733 | CA | THR | E | 396 | 74.722 | 38.601 | 63.116 | 1.00 | 97.05 |
| 3734 | CB | THR | E | 396 | 73.913 | 39.386 | 64.180 | 1.00 | 100.07 |
| 3735 | OG1 | THR | E | 396 | 72.577 | 38.876 | 64.242 | 1.00 | 102.68 |
| 3736 | CG2 | THR | E | 396 | 73.842 | 40.851 | 63.825 | 1.00 | 102.65 |
| 3737 | C | THR | E | 396 | 74.203 | 38.960 | 61.723 | 1.00 | 91.12 |
| 3738 | O | THR | E | 396 | 74.681 | 39.915 | 61.110 | 1.00 | 90.90 |
| 3739 | N | LEU | E | 397 | 73.240 | 38.187 | 61.221 | 1.00 | 86.45 |
| 3740 | CA | LEU | E | 397 | 72.659 | 38.441 | 59.902 | 1.00 | 79.47 |
| 3741 | CB | LEU | E | 397 | 72.512 | 37.139 | 59.110 | 1.00 | 81.51 |
| 3742 | CG | LEU | E | 397 | 71.862 | 37.307 | 57.729 | 1.00 | 83.63 |
| 3743 | CD1 | LEU | E | 397 | 72.785 | 38.126 | 56.839 | 1.00 | 85.44 |
| 3744 | CD2 | LEU | E | 397 | 71.583 | 35.952 | 57.100 | 1.00 | 84.98 |
| 3745 | C | LEU | E | 397 | 71.290 | 39.104 | 60.015 | 1.00 | 76.48 |
| 3746 | O | LEU | E | 397 | 70.466 | 38.710 | 60.840 | 1.00 | 72.31 |
| 3747 | N | THR | E | 398 | 71.052 | 40.107 | 59.175 | 1.00 | 72.73 |
| 3748 | CA | THR | E | 398 | 69.785 | 40.830 | 59.174 | 1.00 | 71.45 |
| 3749 | CB | THR | E | 398 | 69.999 | 42.312 | 59.526 | 1.00 | 75.43 |
| 3750 | OG1 | THR | E | 398 | 70.774 | 42.409 | 60.725 | 1.00 | 79.07 |
| 3751 | CG2 | THR | E | 398 | 68.667 | 43.007 | 59.740 | 1.00 | 78.94 |
| 3752 | C | THR | E | 398 | 69.141 | 40.754 | 57.792 | 1.00 | 67.99 |
| 3753 | O | THR | E | 398 | 69.798 | 41.017 | 56.787 | 1.00 | 66.69 |
| 3754 | N | VAL | E | 399 | 67.858 | 40.401 | 57.747 | 1.00 | 62.75 |
| 3755 | CA | VAL | E | 399 | 67.132 | 40.296 | 56.479 | 1.00 | 58.82 |
| 3756 | CB | VAL | E | 399 | 66.783 | 38.823 | 56.166 | 1.00 | 58.85 |
| 3757 | CG1 | VAL | E | 399 | 66.015 | 38.728 | 54.852 | 1.00 | 58.35 |
| 3758 | CG2 | VAL | E | 399 | 68.061 | 38.000 | 56.090 | 1.00 | 58.63 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3759 | C | VAL | E | 399 | 65.843 | 41.126 | 56.465 | 1.00 | 54.64 |
| 3760 | O | VAL | E | 399 | 65.040 | 41.056 | 57.392 | 1.00 | 56.22 |
| 3761 | N | THR | E | 400 | 65.653 | 41.911 | 55.406 | 1.00 | 50.93 |
| 3762 | CA | THR | E | 400 | 64.464 | 42.754 | 55.268 | 1.00 | 46.52 |
| 3763 | CB | THR | E | 400 | 64.775 | 44.255 | 55.541 | 1.00 | 42.55 |
| 3764 | OG1 | THR | E | 400 | 65.782 | 44.713 | 54.631 | 1.00 | 44.27 |
| 3765 | CG2 | THR | E | 400 | 65.258 | 44.460 | 56.951 | 1.00 | 39.74 |
| 3766 | C | THR | E | 400 | 63.837 | 42.671 | 53.874 | 1.00 | 45.74 |
| 3767 | O | THR | E | 400 | 64.528 | 42.482 | 52.862 | 1.00 | 44.52 |
| 3768 | N | SER | E | 401 | 62.518 | 42.835 | 53.840 | 1.00 | 44.86 |
| 3769 | CA | SER | E | 401 | 61.755 | 42.801 | 52.604 | 1.00 | 45.08 |
| 3770 | CB | SER | E | 401 | 60.984 | 41.482 | 52.509 | 1.00 | 45.89 |
| 3771 | OG | SER | E | 401 | 60.204 | 41.431 | 51.327 | 1.00 | 48.10 |
| 3772 | C | SER | E | 401 | 60.789 | 43.986 | 52.630 | 1.00 | 44.51 |
| 3773 | O | SER | E | 401 | 60.023 | 44.140 | 53.586 | 1.00 | 44.82 |
| 3774 | N | THR | E | 402 | 60.831 | 44.812 | 51.583 | 1.00 | 43.24 |
| 3775 | CA | THR | E | 402 | 59.988 | 46.015 | 51.469 | 1.00 | 42.38 |
| 3776 | CB | THR | E | 402 | 60.854 | 47.254 | 51.142 | 1.00 | 44.65 |
| 3777 | OG1 | THR | E | 402 | 61.834 | 47.439 | 52.174 | 1.00 | 49.48 |
| 3778 | CG2 | THR | E | 402 | 59.996 | 48.504 | 51.019 | 1.00 | 45.75 |
| 3779 | C | THR | E | 402 | 58.942 | 45.879 | 50.365 | 1.00 | 41.16 |
| 3780 | O | THR | E | 402 | 59.290 | 45.639 | 49.216 | 1.00 | 40.47 |
| 3781 | N | LEU | E | 403 | 57.672 | 46.066 | 50.712 | 1.00 | 40.58 |
| 3782 | CA | LEU | E | 403 | 56.571 | 45.935 | 49.749 | 1.00 | 41.03 |
| 3783 | CB | LEU | E | 403 | 55.607 | 44.835 | 50.220 | 1.00 | 42.62 |
| 3784 | CG | LEU | E | 403 | 54.215 | 44.823 | 49.568 | 1.00 | 46.39 |
| 3785 | CD1 | LEU | E | 403 | 54.335 | 44.376 | 48.115 | 1.00 | 48.08 |
| 3786 | CD2 | LEU | E | 403 | 53.279 | 43.894 | 50.337 | 1.00 | 46.83 |
| 3787 | C | LEU | E | 403 | 55.751 | 47.204 | 49.476 | 1.00 | 39.46 |
| 3788 | O | LEU | E | 403 | 55.219 | 47.812 | 50.405 | 1.00 | 38.19 |
| 3789 | N | PRO | E | 404 | 55.634 | 47.616 | 48.194 | 1.00 | 38.61 |
| 3790 | CD | PRO | E | 404 | 56.461 | 47.225 | 47.036 | 1.00 | 38.71 |
| 3791 | CA | PRO | E | 404 | 54.847 | 48.816 | 47.885 | 1.00 | 39.09 |
| 3792 | CB | PRO | E | 404 | 55.142 | 49.064 | 46.408 | 1.00 | 37.63 |
| 3793 | CG | PRO | E | 404 | 56.523 | 48.514 | 46.230 | 1.00 | 36.46 |
| 3794 | C | PRO | E | 404 | 53.375 | 48.488 | 48.120 | 1.00 | 42.18 |
| 3795 | O | PRO | E | 404 | 52.959 | 47.349 | 47.913 | 1.00 | 41.83 |
| 3796 | N | VAL | E | 405 | 52.599 | 49.473 | 48.562 | 1.00 | 45.34 |
| 3797 | CA | VAL | E | 405 | 51.177 | 49.276 | 48.823 | 1.00 | 49.03 |
| 3798 | CB | VAL | E | 405 | 50.890 | 49.210 | 50.337 | 1.00 | 52.48 |
| 3799 | CG1 | VAL | E | 405 | 49.409 | 49.061 | 50.560 | 1.00 | 57.99 |
| 3800 | CG2 | VAL | E | 405 | 51.631 | 48.037 | 50.976 | 1.00 | 55.09 |
| 3801 | C | VAL | E | 405 | 50.360 | 50.418 | 48.223 | 1.00 | 49.13 |
| 3802 | O | VAL | E | 405 | 50.856 | 51.533 | 48.096 | 1.00 | 48.66 |
| 3803 | N | GLY | E | 406 | 49.109 | 50.139 | 47.859 | 1.00 | 48.38 |
| 3804 | CA | GLY | E | 406 | 48.261 | 51.165 | 47.271 | 1.00 | 48.45 |
| 3805 | C | GLY | E | 406 | 47.786 | 52.205 | 48.271 | 1.00 | 50.04 |
| 3806 | O | GLY | E | 406 | 47.328 | 51.859 | 49.365 | 1.00 | 47.47 |
| 3807 | N | THR | E | 407 | 47.878 | 53.479 | 47.896 | 1.00 | 51.68 |
| 3808 | CA | THR | E | 407 | 47.462 | 54.562 | 48.785 | 1.00 | 55.71 |
| 3809 | CB | THR | E | 407 | 47.673 | 55.950 | 48.116 | 1.00 | 55.48 |
| 3810 | OG1 | THR | E | 407 | 49.072 | 56.155 | 47.870 | 1.00 | 55.00 |
| 3811 | CG2 | THR | E | 407 | 47.169 | 57.072 | 49.025 | 1.00 | 55.49 |
| 3812 | C | THR | E | 407 | 46.011 | 54.440 | 49.269 | 1.00 | 59.04 |
| 3813 | O | THR | E | 407 | 45.702 | 54.797 | 50.406 | 1.00 | 59.77 |
| 3814 | N | ARG | E | 408 | 45.124 | 53.927 | 48.422 | 1.00 | 61.55 |
| 3815 | CA | ARG | E | 408 | 43.720 | 53.765 | 48.801 | 1.00 | 64.24 |
| 3816 | CB | ARG | E | 408 | 42.840 | 53.653 | 47.555 | 1.00 | 68.30 |
| 3817 | CG | ARG | E | 408 | 41.754 | 54.706 | 47.451 | 1.00 | 73.28 |
| 3818 | CD | ARG | E | 408 | 42.273 | 55.971 | 46.793 | 1.00 | 78.06 |
| 3819 | NE | ARG | E | 408 | 41.225 | 56.978 | 46.648 | 1.00 | 83.58 |
| 3820 | CZ | ARG | E | 408 | 41.352 | 58.102 | 45.947 | 1.00 | 86.47 |
| 3821 | NH1 | ARG | E | 408 | 42.490 | 58.372 | 45.314 | 1.00 | 88.16 |
| 3822 | NH2 | ARG | E | 408 | 40.340 | 58.961 | 45.876 | 1.00 | 88.17 |
| 3823 | C | ARG | E | 408 | 43.493 | 52.525 | 49.673 | 1.00 | 62.89 |
| 3824 | O | ARG | E | 408 | 42.824 | 52.593 | 50.706 | 1.00 | 64.67 |
| 3825 | N | ASP | E | 409 | 44.045 | 51.394 | 49.241 | 1.00 | 62.78 |
| 3826 | CA | ASP | E | 409 | 43.898 | 50.132 | 49.964 | 1.00 | 60.98 |
| 3827 | CB | ASP | E | 409 | 44.760 | 49.035 | 49.324 | 1.00 | 62.67 |
| 3828 | CG | ASP | E | 409 | 44.393 | 48.764 | 47.872 | 1.00 | 66.61 |
| 3829 | OD1 | ASP | E | 409 | 43.182 | 48.696 | 47.566 | 1.00 | 67.93 |
| 3830 | OD2 | ASP | E | 409 | 45.316 | 48.602 | 47.040 | 1.00 | 67.34 |
| 3831 | C | ASP | E | 409 | 44.268 | 50.245 | 51.441 | 1.00 | 59.43 |
| 3832 | O | ASP | E | 409 | 43.682 | 49.564 | 52.289 | 1.00 | 59.03 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3833 | N | TRP | E | 410 | 45.246 | 51.096 | 51.747 | 1.00 | 56.10 |
| 3834 | CA | TRP | E | 410 | 45.686 | 51.266 | 53.123 | 1.00 | 54.11 |
| 3835 | CB | TRP | E | 410 | 47.124 | 51.782 | 53.170 | 1.00 | 49.10 |
| 3836 | CG | TRP | E | 410 | 47.587 | 52.018 | 54.574 | 1.00 | 43.91 |
| 3837 | CD2 | TRP | E | 410 | 48.217 | 51.063 | 55.436 | 1.00 | 42.68 |
| 3838 | CE2 | TRP | E | 410 | 48.371 | 51.680 | 56.700 | 1.00 | 40.53 |
| 3839 | CE3 | TRP | E | 410 | 48.664 | 49.742 | 55.266 | 1.00 | 41.59 |
| 3840 | CD1 | TRP | E | 410 | 47.397 | 53.144 | 55.325 | 1.00 | 41.48 |
| 3841 | NE1 | TRP | E | 410 | 47.862 | 52.948 | 56.601 | 1.00 | 40.90 |
| 3842 | CZ2 | TRP | E | 410 | 48.952 | 51.021 | 57.793 | 1.00 | 39.91 |
| 3843 | CZ3 | TRP | E | 410 | 49.241 | 49.086 | 56.354 | 1.00 | 41.42 |
| 3844 | CH2 | TRP | E | 410 | 49.378 | 49.730 | 57.603 | 1.00 | 39.69 |
| 3845 | C | TRP | E | 410 | 44.790 | 52.207 | 53.922 | 1.00 | 58.01 |
| 3846 | O | TRP | E | 410 | 44.385 | 51.885 | 55.049 | 1.00 | 54.76 |
| 3847 | N | ILE | E | 411 | 44.495 | 53.368 | 53.336 | 1.00 | 62.03 |
| 3848 | CA | ILE | E | 411 | 43.653 | 54.371 | 53.976 | 1.00 | 67.39 |
| 3849 | CB | ILE | E | 411 | 43.423 | 55.597 | 53.048 | 1.00 | 75.35 |
| 3850 | CG2 | ILE | E | 411 | 42.486 | 56.598 | 53.718 | 1.00 | 78.72 |
| 3851 | CG1 | ILE | E | 411 | 44.757 | 56.278 | 52.725 | 1.00 | 82.75 |
| 3852 | CD1 | ILE | E | 411 | 45.469 | 56.861 | 53.932 | 1.00 | 90.92 |
| 3853 | C | ILE | E | 411 | 42.296 | 53.787 | 54.349 | 1.00 | 65.46 |
| 3854 | O | ILE | E | 411 | 41.662 | 54.238 | 55.302 | 1.00 | 64.43 |
| 3855 | N | GLU | E | 412 | 41.859 | 52.776 | 53.603 | 1.00 | 63.27 |
| 3856 | CA | GLU | E | 412 | 40.566 | 52.154 | 53.867 | 1.00 | 62.05 |
| 3857 | CB | GLU | E | 412 | 39.847 | 51.873 | 52.544 | 1.00 | 63.23 |
| 3858 | CG | GLU | E | 412 | 39.664 | 53.134 | 51.714 | 1.00 | 67.99 |
| 3859 | CD | GLU | E | 412 | 38.635 | 52.983 | 50.614 | 1.00 | 70.92 |
| 3860 | OE1 | GLU | E | 412 | 37.466 | 52.689 | 50.936 | 1.00 | 72.98 |
| 3861 | OE2 | GLU | E | 412 | 38.991 | 53.167 | 49.430 | 1.00 | 73.54 |
| 3862 | C | GLU | E | 412 | 40.620 | 50.897 | 54.739 | 1.00 | 59.89 |
| 3863 | O | GLU | E | 412 | 39.645 | 50.155 | 54.835 | 1.00 | 57.98 |
| 3864 | N | GLY | E | 413 | 41.767 | 50.667 | 55.370 | 1.00 | 58.97 |
| 3865 | CA | GLY | E | 413 | 41.911 | 49.535 | 56.271 | 1.00 | 57.37 |
| 3866 | C | GLY | E | 413 | 42.257 | 48.142 | 55.770 | 1.00 | 57.53 |
| 3867 | O | GLY | E | 413 | 41.905 | 47.163 | 56.437 | 1.00 | 56.74 |
| 3868 | N | GLU | E | 414 | 42.930 | 48.016 | 54.627 | 1.00 | 56.19 |
| 3869 | CA | GLU | E | 414 | 43.296 | 46.684 | 54.151 | 1.00 | 55.41 |
| 3870 | CB | GLU | E | 414 | 43.931 | 46.765 | 52.758 | 1.00 | 56.17 |
| 3871 | CG | GLU | E | 414 | 44.541 | 45.461 | 52.220 | 1.00 | 57.34 |
| 3872 | CD | GLU | E | 414 | 43.528 | 44.333 | 52.004 | 1.00 | 58.54 |
| 3873 | OE1 | GLU | E | 414 | 43.186 | 43.635 | 52.987 | 1.00 | 56.95 |
| 3874 | OE2 | GLU | E | 414 | 43.074 | 44.149 | 50.849 | 1.00 | 55.82 |
| 3875 | C | GLU | E | 414 | 44.288 | 46.122 | 55.165 | 1.00 | 56.82 |
| 3876 | O | GLU | E | 414 | 44.942 | 46.880 | 55.885 | 1.00 | 55.98 |
| 3877 | N | THR | E | 415 | 44.379 | 44.799 | 55.254 | 1.00 | 59.00 |
| 3878 | CA | THR | E | 415 | 45.315 | 44.178 | 56.188 | 1.00 | 62.12 |
| 3879 | CB | THR | E | 415 | 44.576 | 43.344 | 57.258 | 1.00 | 66.90 |
| 3880 | OG1 | THR | E | 415 | 45.502 | 42.474 | 57.924 | 1.00 | 70.89 |
| 3881 | CG2 | THR | E | 415 | 43.468 | 42.532 | 56.620 | 1.00 | 72.94 |
| 3882 | C | THR | E | 415 | 46.315 | 43.295 | 55.448 | 1.00 | 61.10 |
| 3883 | O | THR | E | 415 | 45.935 | 42.460 | 54.627 | 1.00 | 59.50 |
| 3884 | N | TYR | E | 416 | 47.596 | 43.488 | 55.747 | 1.00 | 57.71 |
| 3885 | CA | TYR | E | 416 | 48.656 | 42.734 | 55.093 | 1.00 | 55.26 |
| 3886 | CB | TYR | E | 416 | 49.658 | 43.711 | 54.472 | 1.00 | 54.16 |
| 3887 | CG | TYR | E | 416 | 49.037 | 44.664 | 53.468 | 1.00 | 51.03 |
| 3888 | CD1 | TYR | E | 416 | 48.227 | 45.723 | 53.882 | 1.00 | 51.30 |
| 3889 | CE1 | TYR | E | 416 | 47.625 | 46.577 | 52.948 | 1.00 | 51.25 |
| 3890 | CD2 | TYR | E | 416 | 49.232 | 44.483 | 52.101 | 1.00 | 49.61 |
| 3891 | CE2 | TYR | E | 416 | 48.636 | 45.322 | 51.167 | 1.00 | 48.47 |
| 3892 | CZ | TYR | E | 416 | 47.837 | 46.362 | 51.594 | 1.00 | 49.35 |
| 3893 | OH | TYR | E | 416 | 47.246 | 47.177 | 50.661 | 1.00 | 49.68 |
| 3894 | C | TYR | E | 416 | 49.362 | 41.772 | 56.048 | 1.00 | 56.94 |
| 3895 | O | TYR | E | 416 | 49.313 | 41.952 | 57.267 | 1.00 | 57.94 |
| 3896 | N | GLN | E | 417 | 50.020 | 40.751 | 55.496 | 1.00 | 59.00 |
| 3897 | CA | GLN | E | 417 | 50.712 | 39.770 | 56.328 | 1.00 | 60.37 |
| 3898 | CB | GLN | E | 417 | 49.792 | 38.579 | 56.595 | 1.00 | 64.98 |
| 3899 | CG | GLN | E | 417 | 50.397 | 37.524 | 57.514 | 1.00 | 75.59 |
| 3900 | CD | GLN | E | 417 | 49.481 | 36.330 | 57.719 | 1.00 | 81.03 |
| 3901 | OE1 | GLN | E | 417 | 49.147 | 35.617 | 56.770 | 1.00 | 83.52 |
| 3902 | NE2 | GLN | E | 417 | 49.068 | 36.107 | 58.964 | 1.00 | 84.96 |
| 3903 | C | GLN | E | 417 | 52.050 | 39.252 | 55.789 | 1.00 | 59.14 |
| 3904 | O | GLN | E | 417 | 52.190 | 38.959 | 54.599 | 1.00 | 54.29 |
| 3905 | N | CYS | E | 418 | 53.021 | 39.139 | 56.698 | 1.00 | 58.87 |
| 3906 | CA | CYS | E | 418 | 54.364 | 38.640 | 56.393 | 1.00 | 60.58 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3907 | C | CYS | E | 418 | 54.571 | 37.280 | 57.092 | 1.00 | 62.49 |
| 3908 | O | CYS | E | 418 | 54.319 | 37.140 | 58.297 | 1.00 | 61.82 |
| 3909 | CB | CYS | E | 418 | 55.440 | 39.647 | 56.860 | 1.00 | 60.62 |
| 3910 | SG | CYS | E | 418 | 57.157 | 39.127 | 56.507 | 1.00 | 61.45 |
| 3911 | N | ARG | E | 419 | 55.025 | 36.288 | 56.325 | 1.00 | 66.40 |
| 3912 | CA | ARG | E | 419 | 55.263 | 34.934 | 56.834 | 1.00 | 70.10 |
| 3913 | CB | ARG | E | 419 | 54.324 | 33.954 | 56.122 | 1.00 | 80.07 |
| 3914 | CG | ARG | E | 419 | 54.467 | 32.509 | 56.555 | 1.00 | 96.64 |
| 3915 | CD | ARG | E | 419 | 53.486 | 31.615 | 55.811 | 1.00 | 110.29 |
| 3916 | NE | ARG | E | 419 | 53.654 | 30.208 | 56.166 | 1.00 | 120.83 |
| 3917 | CZ | ARG | E | 419 | 54.761 | 29.506 | 55.940 | 1.00 | 125.91 |
| 3918 | NH1 | ARG | E | 419 | 55.807 | 30.075 | 55.354 | 1.00 | 128.15 |
| 3919 | NH2 | ARG | E | 419 | 54.822 | 28.231 | 56.300 | 1.00 | 128.53 |
| 3920 | C | ARG | E | 419 | 56.725 | 34.511 | 56.633 | 1.00 | 66.93 |
| 3921 | O | ARG | E | 419 | 57.279 | 34.657 | 55.538 | 1.00 | 63.55 |
| 3922 | N | VAL | E | 420 | 57.339 | 33.970 | 57.686 | 1.00 | 63.97 |
| 3923 | CA | VAL | E | 420 | 58.746 | 33.557 | 57.632 | 1.00 | 63.36 |
| 3924 | CB | VAL | E | 420 | 59.551 | 34.243 | 58.761 | 1.00 | 62.17 |
| 3925 | CG1 | VAL | E | 420 | 61.040 | 34.188 | 58.446 | 1.00 | 61.41 |
| 3926 | CG2 | VAL | E | 420 | 59.085 | 35.680 | 58.938 | 1.00 | 62.05 |
| 3927 | C | VAL | E | 420 | 59.001 | 32.042 | 57.728 | 1.00 | 66.17 |
| 3928 | O | VAL | E | 420 | 58.316 | 31.341 | 58.463 | 1.00 | 65.89 |
| 3929 | N | THR | E | 421 | 60.006 | 31.553 | 57.000 | 1.00 | 71.83 |
| 3930 | CA | THR | E | 421 | 60.361 | 30.130 | 57.001 | 1.00 | 78.85 |
| 3931 | CB | THR | E | 421 | 59.863 | 29.427 | 55.720 | 1.00 | 72.35 |
| 3932 | OG1 | THR | E | 421 | 58.435 | 29.330 | 55.753 | 1.00 | 67.72 |
| 3933 | CG2 | THR | E | 421 | 60.464 | 28.032 | 55.601 | 1.00 | 68.11 |
| 3934 | C | THR | E | 421 | 61.871 | 29.904 | 57.098 | 1.00 | 92.35 |
| 3935 | O | THR | E | 421 | 62.587 | 30.037 | 56.104 | 1.00 | 90.13 |
| 3936 | N | HIS | E | 422 | 62.350 | 29.558 | 58.291 | 1.00 | 105.98 |
| 3937 | CA | HIS | E | 422 | 63.777 | 29.303 | 58.500 | 1.00 | 125.40 |
| 3938 | CB | HIS | E | 422 | 64.215 | 29.801 | 59.886 | 1.00 | 138.39 |
| 3939 | CG | HIS | E | 422 | 65.700 | 29.806 | 60.097 | 1.00 | 152.92 |
| 3940 | CD2 | HIS | E | 422 | 66.561 | 30.823 | 60.346 | 1.00 | 159.28 |
| 3941 | ND1 | HIS | E | 422 | 66.465 | 28.659 | 60.066 | 1.00 | 159.35 |
| 3942 | CE1 | HIS | E | 422 | 67.731 | 28.969 | 60.285 | 1.00 | 163.55 |
| 3943 | NE2 | HIS | E | 422 | 67.816 | 30.275 | 60.459 | 1.00 | 163.47 |
| 3944 | C | HIS | E | 422 | 64.027 | 27.800 | 58.377 | 1.00 | 128.69 |
| 3945 | O | HIS | E | 422 | 63.184 | 26.989 | 58.770 | 1.00 | 130.13 |
| 3946 | N | PRO | E | 423 | 65.189 | 27.411 | 57.823 | 1.00 | 131.20 |
| 3947 | CD | PRO | E | 423 | 66.196 | 28.296 | 57.208 | 1.00 | 132.59 |
| 3948 | CA | PRO | E | 423 | 65.562 | 26.003 | 57.637 | 1.00 | 131.93 |
| 3949 | CB | PRO | E | 423 | 66.734 | 26.091 | 56.663 | 1.00 | 133.35 |
| 3950 | CG | PRO | E | 423 | 67.388 | 27.378 | 57.065 | 1.00 | 133.29 |
| 3951 | C | PRO | E | 423 | 65.922 | 25.206 | 58.893 | 1.00 | 131.11 |
| 3952 | O | PRO | E | 423 | 66.442 | 24.095 | 58.786 | 1.00 | 132.03 |
| 3953 | N | HIS | E | 424 | 65.645 | 25.753 | 60.075 | 1.00 | 133.02 |
| 3954 | CA | HIS | E | 424 | 65.973 | 25.046 | 61.311 | 1.00 | 132.77 |
| 3955 | CB | HIS | E | 424 | 67.407 | 25.373 | 61.739 | 1.00 | 136.77 |
| 3956 | CG | HIS | E | 424 | 68.449 | 24.926 | 60.761 | 1.00 | 142.56 |
| 3957 | CD2 | HIS | E | 424 | 69.423 | 25.614 | 60.119 | 1.00 | 144.92 |
| 3958 | ND1 | HIS | E | 424 | 68.568 | 23.617 | 60.346 | 1.00 | 145.06 |
| 3959 | CE1 | HIS | E | 424 | 69.569 | 23.517 | 59.490 | 1.00 | 146.74 |
| 3960 | NE2 | HIS | E | 424 | 70.105 | 24.715 | 59.335 | 1.00 | 146.75 |
| 3961 | C | HIS | E | 424 | 65.038 | 25.294 | 62.493 | 1.00 | 130.66 |
| 3962 | O | HIS | E | 424 | 65.328 | 24.866 | 63.609 | 1.00 | 129.06 |
| 3963 | N | LEU | E | 425 | 63.922 | 25.976 | 62.263 | 1.00 | 128.52 |
| 3964 | CA | LEU | E | 425 | 62.984 | 26.244 | 63.346 | 1.00 | 127.68 |
| 3965 | CB | LEU | E | 425 | 62.744 | 27.752 | 63.475 | 1.00 | 122.13 |
| 3966 | CG | LEU | E | 425 | 62.415 | 28.574 | 62.226 | 1.00 | 116.84 |
| 3967 | CD1 | LEU | E | 425 | 61.176 | 28.046 | 61.515 | 1.00 | 113.26 |
| 3968 | CD2 | LEU | E | 425 | 62.212 | 30.021 | 62.653 | 1.00 | 113.83 |
| 3969 | C | LEU | E | 425 | 61.659 | 25.518 | 63.148 | 1.00 | 128.93 |
| 3970 | O | LEU | E | 425 | 61.371 | 25.028 | 62.057 | 1.00 | 131.16 |
| 3971 | N | PRO | E | 426 | 60.834 | 25.435 | 64.208 | 1.00 | 136.91 |
| 3972 | CD | PRO | E | 426 | 61.018 | 26.022 | 65.548 | 1.00 | 136.67 |
| 3973 | CA | PRO | E | 426 | 59.536 | 24.759 | 64.117 | 1.00 | 140.45 |
| 3974 | CB | PRO | E | 426 | 58.990 | 24.868 | 65.541 | 1.00 | 139.19 |
| 3975 | CG | PRO | E | 426 | 59.595 | 26.143 | 66.035 | 1.00 | 137.44 |
| 3976 | C | PRO | E | 426 | 58.623 | 25.420 | 63.089 | 1.00 | 144.07 |
| 3977 | O | PRO | E | 426 | 59.095 | 25.985 | 62.103 | 1.00 | 146.99 |
| 3978 | N | ARG | E | 427 | 57.317 | 25.354 | 63.315 | 1.00 | 145.89 |
| 3979 | CA | ARG | E | 427 | 56.385 | 25.959 | 62.378 | 1.00 | 144.70 |
| 3980 | CB | ARG | E | 427 | 54.951 | 25.534 | 62.702 | 1.00 | 147.99 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 3981 | CG | ARG | E | 427 | 54.543 | 25.670 | 64.155 | 1.00 | 147.59 |
| 3982 | CD | ARG | E | 427 | 53.145 | 25.104 | 64.339 | 1.00 | 145.57 |
| 3983 | NE | ARG | E | 427 | 52.659 | 25.210 | 65.712 | 1.00 | 142.95 |
| 3984 | CZ | ARG | E | 427 | 51.459 | 24.795 | 66.109 | 1.00 | 141.72 |
| 3985 | NH1 | ARG | E | 427 | 50.623 | 24.246 | 65.236 | 1.00 | 141.18 |
| 3986 | NH2 | ARG | E | 427 | 51.091 | 24.932 | 67.375 | 1.00 | 140.85 |
| 3987 | C | ARG | E | 427 | 56.507 | 27.482 | 62.345 | 1.00 | 138.24 |
| 3988 | O | ARG | E | 427 | 56.422 | 28.152 | 63.372 | 1.00 | 143.94 |
| 3989 | N | ALA | E | 428 | 56.718 | 27.995 | 61.136 | 1.00 | 132.13 |
| 3990 | CA | ALA | E | 428 | 56.887 | 29.417 | 60.824 | 1.00 | 116.50 |
| 3991 | CB | ALA | E | 428 | 56.384 | 29.662 | 59.410 | 1.00 | 118.43 |
| 3992 | C | ALA | E | 428 | 56.300 | 30.487 | 61.757 | 1.00 | 106.31 |
| 3993 | O | ALA | E | 428 | 55.409 | 30.220 | 62.562 | 1.00 | 105.84 |
| 3994 | N | LEU | E | 429 | 56.816 | 31.710 | 61.611 | 1.00 | 97.06 |
| 3995 | CA | LEU | E | 429 | 56.384 | 32.878 | 62.387 | 1.00 | 85.98 |
| 3996 | CB | LEU | E | 429 | 57.592 | 33.735 | 62.784 | 1.00 | 82.03 |
| 3997 | CG | LEU | E | 429 | 58.482 | 33.346 | 63.966 | 1.00 | 80.09 |
| 3998 | CD1 | LEU | E | 429 | 59.680 | 34.282 | 64.029 | 1.00 | 77.75 |
| 3999 | CD2 | LEU | E | 429 | 57.684 | 33.426 | 65.258 | 1.00 | 78.81 |
| 4000 | C | LEU | E | 429 | 55.443 | 33.740 | 61.545 | 1.00 | 83.84 |
| 4001 | O | LEU | E | 429 | 55.520 | 33.722 | 60.318 | 1.00 | 79.28 |
| 4002 | N | MET | E | 430 | 54.571 | 34.503 | 62.201 | 1.00 | 81.86 |
| 4003 | CA | MET | E | 430 | 53.634 | 35.369 | 61.487 | 1.00 | 83.70 |
| 4004 | CB | MET | E | 430 | 52.253 | 34.717 | 61.404 | 1.00 | 95.76 |
| 4005 | CG | MET | E | 430 | 52.204 | 33.489 | 60.515 | 1.00 | 113.32 |
| 4006 | SD | MET | E | 430 | 50.518 | 32.929 | 60.224 | 1.00 | 126.13 |
| 4007 | CE | MET | E | 430 | 50.259 | 31.871 | 61.643 | 1.00 | 136.43 |
| 4008 | C | MET | E | 430 | 53.482 | 36.770 | 62.068 | 1.00 | 77.91 |
| 4009 | O | MET | E | 430 | 53.474 | 36.961 | 63.287 | 1.00 | 74.90 |
| 4010 | N | ARG | E | 431 | 53.359 | 37.744 | 61.169 | 1.00 | 71.46 |
| 4011 | CA | ARG | E | 431 | 53.193 | 39.145 | 61.534 | 1.00 | 66.77 |
| 4012 | CB | ARG | E | 431 | 54.522 | 39.901 | 61.414 | 1.00 | 69.06 |
| 4013 | CG | ARG | E | 431 | 55.678 | 39.280 | 62.179 | 1.00 | 73.40 |
| 4014 | CD | ARG | E | 431 | 55.426 | 39.277 | 63.674 | 1.00 | 78.83 |
| 4015 | NE | ARG | E | 431 | 56.252 | 38.279 | 64.343 | 1.00 | 84.99 |
| 4016 | CZ | ARG | E | 431 | 56.260 | 38.070 | 65.654 | 1.00 | 88.06 |
| 4017 | NH1 | ARG | E | 431 | 55.485 | 38.796 | 66.447 | 1.00 | 91.05 |
| 4018 | NH2 | ARG | E | 431 | 57.034 | 37.127 | 66.170 | 1.00 | 90.16 |
| 4019 | C | ARG | E | 431 | 52.182 | 39.769 | 60.579 | 1.00 | 62.75 |
| 4020 | O | ARG | E | 431 | 52.218 | 39.515 | 59.379 | 1.00 | 59.71 |
| 4021 | N | SER | E | 432 | 51.283 | 40.583 | 61.121 | 1.00 | 59.94 |
| 4022 | CA | SER | E | 432 | 50.264 | 41.261 | 60.322 | 1.00 | 57.77 |
| 4023 | CB | SER | E | 432 | 48.897 | 40.611 | 60.565 | 1.00 | 57.26 |
| 4024 | OG | SER | E | 432 | 48.537 | 40.673 | 61.935 | 1.00 | 56.46 |
| 4025 | C | SER | E | 432 | 50.232 | 42.750 | 60.705 | 1.00 | 56.74 |
| 4026 | O | SER | E | 432 | 50.554 | 43.099 | 61.844 | 1.00 | 55.20 |
| 4027 | N | THR | E | 433 | 49.853 | 43.613 | 59.758 | 1.00 | 56.18 |
| 4028 | CA | THR | E | 433 | 49.799 | 45.065 | 59.987 | 1.00 | 55.28 |
| 4029 | CB | THR | E | 433 | 51.105 | 45.760 | 59.468 | 1.00 | 56.98 |
| 4030 | OG1 | THR | E | 433 | 51.188 | 47.089 | 60.001 | 1.00 | 57.39 |
| 4031 | CG2 | THR | E | 433 | 51.113 | 45.837 | 57.929 | 1.00 | 55.32 |
| 4032 | C | THR | E | 433 | 48.583 | 45.707 | 59.296 | 1.00 | 55.30 |
| 4033 | O | THR | E | 433 | 48.079 | 45.168 | 58.310 | 1.00 | 54.75 |
| 4034 | N | THR | E | 434 | 48.122 | 46.853 | 59.807 | 1.00 | 55.95 |
| 4035 | CA | THR | E | 434 | 46.957 | 47.545 | 59.233 | 1.00 | 56.28 |
| 4036 | CB | THR | E | 434 | 45.636 | 46.801 | 59.570 | 1.00 | 56.19 |
| 4037 | OG1 | THR | E | 434 | 44.527 | 47.432 | 58.904 | 1.00 | 52.38 |
| 4038 | CG2 | THR | E | 434 | 45.393 | 46.820 | 61.082 | 1.00 | 55.15 |
| 4039 | C | THR | E | 434 | 46.812 | 48.984 | 59.736 | 1.00 | 60.68 |
| 4040 | O | THR | E | 434 | 47.432 | 49.373 | 60.725 | 1.00 | 57.57 |
| 4041 | N | LYS | E | 435 | 45.981 | 49.760 | 59.044 | 1.00 | 67.23 |
| 4042 | CA | LYS | E | 435 | 45.729 | 51.151 | 59.402 | 1.00 | 78.09 |
| 4043 | CB | LYS | E | 435 | 44.774 | 51.786 | 58.398 | 1.00 | 77.22 |
| 4044 | CG | LYS | E | 435 | 44.189 | 53.098 | 58.883 | 1.00 | 80.04 |
| 4045 | CD | LYS | E | 435 | 43.010 | 53.537 | 58.035 | 1.00 | 83.45 |
| 4046 | CE | LYS | E | 435 | 42.359 | 54.784 | 58.613 | 1.00 | 86.23 |
| 4047 | NZ | LYS | E | 435 | 41.888 | 54.563 | 60.013 | 1.00 | 88.56 |
| 4048 | C | LYS | E | 435 | 45.119 | 51.265 | 60.794 | 1.00 | 85.24 |
| 4049 | O | LYS | E | 435 | 44.138 | 50.588 | 61.103 | 1.00 | 84.66 |
| 4050 | N | THR | E | 436 | 45.686 | 52.139 | 61.621 | 1.00 | 92.78 |
| 4051 | CA | THR | E | 436 | 45.196 | 52.338 | 62.982 | 1.00 | 106.18 |
| 4052 | CB | THR | E | 436 | 46.331 | 52.761 | 63.929 | 1.00 | 103.07 |
| 4053 | OG1 | THR | E | 436 | 46.728 | 54.105 | 63.630 | 1.00 | 101.29 |
| 4054 | CG2 | THR | E | 436 | 47.530 | 51.837 | 63.765 | 1.00 | 102.11 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4055 | C | THR | E | 436 | 44.122 | 53.418 | 63.042 | 1.00 | 112.73 |
| 4056 | O | THR | E | 436 | 44.316 | 54.521 | 62.532 | 1.00 | 115.77 |
| 4057 | N | SER | E | 437 | 42.991 | 53.097 | 63.667 | 1.00 | 119.90 |
| 4058 | CA | SER | E | 437 | 41.898 | 54.055 | 63.804 | 1.00 | 124.63 |
| 4059 | CB | SER | E | 437 | 40.551 | 53.409 | 63.437 | 1.00 | 129.23 |
| 4060 | OG | SER | E | 437 | 40.186 | 52.382 | 64.344 | 1.00 | 131.96 |
| 4061 | C | SER | E | 437 | 41.856 | 54.587 | 65.239 | 1.00 | 121.09 |
| 4062 | O | SER | E | 437 | 42.777 | 54.351 | 66.024 | 1.00 | 126.46 |
| 4063 | N | GLY | E | 438 | 40.787 | 55.302 | 65.575 | 1.00 | 116.15 |
| 4064 | CA | GLY | E | 438 | 40.666 | 55.866 | 66.908 | 1.00 | 101.55 |
| 4065 | C | GLY | E | 438 | 40.578 | 57.378 | 66.819 | 1.00 | 89.89 |
| 4066 | O | GLY | E | 438 | 40.628 | 57.928 | 65.718 | 1.00 | 92.11 |
| 4067 | N | PRO | E | 439 | 40.453 | 58.083 | 67.952 | 1.00 | 77.89 |
| 4068 | CD | PRO | E | 439 | 40.531 | 57.592 | 69.337 | 1.00 | 75.09 |
| 4069 | CA | PRO | E | 439 | 40.361 | 59.547 | 67.921 | 1.00 | 70.66 |
| 4070 | CB | PRO | E | 439 | 40.224 | 59.910 | 69.398 | 1.00 | 68.23 |
| 4071 | CG | PRO | E | 439 | 40.983 | 58.826 | 70.080 | 1.00 | 70.93 |
| 4072 | C | PRO | E | 439 | 41.569 | 60.210 | 67.260 | 1.00 | 63.65 |
| 4073 | O | PRO | E | 439 | 42.672 | 59.676 | 67.298 | 1.00 | 58.41 |
| 4074 | N | ARG | E | 440 | 41.348 | 61.372 | 66.654 | 1.00 | 55.65 |
| 4075 | CA | ARG | E | 440 | 42.411 | 62.123 | 65.981 | 1.00 | 52.50 |
| 4076 | CB | ARG | E | 440 | 42.034 | 62.377 | 64.521 | 1.00 | 56.09 |
| 4077 | CG | ARG | E | 440 | 42.134 | 61.189 | 63.595 | 1.00 | 61.36 |
| 4078 | CD | ARG | E | 440 | 41.836 | 61.660 | 62.187 | 1.00 | 67.36 |
| 4079 | NE | ARG | E | 440 | 42.138 | 60.660 | 61.169 | 1.00 | 74.49 |
| 4080 | CZ | ARG | E | 440 | 42.011 | 60.873 | 59.862 | 1.00 | 77.29 |
| 4081 | NH1 | ARG | E | 440 | 41.587 | 62.051 | 59.415 | 1.00 | 77.54 |
| 4082 | NH2 | ARG | E | 440 | 42.313 | 59.911 | 59.003 | 1.00 | 79.28 |
| 4083 | C | ARG | E | 440 | 42.662 | 63.482 | 66.641 | 1.00 | 49.13 |
| 4084 | O | ARG | E | 440 | 41.756 | 64.042 | 67.259 | 1.00 | 48.94 |
| 4085 | N | ALA | E | 441 | 43.877 | 64.014 | 66.498 | 1.00 | 42.42 |
| 4086 | CA | ALA | E | 441 | 44.220 | 65.329 | 67.055 | 1.00 | 37.58 |
| 4087 | CB | ALA | E | 441 | 44.294 | 65.258 | 68.567 | 1.00 | 35.93 |
| 4088 | C | ALA | E | 441 | 45.544 | 65.840 | 66.480 | 1.00 | 37.46 |
| 4089 | O | ALA | E | 441 | 46.564 | 65.145 | 66.547 | 1.00 | 32.42 |
| 4090 | N | ALA | E | 442 | 45.504 | 67.051 | 65.905 | 1.00 | 33.89 |
| 4091 | CA | ALA | E | 442 | 46.662 | 67.706 | 65.279 | 1.00 | 32.77 |
| 4092 | CB | ALA | E | 442 | 46.208 | 68.942 | 64.524 | 1.00 | 33.25 |
| 4093 | C | ALA | E | 442 | 47.753 | 68.099 | 66.275 | 1.00 | 33.11 |
| 4094 | O | ALA | E | 442 | 47.462 | 68.511 | 67.394 | 1.00 | 31.07 |
| 4095 | N | PRO | E | 443 | 49.032 | 68.010 | 65.862 | 1.00 | 29.50 |
| 4096 | CD | PRO | E | 443 | 49.550 | 67.553 | 64.556 | 1.00 | 29.35 |
| 4097 | CA | PRO | E | 443 | 50.119 | 68.368 | 66.779 | 1.00 | 29.99 |
| 4098 | CB | PRO | E | 443 | 51.292 | 67.560 | 66.244 | 1.00 | 31.89 |
| 4099 | CG | PRO | E | 443 | 51.081 | 67.644 | 64.724 | 1.00 | 31.79 |
| 4100 | C | PRO | E | 443 | 50.466 | 69.854 | 66.884 | 1.00 | 29.11 |
| 4101 | O | PRO | E | 443 | 50.105 | 70.661 | 66.031 | 1.00 | 25.58 |
| 4102 | N | GLU | E | 444 | 51.176 | 70.187 | 67.957 | 1.00 | 28.41 |
| 4103 | CA | GLU | E | 444 | 51.677 | 71.542 | 68.217 | 1.00 | 29.11 |
| 4104 | CB | GLU | E | 444 | 51.375 | 71.952 | 69.660 | 1.00 | 29.87 |
| 4105 | CG | GLU | E | 444 | 49.893 | 72.039 | 69.982 | 1.00 | 32.22 |
| 4106 | CD | GLU | E | 444 | 49.629 | 71.981 | 71.478 | 1.00 | 35.45 |
| 4107 | OE1 | GLU | E | 444 | 50.474 | 72.471 | 72.259 | 1.00 | 36.47 |
| 4108 | OE2 | GLU | E | 444 | 48.568 | 71.453 | 71.874 | 1.00 | 41.45 |
| 4109 | C | GLU | E | 444 | 53.199 | 71.447 | 68.020 | 1.00 | 26.23 |
| 4110 | O | GLU | E | 444 | 53.805 | 70.458 | 68.431 | 1.00 | 25.42 |
| 4111 | N | VAL | E | 445 | 53.796 | 72.469 | 67.398 | 1.00 | 24.56 |
| 4112 | CA | VAL | E | 445 | 55.239 | 72.526 | 67.113 | 1.00 | 21.27 |
| 4113 | CB | VAL | E | 445 | 55.497 | 72.568 | 65.559 | 1.00 | 21.49 |
| 4114 | CG1 | VAL | E | 445 | 57.007 | 72.684 | 65.274 | 1.00 | 15.51 |
| 4115 | CG2 | VAL | E | 445 | 54.909 | 71.313 | 64.863 | 1.00 | 17.08 |
| 4116 | C | VAL | E | 445 | 55.912 | 73.774 | 67.721 | 1.00 | 23.80 |
| 4117 | O | VAL | E | 445 | 55.443 | 74.909 | 67.508 | 1.00 | 20.16 |
| 4118 | N | TYR | E | 446 | 57.013 | 73.573 | 68.462 | 1.00 | 20.73 |
| 4119 | CA | TYR | E | 446 | 57.774 | 74.681 | 69.058 | 1.00 | 23.83 |
| 4120 | CB | TYR | E | 446 | 57.542 | 74.779 | 70.579 | 1.00 | 26.93 |
| 4121 | CG | TYR | E | 446 | 56.083 | 74.796 | 70.993 | 1.00 | 29.31 |
| 4122 | CD1 | TYR | E | 446 | 55.437 | 73.623 | 71.386 | 1.00 | 31.29 |
| 4123 | CE1 | TYR | E | 446 | 54.088 | 73.628 | 71.750 | 1.00 | 32.15 |
| 4124 | CD2 | TYR | E | 446 | 55.346 | 75.979 | 70.976 | 1.00 | 27.46 |
| 4125 | CE2 | TYR | E | 446 | 54.002 | 75.990 | 71.340 | 1.00 | 30.40 |
| 4126 | CZ | TYR | E | 446 | 53.385 | 74.812 | 71.723 | 1.00 | 30.48 |
| 4127 | OH | TYR | E | 446 | 52.062 | 74.815 | 72.077 | 1.00 | 34.97 |
| 4128 | C | TYR | E | 446 | 59.271 | 74.459 | 68.802 | 1.00 | 24.17 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4129 | O | TYR | E | 446 | 59.779 | 73.341 | 68.964 | 1.00 | 24.87 |
| 4130 | N | ALA | E | 447 | 59.996 | 75.511 | 68.433 | 1.00 | 24.68 |
| 4131 | CA | ALA | E | 447 | 61.425 | 75.347 | 68.154 | 1.00 | 26.37 |
| 4132 | CB | ALA | E | 447 | 61.664 | 75.473 | 66.643 | 1.00 | 25.08 |
| 4133 | C | ALA | E | 447 | 62.324 | 76.323 | 68.915 | 1.00 | 26.86 |
| 4134 | O | ALA | E | 447 | 61.938 | 77.466 | 69.144 | 1.00 | 26.52 |
| 4135 | N | PHE | E | 448 | 63.524 | 75.882 | 69.285 | 1.00 | 28.54 |
| 4136 | CA | PHE | E | 448 | 64.441 | 76.760 | 70.034 | 1.00 | 31.00 |
| 4137 | CB | PHE | E | 448 | 64.345 | 76.530 | 71.558 | 1.00 | 34.68 |
| 4138 | CG | PHE | E | 448 | 62.961 | 76.239 | 72.084 | 1.00 | 39.52 |
| 4139 | CD1 | PHE | E | 448 | 62.491 | 74.931 | 72.149 | 1.00 | 39.13 |
| 4140 | CD2 | PHE | E | 448 | 62.165 | 77.268 | 72.595 | 1.00 | 41.44 |
| 4141 | CE1 | PHE | E | 448 | 61.254 | 74.649 | 72.723 | 1.00 | 43.53 |
| 4142 | CE2 | PHE | E | 448 | 60.923 | 76.998 | 73.173 | 1.00 | 43.52 |
| 4143 | CZ | PHE | E | 448 | 60.466 | 75.683 | 73.240 | 1.00 | 43.04 |
| 4144 | C | PHE | E | 448 | 65.931 | 76.596 | 69.693 | 1.00 | 31.71 |
| 4145 | O | PHE | E | 448 | 66.358 | 75.547 | 69.213 | 1.00 | 29.19 |
| 4146 | N | ALA | E | 449 | 66.711 | 77.634 | 70.005 | 1.00 | 31.19 |
| 4147 | CA | ALA | E | 449 | 68.163 | 77.630 | 69.812 | 1.00 | 32.70 |
| 4148 | CB | ALA | E | 449 | 68.534 | 78.637 | 68.759 | 1.00 | 33.16 |
| 4149 | C | ALA | E | 449 | 68.888 | 77.981 | 71.141 | 1.00 | 33.63 |
| 4150 | O | ALA | E | 449 | 68.431 | 78.845 | 71.888 | 1.00 | 31.26 |
| 4151 | N | THR | E | 450 | 70.006 | 77.309 | 71.427 | 1.00 | 33.05 |
| 4152 | CA | THR | E | 450 | 70.803 | 77.579 | 72.636 | 1.00 | 37.23 |
| 4153 | CB | THR | E | 450 | 71.885 | 76.513 | 72.854 | 1.00 | 34.32 |
| 4154 | OG1 | THR | E | 450 | 72.662 | 76.380 | 71.651 | 1.00 | 28.79 |
| 4155 | CG2 | THR | E | 450 | 71.256 | 75.176 | 73.239 | 1.00 | 34.88 |
| 4156 | C | THR | E | 450 | 71.528 | 78.924 | 72.500 | 1.00 | 39.59 |
| 4157 | O | THR | E | 450 | 72.026 | 79.250 | 71.431 | 1.00 | 37.51 |
| 4158 | N | PRO | E | 451 | 71.623 | 79.703 | 73.593 | 1.00 | 41.56 |
| 4159 | CD | PRO | E | 451 | 71.163 | 79.390 | 74.956 | 1.00 | 45.32 |
| 4160 | CA | PRO | E | 451 | 72.293 | 81.009 | 73.564 | 1.00 | 46.15 |
| 4161 | CB | PRO | E | 451 | 72.016 | 81.586 | 74.952 | 1.00 | 45.83 |
| 4162 | CG | PRO | E | 451 | 70.861 | 80.758 | 75.486 | 1.00 | 47.64 |
| 4163 | C | PRO | E | 451 | 73.790 | 80.892 | 73.301 | 1.00 | 50.47 |
| 4164 | O | PRO | E | 451 | 74.379 | 79.818 | 73.427 | 1.00 | 46.75 |
| 4165 | N | GLU | E | 452 | 74.401 | 82.015 | 72.952 | 1.00 | 54.37 |
| 4166 | CA | GLU | E | 452 | 75.829 | 82.058 | 72.654 | 1.00 | 64.27 |
| 4167 | CB | GLU | E | 452 | 76.112 | 83.164 | 71.638 | 1.00 | 68.97 |
| 4168 | CG | GLU | E | 452 | 77.583 | 83.352 | 71.321 | 1.00 | 76.77 |
| 4169 | CD | GLU | E | 452 | 77.818 | 84.472 | 70.331 | 1.00 | 80.91 |
| 4170 | OE1 | GLU | E | 452 | 77.416 | 85.621 | 70.621 | 1.00 | 82.83 |
| 4171 | OE2 | GLU | E | 452 | 78.407 | 84.202 | 69.263 | 1.00 | 84.33 |
| 4172 | C | GLU | E | 452 | 76.718 | 82.278 | 73.875 | 1.00 | 68.22 |
| 4173 | O | GLU | E | 452 | 76.641 | 83.320 | 74.525 | 1.00 | 67.17 |
| 4174 | N | TRP | E | 453 | 77.561 | 81.292 | 74.178 | 1.00 | 70.63 |
| 4175 | CA | TRP | E | 453 | 78.488 | 81.397 | 75.304 | 1.00 | 74.10 |
| 4176 | CB | TRP | E | 453 | 78.624 | 80.067 | 76.057 | 1.00 | 86.03 |
| 4177 | CG | TRP | E | 453 | 77.387 | 79.619 | 76.768 | 1.00 | 99.68 |
| 4178 | CD2 | TRP | E | 453 | 76.980 | 79.981 | 78.095 | 1.00 | 105.33 |
| 4179 | CE2 | TRP | E | 453 | 75.747 | 79.341 | 78.342 | 1.00 | 107.58 |
| 4180 | CE3 | TRP | E | 453 | 77.539 | 80.786 | 79.098 | 1.00 | 107.98 |
| 4181 | CD1 | TRP | E | 453 | 76.411 | 78.797 | 76.280 | 1.00 | 103.84 |
| 4182 | NE1 | TRP | E | 453 | 75.424 | 78.625 | 77.220 | 1.00 | 107.39 |
| 4183 | CZ2 | TRP | E | 453 | 75.059 | 79.480 | 79.553 | 1.00 | 109.73 |
| 4184 | CZ3 | TRP | E | 453 | 76.855 | 80.925 | 80.302 | 1.00 | 109.81 |
| 4185 | CH2 | TRP | E | 453 | 75.628 | 80.274 | 80.517 | 1.00 | 110.23 |
| 4186 | C | TRP | E | 453 | 79.852 | 81.790 | 74.759 | 1.00 | 69.31 |
| 4187 | O | TRP | E | 453 | 80.375 | 81.153 | 73.846 | 1.00 | 67.34 |
| 4188 | N | PRO | E | 454 | 80.445 | 82.852 | 75.310 | 1.00 | 62.87 |
| 4189 | CD | PRO | E | 454 | 80.008 | 83.623 | 76.486 | 1.00 | 62.38 |
| 4190 | CA | PRO | E | 454 | 81.761 | 83.299 | 74.843 | 1.00 | 58.96 |
| 4191 | CB | PRO | E | 454 | 82.058 | 84.498 | 75.743 | 1.00 | 59.87 |
| 4192 | CG | PRO | E | 454 | 81.314 | 84.172 | 77.004 | 1.00 | 61.26 |
| 4193 | C | PRO | E | 454 | 82.800 | 82.188 | 74.961 | 1.00 | 55.73 |
| 4194 | O | PRO | E | 454 | 82.848 | 81.471 | 75.966 | 1.00 | 52.52 |
| 4195 | N | GLY | E | 455 | 83.621 | 82.052 | 73.923 | 1.00 | 52.40 |
| 4196 | CA | GLY | E | 455 | 84.640 | 81.019 | 73.901 | 1.00 | 51.83 |
| 4197 | C | GLY | E | 455 | 84.374 | 80.018 | 72.789 | 1.00 | 54.21 |
| 4198 | O | GLY | E | 455 | 85.280 | 79.310 | 72.343 | 1.00 | 50.79 |
| 4199 | N | SER | E | 456 | 83.123 | 79.961 | 72.338 | 1.00 | 57.45 |
| 4200 | CA | SER | E | 456 | 82.729 | 79.045 | 71.268 | 1.00 | 65.30 |
| 4201 | CB | SER | E | 456 | 82.289 | 77.701 | 71.860 | 1.00 | 62.00 |
| 4202 | OG | SER | E | 456 | 81.188 | 77.862 | 72.738 | 1.00 | 58.14 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4203 | C | SER | E | 456 | 81.601 | 79.635 | 70.416 | 1.00 | 72.76 |
| 4204 | O | SER | E | 456 | 80.418 | 79.451 | 70.711 | 1.00 | 70.62 |
| 4205 | N | ALA | E | 457 | 81.979 | 80.345 | 69.358 | 1.00 | 78.96 |
| 4206 | CA | ALA | E | 457 | 81.010 | 80.968 | 68.461 | 1.00 | 87.69 |
| 4207 | CB | ALA | E | 457 | 81.272 | 82.472 | 68.373 | 1.00 | 91.65 |
| 4208 | C | ALA | E | 457 | 81.078 | 80.344 | 67.071 | 1.00 | 89.41 |
| 4209 | O | ALA | E | 457 | 80.877 | 81.023 | 66.065 | 1.00 | 92.22 |
| 4210 | N | ASP | E | 458 | 81.356 | 79.045 | 67.024 | 1.00 | 92.00 |
| 4211 | CA | ASP | E | 458 | 81.461 | 78.332 | 65.758 | 1.00 | 90.48 |
| 4212 | CB | ASP | E | 458 | 82.841 | 77.676 | 65.645 | 1.00 | 106.11 |
| 4213 | CG | ASP | E | 458 | 83.969 | 78.692 | 65.582 | 1.00 | 119.98 |
| 4214 | OD1 | ASP | E | 458 | 84.030 | 79.460 | 64.598 | 1.00 | 129.07 |
| 4215 | OD2 | ASP | E | 458 | 84.796 | 78.724 | 66.519 | 1.00 | 129.49 |
| 4216 | C | ASP | E | 458 | 80.370 | 77.278 | 65.550 | 1.00 | 81.51 |
| 4217 | O | ASP | E | 458 | 80.239 | 76.726 | 64.456 | 1.00 | 77.41 |
| 4218 | N | LYS | E | 459 | 79.593 | 77.001 | 66.595 | 1.00 | 73.03 |
| 4219 | CA | LYS | E | 459 | 78.519 | 76.013 | 66.514 | 1.00 | 67.11 |
| 4220 | CB | LYS | E | 459 | 79.076 | 74.599 | 66.718 | 1.00 | 71.84 |
| 4221 | CG | LYS | E | 459 | 79.944 | 74.093 | 65.578 | 1.00 | 79.82 |
| 4222 | CD | LYS | E | 459 | 80.370 | 72.654 | 65.797 | 1.00 | 87.84 |
| 4223 | CE | LYS | E | 459 | 81.167 | 72.135 | 64.612 | 1.00 | 92.81 |
| 4224 | NZ | LYS | E | 459 | 81.582 | 70.722 | 64.814 | 1.00 | 97.59 |
| 4225 | C | LYS | E | 459 | 77.415 | 76.266 | 67.536 | 1.00 | 61.22 |
| 4226 | O | LYS | E | 459 | 77.648 | 76.911 | 68.552 | 1.00 | 58.83 |
| 4227 | N | ARG | E | 460 | 76.217 | 75.753 | 67.251 | 1.00 | 55.33 |
| 4228 | CA | ARG | E | 460 | 75.056 | 75.890 | 68.132 | 1.00 | 50.28 |
| 4229 | CB | ARG | E | 460 | 74.175 | 77.066 | 67.714 | 1.00 | 53.66 |
| 4230 | CG | ARG | E | 460 | 74.828 | 78.422 | 67.734 | 1.00 | 60.04 |
| 4231 | CD | ARG | E | 460 | 75.269 | 78.832 | 69.129 | 1.00 | 65.40 |
| 4232 | NE | ARG | E | 460 | 75.437 | 80.278 | 69.194 | 1.00 | 70.68 |
| 4233 | CZ | ARG | E | 460 | 74.424 | 81.136 | 69.202 | 1.00 | 73.63 |
| 4234 | NH1 | ARG | E | 460 | 73.176 | 80.688 | 69.163 | 1.00 | 75.73 |
| 4235 | NH2 | ARG | E | 460 | 74.656 | 82.440 | 69.217 | 1.00 | 75.96 |
| 4236 | C | ARG | E | 460 | 74.207 | 74.628 | 68.047 | 1.00 | 45.48 |
| 4237 | O | ARG | E | 460 | 74.361 | 73.835 | 67.125 | 1.00 | 45.40 |
| 4238 | N | THR | E | 461 | 73.310 | 74.448 | 69.010 | 1.00 | 40.80 |
| 4239 | CA | THR | E | 461 | 72.417 | 73.299 | 69.007 | 1.00 | 37.55 |
| 4240 | CB | THR | E | 461 | 72.556 | 72.458 | 70.305 | 1.00 | 37.13 |
| 4241 | OG1 | THR | E | 461 | 73.943 | 72.293 | 70.626 | 1.00 | 34.41 |
| 4242 | CG2 | THR | E | 461 | 71.945 | 71.070 | 70.113 | 1.00 | 33.83 |
| 4243 | C | THR | E | 461 | 70.984 | 73.850 | 68.915 | 1.00 | 36.56 |
| 4244 | O | THR | E | 461 | 70.653 | 74.854 | 69.556 | 1.00 | 35.30 |
| 4245 | N | LEU | E | 462 | 70.153 | 73.222 | 68.088 | 1.00 | 32.77 |
| 4246 | CA | LEU | E | 462 | 68.759 | 73.634 | 67.924 | 1.00 | 30.03 |
| 4247 | CB | LEU | E | 462 | 68.423 | 73.872 | 66.447 | 1.00 | 30.85 |
| 4248 | CG | LEU | E | 462 | 69.178 | 74.963 | 65.692 | 1.00 | 32.39 |
| 4249 | CD1 | LEU | E | 462 | 68.628 | 75.042 | 64.282 | 1.00 | 31.88 |
| 4250 | CD2 | LEU | E | 462 | 69.040 | 76.307 | 66.410 | 1.00 | 32.84 |
| 4251 | C | LEU | E | 462 | 67.885 | 72.510 | 68.446 | 1.00 | 27.56 |
| 4252 | O | LEU | E | 462 | 68.276 | 71.351 | 68.382 | 1.00 | 29.87 |
| 4253 | N | ALA | E | 463 | 66.703 | 72.851 | 68.951 | 1.00 | 26.88 |
| 4254 | CA | ALA | E | 463 | 65.781 | 71.859 | 69.488 | 1.00 | 25.80 |
| 4255 | CB | ALA | E | 463 | 65.912 | 71.804 | 70.990 | 1.00 | 27.84 |
| 4256 | C | ALA | E | 463 | 64.320 | 72.111 | 69.116 | 1.00 | 25.76 |
| 4257 | O | ALA | E | 463 | 63.872 | 73.258 | 68.978 | 1.00 | 24.01 |
| 4258 | N | CYS | E | 464 | 63.573 | 71.021 | 68.995 | 1.00 | 24.22 |
| 4259 | CA | CYS | E | 464 | 62.170 | 71.082 | 68.630 | 1.00 | 27.60 |
| 4260 | C | CYS | E | 464 | 61.310 | 70.166 | 69.492 | 1.00 | 26.23 |
| 4261 | O | CYS | E | 464 | 61.708 | 69.041 | 69.794 | 1.00 | 29.44 |
| 4262 | CB | CYS | E | 464 | 62.014 | 70.686 | 67.151 | 1.00 | 25.24 |
| 4263 | SG | CYS | E | 464 | 60.375 | 71.045 | 66.440 | 1.00 | 32.76 |
| 4264 | N | LEU | E | 465 | 60.132 | 70.650 | 69.884 | 1.00 | 28.98 |
| 4265 | CA | LEU | E | 465 | 59.177 | 69.854 | 70.675 | 1.00 | 30.90 |
| 4266 | CB | LEU | E | 465 | 58.906 | 70.509 | 72.037 | 1.00 | 32.92 |
| 4267 | CG | LEU | E | 465 | 57.770 | 69.914 | 72.896 | 1.00 | 34.43 |
| 4268 | CD1 | LEU | E | 465 | 58.106 | 68.484 | 73.337 | 1.00 | 32.30 |
| 4269 | CD2 | LEU | E | 465 | 57.541 | 70.803 | 74.111 | 1.00 | 31.82 |
| 4270 | C | LEU | E | 465 | 57.857 | 69.780 | 69.882 | 1.00 | 30.42 |
| 4271 | O | LEU | E | 465 | 57.324 | 70.822 | 69.485 | 1.00 | 25.94 |
| 4272 | N | ILE | E | 466 | 57.376 | 68.551 | 69.642 | 1.00 | 29.85 |
| 4273 | CA | ILE | E | 466 | 56.128 | 68.255 | 68.911 | 1.00 | 31.63 |
| 4274 | CB | ILE | E | 466 | 56.390 | 67.318 | 67.689 | 1.00 | 34.85 |
| 4275 | CG2 | ILE | E | 466 | 55.158 | 67.283 | 66.778 | 1.00 | 33.84 |
| 4276 | CG1 | ILE | E | 466 | 57.631 | 67.776 | 66.911 | 1.00 | 37.86 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4277 | CD1 | ILE | E | 466 | 57.565 | 69.194 | 66.421 | 1.00 | 44.00 |
| 4278 | C | ILE | E | 466 | 55.212 | 67.499 | 69.897 | 1.00 | 29.24 |
| 4279 | O | ILE | E | 466 | 55.584 | 66.426 | 70.376 | 1.00 | 28.89 |
| 4280 | N | GLN | E | 467 | 54.015 | 68.021 | 70.179 | 1.00 | 27.12 |
| 4281 | CA | GLN | E | 467 | 53.136 | 67.381 | 71.177 | 1.00 | 25.41 |
| 4282 | CB | GLN | E | 467 | 53.458 | 67.958 | 72.567 | 1.00 | 25.39 |
| 4283 | CG | GLN | E | 467 | 53.276 | 69.488 | 72.673 | 1.00 | 25.68 |
| 4284 | CD | GLN | E | 467 | 53.488 | 70.024 | 74.104 | 1.00 | 30.64 |
| 4285 | OE1 | GLN | E | 467 | 54.318 | 69.506 | 74.862 | 1.00 | 28.36 |
| 4286 | NE2 | GLN | E | 467 | 52.748 | 71.078 | 74.462 | 1.00 | 25.57 |
| 4287 | C | GLN | E | 467 | 51.609 | 67.461 | 70.975 | 1.00 | 27.44 |
| 4288 | O | GLN | E | 467 | 51.098 | 68.224 | 70.131 | 1.00 | 22.53 |
| 4289 | N | ASN | E | 468 | 50.914 | 66.670 | 71.797 | 1.00 | 27.39 |
| 4290 | CA | ASN | E | 468 | 49.452 | 66.530 | 71.850 | 1.00 | 31.56 |
| 4291 | CB | ASN | E | 468 | 48.796 | 67.859 | 72.249 | 1.00 | 33.00 |
| 4292 | CG | ASN | E | 468 | 49.191 | 68.309 | 73.650 | 1.00 | 35.28 |
| 4293 | OD1 | ASN | E | 468 | 49.518 | 67.487 | 74.517 | 1.00 | 34.08 |
| 4294 | ND2 | ASN | E | 468 | 49.153 | 69.613 | 73.880 | 1.00 | 28.60 |
| 4295 | C | ASN | E | 468 | 48.743 | 65.970 | 70.610 | 1.00 | 33.55 |
| 4296 | O | ASN | E | A68 | 47.591 | 66.329 | 70.337 | 1.00 | 33.21 |
| 4297 | N | PHE | E | 469 | 49.417 | 65.082 | 69.881 | 1.00 | 35.14 |
| 4298 | CA | PHE | E | 469 | 48.839 | 64.486 | 68.687 | 1.00 | 38.90 |
| 4299 | CB | PHE | E | 469 | 49.828 | 64.595 | 67.514 | 1.00 | 31.54 |
| 4300 | CG | PHE | E | 469 | 51.145 | 63.885 | 67.744 | 1.00 | 27.77 |
| 4301 | CD1 | PHE | E | 469 | 51.296 | 62.529 | 67.412 | 1.00 | 22.68 |
| 4302 | CD2 | PHE | E | 469 | 52.242 | 64.576 | 68.267 | 1.00 | 25.15 |
| 4303 | CE1 | PHE | E | 469 | 52.514 | 61.876 | 67.588 | 1.00 | 23.25 |
| 4304 | CE2 | PHE | E | 469 | 53.477 | 63.934 | 68.455 | 1.00 | 23.98 |
| 4305 | CZ | PHE | E | 469 | 53.620 | 62.579 | 68.113 | 1.00 | 22.63 |
| 4306 | C | PHE | E | 469 | 48.431 | 63.031 | 68.894 | 1.00 | 45.58 |
| 4307 | O | PHE | E | 469 | 48.823 | 62.396 | 69.879 | 1.00 | 42.42 |
| 4308 | N | MET | E | 470 | 47.614 | 62.521 | 67.974 | 1.00 | 50.96 |
| 4309 | CA | MET | E | 470 | 47.166 | 61.134 | 68.002 | 1.00 | 62.33 |
| 4310 | CB | MET | E | 470 | 46.285 | 60.858 | 69.232 | 1.00 | 69.67 |
| 4311 | CG | MET | E | 470 | 44.927 | 61.533 | 69.258 | 1.00 | 79.03 |
| 4312 | SD | MET | E | 470 | 44.100 | 61.325 | 70.877 | 1.00 | 84.15 |
| 4313 | CE | MET | E | 470 | 44.162 | 59.547 | 71.081 | 1.00 | 90.12 |
| 4314 | C | MET | E | 470 | 46.425 | 60.813 | 66.709 | 1.00 | 64.71 |
| 4315 | O | MET | E | 470 | 45.704 | 61.652 | 66.180 | 1.00 | 64.24 |
| 4316 | N | CPR | E | 471 | 46.620 | 59.599 | 66.163 | 1.00 | 64.30 |
| 4317 | CD | CPR | E | 471 | 46.038 | 59.251 | 64.858 | 1.00 | 66.89 |
| 4318 | CA | CPR | E | 471 | 47.469 | 58.503 | 66.649 | 1.00 | 62.62 |
| 4319 | CB | CPR | E | 471 | 47.214 | 57.395 | 65.629 | 1.00 | 64.75 |
| 4320 | CG | CPR | E | 471 | 46.969 | 58.160 | 64.379 | 1.00 | 68.96 |
| 4321 | C | CPR | E | 471 | 48.957 | 58.844 | 66.788 | 1.00 | 56.02 |
| 4322 | O | CPR | E | 471 | 49.357 | 59.993 | 66.615 | 1.00 | 49.44 |
| 4323 | N | GLU | E | 472 | 49.761 | 57.821 | 67.070 | 1.00 | 48.16 |
| 4324 | CA | GLU | E | 472 | 51.203 | 57.958 | 67.304 | 1.00 | 45.13 |
| 4325 | CB | GLU | E | 472 | 51.664 | 56.819 | 68.214 | 1.00 | 49.09 |
| 4326 | CG | GLU | E | 472 | 51.588 | 55.461 | 67.538 | 1.00 | 56.24 |
| 4327 | CD | GLU | E | 472 | 52.026 | 54.329 | 68.443 | 1.00 | 61.85 |
| 4328 | OE1 | GLU | E | 472 | 51.325 | 54.076 | 69.449 | 1.00 | 64.68 |
| 4329 | OE2 | GLU | E | 472 | 53.071 | 53.694 | 68.150 | 1.00 | 65.52 |
| 4330 | C | GLU | E | 472 | 52.192 | 58.055 | 66.130 | 1.00 | 42.85 |
| 4331 | O | GLU | E | 472 | 53.332 | 58.479 | 66.332 | 1.00 | 40.09 |
| 4332 | N | ASP | E | 473 | 51.789 | 57.652 | 64.927 | 1.00 | 40.40 |
| 4333 | CA | ASP | E | 473 | 52.688 | 57.710 | 63.769 | 1.00 | 39.41 |
| 4334 | CB | ASP | E | 473 | 52.154 | 56.830 | 62.636 | 1.00 | 44.54 |
| 4335 | CG | ASP | E | 473 | 51.892 | 55.395 | 63.077 | 1.00 | 50.85 |
| 4336 | OD1 | ASP | E | 473 | 52.724 | 54.818 | 63.819 | 1.00 | 51.55 |
| 4337 | OD2 | ASP | E | 473 | 50.847 | 54.843 | 62.669 | 1.00 | 54.88 |
| 4338 | C | ASP | E | 473 | 52.899 | 59.139 | 63.248 | 1.00 | 37.07 |
| 4339 | O | ASP | E | 473 | 51.939 | 59.845 | 62.925 | 1.00 | 33.75 |
| 4340 | N | ILE | E | 474 | 54.164 | 59.544 | 63.148 | 1.00 | 33.07 |
| 4341 | CA | ILE | E | 474 | 54.512 | 60.885 | 62.696 | 1.00 | 32.66 |
| 4342 | CB | ILE | E | 474 | 54.399 | 61.855 | 63.908 | 1.00 | 32.80 |
| 4343 | CG2 | ILE | E | 474 | 55.472 | 61.522 | 64.940 | 1.00 | 33.95 |
| 4344 | CG1 | ILE | E | 474 | 54.483 | 63.313 | 63.451 | 1.00 | 36.04 |
| 4345 | CD1 | ILE | E | 474 | 54.017 | 64.318 | 64.510 | 1.00 | 36.74 |
| 4346 | C | ILE | E | 474 | 55.927 | 60.945 | 62.055 | 1.00 | 31.59 |
| 4347 | O | ILE | E | 474 | 56.796 | 60.119 | 62.357 | 1.00 | 29.43 |
| 4348 | N | SER | E | 475 | 56.133 | 61.899 | 61.146 | 1.00 | 29.64 |
| 4349 | CA | SER | E | 475 | 57.423 | 62.096 | 60.468 | 1.00 | 29.17 |
| 4350 | CB | SER | E | 475 | 57.273 | 62.023 | 58.938 | 1.00 | 28.49 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4351 | OG | SER | E | 475 | 57.077 | 60.702 | 58.480 | 1.00 | 31.44 |
| 4352 | C | SER | E | 475 | 57.930 | 63.491 | 60.831 | 1.00 | 30.49 |
| 4353 | O | SER | E | 475 | 57.166 | 64.447 | 60.775 | 1.00 | 26.95 |
| 4354 | N | VAL | E | 476 | 59.214 | 63.603 | 61.186 | 1.00 | 30.00 |
| 4355 | CA | VAL | E | 476 | 59.821 | 64.883 | 61.577 | 1.00 | 28.48 |
| 4356 | CB | VAL | E | 476 | 60.319 | 64.830 | 63.058 | 1.00 | 31.52 |
| 4357 | CG1 | VAL | E | 476 | 61.150 | 66.058 | 63.393 | 1.00 | 30.02 |
| 4358 | CG2 | VAL | E | 476 | 59.141 | 64.719 | 64.005 | 1.00 | 32.74 |
| 4359 | C | VAL | E | 476 | 61.027 | 65.182 | 60.702 | 1.00 | 29.70 |
| 4360 | O | VAL | E | 476 | 61.809 | 64.274 | 60.401 | 1.00 | 27.22 |
| 4361 | N | GLN | E | 477 | 61.190 | 66.438 | 60.296 | 1.00 | 27.16 |
| 4362 | CA | GLN | E | 477 | 62.349 | 66.803 | 59.483 | 1.00 | 31.97 |
| 4363 | CB | GLN | E | 477 | 62.064 | 66.516 | 58.003 | 1.00 | 37.01 |
| 4364 | CG | GLN | E | 477 | 60.914 | 67.308 | 57.433 | 1.00 | 45.92 |
| 4365 | CD | GLN | E | 477 | 60.136 | 66.549 | 56.368 | 1.00 | 48.48 |
| 4366 | OE1 | GLN | E | 477 | 59.277 | 67.117 | 55.696 | 1.00 | 48.61 |
| 4367 | NE2 | GLN | E | 477 | 60.430 | 65.258 | 56.218 | 1.00 | 51.80 |
| 4368 | C | GLN | E | 477 | 62.756 | 68.271 | 59.673 | 1.00 | 31.12 |
| 4369 | O | GLN | E | 477 | 61.981 | 69.073 | 60.196 | 1.00 | 29.33 |
| 4370 | N | TRP | E | 478 | 63.981 | 68.600 | 59.264 | 1.00 | 29.28 |
| 4371 | CA | TRP | E | 478 | 64.511 | 69.958 | 59.370 | 1.00 | 30.88 |
| 4372 | CB | TRP | E | 478 | 65.812 | 69.977 | 60.200 | 1.00 | 29.96 |
| 4373 | CG | TRP | E | 478 | 65.635 | 69.716 | 61.673 | 1.00 | 31.71 |
| 4374 | CD2 | TRP | E | 478 | 65.482 | 70.703 | 62.704 | 1.00 | 29.29 |
| 4375 | CE2 | TRP | E | 478 | 65.386 | 70.014 | 63.930 | 1.00 | 31.57 |
| 4376 | CE3 | TRP | E | 478 | 65.419 | 72.103 | 62.708 | 1.00 | 29.61 |
| 4377 | CD1 | TRP | E | 478 | 65.620 | 68.502 | 62.299 | 1.00 | 30.74 |
| 4378 | NE1 | TRP | E | 478 | 65.472 | 68.672 | 63.657 | 1.00 | 33.07 |
| 4379 | CZ2 | TRP | E | 478 | 65.230 | 70.680 | 65.152 | 1.00 | 29.10 |
| 4380 | CZ3 | TRP | E | 478 | 65.262 | 72.763 | 63.922 | 1.00 | 28.35 |
| 4381 | CH2 | TRP | E | 478 | 65.169 | 72.048 | 65.125 | 1.00 | 25.94 |
| 4382 | C | TRP | E | 478 | 64.823 | 70.508 | 57.978 | 1.00 | 30.64 |
| 4383 | O | TRP | E | 478 | 65.231 | 69.762 | 57.099 | 1.00 | 31.16 |
| 4384 | N | LEU | E | 479 | 64.675 | 71.814 | 57.792 | 1.00 | 31.42 |
| 4385 | CA | LEU | E | 479 | 64.973 | 72.426 | 56.499 | 1.00 | 34.53 |
| 4386 | CB | LEU | E | 479 | 63.675 | 72.772 | 55.764 | 1.00 | 38.76 |
| 4387 | CG | LEU | E | 479 | 62.851 | 71.575 | 55.287 | 1.00 | 42.05 |
| 4388 | CD1 | LEU | E | 479 | 61.947 | 71.116 | 56.403 | 1.00 | 44.24 |
| 4389 | CD2 | LEU | E | 479 | 62.018 | 71.976 | 54.077 | 1.00 | 47.35 |
| 4390 | C | LEU | E | 479 | 65.840 | 73.682 | 56.570 | 1.00 | 35.83 |
| 4391 | O | LEU | E | 479 | 65.653 | 74.521 | 57.454 | 1.00 | 35.17 |
| 4392 | N | HIS | E | 480 | 66.787 | 73.808 | 55.640 | 1.00 | 34.34 |
| 4393 | CA | HIS | E | 480 | 67.660 | 74.988 | 55.577 | 1.00 | 38.00 |
| 4394 | CB | HIS | E | 480 | 69.112 | 74.639 | 55.946 | 1.00 | 33.16 |
| 4395 | CG | HIS | E | 480 | 70.011 | 75.837 | 56.056 | 1.00 | 33.78 |
| 4396 | CD2 | HIS | E | 480 | 69.767 | 77.098 | 56.489 | 1.00 | 30.32 |
| 4397 | ND1 | HIS | E | 480 | 71.342 | 75.813 | 55.676 | 1.00 | 34.35 |
| 4398 | CE1 | HIS | E | 480 | 71.873 | 77.010 | 55.864 | 1.00 | 31.66 |
| 4399 | NE2 | HIS | E | 480 | 70.939 | 77.808 | 56.356 | 1.00 | 33.79 |
| 4400 | C | HIS | E | 480 | 67.622 | 75.572 | 54.155 | 1.00 | 41.94 |
| 4401 | O | HIS | E | 480 | 67.555 | 74.824 | 53.174 | 1.00 | 35.70 |
| 4402 | N | ASN | E | 481 | 67.694 | 76.899 | 54.059 | 1.00 | 48.17 |
| 4403 | CA | ASN | E | 481 | 67.625 | 77.598 | 52.776 | 1.00 | 58.93 |
| 4404 | CB | ASN | E | 481 | 68.657 | 77.060 | 51.776 | 1.00 | 60.72 |
| 4405 | CG | ASN | E | 481 | 69.952 | 77.830 | 54.811 | 1.00 | 61.24 |
| 4406 | OD1 | ASN | E | 481 | 69.981 | 79.023 | 51.526 | 1.00 | 61.93 |
| 4407 | ND2 | ASN | E | 481 | 71.035 | 77.152 | 52.164 | 1.00 | 64.87 |
| 4408 | C | ASN | E | 481 | 66.228 | 77.357 | 52.246 | 1.00 | 65.69 |
| 4409 | O | ASN | E | 481 | 65.327 | 78.169 | 52.461 | 1.00 | 68.64 |
| 4410 | N | GLU | E | 482 | 66.050 | 76.230 | 51.566 | 1.00 | 72.83 |
| 4411 | CA | GLU | E | 482 | 64.758 | 75.860 | 51.024 | 1.00 | 80.48 |
| 4412 | CB | GLU | E | 482 | 64.557 | 76.494 | 49.648 | 1.00 | 92.70 |
| 4413 | CG | GLU | E | 482 | 64.352 | 78.000 | 49.684 | 1.00 | 112.13 |
| 4414 | CD | GLU | E | 482 | 63.261 | 78.411 | 50.657 | 1.00 | 122.51 |
| 4415 | OE1 | GLU | E | 482 | 62.162 | 77.818 | 50.601 | 1.00 | 129.74 |
| 4416 | OE2 | GLU | E | 482 | 63.498 | 79.328 | 51.474 | 1.00 | 129.13 |
| 4417 | C | GLU | E | 482 | 64.694 | 74.353 | 50.911 | 1.00 | 77.12 |
| 4418 | O | GLU | E | 482 | 63.643 | 73.781 | 50.627 | 1.00 | 77.23 |
| 4419 | N | VAL | E | 483 | 65.826 | 73.710 | 51.165 | 1.00 | 71.68 |
| 4420 | CA | VAL | E | 483 | 65.910 | 72.262 | 51.064 | 1.00 | 67.32 |
| 4421 | CB | VAL | E | 483 | 67.145 | 71.860 | 50.230 | 1.00 | 69.78 |
| 4422 | CG1 | VAL | E | 483 | 68.419 | 72.301 | 50.947 | 1.00 | 72.14 |
| 4423 | CG2 | VAL | E | 483 | 67.148 | 70.359 | 49.987 | 1.00 | 72.00 |
| 4424 | C | VAL | E | 483 | 65.958 | 71.518 | 52.398 | 1.00 | 61.56 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4425 | O | VAL | E | 483 | 66.356 | 72.061 | 53.424 | 1.00 | 62.55 |
| 4426 | N | GLN | E | 484 | 65.556 | 70.257 | 52.348 | 1.00 | 55.04 |
| 4427 | CA | GLN | E | 484 | 65.532 | 69.360 | 53.490 | 1.00 | 49.37 |
| 4428 | CB | GLN | E | 484 | 64.494 | 68.275 | 53.197 | 1.00 | 47.80 |
| 4429 | CG | GLN | E | 484 | 64.440 | 67.094 | 54.135 | 1.00 | 48.47 |
| 4430 | CD | GLN | E | 484 | 63.381 | 66.090 | 53.687 | 1.00 | 50.97 |
| 4431 | OE1 | GLN | E | 484 | 63.371 | 64.935 | 54.114 | 1.00 | 53.78 |
| 4432 | NE2 | GLN | E | 484 | 62.479 | 66.538 | 52.824 | 1.00 | 50.81 |
| 4433 | C | GLN | E | 484 | 66.928 | 68.751 | 53.731 | 1.00 | 46.11 |
| 4434 | O | GLN | E | 484 | 67.562 | 68.255 | 52.797 | 1.00 | 45.49 |
| 4435 | N | LEU | E | 485 | 67.397 | 68.793 | 54.979 | 1.00 | 41.41 |
| 4436 | CA | LEU | E | 485 | 68.714 | 68.258 | 55.348 | 1.00 | 38.36 |
| 4437 | CB | LEU | E | 485 | 69.183 | 68.867 | 56.678 | 1.00 | 33.52 |
| 4438 | CG | LEU | E | 485 | 69.416 | 70.388 | 56.699 | 1.00 | 33.57 |
| 4439 | CD1 | LEU | E | 485 | 69.658 | 70.876 | 58.133 | 1.00 | 29.64 |
| 4440 | CD2 | LEU | E | 485 | 70.622 | 70.737 | 55.806 | 1.00 | 31.63 |
| 4441 | C | LEU | E | 485 | 68.683 | 66.734 | 55.473 | 1.00 | 40.19 |
| 4442 | O | LEU | E | 485 | 67.619 | 66.138 | 55.611 | 1.00 | 36.32 |
| 4443 | N | PRO | E | 486 | 69.860 | 66.084 | 55.418 | 1.00 | 41.23 |
| 4444 | CD | PRO | E | 486 | 71.166 | 66.668 | 55.060 | 1.00 | 42.72 |
| 4445 | CA | PRO | E | 486 | 69.955 | 64.622 | 55.526 | 1.00 | 45.30 |
| 4446 | CB | PRO | E | 486 | 71.429 | 64.347 | 55.221 | 1.00 | 44.62 |
| 4447 | CG | PRO | E | 486 | 71.836 | 65.518 | 54.355 | 1.00 | 44.13 |
| 4448 | C | PRO | E | 486 | 69.544 | 64.091 | 56.911 | 1.00 | 50.93 |
| 4449 | O | PRO | E | 486 | 69.765 | 64.748 | 57.928 | 1.00 | 46.81 |
| 4450 | N | ASP | E | 487 | 68.961 | 62.895 | 56.934 | 1.00 | 55.76 |
| 4451 | CA | ASP | E | 487 | 68.508 | 62.270 | 58.173 | 1.00 | 62.95 |
| 4452 | CB | ASP | E | 487 | 67.778 | 60.957 | 57.865 | 1.00 | 76.45 |
| 4453 | CG | ASP | E | 487 | 66.357 | 61.178 | 57.379 | 1.00 | 88.17 |
| 4454 | OD1 | ASP | E | 487 | 65.552 | 61.760 | 58.138 | 1.00 | 96.61 |
| 4455 | OD2 | ASP | E | 487 | 66.043 | 60.770 | 56.240 | 1.00 | 95.52 |
| 4456 | C | ASP | E | 487 | 69.595 | 62.004 | 59.214 | 1.00 | 59.87 |
| 4457 | O | ASP | E | 487 | 69.353 | 62.165 | 60.410 | 1.00 | 59.69 |
| 4458 | N | ALA | E | 488 | 70.782 | 61.601 | 58.769 | 1.00 | 56.53 |
| 4459 | CA | ALA | E | 488 | 71.893 | 61.307 | 59.683 | 1.00 | 53.11 |
| 4460 | CB | ALA | E | 488 | 73.109 | 60.836 | 58.892 | 1.00 | 52.44 |
| 4461 | C | ALA | E | 488 | 72.272 | 62.510 | 60.542 | 1.00 | 50.00 |
| 4462 | O | ALA | E | 488 | 72.930 | 62.374 | 61.572 | 1.00 | 49.47 |
| 4463 | N | ARG | E | 489 | 71.838 | 63.685 | 60.103 | 1.00 | 47.07 |
| 4464 | CA | ARG | E | 489 | 72.109 | 64.943 | 60.780 | 1.00 | 44.10 |
| 4465 | CB | ARG | E | 489 | 71.760 | 66.093 | 59.844 | 1.00 | 42.97 |
| 4466 | CG | ARG | E | 489 | 72.915 | 66.601 | 59.031 | 1.00 | 44.05 |
| 4467 | CD | ARG | E | 489 | 73.700 | 67.578 | 59.871 | 1.00 | 44.19 |
| 4468 | NE | ARG | E | 489 | 74.310 | 68.585 | 59.028 | 1.00 | 43.20 |
| 4469 | CZ | ARG | E | 489 | 74.346 | 69.878 | 59.309 | 1.00 | 43.58 |
| 4470 | NH1 | ARG | E | 489 | 73.804 | 70.345 | 60.421 | 1.00 | 43.26 |
| 4471 | NH2 | ARG | E | 489 | 74.928 | 70.706 | 58.463 | 1.00 | 48.04 |
| 4472 | C | ARG | E | 489 | 71.398 | 65.170 | 62.118 | 1.00 | 43.13 |
| 4473 | O | ARG | E | 489 | 71.982 | 65.763 | 63.017 | 1.00 | 42.62 |
| 4474 | N | HIS | E | 490 | 70.143 | 64.732 | 62.239 | 1.00 | 41.88 |
| 4475 | CA | HIS | E | 490 | 69.392 | 64.935 | 63.476 | 1.00 | 41.20 |
| 4476 | CB | HIS | E | 490 | 68.092 | 65.712 | 63.210 | 1.00 | 40.89 |
| 4477 | CG | HIS | E | 490 | 67.075 | 64.952 | 62.412 | 1.00 | 41.89 |
| 4478 | CD2 | HIS | E | 490 | 66.149 | 64.038 | 62.788 | 1.00 | 41.94 |
| 4479 | ND1 | HIS | E | 490 | 66.930 | 65.102 | 61.048 | 1.00 | 42.24 |
| 4480 | CE1 | HIS | E | 490 | 65.959 | 64.317 | 60.620 | 1.00 | 42.31 |
| 4481 | NE2 | HIS | E | 490 | 65.467 | 63.660 | 61.656 | 1.00 | 43.18 |
| 4482 | C | HIS | E | 490 | 69.055 | 63.657 | 64.242 | 1.00 | 41.06 |
| 4483 | O | HIS | E | 490 | 69.158 | 62.545 | 63.714 | 1.00 | 39.58 |
| 4484 | N | SER | E | 491 | 68.649 | 63.839 | 65.496 | 1.00 | 40.14 |
| 4485 | CA | SER | E | 491 | 68.291 | 62.731 | 66.367 | 1.00 | 40.63 |
| 4486 | CB | SER | E | 491 | 69.337 | 62.596 | 67.475 | 1.00 | 41.07 |
| 4487 | OG | SER | E | 491 | 69.090 | 61.458 | 68.274 | 1.00 | 42.41 |
| 4488 | C | SER | E | 491 | 66.901 | 62.999 | 66.958 | 1.00 | 39.90 |
| 4489 | O | SER | E | 491 | 66.680 | 64.015 | 67.624 | 1.00 | 38.92 |
| 4490 | N | THR | E | 492 | 65.975 | 62.074 | 66.726 | 1.00 | 39.06 |
| 4491 | CA | THR | E | 492 | 64.597 | 62.219 | 67.192 | 1.00 | 38.08 |
| 4492 | CB | THR | E | 492 | 63.651 | 62.265 | 65.963 | 1.00 | 37.28 |
| 4493 | OG1 | THR | E | 492 | 64.053 | 63.337 | 65.096 | 1.00 | 37.79 |
| 4494 | CG2 | THR | E | 492 | 62.216 | 62.494 | 66.387 | 1.00 | 37.59 |
| 4495 | C | THR | E | 492 | 64.153 | 61.100 | 68.153 | 1.00 | 38.89 |
| 4496 | O | THR | E | 492 | 64.322 | 59.915 | 67.858 | 1.00 | 36.70 |
| 4497 | N | THR | E | 493 | 63.572 | 61.482 | 69.293 | 1.00 | 39.44 |
| 4498 | CA | THR | E | 493 | 63.122 | 60.508 | 70.292 | 1.00 | 43.18 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4499 | CB | THR | E | 493 | 62.746 | 61.183 | 71.655 | 1.00 | 42.00 |
| 4500 | OG1 | THR | E | 493 | 61.550 | 61.963 | 71.509 | 1.00 | 41.02 |
| 4501 | CG2 | THR | E | 493 | 63.872 | 62.079 | 72.132 | 1.00 | 38.83 |
| 4502 | C | THR | E | 493 | 61.922 | 59.708 | 69.807 | 1.00 | 45.99 |
| 4503 | O | THR | E | 493 | 61.334 | 60.024 | 68.773 | 1.00 | 45.35 |
| 4504 | N | GLN | E | 494 | 61.576 | 58.663 | 70.555 | 1.00 | 49.47 |
| 4505 | CA | GLN | E | 494 | 60.443 | 57.798 | 70.225 | 1.00 | 53.83 |
| 4506 | CB | GLN | E | 494 | 60.722 | 56.367 | 70.702 | 1.00 | 63.57 |
| 4507 | CG | GLN | E | 494 | 61.860 | 55.661 | 69.957 | 1.00 | 80.21 |
| 4508 | CD | GLN | E | 494 | 61.492 | 55.248 | 68.529 | 1.00 | 88.33 |
| 4509 | OE1 | GLN | E | 494 | 60.606 | 54.418 | 68.318 | 1.00 | 93.68 |
| 4510 | NE2 | GLN | E | 494 | 62.178 | 55.827 | 67.547 | 1.00 | 94.08 |
| 4511 | C | GLN | E | 494 | 59.154 | 58.321 | 70.871 | 1.00 | 50.75 |
| 4512 | O | GLN | E | 494 | 59.195 | 58.984 | 71.903 | 1.00 | 47.92 |
| 4513 | N | PRO | E | 495 | 57.993 | 58.033 | 70.264 | 1.00 | 48.68 |
| 4514 | CD | PRO | E | 495 | 57.830 | 57.471 | 68.913 | 1.00 | 46.85 |
| 4515 | CA | PRO | E | 495 | 56.703 | 58.486 | 70.795 | 1.00 | 50.82 |
| 4516 | CB | PRO | E | 495 | 55.705 | 57.872 | 69.821 | 1.00 | 48.84 |
| 4517 | CG | PRO | E | 495 | 56.450 | 57.958 | 68.519 | 1.00 | 46.07 |
| 4518 | C | PRO | E | 495 | 56.395 | 58.123 | 72.249 | 1.00 | 57.66 |
| 4519 | O | PRO | E | 495 | 56.419 | 56.952 | 72.623 | 1.00 | 56.34 |
| 4520 | N | ARG | E | 496 | 56.102 | 59.143 | 73.056 | 1.00 | 64.86 |
| 4521 | CA | ARG | E | 496 | 55.761 | 58.971 | 74.470 | 1.00 | 75.13 |
| 4522 | CB | ARG | E | 496 | 56.806 | 59.647 | 75.363 | 1.00 | 89.34 |
| 4523 | CG | ARG | E | 496 | 58.097 | 58.868 | 75.557 | 1.00 | 111.84 |
| 4524 | CD | ARG | E | 496 | 59.082 | 59.670 | 76.402 | 1.00 | 130.17 |
| 4525 | NE | ARG | E | 496 | 60.262 | 58.899 | 76.788 | 1.00 | 143.77 |
| 4526 | CZ | ARG | E | 496 | 60.245 | 57.874 | 77.636 | 1.00 | 150.08 |
| 4527 | NH1 | ARG | E | 496 | 59.104 | 57.490 | 78.193 | 1.00 | 153.19 |
| 4528 | NH2 | ARG | E | 496 | 61.369 | 57.233 | 77.932 | 1.00 | 153.09 |
| 4529 | C | ARG | E | 496 | 54.387 | 59.587 | 74.756 | 1.00 | 71.94 |
| 4530 | O | ARG | E | 496 | 53.882 | 60.378 | 73.961 | 1.00 | 70.04 |
| 4531 | N | LYS | E | 497 | 53.790 | 59.232 | 75.893 | 1.00 | 69.41 |
| 4532 | CA | LYS | E | 497 | 52.477 | 59.763 | 76.263 | 1.00 | 67.56 |
| 4533 | CB | LYS | E | 497 | 51.633 | 58.696 | 76.960 | 1.00 | 69.70 |
| 4534 | CG | LYS | E | 497 | 51.144 | 57.582 | 76.063 | 1.00 | 73.75 |
| 4535 | CD | LYS | E | 497 | 50.235 | 56.648 | 76.840 | 1.00 | 78.07 |
| 4536 | CE | LYS | E | 497 | 49.830 | 55.443 | 76.011 | 1.00 | 81.83 |
| 4537 | NZ | LYS | E | 497 | 48.947 | 54.524 | 76.783 | 1.00 | 84.03 |
| 4538 | C | LYS | E | 497 | 52.519 | 60.994 | 77.163 | 1.00 | 65.42 |
| 4539 | O | LYS | E | 497 | 53.309 | 61.073 | 78.104 | 1.00 | 64.57 |
| 4540 | N | THR | E | 498 | 51.659 | 61.958 | 76.860 | 1.00 | 66.13 |
| 4541 | CA | THR | E | 498 | 51.562 | 63.167 | 77.659 | 1.00 | 67.23 |
| 4542 | CB | THR | E | 498 | 50.868 | 64.304 | 76.882 | 1.00 | 62.10 |
| 4543 | OG1 | THR | E | 498 | 49.488 | 63.977 | 76.676 | 1.00 | 58.93 |
| 4544 | CG2 | THR | E | 498 | 51.545 | 64.511 | 75.531 | 1.00 | 59.00 |
| 4545 | C | THR | E | 498 | 50.694 | 62.770 | 78.846 | 1.00 | 73.38 |
| 4546 | O | THR | E | 498 | 50.706 | 61.614 | 79.268 | 1.00 | 71.03 |
| 4547 | N | LYS | E | 499 | 49.936 | 63.715 | 79.386 | 1.00 | 80.40 |
| 4548 | CA | LYS | E | 499 | 49.064 | 63.404 | 80.509 | 1.00 | 90.49 |
| 4549 | CB | LYS | E | 499 | 49.214 | 64.460 | 81.606 | 1.00 | 92.39 |
| 4550 | CG | LYS | E | 499 | 50.581 | 64.463 | 82.268 | 1.00 | 95.79 |
| 4551 | CD | LYS | E | 499 | 50.654 | 65.513 | 83.360 | 1.00 | 99.01 |
| 4552 | CE | LYS | E | 499 | 52.000 | 65.489 | 84.065 | 1.00 | 101.21 |
| 4553 | NZ | LYS | E | 499 | 52.101 | 66.549 | 85.112 | 1.00 | 101.75 |
| 4554 | C | LYS | E | 499 | 47.615 | 63.325 | 80.037 | 1.00 | 95.14 |
| 4555 | O | LYS | E | 499 | 46.805 | 64.200 | 80.334 | 1.00 | 96.69 |
| 4556 | N | GLY | E | 500 | 47.299 | 62.270 | 79.291 | 1.00 | 100.25 |
| 4557 | CA | GLY | E | 500 | 45.948 | 62.097 | 78.793 | 1.00 | 107.11 |
| 4558 | C | GLY | E | 500 | 45.891 | 61.899 | 77.293 | 1.00 | 112.65 |
| 4559 | O | GLY | E | 500 | 45.903 | 62.872 | 76.540 | 1.00 | 111.94 |
| 4560 | N | SER | E | 501 | 45.830 | 60.637 | 76.871 | 1.00 | 110.88 |
| 4561 | CA | SER | E | 501 | 45.760 | 60.257 | 75.458 | 1.00 | 110.24 |
| 4562 | CB | SER | E | 501 | 44.314 | 59.916 | 75.085 | 1.00 | 118.16 |
| 4563 | OG | SER | E | 501 | 43.448 | 61.007 | 75.347 | 1.00 | 125.19 |
| 4564 | C | SER | E | 501 | 46.298 | 61.326 | 74.508 | 1.00 | 101.75 |
| 4565 | O | SER | E | 501 | 45.577 | 62.234 | 74.100 | 1.00 | 107.76 |
| 4566 | N | GLY | E | 502 | 47.570 | 61.199 | 74.157 | 1.00 | 94.51 |
| 4567 | CA | GLY | E | 502 | 48.211 | 62.151 | 73.270 | 1.00 | 73.91 |
| 4568 | C | GLY | E | 502 | 49.696 | 61.916 | 73.415 | 1.00 | 62.66 |
| 4569 | O | GLY | E | 502 | 50.165 | 61.654 | 74.517 | 1.00 | 60.83 |
| 4570 | N | PHE | E | 503 | 50.446 | 61.999 | 72.324 | 1.00 | 53.51 |
| 4571 | CA | PHE | E | 503 | 51.881 | 61.758 | 72.398 | 1.00 | 45.16 |
| 4572 | CB | PHE | E | 503 | 52.273 | 60.675 | 71.389 | 1.00 | 43.18 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4573 | CG | PHE | E | 503 | 51.418 | 59.438 | 71.461 | 1.00 | 43.28 |
| 4574 | CD1 | PHE | E | 503 | 50.164 | 59.401 | 70.846 | 1.00 | 42.69 |
| 4575 | CD2 | PHE | E | 503 | 51.856 | 58.314 | 72.164 | 1.00 | 43.22 |
| 4576 | CE1 | PHE | E | 503 | 49.355 | 58.261 | 70.929 | 1.00 | 44.11 |
| 4577 | CE2 | PHE | E | 503 | 51.061 | 57.162 | 72.259 | 1.00 | 45.00 |
| 4578 | CZ | PHE | E | 503 | 49.803 | 57.134 | 71.639 | 1.00 | 45.45 |
| 4579 | C | PHE | E | 503 | 52.750 | 63.002 | 72.186 | 1.00 | 40.94 |
| 4580 | O | PHE | E | 503 | 52.251 | 64.083 | 71.867 | 1.00 | 36.99 |
| 4581 | N | PHE | E | 504 | 54.056 | 62.839 | 72.392 | 1.00 | 36.53 |
| 4582 | CA | PHE | E | 504 | 55.011 | 63.927 | 72.197 | 1.00 | 34.17 |
| 4583 | CB | PHE | E | 504 | 55.150 | 64.783 | 73.473 | 1.00 | 33.02 |
| 4584 | CG | PHE | E | 504 | 56.007 | 64.169 | 74.555 | 1.00 | 31.44 |
| 4585 | CD1 | PHE | E | 504 | 57.388 | 64.321 | 74.537 | 1.00 | 30.38 |
| 4586 | CD2 | PHE | E | 504 | 55.421 | 63.484 | 75.618 | 1.00 | 33.15 |
| 4587 | CE1 | PHE | E | 504 | 58.183 | 63.806 | 75.566 | 1.00 | 30.77 |
| 4588 | CE2 | PHE | E | 504 | 56.197 | 62.961 | 76.658 | 1.00 | 32.98 |
| 4589 | CZ | PHE | E | 504 | 57.589 | 63.125 | 76.629 | 1.00 | 34.03 |
| 4590 | C | PHE | E | 504 | 56.357 | 63.346 | 71.775 | 1.00 | 32.72 |
| 4591 | O | PHE | E | 504 | 56.627 | 62.165 | 72.003 | 1.00 | 31.92 |
| 4592 | N | VAL | E | 505 | 57.187 | 64.183 | 71.159 | 1.00 | 32.75 |
| 4593 | CA | VAL | E | 505 | 58.502 | 63.780 | 70.674 | 2.00 | 31.52 |
| 4594 | CB | VAL | E | 505 | 58.388 | 63.208 | 69.239 | 1.00 | 35.44 |
| 4595 | CG1 | VAL | E | 505 | 57.846 | 64.274 | 68.296 | 1.00 | 37.95 |
| 4596 | CG2 | VAL | E | 505 | 59.732 | 62.742 | 68.751 | 1.00 | 41.10 |
| 4597 | C | VAL | E | 505 | 59.449 | 64.984 | 70.654 | 1.00 | 31.85 |
| 4598 | O | VAL | E | 505 | 58.987 | 66.135 | 70.516 | 1.00 | 29.30 |
| 4599 | N | PHE | E | 506 | 60.754 | 64.707 | 70.803 | 1.00 | 28.71 |
| 4600 | CA | PHE | E | 506 | 61.832 | 65.720 | 70.782 | 1.00 | 28.45 |
| 4601 | CB | PHE | E | 506 | 62.651 | 65.694 | 72.104 | 1.00 | 28.00 |
| 4602 | CG | PHE | E | 506 | 62.063 | 66.519 | 73.233 | 1.00 | 24.95 |
| 4603 | CD1 | PHE | E | 506 | 61.442 | 65.908 | 74.306 | 1.00 | 25.60 |
| 4604 | CD2 | PHE | E | 506 | 62.142 | 67.911 | 73.215 | 1.00 | 26.92 |
| 4605 | CE1 | PHE | E | 506 | 60.898 | 66.669 | 75.362 | 1.00 | 28.81 |
| 4606 | CE2 | PHE | E | 506 | 61.608 | 68.678 | 74.247 | 1.00 | 23.71 |
| 4607 | CZ | PHE | E | 506 | 60.983 | 68.059 | 75.325 | 1.00 | 27.31 |
| 4608 | C | PHE | E | 506 | 62.831 | 65.450 | 69.623 | 1.00 | 27.74 |
| 4609 | O | PHE | E | 506 | 63.066 | 64.297 | 69.259 | 1.00 | 28.16 |
| 4610 | N | SER | E | 507 | 63.434 | 66.504 | 69.071 | 1.00 | 29.65 |
| 4611 | CA | SER | E | 507 | 64.436 | 66.375 | 67.995 | 1.00 | 30.30 |
| 4612 | CB | SER | E | 507 | 63.800 | 66.682 | 66.630 | 1.00 | 31.60 |
| 4613 | OG | SER | E | 507 | 64.697 | 66.396 | 65.567 | 1.00 | 31.08 |
| 4614 | C | SER | E | 507 | 65.617 | 67.335 | 68.251 | 1.00 | 30.60 |
| 4615 | O | SER | E | 507 | 65.402 | 68.458 | 68.707 | 1.00 | 32.07 |
| 4616 | N | ARG | E | 508 | 66.849 | 66.891 | 67.962 | 1.00 | 30.75 |
| 4617 | CA | ARG | E | 508 | 68.079 | 67.696 | 68.167 | 1.00 | 29.75 |
| 4618 | CB | ARG | E | 508 | 68.922 | 67.088 | 69.304 | 1.00 | 30.00 |
| 4619 | CG | ARG | E | 508 | 70.301 | 67.760 | 69.557 | 1.00 | 32.88 |
| 4620 | CD | ARG | E | 508 | 70.980 | 67.169 | 70.803 | 1.00 | 34.69 |
| 4621 | NE | ARG | E | 508 | 72.254 | 67.800 | 71.147 | 1.00 | 35.48 |
| 4622 | CZ | ARG | E | 508 | 73.416 | 67.529 | 70.555 | 1.00 | 39.79 |
| 4623 | NH1 | ARG | E | 508 | 73.480 | 66.627 | 69.578 | 1.00 | 40.94 |
| 4624 | NH2 | ARG | E | 508 | 74.519 | 68.161 | 70.938 | 1.00 | 38.99 |
| 4625 | C | ARG | E | 508 | 68.961 | 67.802 | 66.903 | 1.00 | 28.92 |
| 4626 | O | ARG | E | 508 | 69.278 | 66.788 | 66.280 | 1.00 | 26.42 |
| 4627 | N | LEU | E | 509 | 69.359 | 69.025 | 66.553 | 1.00 | 28.56 |
| 4628 | CA | LEU | E | 509 | 70.191 | 69.291 | 65.377 | 1.00 | 31.29 |
| 4629 | CB | LEU | E | 509 | 69.331 | 69.875 | 64.250 | 1.00 | 32.14 |
| 4630 | CG | LEU | E | 509 | 70.068 | 70.358 | 62.991 | 1.00 | 32.76 |
| 4631 | CD1 | LEU | E | 509 | 70.424 | 69.143 | 62.159 | 1.00 | 33.67 |
| 4632 | CD2 | LEU | E | 509 | 69.201 | 71.305 | 62.173 | 1.00 | 30.25 |
| 4633 | C | LEU | E | 509 | 71.346 | 70.280 | 65.640 | 1.00 | 33.56 |
| 4634 | O | LEU | E | 509 | 71.116 | 71.444 | 65.984 | 1.00 | 31.73 |
| 4635 | N | GLU | E | 510 | 72.580 | 69.823 | 65.453 | 1.00 | 34.78 |
| 4636 | CA | GLU | E | 510 | 73.750 | 70.683 | 65.620 | 1.00 | 38.47 |
| 4637 | CB | GLU | E | 510 | 74.973 | 69.828 | 65.959 | 1.00 | 46.22 |
| 4638 | CG | GLU | E | 510 | 74.824 | 68.975 | 67.216 | 1.00 | 57.53 |
| 4639 | CD | GLU | E | 510 | 75.988 | 68.008 | 67.398 | 1.00 | 64.25 |
| 4640 | OE1 | GLU | E | 510 | 77.153 | 68.454 | 67.284 | 1.00 | 67.97 |
| 4641 | OE2 | GLU | E | 510 | 75.741 | 66.807 | 67.657 | 1.00 | 66.64 |
| 4642 | C | GLU | E | 510 | 74.009 | 71.416 | 64.296 | 1.00 | 38.61 |
| 4643 | O | GLU | E | 510 | 74.010 | 70.780 | 63.240 | 1.00 | 34.67 |
| 4644 | N | VAL | E | 511 | 74.221 | 72.733 | 64.341 | 1.00 | 38.56 |
| 4645 | CA | VAL | E | 511 | 74.491 | 73.500 | 63.118 | 1.00 | 41.34 |
| 4646 | CB | VAL | E | 511 | 73.319 | 74.472 | 62.770 | 1.00 | 40.98 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4647 | CG1 | VAL | E | 511 | 71.999 | 73.704 | 62.748 | 1.00 | 39.52 |
| 4648 | CG2 | VAL | E | 511 | 73.263 | 75.631 | 63.747 | 1.00 | 37.80 |
| 4649 | C | VAL | E | 511 | 75.806 | 74.309 | 63.176 | 1.00 | 46.06 |
| 4650 | O | VAL | E | 511 | 76.202 | 74.783 | 64.245 | 1.00 | 46.29 |
| 4651 | N | THR | E | 512 | 76.478 | 74.457 | 62.028 | 1.00 | 48.02 |
| 4652 | CA | THR | E | 512 | 77.743 | 75.211 | 61.957 | 1.00 | 50.12 |
| 4653 | CB | THR | E | 512 | 78.713 | 74.650 | 60.884 | 1.00 | 49.41 |
| 4654 | OG1 | THR | E | 512 | 78.080 | 74.689 | 59.601 | 1.00 | 49.34 |
| 4655 | CG2 | THR | E | 512 | 79.115 | 73.225 | 61.203 | 1.00 | 49.96 |
| 4656 | C | THR | E | 512 | 77.552 | 76.688 | 61.638 | 1.00 | 52.61 |
| 4657 | O | THR | E | 512 | 76.496 | 77.112 | 61.165 | 1.00 | 52.49 |
| 4658 | N | ARG | E | 513 | 78.596 | 77.464 | 61.893 | 1.00 | 55.29 |
| 4659 | CA | ARG | E | 513 | 78.585 | 78.901 | 61.649 | 1.00 | 60.21 |
| 4660 | CB | ARG | E | 513 | 79.864 | 79.509 | 62.221 | 1.00 | 65.85 |
| 4661 | CG | ARG | E | 513 | 80.011 | 81.002 | 62.030 | 1.00 | 74.98 |
| 4662 | CD | ARG | E | 513 | 81.429 | 81.423 | 62.375 | 1.00 | 82.81 |
| 4663 | NE | ARG | E | 513 | 81.663 | 82.840 | 62.130 | 1.00 | 90.35 |
| 4664 | CZ | ARG | E | 513 | 82.869 | 83.399 | 62.095 | 1.00 | 94.40 |
| 4665 | NH1 | ARG | E | 513 | 83.952 | 82.655 | 62.289 | 1.00 | 96.62 |
| 4666 | NH2 | ARG | E | 513 | 82.994 | 84.700 | 61.859 | 1.00 | 96.84 |
| 4667 | C | ARG | E | 513 | 78.479 | 79.217 | 60.150 | 1.00 | 60.30 |
| 4668 | O | ARG | E | 513 | 77.921 | 80.245 | 59.756 | 1.00 | 58.00 |
| 4669 | N | ALA | E | 514 | 79.026 | 78.338 | 59.317 | 1.00 | 57.96 |
| 4670 | CA | ALA | E | 514 | 78.971 | 78.547 | 57.875 | 1.00 | 58.08 |
| 4671 | CB | ALA | E | 514 | 79.749 | 77.450 | 57.147 | 1.00 | 58.35 |
| 4672 | C | ALA | E | 514 | 77.507 | 78.538 | 57.433 | 1.00 | 56.45 |
| 4673 | O | ALA | E | 514 | 77.098 | 79.322 | 56.572 | 1.00 | 56.60 |
| 4674 | N | GLU | E | 515 | 76.727 | 77.654 | 58.046 | 1.00 | 55.14 |
| 4675 | CA | GLU | E | 515 | 75.315 | 77.522 | 57.735 | 1.00 | 52.06 |
| 4676 | CB | GLU | E | 515 | 74.730 | 76.305 | 58.453 | 1.00 | 53.49 |
| 4677 | CG | GLU | E | 515 | 75.113 | 74.991 | 57.801 | 1.00 | 56.13 |
| 4678 | CD | GLU | E | 515 | 74.556 | 73.781 | 58.526 | 1.00 | 57.51 |
| 4679 | OE1 | GLU | E | 515 | 74.396 | 72.738 | 57.872 | 1.00 | 55.98 |
| 4680 | OE2 | GLU | E | 515 | 74.287 | 73.865 | 59.743 | 1.00 | 58.61 |
| 4681 | C | GLU | E | 515 | 74.496 | 78.754 | 58.062 | 1.00 | 49.61 |
| 4682 | O | GLU | E | 515 | 73.905 | 79.351 | 57.173 | 1.00 | 48.73 |
| 4683 | N | TRP | E | 516 | 74.460 | 79.159 | 59.322 | 1.00 | 49.17 |
| 4684 | CA | TRP | E | 516 | 73.655 | 80.320 | 59.650 | 1.00 | 51.45 |
| 4685 | CB | TRP | E | 516 | 73.513 | 80.476 | 61.175 | 1.00 | 50.49 |
| 4686 | CG | TRP | E | 516 | 74.700 | 80.990 | 61.928 | 1.00 | 51.21 |
| 4687 | CD2 | TRP | E | 516 | 75.479 | 80.271 | 62.894 | 1.00 | 51.56 |
| 4688 | CE2 | TRP | E | 516 | 76.414 | 81.177 | 63.435 | 1.00 | 52.55 |
| 4689 | CE3 | TRP | E | 516 | 75.473 | 78.950 | 63.358 | 1.00 | 52.40 |
| 4690 | CD1 | TRP | E | 516 | 75.188 | 82.262 | 61.916 | 1.00 | 50.20 |
| 4691 | NE1 | TRP | E | 516 | 76.215 | 82.386 | 62.820 | 1.00 | 51.95 |
| 4692 | CZ2 | TRP | E | 516 | 77.337 | 80.806 | 64.419 | 1.00 | 52.88 |
| 4693 | CZ3 | TRP | E | 516 | 76.392 | 78.577 | 64.339 | 1.00 | 52.80 |
| 4694 | CH2 | TRP | E | 516 | 77.310 | 79.504 | 64.858 | 1.00 | 53.87 |
| 4695 | C | TRP | E | 516 | 74.132 | 81.616 | 58.991 | 1.00 | 52.96 |
| 4696 | O | TRP | E | 516 | 73.390 | 82.598 | 58.941 | 1.00 | 51.65 |
| 4697 | N | GLU | E | 517 | 75.354 | 81.616 | 58.463 | 1.00 | 54.49 |
| 4698 | CA | GLU | E | 517 | 75.885 | 82.804 | 57.795 | 1.00 | 57.98 |
| 4699 | CB | GLU | E | 517 | 77.418 | 82.785 | 57.784 | 1.00 | 64.54 |
| 4700 | CG | GLU | E | 517 | 78.046 | 83.025 | 59.150 | 1.00 | 72.90 |
| 4701 | CD | GLU | E | 517 | 79.499 | 83.462 | 59.064 | 1.00 | 77.23 |
| 4702 | OE1 | GLU | E | 517 | 80.301 | 82.750 | 58.420 | 1.00 | 79.55 |
| 4703 | OE2 | GLU | E | 517 | 79.834 | 84.518 | 59.646 | 1.00 | 79.31 |
| 4704 | C | GLU | E | 517 | 75.351 | 82.934 | 56.364 | 1.00 | 55.72 |
| 4705 | O | GLU | E | 517 | 75.138 | 84.044 | 55.873 | 1.00 | 54.39 |
| 4706 | N | ALA | E | 518 | 75.145 | 81.800 | 55.696 | 1.00 | 54.31 |
| 4707 | CA | ALA | E | 518 | 74.595 | 81.802 | 54.343 | 1.00 | 51.90 |
| 4708 | CB | ALA | E | 518 | 74.678 | 80.397 | 53.714 | 1.00 | 52.38 |
| 4709 | C | ALA | E | 518 | 73.134 | 82.243 | 54.452 | 1.00 | 50.21 |
| 4710 | O | ALA | E | 518 | 72.712 | 83.182 | 53.773 | 1.00 | 49.54 |
| 4711 | N | LYS | E | 519 | 72.385 | 81.572 | 55.330 | 1.00 | 49.19 |
| 4712 | CA | LYS | E | 519 | 70.964 | 81.860 | 55.569 | 1.00 | 49.61 |
| 4713 | CB | LYS | E | 519 | 70.113 | 81.040 | 54.596 | 1.00 | 54.65 |
| 4714 | CG | LYS | E | 519 | 68.604 | 81.215 | 54.733 | 1.00 | 64.73 |
| 4715 | CD | LYS | E | 519 | 68.102 | 82.490 | 54.074 | 1.00 | 71.63 |
| 4716 | CE | LYS | E | 519 | 66.583 | 82.473 | 53.977 | 1.00 | 76.82 |
| 4717 | NZ | LYS | E | 519 | 66.045 | 83.703 | 53.341 | 1.00 | 81.92 |
| 4718 | C | LYS | E | 519 | 70.571 | 81.520 | 57.030 | 1.00 | 47.70 |
| 4719 | O | LYS | E | 519 | 70.561 | 80.350 | 57.421 | 1.00 | 40.31 |
| 4720 | N | ASP | E | 520 | 70.235 | 82.540 | 57.818 | 1.00 | 46.14 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4721 | CA | ASP | E | 520 | 69.875 | 82.339 | 59.222 | 1.00 | 49.24 |
| 4722 | CB | ASP | E | 520 | 70.360 | 83.524 | 60.063 | 1.00 | 60.08 |
| 4723 | CG | ASP | E | 520 | 70.163 | 83.298 | 61.559 | 1.00 | 69.20 |
| 4724 | OD1 | ASP | E | 520 | 69.010 | 83.331 | 62.030 | 1.00 | 76.43 |
| 4725 | OD2 | ASP | E | 520 | 71.163 | 83.076 | 62.268 | 1.00 | 74.91 |
| 4726 | C | ASP | E | 520 | 68.387 | 82.088 | 59.507 | 1.00 | 46.03 |
| 4727 | O | ASP | E | 520 | 67.659 | 82.971 | 59.966 | 1.00 | 42.30 |
| 4728 | N | GLU | E | 521 | 67.952 | 80.864 | 59.231 | 1.00 | 42.46 |
| 4729 | CA | GLU | E | 521 | 66.581 | 80.445 | 59.460 | 1.00 | 40.38 |
| 4730 | CB | GLU | E | 521 | 65.621 | 81.080 | 58.443 | 1.00 | 43.57 |
| 4731 | CG | GLU | E | 521 | 64.211 | 80.505 | 58.525 | 1.00 | 48.13 |
| 4732 | CD | GLU | E | 521 | 63.220 | 81.146 | 57.571 | 1.00 | 51.69 |
| 4733 | OE1 | GLU | E | 521 | 63.456 | 81.169 | 56.342 | 1.00 | 52.45 |
| 4734 | OE2 | GLU | E | 521 | 62.179 | 81.618 | 58.063 | 1.00 | 56.05 |
| 4735 | C | GLU | E | 521 | 66.587 | 78.943 | 59.294 | 1.00 | 37.44 |
| 4736 | O | GLU | E | 521 | 67.150 | 78.427 | 58.325 | 1.00 | 37.61 |
| 4737 | N | PHE | E | 522 | 65.996 | 78.239 | 60.254 | 1.00 | 33.16 |
| 4738 | CA | PHE | E | 522 | 65.925 | 76.781 | 60.207 | 1.00 | 31.74 |
| 4739 | CB | PHE | E | 522 | 66.909 | 76.162 | 61.204 | 1.00 | 30.98 |
| 4740 | CG | PHE | E | 522 | 68.347 | 76.551 | 60.954 | 1.00 | 32.27 |
| 4741 | CD1 | PHE | E | 522 | 68.788 | 77.854 | 61.203 | 1.00 | 32.40 |
| 4742 | CD2 | PHE | E | 522 | 69.249 | 75.632 | 60.435 | 1.00 | 29.77 |
| 4743 | CE1 | PHE | E | 522 | 70.103 | 78.227 | 60.935 | 1.00 | 33.87 |
| 4744 | CE2 | PHE | E | 522 | 70.564 | 75.997 | 60.165 | 1.00 | 30.47 |
| 4745 | CZ | PHE | E | 522 | 70.991 | 77.292 | 60.414 | 1.00 | 31.45 |
| 4746 | C | PHE | E | 522 | 64.490 | 76.409 | 60.553 | 1.00 | 30.60 |
| 4747 | O | PHE | E | 522 | 63.878 | 77.029 | 61.428 | 1.00 | 33.98 |
| 4748 | N | ILE | E | 523 | 63.954 | 75.398 | 59.879 | 1.00 | 28.30 |
| 4749 | CA | ILE | E | 523 | 62.580 | 75.011 | 60.107 | 1.00 | 27.92 |
| 4750 | CB | ILE | E | 523 | 61.757 | 75.266 | 58.835 | 1.00 | 28.19 |
| 4751 | CG2 | ILE | E | 523 | 60.363 | 74.670 | 58.982 | 1.00 | 26.26 |
| 4752 | CG1 | ILE | E | 523 | 61.704 | 76.779 | 58.553 | 1.00 | 30.22 |
| 4753 | CD1 | ILE | E | 523 | 61.086 | 77.153 | 57.190 | 1.00 | 29.29 |
| 4754 | C | ILE | E | 523 | 62.348 | 73.573 | 60.549 | 1.00 | 28.49 |
| 4755 | O | ILE | E | 523 | 62.858 | 72.634 | 59.933 | 1.00 | 29.59 |
| 4756 | N | CYS | E | 524 | 61.568 | 73.416 | 61.624 | 1.00 | 28.27 |
| 4757 | CA | CYS | E | 524 | 61.183 | 72.106 | 62.153 | 1.00 | 28.48 |
| 4758 | C | CYS | E | 524 | 59.787 | 71.855 | 61.572 | 1.00 | 28.90 |
| 4759 | O | CYS | E | 524 | 58.899 | 72.706 | 61.716 | 1.00 | 27.78 |
| 4760 | CB | CYS | E | 524 | 61.100 | 72.159 | 63.682 | 1.00 | 29.82 |
| 4761 | SG | CYS | E | 524 | 60.543 | 70.605 | 64.439 | 1.00 | 27.31 |
| 4762 | N | ARG | E | 525 | 59.586 | 70.696 | 60.941 | 1.00 | 29.43 |
| 4763 | CA | ARG | E | 525 | 58.304 | 70.374 | 60.297 | 1.00 | 29.55 |
| 4764 | CB | ARG | E | 525 | 58.438 | 70.569 | 58.770 | 1.00 | 31.86 |
| 4765 | CG | ARG | E | 525 | 57.213 | 70.130 | 57.943 | 1.00 | 35.26 |
| 4766 | CD | ARG | E | 525 | 57.061 | 70.978 | 56.659 | 1.00 | 38.43 |
| 4767 | NE | ARG | E | 525 | 57.847 | 70.486 | 55.533 | 1.00 | 43.93 |
| 4768 | CZ | ARG | E | 525 | 58.141 | 71.202 | 54.442 | 1.00 | 48.33 |
| 4769 | NH1 | ARG | E | 525 | 57.725 | 72.461 | 54.318 | 1.00 | 49.20 |
| 4770 | NH2 | ARG | E | 525 | 58.842 | 70.653 | 53.457 | 1.00 | 48.85 |
| 4771 | C | ARG | E | 525 | 57.794 | 68.959 | 60.570 | 1.00 | 29.28 |
| 4772 | O | ARG | E | 525 | 58.541 | 67.995 | 60.456 | 1.00 | 28.78 |
| 4773 | N | ALA | E | 526 | 56.511 | 68.839 | 60.903 | 1.00 | 27.76 |
| 4774 | CA | ALA | E | 526 | 55.917 | 67.538 | 61.165 | 1.00 | 28.61 |
| 4775 | CB | ALA | E | 526 | 55.304 | 67.516 | 62.574 | 1.00 | 24.71 |
| 4776 | C | ALA | E | 526 | 54.842 | 67.182 | 60.121 | 1.00 | 29.03 |
| 4777 | O | ALA | E | 526 | 54.091 | 68.054 | 59.653 | 1.00 | 30.38 |
| 4778 | N | VAL | E | 527 | 54.784 | 65.902 | 59.760 | 1.00 | 28.02 |
| 4779 | CA | VAL | E | 527 | 53.796 | 65.376 | 58.804 | 1.00 | 29.46 |
| 4780 | CB | VAL | E | 527 | 54.460 | 64.550 | 57.688 | 1.00 | 29.17 |
| 4781 | CG1 | VAL | E | 527 | 53.402 | 63.894 | 56.832 | 1.00 | 30.56 |
| 4782 | CG2 | VAL | E | 527 | 55.338 | 65.445 | 56.830 | 1.00 | 32.84 |
| 4783 | C | VAL | E | 527 | 52.898 | 64.457 | 59.617 | 1.00 | 30.25 |
| 4784 | O | VAL | E | 527 | 53.377 | 63.508 | 60.240 | 1.00 | 29.97 |
| 4785 | N | HIS | E | 528 | 51.598 | 64.730 | 59.612 | 1.00 | 29.14 |
| 4786 | CA | HIS | E | 528 | 50.663 | 63.944 | 60.417 | 1.00 | 28.36 |
| 4787 | CB | HIS | E | 528 | 50.686 | 64.448 | 61.869 | 1.00 | 26.57 |
| 4788 | CG | HIS | E | 528 | 49.859 | 63.632 | 62.820 | 1.00 | 25.28 |
| 4789 | CD2 | HIS | E | 528 | 50.217 | 62.696 | 63.735 | 1.00 | 20.92 |
| 4790 | ND1 | HIS | E | 528 | 48.484 | 63.735 | 62.898 | 1.00 | 23.31 |
| 4791 | CE1 | HIS | E | 528 | 48.029 | 62.899 | 63.816 | 1.00 | 21.33 |
| 4792 | NE2 | HIS | E | 528 | 49.060 | 62.258 | 64.340 | 1.00 | 23.62 |
| 4793 | C | HIS | E | 528 | 49.230 | 63.985 | 59.880 | 1.00 | 31.29 |
| 4794 | O | HIS | E | 528 | 48.732 | 65.017 | 59.420 | 1.00 | 26.35 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4795 | N | GLU | E | 529 | 48.596 | 62.828 | 59.981 | 1.00 | 34.57 |
| 4796 | CA | GLU | E | 529 | 47.244 | 62.551 | 59.536 | 1.00 | 41.33 |
| 4797 | CB | GLU | E | 529 | 46.952 | 61.108 | 59.925 | 1.00 | 45.75 |
| 4798 | CG | GLU | E | 529 | 45.518 | 60.714 | 59.990 | 1.00 | 55.47 |
| 4799 | CD | GLU | E | 529 | 45.398 | 59.251 | 60.316 | 1.00 | 61.74 |
| 4800 | OE1 | GLU | E | 529 | 46.013 | 58.813 | 61.317 | 1.00 | 63.12 |
| 4801 | OE2 | GLU | E | 529 | 44.701 | 58.539 | 59.566 | 1.00 | 67.04 |
| 4802 | C | GLU | E | 529 | 46.080 | 63.462 | 59.963 | 1.00 | 41.97 |
| 4803 | O | GLU | E | 529 | 45.086 | 63.552 | 59.244 | 1.00 | 40.08 |
| 4804 | N | ALA | E | 530 | 46.196 | 64.132 | 61.111 | 1.00 | 42.80 |
| 4805 | CA | ALA | E | 530 | 45.119 | 64.991 | 61.598 | 1.00 | 44.48 |
| 4806 | CB | ALA | E | 530 | 44.874 | 64.716 | 63.075 | 1.00 | 40.93 |
| 4807 | C | ALA | E | 530 | 45.324 | 66.493 | 61.371 | 1.00 | 47.80 |
| 4808 | O | ALA | E | 530 | 44.471 | 67.302 | 61.757 | 1.00 | 47.94 |
| 4809 | N | ALA | E | 531 | 46.433 | 66.866 | 60.735 | 1.00 | 51.96 |
| 4810 | CA | ALA | E | 531 | 46.729 | 68.276 | 60.477 | 1.00 | 58.45 |
| 4811 | CB | ALA | E | 531 | 48.229 | 68.478 | 60.405 | 1.00 | 56.75 |
| 4812 | C | ALA | E | 531 | 46.079 | 68.839 | 59.212 | 1.00 | 64.98 |
| 4813 | O | ALA | E | 531 | 46.747 | 69.492 | 58.409 | 1.00 | 63.46 |
| 4814 | N | SER | E | 532 | 44.782 | 68.597 | 59.039 | 1.00 | 69.81 |
| 4815 | CA | SER | E | 532 | 44.065 | 69.093 | 57.870 | 1.00 | 77.60 |
| 4816 | CB | SER | E | 532 | 42.585 | 68.702 | 57.954 | 1.00 | 82.10 |
| 4817 | OG | SER | E | 532 | 41.999 | 69.133 | 59.169 | 1.00 | 88.06 |
| 4818 | C | SER | E | 532 | 44.204 | 70.610 | 57.781 | 1.00 | 77.53 |
| 4819 | O | SER | E | 532 | 44.295 | 71.291 | 58.802 | 1.00 | 79.21 |
| 4820 | N | CPR | E | 533 | 44.196 | 71.164 | 56.558 | 1.00 | 75.57 |
| 4821 | CD | CPR | E | 533 | 44.012 | 72.618 | 56.394 | 1.00 | 76.76 |
| 4822 | CA | CPR | E | 533 | 44.065 | 70.486 | 55.264 | 1.00 | 73.22 |
| 4823 | CB | CPR | E | 533 | 43.300 | 71.509 | 54.442 | 1.00 | 75.35 |
| 4824 | CG | CPR | E | 533 | 43.942 | 72.780 | 54.887 | 1.00 | 76.72 |
| 4825 | C | CPR | E | 533 | 45.344 | 70.040 | 54.539 | 1.00 | 67.04 |
| 4826 | O | CPR | E | 533 | 45.262 | 69.296 | 53.570 | 1.00 | 67.32 |
| 4827 | N | SER | E | 534 | 46.514 | 70.484 | 54.988 | 1.00 | 60.21 |
| 4828 | CA | SER | E | 534 | 47.770 | 70.124 | 54.312 | 1.00 | 52.87 |
| 4829 | CB | SER | E | 534 | 48.721 | 71.322 | 54.306 | 1.00 | 51.85 |
| 4830 | OG | SER | E | 534 | 49.142 | 71.633 | 55.627 | 1.00 | 50.04 |
| 4831 | C | SER | E | 534 | 48.535 | 68.922 | 54.873 | 1.00 | 48.70 |
| 4832 | O | SER | E | 534 | 49.550 | 68.515 | 54.306 | 1.00 | 45.90 |
| 4833 | N | GLN | E | 535 | 48.061 | 68.362 | 55.979 | 1.00 | 43.65 |
| 4834 | CA | GLN | E | 535 | 48.742 | 67.232 | 56.611 | 1.00 | 41.93 |
| 4835 | CB | GLN | E | 535 | 48.975 | 66.092 | 55.605 | 1.00 | 45.01 |
| 4836 | CG | GLN | E | 535 | 47.828 | 65.836 | 54.635 | 1.00 | 48.63 |
| 4837 | CD | GLN | E | 535 | 46.603 | 65.342 | 55.339 | 1.00 | 49.77 |
| 4838 | OE1 | GLN | E | 535 | 46.668 | 64.370 | 56.093 | 1.00 | 53.34 |
| 4839 | NE2 | GLN | E | 535 | 45.473 | 66.000 | 55.104 | 1.00 | 49.53 |
| 4840 | C | GLN | E | 535 | 50.105 | 67.677 | 57.160 | 1.00 | 39.50 |
| 4841 | O | GLN | E | 535 | 50.971 | 66.840 | 57.408 | 1.00 | 35.51 |
| 4842 | N | THR | E | 536 | 50.284 | 68.982 | 57.364 | 1.00 | 38.07 |
| 4843 | CA | THR | E | 536 | 51.557 | 69.504 | 57.863 | 1.00 | 37.85 |
| 4844 | CB | THR | E | 536 | 52.459 | 69.896 | 56.661 | 1.00 | 41.21 |
| 4845 | OG1 | THR | E | 536 | 53.807 | 70.047 | 57.107 | 1.00 | 49.97 |
| 4846 | CG2 | THR | E | 536 | 52.010 | 71.207 | 56.045 | 1.00 | 42.29 |
| 4847 | C | THR | E | 536 | 51.438 | 70.701 | 58.850 | 1.00 | 37.76 |
| 4848 | O | THR | E | 536 | 50.440 | 71.421 | 58.841 | 1.00 | 37.36 |
| 4849 | N | VAL | E | 537 | 52.455 | 70.871 | 59.703 | 1.00 | 33.49 |
| 4850 | CA | VAL | E | 537 | 52.558 | 71.949 | 60.711 | 1.00 | 31.94 |
| 4851 | CB | VAL | E | 537 | 51.969 | 71.533 | 62.087 | 1.00 | 34.75 |
| 4852 | CG1 | VAL | E | 537 | 52.188 | 72.647 | 63.101 | 1.00 | 37.35 |
| 4853 | CG2 | VAL | E | 537 | 50.487 | 71.218 | 61.973 | 1.00 | 37.52 |
| 4854 | C | VAL | E | 537 | 54.054 | 72.223 | 60.953 | 1.00 | 31.11 |
| 4855 | O | VAL | E | 537 | 54.812 | 71.286 | 61.196 | 1.00 | 31.82 |
| 4856 | N | GLN | E | 538 | 54.482 | 73.485 | 60.921 | 1.00 | 27.29 |
| 4857 | CA | GLN | E | 538 | 55.896 | 73.802 | 61.120 | 1.00 | 26.74 |
| 4858 | CB | GLN | E | 538 | 56.615 | 73.938 | 59.762 | 1.00 | 22.26 |
| 4859 | CG | GLN | E | 538 | 56.263 | 75.227 | 58.993 | 1.00 | 23.99 |
| 4860 | CD | GLN | E | 538 | 56.719 | 75.194 | 57.522 | 1.00 | 27.01 |
| 4861 | OE1 | GLN | E | 538 | 56.503 | 74.201 | 56.809 | 1.00 | 28.74 |
| 4862 | NE2 | GLN | E | 538 | 57.336 | 76.281 | 57.064 | 1.00 | 23.41 |
| 4863 | C | GLN | E | 538 | 56.131 | 75.072 | 61.923 | 1.00 | 27.31 |
| 4864 | O | GLN | E | 538 | 55.203 | 75.821 | 62.226 | 1.00 | 24.69 |
| 4865 | N | ARG | E | 539 | 57.403 | 75.330 | 62.220 | 1.00 | 28.07 |
| 4866 | CA | ARG | E | 539 | 57.806 | 76.487 | 63.008 | 1.00 | 28.94 |
| 4867 | CB | ARG | E | 539 | 57.507 | 76.201 | 64.494 | 1.00 | 36.00 |
| 4868 | CG | ARG | E | 539 | 57.952 | 77.291 | 65.467 | 1.00 | 46.45 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4869 | CD | ARG | E | 539 | 57.247 | 78.604 | 65.172 | 1.00 | 55.30 |
| 4870 | NE | ARG | E | 539 | 57.613 | 79.633 | 66.138 | 1.00 | 66.10 |
| 4871 | CZ | ARG | E | 539 | 57.318 | 80.922 | 66.006 | 1.00 | 70.80 |
| 4872 | NH1 | ARG | E | 539 | 56.650 | 81.344 | 64.940 | 1.00 | 74.33 |
| 4873 | NH2 | ARG | E | 539 | 57.692 | 81.788 | 66.938 | 1.00 | 73.38 |
| 4874 | C | ARG | E | 539 | 59.301 | 76.750 | 62.783 | 1.00 | 26.39 |
| 4875 | O | ARG | E | 539 | 60.102 | 75.840 | 62.871 | 1.00 | 23.82 |
| 4876 | N | ALA | E | 540 | 59.663 | 77.996 | 62.497 | 1.00 | 23.65 |
| 4877 | CA | ALA | E | 540 | 61.055 | 78.384 | 62.228 | 1.00 | 27.79 |
| 4878 | CB | ALA | E | 540 | 61.087 | 79.419 | 61.079 | 1.00 | 25.05 |
| 4879 | C | ALA | E | 540 | 61.761 | 78.983 | 63.451 | 1.00 | 28.70 |
| 4880 | O | ALA | E | 540 | 61.090 | 79.485 | 64.328 | 1.00 | 26.03 |
| 4881 | N | VAL | E | 541 | 63.100 | 78.940 | 63.467 | 1.00 | 31.26 |
| 4882 | CA | VAL | E | 541 | 63.953 | 79.509 | 64.548 | 1.00 | 35.46 |
| 4883 | CB | VAL | E | 541 | 64.641 | 78.462 | 65.467 | 1.00 | 33.28 |
| 4884 | CG1 | VAL | E | 541 | 64.770 | 79.032 | 66.881 | 1.00 | 34.26 |
| 4885 | CG2 | VAL | E | 541 | 63.952 | 77.155 | 65.419 | 1.00 | 35.63 |
| 4886 | C | VAL | E | 541 | 65.171 | 80.216 | 63.955 | 1.00 | 38.02 |
| 4887 | O | VAL | E | 541 | 65.699 | 79.779 | 62.943 | 1.00 | 37.67 |
| 4888 | N | SER | E | 542 | 65.639 | 81.270 | 64.615 | 1.00 | 43.24 |
| 4889 | CA | SER | E | 542 | 66.833 | 81.993 | 64.179 | 1.00 | 49.43 |
| 4890 | CB | SER | E | 542 | 66.514 | 83.458 | 63.879 | 1.00 | 49.50 |
| 4891 | OG | SER | E | 542 | 65.890 | 83.584 | 62.618 | 1.00 | 51.89 |
| 4892 | C | SER | E | 542 | 67.905 | 81.930 | 65.267 | 1.00 | 53.76 |
| 4893 | O | SER | E | 542 | 67.596 | 81.998 | 66.459 | 1.00 | 53.37 |
| 4894 | N | VAL | E | 543 | 69.161 | 81.795 | 64.846 | 1.00 | 58.38 |
| 4895 | CA | VAL | E | 543 | 70.292 | 81.725 | 65.766 | 1.00 | 62.96 |
| 4896 | CB | VAL | E | 543 | 71.511 | 81.008 | 65.112 | 1.00 | 64.04 |
| 4897 | CG1 | VAL | E | 543 | 72.746 | 81.166 | 65.978 | 1.00 | 65.56 |
| 4898 | CG2 | VAL | E | 543 | 71.216 | 79.533 | 64.924 | 1.00 | 64.27 |
| 4899 | C | VAL | E | 543 | 70.736 | 83.109 | 66.234 | 1.00 | 66.13 |
| 4900 | O | VAL | E | 543 | 71.068 | 83.291 | 67.401 | 1.00 | 65.54 |
| 4901 | N | ASN | E | 544 | 70.728 | 84.079 | 65.322 | 1.00 | 69.46 |
| 4902 | CA | ASN | E | 544 | 71.157 | 85.454 | 65.614 | 1.00 | 73.11 |
| 4903 | CB | ASN | E | 544 | 70.448 | 85.997 | 66.857 | 1.00 | 74.36 |
| 4904 | CG | ASN | E | 544 | 69.023 | 86.405 | 66.578 | 1.00 | 75.62 |
| 4905 | OD1 | ASN | E | 544 | 68.757 | 87.150 | 65.636 | 1.00 | 76.58 |
| 4906 | ND2 | ASN | E | 544 | 68.097 | 85.928 | 67.399 | 1.00 | 76.67 |
| 4907 | C | ASN | E | 544 | 72.678 | 85.583 | 65.789 | 1.00 | 73.42 |
| 4908 | O | ASN | E | 544 | 73.276 | 86.449 | 65.116 | 1.00 | 74.44 |
| 4909 | OXT | ASN | E | 544 | 73.260 | 84.826 | 66.596 | 1.00 | 74.02 |
| 4910 | C1 | NAG | E | 1 | 74.208 | 42.744 | 66.666 | 1.00 | 82.55 |
| 4911 | C2 | NAG | E | 1 | 73.256 | 42.591 | 67.848 | 1.00 | 81.88 |
| 4912 | N2 | NAG | E | 1 | 73.521 | 41.349 | 68.549 | 1.00 | 81.79 |
| 4913 | C7 | NAG | E | 1 | 73.357 | 41.283 | 69.868 | 1.00 | 82.45 |
| 4914 | O7 | NAG | E | 1 | 73.601 | 42.229 | 70.618 | 1.00 | 83.14 |
| 4915 | C8 | NAG | E | 1 | 72.834 | 39.976 | 70.444 | 1.00 | 82.01 |
| 4916 | C3 | NAG | E | 1 | 71.815 | 42.623 | 67.323 | 1.00 | 81.55 |
| 4917 | O3 | NAG | E | 1 | 70.901 | 42.571 | 68.408 | 1.00 | 80.92 |
| 4918 | C4 | NAG | E | 1 | 71.569 | 43.901 | 66.503 | 1.00 | 81.71 |
| 4919 | O4 | NAG | E | 1 | 70.282 | 43.820 | 65.857 | 1.00 | 80.43 |
| 4920 | C5 | NAG | E | 1 | 72.664 | 44.082 | 65.433 | 1.00 | 82.64 |
| 4921 | O5 | NAG | E | 1 | 73.981 | 44.005 | 66.029 | 1.00 | 82.54 |
| 4922 | C6 | NAG | E | 1 | 72.575 | 45.417 | 64.711 | 1.00 | 83.25 |
| 4923 | O6 | NAG | E | 1 | 73.504 | 46.355 | 65.236 | 1.00 | 82.73 |
| 4924 | C1 | NAG | E | 2 | 69.294 | 44.687 | 66.301 | 1.00 | 80.32 |
| 4925 | C2 | NAG | E | 2 | 68.535 | 45.256 | 65.098 | 1.00 | 81.34 |
| 4926 | N2 | NAG | E | 2 | 69.443 | 46.022 | 64.264 | 1.00 | 81.90 |
| 4927 | C7 | NAG | E | 2 | 69.608 | 45.703 | 62.982 | 1.00 | 82.24 |
| 4928 | O7 | NAG | E | 2 | 69.603 | 44.540 | 62.574 | 1.00 | 82.01 |
| 4929 | C8 | NAG | E | 2 | 69.804 | 46.848 | 62.000 | 1.00 | 81.90 |
| 4930 | C3 | NAG | E | 2 | 67.382 | 46.144 | 65.581 | 1.00 | 80.82 |
| 4931 | O3 | NAG | E | 2 | 66.599 | 46.550 | 64.469 | 1.00 | 81.61 |
| 4932 | C4 | NAG | E | 2 | 66.488 | 45.406 | 66.589 | 1.00 | 80.33 |
| 4933 | O4 | NAG | E | 2 | 65.575 | 46.350 | 67.194 | 1.00 | 81.00 |
| 4934 | C5 | NAG | E | 2 | 67.345 | 44.754 | 67.693 | 1.00 | 80.59 |
| 4935 | O5 | NAG | E | 2 | 68.395 | 43.939 | 67.124 | 1.00 | 79.64 |
| 4936 | C6 | NAG | E | 2 | 66.532 | 43.846 | 68.595 | 1.00 | 79.37 |
| 4937 | O6 | NAG | E | 2 | 66.431 | 42.537 | 68.049 | 1.00 | 80.19 |
| 4938 | C1 | MAN | E | 3 | 64.233 | 46.291 | 66.839 | 1.00 | 81.19 |
| 4939 | C2 | MAN | E | 3 | 63.376 | 46.653 | 68.060 | 1.00 | 80.99 |
| 4940 | O2 | MAN | E | 3 | 63.777 | 47.918 | 68.565 | 1.00 | 79.78 |
| 4941 | C3 | MAN | E | 3 | 61.897 | 46.706 | 67.674 | 1.00 | 81.60 |
| 4942 | O3 | MAN | E | 3 | 61.119 | 47.126 | 68.788 | 1.00 | 81.97 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 4943 | C4 | MAN | E | 3 | 61.703 | 47.677 | 66.513 | 1.00 | 82.09 |
| 4944 | O4 | MAN | E | 3 | 60.349 | 47.637 | 66.083 | 1.00 | 80.11 |
| 4945 | C5 | MAN | E | 3 | 62.628 | 47.302 | 65.346 | 1.00 | 83.69 |
| 4946 | O5 | MAN | E | 3 | 64.011 | 47.247 | 65.788 | 1.00 | 82.34 |
| 4947 | C6 | MAN | E | 3 | 62.535 | 48.313 | 64.205 | 1.00 | 85.82 |
| 4948 | O6 | MAN | E | 3 | 63.772 | 49.053 | 64.063 | 1.00 | 90.59 |
| 4949 | C1 | MAN | E | 4 | 63.613 | 50.350 | 63.541 | 1.00 | 92.89 |
| 4950 | C2 | MAN | E | 4 | 63.141 | 50.295 | 62.087 | 1.00 | 94.55 |
| 4951 | O2 | MAN | E | 4 | 61.823 | 49.764 | 62.038 | 1.00 | 95.48 |
| 4952 | C3 | MAN | E | 4 | 63.129 | 51.711 | 61.536 | 1.00 | 95.30 |
| 4953 | O3 | MAN | E | 4 | 62.704 | 51.692 | 60.180 | 1.00 | 98.02 |
| 4954 | C4 | MAN | E | 4 | 62.171 | 52.560 | 62.375 | 1.00 | 94.04 |
| 4955 | O4 | MAN | E | 4 | 62.185 | 53.900 | 61.910 | 1.00 | 96.30 |
| 4956 | C5 | MAN | E | 4 | 62.578 | 52.524 | 63.855 | 1.00 | 92.93 |
| 4957 | O5 | MAN | E | 4 | 62.721 | 51.155 | 64.311 | 1.00 | 94.08 |
| 4958 | C6 | MAN | E | 4 | 61.520 | 53.166 | 64.736 | 1.00 | 91.27 |
| 4959 | O6 | MAN | E | 4 | 61.740 | 54.558 | 64.886 | 1.00 | 88.67 |
| 4960 | C1 | NAG | B | 1 | 15.611 | 55.447 | 33.097 | 1.00 | 82.70 |
| 4961 | C2 | NAG | B | 1 | 15.232 | 54.638 | 31.853 | 1.00 | 83.59 |
| 4962 | N2 | NAG | B | 1 | 14.163 | 55.309 | 31.137 | 1.00 | 85.17 |
| 4963 | C7 | NAG | B | 1 | 14.178 | 55.360 | 29.807 | 1.00 | 85.77 |
| 4964 | O7 | NAG | B | 1 | 15.196 | 55.613 | 29.164 | 1.00 | 85.38 |
| 4965 | C8 | NAG | B | 1 | 12.872 | 55.083 | 29.075 | 1.00 | 84.57 |
| 4966 | C3 | NAG | B | 1 | 14.791 | 53.220 | 32.256 | 1.00 | 81.56 |
| 4967 | O3 | NAG | B | 1 | 14.610 | 52.427 | 31.088 | 1.00 | 81.59 |
| 4968 | C4 | NAG | B | 1 | 15.830 | 52.546 | 33.173 | 1.00 | 80.39 |
| 4969 | O4 | NAG | B | 1 | 15.257 | 51.346 | 33.742 | 1.00 | 77.22 |
| 4970 | C5 | NAG | B | 1 | 16.260 | 53.498 | 34.314 | 1.00 | 81.15 |
| 4971 | O5 | NAG | B | 1 | 16.675 | 54.781 | 33.788 | 1.00 | 82.04 |
| 4972 | C6 | NAG | B | 1 | 17.416 | 52.962 | 35.134 | 1.00 | 80.88 |
| 4973 | O6 | NAG | B | 1 | 18.560 | 52.749 | 34.322 | 1.00 | 81.53 |
| 4974 | C1 | NAG | B | 2 | 15.655 | 50.129 | 33.203 | 1.00 | 73.83 |
| 4975 | C2 | NAG | B | 2 | 15.874 | 49.107 | 34.330 | 1.00 | 72.15 |
| 4976 | N2 | NAG | B | 2 | 16.909 | 49.569 | 35.234 | 1.00 | 67.97 |
| 4977 | C7 | NAG | B | 2 | 16.752 | 49.441 | 36.548 | 1.00 | 64.33 |
| 4978 | O7 | NAG | B | 2 | 15.692 | 49.682 | 37.122 | 1.00 | 61.79 |
| 4979 | C8 | NAG | B | 2 | 17.949 | 48.966 | 37.344 | 1.00 | 62.01 |
| 4980 | C3 | NAG | B | 2 | 16.245 | 47.739 | 33.739 | 1.00 | 73.05 |
| 4981 | O3 | NAG | B | 2 | 16.348 | 46.781 | 34.787 | 1.00 | 69.08 |
| 4982 | C4 | NAG | B | 2 | 15.165 | 47.307 | 32.725 | 1.00 | 74.60 |
| 4983 | O4 | NAG | B | 2 | 15.570 | 46.098 | 32.036 | 1.00 | 78.35 |
| 4984 | C5 | NAG | B | 2 | 14.923 | 48.423 | 31.687 | 1.00 | 73.90 |
| 4985 | O5 | NAG | B | 2 | 14.610 | 49.674 | 32.337 | 1.00 | 73.45 |
| 4986 | C6 | NAG | B | 2 | 13.760 | 48.114 | 30.763 | 1.00 | 70.87 |
| 4987 | O6 | NAG | B | 2 | 12.630 | 47.672 | 31.499 | 1.00 | 69.97 |
| 4988 | C1 | MAN | B | 3 | 14.851 | 44.939 | 32.303 | 1.00 | 81.07 |
| 4989 | C2 | MAN | B | 3 | 14.958 | 43.968 | 31.115 | 1.00 | 82.05 |
| 4990 | O2 | MAN | B | 3 | 16.321 | 43.786 | 30.760 | 1.00 | 81.07 |
| 4991 | C3 | MAN | B | 3 | 14.328 | 42.609 | 31.452 | 1.00 | 83.77 |
| 4992 | O3 | MAN | B | 3 | 14.672 | 41.659 | 30.423 | 1.00 | 86.34 |
| 4993 | C4 | MAN | B | 3 | 14.847 | 42.087 | 32.799 | 1.00 | 83.75 |
| 4994 | O4 | MAN | B | 3 | 14.098 | 40.950 | 33.191 | 1.00 | 82.32 |
| 4995 | C5 | MAN | B | 3 | 14.731 | 43.150 | 33.882 | 1.00 | 83.33 |
| 4996 | O5 | MAN | B | 3 | 15.417 | 44.346 | 33.479 | 1.00 | 82.49 |
| 4997 | C6 | MAN | B | 3 | 15.317 | 42.713 | 35.213 | 1.00 | 85.22 |
| 4998 | O6 | MAN | B | 3 | 16.729 | 42.436 | 35.088 | 1.00 | 89.17 |
| 4999 | C1 | MAN | B | 4 | 13.613 | 41.063 | 29.729 | 1.00 | 88.40 |
| 5000 | C2 | MAN | B | 4 | 13.653 | 41.540 | 28.262 | 1.00 | 89.67 |
| 5001 | O2 | MAN | B | 4 | 14.958 | 41.354 | 27.725 | 1.00 | 91.02 |
| 5002 | C3 | MAN | B | 4 | 12.628 | 40.793 | 27.394 | 1.00 | 90.40 |
| 5003 | O3 | MAN | B | 4 | 12.846 | 41.118 | 26.030 | 1.00 | 90.05 |
| 5004 | C4 | MAN | B | 4 | 12.768 | 39.278 | 27.578 | 1.00 | 90.42 |
| 5005 | O4 | MAN | B | 4 | 11.750 | 38.599 | 26.852 | 1.00 | 91.46 |
| 5006 | C5 | MAN | B | 4 | 12.671 | 38.928 | 29.063 | 1.00 | 89.98 |
| 5007 | O5 | MAN | B | 4 | 13.690 | 39.636 | 29.799 | 1.00 | 89.55 |
| 5008 | C6 | MAN | B | 4 | 12.871 | 37.447 | 29.334 | 1.00 | 89.68 |
| 5009 | O6 | MAN | B | 4 | 12.303 | 37.075 | 30.582 | 1.00 | 89.40 |
| 5010 | C1 | MAN | B | 5 | 17.099 | 41.448 | 36.006 | 1.00 | 92.62 |
| 5011 | C2 | MAN | B | 5 | 17.362 | 42.052 | 37.415 | 1.00 | 94.19 |
| 5012 | O2 | MAN | B | 5 | 16.833 | 41.196 | 38.415 | 1.00 | 95.03 |
| 5013 | C3 | MAN | B | 5 | 18.845 | 42.338 | 37.713 | 1.00 | 95.24 |
| 5014 | O3 | MAN | B | 5 | 19.027 | 42.573 | 39.105 | 1.00 | 95.82 |
| 5015 | C4 | MAN | B | 5 | 19.686 | 41.152 | 37.279 | 1.00 | 95.27 |
| 5016 | O4 | MAN | B | 5 | 21.051 | 41.385 | 37.585 | 1.00 | 97.38 |

TABLE I-continued

Atomic coordinates of Crystal 1

| ATOM # | ATOM TYPE | RES | CHN | # | X | Y | Z | OCC | B |
|---|---|---|---|---|---|---|---|---|---|
| 5017 | C5 | MAN | B | 5 | 19.487 | 40.995 | 35.783 | 1.00 | 93.73 |
| 5018 | O5 | MAN | B | 5 | 18.135 | 40.568 | 35.537 | 1.00 | 93.51 |
| 5019 | C6 | MAN | B | 5 | 20.410 | 39.958 | 35.171 | 1.00 | 92.61 |
| 5020 | O6 | MAN | B | 5 | 21.728 | 40.468 | 35.012 | 1.00 | 90.05 |
| 5021 | C1 | NAG | A | 1 | −1.012 | 44.633 | 68.125 | 1.00 | 93.76 |
| 5022 | C2 | NAG | A | 1 | −0.370 | 45.053 | 69.450 | 1.00 | 93.50 |
| 5023 | N2 | NAG | A | 1 | −1.324 | 45.808 | 70.245 | 1.00 | 92.37 |
| 5024 | C7 | NAG | A | 1 | −1.552 | 45.478 | 71.516 | 1.00 | 92.56 |
| 5025 | O7 | NAG | A | 1 | −1.624 | 44.309 | 71.897 | 1.00 | 92.88 |
| 5026 | C8 | NAG | A | 1 | −1.723 | 46.609 | 72.521 | 1.00 | 92.33 |
| 5027 | C3 | NAG | A | 1 | 0.882 | 45.887 | 69.171 | 1.00 | 93.45 |
| 5028 | O3 | NAG | A | 1 | 1.548 | 46.162 | 70.393 | 1.00 | 93.61 |
| 5029 | C4 | NAG | A | 1 | 1.843 | 45.154 | 68.214 | 1.00 | 94.18 |
| 5030 | O4 | NAG | A | 1 | 2.898 | 46.062 | 67.817 | 1.00 | 93.61 |
| 5031 | C5 | NAG | A | 1 | 1.081 | 44.653 | 66.962 | 1.00 | 94.71 |
| 5032 | O5 | NAG | A | 1 | −0.070 | 43.866 | 67.353 | 1.00 | 94.82 |
| 5033 | C6 | NAG | A | 1 | 1.905 | 43.792 | 66.025 | 1.00 | 95.80 |
| 5034 | O6 | NAG | A | 1 | 2.093 | 42.492 | 66.564 | 1.00 | 93.54 |
| 5035 | C1 | NAG | A | 2 | 4.157 | 45.856 | 68.374 | 1.00 | 92.27 |
| 5036 | C2 | NAG | A | 2 | 5.263 | 46.221 | 67.353 | 1.00 | 91.83 |
| 5037 | N2 | NAG | A | 2 | 5.221 | 45.292 | 66.234 | 1.00 | 91.58 |
| 5038 | C7 | NAG | A | 2 | 4.783 | 45.680 | 65.038 | 1.00 | 90.99 |
| 5039 | O7 | NAG | A | 2 | 4.254 | 46.771 | 64.837 | 1.00 | 90.69 |
| 5040 | C8 | NAG | A | 2 | 4.955 | 44.706 | 63.884 | 1.00 | 89.47 |
| 5041 | C3 | NAG | A | 2 | 6.656 | 46.162 | 68.024 | 1.00 | 91.00 |
| 5042 | O3 | NAG | A | 2 | 7.648 | 46.651 | 67.132 | 1.00 | 90.94 |
| 5043 | C4 | NAG | A | 2 | 6.682 | 46.979 | 69.333 | 1.00 | 91.32 |
| 5044 | O4 | NAG | A | 2 | 7.937 | 46.784 | 70.033 | 1.00 | 90.82 |
| 5045 | C5 | NAG | A | 2 | 5.514 | 46.522 | 70.228 | 1.00 | 91.61 |
| 5046 | O5 | NAG | A | 2 | 4.261 | 46.690 | 69.534 | 1.00 | 91.90 |
| 5047 | C6 | NAG | A | 2 | 5.393 | 47.278 | 71.543 | 1.00 | 90.34 |
| 5048 | O6 | NAG | A | 2 | 5.520 | 48.680 | 71.353 | 1.00 | 90.09 |
| 5049 | C1 | MAN | A | 3 | 8.873 | 47.811 | 69.986 | 1.00 | 91.46 |
| 5050 | C2 | MAN | A | 3 | 9.719 | 47.798 | 71.269 | 1.00 | 91.97 |
| 5051 | O2 | MAN | A | 3 | 10.235 | 46.495 | 71.503 | 1.00 | 91.01 |
| 5052 | C3 | MAN | A | 3 | 10.874 | 48.803 | 71.169 | 1.00 | 92.47 |
| 5053 | O3 | MAN | A | 3 | 11.723 | 48.673 | 72.303 | 1.00 | 93.35 |
| 5054 | C4 | MAN | A | 3 | 11.673 | 48.563 | 69.877 | 1.00 | 92.31 |
| 5055 | O4 | MAN | A | 3 | 12.668 | 49.562 | 69.716 | 1.00 | 90.03 |
| 5056 | C5 | MAN | A | 3 | 10.733 | 48.596 | 68.678 | 1.00 | 92.22 |
| 5057 | O5 | MAN | A | 3 | 9.703 | 47.595 | 68.832 | 1.00 | 92.57 |
| 5058 | C6 | MAN | A | 3 | 11.446 | 48.336 | 67.353 | 1.00 | 92.59 |
| 5059 | O6 | MAN | A | 3 | 12.077 | 47.061 | 67.331 | 1.00 | 92.00 |

Another embodiment of the present invention is a 3-D model of a Fc-Cε3/Cε4 region that substantially represents the atomic coordinates specified (i.e., listed) in Table II.

TABLE II

Atomic coordinates of Crystal 2

| ATOM # | ATOM TYPE | RES | CHN | # | X | Y | Z | OCC | B |
|---|---|---|---|---|---|---|---|---|---|
| 1 | CB | VAL | C | 336 | 73.204 | −43.157 | 9.088 | 1.00 | 79.52 |
| 2 | CG1 | VAL | C | 336 | 72.244 | −42.384 | 8.199 | 1.00 | 81.20 |
| 3 | CG2 | VAL | C | 336 | 73.120 | −44.642 | 8.800 | 1.00 | 81.37 |
| 4 | C | VAL | C | 336 | 74.677 | −41.160 | 9.188 | 1.00 | 73.78 |
| 5 | O | VAL | C | 336 | 73.916 | −40.679 | 10.032 | 1.00 | 76.82 |
| 6 | N | VAL | C | 336 | 75.620 | −43.443 | 9.677 | 1.00 | 76.28 |
| 7 | CA | VAL | C | 336 | 74.647 | −42.655 | 8.869 | 1.00 | 77.45 |
| 8 | N | SER | C | 337 | 75.552 | −40.424 | 8.513 | 1.00 | 69.51 |
| 9 | CA | SER | C | 337 | 75.637 | −38.985 | 8.730 | 1.00 | 67.43 |
| 10 | CB | SER | C | 337 | 77.093 | −38.511 | 8.606 | 1.00 | 70.48 |
| 11 | OG | SER | C | 337 | 77.724 | −39.047 | 7.457 | 1.00 | 67.93 |
| 12 | C | SER | C | 337 | 74.727 | −38.219 | 7.757 | 1.00 | 64.81 |
| 13 | O | SER | C | 337 | 74.404 | −38.697 | 6.664 | 1.00 | 66.34 |
| 14 | N | ALA | C | 338 | 74.287 | −37.041 | 8.178 | 1.00 | 60.98 |
| 15 | CA | ALA | C | 338 | 73.418 | −36.215 | 7.353 | 1.00 | 56.77 |
| 16 | CB | ALA | C | 338 | 72.026 | −36.141 | 7.963 | 1.00 | 51.65 |
| 17 | C | ALA | C | 338 | 74.032 | −34.830 | 7.258 | 1.00 | 57.13 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 18 | O | ALA | C | 338 | 74.611 | −34.336 | 8.222 | 1.00 | 51.47 |
| 19 | N | TYR | C | 339 | 73.917 | −34.213 | 6.088 | 1.00 | 58.82 |
| 20 | CA | TYR | C | 339 | 74.478 | −32.889 | 5.873 | 1.00 | 61.04 |
| 21 | CB | TYR | C | 339 | 75.783 | −32.992 | 5.070 | 1.00 | 75.40 |
| 22 | CG | TYR | C | 339 | 76.759 | −34.056 | 5.548 | 1.00 | 95.22 |
| 23 | CD1 | TYR | C | 339 | 76.477 | −35.414 | 5.386 | 1.00 | 103.70 |
| 24 | CE1 | TYR | C | 339 | 77.376 | −36.394 | 5.807 | 1.00 | 110.09 |
| 25 | CD2 | TYR | C | 339 | 77.972 | −33.703 | 6.147 | 1.00 | 103.68 |
| 26 | CE2 | TYR | C | 339 | 78.879 | −34.678 | 6.572 | 1.00 | 110.04 |
| 27 | CZ | TYR | C | 339 | 78.573 | −36.020 | 6.398 | 1.00 | 111.74 |
| 28 | OH | TYR | C | 339 | 79.460 | −36.988 | 6.813 | 1.00 | 114.45 |
| 29 | C | TYR | C | 339 | 73.485 | −31.999 | 5.123 | 1.00 | 56.12 |
| 30 | O | TYR | C | 339 | 72.657 | −32.486 | 4.347 | 1.00 | 53.75 |
| 31 | N | LEU | C | 340 | 73.569 | −30.694 | 5.362 | 1.00 | 48.34 |
| 32 | CA | LEU | C | 340 | 72.686 | −29.740 | 4.706 | 1.00 | 42.91 |
| 33 | CB | LEU | C | 340 | 71.551 | −29.315 | 5.644 | 1.00 | 43.46 |
| 34 | CG | LEU | C | 340 | 70.501 | −28.379 | 5.043 | 1.00 | 44.44 |
| 35 | CD1 | LEU | C | 340 | 69.837 | −29.049 | 3.843 | 1.00 | 45.43 |
| 36 | CD2 | LEU | C | 340 | 69.466 | −28.038 | 6.091 | 1.00 | 44.27 |
| 37 | C | LEU | C | 340 | 73.523 | −28.534 | 4.326 | 1.00 | 40.07 |
| 38 | O | LEU | C | 340 | 74.106 | −27.882 | 5.190 | 1.00 | 40.72 |
| 39 | N | SER | C | 341 | 73.582 | −28.237 | 3.032 | 1.00 | 36.66 |
| 40 | CA | SER | C | 341 | 74.386 | −27.124 | 2.549 | 1.00 | 33.82 |
| 41 | CB | SER | C | 341 | 75.072 | −27.508 | 1.241 | 1.00 | 32.21 |
| 42 | OG | SER | C | 341 | 74.117 | −27.631 | 0.196 | 1.00 | 31.88 |
| 43 | C | SER | C | 341 | 73.578 | −25.862 | 2.315 | 1.00 | 32.39 |
| 44 | O | SER | C | 341 | 72.349 | −25.879 | 2.337 | 1.00 | 33.66 |
| 45 | N | ARG | C | 342 | 74.292 | −24.767 | 2.084 | 1.00 | 30.52 |
| 46 | CA | ARG | C | 342 | 73.676 | −23.483 | 1.809 | 1.00 | 28.98 |
| 47 | CB | ARG | C | 342 | 74.406 | −22.364 | 2.568 | 1.00 | 26.50 |
| 48 | CG | ARG | C | 342 | 74.288 | −22.477 | 4.094 | 1.00 | 24.18 |
| 49 | CD | ARG | C | 342 | 74.904 | −21.300 | 4.830 | 1.00 | 23.05 |
| 50 | NE | ARG | C | 342 | 76.363 | −21.295 | 4.751 | 1.00 | 25.09 |
| 51 | CZ | ARG | C | 342 | 77.162 | −22.066 | 5.489 | 1.00 | 25.32 |
| 52 | NH1 | ARG | C | 342 | 76.640 | −22.911 | 6.373 | 1.00 | 25.20 |
| 53 | NH2 | ARG | C | 342 | 78.483 | −21.992 | 5.348 | 1.00 | 23.96 |
| 54 | C | ARG | C | 342 | 73.795 | −23.293 | 0.303 | 1.00 | 29.56 |
| 55 | O | ARG | C | 342 | 74.580 | −23.976 | −0.354 | 1.00 | 32.78 |
| 56 | N | PRO | C | 343 | 73.002 | −22.387 | −0.276 | 1.00 | 28.77 |
| 57 | CD | PRO | C | 343 | 72.033 | −21.463 | 0.328 | 1.00 | 29.74 |
| 58 | CA | PRO | C | 343 | 73.104 | −22.191 | −1.721 | 1.00 | 29.81 |
| 59 | CB | PRO | C | 343 | 72.041 | −21.137 | −2.018 | 1.00 | 29.18 |
| 60 | CG | PRO | C | 343 | 71.141 | −21.148 | −0.825 | 1.00 | 27.62 |
| 61 | C | PRO | C | 343 | 74.487 | −21.673 | −2.086 | 1.00 | 29.03 |
| 62 | O | PRO | C | 343 | 75.139 | −20.993 | −1.288 | 1.00 | 28.38 |
| 63 | N | SER | C | 344 | 74.927 | −21.992 | −3.295 | 1.00 | 28.15 |
| 64 | CA | SER | C | 344 | 76.209 | −21.507 | −3.764 | 1.00 | 25.97 |
| 65 | CB | SER | C | 344 | 76.664 | −22.278 | −5.006 | 1.00 | 25.79 |
| 66 | OG | SER | C | 344 | 76.196 | −21.656 | −6.190 | 1.00 | 25.69 |
| 67 | C | SER | C | 344 | 75.978 | −20.052 | −4.146 | 1.00 | 23.26 |
| 68 | O | SER | C | 344 | 74.954 | −19.723 | −4.766 | 1.00 | 23.79 |
| 69 | N | PRO | C | 345 | 76.919 | −19.157 | −3.788 | 1.00 | 29.03 |
| 70 | CD | PRO | C | 345 | 78.154 | −19.395 | −3.011 | 1.00 | 24.22 |
| 71 | CA | PRO | C | 345 | 76.746 | −17.737 | −4.137 | 1.00 | 27.02 |
| 72 | CB | PRO | C | 345 | 78.077 | −17.097 | −3.730 | 1.00 | 23.33 |
| 73 | CG | PRO | C | 345 | 78.582 | −17.994 | −2.625 | 1.00 | 22.66 |
| 74 | C | PRO | C | 345 | 76.467 | −17.558 | −5.640 | 1.00 | 26.73 |
| 75 | O | PRO | C | 345 | 75.751 | −16.638 | −6.053 | 1.00 | 27.34 |
| 76 | N | PHE | C | 346 | 77.043 | −18.436 | −6.457 | 1.00 | 30.22 |
| 77 | CA | PHE | C | 346 | 76.842 | −18.356 | −7.901 | 1.00 | 32.11 |
| 78 | CB | PHE | C | 346 | 77.676 | −19.419 | −8.610 | 1.00 | 34.08 |
| 79 | CG | PHE | C | 346 | 77.479 | −19.451 | −10.099 | 1.00 | 35.36 |
| 80 | CD1 | PHE | C | 346 | 77.438 | −18.270 | −10.835 | 1.00 | 36.50 |
| 81 | CD2 | PHE | C | 346 | 77.356 | −20.665 | −10.767 | 1.00 | 36.34 |
| 82 | CE1 | PHE | C | 346 | 77.285 | −18.294 | −12.219 | 1.00 | 37.40 |
| 83 | CE2 | PHE | C | 346 | 77.202 | −20.705 | −12.150 | 1.00 | 37.55 |
| 84 | CZ | PHE | C | 346 | 77.166 | −19.517 | −12.879 | 1.00 | 37.50 |
| 85 | C | PHE | C | 346 | 75.366 | −18.551 | −8.234 | 1.00 | 32.36 |
| 86 | O | PHE | C | 346 | 74.741 | −17.703 | −8.864 | 1.00 | 31.95 |
| 87 | N | ASP | C | 347 | 74.812 | −19.677 | −7.816 | 1.00 | 31.30 |
| 88 | CA | ASP | C | 347 | 73.404 | −19.955 | −8.063 | 1.00 | 33.28 |
| 89 | CB | ASP | C | 347 | 73.032 | −21.303 | −7.460 | 1.00 | 31.13 |
| 90 | CG | ASP | C | 347 | 73.617 | −22.447 | −8.226 | 1.00 | 32.93 |
| 91 | OD1 | ASP | C | 347 | 73.603 | −23.575 | −7.697 | 1.00 | 34.70 |
| 92 | OD2 | ASP | C | 347 | 74.086 | −22.225 | −9.368 | 1.00 | 32.74 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 93 | C | ASP | C | 347 | 72.503 | −18.889 | −7.450 | 1.00 | 32.81 |
| 94 | O | ASP | C | 347 | 71.460 | −18.535 | −7.998 | 1.00 | 32.33 |
| 95 | N | LEU | C | 348 | 72.923 | −18.380 | −6.302 | 1.00 | 34.19 |
| 96 | CA | LEU | C | 348 | 72.147 | −17.393 | −5.579 | 1.00 | 36.34 |
| 97 | CB | LEU | C | 348 | 72.602 | −17.376 | −4.112 | 1.00 | 32.56 |
| 98 | CG | LEU | C | 348 | 71.970 | −16.334 | −3.190 | 1.00 | 32.80 |
| 99 | CD1 | LEU | C | 348 | 70.478 | −16.616 | −3.031 | 1.00 | 26.95 |
| 100 | CD2 | LEU | C | 348 | 72.654 | −16.365 | −1.825 | 1.00 | 30.49 |
| 101 | C | LEU | C | 348 | 72.180 | −15.975 | −6.146 | 1.00 | 37.92 |
| 102 | O | LEU | C | 348 | 71.141 | −15.313 | −6.224 | 1.00 | 42.20 |
| 103 | N | PHE | C | 349 | 73.351 | −15.517 | −6.571 | 1.00 | 39.44 |
| 104 | CA | PHE | C | 349 | 73.476 | −14.142 | −7.040 | 1.00 | 39.77 |
| 105 | CB | PHE | C | 349 | 74.664 | −13.489 | −6.346 | 1.00 | 34.47 |
| 106 | CG | PHE | C | 349 | 74.523 | −13.405 | −4.859 | 1.00 | 29.45 |
| 107 | CD1 | PHE | C | 349 | 75.416 | −14.069 | −4.030 | 1.00 | 27.88 |
| 108 | CD2 | PHE | C | 349 | 73.501 | −12.655 | −4.284 | 1.00 | 27.33 |
| 109 | CE1 | PHE | C | 349 | 75.301 | −13.977 | −2.654 | 1.00 | 24.86 |
| 110 | CE2 | PHE | C | 349 | 73.383 | −12.558 | −2.898 | 1.00 | 24.38 |
| 111 | CZ | PHE | C | 349 | 74.281 | −13.225 | −2.088 | 1.00 | 24.63 |
| 112 | C | PHE | C | 349 | 73.584 | −13.877 | −8.532 | 1.00 | 39.64 |
| 113 | O | PHE | C | 349 | 73.146 | −12.835 | −9.013 | 1.00 | 41.98 |
| 114 | N | ILE | C | 350 | 74.178 | −14.804 | −9.263 | 1.00 | 39.81 |
| 115 | CA | ILE | C | 350 | 74.360 | −14.628 | −10.692 | 1.00 | 41.78 |
| 116 | CB | ILE | C | 350 | 75.739 | −15.199 | −11.106 | 1.00 | 37.74 |
| 117 | CG2 | ILE | C | 350 | 75.963 | −15.050 | −12.593 | 1.00 | 34.94 |
| 118 | CG1 | ILE | C | 350 | 76.837 | −14.493 | −10.311 | 1.00 | 33.45 |
| 119 | CD1 | ILE | C | 350 | 76.672 | −12.988 | −10.240 | 1.00 | 26.38 |
| 120 | C | ILE | C | 350 | 73.251 | −15.342 | −11.456 | 1.00 | 44.47 |
| 121 | O | ILE | C | 350 | 72.467 | −14.733 | −12.197 | 1.00 | 44.18 |
| 122 | N | ARG | C | 351 | 73.196 | −16.645 | −11.236 | 1.00 | 48.10 |
| 123 | CA | ARG | C | 351 | 72.240 | −17.523 | −11.876 | 1.00 | 51.17 |
| 124 | CB | ARG | C | 351 | 72.647 | −18.954 | −11.589 | 1.00 | 49.89 |
| 125 | CG | ARG | C | 351 | 72.518 | −19.841 | −12.763 | 1.00 | 52.26 |
| 126 | CD | ARG | C | 351 | 72.806 | −21.255 | −12.378 | 1.00 | 53.38 |
| 127 | NE | ARG | C | 351 | 72.132 | −22.197 | −13.255 | 1.00 | 56.99 |
| 128 | CZ | ARG | C | 351 | 70.951 | −22.751 | −13.002 | 1.00 | 60.52 |
| 129 | NH1 | ARG | C | 351 | 70.298 | −22.467 | −11.892 | 1.00 | 62.79 |
| 130 | NH2 | ARG | C | 351 | 70.417 | −23.598 | −13.863 | 1.00 | 62.21 |
| 131 | C | ARG | C | 351 | 70.815 | −17.269 | −11.384 | 1.00 | 52.27 |
| 132 | O | ARG | C | 351 | 69.836 | −17.610 | −12.052 | 1.00 | 53.43 |
| 133 | N | LYS | C | 352 | 70.716 | −16.690 | −10.192 | 1.00 | 52.59 |
| 134 | CA | LYS | C | 352 | 69.437 | −16.355 | −9.589 | 1.00 | 53.27 |
| 135 | CB | LYS | C | 352 | 68.735 | −15.291 | −10.428 | 1.00 | 56.02 |
| 136 | CG | LYS | C | 352 | 69.549 | −14.025 | −10.585 | 1.00 | 57.14 |
| 137 | CD | LYS | C | 352 | 68.825 | −12.839 | −9.992 | 1.00 | 58.32 |
| 138 | CE | LYS | C | 352 | 69.698 | −11.600 | −9.998 | 1.00 | 59.65 |
| 139 | NZ | LYS | C | 352 | 70.005 | −11.134 | −11.349 | 1.00 | 61.73 |
| 140 | C | LYS | C | 352 | 68.492 | −17.518 | −9.370 | 1.00 | 50.05 |
| 141 | O | LYS | C | 352 | 67.281 | −17.361 | −9.472 | 1.00 | 52.78 |
| 142 | N | SER | C | 353 | 69.028 | −18.689 | −9.074 | 1.00 | 45.06 |
| 143 | CA | SER | C | 353 | 68.164 | −19.823 | −8.814 | 1.00 | 40.14 |
| 144 | CB | SER | C | 353 | 67.863 | −20.545 | −10.128 | 1.00 | 39.16 |
| 145 | OG | SER | C | 353 | 68.454 | −21.819 | −10.196 | 1.00 | 41.17 |
| 146 | C | SER | C | 353 | 68.891 | −20.696 | −7.798 | 1.00 | 36.20 |
| 147 | O | SER | C | 353 | 69.529 | −21.687 | −8.144 | 1.00 | 34.33 |
| 148 | N | PRO | C | 354 | 68.809 | −20.317 | −6.512 | 1.00 | 30.06 |
| 149 | CD | PRO | C | 354 | 68.064 | −19.164 | −5.994 | 1.00 | 29.08 |
| 150 | CA | PRO | C | 354 | 69.461 | −21.036 | −5.409 | 1.00 | 28.52 |
| 151 | CB | PRO | C | 354 | 69.341 | −20.073 | −4.223 | 1.00 | 27.25 |
| 152 | CG | PRO | C | 354 | 68.910 | −18.771 | −4.828 | 1.00 | 31.87 |
| 153 | C | PRO | C | 354 | 68.818 | −22.357 | −5.071 | 1.00 | 26.22 |
| 154 | O | PRO | C | 354 | 67.624 | −22.539 | −5.269 | 1.00 | 24.00 |
| 155 | N | THR | C | 355 | 69.619 | −23.279 | −4.556 | 1.00 | 23.37 |
| 156 | CA | THR | C | 355 | 69.097 | −24.563 | −4.118 | 1.00 | 23.94 |
| 157 | CB | THR | C | 355 | 69.243 | −25.693 | −5.169 | 1.00 | 22.82 |
| 158 | OG1 | THR | C | 355 | 70.628 | −25.994 | −5.368 | 1.00 | 24.17 |
| 159 | CG2 | THR | C | 355 | 68.606 | −25.295 | −6.482 | 1.00 | 22.26 |
| 160 | C | THR | C | 355 | 69.909 | −24.959 | −2.897 | 1.00 | 23.53 |
| 161 | O | THR | C | 355 | 70.977 | −24.403 | −2.656 | 1.00 | 26.74 |
| 162 | N | ILE | C | 356 | 69.379 | −25.881 | −2.104 | 1.00 | 22.87 |
| 163 | CA | ILE | C | 356 | 70.098 | −26.386 | −0.946 | 1.00 | 24.42 |
| 164 | CB | ILE | C | 356 | 69.489 | −25.901 | 0.388 | 1.00 | 24.26 |
| 165 | CG2 | ILE | C | 356 | 69.507 | −24.384 | 0.423 | 1.00 | 22.48 |
| 166 | CG1 | ILE | C | 356 | 68.062 | −26.425 | 0.557 | 1.00 | 23.83 |
| 167 | CD1 | ILE | C | 356 | 67.376 | −25.891 | 1.805 | 1.00 | 23.59 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 168 | C | ILE | C | 356 | 70.014 | −27.893 | −1.074 | 1.00 | 24.78 |
| 169 | O | ILE | C | 356 | 69.087 | −28.421 | −1.700 | 1.00 | 24.74 |
| 170 | N | THR | C | 357 | 70.990 | −28.589 | −0.511 | 1.00 | 25.36 |
| 171 | CA | THR | C | 357 | 71.002 | −30.034 | −0.633 | 1.00 | 28.25 |
| 172 | CB | THR | C | 357 | 72.119 | −30.471 | −1.601 | 1.00 | 28.81 |
| 173 | OG1 | THR | C | 357 | 71.884 | −29.887 | −2.891 | 1.00 | 27.68 |
| 174 | CG2 | THR | C | 357 | 72.169 | −31.979 | −1.718 | 1.00 | 26.99 |
| 175 | C | THR | C | 357 | 71.174 | −30.766 | 0.680 | 1.00 | 30.81 |
| 176 | O | THR | C | 357 | 72.017 | −30.415 | 1.512 | 1.00 | 28.97 |
| 177 | N | CYS | C | 358 | 70.351 | −31.788 | 0.859 | 1.00 | 35.07 |
| 178 | CA | CYS | C | 358 | 70.413 | −32.611 | 2.052 | 1.00 | 38.49 |
| 179 | C | CYS | C | 358 | 71.126 | −33.875 | 1.611 | 1.00 | 39.66 |
| 180 | O | CYS | C | 358 | 70.606 | −34.636 | 0.793 | 1.00 | 39.70 |
| 181 | CB | CYS | C | 358 | 69.012 | −32.961 | 2.532 | 1.00 | 38.78 |
| 182 | SG | CYS | C | 358 | 68.952 | −33.758 | 4.167 | 1.00 | 40.73 |
| 183 | N | LEU | C | 359 | 72.319 | −34.089 | 2.147 | 1.00 | 42.48 |
| 184 | CA | LEU | C | 359 | 73.106 | −35.256 | 1.786 | 1.00 | 47.01 |
| 185 | CB | LEU | C | 359 | 74.539 | −34.834 | 1.446 | 1.00 | 45.35 |
| 186 | CG | LEU | C | 359 | 75.600 | −35.926 | 1.282 | 1.00 | 43.26 |
| 187 | CD1 | LEU | C | 359 | 75.172 | −36.907 | 0.205 | 1.00 | 40.22 |
| 188 | CD2 | LEU | C | 359 | 76.942 | −35.291 | 0.940 | 1.00 | 41.74 |
| 189 | C | LEU | C | 359 | 73.121 | −36.280 | 2.902 | 1.00 | 50.62 |
| 190 | O | LEU | C | 359 | 73.537 | −35.982 | 4.021 | 1.00 | 53.01 |
| 191 | N | VAL | C | 360 | 72.649 | −37.484 | 2.589 | 1.00 | 57.09 |
| 192 | CA | VAL | C | 360 | 72.625 | −38.584 | 3.544 | 1.00 | 60.77 |
| 193 | CB | VAL | C | 360 | 71.222 | −39.192 | 3.660 | 1.00 | 54.79 |
| 194 | CG1 | VAL | C | 360 | 71.209 | −40.287 | 4.719 | 1.00 | 50.09 |
| 195 | CG2 | VAL | C | 360 | 70.232 | −38.102 | 4.028 | 1.00 | 49.57 |
| 196 | C | VAL | C | 360 | 73.645 | −39.624 | 3.084 | 1.00 | 66.09 |
| 197 | O | VAL | C | 360 | 73.517 | −40.254 | 2.036 | 1.00 | 68.68 |
| 198 | N | VAL | C | 361 | 74.684 | −39.769 | 3.887 | 1.00 | 72.84 |
| 199 | CA | VAL | C | 361 | 75.772 | −40.669 | 3.576 | 1.00 | 86.21 |
| 200 | CB | VAL | C | 361 | 77.111 | −40.001 | 3.995 | 1.00 | 81.20 |
| 201 | CG1 | VAL | C | 361 | 78.285 | −40.921 | 3.732 | 1.00 | 72.20 |
| 202 | CG2 | VAL | C | 361 | 77.286 | −38.689 | 3.224 | 1.00 | 73.37 |
| 203 | C | VAL | C | 361 | 75.641 | −42.064 | 4.184 | 1.00 | 95.70 |
| 204 | O | VAL | C | 361 | 75.985 | −42.275 | 5.352 | 1.00 | 101.67 |
| 205 | N | ASP | C | 362 | 75.104 | −42.998 | 3.390 | 1.00 | 107.30 |
| 206 | CA | ASP | C | 362 | 74.982 | −44.397 | 3.799 | 1.00 | 114.78 |
| 207 | CB | ASP | C | 362 | 76.136 | −44.686 | 4.766 | 1.00 | 115.10 |
| 208 | CG | ASP | C | 362 | 76.138 | −46.083 | 5.304 | 1.00 | 119.86 |
| 209 | OD1 | ASP | C | 362 | 75.131 | −46.802 | 5.151 | 1.00 | 121.37 |
| 210 | OD2 | ASP | C | 362 | 77.167 | −46.451 | 5.907 | 1.00 | 122.05 |
| 211 | C | ASP | C | 362 | 73.631 | −44.817 | 4.386 | 1.00 | 115.78 |
| 212 | O | ASP | C | 362 | 72.784 | −43.984 | 4.699 | 1.00 | 113.26 |
| 213 | N | THR | C | 369 | 64.059 | −47.855 | 2.045 | 1.00 | 98.58 |
| 214 | CA | THR | C | 369 | 63.907 | −46.536 | 1.443 | 1.00 | 95.15 |
| 215 | CB | THR | C | 369 | 62.526 | −46.386 | 0.758 | 1.00 | 98.63 |
| 216 | OG1 | THR | C | 369 | 61.955 | −45.113 | 1.090 | 1.00 | 94.03 |
| 217 | CG2 | THR | C | 369 | 61.584 | −47.499 | 1.203 | 1.00 | 94.35 |
| 218 | C | THR | C | 369 | 64.071 | −45.426 | 2.479 | 1.00 | 92.26 |
| 219 | O | THR | C | 369 | 63.275 | −45.314 | 3.416 | 1.00 | 94.14 |
| 220 | N | VAL | C | 370 | 65.121 | −44.622 | 2.305 | 1.00 | 84.79 |
| 221 | CA | VAL | C | 370 | 65.407 | −43.496 | 3.191 | 1.00 | 76.32 |
| 222 | CB | VAL | C | 370 | 66.826 | −42.936 | 2.986 | 1.00 | 70.88 |
| 223 | CG1 | VAL | C | 370 | 67.063 | −41.775 | 3.941 | 1.00 | 66.16 |
| 224 | CG2 | VAL | C | 370 | 67.859 | −44.023 | 3.194 | 1.00 | 65.91 |
| 225 | C | VAL | C | 370 | 64.437 | −42.383 | 2.845 | 1.00 | 80.28 |
| 226 | O | VAL | C | 370 | 64.079 | −42.203 | 1.684 | 1.00 | 71.60 |
| 227 | N | GLN | C | 371 | 64.038 | −41.613 | 3.845 | 1.00 | 82.78 |
| 228 | CA | GLN | C | 371 | 63.090 | −40.545 | 3.613 | 1.00 | 80.19 |
| 229 | CB | GLN | C | 371 | 61.830 | −40.821 | 4.429 | 1.00 | 86.79 |
| 230 | CG | GLN | C | 371 | 61.043 | −42.043 | 3.976 | 1.00 | 97.90 |
| 231 | CD | GLN | C | 371 | 59.654 | −41.675 | 3.597 | 1.00 | 116.42 |
| 232 | OE1 | GLN | C | 371 | 59.358 | −40.507 | 3.546 | 1.00 | 108.17 |
| 233 | NE2 | GLN | C | 371 | 58.792 | −42.645 | 3.324 | 1.00 | 108.59 |
| 234 | C | GLN | C | 371 | 63.614 | −39.144 | 3.921 | 1.00 | 77.44 |
| 235 | O | GLN | C | 371 | 64.083 | −38.869 | 5.027 | 1.00 | 70.82 |
| 236 | N | LEU | C | 372 | 63.534 | −38.267 | 2.924 | 1.00 | 68.01 |
| 237 | CA | LEU | C | 372 | 63.963 | −36.885 | 3.077 | 1.00 | 56.72 |
| 238 | CB | LEU | C | 372 | 64.990 | −36.506 | 2.005 | 1.00 | 56.21 |
| 239 | CG | LEU | C | 372 | 66.322 | −37.253 | 2.062 | 1.00 | 57.86 |
| 240 | CD1 | LEU | C | 372 | 67.360 | −36.513 | 1.234 | 1.00 | 60.46 |
| 241 | CD2 | LEU | C | 372 | 66.794 | −37.342 | 3.505 | 1.00 | 61.48 |
| 242 | C | LEU | C | 372 | 62.751 | −35.974 | 2.968 | 1.00 | 52.07 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 243 | O | LEU | C | 372 | 62.113 | −35.893 | 1.921 | 1.00 | 48.59 |
| 244 | N | THR | C | 373 | 62.431 | −35.290 | 4.059 | 1.00 | 50.77 |
| 245 | CA | THR | C | 373 | 61.290 | −34.386 | 4.071 | 1.00 | 51.43 |
| 246 | CB | THR | C | 373 | 60.276 | −34.797 | 5.155 | 1.00 | 56.58 |
| 247 | OG1 | THR | C | 373 | 60.004 | −36.198 | 5.043 | 1.00 | 62.93 |
| 248 | CG2 | THR | C | 373 | 58.974 | −34.023 | 4.984 | 1.00 | 62.39 |
| 249 | C | THR | C | 373 | 61.728 | −32.944 | 4.325 | 1.00 | 47.71 |
| 250 | O | THR | C | 373 | 62.489 | −32.665 | 5.255 | 1.00 | 47.66 |
| 251 | N | TRP | C | 374 | 61.231 | −32.028 | 3.502 | 1.00 | 45.68 |
| 252 | CA | TRP | C | 374 | 61.573 | −30.613 | 3.632 | 1.00 | 43.41 |
| 253 | CB | TRP | C | 374 | 61.849 | −29.993 | 2.262 | 1.00 | 39.72 |
| 254 | CG | TRP | C | 374 | 63.034 | −30.529 | 1.575 | 1.00 | 34.75 |
| 255 | CD2 | TRP | C | 374 | 64.388 | −30.185 | 1.835 | 1.00 | 31.82 |
| 256 | CE2 | TRP | C | 374 | 65.193 | −30.937 | 0.961 | 1.00 | 31.02 |
| 257 | CE3 | TRP | C | 374 | 65.012 | −29.297 | 2.724 | 1.00 | 30.25 |
| 258 | CD1 | TRP | C | 374 | 63.054 | −31.459 | 0.584 | 1.00 | 32.43 |
| 259 | NE1 | TRP | C | 374 | 64.346 | −31.714 | 0.201 | 1.00 | 33.19 |
| 260 | CZ2 | TRP | C | 374 | 66.584 | −30.855 | 0.947 | 1.00 | 29.78 |
| 261 | CZ3 | TRP | C | 374 | 66.405 | −29.211 | 2.711 | 1.00 | 32.02 |
| 262 | CH2 | TRP | C | 374 | 67.170 | −29.983 | 1.825 | 1.00 | 28.29 |
| 263 | C | TRP | C | 374 | 60.494 | −29.764 | 4.282 | 1.00 | 44.13 |
| 264 | O | TRP | C | 374 | 59.309 | −30.087 | 4.231 | 1.00 | 47.33 |
| 265 | N | SER | C | 375 | 60.917 | −28.658 | 4.882 | 1.00 | 46.11 |
| 266 | CA | SER | C | 375 | 59.985 | −27.708 | 5.480 | 1.00 | 48.61 |
| 267 | CB | SER | C | 375 | 59.296 | −28.305 | 6.713 | 1.00 | 49.72 |
| 268 | OG | SER | C | 375 | 60.221 | −28.583 | 7.747 | 1.00 | 48.91 |
| 269 | C | SER | C | 375 | 60.688 | −26.398 | 5.841 | 1.00 | 48.35 |
| 270 | O | SER | C | 375 | 61.919 | −26.318 | 5.865 | 1.00 | 49.94 |
| 271 | N | ARG | C | 376 | 59.895 | −25.367 | 6.100 | 1.00 | 47.30 |
| 272 | CA | ARG | C | 376 | 60.432 | −24.060 | 6.452 | 1.00 | 45.60 |
| 273 | CB | ARG | C | 376 | 59.866 | −22.988 | 5.531 | 1.00 | 39.80 |
| 274 | CG | ARG | C | 376 | 60.424 | −23.025 | 4.140 | 1.00 | 33.37 |
| 275 | CD | ARG | C | 376 | 60.421 | −21.625 | 3.567 | 1.00 | 27.79 |
| 276 | NE | ARG | C | 376 | 59.381 | −21.438 | 2.575 | 1.00 | 29.53 |
| 277 | CZ | ARG | C | 376 | 59.035 | −20.256 | 2.082 | 1.00 | 32.86 |
| 278 | NH1 | ARG | C | 376 | 59.648 | −19.152 | 2.496 | 1.00 | 32.68 |
| 279 | NH2 | ARG | C | 376 | 58.076 | −20.175 | 1.169 | 1.00 | 32.09 |
| 280 | C | ARG | C | 376 | 60.104 | −23.690 | 7.885 | 1.00 | 46.09 |
| 281 | O | ARG | C | 376 | 59.017 | −23.985 | 8.371 | 1.00 | 46.19 |
| 282 | N | ALA | C | 377 | 61.036 | −23.030 | 8.560 | 1.00 | 46.10 |
| 283 | CA | ALA | C | 377 | 60.799 | −22.642 | 9.943 | 1.00 | 48.52 |
| 284 | CB | ALA | C | 377 | 61.977 | −21.834 | 10.481 | 1.00 | 53.09 |
| 285 | C | ALA | C | 377 | 59.519 | −21.822 | 10.027 | 1.00 | 49.51 |
| 286 | O | ALA | C | 377 | 58.707 | −22.003 | 10.935 | 1.00 | 52.26 |
| 287 | N | SER | C | 378 | 59.340 | −20.937 | 9.056 | 1.00 | 47.94 |
| 288 | CA | SER | C | 378 | 58.178 | −20.062 | 8.994 | 1.00 | 44.34 |
| 289 | CB | SER | C | 378 | 58.390 | −19.029 | 7.893 | 1.00 | 42.26 |
| 290 | OG | SER | C | 378 | 58.333 | −19.648 | 6.621 | 1.00 | 41.39 |
| 291 | C | SER | C | 378 | 56.831 | −20.769 | 8.759 | 1.00 | 43.69 |
| 292 | O | SER | C | 378 | 55.781 | −20.138 | 8.869 | 1.00 | 40.36 |
| 293 | N | GLY | C | 379 | 56.858 | −22.061 | 8.424 | 1.00 | 41.43 |
| 294 | CA | GLY | C | 379 | 55.622 | −22.794 | 8.190 | 1.00 | 40.32 |
| 295 | C | GLY | C | 379 | 55.070 | −22.683 | 6.778 | 1.00 | 39.92 |
| 296 | O | GLY | C | 379 | 54.064 | −23.312 | 6.453 | 1.00 | 40.32 |
| 297 | N | LYS | C | 380 | 55.729 | −21.891 | 5.936 | 1.00 | 40.07 |
| 298 | CA | LYS | C | 380 | 55.301 | −21.705 | 4.551 | 1.00 | 37.14 |
| 299 | CB | LYS | C | 380 | 55.917 | −20.437 | 3.976 | 1.00 | 38.66 |
| 300 | CG | LYS | C | 380 | 55.756 | −19.253 | 4.870 | 1.00 | 39.31 |
| 301 | CD | LYS | C | 380 | 56.311 | −18.010 | 4.226 | 1.00 | 44.80 |
| 302 | CE | LYS | C | 380 | 56.017 | −16.801 | 5.088 | 1.00 | 46.62 |
| 303 | NZ | LYS | C | 380 | 56.462 | −15.544 | 4.438 | 1.00 | 49.78 |
| 304 | C | LYS | C | 380 | 55.685 | −22.896 | 3.680 | 1.00 | 34.05 |
| 305 | O | LYS | C | 380 | 56.533 | −23.713 | 4.052 | 1.00 | 34.65 |
| 306 | N | PRO | C | 381 | 55.078 | −22.996 | 2.494 | 1.00 | 33.75 |
| 307 | CD | PRO | C | 381 | 54.117 | −22.035 | 1.923 | 1.00 | 32.11 |
| 308 | CA | PRO | C | 381 | 55.342 | −24.097 | 1.557 | 1.00 | 32.65 |
| 309 | CB | PRO | C | 381 | 54.284 | −23.904 | 0.463 | 1.00 | 31.19 |
| 310 | CG | PRO | C | 381 | 53.304 | −22.913 | 1.038 | 1.00 | 31.65 |
| 311 | C | PRO | C | 381 | 56.745 | −24.147 | 0.949 | 1.00 | 32.25 |
| 312 | O | PRO | C | 381 | 57.411 | −23.122 | 0.752 | 1.00 | 35.21 |
| 313 | N | VAL | C | 382 | 57.176 | −25.366 | 0.650 | 1.00 | 33.21 |
| 314 | CA | VAL | C | 382 | 58.457 | −25.595 | 0.008 | 1.00 | 38.73 |
| 315 | CB | VAL | C | 382 | 59.300 | −26.653 | 0.746 | 1.00 | 34.89 |
| 316 | CG1 | VAL | C | 382 | 59.597 | −26.189 | 2.155 | 1.00 | 34.81 |
| 317 | CG2 | VAL | C | 382 | 58.576 | −27.976 | 0.763 | 1.00 | 32.70 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 318 | C | VAL | C | 382 | 58.113 | −26.124 | −1.380 | 1.00 | 45.61 |
| 319 | O | VAL | C | 382 | 57.059 | −26.732 | −1.563 | 1.00 | 40.90 |
| 320 | N | GLN | C | 383 | 58.981 | −25.882 | −2.353 | 1.00 | 52.86 |
| 321 | CA | GLN | C | 383 | 58.741 | −26.356 | −3.706 | 1.00 | 55.17 |
| 322 | CB | GLN | C | 383 | 59.633 | −25.606 | −4.694 | 1.00 | 60.33 |
| 323 | CG | GLN | C | 383 | 59.348 | −24.115 | −4.880 | 1.00 | 81.77 |
| 324 | CD | GLN | C | 383 | 60.512 | −23.420 | −5.552 | 1.00 | 97.82 |
| 325 | OE1 | GLN | C | 383 | 61.274 | −24.057 | −6.283 | 1.00 | 98.24 |
| 326 | NE2 | GLN | C | 383 | 60.663 | −22.116 | −5.317 | 1.00 | 97.83 |
| 327 | C | GLN | C | 383 | 59.039 | −27.851 | −3.810 | 1.00 | 56.59 |
| 328 | O | GLN | C | 383 | 59.159 | −28.550 | −2.805 | 1.00 | 46.16 |
| 329 | N | HIS | C | 384 | 59.155 | −28.326 | −5.044 | 1.00 | 55.08 |
| 330 | CA | HIS | C | 384 | 59.456 | −29.713 | −5.321 | 1.00 | 54.27 |
| 331 | CB | HIS | C | 384 | 59.073 | −30.026 | −6.725 | 1.00 | 75.00 |
| 332 | CG | HIS | C | 384 | 59.115 | −31.468 | −6.988 | 1.00 | 103.49 |
| 333 | CD2 | HIS | C | 384 | 60.113 | −32.167 | −7.530 | 1.00 | 116.20 |
| 334 | ND1 | HIS | C | 384 | 58.157 | −32.325 | −6.587 | 1.00 | 115.56 |
| 335 | CE1 | HIS | C | 384 | 58.547 | −33.569 | −6.874 | 1.00 | 124.41 |
| 336 | NE2 | HIS | C | 384 | 59.710 | −33.473 | −7.433 | 1.00 | 124.67 |
| 337 | C | HIS | C | 384 | 60.935 | −30.014 | −5.192 | 1.00 | 45.61 |
| 338 | O | HIS | C | 384 | 61.756 | −29.203 | −5.590 | 1.00 | 39.79 |
| 339 | N | SER | C | 385 | 61.275 | −31.192 | −4.685 | 1.00 | 39.49 |
| 340 | CA | SER | C | 385 | 62.678 | −31.533 | −4.553 | 1.00 | 36.94 |
| 341 | CB | SER | C | 385 | 63.022 | −31.791 | −3.084 | 1.00 | 33.64 |
| 342 | OG | SER | C | 385 | 62.214 | −32.806 | −2.537 | 1.00 | 33.38 |
| 343 | C | SER | C | 385 | 63.088 | −32.718 | −5.427 | 1.00 | 35.98 |
| 344 | O | SER | C | 385 | 62.259 | −33.530 | −5.835 | 1.00 | 36.43 |
| 345 | N | THR | C | 386 | 64.380 | −32.789 | −5.728 | 1.00 | 38.09 |
| 346 | CA | THR | C | 386 | 64.935 | −33.849 | −6.558 | 1.00 | 39.65 |
| 347 | CB | THR | C | 386 | 65.921 | −33.282 | −7.580 | 1.00 | 37.64 |
| 348 | OG1 | THR | C | 386 | 65.267 | −32.278 | −8.362 | 1.00 | 38.40 |
| 349 | CG2 | THR | C | 386 | 66.432 | −34.389 | −8.497 | 1.00 | 37.95 |
| 350 | C | THR | C | 386 | 65.683 | −34.842 | −5.679 | 1.00 | 40.79 |
| 351 | O | THR | C | 386 | 66.531 | −34.453 | −4.875 | 1.00 | 41.51 |
| 352 | N | ARG | C | 387 | 65.370 | −36.123 | −5.836 | 1.00 | 43.26 |
| 353 | CA | ARG | C | 387 | 66.014 | −37.161 | −5.045 | 1.00 | 47.20 |
| 354 | CB | ARG | C | 387 | 64.945 | −38.051 | −4.405 | 1.00 | 49.49 |
| 355 | CG | ARG | C | 387 | 65.475 | −39.188 | −3.553 | 1.00 | 50.94 |
| 356 | CD | ARG | C | 387 | 64.386 | −40.232 | −3.335 | 1.00 | 53.95 |
| 357 | NE | ARG | C | 387 | 64.885 | −41.417 | −2.644 | 1.00 | 57.78 |
| 358 | CZ | ARG | C | 387 | 65.058 | −41.493 | −1.331 | 1.00 | 58.90 |
| 359 | NH1 | ARG | C | 387 | 64.764 | −40.449 | −0.571 | 1.00 | 61.24 |
| 360 | NH2 | ARG | C | 387 | 65.536 | −42.602 | −0.780 | 1.00 | 59.66 |
| 361 | C | ARG | C | 387 | 66.934 | −37.990 | −5.940 | 1.00 | 49.48 |
| 362 | O | ARG | C | 387 | 66.585 | −38.311 | −7.079 | 1.00 | 49.58 |
| 363 | N | LYS | C | 388 | 68.109 | −38.335 | −5.432 | 1.00 | 52.65 |
| 364 | CA | LYS | C | 388 | 69.042 | −39.121 | −6.222 | 1.00 | 58.02 |
| 365 | CB | LYS | C | 388 | 70.021 | −38.186 | −6.930 | 1.00 | 64.91 |
| 366 | CG | LYS | C | 388 | 71.011 | −38.889 | −7.831 | 1.00 | 74.61 |
| 367 | CD | LYS | C | 388 | 71.938 | −37.894 | −8.493 | 1.00 | 87.05 |
| 368 | CE | LYS | C | 388 | 72.940 | −38.576 | −9.363 | 1.00 | 96.04 |
| 369 | NZ | LYS | C | 388 | 73.853 | −37.628 | −10.017 | 1.00 | 102.63 |
| 370 | C | LYS | C | 388 | 69.796 | −40.118 | −5.350 | 1.00 | 60.41 |
| 371 | O | LYS | C | 388 | 70.413 | −39.732 | −4.361 | 1.00 | 55.74 |
| 372 | N | GLU | C | 389 | 69.734 | −41.400 | −5.711 | 1.00 | 66.45 |
| 373 | CA | GLU | C | 389 | 70.422 | −42.442 | −4.949 | 1.00 | 74.44 |
| 374 | CB | GLU | C | 389 | 69.440 | −43.562 | −4.573 | 1.00 | 76.84 |
| 375 | CG | GLU | C | 389 | 68.368 | −43.127 | −3.566 | 1.00 | 87.65 |
| 376 | CD | GLU | C | 389 | 67.325 | −44.200 | −3.306 | 1.00 | 93.02 |
| 377 | OE1 | GLU | C | 389 | 67.708 | −45.373 | −3.122 | 1.00 | 96.17 |
| 378 | OE2 | GLU | C | 389 | 66.122 | −43.871 | −3.275 | 1.00 | 96.04 |
| 379 | C | GLU | C | 389 | 71.622 | −42.986 | −5.730 | 1.00 | 79.51 |
| 380 | O | GLU | C | 389 | 71.489 | −43.456 | −6.864 | 1.00 | 79.85 |
| 381 | N | GLU | C | 390 | 72.792 | −42.878 | −5.097 | 1.00 | 89.53 |
| 382 | CA | GLU | C | 390 | 74.075 | −43.294 | −5.654 | 1.00 | 100.43 |
| 383 | CB | GLU | C | 390 | 75.047 | −42.130 | −5.645 | 1.00 | 106.78 |
| 384 | CG | GLU | C | 390 | 76.336 | −42.487 | −4.970 | 1.00 | 118.48 |
| 385 | CD | GLU | C | 390 | 76.857 | −41.378 | −4.119 | 1.00 | 124.72 |
| 386 | OE1 | GLU | C | 390 | 76.986 | −40.259 | −4.630 | 1.00 | 128.94 |
| 387 | OE2 | GLU | C | 390 | 77.181 | −41.623 | −2.936 | 1.00 | 129.92 |
| 388 | C | GLU | C | 390 | 74.784 | −44.474 | −4.993 | 1.00 | 103.71 |
| 389 | O | GLU | C | 390 | 75.171 | −44.448 | −3.816 | 1.00 | 105.94 |
| 390 | N | LYS | C | 391 | 74.989 | −45.468 | −5.840 | 1.00 | 112.30 |
| 391 | CA | LYS | C | 391 | 75.655 | −46.728 | −5.586 | 1.00 | 120.76 |
| 392 | CB | LYS | C | 391 | 76.156 | −47.228 | −6.943 | 1.00 | 120.86 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 393 | CG | LYS | C | 391 | 75.371 | −46.630 | −8.149 | 1.00 | 120.67 |
| 394 | CD | LYS | C | 391 | 75.655 | −45.133 | −8.365 | 1.00 | 121.64 |
| 395 | CE | LYS | C | 391 | 74.674 | −44.489 | −9.339 | 1.00 | 122.93 |
| 396 | NZ | LYS | C | 391 | 75.065 | −44.671 | −10.763 | 1.00 | 124.45 |
| 397 | C | LYS | C | 391 | 76.811 | −46.611 | −4.588 | 1.00 | 125.04 |
| 398 | O | LYS | C | 391 | 76.622 | −46.763 | −3.381 | 1.00 | 127.83 |
| 399 | N | GLN | C | 392 | 78.005 | −46.366 | −5.122 | 1.00 | 133.01 |
| 400 | CA | GLN | C | 392 | 79.229 | −46.180 | −4.347 | 1.00 | 142.08 |
| 401 | CB | GLN | C | 392 | 78.902 | −45.606 | −2.959 | 1.00 | 134.74 |
| 402 | CG | GLN | C | 392 | 78.169 | −44.253 | −3.033 | 1.00 | 119.75 |
| 403 | CD | GLN | C | 392 | 79.005 | −43.209 | −3.775 | 1.00 | 112.76 |
| 404 | OE1 | GLN | C | 392 | 79.906 | −43.554 | −4.501 | 1.00 | 108.81 |
| 405 | NE2 | GLN | C | 392 | 78.722 | −41.953 | −3.592 | 1.00 | 108.97 |
| 406 | C | GLN | C | 392 | 80.179 | −47.362 | −4.224 | 1.00 | 151.31 |
| 407 | O | GLN | C | 392 | 79.801 | −48.478 | −3.845 | 1.00 | 156.99 |
| 408 | N | ARG | C | 393 | 81.430 | −47.048 | −4.562 | 1.00 | 159.84 |
| 409 | CA | ARG | C | 393 | 82.577 | −47.946 | −4.568 | 1.00 | 166.06 |
| 410 | CB | ARG | C | 393 | 83.758 | −47.283 | −5.285 | 1.00 | 176.11 |
| 411 | CG | ARG | C | 393 | 83.479 | −46.840 | −6.705 | 1.00 | 186.96 |
| 412 | CD | ARG | C | 393 | 84.741 | −46.326 | −7.377 | 1.00 | 189.49 |
| 413 | NE | ARG | C | 393 | 84.518 | −45.992 | −8.780 | 1.00 | 188.57 |
| 414 | CZ | ARG | C | 393 | 85.460 | −45.525 | −9.592 | 1.00 | 187.83 |
| 415 | NH1 | ARG | C | 393 | 86.692 | −45.336 | −9.140 | 1.00 | 187.52 |
| 416 | NH2 | ARG | C | 393 | 85.171 | −45.247 | −10.856 | 1.00 | 187.34 |
| 417 | C | ARG | C | 393 | 83.030 | −48.276 | −3.172 | 1.00 | 162.11 |
| 418 | O | ARG | C | 393 | 84.084 | −47.798 | −2.751 | 1.00 | 164.19 |
| 419 | N | ASN | C | 394 | 82.267 | −49.083 | −2.446 | 1.00 | 152.05 |
| 420 | CA | ASN | C | 394 | 82.710 | −49.408 | −1.104 | 1.00 | 135.95 |
| 421 | CB | ASN | C | 394 | 83.622 | −48.310 | −0.578 | 1.00 | 122.93 |
| 422 | CG | ASN | C | 394 | 82.872 | −47.020 | −0.310 | 1.00 | 108.25 |
| 423 | OD1 | ASN | C | 394 | 81.814 | −46.761 | −0.889 | 1.00 | 102.60 |
| 424 | ND2 | ASN | C | 394 | 83.418 | −46.202 | 0.573 | 1.00 | 102.03 |
| 425 | C | ASN | C | 394 | 81.601 | −49.571 | −0.110 | 1.00 | 131.36 |
| 426 | O | ASN | C | 394 | 81.736 | −49.126 | 1.026 | 1.00 | 128.19 |
| 427 | N | GLY | C | 395 | 80.509 | −50.203 | −0.497 | 1.00 | 124.33 |
| 428 | CA | GLY | C | 395 | 79.462 | −50.352 | 0.480 | 1.00 | 126.11 |
| 429 | C | GLY | C | 395 | 79.083 | −48.974 | 0.961 | 1.00 | 127.21 |
| 430 | O | GLY | C | 395 | 79.668 | −48.391 | 1.884 | 1.00 | 131.01 |
| 431 | N | THR | C | 396 | 78.105 | −48.433 | 0.269 | 1.00 | 128.48 |
| 432 | CA | THR | C | 396 | 77.587 | −47.142 | 0.604 | 1.00 | 118.39 |
| 433 | CB | THR | C | 396 | 78.533 | −45.972 | 0.240 | 1.00 | 114.05 |
| 434 | OG1 | THR | C | 396 | 79.604 | −45.899 | 1.185 | 1.00 | 108.89 |
| 435 | CG2 | THR | C | 396 | 77.769 | −44.638 | 0.259 | 1.00 | 109.21 |
| 436 | C | THR | C | 396 | 76.344 | −46.950 | −0.182 | 1.00 | 113.46 |
| 437 | O | THR | C | 396 | 76.128 | −47.547 | −1.239 | 1.00 | 115.98 |
| 438 | N | LEU | C | 397 | 75.504 | −46.128 | 0.406 | 1.00 | 102.40 |
| 439 | CA | LEU | C | 397 | 74.291 | −45.718 | −0.214 | 1.00 | 98.26 |
| 440 | CB | LEU | C | 397 | 73.059 | −46.336 | 0.420 | 1.00 | 98.40 |
| 441 | CG | LEU | C | 397 | 71.826 | −45.752 | −0.279 | 1.00 | 90.31 |
| 442 | CD1 | LEU | C | 397 | 71.916 | −45.984 | −1.793 | 1.00 | 83.41 |
| 443 | CD2 | LEU | C | 397 | 70.574 | −46.379 | 0.286 | 1.00 | 83.14 |
| 444 | C | LEU | C | 397 | 74.297 | −44.243 | 0.065 | 1.00 | 94.28 |
| 445 | O | LEU | C | 397 | 74.317 | −43.815 | 1.216 | 1.00 | 100.29 |
| 446 | N | THR | C | 398 | 74.333 | −43.463 | −0.997 | 1.00 | 87.26 |
| 447 | CA | THR | C | 398 | 74.295 | −42.029 | −0.852 | 1.00 | 69.56 |
| 448 | CB | THR | C | 398 | 75.426 | −41.372 | −1.605 | 1.00 | 63.90 |
| 449 | OG1 | THR | C | 398 | 76.633 | −41.503 | −0.846 | 1.00 | 57.93 |
| 450 | CG2 | THR | C | 398 | 75.144 | −39.909 | −1.862 | 1.00 | 57.87 |
| 451 | C | THR | C | 398 | 72.967 | −41.560 | −1.402 | 1.00 | 63.37 |
| 452 | O | THR | C | 398 | 72.556 | −41.940 | −2.493 | 1.00 | 57.90 |
| 453 | N | VAL | C | 399 | 72.291 | −40.743 | −0.615 | 1.00 | 52.98 |
| 454 | CA | VAL | C | 399 | 70.996 | −40.205 | −0.988 | 1.00 | 50.15 |
| 455 | CB | VAL | C | 399 | 69.900 | −40.759 | −0.064 | 1.00 | 50.02 |
| 456 | CG1 | VAL | C | 399 | 68.654 | −39.904 | −0.162 | 1.00 | 49.67 |
| 457 | CG2 | VAL | C | 399 | 69.584 | −42.193 | −0.435 | 1.00 | 51.10 |
| 458 | C | VAL | C | 339 | 71.028 | −38.681 | −0.863 | 1.00 | 46.64 |
| 459 | O | VAL | C | 399 | 71.487 | −38.142 | 0.141 | 1.00 | 50.11 |
| 460 | N | THR | C | 400 | 70.553 | −37.981 | −1.884 | 1.00 | 42.69 |
| 461 | CA | THR | C | 400 | 70.529 | −36.529 | −1.819 | 1.00 | 37.08 |
| 462 | CB | THR | C | 400 | 71.582 | −35.866 | −2.735 | 1.00 | 33.07 |
| 463 | OG1 | THR | C | 400 | 71.301 | −36.201 | −4.098 | 1.00 | 29.38 |
| 464 | CG2 | THR | C | 400 | 72.979 | −36.305 | −2.371 | 1.00 | 29.78 |
| 465 | C | THR | C | 400 | 69.177 | −36.022 | −2.277 | 1.00 | 35.76 |
| 466 | O | THR | C | 400 | 68.513 | −36.666 | −3.085 | 1.00 | 34.07 |
| 467 | N | SER | C | 401 | 68.765 | −34.878 | −1.739 | 1.00 | 33.57 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 468 | CA | SER | C | 401 | 67.516 | −34.240 | −2.140 | 1.00 | 33.40 |
| 469 | CB | SER | C | 401 | 66.408 | −34.443 | −1.108 | 1.00 | 34.11 |
| 470 | OG | SER | C | 401 | 65.228 | −33.764 | −1.510 | 1.00 | 32.31 |
| 471 | C | SER | C | 401 | 67.838 | −32.764 | −2.265 | 1.00 | 33.02 |
| 472 | O | SER | C | 401 | 68.267 | −32.124 | −1.307 | 1.00 | 35.15 |
| 473 | N | THR | C | 402 | 67.651 | −32.232 | −3.461 | 1.00 | 32.49 |
| 474 | CA | THR | C | 402 | 67.962 | −30.843 | −3.721 | 1.00 | 32.69 |
| 475 | CB | THR | C | 402 | 68.817 | −30.720 | −4.989 | 1.00 | 33.95 |
| 476 | OG1 | THR | C | 402 | 70.040 | −31.440 | −4.789 | 1.00 | 37.65 |
| 477 | CG2 | THR | C | 402 | 69.142 | −29.260 | −5.292 | 1.00 | 36.67 |
| 478 | C | THR | C | 402 | 66.690 | −30.043 | −3.858 | 1.00 | 31.23 |
| 479 | O | THR | C | 402 | 65.858 | −30.319 | −4.716 | 1.00 | 32.08 |
| 480 | N | LEU | C | 403 | 66.556 | −29.042 | −3.000 | 1.00 | 30.11 |
| 481 | CA | LEU | C | 403 | 65.375 | −28.195 | −2.961 | 1.00 | 26.66 |
| 482 | CB | LEU | C | 403 | 64.901 | −28.056 | −1.507 | 1.00 | 26.92 |
| 483 | CG | LEU | C | 403 | 63.684 | −27.166 | −1.239 | 1.00 | 27.35 |
| 484 | CD1 | LEU | C | 403 | 62.438 | −27.851 | −1.787 | 1.00 | 22.75 |
| 485 | CD2 | LEU | C | 403 | 63.538 | −26.911 | 0.267 | 1.00 | 23.49 |
| 486 | C | LEU | C | 403 | 65.575 | −26.804 | −3.534 | 1.00 | 23.18 |
| 487 | O | LEU | C | 403 | 66.420 | −26.058 | −3.067 | 1.00 | 25.06 |
| 488 | N | PRO | C | 404 | 64.807 | −26.444 | −4.571 | 1.00 | 27.42 |
| 489 | CD | PRO | C | 404 | 63.912 | −27.303 | −5.362 | 1.00 | 23.38 |
| 490 | CA | PRO | C | 404 | 64.935 | −25.106 | −5.156 | 1.00 | 25.89 |
| 491 | CB | PRO | C | 404 | 63.961 | −25.126 | −6.329 | 1.00 | 25.52 |
| 492 | CG | PRO | C | 404 | 63.827 | −26.579 | −6.668 | 1.00 | 25.10 |
| 493 | C | PRO | C | 404 | 64.437 | −24.182 | −4.047 | 1.00 | 25.48 |
| 494 | O | PRO | C | 404 | 63.480 | −24.523 | −3.347 | 1.00 | 29.06 |
| 495 | N | VAL | C | 405 | 65.073 | −23.031 | −3.876 | 1.00 | 26.36 |
| 496 | CA | VAL | C | 405 | 64.676 | −22.101 | −2.829 | 1.00 | 26.16 |
| 497 | CB | VAL | C | 405 | 65.775 | −22.055 | −1.737 | 1.00 | 25.69 |
| 498 | CG1 | VAL | C | 405 | 65.916 | −20.670 | −1.168 | 1.00 | 25.97 |
| 499 | CG2 | VAL | C | 405 | 65.445 | −23.049 | −0.637 | 1.00 | 24.70 |
| 500 | C | VAL | C | 405 | 64.425 | −20.709 | −3.412 | 1.00 | 25.98 |
| 501 | O | VAL | C | 405 | 64.948 | −20.362 | −4.483 | 1.00 | 21.54 |
| 502 | N | GLY | C | 406 | 63.598 | −19.921 | −2.724 | 1.00 | 27.11 |
| 503 | CA | GLY | C | 406 | 63.306 | −18.574 | −3.181 | 1.00 | 28.30 |
| 504 | C | GLY | C | 406 | 64.482 | −17.664 | −2.870 | 1.00 | 31.73 |
| 505 | O | GLY | C | 406 | 65.049 | −17.738 | −1.779 | 1.00 | 31.42 |
| 506 | N | THR | C | 407 | 64.858 | −16.806 | −3.815 | 1.00 | 34.42 |
| 507 | CA | THR | C | 407 | 65.985 | −15.892 | −3.613 | 1.00 | 39.43 |
| 508 | CB | THR | C | 407 | 66.296 | −15.096 | −4.905 | 1.00 | 40.99 |
| 509 | OG1 | THR | C | 407 | 66.581 | −16.013 | −5.968 | 1.00 | 43.96 |
| 510 | CG2 | THR | C | 407 | 67.507 | −14.190 | −4.698 | 1.00 | 43.53 |
| 511 | C | THR | C | 407 | 65.777 | −14.897 | −2.460 | 1.00 | 40.91 |
| 512 | O | THR | C | 407 | 66.653 | −14.738 | −1.600 | 1.00 | 40.39 |
| 513 | N | ALA | C | 408 | 64.629 | −14.223 | −2.447 | 1.00 | 41.34 |
| 514 | CA | ALA | C | 408 | 64.337 | −13.265 | −1.394 | 1.00 | 40.50 |
| 515 | CB | ALA | C | 408 | 63.059 | −12.507 | −1.711 | 1.00 | 40.79 |
| 516 | C | ALA | C | 408 | 64.206 | −13.992 | −0.060 | 1.00 | 40.50 |
| 517 | O | ALA | C | 408 | 64.793 | −13.575 | 0.938 | 1.00 | 39.47 |
| 518 | N | ASP | C | 409 | 63.442 | −15.083 | −0.053 | 1.00 | 39.67 |
| 519 | CA | ASP | C | 409 | 63.230 | −15.882 | 1.154 | 1.00 | 40.23 |
| 520 | CB | ASP | C | 409 | 62.533 | −17.211 | 0.831 | 1.00 | 46.39 |
| 521 | CG | ASP | C | 409 | 61.126 | −17.033 | 0.296 | 1.00 | 52.67 |
| 522 | OD1 | ASP | C | 409 | 60.407 | −16.138 | 0.787 | 1.00 | 56.39 |
| 523 | OD2 | ASP | C | 409 | 60.734 | −17.807 | −0.604 | 1.00 | 57.10 |
| 524 | C | ASP | C | 409 | 64.543 | −16.214 | 1.846 | 1.00 | 37.91 |
| 525 | O | ASP | C | 409 | 64.675 | −16.064 | 3.061 | 1.00 | 36.82 |
| 526 | N | TRP | C | 410 | 65.508 | −16.686 | 1.060 | 1.00 | 35.24 |
| 527 | CA | TRP | C | 410 | 66.803 | −17.069 | 1.601 | 1.00 | 32.29 |
| 528 | CB | TRP | C | 410 | 67.622 | −17.853 | 0.573 | 1.00 | 29.12 |
| 529 | CG | TRP | C | 410 | 68.961 | −18.179 | 1.118 | 1.00 | 28.87 |
| 530 | CD2 | TRP | C | 410 | 69.299 | −19.320 | 1.920 | 1.00 | 28.01 |
| 531 | CE2 | TRP | C | 410 | 70.619 | −19.112 | 2.404 | 1.00 | 26.28 |
| 532 | CE3 | TRP | C | 410 | 68.623 | −20.497 | 2.271 | 1.00 | 26.80 |
| 533 | CD1 | TRP | C | 410 | 70.061 | −17.352 | 1.139 | 1.00 | 28.03 |
| 534 | NE1 | TRP | C | 410 | 71.055 | −17.904 | 1.919 | 1.00 | 26.70 |
| 535 | CZ2 | TRP | C | 410 | 71.266 | −20.034 | 3.250 | 1.00 | 25.66 |
| 536 | CZ3 | TRP | C | 410 | 69.263 | −21.411 | 3.112 | 1.00 | 27.57 |
| 537 | CH2 | TRP | C | 410 | 70.577 | −21.176 | 3.583 | 1.00 | 25.32 |
| 538 | C | TRP | C | 410 | 67.615 | −15.880 | 2.082 | 1.00 | 34.59 |
| 539 | O | TRP | C | 410 | 68.171 | −15.909 | 3.181 | 1.00 | 33.18 |
| 540 | N | ILE | C | 411 | 67.701 | −14.843 | 1.254 | 1.00 | 36.64 |
| 541 | CA | ILE | C | 411 | 68.450 | −13.650 | 1.615 | 1.00 | 38.60 |
| 542 | CB | ILE | C | 411 | 68.572 | −12.690 | 0.398 | 1.00 | 39.68 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 543 | CG2 | ILE | C | 411 | 68.933 | −11.283 | 0.850 | 1.00 | 37.97 |
| 544 | CG1 | ILE | C | 411 | 69.639 | −13.224 | −0.560 | 1.00 | 38.03 |
| 545 | CD1 | ILE | C | 411 | 69.653 | −12.537 | −1.893 | 1.00 | 41.61 |
| 546 | C | ILE | C | 411 | 67.825 | −12.929 | 2.809 | 1.00 | 38.74 |
| 547 | O | ILE | C | 411 | 68.531 | −12.342 | 3.631 | 1.00 | 40.91 |
| 548 | N | GLU | C | 412 | 66.503 | −12.990 | 2.917 | 1.00 | 39.92 |
| 549 | CA | GLU | C | 412 | 65.833 | −12.333 | 4.023 | 1.00 | 41.70 |
| 550 | CB | GLU | C | 412 | 64.390 | −11.997 | 3.652 | 1.00 | 46.61 |
| 551 | CG | GLU | C | 412 | 64.264 | −10.602 | 3.062 | 1.00 | 51.27 |
| 552 | CD | GLU | C | 412 | 62.967 | −10.397 | 2.320 | 1.00 | 53.83 |
| 553 | OE1 | GLU | C | 412 | 61.937 | −10.925 | 2.789 | 1.00 | 55.67 |
| 554 | OE2 | GLU | C | 412 | 62.976 | −9.703 | 1.276 | 1.00 | 55.76 |
| 555 | C | GLU | C | 412 | 65.888 | −13.120 | 5.316 | 1.00 | 39.67 |
| 556 | O | GLU | C | 412 | 65.359 | −12.667 | 6.329 | 1.00 | 42.17 |
| 557 | N | GLY | C | 413 | 66.507 | −14.303 | 5.286 | 1.00 | 37.28 |
| 558 | CA | GLY | C | 413 | 66.654 | −15.072 | 6.513 | 1.00 | 31.36 |
| 559 | C | GLY | C | 413 | 65.861 | −16.325 | 6.833 | 1.00 | 28.67 |
| 560 | O | GLY | C | 413 | 66.012 | −16.854 | 7.935 | 1.00 | 25.75 |
| 561 | N | GLU | C | 414 | 65.033 | −16.812 | 5.917 | 1.00 | 26.43 |
| 562 | CA | GLU | C | 414 | 64.267 | −18.025 | 6.189 | 1.00 | 25.80 |
| 563 | CB | GLU | C | 414 | 63.475 | −18.426 | 4.490 | 1.00 | 26.03 |
| 564 | CG | GLU | C | 414 | 62.754 | −19.756 | 5.028 | 1.00 | 27.61 |
| 565 | CD | GLU | C | 414 | 61.573 | −19.715 | 5.984 | 1.00 | 29.35 |
| 566 | OE1 | GLU | C | 414 | 61.771 | −19.869 | 7.209 | 1.00 | 29.81 |
| 567 | OE2 | GLU | C | 414 | 60.441 | −19.515 | 5.504 | 1.00 | 28.34 |
| 568 | C | GLU | C | 414 | 65.243 | −19.149 | 6.563 | 1.00 | 26.55 |
| 569 | O | GLU | C | 414 | 66.432 | −19.068 | 6.260 | 1.00 | 27.05 |
| 570 | N | THR | C | 415 | 64.754 | −20.178 | 7.246 | 1.00 | 27.87 |
| 571 | CA | THR | C | 415 | 65.605 | −21.303 | 7.591 | 1.00 | 30.70 |
| 572 | CB | THR | C | 415 | 65.956 | −21.360 | 9.100 | 1.00 | 31.97 |
| 573 | OG1 | THR | C | 415 | 65.599 | −22.641 | 9.620 | 1.00 | 35.77 |
| 574 | CG2 | THR | C | 415 | 65.248 | −20.283 | 9.870 | 1.00 | 34.71 |
| 575 | C | THR | C | 415 | 64.873 | −22.565 | 7.176 | 1.00 | 29.24 |
| 576 | O | THR | C | 415 | 63.701 | −22.758 | 7.510 | 1.00 | 29.70 |
| 577 | N | TYR | C | 416 | 65.574 | −23.401 | 6.414 | 1.00 | 28.85 |
| 578 | CA | TYR | C | 416 | 65.032 | −24.644 | 5.897 | 1.00 | 28.07 |
| 579 | CB | TYR | C | 416 | 65.397 | −24.795 | 4.412 | 1.00 | 25.40 |
| 580 | CG | TYR | C | 416 | 64.931 | −23.623 | 3.571 | 1.00 | 24.40 |
| 581 | CD1 | TYR | C | 416 | 65.539 | −23.382 | 3.691 | 1.00 | 25.39 |
| 582 | CE1 | TYR | C | 416 | 65.086 | −21.273 | 2.969 | 1.00 | 27.33 |
| 583 | CD2 | TYR | C | 416 | 63.853 | −23.738 | 2.700 | 1.00 | 24.40 |
| 584 | CE2 | TYR | C | 416 | 63.393 | −22.636 | 1.973 | 1.00 | 25.75 |
| 585 | CZ | TYR | C | 416 | 64.019 | −21.406 | 2.118 | 1.00 | 25.74 |
| 586 | OH | TYR | C | 416 | 63.580 | −20.300 | 1.429 | 1.00 | 29.35 |
| 587 | C | TYR | C | 416 | 65.484 | −25.865 | 6.690 | 1.00 | 31.15 |
| 588 | O | TYR | C | 416 | 66.559 | −25.882 | 7.306 | 1.00 | 27.91 |
| 589 | N | GLN | C | 417 | 64.641 | −26.889 | 6.647 | 1.00 | 36.01 |
| 590 | CA | GLN | C | 417 | 64.874 | −28.126 | 7.370 | 1.00 | 43.27 |
| 591 | CB | GLN | C | 417 | 63.904 | −28.211 | 8.542 | 1.00 | 54.69 |
| 592 | CG | GLN | C | 417 | 64.512 | −28.141 | 9.921 | 1.00 | 76.67 |
| 593 | CD | GLN | C | 417 | 63.462 | −28.297 | 10.998 | 1.00 | 88.86 |
| 594 | OE1 | GLN | C | 417 | 62.272 | −28.277 | 10.712 | 1.00 | 96.84 |
| 595 | NE2 | GLN | C | 417 | 63.889 | −28.445 | 12.241 | 1.00 | 96.80 |
| 596 | C | GLN | C | 417 | 64.721 | −29.392 | 6.541 | 1.00 | 40.64 |
| 597 | O | GLN | C | 417 | 63.811 | −29.523 | 5.716 | 1.00 | 36.85 |
| 598 | N | CYS | C | 418 | 65.621 | −30.335 | 6.794 | 1.00 | 40.27 |
| 599 | CA | CYS | C | 418 | 65.600 | −31.617 | 6.115 | 1.00 | 41.02 |
| 600 | C | CYS | C | 418 | 65.493 | −32.676 | 7.185 | 1.00 | 42.50 |
| 601 | O | CYS | C | 418 | 66.375 | −32.804 | 8.036 | 1.00 | 41.70 |
| 602 | CB | CYS | C | 418 | 66.878 | −31.850 | 5.316 | 1.00 | 39.66 |
| 603 | SG | CYS | C | 418 | 66.991 | −33.545 | 4.660 | 1.00 | 43.01 |
| 604 | N | ARG | C | 418 | 64.408 | −33.430 | 7.142 | 1.00 | 46.21 |
| 605 | CA | ARG | C | 418 | 64.182 | −34.477 | 8.114 | 1.00 | 49.29 |
| 606 | CB | ARG | C | 418 | 62.781 | −34.335 | 8.684 | 1.00 | 53.13 |
| 607 | CG | ARG | C | 418 | 62.324 | −35.525 | 9.452 | 1.00 | 61.82 |
| 608 | CD | ARG | C | 418 | 61.486 | −35.074 | 10.599 | 1.00 | 69.14 |
| 609 | NE | ARG | C | 418 | 61.340 | −36.132 | 11.578 | 1.00 | 75.24 |
| 610 | CZ | ARG | C | 418 | 60.185 | −36.705 | 11.865 | 1.00 | 78.04 |
| 611 | NH1 | ARG | C | 418 | 59.089 | −36.308 | 11.239 | 1.00 | 79.81 |
| 612 | NH2 | ARG | C | 418 | 60.129 | −37.670 | 12.769 | 1.00 | 79.28 |
| 613 | C | ARG | C | 418 | 64.370 | −35.856 | 7.505 | 1.00 | 48.97 |
| 614 | O | ARG | C | 418 | 63.580 | −36.285 | 6.660 | 1.00 | 46.65 |
| 615 | N | VAL | C | 419 | 65.417 | −36.543 | 7.956 | 1.00 | 50.81 |
| 616 | CA | VAL | C | 419 | 65.749 | −37.880 | 7.466 | 1.00 | 54.76 |
| 617 | CB | VAL | C | 419 | 67.276 | −38.097 | 7.451 | 1.00 | 50.55 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 618 | CG1 | VAL | C | 419 | 67.608 | −39.443 | 6.830 | 1.00 | 47.39 |
| 619 | CG2 | VAL | C | 419 | 67.948 | −36.969 | 6.684 | 1.00 | 48.05 |
| 620 | C | VAL | C | 419 | 65.111 | −38.969 | 8.321 | 1.00 | 63.91 |
| 621 | O | VAL | C | 419 | 65.457 | −39.129 | 9.491 | 1.00 | 62.37 |
| 622 | N | THR | C | 421 | 64.185 | −39.708 | 7.719 | 1.00 | 79.40 |
| 623 | CA | THR | C | 421 | 63.463 | −40.797 | 8.375 | 1.00 | 91.09 |
| 624 | CB | THR | C | 421 | 61.960 | −40.721 | 8.101 | 1.00 | 88.41 |
| 625 | OG1 | THR | C | 421 | 61.416 | −39.538 | 8.691 | 1.00 | 88.70 |
| 626 | CG2 | THR | C | 421 | 61.262 | −41.954 | 8.648 | 1.00 | 89.07 |
| 627 | C | THR | C | 421 | 63.905 | −42.101 | 7.758 | 1.00 | 100.78 |
| 628 | O | THR | C | 421 | 63.735 | −42.293 | 6.559 | 1.00 | 106.84 |
| 629 | N | ALA | C | 422 | 64.428 | −43.027 | 8.542 | 1.00 | 109.58 |
| 630 | CA | ALA | C | 422 | 64.842 | −44.257 | 7.904 | 1.00 | 119.07 |
| 631 | CB | ALA | C | 422 | 66.337 | −44.200 | 7.607 | 1.00 | 135.26 |
| 632 | C | ALA | C | 422 | 64.510 | −45.548 | 8.613 | 1.00 | 124.17 |
| 633 | O | ALA | C | 422 | 63.943 | −45.560 | 9.709 | 1.00 | 132.02 |
| 634 | N | PRO | C | 423 | 64.863 | −46.662 | 7.963 | 1.00 | 116.73 |
| 635 | CD | PRO | C | 423 | 65.458 | −46.658 | 6.618 | 1.00 | 117.90 |
| 636 | CA | PRO | C | 423 | 64.682 | −48.037 | 8.395 | 1.00 | 120.28 |
| 637 | CB | PRO | C | 423 | 65.919 | −48.733 | 7.817 | 1.00 | 115.32 |
| 638 | CG | PRO | C | 423 | 66.443 | −47.776 | 6.712 | 1.00 | 109.60 |
| 639 | C | PRO | C | 423 | 64.544 | −48.222 | 9.905 | 1.00 | 120.60 |
| 640 | O | PRO | C | 423 | 65.451 | −48.736 | 10.561 | 1.00 | 121.92 |
| 641 | N | ALA | C | 424 | 63.395 | −47.789 | 10.428 | 1.00 | 119.17 |
| 642 | CA | ALA | C | 424 | 63.021 | −47.901 | 11.842 | 1.00 | 122.82 |
| 643 | CB | ALA | C | 424 | 62.526 | −49.298 | 12.127 | 1.00 | 128.22 |
| 644 | C | ALA | C | 424 | 64.115 | −47.532 | 12.813 | 1.00 | 123.28 |
| 645 | O | ALA | C | 424 | 64.775 | −48.391 | 13.407 | 1.00 | 130.37 |
| 646 | N | LEU | C | 425 | 64.253 | −46.232 | 13.008 | 1.00 | 122.66 |
| 647 | CA | LEU | C | 425 | 65.280 | −45.711 | 13.864 | 1.00 | 124.17 |
| 648 | CB | LEU | C | 425 | 65.867 | −44.443 | 13.262 | 1.00 | 115.15 |
| 649 | CG | LEU | C | 425 | 66.578 | −44.539 | 11.929 | 1.00 | 103.19 |
| 650 | CD1 | LEU | C | 425 | 66.575 | −43.168 | 11.279 | 1.00 | 96.63 |
| 651 | CD2 | LEU | C | 425 | 67.992 | −45.065 | 12.123 | 1.00 | 96.60 |
| 652 | C | LEU | C | 425 | 64.931 | −45.361 | 15.268 | 1.00 | 130.10 |
| 653 | O | LEU | C | 425 | 63.771 | −45.362 | 15.697 | 1.00 | 126.40 |
| 654 | N | PRO | C | 426 | 65.988 | −45.022 | 15.998 | 1.00 | 128.71 |
| 655 | CD | PRO | C | 426 | 67.341 | −45.317 | 15.482 | 1.00 | 134.02 |
| 656 | CA | PRO | C | 426 | 66.028 | −44.602 | 17.383 | 1.00 | 130.66 |
| 657 | CB | PRO | C | 426 | 67.463 | −44.909 | 17.797 | 1.00 | 132.87 |
| 658 | CG | PRO | C | 426 | 68.238 | −44.800 | 16.536 | 1.00 | 137.39 |
| 659 | C | PRO | C | 426 | 65.740 | −43.123 | 17.234 | 1.00 | 127.72 |
| 660 | O | PRO | C | 426 | 66.635 | −42.283 | 17.325 | 1.00 | 123.61 |
| 661 | N | ALA | C | 427 | 64.479 | −42.840 | 16.921 | 1.00 | 117.33 |
| 662 | CA | ALA | C | 427 | 63.996 | −41.482 | 16.725 | 1.00 | 108.07 |
| 663 | CB | ALA | C | 427 | 64.735 | −40.529 | 17.656 | 1.00 | 117.40 |
| 664 | C | ALA | C | 427 | 64.083 | −41.009 | 15.257 | 1.00 | 97.39 |
| 665 | O | ALA | C | 427 | 63.417 | −41.598 | 14.400 | 1.00 | 95.27 |
| 666 | N | ALA | C | 428 | 64.890 | −39.971 | 14.968 | 1.00 | 84.15 |
| 667 | CA | ALA | C | 428 | 65.025 | −39.403 | 13.595 | 1.00 | 71.53 |
| 668 | CB | ALA | C | 428 | 63.665 | −38.836 | 13.163 | 1.00 | 67.96 |
| 669 | C | ALA | C | 428 | 66.129 | −38.303 | 13.408 | 1.00 | 63.87 |
| 670 | O | ALA | C | 428 | 66.418 | −37.573 | 14.353 | 1.00 | 61.99 |
| 671 | N | LEU | C | 429 | 66.721 | −38.166 | 12.204 | 1.00 | 56.75 |
| 672 | CA | LEU | C | 429 | 67.782 | −37.152 | 11.934 | 1.00 | 54.03 |
| 673 | CB | LEU | C | 429 | 68.878 | −37.717 | 10.995 | 1.00 | 56.24 |
| 674 | CG | LEU | C | 429 | 69.784 | −38.865 | 11.471 | 1.00 | 54.55 |
| 675 | CD1 | LEU | C | 429 | 70.921 | −39.089 | 10.475 | 1.00 | 54.68 |
| 676 | CD2 | LEU | C | 429 | 70.353 | −38.533 | 12.842 | 1.00 | 55.24 |
| 677 | C | LEU | C | 429 | 67.255 | −35.837 | 11.328 | 1.00 | 53.40 |
| 678 | O | LEU | C | 429 | 66.531 | −35.858 | 10.330 | 1.00 | 50.90 |
| 679 | N | MET | C | 430 | 67.631 | −34.696 | 11.910 | 1.00 | 54.52 |
| 680 | CA | MET | C | 430 | 67.154 | −33.408 | 11.400 | 1.00 | 56.27 |
| 681 | CB | MET | C | 430 | 66.074 | −32.840 | 12.313 | 1.00 | 66.16 |
| 682 | CG | MET | C | 430 | 65.125 | −33.864 | 12.788 | 1.00 | 86.24 |
| 683 | SD | MET | C | 430 | 63.661 | −33.177 | 13.538 | 1.00 | 99.53 |
| 684 | CE | MET | C | 430 | 64.186 | −32.952 | 15.166 | 1.00 | 107.62 |
| 685 | C | MET | C | 430 | 68.246 | −32.369 | 11.253 | 1.00 | 51.60 |
| 686 | O | MET | C | 430 | 68.963 | −32.063 | 12.209 | 1.00 | 47.36 |
| 687 | N | ARG | C | 431 | 68.367 | −31.827 | 10.046 | 1.00 | 47.49 |
| 688 | CA | ARG | C | 431 | 69.364 | −30.804 | 9.773 | 1.00 | 43.09 |
| 689 | CB | ARG | C | 431 | 70.336 | −31.267 | 8.683 | 1.00 | 48.34 |
| 690 | CG | ARG | C | 431 | 71.085 | −32.547 | 9.024 | 1.00 | 58.17 |
| 691 | CD | ARG | C | 431 | 72.010 | −32.347 | 10.207 | 1.00 | 66.63 |
| 692 | NE | ARG | C | 431 | 72.510 | −33.619 | 10.713 | 1.00 | 74.01 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 693 | CZ | ARG | C | 431 | 73.336 | −33.736 | 11.746 | 1.00 | 77.89 |
| 694 | NH1 | ARG | C | 431 | 73.759 | −32.651 | 12.385 | 1.00 | 79.90 |
| 695 | NH2 | ARG | C | 431 | 73.734 | −34.937 | 12.143 | 1.00 | 79.91 |
| 696 | C | ARG | C | 431 | 68.629 | −29.562 | 9.315 | 1.00 | 38.83 |
| 697 | O | ARG | C | 431 | 67.539 | −29.645 | 8.738 | 1.00 | 37.99 |
| 698 | N | SER | C | 432 | 69.212 | −28.404 | 9.585 | 1.00 | 34.71 |
| 699 | CA | SER | C | 432 | 68.588 | −27.162 | 9.183 | 1.00 | 33.86 |
| 700 | CB | SER | C | 432 | 67.851 | −26.523 | 10.356 | 1.00 | 34.04 |
| 701 | OG | SER | C | 432 | 68.757 | −26.175 | 11.381 | 1.00 | 35.50 |
| 702 | C | SER | C | 432 | 69.655 | −26.222 | 8.680 | 1.00 | 32.51 |
| 703 | O | SER | C | 432 | 70.811 | −26.331 | 9.063 | 1.00 | 33.75 |
| 704 | N | THR | C | 433 | 69.274 | −25.303 | 7.805 | 1.00 | 30.65 |
| 705 | CA | THR | C | 433 | 70.239 | −24.361 | 7.272 | 1.00 | 28.78 |
| 706 | CB | THR | C | 433 | 70.800 | −24.857 | 5.918 | 1.00 | 28.10 |
| 707 | OG1 | THR | C | 433 | 71.936 | −24.071 | 5.554 | 1.00 | 28.08 |
| 708 | CG2 | THR | C | 433 | 69.756 | −24.764 | 4.823 | 1.00 | 29.19 |
| 709 | C | THR | C | 433 | 69.570 | −23.011 | 7.102 | 1.00 | 28.08 |
| 710 | O | THR | C | 433 | 68.350 | −22.928 | 6.903 | 1.00 | 24.92 |
| 711 | N | THR | C | 434 | 70.355 | −21.952 | 7.229 | 1.00 | 27.74 |
| 712 | CA | THR | C | 434 | 69.823 | −20.604 | 7.059 | 1.00 | 28.79 |
| 713 | CB | THR | C | 434 | 69.259 | −20.021 | 8.374 | 1.00 | 27.23 |
| 714 | OG1 | THR | C | 434 | 68.663 | −18.745 | 8.114 | 1.00 | 24.99 |
| 715 | CG2 | THR | C | 434 | 70.371 | −19.842 | 9.407 | 1.00 | 22.38 |
| 716 | C | THR | C | 434 | 70.953 | −19.724 | 6.589 | 1.00 | 32.80 |
| 717 | O | THR | C | 434 | 72.119 | −20.117 | 6.660 | 1.00 | 27.91 |
| 718 | N | LYS | C | 435 | 70.609 | −18.538 | 6.102 | 1.00 | 40.51 |
| 719 | CA | LYS | C | 435 | 71.638 | −17.630 | 5.637 | 1.00 | 46.89 |
| 720 | CB | LYS | C | 435 | 71.061 | −16.361 | 5.019 | 1.00 | 50.79 |
| 721 | CG | LYS | C | 435 | 72.160 | −15.356 | 4.693 | 1.00 | 64.78 |
| 722 | CD | LYS | C | 435 | 71.640 | −14.076 | 4.078 | 1.00 | 71.13 |
| 723 | CE | LYS | C | 435 | 72.789 | −13.210 | 3.605 | 1.00 | 73.50 |
| 724 | NZ | LYS | C | 435 | 72.472 | −12.513 | 2.320 | 1.00 | 74.41 |
| 725 | C | LYS | C | 435 | 72.495 | −17.236 | 6.816 | 1.00 | 50.18 |
| 726 | O | LYS | C | 435 | 72.000 | −16.775 | 7.839 | 1.00 | 46.63 |
| 727 | N | THR | C | 436 | 73.792 | −17.420 | 6.669 | 1.00 | 53.88 |
| 728 | CA | THR | C | 436 | 74.716 | −17.068 | 7.723 | 1.00 | 56.62 |
| 729 | CB | THR | C | 436 | 76.135 | −17.388 | 7.281 | 1.00 | 58.22 |
| 730 | OG1 | THR | C | 436 | 76.337 | −18.798 | 7.360 | 1.00 | 63.12 |
| 731 | CG2 | THR | C | 436 | 77.143 | −16.678 | 8.137 | 1.00 | 63.91 |
| 732 | C | THR | C | 436 | 74.604 | −15.584 | 8.019 | 1.00 | 60.24 |
| 733 | O | THR | C | 436 | 74.306 | −14.794 | 7.133 | 1.00 | 55.72 |
| 734 | N | SER | C | 437 | 74.810 | −15.169 | 9.255 | 1.00 | 60.67 |
| 735 | CA | SER | C | 437 | 74.729 | −13.744 | 9.441 | 1.00 | 62.74 |
| 736 | CB | SER | C | 437 | 73.501 | −13.342 | 10.259 | 1.00 | 68.24 |
| 737 | OG | SER | C | 437 | 73.631 | −13.712 | 11.611 | 1.00 | 82.68 |
| 738 | C | SER | C | 437 | 76.001 | −13.239 | 10.055 | 1.00 | 60.21 |
| 739 | O | SER | C | 437 | 77.009 | −13.940 | 10.088 | 1.00 | 59.87 |
| 740 | N | GLY | C | 438 | 75.969 | −12.020 | 10.543 | 1.00 | 55.17 |
| 741 | CA | GLY | C | 438 | 77.185 | −11.479 | 11.079 | 1.00 | 47.01 |
| 742 | C | GLY | C | 438 | 77.587 | −10.448 | 10.055 | 1.00 | 43.90 |
| 743 | O | GLY | C | 438 | 76.846 | −10.187 | 9.109 | 1.00 | 42.54 |
| 744 | N | PRO | C | 439 | 78.773 | −9.868 | 10.199 | 1.00 | 42.82 |
| 745 | CD | PRO | C | 439 | 79.773 | −10.205 | 11.223 | 1.00 | 42.58 |
| 746 | CA | PRO | C | 439 | 79.280 | −8.844 | 9.288 | 1.00 | 41.98 |
| 747 | CB | PRO | C | 439 | 80.551 | −8.344 | 9.993 | 1.00 | 42.28 |
| 748 | CG | PRO | C | 439 | 80.476 | −8.909 | 11.391 | 1.00 | 41.79 |
| 749 | C | PRO | C | 439 | 79.580 | −9.325 | 7.870 | 1.00 | 40.11 |
| 750 | O | PRO | C | 439 | 79.757 | −10.511 | 7.629 | 1.00 | 39.54 |
| 751 | N | ARG | C | 440 | 79.632 | −8.374 | 6.942 | 1.00 | 41.27 |
| 752 | CA | ARG | C | 440 | 79.947 | −8.648 | 5.547 | 1.00 | 42.53 |
| 753 | CB | ARG | C | 440 | 78.870 | −8.094 | 4.609 | 1.00 | 46.53 |
| 754 | CG | ARG | C | 440 | 77.458 | −8.346 | 5.039 | 1.00 | 56.85 |
| 755 | CD | ARG | C | 440 | 77.063 | −9.791 | 4.875 | 1.00 | 61.35 |
| 756 | NE | ARG | C | 440 | 75.840 | −10.049 | 5.618 | 1.00 | 66.96 |
| 757 | CZ | ARG | C | 440 | 75.219 | −11.221 | 5.690 | 1.00 | 68.75 |
| 758 | NH1 | ARG | C | 440 | 75.695 | −12.282 | 5.058 | 1.00 | 68.78 |
| 759 | NH2 | ARG | C | 440 | 74.107 | −11.328 | 6.407 | 1.00 | 72.20 |
| 760 | C | ARG | C | 440 | 81.251 | −7.924 | 5.219 | 1.00 | 40.93 |
| 761 | O | ARG | C | 440 | 81.536 | −6.849 | 5.760 | 1.00 | 38.74 |
| 762 | N | ALA | C | 441 | 82.029 | −8.504 | 4.320 | 1.00 | 38.01 |
| 763 | CA | ALA | C | 441 | 83.266 | −7.884 | 3.892 | 1.00 | 34.89 |
| 764 | CB | ALA | C | 441 | 84.399 | −8.227 | 4.855 | 1.00 | 30.09 |
| 765 | C | ALA | C | 441 | 83.551 | −8.437 | 2.512 | 1.00 | 31.63 |
| 766 | O | ALA | C | 441 | 83.631 | −9.646 | 2.335 | 1.00 | 31.43 |
| 767 | N | ALA | C | 442 | 83.693 | −7.558 | 1.532 | 1.00 | 30.94 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 768 | CA | ALA | C | 442 | 83.964 | −7.998 | 0.167 | 1.00 | 32.13 |
| 769 | CB | ALA | C | 442 | 84.008 | −6.804 | −0.777 | 1.00 | 35.52 |
| 770 | C | ALA | C | 442 | 85.285 | −8.746 | 0.119 | 1.00 | 33.23 |
| 771 | O | ALA | C | 442 | 86.167 | −8.512 | 0.947 | 1.00 | 31.88 |
| 772 | N | PRO | C | 443 | 85.437 | −9.657 | −0.853 | 1.00 | 21.83 |
| 773 | CD | PRO | C | 443 | 84.459 | −10.048 | −1.887 | 1.00 | 25.38 |
| 774 | CA | PRO | C | 443 | 86.674 | −10.420 | −0.975 | 1.00 | 25.50 |
| 775 | CB | PRO | C | 443 | 86.220 | −11.691 | −1.666 | 1.00 | 26.94 |
| 776 | CG | PRO | C | 443 | 85.134 | −11.207 | −2.596 | 1.00 | 21.34 |
| 777 | C | PRO | C | 443 | 87.709 | −9.684 | −1.799 | 1.00 | 28.08 |
| 778 | O | PRO | C | 443 | 87.365 | −8.954 | −2.720 | 1.00 | 26.70 |
| 779 | N | GLU | C | 444 | 88.980 | −9.854 | −1.450 | 1.00 | 27.32 |
| 780 | CA | GLU | C | 444 | 90.060 | −9.254 | −2.235 | 1.00 | 26.49 |
| 781 | CB | GLU | C | 444 | 91.169 | −8.728 | −1.312 | 1.00 | 27.65 |
| 782 | CG | GLU | C | 444 | 90.812 | −7.422 | −0.583 | 1.00 | 34.66 |
| 783 | CD | GLU | C | 444 | 91.339 | −7.371 | 0.850 | 1.00 | 37.62 |
| 784 | OE1 | GLU | C | 444 | 92.399 | −7.996 | 1.110 | 1.00 | 32.44 |
| 785 | OE2 | GLU | C | 444 | 90.699 | −6.694 | 1.705 | 1.00 | 38.74 |
| 786 | C | GLU | C | 444 | 90.557 | −10.413 | −3.127 | 1.00 | 26.10 |
| 787 | O | GLU | C | 444 | 90.776 | −11.531 | −2.637 | 1.00 | 25.68 |
| 788 | N | VAL | C | 445 | 90.705 | −10.163 | −4.431 | 1.00 | 25.49 |
| 789 | CA | VAL | C | 445 | 92.132 | −11.202 | −5.364 | 1.00 | 23.72 |
| 790 | CB | VAL | C | 445 | 90.100 | −11.352 | −6.508 | 1.00 | 22.55 |
| 791 | CG1 | VAL | C | 445 | 90.529 | −12.460 | −7.460 | 1.00 | 15.69 |
| 792 | CG2 | VAL | C | 445 | 88.722 | −11.638 | −5.929 | 1.00 | 17.42 |
| 793 | C | VAL | C | 445 | 92.514 | −10.980 | −5.986 | 1.00 | 21.05 |
| 794 | O | VAL | C | 445 | 92.823 | −9.887 | −6.477 | 1.00 | 23.56 |
| 795 | N | TYR | C | 446 | 93.343 | −12.022 | −5.981 | 1.00 | 21.20 |
| 796 | CA | TYR | C | 446 | 94.681 | −11.915 | −6.575 | 1.00 | 30.31 |
| 797 | CB | TYR | C | 446 | 95.748 | −11.779 | −5.489 | 1.00 | 43.70 |
| 798 | CG | TYR | C | 446 | 95.508 | −10.636 | −4.528 | 1.00 | 49.06 |
| 799 | CD1 | TYR | C | 446 | 94.810 | −10.830 | −3.336 | 1.00 | 51.62 |
| 800 | CE1 | TYR | C | 446 | 94.601 | −9.780 | −2.449 | 1.00 | 59.25 |
| 801 | CD2 | TYR | C | 446 | 95.986 | −9.359 | −4.808 | 1.00 | 51.72 |
| 802 | CE2 | TYR | C | 446 | 95.780 | −8.308 | −3.932 | 1.00 | 58.98 |
| 803 | CZ | TYR | C | 446 | 95.089 | −8.526 | −2.755 | 1.00 | 60.63 |
| 804 | OH | TYR | C | 446 | 94.892 | −7.492 | −1.877 | 1.00 | 65.13 |
| 805 | C | TYR | C | 446 | 94.980 | −13.147 | −7.413 | 1.00 | 25.40 |
| 806 | O | TYR | C | 446 | 94.717 | −14.273 | −6.967 | 1.00 | 29.17 |
| 807 | N | ALA | C | 447 | 95.524 | −12.954 | −8.612 | 1.00 | 16.77 |
| 808 | CA | ALA | C | 447 | 95.831 | −14.090 | −9.464 | 1.00 | 20.67 |
| 809 | CB | ALA | C | 447 | 94.882 | −14.122 | −10.675 | 1.00 | 19.82 |
| 810 | C | ALA | C | 447 | 97.266 | −14.043 | −9.941 | 1.00 | 20.86 |
| 811 | O | ALA | C | 447 | 97.795 | −12.973 | −10.216 | 1.00 | 20.16 |
| 812 | N | PHE | C | 448 | 97.900 | −15.200 | −10.049 | 1.00 | 17.69 |
| 813 | CA | PHE | C | 448 | 99.269 | −15.230 | −10.525 | 1.00 | 22.74 |
| 814 | CB | PHE | C | 448 | 100.291 | −15.339 | −9.390 | 1.00 | 28.63 |
| 815 | CG | PHE | C | 448 | 99.798 | −14.870 | −8.066 | 1.00 | 34.86 |
| 816 | CD1 | PHE | C | 448 | 99.018 | −15.701 | −7.275 | 1.00 | 38.18 |
| 817 | CD2 | PHE | C | 448 | 100.148 | −13.608 | −7.584 | 1.00 | 37.09 |
| 818 | CE1 | PHE | C | 448 | 98.586 | −15.287 | −6.020 | 1.00 | 41.41 |
| 819 | CE2 | PHE | C | 448 | 99.720 | −13.182 | −6.327 | 1.00 | 39.42 |
| 820 | CZ | PHE | C | 448 | 98.941 | −14.024 | −5.545 | 1.00 | 41.58 |
| 821 | C | PHE | C | 448 | 99.496 | −16.412 | −11.430 | 1.00 | 20.91 |
| 822 | O | PHE | C | 448 | 98.708 | −17.364 | −11.439 | 1.00 | 21.05 |
| 823 | N | ALA | C | 449 | 100.594 | −16.344 | −12.170 | 1.00 | 19.91 |
| 824 | CA | ALA | C | 449 | 100.991 | −17.405 | −13.067 | 1.00 | 19.89 |
| 825 | CB | ALA | C | 449 | 101.028 | −16.900 | −14.486 | 1.00 | 17.23 |
| 826 | C | ALA | C | 449 | 102.386 | −17.851 | −12.633 | 1.00 | 19.94 |
| 827 | O | ALA | C | 449 | 103.251 | −17.029 | −12.345 | 1.00 | 17.23 |
| 828 | N | THR | C | 450 | 102.603 | −19.154 | −12.583 | 1.00 | 24.30 |
| 829 | CA | THR | C | 450 | 103.908 | −19.660 | −12.210 | 1.00 | 30.69 |
| 830 | CB | THR | C | 450 | 103.849 | −21.126 | −11.806 | 1.00 | 29.58 |
| 831 | OG1 | THR | C | 450 | 103.250 | −21.888 | −12.869 | 1.00 | 31.67 |
| 832 | CG2 | THR | C | 450 | 103.048 | −21.310 | −10.542 | 1.00 | 28.92 |
| 833 | C | THR | C | 450 | 104.806 | −19.557 | −13.429 | 1.00 | 31.94 |
| 834 | O | THR | C | 450 | 104.319 | −19.541 | −14.562 | 1.00 | 31.48 |
| 835 | N | PRO | C | 451 | 106.134 | −19.467 | −13.217 | 1.00 | 36.38 |
| 836 | CD | PRO | C | 451 | 106.886 | −19.261 | −11.962 | 1.00 | 38.78 |
| 837 | CA | PRO | C | 451 | 106.999 | −19.386 | −14.399 | 1.00 | 43.40 |
| 838 | CB | PRO | C | 451 | 108.281 | −18.742 | −13.873 | 1.00 | 40.07 |
| 839 | CG | PRO | C | 451 | 108.336 | −19.156 | −12.430 | 1.00 | 40.19 |
| 840 | C | PRO | C | 451 | 107.256 | −20.763 | −14.986 | 1.00 | 51.80 |
| 841 | O | PRO | C | 451 | 106.641 | −21.761 | −14.589 | 1.00 | 45.25 |
| 842 | N | GLU | C | 452 | 108.179 | −20.791 | −15.936 | 1.00 | 59.84 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 843 | CA | GLU | C | 452 | 108.562 | −22.023 | −16.583 | 1.00 | 70.84 |
| 844 | CB | GLU | C | 452 | 109.087 | −21.762 | −17.991 | 1.00 | 82.23 |
| 845 | CG | GLU | C | 452 | 109.250 | −23.024 | −18.826 | 1.00 | 112.49 |
| 846 | CD | GLU | C | 452 | 109.728 | −22.719 | −20.226 | 1.00 | 128.43 |
| 847 | OE1 | GLU | C | 452 | 109.922 | −21.523 | −20.529 | 1.00 | 138.05 |
| 848 | OE2 | GLU | C | 452 | 109.909 | −23.666 | −21.020 | 1.00 | 137.33 |
| 849 | C | GLU | C | 452 | 109.632 | −22.690 | −15.741 | 1.00 | 70.00 |
| 850 | O | GLU | C | 452 | 110.657 | −22.096 | −15.376 | 1.00 | 63.19 |
| 851 | N | TRP | C | 453 | 109.338 | −23.942 | −15.441 | 1.00 | 68.31 |
| 852 | CA | TRP | C | 453 | 110.145 | −24.828 | −14.638 | 1.00 | 68.31 |
| 853 | CB | TRP | C | 453 | 109.235 | −25.459 | −13.584 | 1.00 | 68.31 |
| 854 | CG | TRP | C | 453 | 109.922 | −26.244 | −12.532 | 1.00 | 78.31 |
| 855 | CD2 | TRP | C | 453 | 110.846 | −25.733 | −11.581 | 1.00 | 118.31 |
| 856 | CE2 | TRP | C | 453 | 111.242 | −26.812 | −10.760 | 1.00 | 118.31 |
| 857 | CE3 | TRP | C | 453 | 111.380 | −24.463 | −11.342 | 1.00 | 118.31 |
| 858 | CD1 | TRP | C | 453 | 109.790 | −27.580 | −12.266 | 1.00 | 118.31 |
| 859 | NE1 | TRP | C | 453 | 110.583 | −27.929 | −11.199 | 1.00 | 118.31 |
| 860 | CZ2 | TRP | C | 453 | 112.153 | −26.653 | −9.712 | 1.00 | 118.31 |
| 861 | CZ3 | TRP | C | 453 | 112.281 | −24.305 | −10.306 | 1.00 | 118.31 |
| 862 | CH2 | TRP | C | 453 | 112.660 | −25.395 | −9.501 | 1.00 | 118.31 |
| 863 | C | TRP | C | 453 | 110.609 | −25.903 | −15.595 | 1.00 | 68.31 |
| 864 | O | TRP | C | 453 | 110.007 | −26.108 | −16.658 | 1.00 | 68.31 |
| 865 | N | PRO | C | 454 | 111.692 | −26.590 | −15.258 | 1.00 | 68.31 |
| 866 | CD | PRO | C | 454 | 112.708 | −26.452 | −14.196 | 1.00 | 68.31 |
| 867 | CA | PRO | C | 454 | 112.050 | −27.617 | −16.213 | 1.00 | 68.31 |
| 868 | CB | PRO | C | 454 | 113.406 | −27.923 | −15.829 | 1.00 | 68.31 |
| 869 | CG | PRO | C | 454 | 113.538 | −27.642 | −14.382 | 1.00 | 68.31 |
| 870 | C | PRO | C | 454 | 111.170 | −28.786 | −15.916 | 1.00 | 68.31 |
| 871 | O | PRO | C | 454 | 111.327 | −29.888 | −16.447 | 1.00 | 68.31 |
| 872 | N | GLY | C | 455 | 110.268 | −28.559 | −14.986 | 1.00 | 68.31 |
| 873 | CA | GLY | C | 455 | 109.365 | −29.627 | −14.670 | 1.00 | 68.31 |
| 874 | C | GLY | C | 455 | 108.607 | −29.802 | −15.966 | 1.00 | 68.31 |
| 875 | O | GLY | C | 455 | 109.052 | −30.452 | −16.928 | 1.00 | 68.31 |
| 876 | N | SER | C | 456 | 107.451 | −29.167 | −15.989 | 1.00 | 68.31 |
| 877 | CA | SER | C | 456 | 106.594 | −29.205 | −17.140 | 1.00 | 68.31 |
| 878 | CB | SER | C | 456 | 105.217 | −29.707 | −16.736 | 1.00 | 78.31 |
| 879 | OG | SER | C | 456 | 104.233 | −29.250 | −17.637 | 1.00 | 88.31 |
| 880 | C | SER | C | 456 | 106.547 | −27.795 | −17.686 | 1.00 | 68.31 |
| 881 | O | SER | C | 456 | 106.257 | −26.816 | −16.978 | 1.00 | 68.31 |
| 882 | N | ALA | C | 457 | 106.854 | −27.713 | −18.967 | 1.00 | 68.31 |
| 883 | CA | ALA | C | 457 | 106.921 | −26.446 | −19.639 | 1.00 | 68.31 |
| 884 | CB | ALA | C | 457 | 108.073 | −26.464 | −20.599 | 1.00 | 78.31 |
| 885 | C | ALA | C | 457 | 105.665 | −26.044 | −20.364 | 1.00 | 68.31 |
| 886 | O | ALA | C | 457 | 104.959 | −25.131 | −19.942 | 1.00 | 68.31 |
| 887 | N | ASP | C | 458 | 105.383 | −26.721 | −21.461 | 1.00 | 68.31 |
| 888 | CA | ASP | C | 458 | 104.233 | −26.355 | −22.237 | 1.00 | 78.31 |
| 889 | CB | ASP | C | 458 | 104.282 | −27.122 | −23.540 | 1.00 | 88.31 |
| 890 | CG | ASP | C | 458 | 105.619 | −26.948 | −24.223 | 1.00 | 118.31 |
| 891 | OD1 | ASP | C | 458 | 106.303 | −25.946 | −23.906 | 1.00 | 118.31 |
| 892 | OD2 | ASP | C | 458 | 105.988 | −27.792 | −25.062 | 1.00 | 118.31 |
| 893 | C | ASP | C | 458 | 102.892 | −26.453 | −21.532 | 1.00 | 68.31 |
| 894 | O | ASP | C | 458 | 101.966 | −27.111 | −21.989 | 1.00 | 68.31 |
| 895 | N | LYS | C | 459 | 102.826 | −25.765 | −20.400 | 1.00 | 62.45 |
| 896 | CA | LYS | C | 459 | 101.649 | −25.633 | −19.565 | 1.00 | 64.90 |
| 897 | CB | LYS | C | 459 | 100.886 | −26.962 | −19.380 | 1.00 | 72.40 |
| 898 | CG | LYS | C | 459 | 101.126 | −27.786 | −18.131 | 1.00 | 81.32 |
| 899 | CD | LYS | C | 459 | 99.925 | −28.726 | −17.868 | 1.00 | 88.03 |
| 900 | CE | LYS | C | 459 | 100.181 | −30.166 | −18.307 | 1.00 | 91.43 |
| 901 | NZ | LYS | C | 459 | 99.054 | −31.070 | −17.915 | 1.00 | 94.56 |
| 902 | C | LYS | C | 459 | 102.131 | −25.025 | −18.278 | 1.00 | 59.42 |
| 903 | O | LYS | C | 459 | 103.281 | −25.154 | −17.871 | 1.00 | 56.62 |
| 904 | N | ARG | C | 460 | 101.257 | −24.274 | −17.674 | 1.00 | 50.41 |
| 905 | CA | ARG | C | 460 | 101.648 | −23.614 | −16.481 | 1.00 | 41.66 |
| 906 | CB | ARG | C | 460 | 102.055 | −22.197 | −16.815 | 1.00 | 43.58 |
| 907 | CG | ARG | C | 460 | 103.253 | −22.158 | −17.733 | 1.00 | 49.61 |
| 908 | CD | ARG | C | 460 | 103.869 | −20.834 | −17.615 | 1.00 | 53.53 |
| 909 | NE | ARG | C | 460 | 105.042 | −20.648 | −18.442 | 1.00 | 57.16 |
| 910 | CZ | ARG | C | 460 | 105.643 | −19.473 | −18.522 | 1.00 | 59.71 |
| 911 | NH1 | ARG | C | 460 | 105.148 | −18.459 | −17.828 | 1.00 | 60.68 |
| 912 | NH2 | ARG | C | 460 | 106.721 | −19.307 | −19.271 | 1.00 | 62.11 |
| 913 | C | ARG | C | 460 | 100.532 | −23.636 | −15.508 | 1.00 | 33.09 |
| 914 | O | ARG | C | 460 | 99.416 | −24.058 | −15.817 | 1.00 | 30.19 |
| 915 | N | THR | C | 461 | 100.829 | −23.177 | −14.311 | 1.00 | 29.07 |
| 916 | CA | THR | C | 461 | 99.816 | −23.195 | −13.305 | 1.00 | 25.36 |
| 917 | CB | THR | C | 461 | 100.315 | −23.942 | −12.058 | 1.00 | 20.38 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 918 | OG1 | THR | C | 461 | 100.628 | −25.295 | −12.421 | 1.00 | 24.76 |
| 919 | CG2 | THR | C | 461 | 99.234 | −23.948 | −10.974 | 1.00 | 17.59 |
| 920 | C | THR | C | 461 | 99.417 | −21.789 | −12.951 | 1.00 | 21.18 |
| 921 | O | THR | C | 461 | 100.262 | −20.902 | −12.820 | 1.00 | 24.70 |
| 922 | N | LEU | C | 462 | 98.122 | −21.569 | −12.830 | 1.00 | 20.59 |
| 923 | CA | LEU | C | 462 | 97.622 | −20.266 | −12.432 | 1.00 | 19.92 |
| 924 | CB | LEU | C | 462 | 96.595 | −19.737 | −13.385 | 1.00 | 18.76 |
| 925 | CG | LEU | C | 462 | 97.029 | −19.621 | −14.846 | 1.00 | 20.91 |
| 926 | CD1 | LEU | C | 462 | 95.898 | −18.982 | −15.647 | 1.00 | 19.18 |
| 927 | CD2 | LEU | C | 462 | 98.310 | −18.796 | −14.961 | 1.00 | 17.26 |
| 928 | C | LEU | C | 462 | 97.082 | −20.454 | −11.043 | 1.00 | 19.00 |
| 929 | O | LEU | C | 462 | 96.523 | −21.513 | −10.719 | 1.00 | 20.66 |
| 930 | N | ALA | C | 463 | 97.221 | −19.438 | −10.210 | 1.00 | 19.05 |
| 931 | CA | ALA | C | 463 | 96.689 | −19.551 | −8.874 | 1.00 | 18.58 |
| 932 | CB | ALA | C | 463 | 97.793 | −19.866 | −7.888 | 1.00 | 17.15 |
| 933 | C | ALA | C | 463 | 95.999 | −18.268 | −8.501 | 1.00 | 19.05 |
| 934 | O | ALA | C | 463 | 96.360 | −17.181 | −8.943 | 1.00 | 18.21 |
| 935 | N | CYS | C | 464 | 94.987 | −18.404 | −7.677 | 1.00 | 19.54 |
| 936 | CA | CYS | C | 464 | 94.238 | −17.255 | −7.270 | 1.00 | 19.71 |
| 937 | C | CYS | C | 464 | 94.086 | −17.293 | −5.774 | 1.00 | 19.73 |
| 938 | O | CYS | C | 464 | 93.850 | −18.350 | −5.183 | 1.00 | 20.65 |
| 939 | CB | CYS | C | 464 | 92.878 | −17.311 | −7.927 | 1.00 | 20.95 |
| 940 | SG | CYS | C | 464 | 91.870 | −15.814 | −7.812 | 1.00 | 20.35 |
| 941 | N | LEU | C | 465 | 94.248 | −16.138 | −5.160 | 1.00 | 18.76 |
| 942 | CA | LEU | C | 465 | 94.097 | −16.039 | −3.720 | 1.00 | 20.88 |
| 943 | CB | LEU | C | 465 | 95.351 | −15.458 | −3.060 | 1.00 | 18.91 |
| 944 | CG | LEU | C | 465 | 95.161 | −14.971 | −1.617 | 1.00 | 19.35 |
| 945 | CD1 | LEU | C | 465 | 94.844 | −16.151 | −0.705 | 1.00 | 19.27 |
| 946 | CD2 | LEU | C | 465 | 96.435 | −14.250 | −1.131 | 1.00 | 20.28 |
| 947 | C | LEU | C | 465 | 92.936 | −15.099 | −3.483 | 1.00 | 18.88 |
| 948 | O | LEU | C | 465 | 92.931 | −13.968 | −3.987 | 1.00 | 21.68 |
| 949 | N | ILE | C | 466 | 91.946 | −15.561 | −2.737 | 1.00 | 17.80 |
| 950 | CA | ILE | C | 466 | 90.793 | −14.726 | −2.436 | 1.00 | 21.70 |
| 951 | CB | ILE | C | 466 | 89.514 | −15.330 | −3.041 | 1.00 | 20.01 |
| 952 | CG2 | ILE | C | 466 | 88.319 | −14.421 | −2.771 | 1.00 | 16.39 |
| 953 | CG1 | ILE | C | 466 | 89.711 | −15.515 | −4.549 | 1.00 | 19.30 |
| 954 | CD1 | ILE | C | 466 | 88.960 | −16.690 | −5.114 | 1.00 | 20.00 |
| 955 | C | ILE | C | 466 | 90.728 | −14.682 | 0.921 | 1.00 | 22.37 |
| 956 | O | ILE | C | 466 | 90.655 | −15.734 | −0.273 | 1.00 | 23.15 |
| 957 | N | GLN | C | 467 | 90.761 | −13.477 | −0.356 | 1.00 | 21.47 |
| 958 | CA | GLN | C | 467 | 90.793 | −13.348 | 1.093 | 1.00 | 25.10 |
| 959 | CB | GLN | C | 467 | 92.255 | −13.279 | 1.557 | 1.00 | 25.32 |
| 960 | CG | GLN | C | 467 | 93.106 | −12.187 | 0.865 | 1.00 | 25.88 |
| 961 | CD | GLN | C | 467 | 94.510 | −12.049 | 1.454 | 1.00 | 27.27 |
| 962 | OE1 | GLN | C | 467 | 95.114 | −13.037 | 1.891 | 1.00 | 28.10 |
| 963 | NE2 | GLN | C | 467 | 95.043 | −10.825 | 1.453 | 1.00 | 25.12 |
| 964 | C | GLN | C | 467 | 90.044 | −12.188 | 1.717 | 1.00 | 27.56 |
| 965 | O | GLN | C | 467 | 89.562 | −11.274 | 1.030 | 1.00 | 28.72 |
| 966 | N | ASN | C | 468 | 89.975 | −12.243 | 3.044 | 1.00 | 27.06 |
| 967 | CA | ASN | C | 468 | 89.323 | −11.235 | 3.869 | 1.00 | 29.09 |
| 968 | CB | ASN | C | 468 | 90.093 | −9.903 | 3.763 | 1.00 | 30.69 |
| 969 | CG | ASN | C | 468 | 91.539 | −10.017 | 4.267 | 1.00 | 31.20 |
| 970 | OD1 | ASN | C | 468 | 91.823 | −10.776 | 5.197 | 1.00 | 31.84 |
| 971 | ND2 | ASN | C | 468 | 92.449 | −9.253 | 3.663 | 1.00 | 29.63 |
| 972 | C | ASN | C | 468 | 87.828 | −11.017 | 3.601 | 1.00 | 30.07 |
| 973 | O | ASN | C | 468 | 87.293 | −9.965 | 3.955 | 1.00 | 30.13 |
| 974 | N | PHE | C | 469 | 87.153 | −11.996 | 2.986 | 1.00 | 33.86 |
| 975 | CA | PHE | C | 469 | 85.708 | −11.872 | 2.725 | 1.00 | 35.51 |
| 976 | CB | PHE | C | 469 | 85.285 | −12.614 | 1.442 | 1.00 | 27.30 |
| 977 | CG | PHE | C | 469 | 85.761 | −14.035 | 1.381 | 1.00 | 21.23 |
| 978 | CD1 | PHE | C | 469 | 84.946 | −15.058 | 1.844 | 1.00 | 18.22 |
| 979 | CD2 | PHE | C | 469 | 86.990 | −14.354 | 0.780 | 1.00 | 19.34 |
| 980 | CE1 | PHE | C | 469 | 85.373 | −16.393 | 1.800 | 1.00 | 19.44 |
| 981 | CE2 | PHE | C | 469 | 87.430 | −15.678 | 0.729 | 1.00 | 19.93 |
| 982 | CZ | PHE | C | 469 | 86.600 | −16.708 | 1.205 | 1.00 | 19.37 |
| 983 | C | PHE | C | 469 | 84.947 | −12.361 | 3.960 | 1.00 | 38.34 |
| 984 | O | PHE | C | 469 | 85.440 | −13.221 | 4.692 | 1.00 | 40.99 |
| 985 | N | MET | C | 470 | 83.756 | −11.821 | 4.205 | 1.00 | 39.80 |
| 986 | CA | MET | C | 470 | 83.068 | −12.172 | 5.438 | 1.00 | 50.04 |
| 987 | CB | MET | C | 470 | 82.335 | −10.961 | 6.006 | 1.00 | 61.54 |
| 988 | CG | MET | C | 470 | 82.399 | −10.905 | 7.538 | 1.00 | 64.53 |
| 989 | SD | MET | C | 470 | 84.083 | −10.913 | 8.216 | 1.00 | 63.70 |
| 990 | CE | MET | C | 470 | 83.775 | −10.460 | 9.903 | 1.00 | 66.09 |
| 991 | C | MET | C | 470 | 82.206 | −13.410 | 5.519 | 1.00 | 51.04 |
| 992 | O | MET | C | 470 | 82.706 | −14.425 | 6.015 | 1.00 | 59.29 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 993 | N | PRO | C | 471 | 80.930 | −13.402 | 5.083 | 1.00 | 40.22 |
| 994 | CD | PRO | C | 471 | 79.748 | −12.585 | 4.767 | 1.00 | 41.27 |
| 995 | CA | PRO | C | 471 | 80.561 | −14.790 | 5.379 | 1.00 | 39.05 |
| 996 | CB | PRO | C | 471 | 79.102 | −14.862 | 4.968 | 1.00 | 36.04 |
| 997 | CG | PRO | C | 471 | 78.612 | −13.481 | 5.275 | 1.00 | 35.83 |
| 998 | C | PRO | C | 471 | 81.499 | −15.652 | 4.534 | 1.00 | 36.75 |
| 999 | O | PRO | C | 471 | 82.086 | −15.162 | 3.570 | 1.00 | 30.45 |
| 1000 | N | GLU | C | 472 | 81.682 | −16.907 | 4.918 | 1.00 | 31.88 |
| 1001 | CA | GLU | C | 472 | 82.612 | −17.778 | 4.215 | 1.00 | 34.09 |
| 1002 | CB | GLU | C | 472 | 83.045 | −18.915 | 5.142 | 1.00 | 39.62 |
| 1003 | CG | GLU | C | 472 | 81.909 | −19.807 | 5.575 | 1.00 | 48.49 |
| 1004 | CD | GLU | C | 472 | 82.322 | −20.798 | 6.636 | 1.00 | 53.73 |
| 1005 | OE1 | GLU | C | 472 | 82.403 | −20.407 | 7.826 | 1.00 | 57.15 |
| 1006 | OE2 | GLU | C | 472 | 82.571 | −21.968 | 6.270 | 1.00 | 57.25 |
| 1007 | C | GLU | C | 472 | 82.125 | −18.356 | 2.900 | 1.00 | 32.29 |
| 1008 | O | GLU | C | 472 | 82.924 | −18.883 | 2.120 | 1.00 | 30.57 |
| 1009 | N | ASP | C | 473 | 80.828 | −18.257 | 2.640 | 1.00 | 31.15 |
| 1010 | CA | ASP | C | 473 | 80.300 | −18.807 | 1.407 | 1.00 | 31.42 |
| 1011 | CB | ASP | C | 473 | 78.779 | −18.781 | 1.422 | 1.00 | 34.90 |
| 1012 | CG | ASP | C | 473 | 78.206 | −19.610 | 2.545 | 1.00 | 36.80 |
| 1013 | OD1 | ASP | C | 473 | 78.753 | −20.694 | 2.827 | 1.00 | 39.88 |
| 1014 | OD2 | ASP | C | 473 | 77.208 | −19.183 | 3.145 | 1.00 | 38.59 |
| 1015 | C | ASP | C | 473 | 80.836 | −18.054 | 0.200 | 1.00 | 28.26 |
| 1016 | O | ASP | C | 473 | 80.695 | −16.830 | 0.084 | 1.00 | 28.47 |
| 1017 | N | ILE | C | 474 | 81.453 | −18.799 | −0.708 | 1.00 | 24.10 |
| 1018 | CA | ILE | C | 474 | 82.033 | −18.184 | −1.878 | 1.00 | 24.19 |
| 1019 | CB | ILE | C | 474 | 83.444 | −17.684 | −1.541 | 1.00 | 20.30 |
| 1020 | CG2 | ILE | C | 474 | 84.385 | −18.864 | −1.423 | 1.00 | 17.49 |
| 1021 | CG1 | ILE | C | 474 | 83.923 | −16.705 | −2.605 | 1.00 | 20.00 |
| 1022 | CD1 | ILE | C | 474 | 84.959 | −15.736 | −2.103 | 1.00 | 20.95 |
| 1023 | C | ILE | C | 474 | 82.112 | −19.134 | −3.076 | 1.00 | 22.89 |
| 1024 | O | ILE | C | 474 | 82.313 | −20.338 | −2.911 | 1.00 | 23.42 |
| 1025 | N | SER | C | 475 | 81.923 | −18.590 | −4.278 | 1.00 | 18.58 |
| 1026 | CA | SER | C | 475 | 82.034 | −19.378 | −5.499 | 1.00 | 19.62 |
| 1027 | CB | SER | C | 475 | 80.762 | −19.295 | −6.340 | 1.00 | 16.92 |
| 1028 | OG | SER | C | 475 | 79.729 | −20.055 | −5.747 | 1.00 | 23.65 |
| 1029 | C | SER | C | 475 | 83.188 | −18.802 | −6.287 | 1.00 | 19.36 |
| 1030 | O | SER | C | 475 | 83.325 | −17.571 | −6.393 | 1.00 | 15.01 |
| 1031 | N | VAL | C | 476 | 84.022 | −19.686 | −6.827 | 1.00 | 18.13 |
| 1032 | CA | VAL | C | 476 | 85.173 | −19.270 | −7.615 | 1.00 | 18.15 |
| 1033 | CB | VAL | C | 476 | 86.511 | −19.753 | −7.005 | 1.00 | 18.21 |
| 1034 | CG1 | VAL | C | 476 | 87.689 | −19.223 | −7.830 | 1.00 | 14.84 |
| 1035 | CG2 | VAL | C | 476 | 86.627 | −19.306 | −5.557 | 1.00 | 16.73 |
| 1036 | C | VAL | C | 476 | 85.062 | −19.933 | −8.960 | 1.00 | 19.06 |
| 1037 | O | VAL | C | 476 | 84.704 | −21.107 | −9.057 | 1.00 | 17.85 |
| 1038 | N | GLN | C | 477 | 85.366 | −19.192 | −10.005 | 1.00 | 22.06 |
| 1039 | CA | GLN | C | 477 | 85.340 | −19.794 | −11.319 | 1.00 | 26.50 |
| 1040 | CB | GLN | C | 477 | 83.956 | −19.623 | −11.977 | 1.00 | 31.23 |
| 1041 | CG | GLN | C | 477 | 83.480 | −18.203 | −12.073 | 1.00 | 42.24 |
| 1042 | CD | GLN | C | 477 | 81.974 | −18.054 | −12.255 | 1.00 | 48.02 |
| 1043 | OE1 | GLN | C | 477 | 81.509 | −17.044 | −12.807 | 1.00 | 51.98 |
| 1044 | NE2 | GLN | C | 477 | 81.202 | −19.028 | −11.773 | 1.00 | 50.40 |
| 1045 | C | GLN | C | 477 | 86.448 | −19.181 | −12.150 | 1.00 | 24.93 |
| 1046 | O | GLN | C | 477 | 87.000 | −18.145 | −11.789 | 1.00 | 24.97 |
| 1047 | N | TRP | C | 478 | 86.812 | −19.860 | −13.230 | 1.00 | 23.75 |
| 1048 | CA | TRP | C | 478 | 87.840 | −19.349 | −14.116 | 1.00 | 22.78 |
| 1049 | CB | TRP | C | 478 | 89.032 | −20.296 | −14.200 | 1.00 | 21.35 |
| 1050 | CG | TRP | C | 478 | 89.812 | −20.399 | −12.930 | 1.00 | 19.56 |
| 1051 | CD2 | TRP | C | 478 | 91.033 | −19.705 | −12.611 | 1.00 | 17.70 |
| 1052 | CE2 | TRP | C | 478 | 91.411 | −20.131 | −11.302 | 1.00 | 18.23 |
| 1053 | CE3 | TRP | C | 478 | 91.799 | −18.725 | −13.257 | 1.00 | 16.63 |
| 1054 | CD1 | TRP | C | 478 | 89.532 | −21.212 | −11.869 | 1.00 | 18.65 |
| 1055 | NE1 | TRP | C | 478 | 90.498 | −21.064 | −10.887 | 1.00 | 18.95 |
| 1056 | CZ2 | TRP | C | 478 | 92.595 | −19.667 | −10.676 | 1.00 | 15.27 |
| 1057 | CZ3 | TRP | C | 478 | 92.965 | −18.251 | −12.628 | 1.00 | 14.75 |
| 1058 | CH2 | TRP | C | 478 | 93.328 | −18.705 | −11.338 | 1.00 | 16.84 |
| 1059 | C | TRP | C | 478 | 87.259 | −19.161 | −15.499 | 1.00 | 23.23 |
| 1060 | O | TRP | C | 478 | 86.446 | −19.963 | −15.960 | 1.00 | 20.20 |
| 1061 | N | LEU | C | 479 | 87.690 | −18.102 | −16.170 | 1.00 | 21.25 |
| 1062 | CA | LEU | C | 479 | 87.170 | −17.825 | −17.491 | 1.00 | 22.83 |
| 1063 | CB | LEU | C | 479 | 86.311 | −16.556 | −17.449 | 1.00 | 26.17 |
| 1064 | CG | LEU | C | 479 | 85.358 | −16.489 | −16.241 | 1.00 | 30.17 |
| 1065 | CD1 | LEU | C | 479 | 84.913 | −15.062 | −15.995 | 1.00 | 34.63 |
| 1066 | CD2 | LEU | C | 479 | 84.164 | −17.371 | −16.485 | 1.00 | 34.81 |
| 1067 | C | LEU | C | 479 | 88.304 | −17.665 | −18.483 | 1.00 | 22.51 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1068 | O | LEU | C | 479 | 89.384 | −17.183 | −18.139 | 1.00 | 20.69 |
| 1069 | N | HIS | C | 480 | 88.059 | −18.090 | −19.712 | 1.00 | 20.17 |
| 1070 | CA | HIS | C | 480 | 89.035 | −17.976 | −20.780 | 1.00 | 25.29 |
| 1071 | CB | HIS | C | 480 | 89.604 | −19.343 | −21.158 | 1.00 | 21.62 |
| 1072 | CG | HIS | C | 480 | 90.739 | −19.248 | −22.134 | 1.00 | 22.58 |
| 1073 | CD2 | HIS | C | 480 | 91.134 | −20.079 | −23.128 | 1.00 | 21.52 |
| 1074 | ND1 | HIS | C | 480 | 91.636 | −18.208 | −22.114 | 1.00 | 23.50 |
| 1075 | CE1 | HIS | C | 480 | 92.549 | −18.398 | −23.057 | 1.00 | 21.02 |
| 1076 | NE2 | HIS | C | 480 | 92.268 | −19.521 | −23.682 | 1.00 | 19.24 |
| 1077 | C | HIS | C | 480 | 88.258 | −17.360 | −21.939 | 1.00 | 30.63 |
| 1078 | O | HIS | C | 480 | 87.149 | −17.799 | −22.236 | 1.00 | 29.01 |
| 1079 | N | ASN | C | 481 | 88.833 | −16.357 | −22.606 | 1.00 | 34.83 |
| 1080 | CA | ASN | C | 481 | 88.082 | −15.641 | −23.637 | 1.00 | 42.90 |
| 1081 | CB | ASN | C | 481 | 87.614 | −16.592 | −24.735 | 1.00 | 40.03 |
| 1082 | CG | ASN | C | 481 | 88.779 | −17.205 | −25.482 | 1.00 | 37.29 |
| 1083 | OD1 | ASN | C | 481 | 89.572 | −16.494 | −26.105 | 1.00 | 31.13 |
| 1084 | ND2 | ASN | C | 481 | 88.909 | −18.526 | −25.399 | 1.00 | 35.93 |
| 1085 | C | ASN | C | 481 | 86.958 | −15.253 | −22.695 | 1.00 | 53.34 |
| 1086 | O | ASN | C | 481 | 87.214 | −15.176 | −21.489 | 1.00 | 56.43 |
| 1087 | N | GLU | C | 482 | 85.740 | −14.968 | −23.111 | 1.00 | 62.40 |
| 1088 | CA | GLU | C | 482 | 84.864 | −14.715 | −21.977 | 1.00 | 64.64 |
| 1089 | CB | GLU | C | 482 | 84.100 | −13.400 | −22.060 | 1.00 | 78.35 |
| 1090 | CG | GLU | C | 482 | 83.467 | −12.991 | −20.715 | 1.00 | 106.38 |
| 1091 | CD | GLU | C | 482 | 84.485 | −12.720 | −19.604 | 1.00 | 121.05 |
| 1092 | OE1 | GLU | C | 482 | 85.705 | −12.781 | −19.866 | 1.00 | 129.63 |
| 1093 | OE2 | GLU | C | 482 | 84.060 | −12.436 | −18.462 | 1.00 | 129.61 |
| 1094 | C | GLU | C | 482 | 83.922 | −15.873 | −21.777 | 1.00 | 59.03 |
| 1095 | O | GLU | C | 482 | 82.712 | −15.711 | −21.729 | 1.00 | 56.94 |
| 1096 | N | VAL | C | 483 | 84.509 | −17.061 | −21.669 | 1.00 | 52.74 |
| 1097 | CA | VAL | C | 483 | 83.748 | −18.278 | −21.444 | 1.00 | 46.52 |
| 1098 | CB | VAL | C | 483 | 83.831 | −19.259 | −22.648 | 1.00 | 48.77 |
| 1099 | CG1 | VAL | C | 483 | 85.238 | −19.772 | −22.825 | 1.00 | 53.46 |
| 1100 | CG2 | VAL | C | 483 | 82.875 | −20.421 | −22.430 | 1.00 | 53.15 |
| 1101 | C | VAL | C | 483 | 84.259 | −18.970 | −20.185 | 1.00 | 38.48 |
| 1102 | O | VAL | C | 483 | 85.456 | −18.987 | −19.889 | 1.00 | 37.91 |
| 1103 | N | GLN | C | 484 | 83.325 | −19.525 | −19.434 | 1.00 | 32.85 |
| 1104 | CA | GLN | C | 484 | 83.643 | −20.197 | −18.193 | 1.00 | 28.21 |
| 1105 | CB | GLN | C | 484 | 82.412 | −20.181 | −17.298 | 1.00 | 28.42 |
| 1106 | CG | GLN | C | 484 | 82.505 | −21.086 | −16.096 | 1.00 | 34.41 |
| 1107 | CD | GLN | C | 484 | 81.486 | −20.757 | −15.012 | 1.00 | 37.83 |
| 1108 | OE1 | GLN | C | 484 | 80.937 | −21.666 | −14.372 | 1.00 | 40.79 |
| 1109 | NE2 | GLN | C | 484 | 81.244 | −19.461 | −14.777 | 1.00 | 38.62 |
| 1110 | C | GLN | C | 484 | 84.144 | −21.617 | −18.411 | 1.00 | 24.70 |
| 1111 | O | GLN | C | 484 | 83.517 | −22.415 | −19.121 | 1.00 | 22.56 |
| 1112 | N | LEU | C | 485 | 85.279 | −21.930 | −17.797 | 1.00 | 20.55 |
| 1113 | CA | LEU | C | 485 | 85.875 | −23.242 | −17.956 | 1.00 | 20.53 |
| 1114 | CB | LEU | C | 485 | 87.359 | −23.197 | −17.613 | 1.00 | 19.49 |
| 1115 | CG | LEU | C | 485 | 88.254 | −22.399 | −18.563 | 1.00 | 19.86 |
| 1116 | CD1 | LEU | C | 485 | 89.621 | −22.173 | −17.910 | 1.00 | 16.73 |
| 1117 | CD2 | LEU | C | 485 | 88.394 | −23.151 | −19.884 | 1.00 | 17.80 |
| 1118 | C | LEU | C | 485 | 85.183 | −24.271 | −17.086 | 1.00 | 21.13 |
| 1119 | O | LEU | C | 485 | 84.597 | −23.945 | −16.054 | 1.00 | 18.30 |
| 1120 | N | PRO | C | 486 | 85.219 | −25.536 | −17.506 | 1.00 | 20.05 |
| 1121 | CD | PRO | C | 486 | 85.787 | −26.024 | −18.775 | 1.00 | 19.33 |
| 1122 | CA | PRO | C | 486 | 84.585 | −26.615 | −16.746 | 1.00 | 23.66 |
| 1123 | CB | PRO | C | 486 | 85.001 | −27.865 | −17.509 | 1.00 | 21.88 |
| 1124 | CG | PRO | C | 486 | 85.128 | −27.364 | −18.931 | 1.00 | 21.50 |
| 1125 | C | PRO | C | 486 | 85.078 | −26.631 | −15.301 | 1.00 | 28.70 |
| 1126 | O | PRO | C | 486 | 86.283 | −26.502 | −15.039 | 1.00 | 30.57 |
| 1127 | N | ASP | C | 487 | 84.145 | −26.799 | −14.367 | 1.00 | 36.18 |
| 1128 | CA | ASP | C | 487 | 84.488 | −26.819 | −12.951 | 1.00 | 41.47 |
| 1129 | CB | ASP | C | 487 | 83.250 | −27.146 | −12.113 | 1.00 | 51.25 |
| 1130 | CG | ASP | C | 487 | 82.174 | −26.086 | −12.236 | 1.00 | 61.07 |
| 1131 | OD1 | ASP | C | 487 | 82.528 | −24.907 | −12.478 | 1.00 | 67.74 |
| 1132 | OD2 | ASP | C | 487 | 80.981 | −26.422 | −12.079 | 1.00 | 67.49 |
| 1133 | C | ASP | C | 487 | 85.608 | −27.796 | −12.619 | 1.00 | 38.82 |
| 1134 | O | ASP | C | 487 | 86.490 | −27.494 | −11.821 | 1.00 | 36.02 |
| 1135 | N | ALA | C | 488 | 85.583 | −28.961 | −13.252 | 1.00 | 37.06 |
| 1136 | CA | ALA | C | 488 | 86.583 | −29.991 | −13.004 | 1.00 | 35.54 |
| 1137 | CB | ALA | C | 488 | 86.201 | −31.260 | −13.746 | 1.00 | 34.70 |
| 1138 | C | ALA | C | 488 | 88.013 | −29.596 | −13.366 | 1.00 | 33.91 |
| 1139 | O | ALA | C | 488 | 88.965 | −30.281 | −12.996 | 1.00 | 33.94 |
| 1140 | N | ARG | C | 489 | 88.181 | −28.494 | −14.087 | 1.00 | 32.78 |
| 1141 | CA | ARG | C | 489 | 89.527 | −28.071 | −14.472 | 1.00 | 30.67 |
| 1142 | CB | ARG | C | 489 | 89.464 | −27.254 | −15.761 | 1.00 | 30.79 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1143 | CG | ARG | C | 489 | 89.774 | −28.111 | −16.991 | 1.00 | 31.30 |
| 1144 | CD | ARG | C | 489 | 91.135 | −27.761 | −17.562 | 1.00 | 31.69 |
| 1145 | NE | ARG | C | 489 | 90.939 | −27.052 | −18.813 | 1.00 | 35.53 |
| 1146 | CZ | ARG | C | 489 | 91.750 | −26.132 | −19.313 | 1.00 | 36.13 |
| 1147 | NH1 | ARG | C | 489 | 92.854 | −25.774 | −18.668 | 1.00 | 35.39 |
| 1148 | NH2 | ARG | C | 489 | 91.438 | −25.576 | −20.475 | 1.00 | 35.63 |
| 1149 | C | ARG | C | 489 | 90.326 | −27.334 | −13.397 | 1.00 | 29.25 |
| 1150 | O | ARG | C | 489 | 91.544 | −27.216 | −13.505 | 1.00 | 27.32 |
| 1151 | N | HIS | C | 490 | 89.648 | −26.870 | −12.352 | 1.00 | 27.01 |
| 1152 | CA | HIS | C | 490 | 90.325 | −26.170 | −11.274 | 1.00 | 27.07 |
| 1153 | CB | HIS | C | 490 | 89.942 | −24.683 | −11.250 | 1.00 | 24.30 |
| 1154 | CG | HIS | C | 490 | 88.518 | −24.435 | −10.834 | 1.00 | 26.61 |
| 1155 | CD2 | HIS | C | 490 | 87.961 | −24.361 | −9.607 | 1.00 | 26.96 |
| 1156 | ND1 | HIS | C | 490 | 87.504 | −24.275 | −11.745 | 1.00 | 26.60 |
| 1157 | CE1 | HIS | C | 490 | 86.359 | −24.109 | −11.089 | 1.00 | 23.01 |
| 1158 | NE2 | HIS | C | 490 | 86.606 | −24.157 | −9.804 | 1.00 | 27.55 |
| 1159 | C | HIS | C | A90 | 90.006 | −26.790 | −9.914 | 1.00 | 28.88 |
| 1160 | O | HIS | C | 490 | 89.030 | −27.528 | −9.748 | 1.00 | 24.79 |
| 1161 | N | SER | C | 491 | 90.843 | −26.462 | −8.938 | 1.00 | 30.63 |
| 1162 | CA | SER | C | 491 | 90.682 | −26.948 | −7.574 | 1.00 | 30.54 |
| 1163 | CB | SER | C | 491 | 91.860 | −27.846 | −7.214 | 1.00 | 33.14 |
| 1164 | OG | SER | C | 491 | 91.664 | −28.456 | −5.961 | 1.00 | 41.58 |
| 1165 | C | SER | C | 491 | 90.660 | −25.730 | −6.662 | 1.00 | 30.19 |
| 1166 | O | SER | C | 491 | 91.466 | −24.817 | −6.822 | 1.00 | 30.75 |
| 1167 | N | THR | C | 492 | 89.727 | −25.697 | −5.722 | 1.00 | 30.71 |
| 1168 | CA | THR | C | 492 | 89.630 | −24.571 | −4.798 | 1.00 | 28.20 |
| 1169 | CB | THR | C | 492 | 88.344 | −23.760 | −5.043 | 1.00 | 25.99 |
| 1170 | OG1 | THR | C | 492 | 88.463 | −23.034 | −6.271 | 1.00 | 26.31 |
| 1171 | CG2 | THR | C | 492 | 88.110 | −22.782 | −3.912 | 1.00 | 26.55 |
| 1172 | C | THR | C | 492 | 89.622 | −25.090 | −3.367 | 1.00 | 27.18 |
| 1173 | O | THR | C | 492 | 88.852 | −25.989 | −3.038 | 1.00 | 25.91 |
| 1174 | N | THR | C | 493 | 90.471 | −24.531 | −2.514 | 1.00 | 27.60 |
| 1175 | CA | THR | C | 493 | 90.544 | −24.979 | −1.118 | 1.00 | 29.86 |
| 1176 | CB | THR | C | 493 | 91.773 | −24.383 | −0.405 | 1.00 | 28.84 |
| 1177 | OG1 | THR | C | 493 | 91.575 | −22.973 | −0.206 | 1.00 | 25.63 |
| 1178 | CG2 | THR | C | 493 | 93.032 | −24.610 | −1.245 | 1.00 | 25.34 |
| 1179 | C | THR | C | 493 | 89.299 | −24.569 | −0.333 | 1.00 | 33.52 |
| 1180 | O | THR | C | 493 | 88.473 | −23.806 | −0.825 | 1.00 | 32.96 |
| 1181 | N | GLN | C | 494 | 89.160 | −25.081 | 0.885 | 1.00 | 37.70 |
| 1182 | CA | GLN | C | 494 | 88.008 | −24.728 | 1.715 | 1.00 | 40.89 |
| 1183 | CB | GLN | C | 494 | 87.701 | −25.826 | 2.739 | 1.00 | 52.33 |
| 1184 | CG | GLN | C | 494 | 87.198 | −27.127 | 2.118 | 1.00 | 72.52 |
| 1185 | CD | GLN | C | 494 | 85.686 | −27.280 | 2.173 | 1.00 | 82.33 |
| 1186 | OE1 | GLN | C | 494 | 85.106 | −27.408 | 3.256 | 1.00 | 89.23 |
| 1187 | NE2 | GLN | C | 494 | 85.037 | −27.274 | 1.007 | 1.00 | 88.21 |
| 1188 | C | GLN | C | 494 | 88.289 | −23.438 | 2.452 | 1.00 | 35.36 |
| 1189 | O | GLN | C | 494 | 89.420 | −23.194 | 2.899 | 1.00 | 32.68 |
| 1190 | N | PRO | C | 495 | 87.260 | −22.588 | 2.575 | 1.00 | 29.55 |
| 1191 | CD | PRO | C | 495 | 85.888 | −22.770 | 2.075 | 1.00 | 25.94 |
| 1192 | CA | PRO | C | 495 | 87.425 | −21.320 | 3.274 | 1.00 | 29.86 |
| 1193 | CB | PRO | C | 495 | 86.006 | −20.865 | 3.552 | 1.00 | 27.12 |
| 1194 | CG | PRO | C | 495 | 85.202 | −21.480 | 2.461 | 1.00 | 24.57 |
| 1195 | C | PRO | C | 495 | 88.146 | −21.654 | 4.544 | 1.00 | 32.54 |
| 1196 | O | PRO | C | 495 | 88.081 | −22.768 | 5.063 | 1.00 | 29.68 |
| 1197 | N | ALA | C | 496 | 88.821 | −20.675 | 5.069 | 1.00 | 38.38 |
| 1198 | CA | ALA | C | 496 | 89.560 | −20.939 | 6.253 | 1.00 | 45.23 |
| 1199 | CB | ALA | C | 496 | 90.760 | −21.813 | 5.925 | 1.00 | 52.88 |
| 1200 | C | ALA | C | 496 | 89.973 | −19.570 | 6.687 | 1.00 | 44.39 |
| 1201 | O | ALA | C | 496 | 90.285 | −18.700 | 5.865 | 1.00 | 42.47 |
| 1202 | N | LYS | C | 497 | 89.953 | −19.382 | 7.994 | 1.00 | 46.04 |
| 1203 | CA | LYS | C | 497 | 90.281 | −18.110 | 8.578 | 1.00 | 51.77 |
| 1204 | CB | LYS | C | 497 | 89.994 | −18.134 | 10.079 | 1.00 | 59.01 |
| 1205 | CG | LYS | C | 497 | 88.520 | −18.324 | 10.434 | 1.00 | 71.26 |
| 1206 | CD | LYS | C | 497 | 88.297 | −18.177 | 11.931 | 1.00 | 80.62 |
| 1207 | CE | LYS | C | 497 | 86.817 | −18.209 | 12.279 | 1.00 | 87.08 |
| 1208 | NZ | LYS | C | 497 | 86.587 | −18.074 | 13.747 | 1.00 | 92.05 |
| 1209 | C | LYS | C | 497 | 91.676 | −17.580 | 8.337 | 1.00 | 53.73 |
| 1210 | O | LYS | C | 497 | 92.671 | −18.314 | 8.305 | 1.00 | 50.77 |
| 1211 | N | THR | C | 498 | 91.673 | −16.261 | 8.166 | 1.00 | 55.49 |
| 1212 | CA | THR | C | 498 | 92.813 | −15.384 | 7.940 | 1.00 | 55.14 |
| 1213 | CB | THR | C | 498 | 92.309 | −13.989 | 7.537 | 1.00 | 57.01 |
| 1214 | OG1 | THR | C | 498 | 91.429 | −13.489 | 8.556 | 1.00 | 59.71 |
| 1215 | CG2 | THR | C | 498 | 91.549 | −14.062 | 6.231 | 1.00 | 60.70 |
| 1216 | C | THR | C | 498 | 93.494 | −15.283 | 9.295 | 1.00 | 58.27 |
| 1217 | O | THR | C | 498 | 93.925 | −16.293 | 9.843 | 1.00 | 54.79 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1218 | N | LYS | C | 499 | 93.596 | −14.074 | 9.837 | 1.00 | 59.56 |
| 1219 | CA | LYS | C | 499 | 94.186 | −13.891 | 11.162 | 1.00 | 65.17 |
| 1220 | CB | LYS | C | 499 | 95.638 | −13.387 | 11.068 | 1.00 | 65.40 |
| 1221 | CG | LYS | C | 499 | 96.515 | −14.114 | 10.060 | 1.00 | 63.87 |
| 1222 | CD | LYS | C | 499 | 97.706 | −14.771 | 10.729 | 1.00 | 67.65 |
| 1223 | CE | LYS | C | 499 | 98.353 | −15.774 | 9.791 | 1.00 | 70.73 |
| 1224 | NZ | LYS | C | 499 | 99.257 | −16.670 | 10.543 | 1.00 | 73.12 |
| 1225 | C | LYS | C | 499 | 93.333 | −12.878 | 11.939 | 1.00 | 70.55 |
| 1226 | O | LYS | C | 499 | 93.860 | −12.062 | 12.680 | 1.00 | 72.22 |
| 1227 | N | GLY | C | 500 | 92.016 | −12.966 | 11.766 | 1.00 | 85.13 |
| 1228 | CA | GLY | C | 500 | 91.048 | −12.071 | 12.396 | 1.00 | 101.43 |
| 1229 | C | GLY | C | 500 | 89.874 | −12.196 | 11.443 | 1.00 | 106.15 |
| 1230 | O | GLY | C | 500 | 90.048 | −11.910 | 10.258 | 1.00 | 116.31 |
| 1231 | N | SER | C | 501 | 88.692 | −12.582 | 11.927 | 1.00 | 105.33 |
| 1232 | CA | SER | C | 501 | 87.574 | −12.835 | 11.019 | 1.00 | 107.99 |
| 1233 | CB | SER | C | 501 | 86.198 | −12.705 | 11.680 | 1.00 | 116.05 |
| 1234 | OG | SER | C | 501 | 85.248 | −13.490 | 10.951 | 1.00 | 104.13 |
| 1235 | C | SER | C | 501 | 87.575 | −12.142 | 9.685 | 1.00 | 103.68 |
| 1236 | O | SER | C | 501 | 87.544 | −10.907 | 9.522 | 1.00 | 113.26 |
| 1237 | N | GLY | C | 502 | 87.638 | −13.077 | 8.753 | 1.00 | 97.40 |
| 1238 | CA | GLY | C | 502 | 87.697 | −12.902 | 7.333 | 1.00 | 74.16 |
| 1239 | C | GLY | C | 502 | 88.241 | −14.279 | 6.986 | 1.00 | 58.84 |
| 1240 | O | GLY | C | 502 | 88.945 | −14.918 | 7.785 | 1.00 | 50.25 |
| 1241 | N | PHE | C | 503 | 87.887 | −14.755 | 5.809 | 1.00 | 43.71 |
| 1242 | CA | PHE | C | 503 | 88.332 | −16.045 | 5.331 | 1.00 | 32.89 |
| 1243 | CB | PHE | C | 503 | 87.129 | −16.939 | 5.044 | 1.00 | 29.57 |
| 1244 | CG | PHE | C | 503 | 86.241 | −17.151 | 6.223 | 1.00 | 27.73 |
| 1245 | CD1 | PHE | C | 503 | 85.380 | −16.147 | 6.653 | 1.00 | 27.27 |
| 1246 | CD2 | PHE | C | 503 | 86.285 | −18.345 | 6.930 | 1.00 | 26.99 |
| 1247 | CE1 | PHE | C | 503 | 84.577 | −16.329 | 7.775 | 1.00 | 27.59 |
| 1248 | CE2 | PHE | C | 503 | 85.484 | −18.540 | 8.061 | 1.00 | 27.64 |
| 1249 | CZ | PHE | C | 503 | 84.628 | −17.528 | 8.485 | 1.00 | 27.08 |
| 1250 | C | PHE | C | 503 | 89.134 | −15.864 | 4.051 | 1.00 | 27.03 |
| 1251 | O | PHE | C | 503 | 89.116 | −14.802 | 3.422 | 1.00 | 27.31 |
| 1252 | N | PHE | C | 504 | 89.852 | −16.915 | 3.682 | 1.00 | 26.28 |
| 1253 | CA | PHE | C | 504 | 90.639 | −16.901 | 2.466 | 1.00 | 26.03 |
| 1254 | CB | PHE | C | 504 | 92.127 | −16.630 | 2.743 | 1.00 | 21.13 |
| 1255 | CG | PHE | C | 504 | 92.867 | −17.802 | 3.330 | 1.00 | 19.18 |
| 1256 | CD1 | PHE | C | 504 | 93.409 | −18.801 | 2.508 | 1.00 | 17.33 |
| 1257 | CD2 | PHE | C | 504 | 93.085 | −17.877 | 4.711 | 1.00 | 20.16 |
| 1258 | CE1 | PHE | C | 504 | 94.159 | −19.870 | 3.059 | 1.00 | 14.38 |
| 1259 | CE2 | PHE | C | 504 | 93.829 | −18.936 | 5.273 | 1.00 | 15.33 |
| 1260 | CZ | PHE | C | 504 | 94.372 | −19.926 | 4.444 | 1.00 | 15.36 |
| 1261 | C | PHE | C | 504 | 90.453 | −18.268 | 1.852 | 1.00 | 25.04 |
| 1262 | O | PHE | C | 504 | 90.145 | −19.244 | 2.550 | 1.00 | 27.80 |
| 1263 | N | VAL | C | 505 | 90.620 | −18.322 | 0.540 | 1.00 | 24.99 |
| 1264 | CA | VAL | C | 505 | 90.480 | −19.551 | −0.198 | 1.00 | 29.23 |
| 1265 | CB | VAL | C | 505 | 89.039 | −19.668 | −0.778 | 1.00 | 28.10 |
| 1266 | CG1 | VAL | C | 505 | 88.916 | −18.903 | −2.071 | 1.00 | 24.07 |
| 1267 | CG2 | VAL | C | 505 | 88.679 | −21.102 | −0.968 | 1.00 | 30.57 |
| 1268 | C | VAL | C | 505 | 91.514 | −19.475 | −1.324 | 1.00 | 25.44 |
| 1269 | O | VAL | C | 505 | 91.836 | −18.388 | −1.799 | 1.00 | 27.94 |
| 1270 | N | PHE | C | 506 | 92.061 | −20.613 | −1.726 | 1.00 | 22.46 |
| 1271 | CA | PHE | C | 506 | 93.026 | −20.632 | −2.817 | 1.00 | 27.75 |
| 1272 | CB | PHE | C | 506 | 94.330 | −21.295 | −2.376 | 1.00 | 30.76 |
| 1273 | CG | PHE | C | 506 | 95.355 | −20.344 | −1.800 | 1.00 | 29.31 |
| 1274 | CD1 | PHE | C | 506 | 95.647 | −20.353 | −0.434 | 1.00 | 29.10 |
| 1275 | CD2 | PHE | C | 506 | 96.073 | −19.488 | −2.630 | 1.00 | 28.63 |
| 1276 | CE1 | PHE | C | 506 | 96.645 | −19.533 | 0.091 | 1.00 | 30.45 |
| 1277 | CE2 | PHE | C | 506 | 97.079 | −18.659 | −2.110 | 1.00 | 32.55 |
| 1278 | CZ | PHE | C | 506 | 97.362 | −18.685 | −0.749 | 1.00 | 32.25 |
| 1279 | C | PHE | C | 506 | 92.443 | −21.439 | −3.972 | 1.00 | 24.97 |
| 1280 | O | PHE | C | 506 | 91.749 | −22.427 | −3.745 | 1.00 | 24.23 |
| 1281 | N | SER | C | 507 | 92.716 | −21.030 | −5.205 | 1.00 | 19.88 |
| 1282 | CA | SER | C | 507 | 92.221 | −21.772 | −6.357 | 1.00 | 18.82 |
| 1283 | CB | SER | C | 507 | 91.076 | −21.016 | −7.040 | 1.00 | 20.07 |
| 1284 | OG | SER | C | 507 | 90.316 | −21.896 | −7.859 | 1.00 | 23.21 |
| 1285 | C | SER | C | 507 | 93.366 | −22.000 | −7.338 | 1.00 | 17.34 |
| 1286 | O | SER | C | 507 | 94.110 | −21.073 | −7.655 | 1.00 | 16.61 |
| 1287 | N | ARG | C | 508 | 93.487 | −23.237 | −7.816 | 1.00 | 16.00 |
| 1288 | CA | ARG | C | 508 | 94.545 | −23.657 | −8.742 | 1.00 | 16.14 |
| 1289 | CB | ARG | C | 508 | 95.287 | −24.827 | −8.092 | 1.00 | 16.55 |
| 1290 | CG | ARG | C | 508 | 96.440 | −25.423 | −8.880 | 1.00 | 19.23 |
| 1291 | CD | ARG | C | 508 | 97.134 | −26.525 | −8.063 | 1.00 | 24.74 |
| 1292 | NE | ARG | C | 508 | 98.297 | −27.055 | −8.765 | 1.00 | 28.42 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1293 | CZ | ARG | C | 508 | 98.236 | −27.898 | −9.790 | 1.00 | 28.54 |
| 1294 | NH1 | ARG | C | 508 | 97.060 | −28.324 | −10.229 | 1.00 | 29.90 |
| 1295 | NH2 | ARG | C | 508 | 99.353 | −28.294 | −10.390 | 1.00 | 28.60 |
| 1296 | C | ARG | C | 508 | 94.006 | −24.073 | −10.138 | 1.00 | 14.18 |
| 1297 | O | ARG | C | 508 | 93.060 | −24.853 | −10.239 | 1.00 | 13.25 |
| 1298 | N | LEU | C | 509 | 94.598 | −23.558 | −11.210 | 1.00 | 14.14 |
| 1299 | CA | LEU | C | 509 | 94.150 | −23.931 | −12.558 | 1.00 | 19.36 |
| 1300 | CB | LEU | C | 509 | 93.265 | −22.842 | −13.171 | 1.00 | 16.34 |
| 1301 | CG | LEU | C | 509 | 92.949 | −23.031 | −14.668 | 1.00 | 19.57 |
| 1302 | CD1 | LEU | C | 509 | 91.999 | −24.227 | −14.858 | 1.00 | 19.04 |
| 1303 | CD2 | LEU | C | 509 | 92.341 | −21.742 | −15.242 | 1.00 | 12.89 |
| 1304 | C | LEU | C | 509 | 95.323 | −24.177 | −13.495 | 1.00 | 20.24 |
| 1305 | O | LEU | C | 509 | 96.087 | −23.252 | −13.784 | 1.00 | 21.24 |
| 1306 | N | GLU | C | 510 | 95.470 | −25.409 | −13.970 | 1.00 | 18.91 |
| 1307 | CA | GLU | C | 510 | 96.541 | −25.739 | −14.907 | 1.00 | 23.95 |
| 1308 | CB | GLU | C | 510 | 96.874 | −27.232 | −14.816 | 1.00 | 27.49 |
| 1309 | CG | GLU | C | 510 | 97.643 | −27.604 | −13.553 | 1.00 | 39.49 |
| 1310 | CD | GLU | C | 510 | 97.822 | −29.095 | −13.360 | 1.00 | 46.42 |
| 1311 | OE1 | GLU | C | 510 | 97.004 | −29.735 | −12.743 | 1.00 | 50.93 |
| 1312 | OE2 | GLU | C | 510 | 98.778 | −29.697 | −13.811 | 1.00 | 50.04 |
| 1313 | C | GLU | C | 510 | 96.111 | −25.387 | −16.339 | 1.00 | 23.25 |
| 1314 | O | GLU | C | 510 | 95.072 | −25.836 | −16.793 | 1.00 | 18.94 |
| 1315 | N | VAL | C | 511 | 96.890 | −24.580 | −17.052 | 1.00 | 23.09 |
| 1316 | CA | VAL | C | 511 | 96.518 | −24.243 | −18.424 | 1.00 | 23.47 |
| 1317 | CB | VAL | C | 511 | 96.447 | −22.707 | −18.638 | 1.00 | 22.07 |
| 1318 | CG1 | VAL | C | 511 | 95.483 | −22.096 | −17.643 | 1.00 | 22.01 |
| 1319 | CG2 | VAL | C | 511 | 97.827 | −22.090 | −18.515 | 1.00 | 19.66 |
| 1320 | C | VAL | C | 511 | 97.500 | −24.845 | −19.429 | 1.00 | 25.21 |
| 1321 | O | VAL | C | 511 | 98.617 | −25.202 | −19.066 | 1.00 | 24.58 |
| 1322 | N | THR | C | 512 | 97.089 | −24.962 | −20.690 | 1.00 | 30.24 |
| 1323 | CA | THR | C | 512 | 97.964 | −25.522 | −21.728 | 1.00 | 32.23 |
| 1324 | CB | THR | C | 512 | 97.211 | −26.478 | −22.646 | 1.00 | 34.13 |
| 1325 | OG1 | THR | C | 512 | 96.227 | −25.740 | −23.386 | 1.00 | 32.58 |
| 1326 | CG2 | THR | C | 512 | 96.530 | −27.578 | −21.829 | 1.00 | 34.63 |
| 1327 | C | THR | C | 512 | 98.550 | −24.434 | −22.614 | 1.00 | 34.98 |
| 1328 | O | THR | C | 512 | 98.059 | −23.302 | −22.641 | 1.00 | 36.66 |
| 1329 | N | ARG | C | 513 | 99.597 | −24.782 | −23.353 | 1.00 | 38.72 |
| 1330 | CA | ARG | C | 513 | 100.240 | −23.817 | −24.231 | 1.00 | 42.83 |
| 1331 | CB | ARG | C | 513 | 101.472 | −24.433 | −24.891 | 1.00 | 49.78 |
| 1332 | CG | ARG | C | 513 | 102.309 | −23.430 | −25.670 | 1.00 | 62.45 |
| 1333 | CD | ARG | C | 513 | 103.403 | −24.107 | −26.476 | 1.00 | 71.11 |
| 1334 | NE | ARG | C | 513 | 104.730 | −23.879 | −25.914 | 1.00 | 79.51 |
| 1335 | CZ | ARG | C | 513 | 105.231 | −22.676 | −25.645 | 1.00 | 83.20 |
| 1336 | NH1 | ARG | C | 513 | 104.514 | −21.586 | −25.881 | 1.00 | 85.26 |
| 1337 | NH2 | ARG | C | 513 | 106.453 | −22.559 | −25.149 | 1.00 | 85.74 |
| 1338 | C | ARG | C | 513 | 99.266 | −23.342 | −25.305 | 1.00 | 41.41 |
| 1339 | O | ARG | C | 513 | 99.248 | −22.161 | −25.668 | 1.00 | 38.31 |
| 1340 | N | ALA | C | 514 | 98.453 | −24.268 | −25.800 | 1.00 | 35.36 |
| 1341 | CA | ALA | C | 514 | 97.482 | −23.968 | −26.838 | 1.00 | 36.35 |
| 1342 | CB | ALA | C | 514 | 96.744 | −25.226 | −27.235 | 1.00 | 31.90 |
| 1343 | C | ALA | C | 514 | 96.500 | −22.927 | −26.344 | 1.00 | 37.00 |
| 1344 | O | ALA | C | 514 | 96.000 | −22.104 | −27.105 | 1.00 | 33.50 |
| 1345 | N | GLU | C | 515 | 96.215 | −22.969 | −25.056 | 1.00 | 34.55 |
| 1346 | CA | GLU | C | 515 | 95.297 | −22.004 | −24.499 | 1.00 | 34.21 |
| 1347 | CB | GLU | C | 515 | 94.753 | −22.505 | −23.156 | 1.00 | 32.86 |
| 1348 | CG | GLU | C | 515 | 93.946 | −23.805 | −23.268 | 1.00 | 37.39 |
| 1349 | CD | GLU | C | 515 | 93.445 | −24.316 | −21.932 | 1.00 | 38.78 |
| 1350 | OE1 | GLU | C | 515 | 92.461 | −23.755 | −21.431 | 1.00 | 42.29 |
| 1351 | OE2 | GLU | C | 515 | 94.035 | −25.268 | −21.376 | 1.00 | 41.87 |
| 1352 | C | GLU | C | 515 | 95.944 | −20.622 | −24.373 | 1.00 | 35.22 |
| 1353 | O | GLU | C | 515 | 95.222 | −19.631 | −24.391 | 1.00 | 33.16 |
| 1354 | N | TRP | C | 516 | 97.278 | −20.506 | −24.270 | 1.00 | 38.37 |
| 1355 | CA | TRP | C | 516 | 97.781 | −19.146 | −24.173 | 1.00 | 48.86 |
| 1356 | CB | TRP | C | 516 | 98.857 | −18.959 | −23.038 | 1.00 | 49.43 |
| 1357 | CG | TRP | C | 516 | 100.245 | −19.638 | −23.041 | 1.00 | 47.39 |
| 1358 | CD2 | TRP | C | 516 | 100.649 | −20.811 | −22.421 | 1.00 | 49.57 |
| 1359 | CE2 | TRP | C | 516 | 102.018 | −21.005 | −22.739 | 1.00 | 50.03 |
| 1360 | CE3 | TRP | C | 516 | 100.018 | −21.735 | −21.607 | 1.00 | 51.43 |
| 1361 | CD1 | TRP | C | 516 | 101.328 | −19.229 | −23.643 | 1.00 | 45.52 |
| 1362 | NE1 | TRP | C | 516 | 102.405 | −19.973 | −23.526 | 1.00 | 47.95 |
| 1363 | CZ2 | TRP | C | 516 | 102.751 | −22.082 | −22.296 | 1.00 | 54.08 |
| 1364 | CZ3 | TRP | C | 516 | 100.753 | −22.821 | −21.152 | 1.00 | 55.00 |
| 1365 | CH2 | TRP | C | 516 | 102.108 | −22.982 | −21.496 | 1.00 | 56.44 |
| 1366 | C | TRP | C | 516 | 98.010 | −18.355 | −25.486 | 1.00 | 52.80 |
| 1367 | O | TRP | C | 516 | 98.105 | −17.132 | −25.403 | 1.00 | 51.23 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1368 | N | GLU | C | 517 | 98.153 | −18.945 | −26.684 | 1.00 | 65.13 |
| 1369 | CA | GLU | C | 517 | 97.997 | −17.960 | −27.763 | 1.00 | 79.46 |
| 1370 | CB | GLU | C | 517 | 99.028 | −17.712 | −28.853 | 1.00 | 86.66 |
| 1371 | CG | GLU | C | 517 | 98.252 | −16.504 | −29.582 | 1.00 | 97.68 |
| 1372 | CD | GLU | C | 517 | 98.847 | −15.901 | −30.776 | 1.00 | 98.23 |
| 1373 | OE1 | GLU | C | 517 | 99.772 | −16.433 | −31.206 | 1.00 | 95.42 |
| 1374 | OE2 | GLU | C | 517 | 98.440 | −14.889 | −31.337 | 1.00 | 94.93 |
| 1375 | C | GLU | C | 517 | 96.717 | −18.210 | −28.495 | 1.00 | 82.34 |
| 1376 | O | GLU | C | 517 | 96.676 | −18.479 | −29.676 | 1.00 | 88.96 |
| 1377 | N | ALA | C | 518 | 95.659 | −18.133 | −27.728 | 1.00 | 77.72 |
| 1378 | CA | ALA | C | 518 | 94.321 | −18.220 | −28.230 | 1.00 | 65.71 |
| 1379 | CB | ALA | C | 518 | 93.577 | −19.366 | −27.591 | 1.00 | 61.60 |
| 1380 | C | ALA | C | 518 | 93.956 | −16.914 | −27.560 | 1.00 | 59.72 |
| 1381 | O | ALA | C | 518 | 93.098 | −16.165 | −28.022 | 1.00 | 54.70 |
| 1382 | N | LYS | C | 519 | 94.683 | −16.666 | −26.465 | 1.00 | 54.33 |
| 1383 | CA | LYS | C | 519 | 94.539 | −15.507 | −25.592 | 1.00 | 50.07 |
| 1384 | CB | LYS | C | 519 | 93.067 | −15.309 | −25.260 | 1.00 | 47.72 |
| 1385 | CG | LYS | C | 519 | 92.759 | −14.085 | −24.440 | 1.00 | 53.48 |
| 1386 | CD | LYS | C | 519 | 92.644 | −12.862 | −25.327 | 1.00 | 56.91 |
| 1387 | CE | LYS | C | 519 | 91.824 | −11.771 | −24.650 | 1.00 | 57.37 |
| 1388 | NZ | LYS | C | 519 | 91.984 | −10.468 | −25.337 | 1.00 | 59.86 |
| 1389 | C | LYS | C | 519 | 95.322 | −15.761 | −24.287 | 1.00 | 48.62 |
| 1390 | O | LYS | C | 519 | 94.944 | −16.611 | −23.475 | 1.00 | 45.82 |
| 1391 | N | ASP | C | 520 | 96.411 | −15.031 | −24.081 | 1.00 | 47.35 |
| 1392 | CA | ASP | C | 520 | 97.194 | −15.206 | −22.867 | 1.00 | 47.95 |
| 1393 | CB | ASP | C | 520 | 98.575 | −14.576 | −23.015 | 1.00 | 53.77 |
| 1394 | CG | ASP | C | 520 | 99.472 | −14.913 | −21.866 | 1.00 | 51.50 |
| 1395 | OD1 | ASP | C | 520 | 98.996 | −15.422 | −20.841 | 1.00 | 53.98 |
| 1396 | OD2 | ASP | C | 520 | 100.645 | −14.654 | −21.987 | 1.00 | 54.69 |
| 1397 | C | ASP | C | 520 | 96.468 | −14.574 | −21.674 | 1.00 | 45.24 |
| 1398 | O | ASP | C | 520 | 97.080 | −14.232 | −20.674 | 1.00 | 51.11 |
| 1399 | N | GLU | C | 521 | 95.153 | −14.436 | −21.776 | 1.00 | 43.17 |
| 1400 | CA | GLU | C | 521 | 94.393 | −13.847 | −20.691 | 1.00 | 38.29 |
| 1401 | CB | GLU | C | 521 | 93.540 | −12.687 | −21.201 | 1.00 | 43.50 |
| 1402 | CG | GLU | C | 521 | 92.848 | −11.967 | −20.037 | 1.00 | 51.55 |
| 1403 | CD | GLU | C | 521 | 92.365 | −10.690 | −20.443 | 1.00 | 56.21 |
| 1404 | OE1 | GLU | C | 521 | 92.725 | −10.458 | −21.482 | 1.00 | 60.23 |
| 1405 | OE2 | GLU | C | 521 | 91.665 | −9.876 | −19.878 | 1.00 | 59.88 |
| 1406 | C | GLU | C | 521 | 93.504 | −14.865 | −19.996 | 1.00 | 30.39 |
| 1407 | O | GLU | C | 521 | 92.779 | −15.603 | −20.644 | 1.00 | 31.53 |
| 1408 | N | PHE | C | 522 | 93.588 | −14.910 | −18.670 | 1.00 | 27.56 |
| 1409 | CA | PHE | C | 522 | 92.770 | −15.807 | −17.870 | 1.00 | 20.71 |
| 1410 | CB | PHE | C | 522 | 93.595 | −16.970 | −17.338 | 1.00 | 15.64 |
| 1411 | CG | PHE | C | 522 | 94.110 | −17.874 | −18.413 | 1.00 | 16.09 |
| 1412 | CD1 | PHE | C | 522 | 95.232 | −17.523 | −19.156 | 1.00 | 15.75 |
| 1413 | CD2 | PHE | C | 522 | 93.436 | −19.050 | −18.729 | 1.00 | 16.97 |
| 1414 | CE1 | PHE | C | 522 | 95.663 | −18.322 | −20.210 | 1.00 | 16.16 |
| 1415 | CE2 | PHE | C | 522 | 93.857 | −19.856 | −19.784 | 1.00 | 15.96 |
| 1416 | CZ | PHE | C | 522 | 94.978 | −19.493 | −20.524 | 1.00 | 15.41 |
| 1417 | C | PHE | C | 522 | 92.145 | −15.023 | −16.715 | 1.00 | 20.73 |
| 1418 | O | PHE | C | 522 | 92.760 | −14.126 | −16.143 | 1.00 | 22.63 |
| 1419 | N | ILE | C | 523 | 90.917 | −15.362 | −16.367 | 1.00 | 22.24 |
| 1420 | CA | ILE | C | 523 | 90.250 | −14.637 | −15.316 | 1.00 | 23.44 |
| 1421 | CB | ILE | C | 523 | 89.052 | −13.857 | −15.899 | 1.00 | 27.73 |
| 1422 | CG2 | ILE | C | 523 | 88.278 | −13.167 | −14.782 | 1.00 | 29.13 |
| 1423 | CG1 | ILE | C | 523 | 89.583 | −12.821 | −16.898 | 1.00 | 29.83 |
| 1424 | CD1 | ILE | C | 523 | 88.567 | −12.225 | −17.763 | 1.00 | 35.31 |
| 1425 | C | ILE | C | 523 | 89.795 | −15.472 | −14.138 | 1.00 | 22.77 |
| 1426 | O | ILE | C | 523 | 89.152 | −16.515 | −14.290 | 1.00 | 22.87 |
| 1427 | N | CYS | C | 524 | 90.168 | −15.011 | −12.953 | 1.00 | 22.54 |
| 1428 | CA | CYS | C | 524 | 89.766 | −15.673 | −11.733 | 1.00 | 21.44 |
| 1429 | C | CYS | C | 524 | 88.594 | −14.823 | −11.249 | 1.00 | 19.09 |
| 1430 | O | CYS | C | 524 | 88.713 | −13.595 | −11.076 | 1.00 | 20.03 |
| 1431 | CB | CYS | C | 524 | 90.897 | −15.669 | −10.699 | 1.00 | 20.47 |
| 1432 | SG | CYS | C | 524 | 90.345 | −16.294 | −9.082 | 1.00 | 16.22 |
| 1433 | N | ARG | C | 525 | 87.456 | −15.468 | −11.040 | 1.00 | 17.64 |
| 1434 | CA | ARG | C | 525 | 86.277 | −14.740 | −10.603 | 1.00 | 22.86 |
| 1435 | CB | ARG | C | 525 | 85.222 | −14.722 | −11.712 | 1.00 | 20.59 |
| 1436 | CG | ARG | C | 525 | 83.885 | −14.241 | −11.240 | 1.00 | 25.52 |
| 1437 | CD | ARG | C | 525 | 83.241 | −13.381 | −12.280 | 1.00 | 28.27 |
| 1438 | NE | ARG | C | 525 | 82.682 | −14.168 | −13.361 | 1.00 | 30.61 |
| 1439 | CZ | ARG | C | 525 | 82.436 | −13.693 | −14.578 | 1.00 | 34.81 |
| 1440 | NH1 | ARG | C | 525 | 82.707 | −12.433 | −14.881 | 1.00 | 37.98 |
| 1441 | NH2 | ARG | C | 525 | 81.903 | −14.478 | −15.497 | 1.00 | 36.72 |
| 1442 | C | ARG | C | 525 | 85.657 | −15.286 | −9.338 | 1.00 | 21.26 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1443 | O | ARG | C | 525 | 85.411 | −16.486 | −9.222 | 1.00 | 19.40 |
| 1444 | N | ALA | C | 526 | 85.378 | −14.378 | −8.412 | 1.00 | 18.08 |
| 1445 | CA | ALA | C | 526 | 84.775 | −14.726 | −7.151 | 1.00 | 19.27 |
| 1446 | CB | ALA | C | 526 | 85.611 | −14.158 | −5.999 | 1.00 | 18.76 |
| 1447 | C | ALA | C | 526 | 83.346 | −14.190 | −7.063 | 1.00 | 19.13 |
| 1448 | O | ALA | C | 526 | 83.090 | −12.999 | −7.327 | 1.00 | 17.81 |
| 1449 | N | VAL | C | 527 | 82.416 | −15.070 | −6.703 | 1.00 | 19.19 |
| 1450 | CA | VAL | C | 527 | 81.037 | −14.650 | −6.526 | 1.00 | 21.46 |
| 1451 | CB | VAL | C | 527 | 80.022 | −15.561 | −7.228 | 1.00 | 21.27 |
| 1452 | CG1 | VAL | C | 527 | 78.605 | −15.092 | −6.887 | 1.00 | 18.25 |
| 1453 | CG2 | VAL | C | 527 | 80.228 | −15.512 | −8.743 | 1.00 | 17.12 |
| 1454 | C | VAL | C | 527 | 80.793 | −14.701 | −5.034 | 1.00 | 21.09 |
| 1455 | O | VAL | C | 527 | 80.843 | −15.767 | −4.396 | 1.00 | 24.71 |
| 1456 | N | HIS | C | 528 | 80.559 | −13.526 | −4.473 | 1.00 | 22.76 |
| 1457 | CA | HIS | C | 528 | 80.328 | −13.402 | −3.051 | 1.00 | 24.19 |
| 1458 | CB | HIS | C | 528 | 81.647 | −13.111 | −2.325 | 1.00 | 22.10 |
| 1459 | CG | HIS | C | 528 | 81.518 | −13.042 | −0.826 | 1.00 | 19.24 |
| 1460 | CD2 | HIS | C | 528 | 81.844 | −13.938 | 0.128 | 1.00 | 20.87 |
| 1461 | ND1 | HIS | C | 528 | 81.033 | −11.930 | −0.189 | 1.00 | 20.78 |
| 1462 | CE1 | HIS | C | 528 | 81.072 | −12.141 | 1.124 | 1.00 | 20.09 |
| 1463 | NE2 | HIS | C | 528 | 81.555 | −13.338 | 1.345 | 1.00 | 20.07 |
| 1464 | C | HIS | C | 528 | 79.322 | −12.291 | −2.824 | 1.00 | 25.21 |
| 1465 | O | HIS | C | 528 | 79.339 | −11.234 | −3.465 | 1.00 | 21.88 |
| 1466 | N | GLU | C | 529 | 78.448 | −12.567 | −1.881 | 1.00 | 28.06 |
| 1467 | CA | GLU | C | 529 | 77.365 | −11.698 | −1.511 | 1.00 | 32.60 |
| 1468 | CB | GLU | C | 529 | 76.559 | −12.457 | −0.472 | 1.00 | 38.68 |
| 1469 | CG | GLU | C | 529 | 76.131 | −11.726 | 0.747 | 1.00 | 50.45 |
| 1470 | CD | GLU | C | 529 | 75.805 | −12.690 | 1.877 | 1.00 | 57.14 |
| 1471 | OE1 | GLU | C | 529 | 75.192 | −12.224 | 2.848 | 1.00 | 59.22 |
| 1472 | OE2 | GLU | C | 529 | 76.165 | −13.895 | 1.799 | 1.00 | 59.35 |
| 1473 | C | GLU | C | 529 | 77.686 | −10.273 | −1.069 | 1.00 | 33.48 |
| 1474 | O | GLU | C | 529 | 76.841 | −9.391 | −1.193 | 1.00 | 32.85 |
| 1475 | N | ALA | C | 530 | 78.896 | −10.026 | −0.583 | 1.00 | 31.33 |
| 1476 | CA | ALA | C | 530 | 79.245 | −8.678 | −0.152 | 1.00 | 30.16 |
| 1477 | CB | ALA | C | 530 | 80.093 | −8.734 | 1.124 | 1.00 | 28.28 |
| 1478 | C | ALA | C | 530 | 79.973 | −7.875 | −1.241 | 1.00 | 33.22 |
| 1479 | O | ALA | C | 530 | 80.187 | −6.688 | −1.081 | 1.00 | 31.00 |
| 1480 | N | ALA | C | 531 | 80.356 | −8.494 | −2.350 | 1.00 | 41.60 |
| 1481 | CA | ALA | C | 531 | 81.042 | −7.765 | −3.434 | 1.00 | 48.25 |
| 1482 | CB | ALA | C | 531 | 81.420 | −8.789 | −4.531 | 1.00 | 40.14 |
| 1483 | C | ALA | C | 531 | 80.182 | −6.600 | −4.051 | 1.00 | 50.69 |
| 1484 | O | ALA | C | 531 | 79.063 | −6.871 | −4.455 | 1.00 | 61.09 |
| 1485 | N | SER | C | 532 | 80.683 | −5.346 | −4.107 | 1.00 | 62.89 |
| 1486 | CA | SER | C | 532 | 80.006 | −4.133 | −4.686 | 1.00 | 80.85 |
| 1487 | CB | SER | C | 532 | 81.081 | −3.398 | −5.515 | 1.00 | 97.49 |
| 1488 | OG | SER | C | 532 | 81.707 | −4.310 | −6.416 | 1.00 | 101.29 |
| 1489 | C | SER | C | 532 | 78.719 | −4.414 | −5.525 | 1.00 | 82.81 |
| 1490 | O | SER | C | 532 | 77.710 | −4.903 | −4.985 | 1.00 | 92.28 |
| 1491 | N | PRO | C | 533 | 78.715 | −4.076 | −6.847 | 1.00 | 72.09 |
| 1492 | CD | PRO | C | 533 | 79.729 | −3.206 | −7.473 | 1.00 | 83.68 |
| 1493 | CA | PRO | C | 533 | 77.634 | −4.274 | −7.817 | 1.00 | 77.82 |
| 1494 | CB | PRO | C | 533 | 78.124 | −3.529 | −9.048 | 1.00 | 77.99 |
| 1495 | CG | PRO | C | 533 | 79.627 | −3.588 | −8.878 | 1.00 | 75.94 |
| 1496 | C | PRO | C | 533 | 77.606 | −5.746 | −8.212 | 1.00 | 77.18 |
| 1497 | O | PRO | C | 533 | 78.680 | −6.314 | −8.453 | 1.00 | 73.31 |
| 1498 | N | SER | C | 534 | 76.438 | −6.376 | −8.305 | 1.00 | 69.70 |
| 1499 | CA | SER | C | 534 | 76.358 | −7.757 | −8.792 | 1.00 | 61.89 |
| 1500 | CB | SER | C | 534 | 76.621 | −7.754 | −10.302 | 1.00 | 64.62 |
| 1501 | OG | SER | C | 534 | 77.543 | −6.740 | −10.680 | 1.00 | 75.36 |
| 1502 | C | SER | C | 534 | 77.165 | −8.878 | −8.142 | 1.00 | 54.32 |
| 1503 | O | SER | C | 534 | 77.442 | −9.898 | −8.775 | 1.00 | 51.84 |
| 1504 | N | GLN | C | 535 | 77.511 | −8.676 | −6.876 | 1.00 | 45.77 |
| 1505 | CA | GLN | C | 535 | 78.228 | −9.653 | −6.070 | 1.00 | 38.19 |
| 1506 | CB | GLN | C | 535 | 77.207 | −10.608 | −5.431 | 1.00 | 36.66 |
| 1507 | CG | GLN | C | 535 | 75.816 | −10.582 | −6.054 | 1.00 | 40.62 |
| 1508 | CD | GLN | C | 535 | 75.029 | −9.291 | −5.843 | 1.00 | 42.08 |
| 1509 | OE1 | GLN | C | 535 | 74.186 | −8.939 | −6.674 | 1.00 | 44.73 |
| 1510 | NE2 | GLN | C | 535 | 75.274 | −8.597 | −4.740 | 1.00 | 40.80 |
| 1511 | C | GLN | C | 535 | 79.335 | −10.450 | −6.764 | 1.00 | 34.50 |
| 1512 | O | GLN | C | 535 | 79.474 | −11.660 | −6.570 | 1.00 | 32.28 |
| 1513 | N | THR | C | 536 | 80.155 | −9.756 | −7.534 | 1.00 | 32.27 |
| 1514 | CA | THR | C | 536 | 81.220 | −10.424 | −8.254 | 1.00 | 31.82 |
| 1515 | CB | THR | C | 536 | 80.757 | −10.698 | −9.692 | 1.00 | 32.46 |
| 1516 | OG1 | THR | C | 536 | 81.838 | −11.221 | −10.464 | 1.00 | 35.52 |
| 1517 | CG2 | THR | C | 536 | 80.260 | −9.420 | −10.327 | 1.00 | 36.27 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1518 | C | THR | C | 536 | 82.508 | −9.596 | −8.261 | 1.00 | 30.84 |
| 1519 | O | THR | C | 536 | 82.468 | −8.377 | −8.370 | 1.00 | 32.10 |
| 1520 | N | VAL | C | 537 | 83.650 | −10.257 | −8.108 | 1.00 | 31.16 |
| 1521 | CA | VAL | C | 537 | 84.943 | −9.572 | −8.128 | 1.00 | 30.07 |
| 1522 | CB | VAL | C | 537 | 85.520 | −9.361 | −6.721 | 1.00 | 31.28 |
| 1523 | CG1 | VAL | C | 537 | 86.764 | −8.490 | −6.814 | 1.00 | 34.77 |
| 1524 | CG2 | VAL | C | 537 | 84.495 | −8.722 | −5.818 | 1.00 | 35.34 |
| 1525 | C | VAL | C | 537 | 85.910 | −10.468 | −8.885 | 1.00 | 26.02 |
| 1526 | O | VAL | C | 537 | 85.952 | −11.675 | −8.637 | 1.00 | 25.53 |
| 1527 | N | GLN | C | 538 | 86.703 | −9.895 | −9.786 | 1.00 | 20.90 |
| 1528 | CA | GLN | C | 538 | 87.619 | −10.724 | −10.556 | 1.00 | 21.95 |
| 1529 | CB | GLN | C | 538 | 86.956 | −11.109 | −11.887 | 1.00 | 20.04 |
| 1530 | CG | GLN | C | 538 | 86.685 | −9.932 | −12.821 | 1.00 | 18.99 |
| 1531 | CD | GLN | C | 538 | 85.853 | −10.324 | −14.034 | 1.00 | 21.83 |
| 1532 | OE1 | GLN | C | 538 | 84.759 | −10.890 | −13.898 | 1.00 | 18.18 |
| 1533 | NE2 | GLN | C | 538 | 86.360 | −10.026 | −15.229 | 1.00 | 20.19 |
| 1534 | C | GLN | C | 538 | 88.975 | −10.108 | −10.839 | 1.00 | 21.40 |
| 1535 | O | GLN | C | 538 | 89.157 | −8.906 | −10.715 | 1.00 | 17.72 |
| 1536 | N | ARG | C | 539 | 89.918 | −10.956 | −11.233 | 1.00 | 18.21 |
| 1537 | CA | ARG | C | 539 | 91.258 | −10.512 | −11.578 | 1.00 | 22.09 |
| 1538 | CB | ARG | C | 539 | 92.228 | −10.745 | −10.419 | 1.00 | 26.18 |
| 1539 | CG | ARG | C | 539 | 92.105 | −9.748 | −9.295 | 1.00 | 39.60 |
| 1540 | CD | ARG | C | 539 | 92.829 | −8.457 | −9.620 | 1.00 | 50.55 |
| 1541 | NE | ARG | C | 539 | 93.095 | −7.729 | −8.392 | 1.00 | 61.94 |
| 1542 | CZ | ARG | C | 539 | 93.676 | −6.541 | −8.326 | 1.00 | 67.98 |
| 1543 | NH1 | ARG | C | 539 | 94.067 | −5.911 | −9.422 | 1.00 | 72.06 |
| 1544 | NH2 | ARG | C | 539 | 93.875 | −5.984 | −7.146 | 1.00 | 71.65 |
| 1545 | C | ARG | C | 539 | 91.761 | −11.270 | −12.790 | 1.00 | 19.62 |
| 1546 | O | ARG | C | 539 | 91.602 | −12.486 | −12.884 | 1.00 | 19.09 |
| 1547 | N | ALA | C | 540 | 92.339 | −10.540 | −13.732 | 1.00 | 17.23 |
| 1548 | CA | ALA | C | 540 | 92.913 | −11.152 | −14.923 | 1.00 | 21.14 |
| 1549 | CB | ALA | C | 540 | 92.844 | −10.192 | −16.099 | 1.00 | 16.43 |
| 1550 | C | ALA | C | 540 | 94.373 | −11.466 | −14.627 | 1.00 | 23.30 |
| 1551 | O | ALA | C | 540 | 95.006 | −10.799 | −13.805 | 1.00 | 20.90 |
| 1552 | N | VAL | C | 541 | 94.903 | −12.477 | −15.293 | 1.00 | 21.36 |
| 1553 | CA | VAL | C | 541 | 96.288 | −12.859 | −15.100 | 1.00 | 29.16 |
| 1554 | CB | VAL | C | 541 | 96.463 | −13.944 | −13.999 | 1.00 | 28.40 |
| 1555 | CG1 | VAL | C | 541 | 96.040 | −15.299 | −14.494 | 1.00 | 29.40 |
| 1556 | CG2 | VAL | C | 541 | 97.907 | −14.000 | −13.563 | 1.00 | 30.46 |
| 1557 | C | VAL | C | 541 | 96.783 | −13.388 | −16.437 | 1.00 | 35.79 |
| 1558 | O | VAL | C | 541 | 96.021 | −14.013 | −17.184 | 1.00 | 29.87 |
| 1559 | N | SER | C | 542 | 98.043 | −13.131 | −16.761 | 1.00 | 32.27 |
| 1560 | CA | SER | C | 542 | 98.528 | −13.651 | −18.011 | 1.00 | 38.37 |
| 1561 | CB | SER | C | 542 | 98.407 | −12.569 | −19.078 | 1.00 | 38.89 |
| 1562 | OG | SER | C | 542 | 99.501 | −11.750 | −19.168 | 1.00 | 39.80 |
| 1563 | C | SER | C | 542 | 99.909 | −14.298 | −17.925 | 1.00 | 42.19 |
| 1564 | O | SER | C | 542 | 100.776 | −13.868 | −17.180 | 1.00 | 39.06 |
| 1565 | N | VAL | C | 543 | 100.089 | −15.379 | −18.656 | 1.00 | 43.61 |
| 1566 | CA | VAL | C | 543 | 101.323 | −16.209 | −18.648 | 1.00 | 46.55 |
| 1567 | CB | VAL | C | 543 | 100.953 | −17.597 | −19.233 | 1.00 | 44.22 |
| 1568 | CG1 | VAL | C | 543 | 102.120 | −18.523 | −19.174 | 1.00 | 45.92 |
| 1569 | CG2 | VAL | C | 543 | 99.757 | −18.172 | −18.508 | 1.00 | 45.26 |
| 1570 | C | VAL | C | 543 | 102.067 | −15.759 | −19.872 | 1.00 | 53.54 |
| 1571 | O | VAL | C | 543 | 102.671 | −16.446 | −20.515 | 1.00 | 54.87 |
| 1572 | N | ASN | C | 544 | 102.355 | −14.689 | −20.314 | 1.00 | 59.76 |
| 1573 | CA | ASN | C | 544 | 102.582 | −14.893 | −21.623 | 1.00 | 63.60 |
| 1574 | CB | ASN | C | 544 | 103.797 | −13.844 | −20.830 | 1.00 | 63.23 |
| 1575 | CG | ASN | C | 544 | 103.236 | −12.086 | −19.032 | 1.00 | 66.79 |
| 1576 | OD1 | ASN | C | 544 | 102.256 | −11.548 | −19.203 | 1.00 | 69.16 |
| 1577 | ND2 | ASN | C | 544 | 104.003 | −11.523 | −17.720 | 1.00 | 68.95 |
| 1578 | C | ASN | C | 544 | 101.900 | −16.640 | −23.336 | 1.00 | 67.91 |
| 1579 | O | ASN | C | 544 | 102.712 | −17.134 | −24.025 | 1.00 | 67.41 |
| 1580 | OXT | ASN | C | 544 | 101.553 | −17.654 | −24.163 | 1.00 | 65.86 |
| 1581 | CB | VAL | D | 336 | 84.302 | −43.159 | 17.931 | 1.00 | 58.76 |
| 1582 | CG1 | VAL | D | 336 | 85.708 | −43.387 | 18.459 | 1.00 | 57.54 |
| 1583 | CG2 | VAL | D | 336 | 83.359 | −42.798 | 19.067 | 1.00 | 58.46 |
| 1584 | C | VAL | D | 336 | 85.338 | −42.408 | 15.815 | 1.00 | 60.25 |
| 1585 | O | VAL | D | 336 | 85.583 | −43.587 | 15.578 | 1.00 | 62.02 |
| 1586 | N | VAL | D | 336 | 82.960 | −41.840 | 16.273 | 1.00 | 59.61 |
| 1587 | CA | VAL | D | 336 | 84.310 | −42.036 | 16.873 | 1.00 | 59.84 |
| 1588 | N | SER | D | 337 | 85.937 | −41.409 | 15.173 | 1.00 | 60.56 |
| 1589 | CA | SER | D | 337 | 86.949 | −41.678 | 14.155 | 1.00 | 61.12 |
| 1590 | CB | SER | D | 337 | 86.878 | −40.630 | 13.038 | 1.00 | 61.70 |
| 1591 | OG | SER | D | 337 | 87.005 | −39.318 | 13.551 | 1.00 | 60.40 |
| 1592 | C | SER | D | 337 | 88.365 | −41.719 | 14.744 | 1.00 | 59.93 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1593 | O | SER | D | 337 | 88.667 | −41.056 | 15.738 | 1.00 | 61.88 |
| 1594 | N | ALA | D | 338 | 89.225 | −42.522 | 14.128 | 1.00 | 58.20 |
| 1595 | CA | ALA | D | 338 | 90.605 | −42.662 | 14.566 | 1.00 | 55.78 |
| 1596 | CB | ALA | D | 338 | 90.850 | −44.079 | 15.070 | 1.00 | 54.94 |
| 1597 | C | ALA | D | 338 | 91.521 | −42.346 | 13.384 | 1.00 | 55.44 |
| 1598 | O | ALA | D | 338 | 91.211 | −42.684 | 12.240 | 1.00 | 55.25 |
| 1599 | N | TYR | D | 339 | 92.637 | −41.677 | 13.658 | 1.00 | 55.77 |
| 1600 | CA | TYR | D | 339 | 93.586 | −41.321 | 12.606 | 1.00 | 56.21 |
| 1601 | CB | TYR | D | 339 | 93.435 | −39.843 | 12.227 | 1.00 | 66.14 |
| 1602 | CG | TYR | D | 339 | 92.010 | −39.373 | 11.983 | 1.00 | 76.80 |
| 1603 | CD1 | TYR | D | 339 | 91.089 | −39.313 | 13.028 | 1.00 | 81.98 |
| 1604 | CE1 | TYR | D | 339 | 89.790 | −38.858 | 12.818 | 1.00 | 87.48 |
| 1605 | CD2 | TYR | D | 339 | 91.592 | −38.967 | 10.713 | 1.00 | 80.76 |
| 1606 | CE2 | TYR | D | 339 | 90.293 | −38.510 | 10.493 | 1.00 | 86.32 |
| 1607 | CZ | TYR | D | 339 | 89.397 | −38.458 | 11.549 | 1.00 | 88.48 |
| 1608 | OH | TYR | D | 339 | 88.114 | −38.002 | 11.342 | 1.00 | 91.63 |
| 1609 | C | TYR | D | 339 | 95.029 | −41.589 | 13.060 | 1.00 | 52.08 |
| 1610 | O | TYR | D | 339 | 95.356 | −41.465 | 14.241 | 1.00 | 50.66 |
| 1611 | N | LEU | D | 340 | 95.887 | −41.957 | 12.114 | 1.00 | 46.59 |
| 1612 | CA | LEU | D | 340 | 97.284 | −42.240 | 12.411 | 1.00 | 42.69 |
| 1613 | CB | LEU | D | 340 | 97.532 | −43.746 | 12.405 | 1.00 | 39.27 |
| 1614 | CG | LEU | D | 340 | 98.949 | −44.171 | 12.796 | 1.00 | 35.03 |
| 1615 | CD1 | LEU | D | 340 | 99.236 | −43.701 | 14.212 | 1.00 | 32.59 |
| 1616 | CD2 | LEU | D | 340 | 99.087 | −45.670 | 12.715 | 1.00 | 31.89 |
| 1617 | C | LEU | D | 340 | 98.143 | −41.576 | 11.347 | 1.00 | 42.71 |
| 1618 | O | LEU | D | 340 | 98.048 | −41.915 | 10.172 | 1.00 | 43.41 |
| 1619 | N | SER | D | 341 | 98.995 | −40.646 | 11.760 | 1.00 | 41.52 |
| 1620 | CA | SER | D | 341 | 99.828 | −39.910 | 10.820 | 1.00 | 41.73 |
| 1621 | CB | SER | D | 341 | 99.876 | −38.435 | 11.222 | 1.00 | 44.12 |
| 1622 | OG | SER | D | 341 | 100.619 | −38.273 | 12.420 | 1.00 | 48.45 |
| 1623 | C | SER | D | 341 | 101.258 | −40.418 | 10.685 | 1.00 | 40.53 |
| 1624 | O | SER | D | 341 | 101.745 | −41.199 | 11.500 | 1.00 | 40.74 |
| 1625 | N | ARG | D | 342 | 101.929 | −39.950 | 9.640 | 1.00 | 35.08 |
| 1626 | CA | ARG | D | 342 | 103.302 | −40.338 | 9.415 | 1.00 | 33.02 |
| 1627 | CB | ARG | D | 342 | 103.570 | −40.544 | 7.922 | 1.00 | 30.94 |
| 1628 | CG | ARG | D | 342 | 102.845 | −41.736 | 7.330 | 1.00 | 29.83 |
| 1629 | CD | ARG | D | 342 | 103.241 | −41.980 | 5.877 | 1.00 | 32.98 |
| 1630 | NE | ARG | D | 342 | 102.761 | −40.945 | 4.958 | 1.00 | 35.86 |
| 1631 | CZ | ARG | D | 342 | 101.495 | −40.795 | 4.570 | 1.00 | 37.69 |
| 1632 | NH1 | ARG | D | 342 | 100.550 | −41.616 | 5.014 | 1.00 | 38.68 |
| 1633 | NH2 | ARG | D | 342 | 101.172 | −39.814 | 3.736 | 1.00 | 40.01 |
| 1634 | C | ARG | D | 342 | 104.178 | −39.221 | 9.955 | 1.00 | 31.34 |
| 1635 | O | ARG | D | 342 | 103.734 | −38.099 | 10.167 | 1.00 | 33.20 |
| 1636 | N | PRO | D | 343 | 105.442 | −39.516 | 10.194 | 1.00 | 29.21 |
| 1637 | CD | PRO | D | 343 | 106.127 | −40.808 | 10.044 | 1.00 | 28.52 |
| 1638 | CA | PRO | D | 343 | 106.318 | −38.463 | 10.711 | 1.00 | 28.69 |
| 1639 | CB | PRO | D | 343 | 107.677 | −39.146 | 10.806 | 1.00 | 26.91 |
| 1640 | CG | PRO | D | 343 | 107.357 | −40.627 | 10.879 | 1.00 | 29.66 |
| 1641 | C | PRO | D | 343 | 106.380 | −37.279 | 9.749 | 1.00 | 27.23 |
| 1642 | O | PRO | D | 343 | 106.330 | −37.460 | 8.542 | 1.00 | 29.08 |
| 1643 | N | SER | D | 344 | 106.489 | −36.069 | 10.272 | 1.00 | 26.12 |
| 1644 | CA | SER | D | 344 | 106.620 | −34.911 | 9.403 | 1.00 | 24.17 |
| 1645 | CB | SER | D | 344 | 106.474 | −33.607 | 10.206 | 1.00 | 25.98 |
| 1646 | OG | SER | D | 344 | 107.721 | −33.192 | 10.755 | 1.00 | 22.47 |
| 1647 | C | SER | D | 344 | 108.049 | −35.009 | 8.852 | 1.00 | 22.06 |
| 1648 | O | SER | D | 344 | 108.982 | −35.365 | 9.583 | 1.00 | 22.60 |
| 1649 | N | PRO | D | 345 | 108.243 | −34.681 | 7.565 | 1.00 | 21.57 |
| 1650 | CD | PRO | D | 345 | 107.213 | −34.265 | 6.597 | 1.00 | 20.34 |
| 1651 | CA | PRO | D | 345 | 109.577 | −34.748 | 6.949 | 1.00 | 22.11 |
| 1652 | CB | PRO | D | 345 | 109.358 | −34.181 | 5.545 | 1.00 | 20.00 |
| 1653 | CG | PRO | D | 345 | 107.912 | −34.446 | 5.267 | 1.00 | 17.37 |
| 1654 | C | PRO | D | 345 | 110.622 | −33.942 | 7.705 | 1.00 | 23.14 |
| 1655 | O | PRO | D | 345 | 111.807 | −34.284 | 7.699 | 1.00 | 23.02 |
| 1656 | N | PHE | D | 346 | 110.170 | −32.859 | 8.332 | 1.00 | 24.41 |
| 1657 | CA | PHE | D | 346 | 111.056 | −31.989 | 9.076 | 1.00 | 25.62 |
| 1658 | CB | PHE | D | 346 | 110.301 | −30.725 | 9.516 | 1.00 | 28.17 |
| 1659 | CG | PHE | D | 346 | 111.101 | −29.811 | 10.414 | 1.00 | 30.36 |
| 1660 | CD1 | PHE | D | 346 | 112.377 | −29.386 | 10.048 | 1.00 | 33.03 |
| 1661 | CD2 | PHE | D | 346 | 110.578 | −29.373 | 11.630 | 1.00 | 33.37 |
| 1662 | CE1 | PHE | D | 346 | 113.115 | −28.543 | 10.874 | 1.00 | 32.20 |
| 1663 | CE2 | PHE | D | 346 | 111.312 | −28.526 | 12.465 | 1.00 | 32.12 |
| 1664 | CZ | PHE | D | 346 | 112.582 | −28.116 | 12.083 | 1.00 | 33.51 |
| 1665 | C | PHE | D | 346 | 111.590 | −32.761 | 10.276 | 1.00 | 25.85 |
| 1666 | O | PHE | D | 346 | 112.805 | −32.849 | 10.473 | 1.00 | 25.72 |
| 1667 | N | ASP | D | 347 | 110.686 | −33.318 | 11.080 | 1.00 | 26.93 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1668 | CA | ASP | D | 347 | 111.096 | −34.104 | 12.244 | 1.00 | 29.39 |
| 1669 | CB | ASP | D | 347 | 109.876 | −34.630 | 12.987 | 1.00 | 26.02 |
| 1670 | CG | ASP | D | 347 | 109.156 | −33.551 | 13.744 | 1.00 | 25.82 |
| 1671 | OD1 | ASP | D | 347 | 108.010 | −33.791 | 14.166 | 1.00 | 22.02 |
| 1672 | OD2 | ASP | D | 347 | 109.737 | −32.462 | 13.933 | 1.00 | 27.72 |
| 1673 | C | ASP | D | 347 | 111.974 | −35.282 | 11.822 | 1.00 | 29.70 |
| 1674 | O | ASP | D | 347 | 112.960 | −35.608 | 12.489 | 1.00 | 30.98 |
| 1675 | N | LEU | D | 348 | 111.621 | −35.897 | 10.697 | 1.00 | 31.01 |
| 1676 | CA | LEU | D | 348 | 112.351 | −37.052 | 10.187 | 1.00 | 32.66 |
| 1677 | CB | LEU | D | 348 | 111.503 | −37.764 | 9.136 | 1.00 | 27.31 |
| 1678 | CG | LEU | D | 348 | 112.056 | −39.069 | 8.555 | 1.00 | 26.43 |
| 1679 | CD1 | LEU | D | 348 | 112.076 | −40.155 | 9.643 | 1.00 | 20.53 |
| 1680 | CD2 | LEU | D | 348 | 111.179 | −39.515 | 7.367 | 1.00 | 21.35 |
| 1681 | C | LEU | D | 348 | 113.746 | −36.792 | 9.607 | 1.00 | 33.63 |
| 1682 | O | LEU | D | 348 | 114.718 | −37.454 | 9.990 | 1.00 | 35.14 |
| 1683 | N | PHE | D | 349 | 113.856 | −35.825 | 8.702 | 1.00 | 33.30 |
| 1684 | CA | PHE | D | 349 | 115.127 | −35.552 | 8.040 | 1.00 | 34.43 |
| 1685 | CB | PHE | D | 349 | 114.855 | −35.273 | 6.568 | 1.00 | 33.49 |
| 1686 | CG | PHE | D | 349 | 114.184 | −36.411 | 5.866 | 1.00 | 34.47 |
| 1687 | CD1 | PHE | D | 349 | 112.891 | −36.281 | 5.362 | 1.00 | 34.39 |
| 1688 | CD2 | PHE | D | 349 | 114.845 | −37.625 | 5.707 | 1.00 | 33.66 |
| 1689 | CE1 | PHE | D | 349 | 112.267 | −37.355 | 4.711 | 1.00 | 33.08 |
| 1690 | CE2 | PHE | D | 349 | 114.237 | −38.690 | 5.067 | 1.00 | 33.68 |
| 1691 | CZ | PHE | D | 349 | 112.945 | −38.558 | 4.563 | 1.00 | 33.38 |
| 1692 | C | PHE | D | 349 | 116.051 | −34.465 | 8.588 | 1.00 | 34.94 |
| 1693 | O | PHE | D | 349 | 117.275 | −34.554 | 8.437 | 1.00 | 33.25 |
| 1694 | N | ILE | D | 350 | 115.478 | −33.444 | 9.213 | 1.00 | 34.20 |
| 1695 | CA | ILE | D | 350 | 116.268 | −32.345 | 9.747 | 1.00 | 33.47 |
| 1696 | CB | ILE | D | 350 | 115.556 | −30.998 | 9.458 | 1.00 | 32.84 |
| 1697 | CG2 | ILE | D | 350 | 116.414 | −29.830 | 9.952 | 1.00 | 30.51 |
| 1698 | CG1 | ILE | D | 350 | 115.262 | −30.876 | 7.956 | 1.00 | 30.26 |
| 1699 | CD1 | ILE | D | 350 | 116.481 | −31.043 | 7.073 | 1.00 | 30.05 |
| 1700 | C | ILE | D | 350 | 116.516 | −32.465 | 11.259 | 1.00 | 36.78 |
| 1701 | O | ILE | D | 350 | 117.657 | −32.542 | 11.721 | 1.00 | 35.60 |
| 1702 | N | ARG | D | 351 | 115.421 | −32.473 | 12.009 | 1.00 | 39.33 |
| 1703 | CA | ARG | D | 351 | 115.431 | −32.561 | 13.455 | 1.00 | 43.08 |
| 1704 | CB | ARG | D | 351 | 114.028 | −32.276 | 13.956 | 1.00 | 46.44 |
| 1705 | CG | ARG | D | 351 | 114.016 | −31.639 | 15.281 | 1.00 | 52.29 |
| 1706 | CD | ARG | D | 351 | 112.931 | −30.623 | 15.361 | 1.00 | 57.72 |
| 1707 | NE | ARG | D | 351 | 111.951 | −30.908 | 16.393 | 1.00 | 64.10 |
| 1708 | CZ | ARG | D | 351 | 112.148 | −31.702 | 17.434 | 1.00 | 68.04 |
| 1709 | NH1 | ARG | D | 351 | 113.277 | −32.308 | 17.594 | 1.00 | 68.89 |
| 1710 | NH2 | ARG | D | 351 | 111.226 | −31.882 | 18.347 | 1.00 | 70.36 |
| 1711 | C | ARG | D | 351 | 115.886 | −33.938 | 13.925 | 1.00 | 45.25 |
| 1712 | O | ARG | D | 351 | 116.347 | −34.109 | 15.055 | 1.00 | 46.32 |
| 1713 | N | LYS | D | 352 | 115.728 | −34.919 | 13.046 | 1.00 | 47.38 |
| 1714 | CA | LYS | D | 352 | 116.129 | −36.286 | 13.319 | 1.00 | 49.55 |
| 1715 | CB | LYS | D | 352 | 117.648 | −36.354 | 13.494 | 1.00 | 58.43 |
| 1716 | CG | LYS | D | 352 | 118.445 | −35.849 | 12.299 | 1.00 | 70.86 |
| 1717 | CD | LYS | D | 352 | 118.428 | −36.832 | 11.171 | 1.00 | 82.29 |
| 1718 | CE | LYS | D | 352 | 119.211 | −36.285 | 10.009 | 1.00 | 89.34 |
| 1719 | NZ | LYS | D | 352 | 119.201 | −37.111 | 8.885 | 1.00 | 93.88 |
| 1720 | C | LYS | D | 352 | 115.445 | −36.939 | 14.513 | 1.00 | 46.54 |
| 1721 | O | LYS | D | 352 | 116.058 | −37.741 | 15.217 | 1.00 | 45.74 |
| 1722 | N | SER | D | 353 | 114.186 | −36.593 | 14.755 | 1.00 | 41.63 |
| 1723 | CA | SER | D | 353 | 113.449 | −37.223 | 15.840 | 1.00 | 38.78 |
| 1724 | CB | SER | D | 353 | 113.643 | −36.484 | 17.167 | 1.00 | 38.10 |
| 1725 | OG | SER | D | 353 | 112.905 | −35.298 | 17.221 | 1.00 | 44.86 |
| 1726 | C | SER | D | 353 | 111.979 | −37.309 | 15.454 | 1.00 | 35.13 |
| 1727 | O | SER | D | 353 | 111.138 | −36.510 | 15.872 | 1.00 | 31.32 |
| 1728 | N | PRO | D | 354 | 111.660 | −38.305 | 14.622 | 1.00 | 31.87 |
| 1729 | CD | PRO | D | 354 | 112.619 | −39.313 | 14.144 | 1.00 | 32.58 |
| 1730 | CA | PRO | D | 354 | 110.310 | −38.575 | 14.117 | 1.00 | 29.81 |
| 1731 | CB | PRO | D | 354 | 110.526 | −39.683 | 13.077 | 1.00 | 30.28 |
| 1732 | CG | PRO | D | 354 | 112.023 | −39.710 | 12.837 | 1.00 | 34.34 |
| 1733 | C | PRO | D | 354 | 109.379 | −39.049 | 15.228 | 1.00 | 28.23 |
| 1734 | O | PRO | D | 354 | 109.829 | −39.591 | 16.234 | 1.00 | 23.37 |
| 1735 | N | THR | D | 355 | 108.083 | −38.831 | 15.033 | 1.00 | 25.66 |
| 1736 | CA | THR | D | 355 | 107.058 | −39.272 | 15.968 | 1.00 | 24.42 |
| 1737 | CB | THR | D | 355 | 100.677 | −38.205 | 17.009 | 1.00 | 27.14 |
| 1738 | OG1 | THR | D | 355 | 106.079 | −37.088 | 16.341 | 1.00 | 34.55 |
| 1739 | CG2 | THR | D | 355 | 107.897 | −37.746 | 17.790 | 1.00 | 31.95 |
| 1740 | C | THR | D | 355 | 105.829 | −39.484 | 15.115 | 1.00 | 25.05 |
| 1741 | O | THR | D | 355 | 105.725 | −38.928 | 14.025 | 1.00 | 24.59 |
| 1742 | N | ILE | D | 356 | 104.899 | −40.295 | 15.587 | 1.00 | 25.15 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1743 | CA | ILE | D | 356 | 103.680 | −40.503 | 14.839 | 1.00 | 24.30 |
| 1744 | CB | ILE | D | 356 | 103.587 | −41.929 | 14.250 | 1.00 | 25.53 |
| 1745 | CG2 | ILE | D | 356 | 104.761 | −42.172 | 13.303 | 1.00 | 28.10 |
| 1746 | CG1 | ILE | D | 356 | 103.567 | −42.969 | 15.368 | 1.00 | 28.57 |
| 1747 | CD1 | ILE | D | 356 | 103.530 | −44.392 | 14.851 | 1.00 | 30.63 |
| 1748 | C | ILE | D | 356 | 102.568 | −40.251 | 15.830 | 1.00 | 24.83 |
| 1749 | O | ILE | D | 356 | 102.751 | −40.424 | 17.046 | 1.00 | 25.59 |
| 1750 | N | THR | D | 357 | 101.419 | −39.829 | 15.318 | 1.00 | 24.58 |
| 1751 | CA | THR | D | 357 | 100.322 | −39.517 | 16.196 | 1.00 | 28.82 |
| 1752 | CB | THR | D | 357 | 100.068 | −38.008 | 16.221 | 1.00 | 28.39 |
| 1753 | OG1 | THR | D | 357 | 101.260 | −37.343 | 16.653 | 1.00 | 27.48 |
| 1754 | CG2 | THR | D | 357 | 98.940 | −37.680 | 17.166 | 1.00 | 26.19 |
| 1755 | C | THR | D | 357 | 99.032 | −40.222 | 15.875 | 1.00 | 31.65 |
| 1756 | O | THR | D | 357 | 98.597 | −40.261 | 14.721 | 1.00 | 28.26 |
| 1757 | N | CYS | D | 358 | 98.446 | −40.788 | 16.928 | 1.00 | 34.06 |
| 1758 | CA | CYS | D | 358 | 97.173 | −41.485 | 16.861 | 1.00 | 37.23 |
| 1759 | C | CYS | D | 358 | 96.170 | −40.442 | 17.389 | 1.00 | 38.61 |
| 1760 | O | CYS | D | 358 | 96.258 | −40.009 | 18.540 | 1.00 | 34.14 |
| 1761 | CB | CYS | D | 358 | 97.173 | −42.755 | 17.759 | 1.00 | 41.17 |
| 1762 | SG | CYS | D | 358 | 95.858 | −43.968 | 17.340 | 1.00 | 49.40 |
| 1763 | N | LEU | D | 359 | 95.240 | −40.023 | 16.532 | 1.00 | 41.57 |
| 1764 | CA | LEU | D | 359 | 94.227 | −39.035 | 16.896 | 1.00 | 43.10 |
| 1765 | CB | LEU | D | 359 | 94.252 | −37.879 | 15.891 | 1.00 | 43.38 |
| 1766 | CG | LEU | D | 359 | 93.075 | −36.900 | 15.931 | 1.00 | 45.36 |
| 1757 | CD1 | LEU | D | 359 | 92.983 | −36.242 | 17.296 | 1.00 | 44.04 |
| 1768 | CD2 | LEU | D | 359 | 93.250 | −35.853 | 14.829 | 1.00 | 45.14 |
| 1769 | C | LEU | D | 359 | 92.839 | −39.669 | 16.942 | 1.00 | 44.26 |
| 1770 | O | LEU | D | 359 | 92.349 | −40.201 | 15.946 | 1.00 | 46.90 |
| 1771 | N | VAL | D | 360 | 92.205 | −39.599 | 18.108 | 1.00 | 49.48 |
| 1772 | CA | VAL | D | 360 | 90.884 | −40.185 | 18.308 | 1.00 | 53.72 |
| 1773 | CB | VAL | D | 360 | 90.901 | −41.138 | 19.516 | 1.00 | 47.04 |
| 1774 | CG1 | VAL | D | 360 | 89.518 | −41.703 | 19.774 | 1.00 | 37.46 |
| 1775 | CG2 | VAL | D | 360 | 91.893 | −42.258 | 19.254 | 1.00 | 38.87 |
| 1776 | C | VAL | D | 360 | 89.793 | −39.144 | 18.509 | 1.00 | 60.67 |
| 1777 | O | VAL | D | 360 | 89.778 | −38.429 | 19.508 | 1.00 | 62.09 |
| 1778 | N | VAL | D | 361 | 88.868 | −39.077 | 17.558 | 1.00 | 70.77 |
| 1779 | CA | VAL | D | 361 | 87.789 | −38.112 | 17.655 | 1.00 | 82.04 |
| 1780 | CB | VAL | D | 361 | 87.603 | −37.358 | 16.310 | 1.00 | 83.57 |
| 1781 | CG1 | VAL | D | 361 | 86.440 | −36.382 | 16.412 | 1.00 | 85.44 |
| 1782 | CG2 | VAL | D | 361 | 88.894 | −36.606 | 15.951 | 1.00 | 85.26 |
| 1783 | C | VAL | D | 361 | 86.456 | −38.713 | 18.112 | 1.00 | 88.45 |
| 1784 | O | VAL | D | 361 | 85.999 | −39.732 | 17.587 | 1.00 | 89.07 |
| 1785 | N | ASP | D | 362 | 85.878 | −38.064 | 19.127 | 1.00 | 94.20 |
| 1786 | CA | ASP | D | 362 | 84.584 | −38.394 | 19.742 | 1.00 | 98.12 |
| 1787 | CB | ASP | D | 362 | 83.524 | −38.556 | 18.643 | 1.00 | 94.20 |
| 1788 | CG | ASP | D | 362 | 82.101 | −38.584 | 19.189 | 1.00 | 93.55 |
| 1789 | OD1 | ASP | D | 362 | 81.912 | −38.869 | 20.393 | 1.00 | 90.67 |
| 1790 | OD2 | ASP | D | 362 | 81.164 | −38.334 | 18.399 | 1.00 | 92.04 |
| 1791 | C | ASP | D | 362 | 84.568 | −39.609 | 20.678 | 1.00 | 101.90 |
| 1792 | O | ASP | D | 362 | 83.662 | −39.760 | 21.505 | 1.00 | 105.44 |
| 1793 | N | SER | D | 366 | 80.153 | −40.832 | 27.991 | 1.00 | 106.80 |
| 1794 | CA | SER | D | 366 | 81.421 | −41.112 | 28.632 | 1.00 | 108.38 |
| 1795 | CB | SER | D | 366 | 82.407 | −39.953 | 28.434 | 1.00 | 105.73 |
| 1796 | OG | SER | D | 366 | 81.961 | −38.778 | 29.085 | 1.00 | 107.86 |
| 1797 | C | SER | D | 366 | 81.337 | −41.429 | 30.115 | 1.00 | 109.15 |
| 1798 | O | SER | D | 366 | 80.475 | −40.948 | 30.866 | 1.00 | 108.59 |
| 1799 | N | ALA | D | 367 | 82.282 | −42.291 | 30.456 | 1.00 | 113.39 |
| 1800 | CA | ALA | D | 367 | 82.624 | −42.848 | 31.753 | 1.00 | 117.11 |
| 1801 | CB | ALA | D | 367 | 81.787 | −44.077 | 32.066 | 1.00 | 117.97 |
| 1802 | C | ALA | D | 367 | 83.969 | −43.282 | 31.204 | 1.00 | 118.02 |
| 1803 | O | ALA | D | 367 | 85.024 | −43.202 | 31.846 | 1.00 | 121.90 |
| 1804 | N | GLY | D | 368 | 83.854 | −43.691 | 29.940 | 1.00 | 117.42 |
| 1805 | CA | GLY | D | 368 | 84.936 | −44.181 | 29.121 | 1.00 | 116.91 |
| 1806 | C | GLY | D | 368 | 86.205 | −43.379 | 29.039 | 1.00 | 115.45 |
| 1807 | O | GLY | D | 368 | 86.224 | −42.140 | 29.021 | 1.00 | 117.93 |
| 1808 | N | THR | D | 369 | 87.270 | −44.169 | 28.983 | 1.00 | 113.64 |
| 1809 | CA | THR | D | 369 | 88.652 | −43.747 | 28.893 | 1.00 | 105.24 |
| 1810 | CB | THR | D | 369 | 89.454 | −44.166 | 30.113 | 1.00 | 102.05 |
| 1811 | OG1 | THR | D | 369 | 89.041 | −43.395 | 31.241 | 1.00 | 99.65 |
| 1812 | CG2 | THR | D | 369 | 90.943 | −43.971 | 29.862 | 1.00 | 99.17 |
| 1813 | C | THR | D | 369 | 89.227 | −44.513 | 27.733 | 1.00 | 101.72 |
| 1814 | O | THR | D | 369 | 89.510 | −45.714 | 27.834 | 1.00 | 100.21 |
| 1815 | N | VAL | D | 370 | 89.407 | −43.823 | 26.627 | 1.00 | 94.52 |
| 1816 | CA | VAL | D | 370 | 89.943 | −44.498 | 25.489 | 1.00 | 94.05 |
| 1817 | CB | VAL | D | 370 | 90.009 | −43.601 | 24.281 | 1.00 | 93.59 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1818 | CG1 | VAL | D | 370 | 90.638 | −44.358 | 23.121 | 1.00 | 95.58 |
| 1819 | CG2 | VAL | D | 370 | 88.614 | −43.138 | 23.934 | 1.00 | 95.91 |
| 1820 | C | VAL | D | 370 | 91.316 | −44.982 | 25.806 | 1.00 | 98.54 |
| 1821 | O | VAL | D | 370 | 92.106 | −44.348 | 26.509 | 1.00 | 89.34 |
| 1822 | N | GLN | D | 371 | 91.601 | −46.149 | 25.301 | 1.00 | 103.00 |
| 1823 | CA | GLN | D | 371 | 92.901 | −46.644 | 25.543 | 1.00 | 93.47 |
| 1824 | CB | GLN | D | 371 | 92.809 | −47.950 | 26.303 | 1.00 | 98.82 |
| 1825 | CG | GLN | D | 371 | 92.491 | −47.726 | 27.783 | 1.00 | 127.66 |
| 1826 | CD | GLN | D | 371 | 93.382 | −48.529 | 28.664 | 1.00 | 150.20 |
| 1827 | OE1 | GLN | D | 371 | 94.073 | −49.371 | 28.166 | 1.00 | 146.09 |
| 1828 | NE2 | GLN | D | 371 | 93.376 | −48.292 | 29.967 | 1.00 | 145.86 |
| 1829 | C | GLN | D | 371 | 93.628 | −46.760 | 24.233 | 1.00 | 83.84 |
| 1830 | O | GLN | D | 371 | 93.175 | −47.413 | 23.296 | 1.00 | 72.59 |
| 1831 | N | LEU | D | 372 | 94.737 | −46.044 | 24.157 | 1.00 | 66.14 |
| 1832 | CA | LEU | D | 372 | 95.554 | −46.071 | 22.967 | 1.00 | 52.66 |
| 1833 | CB | LEU | D | 372 | 96.008 | −44.668 | 22.583 | 1.00 | 51.89 |
| 1834 | CG | LEU | D | 372 | 94.930 | −43.664 | 22.180 | 1.00 | 53.06 |
| 1835 | CD1 | LEU | D | 372 | 95.584 | −42.518 | 21.408 | 1.00 | 53.72 |
| 1836 | CD2 | LEU | D | 372 | 93.885 | −44.336 | 21.308 | 1.00 | 55.34 |
| 1837 | C | LEU | D | 372 | 96.756 | −46.937 | 23.250 | 1.00 | 46.74 |
| 1838 | O | LEU | D | 372 | 97.571 | −46.615 | 24.111 | 1.00 | 46.38 |
| 1839 | N | THR | D | 373 | 96.857 | −48.046 | 22.528 | 1.00 | 45.21 |
| 1840 | CA | THR | D | 373 | 97.971 | −48.967 | 22.701 | 1.00 | 41.72 |
| 1841 | CB | THR | D | 373 | 97.474 | −50.359 | 23.105 | 1.00 | 43.46 |
| 1842 | OG1 | THR | D | 373 | 96.661 | −50.239 | 24.281 | 1.00 | 46.18 |
| 1843 | CG2 | THR | D | 373 | 98.651 | −51.282 | 23.395 | 1.00 | 45.00 |
| 1844 | C | THR | D | 373 | 98.805 | −49.081 | 21.432 | 1.00 | 38.11 |
| 1845 | O | THR | D | 373 | 98.287 | −49.292 | 20.332 | 1.00 | 36.17 |
| 1846 | N | TRP | D | 374 | 100.113 | −48.939 | 21.598 | 1.00 | 34.86 |
| 1847 | CA | TRP | D | 374 | 101.037 | −49.007 | 20.476 | 1.00 | 33.44 |
| 1848 | CB | TRP | D | 374 | 102.095 | −47.920 | 20.597 | 1.00 | 32.81 |
| 1849 | CG | TRP | D | 374 | 101.591 | −46.557 | 20.516 | 1.00 | 32.83 |
| 1850 | CD2 | TRP | D | 374 | 101.322 | −45.829 | 19.320 | 1.00 | 33.68 |
| 1851 | CE2 | TRP | D | 374 | 100.911 | −44.534 | 19.710 | 1.00 | 33.04 |
| 1852 | CE3 | TRP | D | 374 | 101.423 | −46.134 | 17.954 | 1.00 | 32.60 |
| 1853 | CD1 | TRP | D | 374 | 101.313 | −45.721 | 21.555 | 1.00 | 32.05 |
| 1854 | NE1 | TRP | D | 374 | 100.901 | −44.499 | 21.079 | 1.00 | 33.06 |
| 1855 | CZ2 | TRP | D | 374 | 100.552 | −43.554 | 18.777 | 1.00 | 33.06 |
| 1856 | CZ3 | TRP | D | 374 | 101.070 | −45.164 | 17.030 | 1.00 | 33.48 |
| 1857 | CH2 | TRP | D | 374 | 100.655 | −43.880 | 17.447 | 1.00 | 33.73 |
| 1858 | C | TRP | D | 374 | 101.772 | −50.333 | 20.370 | 1.00 | 33.25 |
| 1859 | O | TRP | D | 374 | 101.924 | −51.054 | 21.357 | 1.00 | 34.89 |
| 1860 | N | SER | D | 375 | 102.249 | −50.625 | 19.162 | 1.00 | 31.16 |
| 1861 | CA | SER | D | 375 | 103.021 | −51.828 | 18.898 | 1.00 | 28.86 |
| 1862 | CB | SER | D | 375 | 102.176 | −53.084 | 19.108 | 1.00 | 27.04 |
| 1863 | OG | SER | D | 375 | 101.260 | −53.253 | 18.048 | 1.00 | 31.34 |
| 1864 | C | SER | D | 375 | 103.576 | −51.812 | 17.480 | 1.00 | 27.22 |
| 1865 | O | SER | D | 375 | 103.149 | −51.035 | 16.633 | 1.00 | 25.71 |
| 1866 | N | ARG | D | 376 | 104.547 | −52.673 | 17.228 | 1.00 | 25.11 |
| 1867 | CA | ARG | D | 376 | 105.146 | −52.759 | 15.911 | 1.00 | 23.07 |
| 1868 | CB | ARG | D | 376 | 106.659 | −52.713 | 16.033 | 1.00 | 22.05 |
| 1869 | CG | ARG | D | 376 | 107.163 | −51.371 | 16.491 | 1.00 | 24.33 |
| 1870 | CD | ARG | D | 376 | 108.512 | −51.106 | 15.897 | 1.00 | 23.87 |
| 1871 | NE | ARG | D | 376 | 109.560 | −51.225 | 16.884 | 1.00 | 25.26 |
| 1872 | CZ | ARG | D | 376 | 110.830 | −51.456 | 16.584 | 1.00 | 24.50 |
| 1873 | NH1 | ARG | D | 376 | 111.197 | −51.601 | 15.319 | 1.00 | 23.81 |
| 1874 | NH2 | ARG | D | 376 | 111.729 | −51.519 | 17.554 | 1.00 | 23.95 |
| 1875 | C | ARG | D | 376 | 104.715 | −54.053 | 15.232 | 1.00 | 22.61 |
| 1876 | O | ARG | D | 376 | 104.465 | −55.064 | 15.894 | 1.00 | 21.95 |
| 1877 | N | ALA | D | 377 | 104.601 | −54.025 | 13.914 | 1.00 | 22.97 |
| 1878 | CA | ALA | D | 377 | 104.215 | −55.232 | 13.205 | 1.00 | 23.36 |
| 1879 | CB | ALA | D | 377 | 104.020 | −54.937 | 11.733 | 1.00 | 24.31 |
| 1880 | C | ALA | D | 377 | 105.316 | −56.272 | 13.398 | 1.00 | 24.00 |
| 1881 | O | ALA | D | 377 | 105.035 | −57.475 | 13.411 | 1.00 | 25.37 |
| 1882 | N | SER | D | 378 | 106.557 | −55.809 | 13.568 | 1.00 | 20.38 |
| 1883 | CA | SER | D | 378 | 107.704 | −56.704 | 13.753 | 1.00 | 20.95 |
| 1884 | CB | SER | D | 378 | 108.999 | −55.910 | 13.623 | 1.00 | 18.23 |
| 1885 | OG | SER | D | 378 | 109.177 | −55.118 | 14.780 | 1.00 | 15.18 |
| 1886 | C | SER | D | 378 | 107.683 | −57.414 | 15.119 | 1.00 | 20.53 |
| 1887 | O | SER | D | 378 | 108.291 | −58.475 | 15.306 | 1.00 | 18.81 |
| 1888 | N | GLY | D | 379 | 106.986 | −56.828 | 16.082 | 1.00 | 21.19 |
| 1889 | CA | GLY | D | 379 | 106.922 | −57.432 | 17.400 | 1.00 | 21.66 |
| 1890 | C | GLY | D | 379 | 107.932 | −56.794 | 18.336 | 1.00 | 23.55 |
| 1891 | O | GLY | D | 379 | 107.949 | −57.087 | 19.533 | 1.00 | 20.69 |
| 1892 | N | LYS | D | 380 | 108.772 | −55.914 | 17.797 | 1.00 | 27.56 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1893 | CA | LYS | D | 380 | 109.778 | −55.240 | 18.608 | 1.00 | 30.23 |
| 1894 | CB | LYS | D | 380 | 110.846 | −54.640 | 17.699 | 1.00 | 34.04 |
| 1895 | CG | LYS | D | 380 | 111.669 | −55.700 | 16.986 | 1.00 | 38.18 |
| 1896 | CD | LYS | D | 380 | 112.566 | −55.086 | 15.927 | 1.00 | 43.21 |
| 1897 | CE | LYS | D | 380 | 113.456 | −56.137 | 15.295 | 1.00 | 46.84 |
| 1898 | NZ | LYS | D | 380 | 114.303 | −55.578 | 14.213 | 1.00 | 50.71 |
| 1899 | C | LYS | D | 380 | 109.169 | −54.176 | 19.540 | 1.00 | 28.44 |
| 1900 | O | LYS | D | 380 | 108.017 | −53.770 | 19.377 | 1.00 | 27.95 |
| 1901 | N | PRO | D | 381 | 109.942 | −53.726 | 20.543 | 1.00 | 32.68 |
| 1902 | CD | PRO | D | 381 | 111.325 | −54.149 | 20.818 | 1.00 | 31.16 |
| 1903 | CA | PRO | D | 381 | 109.487 | −52.720 | 21.514 | 1.00 | 31.71 |
| 1904 | CB | PRO | D | 381 | 110.569 | −52.751 | 22.605 | 1.00 | 32.82 |
| 1905 | CG | PRO | D | 381 | 111.427 | −53.959 | 22.292 | 1.00 | 32.21 |
| 1906 | C | PRO | D | 381 | 109.280 | −51.296 | 20.971 | 1.00 | 30.98 |
| 1907 | O | PRO | D | 381 | 109.968 | −50.869 | 20.047 | 1.00 | 32.20 |
| 1908 | N | VAL | D | 382 | 108.332 | −50.580 | 21.585 | 1.00 | 30.88 |
| 1909 | CA | VAL | D | 382 | 107.959 | −49.201 | 21.256 | 1.00 | 29.99 |
| 1910 | CB | VAL | D | 382 | 106.418 | −49.034 | 21.187 | 1.00 | 29.69 |
| 1911 | CG1 | VAL | D | 382 | 105.830 | −49.891 | 20.077 | 1.00 | 30.77 |
| 1912 | CG2 | VAL | D | 382 | 105.799 | −49.417 | 22.536 | 1.00 | 27.36 |
| 1913 | C | VAL | D | 382 | 108.418 | −48.319 | 22.413 | 1.00 | 33.54 |
| 1914 | O | VAL | D | 382 | 108.459 | −48.786 | 23.544 | 1.00 | 29.20 |
| 1915 | N | GLN | D | 383 | 108.738 | −47.051 | 22.171 | 1.00 | 35.30 |
| 1916 | CA | GLN | D | 383 | 109.143 | −46.214 | 23.289 | 1.00 | 35.85 |
| 1917 | CB | GLN | D | 383 | 109.962 | −45.016 | 22.794 | 1.00 | 37.12 |
| 1918 | CG | GLN | D | 383 | 111.250 | −45.364 | 21.997 | 1.00 | 43.44 |
| 1919 | CD | GLN | D | 383 | 111.890 | −44.127 | 21.366 | 1.00 | 51.44 |
| 1920 | OE1 | GLN | D | 383 | 111.574 | −43.000 | 21.745 | 1.00 | 51.02 |
| 1921 | NE2 | GLN | D | 383 | 112.796 | −44.329 | 20.410 | 1.00 | 49.96 |
| 1922 | C | GLN | D | 383 | 107.872 | −45.746 | 24.014 | 1.00 | 37.35 |
| 1923 | O | GLN | D | 383 | 106.765 | −46.211 | 23.725 | 1.00 | 33.75 |
| 1924 | N | HIS | D | 384 | 108.047 | −44.838 | 24.965 | 1.00 | 38.23 |
| 1925 | CA | HIS | D | 384 | 106.954 | −44.273 | 25.751 | 1.00 | 39.29 |
| 1926 | CB | HIS | D | 384 | 107.521 | −43.474 | 26.891 | 1.00 | 46.68 |
| 1927 | CG | HIS | D | 384 | 107.895 | −44.305 | 28.062 | 1.00 | 56.92 |
| 1928 | CD2 | HIS | D | 384 | 109.087 | −44.494 | 28.639 | 1.00 | 60.71 |
| 1929 | ND1 | HIS | D | 384 | 106.975 | −45.037 | 28.770 | 1.00 | 61.31 |
| 1930 | CE1 | HIS | D | 384 | 107.599 | −45.654 | 29.761 | 1.00 | 63.29 |
| 1931 | NE2 | HIS | D | 384 | 108.870 | −45.344 | 29.704 | 1.00 | 63.51 |
| 1932 | C | HIS | D | 384 | 106.116 | −43.328 | 24.925 | 1.00 | 37.38 |
| 1933 | O | HIS | D | 384 | 106.639 | −42.685 | 24.027 | 1.00 | 37.36 |
| 1934 | N | SER | D | 385 | 104.828 | −43.205 | 25.212 | 1.00 | 35.34 |
| 1935 | CA | SER | D | 385 | 104.055 | −42.270 | 24.419 | 1.00 | 36.62 |
| 1936 | CB | SER | D | 385 | 102.950 | −42.994 | 23.654 | 1.00 | 34.30 |
| 1937 | OG | SER | D | 385 | 101.961 | −43.513 | 24.524 | 1.00 | 34.64 |
| 1938 | C | SER | D | 385 | 103.464 | −41.146 | 25.255 | 1.00 | 36.99 |
| 1939 | O | SER | D | 385 | 103.279 | −41.290 | 26.463 | 1.00 | 36.66 |
| 1940 | N | THR | D | 386 | 103.189 | −40.016 | 24.609 | 1.00 | 37.99 |
| 1941 | CA | THR | D | 386 | 102.599 | −38.876 | 25.297 | 1.00 | 38.94 |
| 1942 | CB | THR | D | 386 | 103.190 | −37.550 | 24.797 | 1.00 | 39.42 |
| 1943 | OG1 | THR | D | 386 | 104.586 | −37.485 | 25.115 | 1.00 | 39.55 |
| 1944 | CG2 | THR | D | 386 | 102.463 | −36.370 | 25.453 | 1.00 | 41.52 |
| 1945 | C | THR | D | 386 | 101.106 | −38.876 | 25.009 | 1.00 | 40.30 |
| 1946 | O | THR | D | 386 | 100.709 | −38.962 | 23.851 | 1.00 | 41.11 |
| 1947 | N | ARG | D | 387 | 100.275 | −38.788 | 26.045 | 1.00 | 41.74 |
| 1948 | CA | ARG | D | 387 | 98.823 | −38.782 | 25.848 | 1.00 | 44.37 |
| 1949 | CB | ARG | D | 387 | 98.163 | −39.846 | 26.724 | 1.00 | 46.45 |
| 1950 | CG | ARG | D | 387 | 96.640 | −39.856 | 26.671 | 1.00 | 51.86 |
| 1951 | CD | ARG | D | 387 | 96.089 | −40.681 | 27.822 | 1.00 | 56.86 |
| 1952 | NE | ARG | D | 387 | 94.634 | −40.681 | 27.856 | 1.00 | 62.22 |
| 1953 | CZ | ARG | D | 387 | 93.876 | −41.525 | 27.170 | 1.00 | 65.19 |
| 1954 | NH1 | ARG | D | 387 | 94.441 | −42.441 | 26.395 | 1.00 | 67.20 |
| 1955 | NH2 | ARG | D | 387 | 92.554 | −41.462 | 27.264 | 1.00 | 67.08 |
| 1956 | C | ARG | D | 387 | 98.243 | −37.410 | 26.171 | 1.00 | 45.17 |
| 1957 | O | ARG | D | 387 | 98.637 | −36.771 | 27.143 | 1.00 | 43.23 |
| 1958 | N | LYS | D | 388 | 97.290 | −36.966 | 25.363 | 1.00 | 47.94 |
| 1959 | CA | LYS | D | 388 | 96.710 | −35.655 | 25.571 | 1.00 | 51.55 |
| 1960 | CB | LYS | D | 388 | 97.446 | −34.652 | 24.685 | 1.00 | 52.43 |
| 1961 | CG | LYS | D | 388 | 97.399 | −33.217 | 25.163 | 1.00 | 57.81 |
| 1962 | CD | LYS | D | 388 | 98.411 | −32.396 | 24.396 | 1.00 | 62.53 |
| 1963 | CE | LYS | D | 388 | 98.044 | −30.944 | 24.340 | 1.00 | 65.60 |
| 1964 | NZ | LYS | D | 388 | 98.894 | −30.157 | 23.404 | 1.00 | 69.27 |
| 1965 | C | LYS | D | 388 | 95.210 | −35.632 | 25.302 | 1.00 | 52.36 |
| 1966 | O | LYS | D | 388 | 94.749 | −35.949 | 24.203 | 1.00 | 54.17 |
| 1967 | N | GLU | D | 389 | 94.462 | −35.249 | 26.330 | 1.00 | 55.16 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 1968 | CA | GLU | D | 389 | 93.016 | −35.185 | 26.267 | 1.00 | 60.68 |
| 1969 | CB | GLU | D | 389 | 92.393 | −35.962 | 27.408 | 1.00 | 65.38 |
| 1970 | CG | GLU | D | 389 | 92.534 | −37.433 | 27.311 | 1.00 | 69.45 |
| 1971 | CD | GLU | D | 389 | 91.900 | −38.100 | 28.495 | 1.00 | 71.55 |
| 1972 | OE1 | GLU | D | 389 | 90.741 | −37.762 | 28.808 | 1.00 | 74.14 |
| 1973 | OE2 | GLU | D | 389 | 92.553 | −38.957 | 29.118 | 1.00 | 74.20 |
| 1974 | C | GLU | D | 389 | 92.499 | −33.785 | 26.385 | 1.00 | 61.95 |
| 1975 | O | GLU | D | 389 | 92.979 | −32.988 | 27.192 | 1.00 | 63.87 |
| 1976 | N | GLU | D | 390 | 91.465 | −33.509 | 25.615 | 1.00 | 62.55 |
| 1977 | CA | GLU | D | 390 | 90.856 | −32.210 | 25.673 | 1.00 | 63.25 |
| 1978 | CB | GLU | D | 390 | 91.629 | −31.226 | 24.807 | 1.00 | 65.78 |
| 1979 | CG | GLU | D | 390 | 91.053 | −29.830 | 24.841 | 1.00 | 71.17 |
| 1980 | CD | GLU | D | 390 | 91.756 | −28.888 | 23.895 | 1.00 | 75.70 |
| 1981 | OE1 | GLU | D | 390 | 92.628 | −29.343 | 23.127 | 1.00 | 79.08 |
| 1982 | OE2 | GLU | D | 390 | 91.431 | −27.686 | 23.915 | 1.00 | 78.39 |
| 1983 | C | GLU | D | 390 | 89.415 | −32.277 | 25.212 | 1.00 | 62.17 |
| 1984 | O | GLU | D | 390 | 89.057 | −33.096 | 24.365 | 1.00 | 57.98 |
| 1985 | N | ALA | D | 391 | 88.590 | −31.422 | 25.806 | 1.00 | 60.32 |
| 1986 | CA | ALA | D | 391 | 87.185 | −31.321 | 25.445 | 1.00 | 61.77 |
| 1987 | CB | ALA | D | 391 | 86.311 | −31.346 | 26.690 | 1.00 | 56.32 |
| 1988 | C | ALA | D | 391 | 87.019 | −29.999 | 24.703 | 1.00 | 65.88 |
| 1989 | O | ALA | D | 391 | 87.541 | −28.971 | 25.130 | 1.00 | 65.24 |
| 1990 | N | GLN | D | 392 | 86.316 | −30.031 | 23.578 | 1.00 | 73.73 |
| 1991 | CA | GLN | D | 392 | 86.091 | −28.827 | 22.790 | 1.00 | 85.54 |
| 1992 | CB | GLN | D | 392 | 86.762 | −28.980 | 21.417 | 1.00 | 87.14 |
| 1993 | CG | GLN | D | 392 | 88.269 | −29.304 | 21.503 | 1.00 | 89.01 |
| 1994 | CD | GLN | D | 392 | 88.746 | −30.187 | 20.371 | 1.00 | 89.57 |
| 1995 | OE1 | GLN | D | 392 | 88.596 | −29.839 | 19.194 | 1.00 | 90.63 |
| 1996 | NE2 | GLN | D | 392 | 89.322 | −31.340 | 20.712 | 1.00 | 90.69 |
| 1997 | C | GLN | D | 392 | 84.579 | −28.593 | 22.666 | 1.00 | 92.71 |
| 1998 | O | GLN | D | 392 | 83.817 | −29.514 | 22.364 | 1.00 | 95.47 |
| 1999 | N | ALA | D | 393 | 84.157 | −27.360 | 22.923 | 1.00 | 99.32 |
| 2000 | CA | ALA | D | 393 | 82.749 | −26.971 | 22.889 | 1.00 | 102.86 |
| 2001 | CB | ALA | D | 393 | 82.635 | −25.486 | 22.563 | 1.00 | 106.54 |
| 2002 | C | ALA | D | 393 | 81.787 | −27.773 | 22.007 | 1.00 | 102.98 |
| 2003 | O | ALA | D | 393 | 80.700 | −28.116 | 22.466 | 1.00 | 104.42 |
| 2004 | N | ASN | D | 394 | 82.151 | −28.080 | 20.763 | 1.00 | 100.68 |
| 2005 | CA | ASN | D | 394 | 81.243 | −28.841 | 19.896 | 1.00 | 96.68 |
| 2006 | CB | ASN | D | 394 | 81.908 | −29.146 | 18.545 | 1.00 | 105.70 |
| 2007 | CG | ASN | D | 394 | 83.216 | −29.902 | 18.691 | 1.00 | 112.44 |
| 2008 | OD1 | ASN | D | 394 | 83.697 | −30.119 | 19.801 | 1.00 | 119.49 |
| 2009 | ND2 | ASN | D | 394 | 83.805 | −30.298 | 17.566 | 1.00 | 118.61 |
| 2010 | C | ASN | D | 394 | 80.800 | −30.153 | 20.540 | 1.00 | 92.04 |
| 2011 | O | ASN | D | 394 | 80.397 | −31.082 | 19.844 | 1.00 | 88.18 |
| 2012 | N | GLY | D | 395 | 80.852 | −30.216 | 21.868 | 1.00 | 90.24 |
| 2013 | CA | GLY | D | 395 | 80.493 | −31.433 | 22.567 | 1.00 | 92.32 |
| 2014 | C | GLY | D | 395 | 81.322 | −32.553 | 21.959 | 1.00 | 92.75 |
| 2015 | O | GLY | D | 395 | 80.881 | −33.161 | 20.984 | 1.00 | 97.07 |
| 2016 | N | ALA | D | 396 | 82.514 | −32.818 | 22.512 | 1.00 | 92.57 |
| 2017 | CA | ALA | D | 396 | 83.433 | −33.867 | 22.007 | 1.00 | 95.03 |
| 2018 | CB | ALA | D | 396 | 84.234 | −33.302 | 20.826 | 1.00 | 100.45 |
| 2019 | C | ALA | D | 396 | 84.404 | −34.474 | 23.076 | 1.00 | 93.82 |
| 2020 | O | ALA | D | 396 | 84.026 | −34.614 | 24.236 | 1.00 | 103.77 |
| 2021 | N | LEU | D | 397 | 85.613 | −34.880 | 22.657 | 1.00 | 88.78 |
| 2022 | CA | LEU | D | 397 | 86.716 | −35.433 | 23.501 | 1.00 | 81.50 |
| 2023 | CB | LEU | D | 397 | 86.361 | −36.679 | 24.348 | 1.00 | 76.76 |
| 2024 | CG | LEU | D | 397 | 87.529 | −37.246 | 25.211 | 1.00 | 66.38 |
| 2025 | CD1 | LEU | D | 397 | 87.841 | −36.305 | 26.374 | 1.00 | 61.59 |
| 2026 | CD2 | LEU | D | 397 | 87.173 | −38.627 | 25.763 | 1.00 | 60.43 |
| 2027 | C | LEU | D | 397 | 87.819 | −35.857 | 22.558 | 1.00 | 77.67 |
| 2028 | O | LEU | D | 397 | 87.792 | −36.946 | 21.987 | 1.00 | 78.15 |
| 2029 | N | THR | D | 398 | 88.795 | −34.998 | 22.374 | 1.00 | 70.59 |
| 2030 | CA | THR | D | 398 | 89.855 | −35.382 | 21.495 | 1.00 | 60.99 |
| 2031 | CB | THR | D | 398 | 90.332 | −34.191 | 20.697 | 1.00 | 57.63 |
| 2032 | OG1 | THR | D | 398 | 89.385 | −33.928 | 19.653 | 1.00 | 52.21 |
| 2033 | CG2 | THR | D | 398 | 91.695 | −34.466 | 20.108 | 1.00 | 52.65 |
| 2034 | C | THR | D | 398 | 90.975 | −36.000 | 22.307 | 1.00 | 59.32 |
| 2035 | O | THR | D | 398 | 91.388 | −35.463 | 23.333 | 1.00 | 57.49 |
| 2036 | N | VAL | D | 399 | 91.433 | −37.159 | 21.855 | 1.00 | 55.64 |
| 2037 | CA | VAL | D | 399 | 92.503 | −37.884 | 22.517 | 1.00 | 56.02 |
| 2038 | CB | VAL | D | 399 | 91.985 | −39.221 | 23.086 | 1.00 | 57.65 |
| 2039 | CG1 | VAL | D | 399 | 93.148 | −40.132 | 23.424 | 1.00 | 58.42 |
| 2040 | CG2 | VAL | D | 399 | 91.142 | −38.959 | 24.326 | 1.00 | 58.59 |
| 2041 | C | VAL | D | 399 | 93.625 | −38.150 | 21.520 | 1.00 | 54.61 |
| 2042 | O | VAL | D | 399 | 93.392 | −38.675 | 20.432 | 1.00 | 56.27 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2043 | N | THR | D | 400 | 94.842 | −37.773 | 21.889 | 1.00 | 52.66 |
| 2044 | CA | THR | D | 400 | 95.985 | −37.976 | 21.018 | 1.00 | 47.80 |
| 2045 | CB | THR | D | 400 | 96.492 | −36.652 | 20.423 | 1.00 | 47.20 |
| 2046 | OG1 | THR | D | 400 | 96.787 | −35.732 | 21.478 | 1.00 | 45.27 |
| 2047 | CG2 | THR | D | 400 | 95.458 | −36.046 | 19.520 | 1.00 | 46.58 |
| 2048 | C | THR | D | 400 | 97.138 | −38.615 | 21.764 | 1.00 | 45.04 |
| 2049 | O | THR | D | 400 | 97.379 | −38.328 | 22.935 | 1.00 | 45.60 |
| 2050 | N | SER | D | 401 | 97.850 | −39.494 | 21.077 | 1.00 | 41.32 |
| 2051 | CA | SER | D | 401 | 99.000 | −40.147 | 21.664 | 1.00 | 39.00 |
| 2052 | CB | SER | D | 401 | 98.701 | −41.612 | 21.974 | 1.00 | 38.49 |
| 2053 | OG | SER | D | 401 | 99.827 | −42.238 | 22.560 | 1.00 | 37.23 |
| 2054 | C | SER | D | 401 | 100.086 | −40.034 | 20.617 | 1.00 | 38.33 |
| 2055 | O | SER | D | 401 | 99.910 | −40.468 | 19.474 | 1.00 | 40.49 |
| 2056 | N | THR | D | 402 | 101.193 | −39.405 | 20.993 | 1.00 | 36.95 |
| 2057 | CA | THR | D | 402 | 102.309 | −39.237 | 20.079 | 1.00 | 34.80 |
| 2058 | CB | THR | D | 402 | 102.809 | −37.797 | 20.095 | 1.00 | 34.96 |
| 2059 | OG1 | THR | D | 402 | 101.757 | −36.940 | 19.638 | 1.00 | 35.48 |
| 2060 | CG2 | THR | D | 402 | 104.019 | −37.635 | 19.190 | 1.00 | 33.99 |
| 2061 | C | THR | D | 402 | 103.413 | −40.192 | 20.499 | 1.00 | 32.33 |
| 2062 | O | THR | D | 402 | 103.809 | −40.243 | 21.670 | 1.00 | 33.41 |
| 2063 | N | LEU | D | 403 | 103.894 | −40.965 | 19.534 | 1.00 | 28.92 |
| 2064 | CA | LEU | D | 403 | 104.915 | −41.959 | 19.808 | 1.00 | 26.91 |
| 2065 | CB | LEU | D | 403 | 104.423 | −43.353 | 19.409 | 1.00 | 23.79 |
| 2066 | CG | LEU | D | 403 | 105.441 | −44.503 | 19.467 | 1.00 | 22.05 |
| 2067 | CD1 | LEU | D | 403 | 105.699 | −44.863 | 20.922 | 1.00 | 21.55 |
| 2068 | CD2 | LEU | D | 403 | 104.921 | −45.725 | 18.711 | 1.00 | 18.51 |
| 2069 | C | LEU | D | 403 | 106.219 | −41.700 | 19.118 | 1.00 | 27.42 |
| 2070 | O | LEU | D | 403 | 106.271 | −41.575 | 17.904 | 1.00 | 28.68 |
| 2071 | N | PRO | D | 404 | 107.299 | −41.593 | 19.892 | 1.00 | 21.20 |
| 2072 | CD | PRO | D | 404 | 107.343 | −41.491 | 21.359 | 1.00 | 23.46 |
| 2073 | CA | PRO | D | 404 | 108.603 | −41.366 | 19.285 | 1.00 | 23.91 |
| 2074 | CB | PRO | D | 404 | 109.529 | −41.129 | 20.475 | 1.00 | 22.16 |
| 2075 | CG | PRO | D | 404 | 108.633 | −40.757 | 21.590 | 1.00 | 24.23 |
| 2076 | C | PRO | D | 404 | 108.915 | −42.685 | 18.599 | 1.00 | 26.37 |
| 2077 | O | PRO | D | 404 | 108.584 | −43.754 | 19.114 | 1.00 | 22.62 |
| 2078 | N | VAL | D | 405 | 109.545 | −42.590 | 17.440 | 1.00 | 26.40 |
| 2079 | CA | VAL | D | 405 | 109.911 | −43.739 | 16.639 | 1.00 | 28.32 |
| 2080 | CB | VAL | D | 405 | 109.021 | −43.806 | 15.384 | 1.00 | 35.39 |
| 2081 | CG1 | VAL | D | 405 | 109.824 | −44.275 | 14.174 | 1.00 | 41.63 |
| 2082 | CG2 | VAL | D | 405 | 107.844 | −44.721 | 15.646 | 1.00 | 39.64 |
| 2083 | C | VAL | D | 405 | 111.370 | −43.609 | 16.233 | 1.00 | 26.00 |
| 2084 | O | VAL | D | 405 | 111.921 | −42.517 | 16.221 | 1.00 | 26.43 |
| 2085 | N | GLY | D | 406 | 111.993 | −44.734 | 15.911 | 1.00 | 24.53 |
| 2086 | CA | GLY | D | 406 | 113.388 | −44.723 | 15.514 | 1.00 | 23.32 |
| 2087 | C | GLY | D | 406 | 113.527 | −44.232 | 14.087 | 1.00 | 25.19 |
| 2088 | O | GLY | D | 406 | 112.673 | −44.519 | 13.240 | 1.00 | 26.72 |
| 2089 | N | THR | D | 407 | 114.597 | −43.505 | 13.797 | 1.00 | 25.55 |
| 2090 | CA | THR | D | 407 | 114.774 | −42.990 | 12.451 | 1.00 | 27.30 |
| 2091 | CB | THR | D | 407 | 115.901 | −41.946 | 12.397 | 1.00 | 26.41 |
| 2092 | OG1 | THR | D | 407 | 115.604 | −40.892 | 13.320 | 1.00 | 28.38 |
| 2093 | CG2 | THR | D | 407 | 116.016 | −41.348 | 11.006 | 1.00 | 26.72 |
| 2094 | C | THR | D | 407 | 115.032 | −44.100 | 11.440 | 1.00 | 27.68 |
| 2095 | O | THR | D | 407 | 114.336 | −44.178 | 10.423 | 1.00 | 27.90 |
| 2096 | N | ALA | D | 408 | 116.019 | −44.958 | 11.704 | 1.00 | 28.68 |
| 2097 | CA | ALA | D | 408 | 116.310 | −46.061 | 10.782 | 1.00 | 30.44 |
| 2098 | CB | ALA | D | 408 | 117.518 | −46.863 | 11.253 | 1.00 | 28.90 |
| 2099 | C | ALA | D | 408 | 115.088 | −46.964 | 10.687 | 1.00 | 31.18 |
| 2100 | O | ALA | D | 408 | 114.641 | −47.294 | 9.585 | 1.00 | 37.20 |
| 2101 | N | ASP | D | 409 | 114.542 | −47.346 | 11.843 | 1.00 | 32.70 |
| 2102 | CA | ASP | D | 409 | 113.355 | −48.207 | 11.898 | 1.00 | 36.15 |
| 2103 | CB | ASP | D | 409 | 112.719 | −48.212 | 13.298 | 1.00 | 35.40 |
| 2104 | CG | ASP | D | 409 | 113.551 | −48.951 | 14.335 | 1.00 | 34.21 |
| 2105 | OD1 | ASP | D | 409 | 114.414 | −49.775 | 13.952 | 1.00 | 29.17 |
| 2106 | OD2 | ASP | D | 409 | 113.317 | −48.713 | 15.547 | 1.00 | 30.06 |
| 2107 | C | ASP | D | 409 | 112.277 | −47.744 | 10.922 | 1.00 | 36.19 |
| 2108 | O | ASP | D | 409 | 111.668 | −48.556 | 10.209 | 1.00 | 36.62 |
| 2109 | N | TRP | D | 410 | 112.029 | −46.437 | 10.917 | 1.00 | 34.16 |
| 2110 | CA | TRP | D | 410 | 111.003 | −45.878 | 10.060 | 1.00 | 34.01 |
| 2111 | CB | TRP | D | 410 | 110.588 | −44.476 | 10.550 | 1.00 | 27.80 |
| 2112 | CG | TRP | D | 410 | 109.553 | −43.880 | 9.649 | 1.00 | 22.85 |
| 2113 | CD2 | TRP | D | 410 | 108.131 | −44.073 | 9.724 | 1.00 | 18.78 |
| 2114 | CE2 | TRP | D | 410 | 107.578 | −43.506 | 8.553 | 1.00 | 18.57 |
| 2115 | CE3 | TRP | D | 410 | 107.275 | −44.647 | 10.666 | 1.00 | 18.31 |
| 2116 | CD1 | TRP | D | 410 | 109.789 | −43.223 | 8.474 | 1.00 | 19.77 |
| 2117 | NE1 | TRP | D | 410 | 108.615 | −43.005 | 7.807 | 1.00 | 18.45 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2118 | CZ2 | TRP | D | 410 | 106.196 | −43.532 | 8.281 | 1.00 | 16.19 |
| 2119 | CZ3 | TRP | D | 410 | 105.901 | −44.670 | 10.397 | 1.00 | 17.27 |
| 2120 | CH2 | TRP | D | 410 | 105.380 | −44.104 | 9.219 | 1.00 | 13.16 |
| 2121 | C | TRP | D | 410 | 111.393 | −45.825 | 8.589 | 1.00 | 37.21 |
| 2122 | O | TRP | D | 410 | 110.601 | −46.189 | 7.722 | 1.00 | 34.30 |
| 2123 | N | ILE | D | 411 | 112.606 | −45.369 | 8.308 | 1.00 | 41.96 |
| 2124 | CA | ILE | D | 411 | 113.073 | −45.277 | 6.933 | 1.00 | 46.92 |
| 2125 | CB | ILE | D | 411 | 114.409 | −44.507 | 6.860 | 1.00 | 51.51 |
| 2126 | CG2 | ILE | D | 411 | 115.090 | −44.736 | 5.520 | 1.00 | 56.36 |
| 2127 | CG1 | ILE | D | 411 | 114.140 | −43.017 | 7.087 | 1.00 | 57.51 |
| 2128 | CD1 | ILE | D | 411 | 115.376 | −42.163 | 7.109 | 1.00 | 60.66 |
| 2129 | C | ILE | D | 411 | 113.237 | −46.658 | 6.325 | 1.00 | 47.63 |
| 2130 | O | ILE | D | 411 | 113.088 | −46.844 | 5.110 | 1.00 | 48.49 |
| 2131 | N | GLU | D | 412 | 113.519 | −47.636 | 7.172 | 1.00 | 47.65 |
| 2132 | CA | GLU | D | 412 | 113.689 | −48.979 | 6.671 | 1.00 | 46.71 |
| 2133 | CB | GLU | D | 412 | 114.690 | −49.729 | 7.536 | 1.00 | 52.15 |
| 2134 | CG | GLU | D | 412 | 116.105 | −49.527 | 7.017 | 1.00 | 63.47 |
| 2135 | CD | GLU | D | 412 | 117.153 | −49.863 | 8.039 | 1.00 | 70.47 |
| 2136 | OE1 | GLU | D | 412 | 116.901 | −50.777 | 8.848 | 1.00 | 75.46 |
| 2137 | OE2 | GLU | D | 412 | 118.229 | −49.224 | 8.036 | 1.00 | 73.69 |
| 2138 | C | GLU | D | 412 | 112.390 | −49.750 | 6.485 | 1.00 | 43.10 |
| 2139 | O | GLU | D | 412 | 112.406 | −50.908 | 6.076 | 1.00 | 42.64 |
| 2140 | N | GLY | D | 413 | 111.261 | −49.111 | 6.777 | 1.00 | 39.28 |
| 2141 | CA | GLY | D | 413 | 109.989 | −49.770 | 6.539 | 1.00 | 35.96 |
| 2142 | C | GLY | D | 413 | 109.140 | −50.374 | 7.638 | 1.00 | 33.16 |
| 2143 | O | GLY | D | 413 | 108.111 | −50.981 | 7.340 | 1.00 | 33.66 |
| 2144 | N | GLU | D | 414 | 109.537 | −50.229 | 8.893 | 1.00 | 30.51 |
| 2145 | CA | GLU | D | 414 | 108.734 | −50.791 | 9.974 | 1.00 | 30.95 |
| 2146 | CB | GLU | D | 414 | 109.348 | −50.393 | 11.318 | 1.00 | 30.81 |
| 2147 | CG | GLU | D | 414 | 108.513 | −50.733 | 12.528 | 1.00 | 31.82 |
| 2148 | CD | GLU | D | 414 | 108.434 | −52.229 | 12.785 | 1.00 | 33.37 |
| 2149 | OE1 | GLU | D | 414 | 107.615 | −52.907 | 12.128 | 1.00 | 33.68 |
| 2150 | OE2 | GLU | D | 414 | 109.201 | −52.730 | 13.640 | 1.00 | 32.12 |
| 2151 | C | GLU | D | 414 | 107.307 | −50.245 | 9.868 | 1.00 | 28.76 |
| 2152 | O | GLU | D | 414 | 107.098 | −49.196 | 9.272 | 1.00 | 30.43 |
| 2153 | N | THR | D | 415 | 106.316 | −50.956 | 10.394 | 1.00 | 27.21 |
| 2154 | CA | THR | D | 415 | 104.968 | −50.408 | 10.364 | 1.00 | 25.97 |
| 2155 | CB | THR | D | 415 | 103.988 | −51.196 | 9.449 | 1.00 | 24.41 |
| 2156 | OG1 | THR | D | 415 | 102.912 | −51.724 | 10.234 | 1.00 | 20.80 |
| 2157 | CG2 | THR | D | 415 | 104.705 | −52.294 | 8.694 | 1.00 | 22.85 |
| 2158 | C | THR | D | 415 | 104.469 | −50.400 | 11.798 | 1.00 | 25.60 |
| 2159 | O | THR | D | 415 | 104.609 | −51.392 | 12.524 | 1.00 | 24.52 |
| 2160 | N | TYR | D | 416 | 103.923 | −49.256 | 12.207 | 1.00 | 24.91 |
| 2161 | CA | TYR | D | 416 | 103.420 | −49.065 | 13.564 | 1.00 | 26.87 |
| 2162 | CB | TYR | D | 416 | 103.905 | −47.716 | 14.099 | 1.00 | 22.11 |
| 2163 | CG | TYR | D | 416 | 105.397 | −47.641 | 14.123 | 1.00 | 16.72 |
| 2164 | CD1 | TYR | D | 416 | 106.112 | −47.542 | 12.943 | 1.00 | 15.25 |
| 2165 | CE1 | TYR | D | 416 | 107.489 | −47.539 | 12.941 | 1.00 | 16.98 |
| 2166 | CD2 | TYR | D | 416 | 106.104 | −47.732 | 15.322 | 1.00 | 16.17 |
| 2167 | CE2 | TYR | D | 416 | 107.494 | −47.729 | 15.326 | 1.00 | 17.12 |
| 2168 | CZ | TYR | D | 416 | 108.178 | −47.628 | 14.127 | 1.00 | 15.08 |
| 2169 | OH | TYR | D | 416 | 109.556 | −47.594 | 14.097 | 1.00 | 17.20 |
| 2170 | C | TYR | D | 416 | 101.903 | −49.155 | 13.660 | 1.00 | 32.19 |
| 2171 | O | TYR | D | 416 | 101.191 | −48.882 | 12.698 | 1.00 | 29.70 |
| 2172 | N | GLN | D | 417 | 101.408 | −49.511 | 14.836 | 1.00 | 39.74 |
| 2173 | CA | GLN | D | 417 | 99.974 | −49.676 | 15.020 | 1.00 | 48.73 |
| 2174 | CB | GLN | D | 417 | 99.681 | −51.175 | 14.984 | 1.00 | 60.24 |
| 2175 | CG | GLN | D | 417 | 98.242 | −51.566 | 15.160 | 1.00 | 88.82 |
| 2176 | CD | GLN | D | 417 | 98.042 | −53.062 | 15.141 | 1.00 | 103.17 |
| 2177 | OE1 | GLN | D | 417 | 98.995 | −53.818 | 15.033 | 1.00 | 110.86 |
| 2178 | NE2 | GLN | D | 417 | 96.802 | −53.499 | 15.248 | 1.00 | 111.28 |
| 2179 | C | GLN | D | 417 | 99.447 | −49.049 | 16.322 | 1.00 | 48.07 |
| 2180 | O | GLN | D | 417 | 100.207 | −48.856 | 17.258 | 1.00 | 43.82 |
| 2181 | N | CYS | D | 418 | 98.155 | −48.727 | 16.388 | 1.00 | 47.44 |
| 2182 | CA | CYS | D | 418 | 97.564 | −48.141 | 17.605 | 1.00 | 46.21 |
| 2183 | C | CYS | D | 418 | 96.215 | −48.800 | 17.914 | 1.00 | 44.81 |
| 2184 | O | CYS | D | 418 | 95.310 | −48.681 | 17.112 | 1.00 | 43.60 |
| 2185 | CB | CYS | D | 418 | 97.394 | −46.620 | 17.403 | 1.00 | 48.45 |
| 2186 | SG | CYS | D | 418 | 96.193 | −45.684 | 18.422 | 1.00 | 52.51 |
| 2187 | N | ARG | D | 419 | 96.067 | −49.485 | 19.054 | 1.00 | 44.37 |
| 2188 | CA | ARG | D | 419 | 94.789 | −50.131 | 19.382 | 1.00 | 45.74 |
| 2189 | CB | ARG | D | 419 | 95.003 | −51.555 | 19.935 | 1.00 | 50.56 |
| 2190 | CG | ARG | D | 419 | 93.815 | −52.493 | 19.687 | 1.00 | 59.17 |
| 2191 | CD | ARG | D | 419 | 94.105 | −53.924 | 20.064 | 1.00 | 67.85 |
| 2192 | NE | ARG | D | 419 | 92.927 | −54.774 | 19.956 | 1.00 | 75.46 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2193 | CZ | ARG | D | 419 | 92.892 | −56.022 | 20.395 | 1.00 | 78.71 |
| 2194 | NH1 | ARG | D | 419 | 93.974 | −56.539 | 20.961 | 1.00 | 80.31 |
| 2195 | NH2 | ARG | D | 419 | 91.787 | −56.745 | 20.276 | 1.00 | 80.05 |
| 2196 | C | ARG | D | 419 | 93.977 | −49.286 | 20.370 | 1.00 | 45.32 |
| 2197 | O | ARG | D | 419 | 94.160 | −49.348 | 21.593 | 1.00 | 41.91 |
| 2198 | N | VAL | D | 420 | 93.068 | −48.510 | 19.792 | 1.00 | 48.57 |
| 2199 | CA | VAL | D | 420 | 92.168 | −47.574 | 20.470 | 1.00 | 51.67 |
| 2200 | CB | VAL | D | 420 | 91.663 | −46.570 | 19.397 | 1.00 | 44.30 |
| 2201 | CG1 | VAL | D | 420 | 90.945 | −45.415 | 20.021 | 1.00 | 38.13 |
| 2202 | CG2 | VAL | D | 420 | 92.865 | −46.057 | 18.578 | 1.00 | 35.20 |
| 2203 | C | VAL | D | 420 | 91.027 | −48.344 | 21.159 | 1.00 | 61.39 |
| 2204 | O | VAL | D | 420 | 90.338 | −49.130 | 20.524 | 1.00 | 63.20 |
| 2205 | N | THR | D | 421 | 90.803 | −48.097 | 22.447 | 1.00 | 76.47 |
| 2206 | CA | THR | D | 421 | 89.814 | −48.884 | 23.182 | 1.00 | 96.65 |
| 2207 | CB | THR | D | 421 | 90.480 | −49.487 | 24.440 | 1.00 | 98.36 |
| 2208 | OG1 | THR | D | 421 | 91.842 | −49.800 | 24.141 | 1.00 | 100.21 |
| 2209 | CG2 | THR | D | 421 | 89.775 | −50.764 | 24.882 | 1.00 | 99.48 |
| 2210 | C | THR | D | 421 | 88.458 | −48.356 | 23.631 | 1.00 | 104.30 |
| 2211 | O | THR | D | 421 | 88.220 | −47.152 | 23.761 | 1.00 | 114.30 |
| 2212 | N | HIS | D | 422 | 87.579 | −49.338 | 23.846 | 1.00 | 113.65 |
| 2213 | CA | HIS | D | 422 | 86.229 | −49.168 | 24.373 | 1.00 | 119.44 |
| 2214 | CB | HIS | D | 422 | 85.169 | −48.994 | 23.302 | 1.00 | 131.91 |
| 2215 | CG | HIS | D | 422 | 83.810 | −48.710 | 23.892 | 1.00 | 141.69 |
| 2216 | CD2 | HIS | D | 422 | 83.283 | −47.538 | 24.318 | 1.00 | 144.97 |
| 2217 | ND1 | HIS | D | 422 | 82.935 | −49.696 | 24.235 | 1.00 | 145.14 |
| 2218 | CE1 | HIS | D | 422 | 81.892 | −49.147 | 24.870 | 1.00 | 147.27 |
| 2219 | NE2 | HIS | D | 422 | 82.086 | −47.858 | 24.929 | 1.00 | 147.38 |
| 2220 | C | HIS | D | 422 | 85.837 | −50.396 | 25.191 | 1.00 | 117.96 |
| 2221 | O | HIS | D | 422 | 86.466 | −51.450 | 25.106 | 1.00 | 116.91 |
| 2222 | N | ALA | D | 427 | 83.340 | −52.382 | 19.887 | 1.00 | 98.31 |
| 2223 | CA | ALA | D | 427 | 84.275 | −52.022 | 18.830 | 1.00 | 98.31 |
| 2224 | CB | ALA | D | 427 | 83.753 | −50.826 | 18.043 | 1.00 | 98.31 |
| 2225 | C | ALA | D | 427 | 85.667 | −51.713 | 19.345 | 1.00 | 98.31 |
| 2226 | O | ALA | D | 427 | 85.839 | −51.060 | 20.385 | 1.00 | 98.31 |
| 2227 | N | ALA | D | 428 | 86.640 | −52.199 | 18.573 | 1.00 | 78.31 |
| 2228 | CA | ALA | D | 428 | 88.075 | −52.034 | 18.795 | 1.00 | 78.31 |
| 2229 | CB | ALA | D | 428 | 88.710 | −53.390 | 19.145 | 1.00 | 88.31 |
| 2230 | C | ALA | D | 428 | 88.695 | −51.467 | 17.492 | 1.00 | 78.31 |
| 2231 | O | ALA | D | 428 | 88.902 | −52.207 | 16.524 | 1.00 | 68.31 |
| 2232 | N | LEU | D | 429 | 88.976 | −50.157 | 17.487 | 1.00 | 59.41 |
| 2233 | CA | LEU | D | 429 | 89.559 | −49.423 | 16.346 | 1.00 | 59.29 |
| 2234 | CB | LEU | D | 429 | 89.313 | −47.912 | 16.508 | 1.00 | 61.21 |
| 2235 | CG | LEU | D | 429 | 87.896 | −47.364 | 16.723 | 1.00 | 57.18 |
| 2236 | CD1 | LEU | D | 429 | 87.935 | −45.851 | 16.974 | 1.00 | 54.31 |
| 2237 | CD2 | LEU | D | 429 | 87.048 | −47.684 | 15.501 | 1.00 | 53.35 |
| 2238 | C | LEU | D | 429 | 91.073 | −49.630 | 16.208 | 1.00 | 61.13 |
| 2239 | O | LEU | D | 429 | 91.815 | −49.317 | 17.139 | 1.00 | 61.07 |
| 2240 | N | MET | D | 430 | 91.535 | −50.129 | 15.057 | 1.00 | 59.01 |
| 2241 | CA | MET | D | 430 | 92.973 | −50.340 | 14.827 | 1.00 | 56.60 |
| 2242 | CB | MET | D | 430 | 93.301 | −51.821 | 14.623 | 1.00 | 61.69 |
| 2243 | CG | MET | D | 430 | 93.143 | −52.682 | 15.834 | 1.00 | 74.17 |
| 2244 | SD | MET | D | 430 | 93.820 | −54.333 | 15.603 | 1.00 | 83.89 |
| 2245 | CE | MET | D | 430 | 92.646 | −55.042 | 14.540 | 1.00 | 89.17 |
| 2246 | C | MET | D | 430 | 93.478 | −49.583 | 13.604 | 1.00 | 51.94 |
| 2247 | O | MET | D | 430 | 92.953 | −49.748 | 12.505 | 1.00 | 48.00 |
| 2248 | N | ARG | D | 431 | 94.490 | −48.746 | 13.789 | 1.00 | 46.37 |
| 2249 | CA | ARG | D | 431 | 95.051 | −48.010 | 12.668 | 1.00 | 43.48 |
| 2250 | CB | ARG | D | 431 | 94.880 | −46.500 | 12.872 | 1.00 | 48.10 |
| 2251 | CG | ARG | D | 431 | 93.434 | −46.054 | 13.021 | 1.00 | 58.39 |
| 2252 | CD | ARG | D | 431 | 92.650 | −46.210 | 11.722 | 1.00 | 66.11 |
| 2253 | NE | ARG | D | 431 | 91.227 | −45.966 | 11.925 | 1.00 | 73.29 |
| 2254 | CZ | ARG | D | 431 | 90.309 | −46.087 | 10.975 | 1.00 | 77.87 |
| 2255 | NH1 | ARG | D | 431 | 90.669 | −46.447 | 9.749 | 1.00 | 80.59 |
| 2256 | NH2 | ARG | D | 431 | 89.032 | −45.864 | 11.254 | 1.00 | 80.36 |
| 2257 | C | ARG | D | 431 | 96.531 | −48.359 | 12.575 | 1.00 | 41.06 |
| 2258 | O | ARG | D | 431 | 97.162 | −48.718 | 13.576 | 1.00 | 40.27 |
| 2259 | N | SER | D | 432 | 97.094 | −48.266 | 11.378 | 1.00 | 37.78 |
| 2260 | CA | SER | D | 432 | 98.504 | −48.561 | 11.216 | 1.00 | 35.76 |
| 2261 | CB | SER | D | 432 | 98.685 | −49.992 | 10.719 | 1.00 | 38.17 |
| 2262 | OG | SER | D | 432 | 98.069 | −50.175 | 9.458 | 1.00 | 42.02 |
| 2263 | C | SER | D | 432 | 99.132 | −47.580 | 10.238 | 1.00 | 35.38 |
| 2264 | O | SER | D | 432 | 98.432 | −46.973 | 9.427 | 1.00 | 33.46 |
| 2265 | N | THR | D | 433 | 100.446 | −47.415 | 10.323 | 1.00 | 33.16 |
| 2266 | CA | THR | D | 433 | 101.143 | −46.501 | 9.439 | 1.00 | 30.86 |
| 2267 | CB | THR | D | 433 | 101.224 | −45.076 | 10.038 | 1.00 | 34.58 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2268 | OG1 | THR | D | 433 | 101.869 | −44.199 | 9.104 | 1.00 | 38.31 |
| 2269 | CG2 | THR | D | 433 | 102.023 | −45.083 | 11.335 | 1.00 | 39.77 |
| 2270 | C | THR | D | 433 | 102.548 | −47.005 | 9.174 | 1.00 | 29.98 |
| 2271 | O | THR | D | 433 | 103.163 | −47.644 | 10.031 | 1.00 | 28.11 |
| 2272 | N | THR | D | 434 | 103.051 | −46.709 | 7.980 | 1.00 | 27.76 |
| 2273 | CA | THR | D | 434 | 104.377 | −47.140 | 7.579 | 1.00 | 27.72 |
| 2274 | CB | THR | D | 434 | 104.303 | −48.571 | 6.967 | 1.00 | 25.36 |
| 2275 | OG1 | THR | D | 434 | 105.623 | −49.071 | 6.735 | 1.00 | 25.61 |
| 2276 | CG2 | THR | D | 434 | 103.541 | −48.564 | 5.656 | 1.00 | 22.99 |
| 2277 | C | THR | D | 434 | 104.920 | −46.118 | 6.566 | 1.00 | 30.34 |
| 2278 | O | THR | D | 434 | 104.169 | −45.264 | 6.093 | 1.00 | 30.98 |
| 2279 | N | ALA | D | 435 | 106.217 | −46.191 | 6.262 | 1.00 | 35.79 |
| 2280 | CA | ALA | D | 435 | 106.859 | −45.266 | 5.320 | 1.00 | 43.16 |
| 2281 | CB | ALA | D | 435 | 108.359 | −45.600 | 5.186 | 1.00 | 41.96 |
| 2282 | C | ALA | D | 435 | 106.177 | −45.351 | 3.957 | 1.00 | 50.24 |
| 2283 | O | ALA | D | 435 | 105.976 | −46.442 | 3.438 | 1.00 | 48.00 |
| 2284 | N | THR | D | 436 | 105.830 | −44.202 | 3.383 | 1.00 | 60.35 |
| 2285 | CA | THR | D | 436 | 105.149 | −44.146 | 2.086 | 1.00 | 68.19 |
| 2286 | CB | THR | D | 436 | 104.692 | −42.707 | 1.760 | 1.00 | 73.79 |
| 2287 | OG1 | THR | D | 436 | 103.520 | −42.384 | 2.521 | 1.00 | 81.79 |
| 2288 | CG2 | THR | D | 436 | 104.397 | −42.564 | 0.271 | 1.00 | 82.02 |
| 2289 | C | THR | D | 436 | 106.000 | −44.625 | 0.921 | 1.00 | 70.88 |
| 2290 | O | THR | D | 436 | 107.081 | −44.106 | 0.697 | 1.00 | 69.76 |
| 2291 | N | SER | D | 437 | 105.514 | −45.600 | 0.162 | 1.00 | 75.08 |
| 2292 | CA | SER | D | 437 | 106.290 | −46.074 | −0.975 | 1.00 | 76.09 |
| 2293 | CB | SER | D | 437 | 106.264 | −47.602 | −1.060 | 1.00 | 82.46 |
| 2294 | OG | SER | D | 437 | 104.981 | −48.077 | −1.417 | 1.00 | 96.36 |
| 2295 | C | SER | D | 437 | 105.749 | −45.464 | −2.262 | 1.00 | 72.51 |
| 2296 | O | SER | D | 437 | 104.921 | −44.553 | −2.229 | 1.00 | 76.28 |
| 2297 | N | GLY | D | 438 | 106.214 | −45.967 | −3.397 | 1.00 | 69.15 |
| 2298 | CA | GLY | D | 438 | 105.761 | −45.422 | −4.661 | 1.00 | 60.81 |
| 2299 | C | GLY | D | 438 | 106.840 | −44.514 | −5.221 | 1.00 | 59.98 |
| 2300 | O | GLY | D | 438 | 107.909 | −44.386 | −4.617 | 1.00 | 55.82 |
| 2301 | N | PRO | D | 439 | 106.595 | −43.865 | −6.370 | 1.00 | 49.70 |
| 2302 | CD | PRO | D | 439 | 105.347 | −43.934 | −7.148 | 1.00 | 53.86 |
| 2303 | CA | PRO | D | 439 | 107.574 | −42.967 | −6.999 | 1.00 | 51.46 |
| 2304 | CB | PRO | D | 439 | 106.927 | −42.601 | −8.333 | 1.00 | 51.60 |
| 2305 | CG | PRO | D | 439 | 105.808 | −43.582 | −8.522 | 1.00 | 52.38 |
| 2306 | C | PRO | D | 439 | 107.876 | −41.709 | −6.188 | 1.00 | 52.74 |
| 2307 | O | PRO | D | 439 | 107.096 | −41.318 | −5.329 | 1.00 | 45.42 |
| 2308 | N | ARG | D | 440 | 109.016 | −41.090 | −6.466 | 1.00 | 49.25 |
| 2309 | CA | ARG | D | 440 | 109.416 | −39.860 | −5.789 | 1.00 | 49.30 |
| 2310 | CB | ARG | D | 440 | 110.778 | −39.996 | −5.108 | 1.00 | 58.24 |
| 2311 | CG | ARG | D | 440 | 111.017 | −41.299 | −4.417 | 1.00 | 77.23 |
| 2312 | CD | ARG | D | 440 | 110.317 | −41.366 | −3.089 | 1.00 | 89.95 |
| 2313 | NE | ARG | D | 440 | 110.345 | −42.726 | −2.573 | 1.00 | 99.74 |
| 2314 | CZ | ARG | D | 440 | 109.837 | −43.100 | −1.404 | 1.00 | 104.11 |
| 2315 | NH1 | ARG | D | 440 | 109.255 | −42.215 | −0.610 | 1.00 | 106.70 |
| 2316 | NH2 | ARG | D | 440 | 109.907 | −44.369 | −1.032 | 1.00 | 106.67 |
| 2317 | C | ARG | D | 440 | 109.556 | −38.775 | −6.849 | 1.00 | 44.50 |
| 2318 | O | ARG | D | 440 | 109.949 | −39.050 | −7.983 | 1.00 | 44.01 |
| 2319 | N | ALA | D | 441 | 109.254 | −37.541 | −6.472 | 1.00 | 38.66 |
| 2320 | CA | ALA | D | 441 | 109.371 | −36.423 | −7.392 | 1.00 | 33.20 |
| 2321 | CB | ALA | D | 441 | 108.129 | −36.311 | −8.291 | 1.00 | 29.24 |
| 2322 | C | ALA | D | 441 | 109.515 | −35.194 | −6.543 | 1.00 | 30.32 |
| 2323 | O | ALA | D | 441 | 108.651 | −34.892 | −5.726 | 1.00 | 28.18 |
| 2324 | N | ALA | D | 442 | 110.621 | −34.491 | −6.735 | 1.00 | 31.20 |
| 2325 | CA | ALA | D | 442 | 110.887 | −33.288 | −5.973 | 1.00 | 30.41 |
| 2326 | CB | ALA | D | 442 | 112.202 | −32.676 | −6.397 | 1.00 | 32.65 |
| 2327 | C | ALA | D | 442 | 109.773 | −32.282 | −6.160 | 1.00 | 27.56 |
| 2328 | O | ALA | D | 442 | 109.107 | −32.261 | −7.191 | 1.00 | 30.69 |
| 2329 | N | PRO | D | 443 | 109.559 | −31.426 | −5.149 | 1.00 | 31.87 |
| 2330 | CD | PRO | D | 443 | 110.268 | −31.389 | −3.855 | 1.00 | 28.80 |
| 2331 | CA | PRO | D | 443 | 108.520 | −30.404 | −5.203 | 1.00 | 28.25 |
| 2332 | CB | PRO | D | 443 | 108.225 | −30.137 | −3.728 | 1.00 | 26.31 |
| 2333 | CG | PRO | D | 443 | 109.540 | −30.283 | −3.092 | 1.00 | 26.69 |
| 2334 | C | PRO | D | 443 | 109.012 | −29.156 | −5.918 | 1.00 | 28.79 |
| 2335 | O | PRO | D | 443 | 110.213 | −28.853 | −5.920 | 1.00 | 28.34 |
| 2336 | N | ALA | D | 444 | 108.085 | −28.452 | −6.552 | 1.00 | 28.79 |
| 2337 | CA | ALA | D | 444 | 108.422 | −27.213 | −7.220 | 1.00 | 27.79 |
| 2338 | CB | ALA | D | 444 | 107.777 | −27.155 | −8.608 | 1.00 | 29.15 |
| 2339 | C | ALA | D | 444 | 107.868 | −26.117 | −6.314 | 1.00 | 27.17 |
| 2340 | O | ALA | D | 444 | 106.705 | −26.150 | −5.906 | 1.00 | 22.73 |
| 2341 | N | VAL | D | 445 | 108.692 | −25.127 | −6.019 | 1.00 | 24.17 |
| 2342 | CA | VAL | D | 445 | 108.258 | −24.076 | −5.117 | 1.00 | 23.05 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2343 | CB | VAL | D | 445 | 109.248 | -23.973 | -3.919 | 1.00 | 23.06 |
| 2344 | CG1 | VAL | D | 445 | 108.767 | -22.943 | -2.919 | 1.00 | 19.24 |
| 2345 | CG2 | VAL | D | 445 | 109.404 | -25.327 | -3.252 | 1.00 | 22.11 |
| 2346 | C | VAL | D | 445 | 108.107 | -22.697 | -5.772 | 1.00 | 22.88 |
| 2347 | O | VAL | D | 445 | 108.989 | -22.240 | -6.488 | 1.00 | 25.36 |
| 2348 | N | TYR | D | 446 | 106.982 | -22.038 | -5.517 | 1.00 | 23.09 |
| 2349 | CA | TYR | D | 446 | 106.736 | -20.711 | -6.064 | 1.00 | 27.01 |
| 2350 | CB | TYR | D | 446 | 105.753 | -20.780 | -7.225 | 1.00 | 38.81 |
| 2351 | CG | TYR | D | 446 | 106.163 | -21.714 | -8.328 | 1.00 | 44.60 |
| 2352 | CD1 | TYR | D | 446 | 105.721 | -23.033 | -8.348 | 1.00 | 48.23 |
| 2353 | CE1 | TYR | D | 446 | 106.084 | -23.894 | -9.375 | 1.00 | 56.16 |
| 2354 | CD2 | TYR | D | 446 | 106.988 | -21.278 | -9.362 | 1.00 | 49.16 |
| 2355 | CE2 | TYR | D | 446 | 107.362 | -22.131 | -10.392 | 1.00 | 56.58 |
| 2356 | CZ | TYR | D | 446 | 106.904 | -23.436 | -10.395 | 1.00 | 58.40 |
| 2357 | OH | TYR | D | 446 | 107.262 | -24.284 | -11.418 | 1.00 | 61.65 |
| 2358 | C | TYR | D | 446 | 106.151 | -19.814 | -4.979 | 1.00 | 23.14 |
| 2359 | O | TYR | D | 446 | 105.225 | -20.220 | -4.273 | 1.00 | 23.31 |
| 2360 | N | ALA | D | 447 | 106.679 | -18.601 | -4.849 | 1.00 | 21.13 |
| 2361 | CA | ALA | D | 447 | 106.181 | -17.681 | -3.837 | 1.00 | 22.72 |
| 2362 | CB | ALA | D | 447 | 107.230 | -17.487 | -2.728 | 1.00 | 20.57 |
| 2363 | C | ALA | D | 447 | 105.827 | -16.348 | -4.453 | 1.00 | 21.34 |
| 2364 | O | ALA | D | 447 | 106.469 | -15.909 | -5.404 | 1.00 | 21.81 |
| 2365 | N | PHE | D | 448 | 104.789 | -15.707 | -3.924 | 1.00 | 23.68 |
| 2366 | CA | PHE | D | 448 | 104.389 | -14.405 | -4.446 | 1.00 | 26.16 |
| 2367 | CB | PHE | D | 448 | 103.226 | -14.502 | -5.441 | 1.00 | 26.86 |
| 2368 | CG | PHE | D | 448 | 103.082 | -15.839 | -6.100 | 1.00 | 33.33 |
| 2369 | CD1 | PHE | D | 448 | 102.429 | -16.873 | -5.447 | 1.00 | 33.67 |
| 2370 | CD2 | PHE | D | 448 | 103.551 | -16.050 | -7.404 | 1.00 | 36.40 |
| 2371 | CE1 | PHE | D | 448 | 102.244 | -18.099 | -6.073 | 1.00 | 35.84 |
| 2372 | CE2 | PHE | D | 448 | 103.368 | -17.282 | -8.040 | 1.00 | 36.10 |
| 2373 | CZ | PHE | D | 448 | 102.709 | -18.301 | -7.372 | 1.00 | 36.83 |
| 2374 | C | PHE | D | 448 | 103.942 | -13.480 | -3.338 | 1.00 | 24.19 |
| 2375 | O | PHE | D | 448 | 103.638 | -13.921 | -2.225 | 1.00 | 22.84 |
| 2376 | N | ALA | D | 449 | 103.884 | -12.192 | -3.668 | 1.00 | 23.00 |
| 2377 | CA | ALA | D | 449 | 103.436 | -11.180 | -2.729 | 1.00 | 25.04 |
| 2378 | CB | ALA | D | 449 | 104.545 | -10.184 | -2.470 | 1.00 | 22.47 |
| 2379 | C | ALA | D | 449 | 102.228 | -10.478 | -3.351 | 1.00 | 25.38 |
| 2380 | O | ALA | D | 449 | 102.234 | -10.170 | -4.532 | 1.00 | 23.99 |
| 2381 | N | THR | D | 450 | 101.182 | -10.246 | -2.570 | 1.00 | 25.97 |
| 2382 | CA | THR | D | 450 | 100.029 | -9.551 | -3.107 | 1.00 | 31.11 |
| 2383 | CB | THR | D | 450 | 98.789 | -9.779 | -2.247 | 1.00 | 29.84 |
| 2384 | OG1 | THR | D | 450 | 99.071 | -9.368 | -0.907 | 1.00 | 30.19 |
| 2385 | CG2 | THR | D | 450 | 98.379 | -11.240 | -2.276 | 1.00 | 27.62 |
| 2386 | C | THR | D | 450 | 100.385 | -8.054 | -3.096 | 1.00 | 33.72 |
| 2387 | O | THR | D | 450 | 101.223 | -7.633 | -2.312 | 1.00 | 32.19 |
| 2388 | N | PRO | D | 451 | 99.757 | -7.229 | -3.958 | 1.00 | 43.37 |
| 2389 | CD | PRO | D | 451 | 98.802 | -7.671 | -4.989 | 1.00 | 40.17 |
| 2390 | CA | PRO | D | 451 | 100.009 | -5.780 | -4.057 | 1.00 | 47.07 |
| 2391 | CB | PRO | D | 451 | 99.626 | -5.472 | -5.501 | 1.00 | 44.85 |
| 2392 | CG | PRO | D | 451 | 98.457 | -6.375 | -5.726 | 1.00 | 39.95 |
| 2393 | C | PRO | D | 451 | 99.230 | -4.942 | -3.045 | 1.00 | 48.57 |
| 2394 | O | PRO | D | 451 | 98.251 | -5.423 | -2.476 | 1.00 | 58.15 |
| 2395 | N | GLU | D | 452 | 99.634 | -3.691 | -2.823 | 1.00 | 59.61 |
| 2396 | CA | GLU | D | 452 | 98.912 | -2.900 | -1.830 | 1.00 | 76.39 |
| 2397 | CB | GLU | D | 452 | 99.461 | -1.475 | -1.693 | 1.00 | 91.59 |
| 2398 | CG | GLU | D | 452 | 99.495 | -1.008 | -0.234 | 1.00 | 106.95 |
| 2399 | CD | GLU | D | 452 | 98.796 | 0.331 | 0.010 | 1.00 | 114.98 |
| 2400 | OE1 | GLU | D | 452 | 98.746 | 1.140 | -0.926 | 1.00 | 119.01 |
| 2401 | OE2 | GLU | D | 452 | 98.313 | 0.601 | 1.131 | 1.00 | 119.04 |
| 2402 | C | GLU | D | 452 | 97.420 | -2.862 | -2.140 | 1.00 | 73.61 |
| 2403 | O | GLU | D | 452 | 96.963 | -2.190 | -3.075 | 1.00 | 74.94 |
| 2404 | N | ALA | D | 453 | 96.681 | -3.634 | -1.347 | 1.00 | 75.06 |
| 2405 | CA | ALA | D | 453 | 95.234 | -3.754 | -1.450 | 1.00 | 77.95 |
| 2406 | CB | ALA | D | 453 | 94.763 | -4.941 | -0.605 | 1.00 | 68.06 |
| 2407 | C | ALA | D | 453 | 94.652 | -2.452 | -0.916 | 1.00 | 82.09 |
| 2408 | O | ALA | D | 453 | 95.317 | -1.758 | -0.150 | 1.00 | 72.35 |
| 2409 | N | PRO | D | 454 | 93.420 | -2.081 | -1.317 | 1.00 | 80.89 |
| 2410 | CD | PRO | D | 454 | 92.406 | -2.700 | -2.188 | 1.00 | 82.73 |
| 2411 | CA | PRO | D | 454 | 92.951 | -0.816 | -0.742 | 1.00 | 79.59 |
| 2412 | CB | PRO | D | 454 | 91.664 | -0.518 | -1.506 | 1.00 | 82.68 |
| 2413 | CG | PRO | D | 454 | 91.174 | -1.848 | -1.938 | 1.00 | 90.60 |
| 2414 | C | PRO | D | 454 | 92.717 | -0.999 | 0.741 | 1.00 | 78.04 |
| 2415 | O | PRO | D | 454 | 93.308 | -0.295 | 1.567 | 1.00 | 70.60 |
| 2416 | N | GLY | D | 455 | 91.862 | -1.975 | 1.044 | 1.00 | 74.14 |
| 2417 | CA | GLY | D | 455 | 91.506 | -2.323 | 2.405 | 1.00 | 69.84 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2418 | C | GLY | D | 455 | 92.410 | −1.720 | 3.450 | 1.00 | 67.88 |
| 2419 | O | GLY | D | 455 | 91.942 | −1.066 | 4.379 | 1.00 | 68.02 |
| 2420 | N | ALA | D | 456 | 93.711 | −1.933 | 3.315 | 1.00 | 64.73 |
| 2421 | CA | ALA | D | 456 | 94.627 | −1.366 | 4.281 | 1.00 | 69.01 |
| 2422 | CB | ALA | D | 456 | 94.155 | −1.676 | 5.696 | 1.00 | 76.18 |
| 2423 | C | ALA | D | 456 | 96.025 | −1.884 | 4.080 | 1.00 | 72.19 |
| 2424 | O | ALA | D | 456 | 96.257 | −3.094 | 4.019 | 1.00 | 75.01 |
| 2425 | N | ALA | D | 457 | 96.971 | −0.969 | 3.982 | 1.00 | 72.55 |
| 2426 | CA | ALA | D | 457 | 98.305 | −1.439 | 3.795 | 1.00 | 67.44 |
| 2427 | CB | ALA | D | 457 | 98.694 | −1.307 | 2.400 | 1.00 | 64.13 |
| 2428 | C | ALA | D | 457 | 99.373 | −0.875 | 4.672 | 1.00 | 64.87 |
| 2429 | O | ALA | D | 457 | 99.561 | 0.329 | 4.817 | 1.00 | 56.24 |
| 2430 | N | ASP | D | 458 | 100.042 | −1.849 | 5.257 | 1.00 | 60.83 |
| 2431 | CA | ASP | D | 458 | 101.171 | −1.753 | 6.139 | 1.00 | 57.78 |
| 2432 | CB | ASP | D | 458 | 100.979 | −0.718 | 7.220 | 1.00 | 56.87 |
| 2433 | CG | ASP | D | 458 | 101.804 | 0.486 | 6.928 | 1.00 | 58.78 |
| 2434 | OD1 | ASP | D | 458 | 102.216 | 0.588 | 5.747 | 1.00 | 60.19 |
| 2435 | OD2 | ASP | D | 458 | 102.059 | 1.306 | 7.825 | 1.00 | 60.37 |
| 2436 | C | ASP | D | 458 | 101.246 | −3.160 | 6.626 | 1.00 | 60.03 |
| 2437 | O | ASP | D | 458 | 101.661 | −3.494 | 7.735 | 1.00 | 55.46 |
| 2438 | N | LYS | D | 459 | 100.799 | −3.983 | 5.698 | 1.00 | 64.28 |
| 2439 | CA | LYS | D | 459 | 100.806 | −5.407 | 5.821 | 1.00 | 63.85 |
| 2440 | CB | LYS | D | 459 | 100.092 | −5.881 | 7.091 | 1.00 | 70.20 |
| 2441 | CG | LYS | D | 459 | 98.761 | −5.251 | 7.415 | 1.00 | 84.44 |
| 2442 | CD | LYS | D | 459 | 98.584 | −5.131 | 8.940 | 1.00 | 90.81 |
| 2443 | CE | LYS | D | 459 | 97.858 | −6.323 | 9.559 | 1.00 | 92.48 |
| 2444 | NZ | LYS | D | 459 | 97.782 | −6.211 | 11.051 | 1.00 | 94.09 |
| 2445 | C | LYS | D | 459 | 100.236 | −6.028 | 4.570 | 1.00 | 62.40 |
| 2446 | O | LYS | D | 459 | 99.197 | −5.623 | 4.042 | 1.00 | 63.98 |
| 2447 | N | ARG | D | 460 | 100.973 | −7.016 | 4.094 | 1.00 | 59.57 |
| 2448 | CA | ARG | D | 460 | 100.645 | −7.725 | 2.890 | 1.00 | 48.15 |
| 2449 | CB | ARG | D | 460 | 101.671 | −7.382 | 1.826 | 1.00 | 49.93 |
| 2450 | CG | ARG | D | 460 | 101.681 | −5.918 | 1.481 | 1.00 | 60.38 |
| 2451 | CD | ARG | D | 460 | 102.135 | −5.797 | 0.082 | 1.00 | 65.47 |
| 2452 | NE | ARG | D | 460 | 102.131 | −4.443 | −0.432 | 1.00 | 69.24 |
| 2453 | CZ | ARG | D | 460 | 102.711 | −4.134 | −1.582 | 1.00 | 72.59 |
| 2454 | NH1 | ARG | D | 460 | 103.312 | −5.094 | −2.277 | 1.00 | 73.44 |
| 2455 | NH2 | ARG | D | 460 | 102.689 | −2.892 | −2.040 | 1.00 | 73.63 |
| 2456 | C | ARG | D | 460 | 100.599 | −9.217 | 3.101 | 1.00 | 39.93 |
| 2457 | O | ARG | D | 460 | 100.971 | −9.727 | 4.154 | 1.00 | 39.49 |
| 2458 | N | THR | D | 461 | 100.144 | −9.915 | 2.075 | 1.00 | 34.05 |
| 2459 | CA | THR | D | 461 | 100.028 | −11.348 | 2.151 | 1.00 | 27.97 |
| 2460 | CB | THR | D | 461 | 98.606 | −11.791 | 1.806 | 1.00 | 22.80 |
| 2461 | OG1 | THR | D | 461 | 97.690 | −11.176 | 2.715 | 1.00 | 24.24 |
| 2462 | CG2 | THR | D | 461 | 98.473 | −13.302 | 1.917 | 1.00 | 21.42 |
| 2463 | C | THR | D | 461 | 101.001 | −12.014 | 1.198 | 1.00 | 25.39 |
| 2464 | O | THR | D | 461 | 101.161 | −11.597 | 0.051 | 1.00 | 26.02 |
| 2465 | N | LEU | D | 462 | 101.667 | −13.048 | 1.680 | 1.00 | 24.25 |
| 2466 | CA | LEU | D | 462 | 102.582 | −13.758 | 0.824 | 1.00 | 21.95 |
| 2467 | CB | LEU | D | 462 | 103.963 | −13.871 | 1.471 | 1.00 | 23.05 |
| 2468 | CG | LEU | D | 462 | 104.652 | −12.539 | 1.780 | 1.00 | 26.24 |
| 2469 | CD1 | LEU | D | 462 | 106.075 | −12.803 | 2.297 | 1.00 | 26.42 |
| 2470 | CD2 | LEU | D | 462 | 104.684 | −11.671 | 0.541 | 1.00 | 25.41 |
| 2471 | C | LEU | D | 462 | 101.974 | −15.126 | 0.635 | 1.00 | 22.02 |
| 2472 | O | LEU | D | 462 | 101.299 | −15.655 | 1.528 | 1.00 | 19.08 |
| 2473 | N | ALA | D | 463 | 102.198 | −15.703 | −0.532 | 1.00 | 20.67 |
| 2474 | CA | ALA | D | 463 | 101.650 | −17.011 | −0.787 | 1.00 | 19.01 |
| 2475 | CB | ALA | D | 463 | 100.402 | −16.906 | −1.639 | 1.00 | 18.97 |
| 2476 | C | ALA | D | 463 | 102.672 | −17.873 | −1.461 | 1.00 | 18.21 |
| 2477 | O | ALA | D | 463 | 103.498 | −17.408 | −2.262 | 1.00 | 19.15 |
| 2478 | N | CYS | D | 464 | 102.608 | −19.148 | −1.133 | 1.00 | 20.06 |
| 2479 | CA | CYS | D | 464 | 103.534 | −20.090 | −1.701 | 1.00 | 20.82 |
| 2480 | C | CYS | D | 464 | 102.759 | −21.240 | −2.310 | 1.00 | 19.86 |
| 2481 | O | CYS | D | 464 | 101.787 | −21.726 | −1.728 | 1.00 | 19.97 |
| 2482 | CE | CYS | D | 464 | 104.455 | −20.610 | −0.610 | 1.00 | 20.27 |
| 2483 | SG | CYS | D | 464 | 105.937 | −21.445 | −1.223 | 1.00 | 25.81 |
| 2484 | N | LEU | D | 465 | 103.177 | −21.657 | −3.495 | 1.00 | 18.44 |
| 2485 | CA | LEU | D | 465 | 102.546 | −22.790 | −4.155 | 1.00 | 17.41 |
| 2486 | CB | LEU | D | 465 | 102.020 | −22.411 | −5.546 | 1.00 | 19.89 |
| 2487 | CG | LEU | D | 465 | 101.674 | −23.598 | −6.451 | 1.00 | 20.07 |
| 2488 | CD1 | LEU | D | 465 | 100.538 | −24.409 | −5.837 | 1.00 | 21.22 |
| 2489 | CD2 | LEU | D | 465 | 101.277 | −23.098 | −7.832 | 1.00 | 22.16 |
| 2490 | C | LEU | D | 465 | 103.628 | −23.840 | −4.305 | 1.00 | 16.77 |
| 2491 | O | LEU | D | 465 | 104.685 | −23.567 | −4.889 | 1.00 | 14.24 |
| 2492 | N | ILE | D | 466 | 103.372 | −25.022 | −3.751 | 1.00 | 13.00 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2493 | CA | ILE | D | 466 | 104.309 | −26.123 | −3.826 | 1.00 | 16.12 |
| 2494 | CB | ILE | D | 466 | 104.769 | −26.545 | −2.417 | 1.00 | 14.55 |
| 2495 | CG2 | ILE | D | 466 | 105.794 | −27.660 | −2.526 | 1.00 | 10.81 |
| 2496 | CG1 | ILE | D | 466 | 105.371 | −25.326 | −1.700 | 1.00 | 14.00 |
| 2497 | CD1 | ILE | D | 466 | 105.092 | −25.307 | −0.220 | 1.00 | 13.74 |
| 2498 | C | ILE | D | 466 | 103.553 | −27.249 | −4.512 | 1.00 | 16.81 |
| 2499 | O | ILE | D | 466 | 102.497 | −27.671 | −4.033 | 1.00 | 15.75 |
| 2500 | N | GLN | D | 467 | 104.090 | −27.740 | −5.627 | 1.00 | 17.22 |
| 2501 | CA | GLN | D | 467 | 103.382 | −28.765 | −6.384 | 1.00 | 19.97 |
| 2502 | CB | GLN | D | 467 | 102.502 | −28.087 | −7.442 | 1.00 | 19.16 |
| 2503 | CG | GLN | D | 467 | 103.263 | −27.080 | −8.323 | 1.00 | 18.48 |
| 2504 | CD | GLN | D | 467 | 102.426 | −26.542 | −9.465 | 1.00 | 18.99 |
| 2505 | OE1 | GLN | D | 467 | 101.248 | −26.238 | −9.293 | 1.00 | 21.32 |
| 2506 | NE2 | GLN | D | 467 | 103.028 | −26.414 | −10.633 | 1.00 | 17.55 |
| 2507 | C | GLN | D | 467 | 104.222 | −29.827 | −7.080 | 1.00 | 19.72 |
| 2508 | O | GLN | D | 467 | 105.457 | −29.734 | −7.173 | 1.00 | 20.67 |
| 2509 | N | ASN | D | 468 | 103.506 | −30.835 | −7.573 | 1.00 | 23.97 |
| 2510 | CA | ASN | D | 468 | 104.091 | −31.943 | −8.314 | 1.00 | 27.84 |
| 2511 | CB | ASN | D | 468 | 104.720 | −31.419 | −9.625 | 1.00 | 27.00 |
| 2512 | CG | ASN | D | 468 | 103.695 | −30.754 | −10.553 | 1.00 | 27.40 |
| 2513 | OD1 | ASN | D | 468 | 102.542 | −31.183 | −10.640 | 1.00 | 27.11 |
| 2514 | ND2 | ASN | D | 468 | 104.123 | −29.713 | −11.256 | 1.00 | 26.07 |
| 2515 | C | ASN | D | 468 | 105.113 | −32.781 | −7.528 | 1.00 | 29.45 |
| 2516 | O | ASN | D | 468 | 105.946 | −33.458 | −8.133 | 1.00 | 27.68 |
| 2517 | N | PHE | D | 469 | 105.064 | −32.738 | −6.191 | 1.00 | 37.81 |
| 2518 | CA | PHE | D | 469 | 105.990 | −33.555 | −5.390 | 1.00 | 39.18 |
| 2519 | CB | PHE | D | 469 | 106.314 | −32.880 | −4.041 | 1.00 | 28.73 |
| 2520 | CG | PHE | D | 469 | 105.110 | −32.404 | −3.286 | 1.00 | 18.97 |
| 2521 | CD1 | PHE | D | 469 | 104.477 | −33.237 | −2.381 | 1.00 | 13.64 |
| 2522 | CD2 | PHE | D | 469 | 104.604 | −31.124 | −3.491 | 1.00 | 16.79 |
| 2523 | CE1 | PHE | D | 469 | 103.348 | −32.822 | −1.688 | 1.00 | 15.89 |
| 2524 | CE2 | PHE | D | 469 | 103.470 | −30.689 | −2.808 | 1.00 | 17.93 |
| 2525 | CZ | PHE | D | 469 | 102.839 | −31.542 | −1.897 | 1.00 | 16.09 |
| 2526 | C | PHE | D | 469 | 105.323 | −34.928 | −5.222 | 1.00 | 40.07 |
| 2527 | O | PHE | D | 469 | 104.093 | −35.012 | −5.236 | 1.00 | 46.56 |
| 2528 | N | MET | D | 470 | 106.121 | −35.994 | −5.090 | 1.00 | 42.97 |
| 2529 | CA | MET | D | 470 | 105.557 | −37.347 | −5.006 | 1.00 | 57.79 |
| 2530 | CB | MET | D | 470 | 106.545 | −38.384 | −5.546 | 1.00 | 72.48 |
| 2531 | CG | MET | D | 470 | 105.839 | −39.611 | −6.108 | 1.00 | 78.84 |
| 2532 | SD | MET | D | 470 | 104.764 | −39.310 | −7.518 | 1.00 | 78.19 |
| 2533 | CE | MET | D | 470 | 103.392 | −38.538 | −6.683 | 1.00 | 79.64 |
| 2534 | C | MET | D | 470 | 104.958 | −37.789 | −3.670 | 1.00 | 62.30 |
| 2535 | O | MET | D | 470 | 103.805 | −37.432 | −3.411 | 1.00 | 67.15 |
| 2536 | N | PRO | D | 471 | 105.667 | −38.574 | −2.817 | 1.00 | 39.24 |
| 2537 | CD | PRO | D | 471 | 107.004 | −39.188 | −2.768 | 1.00 | 49.06 |
| 2538 | CA | PRO | D | 471 | 104.872 | −38.849 | −1.608 | 1.00 | 43.81 |
| 2539 | CB | PRO | D | 471 | 105.893 | −39.318 | −0.576 | 1.00 | 41.58 |
| 2540 | CG | PRO | D | 471 | 107.111 | −39.690 | −1.353 | 1.00 | 42.52 |
| 2541 | C | PRO | D | 471 | 104.253 | −37.509 | −1.200 | 1.00 | 42.84 |
| 2542 | O | PRO | D | 471 | 104.849 | −36.445 | −1.423 | 1.00 | 27.32 |
| 2543 | N | GLU | D | 472 | 103.055 | −37.552 | −0.647 | 1.00 | 31.39 |
| 2544 | CA | GLU | D | 472 | 102.383 | −36.336 | −0.252 | 1.00 | 33.33 |
| 2545 | CB | GLU | D | 472 | 100.895 | −36.619 | −0.119 | 1.00 | 36.94 |
| 2546 | CG | GLU | D | 472 | 100.588 | −37.636 | 0.956 | 1.00 | 47.41 |
| 2547 | CD | GLU | D | 472 | 99.134 | −38.019 | 0.966 | 1.00 | 55.20 |
| 2548 | OE1 | GLU | D | 472 | 98.735 | −38.847 | 0.118 | 1.00 | 59.73 |
| 2549 | OE2 | GLU | D | 472 | 98.383 | −37.478 | 1.810 | 1.00 | 60.59 |
| 2550 | C | GLU | D | 472 | 102.900 | −35.709 | 1.045 | 1.00 | 34.51 |
| 2551 | O | GLU | D | 472 | 102.511 | −34.592 | 1.386 | 1.00 | 33.63 |
| 2552 | N | ASP | D | 473 | 103.756 | −36.409 | 1.778 | 1.00 | 36.20 |
| 2553 | CA | ASP | D | 473 | 104.252 | −35.851 | 3.031 | 1.00 | 35.94 |
| 2554 | CB | ASP | D | 473 | 104.963 | −36.919 | 3.850 | 1.00 | 45.24 |
| 2555 | CG | ASP | D | 473 | 104.038 | −38.056 | 4.223 | 1.00 | 55.56 |
| 2556 | OD1 | ASP | D | 473 | 102.862 | −37.791 | 4.566 | 1.00 | 62.37 |
| 2557 | OD2 | ASP | D | 473 | 104.488 | −39.215 | 4.175 | 1.00 | 63.38 |
| 2558 | C | ASP | D | 473 | 105.164 | −34.676 | 2.775 | 1.00 | 31.35 |
| 2559 | O | ASP | D | 473 | 106.143 | −34.788 | 2.037 | 1.00 | 32.19 |
| 2560 | N | ILE | D | 474 | 104.840 | −33.546 | 3.399 | 1.00 | 26.89 |
| 2561 | CA | ILE | D | 474 | 105.621 | −32.339 | 3.187 | 1.00 | 23.96 |
| 2562 | CB | ILE | D | 474 | 105.157 | −31.656 | 1.888 | 1.00 | 19.00 |
| 2563 | CG2 | ILE | D | 474 | 103.797 | −31.023 | 2.101 | 1.00 | 16.45 |
| 2564 | CG1 | ILE | D | 474 | 106.178 | −30.619 | 1.437 | 1.00 | 18.12 |
| 2565 | CD1 | ILE | D | 474 | 106.263 | −30.491 | −0.073 | 1.00 | 18.34 |
| 2566 | C | ILE | D | 474 | 105.537 | −31.328 | 4.328 | 1.00 | 23.39 |
| 2567 | O | ILE | D | 474 | 104.486 | −31.148 | 4.942 | 1.00 | 22.87 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2568 | N | SER | D | 475 | 106.648 | −30.673 | 4.613 | 1.00 | 21.50 |
| 2569 | CA | SER | D | 475 | 106.664 | −29.656 | 5.642 | 1.00 | 21.46 |
| 2570 | CB | SER | D | 475 | 107.722 | −29.966 | 6.702 | 1.00 | 23.45 |
| 2571 | OG | SER | D | 475 | 107.356 | −31.102 | 7.465 | 1.00 | 26.73 |
| 2572 | C | SER | D | 475 | 106.978 | −28.331 | 4.961 | 1.00 | 21.79 |
| 2573 | O | SER | D | 475 | 107.832 | −28.261 | 4.072 | 1.00 | 21.06 |
| 2574 | N | VAL | D | 476 | 106.266 | −27.287 | 5.369 | 1.00 | 22.85 |
| 2575 | CA | VAL | D | 476 | 106.460 | −25.965 | 4.808 | 1.00 | 20.35 |
| 2576 | CB | VAL | D | 476 | 105.181 | −25.430 | 4.144 | 1.00 | 19.82 |
| 2577 | CG1 | VAL | D | 476 | 105.446 | −24.052 | 3.536 | 1.00 | 18.26 |
| 2578 | CG2 | VAL | D | 476 | 104.693 | −26.403 | 3.106 | 1.00 | 18.62 |
| 2579 | C | VAL | D | 476 | 106.782 | −25.024 | 5.946 | 1.00 | 20.30 |
| 2580 | O | VAL | D | 476 | 106.144 | −25.081 | 6.991 | 1.00 | 18.17 |
| 2581 | N | GLN | D | 477 | 107.764 | −24.157 | 5.750 | 1.00 | 24.70 |
| 2582 | CA | GLN | D | 477 | 108.087 | −23.210 | 6.791 | 1.00 | 28.87 |
| 2583 | CB | GLN | D | 477 | 109.187 | −23.781 | 7.715 | 1.00 | 31.89 |
| 2584 | CG | GLN | D | 477 | 110.460 | −24.165 | 7.000 | 1.00 | 38.92 |
| 2585 | CD | GLN | D | 477 | 111.363 | −25.113 | 7.783 | 1.00 | 42.56 |
| 2586 | OE1 | GLN | D | 477 | 112.576 | −25.161 | 7.529 | 1.00 | 45.61 |
| 2587 | NE2 | GLN | D | 477 | 110.789 | −25.888 | 8.707 | 1.00 | 42.71 |
| 2588 | C | GLN | D | 477 | 108.496 | −21.904 | 6.135 | 1.00 | 26.96 |
| 2589 | O | GLN | D | 477 | 108.919 | −21.888 | 4.979 | 1.00 | 27.51 |
| 2590 | N | TRP | D | 478 | 108.321 | −20.802 | 6.854 | 1.00 | 25.62 |
| 2591 | CA | TRP | D | 478 | 108.697 | −19.505 | 6.319 | 1.00 | 24.82 |
| 2592 | CB | TRP | D | 478 | 107.533 | −18.525 | 6.363 | 1.00 | 22.69 |
| 2593 | CG | TRP | D | 478 | 106.414 | −18.869 | 5.449 | 1.00 | 21.50 |
| 2594 | CD2 | TRP | D | 478 | 106.167 | −18.320 | 4.145 | 1.00 | 20.81 |
| 2595 | CE2 | TRP | D | 478 | 104.975 | −18.910 | 3.659 | 1.00 | 22.05 |
| 2596 | CE3 | TRP | D | 478 | 106.816 | −17.359 | 3.355 | 1.00 | 19.62 |
| 2597 | CD1 | TRP | D | 478 | 105.408 | −19.767 | 5.685 | 1.00 | 21.47 |
| 2598 | NE1 | TRP | D | 478 | 104.538 | −19.799 | 4.613 | 1.00 | 22.10 |
| 2599 | CZ2 | TRP | D | 478 | 104.441 | −18.606 | 2.401 | 1.00 | 20.66 |
| 2600 | CZ3 | TRP | D | 478 | 106.288 | −17.054 | 2.106 | 1.00 | 20.65 |
| 2601 | CH2 | TRP | D | 478 | 105.100 | −17.667 | 1.648 | 1.00 | 21.09 |
| 2602 | C | TRP | D | 478 | 109.839 | −18.939 | 7.124 | 1.00 | 25.88 |
| 2603 | O | TRP | D | 478 | 109.906 | −19.106 | 8.354 | 1.00 | 24.55 |
| 2604 | N | LEU | D | 479 | 110.734 | −18.246 | 6.434 | 1.00 | 23.56 |
| 2605 | CA | LEU | D | 479 | 111.864 | −17.672 | 7.126 | 1.00 | 26.44 |
| 2606 | CB | LEU | D | 479 | 113.147 | −18.395 | 6.703 | 1.00 | 26.09 |
| 2607 | CG | LEU | D | 479 | 112.999 | −19.915 | 6.629 | 1.00 | 29.02 |
| 2608 | CD1 | LEU | D | 479 | 114.034 | −20.478 | 5.686 | 1.00 | 30.49 |
| 2609 | CD2 | LEU | D | 479 | 113.136 | −20.526 | 8.003 | 1.00 | 31.07 |
| 2610 | C | LEU | D | 479 | 112.004 | −16.181 | 6.885 | 1.00 | 24.72 |
| 2611 | O | LEU | D | 479 | 111.788 | −15.691 | 5.764 | 1.00 | 22.93 |
| 2612 | N | HIS | D | 480 | 112.305 | −15.476 | 7.973 | 1.00 | 26.44 |
| 2613 | CA | HIS | D | 480 | 112.587 | −14.052 | 7.945 | 1.00 | 29.53 |
| 2614 | CB | HIS | D | 480 | 111.524 | −13.189 | 8.622 | 1.00 | 22.31 |
| 2615 | CG | HIS | D | 480 | 111.736 | −11.708 | 8.361 | 1.00 | 19.78 |
| 2616 | CD2 | HIS | D | 480 | 111.573 | −10.643 | 9.190 | 1.00 | 17.47 |
| 2617 | ND1 | HIS | D | 480 | 112.109 | −11.235 | 7.154 | 1.00 | 20.04 |
| 2618 | CE1 | HIS | D | 480 | 112.182 | −9.891 | 7.209 | 1.00 | 19.70 |
| 2619 | NE2 | HIS | D | 480 | 111.863 | −9.531 | 8.415 | 1.00 | 19.40 |
| 2620 | C | HIS | D | 480 | 113.930 | −13.830 | 8.623 | 1.00 | 34.27 |
| 2621 | O | HIS | D | 480 | 114.336 | −14.551 | 9.547 | 1.00 | 33.24 |
| 2622 | N | ASN | D | 481 | 114.586 | −12.786 | 8.119 | 1.00 | 41.35 |
| 2623 | CA | ASN | D | 481 | 115.924 | −12.340 | 8.472 | 1.00 | 50.42 |
| 2624 | CB | ASN | D | 481 | 116.042 | −11.935 | 9.904 | 1.00 | 47.85 |
| 2625 | CG | ASN | D | 481 | 115.812 | −10.519 | 10.033 | 1.00 | 44.69 |
| 2626 | OD1 | ASN | D | 481 | 116.519 | −9.697 | 9.436 | 1.00 | 42.98 |
| 2627 | ND2 | ASN | D | 481 | 114.787 | −10.188 | 10.761 | 1.00 | 41.33 |
| 2628 | C | ASN | D | 481 | 116.877 | −13.417 | 8.121 | 1.00 | 57.53 |
| 2629 | O | ASN | D | 481 | 118.060 | −13.166 | 7.875 | 1.00 | 62.32 |
| 2630 | N | GLU | D | 482 | 116.263 | −14.589 | 8.001 | 1.00 | 66.57 |
| 2631 | CA | GLU | D | 482 | 116.814 | −15.876 | 7.641 | 1.00 | 74.15 |
| 2632 | CB | GLU | D | 482 | 118.329 | −15.776 | 7.384 | 1.00 | 87.75 |
| 2633 | CG | GLU | D | 482 | 118.730 | −14.787 | 6.236 | 1.00 | 106.73 |
| 2634 | CD | GLU | D | 482 | 118.476 | −15.291 | 4.826 | 1.00 | 117.72 |
| 2635 | OE1 | GLU | D | 482 | 117.807 | −16.329 | 4.668 | 1.00 | 125.73 |
| 2636 | OE2 | GLU | D | 482 | 118.951 | −14.638 | 3.871 | 1.00 | 125.27 |
| 2637 | C | GLU | D | 482 | 116.426 | −16.893 | 8.741 | 1.00 | 70.50 |
| 2638 | O | GLU | D | 482 | 116.625 | −18.094 | 8.580 | 1.00 | 67.38 |
| 2639 | N | VAL | D | 483 | 115.812 | −16.388 | 9.823 | 1.00 | 67.15 |
| 2640 | CA | VAL | D | 483 | 115.320 | −17.169 | 10.989 | 1.00 | 62.15 |
| 2641 | CB | VAL | D | 483 | 115.223 | −16.269 | 12.278 | 1.00 | 69.49 |
| 2642 | CG1 | VAL | D | 483 | 113.855 | −15.580 | 12.345 | 1.00 | 80.52 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2643 | CG2 | VAL | D | 483 | 115.459 | −17.088 | 13.533 | 1.00 | 79.43 |
| 2644 | C | VAL | D | 483 | 113.909 | −17.713 | 10.697 | 1.00 | 55.89 |
| 2645 | O | VAL | D | 483 | 113.143 | −17.105 | 9.960 | 1.00 | 52.84 |
| 2646 | N | GLN | D | 484 | 113.550 | −18.834 | 11.302 | 1.00 | 47.15 |
| 2647 | CA | GLN | D | 484 | 112.239 | −19.419 | 11.057 | 1.00 | 37.83 |
| 2648 | CB | GLN | D | 484 | 112.308 | −20.936 | 11.293 | 1.00 | 37.63 |
| 2649 | CG | GLN | D | 484 | 110.967 | −21.628 | 11.348 | 1.00 | 37.29 |
| 2650 | CD | GLN | D | 484 | 111.048 | −23.138 | 11.206 | 1.00 | 41.38 |
| 2651 | OE1 | GLN | D | 484 | 110.229 | −23.868 | 11.787 | 1.00 | 40.97 |
| 2652 | NE2 | GLN | D | 484 | 112.010 | −23.624 | 10.413 | 1.00 | 42.04 |
| 2653 | C | GLN | D | 484 | 111.127 | −18.782 | 11.889 | 1.00 | 34.54 |
| 2654 | O | GLN | D | 484 | 111.258 | −18.632 | 13.106 | 1.00 | 30.75 |
| 2655 | N | LEU | D | 485 | 110.037 | −18.404 | 11.224 | 1.00 | 32.37 |
| 2656 | CA | LEU | D | 485 | 108.921 | −17.768 | 11.903 | 1.00 | 29.10 |
| 2657 | CB | LEU | D | 485 | 108.069 | −16.979 | 10.903 | 1.00 | 30.92 |
| 2658 | CG | LEU | D | 485 | 108.733 | −15.761 | 10.255 | 1.00 | 30.15 |
| 2659 | CD1 | LEU | D | 485 | 107.903 | −15.281 | 9.073 | 1.00 | 29.71 |
| 2660 | CD2 | LEU | D | 485 | 108.889 | −14.663 | 11.284 | 1.00 | 31.78 |
| 2661 | C | LEU | D | 485 | 108.063 | −18.791 | 12.625 | 1.00 | 26.10 |
| 2662 | O | LEU | D | 485 | 108.047 | −19.967 | 12.273 | 1.00 | 31.91 |
| 2663 | N | PRO | D | 486 | 107.347 | −18.359 | 13.669 | 1.00 | 34.98 |
| 2664 | CD | PRO | D | 486 | 107.346 | −16.994 | 14.233 | 1.00 | 30.33 |
| 2665 | CA | PRO | D | 486 | 106.482 | −19.277 | 14.429 | 1.00 | 33.24 |
| 2666 | CB | PRO | D | 486 | 105.773 | −18.362 | 15.429 | 1.00 | 30.12 |
| 2667 | CG | PRO | D | 486 | 106.730 | −17.198 | 15.586 | 1.00 | 29.96 |
| 2668 | C | PRO | D | 486 | 105.485 | −19.968 | 13.501 | 1.00 | 33.42 |
| 2669 | O | PRO | D | 486 | 104.907 | −19.337 | 12.623 | 1.00 | 36.35 |
| 2670 | N | ASP | D | 487 | 105.282 | −21.260 | 13.702 | 1.00 | 38.11 |
| 2671 | CA | ASP | D | 487 | 104.356 | −22.008 | 12.876 | 1.00 | 44.78 |
| 2672 | CB | ASP | D | 487 | 104.238 | −23.446 | 13.383 | 1.00 | 58.09 |
| 2673 | CG | ASP | D | 487 | 105.553 | −24.188 | 13.322 | 1.00 | 66.60 |
| 2674 | OD1 | ASP | D | 487 | 106.361 | −23.871 | 12.423 | 1.00 | 74.23 |
| 2675 | OD2 | ASP | D | 487 | 105.770 | −25.090 | 14.160 | 1.00 | 74.16 |
| 2676 | C | ASP | D | 487 | 102.964 | −21.385 | 12.805 | 1.00 | 40.96 |
| 2677 | O | ASP | D | 487 | 102.337 | −21.379 | 11.742 | 1.00 | 35.38 |
| 2678 | N | ALA | D | 488 | 102.493 | −20.851 | 13.929 | 1.00 | 34.64 |
| 2679 | CA | ALA | D | 488 | 101.165 | −20.262 | 13.988 | 1.00 | 32.36 |
| 2680 | CB | ALA | D | 488 | 100.828 | −19.904 | 15.424 | 1.00 | 30.93 |
| 2681 | C | ALA | D | 488 | 100.962 | −19.045 | 13.094 | 1.00 | 31.35 |
| 2682 | O | ALA | D | 488 | 99.831 | −18.598 | 12.908 | 1.00 | 30.82 |
| 2683 | N | ARG | D | 489 | 102.044 | −18.502 | 12.545 | 1.00 | 30.84 |
| 2684 | CA | ARG | D | 489 | 101.923 | −17.328 | 11.694 | 1.00 | 29.63 |
| 2685 | CB | ARG | D | 489 | 103.221 | −16.524 | 11.740 | 1.00 | 31.80 |
| 2686 | CG | ARG | D | 489 | 103.136 | −15.363 | 12.722 | 1.00 | 34.08 |
| 2687 | CD | ARG | D | 489 | 103.090 | −14.052 | 11.973 | 1.00 | 37.54 |
| 2688 | NE | ARG | D | 489 | 104.355 | −13.364 | 12.153 | 1.00 | 40.41 |
| 2689 | CZ | ARG | D | 489 | 104.884 | −12.513 | 11.288 | 1.00 | 41.36 |
| 2690 | NH1 | ARG | D | 489 | 104.260 | −12.230 | 10.150 | 1.00 | 39.26 |
| 2691 | NH2 | ARG | D | 489 | 106.049 | −11.947 | 11.579 | 1.00 | 41.86 |
| 2692 | C | ARG | D | 489 | 101.514 | −17.614 | 10.248 | 1.00 | 29.56 |
| 2693 | O | ARG | D | 489 | 101.117 | −16.703 | 9.507 | 1.00 | 29.64 |
| 2694 | N | HIS | D | 490 | 101.592 | −18.871 | 9.838 | 1.00 | 29.01 |
| 2695 | CA | HIS | D | 490 | 101.205 | −19.200 | 8.485 | 1.00 | 28.59 |
| 2696 | CB | HIS | D | 490 | 102.420 | −19.603 | 7.655 | 1.00 | 27.62 |
| 2697 | CG | HIS | D | 490 | 103.022 | −20.913 | 8.062 | 1.00 | 29.57 |
| 2698 | CD2 | HIS | D | 490 | 102.661 | −22.182 | 7.772 | 1.00 | 30.59 |
| 2699 | ND1 | HIS | D | 490 | 104.132 | −20.997 | 8.875 | 1.09 | 32.20 |
| 2700 | CE1 | HIS | D | 490 | 104.430 | −22.274 | 9.067 | 1.00 | 31.66 |
| 2701 | NE2 | HIS | D | 490 | 103.558 | −23.013 | 8.413 | 1.00 | 30.60 |
| 2702 | C | HIS | D | 490 | 100.180 | −20.319 | 8.460 | 1.00 | 29.81 |
| 2703 | O | HIS | D | 490 | 100.004 | −21.042 | 9.433 | 1.00 | 29.04 |
| 2704 | N | SER | D | 491 | 99.505 | −20.449 | 7.326 | 1.00 | 32.13 |
| 2705 | CA | SER | D | 491 | 98.506 | −21.491 | 7.141 | 1.00 | 31.78 |
| 2706 | CB | SER | D | 491 | 97.130 | −20.857 | 6.980 | 1.00 | 32.64 |
| 2707 | OG | SER | D | 491 | 96.158 | −21.843 | 6.724 | 1.00 | 41.02 |
| 2708 | C | SER | D | 491 | 98.882 | −22.272 | 5.888 | 1.00 | 30.25 |
| 2709 | O | SER | D | 491 | 99.239 | −21.683 | 4.872 | 1.00 | 30.83 |
| 2710 | N | THR | D | 492 | 98.828 | −23.596 | 5.966 | 1.00 | 31.72 |
| 2711 | CA | THR | D | 492 | 99.159 | −24.432 | 4.813 | 1.00 | 31.15 |
| 2712 | CB | THR | D | 492 | 100.467 | −25.202 | 5.045 | 1.00 | 27.68 |
| 2713 | OG1 | THR | D | 492 | 101.550 | −24.272 | 5.111 | 1.00 | 29.48 |
| 2714 | CG2 | THR | D | 492 | 100.729 | −26.175 | 3.912 | 1.00 | 29.19 |
| 2715 | C | THR | D | 492 | 98.027 | −25.417 | 4.510 | 1.00 | 28.46 |
| 2716 | O | THR | D | 492 | 97.570 | −26.135 | 5.388 | 1.00 | 26.88 |
| 2717 | N | THR | D | 493 | 97.582 | −25.455 | 3.259 | 1.00 | 27.98 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2718 | CA | THR | D | 493 | 96.489 | −26.344 | 2.888 | 1.00 | 31.37 |
| 2719 | CB | THR | D | 493 | 95.988 | −26.056 | 1.467 | 1.00 | 29.27 |
| 2720 | OG1 | THR | D | 493 | 97.033 | −26.353 | 0.526 | 1.00 | 29.92 |
| 2721 | CG2 | THR | D | 493 | 95.574 | −24.605 | 1.328 | 1.00 | 26.15 |
| 2722 | C | THR | D | 493 | 96.909 | −27.811 | 2.961 | 1.00 | 35.88 |
| 2723 | O | THR | D | 493 | 98.071 | −28.122 | 3.221 | 1.00 | 33.82 |
| 2724 | N | GLN | D | 494 | 95.951 | −28.707 | 2.740 | 1.00 | 38.45 |
| 2725 | CA | GLN | D | 494 | 96.210 | −30.148 | 2.774 | 1.00 | 42.21 |
| 2726 | CB | GLN | D | 494 | 94.966 | −30.897 | 3.255 | 1.00 | 53.01 |
| 2727 | CG | GLN | D | 494 | 94.635 | −30.671 | 4.732 | 1.00 | 72.32 |
| 2728 | CD | GLN | D | 494 | 95.179 | −31.761 | 5.637 | 1.00 | 81.80 |
| 2729 | OE1 | GLN | D | 494 | 94.798 | −32.929 | 5.515 | 1.00 | 88.19 |
| 2730 | NE2 | GLN | D | 494 | 96.070 | −31.390 | 6.555 | 1.00 | 88.00 |
| 2731 | C | GLN | D | 494 | 96.599 | −30.654 | 1.392 | 1.00 | 37.15 |
| 2732 | O | GLN | D | 494 | 96.021 | −30.247 | 0.381 | 1.00 | 35.08 |
| 2733 | N | PRO | D | 495 | 97.587 | −31.553 | 1.333 | 1.00 | 31.66 |
| 2734 | CD | PRO | D | 495 | 98.364 | −32.104 | 2.458 | 1.00 | 28.16 |
| 2735 | CA | PRO | D | 495 | 98.025 | −32.090 | 0.043 | 1.00 | 31.69 |
| 2736 | CB | PRO | D | 495 | 98.900 | −33.275 | 0.431 | 1.00 | 28.40 |
| 2737 | CG | PRO | D | 495 | 99.442 | −32.909 | 1.766 | 1.00 | 27.10 |
| 2738 | C | PRO | D | 495 | 96.824 | −32.522 | −0.792 | 1.00 | 36.94 |
| 2739 | O | PRO | D | 495 | 95.910 | −33.152 | −0.282 | 1.00 | 33.10 |
| 2740 | N | ARG | D | 496 | 96.817 | −32.143 | −2.063 | 1.00 | 44.28 |
| 2741 | CA | ARG | D | 496 | 95.760 | −32.515 | −2.995 | 1.00 | 49.24 |
| 2742 | CB | ARG | D | 496 | 94.865 | −31.325 | −3.315 | 1.00 | 58.73 |
| 2743 | CG | ARG | D | 496 | 93.882 | −30.961 | −2.230 | 1.00 | 81.71 |
| 2744 | CD | ARG | D | 496 | 93.505 | −29.490 | −2.341 | 1.00 | 97.59 |
| 2745 | NE | ARG | D | 496 | 92.211 | −29.202 | −1.735 | 1.00 | 107.02 |
| 2746 | CZ | ARG | D | 496 | 91.070 | −29.154 | −2.414 | 1.00 | 110.88 |
| 2747 | NH1 | ARG | D | 496 | 91.066 | −29.369 | −3.721 | 1.00 | 112.34 |
| 2748 | NH2 | ARG | D | 496 | 89.930 | −28.902 | −1.787 | 1.00 | 112.71 |
| 2749 | C | ARG | D | 496 | 96.450 | −32.965 | −4.265 | 1.00 | 50.02 |
| 2750 | O | ARG | D | 496 | 97.618 | −32.642 | −4.498 | 1.00 | 45.59 |
| 2751 | N | LYS | D | 497 | 95.726 | −33.699 | −5.094 | 1.00 | 52.26 |
| 2752 | CA | LYS | D | 497 | 96.295 | −34.191 | −6.334 | 1.00 | 54.33 |
| 2753 | CB | LYS | D | 497 | 95.645 | −35.509 | −6.713 | 1.00 | 58.16 |
| 2754 | CG | LYS | D | 497 | 95.855 | −36.582 | −5.690 | 1.00 | 69.00 |
| 2755 | CD | LYS | D | 497 | 95.544 | −37.924 | −6.298 | 1.00 | 77.66 |
| 2756 | CE | LYS | D | 497 | 96.035 | −39.055 | −5.422 | 1.00 | 82.83 |
| 2757 | NZ | LYS | D | 497 | 95.336 | −40.328 | −5.749 | 1.00 | 86.20 |
| 2758 | C | LYS | D | 497 | 96.175 | −33.228 | −7.499 | 1.00 | 54.89 |
| 2759 | O | LYS | D | 497 | 95.168 | −32.537 | −7.655 | 1.00 | 55.17 |
| 2760 | N | THR | D | 498 | 97.226 | −33.16 | −8.311 | 1.00 | 59.54 |
| 2761 | CA | THR | D | 498 | 97.291 | −32.357 | −9.502 | 1.00 | 64.65 |
| 2762 | CB | THR | D | 498 | 98.719 | −31.843 | −9.730 | 1.00 | 62.92 |
| 2763 | OG1 | THR | D | 498 | 99.634 | −32.946 | −9.701 | 1.00 | 63.41 |
| 2764 | CG2 | THR | D | 498 | 99.095 | −30.839 | −8.648 | 1.00 | 64.24 |
| 2765 | C | THR | D | 498 | 96.873 | −33.231 | −10.676 | 1.00 | 68.37 |
| 2766 | O | THR | D | 498 | 96.172 | −34.220 | −10.482 | 1.00 | 65.38 |
| 2767 | N | ALA | D | 499 | 97.291 | −32.893 | −11.888 | 1.00 | 75.98 |
| 2768 | CA | ALA | D | 499 | 96.894 | −33.717 | −13.020 | 1.00 | 84.87 |
| 2769 | CB | ALA | D | 499 | 96.951 | −32.909 | −14.307 | 1.00 | 85.48 |
| 2770 | C | ALA | D | 499 | 97.728 | −34.993 | −13.151 | 1.00 | 91.50 |
| 2771 | O | ALA | D | 499 | 98.751 | −35.021 | −13.841 | 1.00 | 90.87 |
| 2772 | N | GLY | D | 500 | 97.276 | −36.040 | −12.462 | 1.00 | 100.76 |
| 2773 | CA | GLY | D | 500 | 97.925 | −37.342 | −12.496 | 1.00 | 112.07 |
| 2774 | C | GLY | D | 500 | 99.430 | −37.420 | −12.325 | 1.00 | 115.03 |
| 2775 | O | GLY | D | 500 | 100.042 | −38.437 | −12.662 | 1.00 | 121.72 |
| 2776 | N | SER | D | 501 | 100.037 | −36.362 | −11.806 | 1.00 | 112.99 |
| 2777 | CA | SER | D | 501 | 101.477 | −36.365 | −11.606 | 1.00 | 113.93 |
| 2778 | CB | SER | D | 501 | 102.110 | −35.137 | −12.268 | 1.00 | 122.02 |
| 2779 | OG | SER | D | 501 | 101.568 | −33.938 | −11.745 | 1.00 | 114.38 |
| 2780 | C | SER | D | 501 | 101.846 | −36.405 | −10.125 | 1.00 | 109.46 |
| 2781 | O | SER | D | 501 | 102.746 | −37.143 | −9.725 | 1.00 | 119.34 |
| 2782 | N | GLY | D | 502 | 101.151 | −35.622 | −9.306 | 1.00 | 102.17 |
| 2783 | CA | GLY | D | 502 | 101.471 | −35.614 | −7.892 | 1.00 | 77.09 |
| 2784 | C | GLY | D | 502 | 100.586 | −34.732 | −7.039 | 1.00 | 59.07 |
| 2785 | O | GLY | D | 502 | 99.392 | −34.618 | −7.302 | 1.00 | 52.94 |
| 2786 | N | PHE | D | 503 | 101.167 | −34.096 | −6.024 | 1.00 | 41.60 |
| 2787 | CA | PHE | D | 503 | 100.387 | −33.254 | −5.121 | 1.00 | 31.06 |
| 2788 | CB | PHE | D | 503 | 100.457 | −33.811 | −3.691 | 1.00 | 27.05 |
| 2789 | CG | PHE | D | 503 | 100.078 | −35.256 | −3.582 | 1.00 | 24.24 |
| 2790 | CD1 | PHE | D | 503 | 100.937 | −36.249 | −4.045 | 1.00 | 21.33 |
| 2791 | CD2 | PHE | D | 503 | 98.853 | −35.630 | −3.031 | 1.00 | 23.74 |
| 2792 | CE1 | PHE | D | 503 | 100.584 | −37.592 | −3.955 | 1.00 | 22.65 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2793 | CE2 | PHE | D | 503 | 98.491 | −36.979 | −2.946 | 1.00 | 24.26 |
| 2794 | CZ | PHE | D | 503 | 99.361 | −37.963 | −3.416 | 1.00 | 22.80 |
| 2795 | C | PHE | D | 503 | 100.818 | −31.793 | −5.098 | 1.00 | 27.82 |
| 2796 | O | PHE | D | 503 | 101.907 | −31.431 | −5.564 | 1.00 | 24.72 |
| 2797 | N | PHE | D | 504 | 99.943 | −30.953 | −4.564 | 1.00 | 22.77 |
| 2798 | CA | PHE | D | 504 | 100.236 | −29.543 | −4.426 | 1.00 | 21.93 |
| 2799 | CB | PHE | D | 504 | 99.610 | −28.709 | −5.552 | 1.00 | 21.65 |
| 2800 | CG | PHE | D | 504 | 98.115 | −28.503 | −5.421 | 1.00 | 21.43 |
| 2801 | CD1 | PHE | D | 504 | 97.594 | −27.457 | −4.655 | 1.00 | 20.42 |
| 2802 | CD2 | PHE | D | 504 | 97.228 | −29.349 | −6.085 | 1.00 | 22.58 |
| 2803 | CE1 | PHE | D | 504 | 96.195 | −27.254 | −4.560 | 1.00 | 22.82 |
| 2804 | CE2 | PHE | D | 504 | 95.841 | −29.159 | −6.001 | 1.00 | 23.97 |
| 2805 | CZ | PHE | D | 504 | 95.321 | −28.108 | −5.234 | 1.00 | 21.75 |
| 2806 | C | PHE | D | 504 | 99.676 | −29.111 | −3.089 | 1.00 | 23.10 |
| 2807 | O | PHE | D | 504 | 98.727 | −29.708 | −2.561 | 1.00 | 20.86 |
| 2808 | N | VAL | D | 505 | 100.277 | −28.063 | −2.545 | 1.00 | 24.54 |
| 2809 | CA | VAL | D | 505 | 99.850 | −27.524 | −1.268 | 1.00 | 25.83 |
| 2810 | CB | VAL | D | 505 | 100.735 | −28.096 | −0.127 | 1.00 | 27.41 |
| 2811 | CG1 | VAL | D | 505 | 102.051 | −27.345 | −0.049 | 1.00 | 28.75 |
| 2812 | CG2 | VAL | D | 505 | 99.999 | −28.042 | 1.175 | 1.00 | 30.79 |
| 2813 | C | VAL | D | 505 | 100.026 | −26.023 | −1.385 | 1.00 | 22.57 |
| 2814 | O | VAL | D | 505 | 100.869 | −25.558 | −2.137 | 1.00 | 26.02 |
| 2815 | N | PHE | D | 506 | 99.215 | −25.257 | −0.681 | 1.00 | 24.53 |
| 2816 | CA | PHE | D | 506 | 99.344 | −23.802 | −0.714 | 1.00 | 25.43 |
| 2817 | CB | PHE | D | 506 | 98.028 | −23.150 | −1.164 | 1.00 | 32.04 |
| 2818 | CG | PHE | D | 506 | 97.908 | −22.931 | −2.656 | 1.00 | 32.17 |
| 2819 | CD1 | PHE | D | 506 | 97.032 | −23.703 | −3.426 | 1.00 | 32.60 |
| 2820 | CD2 | PHE | D | 506 | 98.624 | −21.906 | −3.281 | 1.00 | 33.74 |
| 2821 | CE1 | PHE | D | 506 | 96.862 | −23.442 | −4.800 | 1.00 | 36.42 |
| 2822 | CE2 | PHE | D | 506 | 98.462 | −21.640 | −4.650 | 1.00 | 34.34 |
| 2823 | CZ | PHE | D | 506 | 97.583 | −22.409 | −5.407 | 1.00 | 36.03 |
| 2824 | C | PHE | D | 506 | 99.670 | −23.303 | 0.696 | 1.00 | 22.99 |
| 2825 | O | PHE | D | 506 | 99.201 | −23.873 | 1.679 | 1.00 | 25.82 |
| 2826 | N | SER | D | 507 | 100.459 | −22.239 | 0.810 | 1.00 | 21.70 |
| 2827 | CA | SER | D | 507 | 100.771 | −21.684 | 2.122 | 1.00 | 20.47 |
| 2828 | CB | SER | D | 507 | 102.191 | −22.081 | 2.545 | 1.00 | 19.21 |
| 2829 | OG | SER | D | 507 | 102.400 | −21.769 | 3.911 | 1.00 | 19.37 |
| 2830 | C | SER | D | 507 | 100.610 | −20.151 | 2.102 | 1.00 | 19.36 |
| 2831 | O | SER | D | 507 | 101.117 | −19.477 | 1.206 | 1.00 | 20.55 |
| 2832 | N | ARG | D | 508 | 99.925 | −19.612 | 3.108 | 1.00 | 17.65 |
| 2833 | CA | ARG | D | 508 | 99.635 | −18.174 | 3.229 | 1.00 | 19.20 |
| 2834 | CB | ARG | D | 508 | 98.103 | −18.007 | 3.280 | 1.00 | 19.26 |
| 2835 | CG | ARG | D | 508 | 97.568 | −16.592 | 3.480 | 1.00 | 21.61 |
| 2836 | CD | ARG | D | 508 | 96.040 | −16.572 | 3.359 | 1.00 | 23.81 |
| 2837 | NE | ARG | D | 508 | 95.520 | −15.207 | 3.334 | 1.00 | 27.60 |
| 2838 | CZ | ARG | D | 508 | 95.453 | −14.414 | 4.399 | 1.00 | 31.08 |
| 2839 | NH1 | ARG | D | 508 | 95.868 | −14.852 | 5.579 | 1.00 | 33.14 |
| 2840 | NH2 | ARG | D | 508 | 94.977 | −13.182 | 4.294 | 1.00 | 29.85 |
| 2841 | C | ARG | D | 508 | 100.282 | −17.491 | 4.456 | 1.00 | 19.04 |
| 2842 | O | ARG | D | 508 | 100.049 | −17.904 | 5.591 | 1.00 | 17.68 |
| 2843 | N | LEU | D | 509 | 101.076 | −16.440 | 4.234 | 1.00 | 19.20 |
| 2844 | CA | LEU | D | 509 | 101.724 | −15.718 | 5.332 | 1.00 | 21.98 |
| 2845 | CB | LEU | D | 509 | 103.237 | −15.976 | 5.310 | 1.00 | 23.35 |
| 2846 | CG | LEU | D | 509 | 104.080 | −15.177 | 6.329 | 1.00 | 24.32 |
| 2847 | CD1 | LEU | D | 509 | 103.746 | −15.637 | 7.747 | 1.00 | 24.61 |
| 2848 | CD2 | LEU | D | 509 | 105.566 | −15.378 | 6.062 | 1.00 | 22.80 |
| 2849 | C | LEU | D | 509 | 101.480 | −14.202 | 5.291 | 1.00 | 23.85 |
| 2850 | O | LEU | D | 509 | 101.873 | −13.531 | 4.326 | 1.00 | 24.84 |
| 2851 | N | GLU | D | 510 | 100.836 | −13.678 | 6.336 | 1.00 | 26.14 |
| 2852 | CA | GLU | D | 510 | 100.545 | −12.245 | 6.477 | 1.00 | 28.11 |
| 2853 | CB | GLU | D | 510 | 99.316 | −12.032 | 7.373 | 1.00 | 32.37 |
| 2854 | CG | GLU | D | 510 | 97.989 | −12.301 | 6.655 | 1.00 | 45.11 |
| 2855 | CD | GLU | D | 510 | 96.788 | −12.002 | 7.510 | 1.00 | 50.43 |
| 2856 | OE1 | GLU | D | 510 | 96.848 | −11.767 | 8.624 | 1.00 | 53.01 |
| 2857 | OE2 | GLU | D | 510 | 95.669 | −11.949 | 7.189 | 1.00 | 54.82 |
| 2858 | C | GLU | D | 510 | 101.754 | −11.552 | 7.108 | 1.00 | 26.38 |
| 2859 | O | GLU | D | 510 | 102.120 | −11.861 | 8.239 | 1.00 | 27.04 |
| 2860 | N | VAL | D | 511 | 102.378 | −10.618 | 6.398 | 1.00 | 23.60 |
| 2861 | CA | VAL | D | 511 | 103.535 | −9.952 | 6.970 | 1.00 | 26.83 |
| 2862 | CB | VAL | D | 511 | 104.748 | −9.994 | 6.017 | 1.00 | 24.38 |
| 2863 | CG1 | VAL | D | 511 | 105.048 | −11.425 | 5.633 | 1.00 | 24.14 |
| 2864 | CG2 | VAL | D | 511 | 104.485 | −9.143 | 4.785 | 1.00 | 20.64 |
| 2865 | C | VAL | D | 511 | 103.247 | −8.507 | 7.325 | 1.00 | 30.09 |
| 2866 | O | VAL | D | 511 | 102.256 | −7.938 | 6.870 | 1.00 | 27.41 |
| 2867 | N | THR | D | 512 | 104.129 | −7.910 | 8.120 | 1.00 | 29.92 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2868 | CA | THR | D | 512 | 103.922 | −6.537 | 8.519 | 1.00 | 28.91 |
| 2869 | CB | THR | D | 512 | 104.159 | −6.345 | 10.008 | 1.00 | 30.41 |
| 2870 | OG1 | THR | D | 512 | 105.493 | −6.759 | 10.327 | 1.00 | 31.85 |
| 2871 | CG2 | THR | D | 512 | 103.162 | −7.152 | 10.813 | 1.00 | 30.24 |
| 2872 | C | THR | D | 512 | 104.826 | −5.580 | 7.793 | 1.00 | 31.30 |
| 2873 | O | THR | D | 512 | 105.830 | −5.968 | 7.206 | 1.00 | 32.27 |
| 2874 | N | ARG | D | 513 | 104.462 | −4.309 | 7.846 | 1.00 | 36.09 |
| 2875 | CA | ARG | D | 513 | 105.264 | −3.291 | 7.201 | 1.00 | 41.31 |
| 2876 | CB | ARG | D | 513 | 104.591 | −1.922 | 7.276 | 1.00 | 48.88 |
| 2877 | CG | ARG | D | 513 | 105.357 | −0.841 | 6.518 | 1.00 | 58.36 |
| 2878 | CD | ARG | D | 513 | 104.508 | 0.387 | 6.349 | 1.00 | 64.81 |
| 2879 | NE | ARG | D | 513 | 105.062 | 1.387 | 5.449 | 1.00 | 71.80 |
| 2880 | CZ | ARG | D | 513 | 105.719 | 1.107 | 4.331 | 1.00 | 74.68 |
| 2881 | NH1 | ARG | D | 513 | 105.915 | −0.144 | 3.967 | 1.00 | 77.58 |
| 2882 | NH2 | ARG | D | 513 | 106.192 | 2.084 | 3.579 | 1.00 | 78.08 |
| 2883 | C | ARG | D | 513 | 106.595 | −3.247 | 7.934 | 1.00 | 40.47 |
| 2884 | O | ARG | D | 513 | 107.646 | −3.128 | 7.310 | 1.00 | 41.18 |
| 2885 | N | ALA | D | 514 | 106.554 | −3.358 | 9.260 | 1.00 | 38.65 |
| 2886 | CA | ALA | D | 514 | 107.780 | −3.318 | 10.051 | 1.00 | 41.03 |
| 2887 | CB | ALA | D | 514 | 107.447 | −3.425 | 11.543 | 1.00 | 38.39 |
| 2888 | C | ALA | D | 514 | 108.724 | −4.444 | 9.644 | 1.00 | 41.68 |
| 2889 | O | ALA | D | 514 | 109.939 | −4.275 | 9.631 | 1.00 | 39.39 |
| 2890 | N | GLU | D | 515 | 108.156 | −5.591 | 9.293 | 1.00 | 39.82 |
| 2891 | CA | GLU | D | 515 | 108.960 | −6.744 | 8.916 | 1.00 | 39.13 |
| 2892 | CB | GLU | D | 515 | 108.111 | −8.010 | 8.929 | 1.00 | 38.66 |
| 2893 | CG | GLU | D | 515 | 107.626 | −8.367 | 10.305 | 1.00 | 40.67 |
| 2894 | CD | GLU | D | 515 | 106.777 | −9.599 | 10.298 | 1.00 | 40.77 |
| 2895 | OE1 | GLU | D | 515 | 107.353 | −10.693 | 10.206 | 1.00 | 43.19 |
| 2896 | OE2 | GLU | D | 515 | 105.539 | −9.481 | 10.369 | 1.00 | 43.16 |
| 2897 | C | GLU | D | 515 | 109.670 | −6.625 | 7.583 | 1.00 | 38.23 |
| 2898 | O | GLU | D | 515 | 110.874 | −6.883 | 7.501 | 1.00 | 35.40 |
| 2899 | N | TRP | D | 516 | 108.959 | −6.248 | 6.528 | 1.00 | 37.61 |
| 2900 | CA | TRP | D | 516 | 109.655 | −6.144 | 5.258 | 1.00 | 44.26 |
| 2901 | CB | TRP | D | 516 | 108.696 | −6.264 | 4.069 | 1.00 | 45.87 |
| 2902 | CG | TRP | D | 516 | 107.883 | −5.068 | 3.747 | 1.00 | 45.00 |
| 2903 | CD2 | TRP | D | 516 | 106.483 | −4.910 | 3.973 | 1.00 | 45.91 |
| 2904 | CE2 | TRP | D | 516 | 106.103 | −3.660 | 3.415 | 1.00 | 47.49 |
| 2905 | CE3 | TRP | D | 516 | 105.509 | −5.691 | 4.598 | 1.00 | 48.49 |
| 2906 | CD1 | TRP | D | 516 | 108.298 | −3.948 | 3.082 | 1.00 | 43.80 |
| 2907 | NE1 | TRP | D | 516 | 107.236 | −3.092 | 2.873 | 1.00 | 46.53 |
| 2908 | CZ2 | TRP | D | 516 | 104.780 | −3.183 | 3.452 | 1.00 | 49.77 |
| 2909 | CZ3 | TRP | D | 516 | 104.189 | −5.229 | 4.631 | 1.00 | 52.41 |
| 2910 | CH2 | TRP | D | 516 | 103.843 | −3.980 | 4.068 | 1.00 | 52.43 |
| 2911 | C | TRP | D | 516 | 110.421 | −4.842 | 5.239 | 1.00 | 49.23 |
| 2912 | O | TRP | D | 516 | 111.074 | −4.499 | 4.257 | 1.00 | 45.48 |
| 2913 | N | ALA | D | 517 | 110.340 | −4.108 | 6.339 | 1.00 | 57.16 |
| 2914 | CA | ALA | D | 517 | 111.092 | −2.870 | 6.442 | 1.00 | 68.45 |
| 2915 | CB | ALA | D | 517 | 110.460 | −1.940 | 7.460 | 1.00 | 70.79 |
| 2916 | C | ALA | D | 517 | 112.434 | −3.362 | 6.952 | 1.00 | 74.58 |
| 2917 | O | ALA | D | 517 | 113.484 | −2.805 | 6.646 | 1.00 | 71.45 |
| 2918 | N | GLN | D | 518 | 112.366 | −4.437 | 7.728 | 1.00 | 76.05 |
| 2919 | CA | GLN | D | 518 | 113.535 | −5.047 | 8.335 | 1.00 | 71.37 |
| 2920 | CB | GLN | D | 518 | 113.095 | −6.021 | 9.428 | 1.00 | 59.38 |
| 2921 | CG | GLN | D | 518 | 114.236 | −6.548 | 10.257 | 1.00 | 71.81 |
| 2922 | CD | GLN | D | 518 | 114.034 | −7.953 | 10.691 | 1.00 | 66.68 |
| 2923 | OE1 | GLN | D | 518 | 113.050 | −8.604 | 10.322 | 1.00 | 56.50 |
| 2924 | NE2 | GLN | D | 518 | 114.976 | −8.451 | 11.490 | 1.00 | 57.50 |
| 2925 | C | GLN | D | 518 | 114.385 | −5.785 | 7.313 | 1.00 | 70.74 |
| 2926 | O | GLN | D | 518 | 115.581 | −5.969 | 7.502 | 1.00 | 69.04 |
| 2927 | N | LYS | D | 519 | 113.750 | −6.206 | 6.231 | 1.00 | 70.57 |
| 2928 | CA | LYS | D | 519 | 114.400 | −6.946 | 5.160 | 1.00 | 65.13 |
| 2929 | CB | LYS | D | 519 | 115.089 | −8.195 | 5.706 | 1.00 | 57.49 |
| 2930 | CG | LYS | D | 519 | 115.698 | −9.106 | 4.652 | 1.00 | 57.45 |
| 2931 | CD | LYS | D | 519 | 117.081 | −8.643 | 4.238 | 1.00 | 55.91 |
| 2932 | CE | LYS | D | 519 | 117.855 | −9.772 | 3.583 | 1.00 | 54.01 |
| 2933 | NZ | LYS | D | 519 | 119.163 | −9.311 | 3.061 | 1.00 | 56.42 |
| 2934 | C | LYS | D | 519 | 113.209 | −7.357 | 4.330 | 1.00 | 61.43 |
| 2935 | O | LYS | D | 519 | 112.398 | −8.176 | 4.766 | 1.00 | 65.20 |
| 2936 | N | ASP | D | 520 | 113.080 | −6.770 | 3.150 | 1.00 | 65.58 |
| 2937 | CA | ASP | D | 520 | 111.959 | −7.090 | 2.291 | 1.00 | 70.83 |
| 2938 | CB | ASP | D | 520 | 111.860 | −6.062 | 1.161 | 1.00 | 82.10 |
| 2939 | CG | ASP | D | 520 | 110.593 | −6.213 | 0.348 | 1.00 | 83.59 |
| 2940 | OD1 | ASP | D | 520 | 109.915 | −7.249 | 0.492 | 1.00 | 86.59 |
| 2941 | OD2 | ASP | D | 520 | 110.275 | −5.302 | −0.442 | 1.00 | 85.95 |
| 2942 | C | ASP | D | 520 | 112.099 | −8.500 | 1.712 | 1.00 | 66.62 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 2943 | O | ASP | D | 520 | 111.491 | −8.818 | 0.703 | 1.00 | 75.50 |
| 2944 | N | GLU | D | 521 | 112.888 | −9.353 | 2.356 | 1.00 | 61.31 |
| 2945 | CA | GLU | D | 521 | 113.075 | −10.713 | 1.866 | 1.00 | 56.66 |
| 2946 | CB | GLU | D | 521 | 114.561 | −11.036 | 1.761 | 1.00 | 60.56 |
| 2947 | CG | GLU | D | 521 | 114.843 | −12.441 | 1.280 | 1.00 | 60.46 |
| 2948 | CD | GLU | D | 521 | 115.705 | −12.437 | 0.089 | 1.00 | 62.60 |
| 2949 | OE1 | GLU | D | 521 | 115.338 | −11.712 | −0.793 | 1.00 | 66.84 |
| 2950 | OE2 | GLU | D | 521 | 116.727 | −13.117 | −0.017 | 1.00 | 63.11 |
| 2951 | C | GLU | D | 521 | 112.406 | −11.752 | 2.755 | 1.00 | 48.44 |
| 2952 | O | GLU | D | 521 | 112.592 | −11.758 | 3.970 | 1.00 | 47.48 |
| 2953 | N | PHE | D | 522 | 111.627 | −12.630 | 2.134 | 1.00 | 39.27 |
| 2954 | CA | PHE | D | 522 | 110.931 | −13.687 | 2.850 | 1.00 | 32.78 |
| 2955 | CB | PHE | D | 522 | 109.456 | −13.363 | 2.975 | 1.00 | 27.60 |
| 2956 | CG | PHE | D | 522 | 109.186 | −12.162 | 3.814 | 1.00 | 26.57 |
| 2957 | CD1 | PHE | D | 522 | 109.331 | −10.880 | 3.288 | 1.00 | 25.68 |
| 2958 | CD2 | PHE | D | 522 | 108.796 | −12.307 | 5.141 | 1.00 | 26.40 |
| 2959 | CE1 | PHE | D | 522 | 109.090 | −9.756 | 4.075 | 1.00 | 24.35 |
| 2960 | CE2 | PHE | D | 522 | 108.552 | −11.197 | 5.939 | 1.00 | 24.64 |
| 2961 | CZ | PHE | D | 522 | 108.697 | −9.919 | 5.407 | 1.00 | 25.30 |
| 2962 | C | PHE | D | 522 | 111.126 | −14.999 | 2.122 | 1.00 | 31.20 |
| 2963 | O | PHE | D | 522 | 111.152 | −15.049 | 0.890 | 1.00 | 28.96 |
| 2964 | N | ILE | D | 523 | 111.269 | −16.072 | 2.881 | 1.00 | 28.47 |
| 2965 | CA | ILE | D | 523 | 111.524 | −17.355 | 2.260 | 1.00 | 26.90 |
| 2966 | CB | ILE | D | 523 | 112.945 | −17.830 | 2.627 | 1.00 | 28.69 |
| 2967 | CG2 | ILE | D | 523 | 113.211 | −19.216 | 2.060 | 1.00 | 29.86 |
| 2968 | CG1 | ILE | D | 523 | 113.958 | −16.821 | 2.080 | 1.00 | 29.61 |
| 2969 | CD1 | ILE | D | 523 | 115.378 | −17.211 | 2.279 | 1.00 | 33.42 |
| 2970 | C | ILE | D | 523 | 110.513 | −18.452 | 2.563 | 1.00 | 25.62 |
| 2971 | O | ILE | D | 523 | 110.151 | −18.721 | 3.709 | 1.00 | 21.28 |
| 2972 | N | CYS | D | 524 | 110.025 | −19.060 | 1.498 | 1.00 | 25.10 |
| 2973 | CA | CYS | D | 524 | 109.099 | −20.159 | 1.628 | 1.00 | 24.32 |
| 2974 | C | CYS | D | 524 | 109.964 | −21.389 | 1.422 | 1.00 | 22.96 |
| 2975 | O | CYS | D | 524 | 110.610 | −21.536 | 0.387 | 1.00 | 21.95 |
| 2976 | CB | CYS | D | 524 | 108.014 | −20.097 | 0.558 | 1.00 | 24.32 |
| 2977 | SG | CYS | D | 524 | 107.036 | −21.628 | 0.487 | 1.00 | 24.81 |
| 2978 | N | ARG | D | 525 | 109.979 | −22.267 | 2.413 | 1.00 | 24.42 |
| 2979 | CA | ARG | D | 525 | 110.803 | −23.466 | 2.346 | 1.00 | 26.09 |
| 2980 | CB | ARG | D | 525 | 111.902 | −23.413 | 3.404 | 1.00 | 28.04 |
| 2981 | CG | ARG | D | 525 | 112.582 | −24.742 | 3.621 | 1.00 | 31.80 |
| 2982 | CD | ARG | D | 525 | 114.048 | −24.530 | 3.845 | 1.00 | 36.43 |
| 2983 | NE | ARG | D | 525 | 114.339 | −24.087 | 5.198 | 1.00 | 41.60 |
| 2984 | CZ | ARG | D | 525 | 115.443 | −23.432 | 5.548 | 1.00 | 44.11 |
| 2985 | NH1 | ARG | D | 525 | 116.367 | −23.129 | 4.642 | 1.00 | 44.31 |
| 2986 | NH2 | ARG | D | 525 | 115.627 | −23.093 | 6.814 | 1.00 | 45.90 |
| 2987 | C | ARG | D | 525 | 110.049 | −24.763 | 2.504 | 1.00 | 25.29 |
| 2988 | O | ARG | D | 525 | 109.290 | −24.944 | 3.460 | 1.00 | 24.82 |
| 2989 | N | ALA | D | 526 | 110.298 | −25.677 | 1.572 | 1.00 | 25.81 |
| 2990 | CA | ALA | D | 526 | 109.648 | −26.983 | 1.585 | 1.00 | 25.09 |
| 2991 | CB | ALA | D | 526 | 109.053 | −27.285 | 0.214 | 1.00 | 25.68 |
| 2992 | C | ALA | D | 526 | 110.610 | −28.099 | 1.977 | 1.00 | 26.05 |
| 2993 | O | ALA | D | 526 | 111.703 | −28.228 | 1.407 | 1.00 | 23.12 |
| 2994 | N | VAL | D | 527 | 110.211 | −28.894 | 2.963 | 1.00 | 24.19 |
| 2995 | CA | VAL | D | 527 | 111.029 | −30.022 | 3.361 | 1.00 | 23.43 |
| 2996 | CB | VAL | D | 527 | 111.215 | −30.133 | 4.886 | 1.00 | 24.03 |
| 2997 | CG1 | VAL | D | 527 | 112.062 | −31.377 | 5.212 | 1.00 | 21.66 |
| 2998 | CG2 | VAL | D | 527 | 111.918 | −28.899 | 5.409 | 1.00 | 21.35 |
| 2999 | C | VAL | D | 527 | 110.315 | −31.254 | 2.838 | 1.00 | 23.02 |
| 3000 | O | VAL | D | 527 | 109.193 | −31.574 | 3.238 | 1.00 | 21.06 |
| 3001 | N | HIS | D | 528 | 110.975 | −31.929 | 1.911 | 1.00 | 24.70 |
| 3002 | CA | HIS | D | 528 | 110.408 | −33.108 | 1.291 | 1.00 | 25.12 |
| 3003 | CB | HIS | D | 528 | 109.611 | −32.722 | 0.033 | 1.00 | 22.47 |
| 3004 | CG | HIS | D | 528 | 108.917 | −33.880 | −0.629 | 1.00 | 19.47 |
| 3005 | CD2 | HIS | D | 528 | 107.628 | −34.287 | −0.573 | 1.00 | 19.46 |
| 3006 | ND1 | HIS | D | 528 | 109.573 | −34.742 | −1.472 | 1.00 | 22.85 |
| 3007 | CE1 | HIS | D | 528 | 108.706 | −35.648 | −1.921 | 1.00 | 18.77 |
| 3008 | NE2 | HIS | D | 528 | 107.529 | −35.396 | −1.393 | 1.00 | 18.44 |
| 3009 | C | HIS | D | 528 | 111.549 | −34.037 | 0.954 | 1.00 | 25.23 |
| 3010 | O | HIS | D | 528 | 112.625 | −33.623 | 0.500 | 1.00 | 24.76 |
| 3011 | N | GLU | D | 529 | 111.274 | −35.303 | 1.203 | 1.00 | 28.00 |
| 3012 | CA | GLU | D | 529 | 112.200 | −36.393 | 1.021 | 1.00 | 33.95 |
| 3013 | CB | GLU | D | 529 | 111.517 | −37.644 | 1.564 | 1.00 | 38.38 |
| 3014 | CG | GLU | D | 529 | 111.517 | −38.843 | 0.686 | 1.00 | 46.95 |
| 3015 | CD | GLU | D | 529 | 110.395 | −39.811 | 1.049 | 1.00 | 52.47 |
| 3016 | OE1 | GLU | D | 529 | 110.519 | −40.996 | 0.695 | 1.00 | 54.34 |
| 3017 | OE2 | GLU | D | 529 | 109.392 | −39.391 | 1.674 | 1.00 | 53.62 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3018 | C | GLU | D | 529 | 112.799 | −36.621 | −0.370 | 1.00 | 33.38 |
| 3019 | O | GLU | D | 529 | 113.855 | −37.238 | −0.479 | 1.00 | 33.68 |
| 3020 | N | ALA | D | 530 | 112.163 | −36.119 | −1.426 | 1.00 | 30.72 |
| 3021 | CA | ALA | D | 530 | 112.720 | −36.310 | −2.758 | 1.00 | 30.66 |
| 3022 | CB | ALA | D | 530 | 111.611 | −36.586 | −3.776 | 1.00 | 28.95 |
| 3023 | C | ALA | D | 530 | 113.546 | −35.098 | −3.185 | 1.00 | 31.24 |
| 3024 | O | ALA | D | 530 | 114.274 | −35.160 | −4.166 | 1.00 | 29.75 |
| 3025 | N | ALA | D | 531 | 113.440 | −33.997 | −2.449 | 1.00 | 37.45 |
| 3026 | CA | ALA | D | 531 | 114.205 | −32.796 | −2.787 | 1.00 | 44.88 |
| 3027 | CB | ALA | D | 531 | 113.847 | −31.658 | −1.849 | 1.00 | 37.08 |
| 3028 | C | ALA | D | 531 | 115.693 | −33.096 | −2.700 | 1.00 | 51.68 |
| 3029 | O | ALA | D | 531 | 116.165 | −33.556 | −1.662 | 1.00 | 53.78 |
| 3030 | N | SER | D | 532 | 116.412 | −32.831 | −3.798 | 1.00 | 63.47 |
| 3031 | CA | SER | D | 532 | 117.853 | −33.065 | −3.910 | 1.00 | 75.89 |
| 3032 | CB | SER | D | 532 | 118.410 | −32.337 | −5.129 | 1.00 | 89.24 |
| 3033 | OG | SER | D | 532 | 118.288 | −30.939 | −4.963 | 1.00 | 107.74 |
| 3034 | C | SER | D | 532 | 118.557 | −32.675 | −2.608 | 1.00 | 79.02 |
| 3035 | O | SER | D | 532 | 117.885 | −32.190 | −1.708 | 1.00 | 84.33 |
| 3036 | N | PRO | D | 533 | 119.906 | −32.647 | −2.575 | 1.00 | 67.37 |
| 3037 | CD | PRO | D | 533 | 120.317 | −31.585 | −3.524 | 1.00 | 71.01 |
| 3038 | CA | PRO | D | 533 | 120.659 | −32.364 | −1.354 | 1.00 | 66.78 |
| 3039 | CB | PRO | D | 533 | 121.770 | −31.438 | −1.819 | 1.00 | 64.26 |
| 3040 | CG | PRO | D | 533 | 121.077 | −30.575 | −2.646 | 1.00 | 61.28 |
| 3041 | C | PRO | D | 533 | 119.874 | −31.819 | −0.192 | 1.00 | 63.21 |
| 3042 | O | PRO | D | 533 | 119.169 | −30.809 | −0.296 | 1.00 | 63.96 |
| 3043 | N | SER | D | 534 | 119.976 | −32.550 | 0.909 | 1.00 | 59.36 |
| 3044 | CA | SER | D | 534 | 119.341 | −32.169 | 2.154 | 1.00 | 55.84 |
| 3045 | CB | SER | D | 534 | 120.007 | −30.887 | 2.669 | 1.00 | 58.66 |
| 3046 | OG | SER | D | 534 | 120.519 | −30.090 | 1.609 | 1.00 | 62.91 |
| 3047 | C | SER | D | 534 | 117.820 | −32.024 | 2.181 | 1.00 | 50.75 |
| 3048 | O | SER | D | 534 | 117.285 | −31.302 | 3.023 | 1.00 | 46.95 |
| 3049 | N | GLN | D | 535 | 117.139 | −32.721 | 1.273 | 1.00 | 45.28 |
| 3050 | CA | GLN | D | 535 | 115.675 | −32.735 | 1.179 | 1.00 | 42.16 |
| 3051 | CB | GLN | D | 535 | 115.124 | −33.840 | 2.089 | 1.00 | 42.47 |
| 3052 | CG | GLN | D | 535 | 116.110 | −34.362 | 3.135 | 1.00 | 45.99 |
| 3053 | CD | GLN | D | 535 | 117.286 | −35.179 | 2.584 | 1.00 | 47.90 |
| 3054 | OE1 | GLN | D | 535 | 118.258 | −35.408 | 3.305 | 1.00 | 49.42 |
| 3055 | NE2 | GLN | D | 535 | 117.201 | −35.633 | 1.334 | 1.00 | 49.34 |
| 3056 | C | GLN | D | 535 | 114.956 | −31.417 | 1.464 | 1.00 | 41.19 |
| 3057 | O | GLN | D | 53S | 113.943 | −31.377 | 2.171 | 1.00 | 35.14 |
| 3058 | N | THR | D | 536 | 115.462 | −30.350 | 0.863 | 1.00 | 38.46 |
| 3059 | CA | THR | D | 536 | 114.895 | −29.030 | 1.069 | 1.00 | 37.43 |
| 3060 | CB | THR | D | 536 | 115.705 | −28.309 | 2.169 | 1.00 | 41.75 |
| 3061 | OG1 | THR | D | 536 | 115.227 | −26.974 | 2.326 | 1.00 | 48.07 |
| 3062 | CG2 | THR | D | 536 | 117.181 | −28.272 | 1.801 | 1.00 | 47.08 |
| 3063 | C | THR | D | 536 | 114.892 | −28.199 | −0.221 | 1.00 | 36.89 |
| 3064 | O | THR | D | 536 | 115.839 | −28.259 | −1.002 | 1.00 | 36.77 |
| 3065 | N | VAL | D | 537 | 113.812 | −27.459 | −0.459 | 1.00 | 35.08 |
| 3066 | CA | VAL | D | 537 | 113.699 | −26.597 | −1.639 | 1.00 | 31.91 |
| 3067 | CB | VAL | D | 537 | 112.836 | −27.224 | −2.745 | 1.00 | 34.00 |
| 3068 | CG1 | VAL | D | 537 | 112.888 | −26.342 | −3.995 | 1.00 | 36.07 |
| 3069 | CG2 | VAL | D | 537 | 113.321 | −28.612 | −3.064 | 1.00 | 37.13 |
| 3070 | C | VAL | D | 537 | 113.023 | −25.299 | −1.194 | 1.00 | 28.31 |
| 3071 | O | VAL | D | 537 | 112.021 | −25.337 | −0.478 | 1.00 | 28.85 |
| 3072 | N | GLN | D | 538 | 113.538 | −24.152 | −1.628 | 1.00 | 25.58 |
| 3073 | CA | GLN | D | 538 | 112.953 | −22.898 | −1.192 | 1.00 | 25.35 |
| 3074 | CB | GLN | D | 538 | 113.703 | −22.394 | 0.042 | 1.00 | 23.25 |
| 3075 | CG | GLN | D | 538 | 115.178 | −22.031 | −0.212 | 1.00 | 22.20 |
| 3076 | CD | GLN | D | 538 | 115.931 | −21.689 | 1.073 | 1.00 | 22.08 |
| 3077 | OE1 | GLN | D | 538 | 115.985 | −22.503 | 2.013 | 1.00 | 21.30 |
| 3078 | NE2 | GLN | D | 538 | 116.514 | −20.487 | 1.127 | 1.00 | 20.09 |
| 3079 | C | GLN | D | 538 | 112.931 | −21.801 | −2.244 | 1.00 | 26.14 |
| 3080 | O | GLN | D | 538 | 113.638 | −21.876 | −3.241 | 1.00 | 25.62 |
| 3081 | N | ARG | D | 539 | 112.113 | −20.780 | −2.001 | 1.00 | 26.85 |
| 3082 | CA | ARG | D | 539 | 112.006 | −19.643 | −2.896 | 1.00 | 28.35 |
| 3083 | CB | ARG | D | 539 | 110.784 | −19.779 | −3.795 | 1.00 | 35.17 |
| 3084 | CG | ARG | D | 539 | 110.950 | −20.755 | −4.924 | 1.00 | 48.49 |
| 3085 | CD | ARG | D | 539 | 111.696 | −20.127 | −6.086 | 1.00 | 59.90 |
| 3086 | NE | ARG | D | 539 | 111.400 | −20.857 | −7.308 | 1.00 | 71.51 |
| 3087 | CZ | ARG | D | 539 | 111.932 | −20.594 | −8.493 | 1.00 | 76.82 |
| 3088 | NH1 | ARG | D | 539 | 112.807 | −19.608 | −8.643 | 1.00 | 80.80 |
| 3089 | NH2 | ARG | D | 539 | 111.577 | −21.322 | −9.534 | 1.00 | 79.60 |
| 3090 | C | ARG | D | 539 | 111.883 | −18.369 | −2.093 | 1.00 | 27.26 |
| 3091 | O | ARG | D | 539 | 111.132 | −18.305 | −1.116 | 1.00 | 27.17 |
| 3092 | N | ALA | D | 540 | 112.642 | −17.360 | −2.493 | 1.00 | 24.40 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3093 | CA | ALA | D | 540 | 112.583 | −16.069 | −1.827 | 1.00 | 26.38 |
| 3094 | CB | ALA | D | 540 | 113.930 | −15.366 | −1.914 | 1.00 | 22.49 |
| 3095 | C | ALA | D | 540 | 111.524 | −15.250 | −2.555 | 1.00 | 26.05 |
| 3096 | O | ALA | D | 540 | 111.237 | −15.491 | −3.729 | 1.00 | 26.65 |
| 3097 | N | VAL | D | 541 | 110.938 | −14.291 | −1.852 | 1.00 | 28.11 |
| 3098 | CA | VAL | D | 541 | 109.934 | −13.416 | −2.442 | 1.00 | 34.69 |
| 3099 | CB | VAL | D | 541 | 108.487 | −14.000 | −2.305 | 1.00 | 30.44 |
| 3100 | CG1 | VAL | D | 541 | 107.978 | −13.860 | −0.879 | 1.00 | 30.07 |
| 3101 | CG2 | VAL | D | 541 | 107.562 | −13.301 | −3.277 | 1.00 | 29.98 |
| 3102 | C | VAL | D | 541 | 110.025 | −12.090 | −1.700 | 1.00 | 36.98 |
| 3103 | O | VAL | D | 541 | 110.290 | −12.062 | −0.494 | 1.00 | 33.74 |
| 3104 | N | SER | D | 542 | 109.856 | −10.986 | −2.416 | 1.00 | 37.59 |
| 3105 | CA | SER | D | 542 | 109.875 | −9.696 | −1.752 | 1.00 | 42.24 |
| 3106 | CB | SER | D | 542 | 111.175 | −8.932 | −1.992 | 1.00 | 42.13 |
| 3107 | OG | SER | D | 542 | 111.774 | −9.255 | −3.180 | 1.00 | 44.04 |
| 3108 | C | SER | D | 542 | 108.723 | −8.785 | −2.081 | 1.00 | 44.37 |
| 3109 | O | SER | D | 542 | 108.201 | −8.780 | −3.200 | 1.00 | 43.55 |
| 3110 | N | VAL | D | 543 | 108.358 | −8.050 | −1.026 | 1.00 | 44.73 |
| 3111 | CA | VAL | D | 543 | 107.357 | −7.070 | −1.067 | 1.00 | 50.27 |
| 3112 | CB | VAL | D | 543 | 106.686 | −6.801 | 0.338 | 1.00 | 47.76 |
| 3113 | CG1 | VAL | D | 543 | 105.384 | −5.977 | 0.183 | 1.00 | 47.10 |
| 3114 | CG2 | VAL | D | 543 | 106.392 | −8.124 | 1.009 | 1.00 | 46.15 |
| 3115 | C | VAL | D | 543 | 107.498 | −5.804 | −1.915 | 1.00 | 56.21 |
| 3116 | O | VAL | D | 543 | 107.473 | −4.688 | −1.263 | 1.00 | 58.37 |
| 3117 | N | ASN | D | 544 | 107.904 | −6.235 | −3.231 | 1.00 | 61.50 |
| 3118 | CA | ASN | D | 544 | 107.523 | −5.796 | −4.567 | 1.00 | 65.29 |
| 3119 | CB | ASN | D | 544 | 108.811 | −5.403 | −5.195 | 1.00 | 63.88 |
| 3120 | CG | ASN | D | 544 | 109.607 | −6.481 | −5.571 | 1.00 | 65.88 |
| 3121 | OD1 | ASN | D | 544 | 110.681 | −6.940 | −5.151 | 1.00 | 65.47 |
| 3122 | ND2 | ASN | D | 544 | 108.738 | −7.214 | −6.238 | 1.00 | 65.91 |
| 3123 | C | ASN | D | 544 | 106.319 | −6.317 | −5.802 | 1.00 | 69.40 |
| 3124 | O | ASN | D | 544 | 105.849 | −5.566 | −5.668 | 1.00 | 69.38 |
| 3125 | OXT | ASN | D | 544 | 105.457 | −6.536 | −6.174 | 1.00 | 66.27 |
| 3126 | CB | VAL | A | 336 | 101.298 | −39.041 | 44.890 | 1.00 | 58.63 |
| 3127 | CG1 | VAL | A | 336 | 100.340 | −38.269 | 44.003 | 1.00 | 54.20 |
| 3128 | CG2 | VAL | A | 336 | 101.417 | −40.473 | 44.412 | 1.00 | 54.75 |
| 3129 | C | VAL | A | 336 | 102.484 | −36.897 | 45.250 | 1.00 | 61.47 |
| 3130 | O | VAL | A | 336 | 101.585 | −36.563 | 46.018 | 1.00 | 64.40 |
| 3131 | N | VAL | A | 336 | 103.622 | −39.036 | 45.827 | 1.00 | 59.69 |
| 3132 | CA | VAL | A | 336 | 102.682 | −38.363 | 44.886 | 1.00 | 60.02 |
| 3133 | N | SER | A | 337 | 103.319 | −36.021 | 44.704 | 1.00 | 61.22 |
| 3134 | CA | SER | A | 337 | 103.188 | −34.603 | 44.993 | 1.00 | 60.77 |
| 3135 | CB | SER | A | 337 | 104.568 | −23.939 | 45.083 | 1.00 | 67.00 |
| 3136 | OG | SER | A | 337 | 105.295 | −34.068 | 43.874 | 1.00 | 75.97 |
| 3137 | C | SER | A | 337 | 102.340 | −33.904 | 43.935 | 1.00 | 55.45 |
| 3138 | O | SER | A | 337 | 102.242 | −34.358 | 42.793 | 1.00 | 55.38 |
| 3139 | N | ALA | A | 338 | 101.707 | −32.808 | 44.331 | 1.00 | 48.98 |
| 3140 | CA | ALA | A | 338 | 100.882 | −32.033 | 43.419 | 1.00 | 42.85 |
| 3141 | CB | ALA | A | 338 | 99.421 | −32.143 | 43.807 | 1.00 | 36.84 |
| 3142 | C | ALA | A | 338 | 101.350 | −30.586 | 43.487 | 1.00 | 40.30 |
| 3143 | O | ALA | A | 338 | 101.772 | −30.112 | 44.538 | 1.00 | 39.82 |
| 3144 | N | TYR | A | 339 | 101.297 | −29.897 | 42.352 | 1.00 | 40.43 |
| 3145 | CA | TYR | A | 339 | 101.725 | −28.505 | 42.275 | 1.00 | 42.92 |
| 3146 | CB | TYR | A | 339 | 103.141 | −28.414 | 41.697 | 1.00 | 48.85 |
| 3147 | CG | TYR | A | 339 | 104.154 | −29.372 | 42.298 | 1.00 | 56.05 |
| 3148 | CD1 | TYR | A | 339 | 104.047 | −30.748 | 42.100 | 1.00 | 59.34 |
| 3149 | CE1 | TYR | A | 339 | 104.991 | −31.628 | 42.618 | 1.00 | 61.68 |
| 3150 | CD2 | TYR | A | 339 | 105.240 | −28.899 | 43.038 | 1.00 | 58.84 |
| 3151 | CE2 | TYR | A | 339 | 106.196 | −29.776 | 43.564 | 1.00 | 60.72 |
| 3152 | CZ | TYR | A | 339 | 106.064 | −31.136 | 43.349 | 1.00 | 62.04 |
| 3153 | OH | TYR | A | 339 | 106.996 | −32.001 | 43.874 | 1.00 | 63.20 |
| 3154 | C | TYR | A | 339 | 100.772 | −27.686 | 41.395 | 1.00 | 43.09 |
| 3155 | O | TYR | A | 339 | 100.245 | −28.179 | 40.388 | 1.00 | 41.70 |
| 3156 | N | LEU | A | 340 | 100.550 | −26.435 | 41.783 | 1.00 | 42.05 |
| 3157 | CA | LEU | A | 340 | 99.679 | −25.545 | 41.034 | 1.00 | 38.17 |
| 3158 | C8 | LEU | A | 340 | 98.367 | −25.312 | 41.788 | 1.00 | 37.03 |
| 3159 | CG | LEU | A | 340 | 97.316 | −24.470 | 41.055 | 1.00 | 34.14 |
| 3160 | CD1 | LEU | A | 340 | 97.053 | −25.065 | 39.684 | 1.00 | 33.10 |
| 3161 | CD2 | LEU | A | 340 | 96.032 | −24.414 | 41.868 | 1.00 | 33.40 |
| 3162 | C | LEU | A | 340 | 100.420 | −24.238 | 40.853 | 1.00 | 36.71 |
| 3163 | O | LEU | A | 340 | 100.816 | −23.607 | 41.828 | 1.00 | 34.82 |
| 3164 | N | SER | A | 341 | 100.601 | −23.833 | 39.601 | 1.00 | 37.74 |
| 3165 | CA | SER | A | 341 | 101.333 | −22.602 | 39.295 | 1.00 | 40.53 |
| 3166 | CB | SER | A | 341 | 102.289 | −22.834 | 38.123 | 1.00 | 43.60 |
| 3167 | OG | SER | A | 341 | 101.568 | −22.987 | 36.917 | 1.00 | 45.11 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3168 | C | SER | A | 341 | 100.453 | −21.409 | 38.963 | 1.00 | 39.98 |
| 3169 | O | SER | A | 341 | 99.249 | −21.539 | 38.748 | 1.00 | 44.06 |
| 3170 | N | ARG | A | 342 | 101.070 | −20.239 | 38.930 | 1.00 | 40.02 |
| 3171 | CA | ARG | A | 342 | 100.354 | −19.027 | 38.600 | 1.00 | 37.15 |
| 3172 | CB | ARG | A | 342 | 100.796 | −17.874 | 39.511 | 1.00 | 35.94 |
| 3173 | CG | ARG | A | 342 | 100.478 | −18.065 | 40.996 | 1.00 | 34.26 |
| 3174 | CD | ARG | A | 342 | 100.782 | −16.799 | 41.803 | 1.00 | 35.51 |
| 3175 | NE | ARG | A | 342 | 102.215 | −16.603 | 41.994 | 1.00 | 38.80 |
| 3176 | CZ | ARG | A | 342 | 102.962 | −17.309 | 42.840 | 1.00 | 40.06 |
| 3177 | NH1 | ARG | A | 342 | 102.408 | −18.256 | 43.585 | 1.00 | 41.89 |
| 3178 | NH2 | ARG | A | 342 | 104.262 | −17.081 | 42.936 | 1.00 | 40.62 |
| 3179 | C | ARG | A | 342 | 100.675 | −18.705 | 37.143 | 1.00 | 34.45 |
| 3180 | O | ARG | A | 342 | 101.680 | −19.160 | 36.600 | 1.00 | 32.88 |
| 3181 | N | PRO | A | 343 | 99.812 | −17.932 | 36.482 | 1.00 | 33.62 |
| 3182 | CD | PRO | A | 343 | 98.561 | −17.345 | 36.982 | 1.00 | 32.39 |
| 3183 | CA | PRO | A | 343 | 100.068 | −17.585 | 35.084 | 1.00 | 32.91 |
| 3184 | CB | PRO | A | 343 | 98.927 | −16.634 | 34.732 | 1.00 | 32.51 |
| 3185 | CG | PRO | A | 343 | 97.860 | −16.940 | 35.721 | 1.00 | 33.52 |
| 3186 | C | PRO | A | 343 | 101.419 | −16.883 | 34.939 | 1.00 | 33.12 |
| 3187 | O | PRO | A | 343 | 101.847 | −16.140 | 35.833 | 1.00 | 33.70 |
| 3188 | N | SER | A | 344 | 102.088 | −17.112 | 33.817 | 1.00 | 32.92 |
| 3189 | CA | SER | A | 344 | 103.352 | −16.438 | 33.578 | 1.00 | 33.11 |
| 3190 | CB | SER | A | 344 | 104.068 | −17.032 | 32.365 | 1.00 | 32.63 |
| 3191 | OG | SER | A | 344 | 103.540 | −16.493 | 31.163 | 1.00 | 32.29 |
| 3192 | C | SER | A | 344 | 102.987 | −14.990 | 33.269 | 1.00 | 31.82 |
| 3193 | O | SER | A | 344 | 102.006 | −14.725 | 32.571 | 1.00 | 30.79 |
| 3194 | N | PRO | A | 345 | 103.763 | −14.034 | 33.786 | 1.00 | 32.30 |
| 3195 | CD | PRO | A | 345 | 104.898 | −14.175 | 34.715 | 1.00 | 32.22 |
| 3196 | CA | PRO | A | 345 | 103.458 | −12.625 | 33.514 | 1.00 | 32.11 |
| 3197 | CB | PRO | A | 345 | 104.627 | −11.885 | 34.150 | 1.00 | 31.36 |
| 3198 | CG | PRO | A | 345 | 105.032 | −12.777 | 35.272 | 1.00 | 32.76 |
| 3199 | C | PRO | A | 345 | 103.366 | −12.353 | 32.005 | 1.00 | 32.29 |
| 3200 | O | PRO | A | 345 | 102.629 | −11.473 | 31.566 | 1.00 | 33.44 |
| 3201 | N | PHE | A | 346 | 104.122 | −13.110 | 31.212 | 1.00 | 33.43 |
| 3202 | CA | PHE | A | 346 | 104.115 | −12.930 | 29.758 | 1.00 | 32.58 |
| 3203 | CB | PHE | A | 346 | 105.129 | −13.867 | 29.103 | 1.00 | 32.84 |
| 3204 | CG | PHE | A | 346 | 105.133 | −13.795 | 27.598 | 1.00 | 31.25 |
| 3205 | CD1 | PHE | A | 346 | 105.294 | −12.572 | 26.944 | 1.00 | 32.22 |
| 3206 | CD2 | PHE | A | 346 | 105.001 | −14.949 | 26.838 | 1.00 | 31.24 |
| 3207 | CE1 | PHE | A | 346 | 105.325 | −12.500 | 25.552 | 1.00 | 32.90 |
| 3208 | CE2 | PHE | A | 346 | 105.032 | −14.893 | 25.442 | 1.00 | 32.80 |
| 3209 | CZ | PHE | A | 346 | 105.195 | −13.666 | 24.795 | 1.00 | 32.34 |
| 3210 | C | PHE | A | 346 | 102.732 | −13.215 | 29.192 | 1.00 | 30.35 |
| 3211 | O | PHE | A | 346 | 102.101 | −12.348 | 28.594 | 1.00 | 29.72 |
| 3212 | N | ASP | A | 347 | 102.287 | −14.452 | 29.374 | 1.00 | 30.78 |
| 3213 | CA | ASP | A | 347 | 100.969 | −14.889 | 28.934 | 1.00 | 33.14 |
| 3214 | CB | ASP | A | 347 | 100.676 | −16.310 | 29.437 | 1.00 | 31.82 |
| 3215 | CG | ASP | A | 347 | 101.458 | −17.381 | 28.700 | 1.00 | 31.58 |
| 3216 | OD1 | ASP | A | 347 | 101.471 | −18.537 | 29.190 | 1.00 | 31.54 |
| 3217 | OD2 | ASP | A | 347 | 102.046 | −17.089 | 27.636 | 1.00 | 29.62 |
| 3218 | C | ASP | A | 347 | 99.888 | −13.958 | 29.499 | 1.00 | 33.12 |
| 3219 | O | ASP | A | 347 | 98.911 | −13.660 | 28.817 | 1.00 | 34.85 |
| 3220 | N | LEU | A | 348 | 100.066 | −13.509 | 30.743 | 1.00 | 32.06 |
| 3221 | CA | LEU | A | 348 | 99.086 | −12.647 | 31.413 | 1.00 | 32.23 |
| 3222 | CB | LEU | A | 348 | 99.299 | −12.682 | 32.943 | 1.00 | 28.60 |
| 3223 | CG | LEU | A | 348 | 98.457 | −11.750 | 33.836 | 1.00 | 25.66 |
| 3224 | CD1 | LEU | A | 348 | 96.991 | −12.090 | 33.697 | 1.00 | 20.72 |
| 3225 | CD2 | LEU | A | 348 | 98.891 | −11.871 | 35.311 | 1.00 | 23.01 |
| 3226 | C | LEU | A | 348 | 99.025 | −11.189 | 30.961 | 1.00 | 33.72 |
| 3227 | O | LEU | A | 348 | 97.932 | −10.648 | 30.738 | 1.00 | 34.42 |
| 3228 | N | PHE | A | 349 | 100.179 | −10.548 | 30.807 | 1.00 | 35.21 |
| 3229 | CA | PHE | A | 349 | 100.187 | −9.136 | 30.432 | 1.00 | 35.95 |
| 3230 | CB | PHE | A | 349 | 101.207 | −8.390 | 31.286 | 1.00 | 34.45 |
| 3231 | CG | PHE | A | 349 | 100.896 | −8.432 | 32.743 | 1.00 | 30.91 |
| 3232 | CD1 | PHE | A | 349 | 101.792 | −9.002 | 33.643 | 1.00 | 30.66 |
| 3233 | CD2 | PHE | A | 349 | 99.716 | −7.876 | 33.224 | 1.00 | 30.22 |
| 3234 | CE1 | PHE | A | 349 | 101.487 | −9.052 | 35.004 | 1.00 | 29.27 |
| 3235 | CE2 | PHE | A | 349 | 99.407 | −7.923 | 34.583 | 1.00 | 28.47 |
| 3236 | CZ | PHE | A | 349 | 100.295 | −8.490 | 35.474 | 1.00 | 29.05 |
| 3237 | C | PHE | A | 349 | 100.440 | −8.802 | 28.975 | 1.00 | 34.94 |
| 3238 | O | PHE | A | 349 | 99.914 | −7.821 | 28.467 | 1.00 | 37.77 |
| 3239 | N | ILE | A | 350 | 101.249 | −9.604 | 28.299 | 1.00 | 35.01 |
| 3240 | CA | ILE | A | 350 | 101.558 | −9.319 | 26.907 | 1.00 | 37.91 |
| 3241 | CB | ILE | A | 350 | 103.026 | −9.660 | 26.599 | 1.00 | 30.41 |
| 3242 | CG2 | ILE | A | 350 | 103.345 | −9.303 | 25.155 | 1.00 | 26.48 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3243 | CG1 | ILE | A | 350 | 103.944 | −8.915 | 27.570 | 1.00 | 25.72 |
| 3244 | CD1 | ILE | A | 350 | 103.782 | −7.404 | 27.536 | 1.00 | 20.90 |
| 3245 | C | ILE | A | 350 | 100.666 | −10.085 | 25.939 | 1.00 | 40.10 |
| 3246 | O | ILE | A | 350 | 99.945 | −9.497 | 25.129 | 1.00 | 41.52 |
| 3247 | N | ARG | A | 351 | 100.738 | −11.406 | 26.036 | 1.00 | 43.04 |
| 3248 | CA | ARG | A | 351 | 99.984 | −12.309 | 25.184 | 1.00 | 46.74 |
| 3249 | CB | ARG | A | 351 | 100.513 | −13.716 | 25.385 | 1.00 | 48.81 |
| 3250 | CG | ARG | A | 351 | 100.324 | −14.586 | 24.204 | 1.00 | 55.48 |
| 3251 | CD | ARG | A | 351 | 101.290 | −15.717 | 24.244 | 1.00 | 61.05 |
| 3252 | NE | ARG | A | 351 | 100.823 | −16.813 | 23.416 | 1.00 | 66.61 |
| 3253 | CZ | ARG | A | 351 | 99.994 | −17.757 | 23.835 | 1.00 | 69.38 |
| 3254 | NH1 | ARG | A | 351 | 99.552 | −17.733 | 25.073 | 1.00 | 70.78 |
| 3255 | NH2 | ARG | A | 351 | 99.599 | −18.722 | 23.020 | 1.00 | 71.04 |
| 3256 | C | ARG | A | 351 | 98.493 | −12.258 | 25.494 | 1.00 | 49.12 |
| 3257 | O | ARG | A | 351 | 97.655 | −12.637 | 24.673 | 1.00 | 46.13 |
| 3258 | N | LYS | A | 352 | 98.185 | −11.799 | 26.702 | 1.00 | 49.35 |
| 3259 | CA | LYS | A | 352 | 96.820 | −11.647 | 27.179 | 1.00 | 47.91 |
| 3260 | CB | LYS | A | 352 | 96.094 | −10.596 | 26.349 | 1.00 | 56.01 |
| 3261 | CG | LYS | A | 352 | 96.754 | −9.240 | 26.362 | 1.00 | 72.02 |
| 3262 | CD | LYS | A | 352 | 95.745 | −8.175 | 26.692 | 1.00 | 84.39 |
| 3263 | CE | LYS | A | 352 | 96.411 | −6.843 | 26.939 | 1.00 | 92.52 |
| 3264 | NZ | LYS | A | 352 | 97.089 | −6.316 | 25.764 | 1.00 | 97.68 |
| 3265 | C | LYS | A | 352 | 95.975 | −12.905 | 27.220 | 1.00 | 43.26 |
| 3266 | O | LYS | A | 352 | 94.772 | −12.846 | 26.991 | 1.00 | 39.34 |
| 3267 | N | SER | A | 353 | 96.595 | −14.040 | 27.506 | 1.00 | 39.36 |
| 3268 | CA | SER | A | 353 | 95.856 | −15.289 | 27.602 | 1.00 | 38.88 |
| 3269 | CB | SER | A | 353 | 95.794 | −16.002 | 26.246 | 1.00 | 42.02 |
| 3270 | OG | SER | A | 353 | 97.064 | −16.437 | 25.831 | 1.00 | 51.52 |
| 3271 | C | SER | A | 353 | 96.522 | −16.168 | 28.657 | 1.00 | 34.72 |
| 3272 | O | SER | A | 353 | 97.279 | −17.099 | 28.342 | 1.00 | 36.18 |
| 3273 | N | PRO | A | 354 | 96.236 | −15.873 | 29.940 | 1.00 | 35.76 |
| 3274 | CD | PRO | A | 354 | 95.303 | −14.820 | 30.372 | 1.00 | 33.62 |
| 3275 | CA | PRO | A | 354 | 96.774 | −16.588 | 31.100 | 1.00 | 32.43 |
| 3276 | CB | PRO | A | 354 | 96.307 | −15.743 | 32.291 | 1.00 | 32.73 |
| 3277 | CG | PRO | A | 354 | 95.855 | −14.443 | 31.693 | 1.00 | 33.12 |
| 3278 | C | PRO | A | 354 | 96.267 | −18.022 | 31.220 | 1.00 | 29.33 |
| 3279 | O | PRO | A | 354 | 95.159 | −18.333 | 30.790 | 1.00 | 29.64 |
| 3280 | N | THR | A | 355 | 97.096 | −18.879 | 31.809 | 1.00 | 27.44 |
| 3281 | CA | THR | A | 355 | 96.755 | −20.276 | 32.050 | 1.00 | 26.76 |
| 3282 | CB | THR | A | 355 | 97.202 | −21.215 | 30.898 | 1.00 | 26.18 |
| 3283 | OG1 | THR | A | 355 | 98.620 | −21.130 | 30.731 | 1.00 | 26.80 |
| 3284 | CG2 | THR | A | 355 | 96.513 | −20.841 | 29.595 | 1.00 | 24.64 |
| 3285 | C | THR | A | 355 | 97.466 | −20.729 | 33.323 | 1.00 | 25.17 |
| 3286 | O | THR | A | 355 | 98.543 | −20.221 | 33.659 | 1.00 | 26.05 |
| 3287 | N | ILE | A | 356 | 96.861 | −21.664 | 34.042 | 1.00 | 21.97 |
| 3288 | CA | ILE | A | 356 | 97.480 | −22.167 | 35.248 | 1.00 | 23.26 |
| 3289 | CB | ILE | A | 356 | 96.651 | −21.848 | 36.517 | 1.00 | 22.56 |
| 3290 | CG2 | ILE | A | 356 | 96.610 | −20.339 | 36.746 | 1.00 | 19.80 |
| 3291 | CG1 | ILE | A | 356 | 95.244 | −22.405 | 36.376 | 1.00 | 22.68 |
| 3292 | CD1 | ILE | A | 356 | 94.351 | −22.067 | 37.545 | 1.00 | 25.57 |
| 3293 | C | ILE | A | 356 | 97.626 | −23.659 | 35.041 | 1.00 | 25.78 |
| 3294 | O | ILE | A | 356 | 96.864 | −24.270 | 34.277 | 1.00 | 23.57 |
| 3295 | N | THR | A | 357 | 98.609 | −24.247 | 35.709 | 1.00 | 24.91 |
| 3296 | CA | THR | A | 357 | 98.860 | −25.647 | 35.508 | 1.00 | 26.16 |
| 3297 | CB | THR | A | 357 | 100.158 | −25.813 | 34.708 | 1.00 | 28.55 |
| 3298 | OG1 | THR | A | 357 | 100.010 | −25.155 | 33.439 | 1.00 | 30.47 |
| 3299 | CG2 | THR | A | 357 | 100.475 | −27.272 | 34.501 | 1.00 | 30.13 |
| 3300 | C | THR | A | 357 | 98.947 | −26.453 | 36.774 | 1.00 | 27.93 |
| 3301 | O | THR | A | 357 | 99.660 | −26.091 | 37.717 | 1.00 | 26.42 |
| 3302 | N | CYS | A | 358 | 98.200 | −27.548 | 36.789 | 1.00 | 29.19 |
| 3303 | CA | CYS | A | 358 | 98.215 | −28.450 | 37.922 | 1.00 | 31.73 |
| 3304 | C | CYS | A | 358 | 99.173 | −29.558 | 37.515 | 1.00 | 31.77 |
| 3305 | O | CYS | A | 358 | 98.947 | −30.253 | 36.518 | 1.00 | 31.41 |
| 3306 | CB | CYS | A | 358 | 96.826 | −29.027 | 38.184 | 1.00 | 33.71 |
| 3307 | SG | CYS | A | 358 | 96.658 | −29.845 | 39.807 | 1.00 | 36.97 |
| 3308 | N | LEU | A | 359 | 100.248 | −29.710 | 38.279 | 1.00 | 32.77 |
| 3309 | CA | LEU | A | 359 | 101.255 | −30.709 | 37.968 | 1.00 | 34.78 |
| 3310 | CB | LEU | A | 359 | 102.637 | −30.051 | 37.919 | 1.00 | 32.79 |
| 3311 | CG | LEU | A | 359 | 103.863 | −30.968 | 37.838 | 1.00 | 33.52 |
| 3312 | CD1 | LEU | A | 359 | 103.793 | −31.843 | 36.578 | 1.00 | 30.43 |
| 3313 | CD2 | LEU | A | 359 | 105.129 | −30.115 | 37.829 | 1.00 | 27.35 |
| 3314 | C | LEU | A | 359 | 101.247 | −31.855 | 38.956 | 1.00 | 37.75 |
| 3315 | O | LEU | A | 359 | 101.510 | −31.684 | 40.150 | 1.00 | 39.32 |
| 3316 | N | VAL | A | 360 | 100.943 | −33.039 | 38.457 | 1.00 | 39.85 |
| 3317 | CA | VAL | A | 360 | 100.904 | −34.175 | 39.339 | 1.00 | 42.17 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3318 | CB | VAL | A | 360 | 99.555 | −34.884 | 39.227 | 1.00 | 41.02 |
| 3319 | CG1 | VAL | A | 360 | 99.531 | −36.134 | 40.099 | 1.00 | 42.18 |
| 3320 | CG2 | VAL | A | 360 | 98.460 | −33.911 | 39.681 | 1.00 | 41.18 |
| 3321 | C | VAL | A | 360 | 102.075 | −35.101 | 39.106 | 1.00 | 47.97 |
| 3322 | O | VAL | A | 360 | 102.002 | −36.057 | 38.330 | 1.00 | 43.27 |
| 3323 | N | VAL | A | 361 | 103.189 | −34.716 | 39.735 | 1.00 | 56.36 |
| 3324 | CA | VAL | A | 361 | 104.412 | −35.492 | 39.691 | 1.00 | 62.09 |
| 3325 | CB | VAL | A | 361 | 105.656 | −34.778 | 40.203 | 1.00 | 55.55 |
| 3326 | CG1 | VAL | A | 361 | 106.810 | −35.796 | 40.287 | 1.00 | 49.36 |
| 3327 | CG2 | VAL | A | 361 | 106.032 | −33.650 | 39.261 | 1.00 | 47.61 |
| 3328 | C | VAL | A | 361 | 104.089 | −36.572 | 40.655 | 1.00 | 73.43 |
| 3329 | O | VAL | A | 361 | 104.254 | −36.470 | 41.880 | 1.00 | 78.33 |
| 3330 | N | ASP | A | 362 | 103.569 | −37.608 | 40.046 | 1.00 | 88.15 |
| 3331 | CA | ASP | A | 362 | 103.152 | −38.768 | 40.744 | 1.00 | 105.41 |
| 3332 | CB | ASP | A | 362 | 101.781 | −39.143 | 40.250 | 1.00 | 105.85 |
| 3333 | CG | ASP | A | 362 | 101.143 | −40.136 | 41.128 | 1.00 | 102.39 |
| 3334 | OD1 | ASP | A | 362 | 101.901 | −40.933 | 41.707 | 1.00 | 96.64 |
| 3335 | OD2 | ASP | A | 362 | 99.904 | −40.131 | 41.242 | 1.00 | 97.22 |
| 3336 | C | ASP | A | 362 | 104.162 | −39.865 | 40.464 | 1.00 | 113.28 |
| 3337 | O | ASP | A | 362 | 104.837 | −39.854 | 39.436 | 1.00 | 127.18 |
| 3338 | N | LEU | A | 363 | 104.254 | −40.832 | 41.364 | 1.00 | 121.49 |
| 3339 | CA | LEU | A | 363 | 105.245 | −41.878 | 41.202 | 1.00 | 123.38 |
| 3340 | CB | LEU | A | 363 | 106.218 | −41.778 | 42.378 | 1.00 | 121.49 |
| 3341 | CG | LEU | A | 363 | 106.758 | −40.349 | 42.586 | 1.00 | 112.94 |
| 3342 | CD1 | LEU | A | 363 | 107.325 | −40.194 | 43.990 | 1.00 | 108.80 |
| 3343 | CD2 | LEU | A | 363 | 107.816 | −40.028 | 41.534 | 1.00 | 108.41 |
| 3344 | C | LEU | A | 363 | 104.705 | −43.301 | 41.031 | 1.00 | 121.71 |
| 3345 | O | LEU | A | 363 | 103.612 | −43.484 | 40.492 | 1.00 | 126.40 |
| 3346 | N | ALA | A | 364 | 105.483 | −44.297 | 41.465 | 1.00 | 113.89 |
| 3347 | CA | ALA | A | 364 | 105.102 | −45.710 | 41.341 | 1.00 | 111.38 |
| 3348 | CB | ALA | A | 364 | 104.988 | −46.360 | 42.705 | 1.00 | 115.69 |
| 3349 | C | ALA | A | 364 | 103.790 | −45.857 | 40.588 | 1.00 | 114.99 |
| 3350 | O | ALA | A | 364 | 102.748 | −46.164 | 41.169 | 1.00 | 109.63 |
| 3351 | N | PRO | A | 365 | 103.828 | −45.596 | 39.279 | 1.00 | 98.88 |
| 3352 | CD | PRO | A | 365 | 105.021 | −45.034 | 38.618 | 1.00 | 100.13 |
| 3353 | CA | PRO | A | 365 | 102.681 | −45.681 | 38.372 | 1.00 | 100.71 |
| 3354 | CB | PRO | A | 365 | 103.334 | −45.692 | 36.980 | 1.00 | 95.94 |
| 3355 | CG | PRO | A | 365 | 104.839 | −45.420 | 37.204 | 1.00 | 95.37 |
| 3356 | C | PRO | A | 365 | 101.841 | −46.955 | 38.638 | 1.00 | 100.80 |
| 3357 | O | PRO | A | 365 | 102.278 | −48.047 | 38.282 | 1.00 | 94.65 |
| 3358 | N | SER | A | 366 | 100.663 | −46.814 | 39.269 | 1.00 | 94.94 |
| 3359 | CA | SER | A | 366 | 99.756 | −47.945 | 39.585 | 1.00 | 98.91 |
| 3360 | CB | SER | A | 366 | 99.429 | −47.975 | 41.088 | 1.00 | 100.60 |
| 3361 | OG | SER | A | 366 | 99.382 | −46.669 | 41.638 | 1.00 | 92.37 |
| 3362 | C | SER | A | 366 | 98.453 | −47.891 | 38.774 | 1.00 | 102.47 |
| 3363 | O | SER | A | 366 | 97.349 | −48.053 | 39.314 | 1.00 | 108.72 |
| 3364 | N | ALA | A | 367 | 98.629 | −47.662 | 37.472 | 1.00 | 106.65 |
| 3365 | CA | ALA | A | 367 | 97.561 | −47.560 | 36.480 | 1.00 | 105.97 |
| 3366 | CB | ALA | A | 367 | 97.681 | −48.705 | 35.473 | 1.00 | 101.28 |
| 3367 | C | ALA | A | 367 | 96.163 | −47.527 | 37.084 | 1.00 | 107.03 |
| 3368 | O | ALA | A | 367 | 95.802 | −48.385 | 37.887 | 1.00 | 106.98 |
| 3369 | N | GLY | A | 368 | 95.377 | −46.536 | 36.679 | 1.00 | 106.31 |
| 3370 | CA | GLY | A | 368 | 94.029 | −46.386 | 37.197 | 1.00 | 107.79 |
| 3371 | C | GLY | A | 368 | 93.621 | −44.928 | 37.130 | 1.00 | 109.74 |
| 3372 | O | GLY | A | 368 | 93.067 | −44.370 | 38.077 | 1.00 | 109.76 |
| 3373 | N | THR | A | 369 | 93.936 | −44.324 | 35.989 | 1.00 | 111.35 |
| 3374 | CA | THR | A | 369 | 93.646 | −42.930 | 35.673 | 1.00 | 108.22 |
| 3375 | CB | THR | A | 369 | 92.337 | −42.819 | 34.857 | 1.00 | 110.91 |
| 3376 | OG1 | THR | A | 369 | 91.319 | −42.197 | 35.651 | 1.00 | 116.52 |
| 3377 | CG2 | THR | A | 369 | 91.863 | −44.200 | 34.427 | 1.00 | 116.17 |
| 3378 | C | THR | A | 369 | 93.579 | −41.933 | 36.827 | 1.00 | 102.04 |
| 3379 | O | THR | A | 369 | 92.744 | −42.048 | 37.727 | 1.00 | 104.65 |
| 3380 | N | VAL | A | 370 | 94.476 | −40.952 | 36.787 | 1.00 | 93.76 |
| 3381 | CA | VAL | A | 370 | 94.500 | −39.897 | 37.788 | 1.00 | 90.02 |
| 3382 | CB | VAL | A | 370 | 95.859 | −39.172 | 37.815 | 1.00 | 81.16 |
| 3383 | CG1 | VAL | A | 370 | 95.862 | −38.117 | 38.903 | 1.00 | 68.61 |
| 3384 | CG2 | VAL | A | 370 | 96.977 | −40.175 | 38.051 | 1.00 | 69.43 |
| 3385 | C | VAL | A | 370 | 93.398 | −38.926 | 37.354 | 1.00 | 93.49 |
| 3386 | O | VAL | A | 370 | 93.134 | −38.774 | 36.156 | 1.00 | 94.12 |
| 3387 | N | GLN | A | 371 | 92.761 | −38.278 | 38.328 | 1.00 | 98.10 |
| 3388 | CA | GLN | A | 371 | 91.653 | −37.354 | 38.075 | 1.00 | 94.08 |
| 3389 | CB | GLN | A | 371 | 90.442 | −37.834 | 38.892 | 1.00 | 101.10 |
| 3390 | CG | GLN | A | 371 | 89.054 | −37.682 | 38.282 | 1.00 | 105.16 |
| 3391 | CD | GLN | A | 371 | 88.719 | −38.657 | 37.222 | 1.00 | 121.86 |
| 3392 | OE1 | GLN | A | 371 | 89.580 | −39.054 | 36.560 | 1.00 | 111.58 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3393 | NE2 | GLN | A | 371 | 87.464 | −39.016 | 37.034 | 1.00 | 111.60 |
| 3394 | C | GLN | A | 371 | 91.994 | −35.908 | 38.465 | 1.00 | 88.18 |
| 3395 | O | GLN | A | 371 | 92.276 | −35.635 | 39.628 | 1.00 | 82.08 |
| 3396 | N | LEU | A | 372 | 91.979 | −34.987 | 37.503 | 1.00 | 72.64 |
| 3397 | CA | LEU | A | 372 | 92.252 | −33.579 | 37.804 | 1.00 | 55.06 |
| 3398 | CB | LEU | A | 372 | 93.384 | −33.009 | 36.941 | 1.00 | 48.46 |
| 3399 | CG | LEU | A | 372 | 94.808 | −33.520 | 37.155 | 1.00 | 43.78 |
| 3400 | CD1 | LEU | A | 372 | 95.799 | −32.489 | 36.639 | 1.00 | 44.59 |
| 3401 | CD2 | LEU | A | 372 | 95.047 | −33.763 | 38.624 | 1.00 | 43.71 |
| 3402 | C | LEU | A | 372 | 90.998 | −32.774 | 37.543 | 1.00 | 48.63 |
| 3403 | O | LEU | A | 372 | 90.597 | −32.614 | 36.391 | 1.00 | 44.23 |
| 3404 | N | THR | A | 373 | 90.384 | −32.262 | 38.608 | 1.00 | 43.01 |
| 3405 | CA | THR | A | 373 | 89.160 | −31.472 | 38.486 | 1.00 | 42.42 |
| 3406 | CB | THR | A | 373 | 88.024 | −32.090 | 39.313 | 1.00 | 45.34 |
| 3407 | OG1 | THR | A | 373 | 87.872 | −33.468 | 38.954 | 1.00 | 46.96 |
| 3408 | CG2 | THR | A | 373 | 86.710 | −31.355 | 39.048 | 1.00 | 47.40 |
| 3409 | C | THR | A | 373 | 89.366 | −30.027 | 38.945 | 1.00 | 38.65 |
| 3410 | O | THR | A | 373 | 89.874 | −29.779 | 40.043 | 1.00 | 39.07 |
| 3411 | N | TRP | A | 374 | 88.960 | −29.084 | 38.094 | 1.00 | 35.54 |
| 3412 | CA | TRP | A | 374 | 89.098 | −27.655 | 38.370 | 1.00 | 32.00 |
| 3413 | CB | TRP | A | 374 | 89.508 | −26.892 | 37.100 | 1.00 | 29.56 |
| 3414 | CG | TRP | A | 374 | 90.835 | −27.254 | 36.526 | 1.00 | 29.07 |
| 3415 | CD2 | TRP | A | 374 | 92.107 | −26.757 | 36.940 | 1.00 | 26.97 |
| 3416 | CE2 | TRP | A | 374 | 93.085 | −27.389 | 36.140 | 1.00 | 28.35 |
| 3417 | CE3 | TRP | A | 374 | 92.520 | −25.842 | 37.911 | 1.00 | 25.98 |
| 3418 | CD1 | TRP | A | 374 | 91.079 | −28.140 | 35.516 | 1.00 | 28.23 |
| 3419 | NE1 | TRP | A | 374 | 92.429 | −28.228 | 35.278 | 1.00 | 29.48 |
| 3420 | CZ2 | TRP | A | 374 | 94.452 | −27.132 | 36.281 | 1.00 | 27.07 |
| 3421 | CZ3 | TRP | A | 374 | 93.883 | −25.584 | 38.054 | 1.00 | 26.12 |
| 3422 | CH2 | TRP | A | 374 | 94.831 | −26.228 | 37.242 | 1.00 | 26.16 |
| 3423 | C | TRP | A | 374 | 87.819 | −26.998 | 38.881 | 1.00 | 31.91 |
| 3424 | O | TRP | A | 374 | 86.711 | −27.496 | 38.666 | 1.00 | 30.92 |
| 3425 | N | SER | A | 375 | 87.982 | −25.863 | 39.548 | 1.00 | 29.63 |
| 3426 | CA | SER | A | 375 | 86.845 | −25.087 | 40.018 | 1.00 | 27.90 |
| 3427 | CB | SER | A | 375 | 86.080 | −25.798 | 41.144 | 1.00 | 27.09 |
| 3428 | OG | SER | A | 375 | 86.842 | −25.936 | 42.328 | 1.00 | 29.87 |
| 3429 | C | SER | A | 375 | 87.338 | −23.739 | 40.490 | 1.00 | 27.70 |
| 3430 | O | SER | A | 375 | 88.546 | −23.505 | 40.565 | 1.00 | 27.61 |
| 3431 | N | ARG | A | 376 | 86.400 | −22.852 | 40.795 | 1.00 | 26.72 |
| 3432 | CA | ARG | A | 376 | 86.735 | −21.520 | 41.266 | 1.00 | 26.76 |
| 3433 | CB | ARG | A | 376 | 86.168 | −20.444 | 40.339 | 1.00 | 27.44 |
| 3434 | CG | ARG | A | 376 | 86.831 | −20.365 | 38.991 | 1.00 | 29.05 |
| 3435 | CD | ARG | A | 376 | 86.776 | −18.937 | 38.488 | 1.00 | 30.72 |
| 3436 | NE | ARG | A | 376 | 85.764 | −18.773 | 37.465 | 1.00 | 32.29 |
| 3437 | CZ | ARG | A | 376 | 85.348 | −17.597 | 37.014 | 1.00 | 31.75 |
| 3438 | NH1 | ARG | A | 376 | 85.859 | −16.477 | 37.512 | 1.00 | 28.73 |
| 3439 | NH2 | ARG | A | 376 | 84.436 | −17.552 | 36.049 | 1.00 | 33.27 |
| 3440 | C | ARG | A | 376 | 86.152 | −21.319 | 42.643 | 1.00 | 26.53 |
| 3441 | O | ARG | A | 376 | 85.059 | −21.799 | 42.942 | 1.00 | 28.83 |
| 3442 | N | ALA | A | 377 | 86.869 | −20.588 | 43.480 | 1.00 | 25.21 |
| 3443 | CA | ALA | A | 377 | 86.391 | −20.340 | 44.817 | 1.00 | 23.67 |
| 3444 | CB | ALA | A | 377 | 87.340 | −19.432 | 45.506 | 1.00 | 21.74 |
| 3445 | C | ALA | A | 377 | 85.005 | −19.709 | 44.738 | 1.00 | 23.88 |
| 3446 | O | ALA | A | 377 | 84.114 | −20.022 | 45.538 | 1.00 | 23.51 |
| 3447 | N | SER | A | 378 | 84.832 | −18.824 | 43.754 | 1.00 | 22.76 |
| 3448 | CA | SER | A | 378 | 83.571 | −18.121 | 43.556 | 1.00 | 23.67 |
| 3449 | CB | SER | A | 378 | 83.758 | −17.009 | 42.519 | 1.00 | 24.37 |
| 3450 | OG | SER | A | 378 | 83.886 | −17.555 | 41.211 | 1.00 | 23.05 |
| 3451 | C | SER | A | 378 | 82.412 | −19.031 | 43.122 | 1.00 | 23.98 |
| 3452 | O | SER | A | 378 | 81.250 | −18.655 | 43.255 | 1.00 | 25.54 |
| 3453 | N | GLY | A | 379 | 82.717 | −20.220 | 42.607 | 1.00 | 23.06 |
| 3454 | CA | GLY | A | 379 | 81.657 | −21.111 | 42.161 | 1.00 | 22.60 |
| 3455 | C | GLY | A | 379 | 81.329 | −20.942 | 40.681 | 1.00 | 22.34 |
| 3456 | O | GLY | A | 379 | 80.577 | −21.720 | 40.105 | 1.00 | 22.38 |
| 3457 | N | LYS | A | 380 | 81.905 | −19.918 | 40.063 | 1.00 | 23.53 |
| 3458 | CA | LYS | A | 380 | 81.687 | −19.655 | 38.652 | 1.00 | 24.69 |
| 3459 | CB | LYS | A | 380 | 82.188 | −18.254 | 38.301 | 1.00 | 23.94 |
| 3460 | CG | LYS | A | 380 | 81.372 | −17.162 | 38.953 | 1.00 | 22.63 |
| 3461 | CD | LYS | A | 380 | 82.060 | −15.824 | 38.833 | 1.00 | 25.92 |
| 3462 | CE | LYS | A | 380 | 81.305 | −14.738 | 39.590 | 1.00 | 27.89 |
| 3463 | NZ | LYS | A | 380 | 81.908 | −13.392 | 39.356 | 1.00 | 32.22 |
| 3464 | C | LYS | A | 380 | 82.354 | −20.716 | 37.767 | 1.00 | 26.43 |
| 3465 | O | LYS | A | 380 | 83.255 | −21.451 | 38.199 | 1.00 | 29.36 |
| 3466 | N | PRO | A | 381 | 81.903 | −20.804 | 36.508 | 1.00 | 31.27 |
| 3467 | CD | PRO | A | 381 | 80.940 | −19.848 | 35.939 | 1.00 | 32.85 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3468 | CA | PRO | A | 381 | 82.376 | −21.746 | 35.489 | 1.00 | 31.59 |
| 3469 | CB | PRO | A | 381 | 81.474 | −21.471 | 34.285 | 1.00 | 32.24 |
| 3470 | CG | PRO | A | 381 | 80.360 | −20.617 | 34.810 | 1.00 | 33.41 |
| 3471 | C | PRO | A | 381 | 83.831 | −21.587 | 35.101 | 1.00 | 31.37 |
| 3472 | O | PRO | A | 381 | 84.348 | −20.471 | 35.029 | 1.00 | 34.20 |
| 3473 | N | VAL | A | 382 | 84.478 | −22.722 | 34.859 | 1.00 | 29.99 |
| 3474 | CA | VAL | A | 382 | 85.865 | −22.751 | 34.429 | 1.00 | 31.67 |
| 3475 | CB | VAL | A | 382 | 86.726 | −23.741 | 35.255 | 1.00 | 29.43 |
| 3476 | CG1 | VAL | A | 382 | 86.760 | −23.306 | 36.701 | 1.00 | 26.33 |
| 3477 | CG2 | VAL | A | 382 | 86.173 | −25.164 | 35.124 | 1.00 | 28.12 |
| 3478 | C | VAL | A | 382 | 85.842 | −23.226 | 32.984 | 1.00 | 34.76 |
| 3479 | O | VAL | A | 382 | 84.901 | −23.894 | 32.557 | 1.00 | 30.10 |
| 3480 | N | GLN | A | 383 | 86.875 | −22.882 | 32.231 | 1.00 | 36.04 |
| 3481 | CA | GLN | A | 383 | 86.925 | −23.292 | 30.848 | 1.00 | 36.32 |
| 3482 | CB | GLN | A | 383 | 87.828 | −22.332 | 30.049 | 1.00 | 39.23 |
| 3483 | CG | GLN | A | 383 | 87.373 | −20.848 | 30.009 | 1.00 | 47.36 |
| 3484 | CD | GLN | A | 383 | 88.372 | −19.952 | 29.292 | 1.00 | 57.89 |
| 3485 | OE1 | GLN | A | 383 | 89.040 | −20.391 | 28.352 | 1.00 | 57.63 |
| 3486 | NE2 | GLN | A | 383 | 88.474 | −18.690 | 29.716 | 1.00 | 55.99 |
| 3487 | C | GLN | A | 383 | 87.423 | −24.734 | 30.718 | 1.00 | 36.24 |
| 3488 | O | GLN | A | 383 | 87.589 | −25.452 | 31.705 | 1.00 | 29.87 |
| 3489 | N | HIS | A | 384 | 87.631 | −25.151 | 29.478 | 1.00 | 37.00 |
| 3490 | CA | HIS | A | 384 | 88.131 | −26.492 | 29.163 | 1.00 | 35.65 |
| 3491 | CB | HIS | A | 384 | 87.947 | −26.780 | 27.700 | 1.00 | 41.52 |
| 3492 | CG | HIS | A | 384 | 86.599 | −27.288 | 27.374 | 1.00 | 49.90 |
| 3493 | CD2 | HIS | A | 384 | 85.702 | −26.858 | 26.475 | 1.00 | 53.21 |
| 3494 | ND1 | HIS | A | 384 | 86.046 | −28.374 | 28.010 | 1.00 | 54.30 |
| 3495 | CE1 | HIS | A | 384 | 84.846 | −28.596 | 27.507 | 1.00 | 56.53 |
| 3496 | NE2 | HIS | A | 384 | 84.616 | −27.694 | 26.578 | 1.00 | 55.15 |
| 3497 | C | HIS | A | 384 | 89.610 | −26.607 | 29.442 | 1.00 | 31.75 |
| 3498 | O | HIS | A | 384 | 90.371 | −25.708 | 29.094 | 1.00 | 29.22 |
| 3499 | N | SER | A | 385 | 90.027 | −27.709 | 30.044 | 1.00 | 31.47 |
| 3500 | CA | SER | A | 385 | 91.442 | −27.877 | 30.330 | 1.00 | 33.51 |
| 3501 | CB | SER | A | 385 | 91.627 | −28.239 | 31.803 | 1.00 | 31.96 |
| 3502 | OG | SER | A | 385 | 90.838 | −29.360 | 32.150 | 1.00 | 35.03 |
| 3503 | C | SER | A | 385 | 92.124 | −28.921 | 29.424 | 1.00 | 33.89 |
| 3504 | O | SER | A | 385 | 91.462 | −29.774 | 28.838 | 1.00 | 34.11 |
| 3505 | N | THR | A | 386 | 93.448 | −28.825 | 29.306 | 1.00 | 35.52 |
| 3506 | CA | THR | A | 386 | 94.239 | −29.758 | 28.508 | 1.00 | 34.85 |
| 3507 | CB | THR | A | 386 | 95.317 | −29.045 | 27.679 | 1.00 | 34.93 |
| 3508 | OG1 | THR | A | 386 | 94.700 | −28.100 | 26.794 | 1.00 | 34.77 |
| 3509 | CG2 | THR | A | 386 | 96.105 | −30.065 | 26.859 | 1.00 | 34.72 |
| 3510 | C | THR | A | 386 | 94.954 | −30.707 | 29.452 | 1.00 | 36.51 |
| 3511 | O | THR | A | 386 | 95.614 | −30.269 | 30.389 | 1.00 | 32.26 |
| 3512 | N | ARG | A | 387 | 94.826 | −32.006 | 29.196 | 1.00 | 39.85 |
| 3513 | CA | ARG | A | 387 | 95.450 | −33.026 | 30.030 | 1.00 | 42.82 |
| 3514 | CB | ARG | A | 387 | 94.413 | −34.068 | 30.419 | 1.00 | 40.59 |
| 3515 | CG | ARG | A | 387 | 94.906 | −35.091 | 31.423 | 1.00 | 40.19 |
| 3516 | CD | ARG | A | 387 | 93.973 | −36.286 | 31.439 | 1.00 | 39.93 |
| 3517 | NE | ARG | A | 387 | 94.582 | −37.437 | 32.096 | 1.00 | 42.46 |
| 3518 | CZ | ARG | A | 387 | 94.692 | −37.566 | 33.412 | 1.00 | 42.27 |
| 3519 | NH1 | ARG | A | 387 | 94.228 | −36.615 | 34.212 | 1.00 | 44.24 |
| 3520 | NH2 | ARG | A | 387 | 95.260 | −38.640 | 33.928 | 1.00 | 42.71 |
| 3521 | C | ARG | A | 387 | 96.601 | −33.682 | 29.278 | 1.00 | 46.40 |
| 3522 | O | ARG | A | 387 | 96.515 | −33.902 | 28.076 | 1.00 | 47.76 |
| 3523 | N | LYS | A | 388 | 97.666 | −34.023 | 29.994 | 1.00 | 52.21 |
| 3524 | CA | LYS | A | 388 | 98.841 | −34.592 | 29.347 | 1.00 | 58.52 |
| 3525 | CB | LYS | A | 388 | 99.749 | −33.426 | 28.946 | 1.00 | 61.02 |
| 3526 | CG | LYS | A | 388 | 100.701 | −33.675 | 27.799 | 1.00 | 61.88 |
| 3527 | CD | LYS | A | 388 | 101.401 | −32.377 | 27.396 | 1.00 | 66.02 |
| 3528 | CE | LYS | A | 388 | 102.762 | −32.623 | 26.806 | 1.00 | 68.59 |
| 3529 | NZ | LYS | A | 388 | 103.349 | −31.436 | 26.139 | 1.00 | 70.97 |
| 3530 | C | LYS | A | 388 | 99.616 | −35.597 | 30.211 | 1.00 | 59.76 |
| 3531 | O | LYS | A | 388 | 100.251 | −35.209 | 31.184 | 1.00 | 63.60 |
| 3532 | N | GLU | A | 389 | 99.564 | −36.882 | 29.857 | 1.00 | 61.11 |
| 3533 | CA | GLU | A | 389 | 100.294 | −37.918 | 30.598 | 1.00 | 64.16 |
| 3534 | CB | GLU | A | 389 | 99.428 | −39.184 | 30.789 | 1.00 | 69.67 |
| 3535 | CG | GLU | A | 389 | 98.163 | −39.017 | 31.642 | 1.00 | 77.17 |
| 3536 | CD | GLU | A | 389 | 97.337 | −40.304 | 31.769 | 1.00 | 80.62 |
| 3537 | OE1 | GLU | A | 389 | 97.772 | −41.363 | 31.286 | 1.00 | 82.01 |
| 3538 | OE2 | GLU | A | 389 | 96.244 | −40.262 | 32.360 | 1.00 | 82.68 |
| 3539 | C | GLU | A | 389 | 101.575 | −38.311 | 29.839 | 1.00 | 63.35 |
| 3540 | O | GLU | A | 389 | 101.565 | −38.415 | 28.612 | 1.00 | 61.33 |
| 3541 | N | GLU | A | 390 | 102.679 | −38.495 | 30.563 | 1.00 | 60.52 |
| 3542 | CA | GLU | A | 390 | 103.941 | −38.949 | 29.966 | 1.00 | 58.24 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3543 | CB | GLU | A | 390 | 104.853 | −37.812 | 29.464 | 1.00 | 59.58 |
| 3544 | CG | GLU | A | 390 | 106.227 | −38.313 | 28.901 | 1.00 | 70.26 |
| 3545 | CD | GLU | A | 390 | 107.181 | −37.172 | 28.560 | 1.00 | 76.61 |
| 3546 | OE1 | GLU | A | 390 | 106.856 | −36.019 | 28.909 | 1.00 | 80.89 |
| 3547 | OE2 | GLU | A | 390 | 108.252 | −37.421 | 27.956 | 1.00 | 81.29 |
| 3548 | C | GLU | A | 390 | 104.699 | −39.737 | 31.010 | 1.00 | 57.30 |
| 3549 | O | GLU | A | 390 | 105.255 | −39.180 | 31.960 | 1.00 | 50.15 |
| 3550 | N | LYS | A | 391 | 104.693 | −41.049 | 30.829 | 1.00 | 58.64 |
| 3551 | CA | LYS | A | 391 | 105.396 | −41.943 | 31.719 | 1.00 | 62.79 |
| 3552 | CB | LYS | A | 391 | 104.977 | −43.378 | 31.425 | 1.00 | 59.81 |
| 3553 | CG | LYS | A | 391 | 105.682 | −44.393 | 32.282 | 1.00 | 60.25 |
| 3554 | CD | LYS | A | 391 | 104.960 | −45.718 | 32.269 | 1.00 | 60.93 |
| 3555 | CE | LYS | A | 391 | 105.493 | −46.636 | 33.356 | 1.00 | 61.74 |
| 3556 | NZ | LYS | A | 391 | 104.668 | −47.872 | 33.487 | 1.00 | 62.33 |
| 3557 | C | LYS | A | 391 | 106.881 | −41.726 | 31.434 | 1.00 | 67.79 |
| 3558 | O | LYS | A | 391 | 107.306 | −41.778 | 30.281 | 1.00 | 67.96 |
| 3559 | N | GLN | A | 392 | 107.659 | −41.477 | 32.487 | 1.00 | 76.81 |
| 3560 | CA | GLN | A | 392 | 109.091 | −41.207 | 32.361 | 1.00 | 89.83 |
| 3561 | CB | GLN | A | 392 | 109.361 | −39.834 | 32.997 | 1.00 | 90.98 |
| 3562 | CG | GLN | A | 392 | 108.292 | −38.783 | 32.590 | 1.00 | 92.59 |
| 3563 | CD | GLN | A | 392 | 108.738 | −37.366 | 32.831 | 1.00 | 92.87 |
| 3564 | OE1 | GLN | A | 392 | 109.892 | −37.027 | 32.561 | 1.00 | 93.26 |
| 3565 | NE2 | GLN | A | 392 | 107.832 | −36.518 | 33.325 | 1.00 | 93.32 |
| 3566 | C | GLN | A | 392 | 110.025 | −42.320 | 32.912 | 1.00 | 101.51 |
| 3567 | O | GLN | A | 392 | 109.848 | −42.825 | 34.027 | 1.00 | 98.89 |
| 3568 | N | ARG | A | 393 | 111.002 | −42.691 | 32.078 | 1.00 | 113.96 |
| 3569 | CA | ARG | A | 393 | 111.996 | −43.750 | 32.318 | 1.00 | 118.05 |
| 3570 | CB | ARG | A | 393 | 113.089 | −43.661 | 31.264 | 1.00 | 124.32 |
| 3571 | CG | ARG | A | 393 | 112.782 | −42.599 | 30.242 | 1.00 | 150.76 |
| 3572 | CD | ARG | A | 393 | 113.925 | −42.391 | 29.299 | 1.00 | 161.71 |
| 3573 | NE | ARG | A | 393 | 113.442 | −42.241 | 27.934 | 1.00 | 163.76 |
| 3574 | CZ | ARG | A | 393 | 114.219 | −41.950 | 26.900 | 1.00 | 163.99 |
| 3575 | NH1 | ARG | A | 393 | 115.520 | −41.775 | 27.080 | 1.00 | 163.66 |
| 3576 | NH2 | ARG | A | 393 | 113.697 | −41.844 | 25.688 | 1.00 | 163.73 |
| 3577 | C | ARG | A | 393 | 112.610 | −43.652 | 33.679 | 1.00 | 116.47 |
| 3578 | O | ARG | A | 393 | 113.279 | −44.566 | 34.174 | 1.00 | 110.46 |
| 3579 | N | ASN | A | 394 | 112.385 | −42.510 | 34.282 | 1.00 | 109.95 |
| 3580 | CA | ASN | A | 394 | 112.889 | −42.311 | 35.597 | 1.00 | 101.77 |
| 3581 | CB | ASN | A | 394 | 113.201 | −40.847 | 35.819 | 1.00 | 110.99 |
| 3582 | CG | ASN | A | 394 | 113.942 | −40.630 | 37.095 | 1.00 | 123.78 |
| 3583 | OD1 | ASN | A | 394 | 113.871 | −39.565 | 37.697 | 1.00 | 131.21 |
| 3584 | ND2 | ASN | A | 394 | 114.674 | −41.654 | 37.525 | 1.00 | 131.83 |
| 3585 | C | ASN | A | 394 | 111.814 | −42.765 | 36.573 | 1.00 | 93.77 |
| 3586 | O | ASN | A | 394 | 111.465 | −42.021 | 37.485 | 1.00 | 90.03 |
| 3587 | N | GLY | A | 395 | 111.289 | −43.975 | 36.381 | 1.00 | 87.40 |
| 3588 | CA | GLY | A | 395 | 110.252 | −44.477 | 37.270 | 1.00 | 80.04 |
| 3589 | C | GLY | A | 395 | 109.415 | −43.330 | 37.802 | 1.00 | 77.91 |
| 3590 | O | GLY | A | 395 | 109.534 | −42.946 | 38.974 | 1.00 | 76.51 |
| 3591 | N | THR | A | 396 | 108.576 | −42.774 | 36.931 | 1.00 | 77.57 |
| 3592 | CA | THR | A | 396 | 107.730 | −41.641 | 37.287 | 1.00 | 74.43 |
| 3593 | CB | THR | A | 396 | 108.590 | −40.355 | 37.462 | 1.00 | 73.02 |
| 3594 | OG1 | THR | A | 396 | 109.574 | −40.562 | 38.482 | 1.00 | 72.00 |
| 3595 | CG2 | THR | A | 396 | 107.722 | −39.170 | 37.843 | 1.00 | 71.76 |
| 3596 | C | THR | A | 396 | 106.666 | −41.354 | 36.221 | 1.00 | 73.71 |
| 3597 | O | THR | A | 396 | 106.972 | −41.295 | 35.030 | 1.00 | 76.04 |
| 3598 | N | LEU | A | 397 | 105.416 | −41.196 | 36.656 | 1.00 | 72.32 |
| 3599 | CA | LEU | A | 397 | 104.311 | −40.855 | 35.760 | 1.00 | 71.81 |
| 3600 | CB | LEU | A | 397 | 103.066 | −41.701 | 36.025 | 1.00 | 69.66 |
| 3601 | CG | LEU | A | 397 | 101.834 | −41.130 | 35.314 | 1.00 | 66.42 |
| 3602 | CD1 | LEU | A | 397 | 102.125 | −41.007 | 33.826 | 1.00 | 63.10 |
| 3603 | CD2 | LEU | A | 397 | 100.625 | −42.008 | 35.554 | 1.00 | 61.67 |
| 3604 | C | LEU | A | 397 | 103.946 | −39.402 | 36.027 | 1.00 | 72.38 |
| 3605 | O | LEU | A | 397 | 103.584 | −39.049 | 37.145 | 1.00 | 76.17 |
| 3606 | N | THR | A | 398 | 104.025 | −38.564 | 35.004 | 1.00 | 72.68 |
| 3607 | CA | THR | A | 398 | 103.697 | −37.162 | 35.174 | 1.00 | 65.60 |
| 3608 | CB | THR | A | 398 | 104.826 | −36.264 | 34.649 | 1.00 | 65.00 |
| 3609 | OG1 | THR | A | 398 | 105.910 | −36.279 | 35.586 | 1.00 | 65.63 |
| 3610 | CG2 | THR | A | 398 | 104.337 | −34.830 | 34.460 | 1.00 | 66.38 |
| 3611 | C | THR | A | 398 | 102.402 | −36.811 | 34.475 | 1.00 | 60.62 |
| 3612 | O | THR | A | 398 | 102.188 | −37.154 | 33.310 | 1.00 | 60.18 |
| 3613 | N | VAL | A | 399 | 101.540 | −36.121 | 35.209 | 1.00 | 53.45 |
| 3614 | CA | VAL | A | 399 | 100.244 | −35.700 | 34.710 | 1.00 | 48.87 |
| 3615 | CB | VAL | A | 399 | 99.110 | −36.436 | 35.467 | 1.00 | 43.50 |
| 3616 | CG1 | VAL | A | 399 | 97.794 | −35.683 | 35.344 | 1.00 | 36.66 |
| 3617 | CG2 | VAL | A | 399 | 98.962 | −37.832 | 34.924 | 1.00 | 36.27 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3618 | C | VAL | A | 399 | 100.103 | −34.198 | 34.905 | 1.00 | 46.69 |
| 3619 | O | VAL | A | 399 | 100.419 | −33.668 | 35.970 | 1.00 | 50.98 |
| 3620 | N | THR | A | 400 | 99.654 | −33.507 | 33.868 | 1.00 | 46.03 |
| 3621 | CA | THR | A | 400 | 99.458 | −32.075 | 33.976 | 1.00 | 46.43 |
| 3622 | CB | THR | A | 400 | 100.572 | −31.269 | 33.267 | 1.00 | 44.77 |
| 3623 | OG1 | THR | A | 400 | 100.555 | −31.565 | 31.867 | 1.00 | 44.20 |
| 3624 | CG2 | THR | A | 400 | 101.925 | −31.591 | 33.841 | 1.00 | 40.62 |
| 3625 | C | THR | A | 400 | 98.137 | −31.693 | 33.331 | 1.00 | 44.15 |
| 3626 | O | THR | A | 400 | 97.709 | −32.319 | 32.365 | 1.00 | 44.98 |
| 3627 | N | SER | A | 401 | 97.479 | −30.686 | 33.893 | 1.00 | 40.80 |
| 3628 | CA | SER | A | 401 | 96.244 | −30.173 | 33.320 | 1.00 | 37.55 |
| 3629 | CB | SER | A | 401 | 95.016 | −30.528 | 34.160 | 1.00 | 38.62 |
| 3630 | OG | SER | A | 401 | 93.851 | −29.911 | 33.620 | 1.00 | 38.95 |
| 3631 | C | SER | A | 401 | 96.440 | −28.673 | 33.302 | 1.00 | 34.46 |
| 3632 | O | SER | A | 401 | 96.752 | −28.071 | 34.334 | 1.00 | 33.37 |
| 3633 | N | THR | A | 402 | 96.305 | −28.079 | 32.120 | 1.00 | 29.92 |
| 3634 | CA | THR | A | 402 | 96.466 | −26.641 | 31.981 | 1.00 | 26.73 |
| 3635 | CB | THR | A | 402 | 97.420 | −26.292 | 30.839 | 1.00 | 25.14 |
| 3636 | OG1 | THR | A | 402 | 98.690 | −26.890 | 31.107 | 1.00 | 27.30 |
| 3637 | CG2 | THR | A | 402 | 97.601 | −24.782 | 30.726 | 1.00 | 24.68 |
| 3638 | C | THR | A | 402 | 95.105 | −26.034 | 31.730 | 1.00 | 25.20 |
| 3639 | O | THR | A | 402 | 94.372 | −26.462 | 30.831 | 1.00 | 23.91 |
| 3640 | N | LEU | A | 403 | 94.776 | −25.036 | 32.545 | 1.00 | 23.33 |
| 3641 | CA | LEU | A | 403 | 93.486 | −24.369 | 32.476 | 1.00 | 21.50 |
| 3642 | CB | LEU | A | 403 | 92.794 | −24.439 | 33.838 | 1.00 | 20.24 |
| 3643 | CG | LEU | A | 403 | 91.463 | −23.690 | 33.968 | 1.00 | 20.98 |
| 3644 | CD1 | LEU | A | 403 | 90.382 | −24.482 | 33.237 | 1.00 | 14.91 |
| 3645 | CD2 | LEU | A | 403 | 91.093 | −23.505 | 35.445 | 1.00 | 16.01 |
| 3646 | C | LEU | A | 403 | 93.572 | −22.915 | 32.063 | 1.00 | 20.03 |
| 3647 | O | LEU | A | 403 | 94.243 | −22.113 | 32.714 | 1.00 | 19.98 |
| 3648 | N | PRO | A | 404 | 92.891 | −22.554 | 30.967 | 1.00 | 20.60 |
| 3649 | CD | PRO | A | 404 | 92.180 | −23.448 | 30.043 | 1.00 | 21.20 |
| 3650 | CA | PRO | A | 404 | 92.899 | −21.165 | 30.499 | 1.00 | 23.31 |
| 3651 | CB | PRO | A | 404 | 92.120 | −21.208 | 29.176 | 1.00 | 21.28 |
| 3652 | CG | PRO | A | 404 | 92.134 | −22.650 | 28.761 | 1.00 | 19.80 |
| 3653 | C | PRO | A | 404 | 92.131 | −20.394 | 31.564 | 1.00 | 26.52 |
| 3654 | O | PRO | A | 404 | 91.137 | −20.893 | 32.107 | 1.00 | 26.71 |
| 3655 | N | VAL | A | 405 | 92.565 | −19.180 | 31.856 | 1.00 | 30.20 |
| 3656 | CA | VAL | A | 405 | 91.913 | −18.385 | 32.879 | 1.00 | 32.38 |
| 3657 | CB | VAL | A | 405 | 92.845 | −18.272 | 34.108 | 1.00 | 39.35 |
| 3658 | CG1 | VAL | A | 405 | 92.652 | −16.947 | 34.815 | 1.00 | 45.71 |
| 3659 | CG2 | VAL | A | 405 | 92.582 | −19.440 | 35.055 | 1.00 | 45.35 |
| 3660 | C | VAL | A | 405 | 91.585 | −17.009 | 32.338 | 1.00 | 30.48 |
| 3661 | O | VAL | A | 405 | 92.262 | −16.513 | 31.440 | 1.00 | 28.54 |
| 3662 | N | GLY | A | 406 | 90.538 | −16.397 | 32.872 | 1.00 | 27.33 |
| 3663 | CA | GLY | A | 406 | 90.174 | −15.064 | 32.424 | 1.00 | 27.64 |
| 3664 | C | GLY | A | 406 | 91.199 | −14.060 | 32.920 | 1.00 | 28.54 |
| 3665 | O | GLY | A | 406 | 91.745 | −14.218 | 34.011 | 1.00 | 29.14 |
| 3666 | N | THR | A | 407 | 91.464 | −13.025 | 32.137 | 1.00 | 30.19 |
| 3667 | CA | THR | A | 407 | 92.445 | −12.034 | 32.539 | 1.00 | 32.63 |
| 3668 | CB | THR | A | 407 | 92.833 | −11.128 | 31.358 | 1.00 | 32.16 |
| 3669 | OG1 | THR | A | 407 | 93.382 | −11.938 | 30.305 | 1.00 | 31.09 |
| 3670 | CG2 | THR | A | 407 | 93.880 | −10.101 | 31.795 | 1.00 | 31.39 |
| 3671 | C | THR | A | 407 | 91.961 | −11.181 | 33.699 | 1.00 | 34.46 |
| 3672 | O | THR | A | A07 | 92.648 | −11.062 | 34.721 | 1.00 | 37.68 |
| 3673 | N | ALA | A | 408 | 90.779 | −10.592 | 33.554 | 1.00 | 36.44 |
| 3674 | CA | ALA | A | 408 | 90.233 | −9.762 | 34.621 | 1.00 | 36.85 |
| 3675 | CB | ALA | A | 408 | 88.920 | −9.114 | 34.177 | 1.00 | 38.72 |
| 3676 | C | ALA | A | 408 | 90.016 | −10.612 | 35.875 | 1.00 | 37.94 |
| 3677 | O | ALA | A | 408 | 90.435 | −10.224 | 36.971 | 1.00 | 39.77 |
| 3678 | N | ASP | A | 409 | 89.374 | −11.770 | 35.715 | 1.00 | 38.14 |
| 3679 | CA | ASP | A | 409 | 89.111 | −12.670 | 36.845 | 1.00 | 36.22 |
| 3680 | CB | ASP | A | 409 | 88.677 | −14.061 | 36.366 | 1.00 | 36.58 |
| 3681 | CG | ASP | A | 409 | 87.350 | −14.052 | 35.633 | 1.00 | 36.53 |
| 3682 | OD1 | ASP | A | 409 | 86.495 | −13.196 | 35.947 | 1.00 | 35.73 |
| 3683 | OD2 | ASP | A | 409 | 87.158 | −14.923 | 34.755 | 1.00 | 37.82 |
| 3684 | C | ASP | A | 409 | 90.352 | −12.851 | 37.704 | 1.00 | 35.46 |
| 3685 | O | ASP | A | 409 | 90.307 | −12.699 | 38.927 | 1.00 | 33.98 |
| 3686 | N | TRP | A | A10 | 91.459 | −13.188 | 37.048 | 1.00 | 32.62 |
| 3687 | CA | TRP | A | 410 | 92.708 | −13.416 | 37.745 | 1.00 | 32.51 |
| 3688 | CB | TRP | A | 410 | 93.747 | −14.018 | 36.807 | 1.00 | 30.04 |
| 3689 | CG | TRP | A | 410 | 95.003 | −14.226 | 37.538 | 1.00 | 28.69 |
| 3690 | CD2 | TRP | A | 410 | 95.385 | −15.404 | 38.264 | 1.00 | 27.38 |
| 3691 | CE2 | TRP | A | 410 | 96.601 | −15.112 | 38.930 | 1.00 | 25.36 |
| 3692 | CE3 | TRP | A | A10 | 94.795 | −16.660 | 38.455 | 1.00 | 24.51 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3693 | CD1 | TRP | A | 410 | 95.992 | −13.300 | 37.758 | 1.00 | 27.16 |
| 3694 | NE1 | TRP | A | 410 | 96.960 | −13.828 | 38.592 | 1.00 | 26.67 |
| 3695 | CZ2 | TRP | A | 410 | 97.264 | −16.044 | 39.722 | 1.00 | 24.64 |
| 3696 | CZ3 | TRP | A | 410 | 95.452 | −17.585 | 39.245 | 1.00 | 27.36 |
| 3697 | CH2 | TRP | A | 410 | 96.667 | −17.264 | 39.887 | 1.00 | 25.73 |
| 3698 | C | TRP | A | 410 | 93.294 | −12.168 | 38.397 | 1.00 | 35.22 |
| 3699 | O | TRP | A | 410 | 93.685 | −12.196 | 39.566 | 1.00 | 34.45 |
| 3700 | N | ILE | A | 411 | 93.382 | −11.087 | 37.633 | 1.00 | 37.81 |
| 3701 | CA | ILE | A | 411 | 93.912 | −9.842 | 38.153 | 1.00 | 39.97 |
| 3702 | CB | ILE | A | 411 | 94.055 | −8.812 | 37.012 | 1.00 | 41.23 |
| 3703 | CG2 | ILE | A | 411 | 94.220 | −7.408 | 37.565 | 1.00 | 40.25 |
| 3704 | CG1 | ILE | A | 411 | 95.248 | −9.208 | 36.133 | 1.00 | 40.35 |
| 3705 | CD1 | ILE | A | 411 | 95.660 | −8.160 | 35.149 | 1.00 | 43.84 |
| 3700 | C | ILE | A | 411 | 93.037 | −9.286 | 39.280 | 1.00 | 41.91 |
| 3707 | O | ILE | A | 411 | 93.534 | −8.641 | 40.203 | 1.00 | 42.53 |
| 3708 | N | GLU | A | 412 | 91.735 | −9.551 | 39.219 | 1.00 | 43.22 |
| 3709 | CA | GLU | A | 412 | 90.831 | −9.071 | 40.259 | 1.00 | 45.41 |
| 3710 | CB | GLU | A | 412 | 89.429 | −8.827 | 39.677 | 1.00 | 52.73 |
| 3711 | CG | GLU | A | 412 | 89.281 | −7.423 | 39.076 | 1.00 | 62.38 |
| 3712 | CD | GLU | A | 412 | 88.057 | −7.270 | 38.198 | 1.00 | 68.20 |
| 3713 | OE1 | GLU | A | 412 | 87.034 | −7.922 | 38.499 | 1.00 | 72.25 |
| 3714 | OE2 | GLU | A | 412 | 88.111 | −6.490 | 37.218 | 1.00 | 69.96 |
| 3715 | C | GLU | A | 412 | 90.771 | −9.976 | 41.501 | 1.00 | 42.18 |
| 3716 | O | GLU | A | 412 | 89.975 | −9.739 | 42.414 | 1.00 | 42.18 |
| 3717 | N | GLY | A | 413 | 91.601 | −11.016 | 41.531 | 1.00 | 39.24 |
| 3718 | CA | GLY | A | 413 | 91.651 | −11.866 | 42.707 | 1.00 | 33.20 |
| 3719 | C | GLY | A | 413 | 90.938 | −13.196 | 42.810 | 1.00 | 29.63 |
| 3720 | O | GLY | A | 413 | 90.835 | −13.735 | 43.916 | 1.00 | 29.29 |
| 3721 | N | GLU | A | 414 | 90.442 | −13.749 | 41.709 | 1.00 | 27.01 |
| 3722 | CA | GLU | A | 414 | 89.763 | −15.046 | 41.803 | 1.00 | 25.77 |
| 3723 | CB | GLU | A | 414 | 89.183 | −15.438 | 40.438 | 1.00 | 25.09 |
| 3724 | CG | GLU | A | 414 | 88.655 | −16.866 | 40.357 | 1.00 | 24.31 |
| 3725 | CD | GLU | A | 414 | 87.361 | −17.044 | 41.126 | 1.00 | 25.66 |
| 3726 | OE1 | GLU | A | 414 | 87.429 | −17.263 | 42.362 | 1.00 | 27.47 |
| 3727 | OE2 | GLU | A | 414 | 86.278 | −16.949 | 40.493 | 1.00 | 21.34 |
| 3728 | C | GLU | A | 414 | 90.785 | −16.108 | 42.238 | 1.00 | 24.54 |
| 3729 | O | GLU | A | 414 | 91.984 | −15.946 | 42.014 | 1.00 | 22.52 |
| 3730 | N | THR | A | 415 | 90.344 | −17.181 | 42.882 | 1.00 | 23.55 |
| 3731 | CA | THR | A | 415 | 91.319 | −18.216 | 43.220 | 1.00 | 23.87 |
| 3732 | CB | THR | A | 415 | 91.594 | −18.377 | 44.723 | 1.00 | 23.24 |
| 3733 | OG1 | THR | A | 415 | 91.135 | −19.624 | 45.234 | 1.00 | 24.98 |
| 3734 | CG2 | THR | A | 415 | 90.985 | −17.500 | 45.348 | 1.00 | 22.92 |
| 3735 | C | THR | A | 415 | 90.838 | −19.514 | 42.642 | 1.00 | 24.16 |
| 3736 | O | THR | A | 415 | 89.664 | −19.876 | 42.775 | 1.00 | 21.22 |
| 3737 | N | TYR | A | 416 | 91.759 | −20.199 | 41.962 | 1.00 | 23.86 |
| 3738 | CA | TYR | A | 416 | 91.452 | −21.454 | 41.290 | 1.00 | 27.35 |
| 3739 | CB | TYR | A | 416 | 92.056 | −21.452 | 39.876 | 1.00 | 23.15 |
| 3740 | CG | TYR | A | 416 | 91.586 | −20.289 | 39.021 | 1.00 | 19.79 |
| 3741 | CD1 | TYR | A | 416 | 92.006 | −18.993 | 39.297 | 1.00 | 18.62 |
| 3742 | CE1 | TYR | A | 416 | 91.520 | −17.910 | 38.581 | 1.00 | 20.19 |
| 3743 | CD2 | TYR | A | 416 | 90.664 | −20.475 | 37.988 | 1.00 | 18.25 |
| 3744 | CE2 | TYR | A | 416 | 90.167 | −19.397 | 37.263 | 1.00 | 16.93 |
| 3745 | CZ | TYR | A | 416 | 90.600 | −18.113 | 37.566 | 1.00 | 18.03 |
| 3746 | OH | TYR | A | 416 | 90.120 | −17.015 | 36.877 | 1.00 | 19.55 |
| 3747 | C | TYR | A | 416 | 91.902 | −22.686 | 42.061 | 1.00 | 35.51 |
| 3748 | O | TYR | A | 416 | 92.889 | −22.656 | 42.800 | 1.00 | 30.14 |
| 3749 | N | GLN | A | 417 | 91.171 | −23.773 | 41.862 | 1.00 | 47.68 |
| 3750 | CA | GLN | A | 417 | 91.443 | −25.017 | 42.552 | 1.00 | 58.22 |
| 3751 | CB | GLN | A | 417 | 90.326 | −25.288 | 43.548 | 1.00 | 79.09 |
| 3752 | CG | GLN | A | 417 | 90.684 | −25.101 | 44.993 | 1.00 | 127.13 |
| 3753 | CD | GLN | A | 417 | 89.572 | −25.563 | 45.900 | 1.00 | 150.91 |
| 3754 | OE1 | GLN | A | 417 | 88.517 | −25.953 | 45.432 | 1.00 | 163.75 |
| 3755 | NE2 | GLN | A | 417 | 89.796 | −25.524 | 47.198 | 1.00 | 163.50 |
| 3756 | C | GLN | A | 417 | 91.602 | −26.247 | 41.672 | 1.00 | 52.42 |
| 3757 | O | GLN | A | 417 | 90.889 | −26.439 | 40.685 | 1.00 | 46.61 |
| 3758 | N | CYS | A | 418 | 92.535 | −27.099 | 42.066 | 1.00 | 45.91 |
| 3759 | CA | CYS | A | 418 | 92.796 | −28.328 | 41.346 | 1.00 | 40.74 |
| 3760 | C | CYS | A | 418 | 92.628 | −29.477 | 42.314 | 1.00 | 40.93 |
| 3761 | O | CYS | A | 418 | 93.370 | −29.587 | 43.290 | 1.00 | 39.00 |
| 3762 | CB | CYS | A | 418 | 94.219 | −28.356 | 40.803 | 1.00 | 38.40 |
| 3763 | SG | CYS | A | 418 | 94.652 | −29.963 | 40.054 | 1.00 | 40.69 |
| 3764 | N | ARG | A | 419 | 91.650 | −30.329 | 42.059 | 1.00 | 43.45 |
| 3765 | CA | ARG | A | 419 | 91.448 | −31.463 | 42.931 | 1.00 | 47.83 |
| 3766 | CB | ARG | A | 419 | 89.974 | −31.576 | 43.303 | 1.00 | 55.04 |
| 3767 | CG | ARG | A | 419 | 89.662 | −32.721 | 44.215 | 1.00 | 68.47 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3768 | CD | ARG | A | 419 | 88.540 | −32.357 | 45.160 | 1.00 | 80.91 |
| 3769 | NE | ARG | A | 419 | 88.236 | −33.456 | 46.064 | 1.00 | 89.83 |
| 3770 | CZ | ARG | A | 419 | 87.382 | −34.426 | 45.781 | 1.00 | 93.76 |
| 3771 | NH1 | ARG | A | 419 | 86.748 | −34.416 | 44.622 | 1.00 | 96.06 |
| 3772 | NH2 | ARG | A | 419 | 87.179 | −35.409 | 46.645 | 1.00 | 95.55 |
| 3773 | C | ARG | A | 419 | 91.943 | −32.737 | 42.250 | 1.00 | 44.35 |
| 3774 | O | ARG | A | 419 | 91.423 | −33.140 | 41.213 | 1.00 | 43.28 |
| 3775 | N | VAL | A | 420 | 92.970 | −33.348 | 42.839 | 1.00 | 42.65 |
| 3776 | CA | VAL | A | 420 | 93.565 | −34.581 | 42.325 | 1.00 | 45.33 |
| 3777 | CB | VAL | A | 420 | 95.091 | −34.580 | 42.534 | 1.00 | 41.87 |
| 3778 | CG1 | VAL | A | 420 | 95.706 | −35.804 | 41.889 | 1.00 | 36.30 |
| 3779 | CG2 | VAL | A | 420 | 95.693 | −33.312 | 41.958 | 1.00 | 35.13 |
| 3780 | C | VAL | A | 420 | 92.978 | −35.797 | 43.048 | 1.00 | 51.69 |
| 3781 | O | VAL | A | 420 | 93.243 | −36.018 | 44.229 | 1.00 | 51.34 |
| 3782 | N | THR | A | 421 | 92.186 | −36.579 | 42.324 | 1.00 | 60.99 |
| 3783 | CA | THR | A | 421 | 91.530 | −37.782 | 42.844 | 1.00 | 66.96 |
| 3784 | CB | THR | A | 421 | 90.112 | −37.915 | 42.245 | 1.00 | 67.73 |
| 3785 | OG1 | THR | A | 421 | 89.303 | −36.801 | 42.638 | 1.00 | 72.00 |
| 3786 | CG2 | THR | A | 421 | 89.469 | −39.213 | 42.675 | 1.00 | 70.71 |
| 3787 | C | THR | A | 421 | 92.292 | −39.030 | 42.386 | 1.00 | 73.08 |
| 3788 | O | THR | A | 421 | 92.531 | −39.170 | 41.195 | 1.00 | 70.35 |
| 3789 | N | HIS | A | 422 | 92.690 | −39.943 | 43.268 | 1.00 | 79.51 |
| 3790 | CA | HIS | A | 422 | 93.348 | −41.133 | 42.716 | 1.00 | 88.36 |
| 3791 | CB | HIS | A | 422 | 94.870 | −41.106 | 42.914 | 1.00 | 102.17 |
| 3792 | CG | HIS | A | 422 | 95.315 | −40.806 | 44.314 | 1.00 | 114.88 |
| 3793 | CD2 | HIS | A | 422 | 95.803 | −41.616 | 45.277 | 1.00 | 120.21 |
| 3794 | ND1 | HIS | A | 422 | 95.333 | −39.529 | 44.825 | 1.00 | 120.39 |
| 3795 | CE1 | HIS | A | 422 | 95.823 | −39.565 | 46.056 | 1.00 | 124.22 |
| 3796 | NE2 | HIS | A | 422 | 96.115 | −40.812 | 46.354 | 1.00 | 124.04 |
| 3797 | C | HIS | A | 422 | 92.760 | −42.477 | 43.152 | 1.00 | 88.70 |
| 3798 | O | HIS | A | 422 | 92.118 | −42.582 | 44.186 | 1.00 | 90.24 |
| 3799 | N | PRO | A | 423 | 92.966 | −43.531 | 42.347 | 1.00 | 93.22 |
| 3800 | CD | PRO | A | 423 | 93.891 | −43.556 | 41.195 | 1.00 | 89.39 |
| 3801 | CA | PRO | A | 423 | 92.438 | −44.869 | 42.644 | 1.00 | 96.44 |
| 3802 | CB | PRO | A | 423 | 92.901 | −45.704 | 41.448 | 1.00 | 92.04 |
| 3803 | CG | PRO | A | 423 | 94.160 | −45.024 | 41.003 | 1.00 | 87.57 |
| 3804 | C | PRO | A | 423 | 92.851 | −45.494 | 43.973 | 1.00 | 103.36 |
| 3805 | O | PRO | A | 423 | 92.047 | −46.150 | 44.637 | 1.00 | 104.46 |
| 3806 | N | HIS | A | 424 | 94.100 | −45.272 | 44.357 | 1.00 | 112.06 |
| 3807 | CA | HIS | A | 424 | 94.641 | −45.844 | 45.577 | 1.00 | 121.58 |
| 3808 | CB | HIS | A | 424 | 96.072 | −46.285 | 45.290 | 1.00 | 135.25 |
| 3809 | CG | HIS | A | 424 | 96.186 | −47.159 | 44.069 | 1.00 | 151.70 |
| 3810 | CD2 | HIS | A | 424 | 96.835 | −46.968 | 42.899 | 1.00 | 158.10 |
| 3811 | ND1 | HIS | A | 424 | 95.550 | −48.376 | 43.964 | 1.00 | 158.23 |
| 3812 | CE1 | HIS | A | 424 | 95.804 | −48.901 | 42.775 | 1.00 | 161.34 |
| 3813 | NE2 | HIS | A | 424 | 96.579 | −48.069 | 42.110 | 1.00 | 161.31 |
| 3814 | C | HIS | A | 424 | 94.535 | −44.882 | 46.770 | 1.00 | 122.23 |
| 3815 | O | HIS | A | 424 | 95.140 | −45.070 | 47.825 | 1.00 | 120.55 |
| 3816 | N | LEU | A | 425 | 93.714 | −43.863 | 46.546 | 1.00 | 125.12 |
| 3817 | CA | LEU | A | 425 | 93.312 | −42.771 | 47.447 | 1.00 | 120.26 |
| 3818 | CB | LEU | A | 425 | 91.929 | −42.304 | 47.009 | 1.00 | 117.34 |
| 3819 | CG | LEU | A | 425 | 91.626 | −41.121 | 46.118 | 1.00 | 116.36 |
| 3820 | CD1 | LEU | A | 425 | 90.133 | −40.807 | 46.185 | 1.00 | 116.90 |
| 3821 | CD2 | LEU | A | 425 | 92.445 | −39.959 | 46.564 | 1.00 | 117.34 |
| 3822 | C | LEU | A | 425 | 93.147 | −42.900 | 48.963 | 1.00 | 115.58 |
| 3823 | O | LEU | A | 425 | 92.367 | −43.738 | 49.398 | 1.00 | 119.39 |
| 3824 | N | PRO | A | 426 | 93.844 | −42.080 | 49.791 | 1.00 | 125.99 |
| 3825 | CD | PRO | A | 426 | 95.062 | −41.277 | 49.543 | 1.00 | 124.32 |
| 3826 | CA | PRO | A | 426 | 93.583 | −42.219 | 51.234 | 1.00 | 124.79 |
| 3827 | CB | PRO | A | 426 | 94.906 | −41.827 | 51.896 | 1.00 | 128.20 |
| 3828 | CG | PRO | A | 426 | 95.501 | −40.843 | 50.950 | 1.00 | 125.68 |
| 3829 | C | PRO | A | 426 | 92.539 | −41.100 | 51.356 | 1.00 | 123.53 |
| 3830 | O | PRO | A | 426 | 91.388 | −41.299 | 51.764 | 1.00 | 133.84 |
| 3831 | N | ALA | A | 427 | 93.000 | −39.925 | 50.925 | 1.00 | 126.71 |
| 3832 | CA | ALA | A | 427 | 92.264 | −38.664 | 50.841 | 1.00 | 120.26 |
| 3833 | CB | ALA | A | 427 | 92.808 | −37.656 | 51.848 | 1.00 | 114.78 |
| 3834 | C | ALA | A | 427 | 92.557 | −38.181 | 49.416 | 1.00 | 113.87 |
| 3835 | O | ALA | A | 427 | 93.230 | −38.876 | 48.662 | 1.00 | 116.17 |
| 3836 | N | ALA | A | 428 | 92.084 | −36.996 | 49.046 | 1.00 | 102.29 |
| 3837 | CA | ALA | A | 428 | 92.336 | −36.488 | 47.701 | 1.00 | 95.16 |
| 3838 | CB | ALA | A | 428 | 91.030 | −36.419 | 46.917 | 1.00 | 101.08 |
| 3839 | C | ALA | A | 428 | 93.016 | −35.121 | 47.734 | 1.00 | 90.79 |
| 3840 | O | ALA | A | 428 | 92.457 | −34.156 | 48.246 | 1.00 | 92.80 |
| 3841 | N | LEU | A | 429 | 94.222 | −35.057 | 47.173 | 1.00 | 81.65 |
| 3842 | CA | LEU | A | 429 | 95.031 | −33.841 | 47.129 | 1.00 | 68.49 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3843 | CB | LEU | A | 429 | 96.318 | −34.113 | 46.347 | 1.00 | 65.89 |
| 3844 | CG | LEU | A | 429 | 97.182 | −35.298 | 46.779 | 1.00 | 62.55 |
| 3845 | CD1 | LEU | A | 429 | 98.188 | −35.631 | 45.689 | 1.00 | 62.36 |
| 3846 | CD2 | LEU | A | 429 | 97.886 | −34.965 | 48.075 | 1.00 | 63.43 |
| 3847 | C | LEU | A | 429 | 94.336 | −32.619 | 46.522 | 1.00 | 62.11 |
| 3848 | O | LEU | A | 429 | 93.739 | −32.697 | 45.449 | 1.00 | 55.67 |
| 3849 | N | MET | A | 430 | 94.438 | −31.482 | 47.203 | 1.00 | 54.12 |
| 3850 | CA | MET | A | 430 | 93.834 | −30.249 | 46.713 | 1.00 | 51.64 |
| 3851 | CB | MET | A | 430 | 92.612 | −29.862 | 47.546 | 1.00 | 59.39 |
| 3852 | CG | MET | A | 430 | 91.661 | −30.984 | 47.786 | 1.00 | 70.87 |
| 3853 | SD | MET | A | 430 | 90.010 | −30.459 | 48.267 | 1.00 | 78.57 |
| 3854 | CE | MET | A | 430 | 90.214 | −30.149 | 49.959 | 1.00 | 85.50 |
| 3855 | C | MET | A | 430 | 94.836 | −29.118 | 46.769 | 1.00 | 46.92 |
| 3856 | O | MET | A | 430 | 95.463 | −28.889 | 47.799 | 1.00 | 45.12 |
| 3857 | N | ARG | A | 431 | 94.990 | −28.423 | 45.650 | 1.00 | 43.19 |
| 3858 | CA | ARG | A | 431 | 95.900 | −27.287 | 45.564 | 1.00 | 39.13 |
| 3859 | CB | ARG | A | 431 | 97.055 | −27.574 | 44.598 | 1.00 | 41.41 |
| 3860 | CG | ARG | A | 431 | 97.884 | −28.784 | 44.961 | 1.00 | 47.48 |
| 3861 | CD | ARG | A | 431 | 98.618 | −28.571 | 46.258 | 1.00 | 54.97 |
| 3862 | NE | ARG | A | 431 | 99.125 | −29.832 | 46.780 | 1.00 | 61.39 |
| 3863 | CZ | ARG | A | 431 | 99.820 | −29.947 | 47.905 | 1.00 | 65.79 |
| 3864 | NH1 | ARG | A | 431 | 100.098 | −28.871 | 48.637 | 1.00 | 68.19 |
| 3865 | NH2 | ARG | A | 431 | 100.231 | −31.143 | 48.299 | 1.00 | 68.04 |
| 3866 | C | ARG | A | 431 | 95.094 | −26.119 | 45.034 | 1.00 | 34.68 |
| 3867 | O | ARG | A | 431 | 94.107 | −26.309 | 44.320 | 1.00 | 32.43 |
| 3868 | N | SER | A | 432 | 95.509 | −24.907 | 45.370 | 1.00 | 30.81 |
| 3869 | CA | SER | A | 432 | 94.780 | −23.743 | 44.888 | 1.00 | 31.47 |
| 3870 | CB | SER | A | 432 | 93.739 | −23.304 | 45.923 | 1.00 | 27.79 |
| 3871 | OG | SER | A | 432 | 94.363 | −22.983 | 47.154 | 1.00 | 25.97 |
| 3872 | C | SER | A | 432 | 95.757 | −22.616 | 44.604 | 1.00 | 29.84 |
| 3873 | O | SER | A | 432 | 96.873 | −22.604 | 45.121 | 1.00 | 31.64 |
| 3874 | N | THR | A | 433 | 95.350 | −21.675 | 43.767 | 1.00 | 29.47 |
| 3875 | CA | THR | A | 433 | 96.232 | −20.561 | 43.452 | 1.00 | 30.38 |
| 3876 | CB | THR | A | 433 | 97.069 | −20.846 | 42.187 | 1.00 | 29.29 |
| 3877 | OG1 | THR | A | 433 | 97.874 | −19.708 | 41.892 | 1.00 | 27.04 |
| 3878 | CG2 | THR | A | 433 | 96.166 | −21.142 | 40.997 | 1.00 | 31.54 |
| 3879 | C | THR | A | 433 | 95.452 | −19.275 | 43.252 | 1.00 | 31.27 |
| 3880 | O | THR | A | 433 | 94.293 | −19.294 | 42.836 | 1.00 | 28.74 |
| 3881 | N | THR | A | 434 | 96.098 | −18.160 | 43.561 | 1.00 | 30.38 |
| 3882 | CA | THR | A | 434 | 95.484 | −16.854 | 43.423 | 1.00 | 33.18 |
| 3883 | CB | THR | A | 434 | 94.636 | −16.547 | 44.680 | 1.00 | 31.02 |
| 3884 | OG1 | THR | A | 434 | 93.769 | −15.441 | 44.421 | 1.00 | 32.31 |
| 3885 | CG2 | THR | A | 434 | 95.523 | −16.230 | 45.868 | 1.00 | 28.85 |
| 3886 | C | THR | A | 434 | 96.665 | −15.892 | 43.261 | 1.00 | 38.61 |
| 3887 | O | THR | A | 434 | 97.799 | −16.314 | 43.399 | 1.00 | 35.76 |
| 3888 | N | LYS | A | 435 | 96.420 | −14.619 | 42.979 | 1.00 | 46.15 |
| 3889 | CA | LYS | A | 435 | 97.485 | −13.624 | 42.761 | 1.00 | 53.65 |
| 3890 | CB | LYS | A | 435 | 96.807 | −12.350 | 42.243 | 1.00 | 47.28 |
| 3891 | CG | LYS | A | 435 | 97.692 | −11.178 | 41.863 | 1.00 | 54.25 |
| 3892 | CD | LYS | A | 435 | 96.825 | −9.911 | 41.803 | 1.00 | 50.14 |
| 3893 | CE | LYS | A | 435 | 97.498 | −5.768 | 41.053 | 1.00 | 46.10 |
| 3894 | NZ | LYS | A | 435 | 96.558 | −7.626 | 40.830 | 1.00 | 44.92 |
| 3895 | C | LYS | A | 435 | 98.404 | −13.291 | 43.964 | 1.00 | 61.52 |
| 3896 | O | LYS | A | 435 | 97.912 | −12.996 | 45.049 | 1.00 | 62.52 |
| 3897 | N | THR | A | 436 | 99.728 | −13.330 | 43.764 | 1.00 | 72.25 |
| 3898 | CA | THR | A | 436 | 100.708 | −13.015 | 44.824 | 1.00 | 75.90 |
| 3899 | CB | THR | A | 436 | 102.171 | −13.085 | 44.300 | 1.00 | 77.88 |
| 3900 | OG1 | THR | A | 436 | 102.606 | −14.448 | 44.241 | 1.00 | 83.46 |
| 3901 | CG2 | THR | A | 436 | 103.109 | −12.288 | 45.207 | 1.00 | 83.30 |
| 3902 | C | THR | A | 436 | 100.515 | −11.601 | 45.366 | 1.00 | 74.11 |
| 3903 | O | THR | A | 436 | 100.496 | −10.647 | 44.595 | 1.00 | 82.01 |
| 3904 | N | SER | A | 437 | 100.395 | −11.453 | 46.682 | 1.00 | 76.27 |
| 3905 | CA | SER | A | 437 | 100.229 | −10.119 | 47.249 | 1.00 | 82.72 |
| 3906 | CB | SER | A | 437 | 99.131 | −10.110 | 48.318 | 1.00 | 91.34 |
| 3907 | OG | SER | A | 437 | 99.519 | −10.837 | 49.469 | 1.00 | 93.57 |
| 3908 | C | SER | A | 437 | 101.547 | −9.635 | 47.846 | 1.00 | 79.92 |
| 3909 | O | SER | A | 437 | 102.583 | −10.284 | 47.695 | 1.00 | 79.50 |
| 3910 | N | GLY | A | 438 | 101.513 | −8.498 | 48.527 | 1.00 | 76.82 |
| 3911 | CA | GLY | A | 438 | 102.736 | −7.979 | 49.101 | 1.00 | 70.30 |
| 3912 | C | GLY | A | 438 | 103.188 | −6.807 | 48.264 | 1.00 | 63.47 |
| 3913 | O | GLY | A | 438 | 102.518 | −6.456 | 47.298 | 1.00 | 56.57 |
| 3914 | N | PRO | A | 439 | 104.327 | −6.188 | 48.593 | 1.00 | 59.22 |
| 3915 | CD | PRO | A | 439 | 105.228 | −6.537 | 49.701 | 1.00 | 53.63 |
| 3916 | CA | PRO | A | 439 | 104.839 | −5.037 | 47.843 | 1.00 | 53.88 |
| 3917 | CB | PRO | A | 439 | 106.024 | −4.564 | 48.688 | 1.00 | 53.50 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3918 | CG | PRO | A | 439 | 105.811 | −5.207 | 50.039 | 1.00 | 56.80 |
| 3919 | C | PRO | A | 439 | 105.263 | −5.380 | 46.420 | 1.00 | 54.45 |
| 3920 | O | PRO | A | 439 | 105.489 | −6.546 | 46.092 | 1.00 | 50.57 |
| 3921 | N | ARG | A | 440 | 105.358 | −4.351 | 45.584 | 1.00 | 54.00 |
| 3922 | CA | ARG | A | 440 | 105.770 | −4.503 | 44.195 | 1.00 | 51.48 |
| 3923 | CB | ARG | A | 440 | 104.716 | −3.932 | 43.238 | 1.00 | 57.70 |
| 3924 | CG | ARG | A | 440 | 103.289 | −4.255 | 43.587 | 1.00 | 74.37 |
| 3925 | CD | ARG | A | 440 | 102.943 | −5.677 | 43.247 | 1.00 | 83.89 |
| 3926 | NE | ARG | A | 440 | 101.662 | −6.031 | 43.839 | 1.00 | 91.01 |
| 3927 | CZ | ARG | A | 440 | 101.066 | −7.211 | 43.707 | 1.00 | 93.88 |
| 3928 | NH1 | ARG | A | 440 | 101.628 | −8.174 | 42.993 | 1.00 | 95.21 |
| 3929 | NH2 | ARG | A | 440 | 99.905 | −7.429 | 44.306 | 1.00 | 96.24 |
| 3930 | C | ARG | A | 440 | 107.041 | −3.687 | 44.025 | 1.00 | 47.53 |
| 3931 | O | ARG | A | 440 | 107.215 | −2.658 | 44.671 | 1.00 | 45.93 |
| 3932 | N | ALA | A | 441 | 107.935 | −4.150 | 43.165 | 1.00 | 41.73 |
| 3933 | CA | ALA | A | 441 | 109.158 | −3.417 | 42.883 | 1.00 | 35.62 |
| 3934 | CB | ALA | A | 441 | 110.230 | −3.729 | 43.917 | 1.00 | 30.92 |
| 3935 | C | ALA | A | 441 | 109.595 | −3.856 | 41.505 | 1.00 | 34.08 |
| 3936 | O | ALA | A | 441 | 109.795 | −5.042 | 41.275 | 1.00 | 31.34 |
| 3937 | N | ALA | A | 442 | 109.711 | −2.903 | 40.586 | 1.00 | 34.44 |
| 3938 | CA | ALA | A | 442 | 110.111 | −3.196 | 39.217 | 1.00 | 35.18 |
| 3939 | CB | ALA | A | 442 | 110.174 | −1.907 | 38.399 | 1.00 | 36.60 |
| 3940 | C | ALA | A | 442 | 111.465 | −3.885 | 39.203 | 1.00 | 32.89 |
| 3941 | O | ALA | A | 442 | 112.265 | −3.727 | 40.126 | 1.00 | 35.22 |
| 3942 | N | PRO | A | 443 | 111.739 | −4.666 | 38.150 | 1.00 | 34.30 |
| 3943 | CD | PRO | A | 443 | 110.864 | −5.031 | 37.020 | 1.00 | 30.66 |
| 3944 | CA | PRO | A | 443 | 113.027 | −5.355 | 38.076 | 1.00 | 31.89 |
| 3945 | CB | PRO | A | 443 | 112.698 | −6.607 | 37.265 | 1.00 | 29.90 |
| 3946 | CG | PRO | A | 443 | 111.668 | −6.121 | 36.289 | 1.00 | 28.34 |
| 3947 | C | PRO | A | 443 | 114.078 | −4.490 | 37.389 | 1.00 | 31.60 |
| 3948 | O | PRO | A | 443 | 113.744 | −3.696 | 36.517 | 1.00 | 31.46 |
| 3949 | N | GLU | A | 444 | 115.334 | −4.632 | 37.807 | 1.00 | 33.83 |
| 3950 | CA | GLU | A | 444 | 116.456 | −3.933 | 37.185 | 1.00 | 31.93 |
| 3951 | CB | GLU | A | 444 | 117.553 | −3.642 | 38.216 | 1.00 | 32.25 |
| 3952 | CG | GLU | A | 444 | 117.106 | −2.809 | 39.422 | 1.00 | 38.66 |
| 3953 | CD | GLU | A | 444 | 118.121 | −2.800 | 40.575 | 1.00 | 42.28 |
| 3954 | OE1 | GLU | A | 444 | 119.203 | −3.427 | 40.457 | 1.00 | 41.55 |
| 3955 | OE2 | GLU | A | 444 | 117.824 | −2.162 | 41.610 | 1.00 | 43.89 |
| 3956 | C | GLU | A | 444 | 116.956 | −5.004 | 36.209 | 1.00 | 31.24 |
| 3957 | O | GLU | A | 444 | 117.009 | −6.179 | 36.584 | 1.00 | 28.20 |
| 3958 | N | VAL | A | 445 | 117.298 | −4.627 | 34.974 | 1.00 | 29.56 |
| 3959 | CA | VAL | A | 445 | 117.786 | −5.592 | 33.979 | 1.00 | 27.71 |
| 3960 | CB | VAL | A | 445 | 116.851 | −5.667 | 32.746 | 1.00 | 27.04 |
| 3961 | CG1 | VAL | A | 445 | 117.399 | −6.665 | 31.725 | 1.00 | 23.46 |
| 3962 | CG2 | VAL | A | 445 | 115.463 | −6.066 | 33.171 | 1.00 | 26.61 |
| 3963 | C | VAL | A | 445 | 119.189 | −5.254 | 33.469 | 1.00 | 27.03 |
| 3964 | O | VAL | A | 445 | 119.460 | −4.119 | 33.070 | 1.00 | 31.96 |
| 3965 | N | TYR | A | 446 | 120.078 | −6.243 | 33.459 | 1.00 | 26.48 |
| 3966 | CA | TYR | A | 446 | 121.440 | −6.023 | 32.973 | 1.00 | 31.80 |
| 3967 | CB | TYR | A | 446 | 122.422 | −5.929 | 34.141 | 1.00 | 42.29 |
| 3968 | CG | TYR | A | 446 | 122.063 | −4.883 | 35.168 | 1.00 | 46.44 |
| 3969 | CD1 | TYR | A | 446 | 121.288 | −5.209 | 36.283 | 1.00 | 50.07 |
| 3970 | CE1 | TYR | A | 446 | 120.972 | −4.251 | 37.243 | 1.00 | 56.15 |
| 3971 | CD2 | TYR | A | 446 | 122.506 | −3.568 | 35.036 | 1.00 | 48.26 |
| 3972 | CE2 | TYR | A | 446 | 122.191 | −2.607 | 35.986 | 1.00 | 55.91 |
| 3973 | CZ | TYR | A | 446 | 121.426 | −2.959 | 37.085 | 1.00 | 57.45 |
| 3974 | OH | TYR | A | 446 | 121.118 | −2.024 | 38.037 | 1.00 | 62.17 |
| 3975 | C | TYR | A | 446 | 121.864 | −7.167 | 32.057 | 1.00 | 27.55 |
| 3976 | O | TYR | A | 446 | 121.659 | −8.334 | 32.388 | 1.00 | 29.92 |
| 3977 | N | ALA | A | 447 | 122.457 | −6.842 | 30.914 | 1.00 | 22.57 |
| 3978 | CA | ALA | A | 447 | 122.889 | −7.875 | 29.998 | 1.00 | 24.58 |
| 3979 | CB | ALA | A | 447 | 122.028 | −7.847 | 28.739 | 1.00 | 23.36 |
| 3980 | C | ALA | A | 447 | 124.358 | −7.705 | 29.636 | 1.00 | 23.08 |
| 3981 | O | ALA | A | 447 | 124.854 | −6.588 | 29.559 | 1.00 | 23.03 |
| 3982 | N | PHE | A | 448 | 125.058 | −8.813 | 29.422 | 1.00 | 22.41 |
| 3983 | CA | PHE | A | 448 | 126.465 | −8.733 | 29.061 | 1.00 | 24.13 |
| 3984 | CB | PHE | A | 448 | 127.406 | −8.903 | 30.272 | 1.00 | 26.47 |
| 3985 | CG | PHE | A | 448 | 126.795 | −8.585 | 31.602 | 1.00 | 31.09 |
| 3986 | CD1 | PHE | A | 448 | 126.023 | −9.528 | 32.266 | 1.00 | 34.64 |
| 3987 | CD2 | PHE | A | 448 | 127.036 | −7.358 | 32.221 | 1.00 | 34.72 |
| 3988 | CE1 | PHE | A | 448 | 125.494 | −9.254 | 33.533 | 1.00 | 36.09 |
| 3989 | CE2 | PHE | A | 446 | 126.510 | −7.076 | 33.487 | 1.00 | 36.23 |
| 3990 | CZ | PHE | A | 448 | 125.744 | −8.022 | 34.142 | 1.00 | 35.55 |
| 3991 | C | PHE | A | 448 | 126.830 | −9.815 | 28.069 | 1.00 | 23.72 |
| 3992 | O | PHE | A | 448 | 126.098 | −10.802 | 27.889 | 1.00 | 24.78 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 3993 | N | ALA | A | 449 | 127.985 | −9.638 | 27.442 | 1.00 | 19.96 |
| 3994 | CA | ALA | A | 449 | 128.476 | −10.613 | 26.491 | 1.00 | 23.49 |
| 3995 | CB | ALA | A | 449 | 128.583 | −10.002 | 25.100 | 1.00 | 20.45 |
| 3996 | C | ALA | A | 449 | 129.852 | −11.039 | 26.981 | 1.00 | 26.07 |
| 3997 | O | ALA | A | 449 | 130.652 | −10.212 | 27.397 | 1.00 | 22.86 |
| 3998 | N | THR | A | 450 | 130.131 | −12.330 | 26.949 | 1.00 | 24.00 |
| 3999 | CA | THR | A | 450 | 131.437 | −12.784 | 27.389 | 1.00 | 29.14 |
| 4000 | CB | THR | A | 450 | 131.449 | −14.289 | 27.663 | 1.00 | 29.37 |
| 4001 | OG1 | THR | A | 450 | 131.001 | −14.972 | 26.485 | 1.00 | 26.86 |
| 4002 | CG2 | THR | A | 450 | 130.559 | −14.629 | 28.850 | 1.00 | 28.35 |
| 4003 | C | THR | A | 450 | 132.427 | −12.536 | 26.264 | 1.00 | 32.67 |
| 4004 | O | THR | A | 450 | 132.038 | −12.491 | 25.092 | 1.00 | 26.53 |
| 4005 | N | PRO | A | 451 | 133.713 | −12.330 | 26.605 | 1.00 | 31.71 |
| 4006 | CD | PRO | A | 451 | 134.352 | −12.186 | 27.929 | 1.00 | 34.06 |
| 4007 | CA | PRO | A | 451 | 134.667 | −12.119 | 25.517 | 1.00 | 38.08 |
| 4008 | CB | PRO | A | 451 | 135.853 | −11.442 | 26.200 | 1.00 | 36.59 |
| 4009 | CG | PRO | A | 451 | 135.823 | −11.974 | 27.589 | 1.00 | 36.13 |
| 4010 | C | PRO | A | 451 | 134.991 | −13.521 | 25.002 | 1.00 | 45.77 |
| 4011 | O | PRO | A | 451 | 134.717 | −14.505 | 25.687 | 1.00 | 44.10 |
| 4012 | N | GLU | A | 452 | 135.563 | −13.612 | 23.808 | 1.00 | 52.30 |
| 4013 | CA | GLU | A | 452 | 135.900 | −14.895 | 23.178 | 1.00 | 61.98 |
| 4014 | CB | GLU | A | 452 | 136.656 | −14.627 | 21.870 | 1.00 | 75.30 |
| 4015 | CG | GLU | A | 452 | 137.546 | −15.785 | 21.397 | 1.00 | 95.58 |
| 4016 | CD | GLU | A | 452 | 139.043 | −15.519 | 21.574 | 1.00 | 107.30 |
| 4017 | OE1 | GLU | A | 452 | 139.421 | −14.719 | 22.461 | 1.00 | 114.33 |
| 4018 | OE2 | GLU | A | 452 | 139.845 | −16.128 | 20.829 | 1.00 | 113.87 |
| 4019 | C | GLU | A | 452 | 136.714 | −15.900 | 23.999 | 1.00 | 58.84 |
| 4020 | O | GLU | A | 452 | 137.779 | −15.546 | 24.505 | 1.00 | 61.02 |
| 4021 | N | TRP | A | 453 | 136.239 | −17.147 | 24.129 | 1.00 | 58.23 |
| 4022 | CA | TRP | A | 453 | 137.050 | −18.128 | 24.856 | 1.00 | 60.15 |
| 4023 | CB | TRP | A | 453 | 136.405 | −19.515 | 25.006 | 1.00 | 53.37 |
| 4024 | CG | TRP | A | 453 | 137.175 | −20.349 | 26.027 | 1.00 | 46.22 |
| 4025 | CD2 | TRP | A | 453 | 137.529 | −19.942 | 27.344 | 1.00 | 43.76 |
| 4026 | CE2 | TRP | A | 453 | 138.243 | −20.995 | 27.965 | 1.00 | 41.60 |
| 4027 | CE3 | TRP | A | 453 | 137.365 | −18.744 | 28.073 | 1.00 | 41.85 |
| 4028 | CD1 | TRP | A | 453 | 137.644 | −21.639 | 25.890 | 1.00 | 43.45 |
| 4029 | NE1 | TRP | A | 453 | 138.287 | −22.042 | 27.048 | 1.00 | 40.53 |
| 4030 | CZ2 | TRP | A | 453 | 138.726 | −20.938 | 29.276 | 1.00 | 41.24 |
| 4031 | CZ3 | TRP | A | 453 | 137.837 | −18.674 | 29.380 | 1.00 | 41.79 |
| 4032 | CH2 | TRP | A | 453 | 138.533 | −19.754 | 29.958 | 1.00 | 40.14 |
| 4033 | C | TRP | A | 453 | 138.223 | −18.276 | 23.922 | 1.00 | 67.06 |
| 4034 | O | TRP | A | 453 | 138.040 | −18.359 | 22.701 | 1.00 | 64.25 |
| 4035 | N | PRO | A | 454 | 139.446 | −18.300 | 24.467 | 1.00 | 84.06 |
| 4036 | CD | PRO | A | 454 | 139.889 | −18.326 | 25.870 | 1.00 | 77.96 |
| 4037 | CA | PRO | A | 454 | 140.568 | −18.437 | 23.550 | 1.00 | 88.78 |
| 4038 | CB | PRO | A | 454 | 141.794 | −18.408 | 24.456 | 1.00 | 86.24 |
| 4039 | CG | PRO | A | 454 | 141.291 | −18.875 | 25.763 | 1.00 | 83.96 |
| 4040 | C | PRO | A | 454 | 140.441 | −19.717 | 22.793 | 1.00 | 96.03 |
| 4041 | O | PRO | A | 454 | 139.793 | −20.670 | 23.237 | 1.00 | 99.15 |
| 4042 | N | GLY | A | 455 | 141.057 | −19.722 | 21.627 | 1.00 | 96.34 |
| 4043 | CA | GLY | A | 455 | 140.999 | −20.895 | 20.803 | 1.00 | 106.34 |
| 4044 | C | GLY | A | 455 | 139.665 | −20.992 | 20.113 | 1.00 | 108.48 |
| 4045 | O | GLY | A | 455 | 139.482 | −20.431 | 19.033 | 1.00 | 120.41 |
| 4046 | N | SER | A | 456 | 138.712 | −21.679 | 20.725 | 1.00 | 105.44 |
| 4047 | CA | SER | A | 456 | 137.458 | −21.816 | 20.031 | 1.00 | 91.93 |
| 4048 | CB | SER | A | 456 | 137.119 | −23.290 | 19.804 | 1.00 | 84.99 |
| 4049 | OG | SER | A | 456 | 137.296 | −23.627 | 18.433 | 1.00 | 78.26 |
| 4050 | C | SER | A | 456 | 136.259 | −21.080 | 20.537 | 1.00 | 91.48 |
| 4051 | O | SER | A | 456 | 135.789 | −21.223 | 21.675 | 1.00 | 73.49 |
| 4052 | N | ALA | A | 457 | 135.801 | −20.261 | 19.609 | 1.00 | 86.37 |
| 4053 | CA | ALA | A | 457 | 134.653 | −19.433 | 19.763 | 1.00 | 80.01 |
| 4054 | CB | ALA | A | 457 | 134.917 | −18.303 | 20.729 | 1.00 | 88.23 |
| 4055 | C | ALA | A | 457 | 134.312 | −18.895 | 18.394 | 1.00 | 71.12 |
| 4056 | O | ALA | A | 457 | 135.029 | −18.077 | 17.787 | 1.00 | 55.66 |
| 4057 | N | ASP | A | 458 | 133.227 | −19.483 | 17.918 | 1.00 | 57.99 |
| 4058 | CA | ASP | A | 458 | 132.536 | −19.163 | 16.698 | 1.00 | 48.79 |
| 4059 | CB | ASP | A | 458 | 132.462 | −20.372 | 15.759 | 1.00 | 43.40 |
| 4060 | CG | ASP | A | 458 | 132.707 | −19.999 | 14.295 | 1.00 | 39.93 |
| 4061 | OD1 | ASP | A | 458 | 132.741 | −18.787 | 13.985 | 1.00 | 38.48 |
| 4062 | OD2 | ASP | A | 458 | 132.862 | −20.919 | 13.453 | 1.00 | 38.27 |
| 4063 | C | ASP | A | 458 | 131.213 | −18.987 | 17.457 | 1.00 | 51.91 |
| 4064 | O | ASP | A | 458 | 130.138 | −18.859 | 16.883 | 1.00 | 44.99 |
| 4065 | N | LYS | A | 459 | 131.335 | −19.021 | 18.788 | 1.00 | 59.08 |
| 4066 | CA | LYS | A | 459 | 130.214 | −18.840 | 19.703 | 1.00 | 57.75 |
| 4067 | CB | LYS | A | 459 | 129.652 | −20.184 | 20.202 | 1.00 | 66.56 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4068 | CG | LYS | A | 459 | 128.550 | −20.047 | 21.282 | 1.00 | 86.44 |
| 4069 | CD | LYS | A | 459 | 128.067 | −21.414 | 21.724 | 1.00 | 96.19 |
| 4070 | CE | LYS | A | 459 | 126.930 | −21.294 | 22.589 | 1.00 | 99.69 |
| 4071 | NZ | LYS | A | 459 | 126.291 | −22.598 | 22.930 | 1.00 | 101.19 |
| 4072 | C | LYS | A | 459 | 130.568 | −18.010 | 20.921 | 1.00 | 57.20 |
| 4073 | O | LYS | A | 459 | 131.701 | −18.046 | 21.427 | 1.00 | 56.81 |
| 4074 | N | ARG | A | 460 | 129.580 | −17.226 | 21.350 | 1.00 | 52.69 |
| 4075 | CA | ARG | A | 460 | 129.717 | −16.449 | 22.554 | 1.00 | 39.96 |
| 4076 | CB | ARG | A | 460 | 129.892 | −14.973 | 22.251 | 1.00 | 40.13 |
| 4077 | CG | ARG | A | 460 | 131.130 | −14.702 | 21.439 | 1.00 | 51.61 |
| 4078 | CD | ARG | A | 460 | 131.921 | −13.590 | 22.030 | 1.00 | 57.42 |
| 4079 | NE | ARG | A | 460 | 133.093 | −13.272 | 21.238 | 1.00 | 59.79 |
| 4080 | CZ | ARG | A | 460 | 133.531 | −12.034 | 21.080 | 1.00 | 63.04 |
| 4081 | NH1 | ARG | A | 460 | 132.884 | −11.032 | 21.664 | 1.00 | 64.14 |
| 4082 | NH2 | ARG | A | 460 | 134.598 | −11.799 | 20.339 | 1.00 | 65.38 |
| 4083 | C | ARG | A | 460 | 128.512 | −16.663 | 23.436 | 1.00 | 32.50 |
| 4084 | O | ARG | A | 460 | 127.477 | −17.171 | 23.004 | 1.00 | 31.34 |
| 4085 | N | THR | A | 461 | 128.671 | −16.285 | 24.691 | 1.00 | 32.32 |
| 4086 | CA | THR | A | 461 | 127.605 | −16.432 | 25.644 | 1.00 | 23.46 |
| 4087 | CB | THR | A | 461 | 128.074 | −17.222 | 26.880 | 1.00 | 21.34 |
| 4088 | OG1 | THR | A | 461 | 128.475 | −18.535 | 26.483 | 1.00 | 21.38 |
| 4089 | CG2 | THR | A | 461 | 126.959 | −17.350 | 27.888 | 1.00 | 22.79 |
| 4090 | C | THR | A | 461 | 127.120 | −15.076 | 26.093 | 1.00 | 19.89 |
| 4091 | O | THR | A | 461 | 127.908 | −14.172 | 26.346 | 1.00 | 24.51 |
| 4092 | N | LEU | A | 462 | 125.811 | −14.936 | 26.195 | 1.00 | 22.70 |
| 4093 | CA | LEU | A | 462 | 125.258 | −13.697 | 26.666 | 1.00 | 21.28 |
| 4094 | CB | LEU | A | 462 | 124.239 | −13.141 | 25.665 | 1.00 | 20.39 |
| 4095 | CG | LEU | A | 462 | 124.767 | −12.874 | 24.242 | 1.00 | 20.98 |
| 4096 | CD1 | LEU | A | 462 | 123.640 | −12.281 | 23.394 | 1.00 | 19.70 |
| 4097 | CD2 | LEU | A | 462 | 125.955 | −11.952 | 24.271 | 1.00 | 17.40 |
| 4098 | C | LEU | A | 462 | 124.599 | −14.021 | 27.989 | 1.00 | 19.80 |
| 4099 | O | LEU | A | 462 | 124.092 | −15.133 | 28.199 | 1.00 | 23.19 |
| 4100 | N | ALA | A | 463 | 124.611 | −13.066 | 28.901 | 1.00 | 19.56 |
| 4101 | CA | ALA | A | 463 | 123.989 | −13.322 | 30.178 | 1.00 | 21.56 |
| 4102 | CB | ALA | A | 463 | 125.036 | −13.668 | 31.217 | 1.00 | 20.74 |
| 4103 | C | ALA | A | 463 | 123.209 | −12.108 | 30.599 | 1.00 | 22.55 |
| 4104 | O | ALA | A | 463 | 123.557 | −10.963 | 30.285 | 1.00 | 21.57 |
| 4105 | N | CYS | A | 464 | 122.148 | −12.364 | 31.326 | 1.00 | 19.66 |
| 4106 | CA | CYS | A | 464 | 121.316 | −11.291 | 31.775 | 1.00 | 20.83 |
| 4107 | C | CYS | A | 464 | 121.085 | −11.450 | 33.258 | 1.00 | 21.24 |
| 4108 | O | CYS | A | 464 | 120.854 | −12.557 | 33.745 | 1.00 | 19.95 |
| 4109 | CB | CYS | A | 464 | 119.993 | −11.366 | 31.039 | 1.00 | 20.55 |
| 4110 | SG | CYS | A | 464 | 118.919 | −9.922 | 31.224 | 1.00 | 25.80 |
| 4111 | N | LEU | A | 465 | 121.171 | −10.349 | 33.978 | 1.00 | 19.38 |
| 4112 | CA | LEU | A | 465 | 120.915 | −10.381 | 35.407 | 1.00 | 19.01 |
| 4113 | CB | LEU | A | 465 | 122.088 | −9.808 | 36.199 | 1.00 | 18.24 |
| 4114 | CG | LEU | A | 465 | 121.760 | −9.457 | 37.659 | 1.00 | 20.49 |
| 4115 | CD1 | LEU | A | 465 | 121.435 | −10.721 | 38.447 | 1.00 | 19.78 |
| 4116 | CD2 | LEU | A | 465 | 122.954 | −8.736 | 38.303 | 1.00 | 19.88 |
| 4117 | C | LEU | A | 465 | 119.692 | −9.514 | 35.644 | 1.00 | 17.58 |
| 4118 | O | LEU | A | 465 | 119.670 | −8.338 | 35.257 | 1.00 | 17.02 |
| 4119 | N | ILE | A | 466 | 118.673 | −10.093 | 36.268 | 1.00 | 17.26 |
| 4120 | CA | ILE | A | 466 | 117.451 | −9.356 | 36.567 | 1.00 | 19.01 |
| 4121 | CB | ILE | A | 466 | 116.251 | −9.965 | 35.819 | 1.00 | 19.22 |
| 4122 | CG2 | ILE | A | 466 | 114.989 | −9.156 | 36.098 | 1.00 | 18.37 |
| 4123 | CG1 | ILE | A | 466 | 116.549 | −9.957 | 34.317 | 1.00 | 18.10 |
| 4124 | CD1 | ILE | A | 466 | 115.822 | −11.061 | 33.557 | 1.00 | 21.34 |
| 4125 | C | ILE | A | 466 | 117.273 | −9.449 | 38.068 | 1.00 | 20.84 |
| 4126 | O | ILE | A | 466 | 117.178 | −10.556 | 38.617 | 1.00 | 20.57 |
| 4127 | N | GLN | A | 467 | 117.214 | −8.293 | 38.732 | 1.00 | 24.16 |
| 4128 | CA | GLN | A | 467 | 117.134 | −8.281 | 40.186 | 1.00 | 26.04 |
| 4129 | CB | GLN | A | 467 | 118.554 | −8.178 | 40.755 | 1.00 | 26.93 |
| 4130 | CG | GLN | A | 467 | 119.374 | −6.981 | 40.216 | 1.00 | 28.36 |
| 4131 | CD | GLN | A | 467 | 120.724 | −6.813 | 40.923 | 1.00 | 28.95 |
| 4132 | OE1 | GLN | A | 467 | 121.322 | −7.793 | 41.372 | 1.00 | 28.57 |
| 4133 | NE2 | GLN | A | 467 | 121.214 | −5.577 | 41.006 | 1.00 | 27.56 |
| 4134 | C | GLN | A | 467 | 116.273 | −7.230 | 40.854 | 1.00 | 27.00 |
| 4135 | O | GLN | A | 467 | 115.763 | −6.301 | 40.213 | 1.00 | 28.72 |
| 4136 | N | ASN | A | 468 | 116.130 | −7.401 | 42.166 | 1.00 | 29.10 |
| 4137 | CA | ASN | A | 468 | 115.351 | −6.508 | 43.008 | 1.00 | 32.21 |
| 4138 | CB | ASN | A | 468 | 116.053 | −5.146 | 43.092 | 1.00 | 30.78 |
| 4139 | CG | ASN | A | 468 | 117.466 | −5.253 | 43.659 | 1.00 | 33.15 |
| 4140 | OD1 | ASN | A | 468 | 117.733 | −6.082 | 44.537 | 1.00 | 31.55 |
| 4141 | ND2 | ASN | A | 468 | 118.373 | −4.404 | 43.171 | 1.00 | 32.60 |
| 4142 | C | ASN | A | 468 | 113.873 | −6.319 | 42.617 | 1.00 | 35.40 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4143 | O | ASN | A | 468 | 113.280 | −5.278 | 42.940 | 1.00 | 34.64 |
| 4144 | N | PHE | A | 469 | 113.272 | −7.298 | 41.935 | 1.00 | 42.05 |
| 4145 | CA | PHE | A | 469 | 111.856 | −7.190 | 41.559 | 1.00 | 44.18 |
| 4146 | CB | PHE | A | 469 | 111.609 | −7.857 | 40.194 | 1.00 | 36.79 |
| 4147 | CG | PHE | A | 469 | 112.150 | −9.258 | 40.070 | 1.00 | 25.12 |
| 4148 | CD1 | PHE | A | 469 | 111.368 | −10.339 | 40.422 | 1.00 | 20.07 |
| 4149 | CD2 | PHE | A | 469 | 113.424 | −9.490 | 39.548 | 1.00 | 23.15 |
| 4150 | CE1 | PHE | A | 469 | 111.829 | −11.635 | 40.257 | 1.00 | 20.48 |
| 4151 | CE2 | PHE | A | 469 | 113.902 | −10.777 | 39.377 | 1.00 | 21.30 |
| 4152 | CZ | PHE | A | 469 | 113.103 | −11.857 | 39.733 | 1.00 | 21.55 |
| 4153 | C | PHE | A | 469 | 111.012 | −7.800 | 42.691 | 1.00 | 43.47 |
| 4154 | O | PHE | A | 469 | 111.469 | −8.733 | 43.350 | 1.00 | 54.21 |
| 4155 | N | MET | A | 470 | 109.803 | −7.286 | 42.937 | 1.00 | 45.59 |
| 4156 | CA | MET | A | 470 | 109.034 | −7.789 | 44.079 | 1.00 | 58.70 |
| 4157 | CB | MET | A | 470 | 108.059 | −6.725 | 44.586 | 1.00 | 75.76 |
| 4158 | CG | MET | A | 470 | 108.076 | −6.568 | 46.122 | 1.00 | 78.41 |
| 4159 | SD | MET | A | 470 | 109.672 | −6.858 | 46.915 | 1.00 | 76.79 |
| 4160 | CE | MET | A | 470 | 109.208 | −6.844 | 48.645 | 1.00 | 78.69 |
| 4161 | C | MET | A | 470 | 108.378 | −9.152 | 43.929 | 1.00 | 62.95 |
| 4162 | O | MET | A | 470 | 109.085 | −10.149 | 44.091 | 1.00 | 68.25 |
| 4163 | N | PRO | A | 471 | 107.052 | −9.255 | 43.660 | 1.00 | 40.45 |
| 4164 | CD | PRO | A | 471 | 105.939 | −8.340 | 43.367 | 1.00 | 51.53 |
| 4165 | CA | PRO | A | 471 | 106.640 | −10.661 | 43.556 | 1.00 | 45.25 |
| 4166 | CB | PRO | A | 471 | 105.304 | −10.597 | 42.836 | 1.00 | 42.27 |
| 4167 | CG | PRO | A | 471 | 104.765 | −9.282 | 43.200 | 1.00 | 40.99 |
| 4168 | C | PRO | A | 471 | 107.707 | −11.351 | 42.706 | 1.00 | 44.60 |
| 4169 | O | PRO | A | 471 | 108.293 | −10.732 | 41.799 | 1.00 | 30.57 |
| 4170 | N | GLU | A | 472 | 107.980 | −12.608 | 43.021 | 1.00 | 35.23 |
| 4171 | CA | GLU | A | 472 | 109.003 | −13.352 | 42.315 | 1.00 | 36.71 |
| 4172 | CB | GLU | A | 472 | 109.432 | −14.532 | 43.171 | 1.00 | 39.78 |
| 4173 | CG | GLU | A | 472 | 108.296 | −15.492 | 43.459 | 1.00 | 47.98 |
| 4174 | CD | GLU | A | 472 | 108.691 | −16.571 | 44.449 | 1.00 | 53.69 |
| 4175 | OE1 | GLU | A | 472 | 108.670 | −16.301 | 45.674 | 1.00 | 55.82 |
| 4176 | OE2 | GLU | A | 472 | 109.035 | −17.687 | 43.994 | 1.00 | 57.17 |
| 4177 | C | GLU | A | 472 | 108.588 | −13.850 | 40.935 | 1.00 | 34.89 |
| 4178 | O | GLU | A | 472 | 109.416 | −14.361 | 40.187 | 1.00 | 35.55 |
| 4179 | N | ASP | A | 473 | 107.318 | −13.716 | 40.583 | 1.00 | 36.56 |
| 4180 | CA | ASP | A | 473 | 106.913 | −14.206 | 39.280 | 1.00 | 38.50 |
| 4181 | CB | ASP | A | 473 | 105.398 | −14.265 | 39.171 | 1.00 | 42.42 |
| 4182 | CG | ASP | A | 473 | 104.797 | −15.229 | 40.165 | 1.00 | 46.75 |
| 4183 | OD1 | ASP | A | 473 | 105.392 | −16.310 | 40.385 | 1.00 | 48.54 |
| 4184 | OD2 | ASP | A | 473 | 103.731 | −14.907 | 40.725 | 1.00 | 50.14 |
| 4185 | C | ASP | A | 473 | 107.501 | −13.345 | 38.188 | 1.00 | 34.89 |
| 4186 | O | ASP | A | 473 | 107.324 | −12.119 | 38.182 | 1.00 | 36.42 |
| 4187 | N | ILE | A | 474 | 108.198 | −13.992 | 37.257 | 1.00 | 30.51 |
| 4188 | CA | ILE | A | 474 | 108.835 | −13.252 | 36.181 | 1.00 | 30.92 |
| 4189 | CB | ILE | A | 474 | 110.196 | −12.716 | 36.686 | 1.00 | 26.60 |
| 4190 | CG2 | ILE | A | 474 | 111.191 | −13.874 | 36.819 | 1.00 | 22.70 |
| 4191 | CG1 | ILE | A | 474 | 110.725 | −11.647 | 35.744 | 1.00 | 24.21 |
| 4192 | CD1 | ILE | A | 474 | 111.499 | −10.567 | 36.458 | 1.00 | 23.61 |
| 4193 | C | ILE | A | 474 | 109.045 | −14.070 | 34.904 | 1.00 | 28.50 |
| 4194 | O | ILE | A | 474 | 109.289 | −15.273 | 34.956 | 1.00 | 28.73 |
| 4195 | N | SER | A | 475 | 108.938 | −13.416 | 33.754 | 1.00 | 24.49 |
| 4196 | CA | SER | A | 475 | 109.168 | −14.092 | 32.484 | 1.00 | 25.09 |
| 4197 | CB | SER | A | 475 | 107.940 | −14.002 | 31.568 | 1.00 | 24.10 |
| 4198 | OG | SER | A | 475 | 106.930 | −14.912 | 31.960 | 1.00 | 24.11 |
| 4199 | C | SER | A | 475 | 110.342 | −13.416 | 31.825 | 1.00 | 23.71 |
| 4200 | O | SER | A | 475 | 110.427 | −12.184 | 31.815 | 1.00 | 23.76 |
| 4201 | N | VAL | A | 476 | 111.261 | −14.211 | 31.283 | 1.00 | 20.91 |
| 4202 | CA | VAL | A | 476 | 112.434 | −13.660 | 30.612 | 1.00 | 21.16 |
| 4203 | CB | VAL | A | 476 | 113.762 | −14.118 | 31.272 | 1.00 | 18.95 |
| 4204 | CG1 | VAL | A | 476 | 114.949 | −13.472 | 30.569 | 1.00 | 14.50 |
| 4205 | CG2 | VAL | A | 476 | 113.768 | −13.765 | 32.755 | 1.00 | 16.48 |
| 4206 | C | VAL | A | 476 | 112.445 | −14.192 | 29.211 | 1.00 | 22.04 |
| 4207 | O | VAL | A | 476 | 112.197 | −15.369 | 29.007 | 1.00 | 20.13 |
| 4208 | N | GLN | A | 477 | 112.729 | −13.341 | 28.238 | 1.00 | 23.38 |
| 4209 | CA | GLN | A | 477 | 112.805 | −13.824 | 26.868 | 1.00 | 27.75 |
| 4210 | CB | GLN | A | 477 | 111.444 | −13.682 | 26.157 | 1.00 | 33.01 |
| 4211 | CG | GLN | A | 477 | 110.918 | −12.278 | 26.061 | 1.00 | 47.23 |
| 4212 | CD | GLN | A | 477 | 109.398 | −12.177 | 25.911 | 1.00 | 53.94 |
| 4213 | OE1 | GLN | A | 477 | 108.888 | −11.137 | 25.461 | 1.00 | 58.53 |
| 4214 | NE2 | GLN | A | 477 | 108.669 | −13.225 | 26.303 | 1.00 | 56.18 |
| 4215 | C | GLN | A | 477 | 113.912 | −13.077 | 26.148 | 1.00 | 27.29 |
| 4216 | O | GLN | A | 477 | 114.295 | −11.981 | 26.560 | 1.00 | 27.06 |
| 4217 | N | TRP | A | 478 | 114.474 | −13.696 | 25.114 | 1.00 | 25.81 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4218 | CA | TRP | A | 478 | 115.532 | −13.052 | 24.350 | 1.00 | 22.41 |
| 4219 | CB | TRP | A | 478 | 116.782 | −13.929 | 24.267 | 1.00 | 21.60 |
| 4220 | CG | TRP | A | 478 | 117.490 | −14.128 | 25.578 | 1.00 | 21.48 |
| 4221 | CD2 | TRP | A | 478 | 118.626 | −13.398 | 26.059 | 1.00 | 19.31 |
| 4222 | CE2 | TRP | A | 478 | 118.954 | −13.931 | 27.326 | 1.00 | 22.03 |
| 4223 | CE3 | TRP | A | 478 | 119.393 | −12.345 | 25.544 | 1.00 | 19.89 |
| 4224 | CD1 | TRP | A | 478 | 117.184 | −15.044 | 26.544 | 1.00 | 20.17 |
| 4225 | NE1 | TRP | A | 478 | 118.060 | −14.931 | 27.598 | 1.00 | 20.59 |
| 4226 | CZ2 | TRP | A | 478 | 120.029 | −13.446 | 28.085 | 1.00 | 19.89 |
| 4227 | CZ3 | TRP | A | 478 | 120.458 | −11.861 | 26.301 | 1.00 | 18.81 |
| 4228 | CH2 | TRP | A | 478 | 120.762 | −12.414 | 27.556 | 1.00 | 19.72 |
| 4229 | C | TRP | A | 478 | 115.044 | −12.767 | 22.952 | 1.00 | 23.29 |
| 4230 | O | TRP | A | 478 | 114.316 | −13.562 | 22.355 | 1.00 | 23.55 |
| 4231 | N | LEU | A | 479 | 115.467 | −11.639 | 22.407 | 1.00 | 23.18 |
| 4232 | CA | LEU | A | 479 | 115.031 | −11.288 | 21.074 | 1.00 | 25.23 |
| 4233 | CB | LEU | A | 479 | 114.114 | −10.061 | 21.147 | 1.00 | 29.18 |
| 4234 | CG | LEU | A | 479 | 113.095 | −10.128 | 22.291 | 1.00 | 33.47 |
| 4235 | CD1 | LEU | A | 479 | 112.604 | −8.740 | 22.625 | 1.00 | 36.82 |
| 4236 | CD2 | LEU | A | 479 | 111.942 | −11.035 | 21.912 | 1.00 | 38.14 |
| 4237 | C | LEU | A | 479 | 116.217 | −11.002 | 20.173 | 1.00 | 26.44 |
| 4238 | O | LEU | A | 479 | 117.236 | −10.454 | 20.611 | 1.00 | 25.04 |
| 4239 | N | HIS | A | 480 | 116.101 | −11.401 | 18.917 | 1.00 | 27.16 |
| 4240 | CA | HIS | A | 480 | 117.149 | −11.135 | 17.953 | 1.00 | 28.66 |
| 4241 | CB | HIS | A | 480 | 117.831 | −12.417 | 17.502 | 1.00 | 24.97 |
| 4242 | CG | HIS | A | 480 | 118.994 | −12.160 | 16.596 | 1.00 | 23.35 |
| 4243 | CD2 | HIS | A | 480 | 119.490 | −12.879 | 15.562 | 1.00 | 24.23 |
| 4244 | ND1 | HIS | A | 480 | 119.811 | −11.069 | 16.746 | 1.00 | 21.90 |
| 4245 | CE1 | HIS | A | 480 | 120.779 | −11.121 | 15.840 | 1.00 | 20.80 |
| 4246 | NE2 | HIS | A | 480 | 120.605 | −12.204 | 15.116 | 1.00 | 22.13 |
| 4247 | C | HIS | A | 480 | 116.425 | −10.469 | 16.800 | 1.00 | 32.51 |
| 4248 | O | HIS | A | 480 | 115.374 | −10.951 | 16.371 | 1.00 | 31.11 |
| 4249 | N | ASN | A | 481 | 116.991 | −9.382 | 16.278 | 1.00 | 42.53 |
| 4250 | CA | ASN | A | 481 | 116.288 | −8.621 | 15.257 | 1.00 | 50.66 |
| 4251 | CB | ASN | A | 481 | 115.907 | −9.518 | 14.074 | 1.00 | 47.38 |
| 4252 | CG | ASN | A | 481 | 117.127 | −9.949 | 13.264 | 1.00 | 42.23 |
| 4253 | OD1 | ASN | A | 481 | 117.856 | −9.110 | 12.737 | 1.00 | 40.48 |
| 4254 | ND2 | ASN | A | 481 | 117.358 | −11.252 | 13.167 | 1.00 | 37.32 |
| 4255 | C | ASN | A | 481 | 115.096 | −8.234 | 16.139 | 1.00 | 56.53 |
| 4256 | O | ASN | A | 481 | 115.304 | −7.932 | 17.319 | 1.00 | 67.14 |
| 4257 | N | GLU | A | 482 | 113.867 | −8.224 | 15.647 | 1.00 | 67.49 |
| 4258 | CA | GLU | A | 482 | 112.783 | −7.887 | 16.570 | 1.00 | 75.34 |
| 4259 | CB | GLU | A | 482 | 111.899 | −6.758 | 16.034 | 1.00 | 86.38 |
| 4260 | CG | GLU | A | 482 | 112.533 | −5.381 | 16.107 | 1.00 | 102.03 |
| 4261 | CD | GLU | A | 482 | 113.480 | −5.219 | 17.287 | 1.00 | 110.16 |
| 4262 | OE1 | GLU | A | 482 | 113.475 | −6.068 | 18.206 | 1.00 | 114.48 |
| 4263 | OE2 | GLU | A | 482 | 114.235 | −4.227 | 17.297 | 1.00 | 114.87 |
| 4264 | C | GLU | A | 482 | 111.957 | −9.120 | 16.811 | 1.00 | 72.73 |
| 4265 | O | GLU | A | 482 | 110.768 | −9.050 | 17.103 | 1.00 | 68.90 |
| 4266 | N | VAL | A | 483 | 112.614 | −10.262 | 16.708 | 1.00 | 67.28 |
| 4267 | CA | VAL | A | 483 | 111.930 | −11.518 | 16.874 | 1.00 | 62.50 |
| 4268 | CB | VAL | A | 483 | 112.154 | −12.405 | 15.637 | 1.00 | 68.10 |
| 4269 | CG1 | VAL | A | 483 | 113.206 | −13.469 | 15.929 | 1.00 | 75.51 |
| 4270 | CG2 | VAL | A | 483 | 110.852 | −13.021 | 15.198 | 1.00 | 74.16 |
| 4271 | C | VAL | A | 483 | 112.396 | −12.242 | 18.123 | 1.00 | 57.40 |
| 4272 | O | VAL | A | 483 | 113.562 | −12.183 | 18.512 | 1.00 | 53.44 |
| 4273 | N | GLN | A | 484 | 111.463 | −12.943 | 18.735 | 1.00 | 47.50 |
| 4274 | CA | GLN | A | 484 | 111.743 | −13.692 | 19.937 | 1.00 | 39.94 |
| 4275 | CB | GLN | A | 484 | 110.458 | −13.782 | 20.772 | 1.00 | 41.16 |
| 4276 | CG | GLN | A | 484 | 110.437 | −14.883 | 21.809 | 1.00 | 44.92 |
| 4277 | CD | GLN | A | 484 | 109.376 | −14.692 | 22.881 | 1.00 | 47.77 |
| 4278 | OE1 | GLN | A | 484 | 108.885 | −15.674 | 23.456 | 1.00 | 49.66 |
| 4279 | NH2 | GLN | A | 484 | 109.036 | −13.437 | 23.184 | 1.00 | 49.14 |
| 4280 | C | GLN | A | 484 | 112.301 | −15.073 | 19.604 | 1.00 | 37.25 |
| 4281 | O | GLN | A | 484 | 111.740 | −15.805 | 18.778 | 1.00 | 33.86 |
| 4282 | N | LEU | A | 485 | 113.414 | −15.416 | 20.252 | 1.00 | 33.92 |
| 4283 | CA | LEU | A | 485 | 114.073 | −16.698 | 20.035 | 1.00 | 30.22 |
| 4284 | CB | LEU | A | 485 | 115.531 | −16.626 | 20.491 | 1.00 | 31.41 |
| 4285 | CG | LEU | A | 485 | 116.429 | −15.677 | 19.700 | 1.00 | 31.22 |
| 4286 | CD1 | LEU | A | 485 | 117.683 | −15.373 | 20.499 | 1.00 | 30.02 |
| 4287 | CD2 | LEU | A | 485 | 116.762 | −16.303 | 18.358 | 1.00 | 30.04 |
| 4288 | C | LEU | A | 485 | 113.369 | −17.819 | 20.777 | 1.00 | 28.85 |
| 4289 | O | LEU | A | 485 | 112.725 | −17.596 | 21.802 | 1.00 | 27.80 |
| 4290 | N | PRO | A | 486 | 113.475 | −19.047 | 20.256 | 1.00 | 29.01 |
| 4291 | CD | PRO | A | 486 | 114.166 | −19.400 | 19.002 | 1.00 | 28.57 |
| 4292 | CA | PRO | A | 486 | 112.842 | −20.218 | 20.879 | 1.00 | 30.55 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4293 | CB | PRO | A | 486 | 113.380 | −21.388 | 20.061 | 1.00 | 27.53 |
| 4294 | CG | PRO | A | 486 | 113.615 | −20.780 | 18.702 | 1.00 | 27.31 |
| 4295 | C | PRO | A | 486 | 113.241 | −20.332 | 22.352 | 1.00 | 35.75 |
| 4296 | O | PRO | A | 486 | 114.419 | −20.177 | 22.699 | 1.00 | 36.57 |
| 4297 | N | ASP | A | 487 | 112.264 | −20.615 | 23.210 | 1.00 | 41.55 |
| 4298 | CA | ASP | A | 487 | 112.521 | −20.737 | 24.635 | 1.00 | 45.88 |
| 4299 | CB | ASP | A | 487 | 111.252 | −21.182 | 25.364 | 1.00 | 59.69 |
| 4300 | CG | ASP | A | 487 | 110.126 | −20.179 | 25.230 | 1.00 | 71.93 |
| 4301 | OD1 | ASP | A | 487 | 110.426 | −18.972 | 25.101 | 1.00 | 81.23 |
| 4302 | OD2 | ASP | A | 487 | 108.947 | −20.591 | 25.268 | 1.00 | 80.58 |
| 4303 | C | ASP | A | 487 | 113.664 | −21.694 | 24.962 | 1.00 | 43.48 |
| 4304 | O | ASP | A | 487 | 114.484 | −21.416 | 25.842 | 1.00 | 40.62 |
| 4305 | N | ALA | A | 488 | 113.732 | −22.810 | 24.246 | 1.00 | 39.48 |
| 4306 | CA | ALA | A | 488 | 114.766 | −23.811 | 24.489 | 1.00 | 36.02 |
| 4307 | CB | ALA | A | 488 | 114.505 | −25.045 | 23.619 | 1.00 | 35.75 |
| 4308 | C | ALA | A | 488 | 116.199 | −23.316 | 24.271 | 1.00 | 33.55 |
| 4309 | O | ALA | A | 488 | 117.155 | −23.987 | 24.666 | 1.00 | 33.70 |
| 4310 | N | ARG | A | 489 | 116.356 | −22.153 | 23.647 | 1.00 | 32.99 |
| 4311 | CA | ARG | A | 489 | 117.691 | −21.629 | 23.396 | 1.00 | 32.33 |
| 4312 | CB | ARG | A | 489 | 117.655 | −20.712 | 22.182 | 1.00 | 33.82 |
| 4313 | CG | ARG | A | 489 | 118.128 | −21.433 | 20.927 | 1.00 | 32.25 |
| 4314 | CD | ARG | A | 489 | 119.505 | −20.937 | 20.518 | 1.00 | 32.83 |
| 4315 | NE | ARG | A | 489 | 119.363 | −20.159 | 19.300 | 1.00 | 36.15 |
| 4316 | CZ | ARG | A | 489 | 120.157 | −19.175 | 18.920 | 1.00 | 36.45 |
| 4317 | NH1 | ARG | A | 489 | 121.187 | −18.814 | 19.666 | 1.00 | 35.69 |
| 4318 | NH2 | ARG | A | 489 | 119.911 | −18.560 | 17.773 | 1.00 | 39.55 |
| 4319 | C | ARG | A | 489 | 118.376 | −20.942 | 24.581 | 1.00 | 33.12 |
| 4320 | O | ARG | A | 489 | 119.598 | −20.736 | 24.569 | 1.00 | 32.40 |
| 4321 | N | HIS | A | 490 | 117.607 | −20.614 | 25.613 | 1.00 | 30.60 |
| 4322 | CA | HIS | A | 490 | 118.189 | −19.977 | 26.779 | 1.00 | 31.02 |
| 4323 | CB | HIS | A | 490 | 117.721 | −18.519 | 26.903 | 1.00 | 28.12 |
| 4324 | CG | HIS | A | 490 | 116.260 | −18.383 | 27.230 | 1.00 | 29.50 |
| 4325 | CD2 | HIS | A | 490 | 115.614 | −18.431 | 28.412 | 1.00 | 30.92 |
| 4326 | ND1 | HIS | A | 490 | 115.300 | −18.212 | 26.259 | 1.00 | 31.37 |
| 4327 | CE1 | HIS | A | 490 | 114.110 | −18.158 | 26.840 | 1.00 | 30.70 |
| 4328 | NE2 | HIS | A | 490 | 114.268 | −18.286 | 28.137 | 1.00 | 31.21 |
| 4329 | C | HIS | A | 490 | 117.830 | −20.736 | 28.050 | 1.00 | 30.39 |
| 4330 | O | HIS | A | 490 | 116.913 | −21.549 | 28.064 | 1.00 | 30.21 |
| 4331 | N | SER | A | 491 | 118.557 | −20.445 | 29.121 | 1.00 | 29.79 |
| 4332 | CA | SER | A | 491 | 118.321 | −21.071 | 30.409 | 1.00 | 31.32 |
| 4333 | CB | SER | A | 491 | 119.485 | −21.987 | 30.745 | 1.00 | 31.81 |
| 4334 | OG | SER | A | 491 | 119.302 | −22.587 | 32.001 | 1.00 | 34.05 |
| 4335 | C | SER | A | 491 | 118.200 | −19.962 | 31.436 | 1.00 | 31.03 |
| 4336 | O | SER | A | 491 | 119.010 | −19.042 | 31.454 | 1.00 | 31.34 |
| 4337 | N | THR | A | 492 | 117.179 | −20.033 | 32.278 | 1.00 | 30.48 |
| 4338 | CA | THR | A | 492 | 116.971 | −19.010 | 33.295 | 1.00 | 27.94 |
| 4339 | CB | THR | A | 492 | 115.667 | −18.228 | 33.020 | 1.00 | 29.66 |
| 4340 | OG1 | THR | A | 492 | 115.813 | −17.467 | 31.812 | 1.00 | 29.84 |
| 4341 | CG2 | THR | A | 492 | 115.346 | −17.282 | 34.174 | 1.00 | 28.57 |
| 4342 | C | THR | A | 492 | 116.907 | −19.638 | 34.682 | 1.00 | 28.59 |
| 4343 | O | THR | A | 492 | 116.170 | −20.593 | 34.900 | 1.00 | 24.40 |
| 4344 | N | THR | A | 493 | 117.669 | −19.098 | 35.626 | 1.00 | 29.46 |
| 4345 | CA | THR | A | 493 | 117.674 | −19.660 | 36.981 | 1.00 | 30.70 |
| 4346 | CB | THR | A | 493 | 118.819 | −19.074 | 37.834 | 1.00 | 27.86 |
| 4347 | OG1 | THR | A | 493 | 118.585 | −17.679 | 38.051 | 1.00 | 29.30 |
| 4348 | CG2 | THR | A | 493 | 120.149 | −19.240 | 37.125 | 1.00 | 24.18 |
| 4349 | C | THR | A | 493 | 116.347 | −19.418 | 37.705 | 1.00 | 34.17 |
| 4350 | O | THR | A | 493 | 115.452 | −18.769 | 37.173 | 1.00 | 34.93 |
| 4351 | N | GLN | A | 494 | 116.227 | −19.964 | 38.911 | 1.00 | 41.28 |
| 4352 | CA | GLN | A | 494 | 115.016 | −19.817 | 39.722 | 1.00 | 45.59 |
| 4353 | CB | GLN | A | 494 | 114.811 | −21.058 | 40.602 | 1.00 | 58.58 |
| 4354 | CG | GLN | A | 494 | 114.428 | −22.322 | 39.824 | 1.00 | 80.25 |
| 4355 | CD | GLN | A | 494 | 112.926 | −22.546 | 39.747 | 1.00 | 91.03 |
| 4356 | OE1 | GLN | A | 494 | 112.277 | −22.800 | 40.767 | 1.00 | 97.73 |
| 4357 | NE2 | GLN | A | 494 | 112.363 | −22.459 | 38.541 | 1.00 | 97.43 |
| 4358 | C | GLN | A | 494 | 115.114 | −15.583 | 40.604 | 1.00 | 40.80 |
| 4359 | O | GLN | A | 494 | 116.177 | −18.293 | 41.163 | 1.00 | 39.42 |
| 4360 | N | PRO | A | 495 | 114.007 | −17.833 | 40.736 | 1.00 | 33.07 |
| 4361 | CD | PRO | A | 495 | 112.674 | −18.064 | 40.151 | 1.00 | 32.49 |
| 4362 | CA | PRO | A | 495 | 114.033 | −16.634 | 41.572 | 1.00 | 33.71 |
| 4363 | CB | PRO | A | 495 | 112.564 | −16.257 | 41.700 | 1.00 | 30.63 |
| 4364 | CG | PRO | A | 495 | 111.937 | −16.796 | 40.474 | 1.00 | 30.09 |
| 4365 | C | PRO | A | 495 | 114.652 | −16.940 | 42.937 | 1.00 | 37.50 |
| 4366 | O | PRO | A | 495 | 114.325 | −17.948 | 43.567 | 1.00 | 34.90 |
| 4367 | N | ARG | A | 496 | 115.578 | −16.090 | 43.361 | 1.00 | 41.64 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4368 | CA | ARG | A | 496 | 116.228 | −16.215 | 44.657 | 1.00 | 46.92 |
| 4369 | CB | ARG | A | 496 | 117.685 | −16.633 | 44.511 | 1.00 | 52.99 |
| 4370 | CG | ARG | A | 496 | 117.899 | −18.089 | 44.187 | 1.00 | 70.27 |
| 4371 | CD | ARG | A | 496 | 119.228 | −18.292 | 43.459 | 1.00 | 82.73 |
| 4372 | NE | ARG | A | 496 | 119.748 | −19.645 | 43.635 | 1.00 | 90.76 |
| 4373 | CZ | ARG | A | 496 | 120.627 | −19.986 | 44.573 | 1.00 | 93.76 |
| 4374 | NH1 | ARG | A | 496 | 121.091 | −19.070 | 45.413 | 1.00 | 94.06 |
| 4375 | NH2 | ARG | A | 496 | 121.033 | −21.245 | 44.681 | 1.00 | 95.30 |
| 4376 | C | ARG | A | 496 | 116.175 | −14.851 | 45.327 | 1.00 | 47.85 |
| 4377 | O | ARG | A | 496 | 115.945 | −13.822 | 44.675 | 1.00 | 42.13 |
| 4378 | N | LYS | A | 497 | 116.407 | −14.848 | 46.632 | 1.00 | 50.11 |
| 4379 | CA | LYS | A | 497 | 116.364 | −43.618 | 47.384 | 1.00 | 53.48 |
| 4380 | CB | LYS | A | 497 | 115.843 | −13.892 | 48.785 | 1.00 | 57.22 |
| 4381 | CG | LYS | A | 497 | 114.406 | −14.343 | 48.802 | 1.00 | 68.23 |
| 4382 | CD | LYS | A | 497 | 113.834 | −14.189 | 50.192 | 1.00 | 77.36 |
| 4383 | CE | LYS | A | 497 | 112.374 | −14.589 | 50.236 | 1.00 | 82.47 |
| 4384 | NZ | LYS | A | 497 | 111.892 | −14.714 | 51.637 | 1.00 | 85.77 |
| 4385 | C | LYS | A | 497 | 117.691 | −12.896 | 47.453 | 1.00 | 59.16 |
| 4386 | O | LYS | A | 497 | 118.748 | −13.502 | 47.603 | 1.00 | 53.59 |
| 4387 | N | THR | A | 498 | 117.603 | −11.581 | 47.324 | 1.00 | 68.11 |
| 4388 | CA | THR | A | 498 | 118.745 | −10.695 | 47.377 | 1.00 | 70.45 |
| 4389 | CB | THR | A | 498 | 118.597 | −9.530 | 46.380 | 1.00 | 72.24 |
| 4390 | OG1 | THR | A | 496 | 117.326 | −8.892 | 46.582 | 1.00 | 76.54 |
| 4391 | CG2 | THR | A | 498 | 118.697 | −10.017 | 44.959 | 1.00 | 76.57 |
| 4392 | C | THR | A | 498 | 118.785 | −10.066 | 48.759 | 1.00 | 77.53 |
| 4393 | O | THR | A | 498 | 118.429 | −10.673 | 49.771 | 1.00 | 77.43 |
| 4394 | N | LYS | A | 499 | 119.208 | −8.811 | 48.738 | 1.00 | 89.33 |
| 4395 | CA | LYS | A | 499 | 119.338 | −7.933 | 49.881 | 1.00 | 102.26 |
| 4396 | CB | LYS | A | 499 | 119.946 | −6.622 | 49.391 | 1.00 | 113.56 |
| 4397 | CG | LYS | A | 499 | 119.460 | −6.246 | 47.983 | 1.00 | 122.70 |
| 4398 | CD | LYS | A | 499 | 120.189 | −5.036 | 47.438 | 1.00 | 130.65 |
| 4399 | CE | LYS | A | 499 | 120.167 | −4.997 | 45.911 | 1.00 | 136.06 |
| 4400 | NZ | LYS | A | 499 | 120.919 | −3.823 | 45.377 | 1.00 | 139.16 |
| 4401 | C | LYS | A | 499 | 117.996 | −7.633 | 50.515 | 1.00 | 106.99 |
| 4402 | O | LYS | A | 499 | 117.438 | −6.579 | 50.241 | 1.00 | 111.36 |
| 4403 | N | GLY | A | 500 | 117.484 | −8.523 | 51.360 | 1.00 | 115.14 |
| 4404 | CA | GLY | A | 500 | 116.196 | −8.273 | 51.989 | 1.00 | 123.54 |
| 4405 | C | GLY | A | 500 | 115.322 | −7.275 | 51.239 | 1.00 | 122.36 |
| 4406 | O | GLY | A | 500 | 114.475 | −6.609 | 51.833 | 1.00 | 130.30 |
| 4407 | N | SER | A | 501 | 115.519 | −7.180 | 49.927 | 1.00 | 115.80 |
| 4408 | CA | SER | A | 501 | 114.765 | −6.251 | 49.098 | 1.00 | 116.74 |
| 4409 | CB | SER | A | 501 | 115.710 | −5.299 | 48.348 | 1.00 | 125.90 |
| 4410 | OG | SER | A | 501 | 116.676 | −6.009 | 47.595 | 1.00 | 113.61 |
| 4411 | C | SER | A | 501 | 113.879 | −6.992 | 48.109 | 1.00 | 112.79 |
| 4412 | O | SER | A | 501 | 112.718 | −6.631 | 47.927 | 1.00 | 120.95 |
| 4413 | N | GLY | A | 502 | 114.415 | −8.031 | 47.476 | 1.00 | 106.04 |
| 4414 | CA | GLY | A | 502 | 113.614 | −8.767 | 46.519 | 1.00 | 82.84 |
| 4415 | C | GLY | A | 502 | 114.276 | −9.994 | 45.941 | 1.00 | 65.66 |
| 4416 | O | GLY | A | 502 | 115.043 | −10.679 | 46.619 | 1.00 | 56.20 |
| 4417 | N | PHE | A | 503 | 113.984 | −10.262 | 44.671 | 1.00 | 48.24 |
| 4418 | CA | PHE | A | 503 | 114.533 | −11.432 | 44.008 | 1.00 | 38.90 |
| 4419 | CB | PHE | A | 503 | 113.404 | −12.357 | 43.551 | 1.00 | 38.56 |
| 4420 | CG | PHE | A | 503 | 112.460 | −12.704 | 44.653 | 1.00 | 40.57 |
| 4421 | CD1 | PHE | A | 503 | 111.501 | −11.778 | 45.087 | 1.00 | 41.34 |
| 4422 | CD2 | PHE | A | 503 | 112.476 | −13.982 | 45.213 | 1.00 | 41.81 |
| 4423 | CE1 | PHE | A | 503 | 110.621 | −12.094 | 46.150 | 1.00 | 41.60 |
| 4424 | CE2 | PHE | A | 503 | 111.599 | −14.311 | 46.278 | 1.00 | 43.37 |
| 4425 | CZ | PHE | A | 503 | 110.642 | −13.377 | 46.713 | 1.00 | 42.01 |
| 4426 | C | PHE | A | 503 | 115.409 | −11.112 | 42.803 | 1.00 | 34.57 |
| 4427 | O | PHE | A | 503 | 115.365 | −10.007 | 42.250 | 1.00 | 30.37 |
| 4428 | N | PHE | A | 504 | 116.218 | −12.093 | 42.417 | 1.00 | 27.66 |
| 4429 | CA | PHE | A | 504 | 117.072 | −11.956 | 41.257 | 1.00 | 25.06 |
| 4430 | CB | PHE | A | 504 | 118.522 | −11.636 | 41.638 | 1.00 | 23.33 |
| 4431 | CG | PHE | A | 504 | 119.302 | −12.809 | 42.174 | 1.00 | 20.24 |
| 4432 | CD1 | PHE | A | 504 | 119.939 | −13.714 | 41.314 | 1.00 | 19.36 |
| 4433 | CD2 | PHE | A | 504 | 119.442 | −12.983 | 43.553 | 1.00 | 21.76 |
| 4434 | CE1 | PHE | A | 504 | 120.715 | −14.774 | 41.828 | 1.00 | 18.33 |
| 4435 | CE2 | PHE | A | 504 | 120.208 | −14.030 | 44.081 | 1.00 | 20.70 |
| 4436 | CZ | PHE | A | 504 | 120.846 | −14.931 | 43.216 | 1.00 | 18.59 |
| 4437 | C | PHE | A | 504 | 117.015 | −13.261 | 40.509 | 1.00 | 25.88 |
| 4438 | O | PHE | A | 504 | 116.740 | −14.316 | 41.087 | 1.00 | 24.11 |
| 4439 | N | VAL | A | 505 | 117.262 | −13.178 | 39.213 | 1.00 | 26.55 |
| 4440 | CA | VAL | A | 505 | 117.255 | −14.344 | 38.359 | 1.00 | 26.20 |
| 4441 | CB | VAL | A | 505 | 115.875 | −14.505 | 37.671 | 1.00 | 28.03 |
| 4442 | CG1 | VAL | A | 505 | 115.681 | −13.444 | 36.620 | 1.00 | 28.90 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4443 | CG2 | VAL | A | 505 | 115.753 | −15.868 | 37.075 | 1.00 | 32.35 |
| 4444 | C | VAL | A | 505 | 118.348 | −14.119 | 37.321 | 1.00 | 23.58 |
| 4445 | O | VAL | A | 505 | 118.663 | −12.979 | 36.986 | 1.00 | 23.15 |
| 4446 | N | PHE | A | 506 | 118.946 | −15.194 | 36.832 | 1.00 | 23.34 |
| 4447 | CA | PHE | A | 506 | 119.992 | −15.072 | 35.817 | 1.00 | 24.72 |
| 4448 | CB | PHE | A | 506 | 121.306 | −15.698 | 36.295 | 1.00 | 30.88 |
| 4449 | CG | PHE | A | 506 | 122.222 | −14.759 | 37.035 | 1.00 | 31.54 |
| 4450 | CD1 | PHE | A | 506 | 122.391 | −14.864 | 38.421 | 1.00 | 33.58 |
| 4451 | CD2 | PHE | A | 506 | 122.980 | −13.823 | 36.342 | 1.00 | 31.92 |
| 4452 | CE1 | PHE | A | 506 | 123.320 | −14.058 | 39.095 | 1.00 | 34.59 |
| 4453 | CE2 | PHE | A | 506 | 123.908 | −13.017 | 37.008 | 1.00 | 34.65 |
| 4454 | CZ | PHE | A | 506 | 124.073 | −13.136 | 38.387 | 1.00 | 35.05 |
| 4455 | C | PHE | A | 506 | 119.540 | −15.814 | 34.576 | 1.00 | 21.86 |
| 4456 | O | PHE | A | 506 | 118.902 | −16.856 | 34.675 | 1.00 | 24.94 |
| 4457 | N | SER | A | 507 | 119.862 | −15.288 | 33.403 | 1.00 | 20.47 |
| 4458 | CA | SER | A | 507 | 119.491 | −15.960 | 32.166 | 1.00 | 18.08 |
| 4459 | CB | SER | A | 507 | 118.350 | −15.207 | 31.461 | 1.00 | 17.51 |
| 4460 | OG | SER | A | 507 | 117.829 | −15.968 | 30.378 | 1.00 | 20.98 |
| 4461 | C | SER | A | 507 | 120.714 | −16.043 | 31.286 | 1.00 | 15.74 |
| 4462 | O | SER | A | 507 | 121.414 | −15.064 | 31.078 | 1.00 | 14.26 |
| 4463 | N | ARG | A | 508 | 120.943 | −17.221 | 30.700 | 1.00 | 16.51 |
| 4464 | CA | ARG | A | 508 | 122.084 | −17.487 | 29.830 | 1.00 | 19.19 |
| 4465 | CB | ARG | A | 508 | 122.885 | −18.634 | 30.459 | 1.00 | 18.78 |
| 4466 | CG | ARG | A | 508 | 124.040 | −19.188 | 29.656 | 1.00 | 23.01 |
| 4467 | CD | ARG | A | 508 | 124.789 | −20.280 | 30.447 | 1.00 | 26.67 |
| 4468 | NE | ARG | A | 508 | 126.018 | −20.677 | 29.762 | 1.00 | 30.49 |
| 4469 | CZ | ARG | A | 508 | 126.064 | −21.462 | 28.688 | 1.00 | 29.38 |
| 4470 | NH1 | ARG | A | 508 | 124.951 | −21.954 | 28.170 | 1.00 | 30.76 |
| 4471 | NH2 | ARG | A | 508 | 127.226 | −21.739 | 28.121 | 1.00 | 30.22 |
| 4472 | C | ARG | A | 508 | 121.657 | −17.840 | 28.385 | 1.00 | 18.19 |
| 4473 | O | ARG | A | 508 | 120.784 | −18.674 | 28.184 | 1.00 | 16.71 |
| 4474 | N | LEU | A | 509 | 122.256 | −17.186 | 27.388 | 1.00 | 19.68 |
| 4475 | CA | LEU | A | 509 | 121.941 | −17.472 | 25.980 | 1.00 | 22.67 |
| 4476 | CB | LEU | A | 509 | 121.040 | −16.386 | 25.391 | 1.00 | 23.19 |
| 4477 | CG | LEU | A | 509 | 120.821 | −16.466 | 23.868 | 1.00 | 26.62 |
| 4478 | CD1 | LEU | A | 509 | 119.974 | −17.686 | 23.523 | 1.00 | 24.31 |
| 4479 | CD2 | LEU | A | 509 | 120.138 | −15.188 | 23.358 | 1.00 | 24.23 |
| 4480 | C | LEU | A | 509 | 123.208 | −17.569 | 25.124 | 1.00 | 23.75 |
| 4481 | O | LEU | A | 509 | 123.962 | −16.599 | 25.007 | 1.00 | 25.20 |
| 4482 | N | GLU | A | 510 | 123.440 | −18.731 | 24.530 | 1.00 | 24.94 |
| 4483 | CA | GLU | A | 510 | 124.591 | −18.939 | 23.667 | 1.00 | 28.02 |
| 4484 | CB | GLU | A | 510 | 124.928 | −20.417 | 23.697 | 1.00 | 33.42 |
| 4485 | CG | GLU | A | 510 | 125.672 | −20.868 | 24.983 | 1.00 | 48.31 |
| 4486 | CD | GLU | A | 510 | 125.933 | −22.385 | 25.073 | 1.00 | 55.77 |
| 4487 | OE1 | GLU | A | 510 | 125.078 | −23.125 | 25.488 | 1.00 | 58.30 |
| 4488 | OE2 | GLU | A | 510 | 126.986 | −22.914 | 24.726 | 1.00 | 61.23 |
| 4489 | C | GLU | A | 510 | 124.244 | −18.498 | 22.237 | 1.00 | 25.47 |
| 4490 | O | GLU | A | 510 | 123.246 | −18.944 | 21.689 | 1.00 | 25.48 |
| 4491 | N | VAL | A | 511 | 125.045 | −17.628 | 21.630 | 1.00 | 22.00 |
| 4492 | CA | VAL | A | 511 | 124.740 | −17.185 | 20.272 | 1.00 | 24.92 |
| 4493 | CB | VAL | A | 511 | 124.604 | −15.636 | 20.191 | 1.00 | 20.93 |
| 4494 | CG1 | VAL | A | 511 | 123.552 | −15.159 | 21.188 | 1.00 | 18.59 |
| 4495 | CG2 | VAL | A | 511 | 125.954 | −14.969 | 20.440 | 1.00 | 15.27 |
| 4496 | C | VAL | A | 511 | 125.813 | −17.641 | 19.295 | 1.00 | 24.35 |
| 4497 | O | VAL | A | 511 | 126.905 | −17.998 | 19.709 | 1.00 | 24.46 |
| 4498 | N | THR | A | 512 | 125.517 | −17.638 | 17.997 | 1.00 | 23.08 |
| 4499 | CA | THR | A | 512 | 126.511 | −18.072 | 17.014 | 1.00 | 28.48 |
| 4500 | CB | THR | A | 512 | 125.910 | −18.999 | 15.950 | 1.00 | 25.49 |
| 4501 | OG1 | THR | A | 512 | 124.921 | −18.280 | 15.208 | 1.00 | 23.83 |
| 4502 | CG2 | THR | A | 512 | 125.285 | −20.218 | 16.594 | 1.00 | 23.99 |
| 4503 | C | THR | A | 512 | 127.078 | −16.873 | 16.303 | 1.00 | 33.77 |
| 4504 | O | THR | A | 512 | 126.508 | −15.788 | 16.368 | 1.00 | 27.20 |
| 4505 | N | ARG | A | 513 | 128.197 | −17.078 | 15.619 | 1.00 | 34.77 |
| 4506 | CA | ARG | A | 513 | 128.851 | −16.016 | 14.882 | 1.00 | 38.69 |
| 4507 | CB | ARG | A | 513 | 130.177 | −16.530 | 14.308 | 1.00 | 47.61 |
| 4508 | CG | ARG | A | 513 | 131.040 | −15.466 | 13.661 | 1.00 | 68.49 |
| 4509 | CD | ARG | A | 513 | 132.401 | −16.003 | 13.215 | 1.00 | 83.86 |
| 4510 | NE | ARG | A | 513 | 133.266 | −14.926 | 12.737 | 1.00 | 95.74 |
| 4511 | CZ | ARG | A | 513 | 133.265 | −13.686 | 13.231 | 1.00 | 100.54 |
| 4512 | NH1 | ARG | A | 513 | 132.441 | −13.355 | 14.218 | 1.00 | 102.90 |
| 4513 | NH2 | ARG | A | 513 | 134.086 | −12.768 | 12.740 | 1.00 | 102.48 |
| 4514 | C | ARG | A | 513 | 127.928 | −15.531 | 13.758 | 1.00 | 39.27 |
| 4515 | O | ARG | A | 513 | 127.857 | −14.332 | 13.476 | 1.00 | 34.73 |
| 4516 | N | ALA | A | 514 | 127.222 | −16.463 | 13.124 | 1.00 | 36.15 |
| 4517 | CA | ALA | A | 514 | 126.308 | −16.126 | 12.041 | 1.00 | 34.51 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4518 | CB | ALA | A | 514 | 125.664 | −17.398 | 11.488 | 1.00 | 30.58 |
| 4519 | C | ALA | A | 514 | 125.228 | −15.163 | 12.530 | 1.00 | 35.15 |
| 4520 | O | ALA | A | 514 | 124.819 | −14.253 | 11.809 | 1.00 | 34.79 |
| 4521 | N | GLU | A | 515 | 124.784 | −15.359 | 13.766 | 1.00 | 36.39 |
| 4522 | CA | GLU | A | 515 | 123.748 | −14.511 | 14.330 | 1.00 | 35.38 |
| 4523 | CB | GLU | A | 515 | 123.189 | −15.138 | 15.604 | 1.00 | 34.80 |
| 4524 | CG | GLU | A | 515 | 122.498 | −16.445 | 15.352 | 1.00 | 38.84 |
| 4525 | CD | GLU | A | 515 | 121.924 | −17.045 | 16.613 | 1.00 | 41.13 |
| 4526 | OE1 | GLU | A | 515 | 120.868 | −16.573 | 17.072 | 1.00 | 42.83 |
| 4527 | OE2 | GLU | A | 515 | 122.534 | −17.986 | 17.156 | 1.00 | 43.73 |
| 4528 | C | GLU | A | 515 | 124.160 | −13.081 | 14.610 | 1.00 | 32.91 |
| 4529 | O | GLU | A | 515 | 123.449 | −12.149 | 14.223 | 1.00 | 34.66 |
| 4530 | N | TRP | A | 516 | 125.284 | −12.871 | 15.281 | 1.00 | 32.25 |
| 4531 | CA | TRP | A | 516 | 125.646 | −11.494 | 15.554 | 1.00 | 39.48 |
| 4532 | CB | TRP | A | 516 | 126.532 | −11.379 | 16.797 | 1.00 | 42.20 |
| 4533 | CG | TRP | A | 516 | 127.961 | −11.723 | 16.613 | 1.00 | 44.29 |
| 4534 | CD2 | TRP | A | 516 | 128.618 | −12.895 | 17.101 | 1.00 | 46.49 |
| 4535 | CE2 | TRP | A | 516 | 129.982 | −12.777 | 16.750 | 1.00 | 48.09 |
| 4536 | CE3 | TRP | A | 516 | 128.183 | −14.032 | 17.777 | 1.00 | 49.29 |
| 4537 | CD1 | TRP | A | 516 | 128.921 | −10.963 | 16.014 | 1.00 | 43.86 |
| 4538 | NE1 | TRP | A | 516 | 130.144 | −11.592 | 16.098 | 1.00 | 47.32 |
| 4539 | CZ2 | TRP | A | 516 | 130.916 | −13.756 | 17.093 | 1.00 | 50.92 |
| 4540 | CZ3 | TRP | A | 516 | 129.109 | −14.998 | 18.111 | 1.00 | 52.39 |
| 4541 | CH2 | TRP | A | 516 | 130.461 | −14.860 | 17.758 | 1.00 | 53.07 |
| 4542 | C | TRP | A | 516 | 126.301 | −10.897 | 14.330 | 1.00 | 44.14 |
| 4543 | O | TRP | A | 516 | 126.788 | −9.763 | 14.349 | 1.00 | 39.35 |
| 4544 | N | ALA | A | 517 | 126.280 | −11.675 | 13.253 | 1.00 | 46.02 |
| 4545 | CA | ALA | A | 517 | 126.819 | −11.244 | 11.976 | 1.00 | 53.54 |
| 4546 | CB | ALA | A | 517 | 127.310 | −12.440 | 11.176 | 1.00 | 52.61 |
| 4547 | C | ALA | A | 517 | 125.699 | −10.515 | 11.225 | 1.00 | 58.52 |
| 4548 | O | ALA | A | 517 | 125.974 | −9.584 | 10.478 | 1.00 | 50.10 |
| 4549 | N | GLN | A | 518 | 124.446 | −10.940 | 11.432 | 1.00 | 57.92 |
| 4550 | CA | GLN | A | 518 | 123.278 | −10.308 | 10.797 | 1.00 | 53.77 |
| 4551 | CB | GLN | A | 518 | 121.984 | −11.140 | 10.953 | 1.00 | 42.41 |
| 4552 | CG | GLN | A | 518 | 122.061 | −12.672 | 10.878 | 1.00 | 63.18 |
| 4553 | CD | GLN | A | 518 | 120.889 | −13.354 | 11.617 | 1.00 | 61.65 |
| 4554 | OE1 | GLN | A | 518 | 119.906 | −12.690 | 12.005 | 1.00 | 53.15 |
| 4555 | NE2 | GLN | A | 518 | 120.989 | −14.679 | 11.815 | 1.00 | 54.25 |
| 4556 | C | GLN | A | 518 | 123.002 | −9.004 | 11.533 | 1.00 | 55.47 |
| 4557 | O | GLN | A | 518 | 122.663 | −7.984 | 10.927 | 1.00 | 47.44 |
| 4558 | N | LYS | A | 519 | 123.122 | −9.082 | 12.857 | 1.00 | 57.17 |
| 4559 | CA | LYS | A | 519 | 122.862 | −7.967 | 13.755 | 1.00 | 48.79 |
| 4560 | CB | LYS | A | 519 | 121.346 | −7.835 | 13.943 | 1.00 | 46.07 |
| 4561 | CG | LYS | A | 519 | 120.886 | −6.721 | 14.856 | 1.00 | 52.76 |
| 4562 | CD | LYS | A | 519 | 120.869 | −5.400 | 14.131 | 1.00 | 56.03 |
| 4563 | CE | LYS | A | 519 | 119.932 | −4.421 | 14.825 | 1.00 | 57.45 |
| 4564 | NZ | LYS | A | 519 | 119.932 | −3.094 | 14.153 | 1.00 | 60.89 |
| 4565 | CD | LYS | A | 519 | 123.531 | −8.291 | 15.085 | 1.00 | 44.92 |
| 4566 | O | LYS | A | 519 | 123.138 | −9.245 | 15.759 | 1.00 | 43.71 |
| 4567 | N | ASP | A | 520 | 124.547 | −7.512 | 15.450 | 1.00 | 46.03 |
| 4568 | CA | ASP | A | 520 | 125.258 | −7.738 | 16.703 | 1.00 | 50.34 |
| 4569 | CB | ASP | A | 520 | 126.602 | −7.001 | 16.716 | 1.00 | 54.86 |
| 4570 | CG | ASP | A | 520 | 127.484 | −7.417 | 17.886 | 1.00 | 49.22 |
| 4571 | OD1 | ASP | A | 520 | 126.980 | −8.092 | 18.809 | 1.00 | 48.63 |
| 4572 | OD2 | ASP | A | 520 | 128.681 | −7.067 | 17.890 | 1.00 | 48.49 |
| 4573 | C | ASP | A | 520 | 124.413 | −7.260 | 17.885 | 1.00 | 46.85 |
| 4574 | O | ASP | A | 520 | 124.940 | −6.979 | 18.958 | 1.00 | 55.94 |
| 4575 | N | GLU | A | 521 | 123.102 | −7.171 | 17.693 | 1.00 | 47.52 |
| 4576 | CA | GLU | A | 521 | 122.228 | −6.722 | 18.764 | 1.00 | 44.27 |
| 4577 | CB | GLU | A | 521 | 121.354 | −5.572 | 18.276 | 1.00 | 51.74 |
| 4578 | CG | GLU | A | 521 | 120.412 | −5.036 | 19.332 | 1.00 | 62.88 |
| 4579 | CD | GLU | A | 521 | 120.595 | −3.588 | 19.537 | 1.00 | 69.32 |
| 4580 | OE1 | GLU | A | 521 | 121.725 | −3.253 | 19.759 | 1.00 | 73.69 |
| 4581 | OE2 | GLU | A | 521 | 119.674 | −2.766 | 19.490 | 1.00 | 72.61 |
| 4582 | C | GLU | A | 521 | 121.339 | −7.834 | 19.305 | 1.00 | 37.55 |
| 4583 | O | GLU | A | 521 | 120.670 | −8.533 | 18.546 | 1.00 | 37.86 |
| 4584 | N | PHE | A | 522 | 121.345 | −7.991 | 20.624 | 1.00 | 34.94 |
| 4585 | CA | PHE | A | 522 | 120.527 | −8.997 | 21.286 | 1.00 | 27.30 |
| 4586 | CB | PHE | A | 522 | 121.380 | −10.160 | 21.774 | 1.00 | 22.24 |
| 4587 | CG | PHE | A | 522 | 122.004 | −10.943 | 20.666 | 1.00 | 21.95 |
| 4588 | CD1 | PHE | A | 522 | 123.135 | −10.469 | 20.016 | 1.00 | 22.28 |
| 4589 | CD2 | PHE | A | 522 | 121.426 | −12.123 | 20.228 | 1.00 | 20.53 |
| 4590 | CE1 | PHE | A | 522 | 123.679 | −11.155 | 18.936 | 1.00 | 21.80 |
| 4591 | CE2 | PHE | A | 522 | 121.963 | −12.816 | 19.151 | 1.00 | 21.65 |
| 4592 | CZ | PHE | A | 522 | 123.097 | −12.325 | 18.502 | 1.00 | 19.81 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4593 | C | PHE | A | 522 | 119.801 | −8.355 | 22.451 | 1.00 | 25.32 |
| 4594 | O | PHE | A | 522 | 120.349 | −7.486 | 23.142 | 1.00 | 26.51 |
| 4595 | N | ILE | A | 523 | 118.568 | −8.782 | 22.681 | 1.00 | 27.16 |
| 4596 | CA | ILE | A | 523 | 117.798 | −8.167 | 23.737 | 1.00 | 28.62 |
| 4597 | CB | ILE | A | 523 | 116.613 | −7.375 | 23.129 | 1.00 | 32.25 |
| 4598 | CG2 | ILE | A | 523 | 115.737 | −6.790 | 24.226 | 1.00 | 34.35 |
| 4599 | CG1 | ILE | A | 523 | 117.165 | −6.278 | 22.218 | 1.00 | 34.41 |
| 4600 | CD1 | ILE | A | 523 | 116.142 | −5.329 | 21.713 | 1.00 | 39.74 |
| 4601 | C | ILE | A | 523 | 117.283 | −9.123 | 24.795 | 1.00 | 27.80 |
| 4602 | O | ILE | A | 523 | 116.664 | −10.154 | 24.492 | 1.00 | 27.51 |
| 4603 | N | CYS | A | 524 | 117.573 | −8.779 | 26.043 | 1.00 | 26.79 |
| 4604 | CA | CYS | A | 524 | 117.106 | −9.562 | 27.165 | 1.00 | 25.55 |
| 4605 | C | CYS | A | 524 | 115.864 | −8.820 | 27.647 | 1.00 | 24.31 |
| 4606 | O | CYS | A | 524 | 115.919 | −7.619 | 27.963 | 1.00 | 25.03 |
| 4607 | CB | CYS | A | 524 | 118.159 | −9.615 | 28.277 | 1.00 | 25.40 |
| 4608 | SG | CYS | A | 524 | 117.484 | −10.317 | 29.822 | 1.00 | 24.19 |
| 4609 | N | ARG | A | 525 | 114.740 | −9.518 | 27.687 | 1.00 | 22.50 |
| 4610 | CA | ARG | A | 525 | 113.505 | −8.864 | 28.107 | 1.00 | 26.44 |
| 4611 | CB | ARG | A | 525 | 112.522 | −8.794 | 26.936 | 1.00 | 27.22 |
| 4612 | CG | ARG | A | 525 | 111.121 | −8.413 | 27.359 | 1.00 | 30.02 |
| 4613 | CD | ARG | A | 525 | 110.498 | −7.489 | 26.345 | 1.00 | 34.02 |
| 4614 | NE | ARG | A | 525 | 110.045 | −8.198 | 25.158 | 1.00 | 37.23 |
| 4615 | CZ | ARG | A | 525 | 109.857 | −7.626 | 23.974 | 1.00 | 38.76 |
| 4616 | NH1 | ARG | A | 525 | 110.089 | −6.328 | 23.811 | 1.00 | 39.06 |
| 4617 | NH2 | ARG | A | 525 | 109.439 | −8.356 | 22.950 | 1.00 | 40.37 |
| 4618 | C | ARG | A | 525 | 112.807 | −9.501 | 29.286 | 1.00 | 24.74 |
| 4619 | O | ARG | A | 525 | 112.568 | −10.710 | 29.296 | 1.00 | 24.88 |
| 4620 | N | ALA | A | 526 | 112.447 | −8.668 | 30.255 | 1.00 | 21.83 |
| 4621 | CA | ALA | A | 526 | 111.767 | −9.127 | 31.451 | 1.00 | 24.10 |
| 4622 | CB | ALA | A | 526 | 112.483 | −8.596 | 32.685 | 1.00 | 22.84 |
| 4623 | C | ALA | A | 526 | 110.297 | −8.725 | 31.504 | 1.00 | 24.01 |
| 4624 | O | ALA | A | 526 | 109.961 | −7.550 | 31.367 | 1.00 | 23.34 |
| 4625 | N | VAL | A | 527 | 109.413 | −9.703 | 31.679 | 1.00 | 24.27 |
| 4626 | CA | VAL | A | 527 | 108.006 | −9.380 | 31.797 | 1.00 | 24.58 |
| 4627 | CB | VAL | A | 527 | 107.113 | −10.258 | 30.936 | 1.00 | 25.07 |
| 4628 | CG1 | VAL | A | 527 | 105.646 | −9.904 | 31.206 | 1.00 | 22.70 |
| 4629 | CG2 | VAL | A | 527 | 107.436 | −10.014 | 29.466 | 1.00 | 22.58 |
| 4630 | C | VAL | A | 527 | 107.665 | −9.570 | 33.256 | 1.00 | 24.73 |
| 4631 | O | VAL | A | 527 | 107.755 | −10.668 | 33.813 | 1.00 | 26.04 |
| 4632 | N | HIS | A | 528 | 107.316 | −8.465 | 33.888 | 1.00 | 25.71 |
| 4633 | CA | HIS | A | 528 | 106.982 | −8.474 | 35.292 | 1.00 | 27.34 |
| 4634 | CB | HIS | A | 528 | 108.232 | −8.197 | 36.128 | 1.00 | 26.86 |
| 4635 | CG | HIS | A | 528 | 107.998 | −8.259 | 37.612 | 1.00 | 26.66 |
| 4636 | CD2 | HIS | A | 528 | 108.268 | −9.235 | 38.505 | 1.00 | 26.70 |
| 4637 | ND1 | HIS | A | 528 | 107.451 | −7.214 | 38.311 | 1.00 | 28.32 |
| 4638 | CE1 | HIS | A | 528 | 107.395 | −7.544 | 39.598 | 1.00 | 28.99 |
| 4639 | NE2 | HIS | A | 528 | 107.882 | −8.755 | 39.740 | 1.00 | 29.26 |
| 4640 | C | HIS | A | 528 | 105.914 | −7.424 | 35.534 | 1.00 | 30.79 |
| 4641 | O | HIS | A | 528 | 105.938 | −6.309 | 34.991 | 1.00 | 28.65 |
| 4642 | N | GLU | A | 529 | 104.977 | −7.821 | 36.372 | 1.00 | 35.37 |
| 4643 | CA | GLU | A | 529 | 103.820 | −7.042 | 36.723 | 1.00 | 40.16 |
| 4644 | CB | GLU | A | 529 | 102.951 | −7.927 | 37.610 | 1.00 | 46.25 |
| 4645 | CG | GLU | A | 529 | 102.506 | −7.345 | 38.911 | 1.00 | 57.00 |
| 4646 | CD | GLU | A | 529 | 102.090 | −8.423 | 39.888 | 1.00 | 63.20 |
| 4647 | OE1 | GLU | A | 529 | 101.343 | −8.102 | 40.828 | 1.00 | 65.51 |
| 4648 | OE2 | GLU | A | 529 | 102.516 | −9.587 | 39.717 | 1.00 | 67.73 |
| 4649 | C | GLU | A | 529 | 104.029 | −5.656 | 37.330 | 1.00 | 39.67 |
| 4650 | O | GLU | A | 529 | 103.121 | −4.824 | 37.281 | 1.00 | 40.76 |
| 4651 | N | ALA | A | 530 | 105.209 | −5.396 | 37.884 | 1.00 | 42.59 |
| 4652 | CA | ALA | A | 530 | 105.469 | −4.089 | 38.474 | 1.00 | 42.78 |
| 4653 | CB | ALA | A | 530 | 106.242 | −4.240 | 39.785 | 1.00 | 43.66 |
| 4654 | C | ALA | A | 530 | 106.226 | −3.170 | 37.512 | 1.00 | 45.04 |
| 4655 | O | ALA | A | 530 | 106.358 | −1.977 | 37.770 | 1.00 | 45.66 |
| 4656 | N | ALA | A | 531 | 106.730 | −3.716 | 36.410 | 1.00 | 49.44 |
| 4657 | CA | ALA | A | 531 | 107.446 | −2.906 | 35.420 | 1.00 | 56.07 |
| 4658 | CB | ALA | A | 531 | 108.016 | −3.825 | 34.332 | 1.00 | 50.05 |
| 4659 | C | ALA | A | 531 | 106.468 | −1.883 | 34.804 | 1.00 | 63.25 |
| 4660 | O | ALA | A | 531 | 105.497 | −2.281 | 34.173 | 1.00 | 61.13 |
| 4661 | N | SER | A | 532 | 106.733 | −0.585 | 34.984 | 1.00 | 68.02 |
| 4662 | CA | SER | A | 532 | 105.881 | 0.519 | 34.494 | 1.00 | 77.23 |
| 4663 | CB | SER | A | 532 | 106.772 | 1.713 | 34.138 | 1.00 | 88.37 |
| 4664 | OG | SER | A | 532 | 107.609 | 1.391 | 33.036 | 1.00 | 96.30 |
| 4665 | C | SER | A | 532 | 104.893 | 0.220 | 33.345 | 1.00 | 75.76 |
| 4666 | O | SER | A | 532 | 104.090 | −0.715 | 33.455 | 1.00 | 84.51 |
| 4667 | N | PRO | A | 533 | 104.922 | 1.014 | 32.237 | 1.00 | 73.86 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4668 | CD | PRO | A | 533 | 105.838 | 2.103 | 31.850 | 1.00 | 72.98 |
| 4669 | CA | PRO | A | 533 | 104.027 | 0.790 | 31.118 | 1.00 | 70.43 |
| 4670 | CB | PRO | A | 533 | 104.385 | 1.936 | 30.169 | 1.00 | 70.32 |
| 4671 | CG | PRO | A | 533 | 105.808 | 2.056 | 30.373 | 1.00 | 66.13 |
| 4672 | C | PRO | A | 533 | 104.271 | −0.565 | 30.499 | 1.00 | 68.21 |
| 4673 | O | PRO | A | 533 | 105.418 | −0.968 | 30.241 | 1.00 | 70.93 |
| 4674 | N | SER | A | 534 | 103.162 | −1.260 | 30.286 | 1.00 | 68.47 |
| 4675 | CA | SER | A | 534 | 103.158 | −2.567 | 29.667 | 1.00 | 63.21 |
| 4676 | CB | SER | A | 534 | 103.563 | −2.424 | 28.198 | 1.00 | 66.26 |
| 4677 | OG | SER | A | 534 | 104.416 | −1.310 | 28.001 | 1.00 | 77.59 |
| 4678 | C | SER | A | 534 | 103.964 | −3.676 | 30.332 | 1.00 | 57.35 |
| 4679 | O | SER | A | 534 | 104.356 | −4.634 | 29.671 | 1.00 | 54.48 |
| 4680 | N | GLN | A | 535 | 104.191 | −3.540 | 31.638 | 1.00 | 50.48 |
| 4681 | CA | GLN | A | 535 | 104.900 | −4.535 | 32.453 | 1.00 | 44.37 |
| 4682 | CB | GLN | A | 535 | 103.893 | −5.578 | 32.951 | 1.00 | 44.79 |
| 4683 | CG | GLN | A | 535 | 102.559 | −5.584 | 32.194 | 1.00 | 48.77 |
| 4684 | CD | GLN | A | 535 | 101.651 | −4.382 | 32.472 | 1.00 | 51.12 |
| 4685 | OE1 | GLN | A | 535 | 100.771 | −4.081 | 31.662 | 1.00 | 53.36 |
| 4686 | NE2 | GLN | A | 535 | 101.840 | −3.710 | 33.609 | 1.00 | 51.82 |
| 4687 | C | GLN | A | 535 | 106.089 | −5.233 | 31.794 | 1.00 | 40.35 |
| 4688 | O | GLN | A | 535 | 106.272 | −6.451 | 31.914 | 1.00 | 37.68 |
| 4689 | N | THR | A | 536 | 106.926 | −4.443 | 31.138 | 1.00 | 35.78 |
| 4690 | CA | THR | A | 536 | 108.072 | −4.992 | 30.441 | 1.00 | 37.02 |
| 4691 | CB | THR | A | 536 | 107.707 | −5.153 | 28.945 | 1.00 | 34.14 |
| 4692 | OG1 | THR | A | 536 | 108.861 | −5.521 | 28.195 | 1.00 | 33.95 |
| 4693 | CG2 | THR | A | 536 | 107.161 | −3.854 | 28.399 | 1.00 | 36.03 |
| 4694 | C | THR | A | 536 | 109.319 | −4.113 | 30.610 | 1.00 | 37.26 |
| 4695 | O | THR | A | 536 | 109.226 | −2.899 | 30.605 | 1.00 | 33.61 |
| 4696 | N | VAL | A | 537 | 110.478 | −4.735 | 30.789 | 1.00 | 38.22 |
| 4697 | CA | VAL | A | 537 | 111.739 | −4.004 | 30.924 | 1.00 | 36.69 |
| 4698 | CB | VAL | A | 537 | 112.199 | −3.903 | 32.384 | 1.00 | 44.91 |
| 4699 | CG1 | VAL | A | 537 | 113.437 | −3.029 | 32.468 | 1.00 | 52.00 |
| 4700 | CG2 | VAL | A | 537 | 111.094 | −3.335 | 33.242 | 1.00 | 53.70 |
| 4701 | C | VAL | A | 537 | 112.803 | −4.783 | 30.159 | 1.00 | 36.02 |
| 4702 | O | VAL | A | 537 | 112.890 | −5.999 | 30.297 | 1.00 | 34.60 |
| 4703 | N | GLN | A | 538 | 113.628 | −4.095 | 29.378 | 1.00 | 31.01 |
| 4704 | CA | GLN | A | 538 | 114.627 | −4.799 | 28.594 | 1.00 | 26.46 |
| 4705 | CB | GLN | A | 538 | 114.065 | −5.103 | 27.207 | 1.00 | 25.37 |
| 4706 | CG | GLN | A | 538 | 113.723 | −3.867 | 26.382 | 1.00 | 27.24 |
| 4707 | CD | GLN | A | 538 | 113.064 | −4.221 | 25.069 | 1.00 | 27.39 |
| 4708 | OE1 | GLN | A | 538 | 112.019 | −4.892 | 25.051 | 1.00 | 27.87 |
| 4709 | NE2 | GLN | A | 538 | 113.660 | −3.777 | 23.955 | 1.00 | 27.61 |
| 4710 | C | GLN | A | 538 | 115.962 | −4.102 | 28.430 | 1.00 | 26.60 |
| 4711 | O | GLN | A | 538 | 116.069 | −2.892 | 28.615 | 1.00 | 25.92 |
| 4712 | N | ARG | A | 539 | 116.983 | −4.878 | 28.073 | 1.00 | 27.21 |
| 4713 | CA | ARG | A | 539 | 118.315 | −4.326 | 27.855 | 1.00 | 29.03 |
| 4714 | CB | ARG | A | 539 | 119.207 | −4.551 | 29.073 | 1.00 | 33.82 |
| 4715 | CG | ARG | A | 539 | 118.797 | −3.766 | 30.290 | 1.00 | 45.82 |
| 4716 | CD | ARG | A | 539 | 119.130 | −2.325 | 30.120 | 1.00 | 56.43 |
| 4717 | NE | ARG | A | 539 | 118.854 | −1.626 | 31.347 | 1.00 | 68.65 |
| 4718 | CZ | ARG | A | 539 | 119.056 | −0.336 | 31.508 | 1.00 | 74.27 |
| 4719 | NH1 | ARG | A | 539 | 119.535 | 0.400 | 30.512 | 1.00 | 77.81 |
| 4720 | NH2 | ARG | A | 539 | 118.780 | 0.208 | 32.672 | 1.00 | 77.14 |
| 4721 | C | ARG | A | 539 | 118.953 | −4.975 | 26.648 | 1.00 | 27.49 |
| 4722 | O | ARG | A | 539 | 118.895 | −6.193 | 26.485 | 1.00 | 24.32 |
| 4723 | N | ALA | A | 540 | 119.533 | −4.158 | 25.784 | 1.00 | 25.77 |
| 4724 | CA | ALA | A | 540 | 120.201 | −4.675 | 24.608 | 1.00 | 28.17 |
| 4725 | CB | ALA | A | 540 | 120.137 | −3.665 | 23.461 | 1.00 | 23.76 |
| 4726 | C | ALA | A | 540 | 121.656 | −4.927 | 24.997 | 1.00 | 30.51 |
| 4727 | O | ALA | A | 540 | 122.171 | −4.336 | 25.947 | 1.00 | 28.70 |
| 4728 | N | VAL | A | 541 | 122.313 | −5.814 | 24.265 | 1.00 | 32.38 |
| 4729 | CA | VAL | A | 541 | 123.710 | −6.113 | 24.520 | 1.00 | 35.53 |
| 4730 | CB | VAL | A | 541 | 123.876 | −7.260 | 25.562 | 1.00 | 34.65 |
| 4731 | CG1 | VAL | A | 541 | 123.549 | −8.612 | 24.940 | 1.00 | 37.28 |
| 4732 | CG2 | VAL | A | 541 | 125.293 | −7.253 | 26.111 | 1.00 | 39.82 |
| 4733 | C | VAL | A | 541 | 124.324 | −6.539 | 23.198 | 1.00 | 39.04 |
| 4734 | O | VAL | A | 541 | 123.663 | −7.188 | 22.379 | 1.00 | 35.21 |
| 4735 | N | SER | A | 542 | 125.566 | −6.147 | 22.953 | 1.00 | 37.40 |
| 4736 | CA | SER | A | 542 | 126.201 | −6.574 | 21.713 | 1.00 | 39.79 |
| 4737 | CB | SER | A | 542 | 126.329 | −5.457 | 20.683 | 1.00 | 39.07 |
| 4738 | OG | SER | A | 542 | 126.284 | −4.208 | 21.240 | 1.00 | 43.33 |
| 4739 | C | SER | A | 542 | 127.549 | −7.208 | 21.911 | 1.00 | 41.89 |
| 4740 | O | SER | A | 542 | 128.280 | −6.893 | 22.846 | 1.00 | 36.93 |
| 4741 | N | VAL | A | 543 | 127.848 | −8.127 | 21.004 | 1.00 | 39.71 |
| 4742 | CA | VAL | A | 543 | 129.083 | −8.891 | 20.985 | 1.00 | 42.22 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4743 | CB | VAL | A | 543 | 128.853 | −10.289 | 20.322 | 1.00 | 40.40 |
| 4744 | CG1 | VAL | A | 543 | 130.083 | −11.157 | 20.470 | 1.00 | 39.36 |
| 4745 | CG2 | VAL | A | 543 | 127.637 | −10.974 | 20.926 | 1.00 | 39.75 |
| 4746 | C | VAL | A | 543 | 130.157 | −8.182 | 20.175 | 1.00 | 45.75 |
| 4747 | O | VAL | A | 543 | 130.645 | −8.769 | 19.223 | 1.00 | 49.18 |
| 4748 | N | ASN | A | 544 | 130.551 | −6.948 | 20.531 | 1.00 | 44.39 |
| 4749 | CA | ASN | A | 544 | 131.601 | −6.228 | 19.712 | 1.00 | 42.33 |
| 4750 | CB | ASN | A | 544 | 131.893 | −4.893 | 20.518 | 1.00 | 40.03 |
| 4751 | CG | ASN | A | 544 | 130.636 | −4.269 | 21.042 | 1.00 | 34.18 |
| 4752 | OD1 | ASN | A | 544 | 129.772 | −3.834 | 20.287 | 1.00 | 30.92 |
| 4753 | ND2 | ASN | A | 544 | 130.528 | −4.224 | 22.360 | 1.00 | 31.70 |
| 4754 | C | ASN | A | 544 | 132.877 | −7.140 | 19.163 | 1.00 | 41.76 |
| 4755 | O | ASN | A | 544 | 133.857 | −7.033 | 20.312 | 1.00 | 42.58 |
| 4756 | N | PRO | A | 545 | 132.824 | −8.107 | 17.813 | 1.00 | 46.14 |
| 4757 | CD | PRO | A | 545 | 131.539 | −7.639 | 17.320 | 1.00 | 45.69 |
| 4758 | CA | PRO | A | 545 | 133.175 | −9.132 | 16.606 | 1.00 | 48.68 |
| 4759 | CB | PRO | A | 545 | 133.424 | −10.144 | 17.408 | 1.00 | 48.80 |
| 4760 | CG | PRO | A | 545 | 131.994 | −8.908 | 16.640 | 1.00 | 46.57 |
| 4761 | C | PRO | A | 545 | 132.444 | −10.213 | 15.161 | 1.00 | 51.57 |
| 4762 | O | PRO | A | 545 | 133.076 | −9.953 | 14.343 | 1.00 | 56.79 |
| 4763 | OXT | PRO | A | 545 | 132.030 | −10.461 | 14.166 | 1.00 | 54.39 |
| 4764 | CB | VAL | B | 336 | 111.292 | −40.500 | 56.950 | 1.00 | 66.82 |
| 4765 | CG1 | VAL | B | 336 | 112.704 | −40.638 | 57.493 | 1.00 | 69.03 |
| 4766 | CG2 | VAL | B | 336 | 110.292 | −40.359 | 58.072 | 1.00 | 70.00 |
| 4767 | C | VAL | B | 336 | 112.246 | −39.492 | 54.925 | 1.00 | 61.20 |
| 4768 | O | VAL | B | 336 | 112.565 | −40.629 | 54.585 | 1.00 | 61.82 |
| 4769 | N | VAL | B | 336 | 109.840 | −39.122 | 55.442 | 1.00 | 66.00 |
| 4770 | CA | VAL | B | 336 | 111.208 | −39.284 | 56.016 | 1.00 | 64.64 |
| 4771 | N | SER | B | 337 | 112.765 | −38.400 | 54.376 | 1.00 | 54.79 |
| 4772 | CA | SER | B | 337 | 113.772 | −38.476 | 53.328 | 1.00 | 47.86 |
| 4773 | CB | SER | B | 337 | 113.554 | −37.344 | 52.319 | 1.00 | 47.10 |
| 4774 | OG | SER | B | 337 | 113.425 | −36.095 | 52.978 | 1.00 | 46.57 |
| 4775 | C | SER | B | 337 | 115.188 | −38.405 | 53.921 | 1.00 | 45.14 |
| 4776 | O | SER | B | 337 | 115.403 | −37.859 | 55.007 | 1.00 | 42.62 |
| 4777 | N | ALA | B | 338 | 116.149 | −38.982 | 53.212 | 1.00 | 41.13 |
| 4778 | CA | ALA | B | 338 | 117.536 | −38.971 | 53.652 | 1.00 | 38.74 |
| 4779 | CB | ALA | B | 338 | 117.970 | −40.358 | 54.077 | 1.00 | 37.56 |
| 4780 | C | ALA | B | 338 | 118.374 | −38.494 | 52.485 | 1.00 | 37.95 |
| 4781 | O | ALA | B | 338 | 118.093 | −38.833 | 51.337 | 1.00 | 35.97 |
| 4782 | N | TYR | B | 339 | 119.395 | −37.696 | 52.773 | 1.00 | 38.87 |
| 4783 | CA | TYR | B | 339 | 120.259 | −37.175 | 51.723 | 1.00 | 40.11 |
| 4784 | CB | TYR | B | 339 | 119.916 | −35.717 | 51.408 | 1.00 | 42.80 |
| 4785 | CG | TYR | B | 339 | 118.443 | −35.412 | 51.240 | 1.00 | 49.13 |
| 4786 | CD1 | TYR | B | 339 | 117.568 | −35.494 | 52.318 | 1.00 | 51.74 |
| 4787 | CE1 | TYR | B | 339 | 116.217 | −35.176 | 52.179 | 1.00 | 55.70 |
| 4788 | CD2 | TYR | B | 339 | 117.929 | −35.004 | 50.008 | 1.00 | 51.59 |
| 4789 | CE2 | TYR | B | 339 | 116.582 | −34.682 | 49.857 | 1.00 | 55.45 |
| 4790 | CZ | TYR | B | 339 | 115.730 | −34.770 | 50.947 | 1.00 | 56.59 |
| 4791 | OH | TYR | B | 339 | 114.397 | −34.455 | 50.806 | 1.00 | 59.26 |
| 4792 | C | TYR | B | 339 | 121.723 | −37.260 | 52.137 | 1.00 | 39.32 |
| 4793 | O | TYR | B | 339 | 122.066 | −37.132 | 53.317 | 1.00 | 38.72 |
| 4794 | N | LEU | B | 340 | 122.588 | −37.469 | 51.153 | 1.00 | 39.09 |
| 4795 | CA | LEU | B | 340 | 124.015 | −37.569 | 51.418 | 1.00 | 40.25 |
| 4796 | CB | LEU | B | 340 | 124.465 | −39.028 | 51.344 | 1.00 | 39.62 |
| 4797 | CG | LEU | B | 340 | 125.917 | −39.306 | 51.740 | 1.00 | 39.99 |
| 4798 | CD1 | LEU | B | 340 | 126.158 | −38.828 | 53.159 | 1.00 | 39.47 |
| 4799 | CD2 | LEU | B | 340 | 126.205 | −40.795 | 51.635 | 1.00 | 39.10 |
| 4800 | C | LEU | B | 340 | 124.776 | −36.719 | 50.412 | 1.00 | 40.70 |
| 4801 | O | LEU | B | 340 | 124.707 | −36.942 | 49.200 | 1.00 | 41.27 |
| 4802 | N | SER | B | 341 | 125.502 | −35.733 | 50.920 | 1.00 | 39.57 |
| 4803 | CA | SER | B | 341 | 126.243 | −34.849 | 50.041 | 1.00 | 38.00 |
| 4804 | CB | SER | B | 341 | 126.227 | −33.429 | 50.606 | 1.00 | 39.93 |
| 4805 | OG | SER | B | 341 | 126.863 | −33.390 | 51.871 | 1.00 | 48.15 |
| 4806 | C | SER | B | 341 | 127.677 | −35.288 | 49.810 | 1.00 | 34.22 |
| 4807 | O | SER | B | 341 | 128.159 | −36.239 | 50.426 | 1.00 | 33.57 |
| 4808 | N | ARG | B | 342 | 128.338 | −34.601 | 48.885 | 1.00 | 29.55 |
| 4809 | CA | ARG | B | 342 | 129.735 | −34.854 | 48.573 | 1.00 | 24.20 |
| 4810 | CB | ARG | B | 342 | 129.963 | −34.873 | 47.052 | 1.00 | 22.12 |
| 4811 | CG | ARG | B | 342 | 129.371 | −36.094 | 46.346 | 1.00 | 23.59 |
| 4812 | CD | ARG | B | 342 | 129.748 | −36.157 | 44.865 | 1.00 | 25.79 |
| 4813 | NE | ARG | B | 342 | 129.097 | −35.106 | 44.077 | 1.00 | 30.82 |
| 4814 | CZ | ARG | B | 342 | 127.819 | −35.124 | 43.692 | 1.00 | 32.49 |
| 4815 | NH1 | ARG | B | 342 | 127.030 | −36.145 | 44.014 | 1.00 | 34.00 |
| 4816 | NH2 | ARG | B | 342 | 127.325 | −34.116 | 42.983 | 1.00 | 32.85 |
| 4817 | C | ARG | B | 342 | 130.486 | −33.686 | 49.203 | 1.00 | 20.80 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4818 | O | ARG | B | 342 | 129.885 | −32.679 | 49.550 | 1.00 | 21.00 |
| 4819 | N | PRO | B | 343 | 131.807 | −33.807 | 49.365 | 1.00 | 24.10 |
| 4820 | CD | PRO | B | 343 | 132.657 | −34.964 | 49.035 | 1.00 | 20.95 |
| 4821 | CA | PRO | B | 343 | 132.574 | −32.706 | 49.963 | 1.00 | 22.21 |
| 4822 | CB | PRO | B | 343 | 133.989 | −33.267 | 50.096 | 1.00 | 19.13 |
| 4823 | CG | PRO | B | 343 | 133.857 | −34.749 | 49.894 | 1.00 | 20.93 |
| 4824 | C | PRO | B | 343 | 132.572 | −31.482 | 49.057 | 1.00 | 22.22 |
| 4825 | O | PRO | B | 343 | 132.624 | −31.618 | 47.850 | 1.00 | 25.72 |
| 4826 | N | SER | B | 344 | 132.519 | −30.288 | 49.629 | 1.00 | 24.52 |
| 4827 | CA | SER | B | 344 | 132.558 | −29.084 | 48.809 | 1.00 | 26.08 |
| 4828 | CB | SER | B | 344 | 132.306 | −27.835 | 49.659 | 1.00 | 26.01 |
| 4829 | OG | SER | B | 344 | 133.450 | −27.517 | 50.428 | 1.00 | 30.60 |
| 4830 | C | SER | B | 344 | 133.967 | −29.009 | 48.233 | 1.00 | 24.34 |
| 4831 | O | SER | B | 344 | 134.932 | −29.334 | 48.913 | 1.00 | 24.03 |
| 4832 | N | PRO | B | 345 | 134.108 | −28.575 | 46.975 | 1.00 | 23.08 |
| 4833 | CD | PRO | B | 345 | 133.036 | −28.158 | 46.052 | 1.00 | 22.01 |
| 4834 | CA | PRO | B | 345 | 135.447 | −28.473 | 46.366 | 1.00 | 22.91 |
| 4835 | CB | PRO | B | 345 | 135.180 | −27.910 | 44.966 | 1.00 | 22.50 |
| 4836 | CG | PRO | B | 345 | 133.709 | −28.266 | 44.694 | 1.00 | 20.06 |
| 4837 | C | PRO | B | 345 | 136.381 | −27.553 | 47.174 | 1.00 | 25.08 |
| 4838 | O | PRO | B | 345 | 137.610 | −27.735 | 47.170 | 1.00 | 22.21 |
| 4839 | N | PHE | B | 346 | 135.800 | −26.555 | 47.841 | 1.00 | 28.85 |
| 4840 | CA | PHE | B | 346 | 136.564 | −25.622 | 48.667 | 1.00 | 30.07 |
| 4841 | CB | PHE | B | 346 | 135.649 | −24.528 | 49.236 | 1.00 | 32.97 |
| 4842 | CG | PHE | B | 346 | 136.324 | −23.612 | 50.235 | 1.00 | 36.01 |
| 4843 | CD1 | PHE | B | 346 | 137.490 | −22.928 | 49.897 | 1.00 | 36.80 |
| 4844 | CD2 | PHE | B | 346 | 135.766 | −23.404 | 51.500 | 1.00 | 35.33 |
| 4845 | CE1 | PHE | B | 346 | 138.086 | −22.039 | 50.799 | 1.00 | 38.31 |
| 4846 | CE2 | PHE | B | 346 | 136.354 | −22.520 | 52.404 | 1.00 | 37.90 |
| 4847 | CZ | PHE | B | 346 | 137.519 | −21.836 | 52.051 | 1.00 | 37.56 |
| 4848 | C | PHE | B | 346 | 137.195 | −26.403 | 49.817 | 1.00 | 29.98 |
| 4849 | O | PHE | B | 346 | 138.412 | −26.373 | 49.993 | 1.00 | 29.65 |
| 4850 | N | ASP | B | 347 | 136.364 | −27.099 | 50.594 | 1.00 | 30.63 |
| 4851 | CA | ASP | B | 347 | 136.848 | −27.894 | 51.725 | 1.00 | 30.73 |
| 4852 | CB | ASP | B | 347 | 135.683 | −28.579 | 52.430 | 1.00 | 28.58 |
| 4853 | CG | ASP | B | 347 | 134.948 | −27.658 | 53.364 | 1.00 | 28.99 |
| 4854 | OD1 | ASP | B | 347 | 133.849 | −28.048 | 53.819 | 1.00 | 26.94 |
| 4855 | OD2 | ASP | B | 347 | 135.473 | −26.557 | 53.649 | 1.00 | 29.06 |
| 4856 | C | ASP | B | 347 | 137.836 | −28.966 | 51.271 | 1.00 | 29.99 |
| 4857 | O | ASP | B | 347 | 138.819 | −29.259 | 51.954 | 1.00 | 30.06 |
| 4858 | N | LEU | B | 348 | 137.570 | −29.540 | 50.107 | 1.00 | 29.14 |
| 4859 | CA | LEU | B | 348 | 138.407 | −30.595 | 49.574 | 1.00 | 28.49 |
| 4860 | CB | LEU | B | 348 | 137.605 | −31.398 | 48.552 | 1.00 | 25.00 |
| 4861 | CG | LEU | B | 348 | 138.339 | −32.481 | 47.753 | 1.00 | 21.65 |
| 4862 | CD1 | LEU | B | 348 | 138.720 | −33.620 | 48.677 | 1.00 | 14.78 |
| 4863 | CD2 | LEU | B | 348 | 137.433 | −33.009 | 46.614 | 1.00 | 18.44 |
| 4864 | C | LEU | B | 348 | 139.748 | −30.179 | 48.956 | 1.00 | 30.76 |
| 4865 | O | LEU | B | 348 | 140.741 | −30.890 | 49.126 | 1.00 | 31.51 |
| 4866 | N | PHE | B | 349 | 139.800 | −29.033 | 48.270 | 1.00 | 32.44 |
| 4867 | CA | PHE | B | 349 | 141.038 | −28.612 | 47.611 | 1.00 | 34.05 |
| 4868 | CB | PHE | B | 349 | 140.767 | −28.307 | 46.138 | 1.00 | 29.03 |
| 4869 | CG | PHE | B | 349 | 140.249 | −29.475 | 45.361 | 1.00 | 25.23 |
| 4870 | CD1 | PHE | B | 349 | 138.989 | −29.425 | 44.766 | 1.00 | 22.05 |
| 4871 | CD2 | PHE | B | 349 | 141.014 | −30.622 | 45.210 | 1.00 | 21.74 |
| 4872 | CE1 | PHE | B | 349 | 138.500 | −30.505 | 44.028 | 1.00 | 21.32 |
| 4873 | CE2 | PHE | B | 349 | 140.531 | −31.720 | 44.465 | 1.00 | 20.92 |
| 4874 | CZ | PHE | B | 349 | 139.271 | −31.659 | 43.875 | 1.00 | 19.67 |
| 4875 | C | PHE | B | 349 | 141.801 | −27.427 | 48.202 | 1.00 | 36.28 |
| 4876 | O | PHE | B | 349 | 143.016 | −27.341 | 48.052 | 1.00 | 38.64 |
| 4877 | N | ILE | B | 350 | 141.103 | −26.506 | 48.850 | 1.00 | 39.48 |
| 4878 | CA | ILE | B | 350 | 141.763 | −25.338 | 49.413 | 1.00 | 42.74 |
| 4879 | CB | ILE | B | 350 | 140.883 | −24.073 | 49.175 | 1.00 | 44.32 |
| 4880 | CG2 | ILE | B | 350 | 141.560 | −22.827 | 49.739 | 1.00 | 43.44 |
| 4881 | CG1 | ILE | B | 350 | 140.619 | −23.900 | 47.670 | 1.00 | 44.35 |
| 4882 | CD1 | ILE | B | 350 | 141.868 | −23.699 | 46.831 | 1.00 | 40.58 |
| 4883 | C | ILE | B | 350 | 142.029 | −25.535 | 50.913 | 1.00 | 43.65 |
| 4884 | O | ILE | B | 350 | 143.179 | −25.512 | 51.374 | 1.00 | 44.85 |
| 4885 | N | ARG | B | 351 | 140.949 | −25.746 | 51.655 | 1.00 | 41.98 |
| 4886 | CA | ARG | B | 351 | 140.997 | −25.944 | 53.089 | 1.00 | 40.60 |
| 4887 | CB | ARG | B | 351 | 139.588 | −25.812 | 53.641 | 1.00 | 38.21 |
| 4888 | CG | ARG | B | 351 | 139.533 | −25.283 | 55.035 | 1.00 | 37.55 |
| 4889 | CD | ARG | B | 351 | 138.175 | −24.742 | 55.318 | 1.00 | 38.51 |
| 4890 | NE | ARG | B | 351 | 137.919 | −24.704 | 56.746 | 1.00 | 44.60 |
| 4891 | CZ | ARG | B | 351 | 137.384 | −25.706 | 57.427 | 1.00 | 47.47 |
| 4892 | NH1 | ARG | B | 351 | 137.052 | −26.807 | 56.794 | 1.00 | 50.01 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4893 | NH2 | ARG | B | 351 | 137.183 | −25.620 | 58.733 | 1.00 | 47.59 |
| 4894 | C | ARG | B | 351 | 141.583 | −27.308 | 53.435 | 1.00 | 40.39 |
| 4895 | O | ARG | B | 351 | 142.049 | −27.535 | 54.549 | 1.00 | 37.34 |
| 4896 | N | LYS | B | 352 | 141.544 | −28.214 | 52.466 | 1.00 | 41.33 |
| 4897 | CA | LYS | B | 352 | 142.080 | −29.558 | 52.634 | 1.00 | 44.09 |
| 4898 | CB | LYS | B | 352 | 143.592 | −29.503 | 52.774 | 1.00 | 55.04 |
| 4899 | CG | LYS | B | 352 | 144.269 | −28.782 | 51.644 | 1.00 | 68.19 |
| 4900 | CD | LYS | B | 352 | 145.387 | −29.621 | 51.098 | 1.00 | 79.60 |
| 4901 | CE | LYS | B | 352 | 145.876 | −29.105 | 49.765 | 1.00 | 86.64 |
| 4902 | NZ | LYS | B | 352 | 146.940 | −28.122 | 49.885 | 1.00 | 92.79 |
| 4903 | C | LYS | B | 352 | 141.526 | −30.324 | 53.817 | 1.00 | 39.87 |
| 4904 | O | LYS | B | 352 | 142.262 | −31.028 | 54.499 | 1.00 | 41.55 |
| 4905 | N | SER | B | 353 | 140.235 | −30.188 | 54.068 | 1.00 | 35.10 |
| 4906 | CA | SER | B | 353 | 139.620 | −30.896 | 55.164 | 1.00 | 31.84 |
| 4907 | CB | SER | B | 353 | 139.747 | −30.055 | 56.426 | 1.00 | 31.59 |
| 4908 | OG | SER | B | 353 | 138.691 | −30.273 | 57.308 | 1.00 | 35.63 |
| 4909 | C | SER | B | 353 | 138.179 | −31.138 | 54.743 | 1.00 | 27.68 |
| 4910 | O | SER | B | 353 | 137.264 | −30.418 | 55.134 | 1.00 | 27.48 |
| 4911 | N | PRO | B | 354 | 137.972 | −32.173 | 53.915 | 1.00 | 23.69 |
| 4912 | CD | PRO | B | 354 | 139.032 | −33.040 | 53.382 | 1.00 | 24.04 |
| 4913 | CA | PRO | B | 354 | 136.665 | −32.569 | 53.382 | 1.00 | 23.00 |
| 4914 | CB | PRO | B | 354 | 137.015 | −33.557 | 52.252 | 1.00 | 24.08 |
| 4915 | CG | PRO | B | 354 | 138.488 | −33.377 | 52.016 | 1.00 | 25.98 |
| 4916 | C | PRO | B | 354 | 135.768 | −33.214 | 54.411 | 1.00 | 21.75 |
| 4917 | O | PRO | B | 354 | 136.255 | −33.868 | 55.331 | 1.00 | 17.58 |
| 4918 | N | THR | B | 355 | 134.459 | −33.023 | 54.245 | 1.00 | 20.33 |
| 4919 | CA | THR | B | 355 | 133.450 | −33.614 | 55.121 | 1.00 | 18.07 |
| 4920 | CB | THR | B | 355 | 132.985 | −32.660 | 56.228 | 1.00 | 22.01 |
| 4921 | OG1 | THR | B | 355 | 132.334 | −31.530 | 55.638 | 1.00 | 22.72 |
| 4922 | CG2 | THR | B | 355 | 134.163 | −32.205 | 57.074 | 1.00 | 21.72 |
| 4923 | C | THR | B | 355 | 132.231 | −33.925 | 54.272 | 1.00 | 18.05 |
| 4924 | O | THR | B | 355 | 132.036 | −33.325 | 53.214 | 1.00 | 20.32 |
| 4925 | N | ILE | B | 356 | 131.414 | −34.875 | 54.712 | 1.00 | 19.62 |
| 4926 | CA | ILE | B | 356 | 130.205 | −35.212 | 53.962 | 1.00 | 19.28 |
| 4927 | CB | ILE | B | 356 | 130.264 | −36.623 | 53.338 | 1.00 | 17.62 |
| 4926 | CG2 | ILE | B | 356 | 131.323 | −36.649 | 52.244 | 1.00 | 18.48 |
| 4929 | CG1 | ILE | B | 356 | 130.554 | −37.671 | 54.411 | 1.00 | 13.31 |
| 4930 | CD1 | ILE | B | 356 | 130.486 | −39.110 | 53.882 | 1.00 | 15.90 |
| 4931 | C | ILE | B | 356 | 129.082 | −35.129 | 54.951 | 1.00 | 19.27 |
| 4932 | O | ILE | B | 356 | 129.293 | −35.255 | 56.163 | 1.00 | 20.90 |
| 4933 | N | THR | B | 357 | 127.877 | −34.904 | 54.464 | 1.00 | 21.61 |
| 4934 | CA | THR | B | 357 | 126.793 | −34.769 | 55.404 | 1.00 | 23.70 |
| 4935 | CB | THR | B | 357 | 126.385 | −33.293 | 55.546 | 1.00 | 24.46 |
| 4936 | OG1 | THR | B | 357 | 127.425 | −32.578 | 56.231 | 1.00 | 25.75 |
| 4937 | CG2 | THR | B | 357 | 125.094 | −33.166 | 56.315 | 1.00 | 24.34 |
| 4938 | C | THR | B | 357 | 125.585 | −35.585 | 55.063 | 1.00 | 25.15 |
| 4939 | O | THR | B | 357 | 125.115 | −35.586 | 53.916 | 1.00 | 26.89 |
| 4940 | N | CYS | B | 358 | 125.090 | −36.285 | 56.078 | 1.00 | 26.33 |
| 4941 | CA | CYS | B | 358 | 123.901 | −37.108 | 55.943 | 1.00 | 30.08 |
| 4942 | C | CYS | B | 358 | 122.742 | −36.300 | 56.551 | 1.00 | 29.93 |
| 4943 | O | CYS | B | 358 | 122.790 | −35.962 | 57.736 | 1.00 | 29.65 |
| 4944 | CB | CYS | B | 358 | 124.076 | −38.439 | 56.696 | 1.00 | 31.43 |
| 4945 | SG | CYS | B | 358 | 122.843 | −39.676 | 56.173 | 1.00 | 31.13 |
| 4946 | N | LEU | B | 359 | 121.720 | −35.984 | 55.744 | 1.00 | 31.10 |
| 4947 | CA | LEU | B | 359 | 120.551 | −35.208 | 56.194 | 1.00 | 32.87 |
| 4948 | CB | LEU | B | 359 | 120.394 | −33.963 | 55.301 | 1.00 | 29.84 |
| 4949 | CG | LEU | B | 359 | 119.161 | −33.054 | 55.457 | 1.00 | 28.93 |
| 4950 | CD1 | LEU | B | 359 | 119.155 | −32.424 | 56.846 | 1.00 | 24.70 |
| 4951 | CD2 | LEU | B | 359 | 119.160 | −31.960 | 54.377 | 1.00 | 28.08 |
| 4952 | C | LEU | B | 359 | 119.238 | −36.022 | 56.204 | 1.00 | 35.67 |
| 4953 | O | LEU | B | 359 | 118.858 | −36.608 | 55.188 | 1.00 | 33.02 |
| 4954 | N | VAL | B | 360 | 118.553 | −36.046 | 57.354 | 1.00 | 39.14 |
| 4955 | CA | VAL | B | 360 | 117.277 | −36.779 | 57.530 | 1.00 | 44.40 |
| 4956 | CB | VAL | B | 360 | 117.424 | −37.885 | 58.622 | 1.00 | 47.20 |
| 4957 | CG1 | VAL | B | 360 | 116.077 | −38.532 | 58.913 | 1.00 | 50.37 |
| 4958 | CG2 | VAL | B | 360 | 118.423 | −38.938 | 58.174 | 1.00 | 50.21 |
| 4959 | C | VAL | B | 360 | 116.109 | −35.860 | 57.953 | 1.00 | 48.51 |
| 4960 | O | VAL | B | 360 | 116.257 | −35.098 | 58.903 | 1.00 | 45.20 |
| 4961 | N | VAL | B | 361 | 114.945 | −35.959 | 57.297 | 1.00 | 55.02 |
| 4962 | CA | VAL | B | 361 | 113.773 | −35.115 | 57.641 | 1.00 | 58.42 |
| 4963 | CB | VAL | B | 361 | 113.525 | −34.137 | 56.429 | 1.00 | 53.17 |
| 4964 | CG1 | VAL | B | 361 | 112.445 | −33.124 | 56.751 | 1.00 | 48.58 |
| 4965 | CG2 | VAL | B | 361 | 114.846 | −33.393 | 56.072 | 1.00 | 46.46 |
| 4966 | C | VAL | B | 361 | 112.492 | −35.969 | 58.023 | 1.00 | 69.84 |
| 4967 | O | VAL | B | 361 | 111.892 | −36.555 | 57.125 | 1.00 | 68.56 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 4968 | N | ASP | B | 362 | 112.094 | −36.029 | 59.327 | 1.00 | 84.39 |
| 4969 | CA | ASP | B | 362 | 110.926 | −36.842 | 59.867 | 1.00 | 99.89 |
| 4970 | CB | ASP | B | 362 | 111.407 | −38.258 | 60.127 | 1.00 | 95.22 |
| 4971 | CG | ASP | B | 362 | 112.318 | −38.310 | 61.301 | 1.00 | 91.75 |
| 4972 | OD1 | ASP | B | 362 | 112.821 | −37.222 | 61.644 | 1.00 | 86.42 |
| 4973 | OD2 | ASP | B | 362 | 112.533 | −39.396 | 61.873 | 1.00 | 86.95 |
| 4974 | C | ASP | B | 362 | 110.171 | −36.363 | 61.186 | 1.00 | 109.68 |
| 4975 | O | ASP | B | 362 | 110.349 | −35.231 | 61.610 | 1.00 | 120.75 |
| 4976 | N | LEU | B | 363 | 109.380 | −37.239 | 61.850 | 1.00 | 118.17 |
| 4977 | CA | LEU | B | 363 | 108.572 | −36.882 | 63.061 | 1.00 | 123.34 |
| 4978 | CB | LEU | B | 363 | 107.261 | −36.233 | 62.611 | 1.00 | 124.57 |
| 4979 | CG | LEU | B | 363 | 106.902 | −36.651 | 61.182 | 1.00 | 124.01 |
| 4980 | CD1 | LEU | B | 363 | 105.429 | −36.959 | 61.061 | 1.00 | 121.09 |
| 4981 | CD2 | LEU | B | 363 | 107.319 | −35.546 | 60.218 | 1.00 | 120.83 |
| 4982 | C | LEU | B | 363 | 108.214 | −38.032 | 64.027 | 1.00 | 125.33 |
| 4983 | O | LEU | B | 363 | 107.081 | −38.114 | 64.531 | 1.00 | 125.79 |
| 4984 | N | THR | B | 369 | 114.185 | −41.906 | 68.510 | 1.00 | 89.78 |
| 4985 | CA | THR | B | 369 | 115.618 | −41.750 | 68.275 | 1.00 | 89.29 |
| 4986 | CB | THR | B | 369 | 116.454 | −42.689 | 69.149 | 1.00 | 93.95 |
| 4987 | OG1 | THR | B | 369 | 116.905 | −43.799 | 68.359 | 1.00 | 97.99 |
| 4988 | CG2 | THR | B | 369 | 115.629 | −43.208 | 70.299 | 1.00 | 97.63 |
| 4989 | C | THR | B | 369 | 115.991 | −42.093 | 66.848 | 1.00 | 85.09 |
| 4990 | O | THR | B | 369 | 115.665 | −43.174 | 66.358 | 1.00 | 82.40 |
| 4991 | N | VAL | B | 370 | 116.674 | −41.180 | 66.175 | 1.00 | 79.56 |
| 4992 | CA | VAL | B | 370 | 117.116 | −41.484 | 64.830 | 1.00 | 73.86 |
| 4993 | CB | VAL | B | 370 | 117.084 | −40.277 | 63.889 | 1.00 | 70.59 |
| 4994 | CG1 | VAL | B | 370 | 117.374 | −40.749 | 62.473 | 1.00 | 69.24 |
| 4995 | CG2 | VAL | B | 370 | 115.740 | −39.584 | 63.954 | 1.00 | 71.35 |
| 4996 | C | VAL | B | 370 | 118.561 | −41.940 | 64.958 | 1.00 | 77.99 |
| 4997 | O | VAL | B | 370 | 119.350 | −41.364 | 65.713 | 1.00 | 70.52 |
| 4998 | N | GLN | B | 371 | 118.906 | −42.976 | 64.213 | 1.00 | 81.17 |
| 4999 | CA | GLN | B | 371 | 120.254 | −43.510 | 64.253 | 1.00 | 76.10 |
| 5000 | CB | GLN | B | 371 | 120.200 | −44.999 | 64.567 | 1.00 | 83.81 |
| 5001 | CG | GLN | B | 371 | 119.742 | −45.330 | 65.976 | 1.00 | 95.07 |
| 5002 | CD | GLN | B | 371 | 120.885 | −45.524 | 66.908 | 1.00 | 114.25 |
| 5003 | OE1 | GLN | B | 371 | 122.004 | −45.568 | 66.463 | 1.00 | 106.06 |
| 5004 | NE2 | GLN | B | 371 | 120.623 | −45.659 | 68.201 | 1.00 | 105.53 |
| 5005 | C | GLN | B | 371 | 120.985 | −43.298 | 62.939 | 1.00 | 70.51 |
| 5006 | O | GLN | B | 371 | 120.505 | −43.710 | 61.884 | 1.00 | 65.12 |
| 5007 | N | LEU | B | 372 | 122.138 | −42.637 | 63.004 | 1.00 | 57.06 |
| 5008 | CA | LEU | B | 372 | 122.947 | −42.408 | 61.817 | 1.00 | 42.55 |
| 5009 | CB | LEU | B | 372 | 123.256 | −40.930 | 61.608 | 1.00 | 40.32 |
| 5010 | CG | LEU | B | 372 | 122.113 | −40.054 | 61.114 | 1.00 | 42.39 |
| 5011 | CD1 | LEU | B | 372 | 122.686 | −38.833 | 60.420 | 1.00 | 43.29 |
| 5012 | CD2 | LEU | B | 372 | 121.253 | −40.836 | 60.144 | 1.00 | 45.24 |
| 5013 | C | LEU | B | 372 | 124.253 | −43.154 | 61.961 | 1.00 | 37.85 |
| 5014 | O | LEU | B | 372 | 125.109 | −42.775 | 62.761 | 1.00 | 33.30 |
| 5015 | N | THR | B | 373 | 124.403 | −44.215 | 61.182 | 1.00 | 35.48 |
| 5016 | CA | THR | B | 373 | 125.611 | −44.996 | 61.237 | 1.00 | 33.54 |
| 5017 | CB | THR | B | 373 | 125.264 | −46.460 | 61.488 | 1.00 | 34.70 |
| 5018 | OG1 | THR | B | 373 | 124.413 | −46.550 | 62.640 | 1.00 | 38.60 |
| 5019 | CG2 | THR | B | 373 | 126.527 | −47.261 | 61.740 | 1.00 | 37.39 |
| 5020 | C | THR | B | 373 | 126.419 | −44.852 | 59.946 | 1.00 | 32.24 |
| 5021 | O | THR | B | 373 | 125.874 | −44.982 | 58.847 | 1.00 | 32.43 |
| 5022 | N | TRP | B | 374 | 127.720 | −44.579 | 60.092 | 1.00 | 31.95 |
| 5023 | CA | TRP | B | 374 | 128.633 | −44.415 | 58.954 | 1.00 | 32.28 |
| 5024 | CB | TRP | B | 374 | 129.570 | −43.214 | 59.150 | 1.00 | 31.87 |
| 5025 | CG | TRP | B | 374 | 128.920 | −41.876 | 59.168 | 1.00 | 30.00 |
| 5026 | CD2 | TRP | B | 374 | 128.521 | −41.099 | 58.032 | 1.00 | 26.79 |
| 5027 | CE2 | TRP | B | 374 | 127.955 | −39.898 | 58.533 | 1.00 | 26.80 |
| 5028 | CE3 | TRP | B | 374 | 128.559 | −41.311 | 56.644 | 1.00 | 27.11 |
| 5029 | CD1 | TRP | B | 374 | 128.608 | −41.135 | 60.275 | 1.00 | 27.98 |
| 5030 | NE1 | TRP | B | 374 | 128.033 | −39.940 | 59.900 | 1.00 | 27.47 |
| 5031 | CZ2 | TRP | B | 374 | 127.460 | −38.892 | 57.686 | 1.00 | 26.26 |
| 5032 | CZ3 | TRP | B | 374 | 128.066 | −40.310 | 55.795 | 1.00 | 25.25 |
| 5033 | CH2 | TRP | B | 374 | 127.512 | −39.121 | 56.325 | 1.00 | 27.15 |
| 5034 | C | TRP | B | 374 | 129.540 | −45.616 | 58.710 | 1.00 | 32.24 |
| 5035 | O | TRP | B | 374 | 129.865 | −46.374 | 59.627 | 1.00 | 34.60 |
| 5036 | N | SER | B | 375 | 129.970 | −45.763 | 57.464 | 1.00 | 30.69 |
| 5037 | CA | SER | B | 375 | 130.898 | −46.818 | 57.115 | 1.00 | 29.48 |
| 5038 | CB | SER | B | 375 | 130.238 | −48.192 | 57.212 | 1.00 | 26.91 |
| 5039 | OG | SER | B | 375 | 129.053 | −48.237 | 56.449 | 1.00 | 27.89 |
| 5040 | C | SER | B | 375 | 131.443 | −46.587 | 55.720 | 1.00 | 28.14 |
| 5041 | O | SER | B | 375 | 130.943 | −45.750 | 54.972 | 1.00 | 24.80 |
| 5042 | N | ARG | B | 376 | 132.485 | −47.325 | 55.382 | 1.00 | 26.18 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5043 | CA | ARG | B | 376 | 133.080 | −47.198 | 54.073 | 1.00 | 25.26 |
| 5044 | CB | ARG | B | 376 | 134.581 | −46.950 | 54.200 | 1.00 | 23.42 |
| 5045 | CG | ARG | B | 376 | 134.911 | −45.541 | 54.658 | 1.00 | 23.93 |
| 5046 | CD | ARG | B | 376 | 136.287 | −45.126 | 54.145 | 1.00 | 23.47 |
| 5047 | NE | ARG | B | 376 | 137.311 | −45.281 | 55.156 | 1.00 | 23.44 |
| 5048 | CZ | ARG | B | 376 | 138.611 | −45.309 | 54.901 | 1.00 | 24.76 |
| 5049 | NH1 | ARG | B | 376 | 139.064 | −45.203 | 53.658 | 1.00 | 23.08 |
| 5050 | NH2 | ARG | B | 376 | 139.462 | −45.422 | 55.906 | 1.00 | 26.46 |
| 5051 | C | ARG | B | 376 | 132.824 | −48.466 | 53.296 | 1.00 | 25.04 |
| 5052 | O | ARG | B | 376 | 132.701 | −49.534 | 53.881 | 1.00 | 22.88 |
| 5053 | N | ALA | B | 377 | 132.755 | −48.348 | 51.978 | 1.00 | 25.56 |
| 5054 | CA | ALA | B | 377 | 132.529 | −49.514 | 51.136 | 1.00 | 27.53 |
| 5055 | CB | ALA | B | 377 | 132.324 | −49.092 | 49.682 | 1.00 | 27.98 |
| 5056 | C | ALA | B | 377 | 133.708 | −50.463 | 51.233 | 1.00 | 26.07 |
| 5057 | O | ALA | B | 377 | 133.551 | −51.664 | 51.061 | 1.00 | 29.56 |
| 5058 | N | SER | B | 378 | 134.888 | −49.916 | 51.503 | 1.00 | 25.66 |
| 5059 | CA | SER | B | 378 | 136.101 | −50.720 | 51.610 | 1.00 | 24.27 |
| 5060 | CB | SER | B | 378 | 137.322 | −49.818 | 51.452 | 1.00 | 23.73 |
| 5061 | CG | SER | B | 378 | 137.495 | −49.020 | 52.609 | 1.00 | 24.12 |
| 5062 | C | SER | B | 378 | 136.200 | −51.487 | 52.934 | 1.00 | 22.76 |
| 5063 | O | SER | B | 378 | 136.969 | −52.441 | 53.038 | 1.00 | 23.45 |
| 5064 | N | GLY | B | 379 | 135.428 | −51.072 | 53.939 | 1.00 | 21.00 |
| 5065 | CA | GLY | B | 379 | 135.480 | −51.739 | 55.231 | 1.00 | 20.82 |
| 5066 | C | GLY | B | 379 | 136.431 | −51.046 | 56.200 | 1.00 | 20.50 |
| 5067 | O | GLY | B | 379 | 136.477 | −51.355 | 57.390 | 1.00 | 19.71 |
| 5068 | N | LYS | B | 380 | 137.208 | −50.100 | 55.688 | 1.00 | 21.38 |
| 5069 | CA | LYS | B | 380 | 138.133 | −49.374 | 56.529 | 1.00 | 25.66 |
| 5070 | CB | LYS | B | 380 | 139.101 | −48.572 | 55.665 | 1.00 | 27.59 |
| 5071 | CG | LYS | B | 380 | 140.129 | −49.455 | 54.979 | 1.00 | 29.88 |
| 5072 | CD | LYS | B | 380 | 140.748 | −48.747 | 53.804 | 1.00 | 33.32 |
| 5073 | CE | LYS | B | 380 | 141.558 | −49.709 | 52.939 | 1.00 | 35.39 |
| 5074 | NZ | LYS | B | 380 | 142.200 | −48.992 | 51.806 | 1.00 | 41.04 |
| 5075 | C | LYS | B | 380 | 137.384 | −48.476 | 57.519 | 1.00 | 27.91 |
| 5076 | O | LYS | B | 380 | 136.203 | −48.149 | 57.321 | 1.00 | 26.08 |
| 5077 | N | PRO | B | 381 | 138.066 | −48.078 | 58.605 | 1.00 | 26.39 |
| 5078 | CD | PRO | B | 381 | 139.503 | −48.330 | 58.815 | 1.00 | 28.05 |
| 5079 | CA | PRO | B | 381 | 137.522 | −47.230 | 59.670 | 1.00 | 28.75 |
| 5080 | CB | PRO | B | 381 | 138.665 | −47.154 | 60.695 | 1.00 | 29.86 |
| 5081 | CG | PRO | B | 381 | 139.631 | −48.239 | 60.294 | 1.00 | 30.57 |
| 5082 | C | PRO | B | 381 | 137.119 | −45.839 | 59.222 | 1.00 | 31.38 |
| 5083 | O | PRO | B | 381 | 137.722 | −45.266 | 58.315 | 1.00 | 30.60 |
| 5084 | N | VAL | B | 382 | 136.097 | −45.302 | 59.880 | 1.00 | 33.64 |
| 5085 | CA | VAL | B | 382 | 135.614 | −43.946 | 59.620 | 1.00 | 34.77 |
| 5086 | CB | VAL | B | 382 | 134.088 | −43.883 | 59.421 | 1.00 | 38.40 |
| 5087 | CG1 | VAL | B | 382 | 133.683 | −44.718 | 58.222 | 1.00 | 43.30 |
| 5088 | CG2 | VAL | B | 382 | 133.376 | −44.368 | 60.683 | 1.00 | 41.91 |
| 5089 | C | VAL | B | 382 | 135.920 | −43.161 | 60.872 | 1.00 | 37.23 |
| 5090 | O | VAL | B | 382 | 136.069 | −43.740 | 61.940 | 1.00 | 32.81 |
| 5091 | N | GLN | B | 383 | 135.993 | −41.844 | 60.750 | 1.00 | 41.07 |
| 5092 | CA | GLN | B | 383 | 136.280 | −41.020 | 61.907 | 1.00 | 39.32 |
| 5093 | CB | GLN | B | 383 | 136.976 | −39.726 | 61.472 | 1.00 | 39.39 |
| 5094 | CG | GLN | B | 383 | 138.327 | −39.915 | 60.769 | 1.00 | 44.18 |
| 5095 | CD | GLN | B | 383 | 138.886 | −38.609 | 60.265 | 1.00 | 51.14 |
| 5096 | OE1 | GLN | B | 383 | 138.597 | −37.552 | 60.833 | 1.00 | 50.25 |
| 5097 | NE2 | GLN | B | 383 | 139.696 | −38.659 | 59.208 | 1.00 | 50.43 |
| 5098 | C | GLN | B | 383 | 135.007 | −40.687 | 62.682 | 1.00 | 40.13 |
| 5099 | O | GLN | B | 383 | 133.916 | −41.155 | 62.367 | 1.00 | 36.46 |
| 5100 | N | HIS | B | 384 | 135.172 | −39.872 | 63.710 | 1.00 | 41.72 |
| 5101 | CA | HIS | B | 384 | 134.071 | −39.428 | 64.548 | 1.00 | 42.06 |
| 5102 | CB | HIS | B | 384 | 134.591 | −38.648 | 65.727 | 1.00 | 49.25 |
| 5103 | CG | HIS | B | 384 | 135.050 | −39.493 | 66.839 | 1.00 | 59.53 |
| 5104 | CD2 | HIS | B | 384 | 136.208 | −39.521 | 67.515 | 1.00 | 62.33 |
| 5105 | ND1 | HIS | B | 384 | 134.255 | −40.478 | 67.416 | 1.00 | 63.54 |
| 5106 | CE1 | HIS | B | 384 | 134.912 | −41.055 | 68.381 | 1.00 | 63.96 |
| 5107 | NE2 | HIS | B | 384 | 136.111 | −40.492 | 68.468 | 1.00 | 63.62 |
| 5108 | C | HIS | B | 384 | 133.179 | −38.492 | 63.788 | 1.00 | 40.12 |
| 5109 | O | HIS | B | 384 | 133.679 | −37.642 | 63.046 | 1.00 | 39.73 |
| 5110 | N | SER | B | 385 | 131.868 | −38.604 | 63.975 | 1.00 | 37.03 |
| 5111 | CA | SER | B | 385 | 130.978 | −37.682 | 63.282 | 1.00 | 36.27 |
| 5112 | CB | SER | B | 385 | 129.941 | −38.442 | 62.447 | 1.00 | 33.52 |
| 5113 | OG | SER | B | 385 | 129.230 | −39.396 | 63.213 | 1.00 | 32.48 |
| 5114 | C | SER | B | 385 | 130.282 | −36.711 | 64.235 | 1.00 | 38.82 |
| 5115 | O | SER | B | 385 | 130.270 | −36.916 | 65.437 | 1.00 | 35.61 |
| 5116 | N | THR | B | 386 | 129.725 | −35.637 | 63.689 | 1.00 | 41.09 |
| 5117 | CA | THR | B | 386 | 129.015 | −34.639 | 64.487 | 1.00 | 43.61 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5118 | CB | THR | B | 386 | 129.411 | −33.205 | 64.071 | 1.00 | 46.33 |
| 5119 | OG1 | THR | B | 386 | 130.823 | −33.029 | 64.226 | 1.00 | 53.84 |
| 5120 | CG2 | THR | B | 386 | 128.688 | −32.184 | 64.928 | 1.00 | 53.03 |
| 5121 | C | THR | B | 386 | 127.518 | −34.804 | 64.241 | 1.00 | 43.43 |
| 5122 | O | THR | B | 386 | 127.083 | −34.873 | 63.093 | 1.00 | 44.96 |
| 5123 | N | ARG | B | 387 | 126.731 | −34.858 | 65.311 | 1.00 | 43.10 |
| 5124 | CA | ARG | B | 387 | 125.283 | −35.015 | 65.186 | 1.00 | 44.73 |
| 5125 | CB | ARG | B | 387 | 124.803 | −36.188 | 66.047 | 1.00 | 43.96 |
| 5126 | CG | ARG | B | 387 | 123.311 | −36.474 | 65.940 | 1.00 | 39.16 |
| 5127 | CD | ARG | B | 387 | 122.915 | −37.544 | 66.942 | 1.00 | 39.38 |
| 5128 | NE | ARG | B | 387 | 121.465 | −37.698 | 67.042 | 1.00 | 42.62 |
| 5129 | CZ | ARG | B | 387 | 120.738 | −38.504 | 66.274 | 1.00 | 43.36 |
| 5130 | NH1 | ARG | B | 387 | 121.326 | −39.242 | 65.345 | 1.00 | 44.53 |
| 5131 | NH2 | ARG | B | 387 | 119.421 | −38.563 | 66.425 | 1.00 | 43.51 |
| 5132 | C | ARG | B | 387 | 124.541 | −33.751 | 65.603 | 1.00 | 46.01 |
| 5133 | O | ARG | B | 387 | 124.836 | −33.166 | 66.637 | 1.00 | 45.63 |
| 5134 | N | LYS | B | 388 | 123.561 | −33.336 | 64.810 | 1.00 | 49.89 |
| 5135 | CA | LYS | B | 388 | 122.824 | −32.126 | 65.144 | 1.00 | 54.53 |
| 5136 | CB | LYS | B | 388 | 123.392 | −30.953 | 64.340 | 1.00 | 59.66 |
| 5137 | CG | LYS | B | 388 | 123.197 | −29.618 | 65.008 | 1.00 | 67.19 |
| 5138 | CD | LYS | B | 388 | 123.169 | −28.466 | 64.025 | 1.00 | 75.57 |
| 5139 | CE | LYS | B | 388 | 124.473 | −27.860 | 63.747 | 1.00 | 81.21 |
| 5140 | NZ | LYS | B | 388 | 124.426 | −26.478 | 63.217 | 1.00 | 85.12 |
| 5141 | C | LYS | B | 388 | 121.317 | −32.268 | 64.887 | 1.00 | 54.98 |
| 5142 | O | LYS | B | 388 | 120.898 | −32.566 | 63.768 | 1.00 | 52.71 |
| 5143 | N | GLU | B | 389 | 120.513 | −32.057 | 65.931 | 1.00 | 55.80 |
| 5144 | CA | GLU | B | 389 | 119.051 | −32.158 | 65.840 | 1.00 | 59.38 |
| 5145 | CB | GLU | B | 389 | 118.525 | −33.095 | 66.921 | 1.00 | 62.15 |
| 5146 | CG | GLU | B | 389 | 118.910 | −34.535 | 66.693 | 1.00 | 69.02 |
| 5147 | CD | GLU | B | 389 | 118.441 | −35.435 | 67.803 | 1.00 | 72.87 |
| 5148 | OE1 | GLU | B | 389 | 117.276 | −35.295 | 68.225 | 1.00 | 75.41 |
| 5149 | OE2 | GLU | B | 389 | 119.230 | −36.290 | 68.249 | 1.00 | 74.58 |
| 5150 | C | GLU | B | 389 | 118.349 | −30.808 | 65.945 | 1.00 | 62.37 |
| 5151 | O | GLU | B | 389 | 118.583 | −30.035 | 66.879 | 1.00 | 59.86 |
| 5152 | N | GLU | B | 390 | 117.473 | −30.538 | 64.987 | 1.00 | 68.88 |
| 5153 | CA | GLU | B | 390 | 116.785 | −29.271 | 64.973 | 1.00 | 75.60 |
| 5154 | CB | GLU | B | 390 | 117.501 | −28.288 | 64.062 | 1.00 | 80.71 |
| 5155 | CG | GLU | B | 390 | 117.106 | −26.846 | 64.287 | 1.00 | 97.84 |
| 5156 | CD | GLU | B | 390 | 118.311 | −25.938 | 64.261 | 1.00 | 107.16 |
| 5157 | OE1 | GLU | B | 390 | 119.410 | −26.439 | 63.940 | 1.00 | 113.45 |
| 5158 | OE2 | GLU | B | 390 | 118.166 | −24.733 | 64.559 | 1.00 | 113.55 |
| 5159 | C | GLU | B | 390 | 115.357 | −29.378 | 64.562 | 1.00 | 76.91 |
| 5160 | O | GLU | B | 390 | 115.001 | −29.908 | 63.498 | 1.00 | 75.38 |
| 5161 | N | LYS | B | 391 | 114.544 | −28.838 | 65.448 | 1.00 | 82.02 |
| 5162 | CA | LYS | B | 391 | 113.142 | −28.854 | 65.248 | 1.00 | 92.30 |
| 5163 | CB | LYS | B | 391 | 112.419 | −28.965 | 66.569 | 1.00 | 97.79 |
| 5164 | CG | LYS | B | 391 | 112.339 | −30.416 | 66.979 | 1.00 | 104.43 |
| 5165 | CD | LYS | B | 391 | 111.376 | −30.620 | 68.115 | 1.00 | 108.52 |
| 5166 | CE | LYS | B | 391 | 110.590 | −31.904 | 67.927 | 1.00 | 111.61 |
| 5167 | NZ | LYS | B | 391 | 109.971 | −32.351 | 69.199 | 1.00 | 114.28 |
| 5168 | C | LYS | B | 391 | 112.670 | −27.716 | 64.429 | 1.00 | 98.37 |
| 5169 | O | LYS | B | 391 | 113.065 | −26.546 | 64.568 | 1.00 | 99.33 |
| 5170 | N | GLN | B | 392 | 111.820 | −28.148 | 63.523 | 1.00 | 107.70 |
| 5171 | CA | GLN | B | 392 | 111.249 | −27.306 | 62.539 | 1.00 | 113.69 |
| 5172 | CB | GLN | B | 392 | 111.758 | −27.735 | 61.174 | 1.00 | 114.59 |
| 5173 | CG | GLN | B | 392 | 113.169 | −28.295 | 61.181 | 1.00 | 122.43 |
| 5174 | CD | GLN | B | 392 | 114.165 | −27.287 | 60.697 | 1.00 | 127.18 |
| 5175 | OE1 | GLN | B | 392 | 113.814 | −26.130 | 60.465 | 1.00 | 130.47 |
| 5176 | NE2 | GLN | B | 392 | 115.420 | −27.706 | 60.535 | 1.00 | 130.61 |
| 5177 | C | GLN | B | 392 | 109.751 | −27.297 | 62.497 | 1.00 | 118.37 |
| 5178 | O | GLN | B | 392 | 109.061 | −28.323 | 62.648 | 1.00 | 112.98 |
| 5179 | N | ARG | B | 393 | 109.313 | −26.073 | 62.230 | 1.00 | 125.09 |
| 5180 | CA | ARG | B | 393 | 107.948 | −25.643 | 62.050 | 1.00 | 131.48 |
| 5181 | CB | ARG | B | 393 | 107.947 | −24.306 | 61.313 | 1.00 | 129.00 |
| 5182 | CG | ARG | B | 393 | 107.561 | −23.089 | 62.140 | 1.00 | 129.76 |
| 5183 | CD | ARG | B | 393 | 108.200 | −21.804 | 61.588 | 1.00 | 127.43 |
| 5184 | NE | ARG | B | 393 | 107.221 | −20.745 | 61.332 | 1.00 | 124.50 |
| 5185 | CZ | ARG | B | 393 | 107.529 | −19.466 | 61.127 | 1.00 | 123.25 |
| 5186 | NH1 | ARG | B | 393 | 108.796 | −19.071 | 61.150 | 1.00 | 122.64 |
| 5187 | NH2 | ARG | B | 393 | 106.570 | −18.580 | 60.892 | 1.00 | 122.57 |
| 5188 | C | ARG | B | 393 | 107.342 | −26.672 | 61.157 | 1.00 | 135.36 |
| 5189 | O | ARG | B | 393 | 107.825 | −26.910 | 60.067 | 1.00 | 140.71 |
| 5190 | N | ASN | B | 394 | 106.275 | −27.278 | 61.596 | 1.00 | 136.72 |
| 5191 | CA | ASN | B | 394 | 105.662 | −28.296 | 60.786 | 1.00 | 137.73 |
| 5192 | CB | ASN | B | 394 | 106.234 | −28.383 | 59.402 | 1.00 | 147.16 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5193 | CG | ASN | B | 394 | 105.224 | −28.844 | 58.405 | 1.00 | 155.29 |
| 5194 | OD1 | ASN | B | 394 | 105.598 | −29.242 | 57.321 | 1.00 | 158.97 |
| 5195 | ND2 | ASN | B | 394 | 103.936 | −28.791 | 58.754 | 1.00 | 158.90 |
| 5196 | C | ASN | B | 394 | 105.778 | −29.585 | 61.536 | 1.00 | 133.61 |
| 5197 | O | ASN | B | 394 | 105.502 | −30.665 | 61.022 | 1.00 | 132.85 |
| 5198 | N | GLY | B | 395 | 106.101 | −29.411 | 62.811 | 1.00 | 132.76 |
| 5199 | CA | GLY | B | 395 | 106.258 | −30.527 | 63.701 | 1.00 | 122.21 |
| 5200 | C | GLY | B | 395 | 107.232 | −31.510 | 63.116 | 1.00 | 110.37 |
| 5201 | O | GLY | B | 395 | 107.015 | −32.708 | 63.205 | 1.00 | 113.05 |
| 5202 | N | THR | B | 396 | 108.289 | −31.040 | 62.475 | 1.00 | 96.43 |
| 5203 | CA | THR | B | 396 | 109.218 | −32.017 | 61.967 | 1.00 | 94.82 |
| 5204 | CB | THR | B | 396 | 109.358 | −32.001 | 60.440 | 1.00 | 93.52 |
| 5205 | OG1 | THR | B | 396 | 108.072 | −32.219 | 59.851 | 1.00 | 80.69 |
| 5206 | CG2 | THR | B | 396 | 110.281 | −33.138 | 59.979 | 1.00 | 79.45 |
| 5207 | C | THR | B | 396 | 110.558 | −31.837 | 62.600 | 1.00 | 88.84 |
| 5208 | O | THR | B | 396 | 110.838 | −30.846 | 63.278 | 1.00 | 97.54 |
| 5209 | N | LEU | B | 397 | 111.387 | −32.828 | 62.349 | 1.00 | 83.44 |
| 5210 | CA | LEU | B | 397 | 112.700 | −32.888 | 62.908 | 1.00 | 73.01 |
| 5211 | CB | LEU | B | 397 | 112.714 | −34.064 | 63.875 | 1.00 | 70.15 |
| 5212 | CG | LEU | B | 397 | 114.038 | −34.369 | 64.547 | 1.00 | 66.66 |
| 5213 | CD1 | LEU | B | 397 | 114.417 | −33.203 | 65.436 | 1.00 | 64.69 |
| 5214 | CD2 | LEU | B | 397 | 113.922 | −35.649 | 65.348 | 1.00 | 64.37 |
| 5215 | C | LEU | B | 397 | 113.788 | −33.041 | 61.850 | 1.00 | 65.84 |
| 5216 | O | LEU | B | 397 | 113.648 | −33.814 | 60.908 | 1.00 | 60.95 |
| 5217 | N | THR | B | 398 | 114.861 | −32.273 | 61.992 | 1.00 | 56.33 |
| 5218 | CA | THR | B | 398 | 115.973 | −32.391 | 61.070 | 1.00 | 49.51 |
| 5219 | CB | THR | B | 398 | 116.322 | −31.062 | 60.395 | 1.00 | 49.58 |
| 5220 | OG1 | THR | B | 398 | 115.437 | −30.864 | 59.288 | 1.00 | 51.16 |
| 5221 | CG2 | THR | B | 398 | 117.753 | −31.078 | 59.871 | 1.00 | 51.10 |
| 5222 | C | THR | B | 398 | 117.159 | −32.917 | 61.850 | 1.00 | 45.91 |
| 5223 | O | THR | B | 398 | 117.493 | −32.427 | 62.932 | 1.00 | 45.54 |
| 5224 | N | VAL | B | 399 | 117.773 | −33.947 | 61.289 | 1.00 | 41.73 |
| 5225 | CA | VAL | B | 399 | 118.919 | −34.602 | 61.890 | 1.00 | 37.76 |
| 5226 | CB | VAL | B | 399 | 118.513 | −36.015 | 62.353 | 1.00 | 33.97 |
| 5227 | CG1 | VAL | B | 399 | 119.597 | −36.998 | 62.077 | 1.00 | 35.21 |
| 5228 | CG2 | VAL | B | 399 | 118.207 | −36.001 | 63.818 | 1.00 | 33.98 |
| 5229 | C | VAL | B | 399 | 120.056 | −34.651 | 60.862 | 1.00 | 37.13 |
| 5230 | O | VAL | B | 399 | 119.861 | −35.085 | 59.719 | 1.00 | 34.54 |
| 5231 | N | THR | B | 400 | 121.234 | −34.179 | 61.263 | 1.00 | 37.35 |
| 5232 | CA | THR | B | 400 | 122.375 | −34.164 | 60.363 | 1.00 | 37.63 |
| 5233 | CB | THR | B | 400 | 122.684 | −32.734 | 59.864 | 1.00 | 37.24 |
| 5234 | OG1 | THR | B | 400 | 123.006 | −31.899 | 60.982 | 1.00 | 38.64 |
| 5235 | CG2 | THR | B | 400 | 121.489 | −32.140 | 59.149 | 1.00 | 36.37 |
| 5236 | C | THR | B | 400 | 123.609 | −34.693 | 61.061 | 1.00 | 37.64 |
| 5237 | O | THR | B | 400 | 123.819 | −34.444 | 62.247 | 1.00 | 39.60 |
| 5238 | N | SER | B | 401 | 124.414 | −35.443 | 60.322 | 1.00 | 38.99 |
| 5239 | CA | SER | B | 401 | 125.648 | −35.982 | 60.859 | 1.00 | 38.59 |
| 5240 | CB | SER | B | 401 | 125.570 | −37.507 | 61.032 | 1.00 | 40.46 |
| 5241 | OG | SER | B | 401 | 126.775 | −38.031 | 61.581 | 1.00 | 44.31 |
| 5242 | C | SER | B | 401 | 126.698 | −35.629 | 59.831 | 1.00 | 36.97 |
| 5243 | O | SER | B | 401 | 126.547 | −35.931 | 58.642 | 1.00 | 39.85 |
| 5244 | N | THR | B | 402 | 127.748 | −34.956 | 60.275 | 1.00 | 33.98 |
| 5245 | CA | THR | B | 402 | 128.800 | −34.595 | 59.353 | 1.00 | 31.93 |
| 5246 | CB | THR | B | 402 | 129.135 | −33.111 | 59.430 | 1.00 | 30.75 |
| 5247 | OG1 | THR | B | 402 | 127.952 | −32.353 | 59.149 | 1.00 | 29.46 |
| 5248 | CG2 | THR | B | 402 | 130.208 | −32.757 | 58.390 | 1.00 | 26.59 |
| 5249 | C | THR | B | 402 | 130.016 | −35.424 | 59.670 | 1.00 | 28.79 |
| 5250 | O | THR | B | 402 | 130.470 | −35.468 | 60.818 | 1.00 | 29.09 |
| 5251 | N | LEU | B | 403 | 130.537 | −36.079 | 58.637 | 1.00 | 24.83 |
| 5252 | CA | LEU | B | 403 | 131.680 | −36.953 | 58.773 | 1.00 | 23.04 |
| 5253 | CB | LEU | B | 403 | 131.343 | −38.337 | 58.201 | 1.00 | 19.23 |
| 5254 | CG | LEU | B | 403 | 132.471 | −39.368 | 58.286 | 1.00 | 17.31 |
| 5255 | CD1 | LEU | B | 403 | 132.670 | −39.776 | 59.761 | 1.00 | 16.49 |
| 5256 | CD2 | LEU | B | 403 | 132.107 | −40.597 | 57.465 | 1.00 | 17.39 |
| 5257 | C | LEU | B | 403 | 132.926 | −36.427 | 58.083 | 1.00 | 23.43 |
| 5258 | O | LEU | B | 403 | 132.914 | −36.171 | 56.874 | 1.00 | 24.67 |
| 5259 | N | PRO | B | 404 | 134.020 | −36.249 | 58.847 | 1.00 | 24.04 |
| 5260 | CD | PRO | B | 404 | 134.106 | −36.372 | 60.312 | 1.00 | 25.76 |
| 5261 | CA | PRO | B | 404 | 135.278 | −35.766 | 58.272 | 1.00 | 23.76 |
| 5262 | CB | PRO | B | 404 | 136.199 | −35.569 | 59.478 | 1.00 | 23.41 |
| 5263 | CG | PRO | B | 404 | 135.285 | −35.484 | 60.651 | 1.00 | 24.06 |
| 5264 | C | PRO | B | 404 | 135.749 | −36.932 | 57.428 | 1.00 | 23.40 |
| 5265 | O | PRO | B | 404 | 135.557 | −38.094 | 57.801 | 1.00 | 25.04 |
| 5266 | N | VAL | B | 405 | 136.379 | −36.627 | 56.312 | 1.00 | 22.77 |
| 5267 | CA | VAL | B | 405 | 136.831 | −37.658 | 55.410 | 1.00 | 23.97 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5268 | CB | VAL | B | 405 | 135.867 | −37.693 | 54.201 | 1.00 | 26.17 |
| 5269 | CG1 | VAL | B | 405 | 136.605 | −37.963 | 52.917 | 1.00 | 27.07 |
| 5270 | CG2 | VAL | B | 405 | 134.801 | −38.745 | 54.455 | 1.00 | 25.77 |
| 5271 | C | VAL | B | 405 | 138.276 | −37.415 | 54.986 | 1.00 | 22.53 |
| 5272 | O | VAL | B | 405 | 138.746 | −36.274 | 54.990 | 1.00 | 20.14 |
| 5273 | N | GLY | B | 406 | 138.979 | −38.494 | 54.648 | 1.00 | 21.36 |
| 5274 | CA | GLY | B | 406 | 140.367 | −38.379 | 54.233 | 1.00 | 22.73 |
| 5275 | C | GLY | B | 406 | 140.443 | −37.784 | 52.841 | 1.00 | 25.30 |
| 5276 | O | GLY | B | 406 | 139.651 | −38.151 | 51.973 | 1.00 | 26.82 |
| 5277 | N | THR | B | 407 | 141.391 | −36.882 | 52.604 | 1.00 | 26.51 |
| 5278 | CA | THR | B | 407 | 141.495 | −36.265 | 51.297 | 1.00 | 27.98 |
| 5279 | CB | THR | B | 407 | 142.484 | −35.106 | 51.296 | 1.00 | 29.16 |
| 5280 | OG1 | THR | B | 407 | 142.036 | −34.113 | 52.226 | 1.00 | 25.59 |
| 5281 | CG2 | THR | B | 407 | 142.564 | −34.477 | 49.899 | 1.00 | 30.32 |
| 5282 | C | THR | B | 407 | 141.871 | −37.240 | 50.213 | 1.00 | 29.54 |
| 5283 | O | THR | B | 407 | 141.177 | −37.314 | 49.203 | 1.00 | 33.49 |
| 5284 | N | ALA | B | 408 | 142.954 | −37.989 | 50.394 | 1.00 | 29.81 |
| 5285 | CA | ALA | B | 408 | 143.355 | −38.964 | 49.378 | 1.00 | 30.26 |
| 5286 | CB | ALA | B | 408 | 144.708 | −39.600 | 49.747 | 1.00 | 31.49 |
| 5287 | C | ALA | B | 408 | 142.271 | −40.046 | 49.234 | 1.00 | 30.85 |
| 5288 | O | ALA | B | 408 | 141.936 | −40.447 | 48.116 | 1.00 | 32.88 |
| 5289 | N | ASP | B | 409 | 141.727 | −40.508 | 50.364 | 1.00 | 30.62 |
| 5290 | CA | ASP | B | 409 | 140.679 | −41.531 | 50.364 | 1.00 | 29.36 |
| 5291 | CB | ASP | B | 409 | 140.049 | −41.687 | 51.751 | 1.00 | 30.12 |
| 5292 | CG | ASP | B | 409 | 140.964 | −42.376 | 52.760 | 1.00 | 31.85 |
| 5293 | OD1 | ASP | B | 409 | 141.792 | −43.222 | 52.345 | 1.00 | 32.85 |
| 5294 | OD2 | ASP | B | 409 | 140.823 | −42.082 | 53.980 | 1.00 | 31.04 |
| 5295 | C | ASP | B | 409 | 139.556 | −41.170 | 49.392 | 1.00 | 28.47 |
| 5296 | O | ASP | B | 409 | 139.150 | −41.976 | 48.546 | 1.00 | 26.82 |
| 5297 | N | TRP | B | 410 | 139.051 | −39.947 | 49.528 | 1.00 | 28.07 |
| 5298 | CA | TRP | B | 410 | 137.966 | −39.465 | 48.687 | 1.00 | 25.59 |
| 5299 | CB | TRP | B | 410 | 137.391 | −38.167 | 49.256 | 1.00 | 20.96 |
| 5300 | CG | TRP | B | 410 | 136.304 | −37.636 | 48.402 | 1.00 | 17.54 |
| 5301 | CD2 | TRP | B | 410 | 134.913 | −37.967 | 48.494 | 1.00 | 13.46 |
| 5302 | CE2 | TRP | B | 410 | 134.270 | −37.386 | 47.376 | 1.00 | 12.81 |
| 5303 | CE3 | TRP | B | 410 | 134.142 | −38.678 | 49.426 | 1.00 | 10.66 |
| 5304 | CD1 | TRP | B | 410 | 136.448 | −36.891 | 47.265 | 1.00 | 14.23 |
| 5305 | NE1 | TRP | B | 410 | 135.235 | −36.745 | 46.638 | 1.00 | 13.76 |
| 5306 | CZ2 | TRP | B | 410 | 132.896 | −37.524 | 47.133 | 1.00 | 13.55 |
| 5307 | CZ3 | TRP | B | 410 | 132.769 | −38.817 | 49.193 | 1.00 | 13.98 |
| 5308 | CH2 | TRP | B | 410 | 132.158 | −38.231 | 48.060 | 1.00 | 13.35 |
| 5309 | C | TRP | B | 410 | 138.378 | −39.244 | 47.234 | 1.00 | 26.83 |
| 5310 | O | TRP | B | 410 | 137.654 | −39.622 | 46.314 | 1.00 | 27.77 |
| 5311 | N | ILE | B | 411 | 139.527 | −38.623 | 47.014 | 1.00 | 28.77 |
| 5312 | CA | ILE | B | 411 | 139.966 | −38.378 | 45.648 | 1.00 | 31.11 |
| 5313 | CB | ILE | B | 411 | 141.202 | −37.444 | 45.642 | 1.00 | 28.42 |
| 5314 | CG2 | ILE | B | 411 | 141.867 | −37.411 | 44.264 | 1.00 | 25.18 |
| 5315 | CG1 | ILE | B | 411 | 140.750 | −36.042 | 46.051 | 1.00 | 23.58 |
| 5316 | CD1 | ILE | B | 411 | 141.879 | −35.083 | 46.330 | 1.00 | 25.30 |
| 5317 | C | ILE | B | 411 | 140.251 | −39.687 | 44.912 | 1.00 | 33.01 |
| 5318 | O | ILE | B | 411 | 139.987 | −39.807 | 43.712 | 1.00 | 33.16 |
| 5319 | N | GLU | B | 412 | 140.758 | −40.673 | 45.643 | 1.00 | 34.86 |
| 5320 | CA | GLU | B | 412 | 141.068 | −41.959 | 45.052 | 1.00 | 38.25 |
| 5321 | CB | GLU | B | 412 | 142.164 | −42.639 | 45.865 | 1.00 | 45.78 |
| 5322 | CG | GLU | B | 412 | 143.557 | −42.193 | 45.435 | 1.00 | 54.05 |
| 5323 | CD | GLU | B | 412 | 144.624 | −42.584 | 46.422 | 1.00 | 58.79 |
| 5324 | OE1 | GLU | B | 412 | 144.505 | −43.675 | 47.016 | 1.00 | 60.75 |
| 5325 | OE2 | GLU | B | 412 | 145.585 | −41.804 | 46.599 | 1.00 | 63.00 |
| 5326 | C | GLU | B | 412 | 139.865 | −42.883 | 44.858 | 1.00 | 36.51 |
| 5327 | O | GLU | B | 412 | 140.024 | −44.019 | 44.400 | 1.00 | 38.52 |
| 5328 | N | GLY | B | 413 | 138.669 | −42.412 | 45.209 | 1.00 | 31.68 |
| 5329 | CA | GLY | B | 413 | 137.479 | −43.213 | 44.975 | 1.00 | 26.36 |
| 5330 | C | GLY | B | 413 | 136.694 | −43.897 | 46.081 | 1.00 | 23.30 |
| 5331 | O | GLY | B | 413 | 135.695 | −44.551 | 45.803 | 1.00 | 20.47 |
| 5332 | N | GLU | B | 414 | 137.102 | −43.774 | 47.331 | 1.00 | 20.80 |
| 5333 | CA | GLU | B | 414 | 136.346 | −44.444 | 48.374 | 1.00 | 17.99 |
| 5334 | CB | GLU | B | 414 | 136.913 | −44.070 | 49.743 | 1.00 | 18.62 |
| 5335 | CG | GLU | B | 414 | 136.110 | −44.612 | 50.929 | 1.00 | 21.10 |
| 5336 | CD | GLU | B | 414 | 136.213 | −46.118 | 51.047 | 1.00 | 22.88 |
| 5337 | OE1 | GLU | B | 414 | 135.448 | −46.829 | 50.351 | 1.00 | 24.76 |
| 5338 | OE2 | GLU | B | 414 | 137.076 | −46.587 | 51.825 | 1.00 | 24.35 |
| 5339 | C | GLU | B | 414 | 134.870 | −44.049 | 48.299 | 1.00 | 16.75 |
| 5340 | O | GLU | B | 414 | 134.548 | −42.995 | 47.789 | 1.00 | 15.69 |
| 5341 | N | THR | B | 415 | 133.963 | −44.896 | 48.769 | 1.00 | 15.72 |
| 5342 | CA | THR | B | 415 | 132.557 | −44.491 | 48.773 | 1.00 | 18.07 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5343 | CB | THR | B | 415 | 131.688 | −45.288 | 47.751 | 1.00 | 20.74 |
| 5344 | OG1 | THR | B | 415 | 130.677 | −46.015 | 48.449 | 1.00 | 24.52 |
| 5345 | CG2 | THR | B | 415 | 132.537 | −46.224 | 46.922 | 1.00 | 23.04 |
| 5346 | C | THR | B | 415 | 132.024 | −44.629 | 50.204 | 1.00 | 17.33 |
| 5347 | O | THR | B | 415 | 132.180 | −45.673 | 50.844 | 1.00 | 18.19 |
| 5348 | N | TYR | B | 416 | 131.442 | −43.544 | 50.714 | 1.00 | 17.05 |
| 5349 | CA | TYR | B | 416 | 130.927 | −43.498 | 52.085 | 1.00 | 17.50 |
| 5350 | CB | TYR | B | 416 | 131.280 | −42.149 | 52.727 | 1.00 | 15.39 |
| 5351 | CG | TYR | B | 416 | 132.771 | −41.907 | 52.766 | 1.00 | 12.76 |
| 5352 | CD1 | TYR | B | 416 | 133.473 | −41.657 | 51.591 | 1.00 | 13.93 |
| 5353 | CE1 | TYR | B | 416 | 134.856 | −41.527 | 51.590 | 1.00 | 15.46 |
| 5354 | CD2 | TYR | B | 416 | 133.492 | −42.011 | 53.961 | 1.00 | 10.80 |
| 5355 | CE2 | TYR | B | 416 | 134.897 | −41.875 | 53.973 | 1.00 | 13.21 |
| 5356 | CZ | TYR | B | 416 | 135.568 | −41.632 | 52.777 | 1.00 | 13.84 |
| 5357 | OH | TYR | B | 416 | 136.944 | −41.479 | 52.753 | 1.00 | 16.13 |
| 5358 | C | TYR | B | 416 | 129.440 | −43.770 | 52.199 | 1.00 | 22.38 |
| 5359 | O | TYR | B | 416 | 128.652 | −43.463 | 51.291 | 1.00 | 14.96 |
| 5360 | N | GLN | B | 417 | 129.052 | −44.340 | 53.330 | 1.00 | 31.45 |
| 5361 | CA | GLN | B | 417 | 127.661 | −44.714 | 53.521 | 1.00 | 39.77 |
| 5362 | CB | GLN | B | 417 | 127.527 | −46.222 | 53.329 | 1.00 | 52.62 |
| 5363 | CG | GLN | B | 417 | 126.135 | −46.783 | 53.184 | 1.00 | 87.52 |
| 5364 | CD | GLN | B | 417 | 126.173 | −48.281 | 53.020 | 1.00 | 104.17 |
| 5365 | OE1 | GLN | B | 417 | 127.209 | −48.899 | 53.029 | 1.00 | 111.97 |
| 5366 | NE2 | GLN | B | 417 | 125.065 | −48.855 | 52.869 | 1.00 | 111.68 |
| 5367 | C | GLN | B | 417 | 127.077 | −44.317 | 54.858 | 1.00 | 38.70 |
| 5368 | O | GLN | B | 417 | 127.724 | −44.388 | 55.906 | 1.00 | 31.74 |
| 5369 | N | CYS | B | 418 | 125.825 | −43.897 | 54.790 | 1.00 | 37.30 |
| 5370 | CA | CYS | B | 418 | 125.076 | −43.482 | 55.946 | 1.00 | 33.10 |
| 5371 | C | CYS | B | 418 | 123.837 | −44.339 | 56.035 | 1.00 | 34.71 |
| 5372 | O | CYS | B | 418 | 123.003 | −44.349 | 55.124 | 1.00 | 32.31 |
| 5373 | CB | CYS | B | 418 | 124.678 | −42.026 | 55.803 | 1.00 | 30.53 |
| 5374 | SG | CYS | B | 418 | 123.441 | −41.429 | 57.002 | 1.00 | 35.65 |
| 5375 | N | ARG | B | 419 | 123.721 | −45.063 | 57.139 | 1.00 | 38.83 |
| 5376 | CA | ARG | B | 419 | 122.575 | −45.918 | 57.348 | 1.00 | 44.90 |
| 5377 | CB | ARG | B | 419 | 123.032 | −47.314 | 57.751 | 1.00 | 54.51 |
| 5378 | CG | ARG | B | 419 | 121.892 | −48.276 | 57.986 | 1.00 | 64.89 |
| 5379 | CD | ARG | B | 419 | 122.290 | −49.696 | 57.634 | 1.00 | 75.73 |
| 5380 | NE | ARG | B | 419 | 121.223 | −50.648 | 57.917 | 1.00 | 85.61 |
| 5381 | CZ | ARG | B | 419 | 121.060 | −51.250 | 59.085 | 1.00 | 90.23 |
| 5382 | NH1 | ARG | B | 419 | 121.901 | −51.002 | 60.076 | 1.00 | 92.88 |
| 5383 | NH2 | ARG | B | 419 | 120.054 | −52.093 | 59.259 | 1.00 | 92.28 |
| 5384 | C | ARG | B | 419 | 121.678 | −45.324 | 58.416 | 1.00 | 43.50 |
| 5385 | O | ARG | B | 419 | 122.049 | −45.254 | 59.596 | 1.00 | 45.19 |
| 5386 | N | VAL | B | 420 | 120.497 | −44.889 | 57.989 | 1.00 | 44.24 |
| 5387 | CA | VAL | B | 420 | 119.539 | −44.297 | 58.911 | 1.00 | 51.17 |
| 5388 | CB | VAL | B | 420 | 118.672 | −43.236 | 58.216 | 1.00 | 48.25 |
| 5389 | CG1 | VAL | B | 420 | 117.821 | −42.498 | 59.256 | 1.00 | 45.02 |
| 5390 | CG2 | VAL | B | 420 | 119.565 | −42.265 | 57.459 | 1.00 | 43.64 |
| 5391 | C | VAL | B | 420 | 118.651 | −45.389 | 59.493 | 1.00 | 61.64 |
| 5392 | O | VAL | B | 420 | 117.748 | −45.904 | 58.834 | 1.00 | 55.74 |
| 5393 | N | THR | B | 421 | 118.930 | −45.745 | 60.739 | 1.00 | 76.76 |
| 5394 | CA | THR | B | 421 | 118.179 | −46.785 | 61.413 | 1.00 | 84.89 |
| 5395 | CB | THR | B | 421 | 119.041 | −47.415 | 62.532 | 1.00 | 84.21 |
| 5396 | OG1 | THR | B | 421 | 120.155 | −48.097 | 61.941 | 1.00 | 93.17 |
| 5397 | CG2 | THR | B | 421 | 118.233 | −48.400 | 63.355 | 1.00 | 92.23 |
| 5398 | C | THR | B | 421 | 116.864 | −46.243 | 61.966 | 1.00 | 96.91 |
| 5399 | O | THR | B | 421 | 116.718 | −46.009 | 63.163 | 1.00 | 91.24 |
| 5400 | N | HIS | B | 424 | 110.633 | −45.581 | 59.458 | 1.00 | 124.56 |
| 5401 | CA | HIS | B | 424 | 110.546 | −46.367 | 60.657 | 1.00 | 122.02 |
| 5402 | CB | HIS | B | 424 | 109.225 | −46.260 | 61.369 | 1.00 | 126.05 |
| 5403 | CG | HIS | B | 424 | 109.177 | −47.193 | 62.536 | 1.00 | 138.44 |
| 5404 | CD2 | HIS | B | 424 | 108.463 | −48.315 | 62.756 | 1.00 | 143.66 |
| 5405 | ND1 | HIS | B | 424 | 110.174 | −47.168 | 63.484 | 1.00 | 144.28 |
| 5406 | CE1 | HIS | B | 424 | 110.087 | −48.254 | 64.233 | 1.00 | 146.93 |
| 5407 | NE2 | HIS | B | 424 | 109.065 | −48.967 | 63.816 | 1.00 | 146.68 |
| 5408 | C | HIS | B | 424 | 110.728 | −47.825 | 60.478 | 1.00 | 118.94 |
| 5409 | O | HIS | B | 424 | 111.147 | −48.442 | 61.430 | 1.00 | 112.30 |
| 5410 | N | LEU | B | 425 | 110.324 | −48.389 | 59.340 | 1.00 | 118.31 |
| 5411 | CA | LEU | B | 425 | 110.498 | −49.821 | 59.068 | 1.00 | 118.31 |
| 5412 | CB | LEU | B | 425 | 111.342 | −50.511 | 60.177 | 1.00 | 118.31 |
| 5413 | CG | LEU | B | 425 | 112.450 | −49.694 | 60.914 | 1.00 | 118.31 |
| 5414 | CD1 | LEU | B | 425 | 113.070 | −50.458 | 62.001 | 1.00 | 118.31 |
| 5415 | CD2 | LEU | B | 425 | 113.424 | −49.039 | 60.027 | 1.00 | 118.31 |
| 5416 | C | LEU | B | 425 | 109.167 | −50.545 | 58.907 | 1.00 | 118.31 |
| 5417 | O | LEU | B | 425 | 108.876 | −51.489 | 59.638 | 1.00 | 118.31 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5418 | N | ALA | B | 427 | 111.987 | −48.084 | 55.559 | 1.00 | 63.31 |
| 5419 | CA | ALA | B | 427 | 112.128 | −49.368 | 56.233 | 1.00 | 63.31 |
| 5420 | CB | ALA | B | 427 | 112.152 | −50.497 | 55.222 | 1.00 | 63.31 |
| 5421 | C | ALA | B | 427 | 113.406 | −49.396 | 57.057 | 1.00 | 63.31 |
| 5422 | O | ALA | B | 427 | 113.366 | −49.781 | 58.195 | 1.00 | 63.31 |
| 5423 | N | ALA | B | 428 | 114.529 | −49.051 | 56.417 | 1.00 | 56.34 |
| 5424 | CA | ALA | B | 428 | 115.904 | −48.952 | 56.967 | 1.00 | 57.21 |
| 5425 | CB | ALA | B | 428 | 116.483 | −50.341 | 57.295 | 1.00 | 58.15 |
| 5426 | C | ALA | B | 428 | 116.692 | −48.307 | 55.805 | 1.00 | 56.79 |
| 5427 | O | ALA | B | 428 | 117.195 | −49.008 | 54.932 | 1.00 | 54.53 |
| 5428 | N | LEU | B | 429 | 116.804 | −46.979 | 55.797 | 1.00 | 57.86 |
| 5429 | CA | LEU | B | 429 | 117.459 | −46.263 | 54.693 | 1.00 | 58.00 |
| 5430 | CB | LEU | B | 429 | 116.991 | −44.811 | 54.675 | 1.00 | 62.98 |
| 5431 | CG | LEU | B | 429 | 115.500 | −44.582 | 54.927 | 1.00 | 71.65 |
| 5432 | CD1 | LEU | B | 429 | 115.309 | −43.209 | 55.545 | 1.00 | 76.91 |
| 5433 | CD2 | LEU | B | 429 | 114.707 | −44.724 | 53.641 | 1.00 | 77.18 |
| 5434 | C | LEU | B | 429 | 118.973 | −46.270 | 54.586 | 1.00 | 57.63 |
| 5435 | O | LEU | B | 429 | 119.706 | −46.331 | 55.578 | 1.00 | 53.23 |
| 5436 | N | MET | B | 430 | 119.440 | −46.186 | 53.354 | 1.00 | 59.34 |
| 5437 | CA | MET | B | 430 | 120.859 | −46.168 | 53.151 | 1.00 | 60.72 |
| 5438 | CB | MET | B | 430 | 121.371 | −47.564 | 52.916 | 1.00 | 75.27 |
| 5439 | CG | MET | B | 430 | 122.774 | −47.688 | 53.114 | 1.00 | 102.01 |
| 5440 | SD | MET | B | 430 | 123.184 | −49.415 | 52.896 | 1.00 | 118.87 |
| 5441 | CE | MET | B | 430 | 122.883 | −50.071 | 54.289 | 1.00 | 129.22 |
| 5442 | C | MET | B | 430 | 121.232 | −45.306 | 51.992 | 1.00 | 52.17 |
| 5443 | O | MET | B | 430 | 120.763 | −45.485 | 50.873 | 1.00 | 49.92 |
| 5444 | N | ARG | B | 431 | 122.073 | −44.339 | 52.276 | 1.00 | 42.84 |
| 5445 | CA | ARG | B | 431 | 122.520 | −43.488 | 51.223 | 1.00 | 36.26 |
| 5446 | CB | ARG | B | 431 | 122.129 | −42.049 | 51.506 | 1.00 | 37.15 |
| 5447 | CG | ARG | B | 431 | 120.631 | −41.838 | 51.563 | 1.00 | 41.81 |
| 5448 | CD | ARG | B | 431 | 119.990 | −41.983 | 50.200 | 1.00 | 47.24 |
| 5449 | NE | ARG | B | 431 | 118.545 | −41.794 | 50.250 | 1.00 | 55.73 |
| 5450 | CZ | ARG | B | 431 | 117.758 | −41.858 | 49.180 | 1.00 | 59.70 |
| 5451 | NH1 | ARG | B | 431 | 118.289 | −42.108 | 47.982 | 1.00 | 61.95 |
| 5452 | NH2 | ARG | B | 431 | 116.446 | −41.671 | 49.307 | 1.00 | 60.23 |
| 5453 | C | ARG | B | 431 | 124.021 | −43.658 | 51.164 | 1.00 | 31.89 |
| 5454 | O | ARG | B | 431 | 124.674 | −44.007 | 52.159 | 1.00 | 28.12 |
| 5455 | N | SER | B | 432 | 124.559 | −43.455 | 49.975 | 1.00 | 25.91 |
| 5456 | CA | SER | B | 432 | 125.975 | −43.572 | 49.803 | 1.00 | 23.31 |
| 5457 | CB | SER | B | 432 | 126.319 | −44.945 | 49.229 | 1.00 | 24.07 |
| 5458 | OG | SER | B | 432 | 125.791 | −45.114 | 47.928 | 1.00 | 27.36 |
| 5459 | C | SER | B | 432 | 126.444 | −42.454 | 48.896 | 1.00 | 22.19 |
| 5460 | O | SER | B | 432 | 125.661 | −41.838 | 48.175 | 1.00 | 22.05 |
| 5461 | N | THR | B | 433 | 127.735 | −42.177 | 48.939 | 1.00 | 22.37 |
| 5462 | CA | THR | B | 433 | 128.285 | −41.109 | 48.127 | 1.00 | 19.34 |
| 5463 | CB | THR | B | 433 | 128.211 | −39.749 | 48.887 | 1.00 | 18.15 |
| 5464 | OG1 | THR | B | 433 | 128.756 | −38.707 | 48.072 | 1.00 | 13.63 |
| 5465 | CG2 | THR | B | 433 | 128.993 | −39.823 | 50.202 | 1.00 | 16.41 |
| 5466 | C | THR | B | 433 | 129.724 | −41.447 | 47.811 | 1.00 | 19.63 |
| 5467 | O | THR | B | 433 | 130.385 | −42.152 | 48.571 | 1.00 | 20.15 |
| 5468 | N | THR | B | 434 | 130.206 | −40.938 | 46.688 | 1.00 | 21.95 |
| 5469 | CA | THR | B | 434 | 131.575 | −41.179 | 46.257 | 1.00 | 27.82 |
| 5470 | CB | THR | B | 434 | 131.700 | −42.569 | 45.589 | 1.00 | 28.47 |
| 5471 | OG1 | THR | B | 434 | 133.077 | −42.842 | 45.306 | 1.00 | 28.30 |
| 5472 | CG2 | THR | B | 434 | 130.901 | −42.611 | 44.282 | 1.00 | 28.02 |
| 5473 | C | THR | B | 434 | 131.872 | −40.093 | 45.237 | 1.00 | 29.46 |
| 5474 | O | THR | B | 434 | 130.962 | −39.379 | 44.840 | 1.00 | 29.43 |
| 5475 | N | LYS | B | 435 | 133.121 | −39.941 | 44.815 | 1.00 | 32.54 |
| 5476 | CA | LYS | B | 435 | 133.412 | −38.903 | 43.829 | 1.00 | 36.85 |
| 5477 | CB | LYS | B | 435 | 134.919 | −38.774 | 43.575 | 1.00 | 33.21 |
| 5478 | CG | LYS | B | 435 | 135.500 | −39.891 | 42.723 | 1.00 | 37.12 |
| 5479 | CD | LYS | B | 435 | 137.023 | −39.823 | 42.660 | 1.00 | 39.91 |
| 5480 | CE | LYS | B | 435 | 137.601 | −40.986 | 41.859 | 1.00 | 41.75 |
| 5481 | NZ | LYS | B | 435 | 139.096 | −40.990 | 41.849 | 1.00 | 40.83 |
| 5482 | C | LYS | B | 435 | 132.697 | −39.227 | 42.514 | 1.00 | 43.58 |
| 5483 | O | LYS | B | 435 | 132.358 | −40.380 | 42.228 | 1.00 | 39.60 |
| 5484 | N | THR | B | 436 | 132.480 | −38.183 | 41.727 | 1.00 | 51.48 |
| 5485 | CA | THR | B | 436 | 131.808 | −38.238 | 40.430 | 1.00 | 59.84 |
| 5486 | CB | THR | B | 436 | 131.322 | −36.827 | 40.056 | 1.00 | 62.49 |
| 5487 | OG1 | THR | B | 436 | 130.085 | −36.546 | 40.721 | 1.00 | 67.76 |
| 5488 | CG2 | THR | B | 436 | 131.175 | −36.685 | 38.551 | 1.00 | 69.09 |
| 5489 | C | THR | B | 436 | 132.716 | −38.723 | 39.296 | 1.00 | 65.22 |
| 5490 | O | THR | B | 436 | 133.844 | −38.251 | 39.173 | 1.00 | 61.41 |
| 5491 | N | SER | B | 437 | 132.241 | −39.640 | 38.456 | 1.00 | 68.73 |
| 5492 | CA | SER | B | 437 | 133.083 | −40.083 | 37.349 | 1.00 | 71.75 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5493 | CB | SER | B | 437 | 133.087 | −41.611 | 37.223 | 1.00 | 78.43 |
| 5494 | OG | SER | B | 437 | 131.827 | −42.107 | 36.815 | 1.00 | 97.73 |
| 5495 | C | SER | B | 437 | 132.587 | −39.429 | 36.062 | 1.00 | 69.20 |
| 5496 | O | SER | B | 437 | 131.708 | −38.567 | 36.094 | 1.00 | 69.50 |
| 5497 | N | GLY | B | 438 | 133.145 | −39.828 | 34.931 | 1.00 | 66.08 |
| 5498 | CA | GLY | B | 438 | 132.735 | −39.218 | 33.685 | 1.00 | 57.23 |
| 5499 | C | GLY | B | 438 | 133.840 | −38.288 | 33.234 | 1.00 | 53.04 |
| 5500 | O | GLY | B | 438 | 134.861 | −38.165 | 33.916 | 1.00 | 50.03 |
| 5501 | N | PRO | B | 439 | 133.671 | −37.616 | 32.089 | 1.00 | 52.31 |
| 5502 | CD | PRO | B | 439 | 132.483 | −37.665 | 31.218 | 1.00 | 50.01 |
| 5503 | CA | PRO | B | 439 | 134.690 | −36.694 | 31.569 | 1.00 | 48.74 |
| 5504 | CB | PRO | B | 439 | 134.122 | −36.250 | 30.219 | 1.00 | 49.43 |
| 5505 | CG | PRO | B | 439 | 133.039 | −37.253 | 29.895 | 1.00 | 52.22 |
| 5506 | C | PRO | B | 439 | 134.939 | −35.485 | 32.474 | 1.00 | 47.00 |
| 5507 | O | PRO | B | 439 | 134.111 | −35.146 | 33.320 | 1.00 | 44.02 |
| 5508 | N | ARG | B | 440 | 136.086 | −34.844 | 32.278 | 1.00 | 44.68 |
| 5509 | CA | ARG | B | 440 | 136.449 | −33.647 | 33.023 | 1.00 | 44.39 |
| 5510 | CB | ARG | B | 440 | 137.792 | −33.798 | 33.734 | 1.00 | 50.40 |
| 5511 | CG | ARG | B | 440 | 138.023 | −35.110 | 34.420 | 1.00 | 60.92 |
| 5512 | CD | ARG | B | 440 | 137.195 | −35.254 | 35.671 | 1.00 | 66.96 |
| 5513 | NE | ARG | B | 440 | 137.199 | −36.646 | 36.102 | 1.00 | 73.59 |
| 5514 | CZ | ARG | B | 440 | 136.622 | −37.100 | 37.209 | 1.00 | 76.71 |
| 5515 | NH1 | ARG | B | 440 | 135.983 | −36.275 | 38.020 | 1.00 | 78.15 |
| 5516 | NH2 | ARG | B | 440 | 136.683 | −38.390 | 37.502 | 1.00 | 79.26 |
| 5517 | C | ARG | B | 440 | 136.628 | −32.538 | 31.999 | 1.00 | 40.34 |
| 5518 | O | ARG | B | 440 | 137.078 | −32.784 | 30.870 | 1.00 | 39.59 |
| 5519 | N | ALA | B | 441 | 136.291 | −31.319 | 32.397 | 1.00 | 35.68 |
| 5520 | CA | ALA | B | 441 | 136.458 | −30.160 | 31.526 | 1.00 | 32.37 |
| 5521 | CB | ALA | B | 441 | 135.258 | −29.999 | 30.594 | 1.00 | 28.34 |
| 5522 | C | ALA | B | 441 | 136.581 | −28.967 | 32.453 | 1.00 | 30.38 |
| 5523 | O | ALA | B | 441 | 135.705 | −28.723 | 33.285 | 1.00 | 27.99 |
| 5524 | N | ALA | B | 442 | 137.686 | −28.247 | 32.324 | 1.00 | 32.03 |
| 5525 | CA | ALA | B | 442 | 137.928 | −27.090 | 33.160 | 1.00 | 31.70 |
| 5526 | CB | ALA | B | 442 | 139.276 | −26.469 | 32.817 | 1.00 | 36.00 |
| 5527 | C | ALA | B | 442 | 136.815 | −26.066 | 32.977 | 1.00 | 30.39 |
| 5528 | O | ALA | B | 442 | 136.166 | −26.007 | 31.931 | 1.00 | 33.80 |
| 5529 | N | PRO | B | 443 | 136.579 | −25.243 | 34.004 | 1.00 | 29.60 |
| 5530 | CD | PRO | B | 443 | 137.225 | −25.236 | 35.334 | 1.00 | 27.78 |
| 5531 | CA | PRO | B | 443 | 135.527 | −24.231 | 33.907 | 1.00 | 27.85 |
| 5532 | CB | PRO | B | 443 | 135.131 | −24.003 | 35.369 | 1.00 | 25.03 |
| 5533 | CG | PRO | B | 443 | 136.441 | −24.164 | 36.108 | 1.00 | 20.73 |
| 5534 | C | PRO | B | 443 | 136.070 | −22.960 | 33.282 | 1.00 | 23.37 |
| 5535 | O | PRO | B | 443 | 137.255 | −22.655 | 33.452 | 1.00 | 22.60 |
| 5536 | N | ALA | B | 444 | 135.225 | −22.232 | 32.550 | 1.00 | 19.79 |
| 5537 | CA | ALA | B | 444 | 135.654 | −20.955 | 31.993 | 1.00 | 21.53 |
| 5538 | CB | ALA | B | 444 | 135.079 | −20.733 | 30.591 | 1.00 | 19.88 |
| 5539 | C | ALA | B | 444 | 135.067 | −19.957 | 32.980 | 1.00 | 20.49 |
| 5540 | O | ALA | B | 444 | 133.956 | −20.159 | 33.477 | 1.00 | 19.95 |
| 5541 | N | VAL | B | 445 | 135.788 | −18.882 | 33.272 | 1.00 | 20.73 |
| 5542 | CA | VAL | B | 445 | 135.297 | −17.903 | 34.241 | 1.00 | 24.64 |
| 5543 | CB | VAL | B | 445 | 136.213 | −17.863 | 35.493 | 1.00 | 19.90 |
| 5544 | CG1 | VAL | B | 445 | 135.673 | −16.873 | 36.517 | 1.00 | 12.09 |
| 5545 | CG2 | VAL | B | 445 | 136.325 | −19.256 | 36.086 | 1.00 | 17.39 |
| 5546 | C | VAL | B | 445 | 135.184 | −16.488 | 33.683 | 1.00 | 22.62 |
| 5547 | O | VAL | B | 445 | 136.114 | −15.982 | 33.060 | 1.00 | 25.21 |
| 5548 | N | TYR | B | 446 | 134.041 | −15.848 | 33.915 | 1.00 | 27.52 |
| 5549 | CA | TYR | B | 446 | 133.825 | −14.488 | 33.441 | 1.00 | 35.56 |
| 5550 | CB | TYR | B | 446 | 132.908 | −14.492 | 32.220 | 1.00 | 53.80 |
| 5551 | CG | TYR | B | 446 | 133.371 | −15.387 | 31.094 | 1.00 | 58.78 |
| 5552 | CD1 | TYR | B | 446 | 132.926 | −16.703 | 30.990 | 1.00 | 63.39 |
| 5553 | CE1 | TYR | B | 446 | 133.343 | −17.520 | 29.944 | 1.00 | 72.38 |
| 5554 | CD2 | TYR | B | 446 | 134.249 | −14.912 | 30.124 | 1.00 | 63.25 |
| 5555 | CE2 | TYR | B | 446 | 134.671 | −15.720 | 29.079 | 1.00 | 72.10 |
| 5556 | CZ | TYR | B | 446 | 134.213 | −17.020 | 25.996 | 1.00 | 74.04 |
| 5557 | OH | TYR | B | 446 | 134.617 | −17.821 | 27.959 | 1.00 | 79.47 |
| 5558 | C | TYR | B | 446 | 133.194 | −13.649 | 34.551 | 1.00 | 28.81 |
| 5559 | O | TYR | B | 446 | 132.256 | −14.084 | 35.220 | 1.00 | 33.01 |
| 5560 | N | ALA | B | 447 | 133.711 | −12.445 | 34.754 | 1.00 | 25.58 |
| 5561 | CA | ALA | B | 447 | 133.180 | −11.567 | 35.792 | 1.00 | 27.84 |
| 5562 | CB | ALA | B | 447 | 134.189 | −11.431 | 36.932 | 1.00 | 27.51 |
| 5563 | C | ALA | B | 447 | 132.859 | −10.194 | 35.217 | 1.00 | 26.91 |
| 5564 | O | ALA | B | 447 | 133.580 | −9.694 | 34.350 | 1.00 | 25.24 |
| 5565 | N | PHE | B | 448 | 131.780 | −9.585 | 35.697 | 1.00 | 25.13 |
| 5566 | CA | PHE | B | 448 | 131.397 | −8.264 | 35.216 | 1.00 | 29.34 |
| 5567 | CB | PHE | B | 448 | 130.286 | −8.314 | 34.151 | 1.00 | 34.08 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5568 | CG | PHE | B | 448 | 130.173 | −9.614 | 33.420 | 1.00 | 36.32 |
| 5569 | CD1 | PHE | B | 448 | 129.497 | −10.688 | 33.992 | 1.00 | 37.31 |
| 5570 | CD2 | PHE | B | 448 | 130.691 | −9.754 | 32.133 | 1.00 | 37.04 |
| 5571 | CE1 | PHE | B | 448 | 129.339 | −11.887 | 33.294 | 1.00 | 38.16 |
| 5572 | CE2 | PHE | B | 448 | 130.536 | −10.957 | 31.426 | 1.00 | 38.76 |
| 5573 | CZ | PHE | B | 448 | 129.857 | −12.018 | 32.009 | 1.00 | 38.41 |
| 5574 | C | PHE | B | 448 | 130.889 | −7.393 | 36.336 | 1.00 | 26.89 |
| 5575 | O | PHE | B | 448 | 130.539 | −7.868 | 37.416 | 1.00 | 28.49 |
| 5576 | N | ALA | B | 449 | 130.830 | −6.098 | 36.055 | 1.00 | 27.01 |
| 5577 | CA | ALA | B | 449 | 130.335 | −5.130 | 37.025 | 1.00 | 26.54 |
| 5578 | CB | ALA | B | 449 | 131.424 | −4.139 | 37.382 | 1.00 | 26.44 |
| 5579 | C | ALA | B | 449 | 129.162 | −4.411 | 36.384 | 1.00 | 27.95 |
| 5580 | O | ALA | B | 449 | 129.226 | −4.023 | 35.228 | 1.00 | 27.57 |
| 5581 | N | THR | B | 450 | 128.076 | −4.246 | 37.117 | 1.00 | 29.19 |
| 5582 | CA | THR | B | 450 | 126.950 | −3.555 | 36.544 | 1.00 | 33.18 |
| 5583 | CB | THR | B | 450 | 125.674 | −3.792 | 37.339 | 1.00 | 33.68 |
| 5584 | OG1 | THR | B | 450 | 125.903 | −3.459 | 38.711 | 1.00 | 33.54 |
| 5585 | CG2 | THR | B | 450 | 125.239 | −5.233 | 37.225 | 1.00 | 31.62 |
| 5586 | C | THR | B | 450 | 127.263 | −2.086 | 36.597 | 1.00 | 38.27 |
| 5587 | O | THR | B | 450 | 128.045 | −1.640 | 37.441 | 1.00 | 36.06 |
| 5588 | N | PRO | B | 451 | 126.686 | −1.313 | 35.666 | 1.00 | 39.40 |
| 5589 | CD | PRO | B | 451 | 125.817 | −1.668 | 34.527 | 1.00 | 39.41 |
| 5590 | CA | PRO | B | 451 | 126.958 | 0.116 | 35.708 | 1.00 | 43.76 |
| 5591 | CB | PRO | B | 451 | 126.665 | 0.586 | 34.286 | 1.00 | 42.26 |
| 5592 | CG | PRO | B | 451 | 125.590 | −0.324 | 33.831 | 1.00 | 39.44 |
| 5593 | C | PRO | B | 451 | 125.944 | 0.582 | 36.704 | 1.00 | 50.83 |
| 5594 | O | PRO | B | 451 | 125.033 | −0.158 | 37.068 | 1.00 | 44.91 |
| 5595 | N | GLU | B | 452 | 126.084 | 1.804 | 37.148 | 1.00 | 58.10 |
| 5596 | CA | GLU | B | 452 | 125.166 | 2.292 | 38.138 | 1.00 | 67.01 |
| 5597 | CB | GLU | B | 452 | 125.539 | 3.720 | 38.448 | 1.00 | 82.16 |
| 5598 | CG | GLU | B | 452 | 124.897 | 4.222 | 39.684 | 1.00 | 107.89 |
| 5599 | CD | GLU | B | 452 | 125.349 | 5.611 | 40.008 | 1.00 | 121.95 |
| 5600 | OE1 | GLU | B | 452 | 126.198 | 6.143 | 39.265 | 1.00 | 130.05 |
| 5601 | OE2 | GLU | B | 452 | 124.861 | 6.174 | 41.003 | 1.00 | 129.59 |
| 5602 | C | GLU | B | 452 | 123.669 | 2.203 | 37.797 | 1.00 | 63.67 |
| 5603 | O | GLU | B | 452 | 123.276 | 2.402 | 36.650 | 1.00 | 63.74 |
| 5604 | N | TRP | B | 453 | 122.850 | 1.878 | 38.803 | 1.00 | 56.58 |
| 5605 | CA | TRP | B | 453 | 121.379 | 1.830 | 38.669 | 1.00 | 51.44 |
| 5606 | CB | TRP | B | 453 | 120.753 | 0.506 | 39.179 | 1.00 | 49.16 |
| 5607 | CG | TRP | B | 453 | 119.229 | 0.344 | 38.840 | 1.00 | 46.51 |
| 5608 | CD2 | TRP | B | 453 | 118.667 | −0.164 | 37.618 | 1.00 | 44.75 |
| 5609 | CE2 | TRP | B | A53 | 117.258 | −0.068 | 37.715 | 1.00 | 44.60 |
| 5610 | CE3 | TRP | B | 453 | 119.218 | −0.705 | 36.446 | 1.00 | 43.78 |
| 5611 | CD1 | TRP | B | 453 | 118.154 | 0.725 | 39.613 | 1.00 | 45.26 |
| 5612 | NE1 | TRP | B | 453 | 116.971 | 0.485 | 38.944 | 1.00 | 45.00 |
| 5613 | CZ2 | TRP | B | 453 | 116.396 | −0.471 | 36.687 | 1.00 | 44.29 |
| 5614 | CZ3 | TRP | B | 453 | 118.362 | −1.108 | 35.422 | 1.00 | 44.19 |
| 5615 | CH2 | TRP | B | 453 | 116.968 | −0.994 | 35.554 | 1.00 | 43.58 |
| 5616 | C | TRP | B | 453 | 120.851 | 2.985 | 39.531 | 1.00 | 51.73 |
| 5617 | O | TRP | B | 453 | 121.311 | 3.194 | 40.665 | 1.00 | 49.47 |
| 5618 | N | PRO | B | 454 | 119.876 | 3.748 | 39.010 | 1.00 | 52.64 |
| 5619 | CD | PRO | B | 454 | 119.191 | 3.592 | 37.719 | 1.00 | 47.93 |
| 5620 | CA | PRO | B | 454 | 119.331 | 4.871 | 39.772 | 1.00 | 54.35 |
| 5621 | CB | PRO | B | 454 | 118.222 | 5.423 | 38.872 | 1.00 | 49.88 |
| 5622 | CG | PRO | B | 454 | 117.896 | 4.317 | 37.950 | 1.00 | 45.98 |
| 5623 | C | PRO | B | 454 | 118.840 | 4.482 | 41.147 | 1.00 | 59.81 |
| 5624 | O | PRO | B | 454 | 118.374 | 3.364 | 41.365 | 1.00 | 61.04 |
| 5625 | N | GLY | B | 455 | 118.961 | 5.425 | 42.073 | 1.00 | 63.94 |
| 5626 | CA | GLY | B | 455 | 118.548 | 5.176 | 43.434 | 1.00 | 77.44 |
| 5627 | C | GLY | B | 455 | 119.725 | 4.540 | 44.127 | 1.00 | 82.41 |
| 5628 | O | GLY | B | 455 | 120.533 | 5.233 | 44.739 | 1.00 | 91.93 |
| 5629 | N | SER | B | 456 | 119.839 | 3.221 | 44.025 | 1.00 | 83.94 |
| 5630 | CA | SER | B | 456 | 120.958 | 2.534 | 44.646 | 1.00 | 82.99 |
| 5631 | CB | SER | B | 456 | 121.265 | 1.244 | 43.885 | 1.00 | 81.65 |
| 5632 | OG | SER | B | 456 | 120.068 | 0.551 | 43.556 | 1.00 | 76.75 |
| 5633 | C | SER | B | 456 | 122.166 | 3.488 | 44.642 | 1.00 | 86.31 |
| 5634 | O | SER | B | 456 | 122.614 | 3.898 | 45.704 | 1.00 | 80.34 |
| 5635 | N | ARG | B | 457 | 122.662 | 3.876 | 43.467 | 1.00 | 88.12 |
| 5636 | CA | ARG | B | 457 | 123.796 | 4.808 | 43.382 | 1.00 | 85.63 |
| 5637 | CB | ARG | B | 457 | 123.325 | 6.245 | 43.678 | 1.00 | 91.75 |
| 5638 | CG | ARG | B | 457 | 124.389 | 7.334 | 43.511 | 1.00 | 117.92 |
| 5639 | CD | ARG | B | 457 | 123.911 | 8.684 | 44.035 | 1.00 | 130.94 |
| 5640 | NE | ARG | B | 457 | 124.894 | 9.739 | 43.795 | 1.00 | 135.84 |
| 5641 | CZ | ARG | B | 457 | 124.750 | 11.002 | 44.186 | 1.00 | 136.91 |
| 5642 | NH1 | ARG | B | 457 | 123.660 | 11.373 | 44.843 | 1.00 | 136.91 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5643 | NH2 | ARG | B | 457 | 125.693 | 11.897 | 43.917 | 1.00 | 135.65 |
| 5644 | C | ARG | B | 457 | 124.927 | 4.443 | 44.342 | 1.00 | 82.19 |
| 5645 | O | ARG | B | 457 | 124.713 | 4.266 | 45.535 | 1.00 | 71.12 |
| 5646 | N | ASP | B | 458 | 126.131 | 4.328 | 43.804 | 1.00 | 77.52 |
| 5647 | CA | ASP | B | 458 | 127.317 | 4.006 | 44.578 | 1.00 | 70.75 |
| 5648 | CB | ASP | B | 458 | 127.907 | 5.306 | 45.047 | 1.00 | 68.64 |
| 5649 | CG | ASP | B | 458 | 128.276 | 6.153 | 43.868 | 1.00 | 69.28 |
| 5650 | OD1 | ASP | B | 458 | 129.394 | 5.969 | 43.340 | 1.00 | 70.36 |
| 5651 | OD2 | ASP | B | 458 | 127.424 | 6.952 | 43.424 | 1.00 | 70.63 |
| 5652 | C | ASP | B | 458 | 127.193 | 2.940 | 45.651 | 1.00 | 69.77 |
| 5653 | O | ASP | B | 458 | 126.979 | 3.170 | 46.850 | 1.00 | 71.76 |
| 5654 | N | LYS | B | 459 | 127.354 | 1.746 | 45.093 | 1.00 | 73.30 |
| 5655 | CA | LYS | B | 459 | 127.292 | 0.432 | 45.699 | 1.00 | 74.27 |
| 5656 | CB | LYS | B | 459 | 126.390 | 0.466 | 46.949 | 1.00 | 81.24 |
| 5657 | CG | LYS | B | 459 | 125.216 | −0.496 | 47.013 | 1.00 | 90.86 |
| 5658 | CD | LYS | B | 459 | 124.990 | −0.975 | 48.455 | 1.00 | 93.38 |
| 5659 | CE | LYS | B | 459 | 123.737 | −0.385 | 49.089 | 1.00 | 93.32 |
| 5660 | NZ | LYS | B | 459 | 123.443 | −1.011 | 50.413 | 1.00 | 94.37 |
| 5661 | C | LYS | B | 459 | 126.714 | −0.314 | 44.472 | 1.00 | 69.41 |
| 5662 | O | LYS | B | 459 | 125.588 | −0.065 | 44.043 | 1.00 | 75.24 |
| 5663 | N | ARG | B | 460 | 127.533 | −1.195 | 43.897 | 1.00 | 66.04 |
| 5664 | CA | ARG | B | 460 | 127.234 | −1.918 | 42.672 | 1.00 | 57.95 |
| 5665 | CB | ARG | B | 460 | 128.283 | −1.537 | 41.641 | 1.00 | 58.10 |
| 5666 | CG | ARG | B | 460 | 128.303 | −0.059 | 41.348 | 1.00 | 60.08 |
| 5667 | CD | ARG | B | 460 | 128.888 | 0.123 | 40.003 | 1.00 | 61.32 |
| 5668 | NE | ARG | B | 460 | 128.877 | 1.489 | 39.525 | 1.00 | 61.94 |
| 5669 | CZ | ARG | B | 460 | 129.503 | 1.835 | 38.412 | 1.00 | 64.88 |
| 5670 | NH1 | ARG | B | 460 | 130.155 | 0.901 | 37.726 | 1.00 | 65.49 |
| 5671 | NH2 | ARG | B | 460 | 129.484 | 3.087 | 37.986 | 1.00 | 65.99 |
| 5672 | C | ARG | B | 460 | 127.177 | −3.424 | 42.795 | 1.00 | 50.62 |
| 5673 | O | ARG | B | 460 | 127.497 | −3.987 | 43.836 | 1.00 | 48.95 |
| 5674 | N | THR | B | 461 | 126.774 | −4.076 | 41.711 | 1.00 | 42.06 |
| 5675 | CA | THR | B | 461 | 126.671 | −5.521 | 41.715 | 1.00 | 36.56 |
| 5676 | CB | THR | B | 461 | 125.269 | −5.976 | 41.271 | 1.00 | 36.31 |
| 5677 | OG1 | THR | B | 461 | 124.288 | −5.405 | 42.143 | 1.00 | 36.52 |
| 5678 | CG2 | THR | B | 461 | 125.149 | −7.487 | 41.330 | 1.00 | 33.35 |
| 5679 | C | THR | B | 461 | 127.696 | −6.135 | 40.790 | 1.00 | 34.57 |
| 5680 | O | THR | B | 461 | 127.920 | −5.648 | 39.683 | 1.00 | 35.27 |
| 5681 | N | LEU | B | 462 | 128.335 | −7.195 | 41.252 | 1.00 | 31.12 |
| 5682 | CA | LEU | B | 462 | 129.311 | −7.870 | 40.423 | 1.00 | 28.06 |
| 5683 | CB | LEU | B | 462 | 130.651 | −8.004 | 41.152 | 1.00 | 29.31 |
| 5684 | CG | LEU | B | 462 | 131.304 | −6.679 | 41.565 | 1.00 | 32.87 |
| 5685 | CD1 | LEU | B | 462 | 132.699 | −6.951 | 42.135 | 1.00 | 33.26 |
| 5686 | CD2 | LEU | B | 462 | 131.397 | −5.747 | 40.366 | 1.00 | 33.48 |
| 5687 | C | LEU | B | 462 | 128.724 | −9.232 | 40.148 | 1.00 | 28.77 |
| 5688 | O | LEU | B | 462 | 128.018 | −9.799 | 40.990 | 1.00 | 27.87 |
| 5689 | N | ALA | B | 463 | 128.985 | −9.768 | 38.970 | 1.00 | 25.49 |
| 5690 | CA | ALA | B | 463 | 128.449 | −11.075 | 38.667 | 1.00 | 22.36 |
| 5691 | CB | ALA | B | 463 | 127.234 | −10.955 | 37.779 | 1.00 | 21.53 |
| 5692 | C | ALA | B | 463 | 129.510 | −11.894 | 37.990 | 1.00 | 22.77 |
| 5693 | O | ALA | B | 463 | 130.372 | −11.383 | 37.270 | 1.00 | 23.36 |
| 5694 | N | CYS | B | 464 | 129.443 | −13.184 | 38.228 | 1.00 | 20.78 |
| 5695 | CA | CYS | B | 464 | 130.410 | −14.078 | 37.646 | 1.00 | 19.80 |
| 5696 | C | CYS | B | 464 | 129.685 | −15.214 | 36.957 | 1.00 | 18.69 |
| 5697 | O | CYS | B | 464 | 128.720 | −15.759 | 37.490 | 1.00 | 19.77 |
| 5698 | CB | CYS | B | 464 | 131.295 | −14.644 | 38.743 | 1.00 | 19.66 |
| 5699 | SG | CYS | B | 464 | 132.811 | −15.440 | 38.164 | 1.00 | 25.69 |
| 5700 | N | LEU | B | 465 | 130.136 | −15.549 | 35.760 | 1.00 | 19.11 |
| 5701 | CA | LEU | B | 465 | 129.559 | −16.655 | 35.019 | 1.00 | 18.60 |
| 5702 | CB | LEU | B | 465 | 129.120 | −16.223 | 33.612 | 1.00 | 17.41 |
| 5703 | CG | LEU | B | 465 | 128.832 | −17.376 | 32.638 | 1.00 | 18.43 |
| 5704 | CD1 | LEU | B | 465 | 127.625 | −18.200 | 33.121 | 1.00 | 18.73 |
| 5705 | CD2 | LEU | B | 465 | 128.578 | −16.829 | 31.240 | 1.00 | 16.69 |
| 5706 | C | LEU | B | 465 | 130.657 | −17.709 | 34.896 | 1.00 | 17.14 |
| 5707 | O | LEU | B | 465 | 131.750 | −17.429 | 34.376 | 1.00 | 16.86 |
| 5708 | N | ILE | B | 466 | 130.370 | −18.913 | 35.373 | 1.00 | 16.73 |
| 5709 | CA | ILE | B | 466 | 131.325 | −20.003 | 35.297 | 1.00 | 18.09 |
| 5710 | CB | ILE | B | 466 | 131.712 | −20.475 | 36.707 | 1.00 | 18.05 |
| 5711 | CG2 | ILE | B | 466 | 132.721 | −21.598 | 36.631 | 1.00 | 16.62 |
| 5712 | CG1 | ILE | B | 466 | 132.294 | −19.294 | 37.487 | 1.00 | 18.08 |
| 5713 | CD1 | ILE | B | 466 | 132.172 | −19.441 | 38.984 | 1.00 | 16.30 |
| 5714 | C | ILE | B | 466 | 130.611 | −21.095 | 34.525 | 1.00 | 19.48 |
| 5715 | O | ILE | B | 466 | 129.538 | −21.553 | 34.940 | 1.00 | 18.16 |
| 5716 | N | GLN | B | 467 | 131.198 | −21.520 | 33.404 | 1.00 | 20.42 |
| 5717 | CA | GLN | B | 467 | 130.528 | −22.511 | 32.563 | 1.00 | 23.25 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5718 | CB | GLN | B | 467 | 129.709 | −21.780 | 31.489 | 1.00 | 22.25 |
| 5719 | CG | GLN | B | 467 | 130.515 | −20.750 | 30.670 | 1.00 | 23.87 |
| 5720 | CD | GLN | B | 467 | 129.735 | −20.168 | 29.503 | 1.00 | 25.01 |
| 5721 | OE1 | GLN | B | 467 | 128.523 | −19.934 | 29.599 | 1.00 | 26.97 |
| 5722 | NE2 | GLN | B | 467 | 130.427 | −19.923 | 28.391 | 1.00 | 22.75 |
| 5723 | C | GLN | B | 467 | 131.382 | −23.561 | 31.870 | 1.00 | 25.40 |
| 5724 | O | GLN | B | 467 | 132.617 | −23.497 | 31.858 | 1.00 | 27.12 |
| 5725 | N | ASN | B | 468 | 130.685 | −24.530 | 31.283 | 1.00 | 27.00 |
| 5726 | CA | ASN | B | 468 | 131.297 | −25.611 | 30.524 | 1.00 | 29.37 |
| 5727 | CB | ASN | B | 468 | 132.006 | −25.041 | 29.289 | 1.00 | 29.74 |
| 5728 | CG | ASN | B | 468 | 131.040 | −24.361 | 28.325 | 1.00 | 32.13 |
| 5729 | OD1 | ASN | B | 468 | 129.870 | −24.742 | 28.230 | 1.00 | 31.76 |
| 5730 | ND2 | ASN | B | 468 | 131.531 | −23.370 | 27.590 | 1.00 | 31.12 |
| 5731 | C | ASN | B | 468 | 132.262 | −26.492 | 31.306 | 1.00 | 31.19 |
| 5732 | O | ASN | B | 468 | 133.170 | −27.083 | 30.713 | 1.00 | 28.91 |
| 5733 | N | PHE | B | 469 | 132.074 | −26.588 | 32.623 | 1.00 | 34.25 |
| 5734 | CA | PHE | B | 469 | 132.945 | −27.438 | 33.442 | 1.00 | 37.51 |
| 5735 | CB | PHE | B | 469 | 133.244 | −26.786 | 34.807 | 1.00 | 27.93 |
| 5736 | CG | PHE | B | 469 | 132.022 | −26.326 | 35.560 | 1.00 | 19.74 |
| 5737 | CD1 | PHE | B | 469 | 131.338 | −27.197 | 36.404 | 1.00 | 16.02 |
| 5738 | CD2 | PHE | B | 469 | 131.554 | −25.021 | 35.422 | 1.00 | 15.32 |
| 5739 | CE1 | PHE | B | 469 | 130.197 | −26.778 | 37.093 | 1.00 | 17.05 |
| 5740 | CE2 | PHE | B | 469 | 130.419 | −24.590 | 36.101 | 1.00 | 17.46 |
| 5741 | CZ | PHE | B | 469 | 129.734 | −25.462 | 36.945 | 1.00 | 16.32 |
| 5742 | C | PHE | B | 469 | 132.235 | −28.769 | 33.603 | 1.00 | 41.48 |
| 5743 | O | PHE | B | 469 | 131.009 | −28.793 | 33.688 | 1.00 | 44.97 |
| 5744 | N | MET | B | 470 | 132.944 | −29.891 | 33.631 | 1.00 | 43.30 |
| 5745 | CA | MET | B | 470 | 132.135 | −31.087 | 33.736 | 1.00 | 54.07 |
| 5746 | CB | MET | B | 470 | 132.648 | −32.204 | 32.834 | 1.00 | 69.99 |
| 5747 | CG | MET | B | 470 | 131.824 | −32.304 | 31.518 | 1.00 | 78.44 |
| 5748 | SD | MET | B | 470 | 130.565 | −33.592 | 31.593 | 1.00 | 79.82 |
| 5749 | CE | MET | B | 470 | 130.439 | −34.075 | 29.873 | 1.00 | 83.94 |
| 5750 | C | MET | B | 470 | 131.747 | −31.536 | 35.124 | 1.00 | 57.21 |
| 5751 | O | MET | B | 470 | 130.813 | −30.918 | 35.632 | 1.00 | 62.83 |
| 5752 | N | PRO | B | 471 | 132.394 | −32.541 | 35.784 | 1.00 | 38.71 |
| 5753 | CD | PRO | B | 471 | 133.683 | −33.247 | 35.663 | 1.00 | 42.41 |
| 5754 | CA | PRO | B | 471 | 131.783 | −32.773 | 37.105 | 1.00 | 39.54 |
| 5755 | CB | PRO | B | 471 | 132.958 | −33.070 | 38.014 | 1.00 | 35.89 |
| 5756 | CG | PRO | B | 471 | 134.002 | −33.643 | 37.097 | 1.00 | 37.09 |
| 5757 | C | PRO | B | 471 | 131.096 | −31.485 | 37.507 | 1.00 | 36.96 |
| 5758 | O | PRO | B | 471 | 131.659 | −30.398 | 37.339 | 1.00 | 25.95 |
| 5759 | N | GLU | B | 472 | 129.861 | −31.584 | 37.954 | 1.00 | 31.72 |
| 5760 | CA | GLU | B | 472 | 129.142 | −30.385 | 38.305 | 1.00 | 34.34 |
| 5761 | CB | GLU | B | 472 | 127.648 | −30.680 | 38.307 | 1.00 | 38.99 |
| 5762 | CG | GLU | B | 472 | 127.284 | −31.727 | 39.323 | 1.00 | 50.09 |
| 5763 | CD | GLU | B | 472 | 125.825 | −32.088 | 39.278 | 1.00 | 56.93 |
| 5764 | OE1 | GLU | B | 472 | 125.429 | −32.866 | 38.379 | 1.00 | 60.91 |
| 5765 | OE2 | GLU | B | 472 | 125.069 | −31.583 | 40.137 | 1.00 | 60.63 |
| 5766 | C | GLU | B | 472 | 129.576 | −29.813 | 39.655 | 1.00 | 34.07 |
| 5767 | O | GLU | B | 472 | 129.172 | −28.712 | 40.015 | 1.00 | 34.76 |
| 5768 | N | ASP | B | 473 | 130.403 | −30.538 | 40.403 | 1.00 | 34.03 |
| 5769 | CA | ASP | B | 473 | 130.837 | −30.024 | 41.703 | 1.00 | 33.65 |
| 5770 | CB | ASP | B | 473 | 131.509 | −31.128 | 42.520 | 1.00 | 39.32 |
| 5771 | CG | ASP | B | 473 | 130.573 | −32.286 | 42.778 | 1.00 | 45.06 |
| 5772 | OD1 | ASP | B | 473 | 129.390 | −32.023 | 43.071 | 1.00 | 47.31 |
| 5773 | OD2 | ASP | B | 473 | 131.010 | −33.451 | 42.682 | 1.00 | 50.40 |
| 5774 | C | ASP | B | 473 | 131.761 | −28.836 | 41.535 | 1.00 | 30.32 |
| 5775 | O | ASP | B | 473 | 132.778 | −28.919 | 40.839 | 1.00 | 27.94 |
| 5776 | N | ILE | B | 474 | 131.400 | −27.727 | 42.175 | 1.00 | 23.88 |
| 5777 | CA | ILE | B | 474 | 132.199 | −26.512 | 42.055 | 1.00 | 20.20 |
| 5778 | CB | ILE | B | 474 | 131.799 | −25.754 | 40.772 | 1.00 | 19.14 |
| 5779 | CG2 | ILE | B | 474 | 130.452 | −25.116 | 40.956 | 1.00 | 13.40 |
| 5780 | CG1 | ILE | B | 474 | 132.847 | −24.710 | 40.407 | 1.00 | 15.49 |
| 5781 | CD1 | ILE | B | 474 | 133.131 | −24.643 | 38.899 | 1.00 | 16.21 |
| 5782 | C | ILE | B | 474 | 132.082 | −25.545 | 43.239 | 1.00 | 20.52 |
| 5783 | O | ILE | B | 474 | 131.021 | −25.385 | 43.834 | 1.00 | 21.49 |
| 5784 | N | SER | B | 475 | 133.183 | −24.898 | 43.586 | 1.00 | 22.04 |
| 5785 | CA | SER | B | 475 | 133.136 | −23.929 | 44.666 | 1.00 | 22.09 |
| 5786 | CB | SER | B | 475 | 134.143 | −24.276 | 45.779 | 1.00 | 20.28 |
| 5787 | CG | SER | B | 475 | 133.726 | −25.419 | 46.507 | 1.00 | 19.05 |
| 5788 | C | SER | B | 475 | 133.451 | −22.564 | 44.066 | 1.00 | 20.94 |
| 5789 | O | SER | B | 475 | 134.182 | −22.453 | 43.077 | 1.00 | 20.99 |
| 5790 | N | VAL | B | 476 | 132.842 | −21.531 | 44.621 | 1.00 | 19.97 |
| 5791 | CA | VAL | B | 476 | 133.131 | −20.193 | 44.169 | 1.00 | 23.07 |
| 5792 | CB | VAL | B | 476 | 131.957 | −19.457 | 43.525 | 1.00 | 23.55 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5793 | CG1 | VAL | B | 476 | 132.405 | −18.060 | 43.095 | 1.00 | 22.38 |
| 5794 | CG2 | VAL | B | 476 | 131.453 | −20.211 | 42.333 | 1.00 | 23.27 |
| 5795 | C | VAL | B | 476 | 133.429 | −19.392 | 45.392 | 1.00 | 27.86 |
| 5796 | O | VAL | B | 476 | 132.903 | −19.649 | 46.476 | 1.00 | 27.51 |
| 5797 | N | GLN | B | 477 | 134.271 | −18.398 | 45.210 | 1.00 | 29.47 |
| 5798 | CA | GLN | B | 477 | 134.576 | −17.515 | 46.296 | 1.00 | 32.02 |
| 5799 | CB | GLN | B | 477 | 135.638 | −18.128 | 47.215 | 1.00 | 37.55 |
| 5800 | CG | GLN | B | 477 | 136.935 | −18.475 | 46.545 | 1.00 | 47.27 |
| 5801 | CD | GLN | B | 477 | 137.765 | −19.494 | 47.321 | 1.00 | 54.24 |
| 5802 | OE1 | GLN | B | 477 | 139.008 | −19.455 | 47.285 | 1.00 | 56.47 |
| 5803 | NE2 | GLN | B | 477 | 137.095 | −20.429 | 48.003 | 1.00 | 57.80 |
| 5804 | C | GLN | B | 477 | 135.026 | −16.215 | 45.684 | 1.00 | 30.73 |
| 5805 | O | GLN | B | 477 | 135.525 | −16.180 | 44.555 | 1.00 | 32.53 |
| 5806 | N | TRP | B | 478 | 134.795 | −15.139 | 46.415 | 1.00 | 29.36 |
| 5807 | CA | TRP | B | 478 | 135.181 | −13.835 | 45.935 | 1.00 | 28.79 |
| 5808 | CB | TRP | B | 478 | 133.996 | −12.868 | 45.949 | 1.00 | 26.94 |
| 5809 | CG | TRP | B | 478 | 132.907 | −13.182 | 44.961 | 1.00 | 25.12 |
| 5810 | CD2 | TRP | B | 478 | 132.714 | −12.571 | 43.676 | 1.00 | 24.10 |
| 5811 | CE2 | TRP | B | 478 | 131.574 | −13.163 | 43.096 | 1.00 | 24.20 |
| 5812 | CE3 | TRP | B | 478 | 133.417 | −11.602 | 42.942 | 1.00 | 22.36 |
| 5813 | CD1 | TRP | B | 478 | 131.892 | −14.078 | 45.116 | 1.00 | 24.56 |
| 5814 | NE1 | TRP | B | 478 | 131.080 | −14.070 | 44.003 | 1.00 | 25.72 |
| 5815 | CZ2 | TRP | B | 478 | 131.088 | −12.787 | 41.831 | 1.00 | 24.51 |
| 5816 | CZ3 | TRP | B | 478 | 132.940 | −11.228 | 41.688 | 1.00 | 22.19 |
| 5817 | CH2 | TRP | B | 478 | 131.795 | −11.832 | 41.138 | 1.00 | 22.45 |
| 5818 | C | TRP | B | 478 | 136.279 | −13.302 | 46.823 | 1.00 | 27.69 |
| 5819 | O | TRP | B | 478 | 136.274 | −13.502 | 48.036 | 1.00 | 28.46 |
| 5820 | N | LEU | B | 479 | 137.230 | −12.614 | 46.218 | 1.00 | 25.32 |
| 5821 | CA | LEU | B | 479 | 138.318 | −12.078 | 47.004 | 1.00 | 27.61 |
| 5822 | CB | LEU | B | 479 | 139.624 | −12.772 | 46.608 | 1.00 | 25.46 |
| 5823 | CG | LEU | B | 479 | 139.450 | −14.285 | 46.443 | 1.00 | 26.55 |
| 5824 | CD1 | LEU | B | 479 | 140.527 | −14.844 | 45.568 | 1.00 | 28.40 |
| 5825 | CD2 | LEU | B | 479 | 139.446 | −14.962 | 47.787 | 1.00 | 28.00 |
| 5826 | C | LEU | B | 479 | 138.442 | −10.566 | 46.827 | 1.00 | 29.98 |
| 5827 | O | LEU | B | 479 | 138.197 | −10.016 | 45.737 | 1.00 | 26.34 |
| 5828 | N | HIS | B | 480 | 138.802 | −9.893 | 47.916 | 1.00 | 33.53 |
| 5829 | CA | HIS | B | 480 | 139.001 | −8.453 | 47.878 | 1.00 | 37.77 |
| 5830 | CB | HIS | B | 480 | 137.883 | −7.721 | 48.616 | 1.00 | 31.42 |
| 5831 | CG | HIS | B | 480 | 137.961 | −6.230 | 48.447 | 1.00 | 28.16 |
| 5832 | CD2 | HIS | B | 480 | 137.719 | −5.225 | 49.320 | 1.00 | 26.93 |
| 5833 | ND1 | HIS | B | 480 | 138.362 | −5.661 | 47.271 | 1.00 | 27.87 |
| 5834 | CE1 | HIS | B | 480 | 138.373 | −4.337 | 47.416 | 1.00 | 27.51 |
| 5835 | NE2 | HIS | B | 480 | 137.990 | −4.053 | 48.637 | 1.00 | 27.85 |
| 5836 | C | HIS | B | 480 | 140.347 | −8.119 | 48.499 | 1.00 | 41.53 |
| 5837 | O | HIS | B | 480 | 140.936 | −8.970 | 49.140 | 1.00 | 42.67 |
| 5838 | N | ASN | B | 481 | 140.800 | −6.882 | 48.319 | 1.00 | 49.19 |
| 5839 | CA | ASN | B | 481 | 142.075 | −6.418 | 48.812 | 1.00 | 62.72 |
| 5840 | CB | ASN | B | 481 | 142.015 | −5.857 | 50.233 | 1.00 | 62.64 |
| 5841 | CG | ASN | B | 481 | 143.312 | −5.153 | 50.644 | 1.00 | 63.40 |
| 5842 | OD1 | ASN | B | 481 | 144.289 | −5.104 | 49.885 | 1.00 | 62.32 |
| 5843 | ND2 | ASN | B | 481 | 143.321 | −4.607 | 51.860 | 1.00 | 59.94 |
| 5844 | C | ASN | B | 481 | 143.069 | −7.511 | 48.723 | 1.00 | 72.61 |
| 5845 | O | ASN | B | 481 | 144.164 | −7.177 | 48.444 | 1.00 | 74.22 |
| 5846 | N | GLU | B | 482 | 142.742 | −8.777 | 48.970 | 1.00 | 77.82 |
| 5847 | CA | GLU | B | 482 | 143.701 | −9.852 | 48.782 | 1.00 | 79.35 |
| 5848 | CB | GLU | B | 482 | 145.120 | −9.274 | 48.829 | 1.00 | 92.75 |
| 5849 | CG | GLU | B | 482 | 145.398 | −8.329 | 47.592 | 1.00 | 117.79 |
| 5850 | CD | GLU | B | 482 | 146.783 | −7.891 | 47.507 | 1.00 | 131.66 |
| 5851 | OE1 | GLU | B | 482 | 147.569 | −8.596 | 48.143 | 1.00 | 140.37 |
| 5852 | OE2 | GLU | B | 482 | 147.089 | −6.901 | 46.806 | 1.00 | 139.76 |
| 5853 | C | GLU | B | 482 | 143.481 | −11.023 | 49.724 | 1.00 | 72.74 |
| 5854 | O | GLU | B | 482 | 144.225 | −12.010 | 49.702 | 1.00 | 65.93 |
| 5855 | N | VAL | B | 483 | 142.384 | −10.878 | 50.479 | 1.00 | 61.03 |
| 5856 | CA | VAL | B | 483 | 141.823 | −11.801 | 51.474 | 1.00 | 50.39 |
| 5857 | CB | VAL | B | 483 | 142.016 | −11.176 | 52.924 | 1.00 | 52.94 |
| 5858 | CG1 | VAL | B | 483 | 140.718 | −11.125 | 53.683 | 1.00 | 57.73 |
| 5859 | CG2 | VAL | B | 483 | 143.083 | −11.964 | 53.699 | 1.00 | 56.21 |
| 5860 | C | VAL | B | 483 | 140.313 | −12.023 | 51.070 | 1.00 | 42.26 |
| 5861 | O | VAL | B | 483 | 139.635 | −11.069 | 50.649 | 1.00 | 41.84 |
| 5862 | N | GLN | B | 484 | 139.845 | −13.288 | 51.178 | 1.00 | 36.37 |
| 5863 | CA | GLN | B | 484 | 138.494 | −13.832 | 50.847 | 1.00 | 31.17 |
| 5864 | CE | GLN | B | 484 | 138.549 | −15.379 | 50.936 | 1.00 | 29.33 |
| 5865 | CG | GLN | B | 484 | 137.221 | −16.122 | 51.009 | 1.00 | 30.10 |
| 5866 | CD | GLN | B | 484 | 137.346 | −17.632 | 50.786 | 1.00 | 33.71 |
| 5867 | OE1 | GLN | B | 484 | 136.538 | −18.418 | 51.327 | 1.00 | 33.43 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5868 | NE2 | GLN | B | 484 | 138.334 | −18.051 | 49.971 | 1.00 | 32.80 |
| 5869 | C | GLN | B | 484 | 137.324 | −13.303 | 51.670 | 1.00 | 27.30 |
| 5870 | O | GLN | B | 484 | 137.386 | −13.267 | 52.902 | 1.00 | 24.85 |
| 5871 | N | LEU | B | 485 | 136.256 | −12.907 | 50.975 | 1.00 | 26.34 |
| 5872 | CA | LEU | B | 485 | 135.085 | −12.351 | 51.618 | 1.00 | 24.79 |
| 5873 | CB | LEU | B | 485 | 134.287 | −11.524 | 50.612 | 1.00 | 27.01 |
| 5874 | CG | LEU | B | 485 | 134.993 | −10.289 | 50.046 | 1.00 | 27.23 |
| 5875 | CD1 | LEU | B | 485 | 134.260 | −9.792 | 48.801 | 1.00 | 25.69 |
| 5876 | CD2 | LEU | B | 485 | 135.038 | −9.201 | 51.119 | 1.00 | 25.34 |
| 5877 | C | LEU | B | 485 | 134.203 | −13.418 | 52.216 | 1.00 | 23.94 |
| 5878 | O | LEU | B | 485 | 134.195 | −14.554 | 51.766 | 1.00 | 27.04 |
| 5879 | N | PRO | B | 486 | 133.458 | −13.067 | 53.266 | 1.00 | 25.21 |
| 5880 | CD | PRO | B | 486 | 133.474 | −11.754 | 53.933 | 1.00 | 22.98 |
| 5881 | CA | PRO | B | 486 | 132.552 | −14.013 | 53.929 | 1.00 | 28.24 |
| 5882 | CB | PRO | B | 486 | 131.803 | −13.139 | 54.933 | 1.00 | 26.28 |
| 5883 | CG | PRO | B | 486 | 132.786 | −12.042 | 55.246 | 1.00 | 23.11 |
| 5884 | C | PRO | B | 486 | 131.595 | −14.643 | 52.912 | 1.00 | 32.90 |
| 5885 | O | PRO | B | 486 | 131.080 | −13.956 | 52.026 | 1.00 | 34.80 |
| 5886 | N | ASP | B | 487 | 131.351 | −15.942 | 53.052 | 1.00 | 39.70 |
| 5887 | CA | ASP | B | 487 | 130.465 | −16.659 | 52.145 | 1.00 | 43.06 |
| 5888 | CB | ASP | B | 487 | 130.320 | −18.120 | 52.584 | 1.00 | 56.30 |
| 5889 | CG | ASP | B | 487 | 131.639 | −18.872 | 52.538 | 1.00 | 70.11 |
| 5890 | OD1 | ASP | B | 487 | 132.494 | −18.517 | 51.694 | 1.00 | 79.58 |
| 5891 | OD2 | ASP | B | 487 | 131.820 | −19.822 | 53.330 | 1.00 | 79.55 |
| 5892 | C | ASP | B | 487 | 129.093 | −16.035 | 52.028 | 1.00 | 38.61 |
| 5893 | O | ASP | B | 487 | 128.542 | −15.952 | 50.935 | 1.00 | 37.44 |
| 5894 | N | ALA | B | 488 | 128.552 | −15.586 | 53.154 | 1.00 | 34.78 |
| 5895 | CA | ALA | B | 488 | 127.223 | −14.991 | 53.174 | 1.00 | 32.63 |
| 5896 | CB | ALA | B | 488 | 126.818 | −14.696 | 54.617 | 1.00 | 31.74 |
| 5897 | C | ALA | B | 488 | 127.063 | −13.727 | 52.315 | 1.00 | 31.55 |
| 5898 | O | ALA | B | 488 | 125.931 | −13.284 | 52.085 | 1.00 | 30.35 |
| 5899 | N | ARG | B | 489 | 128.176 | −13.153 | 51.846 | 1.00 | 29.29 |
| 5900 | CA | ARG | B | 489 | 128.109 | −11.938 | 51.037 | 1.00 | 31.13 |
| 5901 | CB | ARG | B | 489 | 129.403 | −11.142 | 51.197 | 1.00 | 31.23 |
| 5902 | CG | ARG | B | 489 | 129.248 | −10.014 | 52.212 | 1.00 | 29.49 |
| 5903 | CD | ARG | B | 489 | 129.248 | −8.675 | 51.507 | 1.00 | 30.08 |
| 5904 | NE | ARG | B | 489 | 130.478 | −7.966 | 51.810 | 1.00 | 32.65 |
| 5905 | CZ | ARG | B | 489 | 131.056 | −7.073 | 51.022 | 1.00 | 35.00 |
| 5906 | NH1 | ARG | B | 489 | 130.527 | −6.757 | 49.846 | 1.00 | 34.07 |
| 5907 | NH2 | ARG | B | 489 | 132.171 | −6.487 | 51.429 | 1.00 | 36.36 |
| 5908 | C | ARG | B | 489 | 127.779 | −12.150 | 49.550 | 1.00 | 30.63 |
| 5909 | O | ARG | B | 489 | 127.431 | −11.204 | 48.826 | 1.00 | 31.49 |
| 5910 | N | HIS | B | 490 | 127.875 | −13.391 | 49.092 | 1.00 | 31.24 |
| 5911 | CA | HIS | B | 490 | 127.557 | −13.663 | 47.705 | 1.00 | 32.96 |
| 5912 | CB | HIS | B | 490 | 128.808 | −14.024 | 46.913 | 1.00 | 31.79 |
| 5913 | CG | HIS | B | 490 | 129.393 | −15.353 | 47.282 | 1.00 | 33.28 |
| 5914 | CD2 | HIS | B | 490 | 129.050 | −16.605 | 46.915 | 1.00 | 31.33 |
| 5915 | ND1 | HIS | B | 490 | 130.464 | −15.478 | 48.144 | 1.00 | 34.30 |
| 5916 | CE1 | HIS | B | 490 | 130.754 | −16.759 | 48.289 | 1.00 | 32.07 |
| 5917 | NE2 | HIS | B | 490 | 129.914 | −17.465 | 47.557 | 1.00 | 31.60 |
| 5918 | C | HIS | B | 490 | 126.542 | −14.786 | 47.578 | 1.00 | 31.79 |
| 5919 | O | HIS | B | 490 | 126.320 | −15.559 | 48.511 | 1.00 | 33.15 |
| 5920 | N | SER | B | 491 | 125.925 | −14.862 | 46.409 | 1.00 | 30.14 |
| 5921 | CA | SER | B | 491 | 124.935 | −15.886 | 46.132 | 1.00 | 33.28 |
| 5922 | CB | SER | B | 491 | 123.566 | −15.240 | 45.936 | 1.00 | 33.65 |
| 5923 | OG | SER | B | 491 | 122.578 | −16.214 | 45.685 | 1.00 | 34.50 |
| 5924 | C | SER | B | 491 | 125.366 | −16.607 | 44.859 | 1.00 | 33.30 |
| 5925 | O | SER | B | 491 | 125.755 | −15.973 | 43.877 | 1.00 | 31.09 |
| 5926 | N | THR | B | 492 | 125.324 | −17.932 | 44.882 | 1.00 | 29.90 |
| 5927 | CA | THR | B | 492 | 125.705 | −18.710 | 43.715 | 1.00 | 28.23 |
| 5928 | CB | THR | B | 492 | 126.989 | −19.520 | 43.973 | 1.00 | 28.26 |
| 5929 | OG1 | THR | B | 492 | 128.095 | −18.624 | 44.093 | 1.00 | 30.09 |
| 5930 | CG2 | THR | B | 492 | 127.259 | −20.474 | 42.821 | 1.00 | 26.56 |
| 5931 | C | THR | B | 492 | 124.583 | −19.666 | 43.311 | 1.00 | 26.25 |
| 5932 | O | THR | B | 492 | 124.069 | −20.407 | 44.139 | 1.00 | 24.59 |
| 5933 | N | THR | B | 493 | 124.212 | −19.658 | 42.032 | 1.00 | 24.72 |
| 5934 | CA | THR | B | 493 | 123.127 | −20.527 | 41.564 | 1.00 | 28.99 |
| 5935 | CB | THR | B | 493 | 122.677 | −20.157 | 40.134 | 1.00 | 22.25 |
| 5936 | OG1 | THR | B | 493 | 123.708 | −20.498 | 39.203 | 1.00 | 22.44 |
| 5937 | CG2 | THR | B | 493 | 122.393 | −18.685 | 40.027 | 1.00 | 17.10 |
| 5938 | C | THR | B | 493 | 123.528 | −22.003 | 41.571 | 1.00 | 29.56 |
| 5939 | O | THR | B | 493 | 124.675 | −22.350 | 41.860 | 1.00 | 30.72 |
| 5940 | N | GLN | B | 494 | 122.578 | −22.872 | 41.256 | 1.00 | 33.82 |
| 5941 | CA | GLN | B | 494 | 122.841 | −24.308 | 41.230 | 1.00 | 38.38 |
| 5942 | CB | GLN | B | 494 | 121.577 | −25.080 | 41.611 | 1.00 | 46.60 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 5943 | CG | GLN | B | 494 | 121.185 | −24.903 | 43.082 | 1.00 | 63.02 |
| 5944 | CD | GLN | B | 494 | 121.666 | −26.042 | 43.967 | 1.00 | 70.83 |
| 5945 | OE1 | GLN | B | 494 | 121.218 | −27.185 | 43.812 | 1.00 | 76.39 |
| 5946 | NE2 | GLN | B | 494 | 122.580 | −25.745 | 44.898 | 1.00 | 74.80 |
| 5947 | C | GLN | B | 494 | 123.327 | −24.749 | 39.861 | 1.00 | 31.84 |
| 5948 | O | GLN | B | 494 | 122.840 | −24.275 | 38.833 | 1.00 | 31.51 |
| 5949 | N | PRO | B | 495 | 124.309 | −25.657 | 39.829 | 1.00 | 30.23 |
| 5950 | CD | PRO | B | 495 | 124.996 | −26.313 | 40.960 | 1.00 | 26.35 |
| 5951 | CA | PRO | B | 495 | 124.819 | −26.122 | 38.541 | 1.00 | 28.60 |
| 5952 | CB | PRO | B | 495 | 125.675 | −27.330 | 38.917 | 1.00 | 25.03 |
| 5953 | CG | PRO | B | 495 | 126.158 | −27.004 | 40.289 | 1.00 | 25.04 |
| 5954 | C | PRO | B | 495 | 123.664 | −26.507 | 37.626 | 1.00 | 29.12 |
| 5955 | O | PRO | B | 495 | 122.708 | −27.141 | 38.059 | 1.00 | 28.99 |
| 5956 | N | ARG | B | 496 | 123.739 | −26.088 | 36.371 | 1.00 | 32.68 |
| 5957 | CA | ARG | B | 496 | 122.731 | −26.415 | 35.373 | 1.00 | 38.21 |
| 5958 | CB | ARG | B | 496 | 121.853 | −25.210 | 35.040 | 1.00 | 43.14 |
| 5959 | CG | ARG | B | 496 | 120.798 | −24.885 | 36.070 | 1.00 | 55.67 |
| 5960 | CD | ARG | B | 496 | 120.406 | −23.412 | 35.997 | 1.00 | 64.78 |
| 5961 | NE | ARG | B | 496 | 118.960 | −23.229 | 36.060 | 1.00 | 71.52 |
| 5962 | CZ | ARG | B | 496 | 118.130 | −23.539 | 35.070 | 1.00 | 74.57 |
| 5963 | NH1 | ARG | B | 496 | 118.605 | −24.042 | 33.942 | 1.00 | 74.02 |
| 5964 | NH2 | ARG | B | 496 | 116.826 | −23.359 | 35.206 | 1.00 | 76.83 |
| 5965 | C | ARG | B | 496 | 123.467 | −26.848 | 34.122 | 1.00 | 38.32 |
| 5966 | O | ARG | B | 496 | 124.669 | −26.618 | 33.966 | 1.00 | 33.97 |
| 5967 | N | LYS | B | 497 | 122.734 | −27.466 | 33.216 | 1.00 | 39.75 |
| 5968 | CA | LYS | B | 497 | 123.338 | −27.942 | 32.001 | 1.00 | 43.81 |
| 5969 | CB | LYS | B | 497 | 122.706 | −29.257 | 31.556 | 1.00 | 45.75 |
| 5970 | CG | LYS | B | 497 | 123.358 | −30.506 | 32.116 | 1.00 | 52.96 |
| 5971 | CD | LYS | B | 497 | 124.747 | −30.742 | 31.521 | 1.00 | 59.61 |
| 5972 | CE | LYS | B | 497 | 125.374 | −32.008 | 32.081 | 1.00 | 64.69 |
| 5973 | NZ | LYS | B | 497 | 126.745 | −32.252 | 31.543 | 1.00 | 67.60 |
| 5974 | C | LYS | B | 497 | 123.263 | −26.992 | 30.857 | 1.00 | 44.72 |
| 5975 | O | LYS | B | 497 | 122.218 | −26.420 | 30.550 | 1.00 | 45.57 |
| 5976 | N | THR | B | 498 | 124.411 | −26.818 | 30.233 | 1.00 | 52.28 |
| 5977 | CA | THR | B | 498 | 124.480 | −26.023 | 29.042 | 1.00 | 62.64 |
| 5978 | CB | THR | B | 498 | 125.909 | −25.472 | 28.806 | 1.00 | 61.10 |
| 5979 | OG1 | THR | B | 498 | 126.853 | −26.549 | 28.762 | 1.00 | 62.16 |
| 5980 | CG2 | THR | B | 498 | 126.294 | −24.517 | 29.929 | 1.00 | 63.07 |
| 5981 | C | THR | B | 498 | 124.093 | −27.108 | 28.028 | 1.00 | 70.60 |
| 5982 | O | THR | B | 498 | 124.485 | −27.083 | 26.862 | 1.00 | 67.52 |
| 5983 | N | LYS | B | 499 | 123.326 | −28.077 | 28.536 | 1.00 | 85.90 |
| 5984 | CA | LYS | B | 499 | 122.776 | −29.216 | 27.795 | 1.00 | 98.58 |
| 5985 | CB | LYS | B | 499 | 121.648 | −28.733 | 26.865 | 1.00 | 105.87 |
| 5986 | CG | LYS | B | 499 | 120.366 | −28.332 | 27.606 | 1.00 | 124.96 |
| 5987 | CD | LYS | B | 499 | 119.956 | −29.393 | 28.627 | 1.00 | 135.56 |
| 5988 | CE | LYS | B | 499 | 118.956 | −28.827 | 29.625 | 1.00 | 139.96 |
| 5989 | NZ | LYS | B | 499 | 118.100 | −29.886 | 30.224 | 1.00 | 141.39 |
| 5990 | C | LYS | B | 499 | 123.690 | −30.170 | 27.032 | 1.00 | 102.20 |
| 5991 | O | LYS | B | 499 | 123.573 | −31.384 | 27.183 | 1.00 | 100.15 |
| 5992 | N | GLY | B | 500 | 124.606 | −29.670 | 26.220 | 1.00 | 106.33 |
| 5993 | CA | GLY | B | 500 | 125.420 | −30.621 | 25.491 | 1.00 | 112.14 |
| 5994 | C | GLY | B | 500 | 126.851 | −30.832 | 25.930 | 1.00 | 112.48 |
| 5995 | O | GLY | B | 500 | 127.408 | −31.919 | 25.753 | 1.00 | 120.00 |
| 5996 | N | SER | B | 501 | 127.440 | −29.802 | 26.520 | 1.00 | 106.76 |
| 5997 | CA | SER | B | 501 | 128.835 | −29.857 | 26.924 | 1.00 | 106.32 |
| 5998 | CB | SER | B | 501 | 129.552 | −28.627 | 26.370 | 1.00 | 113.48 |
| 5999 | OG | SER | B | 501 | 128.997 | −27.440 | 26.908 | 1.00 | 98.25 |
| 6000 | C | SER | B | 501 | 129.122 | −29.981 | 28.419 | 1.00 | 101.13 |
| 6001 | O | SER | B | 501 | 129.979 | −30.768 | 28.826 | 1.00 | 110.45 |
| 6002 | N | GLY | B | 502 | 128.424 | −29.202 | 29.237 | 1.00 | 92.74 |
| 6003 | CA | GLY | B | 502 | 128.673 | −29.268 | 30.662 | 1.00 | 69.39 |
| 6004 | C | GLY | B | 502 | 127.727 | −28.436 | 31.496 | 1.00 | 54.03 |
| 6005 | O | GLY | B | 502 | 126.553 | −28.299 | 31.152 | 1.00 | 46.67 |
| 6006 | N | PHE | B | 503 | 128.246 | −27.873 | 32.587 | 1.00 | 38.53 |
| 6007 | CA | PHE | B | 503 | 127.430 | −27.077 | 33.490 | 1.00 | 28.39 |
| 6008 | CB | PHE | B | 503 | 127.427 | −27.700 | 34.889 | 1.00 | 25.76 |
| 6009 | CG | PHE | B | 503 | 127.041 | −29.145 | 34.899 | 1.00 | 22.08 |
| 6010 | CD1 | PHE | B | 503 | 127.927 | −30.117 | 34.438 | 1.00 | 22.07 |
| 6011 | CD2 | PHE | B | 503 | 125.795 | −29.537 | 35.363 | 1.00 | 21.06 |
| 6012 | CE1 | PHE | B | 503 | 127.569 | −31.465 | 34.413 | 1.00 | 20.79 |
| 6013 | CE2 | PHE | B | 503 | 125.420 | −30.901 | 35.344 | 1.00 | 24.95 |
| 6014 | CZ | PHE | B | 503 | 126.321 | −31.862 | 34.876 | 1.00 | 21.94 |
| 6015 | C | PHE | B | 503 | 127.875 | −25.623 | 33.608 | 1.00 | 23.93 |
| 6016 | O | PHE | B | 503 | 129.007 | −25.256 | 33.255 | 1.00 | 22.77 |
| 6017 | N | PHE | B | 504 | 126.958 | −24.794 | 34.097 | 1.00 | 22.04 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 6018 | CA | PHE | B | 504 | 127.246 | −23.389 | 34.314 | 1.00 | 21.39 |
| 6019 | CB | PHE | B | 504 | 126.679 | −22.509 | 33.188 | 1.00 | 16.98 |
| 6020 | CG | PHE | B | 504 | 125.188 | −22.309 | 33.235 | 1.00 | 18.67 |
| 6021 | CD1 | PHE | B | 504 | 124.620 | −21.315 | 34.044 | 1.00 | 16.56 |
| 6022 | CD2 | PHE | B | 504 | 124.339 | −23.098 | 32.443 | 1.00 | 17.69 |
| 6023 | CE1 | PHE | B | 504 | 123.233 | −21.097 | 34.049 | 1.00 | 15.05 |
| 6024 | CE2 | PHE | B | 504 | 122.945 | −22.882 | 32.447 | 1.00 | 16.63 |
| 6025 | CZ | PHE | B | 504 | 122.398 | −21.883 | 33.255 | 1.00 | 14.59 |
| 6026 | C | PHE | B | 504 | 126.622 | −23.022 | 35.643 | 1.00 | 23.15 |
| 6027 | O | PHE | B | 504 | 125.665 | −23.656 | 36.090 | 1.00 | 20.36 |
| 6028 | N | VAL | B | 505 | 127.186 | −22.002 | 36.274 | 1.00 | 24.21 |
| 6029 | CA | VAL | B | 505 | 126.702 | −21.515 | 37.538 | 1.00 | 23.44 |
| 6030 | CB | VAL | B | 505 | 127.523 | −22.126 | 38.708 | 1.00 | 29.21 |
| 6031 | CG1 | VAL | B | 505 | 128.810 | −21.343 | 38.938 | 1.00 | 30.03 |
| 6032 | CG2 | VAL | B | 505 | 126.697 | −22.166 | 39.947 | 1.00 | 33.88 |
| 6033 | C | VAL | B | 505 | 126.900 | −20.005 | 37.488 | 1.00 | 23.95 |
| 6034 | O | VAL | B | 505 | 127.799 | −19.513 | 36.803 | 1.00 | 25.11 |
| 6035 | N | PHE | B | 506 | 126.055 | −19.262 | 38.190 | 1.00 | 23.80 |
| 6036 | CA | PHE | B | 506 | 126.184 | −17.815 | 38.232 | 1.00 | 23.98 |
| 6037 | CB | PHE | B | 506 | 124.899 | −17.142 | 37.746 | 1.00 | 28.18 |
| 6038 | CG | PHE | B | 506 | 124.858 | −16.861 | 36.262 | 1.00 | 26.71 |
| 6039 | CD1 | PHE | B | 506 | 124.027 | −17.599 | 35.412 | 1.00 | 27.90 |
| 6040 | CD2 | PHE | B | 506 | 125.593 | −15.817 | 35.725 | 1.00 | 25.73 |
| 6041 | CE1 | PHE | B | 506 | 123.927 | −17.284 | 34.049 | 1.00 | 29.83 |
| 6042 | CE2 | PHE | B | 506 | 125.500 | −15.492 | 34.358 | 1.00 | 28.37 |
| 6043 | CZ | PHE | B | 506 | 124.667 | −16.226 | 33.525 | 1.00 | 28.70 |
| 6044 | C | PHE | B | 506 | 126.421 | −17.413 | 39.686 | 1.00 | 22.11 |
| 6045 | O | PHE | B | 506 | 125.868 | −18.040 | 40.598 | 1.00 | 23.27 |
| 6046 | N | SER | B | 507 | 127.231 | −16.379 | 39.905 | 1.00 | 20.19 |
| 6047 | CA | SER | B | 507 | 127.491 | −15.894 | 41.254 | 1.00 | 20.91 |
| 6048 | CB | SER | B | 507 | 128.899 | −16.297 | 41.706 | 1.00 | 20.66 |
| 6049 | OG | SER | B | 507 | 129.081 | −16.015 | 43.083 | 1.00 | 17.96 |
| 6050 | C | SER | B | 507 | 127.330 | −14.367 | 41.289 | 1.00 | 21.84 |
| 6051 | O | SER | B | 507 | 127.876 | −13.646 | 40.443 | 1.00 | 20.78 |
| 6052 | N | ARG | B | 508 | 126.590 | −13.891 | 42.284 | 1.00 | 22.41 |
| 6053 | CA | ARG | B | 508 | 126.283 | −12.474 | 42.464 | 1.00 | 23.95 |
| 6054 | CB | ARG | B | 508 | 124.753 | −12.330 | 42.467 | 1.00 | 25.83 |
| 6055 | CG | ARG | B | 508 | 124.194 | −10.956 | 42.783 | 1.00 | 31.06 |
| 6056 | CD | ARG | B | 508 | 122.661 | −10.954 | 42.662 | 1.00 | 36.51 |
| 6057 | NE | ARG | B | 508 | 122.138 | −9.596 | 42.742 | 1.00 | 43.99 |
| 6058 | CZ | ARG | B | 508 | 122.050 | −8.892 | 43.867 | 1.00 | 46.47 |
| 6059 | NH1 | ARG | B | 508 | 122.440 | −9.428 | 45.015 | 1.00 | 47.24 |
| 6060 | NH2 | ARG | B | 508 | 121.610 | −7.637 | 43.840 | 1.00 | 48.38 |
| 6061 | C | ARG | B | 508 | 126.888 | −11.904 | 43.763 | 1.00 | 23.29 |
| 6062 | O | ARG | B | 508 | 126.745 | −12.491 | 44.834 | 1.00 | 24.23 |
| 6063 | N | LEU | B | 509 | 127.571 | −10.769 | 43.667 | 1.00 | 26.54 |
| 6064 | CA | LEU | B | 509 | 128.170 | −10.141 | 44.844 | 1.00 | 28.86 |
| 6065 | CB | LEU | B | 509 | 129.674 | −10.415 | 44.900 | 1.00 | 28.09 |
| 6066 | CG | LEU | B | 509 | 130.441 | −9.603 | 45.959 | 1.00 | 31.69 |
| 6067 | CD1 | LEU | B | 509 | 130.056 | −10.074 | 47.365 | 1.00 | 29.30 |
| 6068 | CD2 | LEU | B | 509 | 131.958 | −9.745 | 45.731 | 1.00 | 30.27 |
| 6069 | C | LEU | B | 509 | 127.954 | −8.635 | 44.833 | 1.00 | 32.46 |
| 6070 | O | LEU | B | 509 | 128.418 | −7.946 | 43.918 | 1.00 | 32.10 |
| 6071 | N | GLU | B | 510 | 127.253 | −8.123 | 45.840 | 1.00 | 35.34 |
| 6072 | CA | GLU | B | 510 | 127.023 | −6.682 | 45.952 | 1.00 | 37.47 |
| 6073 | CB | GLU | B | 510 | 125.726 | −6.423 | 46.727 | 1.00 | 44.22 |
| 6074 | CG | GLU | B | 510 | 124.465 | −6.733 | 45.915 | 1.00 | 62.51 |
| 6075 | CD | GLU | B | 510 | 123.181 | −6.642 | 46.721 | 1.00 | 71.49 |
| 6076 | OE1 | GLU | B | 510 | 122.743 | −7.604 | 47.302 | 1.00 | 76.31 |
| 6077 | OE2 | GLU | B | 510 | 122.564 | −5.606 | 46.810 | 1.00 | 77.00 |
| 6078 | C | GLU | B | 510 | 128.212 | −6.028 | 46.675 | 1.00 | 36.04 |
| 6079 | O | GLU | B | 510 | 128.598 | −6.468 | 47.745 | 1.00 | 31.78 |
| 6080 | N | VAL | B | 511 | 128.810 | −4.995 | 46.093 | 1.00 | 34.86 |
| 6081 | CA | VAL | B | 511 | 129.926 | −4.335 | 46.761 | 1.00 | 32.43 |
| 6082 | CB | VAL | B | 511 | 131.199 | −4.340 | 45.884 | 1.00 | 31.54 |
| 6083 | CG1 | VAL | B | 511 | 131.521 | −5.765 | 45.479 | 1.00 | 30.78 |
| 6084 | CG2 | VAL | B | 511 | 131.018 | −3.448 | 44.665 | 1.00 | 29.33 |
| 6085 | C | VAL | B | 511 | 129.577 | −2.898 | 47.151 | 1.00 | 33.14 |
| 6086 | O | VAL | B | 511 | 128.641 | −2.314 | 46.608 | 1.00 | 36.08 |
| 6087 | N | THR | B | 512 | 130.316 | −2.329 | 48.101 | 1.00 | 35.99 |
| 6088 | CA | THR | B | 512 | 130.052 | −0.961 | 48.548 | 1.00 | 40.19 |
| 6089 | CB | THR | B | 512 | 130.149 | −0.825 | 50.067 | 1.00 | 38.03 |
| 6090 | OG1 | THR | B | 512 | 131.505 | −1.051 | 50.470 | 1.00 | 38.69 |
| 6091 | CG2 | THR | B | 512 | 129.231 | −1.814 | 50.754 | 1.00 | 36.86 |
| 6092 | C | THR | B | 512 | 131.068 | −0.006 | 47.956 | 1.00 | 42.49 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 6093 | O | THR | B | 512 | 132.138 | −0.425 | 47.520 | 1.00 | 39.51 |
| 6094 | N | ARG | B | 513 | 130.732 | 1.281 | 47.962 | 1.00 | 46.21 |
| 6095 | CA | ARG | B | 513 | 131.619 | 2.305 | 47.422 | 1.00 | 50.39 |
| 6096 | CB | ARG | B | 513 | 130.938 | 3.677 | 47.495 | 1.00 | 57.81 |
| 6097 | CG | ARG | B | 513 | 131.680 | 4.779 | 46.775 | 1.00 | 67.04 |
| 6098 | CD | ARG | B | 513 | 130.838 | 6.048 | 46.651 | 1.00 | 76.30 |
| 6099 | NE | ARG | B | 513 | 131.506 | 7.070 | 45.845 | 1.00 | 84.94 |
| 6100 | CZ | ARG | B | 513 | 132.236 | 6.810 | 44.762 | 1.00 | 88.66 |
| 6101 | NH1 | ARd | B | 513 | 132.405 | 5.563 | 44.353 | 1.00 | 91.11 |
| 6102 | NH2 | ARG | B | 513 | 132.792 | 7.798 | 44.076 | 1.00 | 91.44 |
| 6103 | C | ARG | B | 513 | 132.936 | 2.317 | 48.199 | 1.00 | 46.79 |
| 6104 | O | ARG | B | 513 | 134.013 | 2.448 | 47.609 | 1.00 | 47.40 |
| 6105 | N | ALA | B | 514 | 132.845 | 2.159 | 49.520 | 1.00 | 45.95 |
| 6106 | CA | ALA | B | 514 | 134.031 | 2.150 | 50.374 | 1.00 | 45.92 |
| 6107 | CB | ALA | B | 514 | 133.634 | 1.965 | 51.830 | 1.00 | 46.81 |
| 6108 | C | ALA | B | 514 | 134.981 | 1.040 | 49.947 | 1.00 | 47.39 |
| 6109 | O | ALA | B | 514 | 136.205 | 1.221 | 49.946 | 1.00 | 48.95 |
| 6110 | N | GLU | B | 515 | 134.416 | −0.101 | 49.561 | 1.00 | 47.78 |
| 6111 | CA | GLU | B | 515 | 135.235 | −1.228 | 49.146 | 1.00 | 50.81 |
| 6112 | CB | GLU | B | 515 | 134.382 | −2.480 | 49.031 | 1.00 | 51.26 |
| 6113 | CG | GLU | B | 515 | 133.822 | −2.891 | 50.364 | 1.00 | 53.75 |
| 6114 | CD | GLU | B | 515 | 133.019 | −4.153 | 50.274 | 1.00 | 54.74 |
| 6115 | OE1 | GLU | B | 515 | 133.636 | −5.215 | 50.062 | 1.00 | 55.11 |
| 6116 | OE2 | GLU | B | 515 | 131.777 | −4.083 | 50.402 | 1.00 | 54.80 |
| 6117 | C | GLU | B | 515 | 136.019 | −1.017 | 47.867 | 1.00 | 52.40 |
| 6118 | O | GLU | B | 515 | 137.226 | −1.274 | 47.834 | 1.00 | 47.33 |
| 6119 | N | TRP | B | 516 | 135.376 | −0.534 | 46.813 | 1.00 | 51.56 |
| 6120 | CA | TRP | B | 516 | 136.152 | −0.363 | 45.603 | 1.00 | 56.70 |
| 6121 | CB | TRP | B | 516 | 135.268 | −0.495 | 44.358 | 1.00 | 59.20 |
| 6122 | CG | TRP | B | 516 | 134.457 | 0.698 | 44.006 | 1.00 | 59.06 |
| 6123 | CD2 | TRP | B | 516 | 133.040 | 0.840 | 44.166 | 1.00 | 61.47 |
| 6124 | CE2 | TRP | B | 516 | 132.695 | 2.114 | 43.644 | 1.00 | 63.61 |
| 6125 | CE3 | TRP | B | 516 | 132.039 | 0.024 | 44.703 | 1.00 | 64.73 |
| 6126 | CD1 | TRP | B | 516 | 134.898 | 1.851 | 43.413 | 1.00 | 58.60 |
| 6127 | NE1 | TRP | B | 516 | 133.840 | 2.704 | 43.189 | 1.00 | 63.08 |
| 6128 | CZ2 | TRP | B | 516 | 131.364 | 2.578 | 43.637 | 1.00 | 67.00 |
| 6129 | CZ3 | TRP | B | 516 | 130.720 | 0.488 | 44.696 | 1.00 | 67.60 |
| 6130 | CH2 | TRP | B | 516 | 130.400 | 1.756 | 44.170 | 1.00 | 68.16 |
| 6131 | C | TRP | B | 516 | 137.015 | 0.894 | 45.530 | 1.00 | 60.46 |
| 6132 | O | TRP | B | 516 | 137.457 | 1.266 | 44.451 | 1.00 | 59.34 |
| 6133 | N | ALA | B | 517 | 137.270 | 1.557 | 46.656 | 1.00 | 68.46 |
| 6134 | CA | ALA | B | 517 | 138.154 | 2.726 | 46.612 | 1.00 | 80.94 |
| 6135 | CB | ALA | B | 517 | 137.686 | 3.815 | 47.564 | 1.00 | 87.28 |
| 6136 | C | ALA | B | 517 | 139.519 | 2.220 | 47.042 | 1.00 | 89.89 |
| 6137 | O | ALA | B | 517 | 140.520 | 2.400 | 46.341 | 1.00 | 89.43 |
| 6138 | N | GLN | B | 518 | 139.535 | 1.585 | 48.211 | 1.00 | 93.43 |
| 6139 | CA | GLN | B | 518 | 140.743 | 1.008 | 48.775 | 1.00 | 86.45 |
| 6140 | CB | GLN | B | 518 | 140.408 | −0.088 | 49.761 | 1.00 | 73.51 |
| 6141 | CG | GLN | B | 518 | 140.365 | 0.322 | 51.176 | 1.00 | 91.49 |
| 6142 | CD | GLN | B | 518 | 140.453 | −0.871 | 52.080 | 1.00 | 88.74 |
| 6143 | OE1 | GLN | B | 518 | 141.389 | −1.679 | 51.970 | 1.00 | 81.88 |
| 6144 | NE2 | GLN | B | 518 | 139.486 | −1.003 | 52.990 | 1.00 | 82.23 |
| 6145 | C | GLN | B | 518 | 141.412 | 0.311 | 47.651 | 1.00 | 84.82 |
| 6146 | O | GLN | B | 518 | 142.548 | 0.586 | 47.266 | 1.00 | 77.23 |
| 6147 | N | LYS | B | 519 | 140.655 | −0.651 | 47.165 | 1.00 | 78.47 |
| 6148 | CA | LYS | B | 519 | 141.080 | −1.484 | 46.091 | 1.00 | 68.46 |
| 6149 | CB | LYS | B | 519 | 141.740 | −2.719 | 46.686 | 1.00 | 62.15 |
| 6150 | CG | LYS | B | 519 | 142.567 | −3.523 | 45.716 | 1.00 | 69.17 |
| 6151 | CD | LYS | B | 519 | 143.977 | −2.988 | 45.535 | 1.00 | 70.38 |
| 6152 | CE | LYS | B | 519 | 144.854 | −4.028 | 44.847 | 1.00 | 70.36 |
| 6153 | NZ | LYS | B | 519 | 146.120 | −3.434 | 44.327 | 1.00 | 72.95 |
| 6154 | C | LYS | B | 519 | 139.795 | −1.776 | 45.317 | 1.00 | 64.54 |
| 6155 | O | LYS | B | 519 | 138.810 | −2.287 | 45.848 | 1.00 | 62.63 |
| 6156 | N | ASP | B | 520 | 139.824 | −1.387 | 44.052 | 1.00 | 64.54 |
| 6157 | CA | ASP | B | 520 | 138.689 | −1.506 | 43.147 | 1.00 | 67.27 |
| 6158 | CB | ASP | B | 520 | 138.658 | −0.278 | 42.267 | 1.00 | 75.91 |
| 6159 | CG | ASP | B | 520 | 137.765 | −0.448 | 41.068 | 1.00 | 73.93 |
| 6160 | OD1 | ASP | B | 520 | 137.294 | −1.550 | 40.786 | 1.00 | 74.97 |
| 6161 | OD2 | ASP | B | 520 | 137.513 | 0.528 | 40.364 | 1.00 | 75.65 |
| 6162 | C | ASP | B | 520 | 138.745 | −2.758 | 42.296 | 1.00 | 62.04 |
| 6163 | O | ASP | B | 520 | 138.084 | −2.937 | 41.280 | 1.00 | 70.40 |
| 6164 | N | GLU | B | 521 | 139.576 | −3.645 | 42.751 | 1.00 | 56.68 |
| 6165 | CA | GLU | B | 521 | 139.757 | −4.907 | 42.107 | 1.00 | 53.01 |
| 6166 | CB | GLU | B | 521 | 141.240 | −5.217 | 42.085 | 1.00 | 58.47 |
| 6167 | CG | GLU | B | 521 | 141.565 | −6.588 | 41.578 | 1.00 | 62.07 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 6168 | CD | GLU | B | 521 | 142.455 | −6.523 | 40.416 | 1.00 | 65.14 |
| 6169 | OE1 | GLU | B | 521 | 142.092 | −5.780 | 39.546 | 1.00 | 68.33 |
| 6170 | OE2 | GLU | B | 521 | 143.497 | −7.174 | 40.322 | 1.00 | 66.71 |
| 6171 | C | GLU | B | 521 | 139.021 | −5.963 | 42.913 | 1.00 | 46.26 |
| 6172 | O | GLU | B | 521 | 139.127 | −6.005 | 44.139 | 1.00 | 44.18 |
| 6173 | N | PHE | B | 522 | 138.269 | −6.805 | 42.219 | 1.00 | 38.13 |
| 6174 | CA | PHE | B | 522 | 137.537 | −7.891 | 42.863 | 1.00 | 30.77 |
| 6175 | CB | PHE | B | 522 | 136.046 | −7.586 | 42.922 | 1.00 | 26.87 |
| 6176 | CG | PHE | B | 522 | 135.716 | −6.428 | 43.806 | 1.00 | 23.27 |
| 6177 | CD1 | PHE | B | 522 | 135.892 | −5.126 | 43.356 | 1.00 | 21.08 |
| 6178 | CD2 | PHE | B | 522 | 135.264 | −6.643 | 45.102 | 1.00 | 21.60 |
| 6179 | CE1 | PHE | B | 522 | 135.629 | −4.051 | 44.183 | 1.00 | 23.29 |
| 6180 | CE2 | PHE | B | 522 | 134.994 | −5.578 | 45.951 | 1.00 | 24.07 |
| 6181 | CZ | PHE | B | 522 | 135.176 | −4.273 | 45.492 | 1.00 | 24.51 |
| 6182 | C | PHE | B | 522 | 137.783 | −9.165 | 42.080 | 1.00 | 28.43 |
| 6183 | O | PHE | B | 522 | 137.871 | −9.146 | 40.859 | 1.00 | 23.79 |
| 6184 | N | ILE | B | 523 | 137.893 | −10.278 | 42.785 | 1.00 | 28.23 |
| 6185 | CA | ILE | B | 523 | 138.181 | −11.523 | 42.107 | 1.00 | 27.19 |
| 6186 | CB | ILE | B | 523 | 139.577 | −12.025 | 42.522 | 1.00 | 30.00 |
| 6187 | CG2 | ILE | B | 523 | 139.887 | −13.369 | 41.860 | 1.00 | 30.58 |
| 6188 | CG1 | ILE | B | 523 | 140.619 | −10.976 | 42.129 | 1.00 | 31.77 |
| 6189 | CD1 | ILE | B | 523 | 142.007 | −11.331 | 42.527 | 1.00 | 34.86 |
| 6190 | C | ILE | B | 523 | 137.160 | −12.627 | 42.307 | 1.00 | 24.50 |
| 6191 | O | ILE | B | 523 | 136.758 | −12.951 | 43.428 | 1.00 | 24.03 |
| 6192 | N | CYS | B | 524 | 136.723 | −13.185 | 41.191 | 1.00 | 23.64 |
| 6193 | CA | CYS | B | 524 | 135.793 | −14.285 | 41.235 | 1.00 | 24.51 |
| 6194 | C | CYS | B | 524 | 136.669 | −15.517 | 41.034 | 1.00 | 23.56 |
| 6195 | O | CYS | B | 524 | 137.376 | −15.622 | 40.029 | 1.00 | 20.40 |
| 6196 | CB | CYS | B | 524 | 134.774 | −14.173 | 40.107 | 1.00 | 23.80 |
| 6197 | SG | CYS | B | 524 | 133.849 | −15.718 | 39.897 | 1.00 | 23.52 |
| 6198 | N | ARG | B | 525 | 136.632 | −16.438 | 41.989 | 1.00 | 24.05 |
| 6199 | CA | ARG | B | 525 | 137.454 | −17.632 | 41.893 | 1.00 | 23.97 |
| 6200 | CB | ARG | B | 525 | 138.489 | −17.649 | 43.015 | 1.00 | 27.85 |
| 6201 | CG | ARG | B | 525 | 139.171 | −18.991 | 43.186 | 1.00 | 30.46 |
| 6202 | CD | ARG | B | 525 | 140.626 | −18.795 | 43.497 | 1.00 | 36.39 |
| 6203 | NE | ARG | B | 525 | 140.844 | −18.384 | 44.874 | 1.00 | 42.35 |
| 6204 | CZ | ARG | B | 525 | 141.938 | −17.759 | 45.300 | 1.00 | 44.70 |
| 6205 | NH1 | ARG | B | 525 | 142.914 | −17.463 | 44.450 | 1.00 | 46.71 |
| 6206 | NH2 | ARG | B | 525 | 142.059 | −17.439 | 46.581 | 1.00 | 45.61 |
| 6207 | C | ARG | B | 525 | 136.684 | −18.924 | 41.940 | 1.00 | 21.73 |
| 6208 | O | ARG | B | 525 | 135.879 | −19.139 | 42.844 | 1.00 | 21.63 |
| 6209 | N | ALA | B | 526 | 136.970 | −19.800 | 40.981 | 1.00 | 23.34 |
| 6210 | CA | ALA | B | 526 | 136.315 | −21.103 | 40.915 | 1.00 | 22.36 |
| 6211 | CB | ALA | B | 526 | 135.786 | −21.358 | 39.501 | 1.00 | 22.46 |
| 6212 | C | ALA | B | 526 | 137.265 | −22.220 | 41.302 | 1.00 | 22.51 |
| 6213 | O | ALA | B | 526 | 138.389 | −22.282 | 40.794 | 1.00 | 25.92 |
| 6214 | N | VAL | B | 527 | 136.828 | −23.082 | 42.214 | 1.00 | 21.74 |
| 6215 | CA | VAL | B | 527 | 137.641 | −24.221 | 42.603 | 1.00 | 24.54 |
| 6216 | CB | VAL | B | 527 | 137.750 | −24.408 | 44.132 | 1.00 | 24.53 |
| 6217 | CG1 | VAL | B | 527 | 138.521 | −25.697 | 44.437 | 1.00 | 23.17 |
| 6218 | CG2 | VAL | B | 527 | 138.471 | −23.226 | 44.741 | 1.00 | 22.75 |
| 6219 | C | VAL | B | 527 | 136.945 | −25.418 | 41.998 | 1.00 | 25.59 |
| 6220 | O | VAL | B | 527 | 135.797 | −25.736 | 42.342 | 1.00 | 25.55 |
| 6221 | N | HIS | B | 528 | 137.648 | −26.067 | 41.084 | 1.00 | 23.86 |
| 6222 | CA | HIS | B | 528 | 137.109 | −27.216 | 40.389 | 1.00 | 24.77 |
| 6223 | CB | HIS | B | 528 | 136.368 | −26.772 | 39.121 | 1.00 | 24.30 |
| 6224 | CG | HIS | B | 528 | 135.721 | −27.892 | 38.361 | 1.00 | 22.48 |
| 6225 | CD2 | HIS | B | 528 | 134.428 | −28.285 | 38.291 | 1.00 | 22.87 |
| 6226 | ND1 | HIS | B | 528 | 136.429 | −28.727 | 37.525 | 1.00 | 24.57 |
| 6227 | CE1 | HIS | B | 528 | 135.593 | −29.588 | 36.964 | 1.00 | 24.34 |
| 6228 | NE2 | HIS | B | 528 | 134.376 | −29.342 | 37.410 | 1.00 | 21.27 |
| 6229 | C | HIS | B | 528 | 138.259 | −28.132 | 40.051 | 1.00 | 27.10 |
| 6230 | O | HIS | B | 528 | 139.349 | −27.710 | 39.642 | 1.00 | 25.31 |
| 6231 | N | GLU | B | 529 | 137.963 | −29.400 | 40.236 | 1.00 | 29.47 |
| 6232 | CA | GLU | B | 529 | 138.867 | −30.502 | 40.052 | 1.00 | 34.12 |
| 6233 | CB | GLU | B | 529 | 138.092 | −31.746 | 40.461 | 1.00 | 40.82 |
| 6234 | CG | GLU | B | 529 | 138.222 | −32.938 | 39.594 | 1.00 | 53.09 |
| 6235 | CD | GLU | B | 529 | 137.093 | −33.912 | 39.843 | 1.00 | 59.75 |
| 6236 | OE1 | GLU | B | 529 | 137.216 | −35.071 | 39.405 | 1.00 | 64.15 |
| 6237 | OE2 | GLU | B | 529 | 136.081 | −33.520 | 40.470 | 1.00 | 62.85 |
| 6238 | C | GLU | B | 529 | 139.578 | −30.669 | 38.709 | 1.00 | 32.90 |
| 6239 | O | GLU | B | 529 | 140.661 | −31.252 | 38.663 | 1.00 | 32.95 |
| 6240 | N | ALA | B | 530 | 139.001 | −30.149 | 37.630 | 1.00 | 29.65 |
| 6241 | CA | ALA | B | 530 | 139.627 | −30.266 | 36.321 | 1.00 | 27.50 |
| 6242 | CB | ALA | B | 530 | 138.564 | −30.503 | 35.258 | 1.00 | 26.53 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 6243 | C | ALA | B | 530 | 140.450 | −29.036 | 35.971 | 1.00 | 30.23 |
| 6244 | O | ALA | B | 530 | 141.170 | −29.036 | 34.978 | 1.00 | 28.49 |
| 6245 | N | ALA | B | 531 | 140.342 | −27.983 | 36.772 | 1.00 | 33.58 |
| 6246 | CA | ALA | B | 531 | 141.097 | −26.769 | 36.513 | 1.00 | 40.73 |
| 6247 | CB | ALA | B | 531 | 140.698 | −25.663 | 37.475 | 1.00 | 30.99 |
| 6248 | C | ALA | B | 531 | 142.558 | −27.085 | 36.689 | 1.00 | 48.87 |
| 6249 | O | ALA | B | 531 | 142.965 | −27.534 | 37.763 | 1.00 | 48.19 |
| 6250 | N | SER | B | 532 | 143.385 | −26.855 | 35.660 | 1.00 | 64.68 |
| 6251 | CA | SER | B | 532 | 144.775 | −27.239 | 35.950 | 1.00 | 73.27 |
| 6252 | CB | SER | B | 532 | 145.567 | −27.460 | 34.503 | 1.00 | 86.77 |
| 6253 | OG | SER | B | 532 | 145.864 | −26.373 | 33.647 | 1.00 | 103.60 |
| 6254 | C | SER | B | 532 | 145.696 | −26.409 | 36.603 | 1.00 | 70.12 |
| 6255 | O | SER | B | 532 | 145.019 | −25.346 | 37.242 | 1.00 | 86.67 |
| 6256 | N | PRO | B | 533 | 146.931 | −26.861 | 37.212 | 1.00 | 73.82 |
| 6257 | CD | PRO | B | 533 | 146.446 | −25.921 | 36.711 | 1.00 | 74.28 |
| 6258 | CA | PRO | B | 533 | 147.270 | −25.873 | 37.991 | 1.00 | 69.24 |
| 6259 | CB | PRO | B | 533 | 148.814 | −25.841 | 38.280 | 1.00 | 69.23 |
| 6260 | CG | PRO | B | 533 | 147.917 | −24.666 | 37.229 | 1.00 | 68.88 |
| 6261 | C | PRO | B | 533 | 146.739 | −25.936 | 39.211 | 1.00 | 62.31 |
| 6262 | O | PRO | B | 533 | 145.955 | −25.044 | 39.340 | 1.00 | 65.59 |
| 6263 | N | SER | B | 534 | 146.798 | −26.736 | 40.398 | 1.00 | 55.20 |
| 6264 | CA | SER | B | 534 | 145.994 | −26.359 | 41.705 | 1.00 | 50.24 |
| 6265 | CB | SER | B | 534 | 146.661 | −25.105 | 42.338 | 1.00 | 49.99 |
| 6266 | OG | SER | B | 534 | 147.211 | −24.251 | 41.355 | 1.00 | 46.98 |
| 6267 | C | SER | B | 534 | 144.474 | −26.182 | 41.697 | 1.00 | 44.87 |
| 6268 | O | SER | B | 534 | 143.910 | −25.465 | 42.555 | 1.00 | 35.27 |
| 6269 | N | GLN | B | 535 | 143.827 | −26.831 | 40.736 | 1.00 | 36.37 |
| 6270 | CA | GLN | B | 535 | 142.365 | −26.827 | 40.582 | 1.00 | 31.26 |
| 6271 | CB | GLN | B | 535 | 141.759 | −27.959 | 41.421 | 1.00 | 31.62 |
| 6272 | CG | GLN | B | 535 | 142.684 | −28.550 | 42.495 | 1.00 | 36.49 |
| 6273 | CD | GLN | B | 535 | 143.890 | −29.346 | 41.964 | 1.00 | 37.53 |
| 6274 | OE1 | GLN | B | 535 | 144.835 | −29.572 | 42.712 | 1.00 | 40.33 |
| 6275 | NE2 | GLN | B | 535 | 143.856 | −29.781 | 40.703 | 1.00 | 39.29 |
| 6276 | C | GLN | B | 535 | 141.645 | −25.524 | 40.887 | 1.00 | 28.02 |
| 6277 | O | GLN | B | 535 | 140.612 | −25.491 | 41.556 | 1.00 | 29.88 |
| 6278 | N | THR | B | 536 | 142.161 | −24.439 | 40.340 | 1.00 | 30.33 |
| 6279 | CA | THR | B | 536 | 141.572 | −23.140 | 40.593 | 1.00 | 32.14 |
| 6280 | CB | THR | B | 536 | 142.325 | −22.489 | 41.766 | 1.00 | 29.75 |
| 6281 | OG1 | THR | B | 536 | 141.831 | −21.175 | 41.995 | 1.00 | 33.41 |
| 6282 | CG2 | THR | B | 536 | 143.808 | −22.410 | 41.466 | 1.00 | 33.84 |
| 6283 | C | THR | B | 536 | 141.640 | −22.264 | 39.339 | 1.00 | 28.34 |
| 6284 | O | THR | B | 536 | 142.620 | −22.307 | 38.601 | 1.00 | 31.92 |
| 6285 | N | VAL | B | 537 | 140.585 | −21.498 | 39.080 | 1.00 | 29.13 |
| 6286 | CA | VAL | B | 537 | 140.543 | −20.589 | 37.925 | 1.00 | 31.17 |
| 6287 | CB | VAL | B | 537 | 139.737 | −21.160 | 36.755 | 1.00 | 31.26 |
| 6288 | CG | VAL | B | 537 | 139.848 | −20.223 | 35.565 | 1.00 | 34.10 |
| 6289 | CG2 | VAL | B | 537 | 140.238 | −22.540 | 36.392 | 1.00 | 35.56 |
| 6290 | C | VAL | B | 537 | 139.849 | −19.314 | 38.378 | 1.00 | 28.96 |
| 6291 | O | VAL | B | 537 | 138.800 | −19.379 | 39.017 | 1.00 | 26.67 |
| 6292 | N | GLN | B | 538 | 140.402 | −18.156 | 38.037 | 1.00 | 27.03 |
| 6293 | CA | GLN | B | 538 | 139.800 | −16.908 | 38.498 | 1.00 | 26.20 |
| 6294 | CB | GLN | B | 538 | 140.490 | −16.457 | 39.786 | 1.00 | 27.15 |
| 6295 | CG | GLN | B | 538 | 141.966 | −16.057 | 39.617 | 1.00 | 29.71 |
| 6296 | CD | GLN | B | 538 | 142.674 | −15.831 | 40.952 | 1.00 | 34.16 |
| 6297 | OE1 | GLN | B | 538 | 142.650 | −16.701 | 41.849 | 1.00 | 35.10 |
| 6298 | NE2 | GLN | B | 538 | 143.311 | −14.666 | 41.096 | 1.00 | 34.04 |
| 6299 | C | GLN | B | 538 | 139.827 | −15.755 | 37.506 | 1.00 | 26.88 |
| 6300 | O | GLN | B | 538 | 140.579 | −15.769 | 36.535 | 1.00 | 23.39 |
| 6301 | N | ARG | B | 539 | 138.997 | −14.754 | 37.769 | 1.00 | 27.08 |
| 6302 | CA | ARG | B | 539 | 138.920 | −13.572 | 36.924 | 1.00 | 28.86 |
| 6303 | CB | ARG | B | 539 | 137.747 | −13.665 | 35.953 | 1.00 | 32.92 |
| 6304 | CG | ARG | B | 539 | 137.980 | −14.592 | 34.784 | 1.00 | 46.12 |
| 6305 | CD | ARG | B | 539 | 138.774 | −13.914 | 33.687 | 1.00 | 55.63 |
| 6306 | NE | ARG | B | 539 | 138.592 | −14.632 | 32.435 | 1.00 | 66.23 |
| 6307 | CZ | ARG | B | 539 | 139.128 | −14.270 | 31.280 | 1.00 | 70.76 |
| 6308 | NH1 | ARG | B | 539 | 139.891 | −13.188 | 31.200 | 1.00 | 74.04 |
| 6309 | NH2 | ARG | B | 539 | 138.890 | −14.993 | 30.201 | 1.00 | 74.13 |
| 6310 | C | ARG | B | 539 | 138.743 | −12.338 | 37.785 | 1.00 | 26.30 |
| 6311 | O | ARG | B | 539 | 137.949 | −12.327 | 38.732 | 1.00 | 26.03 |
| 6312 | N | ALA | B | 540 | 139.515 | −11.309 | 37.470 | 1.00 | 24.45 |
| 6313 | CA | ALA | B | 540 | 139.424 | −10.047 | 38.180 | 1.00 | 26.56 |
| 6314 | CB | ALA | B | 540 | 140.771 | −9.342 | 38.194 | 1.00 | 22.95 |
| 6315 | C | ALA | B | 540 | 138.408 | −9.197 | 37.419 | 1.00 | 30.52 |
| 6316 | O | ALA | B | 540 | 138.218 | −9.359 | 36.200 | 1.00 | 24.83 |
| 6317 | N | VAL | B | 541 | 137.754 | −8.298 | 38.142 | 1.00 | 30.94 |

TABLE II-continued

Atomic coordinates of Crystal 2

| ATOM # | ATOM TYPE | RES | CHN | # | X | Y | Z | OCC | B |
|---|---|---|---|---|---|---|---|---|---|
| 6318 | CA | VAL | B | 541 | 136.784 | −7.401 | 37.547 | 1.00 | 35.74 |
| 6319 | CB | VAL | B | 541 | 135.344 | −7.980 | 37.596 | 1.00 | 34.34 |
| 6320 | CG1 | VAL | D | 541 | 134.772 | −7.875 | 38.996 | 1.00 | 34.57 |
| 6321 | CG2 | VAL | B | 541 | 134.463 | −7.246 | 36.591 | 1.00 | 35.62 |
| 6322 | C | VAL | B | 541 | 136.842 | −6.109 | 38.347 | 1.00 | 38.48 |
| 6323 | O | VAL | B | 541 | 137.078 | −6.125 | 39.559 | 1.00 | 39.27 |
| 6324 | N | SER | B | 542 | 136.646 | −4.984 | 37.677 | 1.00 | 41.53 |
| 6325 | CA | SER | B | 542 | 136.691 | −3.744 | 38.399 | 1.00 | 46.05 |
| 6326 | CB | SER | B | 542 | 138.074 | −3.135 | 38.229 | 1.00 | 46.63 |
| 6327 | OG | SER | B | 542 | 138.093 | −2.127 | 37.315 | 1.00 | 44.00 |
| 6328 | C | SER | B | 542 | 135.558 | −2.791 | 38.051 | 1.00 | 48.27 |
| 6329 | O | SER | B | 542 | 135.084 | −2.736 | 36.914 | 1.00 | 48.44 |
| 6330 | N | VAL | B | 543 | 135.112 | −2.083 | 39.085 | 1.00 | 51.78 |
| 6331 | CA | VAL | B | 543 | 134.013 | −1.127 | 39.021 | 1.00 | 57.53 |
| 6332 | CB | VAL | B | 543 | 133.385 | −0.923 | 40.413 | 1.00 | 54.66 |
| 6333 | CG1 | VAL | B | 543 | 132.121 | −0.095 | 40.299 | 1.00 | 53.73 |
| 6334 | CG2 | VAL | B | 543 | 133.117 | −2.250 | 41.064 | 1.00 | 52.68 |
| 6335 | C | VAL | B | 543 | 134.460 | 0.242 | 38.574 | 1.00 | 64.91 |
| 6336 | O | VAL | B | 543 | 134.271 | 1.191 | 39.308 | 1.00 | 64.11 |
| 6337 | N | ASN | B | 544 | 135.027 | 0.372 | 37.387 | 1.00 | 76.78 |
| 6338 | CA | ASN | B | 544 | 135.487 | 1.673 | 36.928 | 1.00 | 84.57 |
| 6339 | CB | ASN | B | 544 | 135.178 | 1.802 | 35.444 | 1.00 | 77.56 |
| 6340 | CG | ASN | B | 544 | 135.817 | 0.695 | 34.642 | 1.00 | 71.46 |
| 6341 | OD1 | ASN | B | 544 | 136.968 | 0.331 | 34.891 | 1.00 | 69.57 |
| 6342 | ND2 | ASN | B | 544 | 135.085 | 0.153 | 33.674 | 1.00 | 69.71 |
| 6343 | C | ASN | B | 544 | 134.904 | 2.850 | 37.726 | 1.00 | 91.44 |
| 6344 | O | ASN | B | 544 | 134.259 | 3.740 | 37.141 | 1.00 | 94.34 |
| 6345 | OXT | ASN | B | 544 | 135.109 | 2.882 | 38.957 | 1.00 | 47.60 |

Another embodiment of the present invention is a 3-D model of a Fc-Cε3/Cε4 region that substantially represents the atomic coordinates specified (i.e., listed) in Table III.

TABLE III

Atomic coordinates of Crystal 3

| ATOM # | ATOM TYPE | RES | CHN | # | X | Y | Z | OCC | B |
|---|---|---|---|---|---|---|---|---|---|
| 1 | CB | VAL | C | 336 | −1.489 | −42.536 | 37.990 | 1.00 | 105.78 |
| 2 | CG1 | VAL | C | 336 | −2.476 | −42.708 | 39.150 | 1.00 | 101.76 |
| 3 | CG2 | VAL | C | 336 | −2.020 | −43.206 | 36.724 | 1.00 | 108.97 |
| 4 | C | VAL | C | 336 | −0.613 | −40.396 | 38.979 | 1.00 | 98.52 |
| 5 | O | VAL | C | 336 | 0.205 | −41.013 | 39.665 | 1.00 | 71.20 |
| 6 | N | VAL | C | 336 | −0.388 | −40.832 | 36.506 | 1.00 | 93.30 |
| 7 | CA | VAL | C | 336 | −1.233 | −41.027 | 37.724 | 1.00 | 105.93 |
| 8 | N | SER | C | 337 | −1.009 | −39.154 | 39.254 | 1.00 | 101.21 |
| 9 | CA | SER | C | 337 | −0.536 | −38.404 | 40.417 | 1.00 | 93.78 |
| 10 | CB | SER | C | 337 | 0.509 | −37.358 | 39.997 | 1.00 | 74.04 |
| 11 | OG | SER | C | 337 | 0.023 | −36.497 | 38.983 | 1.00 | 94.67 |
| 12 | C | SER | C | 337 | −1.722 | −37.724 | 41.117 | 1.00 | 93.56 |
| 13 | O | SER | C | 337 | −2.817 | −37.611 | 40.545 | 1.00 | 77.96 |
| 14 | N | ALA | C | 338 | −1.502 | −37.283 | 42.354 | 1.00 | 98.19 |
| 15 | CA | ALA | C | 338 | −2.550 | −36.629 | 43.135 | 1.00 | 95.98 |
| 16 | CB | ALA | C | 338 | −3.235 | −37.650 | 44.041 | 1.00 | 86.26 |
| 17 | C | ALA | C | 338 | −2.010 | −35.469 | 43.970 | 1.00 | 88.71 |
| 18 | O | ALA | C | 338 | −1.067 | −35.631 | 44.742 | 1.00 | 76.26 |
| 19 | N | TYR | C | 339 | −2.619 | −34.298 | 43.809 | 1.00 | 91.17 |
| 20 | CA | TYR | C | 339 | −2.209 | −33.099 | 44.537 | 1.00 | 85.35 |
| 21 | CB | TYR | C | 339 | −1.898 | −31.947 | 43.562 | 1.00 | 88.31 |
| 22 | CG | TYR | C | 339 | −0.852 | −32.220 | 42.489 | 1.00 | 92.78 |
| 23 | CD1 | TYR | C | 339 | −0.887 | −33.387 | 41.724 | 1.00 | 93.57 |
| 24 | CE1 | TYR | C | 339 | 0.018 | −33.601 | 40.690 | 1.00 | 107.08 |
| 25 | CD2 | TYR | C | 339 | 0.128 | −31.269 | 42.190 | 1.00 | 105.98 |
| 26 | CE2 | TYR | C | 339 | 1.038 | −31.471 | 41.153 | 1.00 | 114.87 |
| 27 | CZ | TYR | C | 339 | 0.975 | −32.641 | 40.407 | 1.00 | 114.64 |
| 28 | OH | TYR | C | 339 | 1.856 | −32.846 | 39.366 | 1.00 | 112.44 |
| 29 | C | TYR | C | 339 | −3.357 | −32.666 | 45.451 | 1.00 | 88.56 |
| 30 | O | TYR | C | 339 | −4.522 | −33.006 | 45.210 | 1.00 | 92.47 |
| 31 | N | LEU | C | 340 | −3.026 | −31.925 | 46.502 | 1.00 | 80.26 |
| 32 | CA | LEU | C | 340 | −4.037 | −31.417 | 47.423 | 1.00 | 69.24 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 33 | CB | LEU | C | 340 | −4.064 | −32.255 | 48.703 | 1.00 | 67.35 |
| 34 | CG | LEU | C | 340 | −5.241 | −31.964 | 49.638 | 1.00 | 65.31 |
| 35 | CD1 | LEU | C | 340 | −6.526 | −32.133 | 48.876 | 1.00 | 57.03 |
| 36 | CD2 | LEU | C | 340 | −5.233 | −32.902 | 50.823 | 1.00 | 43.07 |
| 37 | C | LEU | C | 340 | −3.648 | −29.971 | 47.728 | 1.00 | 65.82 |
| 38 | O | LEU | C | 340 | −2.564 | −29.717 | 48.250 | 1.00 | 75.58 |
| 39 | N | SER | C | 341 | −4.512 | −29.020 | 47.385 | 1.00 | 51.48 |
| 40 | CA | SER | C | 341 | −4.180 | −27.619 | 47.621 | 1.00 | 56.75 |
| 41 | CB | SER | C | 341 | −4.538 | −26.778 | 46.396 | 1.00 | 49.54 |
| 42 | OG | SER | C | 341 | −5.946 | −26.658 | 46.278 | 1.00 | 73.22 |
| 43 | C | SER | C | 341 | −4.853 | −27.023 | 48.856 | 1.00 | 60.13 |
| 44 | O | SER | C | 341 | −5.766 | −27.607 | 49.435 | 1.00 | 71.19 |
| 45 | N | ARG | C | 342 | −4.382 | −25.851 | 49.257 | 1.00 | 46.31 |
| 46 | CA | ARG | C | 342 | −4.933 | −25.155 | 50.406 | 1.00 | 49.52 |
| 47 | CB | ARG | C | 342 | −3.802 | −24.537 | 51.247 | 1.00 | 65.57 |
| 48 | CG | ARG | C | 342 | −2.888 | −25.555 | 51.946 | 1.00 | 66.31 |
| 49 | CD | ARG | C | 342 | −1.834 | −24.887 | 52.826 | 1.00 | 48.06 |
| 50 | NE | ARG | C | 342 | −0.864 | −24.119 | 52.046 | 1.00 | 81.84 |
| 51 | CZ | ARG | C | 342 | 0.186 | −24.633 | 51.403 | 1.00 | 76.24 |
| 52 | NH1 | ARG | C | 342 | 0.441 | −25.933 | 51.428 | 1.00 | 55.59 |
| 53 | NH2 | ARG | C | 342 | 0.988 | −23.836 | 50.718 | 1.00 | 88.16 |
| 54 | C | ARG | C | 342 | −5.889 | −24.054 | 49.955 | 1.00 | 60.85 |
| 55 | O | ARG | C | 342 | −5.990 | −23.746 | 48.770 | 1.00 | 60.22 |
| 56 | N | PRO | C | 343 | −6.611 | −23.448 | 50.902 | 1.00 | 59.14 |
| 57 | CD | PRO | C | 343 | −6.729 | −23.805 | 52.324 | 1.00 | 61.73 |
| 58 | CA | PRO | C | 343 | −7.549 | −22.382 | 50.556 | 1.00 | 38.66 |
| 59 | CB | PRO | C | 343 | −8.197 | −22.042 | 51.900 | 1.00 | 44.57 |
| 60 | CG | PRO | C | 343 | −8.103 | −23.313 | 52.664 | 1.00 | 33.66 |
| 61 | C | PRO | C | 343 | −6.790 | −21.199 | 49.995 | 1.00 | 42.56 |
| 62 | O | PRO | C | 343 | −5.672 | −20.921 | 50.417 | 1.00 | 60.84 |
| 63 | N | SER | C | 344 | −7.363 | −20.514 | 49.019 | 1.00 | 35.99 |
| 64 | CA | SER | C | 344 | −6.672 | −19.345 | 48.527 | 1.00 | 41.83 |
| 65 | CB | SER | C | 344 | −7.293 | −18.825 | 47.231 | 1.00 | 49.12 |
| 66 | OG | SER | C | 344 | −8.614 | −18.376 | 47.426 | 1.00 | 26.86 |
| 67 | C | SER | C | 344 | −6.902 | −18.362 | 49.662 | 1.00 | 42.76 |
| 68 | O | SER | C | 344 | −7.977 | −18.330 | 50.269 | 1.00 | 36.14 |
| 69 | N | PRO | C | 345 | −5.886 | −17.577 | 50.004 | 1.00 | 38.60 |
| 70 | CD | PRO | C | 345 | −4.503 | −17.570 | 49.511 | 1.00 | 25.84 |
| 71 | CA | PRO | C | 345 | −6.087 | −16.620 | 51.095 | 1.00 | 15.78 |
| 72 | CB | PRO | C | 345 | −4.857 | −15.735 | 50.998 | 1.00 | 11.14 |
| 73 | CG | PRO | C | 345 | −3.797 | −16.715 | 50.542 | 1.00 | 64.69 |
| 74 | C | PRO | C | 345 | −7.367 | −15.843 | 50.869 | 1.00 | 35.12 |
| 75 | O | PRO | C | 345 | −8.079 | −15.526 | 51.818 | 1.00 | 34.38 |
| 76 | N | PHE | C | 346 | −7.655 | −15.567 | 49.594 | 1.00 | 33.31 |
| 77 | CA | PHE | C | 346 | −8.836 | −14.804 | 49.193 | 1.00 | 30.80 |
| 78 | CB | PHE | C | 346 | −8.800 | −14.458 | 47.704 | 1.00 | 28.13 |
| 79 | CG | PHE | C | 346 | −10.023 | −13.707 | 47.246 | 1.00 | 61.99 |
| 80 | CD1 | PHE | C | 346 | −10.442 | −12.554 | 47.920 | 1.00 | 41.17 |
| 81 | CD2 | PHE | C | 346 | −10.785 | −14.167 | 46.174 | 1.00 | 72.86 |
| 82 | CE1 | PHE | C | 346 | −11.604 | −11.873 | 47.536 | 1.00 | 52.30 |
| 83 | CE2 | PHE | C | 346 | −11.954 | −13.489 | 45.780 | 1.00 | 46.00 |
| 84 | CZ | PHE | C | 346 | −12.365 | −12.338 | 46.465 | 1.00 | 24.36 |
| 85 | C | PHE | C | 346 | −10.189 | −15.429 | 49.488 | 1.00 | 39.11 |
| 86 | O | PHE | C | 346 | −11.146 | −14.737 | 49.847 | 1.00 | 29.56 |
| 87 | N | ASP | C | 347 | −10.297 | −16.731 | 49.312 | 1.00 | 19.42 |
| 88 | CA | ASP | C | 347 | −11.576 | −17.337 | 49.597 | 1.00 | 40.92 |
| 89 | CB | ASP | C | 347 | −11.589 | −18.829 | 49.282 | 1.00 | 35.55 |
| 90 | CG | ASP | C | 347 | −11.475 | −19.115 | 47.810 | 1.00 | 52.35 |
| 91 | OD1 | ASP | C | 347 | −12.136 | −18.407 | 47.011 | 1.00 | 40.77 |
| 92 | OD2 | ASP | C | 347 | −10.735 | −20.063 | 47.457 | 1.00 | 65.76 |
| 93 | C | ASP | C | 347 | −11.735 | −17.150 | 51.076 | 1.00 | 27.99 |
| 94 | O | ASP | C | 347 | −12.698 | −16.532 | 51.540 | 1.00 | 55.88 |
| 95 | N | LEU | C | 348 | −10.736 | −17.673 | 51.787 | 1.00 | 47.26 |
| 96 | CA | LEU | C | 348 | −10.632 | −17.677 | 53.246 | 1.00 | 57.70 |
| 97 | CB | LEU | C | 348 | −9.285 | −18.271 | 53.625 | 1.00 | 72.86 |
| 98 | CG | LEU | C | 348 | −9.011 | −18.577 | 55.087 | 1.00 | 40.33 |
| 99 | CD1 | LEU | C | 348 | −10.177 | −19.323 | 55.706 | 1.00 | 26.18 |
| 100 | CD2 | LEU | C | 348 | −7.746 | −19.408 | 55.167 | 1.00 | 43.45 |
| 101 | C | LEU | C | 348 | −10.866 | −16.409 | 54.068 | 1.00 | 58.71 |
| 102 | O | LEU | C | 348 | −11.505 | −16.477 | 55.110 | 1.00 | 61.47 |
| 103 | N | PHE | C | 349 | −10.367 | −15.257 | 53.633 | 1.00 | 57.57 |
| 104 | CA | PHE | C | 349 | −10.582 | −14.044 | 54.422 | 1.00 | 50.67 |
| 105 | CB | PHE | C | 349 | −9.244 | −13.364 | 54.703 | 1.00 | 51.49 |
| 106 | CG | PHE | C | 349 | −8.182 | −14.291 | 55.230 | 1.00 | 25.25 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 107 | CD1 | PHE | C | 349 | −7.097 | −14.652 | 54.422 | 1.00 | 22.53 |
| 108 | CD2 | PHE | C | 349 | −8.270 | −14.818 | 56.511 | 1.00 | 25.85 |
| 109 | CE1 | PHE | C | 349 | −6.106 | −15.540 | 54.884 | 1.00 | 34.83 |
| 110 | CE2 | PHE | C | 349 | −7.296 | −15.703 | 56.989 | 1.00 | 37.16 |
| 111 | CZ | PHE | C | 349 | −6.205 | −16.069 | 56.170 | 1.00 | 27.41 |
| 112 | C | PHE | C | 349 | −11.555 | −13.014 | 53.828 | 1.00 | 50.12 |
| 113 | O | PHE | C | 349 | −12.222 | −12.287 | 54.560 | 1.00 | 46.22 |
| 114 | N | ILE | C | 350 | −11.643 | −12.930 | 52.507 | 1.00 | 62.01 |
| 115 | CA | ILE | C | 350 | −12.558 | −11.965 | 51.900 | 1.00 | 32.11 |
| 116 | CB | ILE | C | 350 | −11.940 | −11.312 | 50.711 | 1.00 | 44.84 |
| 117 | CG2 | ILE | C | 350 | −12.732 | −10.064 | 50.357 | 1.00 | 62.43 |
| 118 | CG1 | ILE | C | 350 | −10.480 | −10.977 | 51.020 | 1.00 | 35.91 |
| 119 | CD1 | ILE | C | 350 | −10.300 | −10.090 | 52.210 | 1.00 | 47.74 |
| 120 | C | ILE | C | 350 | −13.867 | −12.592 | 51.470 | 1.00 | 42.85 |
| 121 | O | ILE | C | 350 | −14.910 | −11.983 | 51.608 | 1.00 | 46.34 |
| 122 | N | ARG | C | 351 | −13.825 | −13.810 | 50.946 | 1.00 | 62.16 |
| 123 | CA | ARG | C | 351 | −15.057 | −14.479 | 50.544 | 1.00 | 57.57 |
| 124 | CB | ARG | C | 351 | −14.782 | −15.498 | 49.434 | 1.00 | 59.70 |
| 125 | CG | ARG | C | 351 | −15.554 | −15.253 | 48.141 | 1.00 | 98.57 |
| 126 | CD | ARG | C | 351 | −16.455 | −16.434 | 47.782 | 1.00 | 94.19 |
| 127 | NE | ARG | C | 351 | −17.576 | −16.580 | 48.713 | 1.00 | 96.20 |
| 128 | CZ | ARG | C | 351 | −18.416 | −17.612 | 48.727 | 1.00 | 107.87 |
| 129 | NH1 | ARG | C | 351 | −18.270 | −18.604 | 47.858 | 1.00 | 109.42 |
| 130 | NH2 | ARG | C | 351 | −19.397 | −17.659 | 49.619 | 1.00 | 110.11 |
| 131 | C | ARG | C | 351 | −15.611 | −15.197 | 51.772 | 1.00 | 66.36 |
| 132 | O | ARG | C | 351 | −16.818 | −15.449 | 51.883 | 1.00 | 56.99 |
| 133 | N | LYS | C | 352 | −14.717 | −15.496 | 52.707 | 1.00 | 54.38 |
| 134 | CA | LYS | C | 352 | −15.085 | −16.209 | 53.920 | 1.00 | 70.33 |
| 135 | CB | LYS | C | 352 | −15.858 | −15.309 | 54.884 | 1.00 | 52.90 |
| 136 | CG | LYS | C | 352 | −15.009 | −14.237 | 55.521 | 1.00 | 75.21 |
| 137 | CD | LYS | C | 352 | −15.546 | −13.881 | 56.890 | 1.00 | 94.13 |
| 138 | CE | LYS | C | 352 | −14.763 | −12.738 | 57.503 | 1.00 | 98.72 |
| 139 | NZ | LYS | C | 352 | −14.861 | −11.514 | 56.669 | 1.00 | 105.03 |
| 140 | C | LYS | C | 352 | −15.901 | −17.451 | 53.584 | 1.00 | 65.86 |
| 141 | O | LYS | C | 352 | −17.069 | −17.589 | 53.953 | 1.00 | 36.64 |
| 142 | N | SER | C | 353 | −15.262 | −18.342 | 52.843 | 1.00 | 59.83 |
| 143 | CA | SER | C | 353 | −15.843 | −19.614 | 52.449 | 1.00 | 78.59 |
| 144 | CB | SER | C | 353 | −17.088 | −19.428 | 51.580 | 1.00 | 70.34 |
| 145 | OG | SER | C | 353 | −16.795 | −18.738 | 50.399 | 1.00 | 51.34 |
| 146 | C | SER | C | 353 | −14.749 | −20.351 | 51.695 | 1.00 | 75.61 |
| 147 | O | SER | C | 353 | −14.713 | −20.373 | 50.468 | 1.00 | 67.40 |
| 148 | N | PRO | C | 354 | −13.822 | −20.956 | 52.446 | 1.00 | 64.81 |
| 149 | CD | PRO | C | 354 | −13.722 | −20.838 | 53.909 | 1.00 | 64.44 |
| 150 | CA | PRO | C | 354 | −12.687 | −21.709 | 51.926 | 1.00 | 66.53 |
| 151 | CB | PRO | C | 354 | −11.836 | −21.957 | 53.174 | 1.00 | 63.06 |
| 152 | CG | PRO | C | 354 | −12.253 | −20.881 | 54.102 | 1.00 | 84.68 |
| 153 | C | PRO | C | 354 | −13.066 | −23.013 | 51.263 | 1.00 | 54.67 |
| 154 | O | PRO | C | 354 | −14.152 | −23.528 | 51.480 | 1.00 | 66.06 |
| 155 | N | THR | C | 355 | −12.147 | −23.534 | 50.458 | 1.00 | 36.65 |
| 156 | CA | THR | C | 355 | −12.316 | −24.811 | 49.780 | 1.00 | 53.96 |
| 157 | CB | THR | C | 355 | −13.115 | −24.705 | 48.443 | 1.00 | 45.12 |
| 158 | OG1 | THR | C | 355 | −12.592 | −23.653 | 47.639 | 1.00 | 47.70 |
| 159 | CG2 | THR | C | 355 | −14.561 | −24.437 | 48.701 | 1.00 | 34.95 |
| 160 | C | THR | C | 355 | −10.932 | −25.346 | 49.477 | 1.00 | 48.95 |
| 161 | O | THR | C | 355 | −9.981 | −24.578 | 49.367 | 1.00 | 52.91 |
| 162 | N | ILE | C | 356 | −10.821 | −26.663 | 49.372 | 1.00 | 43.43 |
| 163 | CA | ILE | C | 356 | −9.553 | −27.310 | 49.068 | 1.00 | 52.01 |
| 164 | CB | ILE | C | 356 | −9.017 | −28.124 | 50.279 | 1.00 | 58.41 |
| 165 | CG2 | ILE | C | 356 | −8.571 | −27.186 | 51.377 | 1.00 | 60.32 |
| 166 | CG1 | ILE | C | 356 | −10.103 | −29.053 | 50.820 | 1.00 | 52.66 |
| 167 | CD1 | ILE | C | 356 | −9.701 | −29.811 | 52.058 | 1.00 | 48.82 |
| 168 | C | ILE | C | 356 | −9.869 | −28.242 | 47.917 | 1.00 | 57.21 |
| 169 | O | ILE | C | 356 | −10.957 | −28.807 | 47.867 | 1.00 | 58.80 |
| 170 | N | THR | C | 357 | −8.929 | −28.418 | 47.000 | 1.00 | 46.87 |
| 171 | CA | THR | C | 357 | −9.197 | −29.253 | 45.841 | 1.00 | 44.20 |
| 172 | CB | THR | C | 357 | −9.216 | −28.399 | 44.546 | 1.00 | 42.53 |
| 173 | OG1 | THR | C | 357 | −10.052 | −27.252 | 44.739 | 1.00 | 46.42 |
| 174 | CG2 | THR | C | 357 | −9.755 | −29.201 | 43.380 | 1.00 | 26.07 |
| 175 | C | THR | C | 357 | −8.209 | −30.385 | 45.651 | 1.00 | 53.15 |
| 176 | O | THR | C | 357 | −7.006 | −30.155 | 45.540 | 1.00 | 53.31 |
| 177 | N | CYS | C | 358 | −8.733 | −31.607 | 45.615 | 1.00 | 47.27 |
| 178 | CA | CYS | C | 358 | −7.918 | −32.798 | 45.420 | 1.00 | 60.99 |
| 179 | C | CYS | C | 358 | −7.931 | −32.991 | 43.913 | 1.00 | 60.66 |
| 180 | O | CYS | C | 358 | −8.986 | −33.204 | 43.311 | 1.00 | 67.78 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 181 | CB | CYS | C | 358 | −8.547 | −34.009 | 46.128 | 1.00 | 74.62 |
| 182 | SG | CYS | C | 358 | −7.486 | −35.492 | 46.336 | 1.00 | 84.96 |
| 183 | N | LEU | C | 359 | −6.755 | −32.899 | 43.310 | 1.00 | 43.54 |
| 184 | CA | LEU | C | 359 | −6.619 | −33.024 | 41.875 | 1.00 | 71.90 |
| 185 | CB | LEU | C | 359 | −5.933 | −31.776 | 41.319 | 1.00 | 79.89 |
| 186 | CG | LEU | C | 359 | −5.370 | −31.846 | 39.896 | 1.00 | 76.18 |
| 187 | CD1 | LEU | C | 359 | −6.503 | −32.033 | 38.892 | 1.00 | 87.90 |
| 188 | CD2 | LEU | C | 359 | −4.596 | −30.577 | 39.598 | 1.00 | 77.64 |
| 189 | C | LEU | C | 359 | −5.833 | −34.251 | 41.451 | 1.00 | 84.81 |
| 190 | O | LEU | C | 359 | −4.634 | −34.340 | 41.690 | 1.00 | 88.53 |
| 191 | N | VAL | C | 360 | −6.508 | −35.189 | 40.803 | 1.00 | 92.67 |
| 192 | CA | VAL | C | 360 | −5.850 | −36.392 | 40.323 | 1.00 | 87.21 |
| 193 | CB | VAL | C | 360 | −6.732 | −37.620 | 40.542 | 1.00 | 89.03 |
| 194 | CG1 | VAL | C | 360 | −5.996 | −38.864 | 40.110 | 1.00 | 70.35 |
| 195 | CG2 | VAL | C | 360 | −7.142 | −37.700 | 42.000 | 1.00 | 80.26 |
| 196 | C | VAL | C | 360 | −5.565 | −36.235 | 38.833 | 1.00 | 80.61 |
| 197 | O | VAL | C | 360 | −6.457 | −35.891 | 38.052 | 1.00 | 66.01 |
| 198 | N | VAL | C | 361 | −4.316 | −36.473 | 38.446 | 1.00 | 83.92 |
| 199 | CA | VAL | C | 361 | −3.921 | −36.352 | 37.049 | 1.00 | 97.53 |
| 200 | CB | VAL | C | 361 | −2.747 | −35.365 | 36.890 | 1.00 | 86.37 |
| 201 | CG1 | VAL | C | 361 | −2.314 | −35.289 | 35.431 | 1.00 | 106.76 |
| 202 | CG2 | VAL | C | 361 | −3.155 | −33.999 | 37.387 | 1.00 | 88.36 |
| 203 | C | VAL | C | 361 | −3.505 | −37.697 | 36.466 | 1.00 | 100.35 |
| 204 | O | VAL | C | 361 | −2.540 | −38.297 | 36.921 | 1.00 | 86.78 |
| 205 | N | ASP | C | 362 | −4.237 | −38.165 | 35.457 | 1.00 | 114.98 |
| 206 | CA | ASP | C | 362 | −3.932 | −39.440 | 34.807 | 1.00 | 119.40 |
| 207 | CB | ASP | C | 362 | −5.067 | −40.447 | 35.038 | 1.00 | 120.30 |
| 208 | CG | ASP | C | 362 | −4.650 | −41.883 | 34.748 | 1.00 | 122.32 |
| 209 | OD1 | ASP | C | 362 | −4.092 | −42.143 | 33.661 | 1.00 | 128.90 |
| 210 | OD2 | ASP | C | 362 | −4.885 | −42.756 | 35.609 | 1.00 | 126.95 |
| 211 | C | ASP | C | 362 | −3.750 | −39.210 | 33.305 | 1.00 | 125.15 |
| 212 | O | ASP | C | 362 | −4.672 | −38.750 | 32.623 | 1.00 | 123.00 |
| 213 | N | LEU | C | 363 | −2.563 | −39.531 | 32.796 | 1.00 | 126.28 |
| 214 | CA | LEU | C | 363 | −2.268 | −39.355 | 31.378 | 1.00 | 130.12 |
| 215 | CB | LEU | C | 363 | −0.760 | −39.157 | 31.177 | 1.00 | 124.88 |
| 216 | CG | LEU | C | 363 | −0.143 | −37.878 | 31.759 | 1.00 | 133.28 |
| 217 | CD1 | LEU | C | 363 | 1.363 | −37.946 | 31.625 | 1.00 | 124.47 |
| 218 | CD2 | LEU | C | 363 | −0.684 | −36.643 | 31.039 | 1.00 | 134.46 |
| 219 | C | LEU | C | 363 | −2.763 | −40.520 | 30.511 | 1.00 | 129.36 |
| 220 | O | LEU | C | 363 | −2.816 | −40.410 | 29.288 | 1.00 | 132.15 |
| 221 | N | ALA | C | 364 | −3.133 | −41.629 | 31.145 | 1.00 | 126.02 |
| 222 | CA | ALA | C | 364 | −3.624 | −42.801 | 30.420 | 1.00 | 126.02 |
| 223 | CB | ALA | C | 364 | −2.691 | −43.980 | 30.643 | 1.00 | 122.92 |
| 224 | C | ALA | C | 364 | −5.042 | −43.172 | 30.851 | 1.00 | 129.81 |
| 225 | O | ALA | C | 364 | −5.238 | −44.065 | 31.675 | 1.00 | 130.78 |
| 226 | N | PRO | C | 365 | −6.050 | −42.491 | 30.287 | 1.00 | 134.32 |
| 227 | CD | PRO | C | 365 | −5.898 | −41.398 | 29.308 | 1.00 | 132.82 |
| 228 | CA | PRO | C | 365 | −7.466 | −42.724 | 30.593 | 1.00 | 138.54 |
| 229 | CB | PRO | C | 365 | −8.180 | −41.869 | 29.549 | 1.00 | 141.66 |
| 230 | CG | PRO | C | 365 | −7.240 | −40.713 | 29.375 | 1.00 | 139.13 |
| 231 | C | PRO | C | 365 | −7.917 | −44.189 | 30.548 | 1.00 | 138.14 |
| 232 | O | PRO | C | 365 | −8.397 | −44.662 | 29.520 | 1.00 | 136.69 |
| 233 | N | SER | C | 366 | −7.770 | −44.897 | 31.665 | 1.00 | 140.47 |
| 234 | CA | SER | C | 366 | −8.176 | −46.300 | 31.750 | 1.00 | 139.08 |
| 235 | CB | SER | C | 366 | −7.164 | −47.093 | 32.576 | 1.00 | 129.93 |
| 236 | OG | SER | C | 366 | −6.997 | −46.520 | 33.860 | 1.00 | 132.11 |
| 237 | C | SER | C | 366 | −9.555 | −46.391 | 32.399 | 1.00 | 141.30 |
| 238 | O | SER | C | 366 | −9.800 | −45.776 | 33.438 | 1.00 | 147.59 |
| 239 | N | LYS | C | 367 | −10.450 | −47.166 | 31.791 | 1.00 | 137.90 |
| 240 | CA | LYS | C | 367 | −11.813 | −47.307 | 32.299 | 1.00 | 132.87 |
| 241 | CB | LYS | C | 367 | −12.637 | −48.178 | 31.349 | 1.00 | 132.99 |
| 242 | CG | LYS | C | 367 | −12.705 | −47.623 | 29.932 | 1.00 | 135.82 |
| 243 | CD | LYS | C | 367 | −13.675 | −48.404 | 29.058 | 1.00 | 137.87 |
| 244 | CE | LYS | C | 367 | −15.108 | −48.254 | 29.547 | 1.00 | 138.59 |
| 245 | NZ | LYS | C | 367 | −16.077 | −48.957 | 28.663 | 1.00 | 139.68 |
| 246 | C | LYS | C | 367 | −11.917 | −47.851 | 33.721 | 1.00 | 127.99 |
| 247 | O | LYS | C | 367 | −11.114 | −48.680 | 34.145 | 1.00 | 125.72 |
| 248 | N | GLY | C | 368 | −12.925 | −47.370 | 34.447 | 1.00 | 129.28 |
| 249 | CA | GLY | C | 368 | −13.148 | −47.787 | 35.820 | 1.00 | 122.38 |
| 250 | C | GLY | C | 368 | −13.332 | −46.588 | 36.734 | 1.00 | 132.55 |
| 251 | O | GLY | C | 368 | −12.563 | −45.628 | 36.663 | 1.00 | 134.78 |
| 252 | N | THR | C | 369 | −14.350 | −46.632 | 37.592 | 1.00 | 133.02 |
| 253 | CA | THR | C | 369 | −14.621 | −45.533 | 38.527 | 1.00 | 128.41 |
| 254 | CB | THR | C | 369 | −15.807 | −45.867 | 39.488 | 1.00 | 130.85 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 255 | OG1 | THR | C | 369 | −15.720 | −47.232 | 39.917 | 1.00 | 117.91 |
| 256 | CG2 | THR | C | 369 | −17.134 | −45.637 | 38.819 | 1.00 | 126.17 |
| 257 | C | THR | C | 369 | −13.413 | −45.170 | 39.401 | 1.00 | 127.78 |
| 258 | O | THR | C | 369 | −12.620 | −46.034 | 39.782 | 1.00 | 132.53 |
| 259 | N | VAL | C | 370 | −13.281 | −43.884 | 39.715 | 1.00 | 121.71 |
| 260 | CA | VAL | C | 370 | −12.196 | −43.402 | 40.565 | 1.00 | 105.80 |
| 261 | CB | VAL | C | 370 | −11.370 | −42.299 | 39.867 | 1.00 | 95.87 |
| 262 | CG1 | VAL | C | 370 | −10.127 | −42.000 | 40.680 | 1.00 | 95.34 |
| 263 | CG2 | VAL | C | 370 | −10.996 | −42.729 | 38.464 | 1.00 | 91.87 |
| 264 | C | VAL | C | 370 | −12.825 | −42.814 | 41.831 | 1.00 | 101.95 |
| 265 | O | VAL | C | 370 | −13.603 | −41.863 | 41.758 | 1.00 | 102.73 |
| 266 | N | ASN | C | 371 | −12.506 | −43.385 | 42.988 | 1.00 | 104.31 |
| 267 | CA | ASN | C | 371 | −13.064 | −42.896 | 44.248 | 1.00 | 101.22 |
| 268 | CB | ASN | C | 371 | −13.320 | −44.056 | 45.223 | 1.00 | 109.29 |
| 269 | CG | ASN | C | 371 | −14.526 | −44.896 | 44.834 | 1.00 | 119.67 |
| 270 | OD1 | ASN | C | 371 | −15.649 | −44.397 | 44.755 | 1.00 | 119.25 |
| 271 | ND2 | ASN | C | 371 | −14.296 | −46.183 | 44.596 | 1.00 | 126.17 |
| 272 | C | ASN | C | 371 | −12.157 | −41.877 | 44.922 | 1.00 | 93.08 |
| 273 | O | ASN | C | 371 | −10.961 | −42.116 | 45.101 | 1.00 | 86.80 |
| 274 | N | LEU | C | 372 | −12.737 | −40.737 | 45.282 | 1.00 | 80.34 |
| 275 | CA | LEU | C | 372 | −12.004 | −39.681 | 45.960 | 1.00 | 85.02 |
| 276 | CB | LEU | C | 372 | −11.954 | −38.412 | 45.109 | 1.00 | 86.95 |
| 277 | CG | LEU | C | 372 | −11.142 | −38.486 | 43.815 | 1.00 | 83.93 |
| 278 | CD1 | LEU | C | 372 | −11.026 | −37.101 | 43.216 | 1.00 | 91.95 |
| 279 | CD2 | LEU | C | 372 | −9.764 | −39.036 | 44.101 | 1.00 | 79.32 |
| 280 | C | LEU | C | 372 | −12.723 | −39.412 | 47.272 | 1.00 | 94.51 |
| 281 | O | LEU | C | 372 | −13.669 | −38.626 | 47.335 | 1.00 | 80.05 |
| 282 | N | THR | C | 373 | −12.260 | −40.081 | 48.320 | 1.00 | 94.56 |
| 283 | CA | THR | C | 373 | −12.856 | −39.955 | 49.634 | 1.00 | 91.08 |
| 284 | CB | THR | C | 373 | −12.776 | −41.300 | 50.377 | 1.00 | 102.43 |
| 285 | OG1 | THR | C | 373 | −13.226 | −42.350 | 49.510 | 1.00 | 92.41 |
| 286 | CG2 | THR | C | 373 | −13.641 | −41.268 | 51.632 | 1.00 | 91.87 |
| 287 | C | THR | C | 373 | −12.178 | −38.882 | 50.478 | 1.00 | 83.30 |
| 288 | O | THR | C | 373 | −10.952 | −38.753 | 50.482 | 1.00 | 58.06 |
| 289 | N | TRP | C | 374 | −12.998 | −38.113 | 51.188 | 1.00 | 79.64 |
| 290 | CA | TRP | C | 374 | −12.512 | −37.063 | 52.075 | 1.00 | 87.79 |
| 291 | CB | TRP | C | 374 | −13.267 | −35.758 | 51.843 | 1.00 | 87.84 |
| 292 | CG | TRP | C | 374 | −12.905 | −35.088 | 50.565 | 1.00 | 93.68 |
| 293 | CD2 | TRP | C | 374 | −11.783 | −34.229 | 50.340 | 1.00 | 85.34 |
| 294 | CE2 | TRP | C | 374 | −11.826 | −33.832 | 48.985 | 1.00 | 90.79 |
| 295 | CE3 | TRP | C | 374 | −10.745 | −33.756 | 51.151 | 1.00 | 73.09 |
| 296 | CD1 | TRP | C | 374 | −13.564 | −35.178 | 49.372 | 1.00 | 94.66 |
| 297 | NE1 | TRP | C | 374 | −12.923 | −34.426 | 48.418 | 1.00 | 90.05 |
| 298 | CZ2 | TRP | C | 374 | −10.871 | −32.984 | 48.423 | 1.00 | 82.86 |
| 299 | CZ3 | TRP | C | 374 | −9.796 | −32.914 | 50.593 | 1.00 | 81.31 |
| 300 | CH2 | TRP | C | 374 | −9.866 | −32.536 | 49.240 | 1.00 | 89.56 |
| 301 | C | TRP | C | 374 | −12.702 | −37.485 | 53.525 | 1.00 | 94.29 |
| 302 | O | TRP | C | 374 | −13.519 | −38.350 | 53.825 | 1.00 | 93.69 |
| 303 | N | SER | C | 375 | −11.948 | −36.865 | 54.425 | 1.00 | 96.24 |
| 304 | CA | SER | C | 375 | −12.045 | −37.187 | 55.842 | 1.00 | 80.76 |
| 305 | CB | SER | C | 375 | −11.566 | −38.617 | 56.104 | 1.00 | 68.26 |
| 306 | OG | SER | C | 375 | −10.197 | −38.767 | 55.782 | 1.00 | 76.75 |
| 307 | C | SER | C | 375 | −11.192 | −36.228 | 56.635 | 1.00 | 82.94 |
| 308 | O | SER | C | 375 | −10.244 | −35.642 | 56.109 | 1.00 | 94.52 |
| 309 | N | ARG | C | 376 | −11.534 | −36.066 | 57.904 | 1.00 | 73.68 |
| 310 | CA | ARG | C | 376 | −10.781 | −35.185 | 58.766 | 1.00 | 71.70 |
| 311 | CB | ARG | C | 376 | −11.719 | −34.311 | 59.570 | 1.00 | 62.25 |
| 312 | CG | ARG | C | 376 | −12.511 | −33.346 | 58.736 | 1.00 | 41.33 |
| 313 | CD | ARG | C | 376 | −12.734 | −32.119 | 59.553 | 1.00 | 46.54 |
| 314 | NE | ARG | C | 376 | −14.137 | −31.802 | 59.724 | 1.00 | 48.34 |
| 315 | CZ | ARG | C | 376 | −14.595 | −30.921 | 60.608 | 1.00 | 74.39 |
| 316 | NH1 | ARG | C | 376 | −13.745 | −30.283 | 61.405 | 1.00 | 71.54 |
| 317 | NH2 | ARG | C | 376 | −15.897 | −30.658 | 60.678 | 1.00 | 66.70 |
| 318 | C | ARG | C | 376 | −9.937 | −36.011 | 59.702 | 1.00 | 73.86 |
| 319 | O | ARG | C | 376 | −10.285 | −37.143 | 60.016 | 1.00 | 80.96 |
| 320 | N | ALA | C | 377 | −8.821 | −35.450 | 60.145 | 1.00 | 80.73 |
| 321 | CA | ALA | C | 377 | −7.949 | −36.163 | 61.070 | 1.00 | 79.25 |
| 322 | CB | ALA | C | 377 | −6.629 | −35.420 | 61.226 | 1.00 | 77.18 |
| 323 | C | ALA | C | 377 | −8.659 | −36.271 | 62.417 | 1.00 | 75.29 |
| 324 | O | ALA | C | 377 | −8.513 | −37.259 | 63.129 | 1.00 | 88.49 |
| 325 | N | SER | C | 378 | −9.436 | −35.249 | 62.757 | 1.00 | 68.86 |
| 326 | CA | SER | C | 378 | −10.166 | −35.241 | 64.014 | 1.00 | 76.07 |
| 327 | CB | SER | C | 378 | −10.841 | −33.886 | 64.218 | 1.00 | 71.76 |
| 328 | OG | SER | C | 378 | −11.683 | −33.597 | 63.129 | 1.00 | 71.29 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 329 | C | SER | C | 378 | −11.216 | −36.344 | 64.028 | 1.00 | 81.04 |
| 330 | O | SER | C | 378 | −11.439 | −36.988 | 65.052 | 1.00 | 86.25 |
| 331 | N | GLY | C | 379 | −11.851 | −36.564 | 62.881 | 1.00 | 81.56 |
| 332 | CA | GLY | C | 379 | −12.883 | −37.580 | 62.785 | 1.00 | 81.42 |
| 333 | C | GLY | C | 379 | −14.261 | −36.950 | 62.646 | 1.00 | 90.47 |
| 334 | O | GLY | C | 379 | −15.280 | −37.639 | 62.608 | 1.00 | 82.12 |
| 335 | N | LYS | C | 380 | −14.299 | −35.625 | 62.581 | 1.00 | 93.46 |
| 336 | CA | LYS | C | 380 | −15.562 | −34.928 | 62.429 | 1.00 | 94.10 |
| 337 | CB | LYS | C | 380 | −15.400 | −33.461 | 62.830 | 1.00 | 91.59 |
| 338 | CG | LYS | C | 380 | −14.922 | −33.288 | 64.263 | 1.00 | 86.45 |
| 339 | CD | LYS | C | 380 | −14.888 | −31.831 | 64.665 | 1.00 | 100.98 |
| 340 | CE | LYS | C | 380 | −14.477 | −31.682 | 66.115 | 1.00 | 103.02 |
| 341 | NZ | LYS | C | 380 | −14.577 | −30.268 | 66.559 | 1.00 | 117.14 |
| 342 | C | LYS | C | 380 | −16.026 | −35.061 | 60.975 | 1.00 | 88.57 |
| 343 | O | LYS | C | 380 | −15.267 | −35.48S | 60.101 | 1.00 | 96.07 |
| 344 | N | PRO | C | 381 | −17.289 | −34.709 | 60.702 | 1.00 | 99.97 |
| 345 | CD | PRO | C | 381 | −18.345 | −34.388 | 61.677 | 1.00 | 100.35 |
| 346 | CA | PRO | C | 381 | −17.848 | −34.801 | 59.348 | 1.00 | 103.61 |
| 347 | CB | PRO | C | 381 | −19.345 | −34.571 | 59.576 | 1.00 | 96.29 |
| 348 | CG | PRO | C | 381 | −19.554 | −34.982 | 61.012 | 1.00 | 107.77 |
| 349 | C | PRO | C | 381 | −17.284 | −33.814 | 58.330 | 1.00 | 102.65 |
| 350 | O | PRO | C | 381 | −16.897 | −32.698 | 58.679 | 1.00 | 103.03 |
| 351 | N | VAL | C | 382 | −17.248 | −34.241 | 57.070 | 1.00 | 94.53 |
| 352 | CA | VAL | C | 382 | −16.777 | −33.397 | 55.981 | 1.00 | 85.92 |
| 353 | CB | VAL | C | 382 | −15.772 | −34.153 | 55.065 | 1.00 | 92.34 |
| 354 | CG1 | VAL | C | 382 | −14.527 | −34.538 | 55.848 | 1.00 | 97.90 |
| 355 | CG2 | VAL | C | 382 | −16.421 | −35.391 | 54.493 | 1.00 | 84.11 |
| 356 | C | VAL | C | 382 | −18.024 | −33.015 | 55.176 | 1.00 | 83.04 |
| 357 | O | VAL | C | 382 | −18.933 | −33.828 | 55.025 | 1.00 | 91.87 |
| 358 | N | ASN | C | 383 | −18.079 | −31.786 | 54.672 | 1.00 | 89.89 |
| 359 | CA | ASN | C | 383 | −19.237 | −31.331 | 53.898 | 1.00 | 79.06 |
| 360 | CB | ASN | C | 383 | −19.146 | −29.820 | 53.629 | 1.00 | 89.57 |
| 361 | CG | ASN | C | 383 | −19.061 | −28.993 | 54.902 | 1.00 | 116.70 |
| 362 | OD1 | ASN | C | 383 | −19.088 | −27.760 | 54.857 | 1.00 | 121.80 |
| 363 | ND2 | ASN | C | 383 | −18.953 | −29.666 | 56.042 | 1.00 | 124.80 |
| 364 | C | ASN | C | 383 | −19.374 | −32.072 | 52.563 | 1.00 | 80.35 |
| 365 | O | ASN | C | 383 | −18.692 | −33.070 | 52.311 | 1.00 | 69.13 |
| 366 | N | HIS | C | 384 | −20.259 | −31.565 | 51.708 | 1.00 | 86.01 |
| 367 | CA | HIS | C | 384 | −20.509 | −32.153 | 50.392 | 1.00 | 82.12 |
| 368 | CB | HIS | C | 384 | −21.892 | −31.753 | 49.897 | 1.00 | 92.25 |
| 369 | CG | HIS | C | 384 | −22.959 | −31.916 | 50.924 | 1.00 | 113.42 |
| 370 | CD2 | HIS | C | 384 | −23.757 | −31.008 | 51.532 | 1.00 | 115.82 |
| 371 | ND1 | HIS | C | 384 | −23.274 | −33.138 | 51.477 | 1.00 | 118.05 |
| 372 | CE1 | HIS | C | 384 | −24.220 | −32.974 | 52.384 | 1.00 | 120.18 |
| 373 | NE2 | HIS | C | 384 | −24.531 | −31.691 | 52.437 | 1.00 | 126.19 |
| 374 | C | HIS | C | 384 | −19.481 | −31.698 | 49.371 | 1.00 | 86.56 |
| 375 | O | HIS | C | 384 | −19.427 | −30.511 | 49.029 | 1.00 | 72.45 |
| 376 | N | SER | C | 385 | −18.683 | −32.646 | 48.882 | 1.00 | 88.50 |
| 377 | CA | SER | C | 385 | −17.651 | −32.360 | 47.898 | 1.00 | 65.36 |
| 378 | CB | SER | C | 385 | −16.553 | −33.432 | 47.948 | 1.00 | 74.56 |
| 379 | OG | SER | C | 385 | −17.004 | −34.629 | 48.558 | 1.00 | 78.35 |
| 380 | C | SER | C | 385 | −18.219 | −32.248 | 46.495 | 1.00 | 55.91 |
| 381 | O | SER | C | 385 | −19.374 | −32.590 | 46.243 | 1.00 | 69.53 |
| 382 | N | THR | C | 386 | −17.397 | −31.743 | 45.581 | 1.00 | 82.23 |
| 383 | CA | THR | C | 386 | −17.791 | −31.552 | 44.186 | 1.00 | 74.42 |
| 384 | CB | THR | C | 386 | −17.888 | −30.051 | 43.828 | 1.00 | 67.22 |
| 385 | OG1 | THR | C | 386 | −18.974 | −29.457 | 44.546 | 1.00 | 63.98 |
| 386 | CG2 | THR | C | 386 | −18.123 | −29.869 | 42.348 | 1.00 | 53.95 |
| 387 | C | THR | C | 386 | −16.781 | −32.197 | 43.255 | 1.00 | 69.56 |
| 388 | O | THR | C | 386 | −15.649 | −31.719 | 43.131 | 1.00 | 67.47 |
| 389 | N | ARG | C | 387 | −17.207 | −33.277 | 42.602 | 1.00 | 79.30 |
| 390 | CA | ARG | C | 387 | −16.379 | −34.036 | 41.662 | 1.00 | 84.90 |
| 391 | CB | ARG | C | 387 | −16.821 | −35.505 | 41.665 | 1.00 | 73.84 |
| 392 | CG | ARG | C | 387 | −16.030 | −36.426 | 40.752 | 1.00 | 96.05 |
| 393 | CD | ARG | C | 387 | −16.639 | −37.828 | 40.742 | 1.00 | 90.43 |
| 394 | NE | ARG | C | 387 | −15.914 | −38.731 | 39.855 | 1.00 | 86.64 |
| 395 | CZ | ARG | C | 387 | −14.810 | −39.392 | 40.191 | 1.00 | 104.15 |
| 396 | NH1 | ARG | C | 387 | −14.300 | −39.260 | 41.409 | 1.00 | 108.69 |
| 397 | NH2 | ARG | C | 387 | −14.203 | −40.170 | 39.301 | 1.00 | 105.60 |
| 398 | C | ARG | C | 387 | −16.540 | −33.447 | 40.264 | 1.00 | 77.52 |
| 399 | O | ARG | C | 387 | −17.646 | −33.070 | 39.876 | 1.00 | 67.87 |
| 400 | N | LYS | C | 388 | −15.439 | −33.353 | 39.519 | 1.00 | 73.35 |
| 401 | CA | LYS | C | 388 | −15.486 | −32.809 | 38.166 | 1.00 | 69.06 |
| 402 | CB | LYS | C | 388 | −15.196 | −31.311 | 38.161 | 1.00 | 56.87 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 403 | CG | LYS | C | 388 | −16.076 | −30.498 | 39.082 | 1.00 | 95.72 |
| 404 | CD | LYS | C | 388 | −15.564 | −29.070 | 39.207 | 1.00 | 96.42 |
| 405 | CE | LYS | C | 388 | −16.269 | −28.323 | 40.335 | 1.00 | 100.54 |
| 406 | NZ | LYS | C | 388 | −15.758 | −26.940 | 40.549 | 1.00 | 87.89 |
| 407 | C | LYS | C | 388 | −14.468 | −33.491 | 37.284 | 1.00 | 75.05 |
| 408 | O | LYS | C | 388 | −13.280 | −33.159 | 37.330 | 1.00 | 47.46 |
| 409 | N | GLU | C | 389 | −14.945 | −34.441 | 36.484 | 1.00 | 77.40 |
| 410 | CA | GLU | C | 389 | −14.094 | −35.178 | 35.562 | 1.00 | 81.19 |
| 411 | CB | GLU | C | 389 | −14.630 | −36.607 | 35.378 | 1.00 | 87.35 |
| 412 | CG | GLU | C | 389 | −14.582 | −37.457 | 36.644 | 1.00 | 104.87 |
| 413 | CD | GLU | C | 389 | −15.234 | −38.818 | 36.468 | 1.00 | 112.74 |
| 414 | OE1 | GLU | C | 389 | −14.785 | −39.589 | 35.595 | 1.00 | 111.73 |
| 415 | OE2 | GLU | C | 389 | −16.194 | −39.121 | 37.205 | 1.00 | 110.63 |
| 416 | C | GLU | C | 389 | −14.051 | −34.439 | 34.220 | 1.00 | 85.42 |
| 417 | O | GLU | C | 389 | −15.033 | −34.401 | 33.482 | 1.00 | 93.05 |
| 418 | N | GLU | C | 390 | −12.902 | −33.844 | 33.919 | 1.00 | 88.95 |
| 419 | CA | GLU | C | 390 | −12.720 | −33.092 | 32.686 | 1.00 | 88.21 |
| 420 | CB | GLU | C | 390 | −12.260 | −31.675 | 33.017 | 1.00 | 110.43 |
| 421 | CG | GLU | C | 390 | −11.938 | −30.814 | 31.815 | 1.00 | 128.47 |
| 422 | CD | GLU | C | 390 | −11.558 | −29.412 | 32.221 | 1.00 | 134.79 |
| 423 | OE1 | GLU | C | 390 | −10.628 | −29.267 | 33.041 | 1.00 | 137.71 |
| 424 | OE2 | GLU | C | 390 | −12.191 | −28.457 | 31.727 | 1.00 | 133.68 |
| 425 | C | GLU | C | 390 | −11.695 | −33.784 | 31.806 | 1.00 | 86.83 |
| 426 | O | GLU | C | 390 | −10.491 | −33.520 | 31.892 | 1.00 | 63.26 |
| 427 | N | LYS | C | 391 | −12.187 | −34.663 | 30.945 | 1.00 | 101.68 |
| 428 | CA | LYS | C | 391 | −11.328 | −35.428 | 30.055 | 1.00 | 108.95 |
| 429 | CB | LYS | C | 391 | −12.094 | −36.634 | 29.495 | 1.00 | 116.61 |
| 430 | CG | LYS | C | 391 | −11.210 | −37.789 | 29.030 | 1.00 | 121.06 |
| 431 | CD | LYS | C | 391 | −12.017 | −39.074 | 28.927 | 1.00 | 116.81 |
| 432 | CE | LYS | C | 391 | −11.123 | −40.287 | 28.731 | 1.00 | 120.39 |
| 433 | NZ | LYS | C | 391 | −11.917 | −41.552 | 28.706 | 1.00 | 110.57 |
| 434 | C | LYS | C | 391 | −10.762 | −34.607 | 28.912 | 1.00 | 108.98 |
| 435 | O | LYS | C | 391 | −11.377 | −33.654 | 28.437 | 1.00 | 119.43 |
| 436 | N | GLN | C | 392 | −9.571 | −34.993 | 28.484 | 1.00 | 108.89 |
| 437 | CA | GLN | C | 392 | −8.890 | −34.336 | 27.385 | 1.00 | 123.49 |
| 438 | CB | GLN | C | 392 | −7.824 | −33.384 | 27.922 | 1.00 | 119.65 |
| 439 | CG | GLN | C | 392 | −8.369 | −32.299 | 28.819 | 1.00 | 125.45 |
| 440 | CD | GLN | C | 392 | −7.272 | −31.464 | 29.425 | 1.00 | 125.56 |
| 441 | OE1 | GLN | C | 392 | −6.465 | −30.871 | 28.713 | 1.00 | 115.75 |
| 442 | NE2 | GLN | C | 392 | −7.231 | −31.417 | 30.748 | 1.00 | 117.72 |
| 443 | C | GLN | C | 392 | −8.231 | −35.419 | 26.540 | 1.00 | 138.42 |
| 444 | O | GLN | C | 392 | −7.213 | −35.988 | 26.943 | 1.00 | 145.23 |
| 445 | N | ARG | C | 393 | −8.815 | −35.712 | 25.377 | 1.00 | 143.83 |
| 446 | CA | ARG | C | 393 | −8.265 | −36.729 | 24.478 | 1.00 | 148.53 |
| 447 | CB | ARG | C | 393 | −9.092 | −36.811 | 23.183 | 1.00 | 145.54 |
| 448 | CG | ARG | C | 393 | −10.083 | −35.666 | 22.985 | 1.00 | 147.10 |
| 449 | CD | ARG | C | 393 | −10.762 | −35.746 | 21.627 | 1.00 | 151.42 |
| 450 | NE | ARG | C | 393 | −9.796 | −35.701 | 20.530 | 1.00 | 157.26 |
| 451 | CZ | ARG | C | 393 | −10.114 | −35.788 | 19.241 | 1.00 | 152.19 |
| 452 | NH1 | ARG | C | 393 | −11.379 | −35.925 | 18.873 | 1.00 | 154.22 |
| 453 | NH2 | ARG | C | 393 | −9.164 | −35.735 | 18.317 | 1.00 | 146.55 |
| 454 | C | ARG | C | 393 | −6.799 | −36.417 | 24.159 | 1.00 | 152.47 |
| 455 | O | ARG | C | 393 | −6.109 | −37.200 | 23.496 | 1.00 | 152.34 |
| 456 | N | ASN | C | 394 | −6.339 | −35.265 | 24.644 | 1.00 | 157.12 |
| 457 | CA | ASN | C | 394 | −4.965 | −34.811 | 24.467 | 1.00 | 149.46 |
| 458 | CB | ASN | C | 394 | −4.839 | −33.364 | 24.953 | 1.00 | 147.12 |
| 459 | CG | ASN | C | 394 | −3.449 | −32.792 | 24.745 | 1.00 | 151.90 |
| 460 | OD1 | ASN | C | 394 | −3.086 | −31.787 | 25.357 | 1.00 | 147.69 |
| 461 | ND2 | ASN | C | 394 | −2.669 | −33.421 | 23.872 | 1.00 | 152.93 |
| 462 | C | ASN | C | 394 | −4.056 | −35.712 | 25.302 | 1.00 | 144.10 |
| 463 | O | ASN | C | 394 | −2.838 | −35.553 | 25.309 | 1.00 | 139.35 |
| 464 | N | GLY | C | 395 | −4.665 | −36.661 | 26.005 | 1.00 | 142.49 |
| 465 | CA | GLY | C | 395 | −3.908 | −37.568 | 26.846 | 1.00 | 139.94 |
| 466 | C | GLY | C | 395 | −3.868 | −37.024 | 28.258 | 1.00 | 143.58 |
| 467 | O | GLY | C | 395 | −2.794 | −36.748 | 28.796 | 1.00 | 143.43 |
| 468 | N | THR | C | 396 | −5.048 | −36.869 | 28.855 | 1.00 | 142.98 |
| 469 | CA | THR | C | 396 | −5.171 | −36.336 | 30.206 | 1.00 | 134.69 |
| 470 | CB | THR | C | 396 | −4.687 | −34.849 | 30.264 | 1.00 | 139.14 |
| 471 | OG1 | THR | C | 396 | −3.281 | −34.775 | 29.989 | 1.00 | 141.63 |
| 472 | CG2 | THR | C | 396 | −4.957 | −34.248 | 31.631 | 1.00 | 137.49 |
| 473 | C | THR | C | 396 | −6.625 | −36.391 | 30.695 | 1.00 | 126.31 |
| 474 | O | THR | C | 396 | −7.505 | −35.734 | 30.129 | 1.00 | 122.44 |
| 475 | N | LEU | C | 397 | −6.880 | −37.182 | 31.736 | 1.00 | 120.34 |
| 476 | CA | LEU | C | 397 | −8.224 | −37.269 | 32.308 | 1.00 | 109.38 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 477 | CB | LEU | C | 397 | −8.675 | −38.724 | 32.467 | 1.00 | 87.98 |
| 478 | CG | LEU | C | 397 | −10.015 | −38.923 | 33.202 | 1.00 | 76.29 |
| 479 | CD1 | LEU | C | 397 | −11.122 | −38.167 | 32.499 | 1.00 | 77.99 |
| 480 | CD2 | LEU | C | 397 | −10.360 | −40.390 | 33.276 | 1.00 | 79.38 |
| 481 | C | LEU | C | 397 | −8.245 | −36.586 | 33.675 | 1.00 | 103.75 |
| 482 | O | LEU | C | 397 | −8.088 | −37.236 | 34.705 | 1.00 | 110.47 |
| 483 | N | THR | C | 398 | −8.434 | −35.271 | 33.678 | 1.00 | 99.00 |
| 484 | CA | THR | C | 398 | −8.470 | −34.509 | 34.917 | 1.00 | 93.67 |
| 485 | CB | THR | C | 398 | −8.504 | −32.984 | 34.648 | 1.00 | 112.69 |
| 486 | OG1 | THR | C | 398 | −7.207 | −32.537 | 34.242 | 1.00 | 87.38 |
| 487 | CG2 | THR | C | 398 | −8.924 | −32.223 | 35.899 | 1.00 | 101.93 |
| 488 | C | THR | C | 398 | −9.687 | −34.867 | 35.746 | 1.00 | 86.93 |
| 489 | O | THR | C | 398 | −10.798 | −34.967 | 35.226 | 1.00 | 84.63 |
| 490 | N | VAL | C | 399 | −9.459 | −35.060 | 37.042 | 1.00 | 93.88 |
| 491 | CA | VAL | C | 399 | −10.522 | −35.383 | 37.995 | 1.00 | 92.02 |
| 492 | CB | VAL | C | 399 | −10.576 | −36.898 | 38.325 | 1.00 | 88.67 |
| 493 | CG1 | VAL | C | 399 | −11.730 | −37.177 | 39.274 | 1.00 | 81.68 |
| 494 | CG2 | VAL | C | 399 | −10.747 | −37.708 | 37.057 | 1.00 | 77.97 |
| 495 | C | VAL | C | 399 | −10.236 | −34.613 | 39.280 | 1.00 | 78.97 |
| 496 | O | VAL | C | 399 | −9.258 | −34.885 | 39.965 | 1.00 | 75.46 |
| 497 | N | THR | C | 400 | −11.079 | −33.637 | 39.593 | 1.00 | 72.00 |
| 498 | CA | THR | C | 400 | −10.877 | −32.839 | 40.788 | 1.00 | 51.29 |
| 499 | CB | THR | C | 400 | −10.692 | −31.298 | 40.474 | 1.00 | 51.13 |
| 500 | OG1 | THR | C | 400 | −11.890 | −30.772 | 39.897 | 1.00 | 66.39 |
| 501 | CG2 | THR | C | 400 | −9.530 | −31.044 | 39.522 | 1.00 | 49.07 |
| 502 | C | THR | C | 400 | −12.076 | −32.972 | 41.696 | 1.00 | 79.06 |
| 503 | O | THR | C | 400 | −13.175 | −33.346 | 41.264 | 1.00 | 74.12 |
| 504 | N | SER | C | 401 | −11.849 | −32.673 | 42.967 | 1.00 | 74.01 |
| 505 | CA | SER | C | 401 | −12.906 | −32.696 | 43.958 | 1.00 | 64.91 |
| 506 | CB | SER | C | 401 | −12.866 | −33.978 | 44.777 | 1.00 | 63.30 |
| 507 | OG | SER | C | 401 | −13.999 | −34.037 | 45.624 | 1.00 | 52.16 |
| 508 | C | SER | C | 401 | −12.635 | −31.493 | 44.840 | 1.00 | 60.98 |
| 509 | O | SER | C | 401 | −11.519 | −31.303 | 45.306 | 1.00 | 46.77 |
| 510 | N | THR | C | 402 | −13.654 | −30.670 | 45.037 | 1.00 | 47.43 |
| 511 | CA | THR | C | 402 | −13.519 | −29.473 | 45.845 | 1.00 | 50.30 |
| 512 | CB | THR | C | 402 | −13.882 | −28.227 | 45.025 | 1.00 | 56.12 |
| 513 | OG1 | THR | C | 402 | −12.815 | −27.955 | 44.111 | 1.00 | 54.69 |
| 514 | CG2 | THR | C | 402 | −14.104 | −27.018 | 45.918 | 1.00 | 56.27 |
| 515 | C | THR | C | 402 | −14.383 | −29.544 | 47.092 | 1.00 | 75.40 |
| 516 | O | THR | C | 402 | −15.618 | −29.536 | 47.021 | 1.00 | 56.54 |
| 517 | N | LEU | C | 403 | −13.715 | −29.601 | 48.239 | 1.00 | 69.52 |
| 518 | CA | LEU | C | 403 | −14.403 | −29.706 | 49.504 | 1.00 | 64.31 |
| 519 | CB | LEU | C | 403 | −13.728 | −30.791 | 50.360 | 1.00 | 48.43 |
| 520 | CG | LEU | C | 403 | −14.280 | −30.982 | 51.774 | 1.00 | 77.34 |
| 521 | CD1 | LEU | C | 403 | −15.634 | −31.664 | 51.710 | 1.00 | 56.30 |
| 522 | CD2 | LEU | C | 403 | −13.308 | −31.808 | 52.592 | 1.00 | 85.77 |
| 523 | C | LEU | C | 403 | −14.461 | −28.390 | 50.267 | 1.00 | 67.03 |
| 524 | O | LEU | C | 403 | −13.426 | −27.785 | 50.559 | 1.00 | 51.23 |
| 525 | N | PRO | C | 404 | −15.687 | −27.912 | 50.560 | 1.00 | 73.39 |
| 526 | CD | PRO | C | 404 | −16.957 | −28.386 | 49.979 | 1.00 | 86.08 |
| 527 | CA | PRO | C | 404 | −15.907 | −26.670 | 51.305 | 1.00 | 55.65 |
| 528 | CB | PRO | C | 404 | −17.421 | −26.476 | 51.233 | 1.00 | 50.44 |
| 529 | CG | PRO | C | 404 | −17.794 | −27.121 | 49.950 | 1.00 | 48.97 |
| 530 | C | PRO | C | 404 | −15.453 | −26.954 | 52.731 | 1.00 | 44.85 |
| 531 | O | PRO | C | 404 | −15.791 | −27.992 | 53.302 | 1.00 | 39.42 |
| 532 | N | VAL | C | 405 | −14.676 | −26.042 | 53.294 | 1.00 | 49.79 |
| 533 | CA | VAL | C | 405 | −14.169 | −26.213 | 54.637 | 1.00 | 36.31 |
| 534 | CB | VAL | C | 405 | −12.631 | −26.236 | 54.618 | 1.00 | 47.53 |
| 535 | CG1 | VAL | C | 405 | −12.083 | −26.091 | 56.018 | 1.00 | 86.68 |
| 536 | CG2 | VAL | C | 405 | −12.152 | −27.538 | 54.021 | 1.00 | 72.61 |
| 537 | C | VAL | C | 405 | −14.678 | −25.118 | 55.560 | 1.00 | 32.08 |
| 538 | O | VAL | C | 405 | −15.046 | −24.039 | 55.127 | 1.00 | 43.59 |
| 539 | N | GLY | C | 406 | −14.727 | −25.407 | 56.845 | 1.00 | 55.60 |
| 540 | CA | GLY | C | 406 | −15.180 | −24.400 | 57.776 | 1.00 | 55.19 |
| 541 | C | GLY | C | 406 | −14.062 | −23.398 | 57.935 | 1.00 | 59.64 |
| 542 | O | GLY | C | 406 | −12.881 | −23.763 | 57.971 | 1.00 | 62.46 |
| 543 | N | THR | C | 407 | −14.423 | −22.127 | 58.015 | 1.00 | 41.47 |
| 544 | CA | THR | C | 407 | −13.424 | −21.095 | 58.181 | 1.00 | 57.41 |
| 545 | CB | THR | C | 407 | −14.075 | −19.726 | 58.235 | 1.00 | 50.62 |
| 546 | OG1 | THR | C | 407 | −14.755 | −19.490 | 56.997 | 1.00 | 59.50 |
| 547 | CG2 | THR | C | 407 | −13.035 | −18.651 | 58.435 | 1.00 | 72.87 |
| 548 | C | THR | C | 407 | −12.644 | −21.356 | 59.460 | 1.00 | 73.50 |
| 549 | O | THR | C | 407 | −11.439 | −21.595 | 59.417 | 1.00 | 77.06 |
| 550 | N | ALA | C | 408 | −13.332 | −21.338 | 60.595 | 1.00 | 70.67 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 551 | CA | ALA | C | 408 | −12.676 | −21.586 | 61.875 | 1.00 | 73.16 |
| 552 | CB | ALA | C | 408 | −13.688 | −21.526 | 63.005 | 1.00 | 72.80 |
| 553 | C | ALA | C | 408 | −11.938 | −22.925 | 61.902 | 1.00 | 71.16 |
| 554 | O | ALA | C | 408 | −10.854 | −23.021 | 62.467 | 1.00 | 86.04 |
| 555 | N | ASP | C | 409 | −12.515 | −23.950 | 61.284 | 1.00 | 59.81 |
| 556 | CA | ASP | C | 409 | −11.891 | −25.271 | 61.261 | 1.00 | 77.11 |
| 557 | CB | ASP | C | 409 | −12.749 | −26.256 | 60.465 | 1.00 | 86.06 |
| 558 | CG | ASP | C | 409 | −14.054 | −26.587 | 61.159 | 1.00 | 102.26 |
| 559 | OD1 | ASP | C | 409 | −14.007 | −27.164 | 62.267 | 1.00 | 94.90 |
| 560 | OD2 | ASP | C | 409 | −15.124 | −26.270 | 60.595 | 1.00 | 105.10 |
| 561 | C | ASP | C | 409 | −10.478 | −25.268 | 60.688 | 1.00 | 82.26 |
| 562 | O | ASP | C | 409 | −9.549 | −25.782 | 61.317 | 1.00 | 87.78 |
| 563 | N | TRF | C | 410 | −10.315 | −24.698 | 59.495 | 1.00 | 83.07 |
| 564 | CA | TRP | C | 410 | −9.003 | −24.647 | 58.841 | 1.00 | 72.30 |
| 565 | CB | TRP | C | 410 | −9.131 | −24.144 | 57.395 | 1.00 | 37.77 |
| 566 | CG | TRP | C | 410 | −7.805 | −23.954 | 56.691 | 1.00 | 37.86 |
| 567 | CD2 | TRP | C | 410 | −7.086 | −24.943 | 55.940 | 1.00 | 18.83 |
| 568 | CE2 | TRP | C | 410 | −5.857 | −24.364 | 55.545 | 1.00 | 38.04 |
| 569 | CE3 | TRP | C | 410 | −7.361 | −26.261 | 55.566 | 1.00 | 33.49 |
| 570 | CD1 | TRP | C | 410 | −7.005 | −22.836 | 56.709 | 1.00 | 17.48 |
| 571 | NE1 | TRP | C | 410 | −5.830 | −23.079 | 56.025 | 1.00 | 42.01 |
| 572 | CZ2 | TRP | C | 410 | −4.906 | −25.065 | 54.796 | 1.00 | 38.63 |
| 573 | CZ3 | TRP | C | 410 | −6.413 | −26.958 | 54.820 | 1.00 | 68.26 |
| 574 | CH2 | TRP | C | 410 | −5.201 | −26.357 | 54.446 | 1.00 | 58.98 |
| 575 | C | TRP | C | 410 | −8.026 | −23.756 | 59.593 | 1.00 | 67.15 |
| 576 | O | TRP | C | 410 | −6.828 | −24.053 | 59.673 | 1.00 | 44.43 |
| 577 | N | ILE | C | 411 | −8.545 | −22.663 | 60.139 | 1.00 | 64.66 |
| 578 | CA | ILE | C | 411 | −7.717 | −21.723 | 60.869 | 1.00 | 72.69 |
| 579 | CB | ILE | C | 411 | −8.478 | −20.407 | 61.111 | 1.00 | 68.27 |
| 580 | CG2 | ILE | C | 411 | −7.751 | −19.556 | 62.122 | 1.00 | 74.96 |
| 581 | CG1 | ILE | C | 411 | −8.624 | −19.652 | 59.789 | 1.00 | 67.72 |
| 582 | CD1 | ILE | C | 411 | −9.394 | −18.356 | 59.915 | 1.00 | 75.86 |
| 583 | C | ILE | C | 411 | −7.195 | −22.268 | 62.198 | 1.00 | 75.55 |
| 584 | O | ILE | C | 411 | −6.075 | −21.948 | 62.592 | 1.00 | 69.51 |
| 585 | N | GLU | C | 412 | −7.979 | −23.100 | 62.881 | 1.00 | 66.71 |
| 586 | CA | GLU | C | 412 | −7.537 | −23.630 | 64.162 | 1.00 | 65.94 |
| 587 | CB | GLU | C | 412 | −8.734 | −23.821 | 65.092 | 1.00 | 61.52 |
| 588 | CG | GLU | C | 412 | −9.185 | −22.505 | 65.723 | 1.00 | 88.79 |
| 589 | CD | GLU | C | 412 | −10.519 | −22.595 | 66.447 | 1.00 | 111.05 |
| 590 | OE1 | GLU | C | 412 | −10.699 | −23.533 | 67.248 | 1.00 | 123.78 |
| 591 | OE2 | GLU | C | 412 | −11.382 | −21.718 | 66.226 | 1.00 | 101.99 |
| 592 | C | GLU | C | 412 | −6.651 | −24.879 | 64.120 | 1.00 | 69.54 |
| 593 | O | GLU | C | 412 | −6.227 | −25.382 | 65.168 | 1.00 | 69.11 |
| 594 | N | GLY | C | 413 | −6.352 | −25.379 | 62.924 | 1.00 | 63.59 |
| 595 | CA | GLY | C | 413 | −5.453 | −26.520 | 62.836 | 1.00 | 63.85 |
| 596 | C | GLY | C | 413 | −5.950 | −27.829 | 62.271 | 1.00 | 70.68 |
| 597 | O | GLY | C | 413 | −5.197 | −28.816 | 62.246 | 1.00 | 52.91 |
| 598 | N | GLU | C | 414 | −7.201 | −27.861 | 61.820 | 1.00 | 75.58 |
| 599 | CA | GLU | C | 414 | −7.753 | −29.093 | 61.262 | 1.00 | 73.48 |
| 600 | CB | GLU | C | 414 | −9.213 | −28.901 | 60.862 | 1.00 | 71.78 |
| 601 | CG | GLU | C | 414 | −9.877 | −30.143 | 60.282 | 1.00 | 72.49 |
| 602 | CD | GLU | C | 414 | −10.132 | −31.224 | 61.315 | 1.00 | 73.45 |
| 603 | OE1 | GLU | C | 414 | −9.244 | −32.070 | 61.547 | 1.00 | 92.74 |
| 604 | OE2 | GLU | C | 414 | −11.233 | −31.214 | 61.900 | 1.00 | 49.36 |
| 605 | C | GLU | C | 414 | −6.960 | −29.513 | 60.040 | 1.00 | 67.30 |
| 606 | O | GLU | C | 414 | −6.523 | −28.675 | 59.248 | 1.00 | 67.15 |
| 607 | N | THR | C | 415 | −6.759 | −30.813 | 59.897 | 1.00 | 49.37 |
| 608 | CA | THR | C | 415 | −6.042 | −31.331 | 58.752 | 1.00 | 74.21 |
| 609 | CB | THR | C | 415 | −4.805 | −32.130 | 59.173 | 1.00 | 79.50 |
| 610 | OG1 | THR | C | 415 | −4.582 | −33.188 | 58.232 | 1.00 | 79.72 |
| 611 | CG2 | THR | C | 415 | −4.974 | −32.683 | 60.570 | 1.00 | 93.07 |
| 612 | C | THR | C | 415 | −6.993 | −32.213 | 57.956 | 1.00 | 85.25 |
| 613 | O | THR | C | 415 | −7.544 | −33.181 | 58.491 | 1.00 | 95.54 |
| 614 | N | TYR | C | 416 | −7.196 | −31.868 | 56.683 | 1.00 | 66.34 |
| 615 | CA | TYR | C | 416 | −8.108 | −32.621 | 55.846 | 1.00 | 41.15 |
| 616 | CB | TYR | C | 416 | −8.897 | −31.669 | 54.968 | 1.00 | 29.69 |
| 617 | CG | TYR | C | 416 | −9.718 | −30.694 | 55.769 | 1.00 | 44.40 |
| 618 | CD1 | TYR | C | 416 | −9.126 | −29.618 | 56.416 | 1.00 | 37.72 |
| 619 | CE1 | TYR | C | 416 | −9.880 | −28.753 | 57.194 | 1.00 | 44.13 |
| 620 | CD2 | TYR | C | 416 | −11.090 | −30.874 | 55.918 | 1.00 | 73.31 |
| 621 | CE2 | TYR | C | 416 | −11.849 | −30.011 | 56.696 | 1.00 | 28.70 |
| 622 | CZ | TYR | C | 416 | −11.238 | −28.961 | 57.331 | 1.00 | 21.58 |
| 623 | OH | TYR | C | 416 | −11.998 | −28.123 | 58.121 | 1.00 | 67.60 |
| 624 | C | TYR | C | 416 | −7.387 | −33.650 | 55.010 | 1.00 | 53.89 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 625 | O | TYR | C | 416 | −6.236 | −33.446 | 54.622 | 1.00 | 77.17 |
| 626 | N | GLN | C | 417 | −8.064 | −34.763 | 54.741 | 1.00 | 50.65 |
| 627 | CA | GLN | C | 417 | −7.467 | −35.836 | 53.949 | 1.00 | 74.00 |
| 628 | CB | GLN | C | 417 | −7.159 | −37.036 | 54.857 | 1.00 | 75.49 |
| 629 | CG | GLN | C | 417 | −6.479 | −38.191 | 54.141 | 1.00 | 104.06 |
| 630 | CD | GLN | C | 417 | −6.376 | −39.437 | 54.999 | 1.00 | 114.21 |
| 631 | OE1 | GLN | C | 417 | −7.389 | −40.021 | 55.393 | 1.00 | 119.20 |
| 632 | NE2 | GLN | C | 417 | −5.147 | −39.854 | 55.294 | 1.00 | 104.10 |
| 633 | C | GLN | C | 417 | −8.312 | −36.300 | 52.751 | 1.00 | 70.27 |
| 634 | O | GLN | C | 417 | −9.552 | −36.351 | 52.818 | 1.00 | 56.05 |
| 635 | N | CYS | C | 418 | −7.619 | −36.637 | 51.663 | 1.00 | 49.39 |
| 636 | CA | CYS | C | 418 | −8.253 | −37.102 | 50.437 | 1.00 | 74.43 |
| 637 | C | CYS | C | 418 | −7.720 | −38.493 | 50.123 | 1.00 | 80.59 |
| 638 | O | CYS | C | 418 | −6.510 | −38.680 | 49.970 | 1.00 | 84.76 |
| 639 | CB | CYS | C | 418 | −7.938 | −36.140 | 49.280 | 1.00 | 82.85 |
| 640 | SG | CYS | C | 418 | −8.541 | −36.650 | 47.633 | 1.00 | 103.50 |
| 641 | N | ARG | C | 419 | −8.618 | −39.471 | 50.045 | 1.00 | 76.45 |
| 642 | CA | ARG | C | 419 | −8.210 | −40.833 | 49.742 | 1.00 | 85.74 |
| 643 | CB | ARG | C | 419 | −8.814 | −41.811 | 50.750 | 1.00 | 85.00 |
| 644 | CG | ARG | C | 419 | −8.280 | −43.229 | 50.610 | 1.00 | 96.25 |
| 645 | CD | ARG | C | 419 | −8.641 | −44.091 | 51.819 | 1.00 | 108.36 |
| 646 | NE | ARG | C | 419 | −8.228 | −45.484 | 51.649 | 1.00 | 110.51 |
| 647 | CZ | ARG | C | 419 | −8.731 | −46.308 | 50.733 | 1.00 | 119.05 |
| 648 | NH1 | ARG | C | 419 | −9.673 | −45.886 | 49.897 | 1.00 | 119.40 |
| 649 | NH2 | ARG | C | 419 | −8.292 | −47.557 | 50.651 | 1.00 | 112.03 |
| 650 | C | ARG | C | 419 | −8.637 | −41.191 | 48.326 | 1.00 | 89.47 |
| 651 | O | ARG | C | 419 | −9.818 | −41.117 | 47.983 | 1.00 | 77.50 |
| 652 | N | VAL | C | 420 | −7.661 | −41.572 | 47.508 | 1.00 | 87.24 |
| 653 | CA | VAL | C | 420 | −7.917 | −41.923 | 46.121 | 1.00 | 92.00 |
| 654 | CB | VAL | C | 420 | −6.864 | −41.283 | 45.206 | 1.00 | 94.80 |
| 655 | CG1 | VAL | C | 420 | −7.243 | −41.487 | 43.744 | 1.00 | 94.24 |
| 656 | CG2 | VAL | C | 420 | −6.730 | −39.806 | 45.543 | 1.00 | 89.41 |
| 657 | C | VAL | C | 420 | −7.914 | −43.428 | 45.900 | 1.00 | 95.39 |
| 658 | O | VAL | C | 420 | −6.999 | −44.129 | 46.323 | 1.00 | 91.32 |
| 659 | N | THR | C | 421 | −8.949 | −43.916 | 45.226 | 1.00 | 105.57 |
| 660 | CA | THR | C | 421 | −9.084 | −45.337 | 44.943 | 1.00 | 105.96 |
| 661 | CB | THR | C | 421 | −10.303 | −45.917 | 45.670 | 1.00 | 106.53 |
| 662 | OG1 | THR | C | 421 | −10.198 | −45.637 | 47.071 | 1.00 | 109.60 |
| 663 | CG2 | THR | C | 421 | −10.383 | −47.422 | 45.457 | 1.00 | 114.04 |
| 664 | C | THR | C | 421 | −9.263 | −45.564 | 43.446 | 1.00 | 116.97 |
| 665 | O | THR | C | 421 | −9.894 | −44.758 | 42.760 | 1.00 | 121.36 |
| 666 | N | HIS | C | 422 | −8.700 | −46.657 | 42.941 | 1.00 | 123.28 |
| 667 | CA | HIS | C | 422 | −8.816 | −46.992 | 41.525 | 1.00 | 127.35 |
| 668 | CB | HIS | C | 422 | −7.834 | −46.162 | 40.694 | 1.00 | 121.89 |
| 669 | CG | HIS | C | 422 | −8.036 | −46.290 | 39.215 | 1.00 | 126.17 |
| 670 | CD2 | HIS | C | 422 | −7.193 | −46.668 | 38.228 | 1.00 | 122.77 |
| 671 | ND1 | HIS | C | 422 | −9.242 | −46.010 | 38.602 | 1.00 | 126.70 |
| 672 | CE1 | HIS | C | 422 | −9.128 | −46.211 | 37.301 | 1.00 | 122.30 |
| 673 | NE2 | HIS | C | 422 | −7.895 | −46.611 | 37.048 | 1.00 | 122.98 |
| 674 | C | HIS | C | 422 | −8.550 | −48.481 | 41.313 | 1.00 | 130.53 |
| 675 | O | HIS | C | 422 | −7.701 | −49.070 | 41.984 | 1.00 | 121.00 |
| 676 | N | PRO | C | 423 | −9.283 | −49.109 | 40.377 | 1.00 | 133.99 |
| 677 | CD | PRO | C | 423 | −10.386 | −48.549 | 39.573 | 1.00 | 131.49 |
| 678 | CA | PRO | C | 423 | −9.110 | −50.539 | 40.094 | 1.00 | 138.77 |
| 679 | CB | PRO | C | 423 | −10.318 | −50.861 | 39.208 | 1.00 | 132.51 |
| 680 | CG | PRO | C | 423 | −10.539 | −49.575 | 38.468 | 1.00 | 134.89 |
| 681 | C | PRO | C | 423 | −7.782 | −50.910 | 39.428 | 1.00 | 138.72 |
| 682 | O | PRO | C | 423 | −7.320 | −52.049 | 39.552 | 1.00 | 139.97 |
| 683 | N | HIS | C | 424 | −7.168 | −49.953 | 38.733 | 1.00 | 137.27 |
| 684 | CA | HIS | C | 424 | −5.905 | −50.205 | 38.040 | 1.00 | 137.40 |
| 685 | CB | HIS | C | 424 | −5.922 | −49.529 | 36.661 | 1.00 | 136.77 |
| 686 | CG | HIS | C | 424 | −7.087 | −49.930 | 35.807 | 1.00 | 138.07 |
| 687 | CD2 | HIS | C | 424 | −8.092 | −49.199 | 35.270 | 1.00 | 145.65 |
| 688 | ND1 | HIS | C | 424 | −7.323 | −51.236 | 35.434 | 1.00 | 137.33 |
| 689 | CE1 | HIS | C | 424 | −8.424 | −51.292 | 34.705 | 1.00 | 134.08 |
| 690 | NE2 | HIS | C | 424 | −8.910 | −50.070 | 34.591 | 1.00 | 135.81 |
| 691 | C | HIS | C | 424 | −4.678 | −49.750 | 38.831 | 1.00 | 135.28 |
| 692 | O | HIS | C | 424 | −3.681 | −49.312 | 38.249 | 1.00 | 132.80 |
| 693 | N | LEU | C | 425 | −4.758 | −49.865 | 40.155 | 1.00 | 134.88 |
| 694 | CA | LEU | C | 425 | −3.659 | −49.485 | 41.043 | 1.00 | 136.99 |
| 695 | CB | LEU | C | 425 | −3.733 | −47.996 | 41.381 | 1.00 | 135.42 |
| 696 | CG | LEU | C | 425 | −3.251 | −47.043 | 40.290 | 1.00 | 132.94 |
| 697 | CD1 | LEU | C | 425 | −3.412 | −45.618 | 40.774 | 1.00 | 136.28 |
| 698 | CD2 | LEU | C | 425 | −1.790 | −47.340 | 39.948 | 1.00 | 134.72 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 699 | C | LEU | C | 425 | −3.665 | −50.296 | 42.334 | 1.00 | 130.35 |
| 700 | O | LEU | C | 425 | −4.718 | −50.531 | 42.926 | 1.00 | 131.91 |
| 701 | N | PRO | C | 426 | −2.478 | −50.721 | 42.795 | 1.00 | 128.91 |
| 702 | CD | PRO | C | 426 | −1.148 | −50.343 | 42.283 | 1.00 | 124.12 |
| 703 | CA | PRO | C | 426 | −2.355 | −51.511 | 44.024 | 1.00 | 126.07 |
| 704 | CB | PRO | C | 426 | −0.851 | −51.749 | 44.128 | 1.00 | 127.83 |
| 705 | CG | PRO | C | 426 | −0.276 | −50.510 | 43.506 | 1.00 | 123.31 |
| 706 | C | PRO | C | 426 | −2.919 | −50.789 | 45.245 | 1.00 | 125.11 |
| 707 | O | PRO | C | 426 | −4.123 | −50.826 | 45.500 | 1.00 | 123.79 |
| 708 | N | ARG | C | 427 | −2.038 | −50.136 | 45.996 | 1.00 | 124.94 |
| 709 | CA | ARG | C | 427 | −2.434 | −49.400 | 47.187 | 1.00 | 122.96 |
| 710 | CB | ARG | C | 427 | −1.209 | −49.133 | 48.063 | 1.00 | 126.70 |
| 711 | CG | ARG | C | 427 | −1.508 | −48.379 | 49.344 | 1.00 | 135.59 |
| 712 | CD | ARG | C | 427 | −0.232 | −48.119 | 50.119 | 1.00 | 145.27 |
| 713 | NE | ARG | C | 427 | −0.461 | −47.295 | 51.301 | 1.00 | 148.68 |
| 714 | CZ | ARG | C | 427 | 0.500 | −46.889 | 52.123 | 1.00 | 147.62 |
| 715 | NH1 | ARG | C | 427 | 1.760 | −47.233 | 51.892 | 1.00 | 142.44 |
| 716 | NH2 | ARG | C | 427 | 0.203 | −46.136 | 53.175 | 1.00 | 147.62 |
| 717 | C | ARG | C | 427 | −3.094 | −48.080 | 46.797 | 1.00 | 127.09 |
| 718 | O | ARG | C | 427 | −2.917 | −47.589 | 45.681 | 1.00 | 119.35 |
| 719 | N | ALA | C | 428 | −3.856 | −47.512 | 47.725 | 1.00 | 128.76 |
| 720 | CA | ALA | C | 428 | −4.548 | −46.254 | 47.484 | 1.00 | 119.62 |
| 721 | CB | ALA | C | 428 | −5.800 | −46.179 | 48.347 | 1.00 | 118.62 |
| 722 | C | ALA | C | 428 | −3.644 | −45.060 | 47.769 | 1.00 | 112.45 |
| 723 | O | ALA | C | 428 | −2.650 | −45.171 | 48.486 | 1.00 | 113.64 |
| 724 | N | LEU | C | 429 | −3.997 | −43.917 | 47.194 | 1.00 | 112.17 |
| 725 | CA | LEU | C | 429 | −3.232 | −42.698 | 47.388 | 1.00 | 102.61 |
| 726 | CB | LEU | C | 429 | −3.194 | −41.891 | 46.091 | 1.00 | 101.97 |
| 727 | CG | LEU | C | 429 | −2.348 | −42.469 | 44.958 | 1.00 | 100.73 |
| 728 | CD1 | LEU | C | 429 | −2.469 | −41.572 | 43.744 | 1.00 | 111.29 |
| 729 | CD2 | LEU | C | 429 | −0.886 | −42.579 | 45.397 | 1.00 | 108.24 |
| 730 | C | LEU | C | 429 | −3.850 | −41.858 | 48.497 | 1.00 | 104.87 |
| 731 | O | LEU | C | 429 | −5.064 | −41.904 | 48.722 | 1.00 | 84.00 |
| 732 | N | MET | C | 430 | −3.007 | −41.090 | 49.185 | 1.00 | 110.36 |
| 733 | CA | MET | C | 430 | −3.458 | −40.230 | 50.272 | 1.00 | 101.73 |
| 734 | CB | MET | C | 430 | −3.324 | −40.966 | 51.604 | 1.00 | 107.02 |
| 735 | CG | MET | C | 430 | −4.185 | −42.220 | 51.691 | 1.00 | 126.23 |
| 736 | SD | MET | C | 430 | −3.728 | −43.318 | 53.054 | 1.00 | 144.25 |
| 737 | CE | MET | C | 430 | −2.552 | −44.442 | 52.222 | 1.00 | 123.98 |
| 738 | C | MET | C | 430 | −2.677 | −38.922 | 50.318 | 1.00 | 94.28 |
| 739 | O | MET | C | 430 | −1.464 | −38.892 | 50.088 | 1.00 | 74.35 |
| 740 | N | ARG | C | 431 | −3.397 | −37.841 | 50.601 | 1.00 | 83.11 |
| 741 | CA | ARG | C | 431 | −2.814 | −36.508 | 50.694 | 1.00 | 79.04 |
| 742 | CB | ARG | C | 431 | −3.013 | −35.730 | 49.389 | 1.00 | 80.60 |
| 743 | CG | ARG | C | 431 | −2.653 | −36.501 | 48.145 | 1.00 | 76.98 |
| 744 | CD | ARG | C | 431 | −1.196 | −36.872 | 48.126 | 1.00 | 77.37 |
| 745 | NE | ARG | C | 431 | −0.932 | −37.858 | 47.087 | 1.00 | 91.52 |
| 746 | CZ | ARG | C | 431 | 0.276 | −38.312 | 46.778 | 1.00 | 88.93 |
| 747 | NH1 | ARG | C | 431 | 1.342 | −37.865 | 47.430 | 1.00 | 76.87 |
| 748 | NH2 | ARG | C | 431 | 0.419 | −39.209 | 45.815 | 1.00 | 92.50 |
| 749 | C | ARG | C | 431 | −3.536 | −35.775 | 51.813 | 1.00 | 78.96 |
| 750 | O | ARG | C | 431 | −4.731 | −35.978 | 52.033 | 1.00 | 80.75 |
| 751 | N | SER | C | 432 | −2.810 | −34.921 | 52.519 | 1.00 | 70.71 |
| 752 | CA | SER | C | 432 | −3.400 | −34.154 | 53.602 | 1.00 | 53.76 |
| 753 | CB | SER | C | 432 | −2.979 | −34.740 | 54.941 | 1.00 | 66.03 |
| 754 | OG | SER | C | 432 | −1.569 | −34.780 | 55.045 | 1.00 | 68.60 |
| 755 | C | SER | C | 432 | −2.924 | −32.713 | 53.481 | 1.00 | 60.20 |
| 756 | O | SER | C | 432 | −1.913 | −32.447 | 52.831 | 1.00 | 61.34 |
| 757 | N | THR | C | 433 | −3.643 | −31.786 | 54.102 | 1.00 | 37.60 |
| 758 | CA | THR | C | 433 | −3.274 | −30.385 | 54.015 | 1.00 | 57.51 |
| 759 | CB | THR | C | 433 | −3.904 | −29.738 | 52.771 | 1.00 | 64.69 |
| 760 | OG1 | THR | C | 433 | −3.526 | −28.359 | 52.709 | 1.00 | 52.48 |
| 761 | CG2 | THR | C | 433 | −5.423 | −29.846 | 52.826 | 1.00 | 61.95 |
| 762 | C | THR | C | 433 | −3.716 | −29.614 | 55.242 | 1.00 | 52.56 |
| 763 | O | THR | C | 433 | −4.670 | −30.006 | 55.896 | 1.00 | 55.64 |
| 764 | N | THR | C | 434 | −3.017 | −28.515 | 55.539 | 1.00 | 69.59 |
| 765 | CA | THR | C | 434 | −3.302 | −27.651 | 56.699 | 1.00 | 72.79 |
| 766 | CB | THR | C | 434 | −2.765 | −28.260 | 58.040 | 1.00 | 85.87 |
| 767 | OG1 | THR | C | 434 | −1.636 | −29.105 | 57.780 | 1.00 | 86.20 |
| 768 | CG2 | THR | C | 434 | −3.845 | −29.047 | 58.762 | 1.00 | 74.59 |
| 769 | C | THR | C | 434 | −2.664 | −26.272 | 56.540 | 1.00 | 56.46 |
| 770 | O | THR | C | 434 | −2.681 | −25.454 | 57.466 | 1.00 | 56.38 |
| 771 | N | ARG | C | 440 | 5.359 | −15.979 | 60.002 | 1.00 | 22.82 |
| 772 | CA | ARG | C | 440 | 4.357 | −15.089 | 59.410 | 1.00 | 55.91 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 773 | CB | ARG | C | 440 | 3.076 | −15.058 | 60.266 | 1.00 | 35.97 |
| 774 | CG | ARG | C | 440 | 2.547 | −16.441 | 60.717 | 1.00 | 68.53 |
| 775 | CD | ARG | C | 440 | 1.948 | −17.317 | 59.590 | 1.00 | 70.03 |
| 776 | NE | ARG | C | 440 | 1.778 | −18.711 | 60.023 | 1.00 | 90.79 |
| 777 | CZ | ARG | C | 440 | 1.094 | −19.643 | 59.354 | 1.00 | 86.98 |
| 778 | NH1 | ARG | C | 440 | 0.501 | −19.340 | 58.211 | 1.00 | 92.29 |
| 779 | NH2 | ARG | C | 440 | 1.009 | −20.889 | 59.819 | 1.00 | 92.23 |
| 780 | C | ARG | C | 440 | 4.886 | −13.655 | 59.239 | 1.00 | 48.79 |
| 781 | O | ARG | C | 440 | 5.497 | −13.095 | 60.138 | 1.00 | 49.13 |
| 782 | N | ALA | C | 441 | 4.643 | −13.064 | 58.073 | 1.00 | 54.47 |
| 783 | CA | ALA | C | 441 | 5.088 | −11.695 | 57.770 | 1.00 | 46.37 |
| 784 | CB | ALA | C | 441 | 6.531 | −11.706 | 57.352 | 1.00 | 20.81 |
| 785 | C | ALA | C | 441 | 4.251 | −11.053 | 56.663 | 1.00 | 39.94 |
| 786 | O | ALA | C | 441 | 4.043 | −11.647 | 55.605 | 1.00 | 49.43 |
| 787 | N | ALA | C | 442 | 3.777 | −9.838 | 56.916 | 1.00 | 37.57 |
| 788 | CA | ALA | C | 442 | 2.971 | −9.091 | 55.944 | 1.00 | 39.39 |
| 789 | CB | ALA | C | 442 | 2.470 | −7.796 | 56.556 | 1.00 | 35.44 |
| 790 | C | ALA | C | 442 | 3.760 | −8.780 | 54.674 | 1.00 | 38.53 |
| 791 | O | ALA | C | 442 | 4.973 | −8.680 | 54.699 | 1.00 | 45.10 |
| 792 | N | PRO | C | 443 | 3.064 | −8.622 | 53.543 | 1.00 | 44.52 |
| 793 | CD | PRO | C | 443 | 1.665 | −9.016 | 53.340 | 1.00 | 46.08 |
| 794 | CA | PRO | C | 443 | 3.674 | −8.326 | 52.251 | 1.00 | 40.65 |
| 795 | CB | PRO | C | 443 | 2.659 | −8.883 | 51.253 | 1.00 | 37.36 |
| 796 | CG | PRO | C | 443 | 1.770 | −9.757 | 52.053 | 1.00 | 46.65 |
| 797 | C | PRO | C | 443 | 3.905 | −6.851 | 51.987 | 1.00 | 38.18 |
| 798 | O | PRO | C | 443 | 3.083 | −6.005 | 52.332 | 1.00 | 39.25 |
| 799 | N | ALA | C | 444 | 5.043 | −6.543 | 51.377 | 1.00 | 36.54 |
| 800 | CA | ALA | C | 444 | 5.347 | −5.157 | 50.982 | 1.00 | 30.88 |
| 801 | CB | ALA | C | 444 | 6.878 | −4.878 | 51.104 | 1.00 | 21.64 |
| 802 | C | ALA | C | 444 | 4.846 | −5.128 | 49.513 | 1.00 | 29.06 |
| 803 | O | ALA | C | 444 | 5.123 | −6.053 | 48.730 | 1.00 | 37.58 |
| 804 | N | VAL | C | 445 | 4.075 | −4.116 | 49.147 | 1.00 | 26.08 |
| 805 | CA | VAL | C | 445 | 3.526 | −4.094 | 47.784 | 1.00 | 13.94 |
| 806 | CB | VAL | C | 445 | 1.966 | −4.326 | 47.807 | 1.00 | 37.30 |
| 807 | CG1 | VAL | C | 445 | 1.356 | −4.156 | 46.384 | 1.00 | 12.41 |
| 808 | CG2 | VAL | C | 445 | 1.654 | −5.722 | 48.345 | 1.00 | 23.55 |
| 809 | C | VAL | C | 445 | 3.777 | −2.885 | 46.909 | 1.00 | 30.00 |
| 810 | O | VAL | C | 445 | 3.542 | −1.740 | 47.329 | 1.00 | 19.35 |
| 811 | N | TYR | C | 446 | 4.268 | −3.123 | 45.691 | 1.00 | 25.17 |
| 812 | CA | TYR | C | 446 | 4.442 | −1.982 | 44.778 | 1.00 | 35.46 |
| 813 | CB | TYR | C | 446 | 5.852 | −1.390 | 44.844 | 1.00 | 50.02 |
| 814 | CG | TYR | C | 446 | 5.823 | 0.048 | 44.367 | 1.00 | 92.12 |
| 815 | CD1 | TYR | C | 446 | 4.904 | 0.962 | 44.896 | 1.00 | 91.48 |
| 816 | CE1 | TYR | C | 446 | 4.838 | 2.272 | 44.423 | 1.00 | 86.21 |
| 817 | CD2 | TYR | C | 446 | 6.672 | 0.488 | 43.358 | 1.00 | 92.99 |
| 818 | CE2 | TYR | C | 446 | 6.613 | 1.797 | 42.875 | 1.00 | 81.37 |
| 819 | CZ | TYR | C | 446 | 5.699 | 2.678 | 43.410 | 1.00 | 88.25 |
| 820 | OH | TYR | C | 446 | 5.658 | 3.961 | 42.916 | 1.00 | 96.81 |
| 821 | C | TYR | C | 446 | 4.039 | −2.220 | 43.317 | 1.00 | 40.04 |
| 822 | O | TYR | C | 446 | 4.206 | −3.302 | 42.762 | 1.00 | 29.90 |
| 823 | N | ALA | C | 447 | 3.511 | −1.167 | 42.700 | 1.00 | 30.71 |
| 824 | CA | ALA | C | 447 | 3.006 | −1.242 | 41.337 | 1.00 | 29.44 |
| 825 | CB | ALA | C | 447 | 1.498 | −1.033 | 41.355 | 1.00 | 30.87 |
| 826 | C | ALA | C | 447 | 3.622 | −0.277 | 40.371 | 1.00 | 32.29 |
| 827 | O | ALA | C | 447 | 3.858 | 0.877 | 40.701 | 1.00 | 35.60 |
| 828 | N | PHE | C | 448 | 3.853 | −0.747 | 39.152 | 1.00 | 35.75 |
| 829 | CA | PHE | C | 448 | 4.423 | 0.114 | 38.128 | 1.00 | 35.22 |
| 830 | CB | PHE | C | 448 | 5.855 | −0.293 | 37.814 | 1.00 | 44.80 |
| 831 | CG | PHE | C | 448 | 6.676 | −0.586 | 39.010 | 1.00 | 34.62 |
| 832 | CD1 | PHE | C | 448 | 6.705 | −1.869 | 39.545 | 1.00 | 28.15 |
| 833 | CD2 | PHE | C | 448 | 7.419 | 0.426 | 39.618 | 1.00 | 23.23 |
| 834 | CE1 | PHE | C | 448 | 7.474 | −2.154 | 40.691 | 1.00 | 24.27 |
| 835 | CE2 | PHE | C | 448 | 8.182 | 0.162 | 40.751 | 1.00 | 40.09 |
| 836 | CZ | PHE | C | 448 | 8.208 | −1.139 | 41.292 | 1.00 | 19.06 |
| 837 | C | PHE | C | 448 | 3.649 | 0.069 | 36.826 | 1.00 | 43.18 |
| 838 | O | PHE | C | 448 | 2.974 | −0.912 | 36.526 | 1.00 | 34.74 |
| 839 | N | ALA | C | 449 | 3.802 | 1.136 | 36.052 | 1.00 | 28.16 |
| 840 | CA | ALA | C | 449 | 3.186 | 1.265 | 34.751 | 1.00 | 34.65 |
| 841 | CB | ALA | C | 449 | 2.249 | 2.448 | 34.738 | 1.00 | 33.19 |
| 842 | C | ALA | C | 449 | 4.312 | 1.485 | 33.750 | 1.00 | 43.61 |
| 843 | O | ALA | C | 449 | 5.265 | 2.220 | 34.026 | 1.00 | 43.09 |
| 844 | N | THR | C | 450 | 4.197 | 0.847 | 32.589 | 1.00 | 53.66 |
| 845 | CA | THR | C | 450 | 5.197 | 0.960 | 31.533 | 1.00 | 44.50 |
| 846 | CB | THR | C | 450 | 4.992 | −0.165 | 30.501 | 1.00 | 36.57 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 847 | OG1 | THR | C | 450 | 5.680 | −1.338 | 30.940 | 1.00 | 39.20 |
| 848 | CG2 | THR | C | 450 | 5.501 | 0.222 | 29.147 | 1.00 | 69.58 |
| 849 | C | THR | C | 450 | 5.080 | 2.298 | 30.849 | 1.00 | 35.75 |
| 850 | O | THR | C | 450 | 4.006 | 2.876 | 30.820 | 1.00 | 52.99 |
| 851 | N | PRO | C | 451 | 6.192 | 2.833 | 30.318 | 1.00 | 64.56 |
| 852 | CD | PRO | C | 451 | 7.568 | 2.399 | 30.614 | 1.00 | 65.39 |
| 853 | CA | PRO | C | 451 | 6.203 | 4.125 | 29.611 | 1.00 | 59.82 |
| 854 | CB | PRO | C | 451 | 7.689 | 4.483 | 29.567 | 1.00 | 60.46 |
| 855 | CG | PRO | C | 451 | 8.285 | 3.711 | 30.684 | 1.00 | 73.64 |
| 856 | C | PRO | C | 451 | 5.635 | 3.912 | 28.192 | 1.00 | 55.85 |
| 857 | O | PRO | C | 451 | 5.403 | 2.770 | 27.787 | 1.00 | 36.38 |
| 858 | N | GLU | C | 452 | 5.425 | 4.998 | 27.450 | 1.00 | 66.41 |
| 859 | CA | GLU | C | 452 | 4.910 | 4.959 | 26.068 | 1.00 | 85.71 |
| 860 | CB | GLU | C | 452 | 3.932 | 3.796 | 25.856 | 1.00 | 99.99 |
| 861 | CG | GLU | C | 452 | 4.560 | 2.511 | 25.343 | 1.00 | 94.47 |
| 862 | CD | GLU | C | 452 | 3.797 | 1.281 | 25.801 | 1.00 | 103.77 |
| 863 | OE1 | GLU | C | 452 | 2.639 | 1.095 | 25.372 | 1.00 | 96.18 |
| 864 | OE2 | GLU | C | 452 | 4.351 | 0.502 | 26.603 | 1.00 | 80.28 |
| 865 | C | GLU | C | 452 | 4.199 | 6.252 | 25.709 | 1.00 | 92.49 |
| 866 | O | GLU | C | 452 | 3.105 | 6.223 | 25.142 | 1.00 | 89.42 |
| 867 | N | LYS | C | 459 | −1.468 | −2.550 | 24.530 | 1.00 | 61.46 |
| 868 | CA | LYS | C | 459 | −0.443 | −3.443 | 25.079 | 1.00 | 94.73 |
| 869 | CB | LYS | C | 459 | 0.433 | −3.999 | 23.944 | 1.00 | 104.72 |
| 870 | CG | LYS | C | 459 | −0.133 | −5.239 | 23.251 | 1.00 | 101.29 |
| 871 | CD | LYS | C | 459 | −0.064 | −6.464 | 24.166 | 1.00 | 113.61 |
| 872 | CE | LYS | C | 459 | −0.498 | −7.742 | 23.447 | 1.00 | 116.48 |
| 873 | NZ | LYS | C | 459 | −0.261 | −8.962 | 24.276 | 1.00 | 118.40 |
| 874 | C | LYS | C | 459 | 0.438 | −2.774 | 26.154 | 1.00 | 96.61 |
| 875 | O | LYS | C | 459 | 1.595 | −3.169 | 26.391 | 1.00 | 73.19 |
| 876 | N | ARG | C | 460 | −0.135 | −1.767 | 26.806 | 1.00 | 86.27 |
| 877 | CA | ARG | C | 460 | 0.536 | −1.021 | 27.861 | 1.00 | 67.14 |
| 878 | CB | ARG | C | 460 | −0.179 | 0.312 | 28.042 | 1.00 | 62.32 |
| 879 | CG | ARG | C | 460 | −0.051 | 1.224 | 26.798 | 1.00 | 78.47 |
| 880 | CD | ARG | C | 460 | −0.261 | 0.497 | 25.445 | 1.00 | 59.46 |
| 881 | NE | ARG | C | 460 | −1.600 | −0.083 | 25.277 | 1.00 | 71.21 |
| 882 | CZ | ARG | C | 460 | −2.570 | 0.440 | 24.522 | 1.00 | 73.03 |
| 883 | NH1 | ARG | C | 460 | −2.374 | 1.567 | 23.846 | 1.00 | 80.20 |
| 884 | NH2 | ARG | C | 460 | −3.748 | −0.161 | 24.445 | 1.00 | 60.32 |
| 885 | C | ARG | C | 460 | 0.474 | −1.881 | 29.118 | 1.00 | 58.83 |
| 886 | O | ARG | C | 460 | −0.622 | −2.227 | 29.578 | 1.00 | 53.45 |
| 887 | N | THR | C | 461 | 1.645 | −2.233 | 29.662 | 1.00 | 37.32 |
| 888 | CA | THR | C | 461 | 1.681 | −3.108 | 30.811 | 1.00 | 29.84 |
| 889 | CB | THR | C | 461 | 2.722 | −4.190 | 30.606 | 1.00 | 31.75 |
| 890 | OG1 | THR | C | 461 | 2.864 | −4.443 | 29.204 | 1.00 | 40.42 |
| 891 | CG2 | THR | C | 461 | 2.294 | −5.488 | 31.302 | 1.00 | 45.88 |
| 892 | C | THR | C | 461 | 1.868 | −2.499 | 32.188 | 1.00 | 39.90 |
| 893 | O | THR | C | 461 | 2.524 | −1.472 | 32.364 | 1.00 | 37.50 |
| 894 | N | LEU | C | 462 | 1.241 | −3.152 | 33.163 | 1.00 | 30.35 |
| 895 | CA | LEU | C | 462 | 1.305 | −2.738 | 34.553 | 1.00 | 36.67 |
| 896 | CB | LEU | C | 462 | −0.084 | −2.463 | 35.144 | 1.00 | 36.92 |
| 897 | CG | LEU | C | 462 | −0.942 | −1.430 | 34.419 | 1.00 | 43.30 |
| 898 | CD1 | LEU | C | 462 | −2.317 | −1.379 | 35.076 | 1.00 | 43.17 |
| 899 | CD2 | LEU | C | 462 | −0.266 | −0.063 | 34.455 | 1.00 | 31.35 |
| 900 | C | LEU | C | 462 | 1.934 | −3.914 | 35.259 | 1.00 | 39.39 |
| 901 | O | LEU | C | 462 | 1.604 | −5.076 | 34.980 | 1.00 | 48.25 |
| 902 | N | ALA | C | 463 | 2.859 | −3.611 | 36.162 | 1.00 | 32.39 |
| 903 | CA | ALA | C | 463 | 3.514 | −4.655 | 36.889 | 1.00 | 19.17 |
| 904 | CB | ALA | C | 463 | 4.960 | −4.725 | 36.456 | 1.00 | 40.10 |
| 905 | C | ALA | C | 463 | 3.395 | −4.394 | 38.380 | 1.00 | 36.80 |
| 906 | O | ALA | C | 463 | 3.305 | −3.257 | 38.835 | 1.00 | 33.22 |
| 907 | N | CYS | C | 464 | 3.411 | −5.473 | 39.135 | 1.00 | 34.79 |
| 908 | CA | CYS | C | 464 | 3.291 | −5.390 | 40.570 | 1.00 | 27.33 |
| 909 | C | CYS | C | 464 | 4.286 | −6.337 | 41.197 | 1.00 | 35.41 |
| 910 | O | CYS | C | 464 | 4.368 | −7.507 | 40.828 | 1.00 | 45.88 |
| 911 | CB | CYS | C | 464 | 1.875 | −5.793 | 40.973 | 1.00 | 45.06 |
| 912 | SG | CYS | C | 464 | 1.394 | −5.495 | 42.678 | 1.00 | 60.61 |
| 913 | N | LEU | C | 465 | 5.071 | −5.806 | 42.122 | 1.00 | 27.86 |
| 914 | CA | LEU | C | 465 | 6.027 | −6.600 | 42.862 | 1.00 | 21.20 |
| 915 | CB | LEU | C | 465 | 7.386 | −5.898 | 42.906 | 1.00 | 31.20 |
| 916 | CG | LEU | C | 465 | 8.354 | −6.479 | 43.950 | 1.00 | 34.03 |
| 917 | CD1 | LEU | C | 465 | 8.659 | −7.956 | 43.677 | 1.00 | 31.99 |
| 918 | CD2 | LEU | C | 465 | 9.623 | −5.674 | 43.944 | 1.00 | 29.85 |
| 919 | C | LEU | C | 465 | 5.462 | −6.742 | 44.284 | 1.00 | 37.75 |
| 920 | O | LEU | C | 465 | 5.093 | −5.733 | 44.934 | 1.00 | 36.96 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 921 | N | ILE | C | 466 | 5.380 | −7.985 | 44.753 | 1.00 | 20.39 |
| 922 | CA | ILE | C | 466 | 4.852 | −8.266 | 46.086 | 1.00 | 31.40 |
| 923 | CB | ILE | C | 466 | 3.515 | −9.040 | 45.980 | 1.00 | 56.46 |
| 924 | CG2 | ILE | C | 466 | 2.850 | −9.164 | 47.367 | 1.00 | 42.69 |
| 925 | CG1 | ILE | C | 466 | 2.578 | −8.289 | 45.033 | 1.00 | 46.10 |
| 926 | CD1 | ILE | C | 466 | 1.569 | −9.143 | 44.368 | 1.00 | 36.69 |
| 927 | C | ILE | C | 466 | 5.899 | −9.103 | 46.787 | 1.00 | 38.24 |
| 928 | O | ILE | C | 466 | 6.158 | −10.235 | 46.371 | 1.00 | 38.22 |
| 929 | N | GLN | C | 467 | 6.489 | −8.559 | 47.856 | 1.00 | 33.02 |
| 930 | CA | GLN | C | 467 | 7.581 | −9.264 | 48.534 | 1.00 | 40.80 |
| 931 | CB | GLN | C | 467 | 8.893 | −8.732 | 47.992 | 1.00 | 31.82 |
| 932 | CG | GLN | C | 467 | 8.983 | −7.217 | 48.118 | 1.00 | 20.85 |
| 933 | CD | GLN | C | 467 | 10.345 | −6.670 | 47.709 | 1.00 | 49.75 |
| 934 | OE1 | GLN | C | 467 | 11.038 | −7.240 | 46.857 | 1.00 | 31.87 |
| 935 | NE2 | GLN | C | 467 | 10.724 | −5.544 | 48.303 | 1.00 | 23.70 |
| 936 | C | GLN | C | 467 | 7.675 | −9.252 | 50.050 | 1.00 | 50.67 |
| 937 | O | GLN | C | 467 | 6.951 | −8.528 | 50.743 | 1.00 | 36.86 |
| 938 | N | ASN | C | 468 | 8.601 | −10.075 | 50.536 | 1.00 | 31.50 |
| 939 | CA | ASN | C | 468 | 8.915 | −10.227 | 51.961 | 1.00 | 38.88 |
| 940 | CB | ASN | C | 468 | 9.456 | −8.917 | 52.534 | 1.00 | 39.94 |
| 941 | CG | ASN | C | 468 | 10.621 | −8.382 | 51.753 | 1.00 | 33.87 |
| 942 | OD1 | ASN | C | 468 | 11.439 | −9.134 | 51.241 | 1.00 | 35.12 |
| 943 | ND2 | ASN | C | 468 | 10.710 | −7.072 | 51.669 | 1.00 | 37.89 |
| 944 | C | ASN | C | 468 | 7.761 | −10.688 | 52.820 | 1.00 | 43.89 |
| 945 | O | ASN | C | 468 | 7.549 | −10.171 | 53.910 | 1.00 | 48.24 |
| 946 | N | PHE | C | 469 | 7.023 | −11.672 | 52.337 | 1.00 | 32.95 |
| 947 | CA | PHE | C | 469 | 5.886 | −12.173 | 53.073 | 1.00 | 31.69 |
| 948 | CB | PHE | C | 469 | 4.592 | −11.941 | 52.263 | 1.00 | 38.44 |
| 949 | CG | PHE | C | 469 | 4.539 | −12.691 | 50.935 | 1.00 | 22.12 |
| 950 | CD1 | PHE | C | 469 | 4.219 | −14.047 | 50.887 | 1.00 | 20.00 |
| 951 | CD2 | PHE | C | 469 | 4.815 | −12.031 | 49.735 | 1.00 | 26.68 |
| 952 | CE1 | PHE | C | 469 | 4.175 | −14.742 | 49.669 | 1.00 | 17.24 |
| 953 | CE2 | PHE | C | 469 | 4.773 | −12.708 | 48.512 | 1.00 | 30.08 |
| 954 | CZ | PHE | C | 469 | 4.452 | −14.071 | 48.482 | 1.00 | 30.30 |
| 955 | C | PHE | C | 469 | 6.072 | −13.644 | 53.360 | 1.00 | 39.59 |
| 956 | O | PHE | C | 469 | 6.853 | −14.327 | 52.679 | 1.00 | 34.35 |
| 957 | N | MET | C | 470 | 5.388 | −14.118 | 54.402 | 1.00 | 43.41 |
| 958 | CA | MET | C | 470 | 5.425 | −15.533 | 54.754 | 1.00 | 46.45 |
| 959 | CB | MET | C | 470 | 6.772 | −15.940 | 55.379 | 1.00 | 49.77 |
| 960 | CG | MET | C | 470 | 7.207 | −15.226 | 56.656 | 1.00 | 75.57 |
| 961 | SD | MET | C | 470 | 8.961 | −15.659 | 57.063 | 1.00 | 76.78 |
| 962 | CE | MET | C | 470 | 8.842 | −17.474 | 57.089 | 1.00 | 79.41 |
| 963 | C | MET | C | 470 | 4.256 | −15.880 | 55.652 | 1.00 | 42.01 |
| 964 | O | MET | C | 470 | 3.822 | −15.062 | 56.452 | 1.00 | 46.66 |
| 965 | N | PRO | C | 471 | 3.696 | −17.093 | 55.495 | 1.00 | 38.17 |
| 966 | CD | PRO | C | 471 | 2.517 | −17.519 | 56.263 | 1.00 | 26.66 |
| 967 | CA | PRO | C | 471 | 4.096 | −18.134 | 54.543 | 1.00 | 31.64 |
| 968 | CB | PRO | C | 471 | 3.122 | −19.267 | 54.828 | 1.00 | 44.61 |
| 969 | CG | PRO | C | 471 | 2.654 | −19.001 | 56.223 | 1.00 | 43.16 |
| 970 | C | PRO | C | 471 | 4.005 | −17.681 | 53.098 | 1.00 | 44.54 |
| 971 | O | PRO | C | 471 | 3.721 | −16.515 | 52.822 | 1.00 | 31.87 |
| 972 | N | GLU | C | 472 | 4.220 | −18.626 | 52.182 | 1.00 | 46.00 |
| 973 | CA | GLU | C | 472 | 4.185 | −18.347 | 50.744 | 1.00 | 49.44 |
| 974 | CB | GLU | C | 472 | 4.969 | −19.413 | 49.978 | 1.00 | 43.12 |
| 975 | CG | GLU | C | 472 | 4.299 | −20.760 | 49.962 | 1.00 | 61.29 |
| 976 | CD | GLU | C | 472 | 5.034 | −21.745 | 49.085 | 1.00 | 92.81 |
| 977 | OE1 | GLU | C | 472 | 6.130 | −22.191 | 49.490 | 1.00 | 99.17 |
| 978 | OE2 | GLU | C | 472 | 4.521 | −22.062 | 47.986 | 1.00 | 101.34 |
| 979 | C | GLU | C | 472 | 2.791 | −18.225 | 50.129 | 1.00 | 43.02 |
| 980 | O | GLU | C | 472 | 2.637 | −17.715 | 49.028 | 1.00 | 51.73 |
| 981 | N | ASP | C | 473 | 1.776 | −18.675 | 50.841 | 1.00 | 41.95 |
| 982 | CA | ASP | C | 473 | 0.426 | −18.596 | 50.319 | 1.00 | 38.53 |
| 983 | CB | ASP | C | 473 | −0.558 | −19.268 | 51.276 | 1.00 | 50.79 |
| 984 | CG | ASP | C | 473 | −0.288 | −20.754 | 51.444 | 1.00 | 77.43 |
| 985 | OD1 | ASP | C | 473 | −0.162 | −21.465 | 50.417 | 1.00 | 71.59 |
| 986 | OD2 | ASP | C | 473 | −0.212 | −21.207 | 52.610 | 1.00 | 91.83 |
| 987 | C | ASP | C | 473 | 0.009 | −17.155 | 50.077 | 1.00 | 31.16 |
| 988 | O | ASP | C | 473 | 0.124 | −16.317 | 50.952 | 1.00 | 41.03 |
| 989 | N | ILE | C | 474 | −0.497 | −16.862 | 48.890 | 1.00 | 37.47 |
| 990 | CA | ILE | C | 474 | −0.902 | −15.502 | 48.618 | 1.00 | 33.88 |
| 991 | CB | ILE | C | 474 | 0.379 | −14.603 | 48.352 | 1.00 | 27.68 |
| 992 | CG2 | ILE | C | 474 | 0.968 | −14.870 | 46.946 | 1.00 | 16.39 |
| 993 | CG1 | ILE | C | 474 | 0.027 | −13.124 | 48.479 | 1.00 | 30.48 |
| 994 | CD1 | ILE | C | 474 | 1.237 | −12.255 | 48.657 | 1.00 | 29.60 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 995 | C | ILE | C | 474 | −1.896 | −15.409 | 47.452 | 1.00 | 37.41 |
| 996 | O | ILE | C | 474 | −1.932 | −16.270 | 46.577 | 1.00 | 35.06 |
| 997 | N | SER | C | 475 | −2.701 | −14.352 | 47.466 | 1.00 | 31.03 |
| 998 | CA | SER | C | 475 | −3.681 | −14.091 | 46.426 | 1.00 | 25.55 |
| 999 | CB | SER | C | 475 | −5.105 | −14.225 | 46.977 | 1.00 | 45.18 |
| 1000 | OG | SER | C | 475 | −5.427 | −15.568 | 47.289 | 1.00 | 44.69 |
| 1001 | C | SER | C | 475 | −3.491 | −12.668 | 45.870 | 1.00 | 42.89 |
| 1002 | O | SER | C | 475 | −3.420 | −11.701 | 46.641 | 1.00 | 36.19 |
| 1003 | N | VAL | C | 476 | −3.428 | −12.547 | 44.537 | 1.00 | 33.50 |
| 1004 | CA | VAL | C | 476 | −3.236 | −11.253 | 43.892 | 1.00 | 25.73 |
| 1005 | CB | VAL | C | 476 | −1.992 | −11.266 | 42.998 | 1.00 | 33.29 |
| 1006 | CG1 | VAL | C | 476 | −1.770 | −9.879 | 42.394 | 1.00 | 35.60 |
| 1007 | CG2 | VAL | C | 476 | −0.785 | −11.751 | 43.796 | 1.00 | 6.31 |
| 1008 | C | VAL | C | 476 | −4.426 | −10.872 | 43.022 | 1.00 | 39.25 |
| 1009 | O | VAL | C | 476 | −4.923 | −11.685 | 42.250 | 1.00 | 46.44 |
| 1010 | N | GLN | C | 477 | −4.865 | −9.623 | 43.131 | 1.00 | 41.11 |
| 1011 | CA | GLN | C | 477 | −6.005 | −9.175 | 42.363 | 1.00 | 32.37 |
| 1012 | CB | GLN | C | 477 | −7.267 | −9.132 | 43.227 | 1.00 | 39.60 |
| 1013 | CG | GLN | C | 477 | −7.405 | −10.251 | 44.220 | 1.00 | 53.17 |
| 1014 | CD | GLN | C | 477 | −8.705 | −10.173 | 44.957 | 1.00 | 76.60 |
| 1015 | OE1 | GLN | C | 477 | −9.050 | −9.131 | 45.535 | 1.00 | 58.03 |
| 1016 | NE2 | GLN | C | 477 | −9.450 | −11.273 | 44.943 | 1.00 | 76.40 |
| 1017 | C | GLN | C | 477 | −5.784 | −7.783 | 41.832 | 1.00 | 42.67 |
| 1018 | O | GLN | C | 477 | −5.103 | −6.957 | 42.453 | 1.00 | 37.40 |
| 1019 | N | TRP | C | 478 | −6.388 | −7.527 | 40.676 | 1.00 | 40.22 |
| 1020 | CA | TRP | C | 478 | −6.320 | −6.218 | 40.065 | 1.00 | 27.76 |
| 1021 | CB | TRP | C | 478 | −5.811 | −6.315 | 38.622 | 1.00 | 32.37 |
| 1022 | CG | TRP | C | 478 | −4.340 | −6.589 | 38.549 | 1.00 | 27.78 |
| 1023 | CD2 | TRP | C | 478 | −3.291 | −5.609 | 38.589 | 1.00 | 17.51 |
| 1024 | CE2 | TRP | C | 478 | −2.065 | −6.306 | 38.497 | 1.00 | 24.23 |
| 1025 | CE3 | TRP | C | 478 | −3.271 | −4.214 | 38.685 | 1.00 | 14.67 |
| 1026 | CD1 | TRP | C | 478 | −3.727 | −7.812 | 38.443 | 1.00 | 23.07 |
| 1027 | NE1 | TRP | C | 478 | −2.355 | −7.647 | 38.409 | 1.00 | 39.43 |
| 1028 | CZ2 | TRP | C | 478 | −0.831 | −5.651 | 38.500 | 1.00 | 22.15 |
| 1029 | CZ3 | TRP | C | 478 | −2.041 | −3.560 | 38.687 | 1.00 | 24.75 |
| 1030 | CH2 | TRP | C | 478 | −0.839 | −4.280 | 38.593 | 1.00 | 24.41 |
| 1031 | C | TRP | C | 478 | −7.721 | −5.636 | 40.115 | 1.00 | 37.47 |
| 1032 | O | TRP | C | 478 | −8.703 | −6.351 | 39.971 | 1.00 | 45.14 |
| 1033 | N | LEU | C | 479 | −7.812 | −4.342 | 40.357 | 1.00 | 28.88 |
| 1034 | CA | LEU | C | 479 | −9.089 | −3.691 | 40.413 | 1.00 | 22.53 |
| 1035 | CB | LEU | C | 479 | −9.477 | −3.369 | 41.857 | 1.00 | 51.20 |
| 1036 | CG | LEU | C | 479 | −9.972 | −4.478 | 42.800 | 1.00 | 50.73 |
| 1037 | CD1 | LEU | C | 479 | −8.859 | −5.468 | 43.103 | 1.00 | 55.84 |
| 1038 | CD2 | LEU | C | 479 | −10.479 | −3.826 | 44.090 | 1.00 | 57.36 |
| 1039 | C | LEU | C | 479 | −9.062 | −2.398 | 39.611 | 1.00 | 39.53 |
| 1040 | O | LEU | C | 479 | −8.082 | −1.662 | 39.642 | 1.00 | 31.68 |
| 1041 | N | HIS | C | 480 | −10.151 | −2.139 | 38.885 | 1.00 | 46.09 |
| 1042 | CA | HIS | C | 480 | −10.294 | −0.929 | 38.093 | 1.00 | 45.45 |
| 1043 | CB | HIS | C | 480 | −10.181 | −1.255 | 36.596 | 1.00 | 31.71 |
| 1044 | CG | HIS | C | 480 | −10.199 | −0.040 | 35.730 | 1.00 | 38.21 |
| 1045 | CD2 | HIS | C | 480 | −10.955 | 0.280 | 34.655 | 1.00 | 31.26 |
| 1046 | ND1 | HIS | C | 480 | −9.403 | 1.058 | 35.978 | 1.00 | 49.60 |
| 1047 | CE1 | HIS | C | 480 | −9.672 | 2.005 | 35.099 | 1.00 | 37.92 |
| 1048 | NE2 | HIS | C | 480 | −10.610 | 1.559 | 34.286 | 1.00 | 59.71 |
| 1049 | C | HIS | C | 480 | −11.656 | −0.303 | 38.447 | 1.00 | 60.40 |
| 1050 | O | HIS | C | 480 | −12.694 | −0.982 | 38.430 | 1.00 | 50.49 |
| 1051 | N | ASN | C | 481 | −11.630 | 0.987 | 38.789 | 1.00 | 70.75 |
| 1052 | CA | ASN | C | 481 | −12.827 | 1.730 | 39.203 | 1.00 | 81.01 |
| 1053 | CB | ASN | C | 481 | −14.038 | 1.352 | 38.331 | 1.00 | 68.58 |
| 1054 | CG | ASN | C | 481 | −14.090 | 2.130 | 37.028 | 1.00 | 63.32 |
| 1055 | OD1 | ASN | C | 481 | −14.252 | 3.353 | 37.029 | 1.00 | 59.96 |
| 1056 | ND2 | ASN | C | 481 | −13.950 | 1.427 | 35.913 | 1.00 | 68.24 |
| 1057 | C | ASN | C | 481 | −13.112 | 1.400 | 40.673 | 1.00 | 86.20 |
| 1058 | O | ASN | C | 481 | −13.256 | 2.294 | 41.524 | 1.00 | 90.52 |
| 1059 | N | GLU | C | 482 | −13.174 | 0.099 | 40.951 | 1.00 | 80.55 |
| 1060 | CA | GLU | C | 482 | −13.432 | −0.431 | 42.284 | 1.00 | 83.09 |
| 1061 | CB | GLU | C | 482 | −14.574 | 0.327 | 42.961 | 1.00 | 94.00 |
| 1062 | CG | GLU | C | 482 | −15.737 | 0.691 | 42.036 | 1.00 | 119.48 |
| 1063 | CD | GLU | C | 482 | −16.069 | −0.392 | 41.015 | 1.00 | 127.75 |
| 1064 | OE1 | GLU | C | 482 | −15.288 | −0.579 | 40.055 | 1.00 | 125.21 |
| 1065 | OE2 | GLU | C | 482 | −17.114 | −1.058 | 41.173 | 1.00 | 134.88 |
| 1066 | C | GLU | C | 482 | −13.818 | −1.890 | 42.138 | 1.00 | 69.49 |
| 1067 | O | GLU | C | 482 | −14.063 | −2.594 | 43.113 | 1.00 | 65.85 |
| 1068 | N | VAL | C | 483 | −13.854 | −2.340 | 40.900 | 1.00 | 57.56 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1069 | CA | VAL | C | 483 | −14.237 | −3.705 | 40.628 | 1.00 | 62.68 |
| 1070 | CB | VAL | C | 483 | −15.341 | −3.772 | 39.551 | 1.00 | 51.68 |
| 1071 | CG1 | VAL | C | 483 | −14.848 | −3.126 | 38.248 | 1.00 | 63.80 |
| 1072 | CG2 | VAL | C | 483 | −15.710 | −5.223 | 39.316 | 1.00 | 59.73 |
| 1073 | C | VAL | C | 483 | −13.085 | −4.600 | 40.179 | 1.00 | 56.56 |
| 1074 | O | VAL | C | 483 | −12.270 | −4.233 | 39.325 | 1.00 | 51.82 |
| 1075 | N | GLN | C | 484 | −13.067 | −5.793 | 40.753 | 1.00 | 34.45 |
| 1076 | CA | GLN | C | 484 | −12.078 | −6.805 | 40.475 | 1.00 | 46.35 |
| 1077 | CB | GLN | C | 484 | −12.302 | −7.931 | 41.474 | 1.00 | 42.18 |
| 1078 | CG | GLN | C | 484 | −11.525 | −9.190 | 41.250 | 1.00 | 65.22 |
| 1079 | CD | GLN | C | 484 | −11.729 | −10.152 | 42.388 | 1.00 | 69.01 |
| 1080 | OE1 | GLN | C | 484 | −11.513 | −11.354 | 42.246 | 1.00 | 80.68 |
| 1081 | NE2 | GLN | C | 484 | −12.149 | −9.623 | 43.541 | 1.00 | 75.07 |
| 1082 | C | GLN | C | 484 | −12.168 | −7.320 | 39.028 | 1.00 | 53.79 |
| 1083 | O | GLN | C | 484 | −13.209 | −7.821 | 38.604 | 1.00 | 65.57 |
| 1084 | N | LEU | C | 485 | −11.077 | −7.191 | 38.276 | 1.00 | 51.26 |
| 1085 | CA | LEU | C | 485 | −11.022 | −7.641 | 36.885 | 1.00 | 44.23 |
| 1086 | CB | LEU | C | 485 | −9.776 | −7.101 | 36.184 | 1.00 | 26.69 |
| 1087 | CG | LEU | C | 485 | −9.562 | −5.573 | 36.223 | 1.00 | 57.31 |
| 1088 | CD1 | LEU | C | 485 | −8.265 | −5.224 | 35.488 | 1.00 | 54.55 |
| 1089 | CD2 | LEU | C | 485 | −10.734 | −4.843 | 35.571 | 1.00 | 46.80 |
| 1090 | C | LEU | C | 485 | −10.987 | −9.154 | 36.801 | 1.00 | 51.39 |
| 1091 | O | LEU | C | 485 | −10.588 | −9.830 | 37.745 | 1.00 | 43.54 |
| 1092 | N | PRO | C | 486 | −11.396 | −9.709 | 35.651 | 1.00 | 60.91 |
| 1093 | CD | PRO | C | 486 | −11.819 | −9.043 | 34.409 | 1.00 | 42.07 |
| 1094 | CA | PRO | C | 486 | −11.389 | −11.168 | 35.503 | 1.00 | 49.14 |
| 1095 | CB | PRO | C | 486 | −11.750 | −11.371 | 34.038 | 1.00 | 44.80 |
| 1096 | CG | PRO | C | 486 | −12.556 | −10.140 | 33.717 | 1.00 | 45.92 |
| 1097 | C | PRO | C | 486 | −9.991 | −11.689 | 35.831 | 1.00 | 48.26 |
| 1098 | O | PRO | C | 486 | −8.992 | −11.130 | 35.408 | 1.00 | 45.07 |
| 1099 | N | ASP | C | 487 | −9.925 | −12.766 | 36.588 | 1.00 | 58.27 |
| 1100 | CA | ASP | C | 487 | −8.648 | −13.325 | 36.960 | 1.00 | 63.90 |
| 1101 | CB | ASP | C | 487 | −8.882 | −14.558 | 37.840 | 1.00 | 73.73 |
| 1102 | CG | ASP | C | 487 | −7.682 | −14.895 | 38.705 | 1.00 | 110.89 |
| 1103 | OD1 | ASP | C | 487 | −6.677 | −15.411 | 38.172 | 1.00 | 125.75 |
| 1104 | OD2 | ASP | C | 487 | −7.743 | −14.631 | 39.923 | 1.00 | 116.66 |
| 1105 | C | ASP | C | 487 | −7.771 | −13.677 | 35.742 | 1.00 | 66.13 |
| 1106 | O | ASP | C | 487 | −6.540 | −13.569 | 35.801 | 1.00 | 77.69 |
| 1107 | N | ALA | C | 488 | −8.392 | −14.079 | 34.637 | 1.00 | 57.68 |
| 1108 | CA | ALA | C | 488 | −7.637 | −14.466 | 33.442 | 1.00 | 55.14 |
| 1109 | CB | ALA | C | 488 | −8.534 | −15.254 | 32.496 | 1.00 | 60.39 |
| 1110 | C | ALA | C | 488 | −6.989 | −13.305 | 32.693 | 1.00 | 46.91 |
| 1111 | O | ALA | C | 488 | −6.302 | −13.520 | 31.696 | 1.00 | 51.13 |
| 1112 | N | ARG | C | 489 | −7.224 | −12.082 | 33.168 | 1.00 | 46.61 |
| 1113 | CA | ARG | C | 489 | −6.648 | −10.889 | 32.551 | 1.00 | 50.85 |
| 1114 | CB | ARG | C | 489 | −7.496 | −9.668 | 32.890 | 1.00 | 58.08 |
| 1115 | CG | ARG | C | 489 | −8.595 | −9.407 | 31.891 | 1.00 | 45.22 |
| 1116 | CD | ARG | C | 489 | −8.188 | −8.335 | 30.882 | 1.00 | 24.73 |
| 1117 | NE | ARG | C | 489 | −8.600 | −6.985 | 31.281 | 1.00 | 27.75 |
| 1118 | CZ | ARG | C | 489 | −7.890 | −5.898 | 31.009 | 1.00 | 33.98 |
| 1119 | NH1 | ARG | C | 489 | −6.741 | −6.030 | 30.358 | 1.00 | 67.36 |
| 1120 | NH2 | ARG | C | 489 | −8.330 | −4.684 | 31.352 | 1.00 | 53.20 |
| 1121 | C | ARG | C | 489 | −5.189 | −10.633 | 32.974 | 1.00 | 60.81 |
| 1122 | O | ARG | C | 489 | −4.405 | −10.072 | 32.205 | 1.00 | 62.59 |
| 1123 | N | HIS | C | 490 | −4.825 | −11.049 | 34.186 | 1.00 | 49.48 |
| 1124 | CA | HIS | C | 490 | −3.473 | −10.841 | 34.689 | 1.00 | 30.05 |
| 1125 | CB | HIS | C | 490 | −3.518 | −10.151 | 36.048 | 1.00 | 53.53 |
| 1126 | CG | HIS | C | 490 | −3.983 | −11.036 | 37.167 | 1.00 | 46.29 |
| 1127 | CD2 | HIS | C | 490 | −5.066 | −10.957 | 37.979 | 1.00 | 53.43 |
| 1128 | ND1 | HIS | C | 490 | −3.288 | −12.157 | 37.566 | 1.00 | 50.42 |
| 1129 | CE1 | HIS | C | 490 | −3.918 | −12.731 | 38.574 | 1.00 | 38.46 |
| 1130 | NE2 | HIS | C | 490 | −5.001 | −12.024 | 38.845 | 1.00 | 64.21 |
| 1131 | C | HIS | C | 490 | −2.715 | −12.146 | 34.824 | 1.00 | 41.80 |
| 1132 | O | HIS | C | 490 | −3.311 | −13.233 | 34.856 | 1.00 | 51.94 |
| 1133 | N | SER | C | 491 | −1.394 | −12.034 | 34.903 | 1.00 | 35.13 |
| 1134 | CA | SER | C | 491 | −0.526 | −13.199 | 35.049 | 1.00 | 37.68 |
| 1135 | CB | SER | C | 491 | 0.392 | −13.330 | 33.829 | 1.00 | 30.84 |
| 1136 | OG | SER | C | 491 | 1.056 | −14.585 | 33.822 | 1.00 | 35.78 |
| 1137 | C | SER | C | 491 | 0.319 | −13.057 | 36.329 | 1.00 | 42.71 |
| 1138 | O | SER | C | 491 | 0.913 | −12.001 | 36.568 | 1.00 | 48.12 |
| 1139 | N | THR | C | 492 | 0.370 | −14.116 | 37.143 | 1.00 | 34.23 |
| 1140 | CA | THR | C | 492 | 1.137 | −14.075 | 38.385 | 1.00 | 30.50 |
| 1141 | CB | THR | C | 492 | 0.202 | −14.049 | 39.602 | 1.00 | 31.71 |
| 1142 | OG1 | THR | C | 492 | −0.570 | −12.848 | 39.570 | 1.00 | 51.89 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1143 | CG2 | THR | C | 492 | 0.996 | −14.096 | 40.902 | 1.00 | 41.58 |
| 1144 | C | THR | C | 492 | 2.127 | −15.220 | 38.549 | 1.00 | 26.80 |
| 1145 | O | THR | C | 492 | 1.783 | −16.383 | 38.390 | 1.00 | 38.36 |
| 1146 | N | THR | C | 493 | 3.359 | −14.865 | 38.906 | 1.00 | 35.17 |
| 1147 | CA | THR | C | 493 | 4.467 | −15.809 | 39.099 | 1.00 | 27.22 |
| 1148 | CB | THR | C | 493 | 5.809 | −15.058 | 39.252 | 1.00 | 28.39 |
| 1149 | OG1 | THR | C | 493 | 5.769 | −14.240 | 40.437 | 1.00 | 45.13 |
| 1150 | CG2 | THR | C | 493 | 6.071 | −14.172 | 38.054 | 1.00 | 21.25 |
| 1151 | C | THR | C | 493 | 4.324 | −16.718 | 40.315 | 1.00 | 27.69 |
| 1152 | O | THR | C | 493 | 3.606 | −16.417 | 41.250 | 1.00 | 32.47 |
| 1153 | N | GLN | C | 494 | 5.014 | −17.842 | 40.277 | 1.00 | 38.59 |
| 1154 | CA | GLN | C | 494 | 5.002 | −18.770 | 41.393 | 1.00 | 54.12 |
| 1155 | CB | GLN | C | 494 | 5.598 | −20.115 | 40.966 | 1.00 | 71.41 |
| 1156 | CG | GLN | C | 494 | 4.831 | −20.812 | 39.851 | 1.00 | 92.48 |
| 1157 | CD | GLN | C | 494 | 3.442 | −21.261 | 40.293 | 1.00 | 105.33 |
| 1158 | OE1 | GLN | C | 494 | 3.304 | −22.112 | 41.172 | 1.00 | 112.12 |
| 1159 | NE2 | GLN | C | 494 | 2.407 | −20.687 | 39.684 | 1.00 | 110.63 |
| 1160 | C | GLN | C | 494 | 5.877 | −18.146 | 42.489 | 1.00 | 59.07 |
| 1161 | O | GLN | C | 494 | 6.864 | −17.454 | 42.188 | 1.00 | 50.93 |
| 1162 | N | PRO | C | 495 | 5.519 | −18.364 | 43.770 | 1.00 | 51.34 |
| 1163 | CD | PRO | C | 495 | 4.259 | −18.962 | 44.245 | 1.00 | 57.62 |
| 1164 | CA | PRO | C | 495 | 6.279 | −17.820 | 44.895 | 1.00 | 45.25 |
| 1165 | CB | PRO | C | 495 | 5.533 | −18.367 | 46.102 | 1.00 | 45.66 |
| 1166 | CG | PRO | C | 495 | 4.123 | −18.361 | 45.625 | 1.00 | 37.24 |
| 1167 | C | PRO | C | 495 | 7.729 | −18.260 | 44.870 | 1.00 | 47.61 |
| 1168 | O | PRO | C | 495 | 8.034 | −19.399 | 44.558 | 1.00 | 55.72 |
| 1169 | N | ARG | C | 496 | 8.621 | −17.337 | 45.198 | 1.00 | 55.10 |
| 1170 | CA | ARG | C | 496 | 10.048 | −17.612 | 45.223 | 1.00 | 53.58 |
| 1171 | CB | ARG | C | 496 | 10.704 | −17.076 | 43.961 | 1.00 | 45.73 |
| 1172 | CG | ARG | C | 496 | 10.587 | −17.955 | 42.753 | 1.00 | 39.15 |
| 1173 | CD | ARG | C | 496 | 11.587 | −17.427 | 41.730 | 1.00 | 76.88 |
| 1174 | NE | ARG | C | 496 | 11.931 | −18.397 | 40.697 | 1.00 | 89.37 |
| 1175 | CZ | ARG | C | 496 | 13.114 | −18.446 | 40.091 | 1.00 | 80.00 |
| 1176 | NH1 | ARG | C | 496 | 14.067 | −17.581 | 40.418 | 1.00 | 71.96 |
| 1177 | NH2 | ARG | C | 496 | 13.347 | −19.361 | 39.161 | 1.00 | 82.40 |
| 1178 | C | ARG | C | 496 | 10.691 | −16.945 | 46.441 | 1.00 | 69.59 |
| 1179 | O | ARG | C | 496 | 10.214 | −15.907 | 46.914 | 1.00 | 64.25 |
| 1180 | N | LYS | C | 497 | 11.786 | −17.532 | 46.920 | 1.00 | 63.36 |
| 1181 | CA | LYS | C | 497 | 12.502 | −17.028 | 48.087 | 1.00 | 62.80 |
| 1182 | CB | LYS | C | 497 | 13.454 | −18.095 | 48.623 | 1.00 | 66.07 |
| 1183 | CG | LYS | C | 497 | 12.785 | −19.409 | 48.966 | 1.00 | 75.76 |
| 1184 | CD | LYS | C | 497 | 13.822 | −20.475 | 49.267 | 1.00 | 95.13 |
| 1185 | CE | LYS | C | 497 | 13.165 | −21.828 | 49.497 | 1.00 | 100.34 |
| 1186 | NZ | LYS | C | 497 | 14.174 | −22.884 | 49.778 | 1.00 | 105.51 |
| 1187 | C | LYS | C | 497 | 13.291 | −15.776 | 47.782 | 1.00 | 63.64 |
| 1188 | O | LYS | C | 497 | 14.046 | −15.734 | 46.821 | 1.00 | 59.40 |
| 1189 | N | THR | C | 498 | 13.115 | −14.759 | 48.613 | 1.00 | 66.72 |
| 1190 | CA | THR | C | 498 | 13.815 | −13.497 | 48.440 | 1.00 | 77.51 |
| 1191 | CB | THR | C | 498 | 13.150 | −12.377 | 49.269 | 1.00 | 81.21 |
| 1192 | OG1 | THR | C | 498 | 13.253 | −12.680 | 50.665 | 1.00 | 87.58 |
| 1193 | CG2 | THR | C | 498 | 11.684 | −12.252 | 48.907 | 1.00 | 77.79 |
| 1194 | C | THR | C | 498 | 15.258 | −13.651 | 48.897 | 1.00 | 90.68 |
| 1195 | O | THR | C | 498 | 16.177 | −13.735 | 48.079 | 1.00 | 99.21 |
| 1196 | N | LYS | C | 499 | 15.431 | −13.690 | 50.216 | 1.00 | 98.37 |
| 1197 | CA | LYS | C | 499 | 16.729 | −13.833 | 50.874 | 1.00 | 101.06 |
| 1198 | CB | LYS | C | 499 | 17.716 | −12.758 | 50.395 | 1.00 | 89.87 |
| 1199 | CG | LYS | C | 499 | 18.588 | −13.185 | 49.218 | 1.00 | 99.86 |
| 1200 | CD | LYS | C | 499 | 19.415 | −14.415 | 49.578 | 1.00 | 109.58 |
| 1201 | CE | LYS | C | 499 | 20.296 | −14.863 | 48.422 | 1.00 | 108.04 |
| 1202 | NZ | LYS | C | 499 | 21.106 | −16.065 | 48.776 | 1.00 | 97.35 |
| 1203 | C | LYS | C | 499 | 16.525 | −13.696 | 52.380 | 1.00 | 100.07 |
| 1204 | O | LYS | C | 499 | 16.934 | −12.703 | 52.980 | 1.00 | 93.63 |
| 1205 | N | GLY | C | 500 | 15.872 | −14.690 | 52.978 | 1.00 | 103.12 |
| 1206 | CA | GLY | C | 500 | 15.624 | −14.668 | 54.411 | 1.00 | 102.51 |
| 1207 | C | GLY | C | 500 | 14.276 | −14.097 | 54.822 | 1.00 | 103.54 |
| 1208 | O | GLY | C | 500 | 13.500 | −14.752 | 55.526 | 1.00 | 92.86 |
| 1209 | N | SER | C | 501 | 13.998 | −12.874 | 54.378 | 1.00 | 103.54 |
| 1210 | CA | SER | C | 501 | 12.746 | −12.192 | 54.707 | 1.00 | 104.72 |
| 1211 | CB | SER | C | 501 | 12.726 | −10.795 | 54.075 | 1.00 | 106.33 |
| 1212 | OG | SER | C | 501 | 12.746 | −10.884 | 52.661 | 1.00 | 121.02 |
| 1213 | C | SER | C | 501 | 11.480 | −12.949 | 54.290 | 1.00 | 100.78 |
| 1214 | O | SER | C | 501 | 10.401 | −12.707 | 54.848 | 1.00 | 102.21 |
| 1215 | N | GLY | C | 502 | 11.605 | −13.849 | 53.314 | 1.00 | 84.75 |
| 1216 | CA | GLY | C | 502 | 10.445 | −14.604 | 52.875 | 1.00 | 71.84 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1217 | C | GLY | C | 502 | 10.340 | −14.841 | 51.376 | 1.00 | 59.02 |
| 1218 | O | GLY | C | 502 | 11.293 | −15.274 | 50.739 | 1.00 | 57.77 |
| 1219 | N | PHE | C | 503 | 9.170 | −14.572 | 50.810 | 1.00 | 45.23 |
| 1220 | CA | PHE | C | 503 | 8.956 | −14.778 | 49.380 | 1.00 | 46.72 |
| 1221 | CB | PHE | C | 503 | 7.865 | −15.820 | 49.128 | 1.00 | 29.80 |
| 1222 | CG | PHE | C | 503 | 8.076 | −17.115 | 49.839 | 1.00 | 37.49 |
| 1223 | CD1 | PHE | C | 503 | 7.758 | −17.236 | 51.191 | 1.00 | 39.73 |
| 1224 | CD2 | PHE | C | 503 | 8.577 | −18.230 | 49.156 | 1.00 | 36.19 |
| 1225 | CE1 | PHE | C | 503 | 7.931 | −18.449 | 51.871 | 1.00 | 33.87 |
| 1226 | CE2 | PHE | C | 503 | 8.756 | −19.454 | 49.821 | 1.00 | 56.36 |
| 1227 | CZ | PHE | C | 503 | 8.428 | −19.565 | 51.194 | 1.00 | 30.53 |
| 1228 | C | PHE | C | 503 | 8.553 | −13.525 | 48.610 | 1.00 | 45.18 |
| 1229 | O | PHE | C | 503 | 8.255 | −12.459 | 49.182 | 1.00 | 43.56 |
| 1230 | N | PHE | C | 504 | 8.550 | −13.663 | 47.293 | 1.00 | 29.66 |
| 1231 | CA | PHE | C | 504 | 8.132 | −12.561 | 46.452 | 1.00 | 41.99 |
| 1232 | CB | PHE | C | 504 | 9.324 | −11.731 | 45.970 | 1.00 | 44.16 |
| 1233 | CG | PHE | C | 504 | 10.100 | −12.354 | 44.849 | 1.00 | 50.05 |
| 1234 | CD1 | PHE | C | 504 | 9.690 | −12.192 | 43.527 | 1.00 | 42.22 |
| 1235 | CD2 | PHE | C | 504 | 11.260 | −13.078 | 45.110 | 1.00 | 51.23 |
| 1236 | CE1 | PHE | C | 504 | 10.431 | −12.743 | 42.479 | 1.00 | 42.51 |
| 1237 | CE2 | PHE | C | 504 | 12.008 | −13.632 | 44.080 | 1.00 | 48.52 |
| 1238 | CZ | PHE | C | 504 | 11.596 | −13.465 | 42.758 | 1.00 | 58.54 |
| 1239 | C | PHE | C | 504 | 7.363 | −13.111 | 45.280 | 1.00 | 38.70 |
| 1240 | O | PHE | C | 504 | 7.515 | −14.280 | 44.902 | 1.00 | 34.91 |
| 1241 | N | VAL | C | 505 | 6.524 | −12.258 | 44.724 | 1.00 | 32.68 |
| 1242 | CA | VAL | C | 505 | 5.704 | −12.629 | 43.592 | 1.00 | 18.34 |
| 1243 | CB | VAL | C | 505 | 4.307 | −13.142 | 44.098 | 1.00 | 28.77 |
| 1244 | CG1 | VAL | C | 505 | 3.197 | −12.352 | 43.500 | 1.00 | 37.24 |
| 1245 | CG2 | VAL | C | 505 | 4.147 | −14.625 | 43.802 | 1.00 | 38.26 |
| 1246 | C | VAL | C | 505 | 5.582 | −11.429 | 42.642 | 1.00 | 33.36 |
| 1247 | O | VAL | C | 505 | 5.612 | −10.260 | 43.049 | 1.00 | 32.27 |
| 1248 | N | PHE | C | 506 | 5.488 | −11.723 | 41.360 | 1.00 | 29.48 |
| 1249 | CA | PHE | C | 506 | 5.348 | −10.670 | 40.367 | 1.00 | 37.09 |
| 1250 | CB | PHE | C | 506 | 6.543 | −10.720 | 39.406 | 1.00 | 33.80 |
| 1251 | CG | PHE | C | 506 | 6.447 | −9.776 | 38.224 | 1.00 | 91.20 |
| 1252 | CD1 | PHE | C | 506 | 6.434 | −8.398 | 38.403 | 1.00 | 92.39 |
| 1253 | CD2 | PHE | C | 506 | 6.484 | −10.278 | 36.912 | 1.00 | 87.89 |
| 1254 | CE1 | PHE | C | 506 | 6.474 | −7.533 | 37.280 | 1.00 | 99.43 |
| 1255 | CE2 | PHE | C | 506 | 6.526 | −9.424 | 35.788 | 1.00 | 30.51 |
| 1256 | CZ | PHE | C | 506 | 6.524 | −8.055 | 35.974 | 1.00 | 55.18 |
| 1257 | C | PHE | C | 506 | 4.028 | −10.892 | 39.628 | 1.00 | 36.18 |
| 1258 | O | PHE | C | 506 | 3.613 | −12.025 | 39.407 | 1.00 | 46.44 |
| 1259 | N | SER | C | 507 | 3.347 | −9.813 | 39.278 | 1.00 | 37.67 |
| 1260 | CA | SER | C | 507 | 2.077 | −9.939 | 38.566 | 1.00 | 37.21 |
| 1261 | CB | SER | C | 507 | 0.890 | −9.688 | 39.512 | 1.00 | 49.60 |
| 1262 | OG | SER | C | 507 | −0.345 | −9.894 | 38.848 | 1.00 | 38.51 |
| 1263 | C | SER | C | 507 | 2.002 | −8.971 | 37.388 | 1.00 | 39.50 |
| 1264 | O | SER | C | 507 | 2.290 | −7.771 | 37.512 | 1.00 | 44.36 |
| 1265 | N | ARG | C | 508 | 1.596 | −9.507 | 36.249 | 1.00 | 31.56 |
| 1266 | CA | ARG | C | 508 | 1.480 | −8.713 | 35.027 | 1.00 | 35.50 |
| 1267 | CB | ARG | C | 508 | 2.302 | −9.385 | 33.943 | 1.00 | 27.27 |
| 1268 | CG | ARG | C | 508 | 2.445 | −8.599 | 32.667 | 1.00 | 20.60 |
| 1269 | CD | ARG | C | 508 | 3.446 | −9.310 | 31.772 | 1.00 | 45.09 |
| 1270 | NE | ARG | C | 508 | 3.394 | −8.768 | 30.429 | 1.00 | 45.29 |
| 1271 | CZ | ARG | C | 508 | 2.469 | −9.094 | 29.539 | 1.00 | 50.30 |
| 1272 | NH1 | ARG | C | 508 | 1.524 | −9.973 | 29.856 | 1.00 | 51.15 |
| 1273 | NH2 | ARG | C | 508 | 2.480 | −8.531 | 28.342 | 1.00 | 56.65 |
| 1274 | C | ARG | C | 508 | 0.039 | −8.514 | 34.527 | 1.00 | 36.69 |
| 1275 | O | ARG | C | 508 | −0.765 | −9.454 | 34.492 | 1.00 | 38.55 |
| 1276 | N | LEU | C | 509 | −0.277 | −7.284 | 34.142 | 1.00 | 32.62 |
| 1277 | CA | LEU | C | 509 | −1.611 | −6.940 | 33.635 | 1.00 | 19.57 |
| 1278 | CB | LEU | C | 509 | −2.450 | −6.277 | 34.732 | 1.00 | 36.17 |
| 1279 | CG | LEU | C | 509 | −3.820 | −5.820 | 34.224 | 1.00 | 25.97 |
| 1280 | CD1 | LEU | C | 509 | −4.708 | −7.014 | 34.109 | 1.00 | 27.00 |
| 1281 | CD2 | LEU | C | 509 | −4.417 | −4.774 | 35.171 | 1.00 | 35.53 |
| 1282 | C | LEU | C | 509 | −1.578 | −5.990 | 32.452 | 1.00 | 36.00 |
| 1283 | O | LEU | C | 509 | −1.268 | −4.805 | 32.607 | 1.00 | 38.03 |
| 1284 | N | GLU | C | 510 | −1.923 | −6.496 | 31.274 | 1.00 | 38.10 |
| 1285 | CA | GLU | C | 510 | −1.956 | −5.640 | 30.081 | 1.00 | 38.59 |
| 1286 | CB | GLU | C | 510 | −1.903 | −6.490 | 28.812 | 1.00 | 56.18 |
| 1287 | CG | GLU | C | 510 | −1.021 | −7.724 | 28.909 | 1.00 | 82.07 |
| 1288 | CD | GLU | C | 510 | −0.908 | −8.461 | 27.581 | 1.00 | 84.71 |
| 1289 | OE1 | GLU | C | 510 | −0.369 | −9.594 | 27.555 | 1.00 | 81.91 |
| 1290 | OE2 | GLU | C | 510 | −1.356 | −7.899 | 26.558 | 1.00 | 84.35 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1291 | C | GLU | C | 510 | −3.265 | −4.820 | 30.082 | 1.00 | 41.12 |
| 1292 | O | GLU | C | 510 | −4.338 | −5.395 | 30.194 | 1.00 | 40.16 |
| 1293 | N | VAL | C | 511 | −3.177 | −3.496 | 29.964 | 1.00 | 27.51 |
| 1294 | CA | VAL | C | 511 | −4.369 | −2.668 | 29.956 | 1.00 | 37.08 |
| 1295 | CB | VAL | C | 511 | −4.369 | −1.712 | 31.167 | 1.00 | 44.46 |
| 1296 | CG1 | VAL | C | 511 | −4.255 | −2.534 | 32.429 | 1.00 | 36.42 |
| 1297 | CG2 | VAL | C | 511 | −3.232 | −0.730 | 31.086 | 1.00 | 23.03 |
| 1298 | C | VAL | C | 511 | −4.503 | −1.890 | 28.638 | 1.00 | 49.07 |
| 1299 | O | VAL | C | 511 | −3.505 | −1.697 | 27.937 | 1.00 | 44.47 |
| 1300 | N | THR | C | 512 | −5.726 | −1.437 | 28.320 | 1.00 | 57.05 |
| 1301 | CA | THR | C | 512 | −6.010 | −0.739 | 27.055 | 1.00 | 51.62 |
| 1302 | CB | THR | C | 512 | −7.154 | −1.407 | 26.319 | 1.00 | 35.18 |
| 1303 | OG1 | THR | C | 512 | −8.357 | −1.221 | 27.064 | 1.00 | 49.09 |
| 1304 | CG2 | THR | C | 512 | −6.898 | −2.885 | 26.163 | 1.00 | 57.68 |
| 1305 | C | THR | C | 512 | −6.339 | 0.750 | 27.078 | 1.00 | 52.89 |
| 1306 | O | THR | C | 512 | −6.967 | 1.248 | 28.013 | 1.00 | 54.63 |
| 1307 | N | ARG | C | 513 | −5.936 | 1.439 | 26.006 | 1.00 | 58.94 |
| 1308 | CA | ARG | C | 513 | −6.146 | 2.884 | 25.837 | 1.00 | 60.88 |
| 1309 | CB | ARG | C | 513 | −6.196 | 3.240 | 24.345 | 1.00 | 72.13 |
| 1310 | CG | ARG | C | 513 | −5.214 | 4.324 | 23.903 | 1.00 | 87.22 |
| 1311 | CD | ARG | C | 513 | −5.526 | 5.681 | 24.514 | 1.00 | 86.32 |
| 1312 | NE | ARG | C | 513 | −4.422 | 6.621 | 24.312 | 1.00 | 92.54 |
| 1313 | CZ | ARG | C | 513 | −4.343 | 7.825 | 24.879 | 1.00 | 97.85 |
| 1314 | NH1 | ARG | C | 513 | −5.308 | 8.252 | 25.686 | 1.00 | 96.89 |
| 1315 | NH2 | ARG | C | 513 | −3.289 | 8.596 | 24.655 | 1.00 | 93.80 |
| 1316 | C | ARG | C | 513 | −7.424 | 3.370 | 26.500 | 1.00 | 68.41 |
| 1317 | O | ARG | C | 513 | −7.415 | 4.377 | 27.212 | 1.00 | 69.19 |
| 1318 | N | ALA | C | 514 | −8.515 | 2.643 | 26.255 | 1.00 | 69.65 |
| 1319 | CA | ALA | C | 514 | −9.834 | 2.972 | 26.795 | 1.00 | 68.57 |
| 1320 | CB | ALA | C | 514 | −10.743 | 1.736 | 26.743 | 1.00 | 57.45 |
| 1321 | C | ALA | C | 514 | −9.751 | 3.512 | 28.225 | 1.00 | 83.59 |
| 1322 | O | ALA | C | 514 | −9.696 | 4.736 | 28.440 | 1.00 | 83.31 |
| 1323 | N | GLU | C | 515 | −9.741 | 2.601 | 29.198 | 1.00 | 79.27 |
| 1324 | CA | GLU | C | 515 | −9.655 | 3.001 | 30.596 | 1.00 | 58.46 |
| 1325 | CB | GLU | C | 515 | −9.871 | 1.812 | 31.519 | 1.00 | 41.35 |
| 1326 | CG | GLU | C | 515 | −8.894 | 0.696 | 31.344 | 1.00 | 64.74 |
| 1327 | CD | GLU | C | 515 | −9.346 | −0.294 | 30.312 | 1.00 | 74.66 |
| 1328 | OE1 | GLU | C | 515 | −9.771 | 0.171 | 29.231 | 1.00 | 63.45 |
| 1329 | OE2 | GLU | C | 515 | −9.270 | −1.525 | 30.576 | 1.00 | 67.64 |
| 1330 | C | GLU | C | 515 | −8.295 | 3.603 | 30.863 | 1.00 | 60.09 |
| 1331 | O | GLU | C | 515 | −8.145 | 4.392 | 31.783 | 1.00 | 58.24 |
| 1332 | N | TRP | C | 516 | −7.319 | 3.224 | 30.037 | 1.00 | 73.21 |
| 1333 | CA | TRP | C | 516 | −5.935 | 3.707 | 30.107 | 1.00 | 80.32 |
| 1334 | CB | TRP | C | 516 | −5.142 | 3.121 | 28.931 | 1.00 | 90.49 |
| 1335 | CG | TRP | C | 516 | −3.667 | 3.371 | 28.951 | 1.00 | 113.16 |
| 1336 | CD2 | TRP | C | 516 | −2.849 | 3.795 | 27.850 | 1.00 | 120.04 |
| 1337 | CE2 | TRP | C | 516 | −1.513 | 3.863 | 28.321 | 1.00 | 132.81 |
| 1338 | CE3 | TRP | C | 516 | −3.112 | 4.122 | 26.514 | 1.00 | 115.46 |
| 1339 | CD1 | TRP | C | 516 | −2.820 | 3.203 | 30.011 | 1.00 | 124.82 |
| 1340 | NE1 | TRP | C | 516 | −1.525 | 3.496 | 29.642 | 1.00 | 124.80 |
| 1341 | CZ2 | TRP | C | 516 | −0.440 | 4.249 | 27.499 | 1.00 | 128.02 |
| 1342 | CZ3 | TRP | C | 516 | −2.044 | 4.505 | 25.693 | 1.00 | 127.82 |
| 1343 | CH2 | TRP | C | 516 | −0.725 | 4.564 | 26.193 | 1.00 | 126.25 |
| 1344 | C | TRP | C | 516 | −5.931 | 5.233 | 30.035 | 1.00 | 90.02 |
| 1345 | O | TRP | C | 516 | −4.946 | 5.854 | 29.613 | 1.00 | 63.02 |
| 1346 | N | GLU | C | 517 | −7.061 | 5.813 | 30.445 | 1.00 | 86.75 |
| 1347 | CA | GLU | C | 517 | −7.296 | 7.256 | 30.466 | 1.00 | 93.85 |
| 1348 | CB | GLU | C | 517 | −8.232 | 7.641 | 29.315 | 1.00 | 94.81 |
| 1349 | CG | GLU | C | 517 | −7.614 | 7.339 | 27.951 | 1.00 | 110.76 |
| 1350 | CD | GLU | C | 517 | −8.384 | 7.935 | 26.785 | 1.00 | 115.39 |
| 1351 | OE1 | GLU | C | 517 | −9.516 | 7.476 | 26.519 | 1.00 | 119.26 |
| 1352 | OE2 | GLU | C | 517 | −7.851 | 8.863 | 26.135 | 1.00 | 111.45 |
| 1353 | C | GLU | C | 517 | −7.889 | 7.679 | 31.814 | 1.00 | 90.47 |
| 1354 | O | GLU | C | 517 | −8.072 | 8.872 | 32.082 | 1.00 | 85.79 |
| 1355 | N | ALA | C | 518 | −8.188 | 6.677 | 32.642 | 1.00 | 90.19 |
| 1356 | CA | ALA | C | 518 | −8.730 | 6.846 | 34.000 | 1.00 | 84.71 |
| 1357 | CB | ALA | C | 518 | −10.230 | 6.487 | 34.044 | 1.00 | 84.55 |
| 1358 | C | ALA | C | 518 | −7.927 | 5.841 | 34.821 | 1.00 | 78.01 |
| 1359 | O | ALA | C | 518 | −8.474 | 4.878 | 35.363 | 1.00 | 45.44 |
| 1360 | N | LYS | C | 519 | −6.620 | 6.077 | 34.885 | 1.00 | 79.45 |
| 1361 | CA | LYS | C | 519 | −5.696 | 5.187 | 35.574 | 1.00 | 81.29 |
| 1362 | CB | LYS | C | 519 | −4.253 | 5.527 | 35.207 | 1.00 | 83.32 |
| 1363 | CG | LYS | C | 519 | −3.843 | 5.176 | 33.794 | 1.00 | 93.13 |
| 1364 | CD | LYS | C | 519 | −2.344 | 4.888 | 33.744 | 1.00 | 95.43 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1365 | CE | LYS | C | 519 | −1.786 | 5.027 | 32.353 | 1.00 | 85.54 |
| 1366 | NZ | LYS | C | 519 | −0.325 | 5.170 | 32.392 | 1.00 | 76.75 |
| 1367 | C | LYS | C | 519 | −5.793 | 5.129 | 37.087 | 1.00 | 78.11 |
| 1368 | O | LYS | C | 519 | −5.808 | 4.031 | 37.671 | 1.00 | 66.44 |
| 1369 | N | ASP | C | 520 | −5.818 | 6.302 | 37.717 | 1.00 | 65.18 |
| 1370 | CA | ASP | C | 520 | −5.899 | 6.405 | 39.175 | 1.00 | 92.72 |
| 1371 | CB | ASP | C | 520 | −6.581 | 7.727 | 39.557 | 1.00 | 96.88 |
| 1372 | CG | ASP | C | 520 | −5.859 | 8.945 | 38.989 | 1.00 | 106.91 |
| 1373 | OD1 | ASP | C | 520 | −4.738 | 9.252 | 39.452 | 1.00 | 112.22 |
| 1374 | OD2 | ASP | C | 520 | −6.412 | 9.591 | 38.070 | 1.00 | 107.03 |
| 1375 | C | ASP | C | 520 | −6.664 | 5.214 | 39.774 | 1.00 | 88.34 |
| 1376 | O | ASP | C | 520 | −6.608 | 4.943 | 40.988 | 1.00 | 63.69 |
| 1377 | N | GLU | C | 521 | −7.386 | 4.519 | 38.898 | 1.00 | 77.60 |
| 1378 | CA | GLU | C | 521 | −8.160 | 3.353 | 39.263 | 1.00 | 87.50 |
| 1379 | CB | GLU | C | 521 | −9.560 | 3.393 | 38.611 | 1.00 | 91.07 |
| 1380 | CG | GLU | C | 521 | −10.598 | 4.349 | 39.266 | 1.00 | 87.20 |
| 1381 | CD | GLU | C | 521 | −10.686 | 5.730 | 38.600 | 1.00 | 89.62 |
| 1382 | OE1 | GLU | C | 521 | −10.844 | 5.797 | 37.352 | 1.00 | 81.69 |
| 1383 | OE2 | GLU | C | 521 | −10.611 | 6.744 | 39.334 | 1.00 | 73.98 |
| 1384 | C | GLU | C | 521 | −7.455 | 2.041 | 38.898 | 1.00 | 80.88 |
| 1385 | O | GLU | C | 521 | −8.115 | 1.083 | 38.490 | 1.00 | 100.96 |
| 1386 | N | PHE | C | 522 | −6.126 | 1.992 | 39.018 | 1.00 | 56.95 |
| 1387 | CA | PHE | C | 522 | −5.412 | 0.728 | 38.771 | 1.00 | 51.18 |
| 1388 | CB | PHE | C | 522 | −4.371 | 0.891 | 37.671 | 1.00 | 56.33 |
| 1389 | CG | PHE | C | 522 | −4.971 | 0.827 | 36.299 | 1.00 | 65.58 |
| 1390 | CD1 | PHE | C | 522 | −4.987 | 1.947 | 35.468 | 1.00 | 40.14 |
| 1391 | CD2 | PHE | C | 522 | −5.592 | −0.351 | 35.861 | 1.00 | 53.56 |
| 1392 | CE1 | PHE | C | 522 | −5.609 | 1.898 | 34.237 | 1.00 | 45.12 |
| 1393 | CE2 | PHE | C | 522 | −6.221 | −0.414 | 34.621 | 1.00 | 38.73 |
| 1394 | CZ | PHE | C | 522 | −6.229 | 0.715 | 33.809 | 1.00 | 48.60 |
| 1395 | C | PHE | C | 522 | −4.798 | 0.218 | 40.091 | 1.00 | 52.84 |
| 1396 | O | PHE | C | 522 | −3.785 | 0.735 | 40.595 | 1.00 | 49.62 |
| 1397 | N | ILE | C | 523 | −5.436 | −0.807 | 40.651 | 1.00 | 38.42 |
| 1398 | CA | ILE | C | 523 | −5.032 | −1.337 | 41.928 | 1.00 | 15.86 |
| 1399 | CB | ILE | C | 523 | −6.187 | −1.182 | 42.956 | 1.00 | 44.64 |
| 1400 | CG2 | ILE | C | 523 | −5.835 | −1.883 | 44.272 | 1.00 | 47.67 |
| 1401 | CG1 | ILE | C | 523 | −6.481 | 0.304 | 43.204 | 1.00 | 45.28 |
| 1402 | CD1 | ILE | C | 523 | −7.475 | 0.542 | 44.355 | 1.00 | 25.99 |
| 1403 | C | ILE | C | 523 | −4.581 | −2.773 | 41.946 | 1.00 | 31.06 |
| 1404 | O | ILE | C | 523 | −5.252 | −3.664 | 41.454 | 1.00 | 39.92 |
| 1405 | N | CYS | C | 524 | −3.417 | −2.980 | 42.548 | 1.00 | 41.16 |
| 1406 | CA | CYS | C | 524 | −2.858 | −4.302 | 42.722 | 1.00 | 32.54 |
| 1407 | C | CYS | C | 524 | −3.045 | −4.603 | 44.196 | 1.00 | 38.99 |
| 1408 | O | CYS | C | 524 | −2.471 | −3.933 | 45.043 | 1.00 | 42.91 |
| 1409 | CB | CYS | C | 524 | −1.385 | −4.312 | 42.372 | 1.00 | 35.05 |
| 1410 | SG | CYS | C | 524 | −0.596 | −5.931 | 42.660 | 1.00 | 38.14 |
| 1411 | N | ARG | C | 525 | −3.877 | −5.593 | 44.493 | 1.00 | 34.86 |
| 1412 | CA | ARG | C | 525 | −4.167 | −5.967 | 45.870 | 1.00 | 23.67 |
| 1413 | CB | ARG | C | 525 | −5.652 | −5.769 | 46.150 | 1.00 | 38.72 |
| 1414 | CG | ARG | C | 525 | −6.061 | −6.020 | 47.568 | 1.00 | 48.92 |
| 1415 | CD | ARG | C | 525 | −7.472 | −5.536 | 47.779 | 1.00 | 43.42 |
| 1416 | NE | ARG | C | 525 | −8.446 | −6.465 | 47.235 | 1.00 | 68.57 |
| 1417 | CZ | ARG | C | 525 | −9.723 | −6.171 | 47.052 | 1.00 | 74.03 |
| 1418 | NH1 | ARG | C | 525 | −10.166 | −4.960 | 47.363 | 1.00 | 57.03 |
| 1419 | NH2 | ARG | C | 525 | −10.552 | −7.094 | 46.582 | 1.00 | 69.59 |
| 1420 | C | ARG | C | 525 | −3.786 | −7.409 | 46.183 | 1.00 | 37.68 |
| 1421 | O | ARG | C | 525 | −4.089 | −8.344 | 45.433 | 1.00 | 41.97 |
| 1422 | N | ALA | C | 526 | −3.108 | −7.581 | 47.306 | 1.00 | 30.70 |
| 1423 | CA | ALA | C | 526 | −2.690 | −8.891 | 47.735 | 1.00 | 18.11 |
| 1424 | CB | ALA | C | 526 | −1.211 | −8.880 | 48.037 | 1.00 | 25.89 |
| 1425 | C | ALA | C | 526 | −3.474 | −9.291 | 48.975 | 1.00 | 42.08 |
| 1426 | O | ALA | C | 526 | −3.794 | −8.467 | 49.853 | 1.00 | 37.54 |
| 1427 | N | VAL | C | 527 | −3.787 | −10.577 | 49.039 | 1.00 | 32.28 |
| 1428 | CA | VAL | C | 527 | −4.515 | −11.135 | 50.164 | 1.00 | 32.84 |
| 1429 | CB | VAL | C | 527 | −5.784 | −11.849 | 49.693 | 1.00 | 45.09 |
| 1430 | CG1 | VAL | C | 527 | −6.473 | −12.505 | 50.861 | 1.00 | 44.57 |
| 1431 | CG2 | VAL | C | 527 | −6.715 | −10.849 | 49.033 | 1.00 | 32.75 |
| 1432 | C | VAL | C | 527 | −3.570 | −12.119 | 50.832 | 1.00 | 33.78 |
| 1433 | O | VAL | C | 527 | −3.171 | −13.126 | 50.248 | 1.00 | 38.29 |
| 1434 | N | HIS | C | 528 | −3.182 | −11.786 | 52.056 | 1.00 | 32.00 |
| 1435 | CA | HIS | C | 528 | −2.268 | −12.621 | 52.813 | 1.00 | 36.25 |
| 1436 | CB | HIS | C | 528 | −0.856 | −12.092 | 52.656 | 1.00 | 27.51 |
| 1437 | CG | HIS | C | 528 | 0.181 | −12.998 | 53.218 | 1.00 | 39.81 |
| 1438 | CD2 | HIS | C | 528 | 0.869 | −14.024 | 52.661 | 1.00 | 35.15 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1439 | ND1 | HIS | C | 528 | 0.577 | −12.935 | 54.534 | 1.00 | 25.47 |
| 1440 | CE1 | HIS | C | 528 | 1.465 | −13.887 | 54.766 | 1.00 | 50.05 |
| 1441 | NE2 | HIS | C | 528 | 1.659 | −14.563 | 53.647 | 1.00 | 34.65 |
| 1442 | C | HIS | C | 528 | −2.642 | −12.709 | 54.293 | 1.00 | 42.08 |
| 1443 | O | HIS | C | 528 | −3.086 | −11.730 | 54.901 | 1.00 | 35.28 |
| 1444 | N | GLU | C | 529 | −2.479 | −13.903 | 54.850 | 1.00 | 45.68 |
| 1445 | CA | GLU | C | 529 | −2.784 | −14.189 | 56.249 | 1.00 | 46.76 |
| 1446 | CB | GLU | C | 529 | −2.322 | −15.607 | 56.591 | 1.00 | 47.26 |
| 1447 | CG | GLU | C | 529 | −2.298 | −15.909 | 58.071 | 1.00 | 73.70 |
| 1448 | CD | GLU | C | 529 | −1.749 | −17.279 | 58.360 | 1.00 | 92.01 |
| 1449 | OE1 | GLU | C | 529 | −1.583 | −17.619 | 59.555 | 1.00 | 76.61 |
| 1450 | OE2 | GLU | C | 529 | −1.487 | −18.008 | 57.379 | 1.00 | 84.24 |
| 1451 | C | GLU | C | 529 | −2.174 | −13.237 | 57.269 | 1.00 | 51.31 |
| 1452 | O | GLU | C | 529 | −2.721 | −13.053 | 58.356 | 1.00 | 56.27 |
| 1453 | N | ALA | C | 530 | −1.040 | −12.639 | 56.932 | 1.00 | 52.42 |
| 1454 | CA | ALA | C | 530 | −0.372 | −11.739 | 57.865 | 1.00 | 49.26 |
| 1455 | CB | ALA | C | 530 | 1.123 | −12.071 | 57.891 | 1.00 | 44.68 |
| 1456 | C | ALA | C | 530 | −0.582 | −10.230 | 57.630 | 1.00 | 58.77 |
| 1457 | O | ALA | C | 530 | −0.143 | −9.415 | 58.433 | 1.00 | 53.77 |
| 1458 | N | ALA | C | 531 | −1.261 | −9.852 | 56.555 | 1.00 | 62.98 |
| 1459 | CA | ALA | C | 531 | −1.478 | −8.440 | 56.280 | 1.00 | 61.98 |
| 1460 | CB | ALA | C | 531 | −2.049 | −8.257 | 54.881 | 1.00 | 51.62 |
| 1461 | C | ALA | C | 531 | −2.396 | −7.802 | 57.307 | 1.00 | 68.72 |
| 1462 | O | ALA | C | 531 | −2.668 | −6.606 | 57.248 | 1.00 | 78.77 |
| 1463 | N | SER | C | 532 | −2.859 | −8.600 | 58.258 | 1.00 | 76.48 |
| 1464 | CA | SER | C | 532 | −3.755 | −8.122 | 59.311 | 1.00 | 95.34 |
| 1465 | CB | SER | C | 532 | −3.631 | −9.014 | 60.554 | 1.00 | 100.90 |
| 1466 | OG | SER | C | 532 | −2.311 | −9.008 | 61.067 | 1.00 | 98.09 |
| 1467 | C | SER | C | 532 | −3.551 | −6.657 | 59.716 | 1.00 | 88.35 |
| 1468 | O | SER | C | 532 | −2.425 | −6.174 | 59.817 | 1.00 | 89.54 |
| 1469 | N | PRO | C | 533 | −4.654 | −5.931 | 59.945 | 1.00 | 87.28 |
| 1470 | CD | PRO | C | 533 | −4.629 | −4.488 | 60.240 | 1.00 | 92.00 |
| 1471 | CA | PRO | C | 533 | −6.037 | −6.415 | 59.842 | 1.00 | 83.55 |
| 1472 | CB | PRO | C | 533 | −6.819 | −5.310 | 60.527 | 1.00 | 80.62 |
| 1473 | CG | PRO | C | 533 | −6.083 | −4.092 | 60.052 | 1.00 | 83.88 |
| 1474 | C | PRO | C | 533 | −6.440 | −6.577 | 58.368 | 1.00 | 84.42 |
| 1475 | O | PRO | C | 533 | −5.593 | −6.503 | 57.473 | 1.00 | 94.45 |
| 1476 | N | SER | C | 534 | −7.729 | −6.793 | 58.124 | 1.00 | 71.77 |
| 1477 | CA | SER | C | 534 | −8.251 | −6.932 | 56.761 | 1.00 | 66.09 |
| 1478 | CB | SER | C | 534 | −8.131 | −5.603 | 56.008 | 1.00 | 57.13 |
| 1479 | OG | SER | C | 534 | −6.788 | −5.188 | 55.895 | 1.00 | 55.58 |
| 1480 | C | SER | C | 534 | −7.633 | −8.042 | 55.918 | 1.00 | 49.56 |
| 1481 | O | SER | C | 534 | −8.259 | −8.529 | 54.995 | 1.00 | 56.14 |
| 1482 | N | GLN | C | 535 | −6.415 | −8.444 | 56.244 | 1.00 | 44.12 |
| 1483 | CA | GLN | C | 535 | −5.702 | −9.502 | 55.528 | 1.00 | 42.63 |
| 1484 | CB | GLN | C | 535 | −6.480 | −10.825 | 55.558 | 1.00 | 43.05 |
| 1485 | CG | GLN | C | 535 | −7.394 | −11.027 | 56.761 | 1.00 | 49.89 |
| 1486 | CD | GLN | C | 535 | −6.683 | −10.890 | 58.068 | 1.00 | 56.99 |
| 1487 | OE1 | GLN | C | 535 | −7.302 | −10.587 | 59.083 | 1.00 | 61.29 |
| 1488 | NE2 | GLN | C | 535 | −5.375 | −11.117 | 58.066 | 1.00 | 68.00 |
| 1489 | C | GLN | C | 535 | −5.407 | −9.114 | 54.089 | 1.00 | 45.91 |
| 1490 | O | GLN | C | 535 | −5.288 | −9.974 | 53.214 | 1.00 | 47.62 |
| 1491 | N | THR | C | 536 | −5.296 | −7.818 | 53.832 | 1.00 | 38.66 |
| 1492 | CA | THR | C | 536 | −4.978 | −7.371 | 52.481 | 1.00 | 49.07 |
| 1493 | CB | THR | C | 536 | −6.258 | −7.042 | 51.670 | 1.00 | 57.42 |
| 1494 | OG1 | THR | C | 536 | −6.867 | −5.851 | 52.175 | 1.00 | 47.72 |
| 1495 | CG2 | THR | C | 536 | −7.249 | −8.165 | 51.764 | 1.00 | 56.24 |
| 1496 | C | THR | C | 536 | −4.070 | −6.140 | 52.442 | 1.00 | 50.77 |
| 1497 | O | THR | C | 536 | −4.061 | −5.335 | 53.375 | 1.00 | 44.55 |
| 1498 | N | VAL | C | 537 | −3.299 | −6.023 | 51.361 | 1.00 | 29.60 |
| 1499 | CA | VAL | C | 537 | −2.430 | −4.877 | 51.148 | 1.00 | 31.44 |
| 1500 | CB | VAL | C | 537 | −0.935 | −5.196 | 51.401 | 1.00 | 43.56 |
| 1501 | CG1 | VAL | C | 537 | −0.203 | −3.922 | 51.785 | 1.00 | 27.60 |
| 1502 | CG2 | VAL | C | 537 | −0.785 | −6.237 | 52.470 | 1.00 | 38.57 |
| 1503 | C | VAL | C | 537 | −2.611 | −4.515 | 49.673 | 1.00 | 30.07 |
| 1504 | O | VAL | C | 537 | −2.829 | −5.380 | 48.827 | 1.00 | 39.29 |
| 1505 | N | GLN | C | 538 | −2.499 | −3.241 | 49.348 | 1.00 | 24.18 |
| 1506 | CA | GLN | C | 538 | −2.709 | −2.839 | 47.969 | 1.00 | 34.78 |
| 1507 | CB | GLN | C | 538 | −4.227 | −2.702 | 47.697 | 1.00 | 35.17 |
| 1508 | CG | GLN | C | 538 | −4.890 | −1.502 | 48.395 | 1.00 | 18.53 |
| 1509 | CD | GLN | C | 538 | −6.382 | −1.422 | 48.146 | 1.00 | 48.90 |
| 1510 | OE1 | GLN | C | 538 | −7.128 | −2.373 | 48.406 | 1.00 | 39.45 |
| 1511 | NE2 | GLN | C | 538 | −6.831 | −0.281 | 47.650 | 1.00 | 25.59 |
| 1512 | C | GLN | C | 538 | −2.034 | −1.527 | 47.623 | 1.00 | 34.44 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1513 | O | GLN | C | 538 | −1.813 | −0.656 | 48.482 | 1.00 | 38.59 |
| 1514 | N | ARG | C | 539 | −1.737 | −1.373 | 46.345 | 1.00 | 32.98 |
| 1515 | CA | ARG | C | 539 | −1.119 | −0.147 | 45.869 | 1.00 | 36.74 |
| 1516 | CB | ARG | C | 539 | 0.392 | −0.338 | 45.675 | 1.00 | 40.04 |
| 1517 | CG | ARG | C | 539 | 1.197 | 0.928 | 45.908 | 1.00 | 62.70 |
| 1518 | CD | ARG | C | 539 | 1.963 | 0.829 | 47.232 | 1.00 | 99.44 |
| 1519 | NE | ARG | C | 539 | 1.106 | 0.548 | 48.391 | 1.00 | 110.22 |
| 1520 | CZ | ARG | C | 539 | 1.560 | 0.353 | 49.630 | 1.00 | 105.13 |
| 1521 | NH1 | ARG | C | 539 | 2.857 | 0.407 | 49.879 | 1.00 | 115.51 |
| 1522 | NH2 | ARG | C | 539 | 0.725 | 0.104 | 50.623 | 1.00 | 100.12 |
| 1523 | C | ARG | C | 539 | −1.772 | 0.239 | 44.551 | 1.00 | 29.01 |
| 1524 | O | ARG | C | 539 | −2.126 | −0.617 | 43.755 | 1.00 | 38.75 |
| 1525 | N | ALA | C | 540 | −1.921 | 1.539 | 44.346 | 1.00 | 26.49 |
| 1526 | CA | ALA | C | 540 | −2.540 | 2.078 | 43.147 | 1.00 | 37.52 |
| 1527 | CB | ALA | C | 540 | −3.469 | 3.272 | 43.542 | 1.00 | 19.15 |
| 1528 | C | ALA | C | 540 | −1.457 | 2.539 | 42.179 | 1.00 | 41.59 |
| 1529 | O | ALA | C | 540 | −0.403 | 3.005 | 42.623 | 1.00 | 33.86 |
| 1530 | N | VAL | C | 541 | −1.726 | 2.410 | 40.877 | 1.00 | 46.45 |
| 1531 | CA | VAL | C | 541 | −0.788 | 2.841 | 39.837 | 1.00 | 44.92 |
| 1532 | CB | VAL | C | 541 | −0.381 | 1.706 | 38.907 | 1.00 | 45.35 |
| 1533 | CG1 | VAL | C | 541 | 1.045 | 1.915 | 38.472 | 1.00 | 34.26 |
| 1534 | CG2 | VAL | C | 541 | −0.573 | 0.382 | 39.571 | 1.00 | 57.19 |
| 1535 | C | VAL | C | 541 | −1.432 | 3.918 | 38.975 | 1.00 | 64.37 |
| 1536 | O | VAL | C | 541 | −2.514 | 3.737 | 38.437 | 1.00 | 40.46 |
| 1537 | N | SER | C | 542 | −0.721 | 5.021 | 38.823 | 1.00 | 77.99 |
| 1538 | CA | SER | C | 542 | −1.171 | 6.190 | 38.075 | 1.00 | 92.44 |
| 1539 | CB | SER | C | 542 | −0.409 | 7.405 | 38.601 | 1.00 | 96.88 |
| 1540 | OG | SER | C | 542 | 0.965 | 7.087 | 38.798 | 1.00 | 88.56 |
| 1541 | C | SER | C | 542 | −1.084 | 6.181 | 36.544 | 1.00 | 93.38 |
| 1542 | O | SER | C | 542 | −0.718 | 5.186 | 35.915 | 1.00 | 75.02 |
| 1543 | N | VAL | C | 543 | −1.426 | 7.337 | 35.971 | 1.00 | 111.49 |
| 1544 | CA | VAL | C | 543 | −1.432 | 7.583 | 34.527 | 1.00 | 111.17 |
| 1545 | CB | VAL | C | 543 | −2.300 | 8.819 | 34.166 | 1.00 | 113.66 |
| 1546 | CG1 | VAL | C | 543 | −2.199 | 9.107 | 32.671 | 1.00 | 110.58 |
| 1547 | CG2 | VAL | C | 543 | −3.753 | 8.580 | 34.568 | 1.00 | 105.15 |
| 1548 | C | VAL | C | 543 | −0.035 | 7.802 | 33.972 | 1.00 | 100.62 |
| 1549 | O | VAL | C | 543 | 0.372 | 8.977 | 33.813 | 1.00 | 91.90 |
| 1550 | OXT | VAL | C | 543 | 0.638 | 6.789 | 33.716 | 1.00 | 88.10 |
| 1551 | CB | VAL | D | 336 | 15.755 | −42.116 | 35.528 | 1.00 | 108.98 |
| 1552 | CG1 | VAL | D | 336 | 16.794 | −42.290 | 34.427 | 1.00 | 100.09 |
| 1553 | CG2 | VAL | D | 336 | 16.212 | −42.800 | 36.815 | 1.00 | 105.24 |
| 1554 | C | VAL | D | 336 | 15.057 | −39.954 | 34.490 | 1.00 | 101.74 |
| 1555 | O | VAL | D | 336 | 14.360 | −40.568 | 33.680 | 1.00 | 107.72 |
| 1556 | N | VAL | D | 336 | 14.502 | −40.422 | 36.876 | 1.00 | 77.64 |
| 1557 | CA | VAL | D | 336 | 15.507 | −40.616 | 35.792 | 1.00 | 98.59 |
| 1558 | N | SER | D | 337 | 15.469 | −38.701 | 34.304 | 1.00 | 96.55 |
| 1559 | CA | SER | D | 337 | 15.127 | −37.921 | 33.119 | 1.00 | 101.26 |
| 1560 | CB | SER | D | 337 | 14.105 | −36.843 | 33.484 | 1.00 | 104.37 |
| 1561 | OG | SER | D | 337 | 14.562 | −36.061 | 34.570 | 1.00 | 89.45 |
| 1562 | C | SER | D | 337 | 16.379 | −37.277 | 32.525 | 1.00 | 99.45 |
| 1563 | O | SER | D | 337 | 17.437 | −37.269 | 33.161 | 1.00 | 98.82 |
| 1564 | N | ALA | D | 338 | 16.259 | −36.745 | 31.308 | 1.00 | 93.02 |
| 1565 | CA | ALA | D | 338 | 17.392 | −36.114 | 30.631 | 1.00 | 90.26 |
| 1566 | CB | ALA | D | 338 | 18.116 | −37.133 | 29.741 | 1.00 | 82.08 |
| 1567 | C | ALA | D | 338 | 16.947 | −34.922 | 29.796 | 1.00 | 91.16 |
| 1568 | O | ALA | D | 338 | 16.058 | −35.046 | 28.949 | 1.00 | 105.09 |
| 1569 | N | TYR | D | 339 | 17.579 | −33.773 | 30.041 | 1.00 | 93.59 |
| 1570 | CA | TYR | D | 339 | 17.279 | −32.531 | 29.329 | 1.00 | 78.85 |
| 1571 | CB | TYR | D | 339 | 16.918 | −31.415 | 30.308 | 1.00 | 70.69 |
| 1572 | CG | TYR | D | 339 | 15.755 | −31.688 | 31.240 | 1.00 | 87.57 |
| 1573 | CD1 | TYR | D | 339 | 15.666 | −32.882 | 31.951 | 1.00 | 96.89 |
| 1574 | CE1 | TYR | D | 339 | 14.651 | −33.094 | 32.877 | 1.00 | 112.97 |
| 1575 | CD2 | TYR | D | 339 | 14.786 | −30.710 | 31.476 | 1.00 | 95.27 |
| 1576 | CE2 | TYR | D | 339 | 13.765 | −30.910 | 32.400 | 1.00 | 99.22 |
| 1577 | CZ | TYR | D | 339 | 13.705 | −32.103 | 33.099 | 1.00 | 108.96 |
| 1578 | OH | TYR | D | 339 | 12.713 | −32.296 | 34.033 | 1.00 | 103.91 |
| 1579 | C | TYR | D | 339 | 18.497 | −32.085 | 28.532 | 1.00 | 61.59 |
| 1580 | O | TYR | D | 339 | 19.632 | −32.353 | 28.916 | 1.00 | 62.89 |
| 1581 | N | LEU | D | 340 | 18.255 | −31.404 | 27.418 | 1.00 | 61.60 |
| 1582 | CA | LEU | D | 340 | 19.332 | −30.902 | 26.576 | 1.00 | 68.01 |
| 1583 | CB | LEU | D | 340 | 19.403 | −31.690 | 25.263 | 1.00 | 49.73 |
| 1584 | CG | LEU | D | 340 | 20.683 | −31.422 | 24.462 | 1.00 | 67.03 |
| 1585 | CD1 | LEU | D | 340 | 21.899 | −31.767 | 25.313 | 1.00 | 27.24 |
| 1586 | CD2 | LEU | D | 340 | 20.692 | −32.242 | 23.195 | 1.00 | 38.05 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1587 | C | LEU | D | 340 | 18.995 | −29.446 | 26.311 | 1.00 | 57.64 |
| 1588 | O | LEU | D | 340 | 17.918 | −29.152 | 25.806 | 1.00 | 66.07 |
| 1589 | N | SER | D | 341 | 19.894 | −28.531 | 26.664 | 1.00 | 50.71 |
| 1590 | CA | SER | D | 341 | 19.597 | −27.105 | 26.476 | 1.00 | 73.30 |
| 1591 | CB | SER | D | 341 | 19.838 | −26.316 | 27.775 | 1.00 | 59.12 |
| 1592 | OG | SER | D | 341 | 21.220 | −26.256 | 28.090 | 1.00 | 61.02 |
| 1593 | C | SER | D | 341 | 20.401 | −26.481 | 25.355 | 1.00 | 60.74 |
| 1594 | O | SER | D | 341 | 21.386 | −27.055 | 24.895 | 1.00 | 74.16 |
| 1595 | N | ARG | D | 342 | 19.972 | −25.298 | 24.925 | 1.00 | 53.23 |
| 1596 | CA | ARG | D | 342 | 20.647 | −24.580 | 23.846 | 1.00 | 61.24 |
| 1597 | CB | ARG | D | 342 | 19.620 | −23.899 | 22.934 | 1.00 | 58.98 |
| 1598 | CG | ARG | D | 342 | 18.813 | −24.847 | 22.075 | 1.00 | 62.50 |
| 1599 | CD | ARG | D | 342 | 17.856 | −24.092 | 21.179 | 1.00 | 74.78 |
| 1600 | NE | ARG | D | 342 | 16.827 | −23.387 | 21.934 | 1.00 | 47.29 |
| 1601 | CZ | ARG | D | 342 | 15.750 | −23.958 | 22.461 | 1.00 | 58.60 |
| 1602 | NH1 | ARG | D | 342 | 15.538 | −25.258 | 22.326 | 1.00 | 82.11 |
| 1603 | NH2 | ARG | D | 342 | 14.871 | −23.221 | 23.118 | 1.00 | 77.00 |
| 1604 | C | ARG | D | 342 | 21.617 | −23.539 | 24.388 | 1.00 | 62.05 |
| 1605 | O | ARG | D | 342 | 21.640 | −23.263 | 25.592 | 1.00 | 65.97 |
| 1606 | N | PRO | D | 343 | 22.436 | −22.945 | 23.507 | 1.00 | 53.51 |
| 1607 | CD | PRO | D | 343 | 22.639 | −23.247 | 22.086 | 1.00 | 59.72 |
| 1608 | CA | PRO | D | 343 | 23.393 | −21.937 | 23.957 | 1.00 | 51.22 |
| 1609 | CB | PRO | D | 343 | 24.141 | −21.571 | 22.679 | 1.00 | 56.13 |
| 1610 | CG | PRO | D | 343 | 24.067 | −22.815 | 21.878 | 1.00 | 53.39 |
| 1611 | C | PRO | D | 343 | 22.659 | −20.754 | 24.545 | 1.00 | 54.23 |
| 1612 | O | PRO | D | 343 | 21.555 | −20.405 | 24.109 | 1.00 | 67.21 |
| 1613 | N | SER | D | 344 | 23.263 | −20.164 | 25.564 | 1.00 | 39.66 |
| 1614 | CA | SER | D | 344 | 22.658 | −19.009 | 26.192 | 1.00 | 43.06 |
| 1615 | CB | SER | D | 344 | 23.417 | −18.607 | 27.445 | 1.00 | 53.04 |
| 1616 | OG | SER | D | 344 | 24.757 | −18.291 | 27.104 | 1.00 | 38.14 |
| 1617 | C | SER | D | 344 | 22.853 | −17.940 | 25.160 | 1.00 | 44.56 |
| 1618 | O | SER | D | 344 | 23.848 | −17.951 | 24.413 | 1.00 | 27.72 |
| 1619 | N | PRO | D | 345 | 21.911 | −17.006 | 25.081 | 1.00 | 28.90 |
| 1620 | CD | PRO | D | 345 | 20.510 | −17.000 | 25.534 | 1.00 | 17.68 |
| 1621 | CA | PRO | D | 345 | 22.152 | −15.993 | 24.067 | 1.00 | 15.88 |
| 1622 | CB | PRO | D | 345 | 20.915 | −15.123 | 24.168 | 1.00 | 16.41 |
| 1623 | CG | PRO | D | 345 | 19.831 | −16.153 | 24.478 | 1.00 | 41.71 |
| 1624 | C | PRO | D | 345 | 23.447 | −15.256 | 24.365 | 1.00 | 47.66 |
| 1625 | O | PRO | D | 345 | 24.207 | −14.900 | 23.451 | 1.00 | 36.81 |
| 1626 | N | PHE | D | 346 | 23.712 | −15.067 | 25.654 | 1.00 | 36.68 |
| 1627 | CA | PHE | D | 346 | 24.914 | −14.365 | 26.083 | 1.00 | 33.19 |
| 1628 | CB | PHE | D | 346 | 24.945 | −14.215 | 27.609 | 1.00 | 38.14 |
| 1629 | CG | PHE | D | 346 | 26.186 | −13.529 | 28.108 | 1.00 | 46.70 |
| 1630 | CD1 | PHE | D | 346 | 26.501 | −12.240 | 27.675 | 1.00 | 60.78 |
| 1631 | CD2 | PHE | D | 346 | 27.094 | −14.201 | 28.921 | 1.00 | 33.03 |
| 1632 | CE1 | PHE | D | 346 | 27.712 | −11.635 | 28.038 | 1.00 | 61.26 |
| 1633 | CE2 | PHE | D | 346 | 28.310 | −13.603 | 29.291 | 1.00 | 38.91 |
| 1634 | CZ | PHE | D | 346 | 28.617 | −12.317 | 28.845 | 1.00 | 33.37 |
| 1635 | C | PHE | D | 346 | 26.198 | −15.033 | 25.633 | 1.00 | 39.49 |
| 1636 | O | PHE | D | 346 | 27.153 | −14.369 | 25.200 | 1.00 | 40.46 |
| 1637 | N | ASP | D | 347 | 26.217 | −16.355 | 25.746 | 1.00 | 40.48 |
| 1638 | CA | ASP | D | 347 | 27.386 | −17.125 | 25.366 | 1.00 | 35.45 |
| 1639 | CB | ASP | D | 347 | 27.250 | −18.547 | 25.888 | 1.00 | 40.40 |
| 1640 | CG | ASP | D | 347 | 27.859 | −18.710 | 27.260 | 1.00 | 53.93 |
| 1641 | OD1 | ASP | D | 347 | 27.584 | −19.736 | 27.928 | 1.00 | 70.75 |
| 1642 | OD2 | ASP | D | 347 | 28.627 | −17.807 | 27.656 | 1.00 | 45.65 |
| 1643 | C | ASP | D | 347 | 27.570 | −17.111 | 23.869 | 1.00 | 23.05 |
| 1644 | O | ASP | D | 347 | 28.663 | −16.858 | 23.358 | 1.00 | 31.39 |
| 1645 | N | LEU | D | 348 | 26.468 | −17.349 | 23.181 | 1.00 | 28.43 |
| 1646 | CA | LEU | D | 348 | 26.424 | −17.359 | 21.724 | 1.00 | 25.78 |
| 1647 | CB | LEU | D | 348 | 24.989 | −17.625 | 21.301 | 1.00 | 33.48 |
| 1648 | CG | LEU | D | 348 | 24.723 | −17.937 | 19.848 | 1.00 | 29.86 |
| 1649 | CD1 | LEU | D | 348 | 25.867 | −18.724 | 19.270 | 1.00 | 13.69 |
| 1650 | CD2 | LEU | D | 348 | 23.429 | −18.717 | 19.772 | 1.00 | 29.16 |
| 1651 | C | LEU | D | 348 | 26.916 | −16.071 | 21.062 | 1.00 | 42.85 |
| 1652 | O | LEU | D | 348 | 27.964 | −16.066 | 20.425 | 1.00 | 58.81 |
| 1653 | N | PHE | D | 349 | 26.166 | −14.981 | 21.254 | 1.00 | 59.00 |
| 1654 | CA | PHE | D | 349 | 26.448 | −13.670 | 20.639 | 1.00 | 36.47 |
| 1655 | CB | PHE | D | 349 | 25.148 | −12.886 | 20.475 | 1.00 | 51.07 |
| 1656 | CG | PHE | D | 349 | 23.983 | −13.716 | 20.061 | 1.00 | 24.91 |
| 1657 | CD1 | PHE | D | 349 | 23.103 | −14.201 | 21.006 | 1.00 | 15.37 |
| 1658 | CD2 | PHE | D | 349 | 23.764 | −14.010 | 18.733 | 1.00 | 12.93 |
| 1659 | CE1 | PHE | D | 349 | 22.015 | −14.972 | 20.624 | 1.00 | 55.20 |
| 1660 | CE2 | PHE | D | 349 | 22.693 | −14.768 | 18.351 | 1.00 | 29.61 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1661 | CZ | PHE | D | 349 | 21.817 | −15.254 | 19.292 | 1.00 | 28.17 |
| 1662 | C | PHE | D | 349 | 27.471 | −12.664 | 21.184 | 1.00 | 46.47 |
| 1663 | O | PHE | D | 349 | 28.020 | −11.883 | 20.400 | 1.00 | 43.82 |
| 1664 | N | ILE | D | 350 | 27.694 | −12.622 | 22.495 | 1.00 | 53.26 |
| 1665 | CA | ILE | D | 350 | 28.662 | −11.668 | 23.038 | 1.00 | 42.78 |
| 1666 | CB | ILE | D | 350 | 28.226 | −11.083 | 24.392 | 1.00 | 70.96 |
| 1667 | CG2 | ILE | D | 350 | 29.027 | −9.822 | 24.674 | 1.00 | 47.74 |
| 1668 | CG1 | ILE | D | 350 | 26.734 | −10.752 | 24.392 | 1.00 | 61.48 |
| 1669 | CD1 | ILE | D | 350 | 26.331 | −9.700 | 23.400 | 1.00 | 18.17 |
| 1670 | C | ILE | D | 350 | 30.018 | −12.329 | 23.254 | 1.00 | 45.31 |
| 1671 | O | ILE | D | 350 | 30.997 | −11.917 | 22.654 | 1.00 | 52.57 |
| 1672 | N | ARG | D | 351 | 30.065 | −13.341 | 24.126 | 1.00 | 49.17 |
| 1673 | CA | ARG | D | 351 | 31.298 | −14.081 | 24.428 | 1.00 | 46.84 |
| 1674 | CB | ARG | D | 351 | 31.064 | −15.060 | 25.582 | 1.00 | 66.28 |
| 1675 | CG | ARG | D | 351 | 31.145 | −14.490 | 26.998 | 1.00 | 69.95 |
| 1676 | CD | ARG | D | 351 | 30.662 | −15.548 | 28.015 | 1.00 | 88.52 |
| 1677 | NE | ARG | D | 351 | 31.674 | −16.430 | 28.616 | 1.00 | 79.78 |
| 1678 | CZ | ARG | D | 351 | 32.910 | −16.642 | 28.167 | 1.00 | 75.05 |
| 1679 | NH1 | ARG | D | 351 | 33.362 | −16.037 | 27.079 | 1.00 | 81.99 |
| 1680 | NH2 | ARG | D | 351 | 33.707 | −17.477 | 28.819 | 1.00 | 87.51 |
| 1681 | C | ARG | D | 351 | 31.795 | −14.883 | 23.221 | 1.00 | 56.91 |
| 1682 | O | ARG | D | 351 | 32.982 | −15.221 | 23.118 | 1.00 | 45.81 |
| 1683 | N | LYS | D | 352 | 30.872 | −15.198 | 22.321 | 1.00 | 58.37 |
| 1684 | CA | LYS | D | 352 | 31.185 | −15.960 | 21.121 | 1.00 | 64.66 |
| 1685 | CB | LYS | D | 352 | 31.983 | −15.099 | 20.145 | 1.00 | 68.98 |
| 1686 | CG | LYS | D | 352 | 31.161 | −13.917 | 19.624 | 1.00 | 97.35 |
| 1687 | CD | LYS | D | 352 | 31.761 | −13.267 | 18.391 | 1.00 | 104.99 |
| 1688 | CE | LYS | D | 352 | 30.936 | −12.070 | 17.952 | 1.00 | 105.51 |
| 1689 | NZ | LYS | D | 352 | 30.968 | −10.970 | 18.959 | 1.00 | 107.63 |
| 1690 | C | LYS | D | 352 | 31.908 | −17.263 | 21.428 | 1.00 | 70.23 |
| 1691 | O | LYS | D | 352 | 32.928 | −17.603 | 20.826 | 1.00 | 47.87 |
| 1692 | N | SER | D | 353 | 31.339 | −17.984 | 22.385 | 1.00 | 60.50 |
| 1693 | CA | SER | D | 353 | 31.840 | −19.275 | 22.818 | 1.00 | 64.49 |
| 1694 | CB | SER | D | 353 | 32.992 | −19.114 | 23.824 | 1.00 | 50.55 |
| 1695 | OG | SER | D | 353 | 32.606 | −18.365 | 24.955 | 1.00 | 102.42 |
| 1696 | C | SER | D | 353 | 30.653 | −20.011 | 23.440 | 1.00 | 61.40 |
| 1697 | O | SER | D | 353 | 30.508 | −20.092 | 24.656 | 1.00 | 53.16 |
| 1698 | N | PRO | D | 354 | 29.772 | −20.551 | 22.589 | 1.00 | 63.75 |
| 1699 | CD | PRO | D | 354 | 29.775 | −20.381 | 21.128 | 1.00 | 64.85 |
| 1700 | CA | PRO | D | 354 | 28.576 | −21.286 | 23.015 | 1.00 | 61.87 |
| 1701 | CB | PRO | D | 354 | 27.767 | −21.411 | 21.723 | 1.00 | 46.96 |
| 1702 | CG | PRO | D | 354 | 28.318 | −20.326 | 20.838 | 1.00 | 75.02 |
| 1703 | C | PRO | D | 354 | 28.856 | −22.651 | 23.646 | 1.00 | 49.29 |
| 1704 | O | PRO | D | 354 | 29.948 | −23.197 | 23.503 | 1.00 | 50.89 |
| 1705 | N | THR | D | 355 | 27.856 | −23.179 | 24.346 | 1.00 | 34.78 |
| 1706 | CA | THR | D | 355 | 27.924 | −24.478 | 25.009 | 1.00 | 46.60 |
| 1707 | CB | THR | D | 355 | 28.556 | −24.423 | 26.444 | 1.00 | 46.68 |
| 1708 | OG1 | THR | D | 355 | 27.906 | −23.405 | 27.217 | 1.00 | 54.28 |
| 1709 | CG2 | THR | D | 355 | 30.094 | −24.178 | 26.380 | 1.00 | 16.92 |
| 1710 | C | THR | D | 355 | 26.502 | −24.973 | 25.173 | 1.00 | 59.65 |
| 1711 | O | THR | D | 355 | 25.555 | −24.185 | 25.175 | 1.00 | 62.18 |
| 1712 | N | ILE | D | 356 | 26.354 | −26.285 | 25.294 | 1.00 | 62.47 |
| 1713 | CA | ILE | D | 356 | 25.042 | −26.900 | 25.478 | 1.00 | 57.23 |
| 1714 | CB | ILE | D | 356 | 24.607 | −27.699 | 24.247 | 1.00 | 54.14 |
| 1715 | CG2 | ILE | D | 356 | 24.291 | −26.742 | 23.110 | 1.00 | 64.47 |
| 1716 | CG1 | ILE | D | 356 | 25.711 | −28.696 | 23.868 | 1.00 | 68.80 |
| 1717 | CD1 | ILE | D | 356 | 25.486 | −29.422 | 22.564 | 1.00 | 58.85 |
| 1718 | C | ILE | D | 356 | 25.223 | −27.837 | 26.644 | 1.00 | 52.82 |
| 1719 | O | ILE | D | 356 | 26.308 | −28.404 | 26.807 | 1.00 | 35.17 |
| 1720 | N | THR | D | 357 | 24.172 | −28.018 | 27.442 | 1.00 | 22.18 |
| 1721 | CA | THR | D | 357 | 24.308 | −28.849 | 28.621 | 1.00 | 61.12 |
| 1722 | CB | THR | D | 357 | 24.191 | −27.980 | 29.918 | 1.00 | 68.55 |
| 1723 | OG1 | THR | D | 357 | 25.210 | −26.970 | 29.908 | 1.00 | 64.20 |
| 1724 | CG2 | THR | D | 357 | 24.358 | −28.825 | 31.168 | 1.00 | 53.25 |
| 1725 | C | THR | D | 357 | 23.319 | −29.980 | 28.699 | 1.00 | 62.70 |
| 1726 | O | THR | D | 357 | 22.105 | −29.755 | 28.706 | 1.00 | 68.56 |
| 1727 | N | CYS | D | 358 | 23.847 | −31.201 | 28.755 | 1.00 | 53.32 |
| 1728 | CA | CYS | D | 358 | 23.003 | −32.383 | 28.877 | 1.00 | 72.33 |
| 1729 | C | CYS | D | 358 | 22.893 | −32.598 | 30.383 | 1.00 | 68.15 |
| 1730 | O | CYS | D | 358 | 23.896 | −32.858 | 31.056 | 1.00 | 43.63 |
| 1731 | CB | CYS | D | 358 | 23.664 | −33.595 | 28.211 | 1.00 | 87.13 |
| 1732 | SG | CYS | D | 358 | 22.589 | −35.046 | 27.909 | 1.00 | 71.31 |
| 1733 | N | LEU | D | 359 | 21.677 | −32.467 | 30.902 | 1.00 | 50.64 |
| 1734 | CA | LEU | D | 359 | 21.413 | −32.611 | 32.325 | 1.00 | 47.79 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1735 | CB | LEU | D | 359 | 20.690 | −31.374 | 32.829 | 1.00 | 48.98 |
| 1736 | CG | LEU | D | 359 | 20.001 | −31.467 | 34.191 | 1.00 | 73.55 |
| 1737 | CD1 | LEU | D | 359 | 21.039 | −31.614 | 35.307 | 1.00 | 65.18 |
| 1738 | CD2 | LEU | D | 359 | 19.159 | −30.223 | 34.407 | 1.00 | 76.80 |
| 1739 | C | LEU | D | 359 | 20.569 | −33.822 | 32.675 | 1.00 | 77.06 |
| 1740 | O | LEU | D | 359 | 19.377 | −33.860 | 32.369 | 1.00 | 81.77 |
| 1741 | N | VAL | D | 360 | 21.174 | −34.801 | 33.338 | 1.00 | 79.82 |
| 1742 | CA | VAL | D | 360 | 20.431 | −35.993 | 33.742 | 1.00 | 91.65 |
| 1743 | CB | VAL | D | 360 | 21.286 | −37.256 | 33.593 | 1.00 | 93.51 |
| 1744 | CG1 | VAL | D | 360 | 20.425 | −38.476 | 33.856 | 1.00 | 79.24 |
| 1745 | CG2 | VAL | D | 360 | 21.915 | −37.304 | 32.201 | 1.00 | 89.46 |
| 1746 | C | VAL | D | 360 | 19.985 | −35.873 | 35.204 | 1.00 | 85.42 |
| 1747 | O | VAL | D | 360 | 20.795 | −35.596 | 36.084 | 1.00 | 95.35 |
| 1748 | N | VAL | D | 361 | 18.699 | −36.080 | 35.458 | 1.00 | 89.22 |
| 1749 | CA | VAL | D | 361 | 18.167 | −35.986 | 36.819 | 1.00 | 106.98 |
| 1750 | CB | VAL | D | 361 | 16.997 | −34.973 | 36.905 | 1.00 | 104.29 |
| 1751 | CG1 | VAL | D | 361 | 16.471 | −34.903 | 38.340 | 1.00 | 83.77 |
| 1752 | CG2 | VAL | D | 361 | 17.457 | −33.603 | 36.439 | 1.00 | 98.48 |
| 1753 | C | VAL | D | 361 | 17.660 | −37.326 | 37.358 | 1.00 | 107.84 |
| 1754 | O | VAL | D | 361 | 16.666 | −37.867 | 36.868 | 1.00 | 98.74 |
| 1755 | N | ASP | D | 362 | 18.338 | −37.846 | 38.378 | 1.00 | 116.05 |
| 1756 | CA | ASP | D | 362 | 17.956 | −39.119 | 38.986 | 1.00 | 124.33 |
| 1757 | CB | ASP | D | 362 | 19.087 | −40.143 | 38.849 | 1.00 | 121.23 |
| 1758 | CG | ASP | D | 362 | 18.616 | −41.565 | 39.095 | 1.00 | 122.58 |
| 1759 | OD1 | ASP | D | 362 | 17.935 | −41.799 | 40.113 | 1.00 | 123.71 |
| 1760 | OD2 | ASP | D | 362 | 18.927 | −42.451 | 38.272 | 1.00 | 134.60 |
| 1761 | C | ASP | D | 362 | 17.637 | −38.918 | 40.462 | 1.00 | 118.74 |
| 1762 | O | ASP | D | 362 | 18.497 | −38.516 | 41.241 | 1.00 | 123.38 |
| 1763 | N | LEU | D | 363 | 16.399 | −39.205 | 40.842 | 1.00 | 120.79 |
| 1764 | CA | LEU | D | 363 | 15.982 | −39.046 | 42.224 | 1.00 | 125.68 |
| 1765 | CB | LEU | D | 363 | 14.471 | −38.820 | 42.288 | 1.00 | 125.28 |
| 1766 | CG | LEU | D | 363 | 13.937 | −37.520 | 41.677 | 1.00 | 129.12 |
| 1767 | CD1 | LEU | D | 363 | 12.414 | −37.563 | 41.644 | 1.00 | 123.70 |
| 1768 | CD2 | LEU | D | 363 | 14.429 | −36.322 | 42.487 | 1.00 | 130.99 |
| 1769 | C | LEU | D | 363 | 16.368 | −40.239 | 43.099 | 1.00 | 132.57 |
| 1770 | O | LEU | D | 363 | 16.294 | −40.162 | 44.325 | 1.00 | 137.86 |
| 1771 | N | ALA | D | 364 | 16.780 | −41.338 | 42.474 | 1.00 | 133.10 |
| 1772 | CA | ALA | D | 364 | 17.180 | −42.536 | 43.216 | 1.00 | 136.94 |
| 1773 | CB | ALA | D | 364 | 16.244 | −43.697 | 42.877 | 1.00 | 132.16 |
| 1774 | C | ALA | D | 364 | 18.633 | −42.922 | 42.914 | 1.00 | 136.74 |
| 1775 | O | ALA | D | 364 | 18.897 | −43.813 | 42.104 | 1.00 | 138.88 |
| 1776 | N | PRO | D | 365 | 19.595 | −42.254 | 43.573 | 1.00 | 135.90 |
| 1777 | CD | PRO | D | 365 | 19.385 | −41.174 | 44.555 | 1.00 | 130.17 |
| 1778 | CA | PRO | D | 365 | 21.028 | −42.514 | 43.384 | 1.00 | 134.16 |
| 1779 | CB | PRO | D | 36S | 21.672 | −41.675 | 44.486 | 1.00 | 134.28 |
| 1780 | CG | PRO | D | 365 | 20.740 | −40.508 | 44.599 | 1.00 | 129.87 |
| 1781 | C | PRO | D | 365 | 21.438 | −43.989 | 43.459 | 1.00 | 133.32 |
| 1782 | O | PRO | D | 365 | 21.811 | −44.487 | 44.522 | 1.00 | 137.65 |
| 1783 | N | SER | D | 366 | 21.372 | −44.683 | 42.327 | 1.00 | 134.17 |
| 1784 | CA | SER | D | 366 | 21.757 | −46.089 | 42.271 | 1.00 | 137.38 |
| 1785 | CB | SER | D | 366 | 20.809 | −46.861 | 41.352 | 1.00 | 133.61 |
| 1786 | OG | SER | D | 366 | 20.769 | −46.284 | 40.060 | 1.00 | 136.51 |
| 1787 | C | SER | D | 366 | 23.193 | −46.200 | 41.757 | 1.00 | 138.93 |
| 1788 | O | SER | D | 366 | 23.558 | −45.561 | 40.770 | 1.00 | 147.16 |
| 1789 | N | LYS | D | 367 | 24.003 | −47.014 | 42.425 | 1.00 | 132.33 |
| 1790 | CA | LYS | D | 367 | 25.401 | −47.183 | 42.041 | 1.00 | 133.02 |
| 1791 | CB | LYS | D | 367 | 26.107 | −48.097 | 43.048 | 1.00 | 141.73 |
| 1792 | CG | LYS | D | 367 | 26.039 | −47.591 | 44.485 | 1.00 | 138.03 |
| 1793 | CD | LYS | D | 367 | 26.930 | −48.398 | 45.417 | 1.00 | 136.60 |
| 1794 | CE | LYS | D | 367 | 28.396 | −48.222 | 45.071 | 1.00 | 135.51 |
| 1795 | NZ | LYS | D | 367 | 29.261 | −48.935 | 46.042 | 1.00 | 141.90 |
| 1796 | C | LYS | D | 367 | 25.616 | −47.708 | 40.622 | 1.00 | 124.32 |
| 1797 | O | LYS | D | 367 | 24.869 | −48.552 | 40.135 | 1.00 | 110.94 |
| 1798 | N | GLY | D | 368 | 26.656 | −47.196 | 39.971 | 1.00 | 127.78 |
| 1799 | CA | GLY | D | 368 | 26.977 | −47.599 | 38.613 | 1.00 | 132.10 |
| 1800 | C | GLY | D | 368 | 27.270 | −46.399 | 37.722 | 1.00 | 134.69 |
| 1801 | O | GLY | D | 368 | 26.485 | −45.447 | 37.687 | 1.00 | 123.11 |
| 1802 | N | THR | D | 369 | 28.397 | −46.438 | 37.006 | 1.00 | 135.51 |
| 1803 | CA | THR | D | 369 | 28.789 | −45.342 | 36.108 | 1.00 | 128.38 |
| 1804 | CB | THR | D | 369 | 30.073 | −45.679 | 35.267 | 1.00 | 125.70 |
| 1805 | OG1 | THR | D | 369 | 30.016 | −47.034 | 34.807 | 1.00 | 129.90 |
| 1806 | CG2 | THR | D | 369 | 31.330 | −45.478 | 36.068 | 1.00 | 116.31 |
| 1807 | C | THR | D | 369 | 27.687 | −44.955 | 35.118 | 1.00 | 123.70 |
| 1808 | O | THR | D | 369 | 26.937 | −45.803 | 34.628 | 1.00 | 120.68 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1809 | N | VAL | D | 370 | 27.599 | −43.662 | 34.826 | 1.00 | 115.62 |
| 1810 | CA | VAL | D | 370 | 26.610 | −43.156 | 33.885 | 1.00 | 102.63 |
| 1811 | CB | VAL | D | 370 | 25.711 | −42.083 | 34.530 | 1.00 | 104.13 |
| 1812 | CG1 | VAL | D | 370 | 24.560 | −41.747 | 33.596 | 1.00 | 97.78 |
| 1813 | CG2 | VAL | D | 370 | 25.185 | −42.572 | 35.869 | 1.00 | 92.27 |
| 1814 | C | VAL | D | 370 | 27.358 | −42.529 | 32.716 | 1.00 | 100.15 |
| 1815 | O | VAL | D | 370 | 28.098 | −41.567 | 32.897 | 1.00 | 95.64 |
| 1816 | N | ASN | D | 371 | 27.171 | −43.083 | 31.521 | 1.00 | 102.58 |
| 1817 | CA | ASN | D | 371 | 27.841 | −42.575 | 30.325 | 1.00 | 104.22 |
| 1818 | CB | ASN | D | 371 | 28.171 | −43.724 | 29.358 | 1.00 | 104.22 |
| 1819 | CG | ASN | D | 371 | 29.302 | −44.605 | 29.857 | 1.00 | 114.36 |
| 1820 | OD1 | ASN | D | 371 | 30.410 | −44.131 | 30.106 | 1.00 | 120.72 |
| 1821 | ND2 | ASN | D | 371 | 29.027 | −45.897 | 30.001 | 1.00 | 115.63 |
| 1822 | C | ASN | D | 371 | 27.009 | −41.527 | 29.589 | 1.00 | 108.48 |
| 1823 | O | ASN | D | 371 | 25.830 | −41.741 | 29.293 | 1.00 | 104.61 |
| 1824 | N | LEU | D | 372 | 27.633 | −40.386 | 29.310 | 1.00 | 105.27 |
| 1825 | CA | LEU | D | 372 | 26.978 | −39.305 | 28.585 | 1.00 | 90.17 |
| 1826 | CB | LEU | D | 372 | 26.910 | −38.043 | 29.439 | 1.00 | 81.15 |
| 1827 | CG | LEU | D | 372 | 25.993 | −38.134 | 30.663 | 1.00 | 102.22 |
| 1828 | CD1 | LEU | D | 372 | 25.863 | −36.763 | 31.305 | 1.00 | 109.75 |
| 1829 | CD2 | LEU | D | 372 | 24.622 | −38.645 | 30.249 | 1.00 | 101.63 |
| 1830 | C | LEU | D | 372 | 27.811 | −39.058 | 27.339 | 1.00 | 95.68 |
| 1831 | O | LEU | D | 372 | 28.806 | −38.326 | 27.364 | 1.00 | 72.32 |
| 1832 | N | THR | D | 373 | 27.404 | −39.694 | 26.247 | 1.00 | 100.52 |
| 1833 | CA | THR | D | 373 | 28.122 | −39.574 | 24.988 | 1.00 | 97.24 |
| 1834 | CB | THR | D | 373 | 28.099 | −40.921 | 24.217 | 1.00 | 96.50 |
| 1835 | OG1 | THR | D | 373 | 28.501 | −41.984 | 25.096 | 1.00 | 96.59 |
| 1836 | CG2 | THR | D | 373 | 29.053 | −40.872 | 23.026 | 1.00 | 87.82 |
| 1837 | C | THR | D | 373 | 27.558 | −38.474 | 24.094 | 1.00 | 86.81 |
| 1838 | O | THR | D | 373 | 26.337 | −38.314 | 23.964 | 1.00 | 48.20 |
| 1839 | N | TRP | D | 374 | 28.462 | −37.705 | 23.497 | 1.00 | 79.89 |
| 1840 | CA | TRP | D | 374 | 28.070 | −36.638 | 22.593 | 1.00 | 91.48 |
| 1841 | CB | TRP | D | 374 | 28.814 | −35.339 | 22.911 | 1.00 | 99.08 |
| 1842 | CG | TRP | D | 374 | 28.353 | −34.686 | 24.158 | 1.00 | 87.61 |
| 1843 | CD2 | TRP | D | 374 | 27.228 | −33.818 | 24.296 | 1.00 | 75.56 |
| 1844 | CE2 | TRP | D | 374 | 27.126 | −33.485 | 25.662 | 1.00 | 86.24 |
| 1845 | CE3 | TRP | D | 374 | 26.293 | −33.291 | 23.398 | 1.00 | 67.07 |
| 1846 | CD1 | TRP | D | 374 | 28.877 | −34.839 | 25.405 | 1.00 | 96.56 |
| 1847 | NE1 | TRP | D | 374 | 28.146 | −34.122 | 26.316 | 1.00 | 96.49 |
| 1848 | CZ2 | TRP | D | 374 | 26.123 | −32.646 | 26.156 | 1.00 | 85.35 |
| 1849 | CZ3 | TRP | D | 374 | 25.295 | −32.459 | 23.887 | 1.00 | 83.13 |
| 1850 | CH2 | TRP | D | 374 | 25.219 | −32.144 | 25.256 | 1.00 | 91.51 |
| 1851 | C | TRP | D | 374 | 28.390 | −37.049 | 21.169 | 1.00 | 92.04 |
| 1852 | O | TRP | D | 374 | 29.232 | −37.922 | 20.938 | 1.00 | 81.95 |
| 1853 | N | SER | D | 375 | 27.724 | −36.406 | 20.217 | 1.00 | 88.53 |
| 1854 | CA | SER | D | 375 | 27.943 | −36.701 | 18.805 | 1.00 | 95.24 |
| 1855 | CB | SER | D | 375 | 27.472 | −38.120 | 18.480 | 1.00 | 84.29 |
| 1856 | OG | SER | D | 375 | 26.085 | −38.257 | 18.749 | 1.00 | 77.64 |
| 1857 | C | SER | D | 375 | 27.187 | −35.715 | 17.934 | 1.00 | 87.46 |
| 1858 | O | SER | D | 375 | 26.169 | −35.152 | 18.354 | 1.00 | 78.89 |
| 1859 | N | ARG | D | 376 | 27.688 | −35.512 | 16.721 | 1.00 | 72.60 |
| 1860 | CA | ARG | D | 376 | 27.038 | −34.602 | 15.793 | 1.00 | 78.55 |
| 1861 | CB | ARG | D | 376 | 28.062 | −33.700 | 15.123 | 1.00 | 81.78 |
| 1862 | CG | ARG | D | 376 | 28.767 | −32.759 | 16.063 | 1.00 | 75.19 |
| 1863 | CD | ARG | D | 376 | 29.123 | −31.510 | 15.306 | 1.00 | 77.62 |
| 1864 | NE | ARG | D | 376 | 30.547 | −31.198 | 15.328 | 1.00 | 83.44 |
| 1865 | CZ | ARG | D | 376 | 31.133 | −30.374 | 14.460 | 1.00 | 92.46 |
| 1866 | NH1 | ARG | D | 376 | 30.412 | −29.789 | 13.500 | 1.00 | 79.97 |
| 1867 | NH2 | ARG | D | 376 | 32.436 | −30.125 | 14.553 | 1.00 | 82.49 |
| 1868 | C | ARG | D | 376 | 26.283 | −35.375 | 14.725 | 1.00 | 86.06 |
| 1869 | O | ARG | D | 376 | 26.677 | −36.480 | 14.349 | 1.00 | 94.93 |
| 1870 | N | ALA | D | 377 | 25.197 | −34.792 | 14.233 | 1.00 | 83.87 |
| 1871 | CA | ALA | D | 377 | 24.405 | −35.446 | 13.201 | 1.00 | 87.09 |
| 1872 | CB | ALA | D | 377 | 23.101 | −34.692 | 12.978 | 1.00 | 58.09 |
| 1873 | C | ALA | D | 377 | 25.216 | −35.499 | 11.909 | 1.00 | 78.25 |
| 1874 | O | ALA | D | 377 | 25.055 | −36.403 | 11.095 | 1.00 | 66.16 |
| 1875 | N | SER | D | 378 | 26.095 | −34.525 | 11.728 | 1.00 | 77.12 |
| 1876 | CA | SER | D | 378 | 26.920 | −34.488 | 10.537 | 1.00 | 85.44 |
| 1877 | CB | SER | D | 378 | 27.657 | −33.144 | 10.439 | 1.00 | 84.90 |
| 1878 | OG | SER | D | 378 | 28.535 | −32.944 | 11.535 | 1.00 | 77.62 |
| 1879 | C | SER | D | 378 | 27.928 | −35.628 | 10.583 | 1.00 | 91.29 |
| 1880 | O | SER | D | 378 | 28.214 | −36.260 | 9.558 | 1.00 | 84.06 |
| 1881 | N | GLY | D | 379 | 28.451 | −35.890 | 11.780 | 1.00 | 80.65 |
| 1882 | CA | GLY | D | 379 | 29.442 | −36.936 | 11.940 | 1.00 | 74.38 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1883 | C | GLY | D | 379 | 30.822 | −36.338 | 12.176 | 1.00 | 79.21 |
| 1884 | O | GLY | D | 379 | 31.843 | −37.041 | 12.187 | 1.00 | 60.75 |
| 1885 | N | LYS | D | 380 | 30.861 | −35.022 | 12.361 | 1.00 | 99.94 |
| 1886 | CA | LYS | D | 380 | 32.126 | −34.347 | 12.627 | 1.00 | 97.51 |
| 1887 | CB | LYS | D | 380 | 32.028 | −32.861 | 12.261 | 1.00 | 72.31 |
| 1888 | CG | LYS | D | 380 | 31.654 | −32.641 | 10.806 | 1.00 | 86.77 |
| 1889 | CD | LYS | D | 380 | 31.762 | −31.184 | 10.418 | 1.00 | 115.30 |
| 1890 | CE | LYS | D | 380 | 31.501 | −30.993 | 8.936 | 1.00 | 104.24 |
| 1891 | NZ | LYS | D | 380 | 31.712 | −29.578 | 8.538 | 1.00 | 106.00 |
| 1892 | C | LYS | D | 380 | 32.462 | −34.532 | 14.108 | 1.00 | 80.11 |
| 1893 | O | LYS | D | 380 | 31.614 | −34.941 | 14.905 | 1.00 | 71.27 |
| 1894 | N | PRO | D | 381 | 33.708 | −34.244 | 14.494 | 1.00 | 96.52 |
| 1895 | CD | PRO | D | 381 | 34.861 | −33.892 | 13.650 | 1.00 | 99.31 |
| 1896 | CA | PRO | D | 381 | 34.118 | −34.399 | 15.892 | 1.00 | 100.34 |
| 1897 | CB | PRO | D | 381 | 35.636 | −34.192 | 15.838 | 1.00 | 104.21 |
| 1898 | CG | PRO | D | 381 | 35.996 | −34.528 | 14.412 | 1.00 | 105.84 |
| 1899 | C | PRO | D | 381 | 33.451 | −33.420 | 16.849 | 1.00 | 95.04 |
| 1900 | O | PRO | D | 381 | 33.045 | −32.324 | 16.456 | 1.00 | 100.99 |
| 1901 | N | VAL | D | 382 | 33.345 | −33.837 | 18.107 | 1.00 | 84.05 |
| 1902 | CA | VAL | D | 382 | 32.768 | −33.017 | 19.161 | 1.00 | 84.37 |
| 1903 | CB | VAL | D | 382 | 31.702 | −33.799 | 19.975 | 1.00 | 83.07 |
| 1904 | CG1 | VAL | D | 382 | 30.516 | −34.158 | 19.099 | 1.00 | 76.18 |
| 1905 | CG2 | VAL | D | 382 | 32.307 | −35.050 | 20.538 | 1.00 | 69.32 |
| 1906 | C | VAL | D | 382 | 33.943 | −32.646 | 20.072 | 1.00 | 99.58 |
| 1907 | O | VAL | D | 382 | 34.863 | −33.451 | 20.257 | 1.00 | 93.66 |
| 1908 | N | ASN | D | 383 | 33.925 | −31.432 | 20.626 | 1.00 | 104.87 |
| 1909 | CA | ASN | D | 383 | 35.008 | −30.975 | 21.500 | 1.00 | 99.49 |
| 1910 | CB | ASN | D | 383 | 34.895 | −29.462 | 21.765 | 1.00 | 103.59 |
| 1911 | CG | ASN | D | 383 | 35.002 | −28.622 | 20.494 | 1.00 | 112.35 |
| 1912 | OD1 | ASN | D | 383 | 35.038 | −27.390 | 20.554 | 1.00 | 120.58 |
| 1913 | ND2 | ASN | D | 383 | 35.047 | −29.283 | 19.343 | 1.00 | 115.42 |
| 1914 | C | ASN | D | 383 | 35.013 | −31.725 | 22.835 | 1.00 | 96.54 |
| 1915 | O | ASN | D | 383 | 34.264 | −32.683 | 23.028 | 1.00 | 72.33 |
| 1916 | N | HIS | D | 384 | 35.861 | −31.272 | 23.754 | 1.00 | 94.43 |
| 1917 | CA | HIS | D | 384 | 35.972 | −31.890 | 25.066 | 1.00 | 81.61 |
| 1918 | CB | HIS | D | 384 | 37.312 | −31.518 | 25.685 | 1.00 | 94.68 |
| 1919 | CG | HIS | D | 384 | 38.467 | −31.692 | 24.753 | 1.00 | 110.51 |
| 1920 | CD2 | HIS | D | 384 | 39.362 | −30.801 | 24.266 | 1.00 | 115.09 |
| 1921 | ND1 | HIS | D | 384 | 38.795 | −32.909 | 24.194 | 1.00 | 119.97 |
| 1922 | CE1 | HIS | D | 384 | 39.843 | −32.760 | 23.404 | 1.00 | 119.99 |
| 1923 | NE2 | HIS | D | 384 | 40.207 | −31.490 | 23.430 | 1.00 | 119.41 |
| 1924 | C | HIS | D | 384 | 34.839 | −31.440 | 25.984 | 1.00 | 83.84 |
| 1925 | O | HIS | D | 384 | 34.736 | −30.262 | 26.329 | 1.00 | 88.68 |
| 1926 | N | SER | D | 385 | 33.987 | −32.381 | 26.374 | 1.00 | 57.66 |
| 1927 | CA | SER | D | 385 | 32.876 | −32.076 | 27.256 | 1.00 | 67.02 |
| 1928 | CB | SER | D | 385 | 31.755 | −33.097 | 27.054 | 1.00 | 65.30 |
| 1929 | OG | SER | D | 385 | 32.287 | −34.355 | 26.690 | 1.00 | 90.70 |
| 1930 | C | SER | D | 385 | 33.310 | −32.051 | 28.720 | 1.00 | 75.32 |
| 1931 | O | SER | D | 385 | 34.401 | −32.506 | 29.062 | 1.00 | 60.75 |
| 1932 | N | THR | D | 386 | 32.445 | −31.499 | 29.571 | 1.00 | 72.22 |
| 1933 | CA | THR | D | 386 | 32.703 | −31.392 | 31.003 | 1.00 | 72.79 |
| 1934 | CB | THR | D | 386 | 32.862 | −29.908 | 31.441 | 1.00 | 78.91 |
| 1935 | OG1 | THR | D | 386 | 34.030 | −29.342 | 30.833 | 1.00 | 77.58 |
| 1936 | CG2 | THR | D | 386 | 33.008 | −29.805 | 32.948 | 1.00 | 72.53 |
| 1937 | C | THR | D | 386 | 31.573 | −32.034 | 31.817 | 1.00 | 79.25 |
| 1938 | O | THR | D | 386 | 30.422 | −31.579 | 31.802 | 1.00 | 60.64 |
| 1939 | N | ARG | D | 387 | 31.918 | −33.104 | 32.522 | 1.00 | 76.59 |
| 1940 | CA | ARG | D | 387 | 30.967 | −33.822 | 33.356 | 1.00 | 74.63 |
| 1941 | CB | ARG | D | 387 | 31.325 | −35.308 | 33.338 | 1.00 | 74.42 |
| 1942 | CG | ARG | D | 387 | 30.426 | −36.215 | 34.153 | 1.00 | 88.41 |
| 1943 | CD | ARG | D | 387 | 31.060 | −37.605 | 34.250 | 1.00 | 111.86 |
| 1944 | NE | ARG | D | 387 | 30.260 | −38.536 | 35.041 | 1.00 | 110.24 |
| 1945 | CZ | ARG | D | 387 | 29.182 | −39.167 | 34.592 | 1.00 | 109.65 |
| 1946 | NH1 | ARG | D | 387 | 28.766 | −38.976 | 33.348 | 1.00 | 117.06 |
| 1947 | NH2 | ARG | D | 387 | 28.520 | −39.992 | 35.389 | 1.00 | 110.59 |
| 1948 | C | ARG | D | 387 | 31.035 | −33.246 | 34.784 | 1.00 | 72.74 |
| 1949 | O | ARG | D | 387 | 32.096 | −32.826 | 35.248 | 1.00 | 60.41 |
| 1950 | N | LYS | D | 388 | 29.898 | −33.201 | 35.467 | 1.00 | 54.01 |
| 1951 | CA | LYS | D | 388 | 29.850 | −32.665 | 36.821 | 1.00 | 75.74 |
| 1952 | CB | LYS | D | 388 | 29.581 | −31.165 | 36.799 | 1.00 | 79.98 |
| 1953 | CG | LYS | D | 388 | 30.549 | −30.360 | 35.961 | 1.00 | 104.46 |
| 1954 | CD | LYS | D | 388 | 30.041 | −28.934 | 35.798 | 1.00 | 104.32 |
| 1955 | CE | LYS | D | 388 | 30.882 | −28.154 | 34.803 | 1.00 | 95.19 |
| 1956 | NZ | LYS | D | 388 | 30.320 | −26.803 | 34.581 | 1.00 | 103.25 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 1957 | C | LYS | D | 388 | 28.751 | −33.331 | 37.640 | 1.00 | 88.19 |
| 1958 | O | LYS | D | 388 | 27.590 | −32.936 | 37.564 | 1.00 | 73.06 |
| 1959 | N | GLU | D | 389 | 29.121 | −34.335 | 38.428 | 1.00 | 98.33 |
| 1960 | CA | GLU | D | 389 | 28.159 | −35.048 | 39.260 | 1.00 | 86.86 |
| 1961 | CB | GLU | D | 389 | 28.617 | −36.497 | 39.463 | 1.00 | 104.84 |
| 1962 | CG | GLU | D | 389 | 28.742 | −37.296 | 38.159 | 1.00 | 113.79 |
| 1963 | CD | GLU | D | 389 | 29.358 | −38.669 | 38.361 | 1.00 | 122.68 |
| 1964 | OE1 | GLU | D | 389 | 28.809 | −39.454 | 39.166 | 1.00 | 133.19 |
| 1965 | OE2 | GLU | D | 389 | 30.386 | −38.961 | 37.712 | 1.00 | 116.52 |
| 1966 | C | GLU | D | 389 | 28.043 | −34.327 | 40.590 | 1.00 | 71.26 |
| 1967 | O | GLU | D | 389 | 28.969 | −34.304 | 41.384 | 1.00 | 89.41 |
| 1968 | N | GLU | D | 390 | 26.894 | −33.719 | 40.816 | 1.00 | 79.68 |
| 1969 | CA | GLU | D | 390 | 26.653 | −32.977 | 42.038 | 1.00 | 66.13 |
| 1970 | CB | GLU | D | 390 | 26.257 | −31.545 | 41.682 | 1.00 | 96.06 |
| 1971 | CG | GLU | D | 390 | 25.836 | −30.677 | 42.848 | 1.00 | 119.48 |
| 1972 | CD | GLU | D | 390 | 25.473 | −29.269 | 42.414 | 1.00 | 125.33 |
| 1973 | OE1 | GLU | D | 390 | 24.615 | −29.121 | 41.517 | 1.00 | 134.03 |
| 1974 | OE2 | GLU | D | 390 | 26.047 | −28.310 | 42.969 | 1.00 | 128.86 |
| 1975 | C | GLU | D | 390 | 25.542 | −33.669 | 42.821 | 1.00 | 84.86 |
| 1976 | O | GLU | D | 390 | 24.358 | −33.383 | 42.644 | 1.00 | 64.06 |
| 1977 | N | LYS | D | 391 | 25.941 | −34.584 | 43.696 | 1.00 | 93.57 |
| 1978 | CA | LYS | D | 391 | 24.994 | −35.346 | 44.496 | 1.00 | 101.23 |
| 1979 | CB | LYS | D | 391 | 25.695 | −36.571 | 45.084 | 1.00 | 101.94 |
| 1980 | CG | LYS | D | 391 | 24.754 | −37.708 | 45.430 | 1.00 | 112.94 |
| 1981 | CD | LYS | D | 391 | 25.512 | −39.014 | 45.618 | 1.00 | 104.80 |
| 1982 | CE | LYS | D | 391 | 24.547 | −40.190 | 45.698 | 1.00 | 125.71 |
| 1983 | NZ | LYS | D | 391 | 25.259 | −41.498 | 45.780 | 1.00 | 127.69 |
| 1984 | C | LYS | D | 391 | 24.337 | −34.539 | 45.612 | 1.00 | 105.38 |
| 1985 | O | LYS | D | 391 | 24.943 | −33.639 | 46.190 | 1.00 | 111.04 |
| 1986 | N | GLN | D | 392 | 23.083 | −34.874 | 45.895 | 1.00 | 115.77 |
| 1987 | CA | GLN | D | 392 | 22.300 | −34.225 | 46.940 | 1.00 | 125.09 |
| 1988 | CB | GLN | D | 392 | 21.294 | −33.244 | 46.337 | 1.00 | 121.85 |
| 1989 | CG | GLN | D | 392 | 21.913 | −32.165 | 45.480 | 1.00 | 124.90 |
| 1990 | CD | GLN | D | 392 | 20.873 | −31.307 | 44.793 | 1.00 | 118.38 |
| 1991 | OE1 | GLN | D | 392 | 20.029 | −30.697 | 45.445 | 1.00 | 122.46 |
| 1992 | NE2 | GLN | D | 392 | 20.929 | −31.256 | 43.469 | 1.00 | 105.21 |
| 1993 | C | GLN | D | 392 | 21.542 | −35.318 | 47.681 | 1.00 | 136.05 |
| 1994 | O | GLN | D | 392 | 20.568 | −35.872 | 47.162 | 1.00 | 130.46 |
| 1995 | N | ARG | D | 393 | 21.997 | −35.636 | 48.888 | 1.00 | 143.07 |
| 1996 | CA | ARG | D | 393 | 21.350 | −36.665 | 49.695 | 1.00 | 147.59 |
| 1997 | CB | ARG | D | 393 | 22.049 | −36.795 | 51.051 | 1.00 | 147.15 |
| 1998 | CG | ARG | D | 393 | 23.004 | −35.659 | 51.374 | 1.00 | 150.74 |
| 1999 | CD | ARG | D | 393 | 23.553 | −35.812 | 52.777 | 1.00 | 156.19 |
| 2000 | NE | ARG | D | 393 | 22.489 | −35.781 | 53.778 | 1.00 | 155.97 |
| 2001 | CZ | ARG | D | 393 | 22.699 | −35.849 | 55.088 | 1.00 | 151.36 |
| 2002 | NH1 | ARG | D | 393 | 23.938 | −35.950 | 55.549 | 1.00 | 150.10 |
| 2003 | NH2 | ARG | D | 393 | 21.677 | −35.818 | 55.933 | 1.00 | 147.00 |
| 2004 | C | ARG | D | 393 | 19.875 | −36.326 | 49.889 | 1.00 | 150.27 |
| 2005 | O | ARG | D | 393 | 19.116 | −37.106 | 50.469 | 1.00 | 155.75 |
| 2006 | N | ASN | D | 394 | 19.486 | −35.151 | 49.399 | 1.00 | 153.01 |
| 2007 | CA | ASN | D | 394 | 18.108 | −34.679 | 49.476 | 1.00 | 145.42 |
| 2008 | CB | ASN | D | 394 | 18.026 | −33.229 | 48.996 | 1.00 | 142.86 |
| 2009 | CG | ASN | D | 394 | 16.612 | −32.681 | 49.029 | 1.00 | 140.20 |
| 2010 | OD1 | ASN | D | 394 | 16.306 | −31.679 | 48.380 | 1.00 | 139.59 |
| 2011 | ND2 | ASN | D | 394 | 15.743 | −33.330 | 49.795 | 1.00 | 140.36 |
| 2012 | C | ASN | D | 394 | 17.254 | −35.557 | 48.568 | 1.00 | 143.44 |
| 2013 | O | ASN | D | 394 | 16.032 | −35.417 | 48.514 | 1.00 | 136.41 |
| 2014 | N | GLY | D | 395 | 17.918 | −36.465 | 47.859 | 1.00 | 143.08 |
| 2015 | CA | GLY | D | 395 | 17.228 | −37.350 | 46.942 | 1.00 | 142.75 |
| 2016 | C | GLY | D | 395 | 17.336 | −36.788 | 45.540 | 1.00 | 143.86 |
| 2017 | O | GLY | D | 395 | 16.326 | −36.498 | 44.893 | 1.00 | 138.56 |
| 2018 | N | THR | D | 396 | 18.570 | −36.624 | 45.071 | 1.00 | 141.36 |
| 2019 | CA | THR | D | 396 | 18.820 | −36.082 | 43.741 | 1.00 | 132.93 |
| 2020 | CB | THR | D | 396 | 18.387 | −34.585 | 43.652 | 1.00 | 137.58 |
| 2021 | OG1 | THR | D | 396 | 16.967 | −34.472 | 43.815 | 1.00 | 130.89 |
| 2022 | CG2 | THR | D | 396 | 18.776 | −33.992 | 42.308 | 1.00 | 142.52 |
| 2023 | C | THR | D | 396 | 20.303 | −36.177 | 43.388 | 1.00 | 121.83 |
| 2024 | O | THR | D | 396 | 21.139 | −35.575 | 44.056 | 1.00 | 124.93 |
| 2025 | N | LEU | D | 397 | 20.629 | −36.940 | 42.350 | 1.00 | 114.45 |
| 2026 | CA | LEU | D | 397 | 22.015 | −37.059 | 41.914 | 1.00 | 108.86 |
| 2027 | CB | LEU | D | 397 | 22.439 | −38.525 | 41.793 | 1.00 | 95.99 |
| 2028 | CG | LEU | D | 397 | 23.810 | −38.710 | 41.128 | 1.00 | 92.61 |
| 2029 | CD1 | LEU | D | 397 | 24.873 | −37.961 | 41.906 | 1.00 | 84.95 |
| 2030 | CD2 | LEU | D | 397 | 24.144 | −40.181 | 41.043 | 1.00 | 102.46 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2031 | C | LEU | D | 397 | 22.199 | −36.362 | 40.564 | 1.00 | 112.95 |
| 2032 | O | LEU | D | 397 | 22.184 | −36.999 | 39.508 | 1.00 | 112.52 |
| 2033 | N | THR | D | 398 | 22.364 | −35.045 | 40.609 | 1.00 | 104.59 |
| 2034 | CA | THR | D | 398 | 22.561 | −34.247 | 39.408 | 1.00 | 93.30 |
| 2035 | CB | THR | D | 398 | 22.601 | −32.748 | 39.743 | 1.00 | 95.31 |
| 2036 | OG1 | THR | D | 398 | 21.268 | −32.277 | 39.987 | 1.00 | 84.63 |
| 2037 | CG2 | THR | D | 398 | 23.238 | −31.962 | 38.607 | 1.00 | 95.73 |
| 2038 | C | THR | D | 398 | 23.845 | −34.596 | 38.669 | 1.00 | 93.46 |
| 2039 | O | THR | D | 398 | 24.921 | −34.700 | 39.265 | 1.00 | 70.03 |
| 2040 | N | VAL | D | 399 | 23.711 | −34.776 | 37.359 | 1.00 | 96.28 |
| 2041 | CA | VAL | D | 399 | 24.840 | −35.084 | 36.493 | 1.00 | 94.67 |
| 2042 | CB | VAL | D | 399 | 24.914 | −36.587 | 36.139 | 1.00 | 100.70 |
| 2043 | CG1 | VAL | D | 399 | 26.159 | −36.864 | 35.276 | 1.00 | 73.22 |
| 2044 | CG2 | VAL | D | 399 | 24.945 | −37.418 | 37.416 | 1.00 | 97.61 |
| 2045 | C | VAL | D | 399 | 24.634 | −34.287 | 35.220 | 1.00 | 87.29 |
| 2046 | O | VAL | D | 399 | 23.632 | −34.460 | 34.518 | 1.00 | 74.24 |
| 2047 | N | THR | D | 400 | 25.574 | −33.391 | 34.945 | 1.00 | 87.67 |
| 2048 | CA | THR | D | 400 | 25.508 | −32.561 | 33.758 | 1.00 | 70.32 |
| 2049 | CB | THR | D | 400 | 25.363 | −31.061 | 34.122 | 1.00 | 52.74 |
| 2050 | OG1 | THR | D | 400 | 26.586 | −30.568 | 34.689 | 1.00 | 61.15 |
| 2051 | CG2 | THR | D | 400 | 24.237 | −30.872 | 35.115 | 1.00 | 23.86 |
| 2052 | C | THR | D | 400 | 26.765 | −32.751 | 32.928 | 1.00 | 67.96 |
| 2053 | O | THR | D | 400 | 27.775 | −33.255 | 33.407 | 1.00 | 58.70 |
| 2054 | N | SER | D | 401 | 26.674 | −32.380 | 31.661 | 1.00 | 79.91 |
| 2055 | CA | SER | D | 401 | 27.802 | −32.450 | 30.748 | 1.00 | 76.71 |
| 2056 | CB | SER | D | 401 | 27.742 | −33.710 | 29.881 | 1.00 | 66.01 |
| 2057 | OG | SER | D | 401 | 28.927 | −33.841 | 29.107 | 1.00 | 74.85 |
| 2058 | C | SER | D | 401 | 27.647 | −31.201 | 29.897 | 1.00 | 78.83 |
| 2059 | O | SER | D | 401 | 26.551 | −30.902 | 29.410 | 1.00 | 61.69 |
| 2060 | N | THR | D | 402 | 28.732 | −30.455 | 29.748 | 1.00 | 74.51 |
| 2061 | CA | THR | D | 402 | 28.688 | −29.225 | 28.980 | 1.00 | 66.74 |
| 2062 | CB | THR | D | 402 | 29.016 | −28.006 | 29.875 | 1.00 | 48.69 |
| 2063 | OG1 | THR | D | 402 | 27.882 | −27.732 | 30.709 | 1.00 | 45.21 |
| 2064 | CG2 | THR | D | 402 | 29.344 | −26.786 | 29.029 | 1.00 | 63.22 |
| 2065 | C | THR | D | 402 | 29.642 | −29.295 | 27.817 | 1.00 | 51.33 |
| 2066 | O | THR | D | 402 | 30.852 | −29.334 | 27.998 | 1.00 | 62.20 |
| 2067 | N | LEU | D | 403 | 29.077 | −29.291 | 26.618 | 1.00 | 56.46 |
| 2068 | CA | LEU | D | 403 | 29.863 | −29.375 | 25.393 | 1.00 | 64.98 |
| 2069 | CB | LEU | D | 403 | 29.233 | −30.398 | 24.438 | 1.00 | 53.46 |
| 2070 | CG | LEU | D | 403 | 29.937 | −30.519 | 23.084 | 1.00 | 48.61 |
| 2071 | CD1 | LEU | D | 403 | 31.264 | −31.224 | 23.243 | 1.00 | 51.27 |
| 2072 | CD2 | LEU | D | 403 | 29.036 | −31.280 | 22.129 | 1.00 | 65.29 |
| 2073 | C | LEU | D | 403 | 30.056 | −28.054 | 24.653 | 1.00 | 50.90 |
| 2074 | O | LEU | D | 403 | 29.099 | −27.419 | 24.210 | 1.00 | 40.55 |
| 2075 | N | PRO | D | 404 | 31.309 | −27.615 | 24.535 | 1.00 | 43.68 |
| 2076 | CD | PRO | D | 404 | 32.507 | −28.107 | 25.236 | 1.00 | 73.88 |
| 2077 | CA | PRO | D | 404 | 31.593 | −26.366 | 23.834 | 1.00 | 57.28 |
| 2078 | CB | PRO | D | 404 | 33.103 | −26.196 | 24.024 | 1.00 | 50.33 |
| 2079 | CG | PRO | D | 404 | 33.349 | −26.850 | 25.340 | 1.00 | 80.63 |
| 2080 | C | PRO | D | 404 | 31.220 | −26.590 | 22.376 | 1.00 | 58.60 |
| 2081 | O | PRO | D | 404 | 31.541 | −27.624 | 21.805 | 1.00 | 82.55 |
| 2082 | N | VAL | D | 405 | 30.534 | −25.633 | 21.774 | 1.00 | 73.60 |
| 2083 | CA | VAL | D | 405 | 30.133 | −25.762 | 20.383 | 1.00 | 60.32 |
| 2084 | CB | VAL | D | 405 | 28.604 | −25.756 | 20.267 | 1.00 | 67.75 |
| 2085 | CG1 | VAL | D | 405 | 28.195 | −25.486 | 18.844 | 1.00 | 86.08 |
| 2086 | CG2 | VAL | D | 405 | 28.047 | −27.092 | 20.719 | 1.00 | 52.01 |
| 2087 | C | VAL | D | 405 | 30.712 | −24.647 | 19.516 | 1.00 | 62.52 |
| 2088 | O | VAL | D | 405 | 30.909 | −23.519 | 19.980 | 1.00 | 78.89 |
| 2089 | N | GLY | D | 406 | 30.998 | −24.968 | 18.259 | 1.00 | 59.64 |
| 2090 | CA | GLY | D | 406 | 31.532 | −23.968 | 17.351 | 1.00 | 63.61 |
| 2091 | C | GLY | D | 406 | 30.466 | −22.919 | 17.110 | 1.00 | 65.38 |
| 2092 | O | GLY | D | 406 | 29.284 | −23.251 | 16.969 | 1.00 | 33.62 |
| 2093 | N | THR | D | 407 | 30.865 | −21.654 | 17.072 | 1.00 | 49.63 |
| 2094 | CA | THR | D | 407 | 29.897 | −20.588 | 16.869 | 1.00 | 66.33 |
| 2095 | CB | THR | D | 407 | 30.558 | −19.204 | 16.917 | 1.00 | 74.67 |
| 2096 | OG1 | THR | D | 407 | 31.105 | −18.988 | 18.221 | 1.00 | 99.28 |
| 2097 | CG2 | THR | D | 407 | 29.543 | −18.115 | 16.633 | 1.00 | 81.15 |
| 2098 | C | THR | D | 407 | 29.213 | −20.766 | 15.534 | 1.00 | 71.38 |
| 2099 | O | THR | D | 407 | 27.993 | −20.885 | 15.465 | 1.00 | 73.07 |
| 2100 | N | ALA | D | 408 | 30.001 | −20.802 | 14.469 | 1.00 | 78.88 |
| 2101 | CA | ALA | D | 408 | 29.444 | −20.973 | 13.139 | 1.00 | 72.64 |
| 2102 | CB | ALA | D | 408 | 30.565 | −20.934 | 12.099 | 1.00 | 77.53 |
| 2103 | C | ALA | D | 408 | 28.652 | −22.280 | 13.024 | 1.00 | 72.09 |
| 2104 | O | ALA | D | 408 | 27.579 | −22.303 | 12.433 | 1.00 | 57.11 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2105 | N | ASP | D | 409 | 29.180 | −23.359 | 13.595 | 1.00 | 80.82 |
| 2106 | CA | ASP | D | 409 | 28.519 | −24.656 | 13.540 | 1.00 | 57.62 |
| 2107 | CB | ASP | D | 409 | 29.278 | −25.676 | 14.397 | 1.00 | 79.43 |
| 2108 | CG | ASP | D | 409 | 30.671 | −25.980 | 13.856 | 1.00 | 99.71 |
| 2109 | OD1 | ASP | D | 409 | 30.767 | −26.510 | 12.730 | 1.00 | 104.83 |
| 2110 | OD2 | ASP | D | 409 | 31.670 | −25.693 | 14.553 | 1.00 | 101.64 |
| 2111 | C | ASP | D | 409 | 27.066 | −24.576 | 13.997 | 1.00 | 57.89 |
| 2112 | O | ASP | D | 409 | 26.161 | −24.887 | 13.246 | 1.00 | 55.03 |
| 2113 | N | TRP | D | 410 | 26.835 | −24.144 | 15.229 | 1.00 | 70.07 |
| 2114 | CA | TRP | D | 410 | 25.470 | −24.063 | 15.748 | 1.00 | 70.03 |
| 2115 | CB | TRP | D | 410 | 25.471 | −23.611 | 17.219 | 1.00 | 65.48 |
| 2116 | CG | TRP | D | 410 | 24.088 | −23.401 | 17.808 | 1.00 | 29.36 |
| 2117 | CD2 | TRP | D | 410 | 23.294 | −24.371 | 18.502 | 1.00 | 31.77 |
| 2118 | CE2 | TRP | D | 410 | 22.058 | −23.764 | 18.798 | 1.00 | 16.78 |
| 2119 | CE3 | TRP | D | 410 | 23.508 | −25.699 | 18.896 | 1.00 | 19.69 |
| 2120 | CD1 | TRP | D | 410 | 23.329 | −22.283 | 17.727 | 1.00 | 28.80 |
| 2121 | NE1 | TRP | D | 410 | 22.105 | −22.488 | 18.318 | 1.00 | 30.36 |
| 2122 | CZ2 | TRP | D | 410 | 21.035 | −24.435 | 19.463 | 1.00 | 32.07 |
| 2123 | CZ3 | TRP | D | 410 | 22.497 | −26.360 | 19.553 | 1.00 | 39.38 |
| 2124 | CH2 | TRP | D | 410 | 21.268 | −25.728 | 19.831 | 1.00 | 11.10 |
| 2125 | C | TRP | D | 410 | 24.596 | −23.135 | 14.930 | 1.00 | 74.33 |
| 2126 | O | TRP | D | 410 | 23.431 | −23.432 | 14.690 | 1.00 | 73.16 |
| 2127 | N | ILE | D | 411 | 25.162 | −22.013 | 14.502 | 1.00 | 84.81 |
| 2128 | CA | ILE | D | 411 | 24.423 | −21.035 | 13.721 | 1.00 | 84.99 |
| 2129 | CB | ILE | D | 411 | 25.230 | −19.731 | 13.585 | 1.00 | 89.18 |
| 2130 | CG2 | ILE | D | 411 | 24.604 | −18.833 | 12.536 | 1.00 | 97.29 |
| 2131 | CG1 | ILE | D | 411 | 25.270 | −19.009 | 14.935 | 1.00 | 88.78 |
| 2132 | CD1 | ILE | D | 411 | 26.051 | −17.708 | 14.922 | 1.00 | 95.73 |
| 2133 | C | ILE | D | 411 | 24.008 | −21.518 | 12.332 | 1.00 | 91.19 |
| 2134 | O | ILE | D | 411 | 22.945 | −21.142 | 11.845 | 1.00 | 87.92 |
| 2135 | N | GLU | D | 412 | 24.826 | −22.355 | 11.699 | 1.00 | 93.28 |
| 2136 | CA | GLU | D | 412 | 24.492 | −22.841 | 10.365 | 1.00 | 84.53 |
| 2137 | CB | GLU | D | 412 | 25.769 | −23.041 | 9.544 | 1.00 | 101.44 |
| 2138 | CG | GLU | D | 412 | 26.285 | −21.726 | 8.947 | 1.00 | 116.13 |
| 2139 | CD | GLU | D | 412 | 27.68S | −21.828 | 8.362 | 1.00 | 129.63 |
| 2140 | OE1 | GLU | D | 412 | 27.933 | −22.764 | 7.569 | 1.00 | 140.10 |
| 2141 | OE2 | GLU | D | 412 | 28.534 | −20.965 | 8.690 | 1.00 | 118.74 |
| 2142 | C | GLU | D | 412 | 23.607 | −24.082 | 10.299 | 1.00 | 74.48 |
| 2143 | O | GLU | D | 412 | 23.366 | −24.607 | 9.219 | 1.00 | 86.68 |
| 2144 | N | GLY | D | 413 | 23.118 | −24.549 | 11.444 | 1.00 | 76.85 |
| 2145 | CA | GLY | D | 413 | 22.223 | −25.698 | 11.444 | 1.00 | 74.28 |
| 2146 | C | GLY | D | 413 | 22.674 | −27.035 | 12.008 | 1.00 | 76.65 |
| 2147 | O | GLY | D | 413 | 21.916 | −28.005 | 11.949 | 1.00 | 82.41 |
| 2148 | N | GLU | D | 414 | 23.883 | −27.114 | 12.550 | 1.00 | 65.64 |
| 2149 | CA | GLU | D | 414 | 24.354 | −28.378 | 13.101 | 1.00 | 77.23 |
| 2150 | CB | GLU | D | 414 | 25.797 | −28.240 | 13.602 | 1.00 | 80.96 |
| 2151 | CG | GLU | D | 414 | 26.375 | −29.480 | 14.287 | 1.00 | 87.78 |
| 2152 | CD | GLU | D | 414 | 26.789 | −30.585 | 13.333 | 1.00 | 76.27 |
| 2153 | OE1 | GLU | D | 414 | 25.898 | −31.318 | 12.829 | 1.00 | 62.50 |
| 2154 | OE2 | GLU | D | 414 | 28.019 | −30.702 | 13.108 | 1.00 | 37.65 |
| 2155 | C | GLU | D | 414 | 23.445 | −28.796 | 14.246 | 1.00 | 67.88 |
| 2156 | O | GLU | D | 414 | 22.921 | −27.952 | 14.961 | 1.00 | 69.80 |
| 2157 | N | THR | D | 415 | 23.235 | −30.097 | 14.395 | 1.00 | 63.37 |
| 2158 | CA | THR | D | 415 | 22.421 | −30.598 | 15.479 | 1.00 | 68.87 |
| 2159 | CB | THR | D | 415 | 21.219 | −31.360 | 14.964 | 1.00 | 58.00 |
| 2160 | OG1 | THR | D | 415 | 20.910 | −32.433 | 15.871 | 1.00 | 69.86 |
| 2161 | CG2 | THR | D | 415 | 21.494 | −31.887 | 13.574 | 1.00 | 80.41 |
| 2162 | C | THR | D | 415 | 23.283 | −31.515 | 16.333 | 1.00 | 76.32 |
| 2163 | O | THR | D | 415 | 23.915 | −32.436 | 15.820 | 1.00 | 71.23 |
| 2164 | N | TYR | D | 416 | 23.325 | −31.246 | 17.636 | 1.00 | 75.53 |
| 2165 | CA | TYR | D | 416 | 24.134 | −32.045 | 18.544 | 1.00 | 62.07 |
| 2166 | CB | TYR | D | 416 | 24.929 | −31.136 | 19.473 | 1.00 | 51.85 |
| 2167 | CG | TYR | D | 416 | 25.826 | −30.186 | 18.710 | 1.00 | 24.74 |
| 2168 | CD1 | TYR | D | 416 | 25.295 | −29.077 | 18.033 | 1.00 | 46.37 |
| 2169 | CE1 | TYR | D | 416 | 26.115 | −28.205 | 17.324 | 1.00 | 27.12 |
| 2170 | CD2 | TYR | D | 416 | 27.191 | −30.394 | 18.652 | 1.00 | 38.98 |
| 2171 | CE2 | TYR | D | 416 | 28.025 | −29.525 | 17.941 | 1.00 | 62.30 |
| 2172 | CZ | TYR | D | 416 | 27.482 | −28.435 | 17.282 | 1.00 | 60.88 |
| 2173 | OH | TYR | D | 416 | 28.312 | −27.580 | 16.586 | 1.00 | 64.76 |
| 2174 | C | TYR | D | 416 | 23.298 | −33.039 | 19.334 | 1.00 | 72.68 |
| 2175 | O | TYR | D | 416 | 22.124 | −32.785 | 19.663 | 1.00 | 55.13 |
| 2176 | N | GLN | D | 417 | 23.921 | −34.177 | 19.630 | 1.00 | 67.16 |
| 2177 | CA | GLN | D | 417 | 23.247 | −35.259 | 20.329 | 1.00 | 77.31 |
| 2178 | CB | GLN | D | 417 | 22.996 | −36.408 | 19.349 | 1.00 | 89.08 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2179 | CG | GLN | D | 417 | 22.266 | −37.583 | 19.965 | 1.00 | 102.54 |
| 2180 | CD | GLN | D | 417 | 22.250 | −38.794 | 19.058 | 1.00 | 111.74 |
| 2181 | OE1 | GLN | D | 417 | 23.293 | −39.390 | 18.780 | 1.00 | 116.68 |
| 2182 | NE2 | GLN | D | 417 | 21.062 | −39.167 | 18.588 | 1.00 | 112.76 |
| 2183 | C | GLN | D | 417 | 23.979 | −35.798 | 21.553 | 1.00 | 68.26 |
| 2184 | O | GLN | D | 417 | 25.203 | −35.989 | 21.546 | 1.00 | 62.36 |
| 2185 | N | CYS | D | 418 | 23.198 | −36.074 | 22.591 | 1.00 | 53.68 |
| 2186 | CA | CYS | D | 418 | 23.717 | −36.594 | 23.851 | 1.00 | 78.72 |
| 2187 | C | CYS | D | 418 | 23.138 | −37.988 | 24.073 | 1.00 | 85.08 |
| 2188 | O | CYS | D | 418 | 21.916 | −38.176 | 24.057 | 1.00 | 99.99 |
| 2189 | CB | CYS | D | 418 | 23.313 | −35.651 | 25.003 | 1.00 | 86.02 |
| 2190 | SG | CYS | D | 418 | 23.758 | −36.184 | 26.695 | 1.00 | 96.72 |
| 2191 | N | ARG | D | 419 | 24.011 | −38.969 | 24.263 | 1.00 | 77.42 |
| 2192 | CA | ARG | D | 419 | 23.550 | −40.330 | 24.496 | 1.00 | 94.74 |
| 2193 | CB | ARG | D | 419 | 24.244 | −41.303 | 23.532 | 1.00 | 99.98 |
| 2194 | CG | ARG | D | 419 | 23.703 | −42.728 | 23.586 | 1.00 | 104.35 |
| 2195 | CD | ARG | D | 419 | 24.172 | −43.569 | 22.397 | 1.00 | 100.61 |
| 2196 | NE | ARG | D | 419 | 23.713 | −44.955 | 22.500 | 1.00 | 108.17 |
| 2197 | CZ | ARG | D | 419 | 24.100 | −45.804 | 23.451 | 1.00 | 111.10 |
| 2198 | NH1 | ARG | D | 419 | 24.960 | −45.411 | 24.383 | 1.00 | 110.45 |
| 2199 | NH2 | ARG | D | 419 | 23.621 | −47.044 | 23.475 | 1.00 | 117.41 |
| 2200 | C | ARG | D | 419 | 23.828 | −40.719 | 25.944 | 1.00 | 96.55 |
| 2201 | O | ARG | D | 419 | 24.970 | −40.678 | 26.407 | 1.00 | 96.71 |
| 2202 | N | VAL | D | 420 | 22.767 | −41.085 | 26.653 | 1.00 | 95.97 |
| 2203 | CA | VAL | D | 420 | 22.862 | −41.471 | 28.058 | 1.00 | 98.08 |
| 2204 | CB | VAL | D | 420 | 21.721 | −40.850 | 28.871 | 1.00 | 88.52 |
| 2205 | CG1 | VAL | D | 420 | 21.956 | −41.091 | 30.346 | 1.00 | 96.04 |
| 2206 | CG2 | VAL | D | 420 | 21.614 | −39.368 | 28.566 | 1.00 | 84.94 |
| 2207 | C | VAL | D | 420 | 22.808 | −42.985 | 28.263 | 1.00 | 104.63 |
| 2208 | O | VAL | D | 420 | 21.873 | −43.652 | 27.816 | 1.00 | 117.62 |
| 2209 | N | THR | D | 421 | 23.804 | −43.516 | 28.961 | 1.00 | 111.67 |
| 2210 | CA | THR | D | 421 | 23.883 | −44.948 | 29.229 | 1.00 | 110.89 |
| 2211 | CB | THR | D | 421 | 25.155 | −45.545 | 28.589 | 1.00 | 100.25 |
| 2212 | OG1 | THR | D | 421 | 25.182 | −45.221 | 27.195 | 1.00 | 92.90 |
| 2213 | CG2 | THR | D | 421 | 25.186 | −47.053 | 28.761 | 1.00 | 100.49 |
| 2214 | C | THR | D | 421 | 23.919 | −45.211 | 30.736 | 1.00 | 115.29 |
| 2215 | O | THR | D | 421 | 24.470 | −44.418 | 31.500 | 1.00 | 126.46 |
| 2216 | N | HIS | D | 422 | 23.326 | −46.320 | 31.162 | 1.00 | 118.75 |
| 2217 | CA | HIS | D | 422 | 23.315 | −46.676 | 32.575 | 1.00 | 125.92 |
| 2218 | CB | HIS | D | 422 | 22.265 | −45.842 | 33.326 | 1.00 | 124.91 |
| 2219 | CG | HIS | D | 422 | 22.319 | −45.994 | 34.818 | 1.00 | 133.98 |
| 2220 | CD2 | HIS | D | 422 | 21.368 | −46.355 | 35.712 | 1.00 | 131.99 |
| 2221 | ND1 | HIS | D | 422 | 23.460 | −45.746 | 35.553 | 1.00 | 130.34 |
| 2222 | CE1 | HIS | D | 422 | 23.209 | −45.948 | 36.835 | 1.00 | 125.12 |
| 2223 | NE2 | HIS | D | 422 | 21.947 | −46.318 | 36.958 | 1.00 | 130.82 |
| 2224 | C | HIS | D | 422 | 23.010 | −48.166 | 32.719 | 1.00 | 133.53 |
| 2225 | O | HIS | D | 422 | 22.255 | −48.737 | 31.929 | 1.00 | 128.31 |
| 2226 | N | PRO | D | 423 | 23.611 | −48.821 | 33.724 | 1.00 | 135.34 |
| 2227 | CD | PRO | D | 423 | 24.651 | −48.310 | 34.635 | 1.00 | 132.55 |
| 2228 | CA | PRO | D | 423 | 23.383 | −50.251 | 33.948 | 1.00 | 135.61 |
| 2229 | CB | PRO | D | 423 | 24.488 | −50.621 | 34.937 | 1.00 | 129.04 |
| 2230 | CG | PRO | D | 423 | 24.665 | −49.358 | 35.722 | 1.00 | 131.31 |
| 2231 | C | PRO | D | 423 | 21.985 | −50.596 | 34.477 | 1.00 | 137.23 |
| 2232 | O | PRO | D | 423 | 21.499 | −51.708 | 34.271 | 1.00 | 138.87 |
| 2233 | N | HIS | D | 424 | 21.340 | −49.643 | 35.146 | 1.00 | 137.95 |
| 2234 | CA | HIS | D | 424 | 20.012 | −49.872 | 35.715 | 1.00 | 138.24 |
| 2235 | CB | HIS | D | 424 | 19.916 | −49.220 | 37.100 | 1.00 | 140.25 |
| 2236 | CG | HIS | D | 424 | 20.979 | −49.672 | 38.058 | 1.00 | 150.18 |
| 2237 | CD2 | HIS | D | 424 | 21.934 | −48.977 | 38.723 | 1.00 | 155.59 |
| 2238 | ND1 | HIS | D | 424 | 21.145 | −50.992 | 38.423 | 1.00 | 145.04 |
| 2239 | CE1 | HIS | D | 424 | 22.155 | −51.090 | 39.269 | 1.00 | 139.73 |
| 2240 | NE2 | HIS | D | 424 | 22.651 | −49.882 | 39.468 | 1.00 | 143.35 |
| 2241 | C | HIS | D | 424 | 18.870 | −49.373 | 34.831 | 1.00 | 141.70 |
| 2242 | O | HIS | D | 424 | 17.847 | −48.895 | 35.329 | 1.00 | 144.50 |
| 2243 | N | LEU | D | 425 | 19.052 | −49.492 | 33.519 | 1.00 | 141.46 |
| 2244 | CA | LEU | D | 425 | 18.041 | −49.075 | 32.552 | 1.00 | 136.38 |
| 2245 | CB | LEU | D | 425 | 18.161 | −47.580 | 32.256 | 1.00 | 135.29 |
| 2246 | CG | LEU | D | 425 | 17.577 | −46.628 | 33.298 | 1.00 | 139.06 |
| 2247 | CD1 | LEU | D | 425 | 17.807 | −45.192 | 32.854 | 1.00 | 136.08 |
| 2248 | CD2 | LEU | D | 425 | 16.086 | −46.905 | 33.470 | 1.00 | 135.46 |
| 2249 | C | LEU | D | 425 | 18.165 | −49.857 | 31.251 | 1.00 | 132.64 |
| 2250 | O | LEU | D | 425 | 19.271 | −50.102 | 30.763 | 1.00 | 124.88 |
| 2251 | N | PRO | D | 426 | 17.021 | −50.251 | 30.667 | 1.00 | 135.00 |
| 2252 | CD | PRO | D | 426 | 15.657 | −49.856 | 31.068 | 1.00 | 133.94 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2253 | CA | PRO | D | 426 | 16.993 | −51.011 | 29.412 | 1.00 | 137.36 |
| 2254 | CB | PRO | D | 426 | 15.496 | −51.202 | 29.160 | 1.00 | 131.36 |
| 2255 | CG | PRO | D | 426 | 14.897 | −49.970 | 29.765 | 1.00 | 126.35 |
| 2256 | C | PRO | D | 426 | 17.695 | −50.283 | 28.263 | 1.00 | 138.86 |
| 2257 | O | PRO | D | 426 | 18.922 | −50.334 | 28.138 | 1.00 | 139.47 |
| 2258 | N | ARG | D | 427 | 16.907 | −49.611 | 27.428 | 1.00 | 135.34 |
| 2259 | CA | ARG | D | 427 | 17.438 | −48.864 | 26.292 | 1.00 | 132.33 |
| 2260 | CB | ARG | D | 427 | 16.308 | −48.562 | 25.302 | 1.00 | 136.22 |
| 2261 | CG | ARG | D | 427 | 16.731 | −47.775 | 24.070 | 1.00 | 146.88 |
| 2262 | CD | ARG | D | 427 | 15.524 | −47.452 | 23.204 | 1.00 | 149.34 |
| 2263 | NE | ARG | D | 427 | 15.870 | −46.604 | 22.069 | 1.00 | 152.87 |
| 2264 | CZ | ARG | D | 427 | 14.991 | −46.168 | 21.174 | 1.00 | 157.35 |
| 2265 | NH1 | ARG | D | 427 | 13.712 | −46.503 | 21.286 | 1.00 | 153.62 |
| 2266 | NH2 | ARG | D | 427 | 15.388 | −45.397 | 20.168 | 1.00 | 151.12 |
| 2267 | C | ARG | D | 427 | 18.086 | −47.561 | 26.768 | 1.00 | 127.90 |
| 2268 | O | ARG | D | 427 | 17.837 | −47.103 | 27.887 | 1.00 | 122.40 |
| 2269 | N | ALA | D | 428 | 18.917 | −46.971 | 25.914 | 1.00 | 122.17 |
| 2270 | CA | ALA | D | 428 | 19.608 | −45.729 | 26.249 | 1.00 | 122.10 |
| 2271 | CB | ALA | D | 428 | 20.950 | −45.680 | 25.532 | 1.00 | 121.42 |
| 2272 | C | ALA | D | 428 | 18.782 | −44.494 | 25.892 | 1.00 | 122.18 |
| 2273 | O | ALA | D | 428 | 17.914 | −44.554 | 25.018 | 1.00 | 124.34 |
| 2274 | N | LEU | D | 429 | 19.058 | −43.379 | 26.571 | 1.00 | 119.45 |
| 2275 | CA | LEU | D | 429 | 18.348 | −42.122 | 26.328 | 1.00 | 112.23 |
| 2276 | CB | LEU | D | 429 | 18.185 | −41.334 | 27.630 | 1.00 | 116.17 |
| 2277 | CG | LEU | D | 429 | 17.198 | −41.889 | 28.659 | 1.00 | 112.66 |
| 2278 | CD1 | LEU | D | 429 | 17.198 | −41.001 | 29.893 | 1.00 | 111.33 |
| 2279 | CD2 | LEU | D | 429 | 15.804 | −41.954 | 28.052 | 1.00 | 110.52 |
| 2280 | C | LEU | D | 429 | 19.078 | −41.262 | 25.307 | 1.00 | 111.81 |
| 2281 | O | LEU | D | 429 | 20.309 | −41.291 | 25.222 | 1.00 | 103.47 |
| 2282 | N | MET | D | 430 | 18.309 | −40.492 | 24.542 | 1.00 | 111.14 |
| 2283 | CA | MET | D | 430 | 18.871 | −39.631 | 23.510 | 1.00 | 108.52 |
| 2284 | CB | MET | D | 430 | 18.831 | −40.348 | 22.156 | 1.00 | 111.45 |
| 2285 | CG | MET | D | 430 | 19.661 | −41.626 | 22.108 | 1.00 | 119.21 |
| 2286 | SD | MET | D | 430 | 19.269 | −42.700 | 20.701 | 1.00 | 131.61 |
| 2287 | CE | MET | D | 430 | 18.071 | −43.815 | 21.451 | 1.00 | 123.22 |
| 2288 | C | MET | D | 430 | 18.137 | −38.300 | 23.407 | 1.00 | 103.17 |
| 2289 | O | MET | D | 430 | 16.904 | −38.246 | 23.437 | 1.00 | 87.22 |
| 2290 | N | ARG | D | 431 | 18.915 | −37.229 | 23.287 | 1.00 | 94.69 |
| 2291 | CA | ARG | D | 431 | 18.377 | −35.885 | 23.166 | 1.00 | 79.99 |
| 2292 | CB | ARG | D | 431 | 18.498 | −35.146 | 24.497 | 1.00 | 74.69 |
| 2293 | CG | ARG | D | 431 | 18.018 | −35.932 | 25.694 | 1.00 | 85.37 |
| 2294 | CD | ARG | D | 431 | 16.543 | −36.255 | 25.583 | 1.00 | 106.61 |
| 2295 | NE | ARG | D | 431 | 16.129 | −37.214 | 26.598 | 1.00 | 99.17 |
| 2296 | CZ | ARG | D | 431 | 14.908 | −37.721 | 26.683 | 1.00 | 96.49 |
| 2297 | NH1 | ARG | D | 431 | 13.975 | −37.363 | 25.814 | 1.00 | 92.68 |
| 2298 | NH2 | ARG | D | 431 | 14.621 | −38.588 | 27.638 | 1.00 | 109.79 |
| 2299 | C | ARG | D | 431 | 19.222 | −35.176 | 22.123 | 1.00 | 73.68 |
| 2300 | O | ARG | D | 431 | 20.424 | −35.445 | 22.006 | 1.00 | 60.70 |
| 2301 | N | SER | D | 432 | 18.588 | −34.286 | 21.363 | 1.00 | 65.18 |
| 2302 | CA | SER | D | 432 | 19.278 | −33.504 | 20.337 | 1.00 | 59.29 |
| 2303 | CB | SER | D | 432 | 18.957 | −34.045 | 18.946 | 1.00 | 69.56 |
| 2304 | OG | SER | D | 432 | 17.570 | −33.966 | 18.679 | 1.00 | 78.23 |
| 2305 | C | SER | D | 432 | 18.824 | −32.042 | 20.440 | 1.00 | 73.23 |
| 2306 | O | SER | D | 432 | 17.761 | −31.740 | 21.016 | 1.00 | 60.71 |
| 2307 | N | THR | D | 433 | 19.618 | −31.133 | 19.881 | 1.00 | 63.01 |
| 2308 | CA | THR | D | 433 | 19.278 | −29.718 | 19.948 | 1.00 | 48.63 |
| 2309 | CB | THR | D | 433 | 19.758 | −29.127 | 21.316 | 1.00 | 60.70 |
| 2310 | OG1 | THR | D | 433 | 19.414 | −27.743 | 21.387 | 1.00 | 46.19 |
| 2311 | CG2 | THR | D | 433 | 21.269 | −29.304 | 21.501 | 1.00 | 39.68 |
| 2312 | C | THR | D | 433 | 19.832 | −28.905 | 18.775 | 1.00 | 49.97 |
| 2313 | O | THR | D | 433 | 20.817 | −29.296 | 18.148 | 1.00 | 62.82 |
| 2314 | N | THR | D | 434 | 19.175 | −27.782 | 18.473 | 1.00 | 64.22 |
| 2315 | CA | THR | D | 434 | 19.557 | −26.883 | 17.369 | 1.00 | 67.52 |
| 2316 | CB | THR | D | 434 | 19.170 | −27.447 | 15.969 | 1.00 | 69.61 |
| 2317 | OG1 | THR | D | 434 | 17.935 | −28.159 | 16.069 | 1.00 | 66.43 |
| 2318 | CG2 | THR | D | 434 | 20.251 | −28.342 | 15.408 | 1.00 | 73.07 |
| 2319 | C | THR | D | 434 | 18.848 | −25.540 | 17.501 | 1.00 | 49.46 |
| 2320 | O | THR | D | 434 | 19.008 | −24.659 | 16.652 | 1.00 | 50.82 |
| 2321 | N | ARG | D | 440 | 10.649 | −14.681 | 15.244 | 1.00 | 22.75 |
| 2322 | CA | ARG | D | 440 | 11.666 | −13.839 | 15.887 | 1.00 | 57.97 |
| 2323 | CB | ARG | D | 440 | 12.951 | −13.795 | 15.041 | 1.00 | 34.97 |
| 2324 | CG | ARG | D | 440 | 13.424 | −15.156 | 14.503 | 1.00 | 67.57 |
| 2325 | CD | ARG | D | 440 | 13.969 | −16.118 | 15.573 | 1.00 | 69.97 |
| 2326 | NE | ARG | D | 440 | 14.118 | −17.485 | 15.052 | 1.00 | 89.93 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2327 | CZ | ARG | D | 440 | 14.778 | −18.474 | 15.659 | 1.00 | 85.69 |
| 2328 | NH1 | ARG | D | 440 | 15.369 | −18.271 | 16.824 | 1.00 | 92.86 |
| 2329 | NH2 | ARG | D | 440 | 14.848 | −19.678 | 15.100 | 1.00 | 92.41 |
| 2330 | C | ARG | D | 440 | 11.188 | −12.399 | 16.145 | 1.00 | 50.38 |
| 2331 | O | ARG | D | 440 | 10.615 | −11.762 | 15.269 | 1.00 | 51.18 |
| 2332 | N | ALA | D | 441 | 11.430 | −11.892 | 17.351 | 1.00 | 50.65 |
| 2333 | CA | ALA | D | 441 | 11.029 | −10.529 | 17.717 | 1.00 | 44.25 |
| 2334 | CB | ALA | D | 441 | 9.576 | −10.487 | 18.115 | 1.00 | 11.78 |
| 2335 | C | ALA | D | 441 | 11.879 | −9.990 | 18.860 | 1.00 | 40.45 |
| 2336 | O | ALA | D | 441 | 12.098 | −10.662 | 19.863 | 1.00 | 52.39 |
| 2337 | N | ALA | D | 442 | 12.337 | −8.757 | 18.711 | 1.00 | 36.95 |
| 2338 | CA | ALA | D | 442 | 13.165 | −8.106 | 19.704 | 1.00 | 38.70 |
| 2339 | CB | ALA | D | 442 | 13.706 | −6.803 | 19.140 | 1.00 | 38.08 |
| 2340 | C | ALA | D | 442 | 12.397 | −7.845 | 20.984 | 1.00 | 39.79 |
| 2341 | O | ALA | D | 442 | 11.192 | −7.682 | 20.966 | 1.00 | 43.00 |
| 2342 | N | PRO | D | 443 | 13.102 | −7.784 | 22.121 | 1.00 | 46.38 |
| 2343 | CD | PRO | D | 443 | 14.486 | −8.253 | 22.283 | 1.00 | 40.93 |
| 2344 | CA | PRO | D | 443 | 12.489 | −7.541 | 23.429 | 1.00 | 40.04 |
| 2345 | CB | PRO | D | 443 | 13.473 | −8.199 | 24.401 | 1.00 | 35.44 |
| 2346 | CG | PRO | D | 443 | 14.375 | −9.030 | 23.543 | 1.00 | 45.83 |
| 2347 | C | PRO | D | 443 | 12.293 | −6.076 | 23.785 | 1.00 | 37.92 |
| 2348 | O | PRO | D | 443 | 13.122 | −5.249 | 23.478 | 1.00 | 39.40 |
| 2349 | N | ALA | D | 444 | 11.176 | −5.762 | 24.428 | 1.00 | 39.13 |
| 2350 | CA | ALA | D | 444 | 10.902 | −4.404 | 24.900 | 1.00 | 26.65 |
| 2351 | CB | ALA | D | 444 | 9.399 | −4.097 | 24.803 | 1.00 | 20.65 |
| 2352 | C | ALA | D | 444 | 11.391 | −4.480 | 26.368 | 1.00 | 32.69 |
| 2353 | O | ALA | D | 444 | 11.080 | −5.440 | 27.078 | 1.00 | 38.09 |
| 2354 | N | VAL | D | 445 | 12.181 | −3.503 | 26.826 | 1.00 | 32.15 |
| 2355 | CA | VAL | D | 445 | 12.732 | −3.593 | 28.188 | 1.00 | 10.57 |
| 2356 | CB | VAL | D | 445 | 14.283 | −3.862 | 28.139 | 1.00 | 39.11 |
| 2357 | CG1 | VAL | D | 445 | 14.904 | −3.833 | 29.572 | 1.00 | 14.34 |
| 2358 | CG2 | VAL | D | 445 | 14.573 | −5.214 | 27.464 | 1.00 | 25.23 |
| 2359 | C | VAL | D | 445 | 12.517 | −2.430 | 29.120 | 1.00 | 30.04 |
| 2360 | O | VAL | D | 445 | 12.774 | −1.285 | 28.767 | 1.00 | 23.80 |
| 2361 | N | TYR | D | 446 | 12.033 | −2.714 | 30.326 | 1.00 | 22.48 |
| 2362 | CA | TYR | D | 446 | 11.886 | −1.637 | 31.290 | 1.00 | 33.34 |
| 2363 | CB | TYR | D | 446 | 10.493 | −1.027 | 31.263 | 1.00 | 50.43 |
| 2364 | CG | TYR | D | 446 | 10.558 | 0.379 | 31.835 | 1.00 | 92.60 |
| 2365 | CD1 | TYR | D | 446 | 11.509 | 1.297 | 31.368 | 1.00 | 93.42 |
| 2366 | CE1 | TYR | D | 446 | 11.615 | 2.582 | 31.920 | 1.00 | 87.85 |
| 2367 | CD2 | TYR | D | 446 | 9.715 | 0.781 | 32.865 | 1.00 | 92.46 |
| 2368 | CE2 | TYR | D | 446 | 9.810 | 2.063 | 33.429 | 1.00 | 81.87 |
| 2369 | CZ | TYR | D | 446 | 10.761 | 2.957 | 32.950 | 1.00 | 89.62 |
| 2370 | OH | TYR | D | 446 | 10.846 | 4.222 | 33.492 | 1.00 | 95.26 |
| 2371 | C | TYR | D | 446 | 12.296 | −1.975 | 32.728 | 1.00 | 38.76 |
| 2372 | O | TYR | D | 446 | 12.145 | −3.092 | 33.205 | 1.00 | 28.97 |
| 2373 | N | ALA | D | 447 | 12.817 | −0.973 | 33.420 | 1.00 | 23.01 |
| 2374 | CA | ALA | D | 447 | 13.330 | −1.163 | 34.766 | 1.00 | 24.62 |
| 2375 | CB | ALA | D | 447 | 14.832 | −1.017 | 34.732 | 1.00 | 30.35 |
| 2376 | C | ALA | D | 447 | 12.758 | −0.230 | 35.798 | 1.00 | 30.89 |
| 2377 | O | ALA | D | 447 | 12.566 | 0.943 | 35.538 | 1.00 | 33.50 |
| 2378 | N | PHE | D | 448 | 12.502 | −0.759 | 36.988 | 1.00 | 35.11 |
| 2379 | CA | PHE | D | 448 | 11.948 | 0.051 | 38.067 | 1.00 | 33.98 |
| 2380 | CB | PHE | D | 448 | 10.497 | −0.333 | 38.369 | 1.00 | 42.63 |
| 2381 | CG | PHE | D | 448 | 9.647 | −0.525 | 37.160 | 1.00 | 34.74 |
| 2382 | CD1 | PHE | D | 448 | 9.602 | −1.768 | 36.518 | 1.00 | 25.95 |
| 2383 | CD2 | PHE | D | 448 | 8.920 | 0.543 | 36.633 | 1.00 | 18.64 |
| 2384 | CE1 | PHE | D | 448 | 8.858 | −1.951 | 35.366 | 1.00 | 24.70 |
| 2385 | CE2 | PHE | D | 448 | 8.167 | 0.367 | 35.474 | 1.00 | 42.50 |
| 2386 | CZ | PHE | D | 448 | 8.139 | −0.893 | 34.837 | 1.00 | 21.30 |
| 2387 | C | PHE | D | 448 | 12.722 | −0.084 | 39.373 | 1.00 | 42.45 |
| 2388 | O | PHE | D | 448 | 13.416 | −1.075 | 39.616 | 1.00 | 34.56 |
| 2389 | N | ALA | D | 449 | 12.568 | 0.930 | 40.215 | 1.00 | 28.83 |
| 2390 | CA | ALA | D | 449 | 13.179 | 0.962 | 41.528 | 1.00 | 33.29 |
| 2391 | CB | ALA | D | 449 | 14.147 | 2.113 | 41.646 | 1.00 | 30.58 |
| 2392 | C | ALA | D | 449 | 12.060 | 1.140 | 42.524 | 1.00 | 40.33 |
| 2393 | O | ALA | D | 449 | 11.131 | 1.895 | 42.303 | 1.00 | 42.21 |
| 2394 | N | THR | D | 450 | 12.156 | 0.428 | 43.631 | 1.00 | 51.26 |
| 2395 | CA | THR | D | 450 | 11.162 | 0.505 | 44.683 | 1.00 | 44.45 |
| 2396 | CB | THR | D | 450 | 11.314 | −0.704 | 45.640 | 1.00 | 37.01 |
| 2397 | OG1 | THR | D | 450 | 10.580 | −1.828 | 45.120 | 1.00 | 36.34 |
| 2398 | CG2 | THR | D | 450 | 10.834 | −0.367 | 47.020 | 1.00 | 68.69 |
| 2399 | C | THR | D | 450 | 11.323 | 1.804 | 45.460 | 1.00 | 38.70 |
| 2400 | O | THR | D | 450 | 12.408 | 2.356 | 45.548 | 1.00 | 50.36 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2401 | N | PRO | D | 451 | 10.225 | 2.328 | 46.014 | 1.00 | 66.19 |
| 2402 | CD | PRO | D | 451 | 8.839 | 1.948 | 45.700 | 1.00 | 66.30 |
| 2403 | CA | PRO | D | 451 | 10.257 | 3.568 | 46.798 | 1.00 | 58.85 |
| 2404 | CB | PRO | D | 451 | 8.784 | 3.961 | 46.870 | 1.00 | 61.14 |
| 2405 | CG | PRO | D | 451 | 8.163 | 3.279 | 45.686 | 1.00 | 73.88 |
| 2406 | C | PRO | D | 451 | 10.817 | 3.252 | 48.196 | 1.00 | 57.49 |
| 2407 | O | PRO | D | 451 | 11.014 | 2.073 | 48.539 | 1.00 | 34.17 |
| 2408 | N | GLU | D | 452 | 11.057 | 4.293 | 48.993 | 1.00 | 66.63 |
| 2409 | CA | GLU | D | 452 | 11.565 | 4.161 | 50.372 | 1.00 | 87.05 |
| 2410 | CB | GLU | D | 452 | 12.509 | 2.952 | 50.519 | 1.00 | 100.43 |
| 2411 | CG | GLU | D | 452 | 11.831 | 1.651 | 50.963 | 1.00 | 96.00 |
| 2412 | CD | GLU | D | 452 | 12.546 | 0.417 | 50.438 | 1.00 | 104.32 |
| 2413 | OE1 | GLU | D | 452 | 13.700 | 0.169 | 50.851 | 1.00 | 97.07 |
| 2414 | OE2 | GLU | D | 452 | 11.951 | −0.298 | 49.604 | 1.00 | 79.57 |
| 2415 | C | GLU | D | 452 | 12.301 | 5.411 | 50.825 | 1.00 | 90.88 |
| 2416 | O | GLU | D | 452 | 13.381 | 5.320 | 51.408 | 1.00 | 87.00 |
| 2417 | N | LYS | D | 459 | 17.730 | −3.616 | 51.475 | 1.00 | 63.26 |
| 2418 | CA | LYS | D | 459 | 16.674 | −4.444 | 50.871 | 1.00 | 96.04 |
| 2419 | CB | LYS | D | 459 | 15.777 | −5.044 | 51.969 | 1.00 | 106.23 |
| 2420 | CG | LYS | D | 459 | 16.304 | −6.349 | 52.588 | 1.00 | 101.53 |
| 2421 | CD | LYS | D | 459 | 16.201 | −7.512 | 51.601 | 1.00 | 113.59 |
| 2422 | CE | LYS | D | 459 | 16.591 | −8.839 | 52.242 | 1.00 | 117.13 |
| 2423 | NZ | LYS | D | 459 | 16.319 | −10.000 | 51.340 | 1.00 | 118.78 |
| 2424 | C | LYS | D | 459 | 15.809 | −3.697 | 49.830 | 1.00 | 97.04 |
| 2425 | O | LYS | D | 459 | 14.642 | −4.070 | 49.571 | 1.00 | 71.24 |
| 2426 | N | ARG | D | 460 | 16.409 | −2.659 | 49.236 | 1.00 | 87.47 |
| 2427 | CA | ARG | D | 460 | 15.775 | −1.825 | 48.219 | 1.00 | 63.96 |
| 2428 | CB | ARG | D | 460 | 16.523 | −0.508 | 48.125 | 1.00 | 59.32 |
| 2429 | CG | ARG | D | 460 | 16.402 | 0.333 | 49.425 | 1.00 | 77.94 |
| 2430 | CD | ARG | D | 460 | 16.590 | −0.467 | 50.738 | 1.00 | 56.00 |
| 2431 | NE | ARG | D | 460 | 17.908 | −1.097 | 50.867 | 1.00 | 70.39 |
| 2432 | CZ | ARG | D | 460 | 18.891 | −0.662 | 51.658 | 1.00 | 73.78 |
| 2433 | NH1 | ARG | D | 460 | 18.730 | 0.417 | 52.418 | 1.00 | 80.33 |
| 2434 | NH2 | ARG | D | 460 | 20.052 | −1.306 | 51.688 | 1.00 | 61.48 |
| 2435 | C | ARG | D | 460 | 15.828 | −2.597 | 46.922 | 1.00 | 55.79 |
| 2436 | O | ARG | D | 460 | 16.902 | −2.916 | 46.437 | 1.00 | 49.98 |
| 2437 | N | THR | D | 461 | 14.659 | −2.902 | 46.363 | 1.00 | 40.57 |
| 2438 | CA | THR | D | 461 | 14.607 | −3.713 | 45.162 | 1.00 | 31.13 |
| 2439 | CB | THR | D | 461 | 13.501 | −4.767 | 45.289 | 1.00 | 31.57 |
| 2440 | OG1 | THR | D | 461 | 13.334 | −5.101 | 46.665 | 1.00 | 39.19 |
| 2441 | CG2 | THR | D | 461 | 13.880 | −6.037 | 44.534 | 1.00 | 47.71 |
| 2442 | C | THR | D | 461 | 14.454 | −3.012 | 43.836 | 1.00 | 38.16 |
| 2443 | O | THR | D | 461 | 13.836 | −1.953 | 43.738 | 1.00 | 37.10 |
| 2444 | N | LEU | D | 462 | 15.043 | −3.629 | 42.818 | 1.00 | 23.43 |
| 2445 | CA | LEU | D | 462 | 14.974 | −3.116 | 41.463 | 1.00 | 35.34 |
| 2446 | CB | LEU | D | 462 | 16.368 | −2.834 | 40.887 | 1.00 | 39.80 |
| 2447 | CG | LEU | D | 462 | 17.267 | −1.844 | 41.624 | 1.00 | 42.28 |
| 2448 | CD1 | LEU | D | 462 | 18.609 | −1.830 | 40.955 | 1.00 | 39.02 |
| 2449 | CD2 | LEU | D | 462 | 16.657 | −0.469 | 41.643 | 1.00 | 24.97 |
| 2450 | C | LEU | D | 462 | 14.320 | −4.210 | 40.676 | 1.00 | 35.26 |
| 2451 | O | LEU | D | 462 | 14.601 | −5.385 | 40.894 | 1.00 | 47.30 |
| 2452 | N | ALA | D | 463 | 13.433 | −3.829 | 39.770 | 1.00 | 32.09 |
| 2453 | CA | ALA | D | 463 | 12.742 | −4.804 | 38.966 | 1.00 | 23.23 |
| 2454 | CB | ALA | D | 463 | 11.266 | −4.862 | 39.371 | 1.00 | 40.47 |
| 2455 | C | ALA | D | 463 | 12.871 | −4.463 | 37.516 | 1.00 | 35.36 |
| 2456 | O | ALA | D | 463 | 12.978 | −3.304 | 37.129 | 1.00 | 26.05 |
| 2457 | N | CYS | D | 464 | 12.852 | −5.502 | 36.707 | 1.00 | 36.81 |
| 2458 | CA | CYS | D | 464 | 12.959 | −5.349 | 35.271 | 1.00 | 29.50 |
| 2459 | C | CYS | D | 464 | 11.918 | −6.235 | 34.597 | 1.00 | 36.21 |
| 2460 | O | CYS | D | 464 | 11.784 | −7.418 | 34.917 | 1.00 | 38.88 |
| 2461 | CB | CYS | D | 464 | 14.345 | −5.768 | 34.835 | 1.00 | 45.37 |
| 2462 | SG | CYS | D | 464 | 14.804 | −5.328 | 33.146 | 1.00 | 46.53 |
| 2463 | N | LEU | D | 465 | 11.149 | −5.630 | 33.702 | 1.00 | 34.60 |
| 2464 | CA | LEU | D | 465 | 10.158 | −6.345 | 32.912 | 1.00 | 24.63 |
| 2465 | CB | LEU | D | 465 | 8.822 | −5.603 | 32.918 | 1.00 | 35.42 |
| 2466 | CG | LEU | D | 465 | 7.820 | −6.094 | 31.860 | 1.00 | 36.65 |
| 2467 | CD1 | LEU | D | 465 | 7.469 | −7.560 | 32.103 | 1.00 | 29.41 |
| 2468 | CD2 | LEU | D | 465 | 6.566 | −5.226 | 31.896 | 1.00 | 28.35 |
| 2469 | C | LEU | D | 465 | 10.723 | −6.406 | 31.482 | 1.00 | 27.19 |
| 2470 | O | LEU | D | 465 | 11.085 | −5.391 | 30.911 | 1.00 | 25.59 |
| 2471 | N | ILE | D | 466 | 10.817 | −7.609 | 30.937 | 1.00 | 24.08 |
| 2472 | CA | ILE | D | 466 | 11.321 | −7.827 | 29.591 | 1.00 | 31.94 |
| 2473 | CB | ILE | D | 466 | 12.618 | −8.650 | 29.650 | 1.00 | 56.88 |
| 2474 | CG2 | ILE | D | 466 | 13.270 | −8.733 | 28.264 | 1.00 | 40.58 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2475 | CG1 | ILE | D | 466 | 13.574 | −7.989 | 30.647 | 1.00 | 46.98 |
| 2476 | CD1 | ILE | D | 466 | 14.589 | −8.916 | 31.208 | 1.00 | 38.14 |
| 2477 | C | ILE | D | 466 | 10.241 | −8.597 | 28.856 | 1.00 | 35.34 |
| 2478 | O | ILE | D | 466 | 9.959 | −9.736 | 29.210 | 1.00 | 37.33 |
| 2479 | N | GLN | D | 467 | 9.654 | −7.991 | 27.821 | 1.00 | 38.15 |
| 2480 | CA | GLN | D | 467 | 8.536 | −8.618 | 27.095 | 1.00 | 43.25 |
| 2481 | CB | GLN | D | 467 | 7.227 | −8.087 | 27.672 | 1.00 | 32.45 |
| 2482 | CG | GLN | D | 467 | 7.161 | −6.558 | 27.609 | 1.00 | 25.95 |
| 2483 | CD | GLN | D | 467 | 5.826 | −5.993 | 28.066 | 1.00 | 49.02 |
| 2484 | OE1 | GLN | D | 467 | 5.136 | −6.563 | 28.903 | 1.00 | 32.59 |
| 2485 | NE2 | GLN | D | 467 | 5.473 | −4.854 | 27.526 | 1.00 | 19.30 |
| 2486 | C | GLN | D | 467 | 8.449 | −8.494 | 25.574 | 1.00 | 51.05 |
| 2487 | O | GLN | D | 467 | 9.196 | −7.741 | 24.934 | 1.00 | 36.58 |
| 2488 | N | ASN | D | 468 | 7.489 | −9.251 | 25.030 | 1.00 | 36.35 |
| 2489 | CA | ASN | D | 468 | 7.172 | −9.315 | 23.597 | 1.00 | 35.53 |
| 2490 | CB | ASN | D | 468 | 6.691 | −7.959 | 23.093 | 1.00 | 37.80 |
| 2491 | CG | ASN | D | 468 | 5.546 | −7.445 | 23.881 | 1.00 | 36.27 |
| 2492 | OD1 | ASN | D | 468 | 4.702 | −8.220 | 24.325 | 1.00 | 38.23 |
| 2493 | ND2 | ASN | D | 468 | 5.492 | −6.136 | 24.067 | 1.00 | 34.81 |
| 2494 | C | ASN | D | 468 | 8.317 | −9.765 | 22.721 | 1.00 | 43.85 |
| 2495 | O | ASN | D | 468 | 8.534 | −9.197 | 21.654 | 1.00 | 50.04 |
| 2496 | N | PHE | D | 469 | 9.029 | −10.797 | 23.146 | 1.00 | 30.59 |
| 2497 | CA | PHE | D | 469 | 10.164 | −11.273 | 22.377 | 1.00 | 30.95 |
| 2498 | CB | PHE | D | 469 | 11.479 | −11.118 | 23.192 | 1.00 | 38.62 |
| 2499 | CG | PHE | D | 469 | 11.532 | −11.941 | 24.474 | 1.00 | 21.56 |
| 2500 | CD1 | PHE | D | 469 | 11.855 | −13.309 | 24.442 | 1.00 | 23.22 |
| 2501 | CD2 | PHE | D | 469 | 11.252 | −11.349 | 25.713 | 1.00 | 25.80 |
| 2502 | CE1 | PHE | D | 469 | 11.898 | −14.076 | 25.628 | 1.00 | 19.64 |
| 2503 | CE2 | PHE | D | 469 | 11.289 | −12.100 | 26.904 | 1.00 | 27.52 |
| 2504 | CZ | PHE | D | 469 | 11.613 | −13.461 | 26.858 | 1.00 | 30.93 |
| 2505 | C | PHE | D | 469 | 9.939 | −12.718 | 22.013 | 1.00 | 43.41 |
| 2506 | O | PHE | D | 469 | 9.149 | −13.412 | 22.675 | 1.00 | 42.77 |
| 2507 | N | MET | D | 470 | 10.608 | −13.151 | 20.942 | 1.00 | 46.45 |
| 2508 | CA | MET | D | 470 | 10.551 | −14.535 | 20.494 | 1.00 | 46.47 |
| 2509 | CB | MET | D | 470 | 9.200 | −14.868 | 19.845 | 1.00 | 47.77 |
| 2510 | CG | MET | D | 470 | 8.797 | −14.060 | 18.638 | 1.00 | 74.98 |
| 2511 | SD | MET | D | 470 | 7.063 | −14.426 | 18.189 | 1.00 | 80.27 |
| 2512 | CE | MET | D | 470 | 7.125 | −16.261 | 18.049 | 1.00 | 77.67 |
| 2513 | C | MET | D | 470 | 11.721 | −14.853 | 19.571 | 1.00 | 40.30 |
| 2514 | O | MET | D | 470 | 12.179 | −13.994 | 18.826 | 1.00 | 38.72 |
| 2515 | N | PRO | D | 471 | 12.253 | −16.091 | 19.652 | 1.00 | 40.96 |
| 2516 | CD | PRO | D | 471 | 13.439 | −16.507 | 18.893 | 1.00 | 25.97 |
| 2517 | CA | PRO | D | 471 | 11.814 | −17.178 | 20.545 | 1.00 | 34.07 |
| 2518 | CB | PRO | D | 471 | 12.740 | −18.330 | 20.193 | 1.00 | 39.46 |
| 2519 | CG | PRO | D | 471 | 13.235 | −17.986 | 18.841 | 1.00 | 44.74 |
| 2520 | C | PRO | D | 471 | 11.928 | −16.803 | 22.032 | 1.00 | 47.08 |
| 2521 | O | PRO | D | 471 | 12.264 | −15.663 | 22.387 | 1.00 | 30.99 |
| 2522 | N | GLU | D | 472 | 11.663 | −17.786 | 22.888 | 1.00 | 47.51 |
| 2523 | CA | GLU | D | 472 | 11.686 | −17.599 | 24.332 | 1.00 | 48.67 |
| 2524 | CB | GLU | D | 472 | 10.851 | −18.693 | 25.015 | 1.00 | 44.24 |
| 2525 | CG | GLU | D | 472 | 11.499 | −20.075 | 24.947 | 1.00 | 62.55 |
| 2526 | CD | GLU | D | 472 | 10.753 | −21.097 | 25.769 | 1.00 | 92.39 |
| 2527 | OE1 | GLU | D | 472 | 9.649 | −21.497 | 25.348 | 1.00 | 98.32 |
| 2528 | OE2 | GLU | D | 472 | 11.267 | −21.491 | 26.840 | 1.00 | 101.51 |
| 2529 | C | GLU | D | 472 | 13.082 | −17.569 | 24.947 | 1.00 | 43.19 |
| 2530 | O | GLU | D | 472 | 13.240 | −17.146 | 26.085 | 1.00 | 52.98 |
| 2531 | N | ASP | D | 473 | 14.087 | −18.007 | 24.208 | 1.00 | 37.69 |
| 2532 | CA | ASP | D | 473 | 15.444 | −17.997 | 24.731 | 1.00 | 36.48 |
| 2533 | CB | ASP | D | 473 | 16.416 | −18.637 | 23.734 | 1.00 | 51.20 |
| 2534 | CG | ASP | D | 473 | 16.100 | −20.099 | 23.469 | 1.00 | 76.95 |
| 2535 | OD1 | ASP | D | 473 | 15.905 | −20.874 | 24.438 | 1.00 | 72.60 |
| 2536 | OD2 | ASP | D | 473 | 16.050 | −20.473 | 22.284 | 1.00 | 92.37 |
| 2537 | C | ASP | D | 473 | 15.915 | −16.593 | 25.041 | 1.00 | 30.84 |
| 2538 | G | ASP | D | 473 | 15.898 | −15.719 | 24.173 | 1.00 | 39.27 |
| 2539 | N | ILE | D | 474 | 16.367 | −16.374 | 26.273 | 1.00 | 38.24 |
| 2540 | CA | ILE | D | 474 | 16.828 | −15.044 | 26.655 | 1.00 | 33.45 |
| 2541 | CB | ILE | D | 474 | 15.606 | −14.145 | 26.954 | 1.00 | 21.36 |
| 2542 | CG2 | ILE | D | 474 | 15.045 | −14.481 | 28.320 | 1.00 | 23.24 |
| 2543 | CG1 | ILE | D | 474 | 15.993 | −12.672 | 26.862 | 1.00 | 31.50 |
| 2544 | CD1 | ILE | D | 474 | 14.830 | −11.746 | 26.697 | 1.00 | 25.43 |
| 2545 | C | ILE | D | 474 | 17.809 | −15.036 | 27.838 | 1.00 | 34.60 |
| 2546 | O | ILE | D | 474 | 17.793 | −15.924 | 28.679 | 1.00 | 34.05 |
| 2547 | N | SER | D | 475 | 18.686 | −14.034 | 27.859 | 1.00 | 34.02 |
| 2548 | CA | SER | D | 475 | 19.676 | −13.847 | 28.926 | 1.00 | 28.86 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2549 | CB | SER | D | 475 | 21.100 | −13.968 | 28.378 | 1.00 | 44.91 |
| 2550 | OG | SER | D | 475 | 21.382 | −15.280 | 27.940 | 1.00 | 44.30 |
| 2551 | C | SER | D | 475 | 19.506 | −12.463 | 29.554 | 1.00 | 38.09 |
| 2552 | O | SER | D | 475 | 19.436 | −11.465 | 28.841 | 1.00 | 33.35 |
| 2553 | N | VAL | D | 476 | 19.442 | −12.419 | 30.886 | 1.00 | 32.39 |
| 2554 | CA | VAL | D | 476 | 19.293 | −11.163 | 31.624 | 1.00 | 22.81 |
| 2555 | CB | VAL | D | 476 | 18.048 | −11.173 | 32.506 | 1.00 | 26.91 |
| 2556 | CG1 | VAL | D | 476 | 17.881 | −9.843 | 33.225 | 1.00 | 37.41 |
| 2557 | CG2 | VAL | D | 476 | 16.853 | −11.460 | 31.673 | 1.00 | 14.00 |
| 2558 | C | VAL | D | 476 | 20.499 | −10.885 | 32.514 | 1.00 | 35.82 |
| 2559 | O | VAL | D | 476 | 20.968 | −11.755 | 33.231 | 1.00 | 44.98 |
| 2560 | N | GLN | D | 477 | 20.997 | −9.657 | 32.458 | 1.00 | 41.31 |
| 2561 | CA | GLN | D | 477 | 22.141 | −9.270 | 33.263 | 1.00 | 35.75 |
| 2562 | CB | GLN | D | 477 | 23.391 | −9.194 | 32.401 | 1.00 | 39.45 |
| 2563 | CG | GLN | D | 477 | 23.484 | −10.251 | 31.352 | 1.00 | 47.87 |
| 2564 | CD | GLN | D | 477 | 24.789 | −10.174 | 30.620 | 1.00 | 76.00 |
| 2565 | OE1 | GLN | D | 477 | 25.153 | −9.124 | 30.080 | 1.00 | 54.60 |
| 2566 | NE2 | GLN | D | 477 | 25.516 | −11.285 | 30.597 | 1.00 | 74.22 |
| 2567 | C | GLN | D | 477 | 21.926 | −7.913 | 33.904 | 1.00 | 39.81 |
| 2568 | O | GLN | D | 477 | 21.209 | −7.061 | 33.368 | 1.00 | 39.07 |
| 2569 | N | TRP | D | 478 | 22.544 | −7.726 | 35.066 | 1.00 | 37.41 |
| 2570 | CA | TRP | D | 478 | 22.488 | −6.452 | 35.767 | 1.00 | 19.59 |
| 2571 | CB | TRP | D | 478 | 21.976 | −6.622 | 37.189 | 1.00 | 34.50 |
| 2572 | CG | TRP | D | 478 | 20.479 | −6.864 | 37.275 | 1.00 | 25.01 |
| 2573 | CD2 | TRP | D | 478 | 19.457 | −5.864 | 37.294 | 1.00 | 15.99 |
| 2574 | CE2 | TRP | D | 478 | 18.215 | −6.536 | 37.340 | 1.00 | 23.72 |
| 2575 | CE3 | TRP | D | 478 | 19.470 | −4.464 | 37.275 | 1.00 | 11.76 |
| 2576 | CD1 | TRP | D | 478 | 19.832 | −8.072 | 37.311 | 1.00 | 16.69 |
| 2577 | NE1 | TRP | D | 478 | 18.473 | −7.880 | 37.346 | 1.00 | 34.77 |
| 2578 | CZ2 | TRP | D | 478 | 17.004 | −5.856 | 37.365 | 1.00 | 23.71 |
| 2579 | CZ3 | TRP | D | 478 | 18.268 | −3.785 | 37.295 | 1.00 | 24.64 |
| 2580 | CH2 | TRP | D | 478 | 17.050 | −4.477 | 37.339 | 1.00 | 27.14 |
| 2581 | C | TRP | D | 478 | 23.900 | −5.917 | 35.778 | 1.00 | 33.78 |
| 2582 | O | TRP | D | 478 | 24.854 | −6.669 | 35.937 | 1.00 | 38.04 |
| 2583 | N | LEU | D | 479 | 24.034 | −4.620 | 35.547 | 1.00 | 32.01 |
| 2584 | CA | LEU | D | 479 | 25.344 | −3.986 | 35.550 | 1.00 | 26.74 |
| 2585 | CB | LEU | D | 479 | 25.752 | −3.591 | 34.132 | 1.00 | 47.34 |
| 2586 | CG | LEU | D | 479 | 26.193 | −4.668 | 33.133 | 1.00 | 46.89 |
| 2587 | CD1 | LEU | D | 479 | 25.039 | −5.558 | 32.775 | 1.00 | 52.93 |
| 2588 | CD2 | LEU | D | 479 | 26.733 | −3.991 | 31.890 | 1.00 | 58.41 |
| 2589 | C | LEU | D | 479 | 25.365 | −2.754 | 36.448 | 1.00 | 36.64 |
| 2590 | O | LEU | D | 479 | 24.404 | −2.013 | 36.504 | 1.00 | 33.66 |
| 2591 | N | HIS | D | 480 | 26.463 | −2.563 | 37.169 | 1.00 | 40.85 |
| 2592 | CA | HIS | D | 480 | 26.628 | −1.410 | 38.033 | 1.00 | 42.37 |
| 2593 | CB | HIS | D | 480 | 26.531 | −1.813 | 39.501 | 1.00 | 33.38 |
| 2594 | CG | HIS | D | 480 | 26.571 | −0.652 | 40.438 | 1.00 | 33.44 |
| 2595 | CD2 | HIS | D | 480 | 27.292 | −0.439 | 41.558 | 1.00 | 24.38 |
| 2596 | ND1 | HIS | D | 480 | 25.793 | 0.472 | 40.263 | 1.00 | 45.35 |
| 2597 | CE1 | HIS | D | 480 | 26.033 | 1.328 | 41.234 | 1.00 | 33.57 |
| 2598 | NE2 | HIS | D | 480 | 26.940 | 0.800 | 42.034 | 1.00 | 59.40 |
| 2599 | C | HIS | D | 480 | 27.987 | −0.804 | 37.709 | 1.00 | 57.70 |
| 2600 | O | HIS | D | 480 | 28.988 | −1.511 | 37.646 | 1.00 | 48.10 |
| 2601 | N | ASN | D | 481 | 28.006 | 0.507 | 37.482 | 1.00 | 68.42 |
| 2602 | CA | ASN | D | 481 | 29.227 | 1.222 | 37.102 | 1.00 | 80.77 |
| 2603 | CB | ASN | D | 481 | 30.418 | 0.771 | 37.953 | 1.00 | 66.34 |
| 2604 | CG | ASN | D | 481 | 30.469 | 1.475 | 39.292 | 1.00 | 59.72 |
| 2605 | OD1 | ASN | D | 481 | 30.679 | 2.673 | 39.362 | 1.00 | 55.75 |
| 2606 | ND2 | ASN | D | 481 | 30.271 | 0.732 | 40.354 | 1.00 | 67.95 |
| 2607 | C | ASN | D | 481 | 29.513 | 0.969 | 35.621 | 1.00 | 84.97 |
| 2608 | O | ASN | D | 481 | 29.687 | 1.910 | 34.827 | 1.00 | 90.77 |
| 2609 | N | GLU | D | 482 | 29.531 | −0.310 | 35.261 | 1.00 | 77.71 |
| 2610 | CA | GLU | D | 482 | 29.779 | −0.757 | 33.894 | 1.00 | 81.68 |
| 2611 | CB | GLU | D | 482 | 30.937 | 0.024 | 33.265 | 1.00 | 92.91 |
| 2612 | CG | GLU | D | 482 | 32.116 | 0.306 | 34.212 | 1.00 | 119.14 |
| 2613 | CD | GLU | D | 482 | 32.420 | −0.837 | 35.179 | 1.00 | 127.77 |
| 2614 | OE1 | GLU | D | 482 | 31.624 | −1.050 | 36.121 | 1.00 | 124.99 |
| 2615 | OE2 | GLU | D | 482 | 33.456 | −1.518 | 34.998 | 1.00 | 134.71 |
| 2616 | C | GLU | D | 482 | 30.140 | −2.232 | 33.939 | 1.00 | 70.11 |
| 2617 | O | GLU | D | 482 | 30.391 | −2.870 | 32.919 | 1.00 | 62.83 |
| 2618 | N | VAL | D | 483 | 30.165 | −2.771 | 35.145 | 1.00 | 61.81 |
| 2619 | CA | VAL | D | 483 | 30.515 | −4.156 | 35.329 | 1.00 | 56.55 |
| 2620 | CB | VAL | D | 483 | 31.586 | −4.300 | 36.403 | 1.00 | 46.59 |
| 2621 | CG1 | VAL | D | 483 | 31.073 | −3.725 | 37.717 | 1.00 | 63.87 |
| 2622 | CG2 | VAL | D | 483 | 31.951 | −5.753 | 36.565 | 1.00 | 59.08 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2623 | C | VAL | D | 483 | 29.325 | −5.019 | 35.711 | 1.00 | 53.17 |
| 2624 | O | VAL | D | 483 | 28.499 | −4.654 | 36.547 | 1.00 | 51.85 |
| 2625 | N | GLN | D | 484 | 29.266 | −6.181 | 35.081 | 1.00 | 36.39 |
| 2626 | CA | GLN | D | 484 | 28.244 | −7.185 | 35.301 | 1.00 | 43.61 |
| 2627 | CB | GLN | D | 484 | 28.448 | −8.256 | 34.251 | 1.00 | 38.93 |
| 2628 | CG | GLN | D | 484 | 27.638 | −9.503 | 34.400 | 1.00 | 63.77 |
| 2629 | CD | GLN | D | 484 | 27.817 | −10.404 | 33.203 | 1.00 | 69.17 |
| 2630 | OE1 | GLN | D | 484 | 27.578 | −11.603 | 33.278 | 1.00 | 81.19 |
| 2631 | NE2 | GLN | D | 484 | 28.236 | −9.823 | 32.077 | 1.00 | 75.61 |
| 2632 | C | GLN | D | 484 | 28.315 | −7.785 | 36.708 | 1.00 | 51.27 |
| 2633 | O | GLN | D | 484 | 29.349 | −8.326 | 37.104 | 1.00 | 61.33 |
| 2634 | N | LEU | D | 485 | 27.215 | −7.687 | 37.456 | 1.00 | 48.46 |
| 2635 | CA | LEU | D | 485 | 27.151 | −8.213 | 38.815 | 1.00 | 41.60 |
| 2636 | CB | LEU | D | 485 | 25.926 | −7.668 | 39.552 | 1.00 | 24.59 |
| 2637 | CG | LEU | D | 485 | 25.742 | −6.142 | 39.645 | 1.00 | 55.04 |
| 2638 | CD1 | LEU | D | 485 | 24.479 | −5.828 | 40.432 | 1.00 | 50.40 |
| 2639 | CD2 | LEU | D | 485 | 26.930 | −5.489 | 40.313 | 1.00 | 44.32 |
| 2640 | C | LEU | D | 485 | 27.085 | −9.722 | 38.825 | 1.00 | 47.01 |
| 2641 | O | LEU | D | 485 | 26.678 | −10.332 | 37.851 | 1.00 | 39.93 |
| 2642 | N | PRO | D | 486 | 27.481 | −10.352 | 39.941 | 1.00 | 58.01 |
| 2643 | CD | PRO | D | 486 | 27.912 | −9.790 | 41.232 | 1.00 | 42.36 |
| 2644 | CA | PRO | D | 486 | 27.430 | −11.818 | 40.000 | 1.00 | 47.75 |
| 2645 | CB | PRO | D | 486 | 27.806 | −12.126 | 41.445 | 1.00 | 43.85 |
| 2646 | CG | PRO | D | 486 | 28.629 | −10.964 | 41.844 | 1.00 | 43.40 |
| 2647 | C | PRO | D | 486 | 26.012 | −12.289 | 39.661 | 1.00 | 48.06 |
| 2648 | O | PRO | D | 486 | 25.025 | −11.743 | 40.148 | 1.00 | 45.35 |
| 2649 | N | ASP | D | 487 | 25.915 | −13.306 | 38.827 | 1.00 | 58.33 |
| 2650 | CA | ASP | D | 487 | 24.621 | −13.810 | 38.424 | 1.00 | 63.10 |
| 2651 | CB | ASP | D | 487 | 24.826 | −14.987 | 37.467 | 1.00 | 73.38 |
| 2652 | CG | ASP | D | 487 | 23.626 | −15.232 | 36.578 | 1.00 | 110.72 |
| 2653 | OD1 | ASP | D | 487 | 22.604 | −15.752 | 37.079 | 1.00 | 125.77 |
| 2654 | OD2 | ASP | D | 487 | 23.702 | −14.893 | 35.377 | 1.00 | 116.10 |
| 2655 | C | ASP | D | 487 | 23.730 | −14.214 | 39.612 | 1.00 | 63.32 |
| 2656 | O | ASP | D | 487 | 22.507 | −14.084 | 39.563 | 1.00 | 74.78 |
| 2657 | N | ALA | D | 488 | 24.342 | −14.671 | 40.691 | 1.00 | 55.19 |
| 2658 | CA | ALA | D | 488 | 23.582 | −15.107 | 41.854 | 1.00 | 53.67 |
| 2659 | CB | ALA | D | 488 | 24.459 | −15.971 | 42.745 | 1.00 | 60.44 |
| 2660 | C | ALA | D | 488 | 22.969 | −13.987 | 42.673 | 1.00 | 44.75 |
| 2661 | O | ALA | D | 488 | 22.282 | −14.242 | 43.667 | 1.00 | 51.79 |
| 2662 | N | ARG | D | 489 | 23.227 | −12.749 | 42.270 | 1.00 | 44.89 |
| 2663 | CA | ARG | D | 489 | 22.681 | −11.584 | 42.968 | 1.00 | 50.16 |
| 2664 | CB | ARG | D | 489 | 23.562 | −10.359 | 42.711 | 1.00 | 60.17 |
| 2665 | CG | ARG | D | 489 | 24.690 | −10.188 | 43.714 | 1.00 | 43.88 |
| 2666 | CD | ARG | D | 489 | 24.317 | −9.189 | 44.801 | 1.00 | 22.09 |
| 2667 | NE | ARG | D | 489 | 24.758 | −7.823 | 44.516 | 1.00 | 27.03 |
| 2668 | CZ | ARG | D | 489 | 24.049 | −6.742 | 44.808 | 1.00 | 30.97 |
| 2669 | NH1 | ARG | D | 489 | 22.869 | −6.866 | 45.387 | 1.00 | 66.03 |
| 2670 | NH2 | ARG | D | 489 | 24.522 | −5.533 | 44.524 | 1.00 | 56.01 |
| 2671 | C | ARG | D | 489 | 21.242 | −11.271 | 42.548 | 1.00 | 57.81 |
| 2672 | O | ARG | D | 489 | 20.468 | −10.720 | 43.328 | 1.00 | 60.35 |
| 2673 | N | HIS | D | 490 | 20.884 | −11.624 | 41.320 | 1.00 | 45.21 |
| 2674 | CA | HIS | D | 490 | 19.544 | −11.354 | 40.843 | 1.00 | 38.19 |
| 2675 | CB | HIS | D | 490 | 19.609 | −10.569 | 39.517 | 1.00 | 53.33 |
| 2676 | CG | HIS | D | 490 | 20.045 | −11.390 | 38.343 | 1.00 | 44.86 |
| 2677 | CD2 | HIS | D | 490 | 21.143 | −11.312 | 37.557 | 1.00 | 53.17 |
| 2678 | ND1 | HIS | D | 490 | 19.299 | −12.439 | 37.851 | 1.00 | 50.65 |
| 2679 | CE1 | HIS | D | 490 | 19.916 | −12.970 | 36.812 | 1.00 | 36.65 |
| 2680 | NE2 | HIS | D | 490 | 21.037 | −12.304 | 36.613 | 1.00 | 62.10 |
| 2681 | C | HIS | D | 490 | 18.725 | −12.632 | 40.652 | 1.00 | 42.01 |
| 2682 | O | HIS | D | 490 | 19.270 | −13.730 | 40.587 | 1.00 | 46.12 |
| 2683 | N | SER | D | 491 | 17.411 | −12.469 | 40.556 | 1.00 | 33.71 |
| 2684 | CA | SER | D | 491 | 16.495 | −13.581 | 40.342 | 1.00 | 36.13 |
| 2685 | CB | SER | D | 491 | 15.561 | −13.707 | 41.548 | 1.00 | 29.92 |
| 2686 | OG | SER | D | 491 | 14.861 | −14.932 | 41.520 | 1.00 | 35.89 |
| 2687 | C | SER | D | 491 | 15.659 | −13.360 | 39.065 | 1.00 | 38.06 |
| 2688 | O | SER | D | 491 | 15.050 | −12.305 | 38.890 | 1.00 | 43.59 |
| 2689 | N | THR | D | 492 | 15.613 | −14.356 | 38.185 | 1.00 | 33.54 |
| 2690 | CA | THR | D | 492 | 14.850 | −14.223 | 36.943 | 1.00 | 33.41 |
| 2691 | CB | THR | D | 492 | 15.797 | −14.156 | 35.724 | 1.00 | 29.40 |
| 2692 | OG1 | THR | D | 492 | 16.640 | −13.006 | 35.851 | 1.00 | 48.69 |
| 2693 | CG2 | THR | D | 492 | 14.990 | −14.042 | 34.423 | 1.00 | 41.33 |
| 2694 | C | THR | D | 492 | 13.808 | −15.320 | 36.703 | 1.00 | 26.78 |
| 2695 | O | THR | D | 492 | 14.113 | −16.503 | 36.786 | 1.00 | 37.97 |
| 2696 | N | THR | D | 493 | 12.583 | −14.904 | 36.375 | 1.00 | 35.02 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2697 | CA | THR | D | 493 | 11.450 | −15.797 | 36.113 | 1.00 | 20.49 |
| 2698 | CB | THR | D | 493 | 10.154 | −15.028 | 35.958 | 1.00 | 18.80 |
| 2699 | OG1 | THR | D | 493 | 10.271 | −14.153 | 34.838 | 1.00 | 41.40 |
| 2700 | CG2 | THR | D | 493 | 9.832 | −14.186 | 37.204 | 1.00 | 25.45 |
| 2701 | C | THR | D | 493 | 11.599 | −16.618 | 34.844 | 1.00 | 31.62 |
| 2702 | O | THR | D | 493 | 12.376 | −16.281 | 33.922 | 1.00 | 34.73 |
| 2703 | N | GLN | D | 494 | 10.857 | −17.718 | 34.802 | 1.00 | 40.63 |
| 2704 | CA | GLN | D | 494 | 10.859 | −18.585 | 33.628 | 1.00 | 53.55 |
| 2705 | CB | GLN | D | 494 | 10.227 | −19.942 | 33.964 | 1.00 | 71.55 |
| 2706 | CG | GLN | D | 494 | 10.960 | −20.731 | 35.045 | 1.00 | 91.85 |
| 2707 | CD | GLN | D | 494 | 12.332 | −21.195 | 34.590 | 1.00 | 105.19 |
| 2708 | OE1 | GLN | D | 494 | 12.450 | −22.006 | 33.672 | 1.00 | 111.45 |
| 2709 | NE2 | GLN | D | 494 | 13.378 | −20.676 | 35.227 | 1.00 | 111.17 |
| 2710 | C | GLN | D | 494 | 10.011 | −17.877 | 32.574 | 1.00 | 55.12 |
| 2711 | O | GLN | D | 494 | 9.058 | −17.165 | 32.911 | 1.00 | 47.73 |
| 2712 | N | PRO | D | 495 | 10.361 | −18.039 | 31.289 | 1.00 | 47.03 |
| 2713 | CD | PRO | D | 495 | 11.597 | −18.654 | 30.776 | 1.00 | 55.90 |
| 2714 | CA | PRO | D | 495 | 9.613 | −17.410 | 30.198 | 1.00 | 46.09 |
| 2715 | CB | PRO | D | 495 | 10.346 | −17.896 | 28.955 | 1.00 | 44.77 |
| 2716 | CG | PRO | D | 495 | 11.758 | −17.981 | 29.411 | 1.00 | 36.43 |
| 2717 | C | PRO | D | 495 | 8.135 | −17.805 | 30.187 | 1.00 | 47.81 |
| 2718 | O | PRO | D | 495 | 7.780 | −18.952 | 30.420 | 1.00 | 51.53 |
| 2719 | N | ARG | D | 496 | 7.279 | −16.834 | 29.912 | 1.00 | 53.96 |
| 2720 | CA | ARG | D | 496 | 5.844 | −17.056 | 29.875 | 1.00 | 53.06 |
| 2721 | CB | ARG | D | 496 | 5.208 | −16.551 | 31.167 | 1.00 | 45.71 |
| 2722 | CG | ARG | D | 496 | 5.283 | −17.502 | 32.343 | 1.00 | 42.56 |
| 2723 | CD | ARG | D | 496 | 4.291 | −17.017 | 33.380 | 1.00 | 74.93 |
| 2724 | NE | ARG | D | 496 | 3.917 | −18.055 | 34.331 | 1.00 | 90.18 |
| 2725 | CZ | ARG | D | 496 | 2.729 | −18.120 | 34.927 | 1.00 | 81.55 |
| 2726 | NH1 | ARG | D | 496 | 1.800 | −17.202 | 34.662 | 1.00 | 72.32 |
| 2727 | NH2 | ARG | D | 496 | 2.473 | −19.097 | 35.789 | 1.00 | 83.21 |
| 2728 | C | ARG | D | 496 | 5.222 | −16.313 | 28.695 | 1.00 | 70.63 |
| 2729 | O | ARG | D | 496 | 5.731 | −15.269 | 28.275 | 1.00 | 67.25 |
| 2730 | N | LYS | D | 497 | 4.112 | −16.842 | 28.184 | 1.00 | 64.50 |
| 2731 | CA | LYS | D | 497 | 3.407 | −16.243 | 27.046 | 1.00 | 63.20 |
| 2732 | CB | LYS | D | 497 | 2.415 | −17.241 | 26.453 | 1.00 | 63.75 |
| 2733 | CG | LYS | D | 497 | 3.052 | −18.546 | 26.021 | 1.00 | 75.38 |
| 2734 | CD | LYS | D | 497 | 2.000 | −19.570 | 25.671 | 1.00 | 93.44 |
| 2735 | CE | LYS | D | 497 | 2.627 | −20.914 | 25.363 | 1.00 | 98.70 |
| 2736 | NZ | LYS | D | 497 | 1.592 | −21.921 | 25.015 | 1.00 | 105.20 |
| 2737 | C | LYS | D | 497 | 2.661 | −14.980 | 27.433 | 1.00 | 63.49 |
| 2738 | O | LYS | D | 497 | 1.921 | −14.961 | 28.409 | 1.00 | 60.29 |
| 2739 | N | THR | D | 498 | 2.859 | −13.922 | 26.658 | 1.00 | 68.71 |
| 2740 | CA | THR | D | 498 | 2.194 | −12.646 | 26.920 | 1.00 | 78.42 |
| 2741 | CB | THR | D | 498 | 2.889 | −11.498 | 26.170 | 1.00 | 81.62 |
| 2742 | OG1 | THR | D | 498 | 2.770 | −11.704 | 24.756 | 1.00 | 88.78 |
| 2743 | CG2 | THR | D | 498 | 4.365 | −11.451 | 26.537 | 1.00 | 79.78 |
| 2744 | C | THR | D | 498 | 0.749 | −12.726 | 26.453 | 1.00 | 89.46 |
| 2745 | O | THR | D | 498 | −0.171 | −12.834 | 27.260 | 1.00 | 97.71 |
| 2746 | N | LYS | D | 499 | 0.578 | −12.680 | 25.136 | 1.00 | 98.30 |
| 2747 | CA | LYS | D | 499 | −0.718 | −12.750 | 24.466 | 1.00 | 100.57 |
| 2748 | CB | LYS | D | 499 | −1.673 | −11.676 | 25.001 | 1.00 | 88.79 |
| 2749 | CG | LYS | D | 499 | −2.568 | −12.142 | 26.148 | 1.00 | 100.46 |
| 2750 | CD | LYS | D | 499 | −3.420 | −13.337 | 25.719 | 1.00 | 110.71 |
| 2751 | CE | LYS | D | 499 | −4.318 | −13.839 | 26.845 | 1.00 | 108.57 |
| 2752 | NZ | LYS | D | 499 | −5.165 | −14.992 | 26.403 | 1.00 | 96.62 |
| 2753 | C | LYS | D | 499 | −0.502 | −12.546 | 22.967 | 1.00 | 99.62 |
| 2754 | O | LYS | D | 499 | −0.885 | −11.518 | 22.416 | 1.00 | 92.13 |
| 2755 | N | GLY | D | 500 | 0.128 | −13.525 | 22.320 | 1.00 | 101.93 |
| 2756 | CA | GLY | D | 500 | 0.383 | −13.433 | 20.895 | 1.00 | 100.97 |
| 2757 | C | GLY | D | 500 | 1.748 | −12.871 | 20.526 | 1.00 | 104.17 |
| 2758 | O | GLY | D | 500 | 2.512 | −13.515 | 19.799 | 1.00 | 93.37 |
| 2759 | N | SER | D | 501 | 2.056 | −11.675 | 21.028 | 1.00 | 104.68 |
| 2760 | CA | SER | D | 501 | 3.327 | −11.004 | 20.737 | 1.00 | 103.47 |
| 2761 | CB | SER | D | 501 | 3.384 | −9.644 | 21.444 | 1.00 | 105.66 |
| 2762 | OG | SER | D | 501 | 3.346 | −9.802 | 22.854 | 1.00 | 120.85 |
| 2763 | C | SER | D | 501 | 4.565 | −11.820 | 21.110 | 1.00 | 99.80 |
| 2764 | O | SER | D | 501 | 5.650 | −11.575 | 20.573 | 1.00 | 101.75 |
| 2765 | N | GLY | D | 502 | 4.409 | −12.777 | 22.026 | 1.00 | 83.37 |
| 2766 | CA | GLY | D | 502 | 5.545 | −13.592 | 22.424 | 1.00 | 71.02 |
| 2767 | C | GLY | D | 502 | 5.636 | −13.919 | 23.907 | 1.00 | 60.06 |
| 2768 | O | GLY | D | 502 | 4.664 | −14.359 | 24.523 | 1.00 | 56.60 |
| 2769 | N | PHE | D | 503 | 6.816 | −13.707 | 24.484 | 1.00 | 49.45 |
| 2770 | CA | PHE | D | 503 | 7.021 | −13.994 | 25.900 | 1.00 | 48.97 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2771 | CB | PHE | D | 503 | 8.068 | −15.092 | 26.087 | 1.00 | 34.32 |
| 2772 | CG | PHE | D | 503 | 7.808 | −16.321 | 25.287 | 1.00 | 38.38 |
| 2773 | CD1 | PHE | D | 503 | 8.141 | −16.368 | 23.937 | 1.00 | 37.56 |
| 2774 | CD2 | PHE | D | 503 | 7.277 | −17.458 | 25.896 | 1.00 | 37.86 |
| 2775 | CE1 | PHE | D | 503 | 7.963 | −17.535 | 23.195 | 1.00 | 34.97 |
| 2776 | CE2 | PHE | D | 503 | 7.090 | −18.640 | 25.166 | 1.00 | 56.63 |
| 2777 | CZ | PHE | D | 503 | 7.440 | −18.676 | 23.804 | 1.00 | 33.47 |
| 2778 | C | PHE | D | 503 | 7.464 | −12.806 | 26.738 | 1.00 | 44.15 |
| 2779 | O | PHE | D | 503 | 7.786 | −11.728 | 26.233 | 1.00 | 42.35 |
| 2780 | N | PHE | D | 504 | 7.476 | −13.029 | 28.046 | 1.00 | 37.59 |
| 2781 | CA | PHE | D | 504 | 7.920 | −12.007 | 28.972 | 1.00 | 43.28 |
| 2782 | CB | PHE | D | 504 | 6.740 | −11.182 | 29.501 | 1.00 | 45.17 |
| 2783 | CG | PHE | D | 504 | 5.952 | −11.849 | 30.566 | 1.00 | 50.73 |
| 2784 | CD1 | PHE | D | 504 | 6.362 | −11.782 | 31.893 | 1.00 | 43.85 |
| 2785 | CD2 | PHE | D | 504 | 4.766 | −12.498 | 30.260 | 1.00 | 53.61 |
| 2786 | CE1 | PHE | D | 504 | 5.588 | −12.352 | 32.913 | 1.00 | 43.46 |
| 2787 | CE2 | PHE | D | 504 | 3.980 | −13.076 | 31.271 | 1.00 | 52.61 |
| 2788 | CZ | PHE | D | 504 | 4.392 | −13.002 | 32.596 | 1.00 | 58.74 |
| 2789 | C | PHE | D | 504 | 8.673 | −12.652 | 30.102 | 1.00 | 35.27 |
| 2790 | O | PHE | D | 504 | 8.506 | −13.830 | 30.396 | 1.00 | 34.16 |
| 2791 | N | VAL | D | 505 | 9.531 | −11.866 | 30.719 | 1.00 | 38.59 |
| 2792 | CA | VAL | D | 505 | 10.341 | −12.341 | 31.827 | 1.00 | 21.94 |
| 2793 | CB | VAL | D | 505 | 11.695 | −12.824 | 31.297 | 1.00 | 26.10 |
| 2794 | CG1 | VAL | D | 505 | 12.808 | −12.084 | 31.946 | 1.00 | 39.46 |
| 2795 | CG2 | VAL | D | 505 | 11.824 | −14.319 | 31.489 | 1.00 | 40.57 |
| 2796 | C | VAL | D | 505 | 10.489 | −11.206 | 32.831 | 1.00 | 32.83 |
| 2797 | O | VAL | D | 505 | 10.494 | −10.029 | 32.466 | 1.00 | 30.81 |
| 2798 | N | PHE | D | 506 | 10.561 | −11.565 | 34.102 | 1.00 | 30.08 |
| 2799 | CA | PHE | D | 506 | 10.716 | −10.575 | 35.162 | 1.00 | 35.80 |
| 2800 | CB | PHE | D | 506 | 9.515 | −10.647 | 36.119 | 1.00 | 32.51 |
| 2801 | CG | PHE | D | 506 | 9.634 | −9.773 | 37.356 | 1.00 | 90.85 |
| 2802 | CD1 | PHE | D | 506 | 9.687 | −8.390 | 37.260 | 1.00 | 92.61 |
| 2803 | CD2 | PHE | D | 506 | 9.574 | −10.340 | 38.639 | 1.00 | 88.06 |
| 2804 | CE1 | PHE | D | 506 | 9.663 | −7.591 | 38.435 | 1.00 | 99.85 |
| 2805 | CE2 | PHE | D | 506 | 9.548 | −9.538 | 39.812 | 1.00 | 26.95 |
| 2806 | CZ | PHE | D | 506 | 9.588 | −8.185 | 39.707 | 1.00 | 54.70 |
| 2807 | C | PHE | D | 506 | 12.011 | −10.870 | 35.883 | 1.00 | 30.37 |
| 2808 | O | PHE | D | 506 | 12.389 | −12.017 | 36.023 | 1.00 | 43.00 |
| 2809 | N | SER | D | 507 | 12.717 | −9.831 | 36.305 | 1.00 | 37.14 |
| 2810 | CA | SER | D | 507 | 13.982 | −10.026 | 37.020 | 1.00 | 35.54 |
| 2811 | CB | SER | D | 507 | 15.178 | −9.779 | 36.107 | 1.00 | 45.35 |
| 2812 | OG | SER | D | 507 | 16.338 | −10.187 | 36.790 | 1.00 | 32.92 |
| 2813 | C | SER | D | 507 | 14.072 | −9.123 | 38.245 | 1.00 | 35.27 |
| 2814 | O | SER | D | 507 | 13.749 | −7.932 | 38.201 | 1.00 | 39.92 |
| 2815 | N | ARG | D | 508 | 14.517 | −9.710 | 39.343 | 1.00 | 28.18 |
| 2816 | CA | ARG | D | 508 | 14.637 | −9.002 | 40.616 | 1.00 | 27.20 |
| 2817 | CB | ARG | D | 508 | 13.763 | −9.703 | 41.635 | 1.00 | 27.54 |
| 2818 | CG | ARG | D | 508 | 13.617 | −9.014 | 42.943 | 1.00 | 24.04 |
| 2819 | CD | ARG | D | 508 | 12.626 | −9.799 | 43.811 | 1.00 | 47.88 |
| 2820 | NE | ARG | D | 508 | 12.684 | −9.370 | 45.201 | 1.00 | 44.79 |
| 2821 | CZ | ARG | D | 508 | 13.634 | −9.735 | 46.044 | 1.00 | 49.71 |
| 2822 | NH1 | ARG | D | 508 | 14.596 | −10.555 | 45.636 | 1.00 | 48.49 |
| 2823 | NH2 | ARG | D | 508 | 13.644 | −9.239 | 47.275 | 1.00 | 58.00 |
| 2824 | C | ARG | D | 508 | 16.080 | −8.911 | 41.132 | 1.00 | 33.19 |
| 2825 | O | ARG | D | 508 | 16.849 | −9.882 | 41.103 | 1.00 | 30.13 |
| 2826 | N | LEU | D | 509 | 16.437 | −7.716 | 41.593 | 1.00 | 32.47 |
| 2827 | CA | LEU | D | 509 | 17.769 | −7.425 | 42.123 | 1.00 | 15.75 |
| 2828 | CB | LEU | D | 509 | 18.613 | −6.720 | 41.083 | 1.00 | 31.80 |
| 2829 | CG | LEU | D | 509 | 19.986 | −6.328 | 41.623 | 1.00 | 25.53 |
| 2830 | CD1 | LEU | D | 509 | 20.854 | −7.566 | 41.712 | 1.00 | 26.17 |
| 2831 | CD2 | LEU | D | 509 | 20.619 | −5.263 | 40.708 | 1.00 | 32.66 |
| 2832 | C | LEU | D | 509 | 17.739 | −6.546 | 43.356 | 1.00 | 32.56 |
| 2833 | O | LEU | D | 509 | 17.420 | −5.381 | 43.273 | 1.00 | 36.76 |
| 2834 | N | GLU | D | 510 | 18.075 | −7.110 | 44.503 | 1.00 | 35.48 |
| 2835 | CA | GLU | D | 510 | 18.122 | −6.342 | 45.740 | 1.00 | 32.85 |
| 2836 | CB | GLU | D | 510 | 18.035 | −7.274 | 46.947 | 1.00 | 58.15 |
| 2837 | CG | GLU | D | 510 | 17.125 | −8.498 | 46.774 | 1.00 | 81.75 |
| 2838 | CD | GLU | D | 510 | 16.991 | −9.312 | 48.060 | 1.00 | 83.91 |
| 2839 | OE1 | GLU | D | 510 | 16.411 | −10.419 | 48.020 | 1.00 | 80.75 |
| 2840 | OE2 | GLU | D | 510 | 17.464 | −8.836 | 49.115 | 1.00 | 84.26 |
| 2841 | C | GLU | D | 510 | 19.450 | −5.586 | 45.800 | 1.00 | 37.68 |
| 2842 | O | GLU | D | 510 | 20.508 | −6.187 | 45.668 | 1.00 | 38.08 |
| 2843 | N | VAL | D | 511 | 19.404 | −4.272 | 46.001 | 1.00 | 29.77 |
| 2844 | CA | VAL | D | 511 | 20.622 | −3.472 | 46.057 | 1.00 | 35.57 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2845 | CB | VAL | D | 511 | 20.654 | −2.445 | 44.872 | 1.00 | 43.98 |
| 2846 | CG1 | VAL | D | 511 | 20.540 | −3.189 | 43.551 | 1.00 | 23.80 |
| 2547 | CG2 | VAL | D | 511 | 19.526 | −1.422 | 44.987 | 1.00 | 24.07 |
| 2848 | C | VAL | D | 511 | 20.772 | −2.771 | 47.408 | 1.00 | 43.28 |
| 2849 | O | VAL | D | 511 | 19.777 | −2.537 | 48.097 | 1.00 | 40.08 |
| 2850 | N | THR | D | 512 | 22.010 | −2.417 | 47.772 | 1.00 | 55.57 |
| 2851 | CA | THR | D | 512 | 22.307 | −1.787 | 49.077 | 1.00 | 51.91 |
| 2852 | CB | THR | D | 512 | 23.438 | −2.521 | 49.787 | 1.00 | 33.21 |
| 2853 | OG1 | THR | D | 512 | 24.656 | −2.316 | 49.066 | 1.00 | 49.44 |
| 2854 | CG2 | THR | D | 512 | 23.155 | −4.005 | 49.845 | 1.00 | 58.25 |
| 2855 | C | THR | D | 512 | 22.680 | −0.307 | 49.126 | 1.00 | 50.44 |
| 2856 | O | THR | D | 512 | 23.315 | 0.215 | 48.218 | 1.00 | 49.55 |
| 2857 | N | ARG | D | 513 | 22.293 | 0.335 | 50.229 | 1.00 | 57.25 |
| 2858 | CA | ARG | D | 513 | 22.543 | 1.755 | 50.491 | 1.00 | 59.72 |
| 2859 | CB | ARG | D | 513 | 22.599 | 2.020 | 52.005 | 1.00 | 72.21 |
| 2860 | CG | ARG | D | 513 | 21.655 | 3.105 | 52.524 | 1.00 | 87.02 |
| 2861 | CD | ARG | D | 513 | 22.002 | 4.485 | 51.997 | 1.00 | 86.18 |
| 2862 | NE | ARG | D | 513 | 20.917 | 5.433 | 52.247 | 1.00 | 91.09 |
| 2863 | CZ | ARG | D | 513 | 20.866 | 6.665 | 51.750 | 1.00 | 97.08 |
| 2864 | NH1 | ARG | D | 513 | 21.839 | 7.115 | 50.972 | 1.00 | 97.33 |
| 2865 | NH2 | ARG | D | 513 | 19.831 | 7.445 | 52.022 | 1.00 | 94.75 |
| 2866 | C | ARG | D | 513 | 23.842 | 2.227 | 49.875 | 1.00 | 66.25 |
| 2867 | O | ARG | D | 513 | 23.881 | 3.277 | 49.245 | 1.00 | 68.46 |
| 2868 | N | ALA | D | 514 | 24.902 | 1.449 | 50.071 | 1.00 | 65.50 |
| 2869 | CA | ALA | D | 514 | 26.227 | 1.790 | 49.559 | 1.00 | 66.56 |
| 2870 | CB | ALA | D | 514 | 27.109 | 0.546 | 49.547 | 1.00 | 56.40 |
| 2871 | C | ALA | D | 514 | 26.173 | 2.426 | 48.166 | 1.00 | 81.26 |
| 2872 | O | ALA | D | 514 | 26.153 | 3.655 | 48.035 | 1.00 | 80.99 |
| 2873 | N | GLU | D | 515 | 26.152 | 1.589 | 47.128 | 1.00 | 79.40 |
| 2874 | CA | GLU | D | 515 | 26.073 | 2.079 | 45.759 | 1.00 | 56.16 |
| 2875 | CB | GLU | D | 515 | 26.256 | 0.950 | 44.768 | 1.00 | 38.57 |
| 2876 | CG | GLU | D | 515 | 25.245 | −0.165 | 44.893 | 1.00 | 64.23 |
| 2877 | CD | GLU | D | 515 | 25.681 | −1.257 | 45.855 | 1.00 | 75.43 |
| 2878 | OE1 | GLU | D | 515 | 26.126 | −0.894 | 46.969 | 1.00 | 61.29 |
| 2879 | OE2 | CLU | D | 515 | 25.571 | −2.469 | 45.500 | 1.00 | 64.86 |
| 2880 | C | GLU | D | 515 | 24.718 | 2.719 | 45.536 | 1.00 | 59.61 |
| 2881 | O | GLU | D | 515 | 24.572 | 3.554 | 44.661 | 1.00 | 59.42 |
| 2882 | N | TRP | D | 516 | 23.733 | 2.317 | 46.338 | 1.00 | 73.00 |
| 2883 | CA | TRP | D | 516 | 22.363 | 2.843 | 46.291 | 1.00 | 79.95 |
| 2884 | CB | TRP | D | 516 | 21.549 | 2.208 | 47.427 | 1.00 | 89.62 |
| 2885 | CG | TRP | D | 516 | 20.084 | 2.499 | 47.424 | 1.00 | 112.84 |
| 2886 | CD2 | TRP | D | 516 | 19.276 | 2.876 | 48.549 | 1.00 | 120.19 |
| 2887 | CE2 | TRP | D | 516 | 17.943 | 3.012 | 48.081 | 1.00 | 132.45 |
| 2888 | CE3 | TRP | D | 516 | 19.545 | 3.112 | 49.903 | 1.00 | 115.65 |
| 2889 | CD1 | TRP | D | 516 | 19.236 | 2.421 | 46.355 | 1.00 | 125.29 |
| 2890 | NE1 | TRP | D | 516 | 17.948 | 2.729 | 46.741 | 1.00 | 124.84 |
| 2891 | CZ2 | TRP | D | 516 | 16.880 | 3.378 | 48.925 | 1.00 | 127.78 |
| 2892 | CZ3 | TRP | D | 516 | 18.485 | 3.475 | 50.746 | 1.00 | 127.81 |
| 2893 | CH2 | TRP | D | 516 | 17.170 | 3.604 | 50.249 | 1.00 | 126.46 |
| 2894 | C | TRP | D | 516 | 22.415 | 4.361 | 46.464 | 1.00 | 89.09 |
| 2895 | O | TRP | D | 516 | 21.468 | 4.985 | 46.951 | 1.00 | 58.78 |
| 2896 | N | GLU | D | 517 | 23.556 | 4.928 | 46.074 | 1.00 | 83.80 |
| 2897 | CA | GLU | D | 517 | 23.834 | 6.357 | 46.147 | 1.00 | 93.49 |
| 2898 | CB | GLU | D | 517 | 24.774 | 6.639 | 47.326 | 1.00 | 96.00 |
| 2899 | CG | GLU | D | 517 | 24.132 | 6.293 | 48.672 | 1.00 | 110.25 |
| 2900 | CD | GLU | D | 517 | 24.917 | 6.792 | 49.868 | 1.00 | 114.33 |
| 2901 | OE1 | GLU | D | 517 | 26.031 | 6.280 | 50.110 | 1.00 | 118.49 |
| 2902 | OE2 | GLU | D | 517 | 24.413 | 7.698 | 50.565 | 1.00 | 110.95 |
| 2903 | C | GLU | D | 517 | 24.440 | 6.852 | 44.827 | 1.00 | 90.24 |
| 2904 | O | GLU | D | 517 | 24.633 | 8.056 | 44.620 | 1.00 | 85.35 |
| 2905 | N | ALA | D | 518 | 24.729 | 5.901 | 43.942 | 1.00 | 90.79 |
| 2906 | CA | ALA | D | 518 | 25.274 | 6.151 | 42.599 | 1.00 | 82.83 |
| 2907 | CB | ALA | D | 518 | 26.755 | 5.738 | 42.525 | 1.00 | 82.59 |
| 2908 | C | ALA | D | 518 | 24.442 | 5.225 | 41.739 | 1.00 | 76.16 |
| 2909 | O | ALA | D | 518 | 24.963 | 4.261 | 41.192 | 1.00 | 44.78 |
| 2910 | N | LYS | D | 519 | 23.144 | 5.518 | 41.657 | 1.00 | 77.00 |
| 2911 | CA | LYS | D | 519 | 22.200 | 4.682 | 40.928 | 1.00 | 80.17 |
| 2912 | CB | LYS | D | 519 | 20.759 | 5.027 | 41.309 | 1.00 | 81.73 |
| 2913 | CG | LYS | D | 519 | 20.331 | 4.594 | 42.698 | 1.00 | 93.58 |
| 2914 | CD | LYS | D | 519 | 18.818 | 4.337 | 42.727 | 1.00 | 94.89 |
| 2915 | CE | LYS | D | 519 | 18.252 | 4.413 | 44.125 | 1.00 | 84.11 |
| 2916 | NZ | LYS | D | 519 | 16.800 | 4.638 | 44.096 | 1.00 | 71.60 |
| 2917 | C | LYS | D | 519 | 22.307 | 4.704 | 39.425 | 1.00 | 76.28 |
| 2918 | O | LYS | D | 519 | 22.323 | 3.644 | 38.789 | 1.00 | 65.96 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2919 | N | ASP | D | 520 | 22.351 | 5.907 | 38.861 | 1.00 | 65.40 |
| 2920 | CA | ASP | D | 520 | 22.440 | 6.089 | 37.406 | 1.00 | 92.86 |
| 2921 | CB | ASP | D | 520 | 23.163 | 7.408 | 37.109 | 1.00 | 96.80 |
| 2922 | CG | ASP | D | 520 | 22.474 | 8.610 | 37.755 | 1.00 | 108.05 |
| 2923 | OD1 | ASP | D | 520 | 21.358 | 8.968 | 37.303 | 1.00 | 113.90 |
| 2924 | OD2 | ASP | D | 520 | 23.044 | 9.186 | 38.717 | 1.00 | 106.02 |
| 2925 | C | ASP | D | 520 | 23.159 | 4.908 | 36.740 | 1.00 | 87.36 |
| 2926 | O | ASP | D | 520 | 23.068 | 4.687 | 35.519 | 1.00 | 60.71 |
| 2927 | N | GLU | D | 521 | 23.872 | 4.153 | 37.570 | 1.00 | 75.78 |
| 2928 | CA | GLU | D | 521 | 24.606 | 2.985 | 37.132 | 1.00 | 86.97 |
| 2929 | CB | GLU | D | 521 | 26.010 | 2.946 | 37.773 | 1.00 | 90.41 |
| 2930 | CG | GLU | D | 521 | 27.061 | 3.921 | 37.165 | 1.00 | 86.37 |
| 2931 | CD | GLU | D | 521 | 27.192 | 5.248 | 37.949 | 1.00 | 88.24 |
| 2932 | OE1 | GLU | D | 521 | 27.355 | 5.226 | 39.198 | 1.00 | 80.87 |
| 2933 | OE2 | GLU | D | 521 | 27.148 | 6.312 | 37.292 | 1.00 | 72.10 |
| 2934 | C | GLU | D | 521 | 23.874 | 1.670 | 37.418 | 1.00 | 80.07 |
| 2935 | O | GLU | D | 521 | 24.510 | 0.682 | 37.766 | 1.00 | 100.56 |
| 2936 | N | PHE | D | 522 | 22.547 | 1.650 | 37.294 | 1.00 | 60.66 |
| 2937 | CA | PHE | D | 522 | 21.802 | 0.398 | 37.473 | 1.00 | 47.36 |
| 2938 | CB | PHE | D | 522 | 20.769 | 0.542 | 38.575 | 1.00 | 56.76 |
| 2939 | CG | PHE | D | 522 | 21.349 | 0.363 | 39.939 | 1.00 | 62.71 |
| 2940 | CD1 | PHE | D | 522 | 21.325 | 1.401 | 40.871 | 1.00 | 39.02 |
| 2941 | CD2 | PHE | D | 522 | 21.995 | −0.826 | 40.268 | 1.00 | 48.25 |
| 2942 | CE1 | PHE | D | 522 | 21.940 | 1.264 | 42.105 | 1.00 | 38.23 |
| 2943 | CE2 | PHE | D | 522 | 22.614 | −0.978 | 41.497 | 1.00 | 36.17 |
| 2944 | CZ | PHE | D | 522 | 22.586 | 0.075 | 42.418 | 1.00 | 45.22 |
| 2945 | C | PHE | D | 522 | 21.167 | −0.003 | 36.143 | 1.00 | 43.11 |
| 2946 | O | PHE | D | 522 | 20.172 | 0.565 | 35.702 | 1.00 | 38.28 |
| 2947 | N | ILE | D | 523 | 21.770 | −0.996 | 35.507 | 1.00 | 33.48 |
| 2948 | CA | ILE | D | 523 | 21.344 | −1.440 | 34.190 | 1.00 | 22.71 |
| 2949 | CB | ILE | D | 523 | 22.498 | −1.258 | 33.142 | 1.00 | 42.16 |
| 2950 | CG2 | ILE | D | 523 | 22.105 | −1.858 | 31.810 | 1.00 | 40.59 |
| 2951 | CG1 | ILE | D | 523 | 22.831 | 0.238 | 32.975 | 1.00 | 43.83 |
| 2952 | CD1 | ILE | D | 523 | 23.841 | 0.530 | 31.869 | 1.00 | 22.95 |
| 2953 | C | ILE | D | 523 | 20.843 | −2.860 | 34.077 | 1.00 | 29.41 |
| 2954 | O | ILE | D | 523 | 21.468 | −3.815 | 34.518 | 1.00 | 35.99 |
| 2955 | N | CYS | D | 524 | 19.688 | −2.985 | 33.459 | 1.00 | 38.19 |
| 2956 | CA | CYS | D | 524 | 19.106 | −4.283 | 33.204 | 1.00 | 30.11 |
| 2957 | C | CYS | D | 524 | 19.284 | −4.515 | 31.697 | 1.00 | 33.97 |
| 2958 | O | CYS | D | 524 | 18.716 | −3.816 | 30.881 | 1.00 | 37.96 |
| 2959 | CB | CYS | D | 524 | 17.617 | −4.303 | 33.575 | 1.00 | 34.90 |
| 2960 | SG | CYS | D | 524 | 16.773 | −5.824 | 33.057 | 1.00 | 67.42 |
| 2961 | N | ARG | D | 525 | 20.092 | −5.500 | 31.349 | 1.00 | 31.90 |
| 2962 | CA | ARG | D | 525 | 20.374 | −5.799 | 29.966 | 1.00 | 23.34 |
| 2963 | CB | ARG | D | 525 | 21.862 | −5.620 | 29.700 | 1.00 | 38.27 |
| 2964 | CG | ARG | D | 525 | 22.266 | −5.817 | 28.275 | 1.00 | 47.17 |
| 2965 | CD | ARG | D | 525 | 23.696 | −5.376 | 28.090 | 1.00 | 43.07 |
| 2966 | NE | ARG | D | 525 | 24.651 | −6.358 | 28.560 | 1.00 | 65.25 |
| 2967 | CZ | ARG | D | 525 | 25.929 | −6.094 | 28.790 | 1.00 | 74.13 |
| 2968 | NH1 | ARG | D | 525 | 26.402 | −4.867 | 28.599 | 1.00 | 56.92 |
| 2969 | NH2 | ARG | D | 52S | 26.734 | −7.065 | 29.204 | 1.00 | 69.07 |
| 2970 | C | ARG | D | 525 | 19.964 | −7.204 | 29.566 | 1.00 | 35.31 |
| 2971 | O | ARG | D | 525 | 20.276 | −8.191 | 30.237 | 1.00 | 32.88 |
| 2972 | N | ALA | D | 526 | 19.276 | −7.287 | 28.438 | 1.00 | 28.88 |
| 2973 | CA | ALA | D | 526 | 18.820 | −8.570 | 27.929 | 1.00 | 27.40 |
| 2974 | CB | ALA | D | 526 | 17.307 | −8.530 | 27.633 | 1.00 | 24.16 |
| 2975 | C | ALA | D | 526 | 19.592 | −8.913 | 26.669 | 1.00 | 42.49 |
| 2976 | O | ALA | D | 526 | 19.927 | −8.045 | 25.865 | 1.00 | 34.81 |
| 2977 | N | VAL | D | 527 | 19.884 | −10.195 | 26.522 | 1.00 | 29.29 |
| 2978 | CA | VAL | D | 527 | 20.592 | −10.695 | 25.359 | 1.00 | 29.46 |
| 2979 | CB | VAL | D | 527 | 21.852 | −11.459 | 25.771 | 1.00 | 46.48 |
| 2980 | CG1 | VAL | D | 527 | 22.530 | −12.018 | 24.553 | 1.00 | 41.89 |
| 2981 | CG2 | VAL | D | 527 | 22.799 | −10.532 | 26.524 | 1.00 | 32.52 |
| 2982 | C | VAL | D | 527 | 19.623 | −11.620 | 24.655 | 1.00 | 32.86 |
| 2983 | O | VAL | D | 527 | 19.165 | −12.630 | 25.204 | 1.00 | 35.18 |
| 2984 | N | HIS | D | 528 | 19.290 | −11.245 | 23.431 | 1.00 | 36.03 |
| 2985 | CA | HIS | D | 528 | 18.341 | −11.997 | 22.628 | 1.00 | 35.82 |
| 2986 | CB | HIS | D | 528 | 16.941 | −11.433 | 22.827 | 1.00 | 29.79 |
| 2987 | CG | HIS | D | 528 | 15.872 | −12.257 | 22.199 | 1.00 | 40.76 |
| 2988 | CD2 | HIS | D | 528 | 15.113 | −13.259 | 22.698 | 1.00 | 37.02 |
| 2989 | ND1 | HIS | D | 528 | 15.499 | −12.107 | 20.883 | 1.00 | 27.95 |
| 2990 | CE1 | HIS | D | 528 | 14.550 | −12.981 | 20.600 | 1.00 | 52.47 |
| 2991 | NE2 | HTS | D | 528 | 14.298 | −13.692 | 21.684 | 1.00 | 39.82 |
| 2992 | C | HIS | D | 528 | 18.707 | −11.969 | 21.163 | 1.00 | 38.66 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 2993 | O | HIS | D | 528 | 19.158 | −10.955 | 20.653 | 1.00 | 30.46 |
| 2994 | N | GLU | D | 529 | 18.506 | −13.111 | 20.510 | 1.00 | 49.17 |
| 2995 | CA | GLU | D | 529 | 18.799 | −13.319 | 19.087 | 1.00 | 47.56 |
| 2996 | CB | GLU | D | 529 | 18.311 | −14.696 | 18.658 | 1.00 | 48.34 |
| 2997 | CG | GLU | D | 529 | 18.284 | −14.901 | 17.163 | 1.00 | 71.89 |
| 2998 | CD | GLU | D | 529 | 17.721 | −16.237 | 16.796 | 1.00 | 91.39 |
| 2999 | OE1 | GLU | D | 529 | 17.565 | −16.496 | 15.586 | 1.00 | 76.86 |
| 3000 | OE2 | GLU | D | 529 | 17.439 | −17.023 | 17.725 | 1.00 | 86.34 |
| 3001 | C | GLU | D | 529 | 18.203 | −12.308 | 18.131 | 1.00 | 51.66 |
| 3002 | O | GLU | D | 529 | 18.750 | −12.087 | 17.054 | 1.00 | 53.17 |
| 3003 | N | ALA | D | 530 | 17.083 | −11.701 | 18.518 | 1.00 | 52.22 |
| 3004 | CA | ALA | D | 530 | 16.428 | −10.726 | 17.663 | 1.00 | 49.33 |
| 3005 | CB | ALA | D | 530 | 14.933 | −11.002 | 17.668 | 1.00 | 39.54 |
| 3006 | C | ALA | D | 530 | 16.698 | −9.230 | 17.978 | 1.00 | 59.53 |
| 3007 | O | ALA | D | 530 | 16.276 | −8.341 | 17.232 | 1.00 | 48.78 |
| 3008 | N | ALA | D | 531 | 17.401 | −8.944 | 19.068 | 1.00 | 63.73 |
| 3009 | CA | ALA | D | 531 | 17.665 | −7.554 | 19.425 | 1.00 | 62.65 |
| 3010 | CB | ALA | D | 531 | 18.235 | −7.467 | 20.846 | 1.00 | 48.66 |
| 3011 | C | ALA | D | 531 | 18.611 | −6.881 | 18.428 | 1.00 | 70.14 |
| 3012 | O | ALA | D | 531 | 18.921 | −5.695 | 18.551 | 1.00 | 78.27 |
| 3013 | N | SER | D | 532 | 19.048 | −7.635 | 17.428 | 1.00 | 77.04 |
| 3014 | CA | SER | D | 532 | 19.961 | −7.120 | 16.410 | 1.00 | 94.80 |
| 3015 | CB | SER | D | 532 | 19.817 | −7.924 | 15.118 | 1.00 | 100.34 |
| 3016 | OG | SER | D | 532 | 18.491 | −7.873 | 14.632 | 1.00 | 98.10 |
| 3017 | C | SER | D | 532 | 19.797 | −5.639 | 16.092 | 1.00 | 87.13 |
| 3018 | O | SER | D | 532 | 18.685 | −5.125 | 16.022 | 1.00 | 89.17 |
| 3019 | N | PRO | D | 533 | 20.918 | −4.928 | 15.909 | 1.00 | 87.12 |
| 3020 | CD | PRO | D | 533 | 20.932 | −3.469 | 15.691 | 1.00 | 91.61 |
| 3021 | CA | PRO | D | 533 | 22.286 | −5.451 | 15.989 | 1.00 | 81.82 |
| 3022 | CB | PRO | D | 533 | 23.101 | −4.327 | 15.379 | 1.00 | 79.54 |
| 3023 | CG | PRO | D | 533 | 22.395 | −3.116 | 15.911 | 1.00 | 82.79 |
| 3024 | C | PRO | D | 533 | 22.674 | −5.708 | 17.450 | 1.00 | 82.02 |
| 3025 | O | PRO | D | 533 | 21.823 | −5.675 | 18.341 | 1.00 | 94.02 |
| 3026 | N | SER | D | 534 | 23.955 | −5.954 | 17.690 | 1.00 | 66.69 |
| 3027 | CA | SER | D | 534 | 24.462 | −6.191 | 19.043 | 1.00 | 64.59 |
| 3028 | CB | SER | D | 534 | 24.379 | −4.910 | 19.877 | 1.00 | 60.63 |
| 3029 | OG | SER | D | 534 | 23.049 | −4.455 | 20.002 | 1.00 | 59.22 |
| 3030 | C | SER | D | 534 | 23.820 | −7.336 | 19.824 | 1.00 | 47.47 |
| 3031 | O | SER | D | 534 | 24.441 | −7.883 | 20.715 | 1.00 | 53.23 |
| 3032 | N | GLN | D | 535 | 22.589 | −7.689 | 19.478 | 1.00 | 41.92 |
| 3033 | CA | GLN | D | 535 | 21.849 | −8.767 | 20.112 | 1.00 | 39.56 |
| 3034 | CB | GLN | D | 535 | 22.613 | −10.091 | 20.008 | 1.00 | 44.31 |
| 3035 | CG | GLN | D | 535 | 23.514 | −10.247 | 18.789 | 1.00 | 48.13 |
| 3036 | CD | GLN | D | 535 | 22.798 | −10.029 | 17.496 | 1.00 | 54.41 |
| 3037 | OE1 | GLN | D | 535 | 23.418 | −9.720 | 16.493 | 1.00 | 61.29 |
| 3038 | NE2 | GLN | D | 535 | 21.492 | −10.193 | 17.503 | 1.00 | 68.94 |
| 3039 | C | GLN | D | 535 | 21.534 | −8.466 | 21.572 | 1.00 | 44.42 |
| 3040 | O | GLN | D | 535 | 21.359 | −9.373 | 22.385 | 1.00 | 47.86 |
| 3041 | N | THR | D | 536 | 21.456 | −7.189 | 21.913 | 1.00 | 37.74 |
| 3042 | CA | THR | D | 536 | 21.146 | −6.817 | 23.282 | 1.00 | 48.30 |
| 3043 | CB | THR | D | 536 | 22.435 | −6.569 | 24.120 | 1.00 | 54.14 |
| 3044 | OG1 | THR | D | 536 | 23.088 | −5.379 | 23.670 | 1.00 | 49.20 |
| 3045 | CG2 | THR | D | 536 | 23.398 | −7.725 | 23.992 | 1.00 | 53.35 |
| 3046 | C | THR | D | 536 | 20.262 | −5.562 | 23.377 | 1.00 | 49.54 |
| 3047 | O | THR | D | 536 | 20.241 | −4.729 | 22.477 | 1.00 | 41.01 |
| 3048 | N | VAL | D | 537 | 19.522 | −5.458 | 24.477 | 1.00 | 29.53 |
| 3049 | CA | VAL | D | 537 | 18.668 | −4.322 | 24.740 | 1.00 | 30.57 |
| 3050 | CB | VAL | D | 537 | 17.165 | −4.624 | 24.479 | 1.00 | 39.54 |
| 3051 | CG1 | VAL | D | 537 | 16.404 | −3.335 | 24.220 | 1.00 | 23.02 |
| 3052 | CG2 | VAL | D | 537 | 17.008 | −5.534 | 23.343 | 1.00 | 32.53 |
| 3053 | C | VAL | D | 537 | 18.871 | −4.059 | 26.226 | 1.00 | 29.20 |
| 3054 | O | VAL | D | 537 | 19.099 | −4.993 | 26.989 | 1.00 | 43.17 |
| 3055 | N | GLN | D | 538 | 18.767 | −2.803 | 26.642 | 1.00 | 13.46 |
| 3056 | CA | GLN | D | 538 | 18.997 | −2.482 | 28.043 | 1.00 | 33.32 |
| 3057 | CB | GLN | D | 538 | 20.519 | −2.384 | 28.336 | 1.00 | 34.98 |
| 3058 | CG | GLN | D | 538 | 21.217 | −1.145 | 27.747 | 1.00 | 16.47 |
| 3059 | CD | GLN | D | 538 | 22.705 | −1.161 | 28.004 | 1.00 | 48.20 |
| 3060 | OE1 | GLN | D | 538 | 23.406 | −2.110 | 27.621 | 1.00 | 39.95 |
| 3061 | NE2 | GLN | D | 538 | 23.205 | −0.113 | 28.662 | 1.00 | 19.56 |
| 3062 | C | GLN | D | 538 | 18.338 | −1.199 | 28.477 | 1.00 | 30.03 |
| 3063 | O | GLN | D | 538 | 18.065 | −0.328 | 27.688 | 1.00 | 33.51 |
| 3064 | N | ARG | D | 539 | 18.090 | −1.091 | 29.763 | 1.00 | 31.36 |
| 3065 | CA | ARG | D | 539 | 17.489 | 0.107 | 30.330 | 1.00 | 39.79 |
| 3066 | CB | ARG | D | 539 | 15.969 | −0.075 | 30.546 | 1.00 | 37.18 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3067 | CG | ARG | D | 539 | 15.181 | 1.211 | 30.369 | 1.00 | 61.07 |
| 3068 | CD | ARG | D | 539 | 14.432 | 1.219 | 29.021 | 1.00 | 97.86 |
| 3069 | NE | ARG | D | 539 | 15.289 | 1.001 | 27.845 | 1.00 | 109.24 |
| 3070 | CZ | ARG | D | 539 | 14.836 | 0.911 | 26.593 | 1.00 | 104.02 |
| 3071 | NH1 | ARG | D | 539 | 13.543 | 1.019 | 26.341 | 1.00 | 115.03 |
| 3072 | NH2 | ARG | D | 539 | 15.666 | 0.709 | 25.584 | 1.00 | 99.70 |
| 3073 | C | ARG | D | 539 | 18.170 | 0.400 | 31.673 | 1.00 | 31.91 |
| 3074 | O | ARG | D | 539 | 18.528 | −0.515 | 32.417 | 1.00 | 35.80 |
| 3075 | N | ALA | D | 540 | 18.346 | 1.683 | 31.967 | 1.00 | 25.53 |
| 3076 | CA | ALA | D | 540 | 18.975 | 2.104 | 33.202 | 1.00 | 32.38 |
| 3077 | CB | ALA | D | 540 | 19.915 | 3.256 | 32.932 | 1.00 | 15.41 |
| 3078 | C | ALA | D | 540 | 17.907 | 2.527 | 34.183 | 1.00 | 38.42 |
| 3079 | O | ALA | D | 540 | 16.875 | 3.027 | 33.768 | 1.00 | 35.66 |
| 3080 | N | VAL | D | 541 | 18.157 | 2.307 | 35.474 | 1.00 | 45.05 |
| 3081 | CA | VAL | D | 541 | 17.222 | 2.706 | 36.530 | 1.00 | 45.52 |
| 3082 | CB | VAL | D | 541 | 16.771 | 1.533 | 37.399 | 1.00 | 46.79 |
| 3083 | CG1 | VAL | D | 541 | 15.349 | 1.777 | 37.896 | 1.00 | 28.64 |
| 3084 | CG2 | VAL | D | 541 | 16.916 | 0.241 | 36.641 | 1.00 | 58.23 |
| 3085 | C | VAL | D | 541 | 17.887 | 3.706 | 37.468 | 1.00 | 64.00 |
| 3086 | O | VAL | D | 541 | 18.938 | 3.432 | 38.039 | 1.00 | 38.55 |
| 3087 | N | SER | D | 542 | 17.222 | 4.838 | 37.652 | 1.00 | 76.16 |
| 3086 | CA | SER | D | 542 | 17.695 | 5.942 | 38.476 | 1.00 | 91.73 |
| 3089 | CB | SER | D | 542 | 16.966 | 7.202 | 38.020 | 1.00 | 95.81 |
| 3090 | OG | SER | D | 542 | 15.585 | 6.937 | 37.818 | 1.00 | 88.45 |
| 3091 | C | SER | D | 542 | 17.603 | 5.844 | 40.004 | 1.00 | 92.58 |
| 3092 | O | SER | D | 542 | 17.204 | 4.826 | 40.571 | 1.00 | 73.34 |
| 3093 | N | VAL | D | 543 | 17.980 | 6.952 | 40.645 | 1.00 | 111.72 |
| 3094 | CA | VAL | D | 543 | 17.982 | 7.118 | 42.104 | 1.00 | 112.33 |
| 3095 | CB | VAL | D | 543 | 18.881 | 8.305 | 42.545 | 1.00 | 113.99 |
| 3096 | CG1 | VAL | D | 543 | 18.775 | 6.509 | 44.057 | 1.00 | 111.21 |
| 3097 | CG2 | VAL | D | 543 | 20.331 | 8.043 | 42.143 | 1.00 | 107.41 |
| 3098 | C | VAL | D | 543 | 16.593 | 7.351 | 42.684 | 1.00 | 100.74 |
| 3099 | O | VAL | D | 543 | 16.233 | 8.533 | 42.889 | 1.00 | 88.37 |
| 3100 | OXT | VAL | D | 543 | 15.888 | 6.346 | 42.914 | 1.00 | 91.27 |
| 3101 | CB | VAL | E | 336 | 14.879 | 31.371 | 50.715 | 1.00 | 131.14 |
| 3102 | CG1 | VAL | E | 336 | 15.960 | 32.392 | 51.068 | 1.00 | 128.62 |
| 3103 | CG2 | VAL | E | 336 | 14.993 | 30.943 | 49.253 | 1.00 | 134.58 |
| 3104 | C | VAL | E | 336 | 14.858 | 30.595 | 53.090 | 1.00 | 128.65 |
| 3105 | O | VAL | E | 336 | 14.169 | 31.575 | 53.383 | 1.00 | 124.76 |
| 3106 | N | VAL | E | 336 | 13.988 | 29.093 | 51.275 | 1.00 | 125.80 |
| 3107 | CA | VAL | E | 336 | 14.997 | 30.133 | 51.637 | 1.00 | 129.02 |
| 3108 | N | SER | E | 337 | 15.525 | 29.879 | 53.993 | 1.00 | 128.38 |
| 3109 | CA | SER | E | 337 | 15.496 | 30.193 | 55.417 | 1.00 | 120.77 |
| 3110 | CB | SER | E | 337 | 14.689 | 29.134 | 56.175 | 1.00 | 117.68 |
| 3111 | OG | SER | E | 337 | 15.190 | 27.832 | 55.928 | 1.00 | 127.26 |
| 3112 | C | SER | E | 337 | 16.917 | 30.262 | 55.970 | 1.00 | 122.16 |
| 3113 | O | SER | E | 337 | 17.872 | 29.835 | 55.314 | 1.00 | 118.45 |
| 3114 | N | ALA | E | 338 | 17.051 | 30.804 | 57.177 | 1.00 | 122.10 |
| 3115 | CA | ALA | E | 338 | 18.357 | 30.935 | 57.812 | 1.00 | 118.98 |
| 3116 | CB | ALA | E | 338 | 18.928 | 32.318 | 57.530 | 1.00 | 111.71 |
| 3117 | C | ALA | E | 338 | 18.289 | 30.695 | 59.320 | 1.00 | 117.66 |
| 3118 | O | ALA | E | 338 | 17.523 | 31.354 | 60.027 | 1.00 | 120.88 |
| 3119 | N | TYR | E | 339 | 19.097 | 29.750 | 59.801 | 1.00 | 120.89 |
| 3120 | CA | TYR | E | 339 | 19.158 | 29.403 | 61.227 | 1.00 | 118.87 |
| 3121 | CB | TYR | E | 339 | 18.938 | 27.894 | 61.438 | 1.00 | 120.94 |
| 3122 | CG | TYR | E | 339 | 17.663 | 27.299 | 60.866 | 1.00 | 128.91 |
| 3123 | CD1 | TYR | E | 339 | 17.266 | 27.564 | 59.555 | 1.00 | 127.40 |
| 3124 | CE1 | TYR | E | 339 | 16.138 | 26.954 | 59.007 | 1.00 | 134.75 |
| 3125 | CD2 | TYR | E | 339 | 16.893 | 26.407 | 61.619 | 1.00 | 133.72 |
| 3126 | CE2 | TYR | E | 339 | 15.764 | 25.790 | 61.079 | 1.00 | 130.95 |
| 3127 | CZ | TYR | E | 339 | 15.395 | 26.067 | 59.774 | 1.00 | 132.66 |
| 3128 | OH | TYR | E | 339 | 14.291 | 25.451 | 59.229 | 1.00 | 130.72 |
| 3129 | C | TYR | E | 339 | 20.541 | 29.761 | 61.793 | 1.00 | 113.93 |
| 3130 | O | TYR | E | 339 | 21.533 | 29.807 | 61.058 | 1.00 | 116.78 |
| 3131 | N | LEU | E | 340 | 20.604 | 30.004 | 63.099 | 1.00 | 107.52 |
| 3132 | CA | LEU | E | 340 | 21.868 | 30.322 | 63.760 | 1.00 | 101.76 |
| 3133 | CB | LEU | E | 340 | 21.973 | 31.826 | 64.031 | 1.00 | 101.01 |
| 3134 | CG | LEU | E | 340 | 23.329 | 32.337 | 64.533 | 1.00 | 96.72 |
| 3135 | CD1 | LEU | E | 340 | 24.411 | 31.964 | 63.537 | 1.00 | 91.82 |
| 3136 | CD2 | LEU | E | 340 | 23.282 | 33.842 | 64.720 | 1.00 | 93.44 |
| 3137 | C | LEU | E | 340 | 21.915 | 29.548 | 65.073 | 1.00 | 98.84 |
| 3138 | O | LEU | E | 340 | 21.104 | 29.786 | 65.963 | 1.00 | 98.10 |
| 3139 | N | SER | E | 341 | 22.861 | 28.620 | 65.194 | 1.00 | 102.22 |
| 3140 | CA | SER | E | 341 | 22.968 | 27.808 | 66.403 | 1.00 | 101.36 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3141 | CB | SER | E | 341 | 23.298 | 26.358 | 66.039 | 1.00 | 100.22 |
| 3142 | OG | SER | E | 341 | 24.613 | 26.249 | 65.520 | 1.00 | 100.30 |
| 3143 | C | SER | E | 341 | 23.999 | 28.312 | 67.408 | 1.00 | 100.95 |
| 3144 | O | SER | E | 341 | 24.838 | 29.155 | 67.093 | 1.00 | 100.90 |
| 3145 | N | ARG | E | 342 | 23.919 | 27.769 | 68.622 | 1.00 | 94.47 |
| 3146 | CA | ARG | E | 342 | 24.818 | 28.113 | 69.718 | 1.00 | 89.39 |
| 3147 | CB | ARG | E | 342 | 24.031 | 28.228 | 71.018 | 1.00 | 91.65 |
| 3148 | CG | ARG | E | 342 | 23.085 | 29.413 | 71.080 | 1.00 | 101.75 |
| 3149 | CD | ARG | E | 342 | 22.480 | 29.544 | 72.480 | 1.00 | 104.66 |
| 3150 | NE | ARG | E | 342 | 21.577 | 28.441 | 72.797 | 1.00 | 103.57 |
| 3151 | CZ | ARG | E | 342 | 20.346 | 28.327 | 72.312 | 1.00 | 104.17 |
| 3152 | NH1 | ARG | E | 342 | 19.862 | 29.250 | 71.489 | 1.00 | 105.73 |
| 3153 | NH2 | ARG | E | 342 | 19.602 | 27.283 | 72.646 | 1.00 | 105.71 |
| 3154 | C | ARG | E | 342 | 25.895 | 27.040 | 69.878 | 1.00 | 90.08 |
| 3155 | O | ARG | E | 342 | 25.838 | 26.003 | 69.221 | 1.00 | 94.61 |
| 3156 | N | PRO | E | 343 | 26.894 | 27.276 | 70.753 | 1.00 | 88.43 |
| 3157 | CD | PRO | E | 343 | 27.180 | 28.553 | 71.423 | 1.00 | 90.87 |
| 3158 | CA | PRO | E | 343 | 27.988 | 26.323 | 70.995 | 1.00 | 87.28 |
| 3159 | CB | PRO | E | 343 | 28.993 | 27.135 | 71.805 | 1.00 | 85.08 |
| 3160 | CG | PRO | E | 343 | 28.680 | 28.544 | 71.448 | 1.00 | 101.38 |
| 3161 | C | PRO | E | 343 | 27.511 | 25.125 | 71.798 | 1.00 | 79.67 |
| 3162 | O | PRO | E | 343 | 26.463 | 25.184 | 72.425 | 1.00 | 87.61 |
| 3163 | N | SER | E | 344 | 28.298 | 24.056 | 71.825 | 1.00 | 93.04 |
| 3164 | CA | SER | E | 344 | 27.908 | 22.871 | 72.577 | 1.00 | 88.18 |
| 3165 | CB | SER | E | 344 | 28.140 | 21.616 | 71.726 | 1.00 | 85.61 |
| 3166 | OG | SER | E | 344 | 29.415 | 21.633 | 71.110 | 1.00 | 81.45 |
| 3157 | C | SER | E | 344 | 28.615 | 22.735 | 73.933 | 1.00 | 81.27 |
| 3168 | O | SER | E | 344 | 29.796 | 23.061 | 74.073 | 1.00 | 65.03 |
| 3169 | N | PRO | E | 345 | 27.886 | 22.249 | 74.954 | 1.00 | 75.40 |
| 3170 | CD | PRO | E | 345 | 26.466 | 21.845 | 74.920 | 1.00 | 51.64 |
| 3171 | CA | PRO | E | 345 | 28.450 | 22.072 | 76.300 | 1.00 | 73.77 |
| 3172 | CB | PRO | E | 345 | 27.290 | 21.447 | 77.088 | 1.00 | 69.22 |
| 3173 | CG | PRO | E | 345 | 26.075 | 21.946 | 76.374 | 1.00 | 65.38 |
| 3174 | C | PRO | E | 345 | 29.695 | 21.174 | 76.309 | 1.00 | 82.82 |
| 3175 | O | PRO | E | 345 | 30.466 | 21.184 | 77.272 | 1.00 | 75.10 |
| 3176 | N | PHE | E | 346 | 29.871 | 20.386 | 75.247 | 1.00 | 80.04 |
| 3177 | CA | PHE | E | 346 | 31.024 | 19.485 | 75.136 | 1.00 | 90.36 |
| 3178 | CB | PHE | E | 346 | 30.790 | 18.394 | 74.093 | 1.00 | 94.66 |
| 3179 | CG | PHE | E | 346 | 32.034 | 17.618 | 73.752 | 1.00 | 81.23 |
| 3180 | CD1 | PHE | E | 346 | 32.579 | 16.716 | 74.662 | 1.00 | 77.00 |
| 3181 | CD2 | PHE | E | 346 | 32.680 | 17.815 | 72.534 | 1.00 | 76.33 |
| 3182 | CE1 | PHE | E | 346 | 33.752 | 16.019 | 74.367 | 1.00 | 77.59 |
| 3183 | CE2 | PHE | E | 346 | 33.855 | 17.122 | 72.226 | 1.00 | 79.84 |
| 3184 | CZ | PHE | E | 346 | 34.392 | 16.223 | 73.146 | 1.00 | 75.42 |
| 3185 | C | PHE | E | 346 | 32.250 | 20.278 | 74.724 | 1.00 | 79.15 |
| 3186 | O | PHE | E | 346 | 33.373 | 19.996 | 75.158 | 1.00 | 61.77 |
| 3187 | N | ASP | E | 347 | 32.024 | 21.249 | 73.848 | 1.00 | 72.15 |
| 3188 | CA | ASP | E | 347 | 33.089 | 22.117 | 73.398 | 1.00 | 76.49 |
| 3189 | CB | ASP | E | 347 | 32.659 | 22.847 | 72.126 | 1.00 | 71.98 |
| 3190 | CG | ASP | E | 347 | 32.148 | 21.901 | 71.060 | 1.00 | 93.35 |
| 3191 | OD1 | ASP | E | 347 | 31.631 | 22.374 | 70.023 | 1.00 | 90.86 |
| 3192 | OD2 | ASP | E | 347 | 32.264 | 20.675 | 71.261 | 1.00 | 111.32 |
| 3193 | C | ASP | E | 347 | 33.219 | 23.096 | 74.558 | 1.00 | 68.44 |
| 3194 | O | ASP | E | 347 | 34.010 | 22.902 | 75.479 | 1.00 | 80.50 |
| 3195 | N | LEU | E | 348 | 32.393 | 24.128 | 74.517 | 1.00 | 67.77 |
| 3196 | CA | LEU | E | 348 | 32.369 | 25.155 | 75.542 | 1.00 | 72.93 |
| 3197 | CB | LEU | E | 348 | 30.912 | 25.558 | 75.811 | 1.00 | 67.40 |
| 3198 | CG | LEU | E | 348 | 30.594 | 26.956 | 76.356 | 1.00 | 77.79 |
| 3199 | CD1 | LEU | E | 348 | 30.983 | 28.032 | 75.344 | 1.00 | 67.29 |
| 3200 | CD2 | LEU | E | 348 | 29.111 | 27.049 | 76.641 | 1.00 | 63.75 |
| 3201 | C | LEU | E | 348 | 33.048 | 24.784 | 76.872 | 1.00 | 80.17 |
| 3202 | O | LEU | E | 348 | 34.101 | 25.322 | 77.207 | 1.00 | 89.29 |
| 3203 | N | PHE | E | 349 | 32.468 | 23.839 | 77.605 | 1.00 | 88.90 |
| 3204 | CA | PHE | E | 349 | 32.976 | 23.473 | 78.932 | 1.00 | 88.55 |
| 3205 | CB | PHE | E | 349 | 31.783 | 23.189 | 79.859 | 1.00 | 93.57 |
| 3206 | CG | PHE | E | 349 | 30.757 | 24.290 | 79.883 | 1.00 | 86.78 |
| 3207 | CD1 | PHE | E | 349 | 29.418 | 24.001 | 80.139 | 1.00 | 89.13 |
| 3208 | CD2 | PHE | E | 349 | 31.120 | 25.612 | 79.621 | 1.00 | 85.42 |
| 3209 | CE1 | PHE | E | 349 | 28.450 | 25.011 | 80.128 | 1.00 | 74.97 |
| 3210 | CE2 | PHE | E | 349 | 30.164 | 26.625 | 79.609 | 1.00 | 74.35 |
| 3211 | CZ | PHE | E | 349 | 28.822 | 26.319 | 79.862 | 1.00 | 73.32 |
| 3212 | C | PHE | E | 349 | 34.003 | 22.358 | 79.123 | 1.00 | 88.51 |
| 3213 | O | PHE | E | 349 | 34.498 | 22.178 | 80.241 | 1.00 | 86.14 |
| 3214 | N | ILE | E | 350 | 34.332 | 21.606 | 78.078 | 1.00 | 79.16 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3215 | CA | ILE | E | 350 | 35.301 | 20.525 | 78.256 | 1.00 | 80.44 |
| 3216 | CB | ILE | E | 350 | 34.630 | 19.134 | 78.128 | 1.00 | 71.07 |
| 3217 | CG2 | ILE | E | 350 | 35.493 | 18.088 | 78.818 | 1.00 | 69.10 |
| 3218 | CG1 | ILE | E | 350 | 33.237 | 19.139 | 78.774 | 1.00 | 77.59 |
| 3219 | CD1 | ILE | E | 350 | 33.222 | 19.389 | 80.278 | 1.00 | 86.77 |
| 3220 | C | ILE | E | 350 | 36.469 | 20.582 | 77.268 | 1.00 | 98.96 |
| 3221 | O | ILE | E | 350 | 37.637 | 20.588 | 77.670 | 1.00 | 86.72 |
| 3222 | N | ARG | E | 351 | 36.139 | 20.615 | 75.978 | 1.00 | 105.47 |
| 3223 | CA | ARG | E | 351 | 37.128 | 20.667 | 74.903 | 1.00 | 93.85 |
| 3224 | CB | ARG | E | 351 | 36.462 | 20.239 | 73.591 | 1.00 | 101.78 |
| 3225 | CG | ARG | E | 351 | 37.407 | 19.742 | 72.514 | 1.00 | 104.01 |
| 3226 | CD | ARG | E | 351 | 36.643 | 18.909 | 71.494 | 1.00 | 99.51 |
| 3227 | NE | ARG | E | 351 | 37.480 | 18.498 | 70.372 | 1.00 | 106.80 |
| 3228 | CZ | ARG | E | 351 | 37.809 | 19.291 | 69.357 | 1.00 | 110.91 |
| 3229 | NH1 | ARG | E | 351 | 37.366 | 20.541 | 69.321 | 1.00 | 117.38 |
| 3230 | NH2 | ARG | E | 351 | 38.583 | 18.837 | 68.381 | 1.00 | 101.29 |
| 3231 | C | ARG | E | 351 | 37.723 | 22.079 | 74.779 | 1.00 | 87.32 |
| 3232 | O | ARG | E | 351 | 38.894 | 22.239 | 74.448 | 1.00 | 105.17 |
| 3233 | N | LYS | E | 352 | 36.910 | 23.095 | 75.045 | 1.00 | 87.38 |
| 3234 | CA | LYS | E | 352 | 37.357 | 24.485 | 74.998 | 1.00 | 93.36 |
| 3235 | CB | LYS | E | 352 | 38.520 | 24.696 | 75.967 | 1.00 | 94.63 |
| 3236 | CG | LYS | E | 352 | 38.262 | 24.211 | 77.377 | 1.00 | 85.68 |
| 3237 | CD | LYS | E | 352 | 39.484 | 24.438 | 78.248 | 1.00 | 92.53 |
| 3238 | CE | LYS | E | 352 | 39.268 | 23.900 | 79.648 | 1.00 | 99.62 |
| 3239 | NZ | LYS | E | 352 | 38.997 | 22.437 | 79.626 | 1.00 | 115.97 |
| 3240 | C | LYS | E | 352 | 37.767 | 24.994 | 73.624 | 1.00 | 87.73 |
| 3241 | O | LYS | E | 352 | 38.953 | 25.049 | 73.302 | 1.00 | 68.55 |
| 3242 | N | SER | E | 353 | 36.765 | 25.367 | 72.833 | 1.00 | 77.72 |
| 3243 | CA | SER | E | 353 | 36.929 | 25.919 | 71.483 | 1.00 | 103.77 |
| 3244 | CB | SER | E | 353 | 37.964 | 25.123 | 70.662 | 1.00 | 110.30 |
| 3245 | OG | SER | E | 353 | 37.598 | 23.764 | 70.493 | 1.00 | 121.56 |
| 3246 | C | SER | E | 353 | 35.554 | 25.907 | 70.794 | 1.00 | 105.57 |
| 3247 | O | SER | E | 353 | 35.282 | 25.095 | 69.905 | 1.00 | 109.43 |
| 3248 | N | PRO | E | 354 | 34.664 | 26.816 | 71.217 | 1.00 | 96.44 |
| 3249 | CD | PRO | E | 354 | 34.861 | 27.694 | 72.376 | 1.00 | 97.99 |
| 3250 | CA | PRO | E | 354 | 33.305 | 26.962 | 70.694 | 1.00 | 95.75 |
| 3251 | CB | PRO | E | 354 | 32.670 | 27.948 | 71.666 | 1.00 | 93.49 |
| 3252 | CG | PRO | E | 354 | 33.480 | 27.770 | 72.914 | 1.00 | 103.01 |
| 3253 | C | PRO | E | 354 | 33.204 | 27.464 | 69.260 | 1.00 | 99.25 |
| 3254 | O | PRO | E | 354 | 34.136 | 28.078 | 68.731 | 1.00 | 99.80 |
| 3255 | N | THR | E | 355 | 32.052 | 27.196 | 68.653 | 1.00 | 90.62 |
| 3256 | CA | THR | E | 355 | 31.748 | 27.619 | 67.287 | 1.00 | 101.86 |
| 3257 | CB | THR | E | 355 | 32.259 | 26.601 | 66.202 | 1.00 | 93.22 |
| 3258 | GG1 | THR | E | 355 | 31.852 | 25.271 | 66.550 | 1.00 | 92.95 |
| 3259 | CG2 | THR | E | 355 | 33.772 | 26.659 | 66.060 | 1.00 | 94.53 |
| 3260 | C | THR | E | 355 | 30.230 | 27.745 | 67.148 | 1.00 | 99.64 |
| 3261 | O | THR | E | 355 | 29.468 | 27.138 | 67.906 | 1.00 | 99.91 |
| 3262 | N | ILE | E | 356 | 29.801 | 28.552 | 66.188 | 1.00 | 95.48 |
| 3263 | CA | ILE | E | 356 | 28.390 | 28.744 | 65.920 | 1.00 | 89.41 |
| 3264 | CB | ILE | E | 356 | 27.935 | 30.157 | 66.301 | 1.00 | 89.84 |
| 3265 | CG2 | ILE | E | 356 | 28.006 | 30.316 | 67.813 | 1.00 | 96.40 |
| 3266 | CG1 | ILE | E | 356 | 28.804 | 31.201 | 65.592 | 1.00 | 87.30 |
| 3267 | CD1 | ILE | E | 356 | 28.493 | 32.634 | 65.989 | 1.00 | 95.97 |
| 3268 | C | ILE | E | 356 | 28.234 | 28.533 | 64.430 | 1.00 | 92.60 |
| 3269 | O | ILE | E | 356 | 29.148 | 28.830 | 63.658 | 1.00 | 99.25 |
| 3270 | N | THR | E | 357 | 27.090 | 28.013 | 64.014 | 1.00 | 92.56 |
| 3271 | CA | THR | E | 357 | 26.889 | 27.770 | 62.597 | 1.00 | 100.71 |
| 3272 | CB | THR | E | 357 | 26.787 | 26.260 | 62.307 | 1.00 | 96.69 |
| 3273 | OG1 | THR | E | 357 | 27.905 | 25.580 | 62.892 | 1.00 | 99.95 |
| 3274 | CG2 | THR | E | 357 | 26.776 | 26.010 | 60.802 | 1.00 | 92.52 |
| 3275 | C | THR | E | 357 | 25.659 | 28.452 | 62.011 | 1.00 | 101.74 |
| 3276 | O | THR | E | 357 | 24.535 | 28.239 | 62.476 | 1.00 | 94.25 |
| 3277 | N | CYS | E | 358 | 25.888 | 29.280 | 60.994 | 1.00 | 103.46 |
| 3278 | CA | CYS | E | 358 | 24.808 | 29.974 | 60.296 | 1.00 | 106.01 |
| 3279 | C | CYS | E | 358 | 24.461 | 29.023 | 59.152 | 1.00 | 104.35 |
| 3280 | O | CYS | E | 358 | 25.296 | 28.756 | 58.284 | 1.00 | 105.76 |
| 3281 | CB | CYS | E | 358 | 25.293 | 31.320 | 59.741 | 1.00 | 107.07 |
| 3282 | SG | CYS | E | 358 | 23.980 | 32.451 | 59.170 | 1.00 | 116.20 |
| 3283 | N | LEU | E | 359 | 23.239 | 28.501 | 59.168 | 1.00 | 103.07 |
| 3284 | CA | LEU | E | 359 | 22.786 | 27.551 | 58.156 | 1.00 | 105.76 |
| 3285 | CB | LEU | E | 359 | 22.336 | 26.257 | 58.842 | 1.00 | 107.99 |
| 3286 | CG | LEU | E | 359 | 21.486 | 25.268 | 58.033 | 1.00 | 117.01 |
| 3287 | CD1 | LEU | E | 359 | 22.303 | 24.698 | 56.885 | 1.00 | 118.73 |
| 3288 | CD2 | LEU | E | 359 | 20.988 | 24.149 | 58.941 | 1.00 | 111.15 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3289 | C | LEU | E | 359 | 21.655 | 28.071 | 57.268 | 1.00 | 110.06 |
| 3290 | O | LEU | E | 359 | 20.519 | 28.237 | 57.721 | 1.00 | 106.76 |
| 3291 | N | VAL | E | 360 | 21.965 | 28.313 | 55.998 | 1.00 | 115.81 |
| 3292 | CA | VAL | E | 360 | 20.965 | 28.796 | 55.050 | 1.00 | 119.53 |
| 3293 | CB | VAL | E | 360 | 21.565 | 29.837 | 54.080 | 1.00 | 115.82 |
| 3294 | CG1 | VAL | E | 360 | 20.473 | 30.408 | 53.192 | 1.00 | 106.85 |
| 3295 | CG2 | VAL | E | 360 | 22.248 | 30.944 | 54.868 | 1.00 | 112.82 |
| 3296 | C | VAL | E | 360 | 20.414 | 27.624 | 54.238 | 1.00 | 119.99 |
| 3297 | O | VAL | E | 360 | 21.173 | 26.870 | 53.623 | 1.00 | 117.58 |
| 3298 | N | VAL | E | 361 | 19.093 | 27.472 | 54.243 | 1.00 | 123.77 |
| 3299 | CA | VAL | E | 361 | 18.445 | 26.386 | 53.508 | 1.00 | 131.09 |
| 3300 | CB | VAL | E | 361 | 17.537 | 25.534 | 54.440 | 1.00 | 127.16 |
| 3301 | CG1 | VAL | E | 361 | 16.888 | 24.401 | 53.650 | 1.00 | 118.81 |
| 3302 | CG2 | VAL | E | 361 | 18.356 | 24.965 | 55.590 | 1.00 | 121.65 |
| 3303 | C | VAL | E | 361 | 17.600 | 26.905 | 52.342 | 1.00 | 135.81 |
| 3304 | O | VAL | E | 361 | 16.609 | 27.612 | 52.541 | 1.00 | 127.80 |
| 3305 | N | ASP | E | 362 | 18.003 | 26.545 | 51.125 | 1.00 | 143.67 |
| 3306 | CA | ASP | E | 362 | 17.296 | 26.960 | 49.918 | 1.00 | 147.18 |
| 3307 | CB | ASP | E | 362 | 18.197 | 27.842 | 49.051 | 1.00 | 145.76 |
| 3308 | CG | ASP | E | 362 | 17.421 | 28.616 | 48.009 | 1.00 | 145.36 |
| 3309 | OD1 | ASP | E | 362 | 16.604 | 27.997 | 47.300 | 1.00 | 148.24 |
| 3310 | OD2 | ASP | E | 362 | 17.628 | 29.842 | 47.897 | 1.00 | 145.59 |
| 3311 | C | ASP | E | 362 | 16.877 | 25.725 | 49.125 | 1.00 | 149.00 |
| 3312 | O | ASP | E | 362 | 17.723 | 24.954 | 48.667 | 1.00 | 150.04 |
| 3313 | N | LEU | E | 363 | 15.571 | 25.541 | 48.965 | 1.00 | 153.56 |
| 3314 | CA | LEU | E | 363 | 15.050 | 24.391 | 48.235 | 1.00 | 158.30 |
| 3315 | CB | LEU | E | 363 | 13.620 | 24.077 | 48.701 | 1.00 | 156.24 |
| 3316 | CG | LEU | E | 363 | 13.438 | 23.593 | 50.146 | 1.00 | 155.91 |
| 3317 | CD1 | LEU | E | 363 | 11.959 | 23.516 | 50.478 | 1.00 | 154.03 |
| 3318 | CD2 | LEU | E | 363 | 14.095 | 22.232 | 50.327 | 1.00 | 158.28 |
| 3319 | C | LEU | E | 363 | 15.077 | 24.594 | 46.718 | 1.00 | 158.34 |
| 3320 | O | LEU | E | 363 | 14.927 | 23.639 | 45.956 | 1.00 | 157.11 |
| 3321 | N | ALA | E | 364 | 15.277 | 25.835 | 46.282 | 1.00 | 159.62 |
| 3322 | CA | ALA | E | 364 | 15.322 | 26.147 | 44.854 | 1.00 | 163.17 |
| 3323 | CB | ALA | E | 364 | 14.199 | 27.119 | 44.497 | 1.00 | 158.17 |
| 3324 | C | ALA | E | 364 | 16.677 | 26.736 | 44.449 | 1.00 | 167.84 |
| 3325 | O | ALA | E | 364 | 16.830 | 27.956 | 44.340 | 1.00 | 166.15 |
| 3326 | N | PRO | E | 365 | 17.677 | 25.868 | 44.212 | 1.00 | 171.11 |
| 3327 | CD | PRO | E | 365 | 17.594 | 24.400 | 44.337 | 1.00 | 167.30 |
| 3328 | CA | PRO | E | 365 | 19.032 | 26.276 | 43.819 | 1.00 | 170.93 |
| 3329 | CB | PRO | E | 365 | 19.705 | 24.944 | 43.489 | 1.00 | 168.17 |
| 3330 | CG | PRO | E | 365 | 19.049 | 24.001 | 44.446 | 1.00 | 167.81 |
| 3331 | C | PRO | E | 365 | 19.100 | 27.264 | 42.649 | 1.00 | 169.92 |
| 3332 | O | PRO | E | 365 | 19.233 | 26.859 | 41.495 | 1.00 | 171.19 |
| 3333 | N | SER | E | 366 | 19.012 | 28.556 | 42.954 | 1.00 | 170.99 |
| 3334 | CA | SER | E | 366 | 19.085 | 29.594 | 41.927 | 1.00 | 171.72 |
| 3335 | CB | SER | E | 366 | 18.099 | 30.724 | 42.243 | 1.00 | 167.78 |
| 3336 | OG | SER | E | 366 | 18.323 | 31.257 | 43.536 | 1.00 | 170.13 |
| 3337 | C | SER | E | 366 | 20.514 | 30.139 | 41.868 | 1.00 | 172.58 |
| 3338 | O | SER | E | 366 | 21.117 | 30.425 | 42.903 | 1.00 | 175.93 |
| 3339 | N | LYS | E | 367 | 21.052 | 30.280 | 40.658 | 1.00 | 169.34 |
| 3340 | CA | LYS | E | 367 | 22.420 | 30.766 | 40.471 | 1.00 | 168.91 |
| 3341 | CB | LYS | E | 367 | 22.793 | 30.716 | 38.987 | 1.00 | 167.04 |
| 3342 | CG | LYS | E | 367 | 22.675 | 29.327 | 38.378 | 1.00 | 165.86 |
| 3343 | CD | LYS | E | 367 | 23.248 | 29.271 | 36.969 | 1.00 | 168.17 |
| 3344 | CE | LYS | E | 367 | 24.754 | 29.500 | 36.967 | 1.00 | 169.57 |
| 3345 | NZ | LYS | E | 367 | 25.339 | 29.351 | 35.605 | 1.00 | 168.13 |
| 3346 | C | LYS | E | 367 | 22.683 | 32.169 | 41.023 | 1.00 | 167.17 |
| 3347 | O | LYS | E | 367 | 21.827 | 33.050 | 40.950 | 1.00 | 167.35 |
| 3348 | N | GLY | E | 368 | 23.883 | 32.360 | 41.570 | 1.00 | 165.77 |
| 3349 | CA | GLY | E | 368 | 24.266 | 33.641 | 42.143 | 1.00 | 161.09 |
| 3350 | C | GLY | E | 368 | 24.926 | 33.470 | 43.503 | 1.00 | 161.38 |
| 3351 | O | GLY | E | 368 | 24.403 | 32.755 | 44.360 | 1.00 | 161.44 |
| 3352 | N | THR | E | 369 | 26.073 | 34.121 | 43.705 | 1.00 | 159.13 |
| 3353 | CA | THR | E | 369 | 26.800 | 34.027 | 44.974 | 1.00 | 151.92 |
| 3354 | CB | THR | E | 369 | 28.071 | 34.920 | 44.985 | 1.00 | 149.86 |
| 3355 | OG1 | THR | E | 369 | 27.759 | 36.213 | 44.450 | 1.00 | 147.48 |
| 3356 | CG2 | THR | E | 369 | 29.189 | 34.281 | 44.177 | 1.00 | 147.70 |
| 3357 | C | THR | E | 369 | 25.946 | 34.418 | 46.174 | 1.00 | 150.08 |
| 3358 | O | THR | E | 369 | 25.114 | 35.325 | 46.094 | 1.00 | 150.63 |
| 3359 | N | VAL | E | 370 | 26.160 | 33.721 | 47.286 | 1.00 | 146.39 |
| 3360 | CA | VAL | E | 370 | 25.430 | 33.985 | 48.522 | 1.00 | 138.77 |
| 3361 | CB | VAL | E | 370 | 24.737 | 32.708 | 49.056 | 1.00 | 133.95 |
| 3362 | CG1 | VAL | E | 370 | 23.807 | 33.066 | 50.206 | 1.00 | 131.54 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3363 | CG2 | VAL | E | 370 | 23.968 | 32.020 | 47.936 | 1.00 | 130.58 |
| 3364 | C | VAL | E | 370 | 26.424 | 34.476 | 49.571 | 1.00 | 133.87 |
| 3365 | O | VAL | E | 370 | 27.353 | 33.754 | 49.935 | 1.00 | 130.78 |
| 3366 | N | ASN | E | 371 | 26.233 | 35.704 | 50.048 | 1.00 | 128.83 |
| 3367 | CA | ASN | E | 371 | 27.124 | 36.277 | 51.051 | 1.00 | 127.86 |
| 3368 | CB | ASN | E | 371 | 27.305 | 37.780 | 50.815 | 1.00 | 131.05 |
| 3369 | CG | ASN | E | 371 | 28.142 | 38.082 | 49.589 | 1.00 | 136.74 |
| 3370 | OD1 | ASN | E | 371 | 29.294 | 37.656 | 49.485 | 1.00 | 140.99 |
| 3371 | ND2 | ASN | E | 371 | 27.567 | 38.828 | 48.653 | 1.00 | 137.55 |
| 3372 | C | ASN | E | 371 | 26.643 | 36.056 | 52.479 | 1.00 | 127.96 |
| 3373 | O | ASN | E | 371 | 25.510 | 36.389 | 52.829 | 1.00 | 127.68 |
| 3374 | N | LEU | E | 372 | 27.516 | 35.486 | 53.302 | 1.00 | 121.89 |
| 3375 | CA | LEU | E | 372 | 27.200 | 35.237 | 54.698 | 1.00 | 120.44 |
| 3376 | CB | LEU | E | 372 | 27.281 | 33.742 | 55.018 | 1.00 | 121.70 |
| 3377 | CG | LEU | E | 372 | 26.253 | 32.835 | 54.337 | 1.00 | 123.33 |
| 3378 | CD1 | LEU | E | 372 | 26.372 | 31.420 | 54.887 | 1.00 | 127.50 |
| 3379 | CD2 | LEU | E | 372 | 24.854 | 33.375 | 54.583 | 1.00 | 127.15 |
| 3380 | C | LEU | E | 372 | 28.211 | 36.007 | 55.529 | 1.00 | 122.81 |
| 3381 | O | LEU | E | 372 | 29.295 | 35.506 | 55.827 | 1.00 | 128.48 |
| 3382 | N | THR | E | 373 | 27.846 | 37.234 | 55.890 | 1.00 | 115.02 |
| 3383 | CA | THR | E | 373 | 28.711 | 38.105 | 56.672 | 1.00 | 105.40 |
| 3384 | CB | THR | E | 373 | 28.456 | 39.572 | 56.314 | 1.00 | 111.08 |
| 3385 | OG1 | THR | E | 373 | 28.475 | 39.723 | 54.889 | 1.00 | 107.18 |
| 3386 | CG2 | THR | E | 373 | 29.520 | 40.462 | 56.941 | 1.00 | 108.95 |
| 3387 | C | THR | E | 373 | 28.513 | 37.941 | 58.175 | 1.00 | 110.18 |
| 3388 | O | THR | E | 373 | 27.384 | 37.827 | 58.660 | 1.00 | 109.10 |
| 3389 | N | TRP | E | 374 | 29.621 | 37.925 | 58.909 | 1.00 | 104.03 |
| 3390 | CA | TRP | E | 374 | 29.570 | 37.805 | 60.357 | 1.00 | 103.91 |
| 3391 | CB | TRP | E | 374 | 30.530 | 36.728 | 60.850 | 1.00 | 106.35 |
| 3392 | CG | TRP | E | 374 | 30.067 | 35.345 | 60.558 | 1.00 | 104.34 |
| 3393 | CD2 | TRP | E | 374 | 29.155 | 34.566 | 61.343 | 1.00 | 106.00 |
| 3394 | CE2 | TRP | E | 374 | 29.012 | 33.315 | 60.697 | 1.00 | 110.86 |
| 3395 | CE3 | TRP | E | 374 | 28.446 | 34.802 | 62.534 | 1.00 | 97.93 |
| 3396 | CD1 | TRP | E | 374 | 30.424 | 34.565 | 59.494 | 1.00 | 95.16 |
| 3397 | NE1 | TRP | E | 374 | 29.797 | 33.343 | 59.572 | 1.00 | 99.42 |
| 3398 | CZ2 | TRP | E | 374 | 28.184 | 32.296 | 61.202 | 1.00 | 107.18 |
| 3399 | CZ3 | TRP | E | 374 | 27.621 | 33.787 | 63.038 | 1.00 | 101.06 |
| 3400 | CH2 | TRP | E | 374 | 27.500 | 32.550 | 62.370 | 1.00 | 104.60 |
| 3401 | C | TRP | E | 374 | 29.941 | 39.136 | 60.982 | 1.00 | 102.07 |
| 3402 | O | TRP | E | 374 | 30.549 | 39.984 | 60.334 | 1.00 | 101.96 |
| 3403 | N | SER | E | 375 | 29.566 | 39.316 | 62.242 | 1.00 | 101.28 |
| 3404 | CA | SER | E | 375 | 29.859 | 40.550 | 62.951 | 1.00 | 109.57 |
| 3405 | CB | SER | E | 375 | 29.122 | 41.727 | 62.300 | 1.00 | 109.65 |
| 3406 | OG | SER | E | 375 | 27.715 | 41.567 | 62.394 | 1.00 | 113.39 |
| 3407 | C | SER | E | 375 | 29.432 | 40.430 | 64.406 | 1.00 | 111.42 |
| 3408 | O | SER | E | 375 | 28.561 | 39.626 | 64.743 | 1.00 | 118.39 |
| 3409 | N | ARG | E | 376 | 30.057 | 41.227 | 65.267 | 1.00 | 105.38 |
| 3410 | CA | ARG | E | 376 | 29.719 | 41.224 | 66.677 | 1.00 | 102.33 |
| 3411 | CB | ARG | E | 376 | 30.976 | 41.186 | 67.533 | 1.00 | 88.05 |
| 3412 | CG | ARG | E | 376 | 31.773 | 39.927 | 67.383 | 1.00 | 84.62 |
| 3413 | CD | ARG | E | 376 | 32.476 | 39.658 | 68.691 | 1.00 | 95.80 |
| 3414 | NE | ARG | E | 376 | 33.926 | 39.560 | 68.554 | 1.00 | 111.40 |
| 3415 | CZ | ARG | E | 376 | 34.783 | 39.659 | 69.567 | 1.00 | 103.03 |
| 3416 | NH1 | ARG | E | 376 | 34.346 | 39.865 | 70.803 | 1.00 | 96.15 |
| 3417 | NH2 | ARG | E | 376 | 36.083 | 39.543 | 69.343 | 1.00 | 112.44 |
| 3418 | C | ARG | E | 376 | 28.930 | 42.477 | 67.006 | 1.00 | 105.92 |
| 3419 | O | ARG | E | 376 | 29.088 | 43.511 | 66.354 | 1.00 | 110.13 |
| 3420 | N | ALA | E | 377 | 28.072 | 42.379 | 68.013 | 1.00 | 105.18 |
| 3421 | CA | ALA | E | 377 | 27.274 | 43.515 | 68.429 | 1.00 | 102.97 |
| 3422 | CB | ALA | E | 377 | 26.242 | 43.077 | 69.443 | 1.00 | 102.22 |
| 3423 | C | ALA | E | 377 | 28.199 | 44.559 | 69.035 | 1.00 | 103.45 |
| 3424 | O | ALA | E | 377 | 27.955 | 45.752 | 68.909 | 1.00 | 112.90 |
| 3425 | N | SER | E | 378 | 29.263 | 44.099 | 69.687 | 1.00 | 101.58 |
| 3426 | CA | SER | E | 378 | 30.231 | 44.997 | 70.310 | 1.00 | 108.36 |
| 3427 | CB | SER | E | 378 | 31.244 | 44.201 | 71.141 | 1.00 | 108.11 |
| 3428 | OG | SER | E | 378 | 31.931 | 43.253 | 70.341 | 1.00 | 101.15 |
| 3429 | C | SER | E | 378 | 30.964 | 45.798 | 69.242 | 1.00 | 111.04 |
| 3430 | O | SER | E | 378 | 31.190 | 46.997 | 69.392 | 1.00 | 112.19 |
| 3431 | N | GLY | E | 379 | 31.318 | 45.128 | 68.151 | 1.00 | 109.31 |
| 3432 | CA | GLY | E | 379 | 32.034 | 45.794 | 67.079 | 1.00 | 111.58 |
| 3433 | C | GLY | E | 379 | 33.455 | 45.274 | 66.978 | 1.00 | 115.84 |
| 3434 | O | GLY | E | 379 | 34.250 | 45.747 | 66.162 | 1.00 | 115.01 |
| 3435 | N | LYS | E | 380 | 33.778 | 44.300 | 67.822 | 1.00 | 120.21 |
| 3436 | CA | LYS | E | 380 | 35.100 | 43.703 | 67.819 | 1.00 | 114.76 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3437 | CB | LYS | E | 380 | 35.327 | 42.939 | 69.122 | 1.00 | 104.20 |
| 3438 | CG | LYS | E | 380 | 35.263 | 43.844 | 70.336 | 1.00 | 113.61 |
| 3439 | CD | LYS | E | 380 | 35.671 | 43.130 | 71.600 | 1.00 | 122.57 |
| 3440 | CE | LYS | E | 380 | 35.600 | 44.073 | 72.786 | 1.00 | 122.97 |
| 3441 | NZ | LYS | E | 380 | 36.089 | 43.425 | 74.027 | 1.00 | 135.21 |
| 3442 | C | LYS | E | 380 | 35.208 | 42.780 | 66.613 | 1.00 | 106.95 |
| 3443 | O | LYS | E | 380 | 34.207 | 42.439 | 65.990 | 1.00 | 115.23 |
| 3444 | N | PRO | E | 381 | 36.430 | 42.380 | 66.253 | 1.00 | 120.99 |
| 3445 | CD | PRO | E | 381 | 37.709 | 42.915 | 66.743 | 1.00 | 122.39 |
| 3446 | CA | PRO | E | 381 | 36.645 | 41.498 | 65.103 | 1.00 | 116.60 |
| 3447 | CB | PRO | E | 381 | 38.159 | 41.536 | 64.916 | 1.00 | 117.14 |
| 3448 | CG | PRO | E | 381 | 38.548 | 42.870 | 65.504 | 1.00 | 121.61 |
| 3449 | C | PRO | E | 381 | 36.137 | 40.075 | 65.284 | 1.00 | 110.80 |
| 3450 | O | PRO | E | 381 | 36.070 | 39.567 | 66.399 | 1.00 | 111.36 |
| 3451 | N | VAL | E | 382 | 35.782 | 39.443 | 64.170 | 1.00 | 109.33 |
| 3452 | CA | VAL | E | 382 | 35.303 | 38.064 | 64.162 | 1.00 | 110.05 |
| 3453 | CB | VAL | E | 382 | 33.978 | 37.915 | 63.364 | 1.00 | 114.70 |
| 3454 | CG1 | VAL | E | 382 | 32.869 | 38.735 | 64.019 | 1.00 | 117.44 |
| 3455 | CG2 | VAL | E | 382 | 34.185 | 38.362 | 61.926 | 1.00 | 110.51 |
| 3456 | C | VAL | E | 382 | 36.390 | 37.220 | 63.492 | 1.00 | 116.02 |
| 3457 | O | VAL | E | 382 | 37.035 | 37.670 | 62.542 | 1.00 | 111.26 |
| 3456 | N | ASN | E | 383 | 36.597 | 36.003 | 63.987 | 1.00 | 121.25 |
| 3459 | CA | ASN | E | 383 | 37.628 | 35.132 | 63.432 | 1.00 | 118.24 |
| 3460 | CB | ASN | E | 383 | 37.837 | 33.903 | 64.325 | 1.00 | 129.48 |
| 3461 | CG | ASN | E | 383 | 38.287 | 34.267 | 65.738 | 1.00 | 132.01 |
| 3462 | OD1 | ASN | E | 383 | 38.617 | 33.391 | 66.538 | 1.00 | 136.01 |
| 3463 | ND2 | ASN | E | 383 | 38.297 | 35.558 | 66.048 | 1.00 | 134.54 |
| 3464 | C | ASN | E | 383 | 37.305 | 34.687 | 62.016 | 1.00 | 113.29 |
| 3465 | O | ASN | E | 383 | 36.359 | 35.171 | 61.399 | 1.00 | 101.27 |
| 3466 | N | HIS | E | 384 | 38.101 | 33.755 | 61.510 | 1.00 | 111.70 |
| 3467 | CA | HIS | E | 384 | 37.917 | 33.251 | 60.157 | 1.00 | 113.49 |
| 3468 | CB | HIS | E | 384 | 39.222 | 32.668 | 59.637 | 1.00 | 123.54 |
| 3469 | CG | HIS | E | 384 | 40.401 | 33.554 | 59.859 | 1.00 | 130.20 |
| 3470 | CD2 | HIS | E | 384 | 41.509 | 33.387 | 60.617 | 1.00 | 136.73 |
| 3471 | ND1 | HIS | E | 384 | 40.507 | 34.805 | 59.292 | 1.00 | 134.48 |
| 3472 | CE1 | HIS | E | 384 | 41.629 | 35.372 | 59.693 | 1.00 | 140.98 |
| 3473 | NE2 | HIS | E | 384 | 42.254 | 34.533 | 60.498 | 1.00 | 146.55 |
| 3474 | C | HIS | E | 384 | 36.832 | 32.193 | 60.089 | 1.00 | 112.32 |
| 3475 | O | HIS | E | 384 | 36.963 | 31.104 | 60.653 | 1.00 | 106.01 |
| 3476 | N | SER | E | 385 | 35.763 | 32.521 | 59.378 | 1.00 | 111.38 |
| 3477 | CA | SER | E | 385 | 34.639 | 31.614 | 59.228 | 1.00 | 107.68 |
| 3478 | CB | SER | E | 385 | 33.374 | 32.410 | 58.903 | 1.00 | 107.08 |
| 3479 | OG | SER | E | 385 | 33.696 | 33.618 | 58.230 | 1.00 | 103.43 |
| 3480 | C | SER | E | 385 | 34.890 | 30.558 | 58.164 | 1.00 | 104.81 |
| 3481 | O | SER | E | 385 | 35.815 | 30.666 | 57.359 | 1.00 | 101.44 |
| 3482 | N | THR | E | 386 | 34.047 | 29.536 | 58.173 | 1.00 | 106.14 |
| 3483 | CA | THR | E | 386 | 34.169 | 28.434 | 57.238 | 1.00 | 106.48 |
| 3484 | CB | THR | E | 386 | 34.491 | 27.130 | 57.981 | 1.00 | 105.07 |
| 3485 | OG1 | THR | E | 386 | 35.837 | 27.173 | 58.469 | 1.00 | 113.97 |
| 3486 | CG2 | THR | E | 386 | 34.291 | 25.945 | 57.065 | 1.00 | 112.14 |
| 3487 | C | THR | E | 386 | 32.892 | 28.216 | 56.442 | 1.00 | 106.53 |
| 3488 | O | THR | E | 386 | 31.875 | 27.794 | 56.983 | 1.00 | 112.71 |
| 3489 | N | ARG | E | 387 | 32.956 | 28.490 | 55.148 | 1.00 | 105.46 |
| 3490 | CA | ARG | E | 387 | 31.804 | 28.313 | 54.276 | 1.00 | 111.63 |
| 3491 | CB | ARG | E | 387 | 31.864 | 29.340 | 53.144 | 1.00 | 107.46 |
| 3492 | CG | ARG | E | 387 | 30.675 | 29.325 | 52.205 | 1.00 | 114.19 |
| 3493 | CD | ARG | E | 387 | 30.933 | 30.257 | 51.038 | 1.00 | 120.09 |
| 3494 | NE | ARG | E | 387 | 29.842 | 30.261 | 50.066 | 1.00 | 130.37 |
| 3495 | CZ | ARG | E | 387 | 28.707 | 30.940 | 50.208 | 1.00 | 130.43 |
| 3495 | NH1 | ARG | E | 387 | 28.501 | 31.681 | 51.288 | 1.00 | 137.13 |
| 3497 | NH2 | ARG | E | 387 | 27.775 | 30.881 | 49.266 | 1.00 | 131.16 |
| 3498 | C | ARG | E | 387 | 31.820 | 26.891 | 53.706 | 1.00 | 111.41 |
| 3499 | O | ARG | E | 387 | 32.888 | 26.350 | 53.410 | 1.00 | 109.82 |
| 3500 | N | LYS | E | 388 | 30.640 | 26.288 | 53.560 | 1.00 | 113.37 |
| 3501 | CA | LYS | E | 388 | 30.528 | 24.926 | 53.028 | 1.00 | 116.82 |
| 3502 | CB | LYS | E | 388 | 30.575 | 23.896 | 54.164 | 1.00 | 118.91 |
| 3503 | CG | LYS | E | 388 | 31.767 | 24.010 | 55.100 | 1.00 | 128.88 |
| 3504 | CD | LYS | E | 388 | 31.592 | 23.090 | 56.301 | 1.00 | 124.77 |
| 3505 | CE | LYS | E | 388 | 32.666 | 23.323 | 57.338 | 1.00 | 124.34 |
| 3506 | NZ | LYS | E | 388 | 32.442 | 22.493 | 58.544 | 1.00 | 133.85 |
| 3507 | C | LYS | E | 388 | 29.222 | 24.727 | 52.258 | 1.00 | 119.84 |
| 3508 | O | LYS | E | 388 | 28.180 | 24.445 | 52.857 | 1.00 | 121.55 |
| 3509 | N | GLU | E | 389 | 29.278 | 24.864 | 50.936 | 1.00 | 119.46 |
| 3510 | CA | CLU | E | 389 | 28.095 | 24.683 | 50.100 | 1.00 | 118.79 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3511 | CB | GLU | E | 389 | 28.201 | 25.551 | 48.853 | 1.00 | 122.50 |
| 3512 | CG | GLU | E | 389 | 28.290 | 27.028 | 49.169 | 1.00 | 134.22 |
| 3513 | CD | GLU | E | 389 | 28.568 | 27.861 | 47.941 | 1.00 | 138.76 |
| 3514 | OE1 | GLU | E | 389 | 27.777 | 27.779 | 46.978 | 1.00 | 146.59 |
| 3515 | OE2 | GLU | E | 389 | 29.578 | 28.596 | 47.939 | 1.00 | 137.66 |
| 3516 | C | GLU | E | 389 | 27.950 | 23.218 | 49.703 | 1.00 | 119.13 |
| 3517 | O | GLU | E | 389 | 28.696 | 22.710 | 48.862 | 1.00 | 118.09 |
| 3518 | N | GLU | E | 390 | 26.986 | 22.548 | 50.324 | 1.00 | 119.10 |
| 3519 | CA | GLU | E | 390 | 26.722 | 21.137 | 50.071 | 1.00 | 121.14 |
| 3520 | CB | GLU | E | 390 | 26.662 | 20.389 | 51.403 | 1.00 | 125.75 |
| 3521 | CG | GLU | E | 390 | 26.341 | 18.914 | 51.301 | 1.00 | 144.11 |
| 3522 | CD | GLU | E | 390 | 26.358 | 18.238 | 52.660 | 1.00 | 158.96 |
| 3523 | OE1 | GLU | E | 390 | 25.666 | 18.733 | 53.577 | 1.00 | 163.63 |
| 3524 | OE2 | GLU | E | 390 | 27.062 | 17.216 | 52.813 | 1.00 | 162.75 |
| 3525 | C | GLU | E | 390 | 25.403 | 21.001 | 49.324 | 1.00 | 122.40 |
| 3526 | O | GLU | E | 390 | 24.336 | 20.917 | 49.934 | 1.00 | 113.92 |
| 3527 | N | LYS | E | 391 | 25.487 | 20.980 | 47.999 | 1.00 | 128.57 |
| 3528 | CA | LYS | E | 391 | 24.304 | 20.876 | 47.157 | 1.00 | 134.91 |
| 3529 | CB | LYS | E | 391 | 24.637 | 21.360 | 45.741 | 1.00 | 131.36 |
| 3530 | CG | LYS | E | 391 | 23.426 | 21.808 | 44.940 | 1.00 | 130.15 |
| 3531 | CD | LYS | E | 391 | 23.850 | 22.619 | 43.729 | 1.00 | 134.41 |
| 3532 | CE | LYS | E | 391 | 22.657 | 23.298 | 43.078 | 1.00 | 138.34 |
| 3533 | NZ | LYS | E | 391 | 23.064 | 24.167 | 41.944 | 1.00 | 131.05 |
| 3534 | C | LYS | E | 391 | 23.716 | 19.464 | 47.104 | 1.00 | 139.95 |
| 3535 | O | LYS | E | 391 | 24.435 | 18.464 | 47.192 | 1.00 | 140.10 |
| 3536 | N | GLN | E | 392 | 22.395 | 19.404 | 46.966 | 1.00 | 145.27 |
| 3537 | CA | GLN | E | 392 | 21.668 | 18.145 | 46.885 | 1.00 | 152.43 |
| 3538 | CB | GLN | E | 392 | 20.975 | 17.840 | 48.214 | 1.00 | 153.21 |
| 3539 | CG | GLN | E | 392 | 21.912 | 17.731 | 49.393 | 1.00 | 156.49 |
| 3540 | CD | GLN | E | 392 | 21.171 | 17.568 | 50.698 | 1.00 | 157.89 |
| 3541 | OE1 | GLN | E | 392 | 20.385 | 16.636 | 50.867 | 1.00 | 157.54 |
| 3542 | NE2 | GLN | E | 392 | 21.416 | 18.478 | 51.633 | 1.00 | 155.87 |
| 3543 | C | GLN | E | 392 | 20.618 | 18.287 | 45.797 | 1.00 | 158.73 |
| 3544 | O | GLN | E | 392 | 19.605 | 18.962 | 45.989 | 1.00 | 158.99 |
| 3545 | N | ARG | E | 393 | 20.865 | 17.659 | 44.652 | 1.00 | 163.29 |
| 3546 | CA | ARG | E | 393 | 19.925 | 17.719 | 43.542 | 1.00 | 170.50 |
| 3547 | CB | ARG | E | 393 | 20.422 | 16.855 | 42.378 | 1.00 | 171.96 |
| 3548 | CG | ARG | E | 393 | 21.553 | 15.903 | 42.740 | 1.00 | 178.04 |
| 3549 | CD | ARG | E | 393 | 21.916 | 15.017 | 41.562 | 1.00 | 178.37 |
| 3550 | NE | ARG | E | 393 | 20.779 | 14.204 | 41.139 | 1.00 | 181.46 |
| 3551 | CZ | ARG | E | 393 | 20.806 | 13.344 | 40.126 | 1.00 | 180.84 |
| 3552 | NH1 | ARG | E | 393 | 21.916 | 13.179 | 39.422 | 1.00 | 181.59 |
| 3553 | NH2 | ARG | E | 393 | 19.721 | 12.646 | 39.819 | 1.00 | 181.56 |
| 3554 | C | ARG | E | 393 | 18.544 | 17.254 | 43.997 | 1.00 | 174.63 |
| 3555 | O | ARG | E | 393 | 17.572 | 17.315 | 43.240 | 1.00 | 179.30 |
| 3556 | N | ASN | E | 394 | 18.473 | 16.792 | 45.243 | 1.00 | 175.94 |
| 3557 | CA | ASN | E | 394 | 17.229 | 16.327 | 45.849 | 1.00 | 174.31 |
| 3558 | CB | ASN | E | 394 | 17.526 | 15.655 | 47.194 | 1.00 | 177.32 |
| 3559 | CG | ASN | E | 394 | 16.282 | 15.095 | 47.860 | 1.00 | 176.31 |
| 3560 | OD1 | ASN | E | 394 | 16.280 | 14.823 | 49.060 | 1.00 | 174.63 |
| 3561 | ND2 | ASN | E | 394 | 15.223 | 14.909 | 47.084 | 1.00 | 176.44 |
| 3562 | C | ASN | E | 394 | 16.321 | 17.533 | 46.076 | 1.00 | 172.73 |
| 3563 | O | ASN | E | 394 | 15.191 | 17.398 | 46.544 | 1.00 | 173.40 |
| 3564 | N | GLY | E | 395 | 16.828 | 18.714 | 45.737 | 1.00 | 170.25 |
| 3565 | CA | GLY | E | 395 | 16.062 | 19.931 | 45.922 | 1.00 | 166.99 |
| 3566 | C | GLY | E | 395 | 16.454 | 20.566 | 47.238 | 1.00 | 163.26 |
| 3567 | O | GLY | E | 395 | 15.617 | 20.779 | 48.117 | 1.00 | 158.64 |
| 3568 | N | THR | E | 396 | 17.743 | 20.863 | 47.371 | 1.00 | 161.78 |
| 3569 | CA | THR | E | 396 | 18.271 | 21.461 | 48.586 | 1.00 | 157.48 |
| 3570 | CB | THR | E | 396 | 18.185 | 20.461 | 49.776 | 1.00 | 161.76 |
| 3571 | OG1 | THR | E | 396 | 16.812 | 20.178 | 50.077 | 1.00 | 153.96 |
| 3572 | CG2 | THR | E | 396 | 18.855 | 21.037 | 51.010 | 1.00 | 163.93 |
| 3573 | C | THR | E | 396 | 19.733 | 21.878 | 48.402 | 1.00 | 148.48 |
| 3574 | O | THR | E | 396 | 20.601 | 21.035 | 48.186 | 1.00 | 148.00 |
| 3575 | N | LEU | E | 397 | 19.998 | 23.179 | 48.477 | 1.00 | 146.78 |
| 3576 | CA | LEU | E | 397 | 21.363 | 23.682 | 48.355 | 1.00 | 138.05 |
| 3577 | CB | LEU | E | 397 | 21.453 | 24.813 | 47.326 | 1.00 | 132.67 |
| 3578 | CG | LEU | E | 397 | 22.824 | 25.509 | 47.287 | 1.00 | 134.07 |
| 3579 | CD1 | LEU | E | 397 | 23.935 | 24.494 | 47.022 | 1.00 | 131.87 |
| 3580 | CD2 | LEU | E | 397 | 22.815 | 26.586 | 46.223 | 1.00 | 126.12 |
| 3581 | C | LEU | E | 397 | 21.845 | 24.195 | 49.709 | 1.00 | 136.75 |
| 3582 | O | LEU | E | 397 | 21.809 | 25.397 | 49.984 | 1.00 | 138.18 |
| 3583 | N | THR | E | 398 | 22.293 | 23.273 | 50.553 | 1.00 | 130.11 |
| 3584 | CA | THR | E | 398 | 22.780 | 23.623 | 51.877 | 1.00 | 128.58 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3585 | CB | THR | E | 398 | 23.118 | 22.347 | 52.684 | 1.00 | 126.63 |
| 3586 | OG1 | THR | E | 398 | 21.901 | 21.705 | 53.081 | 1.00 | 130.48 |
| 3587 | CG2 | THR | E | 398 | 23.949 | 22.681 | 53.918 | 1.00 | 130.06 |
| 3588 | C | THR | E | 398 | 24.011 | 24.533 | 51.826 | 1.00 | 128.84 |
| 3589 | O | THR | E | 398 | 24.940 | 24.307 | 51.042 | 1.00 | 129.82 |
| 3590 | N | VAL | E | 399 | 23.999 | 25.573 | 52.657 | 1.00 | 123.84 |
| 3591 | CA | VAL | E | 399 | 25.114 | 26.511 | 52.747 | 1.00 | 124.02 |
| 3592 | CB | VAL | E | 399 | 24.863 | 27.778 | 51.898 | 1.00 | 116.24 |
| 3593 | CG1 | VAL | E | 399 | 26.076 | 28.694 | 51.968 | 1.00 | 117.83 |
| 3594 | CG2 | VAL | E | 399 | 24.583 | 27.392 | 50.457 | 1.00 | 108.35 |
| 3595 | C | VAL | E | 399 | 25.306 | 26.909 | 54.216 | 1.00 | 121.15 |
| 3596 | O | VAL | E | 399 | 24.484 | 27.630 | 54.789 | 1.00 | 113.02 |
| 3597 | N | THR | E | 400 | 26.389 | 26.424 | 54.822 | 1.00 | 115.09 |
| 3598 | CA | THR | E | 400 | 26.677 | 26.716 | 56.223 | 1.00 | 110.29 |
| 3599 | CB | THR | E | 400 | 26.820 | 25.429 | 57.068 | 1.00 | 107.99 |
| 3600 | OG1 | THR | E | 400 | 27.991 | 24.710 | 56.651 | 1.00 | 111.22 |
| 3601 | CG2 | THR | E | 400 | 25.593 | 24.541 | 56.912 | 1.00 | 107.50 |
| 3602 | C | THR | E | 400 | 27.968 | 27.496 | 56.388 | 1.00 | 110.65 |
| 3603 | O | THR | E | 400 | 28.840 | 27.484 | 55.517 | 1.00 | 110.74 |
| 3604 | N | SER | E | 401 | 28.072 | 28.175 | 57.522 | 1.00 | 104.77 |
| 3605 | CA | SER | E | 401 | 29.253 | 28.943 | 57.850 | 1.00 | 102.81 |
| 3606 | CB | SER | E | 401 | 29.035 | 30.427 | 57.564 | 1.00 | 103.01 |
| 3607 | OG | SER | E | 401 | 30.235 | 31.157 | 57.766 | 1.00 | 111.84 |
| 3608 | C | SER | E | 401 | 29.475 | 28.717 | 59.334 | 1.00 | 108.41 |
| 3609 | O | SER | E | 401 | 28.567 | 28.906 | 60.142 | 1.00 | 102.98 |
| 3610 | N | THR | E | 402 | 30.678 | 28.286 | 59.689 | 1.00 | 107.00 |
| 3611 | CA | THR | E | 402 | 31.007 | 28.026 | 61.081 | 1.00 | 94.18 |
| 3612 | CB | THR | E | 402 | 31.543 | 26.598 | 61.260 | 1.00 | 91.07 |
| 3613 | OG1 | THR | E | 402 | 30.466 | 25.662 | 61.102 | 1.00 | 89.89 |
| 3614 | CG2 | THR | E | 402 | 32.166 | 26.435 | 62.633 | 1.00 | 95.79 |
| 3615 | C | THR | E | 402 | 32.040 | 29.012 | 61.572 | 1.00 | 95.84 |
| 3616 | O | THR | E | 402 | 33.183 | 29.007 | 61.120 | 1.00 | 109.43 |
| 3617 | N | LEU | E | 403 | 31.627 | 29.859 | 62.504 | 1.00 | 94.51 |
| 3618 | CA | LEU | E | 403 | 32.514 | 30.867 | 63.052 | 1.00 | 100.82 |
| 3619 | CB | LEU | E | 403 | 31.774 | 32.205 | 63.174 | 1.00 | 88.89 |
| 3620 | CG | LEU | E | 403 | 32.572 | 33.348 | 63.813 | 1.00 | 95.95 |
| 3621 | CD1 | LEU | E | 403 | 33.699 | 33.776 | 62.885 | 1.00 | 101.29 |
| 3622 | CD2 | LEU | E | 403 | 31.653 | 34.519 | 64.098 | 1.00 | 94.36 |
| 3623 | C | LEU | E | 403 | 33.075 | 30.476 | 64.414 | 1.00 | 100.19 |
| 3624 | O | LEU | E | 403 | 32.327 | 30.231 | 65.361 | 1.00 | 105.23 |
| 3625 | N | PRO | E | 404 | 34.408 | 30.390 | 64.523 | 1.00 | 99.99 |
| 3626 | CD | PRO | E | 404 | 35.401 | 30.320 | 63.438 | 1.00 | 103.01 |
| 3627 | CA | PRO | E | 404 | 35.013 | 30.031 | 65.807 | 1.00 | 94.61 |
| 3628 | CB | PRO | E | 404 | 36.488 | 29.849 | 65.452 | 1.00 | 104.91 |
| 3629 | CG | PRO | E | 404 | 36.428 | 29.378 | 64.020 | 1.00 | 99.85 |
| 3630 | C | PRO | E | 404 | 34.780 | 31.205 | 66.749 | 1.00 | 81.64 |
| 3631 | O | PRO | E | 404 | 34.888 | 32.364 | 66.342 | 1.00 | 82.94 |
| 3632 | N | VAL | E | 405 | 34.455 | 30.912 | 67.998 | 1.00 | 73.66 |
| 3633 | CA | VAL | E | 405 | 34.189 | 31.975 | 68.952 | 1.00 | 93.41 |
| 3634 | CB | VAL | E | 405 | 32.707 | 31.956 | 69.394 | 1.00 | 105.26 |
| 3635 | CG1 | VAL | E | 405 | 32.505 | 32.837 | 70.615 | 1.00 | 109.76 |
| 3636 | CG2 | VAL | E | 405 | 31.825 | 32.441 | 68.249 | 1.00 | 111.18 |
| 3637 | C | VAL | E | 405 | 35.076 | 31.891 | 70.177 | 1.00 | 86.65 |
| 3638 | O | VAL | E | 405 | 35.478 | 30.810 | 70.593 | 1.00 | 81.57 |
| 3639 | N | GLY | E | 406 | 35.388 | 33.051 | 70.743 | 1.00 | 90.69 |
| 3640 | CA | GLY | E | 406 | 36.223 | 33.087 | 71.923 | 1.00 | 98.82 |
| 3641 | C | GLY | E | 406 | 35.454 | 32.466 | 73.059 | 1.00 | 97.13 |
| 3642 | O | GLY | E | 406 | 34.262 | 32.702 | 73.197 | 1.00 | 98.98 |
| 3643 | N | THR | E | 407 | 36.126 | 31.659 | 73.865 | 1.00 | 97.85 |
| 3644 | CA | THR | E | 407 | 35.458 | 31.029 | 74.983 | 1.00 | 105.38 |
| 3645 | CB | THR | E | 407 | 36.419 | 30.082 | 75.734 | 1.00 | 111.89 |
| 3646 | OG1 | THR | E | 407 | 36.888 | 29.063 | 74.837 | 1.00 | 110.32 |
| 3647 | CG2 | THR | E | 407 | 35.707 | 29.424 | 76.909 | 1.00 | 117.18 |
| 3648 | C | THR | E | 407 | 34.915 | 32.096 | 75.942 | 1.00 | 108.50 |
| 3649 | O | THR | E | 407 | 33.711 | 32.141 | 76.211 | 1.00 | 109.26 |
| 3650 | N | ALA | E | 408 | 35.791 | 32.963 | 76.444 | 1.00 | 109.91 |
| 3651 | CA | ALA | E | 408 | 35.366 | 34.012 | 77.372 | 1.00 | 108.99 |
| 3652 | CB | ALA | E | 408 | 36.573 | 34.806 | 77.863 | 1.00 | 105.24 |
| 3653 | C | ALA | E | 408 | 34.340 | 34.953 | 76.741 | 1.00 | 110.02 |
| 3654 | O | ALA | E | 408 | 33.404 | 35.394 | 77.413 | 1.00 | 101.76 |
| 3655 | N | ASP | E | 409 | 34.516 | 35.246 | 75.452 | 1.00 | 111.88 |
| 3656 | CA | ASP | E | 409 | 33.614 | 36.144 | 74.728 | 1.00 | 112.36 |
| 3657 | CB | ASP | E | 409 | 34.037 | 36.261 | 73.257 | 1.00 | 114.26 |
| 3658 | CG | ASP | E | 409 | 35.366 | 36.985 | 73.081 | 1.00 | 125.83 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3659 | OD1 | ASP | E | 409 | 35.464 | 38.174 | 73.457 | 1.00 | 128.14 |
| 3660 | OD2 | ASP | E | 409 | 36.314 | 36.361 | 72.563 | 1.00 | 128.19 |
| 3661 | C | ASP | E | 409 | 32.157 | 35.698 | 74.806 | 1.00 | 109.10 |
| 3662 | O | ASP | E | 409 | 31.293 | 36.447 | 75.270 | 1.00 | 115.26 |
| 3663 | N | TRP | E | 410 | 31.881 | 34.483 | 74.353 | 1.00 | 102.42 |
| 3664 | CA | TRP | E | 410 | 30.522 | 33.970 | 74.394 | 1.00 | 104.32 |
| 3665 | CB | TRP | E | 410 | 30.448 | 32.580 | 73.757 | 1.00 | 93.34 |
| 3666 | CG | TRP | E | 410 | 29.076 | 31.974 | 73.842 | 1.00 | 92.10 |
| 3667 | CD2 | TRP | E | 410 | 28.039 | 32.067 | 72.857 | 1.00 | 93.40 |
| 3668 | CE2 | TRP | E | 410 | 26.902 | 31.415 | 73.385 | 1.00 | 93.52 |
| 3669 | CE3 | TRP | E | 410 | 27.959 | 32.640 | 71.578 | 1.00 | 97.42 |
| 3670 | CD1 | TRP | E | 410 | 28.541 | 31.286 | 74.898 | 1.00 | 82.27 |
| 3671 | NE1 | TRP | E | 410 | 27.236 | 30.948 | 74.630 | 1.00 | 85.07 |
| 3672 | CZ2 | TRP | E | 410 | 25.695 | 31.319 | 72.676 | 1.00 | 96.27 |
| 3673 | CZ3 | TRP | E | 410 | 26.756 | 32.545 | 70.872 | 1.00 | 92.07 |
| 3674 | CH2 | TRP | E | 410 | 25.643 | 31.889 | 71.424 | 1.00 | 89.00 |
| 3675 | C | TRP | E | 410 | 29.998 | 33.903 | 75.827 | 1.00 | 111.95 |
| 3676 | O | TRP | E | 410 | 28.859 | 34.292 | 76.103 | 1.00 | 108.55 |
| 3677 | N | ILE | E | 411 | 30.833 | 33.415 | 76.739 | 1.00 | 110.45 |
| 3678 | CA | ILE | E | 411 | 30.448 | 33.289 | 78.137 | 1.00 | 108.33 |
| 3679 | CB | ILE | E | 411 | 31.546 | 32.560 | 78.938 | 1.00 | 111.24 |
| 3680 | CG2 | ILE | E | 411 | 31.270 | 32.651 | 80.434 | 1.00 | 113.02 |
| 3681 | CG1 | ILE | E | 411 | 31.613 | 31.102 | 78.491 | 1.00 | 104.75 |
| 3682 | CD1 | ILE | E | 411 | 32.663 | 30.299 | 79.210 | 1.00 | 115.94 |
| 3683 | C | ILE | E | 411 | 30.118 | 34.612 | 78.831 | 1.00 | 108.47 |
| 3684 | O | ILE | E | 411 | 29.285 | 34.643 | 79.733 | 1.00 | 113.98 |
| 3685 | N | GLU | E | 412 | 30.747 | 35.706 | 78.418 | 1.00 | 108.56 |
| 3686 | CA | GLU | E | 412 | 30.475 | 36.977 | 79.070 | 1.00 | 110.02 |
| 3687 | CB | GLU | E | 412 | 31.769 | 37.779 | 79.188 | 1.00 | 115.73 |
| 3688 | CG | GLU | E | 412 | 32.615 | 37.311 | 80.372 | 1.00 | 136.92 |
| 3689 | CD | GLU | E | 412 | 34.005 | 37.910 | 80.390 | 1.00 | 145.69 |
| 3690 | OE1 | GLU | E | 412 | 34.119 | 39.141 | 80.223 | 1.00 | 149.18 |
| 3691 | OE2 | GLU | E | 412 | 34.979 | 37.148 | 80.581 | 1.00 | 151.00 |
| 3692 | C | GLU | E | 412 | 29.351 | 37.821 | 78.476 | 1.00 | 106.45 |
| 3693 | O | GLU | E | 412 | 29.103 | 38.942 | 78.926 | 1.00 | 103.49 |
| 3694 | N | GLY | E | 413 | 28.662 | 37.288 | 77.473 | 1.00 | 98.00 |
| 3695 | CA | GLY | E | 413 | 27.545 | 38.025 | 76.913 | 1.00 | 96.75 |
| 3696 | C | GLY | E | 413 | 27.623 | 38.543 | 75.492 | 1.00 | 95.78 |
| 3697 | O | GLY | E | 413 | 26.694 | 39.203 | 75.026 | 1.00 | 94.09 |
| 3698 | N | GLU | E | 414 | 28.709 | 38.263 | 74.789 | 1.00 | 91.61 |
| 3699 | CA | GLU | E | 414 | 28.812 | 38.737 | 73.419 | 1.00 | 96.38 |
| 3700 | CB | GLU | E | 414 | 30.169 | 38.371 | 72.826 | 1.00 | 104.10 |
| 3701 | CG | GLU | E | 414 | 30.391 | 38.838 | 71.375 | 1.00 | 114.26 |
| 3702 | CD | GLU | E | 414 | 30.546 | 40.356 | 71.235 | 1.00 | 117.68 |
| 3703 | OE1 | GLU | E | 414 | 29.518 | 41.068 | 71.224 | 1.00 | 116.47 |
| 3704 | OE2 | GLU | E | 414 | 31.700 | 40.839 | 71.143 | 1.00 | 106.02 |
| 3705 | C | GLU | E | 414 | 27.710 | 38.123 | 72.559 | 1.00 | 100.13 |
| 3706 | O | GLU | E | 414 | 27.320 | 36.974 | 72.754 | 1.00 | 99.46 |
| 3707 | N | THR | E | 415 | 27.207 | 38.904 | 71.612 | 1.00 | 101.57 |
| 3708 | CA | THR | E | 415 | 26.174 | 38.438 | 70.700 | 1.00 | 103.30 |
| 3709 | CB | THR | E | 415 | 24.878 | 39.278 | 70.829 | 1.00 | 105.46 |
| 3710 | OG1 | THR | E | 415 | 24.203 | 39.323 | 69.564 | 1.00 | 92.15 |
| 3711 | CG2 | THR | E | 415 | 25.193 | 40.684 | 71.328 | 1.00 | 106.66 |
| 3712 | C | THR | E | 415 | 26.709 | 38.510 | 69.274 | 1.00 | 100.51 |
| 3713 | O | THR | E | 415 | 27.118 | 39.566 | 68.795 | 1.00 | 94.35 |
| 3714 | N | TYR | E | 416 | 26.714 | 37.367 | 68.605 | 1.00 | 97.91 |
| 3715 | CA | TYR | E | 416 | 27.219 | 37.290 | 67.247 | 1.00 | 94.06 |
| 3716 | CB | TYR | E | 416 | 27.998 | 35.987 | 67.068 | 1.00 | 98.50 |
| 3717 | CG | TYR | E | 416 | 29.161 | 35.890 | 68.022 | 1.00 | 99.46 |
| 3718 | CD1 | TYR | E | 416 | 28.958 | 35.624 | 69.383 | 1.00 | 97.24 |
| 3719 | CE1 | TYR | E | 416 | 30.018 | 35.622 | 70.284 | 1.00 | 97.18 |
| 3720 | CD2 | TYR | E | 416 | 30.458 | 36.143 | 67.586 | 1.00 | 97.35 |
| 3721 | CE2 | TYR | E | 416 | 31.525 | 36.143 | 68.476 | 1.00 | 106.83 |
| 3722 | CZ | TYR | E | 416 | 31.300 | 35.885 | 69.823 | 1.00 | 109.01 |
| 3723 | OH | TYR | E | 416 | 32.357 | 35.908 | 70.705 | 1.00 | 120.36 |
| 3724 | C | TYR | E | 416 | 26.106 | 37.390 | 66.224 | 1.00 | 97.67 |
| 3725 | O | TYR | E | 416 | 24.986 | 36.942 | 66.463 | 1.00 | 103.68 |
| 3726 | N | GLN | E | 417 | 26.426 | 37.977 | 65.076 | 1.00 | 98.33 |
| 3727 | CA | GLN | E | 417 | 25.443 | 38.160 | 64.019 | 1.00 | 109.07 |
| 3728 | CB | GLN | E | 417 | 25.083 | 39.644 | 63.906 | 1.00 | 108.19 |
| 3729 | CG | GLN | E | 417 | 24.027 | 39.939 | 62.856 | 1.00 | 128.40 |
| 3730 | CD | GLN | E | 417 | 23.834 | 41.423 | 62.632 | 1.00 | 138.68 |
| 3731 | OE1 | GLN | E | 417 | 24.742 | 42.115 | 62.165 | 1.00 | 138.00 |
| 3732 | NE2 | GLN | E | 417 | 22.647 | 41.925 | 62.967 | 1.00 | 136.21 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3733 | C | GLN | E | 417 | 25.878 | 37.639 | 62.646 | 1.00 | 108.31 |
| 3734 | O | GLN | E | 417 | 27.045 | 37.745 | 62.257 | 1.00 | 108.24 |
| 3735 | N | CYS | E | 418 | 24.914 | 37.083 | 61.918 | 1.00 | 110.05 |
| 3736 | CA | CYS | E | 418 | 25.139 | 36.541 | 60.582 | 1.00 | 113.80 |
| 3737 | C | CYS | E | 418 | 24.240 | 37.280 | 59.598 | 1.00 | 113.59 |
| 3738 | O | CYS | E | 418 | 23.017 | 37.253 | 59.737 | 1.00 | 115.28 |
| 3739 | CB | CYS | E | 418 | 24.801 | 35.043 | 60.558 | 1.00 | 115.96 |
| 3740 | SG | CYS | E | 418 | 24.948 | 34.226 | 58.931 | 1.00 | 122.35 |
| 3741 | N | ARG | E | 419 | 24.837 | 37.949 | 58.617 | 1.00 | 108.55 |
| 3742 | CA | ARG | E | 419 | 24.053 | 38.671 | 57.623 | 1.00 | 106.95 |
| 3743 | CB | ARG | E | 419 | 24.581 | 40.093 | 57.446 | 1.00 | 107.57 |
| 3744 | CG | ARG | E | 419 | 23.726 | 40.950 | 56.535 | 1.00 | 103.95 |
| 3745 | CD | ARG | E | 419 | 24.100 | 42.414 | 56.674 | 1.00 | 120.60 |
| 3746 | NE | ARG | E | 419 | 23.380 | 43.258 | 55.725 | 1.00 | 128.55 |
| 3747 | CZ | ARG | E | 419 | 23.512 | 43.172 | 54.404 | 1.00 | 133.58 |
| 3748 | NH1 | ARG | E | 419 | 24.338 | 42.279 | 53.872 | 1.00 | 128.87 |
| 3749 | NH2 | ARG | E | 419 | 22.817 | 43.979 | 53.613 | 1.00 | 131.09 |
| 3750 | C | ARG | E | 419 | 24.102 | 37.925 | 56.298 | 1.00 | 110.75 |
| 3751 | O | ARG | E | 419 | 25.176 | 37.682 | 55.744 | 1.00 | 114.35 |
| 3752 | N | VAL | E | 420 | 22.929 | 37.558 | 55.797 | 1.00 | 116.06 |
| 3753 | CA | VAL | E | 420 | 22.825 | 36.819 | 54.544 | 1.00 | 122.18 |
| 3754 | CB | VAL | E | 420 | 21.797 | 35.666 | 54.673 | 1.00 | 120.16 |
| 3755 | CG1 | VAL | E | 420 | 21.852 | 34.773 | 53.443 | 1.00 | 116.95 |
| 3756 | CG2 | VAL | E | 420 | 22.076 | 34.857 | 55.931 | 1.00 | 115.66 |
| 3757 | C | VAL | E | 420 | 22.418 | 37.721 | 53.377 | 1.00 | 124.23 |
| 3758 | O | VAL | E | 420 | 21.452 | 38.481 | 53.467 | 1.00 | 126.58 |
| 3759 | N | THR | E | 421 | 23.165 | 37.629 | 52.283 | 1.00 | 127.48 |
| 3760 | CA | THR | E | 421 | 22.891 | 38.425 | 51.098 | 1.00 | 131.53 |
| 3761 | CB | THR | E | 421 | 24.035 | 39.406 | 50.821 | 1.00 | 128.34 |
| 3762 | OG1 | THR | E | 421 | 24.238 | 40.232 | 51.972 | 1.00 | 128.37 |
| 3763 | CG2 | THR | E | 421 | 23.708 | 40.281 | 49.623 | 1.00 | 125.49 |
| 3764 | C | THR | E | 421 | 22.728 | 37.509 | 49.896 | 1.00 | 138.75 |
| 3765 | O | THR | E | 421 | 23.362 | 36.457 | 49.819 | 1.00 | 137.80 |
| 3766 | N | HIS | E | 422 | 21.873 | 37.911 | 48.963 | 1.00 | 143.55 |
| 3767 | CA | HIS | E | 422 | 21.623 | 37.128 | 47.756 | 1.00 | 155.37 |
| 3768 | CB | HIS | E | 422 | 20.700 | 35.936 | 48.077 | 1.00 | 160.43 |
| 3769 | CG | HIS | E | 422 | 20.539 | 34.962 | 46.946 | 1.00 | 161.68 |
| 3770 | CD2 | HIS | E | 422 | 19.432 | 34.506 | 46.312 | 1.00 | 159.04 |
| 3771 | ND1 | HIS | E | 422 | 21.608 | 34.327 | 46.349 | 1.00 | 157.29 |
| 3772 | CE1 | HIS | E | 422 | 21.167 | 33.524 | 45.397 | 1.00 | 156.17 |
| 3773 | NE2 | HIS | E | 422 | 19.850 | 33.614 | 45.354 | 1.00 | 156.88 |
| 3774 | C | HIS | E | 422 | 20.979 | 38.029 | 46.702 | 1.00 | 157.34 |
| 3775 | O | HIS | E | 422 | 20.224 | 38.946 | 47.034 | 1.00 | 155.33 |
| 3776 | N | PRO | E | 423 | 21.284 | 37.788 | 45.415 | 1.00 | 160.72 |
| 3777 | CD | PRO | E | 423 | 22.285 | 36.833 | 44.904 | 1.00 | 158.17 |
| 3778 | CA | PRO | E | 423 | 20.726 | 38.586 | 44.319 | 1.00 | 160.51 |
| 3779 | CB | PRO | E | 423 | 21.602 | 38.192 | 43.133 | 1.00 | 159.29 |
| 3780 | CG | PRO | E | 423 | 21.939 | 36.764 | 43.438 | 1.00 | 159.28 |
| 3781 | C | PRO | E | 423 | 19.236 | 38.345 | 44.048 | 1.00 | 163.54 |
| 3782 | O | PRO | E | 423 | 18.547 | 39.222 | 43.522 | 1.00 | 165.09 |
| 3783 | N | HIS | E | 424 | 18.742 | 37.163 | 44.411 | 1.00 | 164.64 |
| 3784 | CA | HIS | E | 424 | 17.338 | 36.819 | 44.183 | 1.00 | 166.34 |
| 3785 | CB | HIS | E | 424 | 17.226 | 35.359 | 43.727 | 1.00 | 169.48 |
| 3786 | CG | HIS | E | 424 | 18.042 | 35.041 | 42.511 | 1.00 | 173.52 |
| 3787 | CD2 | HIS | E | 424 | 19.034 | 34.140 | 42.314 | 1.00 | 178.74 |
| 3788 | ND1 | HIS | E | 424 | 17.879 | 35.698 | 41.309 | 1.00 | 174.18 |
| 3789 | CE1 | HIS | E | 424 | 18.735 | 35.216 | 40.426 | 1.00 | 171.22 |
| 3790 | NE2 | HIS | E | 424 | 19.448 | 34.269 | 41.010 | 1.00 | 172.01 |
| 3791 | C | HIS | E | 424 | 16.433 | 37.052 | 45.397 | 1.00 | 165.73 |
| 3792 | O | HIS | E | 424 | 15.477 | 36.305 | 45.622 | 1.00 | 165.58 |
| 3793 | N | LEU | E | 425 | 16.738 | 38.090 | 46.172 | 1.00 | 167.68 |
| 3794 | CA | LEU | E | 425 | 15.950 | 38.437 | 47.354 | 1.00 | 166.29 |
| 3795 | CB | LEU | E | 425 | 16.399 | 37.621 | 48.576 | 1.00 | 167.16 |
| 3796 | CG | LEU | E | 425 | 15.924 | 36.166 | 48.689 | 1.00 | 165.54 |
| 3797 | CD1 | LEU | E | 425 | 16.504 | 35.536 | 49.949 | 1.00 | 161.26 |
| 3798 | CD2 | LEU | E | 425 | 14.401 | 36.118 | 48.726 | 1.00 | 162.28 |
| 3799 | C | LEU | E | 425 | 16.057 | 39.929 | 47.666 | 1.00 | 162.72 |
| 3800 | O | LEU | E | 425 | 17.127 | 40.528 | 47.544 | 1.00 | 161.46 |
| 3801 | N | PRO | E | 426 | 14.940 | 40.545 | 48.082 | 1.00 | 162.83 |
| 3802 | CD | PRO | E | 426 | 13.664 | 39.887 | 48.422 | 1.00 | 163.22 |
| 3803 | CA | PRO | E | 426 | 14.896 | 41.972 | 48.413 | 1.00 | 160.31 |
| 3804 | CB | PRO | E | 426 | 13.434 | 42.187 | 48.798 | 1.00 | 160.92 |
| 3805 | CG | PRO | E | 426 | 13.053 | 40.861 | 49.400 | 1.00 | 160.91 |
| 3806 | C | PRO | E | 426 | 15.859 | 42.353 | 49.536 | 1.00 | 160.48 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3807 | O | PRO | E | 426 | 17.044 | 42.588 | 49.302 | 1.00 | 159.17 |
| 3808 | N | ARG | E | 427 | 15.333 | 42.413 | 50.755 | 1.00 | 160.77 |
| 3809 | CA | ARG | E | 427 | 16.128 | 42.757 | 51.927 | 1.00 | 159.32 |
| 3810 | CB | ARG | E | 427 | 15.203 | 43.179 | 53.072 | 1.00 | 159.76 |
| 3811 | CG | ARG | E | 427 | 15.917 | 43.569 | 54.351 | 1.00 | 167.18 |
| 3812 | CD | ARG | E | 427 | 14.916 | 43.914 | 55.436 | 1.00 | 171.33 |
| 3813 | NE | ARG | E | 427 | 15.565 | 44.177 | 56.715 | 1.00 | 172.17 |
| 3814 | CZ | ARG | E | 427 | 14.912 | 44.469 | 57.834 | 1.00 | 173.64 |
| 3815 | NH1 | ARG | E | 427 | 13.587 | 44.536 | 57.831 | 1.00 | 173.53 |
| 3816 | NH2 | ARG | E | 427 | 15.581 | 44.691 | 58.958 | 1.00 | 171.50 |
| 3817 | C | ARG | E | 427 | 16.980 | 41.562 | 52.351 | 1.00 | 155.18 |
| 3818 | O | ARG | E | 427 | 16.692 | 40.420 | 51.988 | 1.00 | 152.78 |
| 3819 | N | ALA | E | 428 | 18.029 | 41.831 | 53.120 | 1.00 | 153.14 |
| 3820 | CA | ALA | E | 428 | 18.922 | 40.780 | 53.587 | 1.00 | 147.40 |
| 3821 | CB | ALA | E | 428 | 20.317 | 41.353 | 53.818 | 1.00 | 145.21 |
| 3822 | C | ALA | E | 428 | 18.401 | 40.141 | 54.869 | 1.00 | 142.55 |
| 3823 | O | ALA | E | 428 | 17.601 | 40.734 | 55.589 | 1.00 | 144.32 |
| 3824 | N | LEU | E | 429 | 18.855 | 38.924 | 55.143 | 1.00 | 136.62 |
| 3825 | CA | LEU | E | 429 | 18.447 | 38.209 | 56.345 | 1.00 | 136.08 |
| 3826 | CB | LEU | E | 429 | 18.307 | 36.713 | 56.052 | 1.00 | 139.05 |
| 3827 | CG | LEU | E | 429 | 17.141 | 36.287 | 55.156 | 1.00 | 140.58 |
| 3828 | CD1 | LEU | E | 429 | 17.193 | 34.778 | 54.935 | 1.00 | 136.57 |
| 3829 | CD2 | LEU | E | 429 | 15.822 | 36.694 | 55.802 | 1.00 | 137.65 |
| 3830 | C | LEU | E | 429 | 19.459 | 38.421 | 57.467 | 1.00 | 135.59 |
| 3831 | O | LEU | E | 429 | 20.648 | 38.620 | 57.213 | 1.00 | 137.04 |
| 3832 | N | MET | E | 430 | 18.983 | 38.377 | 58.709 | 1.00 | 133.60 |
| 3833 | CA | MET | E | 430 | 19.849 | 38.570 | 59.867 | 1.00 | 128.50 |
| 3834 | CB | MET | E | 430 | 19.835 | 40.040 | 60.286 | 1.00 | 130.60 |
| 3835 | CG | MET | E | 430 | 20.346 | 40.973 | 59.206 | 1.00 | 136.15 |
| 3836 | SD | MET | E | 430 | 19.909 | 42.683 | 59.509 | 1.00 | 149.76 |
| 3837 | CE | MET | E | 430 | 18.396 | 42.825 | 58.568 | 1.00 | 149.40 |
| 3838 | C | MET | E | 430 | 19.434 | 37.695 | 61.044 | 1.00 | 124.36 |
| 3839 | O | MET | E | 430 | 18.248 | 37.554 | 61.342 | 1.00 | 122.99 |
| 3840 | N | ARG | E | 431 | 20.428 | 37.105 | 61.701 | 1.00 | 119.17 |
| 3841 | CA | ARG | E | 431 | 20.207 | 36.237 | 62.856 | 1.00 | 108.51 |
| 3842 | CB | ARG | E | 431 | 20.307 | 34.763 | 62.455 | 1.00 | 106.07 |
| 3843 | CG | ARG | E | 431 | 19.534 | 34.386 | 61.206 | 1.00 | 116.42 |
| 3844 | CD | ARG | E | 431 | 18.044 | 34.568 | 61.394 | 1.00 | 125.47 |
| 3845 | NE | ARG | E | 431 | 17.333 | 34.460 | 60.126 | 1.00 | 130.26 |
| 3846 | CZ | ARG | E | 431 | 16.023 | 34.625 | 59.992 | 1.00 | 132.21 |
| 3847 | NH1 | ARG | E | 431 | 15.276 | 34.903 | 61.053 | 1.00 | 132.12 |
| 3848 | NH2 | ARG | E | 431 | 15.460 | 34.524 | 58.797 | 1.00 | 137.61 |
| 3849 | C | ARG | E | 431 | 21.303 | 36.538 | 63.868 | 1.00 | 108.92 |
| 3850 | O | ARG | E | 431 | 22.430 | 36.856 | 63.490 | 1.00 | 118.35 |
| 3851 | N | SER | E | 432 | 20.974 | 36.447 | 65.150 | 1.00 | 101.79 |
| 3852 | CA | SER | E | 432 | 21.951 | 36.691 | 66.206 | 1.00 | 94.40 |
| 3853 | CB | SER | E | 432 | 21.720 | 38.058 | 66.836 | 1.00 | 91.54 |
| 3854 | OG | SER | E | 432 | 20.428 | 38.131 | 67.395 | 1.00 | 109.57 |
| 3855 | C | SER | E | 432 | 21.818 | 35.586 | 67.256 | 1.00 | 95.68 |
| 3856 | O | SER | E | 432 | 20.793 | 34.908 | 67.321 | 1.00 | 86.69 |
| 3857 | N | THR | E | 433 | 22.850 | 35.395 | 68.072 | 1.00 | 89.92 |
| 3858 | CA | THR | E | 433 | 22.811 | 34.343 | 69.078 | 1.00 | 89.28 |
| 3859 | CB | THR | E | 433 | 23.315 | 33.000 | 68.458 | 1.00 | 93.21 |
| 3860 | OG1 | THR | E | 433 | 23.260 | 31.946 | 69.429 | 1.00 | 91.50 |
| 3861 | CG2 | THR | E | 433 | 24.731 | 33.153 | 67.942 | 1.00 | 89.29 |
| 3862 | C | THR | E | 433 | 23.635 | 34.713 | 70.315 | 1.00 | 91.69 |
| 3863 | O | THR | E | 433 | 24.554 | 35.525 | 70.232 | 1.00 | 95.61 |
| 3864 | N | THR | E | 434 | 23.282 | 34.122 | 71.457 | 1.00 | 87.94 |
| 3865 | CA | THR | E | 434 | 23.960 | 34.361 | 72.733 | 1.00 | 97.04 |
| 3866 | CB | THR | E | 434 | 23.606 | 35.748 | 73.323 | 1.00 | 104.32 |
| 3867 | CG1 | THR | E | 434 | 22.313 | 36.154 | 72.865 | 1.00 | 116.24 |
| 3868 | CG2 | THR | E | 434 | 24.622 | 36.776 | 72.918 | 1.00 | 107.18 |
| 3869 | C | THR | E | 434 | 23.590 | 33.300 | 73.773 | 1.00 | 92.94 |
| 3870 | O | THR | E | 434 | 23.987 | 33.381 | 74.939 | 1.00 | 84.37 |
| 3871 | N | ARG | E | 440 | 19.138 | 27.938 | 86.349 | 1.00 | 24.43 |
| 3872 | CA | ARG | E | 440 | 20.157 | 26.891 | 86.240 | 1.00 | 59.49 |
| 3873 | CB | ARG | E | 440 | 21.553 | 27.480 | 86.497 | 1.00 | 41.10 |
| 3874 | CG | ARG | E | 440 | 21.858 | 28.783 | 85.751 | 1.00 | 67.32 |
| 3875 | CD | ARG | E | 440 | 22.087 | 28.609 | 84.244 | 1.00 | 70.00 |
| 3876 | NE | ARG | E | 440 | 22.094 | 29.905 | 83.550 | 1.00 | 91.32 |
| 3877 | CZ | ARG | E | 440 | 22.486 | 30.105 | 82.290 | 1.00 | 86.80 |
| 3878 | NH1 | ARG | E | 440 | 22.918 | 29.094 | 81.547 | 1.00 | 93.08 |
| 3879 | NH2 | ARG | E | 440 | 22.446 | 31.327 | 81.766 | 1.00 | 91.37 |
| 3880 | C | ARG | E | 440 | 19.893 | 25.744 | 87.227 | 1.00 | 53.59 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3881 | O | ARG | E | 440 | 19.577 | 25.990 | 88.410 | 1.00 | 46.19 |
| 3882 | N | ALA | E | 441 | 20.037 | 24.501 | 86.744 | 1.00 | 54.40 |
| 3883 | CA | ALA | E | 441 | 19.799 | 23.318 | 87.584 | 1.00 | 49.83 |
| 3884 | CB | ALA | E | 441 | 18.310 | 23.014 | 87.643 | 1.00 | 25.38 |
| 3885 | C | ALA | E | 441 | 20.543 | 22.093 | 87.080 | 1.00 | 42.21 |
| 3886 | O | ALA | E | 441 | 20.508 | 21.789 | 85.886 | 1.00 | 53.89 |
| 3887 | N | ALA | E | 442 | 21.197 | 21.386 | 87.999 | 1.00 | 30.65 |
| 3888 | CA | ALA | E | 442 | 21.953 | 20.190 | 87.644 | 1.00 | 42.35 |
| 3889 | CB | ALA | E | 442 | 22.739 | 19.692 | 88.865 | 1.00 | 40.91 |
| 3890 | C | ALA | E | 442 | 21.048 | 19.071 | 87.123 | 1.00 | 46.14 |
| 3891 | O | ALA | E | 442 | 19.865 | 19.026 | 87.440 | 1.00 | 51.42 |
| 3892 | N | PRO | E | 443 | 21.596 | 18.158 | 86.308 | 1.00 | 47.31 |
| 3893 | CD | PRO | E | 443 | 22.833 | 18.332 | 85.538 | 1.00 | 46.54 |
| 3894 | CA | PRO | E | 443 | 20.822 | 17.040 | 85.757 | 1.00 | 45.92 |
| 3895 | CB | PRO | E | 443 | 21.552 | 16.717 | 84.445 | 1.00 | 38.44 |
| 3896 | CG | PRO | E | 443 | 22.367 | 17.931 | 84.168 | 1.00 | 49.47 |
| 3897 | C | PRO | E | 443 | 20.805 | 15.805 | 86.663 | 1.00 | 43.87 |
| 3898 | O | PRO | E | 443 | 21.805 | 15.482 | 87.305 | 1.00 | 47.80 |
| 3899 | N | ALA | E | 444 | 19.668 | 15.122 | 86.716 | 1.00 | 36.98 |
| 3900 | CA | ALA | E | 444 | 19.577 | 13.881 | 87.480 | 1.00 | 30.19 |
| 3901 | CB | ALA | E | 444 | 18.163 | 13.746 | 88.121 | 1.00 | 25.02 |
| 3902 | C | ALA | E | 444 | 19.812 | 12.841 | 86.356 | 1.00 | 34.61 |
| 3903 | O | ALA | E | 444 | 19.234 | 12.963 | 85.270 | 1.00 | 44.45 |
| 3904 | N | VAL | E | 445 | 20.658 | 11.840 | 86.590 | 1.00 | 29.92 |
| 3905 | CA | VAL | E | 445 | 20.947 | 10.872 | 85.524 | 1.00 | 10.22 |
| 3906 | CB | VAL | E | 445 | 22.429 | 11.070 | 84.981 | 1.00 | 37.38 |
| 3907 | CG1 | VAL | E | 445 | 22.826 | 9.954 | 84.004 | 1.00 | 12.74 |
| 3908 | CG2 | VAL | E | 445 | 22.553 | 12.421 | 84.268 | 1.00 | 30.05 |
| 3909 | C | VAL | E | 445 | 20.778 | 9.398 | 85.851 | 1.00 | 38.31 |
| 3910 | O | VAL | E | 445 | 21.260 | 8.924 | 86.901 | 1.00 | 29.93 |
| 3911 | N | TYR | E | 446 | 20.091 | 8.671 | 84.957 | 1.00 | 33.94 |
| 3912 | CA | TYR | E | 446 | 19.954 | 7.237 | 85.152 | 1.00 | 34.63 |
| 3913 | CB | TYR | E | 446 | 18.684 | 6.873 | 85.915 | 1.00 | 51.02 |
| 3914 | CG | TYR | E | 446 | 18.887 | 5.515 | 86.568 | 1.00 | 92.06 |
| 3915 | CD1 | TYR | E | 446 | 20.039 | 5.247 | 87.318 | 1.00 | 93.35 |
| 3916 | CE1 | TYR | E | 446 | 20.269 | 3.976 | 87.862 | 1.00 | 88.40 |
| 3917 | CD2 | TYR | E | 446 | 17.978 | 4.485 | 86.388 | 1.00 | 91.37 |
| 3918 | CE2 | TYR | E | 446 | 18.196 | 3.214 | 86.926 | 1.00 | 80.24 |
| 3919 | CZ | TYR | E | 446 | 19.338 | 2.964 | 87.658 | 1.00 | 88.09 |
| 3920 | OH | TYR | E | 446 | 19.534 | 1.708 | 88.187 | 1.00 | 93.84 |
| 3921 | C | TYR | E | 446 | 20.072 | 6.394 | 83.891 | 1.00 | 40.26 |
| 3922 | O | TYR | E | 446 | 19.673 | 6.806 | 82.800 | 1.00 | 37.70 |
| 3923 | N | ALA | E | 447 | 20.620 | 5.196 | 84.056 | 1.00 | 25.54 |
| 3924 | CA | ALA | E | 447 | 20.876 | 4.321 | 82.919 | 1.00 | 30.19 |
| 3925 | CB | ALk | E | 447 | 22.390 | 4.251 | 82.660 | 1.00 | 34.35 |
| 3926 | C | ALA | E | 447 | 20.317 | 2.916 | 83.048 | 1.00 | 37.49 |
| 3927 | O | ALA | E | 447 | 20.378 | 2.315 | 84.103 | 1.00 | 39.95 |
| 3928 | N | PHE | E | 448 | 19.795 | 2.385 | 81.944 | 1.00 | 40.93 |
| 3929 | CA | PHE | E | 448 | 19.211 | 1.057 | 81.960 | 1.00 | 36.89 |
| 3930 | CB | PHE | E | 448 | 17.691 | 1.125 | 81.837 | 1.00 | 43.40 |
| 3931 | CG | PHE | E | 448 | 17.060 | 2.171 | 82.673 | 1.00 | 32.07 |
| 3932 | CDI | PHE | E | 448 | 16.881 | 3.459 | 82.175 | 1.00 | 32.43 |
| 3933 | CD2 | PHE | E | 448 | 16.619 | 1.873 | 83.955 | 1.00 | 21.72 |
| 3934 | CE1 | PHE | E | 448 | 16.266 | 4.443 | 82.952 | 1.00 | 27.43 |
| 3935 | CE2 | PHE | E | 448 | 16.002 | 2.839 | 84.749 | 1.00 | 39.61 |
| 3936 | CZ | PHE | E | 448 | 15.823 | 4.124 | 84.245 | 1.00 | 17.85 |
| 3937 | C | PHE | E | 448 | 19.718 | 0.163 | 80.839 | 1.00 | 43.38 |
| 3938 | O | PHE | E | 448 | 20.176 | 0.627 | 79.793 | 1.00 | 38.12 |
| 3939 | N | ALA | E | 449 | 19.590 | −1.135 | 81.073 | 1.00 | 24.07 |
| 3940 | CA | ALA | E | 449 | 20.000 | −2.125 | 80.112 | 1.00 | 37.84 |
| 3941 | CB | ALA | E | 449 | 21.151 | −2.993 | 80.666 | 1.00 | 31.32 |
| 3942 | C | ALA | E | 449 | 18.783 | −2.982 | 79.841 | 1.00 | 42.98 |
| 3943 | O | ALA | E | 449 | 18.027 | −3.297 | 80.745 | 1.00 | 45.75 |
| 3944 | N | THR | E | 450 | 18.600 | −3.351 | 78.584 | 1.00 | 49.18 |
| 3945 | CA | THR | E | 450 | 17.481 | −4.183 | 78.179 | 1.00 | 47.09 |
| 3946 | CB | THR | E | 450 | 17.305 | −4.099 | 76.653 | 1.00 | 39.86 |
| 3947 | OG1 | THR | E | 450 | 16.521 | −2.946 | 76.342 | 1.00 | 39.37 |
| 3948 | CG2 | THR | E | 450 | 16.635 | −5.341 | 76.115 | 1.00 | 69.96 |
| 3949 | C | THR | E | 450 | 17.699 | −5.635 | 78.579 | 1.00 | 35.67 |
| 3950 | O | THR | E | 450 | 18.835 | −6.088 | 78.673 | 1.00 | 48.47 |
| 3951 | N | PRO | E | 451 | 16.612 | −6.378 | 78.839 | 1.00 | 64.48 |
| 3952 | CD | PRO | E | 451 | 15.267 | −5.855 | 79.114 | 1.00 | 65.82 |
| 3953 | CA | PRO | E | 451 | 16.700 | −7.797 | 79.224 | 1.00 | 62.49 |
| 3954 | CB | PRO | E | 451 | 15.320 | −8.098 | 79.803 | 1.00 | 60.94 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 3955 | CG | PRO | E | 451 | 14.821 | −6.752 | 80.238 | 1.00 | 76.54 |
| 3956 | C | PRO | E | 451 | 16.966 | −8.631 | 77.972 | 1.00 | 59.53 |
| 3957 | O | PRO | E | 451 | 16.920 | −8.095 | 76.852 | 1.00 | 36.13 |
| 3958 | N | GLU | E | 452 | 17.246 | −9.923 | 78.166 | 1.00 | 69.17 |
| 3959 | CA | GLU | E | 452 | 17.525 | −10.872 | 77.074 | 1.00 | 87.05 |
| 3960 | CB | GLU | E | 452 | 18.221 | −10.183 | 75.898 | 1.00 | 100.70 |
| 3961 | CG | GLU | E | 452 | 17.285 | −9.640 | 74.836 | 1.00 | 94.84 |
| 3962 | CD | GLU | E | 452 | 17.879 | −8.434 | 74.130 | 1.00 | 105.15 |
| 3963 | OE1 | GLU | E | 452 | 18.899 | −8.597 | 73.416 | 1.00 | 96.88 |
| 3964 | OE2 | GLU | E | 452 | 17.332 | −7.319 | 74.303 | 1.00 | 80.95 |
| 3965 | C | GLU | E | 452 | 18.405 | −12.033 | 77.532 | 1.00 | 93.87 |
| 3966 | O | GLU | E | 452 | 19.342 | −12.428 | 76.829 | 1.00 | 89.48 |
| 3967 | N | LYS | E | 459 | 22.071 | −6.600 | 69.338 | 1.00 | 66.18 |
| 3968 | CA | LYS | E | 459 | 21.034 | −5.560 | 69.351 | 1.00 | 96.16 |
| 3969 | CB | LYS | E | 459 | 19.886 | −5.960 | 68.412 | 1.00 | 106.77 |
| 3970 | CG | LYS | E | 459 | 20.094 | −5.570 | 66.949 | 1.00 | 102.21 |
| 3971 | CD | LYS | E | 459 | 19.955 | −4.066 | 66.765 | 1.00 | 114.07 |
| 3972 | CE | LYS | E | 459 | 20.006 | −3.674 | 65.297 | 1.00 | 117.62 |
| 3973 | NZ | LYS | E | 459 | 19.694 | −2.228 | 65.105 | 1.00 | 120.52 |
| 3974 | C | LYS | E | 459 | 20.488 | −5.268 | 70.762 | 1.00 | 96.79 |
| 3975 | O | LYS | E | 459 | 19.340 | −4.810 | 70.930 | 1.00 | 73.76 |
| 3976 | N | ARG | E | 460 | 21.330 | −5.532 | 71.764 | 1.00 | 87.73 |
| 3977 | CA | ARG | E | 460 | 21.004 | −5.319 | 73.174 | 1.00 | 67.40 |
| 3978 | CB | ARG | E | 460 | 21.947 | −6.150 | 74.042 | 1.00 | 63.14 |
| 3979 | CG | ARG | E | 460 | 21.770 | −7.673 | 73.838 | 1.00 | 76.05 |
| 3980 | CD | ARG | E | 460 | 21.632 | −8.106 | 72.351 | 1.00 | 59.67 |
| 3981 | NE | ARG | E | 460 | 22.797 | −7.792 | 71.511 | 1.00 | 69.43 |
| 3982 | CZ | ARG | E | 460 | 23.691 | −8.686 | 71.088 | 1.00 | 72.42 |
| 3983 | NH1 | ARG | E | 46D | 23.572 | −9.970 | 71.409 | 1.00 | 81.03 |
| 3984 | NH2 | ARG | E | 460 | 24.724 | −8.297 | 70.359 | 1.00 | 60.75 |
| 3985 | C | ARG | E | 460 | 21.152 | −3.832 | 73.442 | 1.00 | 57.10 |
| 3986 | O | ARG | E | 460 | 22.231 | −3.269 | 73.289 | 1.00 | 49.77 |
| 3987 | N | THR | E | 461 | 20.053 | −3.197 | 73.838 | 1.00 | 41.74 |
| 3988 | CA | THR | E | 461 | 20.051 | −1.756 | 74.047 | 1.00 | 34.59 |
| 3989 | CB | THR | E | 461 | 18.768 | −1.140 | 73.448 | 1.00 | 31.41 |
| 3990 | OG1 | THR | E | 461 | 18.336 | −1.949 | 72.356 | 1.00 | 40.72 |
| 3991 | CG2 | THR | E | 461 | 19.037 | 0.263 | 72.933 | 1.00 | 46.73 |
| 3992 | C | THR | E | 461 | 20.212 | −1.236 | 75.471 | 1.00 | 40.42 |
| 3993 | O | THR | E | 461 | 19.763 | −1.853 | 76.445 | 1.00 | 38.66 |
| 3994 | N | LEU | E | 462 | 20.866 | −0.081 | 75.557 | 1.00 | 29.41 |
| 3995 | CA | LEU | E | 462 | 21.102 | 0.612 | 76.820 | 1.00 | 35.36 |
| 3996 | CB | LEU | E | 462 | 22.596 | 0.848 | 77.083 | 1.00 | 37.96 |
| 3997 | CG | LEU | E | 462 | 23.489 | −0.393 | 77.059 | 1.00 | 43.39 |
| 3998 | CD1 | LEU | E | 462 | 24.919 | 0.033 | 77.217 | 1.00 | 39.82 |
| 3999 | CD2 | LEU | E | 462 | 23.074 | −1.347 | 78.141 | 1.00 | 32.71 |
| 4000 | C | LEU | E | 462 | 20.425 | 1.939 | 76.658 | 1.00 | 33.50 |
| 4001 | O | LEU | E | 462 | 20.501 | 2.569 | 75.603 | 1.00 | 46.97 |
| 4002 | N | ALA | E | 463 | 19.750 | 2.361 | 77.712 | 1.00 | 30.75 |
| 4003 | CA | ALA | E | 463 | 19.047 | 3.608 | 77.667 | 1.00 | 24.66 |
| 4004 | CB | ALA | E | 463 | 17.534 | 3.356 | 77.678 | 1.00 | 38.10 |
| 4005 | C | ALA | E | 463 | 19.460 | 4.457 | 78.836 | 1.00 | 41.57 |
| 4006 | O | ALA | E | 463 | 19.827 | 3.949 | 79.900 | 1.00 | 29.87 |
| 4007 | N | CYS | E | 464 | 19.395 | 5.768 | 78.617 | 1.00 | 38.63 |
| 4008 | CA | CYS | E | 464 | 19.760 | 6.732 | 79.635 | 1.00 | 25.81 |
| 4009 | C | CYS | E | 464 | 18.744 | 7.835 | 79.665 | 1.00 | 36.63 |
| 4010 | O | CYS | E | 464 | 18.419 | 8.410 | 78.625 | 1.00 | 46.30 |
| 4011 | CB | CYS | E | 464 | 21.101 | 7.324 | 79.298 | 1.00 | 47.96 |
| 4012 | SG | CYS | E | 464 | 21.898 | 8.243 | 80.643 | 1.00 | 58.52 |
| 4013 | N | LEU | E | 465 | 18.228 | 8.102 | 80.863 | 1.00 | 34.96 |
| 4014 | CA | LEU | E | 465 | 17.266 | 9.174 | 81.089 | 1.00 | 26.20 |
| 4015 | CB | LEU | E | 465 | 16.108 | 8.705 | 81.964 | 1.00 | 31.06 |
| 4016 | CG | LEU | E | 465 | 15.233 | 9.841 | 82.520 | 1.00 | 31.57 |
| 4017 | CD1 | LEU | E | 465 | 14.643 | 10.702 | 81.395 | 1.00 | 36.25 |
| 4018 | CD2 | LEU | E | 465 | 14.126 | 9.225 | 83.357 | 1.00 | 31.21 |
| 4019 | C | LEU | E | 465 | 18.031 | 10.266 | 81.815 | 1.00 | 35.85 |
| 4020 | O | LEU | E | 465 | 18.703 | 9.993 | 82.823 | 1.00 | 26.12 |
| 4021 | N | ILE | E | 466 | 17.944 | 11.488 | 81.288 | 1.00 | 31.45 |
| 4022 | CA | ILE | E | 466 | 18.636 | 12.638 | 81.865 | 1.00 | 33.30 |
| 4023 | CB | ILE | E | 466 | 19.771 | 13.112 | 80.929 | 1.00 | 57.53 |
| 4024 | CG2 | ILE | E | 466 | 20.604 | 14.183 | 81.629 | 1.00 | 42.41 |
| 4025 | CG1 | ILE | E | 466 | 20.659 | 11.917 | 80.546 | 1.00 | 45.82 |
| 4026 | CD1 | ILE | E | 466 | 21.389 | 12.110 | 79.258 | 1.00 | 37.28 |
| 4027 | C | ILE | E | 466 | 17.608 | 13.736 | 82.029 | 1.00 | 36.00 |
| 4028 | O | ILE | E | 466 | 17.121 | 14.298 | 81.041 | 1.00 | 39.57 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4029 | N | GLN | E | 467 | 17.297 | 14.068 | 83.277 | 1.00 | 34.19 |
| 4030 | CA | GLN | E | 467 | 16.238 | 15.048 | 83.546 | 1.00 | 44.41 |
| 4031 | CB | GLN | E | 467 | 14.952 | 14.280 | 83.863 | 1.00 | 32.36 |
| 4032 | CG | GLN | E | 467 | 15.148 | 13.293 | 85.017 | 1.00 | 20.31 |
| 4033 | CD | GLN | E | 467 | 13.851 | 12.560 | 85.410 | 1.00 | 50.84 |
| 4034 | OE1 | GLN | E | 467 | 12.948 | 12.393 | 84.594 | 1.00 | 38.05 |
| 4035 | NE2 | GLN | E | 467 | 13.775 | 12.099 | 86.652 | 1.00 | 26.90 |
| 4036 | C | GLN | E | 467 | 16.413 | 16.121 | 84.637 | 1.00 | 54.30 |
| 4037 | O | GLN | E | 467 | 17.366 | 16.106 | 85.450 | 1.00 | 38.13 |
| 4038 | N | ASN | E | 468 | 15.436 | 17.037 | 84.633 | 1.00 | 34.90 |
| 4039 | CA | ASN | E | 468 | 15.332 | 18.142 | 85.583 | 1.00 | 39.60 |
| 4040 | CB | ASN | E | 468 | 15.149 | 17.612 | 87.011 | 1.00 | 41.40 |
| 4041 | CG | ASN | E | 468 | 13.969 | 16.674 | 87.127 | 1.00 | 38.63 |
| 4042 | OD1 | ASN | E | 468 | 12.957 | 16.856 | 86.442 | 1.00 | 38.27 |
| 4043 | ND2 | ASN | E | 468 | 14.084 | 15.668 | 87.995 | 1.00 | 34.74 |
| 4044 | C | ASN | E | 468 | 16.515 | 19.083 | 85.553 | 1.00 | 49.99 |
| 4045 | O | ASN | E | 468 | 17.021 | 19.498 | 86.597 | 1.00 | 53.91 |
| 4046 | N | PHE | E | 469 | 16.944 | 19.442 | 84.353 | 1.00 | 36.86 |
| 4047 | CA | PHE | E | 469 | 18.085 | 20.329 | 84.234 | 1.00 | 38.76 |
| 4048 | CB | PHE | E | 469 | 19.276 | 19.603 | 83.526 | 1.00 | 43.00 |
| 4049 | CG | PHE | E | 469 | 18.989 | 19.190 | 82.100 | 1.00 | 23.13 |
| 4050 | CD1 | PHE | E | 469 | 19.028 | 20.127 | 81.056 | 1.00 | 25.24 |
| 4051 | CD2 | PHE | E | 469 | 18.636 | 17.885 | 81.805 | 1.00 | 28.01 |
| 4052 | CE1 | PHE | E | 469 | 18.713 | 19.760 | 79.729 | 1.00 | 20.23 |
| 4053 | CE2 | PHE | E | 469 | 18.316 | 17.514 | 80.478 | 1.00 | 33.95 |
| 4054 | CZ | PHE | E | 469 | 18.358 | 18.459 | 79.445 | 1.00 | 30.84 |
| 4055 | C | PHE | E | 469 | 17.700 | 21.576 | 83.472 | 1.00 | 43.43 |
| 4056 | O | PHE | E | 469 | 16.734 | 21.581 | 82.710 | 1.00 | 41.15 |
| 4057 | N | MET | E | 470 | 18.453 | 22.641 | 83.705 | 1.00 | 47.00 |
| 4058 | CA | MET | E | 470 | 18.231 | 23.882 | 82.989 | 1.00 | 49.91 |
| 4059 | CB | MET | E | 470 | 16.950 | 24.598 | 83.473 | 1.00 | 51.15 |
| 4060 | CG | MET | E | 470 | 16.897 | 24.994 | 84.942 | 1.00 | 74.72 |
| 4061 | SD | MET | E | 470 | 15.223 | 25.580 | 85.346 | 1.00 | 76.41 |
| 4062 | CE | MET | E | 470 | 15.005 | 26.862 | 84.098 | 1.00 | 79.08 |
| 4063 | C | MET | E | 470 | 19.465 | 24.776 | 83.096 | 1.00 | 45.23 |
| 4064 | O | MET | E | 470 | 20.204 | 24.736 | 84.102 | 1.00 | 45.67 |
| 4065 | N | PRO | E | 471 | 19.747 | 25.536 | 82.024 | 1.00 | 38.15 |
| 4066 | CD | PRO | E | 471 | 20.935 | 26.400 | 81.961 | 1.00 | 29.53 |
| 4067 | CA | PRO | E | 471 | 18.992 | 25.590 | 80.759 | 1.00 | 33.78 |
| 4068 | CB | PRO | E | 471 | 19.773 | 26.612 | 79.914 | 1.00 | 44.52 |
| 4069 | CG | PRO | E | 471 | 20.509 | 27.433 | 80.939 | 1.00 | 45.70 |
| 4070 | C | PRO | E | 471 | 18.913 | 24.230 | 80.036 | 1.00 | 47.63 |
| 4071 | O | PRO | E | 471 | 19.360 | 23.189 | 80.535 | 1.00 | 38.19 |
| 4072 | N | GLU | E | 472 | 18.376 | 24.267 | 78.827 | 1.00 | 48.07 |
| 4073 | CA | GLU | E | 472 | 18.212 | 23.072 | 78.022 | 1.00 | 48.57 |
| 4074 | CB | GLU | E | 472 | 17.140 | 23.312 | 76.972 | 1.00 | 40.98 |
| 4075 | CG | GLU | E | 472 | 17.577 | 24.223 | 75.864 | 1.00 | 59.95 |
| 4076 | CD | GLU | E | 472 | 16.535 | 24.300 | 74.774 | 1.00 | 93.48 |
| 4077 | OE1 | GLU | E | 472 | 15.451 | 24.883 | 75.018 | 1.00 | 100.41 |
| 4078 | OE2 | GLU | E | 472 | 16.797 | 23.762 | 73.676 | 1.00 | 100.79 |
| 4079 | C | GLU | E | 472 | 19.477 | 22.566 | 77.320 | 1.00 | 49.83 |
| 4080 | O | GLU | E | 472 | 19.508 | 21.418 | 76.851 | 1.00 | 56.62 |
| 4081 | N | ASP | E | 473 | 20.508 | 23.405 | 77.223 | 1.00 | 48.02 |
| 4082 | CA | ASP | E | 473 | 21.754 | 22.988 | 76.556 | 1.00 | 40.92 |
| 4083 | CB | ASP | E | 473 | 22.748 | 24.144 | 76.520 | 1.00 | 52.90 |
| 4084 | CG | ASP | E | 473 | 22.231 | 25.331 | 75.724 | 1.00 | 77.54 |
| 4085 | OD1 | ASP | E | 473 | 21.773 | 25.117 | 74.584 | 1.00 | 69.70 |
| 4086 | OD2 | ASP | E | 473 | 22.288 | 26.474 | 76.232 | 1.00 | 92.14 |
| 4087 | C | ASP | E | 473 | 22.379 | 21.816 | 77.295 | 1.00 | 33.92 |
| 4088 | O | ASP | E | 473 | 22.585 | 21.881 | 78.514 | 1.00 | 47.40 |
| 4089 | N | ILE | E | 474 | 22.675 | 20.743 | 76.572 | 1.00 | 37.68 |
| 4090 | CA | ILE | E | 474 | 23.274 | 19.566 | 77.224 | 1.00 | 36.64 |
| 4091 | CB | ILE | E | 474 | 22.181 | 18.754 | 77.976 | 1.00 | 28.11 |
| 4092 | CG2 | ILE | E | 474 | 21.333 | 17.967 | 76.980 | 1.00 | 26.97 |
| 4093 | CG1 | ILE | E | 474 | 22.821 | 17.802 | 78.973 | 1.00 | 35.97 |
| 4094 | CD1 | ILE | E | 474 | 21.835 | 17.273 | 80.023 | 1.00 | 28.77 |
| 4095 | C | ILE | E | 474 | 24.015 | 18.658 | 76.245 | 1.00 | 39.45 |
| 4096 | O | ILE | E | 474 | 23.672 | 18.604 | 75.058 | 1.00 | 35.82 |
| 4097 | N | SER | E | 475 | 25.044 | 17.976 | 76.750 | 1.00 | 36.16 |
| 4098 | CA | SER | E | 475 | 25.845 | 17.050 | 75.937 | 1.00 | 30.24 |
| 4099 | CB | SER | E | 475 | 27.293 | 17.531 | 75.843 | 1.00 | 47.39 |
| 4100 | OG | SER | E | 475 | 27.401 | 18.665 | 75.021 | 1.00 | 46.14 |
| 4101 | C | SER | E | 475 | 25.826 | 15.659 | 76.581 | 1.00 | 45.16 |
| 4102 | O | SER | E | 475 | 26.043 | 15.507 | 77.810 | 1.00 | 45.46 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4103 | N | VAL | E | 476 | 25.586 | 14.646 | 75.756 | 1.00 | 30.13 |
| 4104 | CA | VAL | E | 476 | 25.548 | 13.269 | 76.257 | 1.00 | 30.10 |
| 4105 | CB | VAL | E | 476 | 24.167 | 12.607 | 75.973 | 1.00 | 31.56 |
| 4106 | CG1 | VAL | E | 476 | 24.108 | 11.191 | 76.585 | 1.00 | 33.79 |
| 4107 | CG2 | VAL | E | 476 | 23.060 | 13.487 | 76.531 | 1.00 | 15.09 |
| 4108 | C | VAL | E | 476 | 26.636 | 12.392 | 75.622 | 1.00 | 40.86 |
| 4109 | O | VAL | E | 476 | 26.843 | 12.409 | 74.396 | 1.00 | 44.57 |
| 4110 | N | GLN | E | 477 | 27.318 | 11.622 | 76.464 | 1.00 | 39.81 |
| 4111 | CA | GLN | E | 477 | 28.354 | 10.745 | 75.970 | 1.00 | 35.62 |
| 4112 | CB | GLN | E | 477 | 29.725 | 11.324 | 76.257 | 1.00 | 41.56 |
| 4113 | CG | GLN | E | 477 | 29.822 | 12.819 | 76.147 | 1.00 | 55.42 |
| 4114 | CD | GLN | E | 477 | 31.246 | 13.286 | 76.376 | 1.00 | 78.33 |
| 4115 | OE1 | GLN | E | 477 | 31.868 | 12.960 | 77.392 | 1.00 | 60.97 |
| 4116 | NE2 | GLN | E | 477 | 31.776 | 14.041 | 75.424 | 1.00 | 78.04 |
| 4117 | C | GLN | E | 477 | 28.291 | 9.369 | 76.608 | 1.00 | 38.84 |
| 4118 | O | GLN | E | 477 | 27.856 | 9.210 | 77.749 | 1.00 | 30.39 |
| 4119 | N | TRP | E | 478 | 28.737 | 8.380 | 75.841 | 1.00 | 36.98 |
| 4120 | CA | TRP | E | 478 | 28.798 | 7.014 | 76.310 | 1.00 | 25.70 |
| 4121 | CB | TRP | E | 478 | 28.021 | 6.078 | 75.377 | 1.00 | 34.55 |
| 4122 | CG | TRP | E | 478 | 26.517 | 6.214 | 75.516 | 1.00 | 26.76 |
| 4123 | CD2 | TRP | E | 478 | 25.686 | 5.538 | 76.473 | 1.00 | 15.51 |
| 4124 | CE2 | TRP | E | 478 | 24.358 | 5.983 | 76.263 | 1.00 | 23.17 |
| 4125 | CE3 | TRP | E | 478 | 25.937 | 4.600 | 77.488 | 1.00 | 15.20 |
| 4126 | CD1 | TRP | E | 478 | 25.683 | 7.027 | 74.783 | 1.00 | 17.17 |
| 4127 | NE1 | TRP | E | 478 | 24.383 | 6.883 | 75.227 | 1.00 | 39.51 |
| 4128 | CZ2 | TRP | E | 478 | 23.285 | 5.523 | 77.029 | 1.00 | 22.89 |
| 4129 | CZ3 | TRP | E | 478 | 24.865 | 4.141 | 78.253 | 1.00 | 27.63 |
| 4130 | CH2 | TRP | E | 478 | 23.553 | 4.607 | 78.017 | 1.00 | 25.55 |
| 4131 | C | TRP | E | 478 | 30.265 | 6.631 | 76.365 | 1.00 | 38.57 |
| 4132 | O | TRP | E | 478 | 31.067 | 7.029 | 75.508 | 1.00 | 40.04 |
| 4133 | N | LEU | E | 479 | 30.627 | 5.884 | 77.401 | 1.00 | 34.49 |
| 4134 | CA | LEU | E | 479 | 32.010 | 5.468 | 77.559 | 1.00 | 23.93 |
| 4135 | CB | LEU | E | 479 | 32.691 | 6.264 | 78.681 | 1.00 | 47.43 |
| 4136 | CG | LEU | E | 479 | 33.096 | 7.727 | 78.454 | 1.00 | 49.66 |
| 4137 | CD1 | LEU | E | 479 | 31.878 | 8.623 | 78.281 | 1.00 | 53.08 |
| 4138 | CD2 | LEU | E | 479 | 33.916 | 8.187 | 79.649 | 1.00 | 60.27 |
| 4139 | C | LEU | E | 479 | 32.063 | 3.992 | 77.876 | 1.00 | 35.27 |
| 4140 | O | LEU | E | 479 | 31.198 | 3.461 | 78.568 | 1.00 | 36.59 |
| 4141 | N | HIS | E | 480 | 33.064 | 3.323 | 77.331 | 1.00 | 39.23 |
| 4142 | CA | HIS | E | 480 | 33.263 | 1.910 | 77.581 | 1.00 | 43.45 |
| 4143 | CB | HIS | E | 480 | 32.878 | 1.076 | 76.362 | 1.00 | 36.72 |
| 4144 | CG | HIS | E | 480 | 32.962 | −0.400 | 76.593 | 1.00 | 36.29 |
| 4145 | CD2 | HIS | E | 480 | 33.549 | −1.383 | 75.873 | 1.00 | 24.81 |
| 4146 | ND1 | HIS | E | 480 | 32.398 | −1.014 | 77.689 | 1.00 | 48.43 |
| 4147 | CE1 | HIS | E | 480 | 32.636 | −2.313 | 77.638 | 1.00 | 39.55 |
| 4148 | NE2 | HIS | E | 480 | 33.334 | −2.563 | 76.545 | 1.00 | 57.03 |
| 4149 | C | HIS | E | 480 | 34.744 | 1.749 | 77.902 | 1.00 | 61.55 |
| 4150 | O | HIS | E | 480 | 35.611 | 2.253 | 77.166 | 1.00 | 50.85 |
| 4151 | N | ASN | E | 481 | 35.018 | 1.061 | 79.013 | 1.00 | 71.16 |
| 4152 | CA | ASN | E | 481 | 36.381 | 0.842 | 79.505 | 1.00 | 80.14 |
| 4153 | CB | ASN | E | 481 | 37.335 | 0.492 | 78.362 | 1.00 | 66.47 |
| 4154 | CG | ASN | E | 481 | 37.267 | −0.966 | 77.981 | 1.00 | 64.19 |
| 4155 | OD1 | ASN | E | 481 | 37.599 | −1.838 | 78.784 | 1.00 | 60.94 |
| 4156 | ND2 | ASN | E | 481 | 36.831 | −1.245 | 76.758 | 1.00 | 69.42 |
| 4157 | C | ASN | E | 481 | 36.846 | 2.113 | 80.197 | 1.00 | 85.06 |
| 4158 | O | ASN | E | 481 | 37.302 | 2.086 | 81.342 | 1.00 | 91.90 |
| 4159 | N | GLU | E | 482 | 36.701 | 3.229 | 79.493 | 1.00 | 79.85 |
| 4160 | CA | GLU | E | 482 | 37.086 | 4.541 | 79.990 | 1.00 | 81.81 |
| 4161 | CB | GLU | E | 482 | 38.447 | 4.486 | 80.690 | 1.00 | 93.93 |
| 4162 | CG | GLU | E | 482 | 39.489 | 3.578 | 80.023 | 1.00 | 119.15 |
| 4163 | CD | GLU | E | 482 | 39.441 | 3.618 | 78.504 | 1.00 | 127.91 |
| 4164 | OE1 | GLU | E | 482 | 38.482 | 3.072 | 77.918 | 1.00 | 126.04 |
| 4165 | OE2 | GLU | E | 482 | 40.361 | 4.199 | 77.895 | 1.00 | 134.86 |
| 4166 | C | GLU | E | 482 | 37.178 | 5.462 | 78.797 | 1.00 | 66.99 |
| 4167 | O | GLU | E | 482 | 37.474 | 6.642 | 78.926 | 1.00 | 60.13 |
| 4168 | N | VAL | E | 483 | 36.920 | 4.903 | 77.626 | 1.00 | 55.83 |
| 4169 | CA | VAL | E | 483 | 36.998 | 5.669 | 76.404 | 1.00 | 57.97 |
| 4170 | CB | VAL | E | 483 | 37.863 | 4.955 | 75.354 | 1.00 | 48.02 |
| 4171 | CG1 | VAL | E | 483 | 37.281 | 3.600 | 75.042 | 1.00 | 61.25 |
| 4172 | CG2 | VAL | E | 483 | 37.959 | 5.804 | 74.104 | 1.00 | 58.11 |
| 4173 | C | VAL | E | 483 | 35.653 | 5.987 | 75.775 | 1.00 | 54.61 |
| 4174 | O | VAL | E | 483 | 34.784 | 5.129 | 75.638 | 1.00 | 47.77 |
| 4175 | N | GLN | E | 484 | 35.511 | 7.251 | 75.394 | 1.00 | 40.10 |
| 4176 | CA | GLN | E | 484 | 34.327 | 7.776 | 74.751 | 1.00 | 46.86 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4177 | CB | GLN | E | 484 | 34.529 | 9.277 | 74.612 | 1.00 | 40.87 |
| 4178 | CG | GLN | E | 484 | 33.521 | 10.002 | 73.776 | 1.00 | 67.59 |
| 4179 | CD | GLN | E | 484 | 33.732 | 11.496 | 73.854 | 1.00 | 72.67 |
| 4180 | OE1 | GLN | E | 484 | 33.296 | 12.251 | 72.978 | 1.00 | 83.24 |
| 4181 | NE2 | GLN | E | 484 | 34.403 | 11.938 | 74.917 | 1.00 | 77.17 |
| 4182 | C | GLN | E | 484 | 34.082 | 7.118 | 73.387 | 1.00 | 51.89 |
| 4183 | O | GLN | E | 484 | 34.938 | 7.176 | 72.504 | 1.00 | 59.44 |
| 4184 | N | LEU | E | 485 | 32.910 | 6.492 | 73.230 | 1.00 | 55.20 |
| 4185 | CA | LEU | E | 485 | 32.522 | 5.815 | 71.979 | 1.00 | 45.44 |
| 4186 | CB | LEU | E | 485 | 31.304 | 4.925 | 72.201 | 1.00 | 20.02 |
| 4187 | CG | LEU | E | 485 | 31.387 | 3.873 | 73.319 | 1.00 | 54.60 |
| 4188 | CD1 | LEU | E | 485 | 30.094 | 3.096 | 73.376 | 1.00 | 53.22 |
| 4189 | CD2 | LEU | E | 485 | 32.534 | 2.908 | 73.079 | 1.00 | 46.81 |
| 4190 | C | LEU | E | 485 | 32.198 | 6.824 | 70.890 | 1.00 | 48.54 |
| 4191 | O | LEU | E | 485 | 31.845 | 7.952 | 71.176 | 1.00 | 40.90 |
| 4192 | N | PRO | E | 486 | 32.317 | 6.423 | 69.618 | 1.00 | 58.61 |
| 4193 | CD | PRO | E | 486 | 32.577 | 5.068 | 69.100 | 1.00 | 41.44 |
| 4194 | CA | PRO | E | 486 | 32.023 | 7.360 | 68.527 | 1.00 | 48.57 |
| 4195 | CB | PRO | E | 486 | 32.107 | 6.489 | 67.282 | 1.00 | 47.80 |
| 4196 | CG | PRO | E | 486 | 33.014 | 5.365 | 67.695 | 1.00 | 45.51 |
| 4197 | C | PRO | E | 486 | 30.633 | 7.934 | 68.722 | 1.00 | 48.96 |
| 4198 | O | PRO | E | 486 | 29.691 | 7.207 | 69.030 | 1.00 | 45.90 |
| 4199 | N | ASP | E | 487 | 30.502 | 9.235 | 68.532 | 1.00 | 60.24 |
| 4200 | CA | ASP | E | 487 | 29.214 | 9.885 | 68.724 | 1.00 | 65.90 |
| 4201 | CB | ASP | E | 487 | 29.359 | 11.391 | 68.428 | 1.00 | 76.51 |
| 4202 | CG | ASP | E | 487 | 28.286 | 12.236 | 69.109 | 1.00 | 112.34 |
| 4203 | OD1 | ASP | E | 487 | 27.119 | 12.211 | 68.656 | 1.00 | 127.13 |
| 4204 | OD2 | ASP | E | 487 | 28.613 | 12.921 | 70.106 | 1.00 | 117.50 |
| 4205 | C | ASP | E | 487 | 28.089 | 9.262 | 67.878 | 1.00 | 65.39 |
| 4206 | O | ASP | E | 487 | 26.931 | 9.210 | 68.309 | 1.00 | 77.26 |
| 4207 | N | ALA | E | 488 | 28.432 | 8.768 | 66.691 | 1.00 | 56.65 |
| 4208 | CA | ALA | E | 488 | 27.431 | 8.185 | 65.796 | 1.00 | 53.96 |
| 4209 | CB | ALA | E | 488 | 27.976 | 8.091 | 64.397 | 1.00 | 56.94 |
| 4210 | C | ALA | E | 488 | 26.899 | 6.826 | 66.222 | 1.00 | 48.08 |
| 4211 | O | ALA | E | 488 | 26.065 | 6.240 | 65.538 | 1.00 | 58.51 |
| 4212 | N | ARG | E | 489 | 27.377 | 6.327 | 67.352 | 1.00 | 47.30 |
| 4213 | CA | ARG | E | 489 | 26.942 | 5.032 | 67.863 | 1.00 | 50.08 |
| 4214 | CB | ARG | E | 489 | 28.059 | 4.396 | 68.702 | 1.00 | 62.73 |
| 4215 | CG | ARG | E | 489 | 29.001 | 3.512 | 67.911 | 1.00 | 43.53 |
| 4216 | CD | ARG | E | 489 | 28.598 | 2.063 | 68.055 | 1.00 | 16.95 |
| 4217 | NE | ARG | E | 489 | 29.347 | 1.362 | 69.106 | 1.00 | 32.10 |
| 4218 | CZ | ARG | E | 489 | 28.832 | 0.400 | 69.866 | 1.00 | 35.95 |
| 4219 | NH1 | ARG | E | 489 | 27.563 | 0.042 | 69.690 | 1.00 | 70.37 |
| 4220 | NH2 | ARG | E | 489 | 29.569 | −0.212 | 70.785 | 1.00 | 54.29 |
| 4221 | C | ARG | E | 489 | 25.687 | 5.144 | 68.707 | 1.00 | 57.44 |
| 4222 | O | ARG | E | 489 | 24.930 | 4.181 | 68.818 | 1.00 | 61.57 |
| 4223 | N | HIS | E | 490 | 25.476 | 6.311 | 69.312 | 1.00 | 50.39 |
| 4224 | CA | HIS | E | 490 | 24.301 | 6.512 | 70.149 | 1.00 | 39.14 |
| 4225 | CB | HIS | E | 490 | 24.715 | 6.955 | 71.554 | 1.00 | 53.72 |
| 4226 | CG | HIS | E | 490 | 25.169 | 8.377 | 71.629 | 1.00 | 45.41 |
| 4227 | CD2 | HIS | E | 490 | 26.363 | 8.914 | 71.966 | 1.00 | 51.84 |
| 4228 | ND1 | HIS | E | 490 | 24.348 | 9.439 | 71.312 | 1.00 | 53.38 |
| 4229 | CE1 | HIS | E | 490 | 25.017 | 10.569 | 71.447 | 1.00 | 38.24 |
| 4230 | NE2 | HIS | E | 490 | 26.244 | 10.278 | 71.843 | 1.00 | 61.12 |
| 4231 | C | HIS | E | 490 | 23.349 | 7.533 | 69.546 | 1.00 | 38.66 |
| 4232 | O | HIS | E | 490 | 23.741 | 8.326 | 68.700 | 1.00 | 44.59 |
| 4233 | N | SER | E | 491 | 22.098 | 7.495 | 70.003 | 1.00 | 36.93 |
| 4234 | CA | SER | E | 491 | 21.047 | 8.407 | 69.537 | 1.00 | 37.39 |
| 4235 | CB | SER | E | 491 | 19.936 | 7.610 | 68.842 | 1.00 | 29.47 |
| 4236 | OG | SER | E | 491 | 19.114 | 8.482 | 68.105 | 1.00 | 36.39 |
| 4237 | C | SER | E | 491 | 20.466 | 9.177 | 70.722 | 1.00 | 38.16 |
| 4238 | O | SER | E | 491 | 20.093 | 8.579 | 71.742 | 1.00 | 41.77 |
| 4239 | N | THR | E | 492 | 20.382 | 10.496 | 70.584 | 1.00 | 34.94 |
| 4240 | CA | THR | E | 492 | 19.860 | 11.338 | 71.674 | 1.00 | 36.89 |
| 4241 | CB | THR | E | 492 | 20.993 | 12.176 | 72.311 | 1.00 | 32.31 |
| 4242 | OG1 | THR | E | 492 | 21.952 | 11.296 | 72.911 | 1.00 | 48.54 |
| 4243 | CG2 | THR | E | 492 | 20.435 | 13.126 | 73.361 | 1.00 | 40.67 |
| 4244 | C | THR | E | 492 | 18.712 | 12.283 | 71.276 | 1.00 | 32.58 |
| 4245 | O | THR | E | 492 | 18.807 | 13.034 | 70.288 | 1.00 | 41.54 |
| 4246 | N | THR | E | 493 | 17.651 | 12.257 | 72.084 | 1.00 | 34.03 |
| 4247 | CA | THR | E | 493 | 16.430 | 13.054 | 71.845 | 1.00 | 32.29 |
| 4248 | CB | THR | E | 493 | 15.274 | 12.622 | 72.809 | 1.00 | 29.93 |
| 4249 | OG1 | THR | E | 493 | 15.699 | 12.825 | 74.168 | 1.00 | 44.34 |
| 4250 | CG2 | THR | E | 493 | 14.913 | 11.134 | 72.615 | 1.00 | 23.15 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4251 | C | THR | E | 493 | 16.607 | 14.555 | 72.027 | 1.00 | 33.50 |
| 4252 | O | THR | E | 493 | 17.511 | 15.001 | 72.748 | 1.00 | 40.01 |
| 4253 | N | GLN | E | 494 | 15.731 | 15.324 | 71.381 | 1.00 | 39.72 |
| 4254 | CA | GLN | E | 494 | 15.774 | 16.777 | 71.501 | 1.00 | 53.00 |
| 4255 | CB | GLN | E | 494 | 14.892 | 17.434 | 70.433 | 1.00 | 71.23 |
| 4256 | CG | GLN | E | 494 | 15.300 | 17.131 | 69.010 | 1.00 | 89.85 |
| 4257 | CD | GLN | E | 494 | 16.617 | 17.768 | 68.655 | 1.00 | 104.27 |
| 4258 | OE1 | GLN | E | 494 | 16.740 | 18.992 | 68.646 | 1.00 | 111.03 |
| 4259 | NE2 | GLN | E | 494 | 17.618 | 16.944 | 68.367 | 1.00 | 110.42 |
| 4260 | C | GLN | E | 494 | 15.228 | 17.103 | 72.896 | 1.00 | 57.92 |
| 4261 | O | GLN | E | 494 | 14.326 | 16.422 | 73.405 | 1.00 | 52.42 |
| 4262 | N | PRO | E | 495 | 15.773 | 18.139 | 73.543 | 1.00 | 52.31 |
| 4263 | CD | PRO | E | 495 | 16.925 | 18.949 | 73.129 | 1.00 | 57.50 |
| 4264 | CA | PRO | E | 495 | 15.316 | 18.526 | 74.881 | 1.00 | 48.88 |
| 4265 | CB | PRO | E | 495 | 16.130 | 19.778 | 75.176 | 1.00 | 46.82 |
| 4266 | CG | PRO | E | 495 | 17.404 | 19.497 | 74.459 | 1.00 | 40.95 |
| 4267 | C | PRO | E | 495 | 13.822 | 18.810 | 74.913 | 1.00 | 52.54 |
| 4268 | O | PRO | E | 495 | 13.268 | 19.412 | 73.982 | 1.00 | 57.19 |
| 4269 | N | ARG | E | 496 | 13.183 | 18.373 | 75.998 | 1.00 | 56.99 |
| 4270 | CA | ARG | E | 496 | 11.749 | 18.573 | 76.206 | 1.00 | 53.45 |
| 4271 | CB | ARG | E | 496 | 10.995 | 17.294 | 75.895 | 1.00 | 41.60 |
| 4272 | CG | ARG | E | 496 | 10.728 | 17.050 | 74.441 | 1.00 | 43.99 |
| 4273 | CD | ARG | E | 496 | 9.670 | 15.973 | 74.335 | 1.00 | 74.29 |
| 4274 | NE | ARG | E | 496 | 8.996 | 15.960 | 73.044 | 1.00 | 89.87 |
| 4275 | CZ | ARG | E | 496 | 7.734 | 15.578 | 72.878 | 1.00 | 81.46 |
| 4276 | NH1 | ARG | E | 496 | 7.016 | 15.184 | 73.929 | 1.00 | 72.94 |
| 4277 | NH2 | ARG | E | 496 | 7.189 | 15.582 | 71.667 | 1.00 | 84.03 |
| 4278 | C | ARG | E | 496 | 11.453 | 18.980 | 77.655 | 1.00 | 72.40 |
| 4279 | O | ARG | E | 496 | 12.184 | 18.593 | 78.581 | 1.00 | 66.36 |
| 4280 | N | LYS | E | 497 | 10.373 | 19.741 | 77.844 | 1.00 | 65.58 |
| 4281 | CA | LYS | E | 497 | 9.969 | 20.205 | 79.168 | 1.00 | 63.66 |
| 4282 | CB | LYS | E | 497 | 8.935 | 21.313 | 79.034 | 1.00 | 65.15 |
| 4283 | CG | LYS | E | 497 | 9.402 | 22.482 | 78.204 | 1.00 | 77.50 |
| 4284 | CD | LYS | E | 497 | 8.260 | 23.439 | 77.940 | 1.00 | 95.02 |
| 4285 | CE | LYS | E | 497 | 8.691 | 24.559 | 77.021 | 1.00 | 100.20 |
| 4286 | NZ | LYS | E | 497 | 7.569 | 25.494 | 76.747 | 1.00 | 106.98 |
| 4287 | C | LYS | E | 497 | 9.386 | 19.082 | 80.014 | 1.00 | 66.52 |
| 4288 | O | LYS | E | 497 | 8.501 | 18.352 | 79.563 | 1.00 | 64.06 |
| 4289 | N | THR | E | 498 | 9.881 | 18.949 | 81.242 | 1.00 | 68.31 |
| 4290 | CA | THR | E | 498 | 9.397 | 17.914 | 82.145 | 1.00 | 77.42 |
| 4291 | CB | THR | E | 498 | 10.375 | 17.691 | 83.305 | 1.00 | 81.74 |
| 4292 | OG1 | THR | E | 498 | 10.470 | 18.887 | 84.086 | 1.00 | 90.07 |
| 4293 | CG2 | THR | E | 498 | 11.754 | 17.347 | 82.774 | 1.00 | 81.13 |
| 4294 | C | THR | E | 498 | 8.054 | 18.339 | 82.718 | 1.00 | 90.19 |
| 4295 | O | THR | E | 498 | 7.011 | 17.825 | 82.327 | 1.00 | 98.06 |
| 4296 | N | LYS | E | 499 | 8.105 | 19.295 | 83.641 | 1.00 | 99.17 |
| 4297 | CA | LYS | E | 499 | 6.933 | 19.847 | 84.319 | 1.00 | 100.76 |
| 4298 | CB | LYS | E | 499 | 6.093 | 18.738 | 84.976 | 1.00 | 90.04 |
| 4299 | CG | LYS | E | 499 | 4.970 | 18.197 | 84.110 | 1.00 | 99.29 |
| 4300 | CD | LYS | E | 499 | 4.021 | 19.318 | 83.709 | 1.00 | 110.70 |
| 4301 | CE | LYS | E | 499 | 2.887 | 18.819 | 82.816 | 1.00 | 109.22 |
| 4302 | NZ | LYS | E | 499 | 1.946 | 19.919 | 82.434 | 1.00 | 97.69 |
| 4303 | C | LYS | E | 499 | 7.418 | 20.817 | 85.391 | 1.00 | 99.99 |
| 4304 | O | LYS | E | 499 | 7.309 | 20.536 | 86.587 | 1.00 | 94.69 |
| 4305 | N | GLY | E | 500 | 7.972 | 21.948 | 84.956 | 1.00 | 103.65 |
| 4306 | CA | GLY | E | 500 | 8.466 | 22.949 | 85.891 | 1.00 | 102.70 |
| 4307 | C | GLY | E | 500 | 9.946 | 22.849 | 86.231 | 1.00 | 103.96 |
| 4308 | O | GLY | E | 500 | 10.696 | 23.819 | 86.079 | 1.00 | 92.57 |
| 4309 | N | SER | E | 501 | 10.366 | 21.672 | 86.689 | 1.00 | 105.10 |
| 4310 | CA | SER | E | 501 | 11.759 | 21.429 | 87.072 | 1.00 | 104.84 |
| 4311 | CB | SER | E | 501 | 11.923 | 19.990 | 87.586 | 1.00 | 106.18 |
| 4312 | OG | SER | E | 501 | 11.634 | 19.042 | 86.570 | 1.00 | 119.93 |
| 4313 | C | SER | E | 501 | 12.773 | 21.687 | 85.953 | 1.00 | 100.73 |
| 4314 | O | SER | E | 501 | 13.956 | 21.917 | 86.224 | 1.00 | 104.05 |
| 4315 | N | GLY | E | 502 | 12.318 | 21.645 | 84.703 | 1.00 | 85.05 |
| 4316 | CA | GLY | E | 502 | 13.225 | 21.879 | 83.595 | 1.00 | 71.99 |
| 4317 | C | GLY | E | 502 | 13.007 | 20.988 | 82.381 | 1.00 | 61.06 |
| 4318 | O | GLY | E | 502 | 11.879 | 20.837 | 81.892 | 1.00 | 57.67 |
| 4319 | N | PHE | E | 503 | 14.093 | 20.394 | 81.889 | 1.00 | 50.08 |
| 4320 | CA | PHE | E | 503 | 14.014 | 19.531 | 80.718 | 1.00 | 47.53 |
| 4321 | CB | PHE | E | 503 | 14.818 | 20.124 | 79.565 | 1.00 | 34.97 |
| 4322 | CG | PHE | E | 503 | 14.478 | 21.532 | 79.248 | 1.00 | 34.14 |
| 4323 | CD1 | PHE | E | 503 | 14.945 | 22.563 | 80.045 | 1.00 | 39.28 |
| 4324 | CD2 | PHE | E | 503 | 13.720 | 21.834 | 78.122 | 1.00 | 35.29 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4325 | CE1 | PHE | E | 503 | 14.667 | 23.903 | 79.724 | 1.00 | 36.80 |
| 4326 | CE2 | PHE | E | 503 | 13.429 | 23.175 | 77.784 | 1.00 | 56.42 |
| 4327 | CZ | PHE | E | 503 | 13.906 | 24.216 | 78.589 | 1.00 | 29.14 |
| 4328 | C | PHE | E | 503 | 14.516 | 18.118 | 80.941 | 1.00 | 45.32 |
| 4329 | O | PHE | E | 503 | 15.113 | 17.786 | 81.972 | 1.00 | 48.17 |
| 4330 | N | PHE | E | 504 | 14.267 | 17.279 | 79.949 | 1.00 | 37.73 |
| 4331 | CA | PHE | E | 504 | 14.749 | 15.913 | 80.013 | 1.00 | 43.12 |
| 4332 | CB | PHE | E | 504 | 13.657 | 14.967 | 80.533 | 1.00 | 43.59 |
| 4333 | CG | PHE | E | 504 | 12.594 | 14.619 | 79.518 | 1.00 | 51.79 |
| 4334 | CD1 | PHE | E | 504 | 12.797 | 13.588 | 78.601 | 1.00 | 42.13 |
| 4335 | CD2 | PHE | E | 504 | 11.376 | 15.292 | 79.512 | 1.00 | 53.61 |
| 4336 | CE1 | PHE | E | 504 | 11.807 | 13.231 | 77.701 | 1.00 | 40.99 |
| 4337 | CE2 | PHE | E | 504 | 10.376 | 14.945 | 78.616 | 1.00 | 49.58 |
| 4338 | CZ | PHE | E | 504 | 10.589 | 13.910 | 77.708 | 1.00 | 58.24 |
| 4339 | C | PHE | E | 504 | 15.206 | 15.515 | 78.622 | 1.00 | 42.95 |
| 4340 | O | PHE | E | 504 | 14.818 | 16.133 | 77.605 | 1.00 | 43.14 |
| 4341 | N | VAL | E | 505 | 16.057 | 14.499 | 78.589 | 1.00 | 39.19 |
| 4342 | CA | VAL | E | 505 | 16.583 | 13.985 | 77.341 | 1.00 | 17.31 |
| 4343 | CB | VAL | E | 505 | 17.906 | 14.706 | 77.003 | 1.00 | 30.78 |
| 4344 | CG1 | VAL | E | 505 | 19.038 | 13.729 | 76.891 | 1.00 | 41.86 |
| 4345 | CG2 | VAL | E | 505 | 17.734 | 15.514 | 75.726 | 1.00 | 39.87 |
| 4346 | C | VAL | E | 505 | 16.774 | 12.484 | 77.496 | 1.00 | 35.36 |
| 4347 | O | VAL | E | 505 | 17.045 | 11.972 | 78.602 | 1.00 | 35.87 |
| 4348 | N | PHE | E | 506 | 16.596 | 11.770 | 76.393 | 1.00 | 31.26 |
| 4349 | CA | PHE | E | 506 | 16.757 | 10.317 | 76.414 | 1.00 | 39.70 |
| 4350 | CB | PHE | E | 506 | 15.414 | 9.648 | 76.029 | 1.00 | 33.27 |
| 4351 | CG | PHE | E | 506 | 15.484 | 8.149 | 75.817 | 1.00 | 89.88 |
| 4352 | CD1 | PHE | E | 506 | 15.761 | 7.289 | 76.876 | 1.00 | 92.06 |
| 4353 | CD2 | PHE | E | 506 | 15.130 | 7.586 | 74.582 | 1.00 | 85.57 |
| 4354 | CE1 | PHE | E | 506 | 15.664 | 5.879 | 76.707 | 1.00 | 99.63 |
| 4355 | CE2 | PHE | E | 506 | 15.031 | 6.192 | 74.411 | 1.00 | 29.95 |
| 4356 | CZ | PHE | E | 506 | 15.292 | 5.337 | 75.471 | 1.00 | 55.21 |
| 4357 | C | PHE | E | 506 | 17.875 | 9.972 | 75.433 | 1.00 | 34.62 |
| 4358 | O | PHE | E | 506 | 18.036 | 10.647 | 74.399 | 1.00 | 46.36 |
| 4359 | N | SER | E | 507 | 18.660 | 8.955 | 75.773 | 1.00 | 27.86 |
| 4360 | CA | SER | E | 507 | 19.728 | 8.528 | 74.886 | 1.00 | 34.24 |
| 4361 | CB | SER | E | 507 | 21.093 | 9.019 | 75.383 | 1.00 | 49.31 |
| 4362 | OG | SER | E | 507 | 22.118 | 8.718 | 74.441 | 1.00 | 32.85 |
| 4363 | C | SER | E | 507 | 19.758 | 7.021 | 74.713 | 1.00 | 36.50 |
| 4364 | O | SER | E | 507 | 19.691 | 6.248 | 75.690 | 1.00 | 35.74 |
| 4365 | N | ARG | E | 508 | 19.878 | 6.613 | 73.451 | 1.00 | 32.83 |
| 4366 | CA | ARG | E | 508 | 19.908 | 5.192 | 73.107 | 1.00 | 33.40 |
| 4367 | CB | ARG | E | 508 | 18.795 | 4.923 | 72.079 | 1.00 | 25.02 |
| 4368 | CG | ARG | E | 508 | 18.584 | 3.469 | 71.745 | 1.00 | 23.75 |
| 4369 | CD | ARG | E | 508 | 17.330 | 3.310 | 70.917 | 1.00 | 48.60 |
| 4370 | NE | ARG | E | 508 | 17.244 | 1.980 | 70.342 | 1.00 | 44.99 |
| 4371 | CZ | ARG | E | 508 | 17.978 | 1.586 | 69.315 | 1.00 | 49.83 |
| 4372 | NH1 | ARG | E | 508 | 18.832 | 2.441 | 68.758 | 1.00 | 46.73 |
| 4373 | NH2 | ARG | E | 508 | 17.882 | 0.335 | 68.874 | 1.00 | 56.48 |
| 4374 | C | ARG | E | 508 | 21.276 | 4.713 | 72.581 | 1.00 | 33.17 |
| 4375 | O | ARG | E | 508 | 21.944 | 5.399 | 71.790 | 1.00 | 32.30 |
| 4376 | N | LEU | E | 509 | 21.696 | 3.542 | 73.046 | 1.00 | 30.22 |
| 4377 | CA | LEU | E | 509 | 22.966 | 2.967 | 72.607 | 1.00 | 19.42 |
| 4378 | CB | LEU | E | 509 | 24.091 | 3.275 | 73.600 | 1.00 | 35.69 |
| 4379 | CG | LEU | E | 509 | 25.418 | 2.600 | 73.214 | 1.00 | 29.46 |
| 4380 | CD1 | LEU | E | 509 | 26.052 | 3.399 | 72.063 | 1.00 | 33.95 |
| 4381 | CD2 | LEU | E | 509 | 26.363 | 2.547 | 74.400 | 1.00 | 32.04 |
| 4382 | C | LEU | E | 509 | 22.868 | 1.452 | 72.464 | 1.00 | 37.54 |
| 4383 | O | LEU | E | 509 | 22.694 | 0.758 | 73.468 | 1.00 | 35.15 |
| 4384 | N | GLU | E | 510 | 22.975 | 0.950 | 71.222 | 1.00 | 44.66 |
| 4385 | CA | GLU | E | 510 | 22.935 | −0.501 | 70.955 | 1.00 | 35.02 |
| 4386 | CB | GLU | E | 510 | 22.498 | −0.779 | 69.518 | 1.00 | 58.37 |
| 4387 | CG | GLU | E | 510 | 21.419 | 0.153 | 68.957 | 1.00 | 82.86 |
| 4388 | CD | GLU | E | 510 | 20.974 | −0.245 | 67.548 | 1.00 | 84.20 |
| 4389 | OE1 | GLU | E | 510 | 20.238 | 0.536 | 66.903 | 1.00 | 81.25 |
| 4390 | OE2 | GLU | E | 510 | 21.359 | −1.344 | 67.092 | 1.00 | 83.06 |
| 4391 | C | GLU | E | 510 | 24.358 | −1.060 | 71.171 | 1.00 | 38.20 |
| 4392 | O | GLU | E | 510 | 25.325 | −0.547 | 70.640 | 1.00 | 37.55 |
| 4393 | N | VAL | E | 511 | 24.486 | −2.105 | 71.968 | 1.00 | 30.07 |
| 4394 | CA | VAL | E | 511 | 25.800 | −2.674 | 72.246 | 1.00 | 41.21 |
| 4395 | CB | VAL | E | 511 | 26.194 | −2.483 | 73.755 | 1.00 | 45.51 |
| 4396 | CG1 | VAL | E | 511 | 26.172 | −0.984 | 74.103 | 1.00 | 33.88 |
| 4397 | CG2 | VAL | E | 511 | 25.259 | −3.250 | 74.660 | 1.00 | 24.76 |
| 4398 | C | VAL | E | 511 | 25.855 | −4.147 | 71.856 | 1.00 | 46.67 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4399 | O | VAL | E | 511 | 24.812 | −4.789 | 71.769 | 1.00 | 46.28 |
| 4400 | N | THR | E | 512 | 27.064 | −4.679 | 71.638 | 1.00 | 54.85 |
| 4401 | CA | THR | E | 512 | 27.242 | −6.069 | 71.170 | 1.00 | 51.47 |
| 4402 | CB | THR | E | 512 | 28.112 | −6.129 | 69.903 | 1.00 | 35.15 |
| 4403 | OG1 | THR | E | 512 | 29.456 | −5.798 | 70.240 | 1.00 | 50.20 |
| 4404 | CG2 | THR | E | 512 | 27.612 | −5.138 | 68.851 | 1.00 | 58.57 |
| 4405 | C | THR | E | 512 | 27.832 | −7.089 | 72.117 | 1.00 | 50.33 |
| 4406 | O | THR | E | 512 | 28.677 | −6.767 | 72.944 | 1.00 | 50.11 |
| 4407 | N | ARG | E | 513 | 27.385 | −8.332 | 71.949 | 1.00 | 55.00 |
| 4408 | CA | ARG | E | 513 | 27.819 | −9.471 | 72.757 | 1.00 | 58.41 |
| 4409 | CB | ARG | E | 513 | 27.676 | −10.771 | 71.966 | 1.00 | 72.12 |
| 4410 | CG | ARG | E | 513 | 26.850 | −11.858 | 72.640 | 1.00 | 87.83 |
| 4411 | CD | ARG | E | 513 | 27.499 | −12.380 | 73.912 | 1.00 | 86.39 |
| 4412 | NE | ARG | E | 513 | 26.559 | −13.186 | 74.686 | 1.00 | 90.11 |
| 4413 | CZ | ARG | E | 513 | 26.798 | −13.642 | 75.911 | 1.00 | 98.08 |
| 4414 | NH1 | ARG | E | 513 | 27.952 | −13.378 | 76.513 | 1.00 | 98.66 |
| 4415 | NH2 | ARG | E | 513 | 25.873 | −14.349 | 76.545 | 1.00 | 95.42 |
| 4416 | C | ARG | E | 513 | 29.259 | −9.350 | 73.207 | 1.00 | 69.16 |
| 4417 | O | ARG | E | 513 | 29.564 | −9.583 | 74.377 | 1.00 | 70.22 |
| 4418 | N | ALA | E | 514 | 30.142 | −8.999 | 72.268 | 1.00 | 71.12 |
| 4419 | CA | ALA | E | 514 | 31.571 | −8.850 | 72.540 | 1.00 | 67.18 |
| 4420 | CB | ALA | E | 514 | 32.222 | −8.031 | 71.441 | 1.00 | 58.78 |
| 4421 | C | ALA | E | 514 | 31.829 | −8.209 | 73.905 | 1.00 | 81.88 |
| 4422 | O | ALA | E | 514 | 32.023 | −8.922 | 74.895 | 1.00 | 84.05 |
| 4423 | N | GLU | E | 515 | 31.824 | −6.876 | 73.963 | 1.00 | 77.75 |
| 4424 | CA | GLU | E | 515 | 32.055 | −6.181 | 75.225 | 1.00 | 58.12 |
| 4425 | CB | GLU | E | 515 | 32.225 | −4.689 | 75.004 | 1.00 | 43.33 |
| 4426 | CG | GLU | E | 515 | 31.033 | −4.021 | 74.349 | 1.00 | 68.00 |
| 4427 | CD | GLU | E | 515 | 31.129 | −4.034 | 72.841 | 1.00 | 74.49 |
| 4428 | OE1 | GLU | E | 515 | 31.453 | −5.111 | 72.299 | 1.00 | 61.84 |
| 4429 | OE2 | GLU | E | 515 | 30.880 | −2.978 | 72.206 | 1.00 | 62.77 |
| 4430 | C | GLU | E | 515 | 30.884 | −6.414 | 76.163 | 1.00 | 61.91 |
| 4431 | O | GLU | E | 515 | 31.020 | −6.286 | 77.379 | 1.00 | 60.19 |
| 4432 | N | TRP | E | 516 | 29.734 | −6.749 | 75.579 | 1.00 | 74.15 |
| 4433 | CA | TRP | E | 516 | 28.492 | −7.042 | 76.309 | 1.00 | 81.65 |
| 4434 | CB | TRP | E | 516 | 27.409 | −7.449 | 75.299 | 1.00 | 91.26 |
| 4435 | CG | TRP | E | 516 | 26.036 | −7.634 | 75.861 | 1.00 | 113.50 |
| 4436 | CD2 | TRP | E | 516 | 25.135 | −8.718 | 75.597 | 1.00 | 120.21 |
| 4437 | CE2 | TRP | E | 516 | 23.939 | −8.450 | 76.307 | 1.00 | 132.76 |
| 4438 | CE3 | TRP | E | 516 | 25.220 | −9.886 | 74.829 | 1.00 | 115.67 |
| 4439 | CD1 | TRP | E | 516 | 25.372 | −6.780 | 76.695 | 1.00 | 124.78 |
| 4440 | NE1 | TRP | E | 516 | 24.112 | −7.262 | 76.969 | 1.00 | 123.74 |
| 4441 | CZ2 | TRP | E | 516 | 22.829 | −9.315 | 76.271 | 1.00 | 128.75 |
| 4442 | CZ3 | TRP | E | 516 | 24.115 | −10.749 | 74.792 | 1.00 | 128.47 |
| 4443 | CH2 | TRP | E | 516 | 22.936 | −10.455 | 75.510 | 1.00 | 127.51 |
| 4444 | C | TRP | E | 516 | 28.750 | −8.186 | 77.300 | 1.00 | 90.65 |
| 4445 | O | TRP | E | 516 | 27.831 | −8.948 | 77.670 | 1.00 | 59.15 |
| 4446 | N | GLU | E | 517 | 30.022 | −8.290 | 77.693 | 1.00 | 85.03 |
| 4447 | CA | GLU | E | 517 | 30.521 | −9.290 | 78.620 | 1.00 | 93.43 |
| 4448 | CB | GLU | E | 517 | 31.302 | −10.361 | 77.851 | 1.00 | 93.55 |
| 4449 | CG | GLU | E | 517 | 30.414 | −11.122 | 76.885 | 1.00 | 108.99 |
| 4450 | CD | GLU | E | 517 | 31.066 | −12.353 | 76.306 | 1.00 | 113.98 |
| 4451 | OE1 | GLU | E | 517 | 32.034 | −12.201 | 75.535 | 1.00 | 118.04 |
| 4452 | OE2 | GLU | E | 517 | 30.605 | −13.473 | 76.622 | 1.00 | 110.67 |
| 4453 | C | GLU | E | 517 | 31.397 | −8.625 | 79.680 | 1.00 | 91.01 |
| 4454 | O | GLU | E | 517 | 31.823 | −9.270 | 80.628 | 1.00 | 88.18 |
| 4455 | N | ALA | E | 518 | 31.658 | −7.331 | 79.501 | 1.00 | 90.02 |
| 4456 | CA | ALA | E | 518 | 32.451 | −6.509 | 80.429 | 1.00 | 83.16 |
| 4457 | CB | ALA | E | 518 | 33.855 | −6.215 | 79.847 | 1.00 | 82.40 |
| 4458 | C | ALA | E | 518 | 31.630 | −5.231 | 80.501 | 1.00 | 78.98 |
| 4459 | O | ALA | E | 518 | 32.067 | −4.166 | 80.037 | 1.00 | 53.87 |
| 4460 | N | LYS | E | 519 | 30.429 | −5.359 | 81.068 | 1.00 | 79.26 |
| 4461 | CA | LYS | E | 519 | 29.486 | −4.247 | 81.157 | 1.00 | 82.30 |
| 4462 | CB | LYS | E | 519 | 28.075 | −4.741 | 81.493 | 1.00 | 83.13 |
| 4463 | CG | LYS | E | 519 | 27.368 | −5.500 | 80.377 | 1.00 | 93.68 |
| 4464 | CD | LYS | E | 519 | 25.851 | −5.349 | 80.503 | 1.00 | 96.92 |
| 4465 | CE | LYS | E | 519 | 25.096 | −6.450 | 79.782 | 1.00 | 85.56 |
| 4466 | NZ | LYS | E | 519 | 23.713 | −6.540 | 80.277 | 1.00 | 74.60 |
| 4467 | C | LYS | E | 519 | 29.827 | −3.138 | 82.113 | 1.00 | 76.64 |
| 4468 | O | LYS | E | 519 | 29.764 | −1.962 | 81.745 | 1.00 | 66.97 |
| 4469 | N | ASP | E | 520 | 30.150 | −3.516 | 83.345 | 1.00 | 64.80 |
| 4470 | CA | ASP | E | 520 | 30.504 | −2.560 | 84.399 | 1.00 | 93.47 |
| 4471 | CB | ASP | E | 520 | 31.482 | −3.220 | 85.388 | 1.00 | 97.06 |
| 4472 | CG | ASP | E | 520 | 30.913 | −4.492 | 86.016 | 1.00 | 107.65 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4473 | OD1 | ASP | E | 520 | 29.962 | −4.388 | 86.822 | 1.00 | 114.86 |
| 4474 | OD2 | ASP | E | 520 | 31.410 | −5.596 | 85.696 | 1.00 | 106.97 |
| 4475 | C | ASP | E | 520 | 31.121 | −1.280 | 83.813 | 1.00 | 89.53 |
| 4476 | O | ASP | E | 520 | 31.192 | −0.233 | 84.484 | 1.00 | 62.63 |
| 4477 | N | GLU | E | 521 | 31.560 | −1.392 | 82.557 | 1.00 | 81.63 |
| 4478 | CA | GLU | E | 521 | 32.162 | −0.301 | 81.815 | 1.00 | 87.91 |
| 4479 | CB | GLU | E | 521 | 33.406 | −0.787 | 81.043 | 1.00 | 91.51 |
| 4480 | CG | GLU | E | 521 | 34.688 | −1.008 | 81.887 | 1.00 | 88.25 |
| 4481 | CD | GLU | E | 521 | 34.902 | −2.459 | 82.338 | 1.00 | 89.47 |
| 4482 | OE1 | GLU | E | 521 | 34.846 | −3.377 | 81.483 | 1.00 | 81.63 |
| 4483 | OE2 | GLU | E | 521 | 35.142 | −2.672 | 83.547 | 1.00 | 74.83 |
| 4484 | C | GLU | E | 521 | 31.183 | 0.359 | 80.842 | 1.00 | 80.63 |
| 4485 | O | GLU | E | 521 | 31.570 | 0.733 | 79.739 | 1.00 | 102.84 |
| 4486 | N | PHE | E | 522 | 29.918 | 0.492 | 81.224 | 1.00 | 57.90 |
| 4487 | CA | PHE | E | 522 | 28.966 | 1.178 | 80.349 | 1.00 | 47.86 |
| 4488 | CB | PHE | E | 522 | 27.792 | 0.273 | 79.986 | 1.00 | 55.93 |
| 4489 | CG | PHE | E | 522 | 28.095 | −0.635 | 78.837 | 1.00 | 63.10 |
| 4490 | CD1 | PHE | E | 522 | 28.118 | −2.013 | 79.001 | 1.00 | 38.64 |
| 4491 | CD2 | PHE | E | 522 | 28.460 | −0.103 | 77.602 | 1.00 | 50.98 |
| 4492 | CE1 | PHE | E | 522 | 28.515 | −2.851 | 77.957 | 1.00 | 42.78 |
| 4493 | CE2 | PHE | E | 522 | 28.857 | −0.935 | 76.555 | 1.00 | 39.68 |
| 4494 | CZ | PHE | E | 522 | 28.886 | −2.310 | 76.739 | 1.00 | 46.63 |
| 4495 | C | PHE | E | 522 | 28.507 | 2.436 | 81.043 | 1.00 | 45.74 |
| 4496 | O | PHE | E | 522 | 27.682 | 2.403 | 81.960 | 1.00 | 39.55 |
| 4497 | N | ILE | E | 523 | 29.049 | 3.554 | 80.584 | 1.00 | 34.87 |
| 4498 | CA | ILE | E | 523 | 28.756 | 4.824 | 81.203 | 1.00 | 26.43 |
| 4499 | CB | ILE | E | 523 | 30.077 | 5.476 | 81.773 | 1.00 | 44.50 |
| 4500 | CG2 | ILE | E | 523 | 29.804 | 6.895 | 82.310 | 1.00 | 45.76 |
| 4501 | CG1 | ILE | E | 523 | 30.674 | 4.600 | 82.870 | 1.00 | 41.53 |
| 4502 | CD1 | ILE | E | 523 | 31.873 | 5.243 | 83.567 | 1.00 | 31.16 |
| 4503 | C | ILE | E | 523 | 28.058 | 5.863 | 80.359 | 1.00 | 31.35 |
| 4504 | O | ILE | E | 523 | 28.475 | 6.162 | 79.238 | 1.00 | 37.86 |
| 4505 | N | CYS | E | 524 | 27.008 | 6.432 | 80.934 | 1.00 | 38.24 |
| 4506 | CA | CYS | E | 524 | 26.268 | 7.493 | 80.286 | 1.00 | 30.98 |
| 4507 | C | CYS | E | 524 | 26.668 | 8.733 | 81.071 | 1.00 | 41.53 |
| 4508 | O | CYS | E | 524 | 26.420 | 8.818 | 82.287 | 1.00 | 44.75 |
| 4509 | CB | CYS | E | 524 | 24.756 | 7.251 | 80.395 | 1.00 | 35.40 |
| 4510 | SG | CYS | E | 524 | 23.735 | 8.654 | 79.846 | 1.00 | 58.55 |
| 4511 | N | ARG | E | 525 | 27.293 | 9.682 | 80.376 | 1.00 | 36.10 |
| 4512 | CA | ARG | E | 525 | 27.746 | 10.906 | 81.000 | 1.00 | 17.42 |
| 4513 | CB | ARG | E | 525 | 29.263 | 10.966 | 80.946 | 1.00 | 41.29 |
| 4514 | CG | ARG | E | 525 | 29.868 | 12.135 | 81.701 | 1.00 | 52.26 |
| 4515 | CD | ARG | E | 525 | 31.368 | 11.976 | 81.815 | 1.00 | 43.59 |
| 4516 | NE | ARG | E | 525 | 32.042 | 12.278 | 80.556 | 1.00 | 70.40 |
| 4517 | CZ | ARG | E | 525 | 33.300 | 11.945 | 80.296 | 1.00 | 74.49 |
| 4518 | NH1 | ARG | E | 525 | 34.004 | 11.295 | 81.209 | 1.00 | 57.09 |
| 4519 | NH2 | ARG | E | 525 | 33.850 | 12.270 | 79.135 | 1.00 | 71.68 |
| 4520 | C | ARG | E | 525 | 27.170 | 12.128 | 80.334 | 1.00 | 34.31 |
| 4521 | O | ARG | E | 525 | 27.159 | 12.252 | 79.094 | 1.00 | 39.93 |
| 4522 | N | ALA | E | 526 | 26.707 | 13.053 | 81.166 | 1.00 | 32.64 |
| 4523 | CA | ALA | E | 526 | 26.113 | 14.282 | 80.660 | 1.00 | 29.56 |
| 4524 | CB | ALA | E | 526 | 24.692 | 14.490 | 81.256 | 1.00 | 29.22 |
| 4525 | C | ALA | E | 526 | 26.990 | 15.441 | 81.018 | 1.00 | 43.42 |
| 4526 | O | ALA | E | 526 | 27.593 | 15.464 | 82.095 | 1.00 | 43.12 |
| 4527 | N | VAL | E | 527 | 27.062 | 16.401 | 80.102 | 1.00 | 34.08 |
| 4528 | CA | VAL | E | 527 | 27.857 | 17.605 | 80.319 | 1.00 | 36.48 |
| 4529 | CB | VAL | E | 527 | 28.873 | 17.806 | 79.191 | 1.00 | 48.29 |
| 4530 | CG1 | VAL | E | 527 | 29.626 | 19.118 | 79.392 | 1.00 | 47.05 |
| 4531 | CG2 | VAL | E | 527 | 29.860 | 16.640 | 79.192 | 1.00 | 42.41 |
| 4532 | C | VAL | E | 527 | 26.903 | 18.773 | 80.349 | 1.00 | 35.92 |
| 4533 | O | VAL | E | 527 | 26.244 | 19.082 | 79.343 | 1.00 | 46.95 |
| 4534 | N | HIS | E | 528 | 26.820 | 19.419 | 81.501 | 1.00 | 31.45 |
| 4535 | CA | HIS | E | 528 | 25.897 | 20.537 | 81.669 | 1.00 | 38.60 |
| 4536 | CB | HIS | E | 528 | 24.559 | 20.015 | 82.242 | 1.00 | 34.52 |
| 4537 | CG | HIS | E | 528 | 23.490 | 21.059 | 82.331 | 1.00 | 43.46 |
| 4538 | CD2 | HIS | E | 528 | 22.547 | 21.432 | 81.433 | 1.00 | 41.04 |
| 4539 | ND1 | HIS | E | 528 | 23.336 | 21.897 | 83.420 | 1.00 | 26.66 |
| 4540 | CE1 | HIS | E | 528 | 22.344 | 22.741 | 83.182 | 1.00 | 50.17 |
| 4541 | NE2 | HIS | E | 528 | 21.849 | 22.481 | 81.985 | 1.00 | 38.19 |
| 4542 | C | HIS | E | 528 | 26.469 | 21.630 | 82.572 | 1.00 | 41.96 |
| 4543 | O | HIS | E | 528 | 27.099 | 21.352 | 83.610 | 1.00 | 35.50 |
| 4544 | N | GLU | E | 529 | 26.223 | 22.872 | 82.161 | 1.00 | 46.37 |
| 4545 | CA | GLU | E | 529 | 26.694 | 24.057 | 82.876 | 1.00 | 47.44 |
| 4546 | CB | GLU | E | 529 | 26.072 | 25.301 | 82.253 | 1.00 | 46.28 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4547 | CG | GLU | E | 529 | 26.255 | 26.553 | 83.082 | 1.00 | 73.93 |
| 4548 | CD | GLU | E | 529 | 25.526 | 27.732 | 82.483 | 1.00 | 93.10 |
| 4549 | OE1 | GLU | E | 529 | 25.523 | 28.816 | 83.123 | 1.00 | 77.52 |
| 4550 | OE2 | GLU | E | 529 | 24.960 | 27.564 | 81.371 | 1.00 | 84.49 |
| 4551 | C | GLU | E | 529 | 26.442 | 24.093 | 84.381 | 1.00 | 52.66 |
| 4552 | O | GLU | E | 529 | 27.197 | 24.731 | 85.112 | 1.00 | 59.16 |
| 4553 | N | ALA | E | 530 | 25.391 | 23.415 | 84.844 | 1.00 | 56.37 |
| 4554 | CA | ALA | E | 530 | 25.043 | 23.412 | 86.270 | 1.00 | 52.95 |
| 4555 | CB | ALA | E | 530 | 23.536 | 23.611 | 86.421 | 1.00 | 43.40 |
| 4556 | C | ALA | E | 530 | 25.488 | 22.184 | 87.088 | 1.00 | 59.93 |
| 4557 | O | ALA | E | 530 | 25.345 | 22.163 | 88.313 | 1.00 | 50.82 |
| 4558 | N | ALA | E | 531 | 26.038 | 21.170 | 86.429 | 1.00 | 65.39 |
| 4559 | CA | ALA | E | 531 | 26.469 | 19.971 | 87.144 | 1.00 | 63.57 |
| 4560 | CB | ALA | E | 531 | 26.831 | 18.879 | 86.141 | 1.00 | 54.93 |
| 4561 | C | ALA | E | 531 | 27.646 | 20.246 | 88.074 | 1.00 | 69.76 |
| 4562 | O | ALA | E | 531 | 28.094 | 19.354 | 88.800 | 1.00 | 77.13 |
| 4563 | N | SER | E | 532 | 28.135 | 21.486 | 88.047 | 1.00 | 81.02 |
| 4564 | CA | SER | E | 532 | 29.272 | 21.910 | 88.874 | 1.00 | 97.10 |
| 4565 | CB | SER | E | 532 | 29.198 | 23.424 | 89.143 | 1.00 | 102.37 |
| 4566 | OG | SER | E | 532 | 27.997 | 23.785 | 89.808 | 1.00 | 100.11 |
| 4567 | C | SER | E | 532 | 29.402 | 21.155 | 90.205 | 1.00 | 90.56 |
| 4568 | O | SER | E | 532 | 28.411 | 20.877 | 90.879 | 1.00 | 91.17 |
| 4569 | N | PRO | E | 533 | 30.640 | 20.799 | 90.586 | 1.00 | 90.67 |
| 4570 | CD | PRO | E | 533 | 30.930 | 19.992 | 91.788 | 1.00 | 93.78 |
| 4571 | CA | PRO | E | 533 | 31.874 | 21.072 | 89.837 | 1.00 | 84.98 |
| 4572 | CB | PRO | E | 533 | 32.959 | 20.761 | 90.859 | 1.00 | 84.56 |
| 4573 | CG | PRO | E | 533 | 32.377 | 19.563 | 91.556 | 1.00 | 86.67 |
| 4574 | C | PRO | E | 533 | 31.975 | 20.160 | 88.622 | 1.00 | 82.84 |
| 4575 | O | PRO | E | 533 | 31.018 | 19.476 | 88.276 | 1.00 | 94.80 |
| 4576 | N | SER | E | 534 | 33.141 | 20.148 | 87.990 | 1.00 | 70.50 |
| 4577 | CA | SER | E | 534 | 33.400 | 19.307 | 86.819 | 1.00 | 66.68 |
| 4578 | CB | SER | E | 534 | 33.404 | 17.820 | 87.222 | 1.00 | 62.81 |
| 4579 | OG | SER | E | 534 | 32.160 | 17.410 | 87.763 | 1.00 | 61.86 |
| 4580 | C | SER | E | 534 | 32.456 | 19.515 | 85.627 | 1.00 | 52.56 |
| 4581 | O | SER | E | 534 | 32.818 | 19.237 | 84.487 | 1.00 | 59.46 |
| 4582 | N | GLN | E | 535 | 31.253 | 20.007 | 85.882 | 1.00 | 49.35 |
| 4583 | CA | GLN | E | 535 | 30.273 | 20.243 | 84.821 | 1.00 | 44.87 |
| 4584 | CB | GLN | E | 535 | 30.842 | 21.172 | 83.729 | 1.00 | 49.53 |
| 4585 | CG | GLN | E | 535 | 31.872 | 22.209 | 84.224 | 1.00 | 55.02 |
| 4586 | CD | GLN | E | 535 | 31.401 | 23.030 | 85.430 | 1.00 | 60.01 |
| 4587 | OE1 | GLN | E | 535 | 32.220 | 23.553 | 86.189 | 1.00 | 62.85 |
| 4588 | NE2 | GLN | E | 535 | 30.084 | 23.150 | 85.605 | 1.00 | 73.20 |
| 4589 | C | GLN | E | 535 | 29.802 | 18.944 | 84.178 | 1.00 | 48.32 |
| 4590 | O | GLN | E | 535 | 29.408 | 18.928 | 83.013 | 1.00 | 51.60 |
| 4591 | N | THR | E | 536 | 29.847 | 17.847 | 84.927 | 1.00 | 44.42 |
| 4592 | CA | THR | E | 536 | 29.374 | 16.581 | 84.380 | 1.00 | 49.02 |
| 4593 | CB | THR | E | 536 | 30.527 | 15.774 | 83.724 | 1.00 | 58.07 |
| 4594 | CG1 | THR | E | 536 | 31.414 | 15.294 | 84.742 | 1.00 | 50.57 |
| 4595 | CG2 | THR | E | 536 | 31.302 | 16.641 | 82.733 | 1.00 | 56.97 |
| 4596 | C | THR | E | 536 | 28.712 | 15.680 | 85.419 | 1.00 | 52.08 |
| 4597 | O | THR | E | 536 | 29.000 | 15.760 | 86.623 | 1.00 | 50.49 |
| 4598 | N | VAL | E | 537 | 27.811 | 14.828 | 84.940 | 1.00 | 32.07 |
| 4599 | CA | VAL | E | 537 | 27.141 | 13.859 | 85.800 | 1.00 | 35.66 |
| 4600 | CB | VAL | E | 537 | 25.687 | 14.255 | 86.117 | 1.00 | 44.02 |
| 4601 | CG1 | VAL | E | 537 | 25.245 | 13.597 | 87.440 | 1.00 | 33.99 |
| 4602 | CG2 | VAL | E | 537 | 25.565 | 15.744 | 86.215 | 1.00 | 38.82 |
| 4603 | C | VAL | E | 537 | 27.148 | 12.563 | 84.998 | 1.00 | 35.23 |
| 4604 | O | VAL | E | 537 | 27.087 | 12.607 | 83.770 | 1.00 | 44.41 |
| 4605 | N | GLN | E | 538 | 27.226 | 11.420 | 85.672 | 1.00 | 20.30 |
| 4606 | CA | GLN | E | 538 | 27.290 | 10.172 | 84.946 | 1.00 | 32.08 |
| 4607 | CB | GLN | E | 538 | 28.726 | 9.939 | 84.461 | 1.00 | 34.72 |
| 4608 | CG | GLN | E | 538 | 29.682 | 9.538 | 85.582 | 1.00 | 23.12 |
| 4609 | CD | GLN | E | 538 | 31.074 | 9.284 | 85.096 | 1.00 | 49.35 |
| 4610 | OE1 | GLN | E | 538 | 31.677 | 10.134 | 84.421 | 1.00 | 40.70 |
| 4611 | NE2 | GLN | E | 538 | 31.606 | 8.110 | 85.435 | 1.00 | 19.64 |
| 4612 | C | GLN | E | 538 | 26.843 | 8.963 | 85.757 | 1.00 | 35.23 |
| 4513 | O | GLN | E | 538 | 26.979 | 8.918 | 86.971 | 1.00 | 36.60 |
| 4614 | N | ARG | E | 539 | 26.323 | 7.962 | 85.062 | 1.00 | 38.64 |
| 4615 | CA | ARG | E | 539 | 25.871 | 6.756 | 85.733 | 1.00 | 39.58 |
| 4616 | CB | ARG | E | 539 | 24.339 | 6.750 | 85.833 | 1.00 | 43.24 |
| 4617 | CG | ARG | E | 539 | 23.812 | 6.028 | 87.067 | 1.00 | 65.76 |
| 4618 | CD | ARG | E | 539 | 23.270 | 7.022 | 88.095 | 1.00 | 98.87 |
| 4619 | NE | ARG | E | 539 | 24.253 | 8.032 | 88.492 | 1.00 | 109.71 |
| 4620 | CZ | ARG | E | 539 | 24.002 | 9.032 | 89.336 | 1.00 | 105.93 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4621 | NH1 | ARG | E | 539 | 22.797 | 9.163 | 89.877 | 1.00 | 115.82 |
| 4622 | NH2 | ARG | E | 539 | 24.952 | 9.906 | 89.639 | 1.00 | 99.73 |
| 4623 | C | ARG | E | 539 | 26.353 | 5.561 | 84.921 | 1.00 | 34.24 |
| 4624 | O | ARG | E | 539 | 26.445 | 5.631 | 83.703 | 1.00 | 41.60 |
| 4625 | N | ALA | E | 540 | 26.668 | 4.479 | 85.619 | 1.00 | 29.34 |
| 4626 | CA | ALA | E | 540 | 27.154 | 3.254 | 85.016 | 1.00 | 31.29 |
| 4627 | CB | ALA | E | 540 | 28.250 | 2.689 | 85.859 | 1.00 | 17.94 |
| 4628 | C | ALA | E | 540 | 26.025 | 2.249 | 84.924 | 1.00 | 44.04 |
| 4629 | O | ALA | E | 540 | 25.153 | 2.235 | 85.785 | 1.00 | 41.99 |
| 4630 | N | VAL | E | 541 | 26.041 | 1.415 | 83.883 | 1.00 | 49.43 |
| 4631 | CA | VAL | E | 541 | 25.015 | 0.387 | 83.704 | 1.00 | 44.17 |
| 4632 | CB | VAL | E | 541 | 24.249 | 0.540 | 82.394 | 1.00 | 49.06 |
| 4633 | CG1 | VAL | E | 541 | 22.830 | 0.066 | 82.596 | 1.00 | 35.97 |
| 4634 | CG2 | VAL | E | 541 | 24.308 | 1.971 | 81.897 | 1.00 | 56.84 |
| 4635 | C | VAL | E | 541 | 25.688 | −0.971 | 83.664 | 1.00 | 64.94 |
| 4636 | O | VAL | E | 541 | 26.611 | −1.199 | 82.880 | 1.00 | 42.16 |
| 4637 | N | SER | E | 542 | 25.176 | −1.873 | 84.490 | 1.00 | 78.20 |
| 4638 | CA | SER | E | 542 | 25.702 | −3.223 | 84.662 | 1.00 | 92.22 |
| 4639 | CB | SER | E | 542 | 25.281 | −3.715 | 86.046 | 1.00 | 97.33 |
| 4640 | OG | SER | E | 542 | 23.930 | −3.350 | 86.306 | 1.00 | 89.47 |
| 4641 | C | SER | E | 542 | 25.358 | −4.299 | 83.631 | 1.00 | 93.37 |
| 4642 | O | SER | E | 542 | 24.707 | −4.045 | 82.616 | 1.00 | 73.53 |
| 4643 | N | VAL | E | 543 | 25.809 | −5.517 | 83.943 | 1.00 | 112.08 |
| 4644 | CA | VAL | E | 543 | 25.606 | −6.711 | 83.120 | 1.00 | 111.79 |
| 4645 | CB | VAL | E | 543 | 26.613 | −7.840 | 83.496 | 1.00 | 113.96 |
| 4646 | CG1 | VAL | E | 543 | 26.310 | −9.102 | 82.685 | 1.00 | 111.10 |
| 4647 | CG2 | VAL | E | 543 | 28.048 | −7.377 | 83.239 | 1.00 | 105.95 |
| 4648 | C | VAL | E | 543 | 24.192 | −7.268 | 83.231 | 1.00 | 100.43 |
| 4649 | O | VAL | E | 543 | 23.979 | −8.200 | 84.042 | 1.00 | 90.69 |
| 4650 | OXT | VAL | E | 543 | 23.320 | −6.751 | 82.505 | 1.00 | 87.87 |
| 4651 | CB | VAL | F | 336 | 2.666 | 28.593 | 49.373 | 1.00 | 96.54 |
| 4652 | CG1 | VAL | F | 336 | 1.420 | 27.919 | 48.814 | 1.00 | 87.82 |
| 4653 | CG2 | VAL | F | 336 | 2.434 | 30.076 | 49.609 | 1.00 | 101.01 |
| 4654 | C | VAL | F | 336 | 3.328 | 26.435 | 50.432 | 1.00 | 103.40 |
| 4655 | O | VAL | F | 336 | 3.728 | 26.035 | 49.338 | 1.00 | 93.36 |
| 4656 | N | VAL | F | 336 | 4.295 | 28.585 | 51.260 | 1.00 | 100.07 |
| 4657 | CA | VAL | F | 336 | 3.083 | 27.924 | 50.692 | 1.00 | 101.23 |
| 4658 | N | SER | F | 337 | 3.078 | 25.618 | 51.449 | 1.00 | 99.30 |
| 4659 | CA | SER | F | 337 | 3.272 | 24.176 | 51.351 | 1.00 | 99.56 |
| 4660 | CB | SER | F | 337 | 4.486 | 23.759 | 52.184 | 1.00 | 99.88 |
| 4661 | OG | SER | F | 337 | 4.338 | 24.171 | 53.534 | 1.00 | 109.00 |
| 4662 | C | SER | F | 337 | 2.027 | 23.442 | 51.846 | 1.00 | 97.02 |
| 4663 | O | SER | F | 337 | 1.155 | 24.046 | 52.460 | 1.00 | 92.82 |
| 4664 | N | ALA | F | 338 | 1.949 | 22.140 | 51.580 | 1.00 | 102.48 |
| 4665 | CA | ALA | F | 338 | 0.797 | 21.344 | 52.001 | 1.00 | 94.90 |
| 4666 | CB | ALA | F | 338 | −0.229 | 21.275 | 50.865 | 1.00 | 94.69 |
| 4667 | C | ALA | F | 338 | 1.192 | 19.933 | 52.443 | 1.00 | 80.81 |
| 4668 | O | ALA | F | 338 | 1.857 | 19.202 | 51.711 | 1.00 | 77.43 |
| 4669 | N | TYR | F | 339 | 0.769 | 19.565 | 53.649 | 1.00 | 85.80 |
| 4670 | CA | TYR | F | 339 | 1.050 | 18.252 | 54.229 | 1.00 | 77.97 |
| 4671 | CB | TYR | F | 339 | 1.759 | 18.389 | 55.576 | 1.00 | 84.04 |
| 4672 | CG | TYR | F | 339 | 3.034 | 19.201 | 55.590 | 1.00 | 103.08 |
| 4673 | CD1 | TYR | F | 339 | 3.103 | 20.452 | 54.971 | 1.00 | 102.58 |
| 4674 | CE1 | TYR | F | 339 | 4.244 | 21.246 | 55.077 | 1.00 | 106.84 |
| 4675 | CD2 | TYR | F | 339 | 4.147 | 18.760 | 56.312 | 1.00 | 105.86 |
| 4676 | CE2 | TYR | F | 339 | 5.291 | 19.545 | 56.428 | 1.00 | 98.40 |
| 4677 | CZ | TYR | F | 339 | 5.332 | 20.787 | 55.809 | 1.00 | 103.82 |
| 4678 | OH | TYR | F | 339 | 6.445 | 21.583 | 55.942 | 1.00 | 100.78 |
| 4679 | C | TYR | F | 339 | −0.256 | 17.495 | 54.478 | 1.00 | 66.64 |
| 4680 | O | TYR | F | 339 | −1.301 | 18.093 | 54.714 | 1.00 | 76.17 |
| 4681 | N | LEU | F | 340 | −0.183 | 16.174 | 54.446 | 1.00 | 62.07 |
| 4682 | CA | LEU | F | 340 | −1.345 | 15.337 | 54.679 | 1.00 | 41.77 |
| 4683 | CB | LEU | F | 340 | −1.821 | 14.717 | 53.361 | 1.00 | 43.98 |
| 4684 | CG | LEU | F | 340 | −3.144 | 13.961 | 53.376 | 1.00 | 29.76 |
| 4685 | CD1 | LEU | F | 340 | −4.212 | 14.904 | 53.865 | 1.00 | 59.34 |
| 4686 | CD2 | LEU | F | 340 | −3.491 | 13.442 | 51.987 | 1.00 | 41.19 |
| 4687 | C | LEU | F | 340 | −0.909 | 14.239 | 55.630 | 1.00 | 56.45 |
| 4688 | O | LEU | F | 340 | −0.050 | 13.428 | 55.291 | 1.00 | 62.91 |
| 4689 | N | SER | F | 341 | −1.480 | 14.211 | 56.825 | 1.00 | 41.02 |
| 4690 | CA | SER | F | 341 | −1.114 | 13.170 | 57.781 | 1.00 | 66.69 |
| 4691 | CB | SER | F | 341 | −1.028 | 13.748 | 59.183 | 1.00 | 61.32 |
| 4692 | OG | SER | F | 341 | −2.318 | 14.056 | 59.657 | 1.00 | 82.79 |
| 4693 | C | SER | F | 341 | −2.053 | 11.948 | 57.815 | 1.00 | 70.00 |
| 4694 | O | SER | F | 341 | −3.135 | 11.945 | 57.225 | 1.00 | 74.83 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4695 | N | ARG | F | 342 | −1.622 | 10.914 | 58.530 | 1.00 | 50.52 |
| 4696 | CA | ARG | F | 342 | −2.383 | 9.683 | 58.651 | 1.00 | 53.78 |
| 4697 | CB | ARG | F | 342 | −1.460 | 8.466 | 58.441 | 1.00 | 48.40 |
| 4698 | CG | ARG | F | 342 | −1.004 | 8.223 | 57.013 | 1.00 | 61.26 |
| 4699 | CD | ARG | F | 342 | −0.257 | 6.899 | 56.905 | 1.00 | 68.21 |
| 4700 | NE | ARG | F | 342 | 1.001 | 6.969 | 57.632 | 1.00 | 97.81 |
| 4701 | CZ | ARG | F | 342 | 2.090 | 7.573 | 57.173 | 1.00 | 82.00 |
| 4702 | NH1 | ARG | F | 342 | 2.077 | 8.145 | 55.974 | 1.00 | 75.73 |
| 4703 | NH2 | ARG | F | 342 | 3.175 | 7.636 | 57.929 | 1.00 | 72.90 |
| 4704 | C | ARG | F | 342 | −3.066 | 9.568 | 60.022 | 1.00 | 50.66 |
| 4705 | O | ARG | F | 342 | −2.794 | 10.323 | 60.945 | 1.00 | 28.88 |
| 4706 | N | PRO | F | 343 | −3.973 | 8.607 | 60.169 | 1.00 | 36.87 |
| 4707 | CD | PRO | F | 343 | −4.545 | 7.710 | 59.158 | 1.00 | 58.78 |
| 4708 | CA | PRO | F | 343 | −4.655 | 8.439 | 61.443 | 1.00 | 52.81 |
| 4709 | CB | PRO | F | 343 | −5.661 | 7.337 | 61.150 | 1.00 | 63.83 |
| 4710 | CG | PRO | F | 343 | −5.915 | 7.486 | 59.703 | 1.00 | 74.18 |
| 4711 | C | PRO | F | 343 | −3.691 | 8.008 | 62.527 | 1.00 | 42.88 |
| 4712 | O | PRO | F | 343 | −2.651 | 7.442 | 62.245 | 1.00 | 55.45 |
| 4713 | N | SER | F | 344 | −4.056 | 8.263 | 63.773 | 1.00 | 44.29 |
| 4714 | CA | SER | F | 344 | −3.241 | 7.860 | 64.898 | 1.00 | 25.27 |
| 4715 | CB | SER | F | 344 | −3.558 | 8.734 | 66.111 | 1.00 | 43.37 |
| 4716 | OG | SER | F | 344 | −4.616 | 8.182 | 66.881 | 1.00 | 50.20 |
| 4717 | C | SER | F | 344 | −3.587 | 6.399 | 65.215 | 1.00 | 21.07 |
| 4718 | O | SER | F | 344 | −4.752 | 6.063 | 65.418 | 1.00 | 44.71 |
| 4719 | N | PRO | F | 345 | −2.578 | 5.521 | 65.290 | 1.00 | 34.80 |
| 4720 | CD | PRO | F | 345 | −1.142 | 5.852 | 65.377 | 1.00 | 31.59 |
| 4721 | CA | PRO | F | 345 | −2.805 | 4.102 | 65.588 | 1.00 | 21.91 |
| 4722 | CB | PRO | F | 345 | −1.412 | 3.605 | 65.972 | 1.00 | 41.80 |
| 4723 | CG | PRO | F | 345 | −0.498 | 4.501 | 65.201 | 1.00 | 33.93 |
| 4724 | C | PRO | F | 345 | −3.815 | 3.881 | 66.726 | 1.00 | 44.80 |
| 4725 | O | PRO | F | 345 | −4.522 | 2.870 | 66.776 | 1.00 | 39.39 |
| 4726 | N | PHE | F | 346 | −3.870 | 4.830 | 67.649 | 1.00 | 34.33 |
| 4727 | CA | PHE | F | 346 | −4.802 | 4.754 | 68.775 | 1.00 | 50.14 |
| 4728 | CB | PHE | F | 346 | −4.396 | 5.764 | 69.851 | 1.00 | 40.92 |
| 4729 | CG | PHE | F | 346 | −5.466 | 6.037 | 70.851 | 1.00 | 37.48 |
| 4730 | CD1 | PHE | F | 346 | −5.811 | 5.085 | 71.812 | 1.00 | 35.18 |
| 4731 | CD2 | PHE | F | 346 | −6.156 | 7.236 | 70.812 | 1.00 | 8.11 |
| 4732 | CE1 | PHE | F | 346 | −6.839 | 5.325 | 72.731 | 1.00 | 4.47 |
| 4733 | CE2 | PHE | F | 346 | −7.186 | 7.492 | 71.725 | 1.00 | 62.01 |
| 4734 | CZ | PHE | F | 346 | −7.525 | 6.532 | 72.686 | 1.00 | 47.88 |
| 4735 | C | PHE | F | 346 | −6.263 | 5.007 | 68.365 | 1.00 | 52.34 |
| 4736 | O | PHE | F | 346 | −7.163 | 4.199 | 68.668 | 1.00 | 26.91 |
| 4737 | N | ASP | F | 347 | −6.481 | 6.139 | 67.696 | 1.00 | 31.88 |
| 4738 | CA | ASP | F | 347 | −7.808 | 6.520 | 67.239 | 1.00 | 49.46 |
| 4739 | CB | ASP | F | 347 | −7.777 | 7.926 | 66.610 | 1.00 | 40.77 |
| 4740 | CG | ASP | F | 347 | −7.375 | 9.015 | 67.606 | 1.00 | 63.11 |
| 4741 | OD1 | ASP | F | 347 | −7.115 | 10.162 | 67.176 | 1.00 | 54.48 |
| 4742 | OD2 | ASP | F | 347 | −7.319 | 8.734 | 68.819 | 1.00 | 62.53 |
| 4743 | C | ASP | F | 347 | −8.297 | 5.488 | 66.209 | 1.00 | 55.65 |
| 4744 | O | ASP | F | 347 | −9.504 | 5.230 | 66.086 | 1.00 | 51.48 |
| 4745 | N | LEU | F | 348 | −7.355 | 4.880 | 65.497 | 1.00 | 26.60 |
| 4746 | CA | LEU | F | 348 | −7.688 | 3.903 | 64.476 | 1.00 | 24.09 |
| 4747 | CB | LEU | F | 348 | −6.596 | 3.916 | 63.408 | 1.00 | 54.03 |
| 4748 | CG | LEU | F | 348 | −6.500 | 2.871 | 62.301 | 1.00 | 49.87 |
| 4749 | CD1 | LEU | F | 348 | −7.811 | 2.696 | 61.596 | 1.00 | 19.02 |
| 4750 | CD2 | LEU | F | 348 | −5.455 | 3.332 | 61.340 | 1.00 | 11.05 |
| 4751 | C | LEU | F | 348 | −7.942 | 2.473 | 64.935 | 1.00 | 32.08 |
| 4752 | O | LEU | F | 348 | −8.906 | 1.846 | 64.508 | 1.00 | 58.08 |
| 4753 | N | PHE | F | 349 | −7.083 | 1.937 | 65.788 | 1.00 | 33.35 |
| 4754 | CA | PHE | F | 349 | −7.273 | 0.563 | 66.241 | 1.00 | 45.77 |
| 4755 | CB | PHE | F | 349 | −5.925 | −0.148 | 66.359 | 1.00 | 13.79 |
| 4756 | CG | PHE | F | 349 | −5.236 | −0.340 | 65.043 | 1.00 | 66.34 |
| 4757 | CD1 | PHE | F | 349 | −4.113 | 0.422 | 64.715 | 1.00 | 76.12 |
| 4758 | CD2 | PHE | F | 349 | −5.711 | −1.282 | 64.126 | 1.00 | 34.97 |
| 4759 | CE1 | PHE | F | 349 | −3.465 | 0.255 | 63.501 | 1.00 | 41.28 |
| 4760 | CE2 | PHE | F | 349 | −5.071 | −1.465 | 62.899 | 1.00 | 23.52 |
| 4761 | CZ | PHE | F | 349 | −3.943 | −0.691 | 62.588 | 1.00 | 73.03 |
| 4762 | C | PHE | F | 349 | −8.034 | 0.421 | 67.550 | 1.00 | 49.00 |
| 4763 | O | PHE | F | 349 | −8.601 | −0.637 | 67.830 | 1.00 | 49.01 |
| 4764 | N | ILE | F | 350 | −8.056 | 1.483 | 68.349 | 1.00 | 34.84 |
| 4765 | CA | ILE | F | 350 | −8.749 | 1.418 | 69.615 | 1.00 | 47.75 |
| 4766 | CB | ILE | F | 350 | −7.812 | 1.801 | 70.775 | 1.00 | 56.98 |
| 4767 | CG2 | ILE | F | 350 | −8.335 | 1.177 | 72.066 | 1.00 | 61.51 |
| 4768 | CG1 | ILE | F | 350 | −6.396 | 1.260 | 70.521 | 1.00 | 50.83 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4769 | CD1 | ILE | F | 350 | −6.310 | −0.278 | 70.280 | 1.00 | 17.76 |
| 4770 | C | ILE | F | 350 | −9.985 | 2.313 | 69.614 | 1.00 | 60.55 |
| 4771 | O | ILE | F | 350 | −11.095 | 1.844 | 69.378 | 1.00 | 67.45 |
| 4772 | N | ARG | F | 351 | −9.792 | 3.597 | 69.884 | 1.00 | 63.61 |
| 4773 | CA | ARG | F | 351 | −10.892 | 4.547 | 69.889 | 1.00 | 42.93 |
| 4774 | CB | ARG | F | 351 | −10.324 | 5.961 | 69.775 | 1.00 | 59.63 |
| 4775 | CG | ARG | F | 351 | −11.127 | 7.037 | 70.442 | 1.00 | 63.28 |
| 4776 | CD | ARG | F | 351 | −10.198 | 8.148 | 70.848 | 1.00 | 64.45 |
| 4777 | NE | ARG | F | 351 | −10.909 | 9.360 | 71.215 | 1.00 | 94.05 |
| 4778 | CZ | ARG | F | 351 | −11.690 | 10.037 | 70.382 | 1.00 | 106.88 |
| 4779 | NH1 | ARG | F | 351 | −11.858 | 9.617 | 69.135 | 1.00 | 116.43 |
| 4780 | NH2 | ARG | F | 351 | −12.299 | 11.138 | 70.796 | 1.00 | 106.71 |
| 4781 | C | ARG | F | 351 | −11.790 | 4.221 | 68.689 | 1.00 | 41.94 |
| 4782 | O | ARG | F | 351 | −13.012 | 4.232 | 68.793 | 1.00 | 45.57 |
| 4783 | N | LYS | F | 352 | −11.169 | 3.926 | 67.549 | 1.00 | 61.66 |
| 4784 | CA | LYS | F | 352 | −11.870 | 3.554 | 66.313 | 1.00 | 71.23 |
| 4785 | CB | LYS | F | 352 | −12.835 | 2.389 | 66.588 | 1.00 | 45.95 |
| 4786 | CG | LYS | F | 352 | −12.141 | 1.060 | 66.802 | 1.00 | 16.46 |
| 4787 | CD | LYS | F | 352 | −13.117 | −0.094 | 66.920 | 1.00 | 49.58 |
| 4788 | CE | LYS | F | 352 | −12.375 | −1.433 | 66.996 | 1.00 | 73.50 |
| 4789 | NZ | LYS | F | 352 | −11.454 | −1.537 | 68.183 | 1.00 | 66.33 |
| 4790 | C | LYS | F | 352 | −12.597 | 4.638 | 65.506 | 1.00 | 60.62 |
| 4791 | O | LYS | F | 352 | −13.521 | 4.333 | 64.759 | 1.00 | 52.15 |
| 4792 | N | SER | F | 353 | −12.180 | 5.892 | 65.651 | 1.00 | 40.06 |
| 4793 | CA | SER | F | 353 | −12.771 | 6.990 | 64.895 | 1.00 | 71.21 |
| 4794 | CB | SER | F | 353 | −13.665 | 7.872 | 65.786 | 1.00 | 75.55 |
| 4795 | OG | SER | F | 353 | −12.931 | 8.531 | 66.800 | 1.00 | 70.13 |
| 4796 | C | SER | F | 353 | −11.599 | 7.794 | 64.344 | 1.00 | 68.59 |
| 4797 | O | SER | F | 353 | −11.224 | 8.823 | 64.899 | 1.00 | 83.82 |
| 4798 | N | PRO | F | 354 | −11.000 | 7.315 | 63.242 | 1.00 | 68.22 |
| 4799 | CD | PRO | F | 354 | −11.297 | 6.020 | 62.608 | 1.00 | 58.98 |
| 4800 | CA | PRO | F | 354 | −9.858 | 7.953 | 62.583 | 1.00 | 59.86 |
| 4801 | CB | PRO | F | 354 | −9.409 | 6.903 | 61.572 | 1.00 | 67.09 |
| 4802 | CG | PRO | F | 354 | −9.949 | 5.608 | 62.138 | 1.00 | 75.03 |
| 4803 | C | PRO | F | 354 | −10.156 | 9.270 | 61.904 | 1.00 | 54.98 |
| 4804 | O | PRO | F | 354 | −11.296 | 9.577 | 61.583 | 1.00 | 60.20 |
| 4805 | N | THR | F | 355 | −9.096 | 10.035 | 61.680 | 1.00 | 54.20 |
| 4806 | CA | THR | F | 355 | −9.175 | 11.329 | 61.013 | 1.00 | 63.28 |
| 4807 | CB | THR | F | 355 | −9.491 | 12.436 | 62.002 | 1.00 | 59.25 |
| 4808 | OG1 | THR | F | 355 | −8.615 | 12.310 | 63.122 | 1.00 | 46.55 |
| 4809 | CG2 | THR | F | 355 | −10.924 | 12.362 | 62.462 | 1.00 | 40.59 |
| 4810 | C | THR | F | 355 | −7.817 | 11.637 | 60.386 | 1.00 | 49.22 |
| 4811 | O | THR | F | 355 | −6.791 | 11.160 | 60.864 | 1.00 | 58.61 |
| 4812 | N | ILE | F | 356 | −7.820 | 12.417 | 59.311 | 1.00 | 48.34 |
| 4813 | CA | ILE | F | 356 | −6.587 | 12.805 | 58.633 | 1.00 | 40.42 |
| 4814 | CB | ILE | F | 356 | −6.484 | 12.192 | 57.195 | 1.00 | 25.43 |
| 4815 | CG2 | ILE | F | 356 | −6.420 | 10.679 | 57.285 | 1.00 | 67.74 |
| 4816 | CG1 | ILE | F | 356 | −7.677 | 12.605 | 56.333 | 1.00 | 41.98 |
| 4817 | CD1 | ILE | F | 356 | −7.767 | 11.859 | 55.014 | 1.00 | 47.28 |
| 4818 | C | ILE | F | 356 | −6.638 | 14.315 | 58.545 | 1.00 | 57.28 |
| 4819 | O | ILE | F | 356 | −7.710 | 14.894 | 58.445 | 1.00 | 90.47 |
| 4820 | N | THR | F | 357 | −5.489 | 14.965 | 58.580 | 1.00 | 59.80 |
| 4821 | CA | THR | F | 357 | −5.480 | 16.412 | 58.507 | 1.00 | 72.80 |
| 4822 | CB | THR | F | 357 | −4.941 | 17.005 | 59.814 | 1.00 | 67.04 |
| 4823 | OG1 | THR | F | 357 | −5.641 | 16.420 | 60.917 | 1.00 | 62.51 |
| 4824 | CG2 | THR | F | 357 | −5.127 | 18.514 | 59.830 | 1.00 | 56.67 |
| 4825 | C | THR | F | 357 | −4.660 | 16.977 | 57.353 | 1.00 | 77.04 |
| 4826 | O | THR | F | 357 | −3.465 | 16.697 | 57.251 | 1.00 | 86.87 |
| 4827 | N | CYS | F | 358 | −5.308 | 17.757 | 56.484 | 1.00 | 73.03 |
| 4828 | CA | CYS | F | 358 | −4.619 | 18.413 | 55.370 | 1.00 | 62.33 |
| 4829 | C | CYS | F | 358 | −4.178 | 19.725 | 56.002 | 1.00 | 68.25 |
| 4830 | O | CYS | F | 358 | −5.014 | 20.503 | 56.453 | 1.00 | 67.97 |
| 4831 | CB | CYS | F | 358 | −5.577 | 18.711 | 54.200 | 1.00 | 83.68 |
| 4832 | SG | CYS | F | 358 | −4.793 | 19.283 | 52.643 | 1.00 | 60.09 |
| 4833 | N | LEU | F | 359 | −2.875 | 19.962 | 56.051 | 1.00 | 60.16 |
| 4834 | CA | LEU | F | 359 | −2.344 | 21.183 | 56.651 | 1.00 | 74.50 |
| 4835 | CB | LEU | F | 359 | −1.416 | 20.810 | 57.811 | 1.00 | 69.47 |
| 4836 | CG | LEU | F | 359 | −0.426 | 21.869 | 58.271 | 1.00 | 68.45 |
| 4837 | CD1 | LEU | F | 359 | −1.165 | 23.063 | 58.829 | 1.00 | 84.99 |
| 4838 | CD2 | LEU | F | 359 | 0.484 | 21.257 | 59.307 | 1.00 | 58.44 |
| 4839 | C | LEU | F | 359 | −1.599 | 22.073 | 55.648 | 1.00 | 76.30 |
| 4840 | O | LEU | F | 359 | −0.544 | 21.700 | 55.143 | 1.00 | 86.43 |
| 4841 | N | VAL | F | 360 | −2.150 | 23.249 | 55.366 | 1.00 | 79.43 |
| 4842 | CA | VAL | F | 360 | −1.522 | 24.180 | 54.434 | 1.00 | 85.48 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4843 | CB | VAL | F | 360 | -2.571 | 24.849 | 53.513 | 1.00 | 85.65 |
| 4844 | CG1 | VAL | F | 360 | -1.881 | 25.723 | 52.472 | 1.00 | 79.63 |
| 4845 | CG2 | VAL | F | 360 | -3.408 | 23.783 | 52.829 | 1.00 | 91.15 |
| 4846 | C | VAL | F | 360 | -0.785 | 25.267 | 55.218 | 1.00 | 84.65 |
| 4847 | O | VAL | F | 360 | -1.373 | 25.911 | 56.083 | 1.00 | 90.59 |
| 4848 | N | VAL | F | 361 | 0.498 | 25.460 | 54.918 | 1.00 | 88.44 |
| 4849 | CA | VAL | F | 361 | 1.308 | 26.465 | 55.599 | 1.00 | 94.86 |
| 4850 | CB | VAL | F | 361 | 2.568 | 25.838 | 56.246 | 1.00 | 92.15 |
| 4851 | CG1 | VAL | F | 361 | 3.388 | 26.916 | 56.960 | 1.00 | 88.79 |
| 4852 | CG2 | VAL | F | 361 | 2.160 | 24.754 | 57.235 | 1.00 | 91.90 |
| 4853 | C | VAL | F | 361 | 1.749 | 27.579 | 54.650 | 1.00 | 111.75 |
| 4854 | O | VAL | F | 361 | 2.491 | 27.341 | 53.690 | 1.00 | 98.90 |
| 4855 | N | ASP | F | 362 | 1.279 | 28.795 | 54.933 | 1.00 | 121.08 |
| 4856 | CA | ASP | F | 362 | 1.610 | 29.973 | 54.133 | 1.00 | 129.77 |
| 4857 | CB | ASP | F | 362 | 0.349 | 30.550 | 53.477 | 1.00 | 126.14 |
| 4858 | CG | ASP | F | 362 | 0.668 | 31.490 | 52.323 | 1.00 | 125.87 |
| 4859 | OD1 | ASP | F | 362 | 1.488 | 32.414 | 52.503 | 1.00 | 128.80 |
| 4860 | OD2 | ASP | F | 362 | 0.094 | 31.304 | 51.230 | 1.00 | 119.51 |
| 4861 | C | ASP | F | 362 | 2.244 | 31.035 | 55.035 | 1.00 | 133.55 |
| 4862 | O | ASP | F | 362 | 1.608 | 31.526 | 55.972 | 1.00 | 132.84 |
| 4863 | N | LEU | F | 363 | 3.498 | 31.383 | 54.748 | 1.00 | 137.95 |
| 4864 | CA | LEU | F | 363 | 4.217 | 32.381 | 55.535 | 1.00 | 132.39 |
| 4865 | CB | LEU | F | 363 | 5.731 | 32.148 | 55.423 | 1.00 | 124.48 |
| 4866 | CG | LEU | F | 363 | 6.290 | 30.854 | 56.025 | 1.00 | 119.44 |
| 4867 | CD1 | LEU | F | 363 | 7.753 | 30.719 | 55.649 | 1.00 | 119.43 |
| 4868 | CD2 | LEU | F | 363 | 6.124 | 30.859 | 57.537 | 1.00 | 118.14 |
| 4869 | C | LEU | F | 363 | 3.876 | 33.815 | 55.109 | 1.00 | 134.86 |
| 4870 | O | LEU | F | 363 | 4.188 | 34.771 | 55.823 | 1.00 | 137.23 |
| 4871 | N | ALA | F | 364 | 3.232 | 33.960 | 53.952 | 1.00 | 135.61 |
| 4872 | CA | ALA | F | 364 | 2.851 | 35.275 | 53.443 | 1.00 | 133.08 |
| 4873 | CB | ALA | F | 364 | 3.534 | 35.535 | 52.104 | 1.00 | 127.45 |
| 4874 | C | ALA | F | 364 | 1.335 | 35.391 | 53.288 | 1.00 | 137.75 |
| 4875 | O | ALA | F | 364 | 0.799 | 35.206 | 52.192 | 1.00 | 136.10 |
| 4876 | N | PRO | F | 365 | 0.625 | 35.700 | 54.390 | 1.00 | 141.86 |
| 4877 | CD | PRO | F | 365 | 1.177 | 35.868 | 55.749 | 1.00 | 141.03 |
| 4878 | CA | PRO | F | 365 | -0.835 | 35.847 | 54.405 | 1.00 | 140.17 |
| 4879 | CB | PRO | F | 365 | -1.109 | 36.352 | 55.820 | 1.00 | 143.07 |
| 4880 | CG | PRO | F | 365 | -0.041 | 35.669 | 56.624 | 1.00 | 140.07 |
| 4881 | C | PRO | F | 365 | -1.399 | 36.789 | 53.334 | 1.00 | 141.85 |
| 4882 | O | PRO | F | 365 | -1.588 | 37.983 | 53.581 | 1.00 | 142.69 |
| 4883 | N | SER | F | 366 | -1.668 | 36.246 | 52.149 | 1.00 | 140.99 |
| 4884 | CA | SER | F | 366 | -2.225 | 37.029 | 51.049 | 1.00 | 140.74 |
| 4885 | CB | SER | F | 366 | -1.598 | 36.604 | 49.718 | 1.00 | 135.96 |
| 4886 | OG | SER | F | 366 | -1.784 | 35.219 | 49.479 | 1.00 | 133.46 |
| 4887 | C | SER | F | 366 | -3.736 | 36.818 | 51.000 | 1.00 | 146.46 |
| 4888 | O | SER | F | 366 | -4.214 | 35.686 | 51.078 | 1.00 | 151.96 |
| 4889 | N | LYS | F | 367 | -4.484 | 37.908 | 50.866 | 1.00 | 142.15 |
| 4890 | CA | LYS | F | 367 | -5.942 | 37.838 | 50.830 | 1.00 | 139.98 |
| 4891 | CB | LYS | F | 367 | -6.524 | 39.252 | 50.776 | 1.00 | 144.13 |
| 4892 | CG | LYS | F | 367 | -6.087 | 40.137 | 51.940 | 1.00 | 144.20 |
| 4893 | CD | LYS | F | 367 | -6.853 | 41.456 | 51.977 | 1.00 | 142.67 |
| 4894 | CE | LYS | F | 367 | -8.335 | 41.238 | 52.260 | 1.00 | 140.51 |
| 4895 | NZ | LYS | F | 367 | -9.065 | 42.526 | 52.401 | 1.00 | 141.21 |
| 4896 | C | LYS | F | 367 | -6.519 | 36.994 | 49.690 | 1.00 | 138.96 |
| 4897 | O | LYS | F | 367 | -5.988 | 36.977 | 48.578 | 1.00 | 132.76 |
| 4898 | N | GLY | F | 368 | -7.618 | 36.301 | 49.986 | 1.00 | 140.10 |
| 4899 | CA | GLY | F | 368 | -8.274 | 35.448 | 49.008 | 1.00 | 137.38 |
| 4900 | C | GLY | F | 368 | -8.611 | 34.089 | 49.601 | 1.00 | 133.23 |
| 4901 | O | GLY | F | 368 | -7.767 | 33.468 | 50.249 | 1.00 | 133.48 |
| 4902 | N | THR | F | 369 | -9.840 | 33.623 | 49.386 | 1.00 | 130.59 |
| 4903 | CA | THR | F | 369 | -10.277 | 32.329 | 49.913 | 1.00 | 128.07 |
| 4904 | CB | THR | F | 369 | -11.743 | 32.015 | 49.511 | 1.00 | 132.65 |
| 4905 | OG1 | THR | F | 369 | -11.940 | 32.331 | 48.127 | 1.00 | 138.05 |
| 4906 | CG2 | THR | F | 369 | -12.721 | 32.811 | 50.363 | 1.00 | 120.79 |
| 4907 | C | THR | F | 369 | -9.396 | 31.160 | 49.462 | 1.00 | 124.44 |
| 4908 | O | THR | F | 369 | -8.905 | 31.130 | 48.330 | 1.00 | 119.27 |
| 4909 | N | VAL | F | 370 | -9.203 | 30.199 | 50.360 | 1.00 | 118.17 |
| 4910 | CA | VAL | F | 370 | -8.394 | 29.024 | 50.069 | 1.00 | 111.84 |
| 4911 | CB | VAL | F | 370 | -7.267 | 28.851 | 51.116 | 1.00 | 108.70 |
| 4912 | CG1 | VAL | F | 370 | -6.290 | 27.781 | 50.656 | 1.00 | 111.23 |
| 4913 | CG2 | VAL | F | 370 | -6.557 | 30.175 | 51.344 | 1.00 | 86.72 |
| 4914 | C | VAL | F | 370 | -9.296 | 27.791 | 50.108 | 1.00 | 104.98 |
| 4915 | O | VAL | F | 370 | -9.875 | 27.473 | 51.147 | 1.00 | 85.59 |
| 4916 | N | ASN | F | 371 | -9.422 | 27.106 | 48.974 | 1.00 | 103.53 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4917 | CA | ASN | F | 371 | −10.259 | 25.909 | 48.895 | 1.00 | 108.12 |
| 4918 | CB | ASN | F | 371 | −10.924 | 25.808 | 47.519 | 1.00 | 109.51 |
| 4919 | CG | ASN | F | 371 | −11.971 | 26.877 | 47.298 | 1.00 | 117.55 |
| 4920 | OD1 | ASN | F | 371 | −12.937 | 26.984 | 48.058 | 1.00 | 118.25 |
| 4921 | ND2 | ASN | F | 371 | −11.789 | 27.675 | 46.253 | 1.00 | 106.66 |
| 4922 | C | ASN | F | 371 | −9.485 | 24.621 | 49.170 | 1.00 | 106.38 |
| 4923 | O | ASN | F | 371 | −8.430 | 24.373 | 48.581 | 1.00 | 111.35 |
| 4924 | N | LEU | F | 372 | −10.013 | 23.808 | 50.079 | 1.00 | 97.96 |
| 4925 | CA | LEU | F | 372 | −9.386 | 22.539 | 50.424 | 1.00 | 94.66 |
| 4926 | CB | LEU | F | 372 | −8.948 | 22.520 | 51.889 | 1.00 | 83.66 |
| 4927 | CG | LEU | F | 372 | −7.825 | 23.494 | 52.263 | 1.00 | 105.62 |
| 4928 | CD1 | LEU | F | 372 | −7.388 | 23.248 | 53.704 | 1.00 | 102.92 |
| 4929 | CD2 | LEU | F | 372 | −6.644 | 23.306 | 51.309 | 1.00 | 103.83 |
| 4930 | C | LEU | F | 372 | −10.403 | 21.447 | 50.179 | 1.00 | 96.29 |
| 4931 | O | LEU | F | 372 | −11.166 | 21.081 | 51.070 | 1.00 | 108.25 |
| 4932 | N | THR | F | 373 | −10.410 | 20.939 | 48.953 | 1.00 | 92.08 |
| 4933 | CA | THR | F | 373 | −11.332 | 19.889 | 48.541 | 1.00 | 83.61 |
| 4934 | CB | THR | F | 373 | −11.619 | 19.986 | 47.038 | 1.00 | 90.02 |
| 4935 | OG1 | THR | F | 373 | −11.903 | 21.347 | 46.692 | 1.00 | 99.81 |
| 4936 | CG2 | THR | F | 373 | −12.798 | 19.109 | 46.667 | 1.00 | 89.63 |
| 4937 | C | THR | F | 373 | −10.810 | 18.476 | 48.817 | 1.00 | 78.45 |
| 4938 | O | THR | F | 373 | −9.660 | 18.148 | 48.522 | 1.00 | 69.42 |
| 4939 | N | TRP | F | 374 | −11.670 | 17.639 | 49.379 | 1.00 | 65.10 |
| 4940 | CA | TRP | F | 374 | −11.307 | 16.264 | 49.659 | 1.00 | 55.30 |
| 4941 | CB | TRP | F | 374 | −11.832 | 15.853 | 51.030 | 1.00 | 74.05 |
| 4942 | CG | TRP | F | 374 | −11.079 | 16.467 | 52.155 | 1.00 | 90.91 |
| 4943 | CD2 | TRP | F | 374 | −9.880 | 15.960 | 52.733 | 1.00 | 78.71 |
| 4944 | CE2 | TRP | F | 374 | −9.497 | 16.855 | 53.757 | 1.00 | 85.89 |
| 4945 | CE3 | TRP | F | 374 | −9.087 | 14.833 | 52.484 | 1.00 | 76.18 |
| 4946 | CD1 | TRP | F | 374 | −11.375 | 17.626 | 52.827 | 1.00 | 79.64 |
| 4947 | NE1 | TRP | F | 374 | −10.427 | 17.863 | 53.795 | 1.00 | 78.98 |
| 4948 | CZ2 | TRP | F | 374 | −8.349 | 16.655 | 54.534 | 1.00 | 92.81 |
| 4949 | CZ3 | TRP | F | 374 | −7.949 | 14.532 | 53.252 | 1.00 | 71.01 |
| 4950 | CH2 | TRP | F | 374 | −7.590 | 15.539 | 54.267 | 1.00 | 82.90 |
| 4951 | C | TRP | F | 374 | −11.919 | 15.372 | 48.593 | 1.00 | 70.87 |
| 4952 | O | TRP | F | 374 | −12.775 | 15.809 | 47.832 | 1.00 | 92.80 |
| 4953 | N | SER | F | 375 | −11.476 | 14.124 | 48.531 | 1.00 | 71.82 |
| 4954 | CA | SER | F | 375 | −12.021 | 13.168 | 47.574 | 1.00 | 78.28 |
| 4955 | CB | SER | F | 375 | −11.816 | 13.653 | 46.133 | 1.00 | 77.76 |
| 4956 | OG | SER | F | 375 | −10.445 | 13.762 | 45.818 | 1.00 | 83.98 |
| 4957 | C | SER | F | 375 | −11.366 | 11.812 | 47.761 | 1.00 | 69.71 |
| 4958 | O | SER | F | 375 | −10.262 | 11.717 | 48.284 | 1.00 | 73.89 |
| 4959 | N | ARG | F | 376 | −12.062 | 10.761 | 47.347 | 1.00 | 72.56 |
| 4960 | CA | ARG | F | 376 | −11.535 | 9.414 | 47.460 | 1.00 | 68.37 |
| 4961 | CB | ARG | F | 376 | −12.575 | 8.484 | 48.070 | 1.00 | 80.12 |
| 4962 | CG | ARG | F | 376 | −13.010 | 8.842 | 49.480 | 1.00 | 53.43 |
| 4963 | CD | ARG | F | 376 | −13.320 | 7.562 | 50.213 | 1.00 | 58.07 |
| 4964 | NE | ARG | F | 376 | −14.661 | 7.518 | 50.769 | 1.00 | 53.63 |
| 4965 | CZ | ARG | F | 376 | −15.262 | 6.396 | 51.165 | 1.00 | 62.44 |
| 4966 | NH1 | ARG | F | 376 | −14.642 | 5.224 | 51.064 | 1.00 | 30.38 |
| 4967 | NH2 | ARG | F | 376 | −16.489 | 6.441 | 51.659 | 1.00 | 61.59 |
| 4968 | C | ARG | F | 376 | −11.137 | 8.900 | 46.084 | 1.00 | 72.62 |
| 4969 | O | ARG | F | 376 | −11.733 | 9.258 | 45.072 | 1.00 | 55.35 |
| 4970 | N | ALA | F | 377 | −10.119 | 8.056 | 46.048 | 1.00 | 75.94 |
| 4971 | CA | ALA | F | 377 | −9.653 | 7.513 | 44.783 | 1.00 | 81.09 |
| 4972 | CB | ALA | F | 377 | −8.363 | 6.727 | 44.997 | 1.00 | 65.33 |
| 4973 | C | ALA | F | 377 | −10.726 | 6.613 | 44.192 | 1.00 | 75.15 |
| 4974 | O | ALA | F | 377 | −10.864 | 6.511 | 42.972 | 1.00 | 94.88 |
| 4975 | N | SER | F | 378 | −11.487 | 5.968 | 45.067 | 1.00 | 69.04 |
| 4976 | CA | SER | F | 378 | −12.539 | 5.059 | 44.641 | 1.00 | 72.10 |
| 4977 | CB | SER | F | 378 | −13.062 | 4.261 | 45.847 | 1.00 | 59.52 |
| 4978 | OG | SER | F | 378 | −13.572 | 5.113 | 46.856 | 1.00 | 63.08 |
| 4979 | C | SER | F | 378 | −13.682 | 5.822 | 43.972 | 1.00 | 83.13 |
| 4980 | O | SER | F | 378 | −14.241 | 5.374 | 42.969 | 1.00 | 82.58 |
| 4981 | N | GLY | F | 379 | −14.014 | 6.983 | 44.522 | 1.00 | 72.83 |
| 4982 | CA | GLY | F | 379 | −15.095 | 7.772 | 43.963 | 1.00 | 69.95 |
| 4983 | C | GLY | F | 379 | −16.283 | 7.806 | 44.908 | 1.00 | 72.11 |
| 4984 | O | GLY | F | 379 | −17.348 | 8.325 | 44.575 | 1.00 | 31.45 |
| 4985 | N | LYS | F | 380 | −16.106 | 7.234 | 46.094 | 1.00 | 82.31 |
| 4985 | CA | LYS | F | 380 | −17.167 | 7.228 | 47.083 | 1.00 | 75.41 |
| 4987 | CB | LYS | F | 380 | −16.941 | 6.109 | 48.101 | 1.00 | 54.12 |
| 4988 | CG | LYS | F | 380 | −16.887 | 4.727 | 47.468 | 1.00 | 82.09 |
| 4989 | CD | LYS | F | 380 | −16.848 | 3.606 | 48.496 | 1.00 | 71.83 |
| 4990 | CE | LYS | F | 380 | −16.844 | 2.256 | 47.809 | 1.00 | 77.82 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 4991 | Z | LYS | F | 390 | −16.947 | 1.154 | 48.789 | 1.00 | 98.06 |
| 4992 | C | LYS | F | 380 | −17.200 | 8.591 | 47.761 | 1.00 | 75.65 |
| 4993 | O | LYS | F | 380 | −16.332 | 9.431 | 47.534 | 1.00 | 69.78 |
| 4994 | N | PRO | F | 381 | −18.225 | 8.842 | 48.583 | 1.00 | 94.36 |
| 4995 | CD | PRO | F | 381 | −19.488 | 8.094 | 48.687 | 1.00 | 95.22 |
| 4996 | CA | PRO | F | 381 | −18.336 | 10.131 | 49.270 | 1.00 | 95.33 |
| 4997 | CB | PRO | F | 381 | −19.799 | 10.157 | 49.721 | 1.00 | 89.57 |
| 4998 | CG | PRO | F | 381 | −20.485 | 9.209 | 48.775 | 1.00 | 100.53 |
| 4999 | C | PRO | F | 381 | −17.377 | 10.293 | 50.451 | 1.00 | 93.08 |
| 5000 | O | PRO | F | 381 | −16.929 | 9.311 | 51.055 | 1.00 | 84.33 |
| 5001 | N | VAL | F | 382 | −17.066 | 11.546 | 50.765 | 1.00 | 88.63 |
| 5002 | CA | VAL | F | 382 | −16.198 | 11.872 | 51.888 | 1.00 | 77.38 |
| 5003 | CB | VAL | F | 382 | −15.072 | 12.837 | 51.483 | 1.00 | 84.96 |
| 5004 | CG1 | VAL | F | 382 | −14.175 | 12.184 | 50.441 | 1.00 | 99.01 |
| 5005 | CG2 | VAL | F | 382 | −15.668 | 14.133 | 50.961 | 1.00 | 64.32 |
| 5006 | C | VAL | F | 382 | −17.069 | 12.575 | 52.914 | 1.00 | 77.42 |
| 5007 | O | VAL | F | 382 | −17.927 | 13.371 | 52.543 | 1.00 | 77.00 |
| 5008 | N | ASN | F | 383 | −16.842 | 12.295 | 54.196 | 1.00 | 82.94 |
| 5009 | CA | ASN | F | 383 | −17.623 | 12.908 | 55.267 | 1.00 | 76.81 |
| 5010 | CB | ASN | F | 383 | −17.284 | 12.253 | 56.611 | 1.00 | 98.59 |
| 5011 | CG | ASN | F | 383 | −17.528 | 10.750 | 56.612 | 1.00 | 104.90 |
| 5012 | OD1 | ASN | F | 383 | −17.440 | 10.096 | 57.654 | 1.00 | 109.51 |
| 5013 | ND2 | ASN | F | 383 | −17.830 | 10.195 | 55.442 | 1.00 | 100.50 |
| 5014 | C | ASN | F | 383 | −17.449 | 14.429 | 55.382 | 1.00 | 78.00 |
| 5015 | O | ASN | F | 383 | −16.826 | 15.073 | 54.540 | 1.00 | 58.02 |
| 5016 | N | HIS | F | 384 | −18.007 | 14.998 | 56.441 | 1.00 | 79.74 |
| 5017 | CA | HIS | F | 384 | −17.932 | 16.437 | 56.651 | 1.00 | 84.70 |
| 5018 | CB | HIS | F | 384 | −19.060 | 16.886 | 57.575 | 1.00 | 95.64 |
| 5019 | CG | HIS | F | 384 | −20.403 | 16.367 | 57.171 | 1.00 | 115.54 |
| 5020 | CD2 | HIS | F | 384 | −21.272 | 15.552 | 57.814 | 1.00 | 119.84 |
| 5021 | ND1 | HIS | F | 384 | −20.974 | 16.651 | 55.948 | 1.00 | 118.84 |
| 5022 | CE1 | HIS | F | 384 | −22.136 | 16.031 | 55.855 | 1.00 | 121.18 |
| 5023 | NE2 | HIS | F | 384 | −22.340 | 15.357 | 56.974 | 1.00 | 128.43 |
| 5024 | C | HIS | F | 384 | −16.601 | 16.853 | 57.235 | 1.00 | 74.04 |
| 5025 | O | HIS | F | 384 | −16.283 | 16.516 | 58.366 | 1.00 | 76.53 |
| 5026 | N | SER | F | 385 | −15.833 | 17.605 | 56.460 | 1.00 | 72.19 |
| 5027 | CA | SER | F | 385 | −14.520 | 18.057 | 56.904 | 1.00 | 82.22 |
| 5028 | CB | SER | F | 385 | −13.652 | 18.387 | 55.685 | 1.00 | 75.69 |
| 5029 | OG | SER | F | 385 | −14.468 | 18.707 | 54.567 | 1.00 | 51.84 |
| 5030 | C | SER | F | 385 | −14.609 | 19.256 | 57.836 | 1.00 | 83.32 |
| 5031 | O | SER | F | 385 | −15.649 | 19.910 | 57.917 | 1.00 | 83.86 |
| 5032 | N | THR | F | 386 | −13.509 | 19.535 | 58.531 | 1.00 | 79.30 |
| 5033 | CA | THR | F | 386 | −13.437 | 20.647 | 59.471 | 1.00 | 79.21 |
| 5034 | CB | THR | F | 386 | −13.224 | 20.151 | 60.921 | 1.00 | 83.15 |
| 5035 | OG1 | THR | F | 386 | −14.368 | 19.401 | 61.351 | 1.00 | 74.99 |
| 5036 | CG2 | THR | F | 386 | −12.993 | 21.333 | 61.858 | 1.00 | 90.51 |
| 5037 | C | THR | F | 386 | −12.287 | 21.583 | 59.141 | 1.00 | 81.48 |
| 5038 | O | THR | F | 386 | −11.123 | 21.225 | 59.314 | 1.00 | 101.36 |
| 5039 | N | ARG | F | 387 | −12.613 | 22.784 | 58.677 | 1.00 | 76.09 |
| 5040 | CA | ARG | F | 387 | −11.600 | 23.784 | 58.338 | 1.00 | 88.49 |
| 5041 | CB | ARG | F | 387 | −12.115 | 24.626 | 57.171 | 1.00 | 79.29 |
| 5042 | CG | ARG | F | 387 | −11.201 | 25.718 | 56.654 | 1.00 | 85.85 |
| 5043 | CD | ARG | F | 387 | −11.965 | 26.600 | 55.653 | 1.00 | 89.87 |
| 5044 | NE | ARG | F | 387 | −11.174 | 27.716 | 55.154 | 1.00 | 94.95 |
| 5045 | CZ | ARG | F | 387 | −10.304 | 27.623 | 54.156 | 1.00 | 99.78 |
| 5046 | NH1 | ARG | F | 387 | −10.123 | 26.461 | 53.544 | 1.00 | 102.11 |
| 5047 | NH2 | ARG | F | 387 | −9.603 | 28.687 | 53.781 | 1.00 | 106.97 |
| 5048 | C | ARG | F | 387 | −11.311 | 24.648 | 59.579 | 1.00 | 85.06 |
| 5049 | O | ARG | F | 387 | −12.209 | 24.918 | 60.373 | 1.00 | 96.97 |
| 5050 | N | LYS | F | 388 | −10.058 | 25.057 | 59.760 | 1.00 | 86.69 |
| 5051 | CA | LYS | F | 388 | −9.675 | 25.869 | 60.920 | 1.00 | 89.41 |
| 5052 | CB | LYS | F | 388 | −9.249 | 24.978 | 62.085 | 1.00 | 76.57 |
| 5053 | CG | LYS | F | 388 | −10.228 | 23.882 | 62.430 | 1.00 | 82.92 |
| 5054 | CD | LYS | F | 388 | −9.592 | 22.909 | 63.401 | 1.00 | 100.07 |
| 5055 | CE | LYS | F | 388 | −10.469 | 21.695 | 63.625 | 1.00 | 89.47 |
| 5056 | NZ | LYS | F | 388 | −9.803 | 20.709 | 64.515 | 1.00 | 97.50 |
| 5057 | C | LYS | F | 388 | −8.515 | 26.793 | 60.585 | 1.00 | 102.71 |
| 5058 | O | LYS | F | 388 | −7.348 | 26.389 | 60.652 | 1.00 | 107.12 |
| 5059 | N | GLU | F | 389 | −8.832 | 28.032 | 60.231 | 1.00 | 106.16 |
| 5060 | CA | GLU | F | 389 | −7.798 | 29.001 | 59.892 | 1.00 | 108.92 |
| 5061 | CB | GLU | F | 389 | −8.336 | 30.028 | 58.886 | 1.00 | 102.64 |
| 5062 | CG | GLU | F | 389 | −8.795 | 29.427 | 57.560 | 1.00 | 104.58 |
| 5063 | CD | GLU | F | 389 | −9.505 | 30.434 | 56.672 | 1.00 | 118.51 |
| 5064 | OE1 | GLU | F | 389 | −8.889 | 31.465 | 56.329 | 1.00 | 123.48 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5065 | OE2 | GLU | F | 389 | −10.681 | 30.195 | 56.319 | 1.00 | 122.23 |
| 5066 | C | GLU | F | 389 | −7.304 | 29.692 | 61.162 | 1.00 | 104.28 |
| 5067 | O | GLU | F | 389 | −8.022 | 30.473 | 61.788 | 1.00 | 103.05 |
| 5068 | N | GLU | F | 390 | −6.072 | 29.372 | 61.539 | 1.00 | 107.15 |
| 5069 | CA | GLU | F | 390 | −5.442 | 29.928 | 62.721 | 1.00 | 94.35 |
| 5070 | CB | GLU | F | 390 | −4.944 | 28.785 | 63.601 | 1.00 | 97.62 |
| 5071 | CG | GLU | F | 390 | −4.159 | 29.208 | 64.820 | 1.00 | 115.78 |
| 5072 | CD | GLU | F | 390 | −3.727 | 28.022 | 65.657 | 1.00 | 126.34 |
| 5073 | OE1 | GLU | F | 390 | −3.091 | 27.099 | 65.101 | 1.00 | 134.09 |
| 5074 | OE2 | GLU | F | 390 | −4.024 | 28.010 | 66.871 | 1.00 | 136.96 |
| 5075 | C | GLU | F | 390 | −4.281 | 30.808 | 62.269 | 1.00 | 100.11 |
| 5076 | O | GLU | F | 390 | −3.170 | 30.325 | 62.040 | 1.00 | 90.59 |
| 5077 | N | LYS | F | 391 | −4.546 | 32.104 | 62.134 | 1.00 | 107.80 |
| 5078 | CA | LYS | F | 391 | −3.522 | 33.045 | 61.696 | 1.00 | 108.53 |
| 5079 | CB | LYS | F | 391 | −4.172 | 34.303 | 61.128 | 1.00 | 108.68 |
| 5080 | CG | LYS | F | 391 | −3.312 | 35.105 | 60.167 | 1.00 | 106.81 |
| 5081 | CD | LYS | F | 391 | −4.177 | 36.091 | 59.401 | 1.00 | 106.38 |
| 5082 | CE | LYS | F | 391 | −3.422 | 36.738 | 58.268 | 1.00 | 102.68 |
| 5083 | NZ | LYS | F | 391 | −4.319 | 37.601 | 57.452 | 1.00 | 100.29 |
| 5084 | C | LYS | F | 391 | −2.567 | 33.438 | 62.815 | 1.00 | 103.07 |
| 5085 | O | LYS | F | 391 | −2.920 | 33.443 | 63.995 | 1.00 | 98.06 |
| 5086 | N | GLN | F | 392 | −1.349 | 33.769 | 62.414 | 1.00 | 111.17 |
| 5087 | CA | GLN | F | 392 | −0.305 | 34.181 | 63.337 | 1.00 | 128.29 |
| 5088 | CB | GLN | F | 392 | 0.656 | 33.024 | 63.608 | 1.00 | 127.34 |
| 5089 | CG | GLN | F | 392 | −0.006 | 31.786 | 64.177 | 1.00 | 128.47 |
| 5090 | CD | GLN | F | 392 | 0.957 | 30.626 | 64.290 | 1.00 | 133.55 |
| 5091 | OE1 | GLN | F | 392 | 1.997 | 30.731 | 64.941 | 1.00 | 130.39 |
| 5092 | NE2 | GLN | F | 392 | 0.618 | 29.510 | 63.655 | 1.00 | 130.20 |
| 5093 | C | GLN | F | 392 | 0.454 | 35.325 | 62.686 | 1.00 | 130.81 |
| 5094 | O | GLN | F | 392 | 1.238 | 35.109 | 61.760 | 1.00 | 125.63 |
| 5095 | N | ARG | F | 393 | 0.209 | 36.541 | 63.162 | 1.00 | 137.36 |
| 5096 | CA | ARG | F | 393 | 0.883 | 37.717 | 62.624 | 1.00 | 147.76 |
| 5097 | CB | ARG | F | 393 | 0.464 | 38.965 | 63.410 | 1.00 | 146.27 |
| 5098 | CG | ARG | F | 393 | −0.285 | 38.669 | 64.703 | 1.00 | 153.49 |
| 5099 | CD | ARG | F | 393 | −0.531 | 39.942 | 65.481 | 1.00 | 152.48 |
| 5100 | NE | ARG | F | 393 | 0.723 | 40.619 | 65.789 | 1.00 | 153.98 |
| 5101 | CZ | ARG | F | 393 | 0.804 | 41.797 | 66.390 | 1.00 | 151.67 |
| 5102 | NH1 | ARG | F | 393 | −0.307 | 42.427 | 66.747 | 1.00 | 157.03 |
| 5103 | NH2 | ARG | F | 393 | 1.990 | 42.343 | 66.627 | 1.00 | 151.97 |
| 5104 | C | ARG | F | 393 | 2.404 | 37.525 | 62.673 | 1.00 | 152.19 |
| 5105 | O | ARG | F | 393 | 3.172 | 38.346 | 62.164 | 1.00 | 154.97 |
| 5106 | N | ASN | F | 394 | 2.823 | 36.422 | 63.289 | 1.00 | 153.18 |
| 5107 | CA | ASN | F | 394 | 4.232 | 36.070 | 63.407 | 1.00 | 148.03 |
| 5108 | CB | ASN | F | 394 | 4.381 | 34.854 | 64.325 | 1.00 | 147.72 |
| 5109 | CC | ASN | F | 394 | 5.826 | 34.441 | 64.523 | 1.00 | 150.70 |
| 5110 | OD1 | ASN | F | 394 | 6.109 | 33.321 | 64.952 | 1.00 | 151.54 |
| 5111 | ND2 | ASN | F | 394 | 6.750 | 35.348 | 64.224 | 1.00 | 153.56 |
| 5112 | C | ASN | F | 394 | 4.752 | 35.723 | 62.012 | 1.00 | 145.97 |
| 5113 | O | ASN | F | 394 | 5.934 | 35.434 | 61.828 | 1.00 | 145.63 |
| 5114 | N | GLY | F | 395 | 3.853 | 35.763 | 61.034 | 1.00 | 144.18 |
| 5115 | CA | GLY | F | 395 | 4.220 | 35.432 | 59.672 | 1.00 | 141.07 |
| 5116 | C | GLY | F | 395 | 3.888 | 33.974 | 59.426 | 1.00 | 141.09 |
| 5117 | O | GLY | F | 395 | 4.769 | 33.168 | 59.119 | 1.00 | 137.94 |
| 5118 | N | THR | F | 396 | 2.607 | 33.640 | 59.571 | 1.00 | 141.92 |
| 5119 | CA | THR | F | 396 | 2.130 | 32.273 | 59.382 | 1.00 | 135.95 |
| 5120 | CB | THR | F | 396 | 2.725 | 31.325 | 60.469 | 1.00 | 140.54 |
| 5121 | OG1 | THR | F | 396 | 4.151 | 31.249 | 60.323 | 1.00 | 144.65 |
| 5122 | CG2 | THR | F | 396 | 2.128 | 29.922 | 60.352 | 1.00 | 137.02 |
| 5123 | C | THR | F | 396 | 0.597 | 32.182 | 59.446 | 1.00 | 124.83 |
| 5124 | O | THR | F | 396 | −0.004 | 32.434 | 60.491 | 1.00 | 127.16 |
| 5125 | N | LEU | F | 397 | −0.033 | 31.824 | 58.330 | 1.00 | 124.72 |
| 5126 | CA | LEU | F | 397 | −1.486 | 31.674 | 58.297 | 1.00 | 114.50 |
| 5127 | CB | LEU | F | 397 | −2.088 | 32.433 | 57.116 | 1.00 | 109.07 |
| 5128 | CG | LEU | F | 397 | −3.581 | 32.147 | 56.921 | 1.00 | 101.75 |
| 5129 | CD1 | LEU | F | 397 | −4.328 | 32.486 | 58.206 | 1.00 | 105.22 |
| 5130 | CD2 | LEU | F | 397 | −4.117 | 32.937 | 55.735 | 1.00 | 91.73 |
| 5131 | C | LEU | F | 397 | −1.878 | 30.197 | 58.193 | 1.00 | 110.35 |
| 5132 | O | LEU | F | 397 | −2.212 | 29.703 | 57.112 | 1.00 | 96.73 |
| 5133 | N | THR | F | 398 | −1.834 | 29.498 | 59.323 | 1.00 | 104.94 |
| 5134 | CA | THR | F | 398 | −2.177 | 28.082 | 59.360 | 1.00 | 101.14 |
| 5135 | CB | THR | F | 398 | −1.985 | 27.500 | 60.776 | 1.00 | 104.58 |
| 5136 | OG1 | THR | F | 398 | −0.584 | 27.364 | 61.049 | 1.00 | 99.31 |
| 5137 | CG2 | THR | F | 398 | −2.675 | 26.142 | 60.900 | 1.00 | 99.27 |
| 5138 | C | THR | F | 398 | −3.614 | 27.824 | 58.921 | 1.00 | 95.26 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5139 | O | THR | F | 398 | −4.526 | 28.553 | 59.299 | 1.00 | 102.21 |
| 5140 | N | VAL | F | 399 | −3.800 | 26.782 | 58.118 | 1.00 | 99.78 |
| 5141 | CA | VAL | F | 399 | −5.119 | 26.400 | 57.625 | 1.00 | 97.95 |
| 5142 | CB | VAL | F | 399 | −5.405 | 26.998 | 56.226 | 1.00 | 92.18 |
| 5143 | CG1 | VAL | F | 399 | −6.798 | 26.597 | 55.768 | 1.00 | 91.84 |
| 5144 | CG2 | VAL | F | 399 | −5.277 | 28.512 | 56.263 | 1.00 | 94.00 |
| 5145 | C | VAL | F | 399 | −5.199 | 24.878 | 57.524 | 1.00 | 92.06 |
| 5146 | O | VAL | F | 399 | −4.636 | 24.276 | 56.611 | 1.00 | 76.84 |
| 5147 | N | THR | F | 400 | −5.900 | 24.260 | 58.467 | 1.00 | 82.96 |
| 5148 | CA | THR | F | 400 | −6.040 | 22.810 | 58.467 | 1.00 | 86.45 |
| 5149 | CB | THR | F | 400 | −5.623 | 22.194 | 59.819 | 1.00 | 83.36 |
| 5150 | OG1 | THR | F | 400 | −6.623 | 22.486 | 60.804 | 1.00 | 57.43 |
| 5151 | CG2 | THR | F | 400 | −4.285 | 22.752 | 60.270 | 1.00 | 81.73 |
| 5152 | C | THR | F | 400 | −7.472 | 22.350 | 58.186 | 1.00 | 93.97 |
| 5153 | O | THR | F | 400 | −8.440 | 23.084 | 58.382 | 1.00 | 79.99 |
| 5154 | N | SER | F | 401 | −7.587 | 21.116 | 57.718 | 1.00 | 90.56 |
| 5155 | CA | SER | F | 401 | −8.872 | 20.514 | 57.423 | 1.00 | 74.05 |
| 5156 | CB | SER | F | 401 | −9.126 | 20.498 | 55.914 | 1.00 | 70.49 |
| 5157 | OG | SER | F | 401 | −10.384 | 19.916 | 55.619 | 1.00 | 83.29 |
| 5158 | C | SER | F | 401 | −8.764 | 19.094 | 57.949 | 1.00 | 82.44 |
| 5159 | O | SER | F | 401 | −7.828 | 18.372 | 57.603 | 1.00 | 85.12 |
| 5160 | N | THR | F | 402 | −9.697 | 18.700 | 58.806 | 1.00 | 66.71 |
| 5161 | CA | THR | F | 402 | −9.671 | 17.356 | 59.355 | 1.00 | 57.97 |
| 5162 | CB | THR | F | 402 | −9.675 | 17.380 | 60.878 | 1.00 | 52.04 |
| 5163 | OG1 | THR | F | 402 | −8.406 | 17.853 | 61.351 | 1.00 | 77.34 |
| 5164 | CG2 | THR | F | 402 | −9.937 | 15.992 | 61.428 | 1.00 | 50.55 |
| 5165 | C | THR | F | 402 | −10.852 | 16.538 | 58.875 | 1.00 | 66.53 |
| 5166 | O | THR | F | 402 | −11.991 | 16.798 | 59.242 | 1.00 | 81.35 |
| 5167 | N | LEU | F | 403 | −10.566 | 15.540 | 58.053 | 1.00 | 66.54 |
| 5168 | CA | LEU | F | 403 | −11.602 | 14.677 | 57.510 | 1.00 | 73.55 |
| 5169 | CB | LEU | F | 403 | −11.293 | 14.361 | 56.042 | 1.00 | 54.45 |
| 5170 | CG | LEU | F | 403 | −12.270 | 13.402 | 55.359 | 1.00 | 73.80 |
| 5171 | CD1 | LEU | F | 403 | −13.594 | 14.126 | 55.080 | 1.00 | 63.90 |
| 5172 | CD2 | LEU | F | 403 | −11.652 | 12.880 | 54.072 | 1.00 | 54.07 |
| 5173 | C | LEU | F | 403 | −11.775 | 13.366 | 58.289 | 1.00 | 69.11 |
| 5174 | O | LEU | F | 403 | −10.829 | 12.583 | 58.449 | 1.00 | 64.80 |
| 5175 | N | PRO | F | 404 | −12.983 | 13.127 | 58.812 | 1.00 | 49.56 |
| 5176 | CD | PRO | F | 404 | −14.047 | 14.093 | 59.108 | 1.00 | 58.67 |
| 5177 | CA | PRO | F | 404 | −13.192 | 11.880 | 59.550 | 1.00 | 64.58 |
| 5178 | CB | PRO | F | 404 | −14.547 | 12.093 | 60.216 | 1.00 | 61.68 |
| 5179 | CG | PRO | F | 404 | −14.560 | 13.584 | 60.435 | 1.00 | 71.46 |
| 5180 | C | PRO | F | 404 | −13.206 | 10.777 | 58.507 | 1.00 | 43.66 |
| 5181 | O | PRO | F | 404 | −13.728 | 10.959 | 57.411 | 1.00 | 56.01 |
| 5182 | N | VAL | F | 405 | −12.629 | 9.637 | 58.843 | 1.00 | 37.31 |
| 5183 | CA | VAL | F | 405 | −12.552 | 8.543 | 57.897 | 1.00 | 49.22 |
| 5184 | CB | VAL | F | 405 | −11.076 | 8.290 | 57.494 | 1.00 | 66.56 |
| 5185 | CG1 | VAL | F | 405 | −10.945 | 6.957 | 56.789 | 1.00 | 81.81 |
| 5186 | CG2 | VAL | F | 405 | −10.580 | 9.414 | 56.596 | 1.00 | 68.98 |
| 5187 | C | VAL | F | 405 | −13.130 | 7.254 | 58.430 | 1.00 | 29.05 |
| 5188 | O | VAL | F | 405 | −13.085 | 6.982 | 59.629 | 1.00 | 66.63 |
| 5189 | N | GLY | F | 406 | −13.643 | 6.439 | 57.523 | 1.00 | 27.33 |
| 5190 | CA | GLY | F | 406 | −14.207 | 5.169 | 57.928 | 1.00 | 45.20 |
| 5191 | C | GLY | F | 406 | −13.096 | 4.260 | 58.406 | 1.00 | 60.14 |
| 5192 | O | GLY | F | 406 | −12.074 | 4.148 | 57.744 | 1.00 | 53.24 |
| 5193 | N | THR | F | 407 | −13.282 | 3.628 | 59.560 | 1.00 | 65.67 |
| 5194 | CA | THR | F | 407 | −12.282 | 2.728 | 60.091 | 1.00 | 48.48 |
| 5195 | CB | THR | F | 407 | −12.775 | 2.067 | 61.369 | 1.00 | 63.64 |
| 5196 | OG1 | THR | F | 407 | −13.025 | 3.076 | 62.354 | 1.00 | 99.17 |
| 5197 | CG2 | THR | F | 407 | −11.737 | 1.097 | 61.899 | 1.00 | 70.93 |
| 5198 | C | THR | F | 407 | −11.951 | 1.652 | 59.060 | 1.00 | 60.45 |
| 5199 | O | THR | F | 407 | −10.801 | 1.511 | 58.644 | 1.00 | 54.03 |
| 5200 | N | ALA | F | 408 | −12.958 | 0.901 | 58.630 | 1.00 | 70.64 |
| 5201 | CA | ALA | F | 408 | −12.738 | −0.154 | 57.647 | 1.00 | 72.62 |
| 5202 | CB | ALA | F | 408 | −14.019 | −0.956 | 57.438 | 1.00 | 79.42 |
| 5203 | C | ALA | F | 408 | −12.235 | 0.400 | 56.308 | 1.00 | 59.63 |
| 5204 | O | ALA | F | 408 | −11.466 | −0.258 | 55.616 | 1.00 | 44.96 |
| 5205 | N | ASP | F | 409 | −12.657 | 1.607 | 55.948 | 1.00 | 43.66 |
| 5206 | CA | ASP | F | 409 | −12.234 | 2.219 | 54.688 | 1.00 | 49.42 |
| 5207 | CB | ASP | F | 409 | −12.896 | 3.575 | 54.485 | 1.00 | 56.66 |
| 5208 | CG | ASP | F | 409 | −14.385 | 3.460 | 54.246 | 1.00 | 80.40 |
| 5209 | OD1 | ASP | F | 409 | −14.770 | 2.787 | 53.270 | 1.00 | 82.84 |
| 5210 | OD2 | ASP | F | 409 | −15.169 | 4.033 | 55.031 | 1.00 | 79.65 |
| 5211 | C | ASP | F | 409 | −10.743 | 2.391 | 54.626 | 1.00 | 63.89 |
| 5212 | O | ASP | F | 409 | −10.098 | 1.931 | 53.685 | 1.00 | 77.91 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5213 | N | TRP | F | 410 | −10.189 | 3.057 | 55.634 | 1.00 | 74.65 |
| 5214 | CA | TRP | F | 410 | −8.747 | 3.272 | 55.692 | 1.00 | 56.50 |
| 5215 | CB | TRP | F | 410 | −8.365 | 4.146 | 56.893 | 1.00 | 38.06 |
| 5216 | CG | TRP | F | 410 | −6.893 | 4.373 | 57.002 | 1.00 | 51.55 |
| 5217 | CD2 | TRP | F | 410 | −6.143 | 5.469 | 56.443 | 1.00 | 34.92 |
| 5218 | CE2 | TRP | F | 410 | −4.774 | 5.200 | 56.671 | 1.00 | 21.41 |
| 5219 | CE3 | TRP | F | 410 | −6.494 | 6.651 | 55.772 | 1.00 | 36.50 |
| 5220 | CD1 | TRP | F | 410 | −5.967 | 3.514 | 57.542 | 1.00 | 36.24 |
| 5221 | NE1 | TRP | F | 410 | −4.693 | 4.006 | 57.342 | 1.00 | 51.71 |
| 5222 | CZ2 | TRP | F | 410 | −3.762 | 6.072 | 56.250 | 1.00 | 51.84 |
| 5223 | CZ3 | TRP | F | 410 | −5.473 | 7.523 | 55.348 | 1.00 | 36.00 |
| 5224 | CH2 | TRP | F | 410 | −4.132 | 7.226 | 55.591 | 1.00 | 12.92 |
| 5225 | C | TRP | F | 410 | −8.026 | 1.938 | 55.777 | 1.00 | 47.92 |
| 5226 | O | TRP | F | 410 | −7.098 | 1.681 | 55.022 | 1.00 | 46.31 |
| 5227 | N | ILE | F | 411 | −8.480 | 1.080 | 56.674 | 1.00 | 50.97 |
| 5228 | CA | ILE | F | 411 | −7.866 | −0.222 | 56.856 | 1.00 | 63.10 |
| 5229 | CB | ILE | F | 411 | −8.563 | −0.992 | 57.997 | 1.00 | 69.10 |
| 5230 | CG2 | ILE | F | 411 | −8.026 | −2.408 | 58.085 | 1.00 | 80.36 |
| 5231 | CG1 | ILE | F | 411 | −8.334 | −0.259 | 59.316 | 1.00 | 71.23 |
| 5232 | CD1 | ILE | F | 411 | −8.942 | −0.948 | 60.509 | 1.00 | 90.98 |
| 5233 | C | ILE | F | 411 | −7.821 | −1.109 | 55.617 | 1.00 | 69.42 |
| 5234 | O | ILE | F | 411 | −6.859 | −1.858 | 55.431 | 1.00 | 88.03 |
| 5235 | N | GLU | F | 412 | −8.838 | −1.033 | 54.761 | 1.00 | 80.20 |
| 5236 | CA | GLU | F | 412 | −8.860 | −1.885 | 53.570 | 1.00 | 71.25 |
| 5237 | CB | GLU | F | 412 | −10.296 | −2.308 | 53.256 | 1.00 | 81.03 |
| 5238 | CG | GLU | F | 412 | −10.744 | −3.504 | 54.104 | 1.00 | 104.84 |
| 5239 | CD | GLU | F | 412 | −12.235 | −3.785 | 54.026 | 1.00 | 108.71 |
| 5240 | OE1 | GLU | F | 412 | −12.771 | −3.851 | 52.900 | 1.00 | 110.33 |
| 5241 | OE2 | GLU | F | 412 | −12.867 | −3.952 | 55.095 | 1.00 | 117.41 |
| 5242 | C | GLU | F | 412 | −8.166 | −1.371 | 52.312 | 1.00 | 64.66 |
| 5243 | O | GLU | F | 412 | −8.158 | −2.047 | 51.291 | 1.00 | 60.05 |
| 5244 | N | GLY | F | 413 | −7.585 | −0.181 | 52.365 | 1.00 | 54.86 |
| 5245 | CA | GLY | F | 413 | −6.867 | 0.273 | 51.201 | 1.00 | 40.80 |
| 5246 | C | GLY | F | 413 | −7.274 | 1.569 | 50.563 | 1.00 | 57.10 |
| 5247 | O | GLY | F | 413 | −6.629 | 2.024 | 49.610 | 1.00 | 53.46 |
| 5248 | N | GLU | F | 414 | −8.325 | 2.188 | 51.081 | 1.00 | 48.49 |
| 5249 | CA | GLU | F | 414 | −8.780 | 3.429 | 50.484 | 1.00 | 52.40 |
| 5250 | CB | GLU | F | 414 | −10.035 | 3.925 | 51.193 | 1.00 | 71.18 |
| 5251 | CG | GLU | F | 414 | −10.590 | 5.248 | 50.663 | 1.00 | 69.16 |
| 5252 | CD | GLU | F | 414 | −11.267 | 5.112 | 49.315 | 1.00 | 78.19 |
| 5253 | OE1 | GLU | F | 414 | −10.574 | 5.166 | 48.275 | 1.00 | 76.10 |
| 5254 | OE2 | GLU | F | 414 | −12.504 | 4.943 | 49.304 | 1.00 | 84.94 |
| 5255 | C | GLU | F | 414 | −7.710 | 4.496 | 50.550 | 1.00 | 41.29 |
| 5256 | O | GLU | F | 414 | −6.967 | 4.570 | 51.527 | 1.00 | 74.50 |
| 5257 | N | THR | F | 415 | −7.628 | 5.313 | 49.506 | 1.00 | 28.38 |
| 5258 | CA | THR | F | 415 | −6.684 | 6.426 | 49.456 | 1.00 | 51.93 |
| 5259 | CB | THR | F | 415 | −5.700 | 6.295 | 48.252 | 1.00 | 30.02 |
| 5260 | OG1 | THR | F | 415 | −5.331 | 7.599 | 47.779 | 1.00 | 43.30 |
| 5261 | CG2 | THR | F | 415 | −6.303 | 5.471 | 47.158 | 1.00 | 49.19 |
| 5262 | C | THR | F | 415 | −7.448 | 7.758 | 49.387 | 1.00 | 46.38 |
| 5263 | O | THR | F | 415 | −8.251 | 7.969 | 48.488 | 1.00 | 72.47 |
| 5264 | N | TYR | F | 416 | −7.199 | 8.642 | 50.354 | 1.00 | 59.48 |
| 5265 | CA | TYR | F | 416 | −7.865 | 9.942 | 50.434 | 1.00 | 40.83 |
| 5266 | CB | TYR | F | 416 | −8.205 | 10.266 | 51.897 | 1.00 | 33.03 |
| 5267 | CG | TYR | F | 416 | −9.135 | 9.234 | 52.514 | 1.00 | 63.31 |
| 5268 | CD1 | TYR | F | 416 | −8.663 | 7.967 | 52.865 | 1.00 | 66.35 |
| 5269 | CE1 | TYR | F | 416 | −9.524 | 6.977 | 53.355 | 1.00 | 58.00 |
| 5270 | CD2 | TYR | F | 416 | −10.499 | 9.491 | 52.675 | 1.00 | 51.69 |
| 5271 | CE2 | TYR | F | 416 | −11.362 | 8.510 | 53.164 | 1.00 | 46.44 |
| 5272 | CZ | TYR | F | 416 | −10.868 | 7.257 | 53.498 | 1.00 | 63.07 |
| 5273 | OH | TYR | F | 416 | −11.711 | 6.273 | 53.970 | 1.00 | 84.79 |
| 5274 | C | TYR | F | 416 | −7.034 | 11.064 | 49.838 | 1.00 | 56.48 |
| 5275 | O | TYR | F | 416 | −5.816 | 11.090 | 49.980 | 1.00 | 54.19 |
| 5276 | N | GLN | F | 417 | −7.705 | 12.003 | 49.179 | 1.00 | 58.49 |
| 5277 | CA | GLN | F | 417 | −7.017 | 13.119 | 48.541 | 1.00 | 79.18 |
| 5278 | CB | GLN | F | 417 | −7.113 | 12.973 | 47.020 | 1.00 | 80.78 |
| 5279 | CG | GLN | F | 417 | −6.420 | 14.067 | 46.233 | 1.00 | 84.58 |
| 5280 | CD | GLN | F | 417 | −6.742 | 13.998 | 44.754 | 1.00 | 112.78 |
| 5281 | OE1 | GLN | F | 417 | −7.884 | 14.223 | 44.344 | 1.00 | 118.06 |
| 5282 | NE2 | GLN | F | 417 | −5.737 | 13.680 | 43.943 | 1.00 | 119.13 |
| 5283 | C | GLN | F | 417 | −7.509 | 14.515 | 48.951 | 1.00 | 78.56 |
| 5284 | O | GLN | F | 417 | −8.703 | 14.749 | 49.136 | 1.00 | 59.68 |
| 5285 | N | CYS | F | 418 | −6.558 | 15.435 | 49.079 | 1.00 | 82.94 |
| 5286 | CA | CYS | F | 418 | −6.830 | 16.818 | 49.444 | 1.00 | 79.47 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5287 | C | CYS | F | 418 | −6.388 | 17.700 | 48.276 | 1.00 | 82.23 |
| 5288 | O | CYS | F | 418 | −5.227 | 17.663 | 47.872 | 1.00 | 80.72 |
| 5289 | CB | CYS | F | 418 | −6.032 | 17.202 | 50.700 | 1.00 | 63.12 |
| 5290 | SG | CYS | F | 418 | −6.199 | 18.950 | 51.204 | 1.00 | 98.27 |
| 5291 | N | ARG | F | 419 | −7.310 | 18.473 | 47.716 | 1.00 | 77.05 |
| 5292 | CA | ARG | F | 419 | −6.961 | 19.372 | 46.621 | 1.00 | 85.62 |
| 5293 | CB | ARG | F | 419 | −7.932 | 19.211 | 45.453 | 1.00 | 98.01 |
| 5294 | CG | ARG | F | 419 | −7.562 | 20.037 | 44.228 | 1.00 | 92.01 |
| 5295 | CD | ARG | F | 419 | −8.342 | 19.560 | 43.002 | 1.00 | 102.18 |
| 5296 | NE | ARG | F | 419 | −8.078 | 20.419 | 41.837 | 1.00 | 114.89 |
| 5297 | CZ | ARG | F | 419 | −8.404 | 21.707 | 41.753 | 1.00 | 117.10 |
| 5298 | NH1 | ARG | F | 419 | −9.010 | 22.313 | 42.768 | 1.00 | 116.92 |
| 5299 | NH2 | ARG | F | 419 | −8.122 | 22.393 | 40.652 | 1.00 | 114.84 |
| 5300 | C | ARG | F | 419 | −6.993 | 20.812 | 47.131 | 1.00 | 87.56 |
| 5301 | O | ARG | F | 419 | −8.019 | 21.292 | 47.610 | 1.00 | 90.72 |
| 5302 | N | VAL | F | 420 | −5.863 | 21.498 | 47.034 | 1.00 | 88.01 |
| 5303 | CA | VAL | F | 420 | −5.778 | 22.869 | 47.502 | 1.00 | 88.70 |
| 5304 | CB | VAL | F | 420 | −4.485 | 23.074 | 48.268 | 1.00 | 77.59 |
| 5305 | CG1 | VAL | F | 420 | −4.492 | 24.423 | 48.952 | 1.00 | 85.28 |
| 5306 | CG2 | VAL | F | 420 | −4.320 | 21.961 | 49.270 | 1.00 | 80.73 |
| 5307 | C | VAL | F | 420 | −5.855 | 23.868 | 46.348 | 1.00 | 102.92 |
| 5308 | O | VAL | F | 420 | −5.160 | 23.725 | 45.336 | 1.00 | 91.47 |
| 5309 | N | THR | F | 421 | −6.712 | 24.875 | 46.511 | 1.00 | 104.93 |
| 5310 | CA | THR | F | 421 | −6.910 | 25.913 | 45.499 | 1.00 | 111.53 |
| 5311 | CB | THR | F | 421 | −8.339 | 25.856 | 44.920 | 1.00 | 110.83 |
| 5312 | OG1 | THR | F | 421 | −8.592 | 24.545 | 44.396 | 1.00 | 110.25 |
| 5313 | CG2 | THR | F | 421 | −8.505 | 26.882 | 43.813 | 1.00 | 112.88 |
| 5314 | C | THR | F | 421 | −6.683 | 27.300 | 46.102 | 1.00 | 116.65 |
| 5315 | O | THR | F | 421 | −6.977 | 27.532 | 47.277 | 1.00 | 121.79 |
| 5316 | N | HIS | F | 422 | −6.158 | 28.217 | 45.292 | 1.00 | 121.56 |
| 5317 | CA | HIS | F | 422 | −5.887 | 29.581 | 45.745 | 1.00 | 130.48 |
| 5318 | CB | HIS | F | 422 | −4.611 | 29.612 | 46.602 | 1.00 | 128.92 |
| 5319 | CG | HIS | F | 422 | −4.365 | 30.924 | 47.285 | 1.00 | 129.50 |
| 5320 | CD2 | HIS | F | 422 | −3.303 | 31.763 | 47.250 | 1.00 | 134.15 |
| 5321 | ND1 | HIS | F | 422 | −5.285 | 31.509 | 48.130 | 1.00 | 126.50 |
| 5322 | CE1 | HIS | F | 422 | −4.801 | 32.652 | 48.583 | 1.00 | 128.16 |
| 5323 | NE2 | HIS | F | 422 | −3.599 | 32.829 | 48.065 | 1.00 | 137.39 |
| 5324 | C | HIS | F | 422 | −5.730 | 30.512 | 44.541 | 1.00 | 129.44 |
| 5325 | O | HIS | F | 422 | −5.224 | 30.103 | 43.496 | 1.00 | 129.99 |
| 5326 | N | PRO | F | 423 | −6.171 | 31.778 | 44.674 | 1.00 | 137.11 |
| 5327 | CD | PRO | F | 423 | −6.896 | 32.348 | 45.826 | 1.00 | 134.74 |
| 5328 | CA | PRO | F | 423 | −6.076 | 32.764 | 43.590 | 1.00 | 132.90 |
| 5329 | CB | PRO | F | 423 | −6.973 | 33.898 | 44.082 | 1.00 | 129.07 |
| 5330 | CG | PRO | F | 423 | −6.791 | 33.836 | 45.570 | 1.00 | 130.91 |
| 5331 | C | PRO | F | 423 | −4.659 | 33.248 | 43.277 | 1.00 | 134.76 |
| 5332 | O | PRO | F | 423 | −4.379 | 33.677 | 42.159 | 1.00 | 133.55 |
| 5333 | N | HIS | F | 424 | −3.768 | 33.176 | 44.260 | 1.00 | 137.33 |
| 5334 | CA | HIS | F | 424 | −2.392 | 33.627 | 44.071 | 1.00 | 134.19 |
| 5335 | CB | HIS | F | 424 | −1.914 | 34.375 | 45.322 | 1.00 | 138.82 |
| 5336 | CG | HIS | F | 424 | −2.802 | 35.514 | 45.720 | 1.00 | 139.59 |
| 5337 | CD2 | HIS | F | 424 | −3.473 | 35.762 | 46.869 | 1.00 | 143.87 |
| 5338 | ND1 | HIS | F | 424 | −3.088 | 36.563 | 44.874 | 1.00 | 137.50 |
| 5339 | CE1 | HIS | F | 424 | −3.898 | 37.409 | 45.485 | 1.00 | 137.42 |
| 5340 | NE2 | HIS | F | 424 | −4.147 | 36.947 | 46.697 | 1.00 | 138.15 |
| 5341 | C | HIS | F | 424 | −1.418 | 32.492 | 43.742 | 1.00 | 134.99 |
| 5342 | O | HIS | F | 424 | −0.254 | 32.528 | 44.148 | 1.00 | 139.57 |
| 5343 | N | LEU | F | 425 | −1.896 | 31.490 | 43.009 | 1.00 | 133.60 |
| 5344 | CA | LEU | F | 425 | −1.065 | 30.355 | 42.611 | 1.00 | 134.43 |
| 5345 | CB | LEU | F | 425 | −1.039 | 29.284 | 43.707 | 1.00 | 138.14 |
| 5346 | CG | LEU | F | 425 | −0.115 | 29.530 | 44.904 | 1.00 | 141.99 |
| 5347 | CD1 | LEU | F | 425 | −0.240 | 28.377 | 45.889 | 1.00 | 143.98 |
| 5348 | CD2 | LEU | F | 425 | 1.325 | 29.664 | 44.428 | 1.00 | 135.09 |
| 5349 | C | LEU | F | 425 | −1.563 | 29.735 | 41.310 | 1.00 | 135.04 |
| 5350 | O | LEU | F | 425 | −2.769 | 29.596 | 41.099 | 1.00 | 127.50 |
| 5351 | N | PRO | F | 426 | −0.631 | 29.339 | 40.425 | 1.00 | 137.00 |
| 5352 | CD | PRO | F | 426 | 0.823 | 29.286 | 40.665 | 1.00 | 133.29 |
| 5353 | CA | PRO | F | 426 | −0.967 | 28.729 | 39.132 | 1.00 | 134.10 |
| 5354 | CB | PRO | F | 426 | 0.404 | 28.471 | 38.508 | 1.00 | 135.47 |
| 5355 | CG | PRO | F | 426 | 1.266 | 28.199 | 39.710 | 1.00 | 134.92 |
| 5356 | C | PRO | F | 426 | −1.794 | 27.453 | 39.269 | 1.00 | 130.76 |
| 5357 | O | PRO | F | 426 | −3.013 | 27.506 | 39.439 | 1.00 | 125.26 |
| 5358 | N | ARG | F | 427 | −1.121 | 26.310 | 39.189 | 1.00 | 128.50 |
| 5359 | CA | ARG | F | 427 | −1.780 | 25.016 | 39.307 | 1.00 | 126.30 |
| 5360 | CB | ARG | F | 427 | −0.852 | 23.919 | 38.781 | 1.00 | 130.15 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5361 | CG | ARG | F | 427 | −1.419 | 22.516 | 38.863 | 1.00 | 137.40 |
| 5362 | CD | ARG | F | 427 | −0.395 | 21.499 | 38.393 | 1.00 | 144.22 |
| 5363 | NE | ARG | F | 427 | −0.860 | 20.126 | 38.568 | 1.00 | 151.28 |
| 5364 | CZ | ARG | F | 427 | −0.146 | 19.049 | 38.252 | 1.00 | 149.17 |
| 5365 | NH1 | ARG | F | 427 | 1.070 | 19.187 | 37.741 | 1.00 | 151.48 |
| 5366 | NH2 | ARG | F | 427 | −0.643 | 17.835 | 38.450 | 1.00 | 143.17 |
| 5367 | C | ARG | F | 427 | −2.142 | 24.745 | 40.768 | 1.00 | 123.55 |
| 5368 | O | ARG | F | 427 | −1.615 | 25.394 | 41.676 | 1.00 | 119.18 |
| 5369 | N | ALA | F | 428 | −3.039 | 23.786 | 40.986 | 1.00 | 120.67 |
| 5370 | CA | ALA | F | 428 | −3.484 | 23.428 | 42.333 | 1.00 | 122.87 |
| 5371 | CB | ALA | F | 428 | −4.936 | 22.956 | 42.295 | 1.00 | 121.65 |
| 5372 | C | ALA | F | 428 | −2.609 | 22.350 | 42.966 | 1.00 | 117.70 |
| 5373 | O | ALA | F | 428 | −1.973 | 21.564 | 42.267 | 1.00 | 118.01 |
| 5374 | N | LEU | F | 429 | −2.587 | 22.318 | 44.295 | 1.00 | 114.46 |
| 5375 | CA | LEU | F | 429 | −1.796 | 21.336 | 45.031 | 1.00 | 108.33 |
| 5376 | CB | LEU | F | 429 | −1.283 | 21.936 | 46.344 | 1.00 | 114.65 |
| 5377 | CG | LEU | F | 429 | −0.205 | 23.017 | 46.232 | 1.00 | 108.87 |
| 5378 | CD1 | LEU | F | 429 | 0.167 | 23.522 | 47.612 | 1.00 | 98.13 |
| 5379 | CD2 | LEU | F | 429 | 1.014 | 22.438 | 45.531 | 1.00 | 113.68 |
| 5380 | C | LEU | F | 429 | −2.623 | 20.095 | 45.331 | 1.00 | 108.66 |
| 5381 | O | LEU | F | 429 | −3.842 | 20.170 | 45.492 | 1.00 | 111.03 |
| 5382 | N | MET | F | 430 | −1.952 | 18.952 | 45.408 | 1.00 | 103.16 |
| 5383 | CA | MET | F | 430 | −2.631 | 17.694 | 45.679 | 1.00 | 103.89 |
| 5384 | CB | MET | F | 430 | −2.982 | 17.003 | 44.362 | 1.00 | 108.77 |
| 5385 | CG | MET | F | 430 | −3.936 | 17.810 | 43.492 | 1.00 | 111.82 |
| 5386 | SD | MET | F | 430 | −4.003 | 17.223 | 41.792 | 1.00 | 136.14 |
| 5387 | CE | MET | F | 430 | −2.780 | 18.282 | 41.009 | 1.00 | 120.58 |
| 5388 | C | MET | F | 430 | −1.779 | 16.771 | 46.538 | 1.00 | 101.30 |
| 5389 | O | MET | F | 430 | −0.579 | 16.629 | 46.307 | 1.00 | 106.77 |
| 5390 | N | ARG | F | 431 | −2.414 | 16.157 | 47.534 | 1.00 | 98.83 |
| 5391 | CA | ARG | F | 431 | −1.748 | 15.237 | 48.454 | 1.00 | 76.76 |
| 5392 | CB | ARG | F | 431 | −1.475 | 15.916 | 49.801 | 1.00 | 65.43 |
| 5393 | CG | ARG | F | 431 | −0.852 | 17.293 | 49.682 | 1.00 | 72.47 |
| 5394 | CD | ARG | F | 431 | 0.494 | 17.247 | 48.996 | 1.00 | 99.75 |
| 5395 | NE | ARG | F | 431 | 0.949 | 18.579 | 48.622 | 1.00 | 88.46 |
| 5396 | CZ | ARG | F | 431 | 2.096 | 18.828 | 48.002 | 1.00 | 100.03 |
| 5397 | NH1 | ARG | F | 431 | 2.911 | 17.829 | 47.684 | 1.00 | 102.09 |
| 5398 | NH2 | ARG | F | 431 | 2.426 | 20.076 | 47.699 | 1.00 | 92.10 |
| 5399 | C | ARG | F | 431 | −2.674 | 14.061 | 48.682 | 1.00 | 74.45 |
| 5400 | O | ARG | F | 431 | −3.894 | 14.222 | 48.708 | 1.00 | 76.68 |
| 5401 | N | SER | F | 432 | −2.093 | 12.880 | 48.842 | 1.00 | 61.85 |
| 5402 | CA | SER | F | 432 | −2.874 | 11.681 | 49.079 | 1.00 | 60.88 |
| 5403 | CB | SER | F | 432 | −2.908 | 10.814 | 47.821 | 1.00 | 62.73 |
| 5404 | OG | SER | F | 432 | −1.610 | 10.472 | 47.391 | 1.00 | 57.83 |
| 5405 | C | SER | F | 432 | −2.244 | 10.926 | 50.232 | 1.00 | 59.71 |
| 5406 | O | SER | F | 432 | −1.084 | 11.162 | 50.554 | 1.00 | 64.28 |
| 5407 | N | THR | F | 433 | −3.004 | 10.037 | 50.866 | 1.00 | 50.42 |
| 5408 | CA | THR | F | 433 | −2.475 | 9.274 | 51.981 | 1.00 | 43.65 |
| 5409 | CB | THR | F | 433 | −2.676 | 10.063 | 53.284 | 1.00 | 55.79 |
| 5410 | CG1 | THR | F | 433 | −2.115 | 9.337 | 54.379 | 1.00 | 72.89 |
| 5411 | CG2 | THR | F | 433 | −4.150 | 10.306 | 53.539 | 1.00 | 59.03 |
| 5412 | C | THR | F | 433 | −3.117 | 7.885 | 52.083 | 1.00 | 57.50 |
| 5413 | O | THR | F | 433 | −4.226 | 7.690 | 51.594 | 1.00 | 56.97 |
| 5414 | N | THR | F | 434 | −2.412 | 6.927 | 52.697 | 1.00 | 47.97 |
| 5415 | CA | THR | F | 434 | −2.905 | 5.549 | 52.863 | 1.00 | 44.34 |
| 5416 | CB | THR | F | 434 | −2.924 | 4.743 | 51.526 | 1.00 | 66.02 |
| 5417 | OG1 | THR | F | 434 | −1.951 | 5.267 | 50.618 | 1.00 | 81.67 |
| 5418 | CG2 | THR | F | 434 | −4.277 | 4.782 | 50.889 | 1.00 | 73.57 |
| 5419 | C | THR | F | 434 | −2.079 | 4.728 | 53.846 | 1.00 | 46.92 |
| 5420 | O | THR | F | 434 | −2.259 | 3.503 | 53.963 | 1.00 | 36.65 |
| 5421 | N | ARG | F | 440 | 6.916 | −2.872 | 57.130 | 1.00 | 22.92 |
| 5422 | CA | ARG | F | 440 | 6.161 | −3.072 | 58.376 | 1.00 | 59.46 |
| 5423 | CB | ARC | F | 440 | 4.753 | −3.659 | 58.079 | 1.00 | 37.39 |
| 5424 | CG | ARG | F | 440 | 3.967 | −2.961 | 56.952 | 1.00 | 68.37 |
| 5425 | CD | ARG | F | 440 | 3.461 | −1.537 | 57.263 | 1.00 | 70.36 |
| 5426 | NE | ARG | F | 440 | 3.019 | −0.835 | 56.044 | 1.00 | 90.64 |
| 5427 | CZ | ARG | F | 440 | 2.345 | 0.321 | 56.013 | 1.00 | 86.65 |
| 5428 | NH1 | ARG | F | 440 | 2.009 | 0.936 | 57.138 | 1.00 | 93.06 |
| 5429 | NH2 | ARG | F | 440 | 2.007 | 0.873 | 54.848 | 1.00 | 93.47 |
| 5430 | C | ARG | F | 440 | 6.886 | −3.981 | 59.401 | 1.00 | 49.79 |
| 5431 | O | ARG | F | 440 | 7.415 | −5.027 | 59.054 | 1.00 | 45.10 |
| 5432 | N | ALA | F | 441 | 6.908 | −3.575 | 60.669 | 1.00 | 53.67 |
| 5433 | CA | ALA | F | 441 | 7.556 | −4.369 | 61.722 | 1.00 | 47.65 |
| 5434 | CB | ALA | F | 441 | 9.054 | −4.145 | 61.725 | 1.00 | 22.80 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5435 | C | ALA | F | 441 | 7.013 | −4.030 | 63.087 | 1.00 | 38.20 |
| 5436 | O | ALA | F | 441 | 6.884 | −2.862 | 63.423 | 1.00 | 43.69 |
| 5437 | N | ALA | F | 442 | 6.725 | −5.070 | 63.869 | 1.00 | 34.40 |
| 5438 | CA | ALA | F | 442 | 6.190 | −4.911 | 65.226 | 1.00 | 40.27 |
| 5439 | CB | ALA | F | 442 | 5.750 | −6.244 | 65.780 | 1.00 | 37.81 |
| 5440 | C | ALA | F | 442 | 7.200 | −4.269 | 66.173 | 1.00 | 39.77 |
| 5441 | O | ALA | F | 442 | 8.394 | −4.387 | 65.997 | 1.00 | 38.08 |
| 5442 | N | PRO | F | 443 | 6.706 | −3.568 | 67.198 | 1.00 | 49.02 |
| 5443 | CD | PRO | F | 443 | 5.316 | −3.117 | 67.362 | 1.00 | 43.08 |
| 5444 | CA | PRO | F | 443 | 7.567 | −2.900 | 68.175 | 1.00 | 46.02 |
| 5445 | CB | PRO | F | 443 | 6.670 | −1.790 | 68.719 | 1.00 | 36.70 |
| 5446 | CG | PRO | F | 443 | 5.529 | −1.708 | 67.747 | 1.00 | 46.98 |
| 5447 | C | PRO | F | 443 | 8.049 | −3.794 | 69.314 | 1.00 | 39.39 |
| 5448 | O | PRO | F | 443 | 7.313 | −4.651 | 69.789 | 1.00 | 33.60 |
| 5449 | N | ALA | F | 444 | 9.294 | −3.602 | 69.727 | 1.00 | 33.87 |
| 5450 | CA | ALA | F | 444 | 9.815 | −4.336 | 70.878 | 1.00 | 29.28 |
| 5451 | CB | ALA | F | 444 | 11.316 | −4.710 | 70.679 | 1.00 | 28.84 |
| 5452 | C | ALA | F | 444 | 9.616 | −3.281 | 72.001 | 1.00 | 31.84 |
| 5453 | O | ALA | F | 444 | 9.922 | −2.088 | 71.813 | 1.00 | 33.65 |
| 5454 | N | VAL | F | 445 | 9.078 | −3.713 | 73.143 | 1.00 | 30.76 |
| 5455 | CA | VAL | F | 445 | 8.771 | −2.780 | 74.231 | 1.00 | 19.39 |
| 5456 | CB | VAL | F | 445 | 7.205 | −2.609 | 74.392 | 1.00 | 38.54 |
| 5457 | CG1 | VAL | F | 445 | 6.879 | −1.727 | 75.633 | 1.00 | 12.09 |
| 5458 | CG2 | VAL | F | 445 | 6.606 | −2.006 | 73.117 | 1.00 | 19.41 |
| 5459 | C | VAL | F | 445 | 9.315 | −3.075 | 75.613 | 1.00 | 32.66 |
| 5460 | O | VAL | F | 445 | 9.170 | −4.189 | 76.144 | 1.00 | 20.01 |
| 5461 | N | TYR | F | 446 | 9.938 | −2.065 | 76.214 | 1.00 | 29.25 |
| 5462 | CA | TYR | F | 446 | 10.427 | −2.262 | 77.572 | 1.00 | 35.78 |
| 5463 | CB | TYR | F | 446 | 11.866 | −2.765 | 77.608 | 1.00 | 50.40 |
| 5464 | CG | TYR | F | 446 | 12.110 | −3.441 | 78.949 | 1.00 | 93.03 |
| 5465 | CD1 | TYR | F | 446 | 11.243 | −4.440 | 79.413 | 1.00 | 93.48 |
| 5466 | CE1 | TYR | F | 446 | 11.429 | −5.037 | 80.661 | 1.00 | 86.20 |
| 5467 | CD2 | TYR | F | 446 | 13.166 | −3.064 | 79.772 | 1.00 | 92.10 |
| 5468 | CE2 | TYR | F | 446 | 13.358 | −3.656 | 81.020 | 1.00 | 81.32 |
| 5469 | CZ | TYR | F | 446 | 12.491 | −4.638 | 81.456 | 1.00 | 87.69 |
| 5470 | OH | TYR | F | 446 | 12.708 | −5.215 | 82.687 | 1.00 | 95.34 |
| 5471 | C | TYR | F | 446 | 10.266 | −1.081 | 78.502 | 1.00 | 37.31 |
| 5472 | O | TYR | F | 446 | 10.419 | 0.072 | 78.103 | 1.00 | 33.23 |
| 5473 | N | ALA | F | 447 | 9.958 | −1.398 | 79.760 | 1.00 | 23.43 |
| 5474 | CA | ALA | F | 447 | 9.680 | −0.373 | 80.779 | 1.00 | 32.22 |
| 5475 | CB | ALA | F | 447 | 8.206 | −0.478 | 81.205 | 1.00 | 31.87 |
| 5476 | C | ALA | F | 447 | 10.565 | −0.369 | 82.015 | 1.00 | 34.43 |
| 5477 | O | ALA | F | 447 | 10.885 | −1.419 | 82.568 | 1.00 | 37.67 |
| 5478 | N | PHE | F | 448 | 10.945 | 0.824 | 82.461 | 1.00 | 39.14 |
| 5479 | CA | PHE | F | 448 | 11.796 | 0.919 | 83.646 | 1.00 | 39.00 |
| 5480 | CB | PHE | F | 448 | 13.209 | 1.381 | 83.279 | 1.00 | 44.86 |
| 5481 | CG | PHE | F | 448 | 13.772 | 0.713 | 82.063 | 1.00 | 35.87 |
| 5482 | CD1 | PHE | F | 448 | 13.565 | 1.270 | 80.789 | 1.00 | 33.15 |
| 5483 | CD2 | PHE | F | 448 | 14.522 | −0.451 | 82.183 | 1.00 | 23.74 |
| 5484 | CE1 | PHE | F | 448 | 14.103 | 0.682 | 79.649 | 1.00 | 25.05 |
| 5485 | CE2 | PHE | F | 448 | 15.064 | −1.048 | 81.055 | 1.00 | 42.18 |
| 5486 | CZ | PHE | F | 448 | 14.851 | −0.473 | 79.775 | 1.00 | 21.25 |
| 5487 | C | PHE | F | 448 | 11.270 | 1.864 | 84.692 | 1.00 | 41.18 |
| 5488 | O | PHE | F | 448 | 10.497 | 2.775 | 84.400 | 1.00 | 35.86 |
| 5489 | N | ALA | F | 449 | 11.710 | 1.632 | 85.923 | 1.00 | 30.94 |
| 5490 | CA | ALA | F | 449 | 11.339 | 2.483 | 87.051 | 1.00 | 37.16 |
| 5491 | CB | ALA | F | 449 | 10.534 | 1.693 | 88.092 | 1.00 | 30.37 |
| 5492 | C | ALA | F | 449 | 12.632 | 2.991 | 87.664 | 1.00 | 42.46 |
| 5493 | O | ALA | F | 449 | 13.594 | 2.241 | 87.813 | 1.00 | 46.11 |
| 5494 | N | THR | F | 450 | 12.651 | 4.272 | 88.009 | 1.00 | 51.08 |
| 5495 | CA | THR | F | 450 | 13.812 | 4.906 | 88.623 | 1.00 | 45.62 |
| 5496 | CB | THR | F | 450 | 13.642 | 6.436 | 88.608 | 1.00 | 40.77 |
| 5497 | OG1 | THR | F | 450 | 14.054 | 6.956 | 87.335 | 1.00 | 37.30 |
| 5498 | CG2 | THR | F | 450 | 14.444 | 7.081 | 89.718 | 1.00 | 70.03 |
| 5499 | C | THR | F | 450 | 13.988 | 4.443 | 90.063 | 1.00 | 36.82 |
| 5500 | O | THR | F | 450 | 13.018 | 4.118 | 90.738 | 1.00 | 47.68 |
| 5501 | N | PRO | F | 451 | 15.244 | 4.390 | 90.546 | 1.00 | 68.47 |
| 5502 | CD | PRO | F | 451 | 16.476 | 4.468 | 89.745 | 1.00 | 66.43 |
| 5503 | CA | PRO | F | 451 | 15.560 | 3.970 | 91.924 | 1.00 | 63.12 |
| 5504 | CB | PRO | F | 451 | 17.070 | 3.711 | 91.878 | 1.00 | 62.14 |
| 5505 | CG | PRO | F | 451 | 17.350 | 3.451 | 90.443 | 1.00 | 75.08 |
| 5506 | C | PRO | F | 451 | 15.223 | 5.124 | 92.871 | 1.00 | 58.66 |
| 5507 | O | PRO | F | 451 | 14.937 | 6.228 | 92.397 | 1.00 | 32.12 |
| 5508 | N | GLU | F | 452 | 15.269 | 4.860 | 94.183 | 1.00 | 70.37 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5509 | CA | GLU | F | 452 | 14.976 | 5.850 | 95.237 | 1.00 | 87.12 |
| 5510 | CB | GLU | F | 452 | 13.897 | 6.847 | 94.793 | 1.00 | 99.69 |
| 5511 | CG | GLU | F | 452 | 14.442 | 8.111 | 94.144 | 1.00 | 94.75 |
| 5512 | CD | GLU | F | 452 | 13.470 | 8.701 | 93.140 | 1.00 | 103.97 |
| 5513 | OE1 | GLU | F | 452 | 12.388 | 9.162 | 93.562 | 1.00 | 95.18 |
| 5514 | DE2 | GLU | F | 452 | 13.788 | 8.693 | 91.928 | 1.00 | 79.99 |
| 5515 | C | GLU | F | 452 | 14.506 | 5.189 | 96.526 | 1.00 | 93.15 |
| 5516 | O | GLU | F | 452 | 13.544 | 5.651 | 97.148 | 1.00 | 90.39 |
| 5517 | N | LYS | F | 459 | 8.061 | 12.454 | 92.552 | 1.00 | 64.44 |
| 5518 | CA | LYS | F | 459 | 8.819 | 12.681 | 91.320 | 1.00 | 95.03 |
| 5519 | CB | LYS | F | 459 | 9.796 | 13.846 | 91.519 | 1.00 | 105.76 |
| 5520 | CG | LYS | F | 459 | 9.191 | 15.225 | 91.264 | 1.00 | 101.04 |
| 5521 | CD | LYS | F | 459 | 8.946 | 15.463 | 89.781 | 1.00 | 112.59 |
| 5522 | CE | LYS | F | 459 | 8.498 | 16.895 | 89.505 | 1.00 | 117.06 |
| 5523 | NZ | LYS | F | 459 | 8.426 | 17.187 | 88.038 | 1.00 | 118.81 |
| 5524 | C | LYS | F | 459 | 9.575 | 11.436 | 90.827 | 1.00 | 95.43 |
| 5525 | O | LYS | F | 459 | 10.592 | 11.539 | 90.118 | 1.00 | 72.06 |
| 5526 | N | ARG | F | 460 | 9.052 | 10.269 | 91.198 | 1.00 | 85.99 |
| 5527 | CA | ARG | F | 460 | 9.624 | 8.976 | 90.825 | 1.00 | 66.76 |
| 5528 | CB | ARG | F | 460 | 9.091 | 7.902 | 91.776 | 1.00 | 62.65 |
| 5529 | CG | ARG | F | 460 | 9.543 | 8.126 | 93.230 | 1.00 | 77.13 |
| 5530 | CD | ARG | F | 460 | 9.466 | 9.607 | 93.710 | 1.00 | 57.62 |
| 5531 | NE | ARG | F | 460 | 8.104 | 10.152 | 93.721 | 1.00 | 72.17 |
| 5532 | CZ | ARC | F | 460 | 7.352 | 10.318 | 94.811 | 1.00 | 73.85 |
| 5533 | NH1 | ARG | F | 460 | 7.814 | 9.990 | 96.016 | 1.00 | 79.37 |
| 5534 | NH2 | ARG | F | 460 | 6.123 | 10.806 | 94.692 | 1.00 | 63.60 |
| 5535 | C | ARG | F | 460 | 9.226 | 8.704 | 89.374 | 1.00 | 58.49 |
| 5536 | O | ARG | F | 460 | 8.034 | 8.618 | 89.055 | 1.00 | 50.61 |
| 5537 | N | THR | F | 461 | 10.227 | 8.567 | 88.498 | 1.00 | 43.43 |
| 5538 | CA | THR | F | 461 | 9.955 | 8.389 | 87.072 | 1.00 | 32.32 |
| 5539 | CB | THR | F | 461 | 10.882 | 9.271 | 86.213 | 1.00 | 32.09 |
| 5540 | CG1 | THR | F | 461 | 11.260 | 10.440 | 86.944 | 1.00 | 40.18 |
| 5541 | CG2 | THR | F | 461 | 10.162 | 9.729 | 84.966 | 1.00 | 45.95 |
| 5542 | C | THR | F | 461 | 9.992 | 6.990 | 86.489 | 1.00 | 41.97 |
| 5543 | O | THR | F | 461 | 10.780 | 6.128 | 86.892 | 1.00 | 40.42 |
| 5544 | N | LEU | F | 462 | 9.095 | 6.782 | 85.534 | 1.00 | 32.08 |
| 5545 | CA | LEU | F | 462 | 8.990 | 5.516 | 84.837 | 1.00 | 36.60 |
| 5546 | CB | LEU | F | 462 | 7.572 | 4.959 | 84.929 | 1.00 | 40.47 |
| 5547 | CG | LEU | F | 462 | 6.985 | 4.731 | 86.315 | 1.00 | 43.40 |
| 5548 | CD1 | LEU | F | 462 | 5.556 | 4.222 | 86.155 | 1.00 | 41.56 |
| 5549 | CD2 | LEU | F | 462 | 7.834 | 3.743 | 87.095 | 1.00 | 33.31 |
| 5550 | C | LEU | F | 462 | 9.319 | 5.831 | 83.391 | 1.00 | 38.33 |
| 5551 | O | LEU | F | 462 | 8.873 | 6.846 | 82.838 | 1.00 | 49.03 |
| 5552 | N | ALA | F | 463 | 10.109 | 4.970 | 82.781 | 1.00 | 31.53 |
| 5553 | CA | ALA | F | 463 | 10.487 | 5.191 | 81.418 | 1.00 | 23.88 |
| 5554 | CB | ALA | F | 463 | 11.967 | 5.498 | 81.351 | 1.00 | 40.72 |
| 5555 | C | ALA | F | 463 | 10.167 | 3.970 | 80.570 | 1.00 | 44.96 |
| 5556 | O | ALA | F | 463 | 10.220 | 2.805 | 81.032 | 1.00 | 33.62 |
| 5557 | N | CYS | F | 464 | 9.864 | 4.245 | 79.307 | 1.00 | 40.02 |
| 5558 | CA | CYS | F | 464 | 9.532 | 3.188 | 78.381 | 1.00 | 29.04 |
| 5559 | C | CYS | F | 464 | 10.271 | 3.387 | 77.074 | 1.00 | 33.67 |
| 5560 | O | CYS | F | 464 | 10.256 | 4.477 | 76.495 | 1.00 | 39.49 |
| 5561 | CB | CYS | F | 464 | 8.037 | 3.215 | 78.141 | 1.00 | 46.62 |
| 5562 | SG | CYS | F | 464 | 7.335 | 1.789 | 77.278 | 1.00 | 59.01 |
| 5563 | N | LEU | F | 465 | 10.931 | 2.326 | 76.634 | 1.00 | 23.84 |
| 5564 | CA | LEU | F | 465 | 11.656 | 2.334 | 75.386 | 1.00 | 24.39 |
| 5565 | CB | LEU | F | 465 | 13.078 | 1.766 | 75.549 | 1.00 | 33.76 |
| 5566 | CG | LEU | F | 465 | 13.789 | 1.435 | 74.216 | 1.00 | 30.49 |
| 5567 | CD1 | LEU | F | 465 | 13.979 | 2.704 | 73.356 | 1.00 | 30.91 |
| 5568 | CD2 | LEU | F | 465 | 15.135 | 0.803 | 74.507 | 1.00 | 27.47 |
| 5569 | C | LEU | F | 465 | 10.852 | 1.457 | 74.434 | 1.00 | 35.18 |
| 5570 | O | LEU | F | 465 | 10.510 | 0.300 | 74.755 | 1.00 | 23.38 |
| 5571 | N | ILE | F | 466 | 10.528 | 2.022 | 73.274 | 1.00 | 25.89 |
| 5572 | CA | ILE | F | 466 | 9.755 | 1.307 | 72.256 | 1.00 | 33.05 |
| 5573 | CB | ILE | F | 466 | 8.364 | 1.963 | 72.093 | 1.00 | 56.38 |
| 5574 | CG2 | ILE | F | 466 | 7.464 | 1.098 | 71.215 | 1.00 | 37.66 |
| 5575 | CG1 | ILE | F | 466 | 7.728 | 2.136 | 73.471 | 1.00 | 45.76 |
| 5576 | CD1 | ILE | F | 466 | 6.754 | 3.242 | 73.561 | 1.00 | 34.74 |
| 5577 | C | ILE | F | 466 | 10.569 | 1.414 | 70.962 | 1.00 | 38.49 |
| 5578 | O | ILE | F | 466 | 10.774 | 2.514 | 70.423 | 1.00 | 36.24 |
| 5579 | N | GLN | F | 467 | 11.013 | 0.269 | 70.461 | 1.00 | 28.36 |
| 5580 | CA | GLN | F | 467 | 11.879 | 0.261 | 69.287 | 1.00 | 43.20 |
| 5581 | CB | GLN | F | 467 | 13.327 | 0.240 | 69.779 | 1.00 | 32.88 |
| 5582 | CG | GLN | F | 467 | 13.606 | −0.952 | 70.670 | 1.00 | 17.05 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5583 | CD | GLN | F | 467 | 15.069 | −1.080 | 71.037 | 1.00 | 46.49 |
| 5584 | OE1 | GLN | F | 467 | 15.802 | −0.090 | 71.108 | 1.00 | 28.71 |
| 5585 | NE2 | GLN | F | 467 | 15.499 | −2.304 | 71.285 | 1.00 | 20.71 |
| 5586 | C | GLN | F | 467 | 11.732 | −0.830 | 68.205 | 1.00 | 52.19 |
| 5587 | O | GLN | F | 467 | 11.039 | −1.849 | 68.372 | 1.00 | 32.49 |
| 5588 | N | ASN | F | 468 | 12.445 | −0.584 | 67.102 | 1.00 | 35.89 |
| 5589 | CA | ASN | F | 468 | 12.510 | −1.468 | 65.943 | 1.00 | 39.79 |
| 5590 | CB | ASN | F | 468 | 13.098 | −2.824 | 66.341 | 1.00 | 39.69 |
| 5591 | CG | ASN | F | 468 | 14.469 | −2.704 | 66.958 | 1.00 | 35.32 |
| 5592 | OD1 | ASN | F | 468 | 15.232 | −1.794 | 66.634 | 1.00 | 33.94 |
| 5593 | ND2 | ASN | F | 468 | 14.791 | −3.627 | 67.852 | 1.00 | 34.32 |
| 5594 | C | ASN | F | 468 | 11.171 | −1.689 | 65.244 | 1.00 | 46.77 |
| 5595 | Q | ASN | F | 468 | 10.854 | −2.801 | 64.826 | 1.00 | 44.68 |
| 5596 | N | PHE | F | 469 | 10.404 | −0.618 | 65.080 | 1.00 | 32.80 |
| 5597 | CA | PHE | F | 469 | 9.099 | −0.735 | 64.472 | 1.00 | 31.45 |
| 5598 | CB | PHE | F | 469 | 7.998 | −0.333 | 65.494 | 1.00 | 38.76 |
| 5599 | CG | PHE | F | 469 | 8.059 | 1.121 | 65.940 | 1.00 | 24.41 |
| 5600 | CD1 | PHE | F | 469 | 7.614 | 2.140 | 65.113 | 1.00 | 22.07 |
| 5601 | CD2 | PHE | F | 469 | 8.603 | 1.476 | 67.173 | 1.00 | 26.75 |
| 5602 | CE1 | PHE | F | 469 | 7.718 | 3.479 | 65.506 | 1.00 | 18.51 |
| 5603 | CE2 | PHE | F | 469 | 8.698 | 2.819 | 67.550 | 1.00 | 25.84 |
| 5604 | CZ | PHE | F | 469 | 8.260 | 3.810 | 66.716 | 1.00 | 24.07 |
| 5605 | C | PHE | F | 469 | 9.017 | 0.129 | 63.243 | 1.00 | 37.77 |
| 5606 | O | PHE | F | 469 | 9.730 | 1.102 | 63.121 | 1.00 | 30.48 |
| 5607 | N | MET | F | 470 | 8.157 | −0.266 | 62.313 | 1.00 | 45.91 |
| 5608 | CA | MET | F | 470 | 7.931 | 0.501 | 61.091 | 1.00 | 44.88 |
| 5609 | CB | MET | F | 470 | 9.072 | 0.321 | 60.084 | 1.00 | 49.40 |
| 5610 | CG | MET | F | 470 | 9.316 | −1.093 | 59.614 | 1.00 | 72.59 |
| 5611 | SD | MET | F | 470 | 10.813 | −1.163 | 58.630 | 1.00 | 71.05 |
| 5612 | CE | MET | F | 470 | 10.511 | 0.166 | 57.447 | 1.00 | 73.06 |
| 5613 | C | MET | F | 470 | 6.602 | 0.125 | 60.462 | 1.00 | 40.20 |
| 5614 | O | MET | F | 470 | 6.177 | −1.023 | 60.512 | 1.00 | 40.38 |
| 5615 | N | PRO | F | 471 | 5.916 | 1.108 | 59.874 | 1.00 | 38.65 |
| 5616 | CD | PRO | F | 471 | 4.548 | 0.919 | 59.369 | 1.00 | 24.56 |
| 5617 | CA | PRO | F | 471 | 6.318 | 2.522 | 59.765 | 1.00 | 35.03 |
| 5618 | CB | PRO | F | 471 | 5.155 | 3.166 | 59.009 | 1.00 | 45.43 |
| 5619 | CG | PRO | F | 471 | 4.459 | 2.019 | 58.350 | 1.00 | 42.23 |
| 5620 | C | PRO | F | 471 | 6.533 | 3.214 | 61.102 | 1.00 | 43.15 |
| 5621 | O | PRO | F | 471 | 6.431 | 2.599 | 62.154 | 1.00 | 31.79 |
| 5622 | N | GLU | F | 472 | 6.784 | 4.515 | 61.045 | 1.00 | 44.87 |
| 5623 | CA | GLU | F | 472 | 7.044 | 5.307 | 62.248 | 1.00 | 46.43 |
| 5624 | CB | GLU | F | 472 | 7.800 | 6.572 | 61.874 | 1.00 | 36.75 |
| 5625 | CG | GLU | F | 472 | 6.967 | 7.581 | 61.127 | 1.00 | 58.49 |
| 5626 | CD | GLU | F | 472 | 7.699 | 8.891 | 60.915 | 1.00 | 91.09 |
| 5627 | OE1 | GLU | F | 472 | 8.633 | 8.921 | 60.086 | 1.00 | 99.09 |
| 5628 | OE2 | GLU | F | 472 | 7.350 | 9.889 | 61.584 | 1.00 | 98.90 |
| 5629 | C | GLU | F | 472 | 5.804 | 5.703 | 63.057 | 1.00 | 45.78 |
| 5630 | O | GLU | F | 472 | 5.922 | 6.147 | 64.197 | 1.00 | 51.53 |
| 5631 | N | ASP | F | 473 | 4.617 | 5.561 | 62.470 | 1.00 | 48.55 |
| 5632 | CA | ASP | F | 473 | 3.388 | 5.923 | 63.176 | 1.00 | 41.48 |
| 5633 | CB | ASP | F | 473 | 2.179 | 5.753 | 62.255 | 1.00 | 50.07 |
| 5634 | CG | ASP | F | 473 | 2.245 | 6.656 | 61.040 | 1.00 | 75.11 |
| 5635 | OD1 | ASP | F | 473 | 2.492 | 7.870 | 61.205 | 1.00 | 68.98 |
| 5636 | OD2 | ASP | F | 473 | 2.042 | 6.150 | 59.919 | 1.00 | 91.01 |
| 5637 | C | ASP | F | 473 | 3.221 | 5.049 | 64.412 | 1.00 | 33.58 |
| 5638 | O | ASP | F | 473 | 3.299 | 3.813 | 64.331 | 1.00 | 40.74 |
| 5639 | N | ILE | F | 474 | 2.996 | 5.683 | 65.556 | 1.00 | 33.67 |
| 5640 | CA | ILE | F | 474 | 2.825 | 4.915 | 66.775 | 1.00 | 30.75 |
| 5641 | CB | ILE | F | 474 | 4.224 | 4.399 | 67.263 | 1.00 | 25.91 |
| 5642 | CG2 | ILE | F | 474 | 5.041 | 5.560 | 67.819 | 1.00 | 22.95 |
| 5643 | CG1 | ILE | F | 474 | 4.047 | 3.286 | 68.299 | 1.00 | 28.19 |
| 5644 | CD1 | ILE | F | 474 | 5.237 | 2.452 | 68.488 | 1.00 | 24.73 |
| 5645 | C | ILE | F | 474 | 2.090 | 5.693 | 67.881 | 1.00 | 35.29 |
| 5646 | O | ILE | F | 474 | 2.104 | 6.923 | 67.913 | 1.00 | 32.10 |
| 5647 | N | SER | F | 475 | 1.428 | 4.956 | 68.768 | 1.00 | 34.14 |
| 5648 | CA | SER | F | 475 | 0.679 | 5.535 | 69.886 | 1.00 | 24.96 |
| 5649 | CB | SER | F | 475 | −0.829 | 5.328 | 69.703 | 1.00 | 47.65 |
| 5650 | OG | SER | F | 475 | −1.335 | 6.073 | 68.609 | 1.00 | 43.08 |
| 5651 | C | SER | F | 475 | 1.117 | 4.880 | 71.179 | 1.00 | 37.27 |
| 5652 | O | SER | F | 475 | 1.217 | 3.650 | 71.281 | 1.00 | 31.93 |
| 5653 | N | VAL | F | 476 | 1.377 | 5.716 | 72.176 | 1.00 | 33.03 |
| 5654 | CA | VAL | F | 476 | 1.827 | 5.229 | 73.483 | 1.00 | 27.14 |
| 5655 | CB | VAL | F | 476 | 3.213 | 5.797 | 73.845 | 1.00 | 29.82 |
| 5656 | CG1 | VAL | F | 476 | 3.674 | 5.241 | 75.161 | 1.00 | 32.95 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5657 | CG2 | VAL | F | 476 | 4.218 | 5.470 | 72.720 | 1.00 | 11.57 |
| 5658 | C | VAL | F | 476 | 0.864 | 5.591 | 74.598 | 1.00 | 36.55 |
| 5659 | O | VAL | F | 476 | 0.408 | 6.720 | 74.713 | 1.00 | 41.99 |
| 5660 | N | GLN | F | 477 | 0.553 | 4.615 | 75.429 | 1.00 | 40.98 |
| 5661 | CA | GLN | F | 477 | −0.352 | 4.854 | 76.540 | 1.00 | 36.63 |
| 5662 | CB | GLN | F | 477 | −1.716 | 4.251 | 76.256 | 1.00 | 40.08 |
| 5663 | CG | GLN | F | 477 | −2.131 | 4.328 | 74.818 | 1.00 | 53.66 |
| 5664 | CD | GLN | F | 477 | −3.532 | 3.802 | 74.645 | 1.00 | 79.02 |
| 5665 | OE1 | GLN | F | 477 | −3.845 | 2.665 | 75.031 | 1.00 | 60.36 |
| 5666 | NE2 | GLN | F | 477 | −4.398 | 4.628 | 74.073 | 1.00 | 80.75 |
| 5667 | C | GLN | F | 477 | 0.141 | 4.245 | 77.836 | 1.00 | 43.30 |
| 5668 | O | GLN | F | 477 | 0.828 | 3.212 | 77.853 | 1.00 | 42.11 |
| 5669 | N | TRP | F | 478 | −0.224 | 4.884 | 78.932 | 1.00 | 36.93 |
| 5670 | CA | TRP | F | 478 | 0.141 | 4.350 | 80.227 | 1.00 | 29.26 |
| 5671 | CB | TRP | F | 478 | 0.920 | 5.389 | 81.053 | 1.00 | 32.16 |
| 5672 | CG | TRP | F | 478 | 2.324 | 5.581 | 80.581 | 1.00 | 23.69 |
| 5673 | CD2 | TRP | F | 478 | 3.469 | 4.844 | 81.008 | 1.00 | 16.93 |
| 5674 | CE2 | TRP | F | 478 | 4.596 | 5.404 | 80.372 | 1.00 | 15.88 |
| 5675 | CE3 | TRP | F | 478 | 3.655 | 3.755 | 81.870 | 1.00 | 20.04 |
| 5676 | CD1 | TRP | F | 478 | 2.791 | 6.534 | 79.698 | 1.00 | 23.66 |
| 5677 | NE1 | TRP | F | 478 | 4.162 | 6.433 | 79.575 | 1.00 | 33.00 |
| 5678 | CZ2 | TRP | F | 478 | 5.868 | 4.920 | 80.580 | 1.00 | 18.49 |
| 5679 | CZ3 | TRP | F | 478 | 4.927 | 3.275 | 82.067 | 1.00 | 22.36 |
| 5680 | CH2 | TRP | F | 478 | 6.017 | 3.858 | 81.425 | 1.00 | 20.77 |
| 5681 | C | TRP | F | 478 | −1.170 | 3.948 | 80.902 | 1.00 | 37.25 |
| 5682 | O | TRP | F | 478 | −2.205 | 4.581 | 80.716 | 1.00 | 38.33 |
| 5683 | N | LEU | F | 479 | −1.126 | 2.867 | 81.657 | 1.00 | 32.99 |
| 5684 | CA | LEU | F | 479 | −2.316 | 2.386 | 82.345 | 1.00 | 22.88 |
| 5685 | CB | LEU | F | 479 | −2.897 | 1.151 | 81.643 | 1.00 | 47.71 |
| 5686 | CG | LEU | F | 479 | −3.656 | 1.284 | 80.317 | 1.00 | 48.59 |
| 5687 | CD1 | LEU | F | 479 | −2.745 | 1.763 | 79.210 | 1.00 | 57.07 |
| 5688 | CD2 | LEU | F | 479 | −4.235 | −0.064 | 79.964 | 1.00 | 58.33 |
| 5689 | C | LEU | F | 479 | −1.966 | 2.015 | 83.770 | 1.00 | 38.19 |
| 5690 | O | LEU | F | 479 | −0.885 | 1.467 | 84.048 | 1.00 | 34.74 |
| 5691 | N | HIS | F | 480 | −2.880 | 2.332 | 84.675 | 1.00 | 42.33 |
| 5692 | CA | HIS | F | 480 | −2.697 | 2.020 | 86.086 | 1.00 | 43.56 |
| 5693 | CB | HIS | F | 480 | −2.372 | 3.299 | 86.878 | 1.00 | 35.97 |
| 5694 | CG | HIS | F | 480 | −2.060 | 3.050 | 88.325 | 1.00 | 40.08 |
| 5695 | CD2 | HIS | F | 480 | −2.563 | 3.601 | 89.451 | 1.00 | 26.66 |
| 5696 | ND1 | HIS | F | 480 | −1.146 | 2.102 | 88.738 | 1.00 | 49.12 |
| 5697 | CE1 | HIS | F | 480 | −1.108 | 2.076 | 90.058 | 1.00 | 36.08 |
| 5698 | NE2 | HIS | F | 480 | −1.959 | 2.974 | 90.515 | 1.00 | 57.71 |
| 5699 | C | HIS | F | 480 | −3.999 | 1.369 | 86.560 | 1.00 | 58.23 |
| 5700 | O | HIS | F | 480 | −5.093 | 1.895 | 86.345 | 1.00 | 51.82 |
| 5701 | N | ASN | F | 481 | −3.863 | 0.208 | 87.190 | 1.00 | 69.65 |
| 5702 | CA | ASN | F | 481 | −5.005 | −0.573 | 87.663 | 1.00 | 81.31 |
| 5703 | CB | ASN | F | 481 | −6.082 | 0.328 | 88.279 | 1.00 | 67.12 |
| 5704 | CG | ASN | F | 481 | −5.779 | 0.682 | 89.719 | 1.00 | 65.17 |
| 5705 | OD1 | ASN | F | 481 | −5.753 | −0.196 | 90.595 | 1.00 | 59.85 |
| 5706 | ND2 | ASN | F | 481 | −5.531 | 1.964 | 89.975 | 1.00 | 69.46 |
| 5707 | C | ASN | F | 481 | −5.576 | −1.341 | 86.482 | 1.00 | 86.09 |
| 5708 | O | ASN | F | 481 | −5.755 | −2.565 | 86.542 | 1.00 | 90.49 |
| 5709 | N | GLU | F | 482 | −5.826 | −0.608 | 85.400 | 1.00 | 81.41 |
| 5710 | CA | GLU | F | 482 | −6.380 | −1.155 | 84.167 | 1.00 | 82.36 |
| 5711 | CB | GLU | F | 482 | −7.516 | −2.137 | 84.470 | 1.00 | 93.12 |
| 5712 | CG | GLU | F | 482 | −8.453 | −1.725 | 85.624 | 1.00 | 118.61 |
| 5713 | CD | GLU | F | 482 | −8.757 | −0.226 | 85.676 | 1.00 | 127.30 |
| 5714 | OE1 | GLU | F | 482 | −7.858 | 0.559 | 86.052 | 1.00 | 125.27 |
| 5715 | OE2 | GLU | F | 482 | −9.897 | 0.169 | 85.343 | 1.00 | 133.64 |
| 5716 | C | GLU | F | 482 | −6.935 | 0.003 | 83.360 | 1.00 | 70.78 |
| 5717 | O | GLU | F | 482 | −7.437 | −0.177 | 82.250 | 1.00 | 64.33 |
| 5718 | N | VAL | F | 483 | −6.837 | 1.197 | 83.931 | 1.00 | 59.20 |
| 5719 | CA | VAL | F | 483 | −7.360 | 2.379 | 83.282 | 1.00 | 59.92 |
| 5720 | CB | VAL | F | 483 | −8.246 | 3.188 | 84.238 | 1.00 | 51.07 |
| 5721 | CG1 | VAL | F | 483 | −7.447 | 3.611 | 85.466 | 1.00 | 62.71 |
| 5722 | CG2 | VAL | F | 483 | −8.778 | 4.410 | 83.516 | 1.00 | 61.36 |
| 5723 | C | VAL | F | 483 | −6.285 | 3.297 | 82.739 | 1.00 | 54.89 |
| 5724 | O | VAL | F | 483 | −5.286 | 3.585 | 83.414 | 1.00 | 49.93 |
| 5725 | N | GLN | F | 484 | −6.534 | 3.766 | 81.521 | 1.00 | 35.35 |
| 5726 | CA | GLN | F | 484 | −5.638 | 4.647 | 80.799 | 1.00 | 47.09 |
| 5727 | CB | GLN | F | 484 | −6.160 | 4.769 | 79.374 | 1.00 | 42.86 |
| 5728 | CG | GLN | F | 484 | −5.555 | 5.833 | 78.509 | 1.00 | 66.01 |
| 5729 | CD | GLN | F | 484 | −6.060 | 5.720 | 77.087 | 1.00 | 69.56 |
| 5730 | OE1 | GLN | F | 484 | −6.009 | 6.671 | 76.317 | 1.00 | 81.01 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5731 | NE2 | GLN | F | 484 | −6.542 | 4.536 | 76.730 | 1.00 | 77.22 |
| 5732 | C | GLN | F | 484 | −5.542 | 6.010 | 81.472 | 1.00 | 54.76 |
| 5733 | O | GLN | F | 484 | −6.556 | 6.682 | 81.650 | 1.00 | 65.85 |
| 5734 | N | LEU | F | 485 | −4.327 | 6.407 | 81.861 | 1.00 | 54.13 |
| 5735 | CA | LEU | F | 485 | −4.098 | 7.706 | 82.507 | 1.00 | 45.04 |
| 5736 | CB | LEU | F | 485 | −2.698 | 7.760 | 83.112 | 1.00 | 23.90 |
| 5737 | CG | LEU | F | 485 | −2.274 | 6.641 | 84.076 | 1.00 | 56.33 |
| 5738 | CD1 | LEU | F | 485 | −0.850 | 6.875 | 84.562 | 1.00 | 52.11 |
| 5739 | CD2 | LEU | F | 485 | −3.204 | 6.607 | 85.271 | 1.00 | 44.34 |
| 5740 | C | LEU | F | 485 | −4.256 | 8.859 | 81.496 | 1.00 | 52.92 |
| 5741 | O | LEU | F | 485 | −4.176 | 8.664 | 80.271 | 1.00 | 45.42 |
| 5742 | N | PRO | F | 486 | −4.499 | 10.074 | 82.002 | 1.00 | 59.77 |
| 5743 | CD | PRO | F | 486 | −4.610 | 10.483 | 83.414 | 1.00 | 40.26 |
| 5744 | CA | PRO | F | 486 | −4.662 | 11.220 | 81.103 | 1.00 | 48.58 |
| 5745 | CB | PRO | F | 486 | −4.798 | 12.404 | 82.068 | 1.00 | 48.48 |
| 5746 | CG | PRO | F | 486 | −5.374 | 11.771 | 83.305 | 1.00 | 43.16 |
| 5747 | C | PRO | F | 486 | −3.432 | 11.320 | 80.227 | 1.00 | 46.76 |
| 5748 | O | PRO | F | 486 | −2.310 | 11.151 | 80.698 | 1.00 | 41.39 |
| 5749 | N | ASP | F | 487 | −3.644 | 11.589 | 78.947 | 1.00 | 61.73 |
| 5750 | CA | ASP | F | 487 | −2.528 | 11.681 | 78.020 | 1.00 | 64.88 |
| 5751 | CB | ASP | F | 487 | −3.061 | 11.955 | 76.610 | 1.00 | 72.37 |
| 5752 | CG | ASP | F | 487 | −2.072 | 11.556 | 75.523 | 1.00 | 111.82 |
| 5753 | OD1 | ASP | F | 487 | −1.061 | 12.267 | 75.329 | 1.00 | 126.89 |
| 5754 | OD2 | ASP | F | 487 | −2.301 | 10.517 | 74.864 | 1.00 | 116.87 |
| 5755 | C | ASP | F | 487 | −1.499 | 12.741 | 78.438 | 1.00 | 63.58 |
| 5756 | O | ASP | F | 487 | −0.297 | 12.576 | 78.210 | 1.00 | 77.14 |
| 5757 | N | ALA | F | 488 | −1.966 | 13.809 | 79.076 | 1.00 | 56.97 |
| 5758 | CA | ALA | F | 488 | −1.081 | 14.902 | 79.494 | 1.00 | 57.12 |
| 5759 | CB | ALA | F | 488 | −1.898 | 16.150 | 79.789 | 1.00 | 59.32 |
| 5760 | C | ALA | F | 488 | −0.188 | 14.587 | 80.685 | 1.00 | 48.57 |
| 5761 | O | ALA | F | 488 | 0.583 | 15.438 | 81.121 | 1.00 | 58.02 |
| 5762 | N | ARG | F | 489 | −0.301 | 13.375 | 81.213 | 1.00 | 46.30 |
| 5763 | CA | ARG | F | 489 | 0.509 | 12.948 | 82.345 | 1.00 | 49.34 |
| 5764 | CB | ARG | F | 489 | −0.220 | 11.854 | 83.117 | 1.00 | 59.76 |
| 5765 | CG | ARG | F | 489 | −1.088 | 12.376 | 84.232 | 1.00 | 45.56 |
| 5766 | CD | ARG | F | 489 | −0.331 | 12.280 | 85.530 | 1.00 | 23.74 |
| 5767 | NE | ARG | F | 489 | −0.637 | 11.060 | 86.275 | 1.00 | 31.24 |
| 5768 | CZ | ARG | F | 489 | 0.237 | 10.456 | 87.077 | 1.00 | 34.30 |
| 5769 | NH1 | ARG | F | 489 | 1.450 | 10.963 | 87.201 | 1.00 | 67.21 |
| 5770 | NH2 | ARG | F | 489 | −0.105 | 9.375 | 87.780 | 1.00 | 53.88 |
| 5771 | C | ARG | F | 489 | 1.884 | 12.422 | 81.902 | 1.00 | 62.23 |
| 5772 | O | ARG | F | 489 | 2.868 | 12.489 | 82.658 | 1.00 | 64.71 |
| 5773 | N | HIS | F | 490 | 1.958 | 11.898 | 80.681 | 1.00 | 51.92 |
| 5774 | CA | HIS | F | 490 | 3.217 | 11.361 | 80.182 | 1.00 | 37.37 |
| 5775 | CB | HIS | F | 490 | 3.023 | 9.903 | 79.735 | 1.00 | 53.08 |
| 5776 | CG | HIS | F | 490 | 2.282 | 9.760 | 78.441 | 1.00 | 45.54 |
| 5777 | CD2 | HIS | F | 490 | 1.077 | 9.215 | 78.161 | 1.00 | 51.16 |
| 5778 | ND1 | HIS | F | 490 | 2.779 | 10.228 | 77.241 | 1.00 | 53.31 |
| 5779 | CE1 | HIS | F | 490 | 1.913 | 9.977 | 76.276 | 1.00 | 36.37 |
| 5780 | NE2 | HIS | F | 490 | 0.870 | 9.363 | 76.808 | 1.00 | 62.11 |
| 5781 | C | HIS | F | 490 | 3.760 | 12.186 | 79.021 | 1.00 | 40.32 |
| 5782 | O | HIS | F | 490 | 3.020 | 12.943 | 78.387 | 1.00 | 45.93 |
| 5783 | N | SER | F | 491 | 5.058 | 12.030 | 78.760 | 1.00 | 37.17 |
| 5784 | CA | SER | F | 491 | 5.730 | 12.719 | 77.663 | 1.00 | 35.24 |
| 5785 | CB | SER | F | 491 | 6.804 | 13.646 | 78.213 | 1.00 | 33.91 |
| 5786 | OG | SER | F | 491 | 7.183 | 14.579 | 77.212 | 1.00 | 37.23 |
| 5787 | C | SER | F | 491 | 6.363 | 11.702 | 76.715 | 1.00 | 38.07 |
| 5788 | O | SER | F | 491 | 7.050 | 10.768 | 77.149 | 1.00 | 48.33 |
| 5789 | N | THR | F | 492 | 6.148 | 11.887 | 75.420 | 1.00 | 33.02 |
| 5790 | CA | THR | F | 492 | 6.697 | 10.955 | 74.421 | 1.00 | 33.94 |
| 5791 | CB | THR | F | 492 | 5.580 | 10.111 | 73.770 | 1.00 | 28.01 |
| 5792 | OG1 | THR | F | 492 | 4.945 | 9.304 | 74.764 | 1.00 | 51.67 |
| 5793 | CG2 | THR | F | 492 | 6.140 | 9.222 | 72.700 | 1.00 | 38.93 |
| 5794 | C | THR | F | 492 | 7.485 | 11.631 | 73.307 | 1.00 | 31.06 |
| 5795 | O | THR | F | 492 | 7.014 | 12.590 | 72.686 | 1.00 | 36.18 |
| 5796 | N | THR | F | 493 | 8.674 | 11.088 | 73.044 | 1.00 | 36.31 |
| 5797 | CA | THR | F | 493 | 9.604 | 11.602 | 72.020 | 1.00 | 28.21 |
| 5798 | CB | THR | F | 493 | 10.991 | 10.906 | 72.125 | 1.00 | 27.77 |
| 5799 | OG1 | THR | F | 493 | 10.845 | 9.504 | 71.864 | 1.00 | 41.11 |
| 5800 | CG2 | THR | F | 493 | 11.582 | 11.076 | 73.528 | 1.00 | 22.41 |
| 5801 | C | THR | F | 493 | 9.137 | 11.436 | 70.583 | 1.00 | 29.33 |
| 5802 | O | THR | F | 493 | 8.311 | 10.587 | 70.277 | 1.00 | 39.92 |
| 5803 | N | GLN | F | 494 | 9.665 | 12.262 | 69.699 | 1.00 | 40.16 |
| 5804 | CA | GLN | F | 494 | 9.345 | 12.138 | 68.287 | 1.00 | 52.56 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5805 | CB | GLN | F | 494 | 9.820 | 13.376 | 67.522 | 1.00 | 68.75 |
| 5806 | CG | GLN | F | 494 | 9.183 | 14.671 | 67.995 | 1.00 | 90.43 |
| 5807 | CD | GLN | F | 494 | 7.707 | 14.735 | 67.678 | 1.00 | 104.31 |
| 5808 | OE1 | GLN | F | 494 | 7.316 | 14.748 | 66.511 | 1.00 | 110.66 |
| 5809 | NE2 | GLN | F | 494 | 6.875 | 14.775 | 68.714 | 1.00 | 109.52 |
| 5810 | C | GLN | F | 494 | 10.095 | 10.890 | 67.779 | 1.00 | 55.65 |
| 5811 | O | GLN | F | 494 | 11.185 | 10.565 | 68.263 | 1.00 | 46.25 |
| 5812 | N | PRO | F | 495 | 9.498 | 10.157 | 66.825 | 1.00 | 51.05 |
| 5813 | CD | PRO | F | 495 | 8.123 | 10.300 | 66.308 | 1.00 | 57.93 |
| 5814 | CA | PRO | F | 495 | 10.126 | 8.961 | 66.272 | 1.00 | 46.76 |
| 5815 | CB | PRO | F | 495 | 9.117 | 8.502 | 65.219 | 1.00 | 45.08 |
| 5816 | CG | PRO | F | 495 | 7.832 | 8.915 | 65.785 | 1.00 | 33.88 |
| 5817 | C | PRO | F | 495 | 11.501 | 9.266 | 65.672 | 1.00 | 48.72 |
| 5818 | O | PRO | F | 495 | 11.717 | 10.314 | 65.061 | 1.00 | 55.35 |
| 5819 | N | ARG | F | 496 | 12.424 | 8.335 | 65.862 | 1.00 | 53.19 |
| 5820 | CA | ARG | F | 496 | 13.782 | 8.477 | 65.368 | 1.00 | 51.90 |
| 5821 | CB | ARG | F | 496 | 14.702 | 8.945 | 66.493 | 1.00 | 39.69 |
| 5822 | CG | ARG | F | 496 | 14.683 | 10.409 | 66.769 | 1.00 | 35.70 |
| 5823 | CD | ARG | F | 496 | 15.908 | 10.731 | 67.603 | 1.00 | 73.07 |
| 5824 | NE | ARG | F | 496 | 16.285 | 12.137 | 67.560 | 1.00 | 88.41 |
| 5825 | CZ | ARG | F | 496 | 17.538 | 12.564 | 67.669 | 1.00 | 80.22 |
| 5826 | NH1 | ARG | F | 496 | 18.522 | 11.683 | 67.821 | 1.00 | 71.41 |
| 5827 | NH2 | ARG | F | 496 | 17.810 | 13.865 | 67.630 | 1.00 | 82.93 |
| 5828 | C | ARG | F | 496 | 14.300 | 7.144 | 64.829 | 1.00 | 69.50 |
| 5829 | O | ARG | F | 496 | 13.904 | 6.076 | 65.308 | 1.00 | 63.33 |
| 5830 | N | LYS | F | 497 | 15.196 | 7.218 | 63.845 | 1.00 | 63.42 |
| 5831 | CA | LYS | F | 497 | 15.773 | 6.029 | 63.228 | 1.00 | 64.71 |
| 5832 | CB | LYS | F | 497 | 16.467 | 6.402 | 61.924 | 1.00 | 65.33 |
| 5833 | CG | LYS | F | 497 | 15.578 | 7.134 | 60.950 | 1.00 | 76.45 |
| 5834 | CD | LYS | F | 497 | 16.390 | 7.647 | 59.773 | 1.00 | 95.93 |
| 5835 | CE | LYS | F | 497 | 15.534 | 8.462 | 58.821 | 1.00 | 99.81 |
| 5836 | NZ | LYS | F | 497 | 16.335 | 8.980 | 57.678 | 1.00 | 106.12 |
| 5837 | C | LYS | F | 497 | 16.768 | 5.324 | 64.145 | 1.00 | 64.93 |
| 5838 | O | LYS | F | 497 | 17.671 | 5.948 | 64.698 | 1.00 | 56.82 |
| 5839 | N | THR | F | 498 | 16.584 | 4.016 | 64.301 | 1.00 | 67.46 |
| 5840 | CA | THR | F | 498 | 17.453 | 3.208 | 65.136 | 1.00 | 76.46 |
| 5841 | CB | THR | F | 498 | 16.803 | 1.853 | 65.469 | 1.00 | 79.44 |
| 5842 | OG1 | THR | F | 498 | 16.615 | 1.097 | 64.269 | 1.00 | 88.21 |
| 5843 | CG2 | THR | F | 498 | 15.469 | 2.056 | 66.128 | 1.00 | 77.20 |
| 5844 | C | THR | F | 498 | 18.763 | 2.957 | 64.397 | 1.00 | 90.68 |
| 5845 | O | THR | F | 498 | 19.787 | 3.564 | 64.710 | 1.00 | 99.00 |
| 5846 | N | LYS | F | 499 | 18.705 | 2.060 | 63.414 | 1.00 | 97.91 |
| 5847 | CA | LYS | F | 499 | 19.839 | 1.673 | 62.577 | 1.00 | 99.33 |
| 5848 | CB | LYS | F | 499 | 21.026 | 1.206 | 63.425 | 1.00 | 87.83 |
| 5849 | CG | LYS | F | 499 | 22.027 | 2.300 | 63.767 | 1.00 | 100.01 |
| 5850 | CD | LYS | F | 499 | 22.608 | 2.918 | 62.501 | 1.00 | 109.25 |
| 5851 | CE | LYS | F | 499 | 23.604 | 4.024 | 62.813 | 1.00 | 107.08 |
| 5852 | NZ | LYS | F | 499 | 24.186 | 4.607 | 61.574 | 1.00 | 96.65 |
| 5853 | C | LYS | F | 499 | 19.397 | 0.534 | 61.665 | 1.00 | 100.40 |
| 5854 | O | LYS | F | 499 | 19.827 | −0.605 | 61.833 | 1.00 | 92.82 |
| 5855 | N | GLY | F | 500 | 18.517 | 0.848 | 60.715 | 1.00 | 103.69 |
| 5856 | CA | GLY | F | 500 | 18.027 | −0.153 | 59.782 | 1.00 | 102.32 |
| 5857 | C | GLY | F | 500 | 16.717 | −0.816 | 60.176 | 1.00 | 102.83 |
| 5858 | O | GLY | F | 500 | 15.750 | −0.820 | 59.410 | 1.00 | 93.06 |
| 5859 | N | SER | F | 501 | 16.686 | −1.381 | 61.378 | 1.00 | 102.97 |
| 5860 | CA | SER | F | 501 | 15.501 | −2.067 | 61.885 | 1.00 | 102.87 |
| 5861 | CB | SER | F | 501 | 15.775 | −2.624 | 63.283 | 1.00 | 106.03 |
| 5862 | OG | SER | F | 501 | 16.028 | −1.578 | 64.208 | 1.00 | 120.41 |
| 5863 | C | SER | F | 501 | 14.242 | −1.203 | 61.929 | 1.00 | 98.77 |
| 5864 | O | SER | F | 501 | 13.127 | −1.733 | 61.945 | 1.00 | 100.51 |
| 5865 | N | GLY | F | 502 | 14.409 | 0.117 | 61.963 | 1.00 | 83.32 |
| 5866 | CA | GLY | F | 502 | 13.245 | 0.986 | 61.996 | 1.00 | 69.17 |
| 5867 | C | GLY | F | 502 | 13.376 | 2.218 | 62.866 | 1.00 | 55.16 |
| 5868 | O | GLY | F | 502 | 14.333 | 2.973 | 62.748 | 1.00 | 54.48 |
| 5869 | N | PHE | F | 503 | 12.399 | 2.434 | 63.734 | 1.00 | 44.47 |
| 5870 | CA | PHE | F | 503 | 12.417 | 3.593 | 64.621 | 1.00 | 44.82 |
| 5871 | CB | PHE | F | 503 | 11.274 | 4.557 | 64.308 | 1.00 | 28.47 |
| 5872 | CG | PHE | F | 503 | 11.188 | 4.961 | 62.881 | 1.00 | 36.90 |
| 5873 | CD1 | PHE | F | 503 | 10.634 | 4.106 | 61.925 | 1.00 | 37.54 |
| 5874 | CD2 | PHE | F | 503 | 11.644 | 6.208 | 62.480 | 1.00 | 34.68 |
| 5875 | CE1 | PHE | F | 503 | 10.539 | 4.492 | 60.593 | 1.00 | 32.47 |
| 5876 | CE2 | PHE | F | 503 | 11.552 | 6.608 | 61.138 | 1.00 | 51.83 |
| 5877 | CZ | PHE | F | 503 | 11.000 | 5.750 | 60.197 | 1.00 | 29.96 |
| 5878 | C | PHE | F | 503 | 12.299 | 3.216 | 66.091 | 1.00 | 40.43 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5879 | O | PHE | F | 503 | 12.043 | 2.059 | 66.462 | 1.00 | 36.91 |
| 5880 | N | PHE | F | 504 | 12.506 | 4.224 | 66.923 | 1.00 | 32.84 |
| 5881 | CA | PHE | F | 504 | 12.373 | 4.061 | 68.362 | 1.00 | 42.31 |
| 5882 | CB | PHE | F | 504 | 13.732 | 3.760 | 69.024 | 1.00 | 40.81 |
| 5883 | CG | PHE | F | 504 | 14.611 | 4.968 | 69.214 | 1.00 | 49.30 |
| 5884 | CD1 | PHE | F | 504 | 14.433 | 5.805 | 70.305 | 1.00 | 41.25 |
| 5885 | CD2 | PHE | F | 504 | 15.610 | 5.263 | 68.304 | 1.00 | 47.18 |
| 5886 | CE1 | PHE | F | 504 | 15.236 | 6.908 | 70.476 | 1.00 | 41.39 |
| 5887 | CE2 | PHE | F | 504 | 16.413 | 6.358 | 68.466 | 1.00 | 46.22 |
| 5888 | CZ | PHE | F | 504 | 16.233 | 7.190 | 69.553 | 1.00 | 57.79 |
| 5889 | C | PHE | F | 504 | 11.745 | 5.321 | 68.953 | 1.00 | 37.24 |
| 5890 | O | PHE | F | 504 | 11.816 | 6.414 | 68.386 | 1.00 | 27.43 |
| 5891 | N | VAL | F | 505 | 11.116 | 5.139 | 70.100 | 1.00 | 35.18 |
| 5892 | CA | VAL | F | 505 | 10.475 | 6.238 | 70.787 | 1.00 | 17.15 |
| 5893 | CB | VAL | F | 505 | 8.949 | 6.274 | 70.380 | 1.00 | 35.10 |
| 5894 | CG1 | VAL | F | 505 | 8.052 | 6.093 | 71.586 | 1.00 | 38.82 |
| 5895 | CG2 | VAL | F | 505 | 8.629 | 7.557 | 69.626 | 1.00 | 33.60 |
| 5896 | C | VAL | F | 505 | 10.664 | 5.966 | 72.276 | 1.00 | 33.35 |
| 5897 | O | VAL | F | 505 | 10.776 | 4.795 | 72.722 | 1.00 | 29.67 |
| 5898 | N | PHE | F | 506 | 10.717 | 7.053 | 73.032 | 1.00 | 26.17 |
| 5899 | CA | PHE | F | 506 | 10.885 | 6.975 | 74.473 | 1.00 | 32.56 |
| 5900 | CB | PHE | F | 506 | 12.217 | 7.658 | 74.855 | 1.00 | 32.24 |
| 5901 | CG | PHE | F | 506 | 12.454 | 7.835 | 76.357 | 1.00 | 91.51 |
| 5902 | CD1 | PHE | F | 506 | 12.619 | 6.731 | 77.191 | 1.00 | 93.25 |
| 5903 | CD2 | PHE | F | 506 | 12.631 | 9.117 | 76.916 | 1.00 | 87.15 |
| 5904 | CE1 | PHE | F | 506 | 12.970 | 6.899 | 78.553 | 1.00 | 97.87 |
| 5905 | CE2 | PHE | F | 506 | 12.980 | 9.285 | 78.275 | 1.00 | 30.19 |
| 5906 | CZ | PHE | F | 506 | 13.152 | 8.180 | 79.086 | 1.00 | 53.67 |
| 5907 | C | PHE | F | 506 | 9.684 | 7.688 | 75.090 | 1.00 | 33.07 |
| 5908 | O | PHE | F | 506 | 9.165 | 8.667 | 74.543 | 1.00 | 41.65 |
| 5909 | N | SER | F | 507 | 9.225 | 7.181 | 76.224 | 1.00 | 35.19 |
| 5910 | CA | SER | F | 507 | 8.112 | 7.822 | 76.921 | 1.00 | 35.44 |
| 5911 | CB | SER | F | 507 | 6.818 | 7.038 | 76.718 | 1.00 | 48.53 |
| 5912 | OG | SER | F | 507 | 5.744 | 7.733 | 77.300 | 1.00 | 33.19 |
| 5913 | C | SER | F | 507 | 8.397 | 7.955 | 78.409 | 1.00 | 38.25 |
| 5914 | O | SER | F | 507 | 8.877 | 7.012 | 79.059 | 1.00 | 40.97 |
| 5915 | N | ARG | F | 508 | 8.091 | 9.137 | 78.933 | 1.00 | 31.22 |
| 5916 | CA | ARG | F | 508 | 8.306 | 9.438 | 80.344 | 1.00 | 34.23 |
| 5917 | CB | ARG | F | 508 | 9.194 | 10.679 | 80.434 | 1.00 | 27.79 |
| 5918 | CG | ARG | F | 508 | 9.667 | 11.024 | 81.833 | 1.00 | 25.62 |
| 5919 | CD | ARG | F | 508 | 10.702 | 12.146 | 81.760 | 1.00 | 47.46 |
| 5920 | NE | ARG | F | 508 | 10.951 | 12.699 | 83.086 | 1.00 | 49.21 |
| 5921 | CZ | ARG | F | 508 | 10.131 | 13.540 | 83.700 | 1.00 | 52.34 |
| 5922 | NH1 | ARG | F | 508 | 9.012 | 13.931 | 83.088 | 1.00 | 51.38 |
| 5923 | NH2 | ARG | F | 508 | 10.408 | 13.958 | 84.931 | 1.00 | 56.66 |
| 5924 | C | ARG | F | 508 | 7.003 | 9.651 | 81.153 | 1.00 | 33.30 |
| 5925 | O | ARG | F | 508 | 6.081 | 10.343 | 80.723 | 1.00 | 34.06 |
| 5926 | N | LEU | F | 509 | 6.941 | 9.059 | 82.334 | 1.00 | 31.63 |
| 5927 | CA | LEU | F | 509 | 5.767 | 9.223 | 83.196 | 1.00 | 22.54 |
| 5928 | CB | LEU | F | 509 | 4.850 | 8.014 | 83.107 | 1.00 | 35.73 |
| 5929 | CG | LEU | F | 509 | 3.645 | 8.079 | 84.054 | 1.00 | 24.61 |
| 5930 | CD1 | LEU | F | 509 | 2.613 | 9.022 | 83.441 | 1.00 | 28.85 |
| 5931 | CD2 | LEU | F | 509 | 3.031 | 6.697 | 84.243 | 1.00 | 32.23 |
| 5932 | C | LEU | F | 509 | 6.148 | 9.367 | 84.656 | 1.00 | 37.52 |
| 5933 | O | LEU | F | 509 | 6.642 | 8.404 | 85.264 | 1.01 | 37.55 |
| 5934 | N | GLU | F | 510 | 5.911 | 10.554 | 85.219 | 1.00 | 40.23 |
| 5935 | CA | GLU | F | 510 | 6.203 | 10.781 | 86.637 | 1.00 | 35.97 |
| 5936 | CB | GLU | F | 510 | 6.352 | 12.279 | 86.918 | 1.00 | 57.44 |
| 5937 | CG | GLU | F | 510 | 7.052 | 13.087 | 85.826 | 1.00 | 82.28 |
| 5938 | CD | GLU | F | 510 | 7.283 | 14.540 | 86.227 | 1.00 | 84.36 |
| 5939 | OE1 | GLU | F | 510 | 7.669 | 15.357 | 85.359 | 1.00 | 82.44 |
| 5940 | OE2 | GLU | F | 510 | 7.081 | 14.862 | 87.416 | 1.00 | 83.19 |
| 5941 | C | GLU | F | 510 | 5.028 | 10.214 | 87.471 | 1.00 | 38.91 |
| 5942 | O | GLU | F | 510 | 3.877 | 10.546 | 87.219 | 1.00 | 38.85 |
| 5943 | N | VAL | F | 511 | 5.317 | 9.339 | 88.432 | 1.00 | 26.92 |
| 5944 | CA | VAL | F | 511 | 4.280 | 8.779 | 89.296 | 1.00 | 39.82 |
| 5945 | CB | VAL | F | 511 | 4.188 | 7.248 | 89.121 | 1.00 | 45.66 |
| 5946 | CG1 | VAL | F | 511 | 3.885 | 6.929 | 87.674 | 1.00 | 33.50 |
| 5947 | CG2 | VAL | F | 511 | 5.469 | 6.577 | 89.571 | 1.00 | 20.40 |
| 5948 | C | VAL | F | 511 | 4.473 | 9.146 | 90.796 | 1.00 | 48.11 |
| 5949 | O | VAL | F | 511 | 5.590 | 9.464 | 91.240 | 1.00 | 40.92 |
| 5950 | N | THR | F | 512 | 3.387 | 9.088 | 91.570 | 1.00 | 54.65 |
| 5951 | CA | THR | F | 512 | 3.431 | 9.490 | 92.987 | 1.00 | 53.87 |
| 5952 | CB | THR | F | 512 | 2.345 | 10.525 | 93.288 | 1.00 | 37.98 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 5953 | OG1 | THR | F | 512 | 1.056 | 9.897 | 93.184 | 1.00 | 53.60 |
| 5954 | CG2 | THR | F | 512 | 2.415 | 11.683 | 92.290 | 1.00 | 58.40 |
| 5955 | C | THR | F | 512 | 3.300 | 8.420 | 94.058 | 1.00 | 50.85 |
| 5956 | O | THR | F | 512 | 2.590 | 7.429 | 93.879 | 1.00 | 52.93 |
| 5957 | N | ARG | F | 513 | 3.973 | 8.664 | 95.182 | 1.00 | 55.19 |
| 5958 | CA | ARG | F | 513 | 3.972 | 7.760 | 96.341 | 1.00 | 61.22 |
| 5959 | CB | ARG | F | 513 | 4.230 | 8.547 | 97.632 | 1.00 | 71.96 |
| 5960 | CG | ARG | F | 513 | 5.406 | 8.065 | 98.461 | 1.00 | 85.45 |
| 5961 | CD | ARG | F | 513 | 5.177 | 6.680 | 99.021 | 1.00 | 85.51 |
| 5962 | NE | ARG | F | 513 | 6.412 | 6.118 | 99.562 | 1.00 | 90.26 |
| 5963 | CZ | ARG | F | 513 | 6.538 | 4.865 | 99.992 | 1.00 | 96.83 |
| 5964 | NH1 | ARG | F | 513 | 5.506 | 4.029 | 99.954 | 1.00 | 96.73 |
| 5965 | NH2 | ARG | F | 513 | 7.705 | 4.444 | 100.451 | 1.00 | 93.86 |
| 5966 | C | ARG | F | 513 | 2.661 | 6.997 | 96.499 | 1.00 | 67.70 |
| 5967 | O | ARG | F | 513 | 2.669 | 5.784 | 96.710 | 1.00 | 66.74 |
| 5968 | N | ALA | F | 514 | 1.544 | 7.722 | 96.410 | 1.00 | 68.41 |
| 5969 | CA | ALA | F | 514 | 0.210 | 7.136 | 96.548 | 1.00 | 69.32 |
| 5970 | CB | ALA | F | 514 | −0.844 | 8.077 | 95.952 | 1.00 | 58.71 |
| 5971 | C | ALA | F | 514 | 0.115 | 5.752 | 95.895 | 1.00 | 83.19 |
| 5972 | O | ALA | F | 514 | 0.291 | 4.731 | 96.575 | 1.00 | 84.32 |
| 5973 | N | GLU | F | 515 | −0.158 | 5.716 | 94.589 | 1.00 | 78.18 |
| 5974 | CA | GLU | F | 515 | −0.259 | 4.446 | 93.877 | 1.00 | 56.73 |
| 5975 | CB | GLU | F | 515 | −0.791 | 4.645 | 92.462 | 1.00 | 44.11 |
| 5976 | CG | GLU | F | 515 | 0.047 | 5.572 | 91.596 | 1.00 | 67.17 |
| 5977 | CD | GLU | F | 515 | −0.373 | 7.023 | 91.711 | 1.00 | 74.51 |
| 5978 | OE1 | GLU | F | 515 | −0.557 | 7.493 | 92.856 | 1.00 | 64.50 |
| 5979 | OE2 | GLU | F | 515 | −0.509 | 7.694 | 90.658 | 1.00 | 64.98 |
| 5980 | C | GLU | F | 515 | 1.107 | 3.810 | 93.820 | 1.00 | 59.77 |
| 5981 | O | GLU | F | 515 | 1.220 | 2.602 | 93.703 | 1.00 | 58.30 |
| 5982 | N | TRP | F | 516 | 2.143 | 4.640 | 93.913 | 1.00 | 73.13 |
| 5983 | CA | TRP | F | 516 | 3.545 | 4.202 | 93.897 | 1.00 | 80.83 |
| 5984 | CB | TRP | F | 516 | 4.449 | 5.419 | 94.129 | 1.00 | 89.52 |
| 5985 | CG | TRP | F | 516 | 5.910 | 5.181 | 93.976 | 1.00 | 111.71 |
| 5986 | CD2 | TRP | F | 516 | 6.951 | 5.622 | 94.861 | 1.00 | 119.47 |
| 5987 | CE2 | TRP | F | 516 | 8.180 | 5.218 | 94.294 | 1.00 | 133.17 |
| 5988 | CE3 | TRP | F | 516 | 6.965 | 6.321 | 96.074 | 1.00 | 115.16 |
| 5989 | CD1 | TRP | F | 516 | 6.528 | 4.549 | 92.944 | 1.00 | 123.91 |
| 5990 | NE1 | TRP | F | 516 | 7.892 | 4.564 | 93.124 | 1.00 | 125.08 |
| 5991 | CZ2 | TRP | F | 516 | 9.420 | 5.488 | 94.903 | 1.00 | 128.80 |
| 5992 | CZ3 | TRP | F | 516 | 8.198 | 6.593 | 96.681 | 1.00 | 127.50 |
| 5993 | CH2 | TRP | F | 516 | 9.407 | 6.175 | 96.091 | 1.00 | 125.96 |
| 5994 | C | TRP | F | 516 | 3.763 | 3.161 | 94.999 | 1.00 | 90.08 |
| 5995 | O | TRP | F | 516 | 4.881 | 2.993 | 95.523 | 1.00 | 64.03 |
| 5996 | N | GLU | F | 517 | 2.665 | 2.487 | 95.343 | 1.00 | 84.09 |
| 5997 | CA | GLU | F | 517 | 2.615 | 1.449 | 96.366 | 1.00 | 93.95 |
| 5998 | CB | GLU | F | 517 | 1.950 | 2.005 | 97.630 | 1.00 | 94.54 |
| 5999 | CG | GLU | F | 517 | 2.761 | 3.145 | 98.245 | 1.00 | 110.13 |
| 6000 | CD | GLU | F | 517 | 2.294 | 3.558 | 99.634 | 1.00 | 115.68 |
| 6001 | OE1 | GLU | F | 517 | 1.176 | 4.104 | 99.750 | 1.00 | 121.10 |
| 6002 | OE2 | GLU | F | 517 | 3.050 | 3.340 | 100.608 | 1.00 | 110.15 |
| 6003 | C | GLU | F | 517 | 1.858 | 0.217 | 95.843 | 1.00 | 91.69 |
| 6004 | O | GLU | F | 517 | 1.796 | −0.828 | 96.508 | 1.00 | 85.99 |
| 6005 | N | ALA | F | 518 | 1.285 | 0.366 | 94.646 | 1.00 | 90.56 |
| 6006 | CA | ALA | F | 518 | 0.549 | −0.688 | 93.940 | 1.00 | 83.00 |
| 6007 | CB | ALA | F | 518 | −0.967 | −0.422 | 93.978 | 1.00 | 82.74 |
| 6008 | C | ALA | F | 518 | 1.063 | −0.551 | 92.518 | 1.00 | 79.00 |
| 6009 | O | ALA | F | 518 | 0.301 | −0.196 | 91.619 | 1.00 | 51.54 |
| 6010 | N | LYS | F | 519 | 2.363 | −0.816 | 92.340 | 1.00 | 80.58 |
| 6011 | CA | LYS | F | 519 | 3.045 | −0.687 | 91.048 | 1.00 | 81.38 |
| 6012 | CB | LYS | F | 519 | 4.562 | −0.723 | 91.232 | 1.00 | 82.97 |
| 6013 | CG | LYS | F | 519 | 5.158 | 0.498 | 91.904 | 1.00 | 93.50 |
| 6014 | CD | LYS | F | 519 | 6.589 | 0.725 | 91.413 | 1.00 | 95.53 |
| 6015 | CE | LYS | F | 519 | 7.395 | 1.577 | 92.369 | 1.00 | 85.29 |
| 6016 | NZ | LYS | F | 519 | 8.845 | 1.419 | 92.134 | 1.00 | 74.65 |
| 6017 | C | LYS | F | 519 | 2.692 | −1.692 | 89.978 | 1.00 | 77.08 |
| 6018 | O | LYS | F | 519 | 2.443 | −1.309 | 88.823 | 1.00 | 65.73 |
| 6019 | N | ASP | F | 520 | 2.707 | −2.971 | 90.354 | 1.00 | 65.62 |
| 6020 | CA | ASP | F | 520 | 2.390 | −4.064 | 89.427 | 1.00 | 94.02 |
| 6021 | CB | ASP | F | 520 | 1.832 | −5.259 | 90.209 | 1.00 | 96.95 |
| 6022 | CG | ASP | F | 520 | 2.787 | −5.749 | 91.280 | 1.00 | 105.58 |
| 6023 | OD1 | ASP | F | 520 | 3.846 | −6.306 | 90.926 | 1.00 | 112.49 |
| 6024 | OD2 | ASP | F | 520 | 2.481 | −5.569 | 92.477 | 1.00 | 106.38 |
| 6025 | C | ASP | F | 520 | 1.386 | −3.616 | 88.352 | 1.00 | 89.47 |
| 6026 | O | ASP | F | 520 | 1.210 | −4.277 | 87.314 | 1.00 | 65.20 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6027 | N | GLU | F | 521 | 0.730 | −2.490 | 88.635 | 1.00 | 79.91 |
| 6028 | CA | GLU | F | 521 | −0.243 | −1.887 | 87.745 | 1.00 | 87.65 |
| 6029 | CB | GLU | F | 521 | −1.490 | −1.422 | 88.531 | 1.00 | 89.45 |
| 6030 | CG | GLU | F | 521 | −2.472 | −2.530 | 88.952 | 1.00 | 86.15 |
| 6031 | CD | GLU | F | 521 | −2.262 | −3.040 | 90.383 | 1.00 | 88.36 |
| 6032 | OE1 | GLU | F | 521 | −2.176 | −2.205 | 91.312 | 1.00 | 81.34 |
| 6033 | OE2 | GLU | F | 521 | −2.202 | −4.276 | 90.581 | 1.00 | 73.99 |
| 6034 | C | GLU | F | 521 | 0.340 | −0.708 | 86.951 | 1.00 | 80.37 |
| 6035 | O | GLU | F | 521 | −0.348 | 0.286 | 86.733 | 1.00 | 101.77 |
| 6036 | N | PHE | F | 522 | 1.602 | −0.792 | 86.540 | 1.00 | 55.63 |
| 6037 | CA | PHE | F | 522 | 2.159 | 0.274 | 85.713 | 1.00 | 46.37 |
| 6038 | CB | PHE | F | 522 | 3.388 | 0.885 | 86.364 | 1.00 | 54.99 |
| 6039 | CG | PHE | F | 522 | 3.044 | 1.906 | 87.388 | 1.00 | 62.14 |
| 6040 | CD1 | PHE | F | 522 | 3.345 | 1.697 | 88.733 | 1.00 | 42.52 |
| 6041 | CD2 | PHE | F | 522 | 2.335 | 3.049 | 87.021 | 1.00 | 48.88 |
| 6042 | CE1 | PHE | F | 522 | 2.932 | 2.616 | 89.711 | 1.00 | 47.39 |
| 6043 | CE2 | PHE | F | 522 | 1.917 | 3.975 | 87.972 | 1.00 | 38.85 |
| 6044 | CZ | PHE | F | 522 | 2.211 | 3.763 | 89.324 | 1.00 | 49.73 |
| 6045 | C | PHE | F | 522 | 2.463 | −0.293 | 84.332 | 1.00 | 47.67 |
| 6046 | O | PHE | F | 522 | 3.441 | −1.016 | 84.119 | 1.00 | 41.16 |
| 6047 | N | ILE | F | 523 | 1.590 | 0.037 | 83.387 | 1.00 | 40.80 |
| 6048 | CA | ILE | F | 523 | 1.703 | −0.478 | 82.027 | 1.00 | 25.44 |
| 6049 | CB | ILE | F | 523 | 0.437 | −1.276 | 81.653 | 1.00 | 43.20 |
| 6050 | CG2 | ILE | F | 523 | 0.486 | −1.693 | 80.181 | 1.00 | 45.17 |
| 6051 | CG1 | ILE | F | 523 | 0.318 | −2.506 | 82.565 | 1.00 | 44.10 |
| 6052 | CD1 | ILE | F | 523 | −0.808 | −3.463 | 82.164 | 1.00 | 28.41 |
| 6053 | C | ILE | F | 523 | 1.952 | 0.519 | 80.920 | 1.00 | 31.86 |
| 6054 | O | ILE | F | 523 | 1.249 | 1.516 | 80.785 | 1.00 | 36.69 |
| 6055 | N | CYS | F | 524 | 2.970 | 0.225 | 80.123 | 1.00 | 39.95 |
| 6056 | CA | CYS | F | 524 | 3.316 | 1.051 | 78.975 | 1.00 | 30.16 |
| 6057 | C | CYS | F | 524 | 2.847 | 0.217 | 77.796 | 1.00 | 37.34 |
| 6058 | O | CYS | F | 524 | 3.350 | −0.883 | 77.553 | 1.00 | 37.99 |
| 6059 | CB | CYS | F | 524 | 4.825 | 1.297 | 78.903 | 1.00 | 30.66 |
| 6060 | SG | CYS | F | 524 | 5.341 | 2.179 | 77.407 | 1.00 | 58.20 |
| 6061 | N | ARG | F | 525 | 1.851 | 0.742 | 77.093 | 1.00 | 33.22 |
| 6062 | CA | ARG | F | 525 | 1.290 | 0.077 | 75.937 | 1.00 | 21.61 |
| 6063 | CB | ARG | F | 525 | −0.186 | −0.200 | 76.184 | 1.00 | 38.37 |
| 6064 | CG | ARG | F | 525 | −0.847 | −1.011 | 75.115 | 1.00 | 49.43 |
| 6065 | CD | ARG | F | 525 | −2.184 | −1.466 | 75.590 | 1.00 | 42.86 |
| 6066 | NE | ARG | F | 525 | −3.173 | −0.404 | 75.514 | 1.00 | 69.35 |
| 6067 | CZ | ARG | F | 525 | −4.355 | −0.446 | 76.119 | 1.00 | 74.70 |
| 6068 | NH1 | ARG | F | 525 | −4.689 | −1.503 | 76.851 | 1.00 | 57.57 |
| 6069 | NH2 | ARG | F | 525 | −5.199 | 0.570 | 75.990 | 1.00 | 70.99 |
| 6070 | C | ARG | F | 525 | 1.462 | 0.867 | 74.631 | 1.00 | 34.01 |
| 6071 | O | ARG | F | 525 | 1.190 | 2.074 | 74.564 | 1.00 | 34.83 |
| 6072 | N | ALA | F | 526 | 1.917 | 0.170 | 73.592 | 1.00 | 26.25 |
| 6073 | CA | ALA | F | 526 | 2.098 | 0.809 | 72.302 | 1.00 | 29.52 |
| 6074 | CB | ALA | F | 526 | 3.509 | 0.536 | 71.744 | 1.00 | 23.55 |
| 6075 | C | ALA | F | 526 | 1.062 | 0.294 | 71.334 | 1.00 | 43.05 |
| 6076 | O | ALA | F | 526 | 0.711 | −0.880 | 71.373 | 1.00 | 40.17 |
| 6077 | N | VAL | F | 527 | 0.586 | 1.184 | 70.474 | 1.00 | 25.00 |
| 6078 | CA | VAL | F | 527 | −0.379 | 0.824 | 69.470 | 1.00 | 38.08 |
| 6079 | CB | VAL | F | 527 | −1.661 | 1.699 | 69.578 | 1.00 | 46.40 |
| 6080 | CG1 | VAL | F | 527 | −2.614 | 1.380 | 68.442 | 1.00 | 46.38 |
| 6081 | CG2 | VAL | F | 527 | −2.343 | 1.423 | 70.897 | 1.00 | 36.99 |
| 6082 | C | VAL | F | 527 | 0.308 | 1.027 | 68.128 | 1.00 | 33.91 |
| 6083 | O | VAL | F | 527 | 0.692 | 2.149 | 67.769 | 1.00 | 29.12 |
| 6084 | N | HIS | F | 528 | 0.459 | −0.073 | 67.394 | 1.00 | 30.94 |
| 6085 | CA | HIS | F | 528 | 1.118 | −0.031 | 66.105 | 1.00 | 32.55 |
| 6086 | CB | HIS | F | 528 | 2.615 | −0.331 | 66.295 | 1.00 | 30.88 |
| 6087 | CG | HIS | F | 528 | 3.432 | −0.121 | 65.058 | 1.00 | 44.30 |
| 6088 | CD2 | HIS | F | 528 | 4.056 | 0.983 | 64.581 | 1.00 | 38.00 |
| 6089 | ND1 | HIS | F | 528 | 3.615 | −1.103 | 64.107 | 1.00 | 28.02 |
| 6090 | CE1 | HIS | F | 528 | 4.309 | −0.610 | 63.099 | 1.00 | 49.23 |
| 6091 | NE2 | HIS | F | 528 | 4.589 | 0.653 | 63.361 | 1.00 | 34.20 |
| 6092 | C | HIS | F | 528 | 0.509 | −0.995 | 65.106 | 1.00 | 37.36 |
| 6093 | O | HIS | F | 528 | 0.161 | −2.125 | 65.456 | 1.00 | 34.17 |
| 6094 | N | GLU | F | 529 | 0.411 | −0.539 | 63.857 | 1.00 | 44.16 |
| 6095 | CA | GLU | F | 529 | −0.159 | −1.317 | 62.757 | 1.00 | 45.71 |
| 6096 | CB | GLU | F | 529 | 0.020 | −0.548 | 61.455 | 1.00 | 42.99 |
| 6097 | CG | GLU | F | 529 | −0.253 | −1.370 | 60.217 | 1.00 | 70.99 |
| 6098 | CD | GLU | F | 529 | 0.028 | −0.594 | 58.958 | 1.00 | 91.74 |
| 6099 | OE1 | GLU | F | 529 | −0.085 | −1.182 | 57.855 | 1.00 | 78.05 |
| 6100 | OE2 | GLU | F | 529 | 0.358 | 0.611 | 59.079 | 1.00 | 81.73 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6101 | C | GLU | F | 529 | 0.383 | −2.738 | 62.567 | 1.00 | 50.88 |
| 6102 | O | GLU | F | 529 | −0.322 | −3.628 | 62.075 | 1.00 | 52.03 |
| 6103 | N | ALA | F | 530 | 1.627 | −2.956 | 62.969 | 1.00 | 52.28 |
| 6104 | CA | ALA | F | 530 | 2.251 | −4.258 | 62.804 | 1.00 | 46.43 |
| 6105 | CB | ALA | F | 530 | 3.659 | −4.074 | 62.266 | 1.00 | 39.82 |
| 6106 | C | ALA | F | 530 | 2.276 | −5.158 | 64.030 | 1.00 | 55.12 |
| 6107 | O | ALA | F | 530 | 2.667 | −6.310 | 63.926 | 1.00 | 47.94 |
| 6108 | N | ALA | F | 531 | 1.850 | −4.658 | 65.186 | 1.00 | 62.47 |
| 6109 | CA | ALA | F | 531 | 1.867 | −5.478 | 66.400 | 1.00 | 64.22 |
| 6110 | CB | ALA | F | 531 | 1.568 | −4.603 | 67.635 | 1.00 | 46.47 |
| 6111 | C | ALA | F | 531 | 0.881 | −6.651 | 66.314 | 1.00 | 69.72 |
| 6112 | O | ALA | F | 531 | 0.814 | −7.490 | 67.214 | 1.00 | 77.75 |
| 6113 | N | SER | F | 532 | 0.133 | −6.709 | 65.218 | 1.00 | 78.84 |
| 6114 | CA | SER | F | 532 | −0.856 | −7.762 | 64.999 | 1.00 | 96.54 |
| 6115 | CB | SER | F | 532 | −1.064 | −7.985 | 63.489 | 1.00 | 101.31 |
| 6116 | OG | SER | F | 532 | 0.140 | −8.358 | 62.835 | 1.00 | 99.05 |
| 6117 | C | SER | F | 532 | −0.529 | −9.096 | 65.685 | 1.00 | 88.77 |
| 6118 | O | SER | F | 532 | 0.620 | −9.535 | 65.711 | 1.00 | 88.99 |
| 6119 | N | PRO | F | 533 | −1.548 | −9.747 | 66.265 | 1.00 | 88.15 |
| 6120 | CD | PRO | F | 533 | −1.384 | −10.984 | 67.048 | 1.00 | 94.33 |
| 6121 | CA | PRO | F | 533 | −2.943 | −9.297 | 66.299 | 1.00 | 82.10 |
| 6122 | CB | PRO | F | 533 | −3.677 | −10.541 | 66.761 | 1.00 | 83.86 |
| 6123 | CG | PRO | F | 533 | −2.714 | −11.088 | 67.785 | 1.00 | 85.45 |
| 6124 | C | PRO | F | 933 | −3.101 | −8.152 | 67.292 | 1.00 | 82.26 |
| 6125 | O | PRO | F | 533 | −2.109 | −7.613 | 67.778 | 1.00 | 93.84 |
| 6126 | N | SER | F | 534 | −4.347 | −7.793 | 67.592 | 1.00 | 71.20 |
| 6127 | CA | SER | F | 534 | −4.655 | −6.725 | 68.544 | 1.00 | 64.68 |
| 6128 | CB | SER | F | 534 | −4.237 | −7.155 | 69.963 | 1.00 | 63.02 |
| 6129 | OG | SER | F | 534 | −2.832 | −7.414 | 70.055 | 1.00 | 62.20 |
| 6130 | C | SER | F | 534 | −4.049 | −5.350 | 68.226 | 1.00 | 48.78 |
| 6131 | O | SER | F | 534 | −4.563 | −4.343 | 68.676 | 1.00 | 55.26 |
| 6132 | N | GLN | F | 535 | −2.960 | −5.314 | 67.464 | 1.00 | 42.41 |
| 6133 | CA | GLN | F | 535 | −2.295 | −4.070 | 67.087 | 1.00 | 39.14 |
| 6134 | CB | GLN | F | 535 | −3.261 | −3.127 | 66.345 | 1.00 | 44.77 |
| 6135 | CG | GLN | F | 535 | −4.395 | −3.812 | 65.563 | 1.00 | 52.84 |
| 6136 | CD | GLN | F | 535 | −3.900 | −4.845 | 64.581 | 1.00 | 56.65 |
| 6137 | OE1 | GLN | F | 535 | −4.632 | −5.752 | 64.206 | 1.00 | 54.31 |
| 6138 | NE2 | GLN | F | 535 | −2.645 | −4.716 | 64.161 | 1.00 | 72.96 |
| 6139 | C | GLN | F | 535 | −1.709 | −3.341 | 68.302 | 1.00 | 45.62 |
| 6140 | O | GLN | F | 535 | −1.577 | −2.111 | 68.325 | 1.00 | 41.04 |
| 6141 | N | THR | F | 536 | −1.360 | −4.101 | 69.330 | 1.00 | 44.20 |
| 6142 | CA | THR | F | 536 | −0.761 | −3.499 | 70.516 | 1.00 | 48.90 |
| 6143 | CB | THR | F | 536 | −1.822 | −3.125 | 71.601 | 1.00 | 56.86 |
| 6144 | OG1 | THR | F | 536 | −2.321 | −4.309 | 72.234 | 1.00 | 49.80 |
| 6145 | CG2 | THR | F | 536 | −2.966 | −2.342 | 70.986 | 1.00 | 57.33 |
| 6146 | C | THR | F | 536 | 0.280 | −4.384 | 71.186 | 1.00 | 46.47 |
| 6147 | O | THR | F | 536 | 0.246 | −5.604 | 71.073 | 1.00 | 44.81 |
| 6148 | N | VAL | F | 537 | 1.227 | −3.740 | 71.854 | 1.00 | 30.54 |
| 6149 | CA | VAL | F | 537 | 2.267 | −4.440 | 72.611 | 1.00 | 37.39 |
| 6150 | CB | VAL | F | 537 | 3.639 | −4.412 | 71.914 | 1.00 | 42.16 |
| 6151 | CG1 | VAL | F | 537 | 4.452 | −5.584 | 72.379 | 1.00 | 26.71 |
| 6152 | CG2 | VAL | F | 537 | 3.477 | −4.427 | 70.430 | 1.00 | 39.65 |
| 6153 | C | VAL | F | 537 | 2.375 | −3.658 | 73.917 | 1.00 | 32.11 |
| 6154 | O | VAL | F | 537 | 2.186 | −2.442 | 73.936 | 1.00 | 42.14 |
| 6155 | N | GLN | F | 538 | 2.694 | −4.343 | 74.996 | 1.00 | 25.80 |
| 6156 | CA | GLN | F | 538 | 2.756 | −3.678 | 76.294 | 1.00 | 38.76 |
| 6157 | CB | GLN | F | 538 | 1.343 | −3.555 | 76.883 | 1.00 | 31.13 |
| 6158 | CG | GLN | F | 538 | 0.740 | −4.879 | 77.322 | 1.00 | 19.62 |
| 6159 | CD | GLN | F | 538 | −0.671 | −4.724 | 77.907 | 1.00 | 51.49 |
| 6160 | OE1 | GLN | F | 538 | −1.571 | −4.186 | 77.246 | 1.00 | 37.71 |
| 6161 | NE2 | GLN | F | 538 | −0.873 | −5.201 | 79.154 | 1.00 | 25.39 |
| 6162 | C | GLN | F | 538 | 3.644 | −4.379 | 77.312 | 1.00 | 35.38 |
| 6163 | O | GLN | F | 538 | 3.841 | −5.589 | 77.269 | 1.00 | 38.69 |
| 6164 | N | ARG | F | 539 | 4.179 | −3.595 | 78.236 | 1.00 | 35.14 |
| 6165 | CA | ARG | F | 539 | 5.038 | −4.140 | 79.270 | 1.00 | 37.99 |
| 6166 | CB | ARG | F | 539 | 6.515 | −3.904 | 78.936 | 1.00 | 36.20 |
| 6167 | CG | ARG | F | 539 | 7.435 | −5.011 | 79.442 | 1.00 | 62.55 |
| 6168 | CD | ARG | F | 539 | 7.946 | −5.887 | 78.305 | 1.00 | 96.87 |
| 6169 | NE | ARG | F | 539 | 6.874 | −6.490 | 77.507 | 1.00 | 108.47 |
| 6170 | CZ | ARG | F | 539 | 7.077 | −7.242 | 76.424 | 1.00 | 104.84 |
| 6171 | NH1 | ARG | F | 539 | 8.310 | −7.488 | 76.004 | 1.00 | 114.60 |
| 6172 | NH2 | ARG | F | 539 | 6.052 | −7.752 | 75.757 | 1.00 | 97.72 |
| 6173 | C | ARG | F | 539 | 4.679 | −3.490 | 80.593 | 1.00 | 31.31 |
| 6174 | O | ARG | F | 539 | 4.347 | −2.319 | 80.637 | 1.00 | 35.37 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6175 | N | ALA | F | 540 | 4.721 | −4.287 | 81.657 | 1.00 | 27.22 |
| 6176 | CA | ALA | F | 540 | 4.423 | −3.830 | 83.011 | 1.00 | 34.70 |
| 6177 | CB | ALA | F | 540 | 3.676 | −4.915 | 83.781 | 1.00 | 15.99 |
| 6178 | C | ALA | F | 540 | 5.724 | −3.490 | 83.750 | 1.00 | 44.26 |
| 6179 | O | ALA | F | 540 | 6.764 | −4.111 | 83.499 | 1.00 | 38.34 |
| 6180 | N | VAL | F | 541 | 5.661 | −2.495 | 84.637 | 1.00 | 47.07 |
| 6181 | CA | VAL | F | 541 | 6.813 | −2.097 | 85.431 | 1.00 | 42.79 |
| 6182 | CB | VAL | F | 541 | 7.208 | −0.654 | 85.209 | 1.00 | 44.69 |
| 6183 | CG1 | VAL | F | 541 | 8.700 | −0.524 | 85.373 | 1.00 | 33.65 |
| 6184 | CG2 | VAL | F | 541 | 6.730 | −0.173 | 83.883 | 1.00 | 55.08 |
| 6185 | C | VAL | F | 541 | 6.455 | −2.239 | 86.913 | 1.00 | 66.26 |
| 6186 | O | VAL | F | 541 | 5.446 | −1.690 | 87.399 | 1.00 | 45.59 |
| 6187 | N | SER | F | 542 | 7.321 | −2.951 | 87.623 | 1.00 | 77.09 |
| 6188 | CA | SER | F | 542 | 7.159 | −3.264 | 89.036 | 1.00 | 92.06 |
| 6189 | CB | SER | F | 542 | 7.973 | −4.526 | 89.332 | 1.00 | 96.77 |
| 6190 | OG | SER | F | 542 | 9.239 | −4.475 | 88.673 | 1.00 | 86.91 |
| 6191 | C | SER | F | 542 | 7.506 | −2.192 | 90.071 | 1.00 | 93.26 |
| 6192 | O | SER | F | 542 | 7.855 | −1.053 | 89.741 | 1.00 | 73.69 |
| 6193 | N | VAL | F | 543 | 7.414 | −2.609 | 91.336 | 1.00 | 111.85 |
| 6194 | CA | VAL | F | 543 | 7.696 | −1.781 | 92.514 | 1.00 | 111.96 |
| 6195 | CB | VAL | F | 543 | 7.069 | −2.393 | 93.799 | 1.00 | 113.84 |
| 6196 | CG1 | VAL | F | 543 | 7.459 | −1.565 | 95.019 | 1.00 | 110.82 |
| 6197 | CG2 | VAL | F | 543 | 5.552 | −2.447 | 93.669 | 1.00 | 107.62 |
| 6198 | C | VAL | F | 543 | 9.189 | −1.582 | 92.755 | 1.00 | 100.98 |
| 6199 | O | VAL | F | 543 | 9.766 | −2.331 | 93.578 | 1.00 | 91.87 |
| 6200 | OXT | VAL | F | 543 | 9.762 | −0.682 | 92.109 | 1.00 | 87.66 |
| 6201 | CB | VAL | A | 336 | 14.109 | 29.622 | 27.440 | 1.00 | 97.65 |
| 6202 | CG1 | VAL | A | 336 | 15.388 | 28.964 | 27.923 | 1.00 | 81.70 |
| 6203 | CG2 | VAL | A | 336 | 14.312 | 31.113 | 27.248 | 1.00 | 97.11 |
| 6204 | C | VAL | A | 336 | 13.387 | 27.488 | 26.371 | 1.00 | 89.07 |
| 6205 | O | VAL | A | 336 | 12.983 | 27.084 | 27.465 | 1.00 | 68.00 |
| 6206 | N | VAL | A | 336 | 12.464 | 29.673 | 25.547 | 1.00 | 74.36 |
| 6207 | CA | VAL | A | 336 | 13.659 | 28.974 | 26.116 | 1.00 | 90.76 |
| 6208 | N | SER | A | 337 | 13.623 | 26.677 | 25.349 | 1.00 | 88.54 |
| 6209 | CA | SER | A | 337 | 13.400 | 25.240 | 25.432 | 1.00 | 60.95 |
| 6210 | CB | SER | A | 337 | 12.197 | 24.853 | 24.573 | 1.00 | 74.47 |
| 6211 | OG | SER | A | 337 | 12.376 | 25.244 | 23.220 | 1.00 | 74.83 |
| 6212 | C | SER | A | 337 | 14.642 | 24.513 | 24.943 | 1.00 | 64.79 |
| 6213 | O | SER | A | 337 | 15.517 | 25.126 | 24.343 | 1.00 | 58.16 |
| 6214 | N | ALA | A | 338 | 14.719 | 23.208 | 25.199 | 1.00 | 82.47 |
| 6215 | CA | ALA | A | 338 | 15.870 | 22.405 | 24.786 | 1.00 | 66.22 |
| 6216 | CB | ALA | A | 338 | 16.859 | 22.296 | 25.942 | 1.00 | 59.04 |
| 6217 | C | ALA | A | 338 | 15.464 | 21.012 | 24.311 | 1.00 | 31.22 |
| 6218 | O | ALA | A | 338 | 14.815 | 20.274 | 25.035 | 1.00 | 54.26 |
| 6219 | N | TYR | A | 339 | 15.856 | 20.665 | 23.089 | 1.00 | 57.50 |
| 6220 | CA | TYR | A | 339 | 15.547 | 19.363 | 22.492 | 1.00 | 57.67 |
| 6221 | CB | TYR | A | 339 | 14.860 | 19.528 | 21.141 | 1.00 | 47.17 |
| 6222 | CG | TYR | A | 339 | 13.588 | 20.341 | 21.156 | 1.00 | 94.68 |
| 6223 | CD1 | TYR | A | 339 | 13.543 | 21.586 | 21.783 | 1.00 | 93.45 |
| 6224 | CE1 | TYR | A | 339 | 12.411 | 22.385 | 21.719 | 1.00 | 97.71 |
| 6225 | CD2 | TYR | A | 339 | 12.452 | 19.906 | 20.464 | 1.00 | 87.99 |
| 6226 | CE2 | TYR | A | 339 | 11.308 | 20.700 | 20.389 | 1.00 | 98.63 |
| 6227 | CZ | TYR | A | 339 | 11.300 | 21.945 | 21.020 | 1.00 | 97.34 |
| 6228 | OH | TYR | A | 339 | 10.210 | 22.783 | 20.937 | 1.00 | 85.94 |
| 6229 | C | TYR | A | 339 | 16.813 | 18.555 | 22.256 | 1.00 | 58.21 |
| 6230 | O | TYR | A | 339 | 17.858 | 19.112 | 21.958 | 1.00 | 60.36 |
| 6231 | N | LEU | A | 340 | 16.705 | 17.237 | 22.377 | 1.00 | 64.94 |
| 6232 | CA | LEU | A | 340 | 17.831 | 16.345 | 22.147 | 1.00 | 41.25 |
| 6233 | CB | LEU | A | 340 | 18.292 | 15.719 | 23.465 | 1.00 | 34.03 |
| 6234 | CG | LEU | A | 340 | 19.629 | 14.964 | 23.405 | 1.00 | 48.49 |
| 6235 | CD1 | LEU | A | 340 | 20.700 | 15.864 | 22.818 | 1.00 | 51.46 |
| 6236 | CD2 | LEU | A | 340 | 20.030 | 14.518 | 24.798 | 1.00 | 46.32 |
| 6237 | C | LEU | A | 340 | 17.396 | 15.254 | 21.174 | 1.00 | 37.79 |
| 6238 | O | LEU | A | 340 | 16.569 | 14.420 | 21.515 | 1.00 | 40.56 |
| 6239 | N | SER | A | 341 | 17.951 | 15.262 | 19.968 | 1.00 | 24.71 |
| 6240 | CA | SER | A | 341 | 17.589 | 14.268 | 18.975 | 1.00 | 47.02 |
| 6241 | CB | SER | A | 341 | 17.536 | 14.913 | 17.602 | 1.00 | 42.64 |
| 6242 | OG | SER | A | 341 | 18.837 | 15.182 | 17.139 | 1.00 | 61.52 |
| 6243 | C | SER | A | 341 | 18.538 | 13.075 | 18.926 | 1.00 | 50.06 |
| 6244 | O | SER | A | 341 | 19.644 | 13.142 | 19.436 | 1.00 | 43.33 |
| 6245 | N | ARG | A | 342 | 18.083 | 11.992 | 18.301 | 1.00 | 40.93 |
| 6246 | CA | ARG | A | 342 | 18.857 | 10.772 | 18.147 | 1.00 | 32.48 |
| 6247 | CB | ARG | A | 342 | 17.947 | 9.554 | 18.286 | 1.00 | 40.43 |
| 6248 | CG | ARG | A | 342 | 17.402 | 9.335 | 19.681 | 1.00 | 36.77 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6249 | CD | ARG | A | 342 | 16.666 | 8.022 | 19.749 | 1.00 | 19.71 |
| 6250 | NE | ARG | A | 342 | 15.425 | 8.106 | 18.990 | 1.00 | 75.82 |
| 6251 | CZ | ARG | A | 342 | 14.322 | 8.704 | 19.428 | 1.00 | 69.92 |
| 6252 | NH1 | ARC | A | 342 | 14.297 | 9.262 | 20.633 | 1.00 | 67.66 |
| 6253 | NH2 | ARG | A | 342 | 13.255 | 8.771 | 18.648 | 1.00 | 73.45 |
| 6254 | C | ARG | A | 342 | 19.543 | 10.741 | 16.784 | 1.00 | 46.33 |
| 6255 | O | ARG | A | 342 | 19.323 | 11.622 | 15.959 | 1.00 | 39.31 |
| 6256 | N | PRO | A | 343 | 20.397 | 9.734 | 16.539 | 1.00 | 54.84 |
| 6257 | CD | PRO | A | 343 | 20.916 | 8.748 | 17.502 | 1.00 | 52.58 |
| 6258 | CA | PRO | A | 343 | 21.101 | 9.614 | 15.257 | 1.00 | 47.67 |
| 6259 | CB | PRO | A | 343 | 22.064 | 8.443 | 15.479 | 1.00 | 35.51 |
| 6260 | CG | PRO | A | 343 | 22.293 | 8.459 | 16.943 | 1.00 | 74.02 |
| 6261 | C | PRO | A | 343 | 20.121 | 9.270 | 14.171 | 1.00 | 29.31 |
| 6262 | O | PRO | A | 343 | 19.113 | 8.629 | 14.433 | 1.00 | 48.93 |
| 6263 | N | SER | A | 344 | 20.416 | 9.701 | 12.951 | 1.00 | 33.67 |
| 6264 | CA | SER | A | 344 | 19.566 | 9.352 | 11.821 | 1.00 | 27.70 |
| 6265 | CB | SER | A | 344 | 19.979 | 10.088 | 10.582 | 1.00 | 20.64 |
| 6266 | OG | SER | A | 344 | 21.100 | 9.440 | 10.054 | 1.00 | 21.15 |
| 6267 | C | SER | A | 344 | 19.916 | 7.907 | 11.596 | 1.00 | 19.65 |
| 6268 | O | SER | A | 344 | 21.056 | 7.519 | 11.797 | 1.00 | 51.37 |
| 6269 | N | PRO | A | 345 | 18.955 | 7.085 | 11.211 | 1.00 | 27.61 |
| 6270 | CD | PRO | A | 345 | 17.502 | 7.222 | 11.383 | 1.00 | 45.79 |
| 6271 | CA | PRO | A | 345 | 19.326 | 5.688 | 10.989 | 1.00 | 22.83 |
| 6272 | CB | PRO | A | 345 | 17.972 | 5.017 | 10.731 | 1.00 | 26.43 |
| 6273 | CC | PRO | A | 345 | 17.076 | 5.792 | 11.657 | 1.00 | 34.75 |
| 6274 | C | PRO | A | 345 | 20.319 | 5.502 | 9.831 | 1.00 | 18.52 |
| 6275 | O | PRO | A | 345 | 21.036 | 4.520 | 9.779 | 1.00 | 35.15 |
| 6276 | N | PHE | A | 346 | 20.362 | 6.450 | 8.901 | 1.00 | 27.17 |
| 6277 | CA | PHE | A | 346 | 21.288 | 6.350 | 7.780 | 1.00 | 32.56 |
| 6278 | CB | PHE | A | 346 | 20.963 | 7.415 | 6.742 | 1.00 | 55.54 |
| 6279 | CG | PHE | A | 346 | 21.917 | 7.440 | 5.587 | 1.00 | 40.83 |
| 6280 | CD1 | PHE | A | 346 | 22.135 | 6.295 | 4.823 | 1.00 | 19.60 |
| 6281 | CD2 | PHE | A | 346 | 22.585 | 8.607 | 5.256 | 1.00 | 13.01 |
| 6282 | CE1 | PHE | A | 346 | 23.020 | 6.327 | 3.727 | 1.00 | 18.42 |
| 6283 | CE2 | PHE | A | 346 | 23.451 | 8.644 | 4.177 | 1.00 | 25.47 |
| 6284 | CZ | PHE | A | 346 | 23.666 | 7.510 | 3.414 | 1.00 | 11.65 |
| 6285 | C | PHE | A | 346 | 22.761 | 6.497 | 8.198 | 1.00 | 43.76 |
| 6286 | O | PHE | A | 346 | 23.627 | 5.721 | 7.770 | 1.00 | 19.96 |
| 6287 | N | ASP | A | 347 | 23.001 | 7.526 | 9.012 | 1.00 | 26.54 |
| 6288 | CA | ASP | A | 347 | 24.306 | 7.912 | 9.573 | 1.00 | 34.82 |
| 6289 | CB | ASP | A | 347 | 24.176 | 9.228 | 10.350 | 1.00 | 19.91 |
| 6290 | CG | ASP | A | 347 | 24.169 | 10.442 | 9.470 | 1.00 | 37.79 |
| 6291 | OD1 | ASP | A | 347 | 23.764 | 11.514 | 9.976 | 1.00 | 35.72 |
| 6292 | OD2 | ASP | A | 347 | 24.571 | 10.333 | 8.294 | 1.00 | 75.06 |
| 6293 | C | ASP | A | 347 | 24.828 | 6.869 | 10.553 | 1.00 | 45.95 |
| 6294 | O | ASP | A | 347 | 26.041 | 6.742 | 10.762 | 1.00 | 49.04 |
| 6295 | N | LEU | A | 348 | 23.884 | 6.157 | 11.167 | 1.00 | 32.97 |
| 6296 | A | LEU | A | 348 | 24.166 | 5.133 | 12.158 | 1.00 | 44.34 |
| 6297 | CB | LEU | A | 348 | 23.044 | 5.126 | 13.214 | 1.00 | 43.82 |
| 6298 | CG | LEU | A | 348 | 22.979 | 3.999 | 14.260 | 1.00 | 58.65 |
| 6299 | CD1 | LEU | A | 348 | 24.059 | 4.142 | 15.345 | 1.00 | 3.70 |
| 6300 | CD2 | LEU | A | 348 | 21.617 | 4.038 | 14.893 | 1.00 | 43.52 |
| 6301 | C | LEU | A | 348 | 24.342 | 3.722 | 11.588 | 1.00 | 42.92 |
| 6302 | O | LEU | A | 348 | 25.238 | 2.998 | 12.015 | 1.00 | 45.64 |
| 6303 | N | PHE | A | 349 | 23.493 | 3.340 | 10.635 | 1.00 | 27.98 |
| 6304 | CA | PHE | A | 349 | 23.551 | 2.010 | 10.042 | 1.00 | 33.86 |
| 6305 | CB | PHE | A | 349 | 22.141 | 1.406 | 10.020 | 1.00 | 24.60 |
| 6306 | CG | PHE | A | 349 | 21.486 | 1.342 | 11.363 | 1.00 | 29.72 |
| 6307 | CD1 | PHE | A | 349 | 20.141 | 1.681 | 11.504 | 1.00 | 59.58 |
| 6308 | CD2 | PHE | A | 349 | 22.168 | 0.846 | 12.469 | 1.00 | 29.11 |
| 6309 | CE1 | PHE | A | 349 | 19.479 | 1.517 | 12.732 | 1.00 | 21.24 |
| 6310 | CE2 | PHE | A | 349 | 21.525 | 0.671 | 13.698 | 1.00 | 29.42 |
| 6311 | CZ | PHE | A | 349 | 20.178 | 1.003 | 13.834 | 1.00 | 40.15 |
| 6312 | C | PHE | A | 349 | 24.179 | 1.912 | 8.643 | 1.00 | 40.65 |
| 6313 | O | PHE | A | 349 | 24.403 | 0.812 | 8.131 | 1.00 | 45.16 |
| 6314 | N | ILE | A | 350 | 24.460 | 3.041 | 8.014 | 1.00 | 38.63 |
| 6315 | CA | ILE | A | 350 | 25.065 | 2.990 | 6.695 | 1.00 | 47.73 |
| 6316 | CB | ILE | A | 350 | 24.078 | 3.480 | 5.629 | 1.00 | 61.04 |
| 6317 | CG2 | ILE | A | 350 | 24.617 | 3.179 | 4.255 | 1.00 | 41.84 |
| 6318 | CG1 | ILE | A | 350 | 22.733 | 2.779 | 5.808 | 1.00 | 74.70 |
| 6319 | CD1 | ILE | A | 350 | 22.814 | 1.255 | 5.794 | 1.00 | 19.05 |
| 6320 | C | ILE | A | 350 | 26.365 | 3.802 | 6.603 | 1.00 | 56.12 |
| 6321 | O | ILE | A | 350 | 27.421 | 3.267 | 6.299 | 1.00 | 42.08 |
| 6322 | N | ARG | A | 351 | 26.280 | 5.096 | 6.870 | 1.00 | 53.68 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6323 | CA | ARG | A | 351 | 27.442 | 5.973 | 6.814 | 1.00 | 26.75 |
| 6324 | CB | ARG | A | 351 | 26.978 | 7.417 | 6.558 | 1.00 | 37.32 |
| 6325 | CG | ARG | A | 351 | 28.076 | 8.457 | 6.446 | 1.00 | 48.89 |
| 6326 | CD | ARG | A | 351 | 27.544 | 9.842 | 6.780 | 1.00 | 58.45 |
| 6327 | NE | ARG | A | 351 | 28.421 | 10.905 | 6.315 | 1.00 | 93.16 |
| 6328 | CZ | ARG | A | 351 | 29.713 | 10.991 | 6.606 | 1.00 | 78.46 |
| 6329 | NH1 | ARG | A | 351 | 30.282 | 10.072 | 7.368 | 1.00 | 81.39 |
| 6330 | NH2 | ARG | A | 351 | 30.439 | 11.989 | 6.125 | 1.00 | 83.96 |
| 6331 | C | ARG | A | 351 | 28.182 | 5.863 | 8.145 | 1.00 | 49.48 |
| 6332 | O | ARG | A | 351 | 29.057 | 6.675 | 8.460 | 1.00 | 53.74 |
| 6333 | N | LYS | A | 352 | 27.812 | 4.838 | 8.911 | 1.00 | 51.18 |
| 6334 | CA | LYS | A | 352 | 28.369 | 4.538 | 10.236 | 1.00 | 50.09 |
| 6335 | CB | LYS | A | 352 | 29.238 | 3.291 | 10.148 | 1.00 | 23.95 |
| 6336 | CG | LYS | A | 352 | 28.496 | 2.134 | 9.497 | 1.00 | 59.78 |
| 6337 | CD | LYS | A | 352 | 29.375 | 0.923 | 9.260 | 1.00 | 71.28 |
| 6338 | CE | LYS | A | 352 | 28.609 | −0.168 | 8.520 | 1.00 | 76.16 |
| 6339 | NZ | LYS | A | 352 | 28.101 | 0.281 | 7.179 | 1.00 | 72.76 |
| 6340 | C | LYS | A | 352 | 29.112 | 5.613 | 11.035 | 1.00 | 41.33 |
| 6341 | O | LYS | A | 352 | 30.097 | 5.306 | 11.696 | 1.00 | 34.90 |
| 6342 | N | SER | A | 353 | 28.620 | 6.853 | 10.988 | 1.00 | 31.41 |
| 6343 | CA | SER | A | 353 | 29.196 | 7.965 | 11.734 | 1.00 | 62.52 |
| 6344 | CB | SER | A | 353 | 30.105 | 8.823 | 10.837 | 1.00 | 42.53 |
| 6345 | OG | SER | A | 353 | 29.387 | 9.418 | 9.777 | 1.00 | 93.24 |
| 6346 | C | SER | A | 353 | 28.020 | 8.782 | 12.294 | 1.00 | 53.70 |
| 6347 | O | SER | A | 353 | 27.632 | 9.815 | 11.768 | 1.00 | 52.38 |
| 6348 | N | PRO | A | 354 | 27.434 | 8.304 | 13.388 | 1.00 | 49.04 |
| 6349 | CD | PRO | A | 354 | 27.704 | 7.003 | 14.027 | 1.00 | 37.34 |
| 6350 | CA | PRO | A | 354 | 26.305 | 8.963 | 14.033 | 1.00 | 40.98 |
| 6351 | CB | PRO | A | 354 | 25.831 | 7.918 | 15.042 | 1.00 | 54.87 |
| 6352 | CG | PRO | A | 354 | 26.366 | 6.633 | 14.523 | 1.00 | 47.43 |
| 6353 | C | PRO | A | 354 | 26.631 | 10.271 | 14.728 | 1.00 | 38.29 |
| 6354 | O | PRO | A | 354 | 27.779 | 10.565 | 15.033 | 1.00 | 64.30 |
| 6355 | N | THR | A | 355 | 25.582 | 11.038 | 14.993 | 1.00 | 46.72 |
| 6356 | CA | THR | A | 355 | 25.676 | 12.297 | 15.703 | 1.00 | 30.95 |
| 6357 | CB | THR | A | 355 | 26.029 | 13.469 | 14.751 | 1.00 | 25.78 |
| 6358 | OG1 | THR | A | 355 | 25.149 | 13.460 | 13.626 | 1.00 | 72.89 |
| 6359 | CG2 | THR | A | 355 | 27.462 | 13.374 | 14.298 | 1.00 | 24.61 |
| 6360 | C | THR | A | 355 | 24.324 | 12.574 | 16.383 | 1.00 | 31.02 |
| 6361 | O | THR | A | 355 | 23.300 | 12.045 | 15.977 | 1.00 | 52.20 |
| 6362 | N | ILE | A | 356 | 24.342 | 13.381 | 17.434 | 1.00 | 46.29 |
| 6363 | CA | ILE | A | 356 | 23.141 | 13.769 | 18.147 | 1.00 | 33.61 |
| 6364 | CB | ILE | A | 356 | 23.096 | 13.143 | 19.557 | 1.00 | 29.88 |
| 6365 | CG2 | ILE | A | 356 | 22.951 | 11.637 | 19.459 | 1.00 | 33.72 |
| 6366 | CG1 | ILE | A | 356 | 24.352 | 13.523 | 20.339 | 1.00 | 33.45 |
| 6367 | CD1 | ILE | A | 356 | 24.434 | 12.907 | 21.727 | 1.00 | 33.56 |
| 6368 | C | ILE | A | 356 | 23.204 | 15.303 | 18.260 | 1.00 | 61.79 |
| 6369 | O | ILE | A | 356 | 24.278 | 15.876 | 18.423 | 1.00 | 43.23 |
| 6370 | N | THR | A | 357 | 22.060 | 15.972 | 18.179 | 1.00 | 54.78 |
| 6371 | CA | THR | A | 357 | 22.051 | 17.428 | 18.256 | 1.00 | 42.46 |
| 6372 | CB | THR | A | 357 | 21.491 | 18.038 | 16.950 | 1.00 | 30.75 |
| 6373 | OG1 | THR | A | 357 | 22.172 | 17.482 | 15.825 | 1.00 | 45.99 |
| 6374 | CG2 | THR | A | 357 | 21.679 | 19.535 | 16.954 | 1.00 | 34.50 |
| 6375 | C | THR | A | 357 | 21.245 | 18.011 | 19.408 | 1.00 | 21.50 |
| 6376 | O | THR | A | 357 | 20.049 | 17.774 | 19.506 | 1.00 | 58.81 |
| 6377 | N | CYS | A | 358 | 21.887 | 18.792 | 20.261 | 1.00 | 31.05 |
| 6378 | CA | CYS | A | 358 | 21.178 | 19.445 | 21.360 | 1.00 | 44.18 |
| 6379 | C | CYS | A | 358 | 20.780 | 20.773 | 20.732 | 1.00 | 49.36 |
| 6380 | O | CYS | A | 358 | 21.631 | 21.504 | 20.238 | 1.00 | 40.60 |
| 6381 | CB | CYS | A | 358 | 22.104 | 19.688 | 22.560 | 1.00 | 57.29 |
| 6382 | SG | CYS | A | 358 | 21.318 | 20.208 | 24.132 | 1.00 | 46.68 |
| 6383 | N | LEU | A | 359 | 19.488 | 21.067 | 20.719 | 1.00 | 39.30 |
| 6384 | CA | LEU | A | 359 | 18.989 | 22.295 | 20.127 | 1.00 | 38.23 |
| 6385 | CB | LEU | A | 359 | 18.054 | 21.950 | 18.973 | 1.00 | 51.74 |
| 6386 | CG | LEU | A | 359 | 17.116 | 23.019 | 18.435 | 1.00 | 55.54 |
| 6387 | CD1 | LEU | A | 359 | 17.902 | 24.144 | 17.824 | 1.00 | 74.13 |
| 6388 | CD2 | LEU | A | 359 | 16.208 | 22.391 | 17.411 | 1.00 | 55.08 |
| 6389 | C | LEU | A | 359 | 18.269 | 23.161 | 21.145 | 1.00 | 46.76 |
| 6390 | O | LEU | A | 359 | 17.253 | 22.779 | 21.701 | 1.00 | 48.59 |
| 6391 | N | VAL | A | 360 | 18.812 | 24.339 | 21.400 | 1.00 | 65.80 |
| 6392 | CA | VAL | A | 360 | 18.195 | 25.248 | 22.360 | 1.00 | 75.00 |
| 6393 | CB | VAL | A | 360 | 19.243 | 25.877 | 23.304 | 1.00 | 77.67 |
| 6394 | CG1 | VAL | A | 360 | 18.551 | 26.729 | 24.331 | 1.00 | 68.72 |
| 6395 | CG2 | VAL | A | 360 | 20.062 | 24.789 | 23.990 | 1.00 | 68.28 |
| 6396 | C | VAL | A | 360 | 17.489 | 26.356 | 21.596 | 1.00 | 68.89 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6397 | O | VAL | A | 360 | 18.091 | 27.008 | 20.754 | 1.00 | 55.93 |
| 6398 | N | VAL | A | 361 | 16.209 | 26.554 | 21.893 | 1.00 | 79.80 |
| 6399 | CA | VAL | A | 361 | 15.401 | 27.566 | 21.227 | 1.00 | 77.83 |
| 6400 | CB | VAL | A | 361 | 14.101 | 26.960 | 20.635 | 1.00 | 63.41 |
| 6401 | CG1 | VAL | A | 361 | 13.275 | 28.052 | 19.976 | 1.00 | 73.64 |
| 6402 | CG2 | VAL | A | 361 | 14.437 | 25.871 | 19.616 | 1.00 | 66.95 |
| 6403 | C | VAL | A | 361 | 15.007 | 28.682 | 22.178 | 1.00 | 92.94 |
| 6404 | O | VAL | A | 361 | 14.294 | 28.457 | 23.154 | 1.00 | 96.67 |
| 6405 | N | ASP | A | 362 | 15.475 | 29.888 | 21.884 | 1.00 | 107.05 |
| 6406 | CA | ASP | A | 362 | 15.156 | 31.046 | 22.704 | 1.00 | 113.13 |
| 6407 | CB | ASP | A | 362 | 16.420 | 31.601 | 23.351 | 1.00 | 106.60 |
| 6408 | CG | ASP | A | 362 | 16.115 | 32.546 | 24.484 | 1.00 | 111.13 |
| 6409 | OD1 | ASP | A | 362 | 15.266 | 33.440 | 24.295 | 1.00 | 125.53 |
| 6410 | OD2 | ASP | A | 362 | 16.723 | 32.395 | 25.564 | 1.00 | 113.41 |
| 6411 | C | ASP | A | 362 | 14.520 | 32.116 | 21.823 | 1.00 | 113.10 |
| 6412 | O | ASP | A | 362 | 15.143 | 32.601 | 20.876 | 1.00 | 112.91 |
| 6413 | N | LEU | A | 363 | 13.278 | 32.479 | 22.132 | 1.00 | 119.77 |
| 6414 | CA | LEU | A | 363 | 12.569 | 33.492 | 21.352 | 1.00 | 124.48 |
| 6415 | CB | LEU | A | 363 | 11.048 | 33.275 | 21.451 | 1.00 | 118.61 |
| 6416 | CG | LEU | A | 363 | 10.453 | 32.017 | 20.798 | 1.00 | 113.84 |
| 6417 | CD1 | LEU | A | 363 | 8.990 | 31.894 | 21.175 | 1.00 | 108.31 |
| 6418 | CD2 | LEU | A | 363 | 10.601 | 32.081 | 19.282 | 1.00 | 119.45 |
| 6419 | C | LEU | A | 363 | 12.930 | 34.919 | 21.789 | 1.00 | 126.79 |
| 6420 | O | LEU | A | 363 | 12.620 | 35.888 | 21.089 | 1.00 | 132.00 |
| 6421 | N | ALA | A | 364 | 13.593 | 35.043 | 22.939 | 1.00 | 124.92 |
| 6422 | CA | ALA | A | 364 | 13.998 | 36.349 | 23.454 | 1.00 | 118.39 |
| 6423 | CB | ALA | A | 364 | 13.317 | 36.611 | 24.789 | 1.00 | 115.51 |
| 6424 | C | ALA | A | 364 | 15.520 | 36.447 | 23.608 | 1.00 | 120.92 |
| 6425 | O | ALA | A | 364 | 16.058 | 36.273 | 24.702 | 1.00 | 118.82 |
| 6426 | N | PRO | A | 365 | 16.232 | 36.736 | 22.505 | 1.00 | 125.28 |
| 6427 | CD | PRO | A | 365 | 15.681 | 36.944 | 21.151 | 1.00 | 130.28 |
| 6428 | CA | PRO | A | 365 | 17.694 | 36.861 | 22.495 | 1.00 | 120.86 |
| 6429 | CB | PRO | A | 365 | 17.981 | 37.378 | 21.088 | 1.00 | 132.31 |
| 6430 | CG | PRO | A | 365 | 16.692 | 36.733 | 20.273 | 1.00 | 137.33 |
| 6431 | C | PRO | A | 365 | 18.269 | 37.780 | 23.571 | 1.00 | 127.80 |
| 6432 | O | PRO | A | 365 | 18.484 | 38.973 | 23.333 | 1.00 | 129.72 |
| 6433 | N | SER | A | 366 | 18.517 | 37.223 | 24.753 | 1.00 | 123.94 |
| 6434 | CA | SER | A | 366 | 19.085 | 37.999 | 25.850 | 1.00 | 131.57 |
| 6435 | CB | SER | A | 366 | 18.445 | 37.595 | 27.180 | 1.00 | 117.41 |
| 6436 | OG | SER | A | 366 | 18.593 | 36.208 | 27.415 | 1.00 | 132.63 |
| 6437 | C | SER | A | 366 | 20.594 | 37.762 | 25.896 | 1.00 | 135.14 |
| 6438 | O | SER | A | 366 | 21.057 | 36.623 | 25.794 | 1.00 | 132.51 |
| 6439 | N | LYS | A | 367 | 21.356 | 38.841 | 26.046 | 1.00 | 132.85 |
| 6440 | CA | LYS | A | 367 | 22.812 | 38.752 | 26.082 | 1.00 | 131.65 |
| 6441 | CB | LYS | A | 367 | 23.420 | 40.159 | 26.152 | 1.00 | 129.49 |
| 6442 | CG | LYS | A | 367 | 23.009 | 41.059 | 24.991 | 1.00 | 136.43 |
| 6443 | CD | LYS | A | 367 | 23.784 | 42.371 | 24.973 | 1.00 | 134.09 |
| 6444 | CE | LYS | A | 367 | 25.263 | 42.142 | 24.705 | 1.00 | 125.96 |
| 6445 | NZ | LYS | A | 367 | 26.005 | 43.428 | 24.584 | 1.00 | 126.00 |
| 6446 | C | LYS | A | 367 | 23.368 | 37.885 | 27.213 | 1.00 | 128.60 |
| 6447 | O | LYS | A | 367 | 22.824 | 37.849 | 28.319 | 1.00 | 113.08 |
| 6448 | N | GLY | A | 368 | 24.462 | 37.191 | 26.911 | 1.00 | 127.03 |
| 6449 | CA | GLY | A | 368 | 25.104 | 36.320 | 27.878 | 1.00 | 121.71 |
| 6450 | C | GLY | A | 368 | 25.422 | 34.969 | 27.264 | 1.00 | 122.18 |
| 6451 | O | GLY | A | 368 | 24.577 | 34.377 | 26.593 | 1.00 | 123.56 |
| 6452 | N | THR | A | 369 | 26.639 | 34.479 | 27.486 | 1.00 | 118.65 |
| 6453 | CA | THR | A | 369 | 27.050 | 33.185 | 26.945 | 1.00 | 110.95 |
| 6454 | CB | THR | A | 369 | 28.508 | 32.841 | 27.349 | 1.00 | 110.46 |
| 6455 | OG1 | THR | A | 369 | 28.710 | 33.139 | 28.736 | 1.00 | 109.44 |
| 6456 | CG2 | THR | A | 369 | 29.500 | 33.631 | 26.509 | 1.00 | 99.62 |
| 6457 | C | THR | A | 369 | 26.137 | 32.035 | 27.385 | 1.00 | 106.66 |
| 6458 | O | THR | A | 369 | 25.632 | 32.010 | 28.508 | 1.00 | 94.11 |
| 6459 | N | VAL | A | 370 | 25.924 | 31.086 | 26.482 | 1.00 | 104.89 |
| 6460 | CA | VAL | A | 370 | 25.090 | 29.928 | 26.768 | 1.00 | 91.70 |
| 6461 | CB | VAL | A | 370 | 23.986 | 29.755 | 25.710 | 1.00 | 91.21 |
| 6462 | CG1 | VAL | A | 370 | 23.013 | 28.678 | 26.157 | 1.00 | 88.89 |
| 6463 | CG2 | VAL | A | 370 | 23.275 | 31.073 | 25.476 | 1.00 | 83.94 |
| 6464 | C | VAL | A | 370 | 25.987 | 28.700 | 26.723 | 1.00 | 84.01 |
| 6465 | O | VAL | A | 370 | 26.577 | 28.409 | 25.682 | 1.00 | 73.24 |
| 6466 | N | ASN | A | 371 | 26.091 | 27.987 | 27.842 | 1.00 | 77.00 |
| 6467 | CA | ASN | A | 371 | 26.926 | 26.794 | 27.908 | 1.00 | 76.93 |
| 6468 | CB | ASN | A | 371 | 27.588 | 26.685 | 29.280 | 1.00 | 91.60 |
| 6469 | CG | ASN | A | 371 | 28.685 | 27.706 | 29.479 | 1.00 | 94.66 |
| 6470 | OD1 | ASN | A | 371 | 29.643 | 27.758 | 28.706 | 1.00 | 101.42 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6471 | ND2 | ASN | A | 371 | 28.558 | 28.521 | 30.521 | 1.00 | 88.75 |
| 6472 | C | ASN | A | 371 | 26.151 | 25.515 | 27.629 | 1.00 | 72.12 |
| 6473 | O | ASN | A | 371 | 25.117 | 25.259 | 28.243 | 1.00 | 73.98 |
| 6474 | N | LEU | A | 372 | 26.652 | 24.722 | 26.689 | 1.00 | 69.63 |
| 6475 | A | LEU | A | 372 | 26.027 | 23.451 | 26.343 | 1.00 | 70.37 |
| 6476 | CB | LEU | A | 372 | 25.580 | 23.430 | 24.879 | 1.00 | 75.60 |
| 6477 | CG | LEU | A | 372 | 24.456 | 24.394 | 24.487 | 1.00 | 94.74 |
| 6478 | CD1 | LEU | A | 372 | 24.069 | 24.114 | 23.049 | 1.00 | 92.87 |
| 6479 | CD2 | LEU | A | 372 | 23.246 | 24.222 | 25.399 | 1.00 | 83.17 |
| 6480 | C | LEU | A | 372 | 27.051 | 22.361 | 26.579 | 1.00 | 63.16 |
| 6481 | O | LEU | A | 372 | 27.857 | 22.059 | 25.713 | 1.00 | 60.65 |
| 6482 | N | THR | A | 373 | 27.015 | 21.780 | 27.766 | 1.00 | 57.73 |
| 6483 | CA | THR | A | 373 | 27.943 | 20.731 | 28.133 | 1.00 | 60.22 |
| 6484 | CB | THR | A | 373 | 28.252 | 20.813 | 29.650 | 1.00 | 68.12 |
| 6485 | OG1 | THR | A | 373 | 28.513 | 22.172 | 30.007 | 1.00 | 88.57 |
| 6486 | CG2 | THR | A | 373 | 29.462 | 19.973 | 30.007 | 1.00 | 60.05 |
| 6487 | C | THR | A | 373 | 27.387 | 19.333 | 27.807 | 1.00 | 46.29 |
| 6488 | O | THR | A | 373 | 26.214 | 19.061 | 28.005 | 1.00 | 44.15 |
| 6489 | N | TRP | A | 374 | 28.242 | 18.459 | 27.300 | 1.00 | 28.34 |
| 6490 | CA | TRP | A | 374 | 27.868 | 17.087 | 27.007 | 1.00 | 39.27 |
| 6491 | CB | TRP | A | 374 | 28.374 | 16.659 | 25.636 | 1.00 | 45.50 |
| 6492 | CG | TRP | A | 374 | 27.646 | 17.275 | 24.543 | 1.00 | 52.83 |
| 6493 | CD2 | TRP | A | 374 | 26.413 | 16.824 | 24.013 | 1.00 | 47.47 |
| 6494 | CE2 | TRP | A | 374 | 26.036 | 17.733 | 23.002 | 1.00 | 72.78 |
| 6495 | CE3 | TRP | A | 374 | 25.580 | 15.741 | 24.296 | 1.00 | 35.10 |
| 6496 | CD1 | TRP | A | 374 | 27.973 | 18.412 | 23.863 | 1.00 | 60.86 |
| 6497 | NE1 | TRP | A | 374 | 27.009 | 18.696 | 22.931 | 1.00 | 77.42 |
| 6498 | CZ2 | TRP | A | 374 | 24.861 | 17.586 | 22.270 | 1.00 | 66.34 |
| 6499 | CZ3 | TRP | A | 374 | 24.413 | 15.596 | 23.572 | 1.00 | 62.29 |
| 6500 | CH2 | TRP | A | 374 | 24.064 | 16.514 | 22.568 | 1.00 | 54.60 |
| 6501 | C | TRP | A | 374 | 28.496 | 16.180 | 28.047 | 1.00 | 58.65 |
| 6502 | O | TRP | A | 374 | 29.437 | 16.572 | 28.741 | 1.00 | 69.05 |
| 6503 | N | SER | A | 375 | 27.972 | 14.965 | 28.152 | 1.00 | 59.05 |
| 6504 | CA | SER | A | 375 | 28.492 | 13.985 | 29.097 | 1.00 | 63.21 |
| 6505 | CB | SER | A | 375 | 28.277 | 14.439 | 30.541 | 1.00 | 44.90 |
| 6506 | OG | SER | A | 375 | 26.910 | 14.695 | 30.800 | 1.00 | 60.59 |
| 6507 | C | SER | A | 375 | 27.804 | 12.663 | 28.888 | 1.00 | 51.42 |
| 6508 | O | SER | A | 375 | 26.700 | 12.610 | 28.367 | 1.00 | 59.36 |
| 6509 | N | ARG | A | 376 | 28.473 | 11.592 | 29.283 | 1.00 | 46.69 |
| 6510 | CA | ARG | A | 376 | 27.909 | 10.258 | 29.157 | 1.00 | 56.90 |
| 6511 | CB | ARG | A | 376 | 28.922 | 9.288 | 28.561 | 1.00 | 63.66 |
| 6512 | CG | ARG | A | 376 | 29.462 | 9.663 | 27.219 | 1.00 | 24.02 |
| 6513 | CD | ARG | A | 376 | 29.752 | 8.383 | 26.510 | 1.00 | 27.29 |
| 6514 | NE | ARG | A | 376 | 31.070 | 8.350 | 25.945 | 1.00 | 49.17 |
| 6515 | CZ | ARG | A | 376 | 31.630 | 7.236 | 25.529 | 1.00 | 57.99 |
| 6516 | NH1 | ARG | A | 376 | 30.938 | 6.114 | 25.633 | 1.00 | 24.51 |
| 6517 | NH2 | ARG | A | 376 | 32.873 | 7.251 | 25.058 | 1.00 | 34.15 |
| 6518 | C | ARG | A | 376 | 27.497 | 9.746 | 30.529 | 1.00 | 45.32 |
| 6519 | O | ARG | A | 376 | 28.027 | 10.167 | 31.549 | 1.00 | 52.55 |
| 6520 | N | ALA | A | 377 | 26.561 | 8.814 | 30.542 | 1.00 | 52.65 |
| 6521 | CA | ALA | A | 377 | 26.082 | 8.261 | 31.790 | 1.00 | 53.91 |
| 6522 | CB | ALA | A | 377 | 24.822 | 7.468 | 31.546 | 1.00 | 18.78 |
| 6523 | C | ALA | A | 377 | 27.144 | 7.375 | 32.394 | 1.00 | 44.90 |
| 6524 | O | ALA | A | 377 | 27.263 | 7.266 | 33.612 | 1.00 | 67.59 |
| 6525 | N | SER | A | 378 | 27.919 | 6.744 | 31.526 | 1.00 | 54.17 |
| 6526 | CA | SER | A | 378 | 28.964 | 5.829 | 31.953 | 1.00 | 47.05 |
| 6527 | CB | SER | A | 378 | 29.510 | 5.048 | 30.753 | 1.00 | 18.68 |
| 6528 | OG | SER | A | 378 | 30.055 | 5.934 | 29.795 | 1.00 | 66.32 |
| 6529 | C | SER | A | 378 | 30.082 | 6.594 | 32.611 | 1.00 | 55.65 |
| 6530 | O | SER | A | 378 | 30.663 | 6.137 | 33.586 | 1.00 | 46.56 |
| 6531 | N | GLY | A | 379 | 30.377 | 7.769 | 32.068 | 1.00 | 53.62 |
| 6532 | CA | GLY | A | 379 | 31.442 | 8.591 | 32.605 | 1.00 | 31.19 |
| 6533 | C | GLY | A | 379 | 32.612 | 8.603 | 31.648 | 1.00 | 50.79 |
| 6534 | O | GLY | A | 379 | 33.644 | 9.194 | 31.924 | 1.00 | 50.13 |
| 6535 | N | LYS | A | 380 | 32.463 | 7.933 | 30.514 | 1.00 | 61.32 |
| 6536 | CA | LYS | A | 380 | 33.529 | 7.922 | 29.537 | 1.00 | 47.97 |
| 6537 | CB | LYS | A | 380 | 33.307 | 6.809 | 28.520 | 1.00 | 55.07 |
| 6538 | CG | LYS | A | 380 | 33.251 | 5.449 | 29.136 | 1.00 | 55.31 |
| 6539 | CD | LYS | A | 380 | 33.236 | 4.375 | 28.086 | 1.00 | 61.61 |
| 6540 | CE | LYS | A | 380 | 33.199 | 2.996 | 28.721 | 1.00 | 75.99 |
| 6541 | NZ | LYS | A | 380 | 33.326 | 1.937 | 27.689 | 1.00 | 22.57 |
| 6542 | C | LYS | A | 380 | 33.558 | 9.284 | 28.847 | 1.00 | 48.02 |
| 6543 | O | LYS | A | 380 | 32.623 | 10.067 | 28.960 | 1.00 | 32.40 |
| 6544 | N | PRO | A | 381 | 34.647 | 9.589 | 28.138 | 1.00 | 61.80 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6545 | CD | PRO | A | 381 | 35.893 | 8.813 | 28.059 | 1.00 | 70.59 |
| 6546 | CA | PRO | A | 381 | 34.797 | 10.863 | 27.435 | 1.00 | 57.80 |
| 6547 | CB | PRO | A | 381 | 36.246 | 10.813 | 26.945 | 1.00 | 41.55 |
| 6548 | CG | PRO | A | 381 | 36.902 | 9.897 | 27.902 | 1.00 | 84.71 |
| 6549 | C | PRO | A | 381 | 33.829 | 11.028 | 26.269 | 1.00 | 60.19 |
| 6550 | O | PRO | A | 381 | 33.363 | 10.039 | 25.684 | 1.00 | 59.27 |
| 6551 | N | VAL | A | 382 | 33.544 | 12.285 | 25.938 | 1.00 | 30.88 |
| 6552 | CA | VAL | A | 382 | 32.680 | 12.627 | 24.805 | 1.00 | 49.36 |
| 6553 | CB | VAL | A | 382 | 31.534 | 13.613 | 25.207 | 1.00 | 51.98 |
| 6554 | CG1 | VAL | A | 382 | 30.644 | 12.968 | 26.263 | 1.00 | 43.55 |
| 6555 | CG2 | VAL | A | 382 | 32.107 | 14.949 | 25.717 | 1.00 | 61.37 |
| 6556 | C | VAL | A | 382 | 33.578 | 13.292 | 23.760 | 1.00 | 54.52 |
| 6557 | O | VAL | A | 382 | 34.542 | 13.962 | 24.118 | 1.00 | 55.64 |
| 6558 | N | ASN | A | 383 | 33.286 | 13.093 | 22.478 | 1.00 | 61.61 |
| 6559 | CA | ASN | A | 383 | 34.090 | 13.692 | 21.412 | 1.00 | 43.73 |
| 6560 | CB | ASN | A | 383 | 33.722 | 13.068 | 20.063 | 1.00 | 54.06 |
| 6561 | CG | ASN | A | 383 | 33.921 | 11.566 | 20.039 | 1.00 | 85.38 |
| 6562 | OD1 | ASN | A | 383 | 33.800 | 10.926 | 18.989 | 1.00 | 76.14 |
| 6563 | ND2 | ASN | A | 383 | 34.226 | 10.992 | 21.197 | 1.00 | 110.09 |
| 6564 | C | ASN | A | 383 | 33.941 | 15.223 | 21.319 | 1.00 | 57.46 |
| 6565 | O | ASN | A | 383 | 33.299 | 15.851 | 22.148 | 1.00 | 52.55 |
| 6566 | N | HIS | A | 384 | 34.541 | 15.816 | 20.296 | 1.00 | 69.28 |
| 6567 | CA | HIS | A | 384 | 34.479 | 17.261 | 20.095 | 1.00 | 69.08 |
| 6568 | CB | HIS | A | 384 | 35.626 | 17.715 | 19.188 | 1.00 | 88.41 |
| 6569 | CG | HIS | A | 384 | 36.962 | 17.169 | 19.582 | 1.00 | 108.13 |
| 6570 | CD2 | HIS | A | 384 | 37.812 | 16.341 | 18.929 | 1.00 | 108.34 |
| 6571 | ND1 | HIS | A | 384 | 37.558 | 17.455 | 20.792 | 1.00 | 107.76 |
| 6572 | CE1 | HIS | A | 384 | 38.717 | 16.826 | 20.868 | 1.00 | 104.70 |
| 6573 | NE2 | HIS | A | 384 | 38.895 | 16.143 | 19.750 | 1.00 | 111.44 |
| 6574 | C | HIS | A | 384 | 33.147 | 17.678 | 19.460 | 1.00 | 55.51 |
| 6575 | O | HIS | A | 384 | 32.852 | 17.345 | 18.311 | 1.00 | 55.51 |
| 6576 | N | SER | A | 385 | 32.364 | 18.434 | 20.211 | 1.00 | 40.38 |
| 6577 | CA | SER | A | 385 | 31.074 | 18.891 | 19.757 | 1.00 | 45.31 |
| 6578 | CB | SER | A | 385 | 30.168 | 19.127 | 20.970 | 1.00 | 41.61 |
| 6579 | OG | SER | A | 385 | 30.934 | 19.438 | 22.125 | 1.00 | 75.19 |
| 6580 | C | SER | A | 385 | 31.184 | 20.142 | 18.887 | 1.00 | 60.17 |
| 6581 | O | SER | A | 385 | 32.208 | 20.823 | 18.871 | 1.00 | 38.74 |
| 6582 | N | THR | A | 386 | 30.111 | 20.432 | 18.158 | 1.00 | 60.87 |
| 6583 | CA | THR | A | 386 | 30.061 | 21.569 | 17.258 | 1.00 | 50.67 |
| 6584 | CB | THR | A | 386 | 29.839 | 21.110 | 15.805 | 1.00 | 62.55 |
| 6585 | OG1 | THR | A | 386 | 30.955 | 20.333 | 15.367 | 1.00 | 43.78 |
| 6586 | CG2 | THR | A | 386 | 29.665 | 22.308 | 14.895 | 1.00 | 74.93 |
| 6587 | C | THR | A | 386 | 28.942 | 22.530 | 17.598 | 1.00 | 52.65 |
| 6588 | O | THR | A | 386 | 27.769 | 22.200 | 17.423 | 1.00 | 80.59 |
| 6589 | N | ARG | A | 387 | 29.306 | 23.723 | 18.058 | 1.00 | 47.92 |
| 6590 | CA | ARG | A | 387 | 28.330 | 24.758 | 18.404 | 1.00 | 71.46 |
| 6591 | CB | ARG | A | 387 | 28.891 | 25.615 | 19.543 | 1.00 | 42.76 |
| 6592 | CG | ARG | A | 387 | 27.947 | 26.641 | 20.119 | 1.00 | 33.12 |
| 6593 | CD | ARG | A | 387 | 28.683 | 27.492 | 21.156 | 1.00 | 65.41 |
| 6594 | NE | ARG | A | 387 | 27.879 | 28.607 | 21.661 | 1.00 | 86.56 |
| 6595 | CZ | ARG | A | 387 | 27.026 | 28.518 | 22.674 | 1.00 | 90.30 |
| 6596 | NH1 | ARG | A | 387 | 26.864 | 27.362 | 23.307 | 1.00 | 96.37 |
| 6597 | NH2 | ARG | A | 387 | 26.322 | 29.597 | 23.042 | 1.00 | 82.77 |
| 6598 | C | ARG | A | 387 | 28.017 | 25.628 | 17.169 | 1.00 | 68.77 |
| 6599 | O | ARG | A | 387 | 28.894 | 25.897 | 16.347 | 1.00 | 56.25 |
| 6600 | N | LYS | A | 388 | 26.762 | 26.048 | 17.029 | 1.00 | 67.73 |
| 6601 | CA | LYS | A | 388 | 26.352 | 26.878 | 15.891 | 1.00 | 64.85 |
| 6602 | CB | LYS | A | 388 | 25.883 | 26.015 | 14.710 | 1.00 | 52.23 |
| 6603 | CG | LYS | A | 388 | 26.861 | 24.935 | 14.283 | 1.00 | 75.10 |
| 6604 | CD | LYS | A | 388 | 26.188 | 23.954 | 13.343 | 1.00 | 86.01 |
| 6605 | CE | LYS | A | 388 | 27.078 | 22.762 | 13.069 | 1.00 | 96.15 |
| 6606 | NZ | LYS | A | 388 | 26.403 | 21.759 | 12.206 | 1.00 | 102.42 |
| 6607 | C | LYS | A | 388 | 25.217 | 27.802 | 16.281 | 1.00 | 67.05 |
| 6608 | O | LYS | A | 388 | 24.058 | 27.385 | 16.303 | 1.00 | 92.62 |
| 6609 | N | GLU | A | 389 | 25.547 | 29.054 | 16.583 | 1.00 | 77.23 |
| 6610 | CA | GLU | A | 389 | 24.539 | 30.042 | 16.957 | 1.00 | 76.76 |
| 6611 | CB | GLU | A | 389 | 25.116 | 31.036 | 17.962 | 1.00 | 79.01 |
| 6612 | CG | GLU | A | 389 | 25.554 | 30.391 | 19.267 | 1.00 | 93.30 |
| 6613 | CD | GLU | A | 389 | 26.281 | 31.350 | 20.185 | 1.00 | 104.60 |
| 6614 | OE1 | GLU | A | 389 | 25.692 | 32.389 | 20.551 | 1.00 | 116.57 |
| 6615 | OE2 | GLU | A | 389 | 27.443 | 31.062 | 20.542 | 1.00 | 111.47 |
| 6616 | C | GLU | A | 389 | 24.060 | 30.769 | 15.708 | 1.00 | 69.14 |
| 6617 | O | GLU | A | 389 | 24.784 | 31.576 | 15.125 | 1.00 | 75.28 |
| 6618 | N | GLU | A | 390 | 22.836 | 30.453 | 15.300 | 1.00 | 80.41 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6619 | CA | GLU | A | 390 | 22.213 | 31.026 | 14.116 | 1.00 | 72.19 |
| 6620 | CB | GLU | A | 390 | 21.711 | 29.898 | 13.217 | 1.00 | 79.43 |
| 6621 | CG | GLU | A | 390 | 20.928 | 30.328 | 12.004 | 1.00 | 97.94 |
| 6622 | CD | GLU | A | 390 | 20.500 | 29.141 | 11.161 | 1.00 | 116.18 |
| 6623 | OE1 | GLU | A | 390 | 19.834 | 28.231 | 11.698 | 1.00 | 122.24 |
| 6624 | OE2 | GLU | A | 390 | 20.835 | 29.113 | 9.959 | 1.00 | 125.52 |
| 6625 | C | GLU | A | 390 | 21.055 | 31.898 | 14.561 | 1.00 | 82.19 |
| 6626 | O | GLU | A | 390 | 19.945 | 31.417 | 14.757 | 1.00 | 48.43 |
| 6627 | N | LYS | A | 391 | 21.333 | 33.187 | 14.722 | 1.00 | 93.50 |
| 6628 | CA | LYS | A | 391 | 20.339 | 34.158 | 15.162 | 1.00 | 87.45 |
| 6629 | CB | LYS | A | 391 | 21.045 | 35.408 | 15.694 | 1.00 | 86.13 |
| 6630 | CG | LYS | A | 391 | 20.219 | 36.248 | 16.646 | 1.00 | 101.67 |
| 6631 | CD | LYS | A | 391 | 21.105 | 37.213 | 17.430 | 1.00 | 83.92 |
| 6632 | CE | LYS | A | 391 | 20.349 | 37.823 | 18.608 | 1.00 | 97.41 |
| 6633 | NZ | LYS | A | 391 | 21.201 | 38.692 | 19.472 | 1.00 | 81.56 |
| 6634 | C | LYS | A | 391 | 19.363 | 34.550 | 14.058 | 1.00 | 78.48 |
| 6635 | O | LYS | A | 391 | 19.677 | 34.512 | 12.873 | 1.00 | 86.58 |
| 6636 | N | GLN | A | 392 | 18.161 | 34.912 | 14.471 | 1.00 | 88.54 |
| 6637 | CA | GLN | A | 392 | 17.126 | 35.330 | 13.545 | 1.00 | 112.73 |
| 6638 | CB | GLN | A | 392 | 16.157 | 34.183 | 13.276 | 1.00 | 116.22 |
| 6639 | CG | GLN | A | 392 | 16.803 | 32.958 | 12.679 | 1.00 | 121.86 |
| 6640 | CD | GLN | A | 392 | 15.827 | 31.815 | 12.563 | 1.00 | 124.15 |
| 6641 | OE1 | GLN | A | 392 | 14.803 | 31.920 | 11.882 | 1.00 | 108.69 |
| 6642 | NE2 | GLN | A | 392 | 16.132 | 30.715 | 13.235 | 1.00 | 120.56 |
| 6643 | C | OLN | A | 392 | 16.384 | 36.482 | 14.201 | 1.00 | 119.72 |
| 6644 | O | GLN | A | 392 | 15.605 | 36.274 | 15.127 | 1.00 | 112.14 |
| 6645 | N | ARG | A | 393 | 16.640 | 37.699 | 13.731 | 1.00 | 129.51 |
| 6646 | CA | ARG | A | 393 | 15.985 | 38.881 | 14.284 | 1.00 | 136.28 |
| 6647 | CB | ARG | A | 393 | 16.407 | 40.137 | 13.507 | 1.00 | 137.35 |
| 6648 | CG | ARG | A | 393 | 17.152 | 39.854 | 12.204 | 1.00 | 146.68 |
| 6649 | CD | ARG | A | 393 | 17.428 | 41.137 | 11.442 | 1.00 | 143.26 |
| 6650 | NE | ARG | A | 393 | 16.189 | 41.840 | 11.122 | 1.00 | 141.13 |
| 6651 | CZ | ARG | A | 393 | 16.131 | 43.003 | 10.483 | 1.00 | 148.31 |
| 6652 | NH1 | ARG | A | 393 | 17.248 | 43.602 | 10.089 | 1.00 | 154.07 |
| 6653 | NH2 | ARG | A | 393 | 14.957 | 43.572 | 10.241 | 1.00 | 143.90 |
| 6654 | C | ARG | A | 393 | 14.468 | 38.707 | 14.242 | 1.00 | 138.18 |
| 6655 | O | ARG | A | 393 | 13.717 | 39.534 | 14.762 | 1.00 | 137.73 |
| 6656 | N | ASN | A | 394 | 14.035 | 37.614 | 13.618 | 1.00 | 140.39 |
| 6657 | CA | ASN | A | 394 | 12.626 | 37.272 | 13.500 | 1.00 | 133.41 |
| 6658 | CB | ASN | A | 394 | 12.473 | 36.057 | 12.581 | 1.00 | 133.17 |
| 6659 | CG | ASN | A | 394 | 11.026 | 35.654 | 12.379 | 1.00 | 144.54 |
| 6660 | OD1 | ASN | A | 394 | 10.735 | 34.536 | 11.952 | 1.00 | 141.95 |
| 6661 | ND2 | ASN | A | 394 | 10.109 | 36.569 | 12.675 | 1.00 | 150.84 |
| 6662 | C | ASN | A | 394 | 12.093 | 36.930 | 14.891 | 1.00 | 132.70 |
| 6663 | O | ASN | A | 394 | 10.905 | 36.671 | 15.071 | 1.00 | 130.82 |
| 6664 | N | GLY | A | 395 | 12.986 | 36.940 | 15.874 | 1.00 | 133.83 |
| 6665 | CA | GLY | A | 395 | 12.603 | 36.605 | 17.232 | 1.00 | 131.97 |
| 6666 | C | GLY | A | 395 | 12.899 | 35.134 | 17.460 | 1.00 | 136.58 |
| 6667 | O | GLY | A | 395 | 11.996 | 34.344 | 17.750 | 1.00 | 133.07 |
| 6668 | N | THR | A | 396 | 14.174 | 34.771 | 17.320 | 1.00 | 132.72 |
| 6669 | CA | THR | A | 396 | 14.619 | 33.389 | 17.485 | 1.00 | 131.16 |
| 6670 | CB | THR | A | 396 | 14.018 | 32.465 | 16.362 | 1.00 | 134.07 |
| 6671 | OG1 | THR | A | 396 | 12.589 | 32.387 | 16.488 | 1.00 | 119.63 |
| 6672 | CG2 | THR | A | 396 | 14.599 | 31.059 | 16.449 | 1.00 | 125.03 |
| 6673 | C | THR | A | 396 | 16.153 | 33.287 | 17.419 | 1.00 | 128.93 |
| 6674 | O | THR | A | 396 | 16.749 | 33.548 | 16.367 | 1.00 | 130.12 |
| 6675 | N | LEU | A | 397 | 16.786 | 32.916 | 18.537 | 1.00 | 130.85 |
| 6676 | CA | LEU | A | 397 | 18.245 | 32.743 | 18.579 | 1.00 | 111.18 |
| 6677 | CB | LEU | A | 397 | 18.870 | 33.489 | 19.765 | 1.00 | 99.32 |
| 6678 | CG | LEU | A | 397 | 20.370 | 33.199 | 19.947 | 1.00 | 100.71 |
| 6679 | CD1 | LEU | A | 397 | 21.123 | 33.544 | 18.671 | 1.00 | 85.60 |
| 6680 | CD2 | LEU | A | 397 | 20.921 | 33.976 | 21.129 | 1.00 | 81.32 |
| 6681 | C | LEU | A | 397 | 18.596 | 31.257 | 18.677 | 1.00 | 95.49 |
| 6682 | O | LEU | A | 397 | 18.844 | 30.732 | 19.762 | 1.00 | 87.41 |
| 6683 | N | THR | A | 398 | 18.617 | 30.584 | 17.534 | 1.00 | 97.30 |
| 6684 | CA | THR | A | 398 | 18.929 | 29.164 | 17.496 | 1.00 | 86.70 |
| 6685 | CB | THR | A | 398 | 18.725 | 28.590 | 16.079 | 1.00 | 65.98 |
| 6686 | OG1 | THR | A | 398 | 17.322 | 28.442 | 15.830 | 1.00 | 104.94 |
| 6687 | CG2 | THR | A | 398 | 19.404 | 27.249 | 15.935 | 1.00 | 89.01 |
| 6688 | C | THR | A | 398 | 20.347 | 28.873 | 17.944 | 1.00 | 79.14 |
| 6689 | O | THR | A | 398 | 21.276 | 29.577 | 17.584 | 1.00 | 80.43 |
| 6690 | N | VAL | A | 399 | 20.498 | 27.834 | 18.750 | 1.00 | 75.34 |
| 6691 | CA | VAL | A | 399 | 21.807 | 27.417 | 19.226 | 1.00 | 81.46 |
| 6692 | CB | VAL | A | 399 | 22.106 | 27.997 | 20.630 | 1.00 | 83.97 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6693 | CG1 | VAL | A | 399 | 23.511 | 27.592 | 21.094 | 1.00 | 49.89 |
| 6694 | CG2 | VAL | A | 399 | 21.979 | 29.505 | 20.592 | 1.00 | 94.04 |
| 6695 | C | VAL | A | 399 | 21.838 | 25.888 | 19.275 | 1.00 | 74.77 |
| 6696 | O | VAL | A | 399 | 21.205 | 25.270 | 20.131 | 1.00 | 58.82 |
| 6697 | N | THR | A | 400 | 22.559 | 25.282 | 18.338 | 1.00 | 49.71 |
| 6698 | CA | THR | A | 400 | 22.658 | 23.830 | 18.294 | 1.00 | 58.22 |
| 6699 | CB | THR | A | 400 | 22.205 | 23.245 | 16.911 | 1.00 | 64.49 |
| 6700 | OG1 | THR | A | 400 | 23.151 | 23.593 | 15.896 | 1.00 | 53.14 |
| 6701 | CG2 | THR | A | 400 | 20.857 | 23.781 | 16.502 | 1.00 | 52.59 |
| 6702 | C | THR | A | 400 | 24.081 | 23.337 | 18.564 | 1.00 | 77.01 |
| 6703 | O | THR | A | 400 | 25.061 | 24.053 | 18.374 | 1.00 | 66.92 |
| 6704 | N | SER | A | 401 | 24.183 | 22.101 | 19.027 | 1.00 | 80.17 |
| 6705 | CA | SER | A | 401 | 25.474 | 21.495 | 19.286 | 1.00 | 62.63 |
| 6706 | CB | SER | A | 401 | 25.782 | 21.475 | 20.785 | 1.00 | 71.57 |
| 6707 | OG | SER | A | 401 | 27.104 | 21.018 | 21.008 | 1.00 | 51.82 |
| 6708 | C | SER | A | 401 | 25.351 | 20.083 | 18.741 | 1.00 | 58.63 |
| 6709 | O | SER | A | 401 | 24.368 | 19.393 | 19.014 | 1.00 | 54.22 |
| 6710 | N | THR | A | 402 | 26.326 | 19.667 | 17.942 | 1.00 | 46.51 |
| 6711 | CA | THR | A | 402 | 26.285 | 18.336 | 17.369 | 1.00 | 30.72 |
| 6712 | CB | THR | A | 402 | 26.264 | 18.379 | 15.845 | 1.00 | 24.93 |
| 6713 | OG1 | THR | A | 402 | 25.020 | 18.940 | 15.405 | 1.00 | 50.80 |
| 6714 | CG2 | THR | A | 402 | 26.430 | 16.977 | 15.273 | 1.00 | 18.90 |
| 6715 | C | THR | A | 402 | 27.448 | 17.507 | 17.827 | 1.00 | 39.29 |
| 6716 | O | THR | A | 402 | 28.595 | 17.788 | 17.493 | 1.00 | 52.58 |
| 6717 | N | LEU | A | 403 | 27.128 | 16.465 | 18.583 | 1.00 | 46.74 |
| 6718 | CA | LEU | A | 403 | 28.121 | 15.566 | 19.134 | 1.00 | 44.80 |
| 6719 | CB | LEU | A | 403 | 27.761 | 15.225 | 20.592 | 1.00 | 23.02 |
| 6720 | CG | LEU | A | 403 | 28.720 | 14.293 | 21.337 | 1.00 | 54.05 |
| 6721 | CD1 | LEU | A | 403 | 30.065 | 14.992 | 21.585 | 1.00 | 45.90 |
| 6722 | CD2 | LEU | A | 403 | 28.072 | 13.854 | 22.637 | 1.00 | 26.60 |
| 6723 | C | LEU | A | 403 | 28.278 | 14.267 | 18.349 | 1.00 | 52.02 |
| 6724 | O | LEU | A | 403 | 27.319 | 13.520 | 18.173 | 1.00 | 49.56 |
| 6725 | N | PRO | A | 404 | 29.494 | 13.990 | 17.855 | 1.00 | 44.49 |
| 6726 | CD | PRO | A | 404 | 30.626 | 14.905 | 17.681 | 1.00 | 47.65 |
| 6727 | CA | PRO | A | 404 | 29.733 | 12.756 | 17.112 | 1.00 | 47.82 |
| 6728 | CB | PRO | A | 404 | 31.124 | 12.967 | 16.542 | 1.00 | 30.99 |
| 6729 | CG | PRO | A | 404 | 31.183 | 14.442 | 16.373 | 1.00 | 65.78 |
| 6730 | C | PRO | A | 404 | 29.701 | 11.656 | 18.156 | 1.00 | 43.82 |
| 6731 | O | PRO | A | 404 | 30.208 | 11.822 | 19.276 | 1.00 | 36.67 |
| 6732 | N | VAL | A | 405 | 29.103 | 10.532 | 17.809 | 1.00 | 37.87 |
| 6733 | CA | VAL | A | 405 | 28.988 | 9.462 | 18.777 | 1.00 | 30.06 |
| 6734 | CB | VAL | A | 405 | 27.471 | 9.253 | 19.195 | 1.00 | 43.69 |
| 6735 | CG1 | VAL | A | 405 | 27.261 | 7.906 | 19.823 | 1.00 | 33.37 |
| 6736 | CG2 | VAL | A | 405 | 27.049 | 10.319 | 20.201 | 1.00 | 33.67 |
| 6737 | C | VAL | A | 405 | 29.551 | 8.201 | 18.221 | 1.00 | 23.92 |
| 6738 | O | VAL | A | 405 | 29.512 | 7.972 | 17.021 | 1.00 | 53.54 |
| 6739 | N | GLY | A | 406 | 30.077 | 7.368 | 19.097 | 1.00 | 19.69 |
| 6740 | CA | GLY | A | 406 | 30.611 | 6.111 | 18.627 | 1.00 | 32.71 |
| 6741 | C | GLY | A | 406 | 29.485 | 5.233 | 18.160 | 1.00 | 28.14 |
| 6742 | O | GLY | A | 406 | 28.468 | 5.181 | 18.832 | 1.00 | 35.74 |
| 6743 | N | THR | A | 407 | 29.660 | 4.552 | 17.023 | 1.00 | 50.71 |
| 6744 | CA | THR | A | 407 | 28.641 | 3.648 | 16.469 | 1.00 | 29.52 |
| 6745 | CB | THR | A | 407 | 29.112 | 3.020 | 15.174 | 1.00 | 28.88 |
| 6746 | OG1 | THR | A | 407 | 29.386 | 4.048 | 14.219 | 1.00 | 88.87 |
| 6747 | CG2 | THR | A | 407 | 28.067 | 2.094 | 14.634 | 1.00 | 35.03 |
| 6748 | C | THR | A | 407 | 28.295 | 2.526 | 17.450 | 1.00 | 42.68 |
| 6749 | O | THR | A | 407 | 27.128 | 2.330 | 17.783 | 1.00 | 55.38 |
| 6750 | N | ALA | A | 408 | 29.306 | 1.802 | 17.919 | 1.00 | 44.48 |
| 6751 | CA | ALA | A | 408 | 29.082 | 0.722 | 18.871 | 1.00 | 47.33 |
| 6752 | CB | ALA | A | 408 | 30.371 | −0.045 | 19.123 | 1.00 | 57.64 |
| 6753 | C | ALA | A | 408 | 28.538 | 1.267 | 20.188 | 1.00 | 52.22 |
| 6754 | O | ALA | A | 408 | 27.673 | 0.659 | 20.804 | 1.00 | 61.42 |
| 6755 | N | ASP | A | 409 | 29.048 | 2.415 | 20.614 | 1.00 | 53.49 |
| 6756 | CA | ASP | A | 409 | 28.608 | 3.039 | 21.855 | 1.00 | 44.40 |
| 6757 | CB | ASP | A | 409 | 29.294 | 4.391 | 22.050 | 1.00 | 68.65 |
| 6758 | CG | ASP | A | 409 | 30.796 | 4.262 | 22.286 | 1.00 | 74.33 |
| 6759 | OD1 | ASP | A | 409 | 31.193 | 3.703 | 23.324 | 1.00 | 63.70 |
| 6760 | OD2 | ASP | A | 409 | 31.584 | 4.716 | 21.432 | 1.00 | 84.08 |
| 6761 | C | ASP | A | 409 | 27.112 | 3.225 | 21.888 | 1.00 | 34.33 |
| 6762 | O | ASP | A | 409 | 26.455 | 2.738 | 22.794 | 1.00 | 40.29 |
| 6763 | N | TRP | A | 410 | 26.566 | 3.925 | 20.898 | 1.00 | 45.39 |
| 6764 | CA | TRP | A | 410 | 25.114 | 4.159 | 20.846 | 1.00 | 66.23 |
| 6765 | CB | TRP | A | 410 | 24.744 | 5.112 | 19.697 | 1.00 | 49.11 |
| 6766 | CG | TRP | A | 410 | 23.255 | 5.364 | 19.571 | 1.00 | 40.44 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6767 | CD2 | TRP | A | 410 | 22.504 | 6.428 | 20.182 | 1.00 | 46.99 |
| 6768 | CE2 | TRP | A | 410 | 21.143 | 6.213 | 19.868 | 1.00 | 17.02 |
| 6769 | CE3 | TRP | A | 410 | 22.846 | 7.543 | 20.969 | 1.00 | 30.75 |
| 6770 | CD1 | TRP | A | 410 | 22.333 | 4.577 | 18.916 | 1.00 | 14.13 |
| 6771 | NE1 | TRP | A | 410 | 21.069 | 5.080 | 19.095 | 1.00 | 34.04 |
| 6772 | CZ2 | TRP | A | 410 | 20.132 | 7.068 | 20.316 | 1.00 | 22.48 |
| 6773 | CZ3 | TRP | A | 410 | 21.818 | 8.397 | 21.416 | 1.00 | 24.93 |
| 6774 | CH2 | TRP | A | 410 | 20.491 | 8.151 | 21.087 | 1.00 | 35.38 |
| 6775 | C | TRP | A | 410 | 24.323 | 2.859 | 20.704 | 1.00 | 54.69 |
| 6776 | O | TRP | A | 410 | 23.301 | 2.676 | 21.340 | 1.00 | 49.85 |
| 6777 | N | ILE | A | 411 | 24.803 | 1.960 | 19.867 | 1.00 | 40.24 |
| 6778 | CA | ILE | A | 411 | 24.147 | 0.693 | 19.664 | 1.00 | 44.04 |
| 6779 | CB | ILE | A | 411 | 24.835 | −0.053 | 18.521 | 1.00 | 52.88 |
| 6780 | CG2 | ILE | A | 411 | 24.338 | −1.477 | 18.434 | 1.00 | 56.95 |
| 6781 | CG1 | ILE | A | 411 | 24.593 | 0.705 | 17.223 | 1.00 | 53.79 |
| 6782 | CD1 | ILE | A | 411 | 25.162 | 0.036 | 16.004 | 1.00 | 77.28 |
| 6783 | C | ILE | A | 411 | 24.112 | −0.210 | 20.902 | 1.00 | 62.30 |
| 6784 | O | ILE | A | 411 | 23.198 | −1.006 | 21.058 | 1.00 | 65.52 |
| 6785 | N | GLU | A | 412 | 25.093 | −0.103 | 21.789 | 1.00 | 67.84 |
| 6786 | CA | GLU | A | 412 | 25.104 | −0.972 | 22.964 | 1.00 | 55.63 |
| 6787 | CB | GLU | A | 412 | 26.533 | −1.430 | 23.259 | 1.00 | 50.90 |
| 6788 | CG | GLU | A | 412 | 26.970 | −2.586 | 22.370 | 1.00 | 75.45 |
| 6789 | CD | GLU | A | 412 | 28.450 | −2.903 | 22.472 | 1.00 | 88.36 |
| 6790 | OE1 | GLU | A | 412 | 28.954 | −3.000 | 23.607 | 1.00 | 103.04 |
| 6791 | OE2 | GLU | A | 412 | 29.106 | −3.065 | 21.419 | 1.00 | 97.23 |
| 6792 | C | GLU | A | 412 | 24.431 | −0.420 | 24.225 | 1.00 | 62.77 |
| 6793 | O | GLU | A | 412 | 24.455 | −1.054 | 25.283 | 1.00 | 55.07 |
| 6794 | N | GLY | A | 413 | 23.844 | 0.767 | 24.118 | 1.00 | 39.08 |
| 6795 | CA | GLY | A | 413 | 23.112 | 1.293 | 25.240 | 1.00 | 29.41 |
| 6796 | C | GLY | A | 413 | 23.574 | 2.540 | 25.925 | 1.00 | 44.24 |
| 6797 | O | GLY | A | 413 | 22.963 | 2.970 | 26.905 | 1.00 | 43.94 |
| 6798 | N | GLU | A | 414 | 24.650 | 3.132 | 25.441 | 1.00 | 38.24 |
| 6799 | CA | GLU | A | 414 | 25.132 | 4.342 | 26.080 | 1.00 | 47.61 |
| 6800 | CB | GLU | A | 414 | 26.422 | 4.802 | 25.403 | 1.00 | 48.32 |
| 6801 | CG | GLU | A | 414 | 27.006 | 6.084 | 25.957 | 1.00 | 66.94 |
| 6802 | CD | GLU | A | 414 | 27.677 | 5.910 | 27.308 | 1.00 | 65.43 |
| 6803 | OE1 | GLU | A | 414 | 26.998 | 6.039 | 28.348 | 1.00 | 61.63 |
| 6804 | OE2 | GLU | A | 414 | 28.897 | 5.643 | 27.319 | 1.00 | 47.35 |
| 6805 | C | GLU | A | 414 | 24.058 | 5.432 | 25.995 | 1.00 | 44.26 |
| 6806 | O | GLU | A | 414 | 23.321 | 5.511 | 25.017 | 1.00 | 56.23 |
| 6807 | N | THR | A | 415 | 23.964 | 6.249 | 27.036 | 1.00 | 35.47 |
| 6808 | CA | THR | A | 415 | 23.011 | 7.346 | 27.096 | 1.00 | 45.34 |
| 6809 | CB | THR | A | 415 | 22.002 | 7.187 | 28.302 | 1.00 | 55.20 |
| 6810 | OG1 | THR | A | 415 | 21.636 | 8.478 | 28.825 | 1.00 | 28.96 |
| 6811 | CG2 | THR | A | 415 | 22.593 | 6.319 | 29.391 | 1.00 | 55.44 |
| 6812 | C | THR | A | 415 | 23.777 | 8.659 | 27.216 | 1.00 | 61.57 |
| 6813 | O | THR | A | 415 | 24.526 | 8.874 | 28.180 | 1.00 | 30.09 |
| 6814 | N | TYR | A | 416 | 23.577 | 9.527 | 26.221 | 1.00 | 50.63 |
| 6815 | CA | TYR | A | 416 | 24.244 | 10.826 | 26.149 | 1.00 | 45.99 |
| 6816 | CB | TYR | A | 416 | 24.583 | 11.138 | 24.684 | 1.00 | 29.34 |
| 6817 | CG | TYR | A | 416 | 25.520 | 10.116 | 24.113 | 1.00 | 57.58 |
| 6818 | CD1 | TYR | A | 416 | 25.037 | 8.882 | 23.665 | 1.00 | 33.69 |
| 6819 | CE1 | TYR | A | 416 | 25.907 | 7.899 | 23.208 | 1.00 | 56.33 |
| 6820 | CD2 | TYR | A | 416 | 26.907 | 10.345 | 24.086 | 1.00 | 54.02 |
| 6821 | CE2 | TYR | A | 416 | 27.781 | 9.377 | 23.628 | 1.00 | 29.42 |
| 6822 | CZ | TYR | A | 416 | 27.278 | 8.152 | 23.187 | 1.00 | 60.20 |
| 6823 | OH | TYR | A | 416 | 28.143 | 7.192 | 22.707 | 1.00 | 49.83 |
| 6824 | C | TYR | A | 416 | 23.429 | 11.950 | 26.771 | 1.00 | 53.64 |
| 6825 | O | TYR | A | 416 | 22.201 | 11.969 | 26.645 | 1.00 | 44.31 |
| 6826 | N | GLN | A | 417 | 24.123 | 12.875 | 27.442 | 1.00 | 50.28 |
| 6827 | CA | GLN | A | 417 | 23.477 | 14.007 | 28.112 | 1.00 | 60.65 |
| 6828 | CB | GLN | A | 417 | 23.565 | 13.826 | 29.626 | 1.00 | 67.31 |
| 6829 | CG | GLN | A | 417 | 22.898 | 14.939 | 30.419 | 1.00 | 86.27 |
| 6830 | CD | GLN | A | 417 | 23.233 | 14.886 | 31.896 | 1.00 | 81.77 |
| 6831 | OE1 | GLN | A | 417 | 24.375 | 15.137 | 32.296 | 1.00 | 83.90 |
| 6832 | NE2 | GLN | A | 417 | 22.240 | 14.551 | 32.717 | 1.00 | 80.88 |
| 6833 | C | GLN | A | 417 | 24.012 | 15.403 | 27.740 | 1.00 | 52.97 |
| 6834 | O | GLN | A | 417 | 25.211 | 15.608 | 27.571 | 1.00 | 53.08 |
| 6835 | N | CYS | A | 418 | 23.090 | 16.352 | 27.622 | 1.00 | 54.13 |
| 6836 | CA | CYS | A | 418 | 23.387 | 17.738 | 27.287 | 1.00 | 38.25 |
| 6837 | C | CYS | A | 418 | 22.940 | 18.614 | 28.459 | 1.00 | 60.36 |
| 6838 | O | CYS | A | 418 | 21.775 | 18.595 | 28.864 | 1.00 | 59.54 |
| 6839 | CB | CYS | A | 418 | 22.619 | 18.155 | 26.025 | 1.00 | 52.29 |
| 6840 | SG | CYS | A | 418 | 22.783 | 19.914 | 25.527 | 1.00 | 73.20 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6841 | N | ARG | A | 419 | 23.869 | 19.373 | 29.019 | 1.00 | 50.16 |
| 6842 | CA | ARG | A | 419 | 23.529 | 20.249 | 30.120 | 1.00 | 73.04 |
| 6843 | CB | ARG | A | 419 | 24.505 | 20.055 | 31.284 | 1.00 | 58.22 |
| 6844 | CG | ARG | A | 419 | 24.130 | 20.840 | 32.522 | 1.00 | 85.85 |
| 6845 | CD | ARG | A | 419 | 24.907 | 20.371 | 33.735 | 1.00 | 94.99 |
| 6846 | NE | ARG | A | 419 | 24.636 | 21.192 | 34.915 | 1.00 | 99.28 |
| 6847 | CZ | ARG | A | 419 | 25.002 | 22.465 | 35.042 | 1.00 | 112.89 |
| 6848 | NH1 | ARG | A | 419 | 25.657 | 23.071 | 34.060 | 1.00 | 109.03 |
| 6849 | NH2 | ARG | A | 419 | 24.720 | 23.133 | 36.156 | 1.00 | 110.73 |
| 6850 | C | ARG | A | 419 | 23.571 | 21.681 | 29.606 | 1.00 | 80.10 |
| 6851 | O | ARG | A | 419 | 24.579 | 22.129 | 29.061 | 1.00 | 92.97 |
| 6852 | N | VAL | A | 420 | 22.459 | 22.389 | 29.767 | 1.00 | 82.90 |
| 6853 | CA | VAL | A | 420 | 22.359 | 23.766 | 29.313 | 1.00 | 76.36 |
| 6854 | CB | VAL | A | 420 | 21.042 | 23.976 | 28.584 | 1.00 | 65.31 |
| 6855 | CG1 | VAL | A | 420 | 21.016 | 25.345 | 27.948 | 1.00 | 70.82 |
| 6856 | CG2 | VAL | A | 420 | 20.872 | 22.886 | 27.544 | 1.00 | 48.05 |
| 6857 | C | VAL | A | 420 | 22.468 | 24.773 | 30.459 | 1.00 | 84.49 |
| 6858 | O | VAL | A | 420 | 21.767 | 24.665 | 31.464 | 1.00 | 77.96 |
| 6859 | N | THR | A | 421 | 23.358 | 25.749 | 30.298 | 1.00 | 98.94 |
| 6860 | CA | THR | A | 421 | 23.576 | 26.782 | 31.309 | 1.00 | 98.19 |
| 6861 | CB | THR | A | 421 | 25.004 | 26.703 | 31.884 | 1.00 | 101.90 |
| 6862 | OG1 | THR | A | 421 | 25.221 | 25.399 | 32.430 | 1.00 | 97.61 |
| 6863 | CG2 | THR | A | 421 | 25.207 | 27.739 | 32.983 | 1.00 | 99.81 |
| 6864 | C | THR | A | 421 | 23.378 | 28.167 | 30.705 | 1.00 | 97.17 |
| 6865 | O | THR | A | 421 | 23.700 | 28.398 | 29.538 | 1.00 | 97.95 |
| 6866 | N | HIS | A | 422 | 22.843 | 29.080 | 31.509 | 1.00 | 104.24 |
| 6867 | CA | HIS | A | 422 | 22.603 | 30.450 | 31.071 | 1.00 | 117.24 |
| 6868 | CB | HIS | A | 422 | 21.327 | 30.528 | 30.226 | 1.00 | 117.85 |
| 6869 | CG | HIS | A | 422 | 21.105 | 31.867 | 29.591 | 1.00 | 128.97 |
| 6870 | CD2 | HIS | A | 422 | 20.060 | 32.726 | 29.659 | 1.00 | 127.23 |
| 6871 | ND1 | HIS | A | 422 | 22.034 | 32.459 | 28.762 | 1.00 | 133.63 |
| 6872 | CE1 | HIS | A | 422 | 21.571 | 33.624 | 28.346 | 1.00 | 129.71 |
| 6873 | NE2 | HIS | A | 422 | 20.375 | 33.810 | 28.876 | 1.00 | 125.81 |
| 6874 | C | HIS | A | 422 | 22.473 | 31.361 | 32.287 | 1.00 | 119.78 |
| 6875 | O | HIS | A | 422 | 21.981 | 30.941 | 33.335 | 1.00 | 113.49 |
| 6876 | N | PRO | A | 423 | 22.919 | 32.624 | 32.162 | 1.00 | 121.86 |
| 6877 | CD | PRO | A | 423 | 23.637 | 33.209 | 31.015 | 1.00 | 121.83 |
| 6878 | CA | PRO | A | 423 | 22.845 | 33.586 | 33.264 | 1.00 | 120.31 |
| 6879 | CB | PRO | A | 423 | 23.767 | 34.710 | 32.795 | 1.00 | 115.02 |
| 6880 | CG | PRO | A | 423 | 23.574 | 34.689 | 31.315 | 1.00 | 125.02 |
| 6881 | C | PRO | A | 423 | 21.433 | 34.082 | 33.571 | 1.00 | 123.65 |
| 6882 | O | PRO | A | 423 | 21.150 | 34.497 | 34.694 | 1.00 | 134.50 |
| 6883 | N | HIS | A | 424 | 20.547 | 34.030 | 32.581 | 1.00 | 124.60 |
| 6884 | CA | HIS | A | 424 | 19.181 | 34.502 | 32.772 | 1.00 | 124.40 |
| 6885 | CB | HIS | A | 424 | 18.726 | 35.280 | 31.530 | 1.00 | 128.87 |
| 6886 | CG | HIS | A | 424 | 19.638 | 36.409 | 31.157 | 1.00 | 126.32 |
| 6887 | CD2 | HIS | A | 424 | 20.318 | 36.666 | 30.014 | 1.00 | 129.32 |
| 6888 | ND1 | HIS | A | 424 | 19.940 | 37.440 | 32.022 | 1.00 | 128.09 |
| 6889 | CE1 | HIS | A | 424 | 20.768 | 38.281 | 31.428 | 1.00 | 124.74 |
| 6890 | NE2 | HIS | A | 424 | 21.013 | 37.835 | 30.209 | 1.00 | 124.87 |
| 6891 | C | HIS | A | 424 | 18.185 | 33.384 | 33.091 | 1.00 | 121.46 |
| 6892 | O | HIS | A | 424 | 17.019 | 33.443 | 32.689 | 1.00 | 124.79 |
| 6893 | N | LEU | A | 425 | 18.650 | 32.371 | 33.819 | 1.00 | 120.43 |
| 6894 | CA | LEU | A | 425 | 17.806 | 31.242 | 34.210 | 1.00 | 120.50 |
| 6895 | CB | LEU | A | 425 | 17.778 | 30.182 | 33.112 | 1.00 | 119.10 |
| 6896 | CG | LEU | A | 425 | 16.884 | 30.484 | 31.911 | 1.00 | 126.47 |
| 6897 | CD1 | LEU | A | 425 | 16.990 | 29.347 | 30.916 | 1.00 | 130.62 |
| 6898 | CD2 | LEU | A | 425 | 15.444 | 30.659 | 32.367 | 1.00 | 124.72 |
| 6899 | C | LEU | A | 425 | 18.279 | 30.602 | 35.509 | 1.00 | 115.70 |
| 6900 | O | LEU | A | 425 | 19.477 | 30.422 | 35.722 | 1.00 | 110.50 |
| 6901 | N | PRO | A | 426 | 17.334 | 30.230 | 36.387 | 1.00 | 112.48 |
| 6902 | CD | PRO | A | 426 | 15.881 | 30.198 | 36.143 | 1.00 | 115.21 |
| 6903 | CA | PRO | A | 426 | 17.656 | 29.609 | 37.676 | 1.00 | 115.20 |
| 6904 | CB | PRO | A | 426 | 16.281 | 29.368 | 38.293 | 1.00 | 120.20 |
| 6905 | CG | PRO | A | 426 | 15.422 | 29.116 | 37.093 | 1.00 | 119.54 |
| 6906 | C | PRO | A | 426 | 18.459 | 28.327 | 37.531 | 1.00 | 117.25 |
| 6907 | O | PRO | A | 426 | 19.680 | 28.361 | 37.376 | 1.00 | 123.34 |
| 6908 | N | ARG | A | 427 | 17.762 | 27.197 | 37.584 | 1.00 | 113.18 |
| 6909 | CA | ARG | A | 427 | 18.397 | 25.895 | 37.456 | 1.00 | 106.65 |
| 6910 | CB | ARG | A | 427 | 17.449 | 24.812 | 37.972 | 1.00 | 112.50 |
| 6911 | CG | ARG | A | 427 | 18.000 | 23.404 | 37.895 | 1.00 | 124.74 |
| 6912 | CD | ARG | A | 427 | 16.965 | 22.394 | 38.348 | 1.00 | 126.08 |
| 6913 | NE | ARG | A | 427 | 17.422 | 21.020 | 38.161 | 1.00 | 133.59 |
| 6914 | CZ | ARG | A | 427 | 16.701 | 19.946 | 38.468 | 1.00 | 136.27 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6915 | NH1 | ARG | A | 427 | 15.486 | 20.090 | 38.977 | 1.00 | 140.77 |
| 6916 | NH2 | ARG | A | 427 | 17.191 | 18.730 | 38.266 | 1.00 | 130.19 |
| 6917 | C | ARG | A | 427 | 18.762 | 25.624 | 35.996 | 1.00 | 104.24 |
| 6918 | O | ARG | A | 427 | 18.233 | 26.258 | 35.084 | 1.00 | 101.06 |
| 6919 | N | ALA | A | 428 | 19.670 | 24.679 | 35.779 | 1.00 | 108.28 |
| 6920 | CA | ALA | A | 428 | 20.100 | 24.326 | 34.430 | 1.00 | 107.24 |
| 6921 | CB | ALA | A | 428 | 21.541 | 23.811 | 34.457 | 1.00 | 103.30 |
| 6922 | C | ALA | A | 428 | 19.191 | 23.280 | 33.791 | 1.00 | 90.64 |
| 6923 | O | ALA | A | 428 | 18.490 | 22.538 | 34.480 | 1.00 | 76.78 |
| 6924 | N | LEU | A | 429 | 19.210 | 23.229 | 32.466 | 1.00 | 81.72 |
| 6925 | CA | LEU | A | 429 | 18.408 | 22.271 | 31.726 | 1.00 | 80.58 |
| 6926 | CB | LEU | A | 429 | 17.908 | 22.892 | 30.426 | 1.00 | 87.47 |
| 6927 | CG | LEU | A | 429 | 16.841 | 23.971 | 30.566 | 1.00 | 98.00 |
| 6928 | CD1 | LEU | A | 429 | 16.468 | 24.495 | 29.186 | 1.00 | 86.76 |
| 6929 | CD2 | LEU | A | 429 | 15.631 | 23.395 | 31.276 | 1.00 | 72.37 |
| 6930 | C | LEU | A | 429 | 19.211 | 21.020 | 31.400 | 1.00 | 84.94 |
| 6931 | O | LEU | A | 429 | 20.415 | 21.088 | 31.155 | 1.00 | 81.40 |
| 6932 | N | MET | A | 430 | 18.533 | 19.877 | 31.390 | 1.00 | 69.11 |
| 6933 | CA | MET | A | 430 | 19.186 | 18.619 | 31.082 | 1.00 | 84.70 |
| 6934 | CB | MET | A | 430 | 19.531 | 17.898 | 32.374 | 1.00 | 91.38 |
| 6935 | CG | MET | A | 430 | 20.488 | 18.683 | 33.241 | 1.00 | 96.27 |
| 6936 | SD | MET | A | 430 | 20.523 | 18.111 | 34.941 | 1.00 | 120.06 |
| 6937 | CE | MET | A | 430 | 19.317 | 19.201 | 35.715 | 1.00 | 97.17 |
| 6938 | C | MET | A | 430 | 18.323 | 17.732 | 30.203 | 1.00 | 78.85 |
| 6939 | O | MET | A | 430 | 17.115 | 17.628 | 30.409 | 1.00 | 80.63 |
| 6940 | N | ARG | A | 431 | 18.959 | 17.104 | 29.217 | 1.00 | 65.81 |
| 6941 | CA | ARG | A | 431 | 18.286 | 16.211 | 28.279 | 1.00 | 51.41 |
| 6942 | CB | ARG | A | 431 | 18.017 | 16.912 | 26.949 | 1.00 | 65.17 |
| 6943 | CG | ARG | A | 431 | 17.360 | 18.257 | 27.057 | 1.00 | 70.07 |
| 6944 | CD | ARG | A | 431 | 15.981 | 18.181 | 27.666 | 1.00 | 68.72 |
| 6945 | NE | ARG | A | 431 | 15.544 | 19.521 | 28.034 | 1.00 | 92.79 |
| 6946 | CZ | ARG | A | 431 | 14.412 | 19.794 | 28.662 | 1.00 | 77.45 |
| 6947 | NH1 | ARG | A | 431 | 13.590 | 18.814 | 28.999 | 1.00 | 101.17 |
| 6948 | NH2 | ARG | A | 431 | 14.105 | 21.048 | 28.953 | 1.00 | 88.78 |
| 6949 | C | ARG | A | 431 | 19.192 | 15.020 | 28.007 | 1.00 | 66.61 |
| 6950 | O | ARG | A | 431 | 20.412 | 15.157 | 27.947 | 1.00 | 73.26 |
| 6951 | N | SER | A | 432 | 18.586 | 13.855 | 27.822 | 1.00 | 50.22 |
| 6952 | CA | SER | A | 432 | 19.331 | 12.640 | 27.562 | 1.00 | 45.42 |
| 6953 | CB | SER | A | 432 | 19.413 | 11.794 | 28.844 | 1.00 | 47.26 |
| 6954 | OG | SER | A | 432 | 18.146 | 11.364 | 29.291 | 1.00 | 44.37 |
| 6955 | C | SER | A | 432 | 18.673 | 11.859 | 26.431 | 1.00 | 33.26 |
| 6956 | O | SER | A | 432 | 17.500 | 12.022 | 26.181 | 1.00 | 32.61 |
| 6957 | N | THR | A | 433 | 19.435 | 11.015 | 25.744 | 1.00 | 36.74 |
| 6958 | CA | THR | A | 433 | 18.881 | 10.244 | 24.643 | 1.00 | 29.62 |
| 6959 | CB | THR | A | 433 | 19.040 | 11.051 | 23.318 | 1.00 | 24.21 |
| 6960 | OG1 | THR | A | 433 | 18.497 | 10.307 | 22.230 | 1.00 | 56.37 |
| 6961 | CG2 | THR | A | 433 | 20.523 | 11.344 | 23.031 | 1.00 | 37.77 |
| 6962 | C | THR | A | 433 | 19.541 | 8.843 | 24.542 | 1.00 | 41.85 |
| 6963 | O | THR | A | 433 | 20.634 | 8.639 | 25.053 | 1.00 | 39.69 |
| 6964 | N | THR | A | 434 | 18.854 | 7.881 | 23.923 | 1.00 | 26.70 |
| 6965 | CA | THR | A | 434 | 19.359 | 6.520 | 23.750 | 1.00 | 26.94 |
| 6966 | CB | THR | A | 434 | 19.324 | 5.664 | 25.072 | 1.00 | 59.23 |
| 6967 | OG1 | THR | A | 434 | 18.313 | 6.141 | 25.964 | 1.00 | 59.02 |
| 6968 | CG2 | THR | A | 434 | 20.658 | 5.686 | 25.770 | 1.00 | 60.10 |
| 6969 | C | THR | A | 434 | 18.588 | 5.751 | 22.703 | 1.00 | 18.42 |
| 6970 | O | THR | A | 434 | 18.827 | 4.559 | 22.475 | 1.00 | 24.01 |
| 6971 | N | ARG | A | 440 | 9.329 | −1.211 | 19.273 | 1.00 | 19.07 |
| 6972 | CA | ARG | A | 440 | 10.091 | −1.366 | 18.019 | 1.00 | 57.00 |
| 6973 | CB | ARG | A | 440 | 11.482 | −1.984 | 18.289 | 1.00 | 33.97 |
| 6974 | CG | ARG | A | 440 | 12.299 | −1.331 | 19.435 | 1.00 | 66.45 |
| 6975 | CD | ARG | A | 440 | 12.817 | 0.098 | 19.156 | 1.00 | 69.28 |
| 6976 | NE | ARG | A | 440 | 13.265 | 0.773 | 20.387 | 1.00 | 91.51 |
| 6977 | CZ | ARG | A | 440 | 13.969 | 1.908 | 20.438 | 1.00 | 86.39 |
| 6978 | NH1 | ARG | A | 440 | 14.327 | 2.529 | 19.320 | 1.00 | 93.66 |
| 6979 | NH2 | ARG | A | 440 | 14.327 | 2.420 | 21.615 | 1.00 | 90.26 |
| 6980 | C | ARG | A | 440 | 9.341 | −2.234 | 17.001 | 1.00 | 45.11 |
| 6981 | O | ARG | A | 440 | 8.798 | −3.254 | 17.359 | 1.00 | 45.25 |
| 6982 | N | ALA | A | 441 | 9.297 | −1.814 | 15.736 | 1.00 | 52.35 |
| 6983 | CA | ALA | A | 441 | 8.615 | −2.575 | 14.665 | 1.00 | 45.98 |
| 6984 | CB | ALA | A | 441 | 7.145 | −2.271 | 14.639 | 1.00 | 14.54 |
| 6985 | C | ALA | A | 441 | 9.178 | −2.262 | 13.298 | 1.00 | 37.94 |
| 6986 | O | ALA | A | 441 | 9.354 | −1.087 | 12.966 | 1.00 | 47.71 |
| 6987 | N | ALA | A | 442 | 9.436 | −3.307 | 12.506 | 1.00 | 27.45 |
| 6988 | CA | ALA | A | 442 | 9.986 | −3.132 | 11.154 | 1.00 | 38.13 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 6989 | CB | ALA | A | 442 | 10.394 | −4.465 | 10.563 | 1.00 | 33.69 |
| 6990 | C | ALA | A | 442 | 8.996 | −2.443 | 10.218 | 1.00 | 39.00 |
| 6991 | O | ALA | A | 442 | 7.791 | −2.513 | 10.408 | 1.00 | 36.52 |
| 6992 | N | PRO | A | 443 | 9.508 | −1.748 | 9.193 | 1.00 | 46.59 |
| 6993 | CD | PRO | A | 443 | 10.908 | −1.325 | 9.018 | 1.00 | 46.47 |
| 6994 | CA | PRO | A | 443 | 8.647 | −1.050 | 8.238 | 1.00 | 42.29 |
| 6995 | CB | PRO | A | 443 | 9.532 | 0.101 | 7.738 | 1.00 | 34.34 |
| 6996 | CG | PRO | A | 443 | 10.745 | 0.107 | 8.647 | 1.00 | 47.95 |
| 6997 | C | PRO | A | 443 | 8.177 | −1.930 | 7.067 | 1.00 | 40.31 |
| 6998 | O | PRO | A | 443 | 8.896 | −2.805 | 6.588 | 1.00 | 34.38 |
| 6999 | N | ALA | A | 444 | 6.946 | −1.692 | 6.640 | 1.00 | 35.96 |
| 7000 | CA | ALA | A | 444 | 6.362 | −2.375 | 5.497 | 1.00 | 26.03 |
| 7001 | CB | ALA | A | 444 | 4.824 | −2.643 | 5.740 | 1.00 | 25.17 |
| 7002 | C | ALA | A | 444 | 6.610 | −1.321 | 4.391 | 1.00 | 30.36 |
| 7003 | O | ALA | A | 444 | 6.363 | −0.114 | 4.581 | 1.00 | 31.32 |
| 7004 | N | VAL | A | 445 | 7.114 | −1.763 | 3.244 | 1.00 | 32.09 |
| 7005 | CA | VAL | A | 445 | 7.455 | −0.820 | 2.196 | 1.00 | 19.18 |
| 7006 | CB | VAL | A | 445 | 9.027 | −0.687 | 2.062 | 1.00 | 36.59 |
| 7007 | CG1 | VAL | A | 445 | 9.403 | 0.179 | 0.842 | 1.00 | 13.28 |
| 7008 | CG2 | VAL | A | 445 | 9.615 | −0.085 | 3.346 | 1.00 | 16.99 |
| 7009 | C | VAL | A | 445 | 6.893 | −1.107 | 0.837 | 1.00 | 35.69 |
| 7010 | O | VAL | A | 445 | 6.962 | −2.260 | 0.369 | 1.00 | 20.82 |
| 7011 | N | TYR | A | 446 | 6.322 | −0.063 | 0.214 | 1.00 | 25.86 |
| 7012 | CA | TYR | A | 446 | 5.817 | −0.208 | −1.155 | 1.00 | 34.00 |
| 7013 | CB | TYR | A | 446 | 4.364 | −0.678 | −1.197 | 1.00 | 47.44 |
| 7014 | CG | TYR | A | 446 | 4.107 | −1.347 | −2.538 | 1.00 | 92.25 |
| 7015 | CD1 | TYR | A | 446 | 4.961 | −2.353 | −3.012 | 1.00 | 92.40 |
| 7016 | CE1 | TYR | A | 446 | 4.764 | −2.935 | −4.271 | 1.00 | 87.40 |
| 7017 | CD2 | TYR | A | 446 | 3.055 | −0.946 | −3.357 | 1.00 | 91.33 |
| 7018 | CE2 | TYR | A | 446 | 2.847 | −1.518 | −4.616 | 1.00 | 79.48 |
| 7019 | CZ | TYR | A | 446 | 3.701 | −2.511 | −5.066 | 1.00 | 88.42 |
| 7020 | OH | TYR | A | 446 | 3.469 | −3.085 | −6.297 | 1.00 | 94.26 |
| 7021 | C | TYR | A | 446 | 6.004 | 0.990 | −2.094 | 1.00 | 35.64 |
| 7022 | O | TYR | A | 446 | 5.860 | 2.139 | −1.730 | 1.00 | 29.60 |
| 7023 | N | ALA | A | 447 | 6.294 | 0.685 | −3.341 | 1.00 | 19.90 |
| 7024 | CA | ALA | A | 447 | 6.590 | 1.709 | −4.333 | 1.00 | 29.40 |
| 7025 | CB | ALA | A | 447 | 8.074 | 1.588 | −4.751 | 1.00 | 30.03 |
| 7026 | C | ALA | A | 447 | 5.717 | 1.719 | −5.569 | 1.00 | 30.63 |
| 7027 | O | ALA | A | 447 | 5.401 | 0.687 | −6.134 | 1.00 | 31.44 |
| 7028 | N | PHE | A | 448 | 5.364 | 2.915 | −6.006 | 1.00 | 37.60 |
| 7029 | CA | PHE | A | 448 | 4.523 | 3.049 | −7.178 | 1.00 | 39.37 |
| 7030 | CB | PHE | A | 448 | 3.130 | 3.554 | −6.791 | 1.00 | 43.54 |
| 7031 | CG | PHE | A | 448 | 2.557 | 2.884 | −5.594 | 1.00 | 33.11 |
| 7032 | CD1 | PHE | A | 448 | 2.780 | 3.418 | −4.325 | 1.00 | 27.84 |
| 7033 | CD2 | PHE | A | 448 | 1.772 | 1.736 | −5.731 | 1.00 | 24.07 |
| 7034 | CE1 | PHE | A | 448 | 2.231 | 2.828 | −3.191 | 1.00 | 23.13 |
| 7035 | CE2 | PHE | A | 448 | 1.212 | 1.133 | −4.617 | 1.00 | 42.41 |
| 7036 | CZ | PHE | A | 448 | 1.444 | 1.688 | −3.328 | 1.00 | 23.26 |
| 7037 | C | PHE | A | 448 | 5.096 | 4.001 | −8.207 | 1.00 | 39.57 |
| 7038 | O | PHE | A | 448 | 5.928 | 4.861 | −7.893 | 1.00 | 25.58 |
| 7039 | N | ALA | A | 449 | 4.630 | 3.816 | −9.441 | 1.00 | 28.81 |
| 7040 | CA | ALA | A | 449 | 5.001 | 4.655 | −10.570 | 1.00 | 35.20 |
| 7041 | CB | ALA | A | 449 | 5.752 | 3.852 | −11.631 | 1.00 | 27.82 |
| 7042 | C | ALA | A | 449 | 3.715 | 5.189 | −11.150 | 1.00 | 40.45 |
| 7043 | O | ALA | A | 449 | 2.734 | 4.478 | −11.258 | 1.00 | 38.46 |
| 7044 | N | THR | A | 450 | 3.733 | 6.460 | −11.521 | 1.00 | 51.24 |
| 7045 | CA | THR | A | 450 | 2.571 | 7.114 | −12.126 | 1.00 | 46.00 |
| 7046 | CB | THR | A | 450 | 2.761 | 8.651 | −12.078 | 1.00 | 37.95 |
| 7047 | OG1 | THR | A | 450 | 2.340 | 9.130 | −10.793 | 1.00 | 36.50 |
| 7048 | CG2 | THR | A | 450 | 1.997 | 9.343 | −13.176 | 1.00 | 67.63 |
| 7049 | C | THR | A | 450 | 2.362 | 6.660 | −13.570 | 1.00 | 30.68 |
| 7050 | O | THR | A | 450 | 3.298 | 6.270 | −14.249 | 1.00 | 47.43 |
| 7051 | N | PRO | A | 451 | 1.115 | 6.674 | −14.045 | 1.00 | 62.71 |
| 7052 | CD | PRO | A | 451 | −0.106 | 6.747 | −13.229 | 1.00 | 61.82 |
| 7053 | CA | PRO | A | 451 | 0.791 | 6.277 | −15.424 | 1.00 | 60.45 |
| 7054 | CB | PRO | A | 451 | −0.721 | 6.069 | −15.379 | 1.00 | 58.36 |
| 7055 | CG | PRO | A | 451 | −1.002 | 5.798 | −13.946 | 1.00 | 73.35 |
| 7056 | C | PRO | A | 451 | 1.155 | 7.419 | −16.384 | 1.00 | 54.00 |
| 7057 | O | PRO | A | 451 | 1.448 | 8.517 | −15.938 | 1.00 | 31.14 |
| 7058 | N | GLU | A | 452 | 1.119 | 7.158 | −17.688 | 1.00 | 66.74 |
| 7059 | CA | GLU | A | 452 | 1.429 | 8.166 | −18.718 | 1.00 | 86.66 |
| 7060 | CB | GLU | A | 452 | 2.517 | 9.144 | −18.253 | 1.00 | 99.83 |
| 7061 | CG | GLU | A | 452 | 2.002 | 10.418 | −17.591 | 1.00 | 93.13 |
| 7062 | CD | GLU | A | 452 | 2.994 | 10.973 | −16.579 | 1.00 | 103.21 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7063 | OE1 | GLU | A | 452 | 4.102 | 11.400 | −16.992 | 1.00 | 95.04 |
| 7064 | OE2 | OLU | A | 452 | 2.667 | 10.969 | −15.368 | 1.00 | 77.20 |
| 7065 | C | GLU | A | 452 | 1.898 | 7.520 | −20.013 | 1.00 | 91.89 |
| 7066 | O | GLU | A | 452 | 2.878 | 7.966 | −20.617 | 1.00 | 86.42 |
| 7067 | N | LYS | A | 459 | 8.465 | 14.600 | −15.956 | 1.00 | 63.18 |
| 7068 | CA | LYS | A | 459 | 7.724 | 14.844 | −14.718 | 1.00 | 94.85 |
| 7069 | CB | LYS | A | 459 | 6.778 | 16.040 | −14.911 | 1.00 | 105.30 |
| 7070 | CG | LYS | A | 459 | 7.411 | 17.404 | −14.648 | 1.00 | 100.14 |
| 7071 | CD | LYS | A | 459 | 7.658 | 17.611 | −13.157 | 1.00 | 112.41 |
| 7072 | CE | LYS | A | 459 | 8.147 | 19.023 | −12.854 | 1.00 | 116.05 |
| 7073 | NZ | LYS | A | 459 | 8.225 | 19.284 | −11.385 | 1.00 | 118.24 |
| 7074 | C | LYS | A | 459 | 6.934 | 13.607 | −14.239 | 1.00 | 96.66 |
| 7075 | O | LYS | A | 459 | 5.909 | 13.722 | −13.533 | 1.00 | 71.47 |
| 7076 | N | ARG | A | 460 | 7.431 | 12.430 | −14.626 | 1.00 | 87.35 |
| 7077 | CA | ARG | A | 460 | 6.834 | 11.144 | −14.269 | 1.00 | 65.80 |
| 7078 | CB | ARG | A | 460 | 7.340 | 10.086 | −15.241 | 1.00 | 63.38 |
| 7079 | CG | ARG | A | 460 | 6.879 | 10.334 | −16.689 | 1.00 | 75.43 |
| 7080 | CD | ARG | A | 460 | 6.998 | 11.802 | −17.153 | 1.00 | 57.00 |
| 7081 | NE | ARG | A | 460 | 8.375 | 12.317 | −17.166 | 1.00 | 71.26 |
| 7082 | CZ | ARG | A | 460 | 9.124 | 12.482 | −18.257 | 1.00 | 70.41 |
| 7083 | NH1 | ARG | A | 460 | 8.648 | 12.184 | −19.458 | 1.00 | 76.76 |
| 7084 | NH2 | ARG | A | 460 | 10.363 | 12.937 | −18.142 | 1.00 | 61.45 |
| 7085 | C | ARG | A | 460 | 7.235 | 10.843 | −12.826 | 1.00 | 57.07 |
| 7086 | O | ARG | A | 460 | 8.427 | 10.751 | −12.510 | 1.00 | 51.42 |
| 7087 | N | THR | A | 461 | 6.237 | 10.704 | −11.951 | 1.00 | 37.01 |
| 7088 | CA | THR | A | 461 | 6.504 | 10.502 | −10.530 | 1.00 | 29.34 |
| 7089 | CB | THR | A | 461 | 5.588 | 11.415 | −9.667 | 1.00 | 34.39 |
| 7090 | OG1 | THR | A | 461 | 5.212 | 12.583 | −10.411 | 1.00 | 39.96 |
| 7091 | CG2 | THR | A | 461 | 6.315 | 11.861 | −8.413 | 1.00 | 43.07 |
| 7092 | C | THR | A | 461 | 6.450 | 9.087 | −9.942 | 1.00 | 38.47 |
| 7093 | O | THR | A | 461 | 5.670 | 8.214 | −10.341 | 1.00 | 37.78 |
| 7094 | N | LEU | A | 462 | 7.327 | 8.873 | −8.981 | 1.00 | 24.91 |
| 7095 | CA | LEU | A | 462 | 7.428 | 7.604 | −8.294 | 1.00 | 36.43 |
| 7096 | CB | LEU | A | 462 | 8.842 | 7.023 | −8.403 | 1.00 | 38.42 |
| 7097 | CG | LEU | A | 462 | 9.392 | 6.821 | −9.806 | 1.00 | 41.39 |
| 7098 | CD1 | LEU | A | 462 | 10.818 | 6.329 | −9.679 | 1.00 | 41.57 |
| 7099 | CD2 | LEU | A | 462 | 8.524 | 5.843 | −10.595 | 1.00 | 31.18 |
| 7100 | C | LEU | A | 462 | 7.125 | 7.907 | −6.853 | 1.00 | 31.45 |
| 7101 | O | LEU | A | 462 | 7.609 | 8.876 | −6.289 | 1.00 | 39.74 |
| 7102 | N | ALA | A | 463 | 6.314 | 7.064 | −6.259 | 1.00 | 31.91 |
| 7103 | CA | ALA | A | 463 | 5.935 | 7.267 | −4.895 | 1.00 | 22.60 |
| 7104 | CB | ALA | A | 463 | 4.452 | 7.624 | −4.830 | 1.00 | 40.28 |
| 7105 | C | ALA | A | 463 | 6.238 | 6.022 | −4.072 | 1.00 | 38.21 |
| 7106 | O | ALA | A | 463 | 6.248 | 4.886 | −4.554 | 1.00 | 26.13 |
| 7107 | N | CYS | A | 464 | 6.507 | 6.261 | −2.807 | 1.00 | 38.55 |
| 7108 | CA | CYS | A | 464 | 6.823 | 5.194 | −1.902 | 1.00 | 25.75 |
| 7109 | C | CYS | A | 464 | 6.073 | 5.406 | −0.584 | 1.00 | 37.08 |
| 7110 | O | CYS | A | 464 | 6.112 | 6.489 | 0.013 | 1.00 | 38.19 |
| 7111 | CB | CYS | A | 464 | 8.312 | 5.193 | −1.647 | 1.00 | 41.53 |
| 7112 | SG | CYS | A | 464 | 8.962 | 3.725 | −0.831 | 1.00 | 57.84 |
| 7113 | N | LEU | A | 465 | 5.364 | 4.365 | −0.164 | 1.00 | 25.80 |
| 7114 | CA | LEU | A | 465 | 4.670 | 4.379 | 1.101 | 1.00 | 23.10 |
| 7115 | CB | LEU | A | 46S | 3.238 | 3.834 | 0.959 | 1.00 | 36.48 |
| 7116 | CG | LEU | A | 465 | 2.513 | 3.511 | 2.284 | 1.00 | 33.06 |
| 7117 | CD1 | LEU | A | 465 | 2.389 | 4.159 | 3.156 | 1.00 | 30.11 |
| 7118 | CD2 | LEU | A | 465 | 1.147 | 2.939 | 1.989 | 1.00 | 27.23 |
| 7119 | C | LEU | A | 465 | 5.476 | 3.487 | 2.028 | 1.00 | 32.21 |
| 7120 | O | LEU | A | 465 | 5.830 | 2.363 | 1.668 | 1.00 | 34.72 |
| 7121 | N | ILE | A | 466 | 5.772 | 4.006 | 3.210 | 1.00 | 16.05 |
| 7122 | CA | ILE | A | 466 | 6.553 | 3.273 | 4.213 | 1.00 | 31.66 |
| 7123 | CB | ILE | A | 466 | 7.949 | 3.916 | 4.378 | 1.00 | 54.27 |
| 7124 | CG2 | ILE | A | 466 | 8.838 | 3.056 | 5.275 | 1.00 | 33.58 |
| 7125 | CG1 | ILE | A | 466 | 8.591 | 4.067 | 2.997 | 1.00 | 45.60 |
| 7126 | CD1 | ILE | A | 466 | 9.590 | 5.158 | 2.920 | 1.00 | 37.54 |
| 7127 | C | ILE | A | 466 | 5.766 | 3.365 | 5.508 | 1.00 | 38.24 |
| 7128 | O | ILE | A | 466 | 5.618 | 4.449 | 6.056 | 1.00 | 38.70 |
| 7129 | N | GLN | A | 467 | 5.281 | 2.226 | 6.001 | 1.00 | 30.62 |
| 7130 | CA | GLN | A | 467 | 4.412 | 2.216 | 7.187 | 1.00 | 38.58 |
| 7131 | CB | GLN | A | 467 | 2.956 | 2.218 | 6.726 | 1.00 | 31.01 |
| 7132 | CG | GLN | A | 467 | 2.639 | 1.050 | 5.812 | 1.00 | 19.90 |
| 7133 | CD | GLN | A | 467 | 1.177 | 0.999 | 5.394 | 1.00 | 47.21 |
| 7134 | OE1 | GLN | A | 467 | 0.498 | 2.026 | 5.333 | 1.00 | 27.93 |
| 7135 | NE2 | GLN | A | 467 | 0.691 | −0.199 | 5.081 | 1.00 | 13.08 |
| 7136 | C | GLN | A | 467 | 4.526 | 1.122 | 8.242 | 1.00 | 47.07 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7137 | O | GLN | A | 467 | 5.159 | 0.086 | 8.055 | 1.00 | 31.16 |
| 7138 | N | ASN | A | 468 | 3.832 | 1.374 | 9.346 | 1.00 | 25.43 |
| 7139 | CA | ASN | A | 468 | 3.757 | 0.481 | 10.502 | 1.00 | 38.81 |
| 7140 | CB | ASN | A | 468 | 3.132 | −0.871 | 10.121 | 1.00 | 39.32 |
| 7141 | CG | ASN | A | 468 | 1.764 | −0.725 | 9.503 | 1.00 | 34.76 |
| 7142 | OD1 | ASN | A | 468 | 1.009 | 0.175 | 9.855 | 1.00 | 33.64 |
| 7143 | ND2 | ASN | A | 468 | 1.439 | −1.609 | 8.565 | 1.00 | 36.48 |
| 7144 | C | ASN | A | 468 | 5.089 | 0.219 | 11.175 | 1.00 | 44.09 |
| 7145 | O | ASN | A | 468 | 5.381 | −0.913 | 11.551 | 1.00 | 50.95 |
| 7146 | N | PHE | A | 469 | 5.890 | 1.257 | 11.340 | 1.00 | 27.11 |
| 7147 | CA | PHE | A | 469 | 7.180 | 1.104 | 11.939 | 1.00 | 28.67 |
| 7148 | CB | PHE | A | 469 | 8.281 | 1.502 | 10.932 | 1.00 | 37.06 |
| 7149 | CG | PHE | A | 469 | 8.264 | 2.967 | 10.514 | 1.00 | 19.43 |
| 7150 | CD1 | PHE | A | 469 | 8.798 | 3.967 | 11.339 | 1.00 | 23.43 |
| 7151 | CD2 | PHE | A | 469 | 7.697 | 3.351 | 9.309 | 1.00 | 26.45 |
| 7152 | CE1 | PHE | A | 469 | 8.760 | 5.320 | 10.979 | 1.00 | 13.54 |
| 7153 | CE2 | PHE | A | 469 | 7.656 | 4.710 | 8.933 | 1.00 | 28.53 |
| 7154 | CZ | PHE | A | 469 | 8.186 | 5.686 | 9.773 | 1.00 | 27.22 |
| 7155 | C | PHE | A | 469 | 7.282 | 1.933 | 13.203 | 1.00 | 37.71 |
| 7156 | O | PHE | A | 469 | 6.563 | 2.918 | 13.364 | 1.00 | 30.18 |
| 7157 | N | MET | A | 470 | 8.167 | 1.511 | 14.104 | 1.00 | 42.12 |
| 7158 | CA | MET | A | 470 | 8.405 | 2.241 | 15.340 | 1.00 | 47.11 |
| 7159 | CB | MET | A | 470 | 7.234 | 2.082 | 16.332 | 1.00 | 51.01 |
| 7160 | CG | MET | A | 470 | 6.952 | 0.696 | 16.816 | 1.00 | 71.30 |
| 7161 | SD | MET | A | 470 | 5.475 | 0.671 | 17.838 | 1.00 | 74.66 |
| 7162 | CE | MET | A | 470 | 5.801 | 1.976 | 19.004 | 1.00 | 73.16 |
| 7163 | C | MET | A | 470 | 9.720 | 1.848 | 15.990 | 1.00 | 36.61 |
| 7164 | O | MET | A | 470 | 10.132 | 0.708 | 15.911 | 1.00 | 36.62 |
| 7165 | N | PRO | A | 471 | 10.420 | 2.820 | 16.599 | 1.00 | 38.20 |
| 7166 | CD | PRO | A | 471 | 11.800 | 2.625 | 17.066 | 1.00 | 21.97 |
| 7167 | CA | PRO | A | 471 | 10.048 | 4.248 | 16.707 | 1.00 | 34.63 |
| 7168 | CB | PRO | A | 471 | 11.232 | 4.866 | 17.444 | 1.00 | 41.46 |
| 7169 | CG | PRO | A | 471 | 11.921 | 3.715 | 18.070 | 1.00 | 43.42 |
| 7170 | C | PRO | A | 471 | 9.837 | 4.951 | 15.355 | 1.00 | 42.83 |
| 7171 | O | PRO | A | 471 | 9.927 | 4.345 | 14.280 | 1.00 | 26.85 |
| 7172 | N | GLU | A | 472 | 9.596 | 6.251 | 15.426 | 1.00 | 45.14 |
| 7173 | CA | GLU | A | 472 | 9.367 | 7.075 | 14.238 | 1.00 | 47.03 |
| 7174 | CB | GLU | A | 472 | 8.640 | 8.363 | 14.618 | 1.00 | 37.83 |
| 7175 | CG | GLU | A | 472 | 9.498 | 9.334 | 15.391 | 1.00 | 61.51 |
| 7176 | CD | GLU | A | 472 | 8.800 | 10.659 | 15.635 | 1.00 | 92.98 |
| 7177 | OE1 | GLU | A | 472 | 7.877 | 10.701 | 16.478 | 1.00 | 98.41 |
| 7178 | OE2 | GLU | A | 472 | 9.171 | 11.658 | 14.974 | 1.00 | 100.85 |
| 7179 | C | GLU | A | 472 | 10.632 | 7.450 | 13.452 | 1.00 | 44.26 |
| 7180 | O | GLU | A | 472 | 10.525 | 7.920 | 12.328 | 1.00 | 52.93 |
| 7181 | N | ASP | A | 473 | 11.815 | 7.250 | 14.027 | 1.00 | 40.61 |
| 7182 | CA | ASP | A | 473 | 13.053 | 7.585 | 13.337 | 1.00 | 37.05 |
| 7183 | CB | ASP | A | 473 | 14.263 | 7.376 | 14.257 | 1.00 | 48.50 |
| 7184 | CG | ASP | A | 473 | 14.236 | 8.282 | 15.479 | 1.00 | 75.31 |
| 7185 | OD1 | ASP | A | 473 | 14.049 | 9.512 | 15.327 | 1.00 | 72.41 |
| 7186 | OD2 | ASP | A | 473 | 14.410 | 7.760 | 16.596 | 1.00 | 87.88 |
| 7187 | C | ASP | A | 473 | 13.219 | 6.748 | 12.087 | 1.00 | 27.05 |
| 7188 | O | ASP | A | 473 | 13.158 | 5.538 | 12.136 | 1.00 | 36.05 |
| 7189 | N | ILE | A | 474 | 13.437 | 7.393 | 10.951 | 1.00 | 35.06 |
| 7190 | CA | ILE | A | 474 | 13.587 | 6.634 | 9.722 | 1.00 | 32.66 |
| 7191 | CB | ILE | A | 474 | 12.183 | 6.170 | 9.206 | 1.00 | 26.96 |
| 7192 | CG2 | ILE | A | 474 | 11.408 | 7.344 | 8.625 | 1.00 | 21.47 |
| 7193 | CG1 | ILE | A | 474 | 12.344 | 5.057 | 8.183 | 1.00 | 28.76 |
| 7194 | CD1 | ILE | A | 474 | 11.130 | 4.208 | 8.050 | 1.00 | 23.53 |
| 7195 | C | ILE | A | 474 | 14.328 | 7.413 | 8.650 | 1.00 | 34.10 |
| 7196 | O | ILE | A | 474 | 14.325 | 8.638 | 8.655 | 1.00 | 31.84 |
| 7197 | N | SER | A | 475 | 14.975 | 6.679 | 7.744 | 1.00 | 37.55 |
| 7198 | CA | SER | A | 475 | 15.750 | 7.252 | 6.622 | 1.00 | 30.45 |
| 7199 | CB | SER | A | 475 | 17.257 | 6.988 | 6.795 | 1.00 | 44.67 |
| 7200 | OG | SER | A | 475 | 17.778 | 7.699 | 7.901 | 1.00 | 41.42 |
| 7201 | C | SER | A | 475 | 15.282 | 6.632 | 5.322 | 1.00 | 34.83 |
| 7202 | O | SER | A | 475 | 15.144 | 5.418 | 5.216 | 1.00 | 31.77 |
| 7203 | N | VAL | A | 476 | 15.022 | 7.491 | 4.344 | 1.00 | 27.36 |
| 7204 | CA | VAL | A | 476 | 14.563 | 7.060 | 3.023 | 1.00 | 28.49 |
| 7205 | CB | VAL | A | 476 | 13.216 | 7.694 | 2.666 | 1.00 | 21.81 |
| 7206 | CG1 | VAL | A | 476 | 12.726 | 7.119 | 1.367 | 1.00 | 34.02 |
| 7207 | CG2 | VAL | A | 476 | 12.218 | 7.423 | 3.775 | 1.00 | 13.18 |
| 7208 | C | VAL | A | 476 | 15.551 | 7.383 | 1.910 | 1.00 | 34.57 |
| 7209 | O | VAL | A | 476 | 16.071 | 8.469 | 1.833 | 1.00 | 39.54 |
| 7210 | N | GLN | A | 477 | 15.816 | 6.419 | 1.046 | 1.00 | 40.76 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7211 | CA | GLN | A | 477 | 16.746 | 6.649 | −0.056 | 1.00 | 36.04 |
| 7212 | CB | GLN | A | 477 | 18.101 | 6.016 | 0.214 | 1.00 | 39.36 |
| 7213 | CG | GLN | A | 477 | 18.522 | 6.062 | 1.647 | 1.00 | 54.51 |
| 7214 | CD | GLN | A | 477 | 19.907 | 5.513 | 1.815 | 1.00 | 77.37 |
| 7215 | OE1 | GLN | A | 477 | 20.206 | 4.376 | 1.424 | 1.00 | 59.24 |
| 7216 | NE2 | GLN | A | 477 | 20.776 | 6.320 | 2.389 | 1.00 | 79.44 |
| 7217 | C | GLN | A | 477 | 16.246 | 6.051 | −1.334 | 1.00 | 40.03 |
| 7218 | O | GLN | A | 477 | 15.555 | 5.024 | −1.326 | 1.00 | 38.88 |
| 7219 | N | TRP | A | 478 | 16.604 | 6.702 | −2.431 | 1.00 | 33.44 |
| 7220 | CA | TRP | A | 478 | 16.242 | 6.213 | −3.749 | 1.00 | 27.68 |
| 7221 | CB | TRP | A | 478 | 15.505 | 7.290 | −4.561 | 1.00 | 31.64 |
| 7222 | CG | TRP | A | 478 | 14.092 | 7.528 | −4.114 | 1.00 | 24.65 |
| 7223 | CD2 | TRP | A | 478 | 12.924 | 6.807 | −4.550 | 1.00 | 17.54 |
| 7224 | CE2 | TRP | A | 478 | 11.816 | 7.336 | −3.838 | 1.00 | 19.07 |
| 7225 | CE3 | TRP | A | 478 | 12.708 | 5.763 | −5.469 | 1.00 | 16.35 |
| 7226 | CD1 | TRP | A | 478 | 13.656 | 8.443 | −3.182 | 1.00 | 20.84 |
| 7227 | NE1 | TRP | A | 478 | 12.288 | 8.327 | −3.015 | 1.00 | 35.01 |
| 7228 | CZ2 | TRP | A | 478 | 10.522 | 6.856 | −4.016 | 1.00 | 18.75 |
| 7229 | CZ3 | TRP | A | 478 | 11.419 | 5.283 | −5.639 | 1.00 | 23.21 |
| 7230 | CH2 | TRP | A | 478 | 10.343 | 5.826 | −4.916 | 1.00 | 20.34 |
| 7231 | C | TRP | A | 478 | 17.535 | 5.792 | −4.447 | 1.00 | 34.76 |
| 7232 | O | TRP | A | 478 | 18.569 | 6.433 | −4.320 | 1.00 | 32.91 |
| 7233 | N | LEU | A | 479 | 17.476 | 4.687 | −5.166 | 1.00 | 31.43 |
| 7234 | CA | LEU | A | 479 | 18.640 | 4.198 | −5.873 | 1.00 | 18.11 |
| 7235 | CB | LEU | A | 479 | 19.186 | 2.938 | −5.187 | 1.00 | 45.21 |
| 7236 | CG | LEU | A | 479 | 19.958 | 3.043 | −3.862 | 1.00 | 45.96 |
| 7237 | CD1 | LEU | A | 479 | 19.059 | 3.497 | −2.744 | 1.00 | 56.33 |
| 7238 | CD2 | LEU | A | 479 | 20.530 | 1.709 | −3.519 | 1.00 | 54.53 |
| 7239 | C | LEU | A | 479 | 18.278 | 3.876 | −7.311 | 1.00 | 34.59 |
| 7240 | O | LEU | A | 479 | 17.183 | 3.385 | −7.600 | 1.00 | 30.64 |
| 7241 | N | HIS | A | 480 | 19.197 | 4.187 | −8.216 | 1.00 | 40.79 |
| 7242 | CA | HIS | A | 480 | 19.019 | 3.896 | −9.633 | 1.00 | 42.96 |
| 7243 | CB | HIS | A | 480 | 18.743 | 5.179 | −10.417 | 1.00 | 31.00 |
| 7244 | CG | HIS | A | 480 | 18.414 | 4.948 | −11.863 | 1.00 | 37.31 |
| 7245 | CD2 | HIS | A | 480 | 18.921 | 5.496 | −12.989 | 1.00 | 23.09 |
| 7246 | ND1 | HIS | A | 480 | 17.494 | 4.012 | −12.280 | 1.00 | 49.78 |
| 7247 | CE1 | HIS | A | 480 | 17.455 | 3.986 | −13.600 | 1.00 | 35.97 |
| 7248 | NE2 | HIS | A | 480 | 18.314 | 4.877 | −14.054 | 1.00 | 57.03 |
| 7249 | C | HIS | A | 480 | 20.306 | 3.205 | −10.107 | 1.00 | 60.01 |
| 7250 | O | HIS | A | 480 | 21.406 | 3.690 | −9.857 | 1.00 | 49.81 |
| 7251 | N | ASN | A | 481 | 20.152 | 2.059 | −10.770 | 1.00 | 69.15 |
| 7252 | CA | ASN | A | 481 | 21.274 | 1.256 | −11.248 | 1.00 | 78.90 |
| 7253 | CB | ASN | A | 481 | 22.367 | 2.136 | −11.848 | 1.00 | 64.79 |
| 7254 | CG | ASN | A | 481 | 22.085 | 2.500 | −13.281 | 1.00 | 63.79 |
| 7255 | OD1 | ASN | A | 481 | 22.051 | 1.636 | −14.160 | 1.00 | 58.62 |
| 7256 | ND2 | ASN | A | 481 | 21.867 | 3.779 | −13.531 | 1.00 | 69.79 |
| 7257 | C | ASN | A | 481 | 21.830 | 0.454 | −10.084 | 1.00 | 85.44 |
| 7258 | O | ASN | A | 481 | 21.967 | −0.775 | −10.158 | 1.00 | 90.76 |
| 7259 | N | GLU | A | 482 | 22.124 | 1.167 | −9.003 | 1.00 | 80.75 |
| 7260 | CA | GLU | A | 482 | 22.659 | 0.586 | −7.777 | 1.00 | 82.04 |
| 7261 | CB | GLU | A | 482 | 23.762 | −0.417 | −8.091 | 1.00 | 90.73 |
| 7262 | CG | GLU | A | 482 | 24.686 | −0.011 | −9.241 | 1.00 | 116.62 |
| 7263 | CD | GLU | A | 482 | 25.012 | 1.474 | −9.269 | 1.00 | 125.29 |
| 7264 | OE1 | GLU | A | 482 | 24.120 | 2.275 | −9.621 | 1.00 | 121.29 |
| 7265 | OE2 | GLU | A | 482 | 26.163 | 1.838 | −8.939 | 1.00 | 134.03 |
| 7266 | C | GLU | A | 482 | 23.227 | 1.711 | −6.935 | 1.00 | 70.12 |
| 7267 | O | GLU | A | 482 | 23.703 | 1.497 | −5.815 | 1.00 | 59.67 |
| 7268 | N | VAL | A | 483 | 23.156 | 2.916 | −7.487 | 1.00 | 59.75 |
| 7269 | CA | VAL | A | 483 | 23.682 | 4.080 | −6.814 | 1.00 | 59.97 |
| 7270 | CB | VAL | A | 483 | 24.610 | 4.882 | −7.764 | 1.00 | 51.60 |
| 7271 | CG1 | VAL | A | 483 | 23.834 | 5.335 | −9.004 | 1.00 | 62.07 |
| 7272 | CG2 | VAL | A | 483 | 25.169 | 6.084 | −7.041 | 1.00 | 59.35 |
| 7273 | C | VAL | A | 483 | 22.612 | 5.006 | −6.252 | 1.00 | 51.51 |
| 7274 | O | VAL | A | 483 | 21.622 | 5.311 | −6.895 | 1.00 | 46.03 |
| 7275 | N | GLN | A | 484 | 22.859 | 5.450 | −5.033 | 1.00 | 36.95 |
| 7276 | CA | GLN | A | 484 | 21.997 | 6.361 | −4.310 | 1.00 | 48.07 |
| 7277 | CB | GLN | A | 484 | 22.523 | 6.436 | −2.881 | 1.00 | 42.66 |
| 7278 | CG | GLN | A | 484 | 21.939 | 7.499 | −2.000 | 1.00 | 66.92 |
| 7279 | CD | GLN | A | 464 | 22.464 | 7.383 | −0.585 | 1.00 | 70.16 |
| 7280 | OE1 | GLN | A | 484 | 22.437 | 8.347 | 0.180 | 1.00 | 78.95 |
| 7281 | NE2 | GLN | A | 484 | 22.941 | 6.191 | −0.226 | 1.00 | 75.79 |
| 7282 | C | GLN | A | 484 | 21.958 | 7.750 | −4.977 | 1.00 | 51.52 |
| 7283 | O | GLN | A | 484 | 22.986 | 8.390 | −5.158 | 1.00 | 61.21 |
| 7284 | N | LEU | A | 485 | 20.762 | 8.199 | −5.348 | 1.00 | 52.72 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7285 | CA | LEU | A | 485 | 20.578 | 9.493 | −6.003 | 1.00 | 40.44 |
| 7286 | CB | LEU | A | 485 | 19.177 | 9.594 | −6.632 | 1.00 | 21.77 |
| 7287 | CG | LEU | A | 485 | 18.707 | 8.490 | −7.565 | 1.00 | 51.83 |
| 7288 | CD1 | LEU | A | 485 | 17.293 | 8.763 | −8.019 | 1.00 | 52.68 |
| 7289 | CD2 | LEU | A | 485 | 19.614 | 8.434 | −8.747 | 1.00 | 44.40 |
| 7290 | C | LEU | A | 485 | 20.746 | 10.608 | −4.979 | 1.00 | 49.82 |
| 7291 | O | LEU | A | 485 | 20.616 | 10.394 | −3.769 | 1.00 | 44.24 |
| 7292 | N | PRO | A | 486 | 21.036 | 11.823 | −5.453 | 1.00 | 58.14 |
| 7293 | CD | PRO | A | 486 | 21.140 | 12.260 | −6.853 | 1.00 | 40.04 |
| 7294 | CA | PRO | A | 486 | 21.211 | 12.949 | −4.535 | 1.00 | 46.99 |
| 7295 | CB | PRO | A | 486 | 21.387 | 14.140 | −5.482 | 1.00 | 45.43 |
| 7296 | CG | PRO | A | 486 | 21.915 | 13.523 | −6.715 | 1.00 | 38.89 |
| 7297 | C | PRO | A | 486 | 19.970 | 13.079 | −3.664 | 1.00 | 43.24 |
| 7298 | O | PRO | A | 486 | 18.849 | 13.001 | −4.156 | 1.00 | 42.09 |
| 7299 | N | ASP | A | 487 | 20.174 | 13.285 | −2.373 | 1.00 | 57.53 |
| 7300 | CA | ASP | A | 487 | 19.057 | 13.424 | −1.443 | 1.00 | 63.24 |
| 7301 | CB | ASP | A | 487 | 19.600 | 13.671 | −0.032 | 1.00 | 71.40 |
| 7302 | CG | ASP | A | 487 | 18.613 | 13.283 | 1.050 | 1.00 | 110.84 |
| 7303 | OD1 | ASP | A | 487 | 17.614 | 14.007 | 1.248 | 1.00 | 126.96 |
| 7304 | OD2 | ASP | A | 487 | 18.835 | 12.242 | 1.700 | 1.00 | 115.45 |
| 7305 | C | ASP | A | 487 | 18.050 | 14.526 | −1.838 | 1.00 | 63.62 |
| 7306 | O | ASP | A | 487 | 16.846 | 14.391 | −1.589 | 1.00 | 76.74 |
| 7307 | N | ALA | A | 488 | 18.530 | 15.593 | −2.476 | 1.00 | 54.65 |
| 7308 | CA | ALA | A | 488 | 17.674 | 16.706 | −2.873 | 1.00 | 52.29 |
| 7309 | CB | ALA | A | 488 | 18.524 | 17.921 | −3.169 | 1.00 | 57.53 |
| 7310 | C | ALA | A | 488 | 16.762 | 16.410 | −4.055 | 1.00 | 43.17 |
| 7311 | O | ALA | A | 488 | 15.981 | 17.253 | −4.459 | 1.00 | 52.06 |
| 7312 | N | ARG | A | 489 | 16.869 | 15.213 | −4.608 | 1.00 | 42.74 |
| 7313 | CA | ARG | A | 489 | 16.055 | 14.807 | −5.739 | 1.00 | 48.03 |
| 7314 | CB | ARG | A | 489 | 16.773 | 13.701 | −6.509 | 1.00 | 59.21 |
| 7315 | CG | ARG | A | 489 | 17.645 | 14.196 | −7.627 | 1.00 | 43.25 |
| 7316 | CD | ARG | A | 489 | 16.884 | 14.134 | −8.941 | 1.00 | 22.93 |
| 7317 | NE | ARG | A | 489 | 17.161 | 12.918 | −9.716 | 1.00 | 22.53 |
| 7318 | CZ | ARG | A | 489 | 16.269 | 12.364 | −10.523 | 1.00 | 26.38 |
| 7319 | NH1 | ARG | A | 489 | 15.071 | 12.907 | −10.633 | 1.00 | 66.05 |
| 7320 | NH2 | ARG | A | 489 | 16.574 | 11.309 | −11.249 | 1.00 | 49.23 |
| 7321 | C | ARG | A | 489 | 14.676 | 14.320 | −5.314 | 1.00 | 58.55 |
| 7322 | O | ARG | A | 489 | 13.701 | 14.452 | −6.067 | 1.00 | 60.44 |
| 7323 | N | HIS | A | 490 | 14.591 | 13.756 | −4.108 | 1.00 | 49.48 |
| 7324 | CA | HIS | A | 490 | 13.316 | 13.250 | −3.601 | 1.00 | 35.00 |
| 7325 | CB | HIS | A | 490 | 13.458 | 11.790 | −3.161 | 1.00 | 51.16 |
| 7326 | CG | HIS | A | 490 | 14.201 | 11.609 | −1.871 | 1.00 | 46.94 |
| 7327 | CD2 | HIS | A | 490 | 15.398 | 11.038 | −1.604 | 1.00 | 52.00 |
| 7328 | ND1 | HIS | A | 490 | 13.717 | 12.057 | −0.660 | 1.00 | 52.57 |
| 7329 | CE1 | HIS | A | 490 | 14.582 | 11.773 | 0.295 | 1.00 | 30.20 |
| 7330 | NE2 | HIS | A | 490 | 15.612 | 11.157 | −0.251 | 1.00 | 56.19 |
| 7331 | C | HIS | A | 490 | 12.791 | 14.079 | −2.444 | 1.00 | 37.38 |
| 7332 | O | HIS | A | 490 | 13.534 | 14.821 | −1.817 | 1.00 | 39.90 |
| 7333 | N | SER | A | 491 | 11.496 | 13.944 | −2.177 | 1.00 | 38.83 |
| 7334 | CA | SER | A | 491 | 10.835 | 14.653 | −1.087 | 1.00 | 35.25 |
| 7335 | CB | SER | A | 491 | 9.782 | 15.593 | −1.661 | 1.00 | 22.49 |
| 7336 | OG | SER | A | 491 | 9.321 | 16.459 | −0.661 | 1.00 | 31.32 |
| 7337 | C | SER | A | 491 | 10.187 | 13.638 | −0.120 | 1.00 | 38.73 |
| 7338 | O | SER | A | 491 | 9.487 | 12.716 | −0.540 | 1.00 | 46.36 |
| 7339 | N | THR | A | 492 | 10.439 | 13.793 | 1.174 | 1.00 | 31.40 |
| 7340 | CA | THR | A | 492 | 9.859 | 12.870 | 2.166 | 1.00 | 33.02 |
| 7341 | CB | THR | A | 492 | 10.953 | 11.986 | 2.803 | 1.00 | 25.72 |
| 7342 | OG1 | THR | A | 492 | 11.558 | 11.177 | 1.789 | 1.00 | 52.19 |
| 7343 | CG2 | THR | A | 492 | 10.371 | 11.088 | 3.860 | 1.00 | 38.45 |
| 7344 | C | THR | A | 492 | 9.061 | 13.544 | 3.286 | 1.00 | 29.74 |
| 7345 | O | THR | A | 492 | 9.542 | 14.476 | 3.918 | 1.00 | 39.25 |
| 7346 | N | THR | A | 493 | 7.856 | 13.032 | 3.534 | 1.00 | 32.04 |
| 7347 | CA | THR | A | 493 | 6.936 | 13.564 | 4.558 | 1.00 | 23.89 |
| 7348 | CB | THR | A | 493 | 5.526 | 12.920 | 4.448 | 1.00 | 27.71 |
| 7349 | OG1 | THR | A | 493 | 5.628 | 11.505 | 4.675 | 1.00 | 44.17 |
| 7350 | CG2 | THR | A | 493 | 4.927 | 13.149 | 3.087 | 1.00 | 24.08 |
| 7351 | C | THR | A | 493 | 7.389 | 13.341 | 5.998 | 1.00 | 26.16 |
| 7352 | O | THR | A | 493 | 8.165 | 12.436 | 6.280 | 1.00 | 35.55 |
| 7353 | N | GLN | A | 494 | 6.901 | 14.180 | 6.902 | 1.00 | 35.33 |
| 7354 | CA | GLN | A | 494 | 7.206 | 14.039 | 8.312 | 1.00 | 52.29 |
| 7355 | CB | GLN | A | 494 | 6.764 | 15.283 | 9.075 | 1.00 | 68.27 |
| 7356 | CG | GLN | A | 494 | 7.440 | 16.559 | 8.619 | 1.00 | 89.28 |
| 7357 | CD | GLN | A | 494 | 8.918 | 16.582 | 8.942 | 1.00 | 102.95 |
| 7358 | OE1 | GLN | A | 494 | 9.306 | 16.558 | 10.110 | 1.00 | 110.63 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7359 | NE2 | GLN | A | 494 | 9.755 | 16.626 | 7.909 | 1.00 | 108.81 |
| 7360 | C | GLN | A | 494 | 6.441 | 12.808 | 8.825 | 1.00 | 55.47 |
| 7361 | O | GLN | A | 494 | 5.346 | 12.511 | 8.351 | 1.00 | 45.42 |
| 7362 | N | PRO | A | 495 | 7.027 | 12.067 | 9.784 | 1.00 | 49.88 |
| 7363 | CD | PRO | A | 495 | 8.410 | 12.156 | 10.286 | 1.00 | 54.18 |
| 7364 | CA | PRO | A | 495 | 6.366 | 10.880 | 10.322 | 1.00 | 46.31 |
| 7365 | CB | PRO | A | 495 | 7.367 | 10.361 | 11.351 | 1.00 | 45.53 |
| 7366 | CG | PRO | A | 495 | 8.663 | 10.743 | 10.781 | 1.00 | 35.30 |
| 7367 | C | PRO | A | 495 | 5.010 | 11.211 | 10.921 | 1.00 | 46.21 |
| 7368 | O | PRO | A | 495 | 4.835 | 12.253 | 11.534 | 1.00 | 54.26 |
| 7369 | N | ARG | A | 496 | 4.054 | 10.310 | 10.711 | 1.00 | 54.47 |
| 7370 | CA | ARG | A | 496 | 2.687 | 10.453 | 11.196 | 1.00 | 49.75 |
| 7371 | CB | ARG | A | 496 | 1.780 | 10.944 | 10.081 | 1.00 | 34.31 |
| 7372 | CG | ARG | A | 496 | 1.837 | 12.390 | 9.827 | 1.00 | 33.42 |
| 7373 | CD | ARG | A | 496 | 0.627 | 12.752 | 8.979 | 1.00 | 74.29 |
| 7374 | NE | ARG | A | 496 | 0.291 | 14.171 | 9.032 | 1.00 | 87.92 |
| 7375 | CZ | ARG | A | 496 | −0.946 | 14.634 | 8.922 | 1.00 | 79.55 |
| 7376 | NH1 | ARG | A | 496 | −1.949 | 13.780 | 8.759 | 1.00 | 69.48 |
| 7377 | NH2 | ARG | A | 496 | −1.178 | 15.944 | 8.972 | 1.00 | 82.69 |
| 7378 | C | ARG | A | 496 | 2.153 | 9.117 | 11.703 | 1.00 | 68.56 |
| 7379 | O | ARG | A | 496 | 2.522 | 8.056 | 11.183 | 1.00 | 61.50 |
| 7380 | N | LYS | A | 497 | 1.266 | 9.184 | 12.697 | 1.00 | 62.57 |
| 7381 | CA | LYS | A | 497 | 0.675 | 7.999 | 13.306 | 1.00 | 61.98 |
| 7382 | CB | LYS | A | 497 | −0.015 | 8.373 | 14.612 | 1.00 | 63.37 |
| 7383 | CG | LYS | A | 497 | 0.890 | 9.039 | 15.616 | 1.00 | 74.64 |
| 7384 | CD | LYS | A | 497 | 0.088 | 9.582 | 16.792 | 1.00 | 94.10 |
| 7385 | CE | LYS | A | 497 | 0.965 | 10.379 | 17.739 | 1.00 | 99.16 |
| 7386 | NZ | LYS | A | 497 | 0.181 | 10.926 | 18.886 | 1.00 | 104.96 |
| 7387 | C | LYS | A | 497 | −0.329 | 7.330 | 12.389 | 1.00 | 63.98 |
| 7388 | O | LYS | A | 497 | −1.218 | 7.992 | 11.855 | 1.00 | 58.78 |
| 7389 | N | THR | A | 498 | −0.182 | 6.018 | 12.217 | 1.00 | 66.79 |
| 7390 | CA | THR | A | 498 | −1.074 | 5.241 | 11.371 | 1.00 | 76.02 |
| 7391 | CB | THR | A | 498 | −0.458 | 3.871 | 11.020 | 1.00 | 79.35 |
| 7392 | OG1 | THR | A | 498 | −0.288 | 3.095 | 12.214 | 1.00 | 87.55 |
| 7393 | CG2 | THR | A | 498 | 0.884 | 4.050 | 10.361 | 1.00 | 77.59 |
| 7394 | C | THR | A | 498 | −2.388 | 5.008 | 12.108 | 1.00 | 89.23 |
| 7395 | O | THR | A | 498 | −3.399 | 5.634 | 11.805 | 1.00 | 96.71 |
| 7396 | N | LYS | A | 499 | −2.347 | 4.100 | 13.078 | 1.00 | 97.32 |
| 7397 | CA | LYS | A | 499 | −3.494 | 3.723 | 13.907 | 1.00 | 99.83 |
| 7398 | CB | LYS | A | 499 | −4.690 | 3.291 | 13.050 | 1.00 | 87.50 |
| 7399 | CG | LYS | A | 499 | −5.665 | 4.411 | 12.730 | 1.00 | 98.15 |
| 7400 | CD | LYS | A | 499 | −6.234 | 5.023 | 14.008 | 1.00 | 108.06 |
| 7401 | CE | LYS | A | 499 | −7.211 | 6.155 | 13.710 | 1.00 | 106.43 |
| 7402 | NZ | LYS | A | 499 | −7.774 | 6.740 | 14.955 | 1.00 | 96.58 |
| 7403 | C | LYS | A | 499 | −3.077 | 2.561 | 14.800 | 1.00 | 99.20 |
| 7404 | O | LYS | A | 499 | −3.530 | 1.435 | 14.608 | 1.00 | 92.05 |
| 7405 | N | GLY | A | 500 | −2.198 | 2.843 | 15.759 | 1.00 | 103.35 |
| 7406 | CA | GLY | A | 500 | −1.722 | 1.817 | 16.674 | 1.00 | 102.41 |
| 7407 | C | GLY | A | 500 | −0.425 | 1.123 | 16.267 | 1.00 | 103.34 |
| 7408 | O | GLY | A | 500 | 0.543 | 1.069 | 17.036 | 1.00 | 91.80 |
| 7409 | N | SER | A | 501 | −0.404 | 0.588 | 15.052 | 1.00 | 102.87 |
| 7410 | CA | SER | A | 501 | 0.764 | −0.121 | 14.539 | 1.00 | 102.92 |
| 7411 | CB | SER | A | 501 | 0.478 | −0.663 | 13.136 | 1.00 | 105.20 |
| 7412 | OG | SER | A | 501 | 0.234 | 0.396 | 12.225 | 1.00 | 120.04 |
| 7413 | C | SER | A | 501 | 2.037 | 0.721 | 14.505 | 1.00 | 98.79 |
| 7414 | O | SER | A | 501 | 3.137 | 0.166 | 14.466 | 1.00 | 100.92 |
| 7415 | N | GLY | A | 502 | 1.895 | 2.046 | 14.503 | 1.00 | 82.41 |
| 7416 | CA | GLY | A | 502 | 3.071 | 2.902 | 14.486 | 1.00 | 69.28 |
| 7417 | C | GLY | A | 502 | 2.984 | 4.133 | 13.604 | 1.00 | 56.21 |
| 7418 | O | GLY | A | 502 | 2.039 | 4.901 | 13.698 | 1.00 | 57.94 |
| 7419 | N | PHE | A | 503 | 3.979 | 4.333 | 12.747 | 1.00 | 44.22 |
| 7420 | CA | PHE | A | 503 | 3.986 | 5.491 | 11.862 | 1.00 | 46.46 |
| 7421 | CB | PHE | A | 503 | 5.149 | 6.437 | 12.186 | 1.00 | 28.45 |
| 7422 | CG | PHE | A | 503 | 5.242 | 6.830 | 13.620 | 1.00 | 35.32 |
| 7423 | CD1 | PHE | A | 503 | 5.787 | 5.950 | 14.564 | 1.00 | 37.48 |
| 7424 | CD2 | PHE | A | 503 | 4.817 | 8.084 | 14.033 | 1.00 | 28.40 |
| 7425 | CE1 | PHE | A | 503 | 5.903 | 6.323 | 15.902 | 1.00 | 34.50 |
| 7426 | CE2 | PHE | A | 503 | 4.928 | 8.471 | 15.375 | 1.00 | 53.80 |
| 7427 | CZ | PHE | A | 503 | 5.472 | 7.595 | 16.317 | 1.00 | 29.91 |
| 7428 | C | PHE | A | 503 | 4.073 | 5.156 | 10.379 | 1.00 | 39.50 |
| 7429 | O | PHE | A | 503 | 4.272 | 4.020 | 9.979 | 1.00 | 36.44 |
| 7430 | N | PHE | A | 504 | 3.900 | 6.185 | 9.566 | 1.00 | 31.61 |
| 7431 | CA | PHE | A | 504 | 4.009 | 6.035 | 8.125 | 1.00 | 40.63 |
| 7432 | CB | PHE | A | 504 | 2.653 | 5.778 | 7.465 | 1.00 | 38.26 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7433 | CG | PHE | A | 504 | 1.803 | 7.002 | 7.308 | 1.00 | 47.15 |
| 7434 | CD1 | PHE | A | 504 | 1.985 | 7.851 | 6.223 | 1.00 | 39.11 |
| 7435 | CD2 | PHE | A | 504 | 0.806 | 7.300 | 8.231 | 1.00 | 48.11 |
| 7436 | CE1 | PHE | A | 504 | 1.202 | 8.961 | 6.058 | 1.00 | 39.37 |
| 7437 | CE2 | PHE | A | 504 | 0.008 | 8.418 | 8.073 | 1.00 | 44.73 |
| 7438 | CZ | PHE | A | 504 | 0.203 | 9.251 | 6.986 | 1.00 | 55.17 |
| 7439 | C | PHE | A | 504 | 4.656 | 7.279 | 7.547 | 1.00 | 34.24 |
| 7440 | O | PHE | A | 504 | 4.638 | 8.357 | 8.133 | 1.00 | 22.63 |
| 7441 | N | VAL | A | 505 | 5.251 | 7.097 | 6.382 | 1.00 | 34.19 |
| 7442 | CA | VAL | A | 505 | 5.928 | 8.181 | 5.712 | 1.00 | 15.23 |
| 7443 | CB | VAL | A | 505 | 7.460 | 8.179 | 6.105 | 1.00 | 31.61 |
| 7444 | CG1 | VAL | A | 505 | 8.347 | 8.020 | 4.883 | 1.00 | 35.79 |
| 7445 | CG2 | VAL | A | 505 | 7.793 | 9.435 | 6.896 | 1.00 | 35.15 |
| 7446 | C | VAL | A | 505 | 5.719 | 7.950 | 4.254 | 1.00 | 29.07 |
| 7447 | O | VAL | A | 505 | 5.545 | 6.819 | 3.813 | 1.00 | 30.23 |
| 7448 | N | PHE | A | 506 | 5.696 | 9.046 | 3.516 | 1.00 | 30.48 |
| 7449 | CA | PHE | A | 506 | 5.545 | 9.009 | 2.054 | 1.00 | 37.83 |
| 7450 | CB | PHE | A | 506 | 4.238 | 9.708 | 1.673 | 1.00 | 29.72 |
| 7451 | CG | PHE | A | 506 | 4.017 | 9.896 | 0.188 | 1.00 | 91.37 |
| 7452 | CD1 | PHE | A | 506 | 3.830 | 8.804 | −0.651 | 1.00 | 91.11 |
| 7453 | CD2 | PHE | A | 506 | 3.852 | 11.188 | −0.353 | 1.00 | 86.35 |
| 7454 | CE1 | PHE | A | 506 | 3.464 | 8.997 | −2.004 | 1.00 | 97.40 |
| 7455 | CE2 | PHE | A | 506 | 3.488 | 11.378 | −1.695 | 1.00 | 23.90 |
| 7456 | CZ | PHE | A | 506 | 3.291 | 10.288 | −2.513 | 1.00 | 53.04 |
| 7457 | C | PHE | A | 506 | 6.757 | 9.710 | 1.438 | 1.00 | 30.60 |
| 7458 | O | PHE | A | 506 | 7.288 | 10.672 | 1.989 | 1.00 | 40.35 |
| 7459 | N | SER | A | 507 | 7.221 | 9.187 | 0.318 | 1.00 | 29.80 |
| 7460 | CA | SER | A | 507 | 8.346 | 9.796 | −0.379 | 1.00 | 30.22 |
| 7461 | CB | SER | A | 507 | 9.610 | 8.997 | −0.166 | 1.00 | 45.83 |
| 7462 | OG | SER | A | 507 | 10.687 | 9.740 | −0.679 | 1.00 | 36.32 |
| 7463 | C | SER | A | 507 | 8.078 | 9.947 | −1.881 | 1.00 | 36.28 |
| 7464 | O | SER | A | 507 | 7.604 | 9.026 | −2.548 | 1.00 | 35.98 |
| 7465 | N | ARG | A | 508 | 8.411 | 11.124 | −2.399 | 1.00 | 28.69 |
| 7466 | CA | ARG | A | 508 | 8.186 | 11.456 | −3.791 | 1.00 | 30.30 |
| 7467 | CB | ARG | A | 508 | 7.320 | 12.708 | −3.853 | 1.00 | 25.75 |
| 7468 | CG | ARG | A | 508 | 6.835 | 13.082 | −5.231 | 1.00 | 24.27 |
| 7469 | CD | ARG | A | 508 | 5.851 | 14.262 | −5.144 | 1.00 | 43.29 |
| 7470 | NE | ARG | A | 508 | 5.594 | 14.833 | −6.459 | 1.00 | 43.70 |
| 7471 | CZ | ARG | A | 508 | 6.433 | 15.650 | −7.074 | 1.00 | 49.03 |
| 7472 | NH1 | ARC | A | 508 | 7.559 | 15.993 | −6.463 | 1.00 | 47.14 |
| 7473 | NH2 | ARG | A | 508 | 6.177 | 16.071 | −8.311 | 1.00 | 55.31 |
| 7474 | C | ARG | A | 508 | 9.468 | 11.667 | −4.572 | 1.00 | 33.08 |
| 7475 | O | ARC | A | 508 | 10.373 | 12.337 | −4.099 | 1.00 | 36.27 |
| 7476 | N | LEU | A | 509 | 9.532 | 11.084 | −5.770 | 1.00 | 30.30 |
| 7477 | CA | LEU | A | 509 | 10.695 | 11.213 | −6.653 | 1.00 | 18.67 |
| 7478 | CB | LEU | A | 509 | 11.613 | 9.999 | −6.546 | 1.00 | 30.26 |
| 7479 | CG | LEU | A | 509 | 12.819 | 10.057 | −7.495 | 1.00 | 21.03 |
| 7480 | CD1 | LEU | A | 509 | 13.843 | 10.971 | −6.920 | 1.00 | 24.21 |
| 7481 | CD2 | LEU | A | 509 | 13.427 | 8.679 | −7.707 | 1.00 | 32.52 |
| 7482 | C | LEU | A | 509 | 10.310 | 11.378 | −8.120 | 1.00 | 34.43 |
| 7483 | O | LEU | A | 509 | 9.809 | 10.457 | −8.748 | 1.00 | 32.49 |
| 7484 | N | GLU | A | 510 | 10.555 | 12.562 | −8.663 | 1.00 | 37.87 |
| 7485 | CA | GLU | A | 510 | 10.272 | 12.816 | −10.073 | 1.00 | 36.18 |
| 7486 | CB | GLU | A | 510 | 10.147 | 14.326 | −10.325 | 1.00 | 58.29 |
| 7487 | CG | GLU | A | 510 | 9.469 | 15.131 | −9.222 | 1.00 | 80.51 |
| 7488 | CD | GLU | A | 510 | 9.278 | 16.596 | −9.605 | 1.00 | 82.93 |
| 7489 | OE1 | GLU | A | 510 | 8.923 | 17.419 | −8.731 | 1.00 | 79.88 |
| 7490 | OE2 | GLU | A | 510 | 9.481 | 16.925 | −10.789 | 1.00 | 82.54 |
| 7491 | C | GLU | A | 510 | 11.437 | 12.261 | −10.913 | 1.00 | 37.70 |
| 7492 | O | GLU | A | 510 | 12.593 | 12.595 | −10.655 | 1.00 | 34.60 |
| 7493 | N | VAL | A | 511 | 11.133 | 11.417 | −11.900 | 1.00 | 28.55 |
| 7494 | CA | VAL | A | 511 | 12.164 | 10.839 | −12.759 | 1.00 | 36.09 |
| 7495 | CB | VAL | A | 511 | 12.231 | 9.311 | −12.588 | 1.00 | 42.08 |
| 7496 | CG1 | VAL | A | 511 | 12.462 | 8.972 | −11.126 | 1.00 | 29.92 |
| 7497 | CG2 | VAL | A | 511 | 10.968 | 8.675 | −13.073 | 1.00 | 23.00 |
| 7498 | C | VAL | A | 511 | 11.983 | 11.218 | −14.249 | 1.00 | 47.75 |
| 7499 | O | VAL | A | 511 | 10.876 | 11.560 | −14.687 | 1.00 | 39.14 |
| 7500 | N | THR | A | 512 | 13.070 | 11.147 | −15.025 | 1.00 | 55.18 |
| 7501 | CA | THR | A | 512 | 13.042 | 11.556 | −16.441 | 1.00 | 53.05 |
| 7502 | CB | THR | A | 512 | 14.162 | 12.548 | −16.742 | 1.00 | 38.04 |
| 7503 | OG1 | THR | A | 512 | 15.422 | 11.881 | −16.649 | 1.00 | 50.26 |
| 7504 | CG2 | THR | A | 512 | 14.138 | 13.700 | −15.739 | 1.00 | 61.22 |
| 7505 | C | THR | A | 512 | 13.136 | 10.491 | −17.517 | 1.00 | 49.55 |
| 7506 | O | THR | A | 512 | 13.791 | 9.476 | −17.341 | 1.00 | 50.93 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7507 | N | ARG | A | 513 | 12.488 | 10.766 | −18.646 | 1.00 | 55.44 |
| 7508 | CA | ARG | A | 513 | 12.462 | 9.869 | −19.802 | 1.00 | 57.63 |
| 7509 | CB | ARG | A | 513 | 12.227 | 10.672 | −21.080 | 1.00 | 71.02 |
| 7510 | CG | ARG | A | 513 | 11.042 | 10.219 | −21.917 | 1.00 | 84.86 |
| 7511 | CD | ARG | A | 513 | 11.237 | 8.839 | −22.503 | 1.00 | 82.57 |
| 7512 | NE | ARG | A | 513 | 9.986 | 8.320 | −23.046 | 1.00 | 87.45 |
| 7513 | CZ | ARG | A | 513 | 9.822 | 7.078 | −23.487 | 1.00 | 96.00 |
| 7514 | NH1 | ARG | A | 513 | 10.833 | 6.216 | −23.459 | 1.00 | 97.75 |
| 7515 | NH2 | ARG | A | 513 | 8.638 | 6.692 | −23.935 | 1.00 | 91.66 |
| 7516 | C | ARG | A | 513 | 13.740 | 9.073 | −19.972 | 1.00 | 66.05 |
| 7517 | O | ARG | A | 513 | 13.691 | 7.870 | −20.201 | 1.00 | 63.28 |
| 7518 | N | ALA | A | 514 | 14.879 | 9.765 | −19.874 | 1.00 | 68.56 |
| 7519 | CA | ALA | A | 514 | 16.200 | 9.159 | −20.027 | 1.00 | 65.06 |
| 7520 | CB | ALA | A | 514 | 17.262 | 10.075 | −19.436 | 1.00 | 56.17 |
| 7521 | C | ALA | A | 514 | 16.275 | 7.775 | −19.398 | 1.00 | 79.69 |
| 7522 | O | ALA | A | 514 | 16.092 | 6.767 | −20.088 | 1.00 | 80.99 |
| 7523 | N | GLU | A | 515 | 16.539 | 7.721 | −18.093 | 1.00 | 78.09 |
| 7524 | CA | GLU | A | 515 | 16.624 | 6.442 | −17.395 | 1.00 | 59.32 |
| 7525 | CB | GLU | A | 515 | 17.172 | 6.627 | −15.986 | 1.00 | 44.77 |
| 7526 | CG | GLU | A | 515 | 16.352 | 7.554 | −15.109 | 1.00 | 67.21 |
| 7527 | CD | GLU | A | 515 | 16.805 | 8.983 | −15.196 | 1.00 | 73.23 |
| 7528 | OE1 | GLU | A | 515 | 17.013 | 9.441 | −16.333 | 1.00 | 62.38 |
| 7529 | OE2 | GLU | A | 515 | 16.946 | 9.643 | −14.134 | 1.00 | 64.91 |
| 7530 | C | GLU | A | 515 | 15.244 | 5.827 | −17.338 | 1.00 | 59.74 |
| 7531 | O | GLU | A | 515 | 15.115 | 4.623 | −17.239 | 1.00 | 60.30 |
| 7532 | N | TRP | A | 516 | 14.220 | 6.674 | −17.419 | 1.00 | 72.22 |
| 7533 | CA | TRP | A | 516 | 12.809 | 6.270 | −17.406 | 1.00 | 80.61 |
| 7534 | CB | TRP | A | 516 | 11.934 | 7.512 | −17.632 | 1.00 | 89.98 |
| 7535 | CG | TRP | A | 516 | 10.471 | 7.309 | −17.476 | 1.00 | 111.55 |
| 7536 | CD2 | TRP | A | 516 | 9.440 | 7.782 | −18.351 | 1.00 | 118.45 |
| 7537 | CE2 | TRP | A | 516 | 8.203 | 7.401 | −17.785 | 1.00 | 132.31 |
| 7538 | CE3 | TRP | A | 516 | 9.439 | 8.493 | −19.555 | 1.00 | 113.78 |
| 7539 | CD1 | TRP | A | 516 | 9.842 | 6.680 | −16.449 | 1.00 | 123.87 |
| 7540 | NE1 | TRP | A | 516 | 8.478 | 6.729 | −16.624 | 1.00 | 124.82 |
| 7541 | CZ2 | TRP | A | 516 | 6.973 | 7.707 | −18.386 | 1.00 | 127.95 |
| 7542 | CZ3 | TRP | A | 516 | 8.214 | 8.802 | −20.154 | 1.00 | 126.79 |
| 7543 | CH2 | TRP | A | 516 | 7.000 | 8.407 | −19.565 | 1.00 | 125.82 |
| 7544 | C | TRP | A | 516 | 12.572 | 5.250 | −18.519 | 1.00 | 89.33 |
| 7545 | O | TRP | A | 516 | 11.453 | 5.114 | −19.045 | 1.00 | 62.06 |
| 7546 | N | GLU | A | 517 | 13.654 | 4.559 | −18.872 | 1.00 | 81.84 |
| 7547 | CA | GLU | A | 517 | 13.677 | 3.541 | −19.903 | 1.00 | 92.39 |
| 7548 | CB | GLU | A | 517 | 14.353 | 4.100 | −21.159 | 1.00 | 94.37 |
| 7549 | CG | GLU | A | 517 | 13.566 | 5.260 | −21.763 | 1.00 | 108.23 |
| 7550 | CD | GLU | A | 517 | 14.047 | 5.666 | −23.139 | 1.00 | 113.35 |
| 7551 | OE1 | GLU | A | 517 | 15.176 | 6.184 | −23.248 | 1.00 | 119.13 |
| 7552 | OE2 | GLU | A | 517 | 13.290 | 5.468 | −24.112 | 1.00 | 108.81 |
| 7553 | C | GLU | A | 517 | 14.403 | 2.289 | −19.397 | 1.00 | 90.98 |
| 7554 | O | GLU | A | 517 | 14.434 | 1.255 | −20.075 | 1.00 | 87.10 |
| 7555 | N | ALA | A | 518 | 14.985 | 2.403 | −18.202 | 1.00 | 90.00 |
| 7556 | CA | ALA | A | 518 | 15.702 | 1.313 | −17.511 | 1.00 | 83.44 |
| 7557 | CB | ALA | A | 518 | 17.236 | 1.533 | −17.565 | 1.00 | 81.91 |
| 7558 | C | ALA | A | 518 | 15.201 | 1.444 | −16.075 | 1.00 | 78.61 |
| 7559 | O | ALA | A | 518 | 15.973 | 1.771 | −15.161 | 1.00 | 50.61 |
| 7560 | N | LYS | A | 519 | 13.898 | 1.207 | −15.904 | 1.00 | 79.13 |
| 7561 | CA | LYS | A | 519 | 13.225 | 1.345 | −14.615 | 1.00 | 80.94 |
| 7562 | CB | LYS | A | 519 | 11.706 | 1.355 | −14.800 | 1.00 | 82.60 |
| 7563 | CG | LYS | A | 519 | 11.137 | 2.593 | −15.454 | 1.00 | 91.52 |
| 7564 | CD | LYS | A | 519 | 9.708 | 2.824 | −14.971 | 1.00 | 94.73 |
| 7565 | CE | LYS | A | 519 | 8.925 | 3.719 | −15.906 | 1.00 | 85.19 |
| 7566 | NZ | LYS | A | 519 | 7.476 | 3.604 | −15.678 | 1.00 | 75.34 |
| 7567 | C | LYS | A | 519 | 13.570 | 0.321 | −13.554 | 1.00 | 76.55 |
| 7568 | O | LYS | A | 519 | 13.867 | 0.684 | −12.406 | 1.00 | 64.86 |
| 7569 | N | ASP | A | 520 | 13.500 | −0.952 | −13.933 | 1.00 | 65.62 |
| 7570 | CA | ASP | A | 520 | 13.796 | −2.062 | −13.030 | 1.00 | 91.97 |
| 7571 | CB | ASP | A | 520 | 14.342 | −3.246 | −13.839 | 1.00 | 94.70 |
| 7572 | CG | ASP | A | 520 | 13.376 | −3.709 | −14.925 | 1.00 | 105.93 |
| 7573 | OD1 | ASP | A | 520 | 12.305 | −4.258 | −14.578 | 1.00 | 115.16 |
| 7574 | OD2 | ASP | A | 520 | 13.681 | −3.519 | −16.124 | 1.00 | 104.35 |
| 7575 | C | ASP | A | 520 | 14.802 | −1.639 | −11.959 | 1.00 | 87.18 |
| 7576 | O | ASP | A | 520 | 14.961 | −2.300 | −10.927 | 1.00 | 62.77 |
| 7577 | N | GLU | A | 521 | 15.479 | −0.526 | −12.235 | 1.00 | 78.09 |
| 7578 | CA | GLU | A | 521 | 16.467 | 0.043 | −11.345 | 1.00 | 86.91 |
| 7579 | CB | GLU | A | 521 | 17.726 | 0.487 | −12.121 | 1.00 | 90.01 |
| 7580 | CG | GLU | A | 521 | 18.696 | −0.643 | −12.552 | 1.00 | 86.13 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7581 | CD | GLU | A | 521 | 18.488 | -1.132 | -13.998 | 1.00 | 89.45 |
| 7582 | OE1 | GLU | A | 521 | 18.426 | -0.282 | -14.921 | 1.00 | 81.24 |
| 7583 | OE2 | GLU | A | 521 | 18.408 | -2.368 | -14.212 | 1.00 | 75.99 |
| 7584 | C | GLU | A | 521 | 15.925 | 1.214 | -10.534 | 1.00 | 79.77 |
| 7585 | O | GLU | A | 521 | 16.650 | 2.174 | -10.290 | 1.00 | 101.44 |
| 7586 | N | PHE | A | 522 | 14.657 | 1.161 | -10.131 | 1.00 | 56.96 |
| 7587 | CA | PHE | A | 522 | 14.116 | 2.227 | -9.271 | 1.00 | 49.66 |
| 7588 | CB | PHE | A | 522 | 12.893 | 2.884 | -9.906 | 1.00 | 57.80 |
| 7589 | CG | PHE | A | 522 | 13.255 | 3.921 | -10.928 | 1.00 | 63.50 |
| 7590 | CD1 | PHE | A | 522 | 12.910 | 3.760 | -12.278 | 1.00 | 40.15 |
| 7591 | CD2 | PHE | A | 522 | 14.032 | 5.013 | -10.555 | 1.00 | 47.53 |
| 7592 | CE1 | PHE | A | 522 | 13.343 | 4.670 | -13.241 | 1.00 | 43.95 |
| 7593 | CE2 | PHE | A | 522 | 14.475 | 5.933 | -11.508 | 1.00 | 39.52 |
| 7594 | CZ | PHE | A | 522 | 14.130 | 5.761 | -12.859 | 1.00 | 48.11 |
| 7595 | C | PHE | A | 522 | 13.799 | 1.675 | -7.885 | 1.00 | 44.79 |
| 7596 | O | PHE | A | 522 | 12.783 | 1.036 | -7.661 | 1.00 | 42.66 |
| 7597 | N | ILE | A | 523 | 14.699 | 1.926 | -6.953 | 1.00 | 30.95 |
| 7598 | CA | ILE | A | 523 | 14.556 | 1.418 | -5.608 | 1.00 | 19.91 |
| 7599 | CB | ILE | A | 523 | 15.799 | 0.584 | -5.232 | 1.00 | 40.81 |
| 7600 | CG2 | ILE | A | 523 | 15.725 | 0.149 | -3.774 | 1.00 | 40.66 |
| 7601 | CG1 | ILE | A | 523 | 15.925 | -0.607 | -6.178 | 1.00 | 42.46 |
| 7602 | CD1 | ILE | A | 523 | 17.025 | -1.531 | -5.791 | 1.00 | 25.98 |
| 7603 | C | ILE | A | 523 | 14.333 | 2.416 | -4.477 | 1.00 | 31.65 |
| 7604 | O | ILE | A | 523 | 15.083 | 3.381 | -4.292 | 1.00 | 31.06 |
| 7605 | N | CYS | A | 524 | 13.291 | 2.153 | -3.706 | 1.00 | 38.39 |
| 7606 | CA | CYS | A | 524 | 12.984 | 2.966 | -2.546 | 1.00 | 31.78 |
| 7607 | C | CYS | A | 524 | 13.449 | 2.119 | -1.355 | 1.00 | 36.00 |
| 7608 | O | CYS | A | 524 | 12.937 | 1.019 | -1.133 | 1.00 | 39.08 |
| 7609 | CB | CYS | A | 524 | 11.487 | 3.240 | -2.471 | 1.00 | 34.13 |
| 7610 | SG | CYS | A | 524 | 10.971 | 4.038 | -0.922 | 1.00 | 47.41 |
| 7611 | N | ARG | A | 525 | 14.445 | 2.624 | -0.628 | 1.00 | 30.57 |
| 7612 | CA | ARG | A | 525 | 15.007 | 1.934 | 0.525 | 1.00 | 18.57 |
| 7613 | CB | ARG | A | 525 | 16.472 | 1.619 | 0.263 | 1.00 | 39.35 |
| 7614 | CG | ARG | A | 525 | 17.126 | 0.795 | 1.335 | 1.00 | 50.16 |
| 7615 | CD | ARG | A | 525 | 18.457 | 0.289 | 0.866 | 1.00 | 42.43 |
| 7616 | NE | ARG | A | 525 | 19.465 | 1.324 | 0.925 | 1.00 | 67.97 |
| 7617 | CZ | ARG | A | 525 | 20.638 | 1.243 | 0.317 | 1.00 | 73.67 |
| 7618 | NH1 | ARG | A | 525 | 20.938 | 0.164 | -0.404 | 1.00 | 55.98 |
| 7619 | NH2 | ARG | A | 525 | 21.504 | 2.243 | 0.441 | 1.00 | 67.69 |
| 7620 | C | ARG | A | 525 | 14.891 | 2.701 | 1.834 | 1.00 | 30.50 |
| 7621 | O | ARG | A | 525 | 15.245 | 3.874 | 1.940 | 1.00 | 28.83 |
| 7622 | N | ALA | A | 526 | 14.390 | 2.013 | 2.846 | 1.00 | 25.47 |
| 7623 | CA | ALA | A | 526 | 14.234 | 2.624 | 4.154 | 1.00 | 27.44 |
| 7624 | CB | ALA | A | 526 | 12.800 | 2.397 | 4.710 | 1.00 | 22.97 |
| 7625 | C | ALA | A | 526 | 15.259 | 2.042 | 5.120 | 1.00 | 41.86 |
| 7626 | O | ALA | A | 526 | 15.581 | 0.851 | 5.075 | 1.00 | 34.73 |
| 7627 | N | VAL | A | 527 | 15.773 | 2.908 | 5.977 | 1.00 | 22.17 |
| 7628 | CA | VAL | A | 527 | 16.721 | 2.513 | 6.970 | 1.00 | 33.89 |
| 7629 | CB | VAL | A | 527 | 18.011 | 3.363 | 6.866 | 1.00 | 45.57 |
| 7630 | CG1 | VAL | A | 527 | 18.991 | 3.001 | 7.990 | 1.00 | 42.98 |
| 7631 | CG2 | VAL | A | 527 | 18.651 | 3.115 | 5.514 | 1.00 | 32.22 |
| 7632 | C | VAL | A | 527 | 16.051 | 2.693 | 8.327 | 1.00 | 35.36 |
| 7633 | O | VAL | A | 527 | 15.741 | 3.810 | 8.740 | 1.00 | 39.21 |
| 7634 | N | HIS | A | 528 | 15.828 | 1.582 | 9.015 | 1.00 | 26.43 |
| 7635 | CA | HIS | A | 528 | 15.191 | 1.638 | 10.314 | 1.00 | 34.99 |
| 7636 | CB | HIS | A | 528 | 13.680 | 1.407 | 10.135 | 1.00 | 32.76 |
| 7637 | CG | HIS | A | 528 | 12.884 | 1.615 | 11.383 | 1.00 | 42.35 |
| 7638 | CD2 | HIS | A | 528 | 12.249 | 2.712 | 11.857 | 1.00 | 36.95 |
| 7639 | ND1 | HIS | A | 528 | 12.709 | 0.628 | 12.329 | 1.00 | 25.78 |
| 7640 | CE1 | HIS | A | 528 | 11.998 | 1.114 | 13.331 | 1.00 | 50.03 |
| 7641 | NE2 | HIS | A | 528 | 11.705 | 2.376 | 13.070 | 1.00 | 31.55 |
| 7642 | C | HIS | A | 528 | 15.786 | 0.637 | 11.321 | 1.00 | 36.81 |
| 7643 | O | HIS | A | 528 | 16.110 | -0.493 | 10.972 | 1.00 | 33.44 |
| 7644 | N | GLU | A | 529 | 15.913 | 1.078 | 12.566 | 1.00 | 42.71 |
| 7645 | CA | GLU | A | 529 | 16.468 | 0.280 | 13.660 | 1.00 | 44.11 |
| 7646 | CB | GLU | A | 529 | 16.317 | 1.043 | 14.982 | 1.00 | 39.42 |
| 7647 | CG | GLU | A | 529 | 16.564 | 0.216 | 16.208 | 1.00 | 71.11 |
| 7648 | CD | GLU | A | 529 | 16.276 | 0.987 | 17.480 | 1.00 | 91.81 |
| 7649 | OE1 | GLU | A | 529 | 16.371 | 0.392 | 18.586 | 1.00 | 72.57 |
| 7650 | OE2 | GLU | A | 529 | 15.955 | 2.193 | 17.362 | 1.00 | 83.20 |
| 7651 | C | GLU | A | 529 | 15.872 | -1.108 | 13.631 | 1.00 | 49.21 |
| 7652 | O | GLU | A | 529 | 16.525 | -2.008 | 14.339 | 1.00 | 53.15 |
| 7653 | N | ALA | A | 530 | 14.630 | -1.289 | 13.408 | 1.00 | 53.79 |
| 7654 | CA | ALA | A | 530 | 13.975 | -2.579 | 13.566 | 1.00 | 47.94 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7655 | CB | ALA | A | 530 | 12.584 | −2.373 | 14.125 | 1.00 | 41.56 |
| 7656 | C | ALA | A | 530 | 13.902 | −3.460 | 12.331 | 1.00 | 55.21 |
| 7657 | O | ALA | A | 530 | 13.430 | −4.577 | 12.421 | 1.00 | 47.33 |
| 7658 | N | ALA | A | 531 | 14.367 | −2.977 | 11.185 | 1.00 | 63.49 |
| 7659 | CA | ALA | A | 531 | 14.319 | −3.774 | 9.963 | 1.00 | 60.54 |
| 7660 | CB | ALA | A | 531 | 14.634 | −2.901 | 8.767 | 1.00 | 48.75 |
| 7661 | C | ALA | A | 531 | 15.278 | −4.960 | 10.027 | 1.00 | 66.77 |
| 7662 | O | ALA | A | 531 | 15.328 | −5.784 | 9.121 | 1.00 | 77.77 |
| 7663 | N | SER | A | 532 | 16.025 | −5.046 | 11.117 | 1.00 | 77.67 |
| 7664 | CA | SER | A | 532 | 16.985 | −6.127 | 11.323 | 1.00 | 95.48 |
| 7665 | CB | SER | A | 532 | 17.188 | −6.370 | 12.834 | 1.00 | 101.68 |
| 7666 | OG | SER | A | 532 | 15.990 | −6.737 | 13.499 | 1.00 | 97.71 |
| 7667 | C | SER | A | 532 | 16.627 | −7.445 | 10.615 | 1.00 | 88.19 |
| 7668 | O | SER | A | 532 | 15.466 | −7.858 | 10.580 | 1.00 | 87.77 |
| 7669 | N | PRO | A | 533 | 17.635 | −8.112 | 10.023 | 1.00 | 88.00 |
| 7670 | CD | PRO | A | 533 | 17.445 | −9.334 | 9.223 | 1.00 | 92.52 |
| 7671 | CA | PRO | A | 533 | 19.044 | −7.698 | 9.993 | 1.00 | 82.72 |
| 7672 | CB | PRO | A | 533 | 19.744 | −8.950 | 9.512 | 1.00 | 82.73 |
| 7673 | CG | PRO | A | 533 | 18.769 | −9.453 | 8.467 | 1.00 | 82.53 |
| 7674 | C | PRO | A | 533 | 19.236 | −6.547 | 9.021 | 1.00 | 61.34 |
| 7675 | O | PRO | A | 533 | 18.263 | −5.977 | 8.539 | 1.00 | 93.78 |
| 7676 | N | SER | A | 534 | 20.488 | −6.212 | 8.736 | 1.00 | 69.49 |
| 7677 | CA | SER | A | 534 | 20.811 | −5.142 | 7.799 | 1.00 | 62.83 |
| 7678 | CB | SER | A | 534 | 20.361 | −5.541 | 6.389 | 1.00 | 61.59 |
| 7679 | OG | SER | A | 534 | 18.946 | −5.725 | 6.300 | 1.00 | 53.66 |
| 7680 | C | SER | A | 534 | 20.251 | −3.755 | 8.135 | 1.00 | 48.90 |
| 7681 | O | SER | A | 534 | 20.795 | −2.757 | 7.692 | 1.00 | 56.03 |
| 7682 | N | GLN | A | 535 | 19.164 | −3.698 | 8.901 | 1.00 | 43.00 |
| 7683 | CA | GLN | A | 535 | 18.514 | −2.445 | 9.295 | 1.00 | 40.23 |
| 7684 | CB | GLN | A | 535 | 19.492 | −1.517 | 10.040 | 1.00 | 41.64 |
| 7685 | CG | GLN | A | 535 | 20.604 | −2.230 | 10.813 | 1.00 | 53.29 |
| 7686 | CD | GLN | A | 535 | 20.082 | −3.271 | 11.778 | 1.00 | 57.27 |
| 7687 | OE1 | GLN | A | 535 | 20.797 | −4.197 | 12.140 | 1.00 | 58.57 |
| 7688 | NE2 | GLN | A | 535 | 18.831 | −3.125 | 12.200 | 1.00 | 71.74 |
| 7689 | C | GLN | A | 535 | 17.920 | −1.700 | 8.093 | 1.00 | 47.00 |
| 7690 | O | GLN | A | 535 | 17.778 | −0.477 | 8.103 | 1.00 | 45.23 |
| 7691 | N | THR | A | 536 | 17.571 | −2.440 | 7.049 | 1.00 | 41.10 |
| 7692 | CA | THR | A | 536 | 16.976 | −1.818 | 5.880 | 1.00 | 49.30 |
| 7693 | CB | THR | A | 536 | 18.048 | −1.461 | 4.787 | 1.00 | 57.78 |
| 7694 | OG1 | THR | A | 536 | 18.549 | −2.652 | 4.167 | 1.00 | 44.35 |
| 7695 | CG2 | THR | A | 536 | 19.196 | −0.689 | 5.400 | 1.00 | 60.08 |
| 7696 | C | THR | A | 536 | 15.897 | −2.672 | 5.222 | 1.00 | 47.58 |
| 7697 | O | THR | A | 536 | 15.853 | −3.891 | 5.370 | 1.00 | 44.50 |
| 7698 | N | VAL | A | 537 | 15.007 | −1.995 | 4.517 | 1.00 | 29.17 |
| 7699 | CA | VAL | A | 537 | 13.940 | −2.646 | 3.763 | 1.00 | 35.90 |
| 7700 | CB | VAL | A | 537 | 12.561 | −2.580 | 4.478 | 1.00 | 41.15 |
| 7701 | CG1 | VAL | A | 537 | 11.677 | −3.708 | 3.972 | 1.00 | 30.12 |
| 7702 | CG2 | VAL | A | 537 | 12.721 | −2.662 | 5.974 | 1.00 | 34.69 |
| 7703 | C | VAL | A | 537 | 13.857 | −1.851 | 2.457 | 1.00 | 27.47 |
| 7704 | O | VAL | A | 537 | 14.061 | −0.650 | 2.436 | 1.00 | 39.51 |
| 7705 | N | CLN | A | 538 | 13.566 | −2.521 | 1.363 | 1.00 | 25.74 |
| 7706 | CA | GLN | A | 538 | 13.511 | −1.822 | 0.086 | 1.00 | 34.48 |
| 7707 | CB | GLN | A | 538 | 14.913 | −1.699 | −0.474 | 1.00 | 30.38 |
| 7708 | CG | GLN | A | 538 | 15.449 | −3.024 | −0.979 | 1.00 | 24.94 |
| 7709 | CD | GLN | A | 538 | 16.846 | −2.904 | −1.530 | 1.00 | 46.11 |
| 7710 | OE1 | GLN | A | 538 | 17.721 | −2.413 | −0.848 | 1.00 | 30.91 |
| 7711 | NE2 | GLN | A | 538 | 17.059 | −3.349 | −2.771 | 1.00 | 22.16 |
| 7712 | C | GLN | A | 538 | 12.633 | −2.498 | −0.948 | 1.00 | 28.23 |
| 7713 | O | GLN | A | 538 | 12.483 | −3.705 | −0.949 | 1.00 | 33.57 |
| 7714 | N | ARG | A | 539 | 12.065 | −1.701 | −1.840 | 1.00 | 33.66 |
| 7715 | CA | ARG | A | 539 | 11.194 | −2.227 | −2.880 | 1.00 | 36.42 |
| 7716 | CB | ARG | A | 539 | 9.722 | −1.957 | −2.527 | 1.00 | 32.62 |
| 7717 | CG | ARG | A | 539 | 8.756 | −3.004 | −3.058 | 1.00 | 64.59 |
| 7718 | CD | ARG | A | 539 | 8.220 | −3.892 | −1.930 | 1.00 | 99.15 |
| 7719 | NE | ARG | A | 539 | 9.276 | −4.534 | −1.145 | 1.00 | 106.67 |
| 7720 | CZ | ARG | A | 539 | 9.051 | −5.300 | −0.079 | 1.00 | 102.90 |
| 7721 | NH1 | ARG | A | 539 | 7.812 | −5.524 | 0.333 | 1.00 | 113.57 |
| 7722 | NH2 | ARG | A | 539 | 10.061 | −5.838 | 0.582 | 1.00 | 96.32 |
| 7723 | C | ARG | A | 539 | 11.567 | −1.556 | −4.194 | 1.00 | 31.53 |
| 7724 | O | ARG | A | 539 | 11.924 | −0.381 | −4.225 | 1.00 | 39.29 |
| 7725 | N | ALA | A | 540 | 11.517 | −2.318 | −5.276 | 1.00 | 27.13 |
| 7726 | CA | ALA | A | 540 | 11.812 | −1.800 | −6.613 | 1.00 | 29.07 |
| 7727 | CB | ALA | A | 540 | 12.590 | −2.817 | −7.402 | 1.00 | 18.08 |
| 7728 | C | ALA | A | 540 | 10.507 | −1.476 | −7.353 | 1.00 | 37.25 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7729 | O | ALA | A | 540 | 9.474 | -2.129 | -7.137 | 1.00 | 32.16 |
| 7730 | N | VAL | A | 541 | 10.566 | -0.461 | -8.211 | 1.00 | 45.41 |
| 7731 | CA | VAL | A | 541 | 9.426 | -0.042 | -9.017 | 1.00 | 42.02 |
| 7732 | CB | VAL | A | 541 | 9.039 | 1.409 | -8.794 | 1.00 | 43.03 |
| 7733 | CG1 | VAL | A | 541 | 7.552 | 1.565 | -8.980 | 1.00 | 30.36 |
| 7734 | CG2 | VAL | A | 541 | 9.510 | 1.874 | -7.460 | 1.00 | 55.85 |
| 7735 | C | VAL | A | 541 | 9.792 | -0.172 | -10.490 | 1.00 | 64.37 |
| 7736 | O | VAL | A | 541 | 10.818 | 0.357 | -10.951 | 1.00 | 37.95 |
| 7737 | N | SER | A | 542 | 8.912 | -0.854 | -11.213 | 1.00 | 77.79 |
| 7738 | CA | SER | A | 542 | 9.051 | -1.158 | -12.634 | 1.00 | 93.05 |
| 7739 | CB | SER | A | 542 | 8.203 | -2.399 | -12.935 | 1.00 | 96.55 |
| 7740 | QG | SER | A | 542 | 6.937 | -2.326 | -12.279 | 1.00 | 88.99 |
| 7741 | C | SER | A | 542 | 8.721 | -0.070 | -13.662 | 1.00 | 92.88 |
| 7742 | O | SER | A | 542 | 8.394 | 1.071 | -13.325 | 1.00 | 71.52 |
| 7743 | N | VAL | A | 543 | 8.802 | -0.479 | -14.930 | 1.00 | 110.97 |
| 7744 | CA | VAL | A | 543 | 8.536 | 0.365 | -16.098 | 1.00 | 111.52 |
| 7745 | CB | VAL | A | 543 | 9.150 | -0.244 | -17.386 | 1.00 | 112.44 |
| 7746 | CG1 | VAL | A | 543 | 8.776 | 0.598 | -18.594 | 1.00 | 109.64 |
| 7747 | CG2 | VAL | A | 543 | 10.660 | -0.327 | -17.257 | 1.00 | 106.31 |
| 7748 | C | VAL | A | 543 | 7.046 | 0.591 | -16.336 | 1.00 | 101.00 |
| 7749 | O | VAL | A | 543 | 6.453 | -0.134 | -17.166 | 1.00 | 90.71 |
| 7750 | OXT | VAL | A | 543 | 6.490 | 1.487 | -15.677 | 1.00 | 88.48 |
| 7751 | CB | VAL | B | 336 | 0.571 | 34.065 | 24.483 | 1.00 | 99.33 |
| 7752 | CG1 | VAL | B | 336 | -0.500 | 35.040 | 24.012 | 1.00 | 82.86 |
| 7753 | CG2 | VAL | B | 336 | 0.427 | 33.743 | 25.967 | 1.00 | 100.15 |
| 7754 | C | VAL | B | 335 | 0.696 | 33.140 | 22.198 | 1.00 | 99.99 |
| 7755 | O | VAL | B | 336 | 1.438 | 34.073 | 21.876 | 1.00 | 95.14 |
| 7756 | N | VAL | B | 336 | 1.504 | 31.774 | 24.113 | 1.00 | 96.83 |
| 7757 | CA | VAL | B | 336 | 0.489 | 32.775 | 23.660 | 1.00 | 100.73 |
| 7758 | N | SER | B | 337 | 0.034 | 32.392 | 21.321 | 1.00 | 96.88 |
| 7759 | CA | SER | B | 337 | 0.127 | 32.607 | 19.882 | 1.00 | 90.10 |
| 7760 | CB | SER | B | 337 | 0.952 | 31.484 | 19.237 | 1.00 | 84.51 |
| 7761 | OG | SER | B | 337 | 0.394 | 30.209 | 19.511 | 1.00 | 93.78 |
| 7762 | C | SER | B | 337 | -1.269 | 32.662 | 19.255 | 1.00 | 89.87 |
| 7763 | O | SER | B | 337 | -2.258 | 32.249 | 19.872 | 1.00 | 76.75 |
| 7764 | N | ALA | B | 338 | -1.345 | 33.175 | 18.030 | 1.00 | 88.27 |
| 7765 | CA | ALA | B | 338 | -2.621 | 33.282 | 17.337 | 1.00 | 79.71 |
| 7766 | CB | ALA | B | 338 | -3.189 | 34.685 | 17.530 | 1.00 | 84.93 |
| 7767 | C | ALA | B | 338 | -2.511 | 32.953 | 15.846 | 1.00 | 77.82 |
| 7768 | O | ALA | B | 338 | -1.700 | 33.547 | 15.130 | 1.00 | 79.41 |
| 7769 | N | TYR | B | 339 | -3.331 | 32.001 | 15.391 | 1.00 | 82.68 |
| 7770 | CA | TYR | B | 339 | -3.356 | 31.578 | 13.985 | 1.00 | 80.02 |
| 7771 | CB | TYR | B | 339 | -3.134 | 30.069 | 13.855 | 1.00 | 70.64 |
| 7772 | CG | TYR | B | 339 | -1.888 | 29.515 | 14.499 | 1.00 | 92.81 |
| 7773 | CD1 | TYR | B | 339 | -1.536 | 29.859 | 15.803 | 1.00 | 92.18 |
| 7774 | CE1 | TYR | B | 339 | -0.453 | 29.264 | 16.439 | 1.00 | 94.00 |
| 7775 | CD2 | TYR | B | 339 | -1.113 | 28.559 | 13.838 | 1.00 | 115.23 |
| 7776 | CE2 | TYR | B | 339 | -0.025 | 27.953 | 14.466 | 1.00 | 120.08 |
| 7777 | CZ | TYR | B | 339 | 0.295 | 28.311 | 15.771 | 1.00 | 110.56 |
| 7778 | OH | TYR | B | 339 | 1.341 | 27.698 | 16.421 | 1.00 | 116.97 |
| 7779 | C | TYR | B | 339 | -4.715 | 31.906 | 13.355 | 1.00 | 75.07 |
| 7780 | O | TYR | B | 339 | -5.743 | 31.919 | 14.037 | 1.00 | 63.09 |
| 7781 | N | LEU | B | 340 | -4.716 | 32.147 | 12.048 | 1.00 | 72.85 |
| 7782 | CA | LEU | B | 340 | -5.942 | 32.463 | 11.322 | 1.00 | 45.88 |
| 7783 | CB | LEU | B | 340 | -5.978 | 33.952 | 10.971 | 1.00 | 60.56 |
| 7784 | CG | LEU | B | 340 | -7.299 | 34.472 | 10.415 | 1.00 | 68.85 |
| 7785 | CD1 | LEU | B | 340 | -8.394 | 34.241 | 11.446 | 1.00 | 48.75 |
| 7786 | CD2 | LEU | B | 340 | -7.176 | 35.934 | 10.063 | 1.00 | 47.35 |
| 7787 | C | LEU | B | 340 | -5.951 | 31.641 | 10.050 | 1.00 | 39.92 |
| 7788 | O | LEU | B | 340 | -5.122 | 31.858 | 9.181 | 1.00 | 46.63 |
| 7789 | N | SER | B | 341 | -6.899 | 30.716 | 9.927 | 1.00 | 41.33 |
| 7790 | CA | SER | B | 341 | -6.951 | 29.852 | 8.754 | 1.00 | 63.05 |
| 7791 | CB | SER | B | 341 | -7.335 | 28.426 | 9.163 | 1.00 | 76.17 |
| 7792 | OG | SER | B | 341 | -8.678 | 28.369 | 9.623 | 1.00 | 92.91 |
| 7793 | C | SER | B | 341 | -7.911 | 30.343 | 7.692 | 1.00 | 61.68 |
| 7794 | O | SER | B | 341 | -8.693 | 31.257 | 7.925 | 1.00 | 75.53 |
| 7795 | N | ARG | B | 342 | -7.832 | 29.727 | 6.516 | 1.00 | 57.26 |
| 7796 | CA | ARG | B | 342 | -8.701 | 30.045 | 5.389 | 1.00 | 37.11 |
| 7797 | CB | ARG | B | 342 | -7.891 | 30.059 | 4.097 | 1.00 | 53.81 |
| 7798 | CG | ARG | B | 342 | -6.902 | 31.203 | 3.986 | 1.00 | 20.59 |
| 7799 | CD | ARG | B | 342 | -6.249 | 31.199 | 2.629 | 1.00 | 33.50 |
| 7800 | NE | ARG | B | 342 | -5.374 | 30.045 | 2.448 | 1.00 | 67.73 |
| 7801 | CZ | ARG | B | 342 | -4.153 | 29.941 | 2.968 | 1.00 | 77.54 |
| 7802 | NH1 | ARG | B | 342 | -3.652 | 30.927 | 3.702 | 1.00 | 42.62 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7803 | NH2 | ARG | B | 342 | −3.436 | 28.847 | 2.758 | 1.00 | 54.98 |
| 7804 | C | ARG | B | 342 | −9.798 | 28.987 | 5.279 | 1.00 | 56.31 |
| 7805 | O | ARG | B | 342 | −9.796 | 27.985 | 6.002 | 1.00 | 61.39 |
| 7806 | N | PRO | B | 343 | −10.760 | 29.197 | 4.376 | 1.00 | 60.92 |
| 7807 | CD | PRO | B | 343 | −11.023 | 30.407 | 3.579 | 1.00 | 52.16 |
| 7808 | CA | PRO | B | 343 | −11.836 | 28.215 | 4.217 | 1.00 | 45.50 |
| 7809 | CB | PRO | B | 343 | −12.830 | 28.924 | 3.291 | 1.00 | 57.36 |
| 7810 | CG | PRO | B | 343 | −12.518 | 30.377 | 3.450 | 1.00 | 69.47 |
| 7811 | C | PRO | B | 343 | −11.251 | 26.999 | 3.533 | 1.00 | 18.51 |
| 7812 | O | PRO | B | 343 | −10.307 | 27.118 | 2.776 | 1.00 | 46.20 |
| 7813 | N | SER | B | 344 | −11.793 | 25.824 | 3.788 | 1.00 | 36.64 |
| 7814 | CA | SER | B | 344 | −11.303 | 24.655 | 3.080 | 1.00 | 11.57 |
| 7815 | CB | SER | B | 344 | −11.773 | 23.390 | 3.763 | 1.00 | 31.55 |
| 7816 | OG | SER | B | 344 | −13.173 | 23.403 | 3.895 | 1.00 | 29.68 |
| 7817 | C | SER | B | 344 | −11.926 | 24.726 | 1.675 | 1.00 | 41.09 |
| 7818 | O | SER | B | 344 | −12.949 | 25.388 | 1.446 | 1.00 | 17.90 |
| 7819 | N | PRO | B | 345 | −11.281 | 24.103 | 0.694 | 1.00 | 39.33 |
| 7820 | CD | PRO | B | 345 | −9.843 | 23.807 | 0.571 | 1.00 | 29.72 |
| 7821 | CA | PRO | B | 345 | −11.916 | 24.181 | −0.621 | 1.00 | 38.41 |
| 7822 | CB | PRO | B | 345 | −10.946 | 23.407 | −1.499 | 1.00 | 55.32 |
| 7823 | CG | PRO | B | 345 | −9.627 | 23.837 | −0.936 | 1.00 | 46.75 |
| 7824 | C | PRO | B | 345 | −13.306 | 23.547 | −0.566 | 1.00 | 28.80 |
| 7825 | O | PRO | B | 345 | −14.240 | 24.038 | −1.168 | 1.00 | 34.43 |
| 7826 | N | PHE | B | 346 | −13.426 | 22.463 | 0.186 | 1.00 | 24.50 |
| 7827 | CA | PHE | B | 346 | −14.675 | 21.741 | 0.340 | 1.00 | 39.53 |
| 7828 | CB | PHE | B | 346 | −14.477 | 20.581 | 1.321 | 1.00 | 45.16 |
| 7829 | CG | PHE | B | 346 | −15.721 | 19.794 | 1.594 | 1.00 | 39.81 |
| 7830 | CD1 | PHE | B | 346 | −16.388 | 19.138 | 0.561 | 1.00 | 51.28 |
| 7831 | CD2 | PHE | B | 346 | −16.230 | 19.705 | 2.884 | 1.00 | 55.01 |
| 7832 | CE1 | PHE | B | 346 | −17.550 | 18.404 | 0.816 | 1.00 | 39.76 |
| 7833 | CE2 | PHE | B | 346 | −17.393 | 18.972 | 3.150 | 1.00 | 58.89 |
| 7834 | CZ | PHE | B | 346 | −18.049 | 18.323 | 2.112 | 1.00 | 42.14 |
| 7835 | C | PHE | B | 346 | −15.772 | 22.666 | 0.836 | 1.00 | 36.27 |
| 7836 | O | PHE | B | 346 | −16.757 | 22.892 | 0.147 | 1.00 | 47.27 |
| 7837 | N | ASP | B | 347 | −15.594 | 23.190 | 2.042 | 1.00 | 58.35 |
| 7838 | CA | ASP | B | 347 | −16.549 | 24.117 | 2.638 | 1.00 | 57.62 |
| 7839 | CB | ASP | B | 347 | −15.943 | 24.761 | 3.882 | 1.00 | 76.37 |
| 7840 | CG | ASP | B | 347 | −16.066 | 23.889 | 5.109 | 1.00 | 61.33 |
| 7841 | OD1 | ASP | B | 347 | −15.453 | 24.241 | 6.143 | 1.00 | 84.58 |
| 7842 | OD2 | ASP | B | 347 | −16.779 | 22.864 | 5.037 | 1.00 | 55.08 |
| 7843 | C | ASP | B | 347 | −16.897 | 25.208 | 1.641 | 1.00 | 53.73 |
| 7844 | O | ASP | B | 347 | −18.062 | 25.489 | 1.372 | 1.00 | 88.97 |
| 7845 | N | LEU | B | 348 | −15.863 | 25.818 | 1.094 | 1.00 | 45.95 |
| 7846 | CA | LEU | B | 348 | −16.028 | 26.876 | 0.117 | 1.00 | 63.55 |
| 7847 | CB | LEU | B | 348 | −14.645 | 27.447 | −0.256 | 1.00 | 63.87 |
| 7848 | CG | LEU | B | 348 | −14.535 | 28.560 | −1.310 | 1.00 | 53.30 |
| 7849 | CD1 | LEU | B | 348 | −15.484 | 29.675 | −0.953 | 1.00 | 74.79 |
| 7850 | CD2 | LEU | B | 348 | −13.116 | 29.091 | −1.387 | 1.00 | 35.08 |
| 7851 | C | LEU | B | 348 | −16.786 | 26.486 | −1.164 | 1.00 | 66.00 |
| 7852 | O | LEU | B | 348 | −17.781 | 27.127 | −1.513 | 1.00 | 66.26 |
| 7853 | N | PHE | B | 349 | −16.333 | 25.432 | −1.844 | 1.00 | 63.72 |
| 7854 | CA | PHE | B | 349 | −16.921 | 25.028 | −3.124 | 1.00 | 48.47 |
| 7855 | CB | PHE | B | 349 | −15.812 | 24.615 | −4.088 | 1.00 | 43.25 |
| 7856 | CG | PHE | B | 349 | −14.818 | 25.697 | −4.365 | 1.00 | 54.43 |
| 7857 | CD1 | PHE | B | 349 | −13.499 | 25.569 | −3.954 | 1.00 | 52.21 |
| 7858 | CD2 | PHE | B | 349 | −15.185 | 26.825 | −5.076 | 1.00 | 41.36 |
| 7859 | CE1 | PHE | B | 349 | −12.566 | 26.544 | −4.257 | 1.00 | 51.40 |
| 7860 | CE2 | PHE | B | 349 | −14.252 | 27.812 | −5.386 | 1.00 | 44.15 |
| 7861 | CZ | PHE | B | 349 | −12.945 | 27.671 | −4.980 | 1.00 | 42.96 |
| 7862 | C | PHE | B | 349 | −18.016 | 23.984 | −3.239 | 1.00 | 48.27 |
| 7863 | O | PHE | B | 349 | −18.757 | 24.013 | −4.218 | 1.00 | 69.00 |
| 7864 | N | ILE | B | 350 | −18.133 | 23.058 | −2.296 | 1.00 | 28.27 |
| 7865 | CA | ILE | B | 350 | −19.167 | 22.025 | −2.426 | 1.00 | 58.41 |
| 7866 | CB | ILE | B | 350 | −18.581 | 20.602 | −2.241 | 1.00 | 47.01 |
| 7867 | CG2 | ILE | B | 350 | −19.559 | 19.569 | −2.785 | 1.00 | 42.41 |
| 7868 | CG1 | ILE | B | 350 | −17.249 | 20.489 | −2.982 | 1.00 | 46.42 |
| 7869 | CD1 | ILE | B | 350 | −17.296 | 21.034 | −4.419 | 1.00 | 31.03 |
| 7870 | C | ILE | B | 350 | −20.318 | 22.200 | −1.448 | 1.00 | 69.29 |
| 7871 | O | ILE | B | 350 | −21.479 | 21.923 | −1.762 | 1.00 | 61.84 |
| 7872 | N | ARG | B | 351 | −19.972 | 22.651 | −0.252 | 1.00 | 67.32 |
| 7873 | CA | ARG | B | 351 | −20.931 | 22.895 | 0.805 | 1.00 | 45.53 |
| 7874 | CB | ARG | B | 351 | −20.208 | 22.733 | 2.151 | 1.00 | 49.16 |
| 7875 | CG | ARG | B | 351 | −21.099 | 22.382 | 3.329 | 1.00 | 64.14 |
| 7876 | CD | ARG | B | 351 | −20.516 | 21.212 | 4.118 | 1.00 | 79.75 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7877 | NE | ARG | B | 351 | −21.222 | 20.984 | 5.378 | 1.00 | 81.32 |
| 7878 | CZ | ARG | B | 351 | −20.965 | 21.631 | 6.512 | 1.00 | 83.13 |
| 7879 | NH1 | ARG | B | 351 | −20.008 | 22.549 | 6.559 | 1.00 | 84.78 |
| 7880 | NH2 | ARG | B | 351 | −21.682 | 21.377 | 7.600 | 1.00 | 86.80 |
| 7881 | C | ARG | B | 351 | −21.456 | 24.336 | 0.589 | 1.00 | 54.49 |
| 7882 | O | ARG | B | 351 | −22.603 | 24.659 | 0.925 | 1.00 | 25.61 |
| 7883 | N | LYS | B | 352 | −20.606 | 25.182 | 0.000 | 1.00 | 43.89 |
| 7884 | CA | LYS | B | 352 | −20.939 | 26.572 | −0.297 | 1.00 | 40.18 |
| 7885 | CB | LYS | B | 352 | −22.159 | 26.626 | −1.206 | 1.00 | 55.57 |
| 7886 | CG | LYS | B | 352 | −21.824 | 26.289 | −2.658 | 1.00 | 76.26 |
| 7887 | CD | LYS | B | 352 | −23.003 | 26.519 | −3.582 | 1.00 | 76.83 |
| 7888 | CE | LYS | B | 352 | −22.655 | 26.112 | −4.990 | 1.00 | 86.41 |
| 7889 | NZ | LYS | B | 352 | −22.304 | 24.667 | −5.025 | 1.00 | 95.23 |
| 7890 | C | LYS | B | 352 | −21.152 | 27.509 | 0.884 | 1.00 | 61.57 |
| 7891 | O | LYS | B | 352 | −21.735 | 28.576 | 0.731 | 1.00 | 55.31 |
| 7892 | N | SER | B | 353 | −20.657 | 27.116 | 2.054 | 1.00 | 68.48 |
| 7893 | CA | SER | B | 353 | −20.782 | 27.911 | 3.268 | 1.00 | 63.96 |
| 7894 | CB | SER | B | 353 | −21.887 | 27.324 | 4.155 | 1.00 | 45.74 |
| 7895 | OG | SER | B | 353 | −21.631 | 25.963 | 4.422 | 1.00 | 89.38 |
| 7896 | C | SER | B | 353 | −19.424 | 27.922 | 3.988 | 1.00 | 48.95 |
| 7897 | O | SER | B | 353 | −19.153 | 27.125 | 4.878 | 1.00 | 55.64 |
| 7898 | N | PRO | B | 354 | −18.548 | 28.840 | 3.595 | 1.00 | 50.17 |
| 7899 | CD | PRO | B | 354 | −18.652 | 29.686 | 2.401 | 1.00 | 54.36 |
| 7900 | CA | PRO | B | 354 | −17.220 | 28.953 | 4.192 | 1.00 | 60.06 |
| 7901 | CB | PRO | B | 354 | −16.470 | 29.833 | 3.189 | 1.00 | 61.65 |
| 7902 | CG | PRO | B | 354 | −17.247 | 29.674 | 1.914 | 1.00 | 57.64 |
| 7903 | C | PRO | B | 354 | −17.148 | 29.532 | 5.604 | 1.00 | 49.68 |
| 7904 | O | PRO | B | 354 | −18.046 | 30.231 | 6.067 | 1.00 | 52.39 |
| 7905 | N | THR | B | 355 | −16.048 | 29.222 | 6.276 | 1.00 | 49.93 |
| 7906 | CA | THR | B | 355 | −15.765 | 29.722 | 7.619 | 1.00 | 54.21 |
| 7907 | CB | THR | B | 355 | −16.303 | 28.784 | 8.763 | 1.00 | 39.64 |
| 7908 | OG1 | THR | B | 355 | −15.899 | 27.438 | 8.530 | 1.00 | 53.04 |
| 7909 | CG2 | THR | B | 355 | −17.817 | 28.847 | 8.855 | 1.00 | 56.66 |
| 7910 | C | THR | B | 355 | −14.250 | 29.865 | 7.782 | 1.00 | 36.12 |
| 7911 | O | THR | B | 355 | −13.471 | 29.236 | 7.065 | 1.00 | 52.27 |
| 7912 | N | ILE | B | 356 | −13.842 | 30.731 | 8.698 | 1.00 | 35.56 |
| 7913 | CA | ILE | B | 356 | −12.426 | 30.923 | 8.988 | 1.00 | 43.48 |
| 7914 | CB | ILE | B | 356 | −11.912 | 32.306 | 8.523 | 1.00 | 38.65 |
| 7915 | CG2 | ILE | B | 356 | −11.884 | 32.359 | 7.001 | 1.00 | 29.77 |
| 7916 | CG1 | ILE | B | 356 | −12.793 | 33.419 | 9.089 | 1.00 | 59.41 |
| 7917 | CD1 | ILE | B | 356 | −12.426 | 34.793 | 8.595 | 1.00 | 39.09 |
| 7918 | C | ILE | B | 356 | −12.352 | 30.803 | 10.497 | 1.00 | 59.92 |
| 7919 | O | ILE | B | 356 | −13.318 | 31.139 | 11.197 | 1.00 | 57.76 |
| 7920 | N | THR | B | 357 | −11.232 | 30.305 | 11.006 | 1.00 | 60.33 |
| 7921 | CA | THR | B | 357 | −11.101 | 30.116 | 12.445 | 1.00 | 57.82 |
| 7922 | CB | THR | B | 357 | −11.029 | 28.607 | 12.798 | 1.00 | 60.86 |
| 7923 | OG1 | THR | B | 357 | −12.144 | 27.928 | 12.208 | 1.00 | 77.83 |
| 7924 | CG2 | THR | B | 357 | −11.048 | 28.399 | 14.307 | 1.00 | 37.98 |
| 7925 | C | THR | B | 357 | −9.884 | 30.795 | 13.040 | 1.00 | 45.28 |
| 7926 | O | THR | B | 357 | −8.756 | 30.487 | 12.658 | 1.00 | 52.84 |
| 7927 | N | CYS | B | 358 | −10.122 | 31.709 | 13.977 | 1.00 | 36.01 |
| 7928 | CA | CYS | B | 358 | −9.036 | 32.397 | 14.675 | 1.00 | 52.93 |
| 7929 | C | CYS | B | 358 | −8.761 | 31.503 | 15.875 | 1.00 | 68.31 |
| 7930 | O | CYS | B | 358 | −9.626 | 31.332 | 16.735 | 1.00 | 66.15 |
| 7931 | CB | CYS | B | 358 | −9.484 | 33.783 | 15.163 | 1.00 | 83.93 |
| 7932 | SG | CYS | B | 358 | −8.150 | 34.899 | 15.733 | 1.00 | 67.59 |
| 7933 | N | LEU | B | 359 | −7.564 | 30.928 | 15.921 | 1.00 | 66.86 |
| 7934 | CA | LEU | B | 359 | −7.183 | 30.021 | 16.997 | 1.00 | 66.88 |
| 7935 | CB | LEU | B | 359 | −6.731 | 28.685 | 16.395 | 1.00 | 68.38 |
| 7936 | CG | LEU | B | 359 | −5.961 | 27.713 | 17.295 | 1.00 | 78.91 |
| 7937 | CD1 | LEU | B | 359 | −6.868 | 27.170 | 18.397 | 1.00 | 61.66 |
| 7938 | CD2 | LEU | B | 359 | −5.421 | 26.576 | 16.453 | 1.00 | 86.83 |
| 7939 | C | LEU | B | 359 | −6.081 | 30.569 | 17.900 | 1.00 | 76.91 |
| 7940 | O | LEU | B | 359 | −4.927 | 30.694 | 17.479 | 1.00 | 83.78 |
| 7941 | N | VAL | B | 360 | −6.437 | 30.882 | 19.145 | 1.00 | 79.46 |
| 7942 | CA | VAL | B | 360 | −5.463 | 31.391 | 20.111 | 1.00 | 90.42 |
| 7943 | CB | VAL | B | 360 | −6.075 | 32.479 | 21.009 | 1.00 | 83.66 |
| 7944 | CG1 | VAL | B | 360 | −4.999 | 33.056 | 21.914 | 1.00 | 76.91 |
| 7945 | CG2 | VAL | B | 360 | −6.709 | 33.565 | 20.157 | 1.00 | 78.58 |
| 7946 | C | VAL | B | 360 | −4.950 | 30.263 | 21.013 | 1.00 | 87.53 |
| 7947 | O | VAL | B | 360 | −5.738 | 29.578 | 21.670 | 1.00 | 62.36 |
| 7948 | N | VAL | B | 361 | −3.632 | 30.075 | 21.040 | 1.00 | 85.23 |
| 7949 | CA | VAL | B | 361 | −3.027 | 29.029 | 21.861 | 1.00 | 93.88 |
| 7950 | CB | VAL | B | 361 | −2.108 | 28.118 | 21.010 | 1.00 | 77.61 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 7951 | CG1 | VAL | B | 361 | -1.502 | 27.025 | 21.876 | 1.00 | 75.42 |
| 7952 | CG2 | VAL | B | 361 | -2.904 | 27.509 | 19.876 | 1.00 | 82.46 |
| 7953 | C | VAL | B | 361 | -2.222 | 29.592 | 23.035 | 1.00 | 96.91 |
| 7954 | O | VAL | B | 361 | -1.229 | 30.291 | 22.843 | 1.00 | 96.34 |
| 7955 | N | ASP | B | 362 | -2.660 | 29.279 | 24.251 | 1.00 | 101.75 |
| 7956 | CA | ASP | B | 362 | -1.986 | 29.742 | 25.461 | 1.00 | 115.06 |
| 7957 | CB | ASP | B | 362 | -2.900 | 30.692 | 26.243 | 1.00 | 117.05 |
| 7958 | CG | ASP | B | 362 | -2.145 | 31.513 | 27.268 | 1.00 | 114.74 |
| 7959 | OD1 | ASP | B | 362 | -1.364 | 30.929 | 28.046 | 1.00 | 125.23 |
| 7960 | OD2 | ASP | B | 362 | -2.336 | 32.745 | 27.299 | 1.00 | 95.60 |
| 7961 | C | ASP | B | 362 | -1.615 | 28.546 | 26.344 | 1.00 | 122.47 |
| 7962 | O | ASP | B | 362 | -2.496 | 27.822 | 26.815 | 1.00 | 130.06 |
| 7963 | N | LEU | B | 363 | -0.318 | 28.341 | 26.567 | 1.00 | 125.37 |
| 7964 | CA | LEU | B | 363 | 0.150 | 27.224 | 27.391 | 1.00 | 126.16 |
| 7965 | CB | LEU | B | 363 | 1.581 | 26.841 | 26.995 | 1.00 | 118.16 |
| 7966 | CG | LEU | B | 363 | 1.796 | 26.275 | 25.588 | 1.00 | 123.59 |
| 7967 | CD1 | LEU | B | 363 | 3.286 | 26.128 | 25.328 | 1.00 | 122.61 |
| 7968 | CD2 | LEU | B | 363 | 1.090 | 24.931 | 25.445 | 1.00 | 124.19 |
| 7969 | C | LEU | B | 363 | 0.092 | 27.514 | 28.899 | 1.00 | 132.82 |
| 7970 | O | LEU | B | 363 | 0.252 | 26.604 | 29.717 | 1.00 | 132.37 |
| 7971 | N | ALA | B | 364 | -0.140 | 28.775 | 29.261 | 1.00 | 134.07 |
| 7972 | CA | ALA | B | 364 | -0.224 | 29.177 | 30.666 | 1.00 | 131.46 |
| 7973 | CB | ALA | B | 364 | 0.911 | 30.145 | 31.000 | 1.00 | 132.78 |
| 7974 | C | ALA | B | 364 | -1.575 | 29.824 | 30.982 | 1.00 | 131.92 |
| 7975 | O | ALA | B | 364 | -1.698 | 31.051 | 31.013 | 1.00 | 123.56 |
| 7976 | N | PRO | B | 365 | -2.608 | 28.998 | 31.231 | 1.00 | 136.40 |
| 7977 | CD | PRO | B | 365 | -2.563 | 27.523 | 31.189 | 1.00 | 141.11 |
| 7978 | CA | PRO | B | 365 | -3.964 | 29.461 | 31.546 | 1.00 | 138.63 |
| 7979 | CB | PRO | B | 365 | -4.686 | 28.168 | 31.926 | 1.00 | 135.10 |
| 7980 | CG | PRO | B | 365 | -4.029 | 27.156 | 31.044 | 1.00 | 139.44 |
| 7981 | C | PRO | B | 365 | -4.051 | 30.519 | 32.650 | 1.00 | 140.40 |
| 7982 | O | PRO | B | 365 | -4.226 | 30.188 | 33.825 | 1.00 | 142.74 |
| 7983 | N | SER | B | 366 | -3.930 | 31.788 | 32.267 | 1.00 | 138.41 |
| 7984 | CA | SER | B | 366 | -4.017 | 32.892 | 33.221 | 1.00 | 138.39 |
| 7985 | CB | SER | B | 366 | -2.994 | 33.982 | 32.873 | 1.00 | 135.85 |
| 7986 | OG | SER | B | 366 | -3.166 | 34.457 | 31.548 | 1.00 | 134.58 |
| 7987 | C | SER | B | 366 | -5.435 | 33.469 | 33.192 | 1.00 | 142.53 |
| 7988 | O | SER | B | 366 | -5.982 | 33.739 | 32.122 | 1.00 | 149.05 |
| 7989 | N | LYS | B | 367 | -6.027 | 33.654 | 34.368 | 1.00 | 139.13 |
| 7990 | CA | LYS | B | 367 | -7.385 | 34.180 | 34.467 | 1.00 | 132.30 |
| 7991 | CB | LYS | B | 367 | -7.817 | 34.233 | 35.934 | 1.00 | 133.18 |
| 7992 | CG | LYS | B | 367 | -7.749 | 32.881 | 36.630 | 1.00 | 136.25 |
| 7993 | CD | LYS | B | 367 | -8.367 | 32.920 | 38.019 | 1.00 | 135.04 |
| 7994 | CE | LYS | B | 367 | -9.863 | 33.189 | 37.949 | 1.00 | 134.10 |
| 7995 | NZ | LYS | B | 367 | -10.498 | 33.146 | 39.292 | 1.00 | 136.62 |
| 7996 | C | LYS | B | 367 | -7.562 | 35.552 | 33.821 | 1.00 | 130.84 |
| 7997 | O | LYS | B | 367 | -6.663 | 36.398 | 33.857 | 1.00 | 132.74 |
| 7998 | N | GLY | B | 368 | -8.738 | 35.754 | 33.231 | 1.00 | 132.34 |
| 7999 | CA | GLY | B | 368 | -9.056 | 37.007 | 32.566 | 1.00 | 132.65 |
| 8000 | C | GLY | B | 368 | -9.679 | 36.773 | 31.198 | 1.00 | 128.67 |
| 8001 | O | GLY | B | 368 | -9.152 | 35.996 | 30.399 | 1.00 | 129.21 |
| 8002 | N | THR | B | 369 | -10.800 | 37.436 | 30.923 | 1.00 | 121.65 |
| 8003 | CA | THR | B | 369 | -11.479 | 37.288 | 29.637 | 1.00 | 119.67 |
| 8004 | CB | THR | B | 369 | -12.724 | 38.213 | 29.534 | 1.00 | 121.49 |
| 8005 | OG1 | THR | B | 369 | -12.398 | 39.525 | 30.014 | 1.00 | 124.59 |
| 8006 | CG2 | THR | B | 369 | -13.884 | 37.644 | 30.333 | 1.00 | 120.88 |
| 8007 | C | THR | B | 369 | -10.561 | 37.590 | 28.453 | 1.00 | 122.03 |
| 8008 | O | THR | B | 369 | -9.705 | 38.476 | 28.521 | 1.00 | 123.54 |
| 8009 | N | VAL | B | 370 | -10.745 | 36.842 | 27.369 | 1.00 | 116.41 |
| 8010 | CA | VAL | B | 370 | -9.952 | 37.029 | 26.161 | 1.00 | 105.79 |
| 8011 | CB | VAL | B | 370 | -9.281 | 35.711 | 25.722 | 1.00 | 101.65 |
| 8012 | CG1 | VAL | B | 370 | -8.282 | 35.978 | 24.602 | 1.00 | 94.80 |
| 8013 | CG2 | VAL | B | 370 | -8.596 | 35.063 | 26.908 | 1.00 | 103.04 |
| 8014 | C | VAL | B | 370 | -10.898 | 37.492 | 25.063 | 1.00 | 100.41 |
| 8015 | O | VAL | B | 370 | -11.858 | 36.797 | 24.736 | 1.00 | 102.41 |
| 8016 | N | ASN | B | 371 | -10.633 | 38.669 | 24.504 | 1.00 | 97.19 |
| 8017 | CA | ASN | B | 371 | -11.478 | 39.214 | 23.451 | 1.00 | 90.26 |
| 8018 | CB | ASN | B | 371 | -11.610 | 40.735 | 23.596 | 1.00 | 102.33 |
| 8019 | CG | ASN | B | 371 | -12.495 | 41.144 | 24.761 | 1.00 | 110.16 |
| 8020 | OD1 | ASN | B | 371 | -13.657 | 40.741 | 24.850 | 1.00 | 116.69 |
| 8021 | ND2 | ASN | B | 371 | -11.949 | 41.960 | 25.655 | 1.00 | 112.10 |
| 8022 | C | ASN | B | 371 | -10.946 | 38.905 | 22.062 | 1.00 | 82.28 |
| 8023 | O | ASN | B | 371 | -9.804 | 39.217 | 21.756 | 1.00 | 57.00 |
| 8024 | N | LEU | B | 372 | -11.790 | 38.296 | 21.231 | 1.00 | 90.31 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8025 | CA | LEU | B | 372 | −11.441 | 37.966 | 19.848 | 1.00 | 87.12 |
| 8026 | CB | LEU | B | 372 | −11.558 | 36.461 | 19.598 | 1.00 | 83.98 |
| 8027 | CG | LEU | B | 372 | −10.583 | 35.571 | 20.373 | 1.00 | 83.03 |
| 8028 | CD1 | LEU | B | 372 | −10.695 | 34.146 | 19.870 | 1.00 | 87.88 |
| 8029 | CD2 | LEU | B | 372 | −9.163 | 36.063 | 20.180 | 1.00 | 89.82 |
| 8030 | C | LEU | B | 372 | −12.417 | 38.712 | 18.953 | 1.00 | 73.81 |
| 8031 | O | LEU | B | 372 | −13.514 | 38.237 | 18.702 | 1.00 | 69.33 |
| 8032 | N | THR | B | 373 | −12.008 | 39.887 | 18.488 | 1.00 | 76.61 |
| 8033 | CA | THR | B | 373 | −12.846 | 40.729 | 17.642 | 1.00 | 63.94 |
| 8034 | CB | THR | B | 373 | −12.626 | 42.227 | 17.984 | 1.00 | 72.89 |
| 8035 | OG1 | THR | B | 373 | −12.741 | 42.406 | 19.397 | 1.00 | 77.01 |
| 8036 | CG2 | THR | B | 373 | −13.663 | 43.104 | 17.312 | 1.00 | 52.40 |
| 8037 | C | THR | B | 373 | −12.581 | 40.511 | 16.156 | 1.00 | 53.99 |
| 8038 | O | THR | B | 373 | −11.441 | 40.387 | 15.730 | 1.00 | 49.04 |
| 8039 | N | TRP | B | 374 | −13.657 | 40.459 | 15.377 | 1.00 | 55.83 |
| 8040 | CA | TRP | B | 374 | −13.569 | 40.281 | 13.933 | 1.00 | 55.67 |
| 8041 | CB | TRP | B | 374 | −14.535 | 39.205 | 13.457 | 1.00 | 48.86 |
| 8042 | CG | TRP | B | 374 | −14.131 | 37.840 | 13.842 | 1.00 | 51.61 |
| 8043 | CD2 | TRP | B | 374 | −13.185 | 37.011 | 13.166 | 1.00 | 56.20 |
| 8044 | CE2 | TRP | B | 374 | −13.081 | 35.814 | 13.902 | 1.00 | 64.36 |
| 8045 | CE3 | TRP | B | 374 | −12.412 | 37.164 | 12.008 | 1.00 | 14.32 |
| 8046 | CD1 | TRP | B | 374 | −14.554 | 37.137 | 14.925 | 1.00 | 45.59 |
| 8047 | NE1 | TRP | B | 374 | −13.930 | 35.918 | 14.971 | 1.00 | 67.43 |
| 8048 | CZ2 | TRP | B | 374 | −12.232 | 34.773 | 13.522 | 1.00 | 56.50 |
| 8049 | CZ3 | TRP | B | 374 | −11.564 | 36.125 | 11.630 | 1.00 | 57.00 |
| 8050 | CH2 | TRP | B | 374 | −11.483 | 34.946 | 12.386 | 1.00 | 68.58 |
| 8051 | C | TRP | B | 374 | −13.896 | 41.579 | 13.218 | 1.00 | 56.61 |
| 8052 | O | TRP | B | 374 | −14.565 | 42.448 | 13.772 | 1.00 | 50.51 |
| 8053 | N | SER | B | 375 | −13.425 | 41.702 | 11.982 | 1.00 | 49.40 |
| 8054 | CA | SER | B | 375 | −13.657 | 42.893 | 11.174 | 1.00 | 46.03 |
| 8055 | CB | SER | B | 375 | −12.937 | 44.106 | 11.763 | 1.00 | 35.18 |
| 8056 | OG | SER | B | 375 | −11.550 | 43.872 | 11.902 | 1.00 | 66.68 |
| 8057 | C | SER | B | 375 | −13.172 | 42.682 | 9.753 | 1.00 | 64.17 |
| 8058 | O | SER | B | 375 | −12.296 | 41.854 | 9.496 | 1.00 | 68.13 |
| 8059 | N | ARG | B | 376 | −13.753 | 43.437 | 8.829 | 1.00 | 66.59 |
| 8060 | CA | ARG | B | 376 | −13.375 | 43.353 | 7.431 | 1.00 | 48.38 |
| 8061 | CB | ARG | B | 376 | −14.607 | 43.287 | 6.552 | 1.00 | 61.57 |
| 8062 | CG | ARG | B | 376 | −15.407 | 42.039 | 6.747 | 1.00 | 35.07 |
| 8063 | CD | ARG | B | 376 | −16.052 | 41.692 | 5.455 | 1.00 | 33.26 |
| 8064 | NE | ARG | B | 376 | −17.489 | 41.599 | 5.580 | 1.00 | 59.45 |
| 8065 | CZ | ARG | B | 376 | −18.330 | 41.698 | 4.561 | 1.00 | 49.71 |
| 8066 | NH1 | ARG | B | 376 | −17.879 | 41.905 | 3.327 | 1.00 | 3.70 |
| 8067 | NH2 | ARG | B | 376 | −19.625 | 41.582 | 4.789 | 1.00 | 27.73 |
| 8068 | C | ARG | B | 376 | −12.546 | 44.560 | 7.051 | 1.00 | 50.06 |
| 8069 | O | ARG | B | 376 | −12.655 | 45.628 | 7.655 | 1.00 | 51.13 |
| 8070 | N | ALA | B | 377 | −11.701 | 44.377 | 6.049 | 1.00 | 48.63 |
| 8071 | CA | ALA | B | 377 | −10.832 | 45.444 | 5.588 | 1.00 | 44.03 |
| 8072 | CB | ALA | B | 377 | −9.747 | 44.863 | 4.703 | 1.00 | 24.46 |
| 8073 | C | ALA | B | 377 | −11.657 | 46.485 | 4.836 | 1.00 | 54.71 |
| 8074 | O | ALA | B | 377 | −11.288 | 47.650 | 4.760 | 1.00 | 58.35 |
| 8075 | N | SER | B | 378 | −12.784 | 46.046 | 4.293 | 1.00 | 45.13 |
| 8076 | CA | SER | B | 378 | −13.678 | 46.915 | 3.558 | 1.00 | 40.60 |
| 8077 | CB | SER | B | 378 | −14.694 | 46.081 | 2.787 | 1.00 | 57.52 |
| 8078 | OG | SER | B | 378 | −15.369 | 45.195 | 3.670 | 1.00 | 34.41 |
| 8079 | C | SER | B | 378 | −14.440 | 47.796 | 4.533 | 1.00 | 58.48 |
| 8080 | O | SER | B | 378 | −14.749 | 48.953 | 4.237 | 1.00 | 45.08 |
| 8081 | N | GLY | B | 379 | −14.755 | 47.234 | 5.696 | 1.00 | 33.55 |
| 8082 | CA | GLY | B | 379 | −15.510 | 47.968 | 6.685 | 1.00 | 34.12 |
| 8083 | C | GLY | B | 379 | −16.951 | 47.506 | 6.707 | 1.00 | 40.51 |
| 8084 | O | GLY | B | 379 | −17.783 | 48.102 | 7.387 | 1.00 | 63.43 |
| 8085 | N | LYS | B | 380 | −17.256 | 46.455 | 5.951 | 1.00 | 53.62 |
| 8086 | CA | LYS | B | 380 | −18.604 | 4S.898 | 5.933 | 1.00 | 69.08 |
| 8087 | CB | LYS | B | 380 | −18.825 | 45.079 | 4.667 | 1.00 | 41.89 |
| 8088 | CG | LYS | B | 380 | −18.664 | 45.901 | 3.434 | 1.00 | 48.18 |
| 8089 | CD | LYS | B | 380 | −19.024 | 45.138 | 2.192 | 1.00 | 80.05 |
| 8090 | CE | LYS | B | 380 | −16.936 | 46.025 | 0.959 | 1.00 | 42.13 |
| 8091 | NZ | LYS | B | 380 | −19.347 | 45.255 | −0.243 | 1.00 | 95.98 |
| 8092 | C | LYS | B | 380 | −18.783 | 45.034 | 7.181 | 1.00 | 51.52 |
| 8093 | O | LYS | B | 380 | −17.806 | 44.692 | 7.854 | 1.00 | 31.44 |
| 8094 | N | PRO | B | 381 | −20.036 | 44.680 | 7.509 | 1.00 | 62.90 |
| 8095 | CD | PRO | B | 381 | −21.296 | 45.156 | 6.930 | 1.00 | 50.25 |
| 8096 | CA | PRO | B | 381 | −20.309 | 43.866 | 8.692 | 1.00 | 64.54 |
| 8097 | CB | PRO | B | 381 | −21.830 | 43.961 | 8.829 | 1.00 | 38.05 |
| 8098 | CG | PRO | B | 381 | −22.161 | 45.231 | 8.151 | 1.00 | 51.11 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8099 | C | PRO | B | 381 | −19.831 | 42.430 | 8.603 | 1.00 | 57.70 |
| 8100 | O | PRO | B | 381 | −19.739 | 41.858 | 7.519 | 1.00 | 43.65 |
| 8101 | N | VAL | B | 382 | −19.516 | 41.869 | 9.764 | 1.00 | 38.89 |
| 8102 | CA | VAL | B | 382 | −19.090 | 40.487 | 9.868 | 1.00 | 55.87 |
| 8103 | CB | VAL | B | 382 | −17.827 | 40.348 | 10.772 | 1.00 | 66.54 |
| 8104 | CG1 | VAL | B | 382 | −16.662 | 41.124 | 10.174 | 1.00 | 50.65 |
| 6105 | CG2 | VAL | B | 382 | −18.125 | 40.842 | 12.177 | 1.00 | 41.22 |
| 8106 | C | VAL | B | 382 | −20.269 | 39.737 | 10.503 | 1.00 | 63.82 |
| 8107 | O | VAL | B | 382 | −20.981 | 40.309 | 11.320 | 1.00 | 56.83 |
| 8108 | N | ASN | B | 383 | −20.490 | 38.478 | 10.120 | 1.00 | 65.17 |
| 8109 | CA | ASN | B | 383 | −21.593 | 37.693 | 10.685 | 1.00 | 48.83 |
| 8110 | CB | ASN | B | 383 | −21.798 | 36.400 | 9.889 | 1.00 | 71.38 |
| 8111 | CG | ASN | B | 383 | −22.155 | 36.657 | 8.440 | 1.00 | 96.04 |
| 8112 | OD1 | ASN | B | 383 | −22.493 | 35.737 | 7.692 | 1.00 | 87.06 |
| 8113 | ND2 | ASN | B | 383 | −22.074 | 37.917 | 8.030 | 1.00 | 121.07 |
| 8114 | C | ASN | B | 383 | −21.348 | 37.353 | 12.156 | 1.00 | 69.00 |
| 8115 | O | ASN | B | 383 | −20.441 | 37.908 | 12.780 | 1.00 | 40.50 |
| 8116 | N | HIS | B | 384 | −22.160 | 36.443 | 12.697 | 1.00 | 77.18 |
| 8117 | CA | HIS | B | 384 | −22.055 | 36.011 | 14.093 | 1.00 | 73.12 |
| 8118 | CB | HIS | B | 384 | −23.394 | 35.463 | 14.575 | 1.00 | 97.81 |
| 8119 | CG | HIS | B | 384 | −24.550 | 36.352 | 14.252 | 1.00 | 119.17 |
| 8120 | CD2 | HIS | B | 384 | −25.630 | 36.158 | 13.459 | 1.00 | 122.68 |
| 8121 | ND1 | HIS | B | 384 | −24.662 | 37.634 | 14.747 | 1.00 | 128.12 |
| 8122 | CE1 | HIS | B | 384 | −25.762 | 38.192 | 14.273 | 1.00 | 124.38 |
| 8123 | NE2 | HIS | B | 384 | −26.368 | 37.317 | 13.489 | 1.00 | 124.66 |
| 8124 | C | HIS | B | 384 | −21.003 | 34.935 | 14.245 | 1.00 | 58.78 |
| 8125 | O | HIS | B | 384 | −21.117 | 33.862 | 13.657 | 1.00 | 68.20 |
| 8126 | N | SER | B | 385 | −19.989 | 35.221 | 15.050 | 1.00 | 54.38 |
| 8127 | CA | SER | B | 385 | −18.899 | 34.280 | 15.278 | 1.00 | 64.86 |
| 8128 | CB | SER | B | 385 | −17.600 | 35.043 | 15.577 | 1.00 | 59.44 |
| 8129 | OG | SER | B | 385 | −17.867 | 36.305 | 16.167 | 1.00 | 72.82 |
| 8130 | C | SER | B | 385 | −19.201 | 33.289 | 16.396 | 1.00 | 70.55 |
| 8131 | O | SER | B | 385 | −20.134 | 33.477 | 17.181 | 1.00 | 50.47 |
| 8132 | N | THR | B | 386 | −18.406 | 32.226 | 16.457 | 1.00 | 71.83 |
| 8133 | CA | THR | B | 386 | −18.578 | 31.195 | 17.472 | 1.00 | 70.85 |
| 8134 | CB | THR | B | 386 | −18.964 | 29.861 | 16.841 | 1.00 | 65.88 |
| 8135 | OG1 | THR | B | 386 | −20.271 | 29.967 | 16.280 | 1.00 | 63.91 |
| 8136 | CG2 | THR | B | 386 | −18.962 | 28.773 | 17.874 | 1.00 | 72.82 |
| 8137 | C | THR | B | 386 | −17.317 | 30.978 | 18.290 | 1.00 | 78.13 |
| 8138 | O | THR | B | 386 | −16.317 | 30.472 | 17.779 | 1.00 | 90.36 |
| 8139 | N | ARG | B | 387 | −17.383 | 31.352 | 19.565 | 1.00 | 85.81 |
| 8140 | CA | ARG | B | 387 | −16.262 | 31.208 | 20.496 | 1.00 | 79.09 |
| 8141 | CB | ARG | B | 387 | −16.329 | 32.330 | 21.529 | 1.00 | 57.85 |
| 8142 | CG | ARG | B | 387 | −15.189 | 32.381 | 22.528 | 1.00 | 87.40 |
| 8143 | CD | ARG | B | 387 | −15.476 | 33.438 | 23.610 | 1.00 | 92.57 |
| 8144 | NE | ARG | B | 387 | −14.452 | 33.467 | 24.653 | 1.00 | 98.81 |
| 8145 | CZ | ARG | B | 387 | −13.273 | 34.065 | 24.528 | 1.00 | 103.88 |
| 8146 | NH1 | ARG | B | 387 | −12.967 | 34.699 | 23.407 | 1.00 | 106.78 |
| 8147 | NH2 | ARG | B | 387 | −12.390 | 34.011 | 25.515 | 1.00 | 100.96 |
| 8148 | C | ARG | B | 387 | −16.333 | 29.846 | 21.193 | 1.00 | 60.01 |
| 8149 | O | ARG | B | 397 | −17.407 | 29.404 | 21.568 | 1.00 | 51.34 |
| 8150 | N | LYS | B | 388 | −15.197 | 29.178 | 21.361 | 1.00 | 63.19 |
| 8151 | CA | LYS | B | 388 | −15.174 | 27.861 | 22.003 | 1.00 | 70.73 |
| 8152 | CB | LYS | B | 388 | −15.230 | 26.738 | 20.957 | 1.00 | 86.49 |
| 8153 | CG | LYS | B | 388 | −16.353 | 26.850 | 19.943 | 1.00 | 94.12 |
| 8154 | CD | LYS | B | 388 | −16.144 | 25.879 | 18.790 | 1.00 | 92.40 |
| 8155 | CE | LYS | B | 388 | −17.129 | 26.150 | 17.662 | 1.00 | 93.33 |
| 8156 | NZ | LYS | B | 388 | −16.923 | 25.237 | 16.504 | 1.00 | 99.04 |
| 8157 | C | LYS | B | 388 | −13.908 | 27.681 | 22.819 | 1.00 | 78.24 |
| 8158 | O | LYS | B | 388 | −12.857 | 27.348 | 22.274 | 1.00 | 91.49 |
| 8159 | N | GLU | B | 389 | −14.007 | 27.897 | 24.123 | 1.00 | 78.13 |
| 8160 | CA | GLU | B | 389 | −12.857 | 27.734 | 24.998 | 1.00 | 83.37 |
| 8161 | CB | GLU | B | 389 | −12.976 | 28.674 | 26.192 | 1.00 | 85.00 |
| 8162 | CG | GLU | B | 389 | −12.969 | 30.139 | 25.805 | 1.00 | 101.03 |
| 8163 | CD | GLU | B | 389 | −13.240 | 31.055 | 26.982 | 1.00 | 109.85 |
| 8164 | OE1 | GLU | B | 389 | −12.495 | 30.981 | 27.980 | 1.00 | 104.69 |
| 8165 | OE2 | GLU | B | 389 | −14.199 | 31.855 | 26.910 | 1.00 | 123.28 |
| 8166 | C | GLU | B | 389 | −12.775 | 26.284 | 25.464 | 1.00 | 85.10 |
| 8167 | O | GLU | B | 389 | −13.599 | 25.822 | 26.253 | 1.00 | 92.70 |
| 8168 | N | GLU | B | 390 | −11.780 | 25.571 | 24.947 | 1.00 | 88.84 |
| 8169 | CA | GLU | B | 390 | −11.558 | 24.165 | 25.276 | 1.00 | 97.99 |
| 8170 | CB | GLU | B | 390 | −11.467 | 23.341 | 23.983 | 1.00 | 110.22 |
| 8171 | CG | GLU | B | 390 | −11.142 | 21.862 | 24.179 | 1.00 | 112.58 |
| 8172 | CD | GLU | B | 390 | −11.109 | 21.094 | 22.864 | 1.00 | 119.77 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8173 | OE1 | GLU | B | 390 | −10.371 | 21.514 | 21.950 | 1.00 | 114.74 |
| 8174 | OE2 | GLU | B | 390 | −11.819 | 20.072 | 22.742 | 1.00 | 122.02 |
| 8175 | C | GLU | B | 390 | −10.271 | 24.017 | 26.086 | 1.00 | 90.56 |
| 8176 | O | GLU | B | 390 | −9.188 | 23.835 | 25.529 | 1.00 | 79.93 |
| 8177 | N | LYS | B | 391 | −10.402 | 24.085 | 27.404 | 1.00 | 96.02 |
| 8178 | CA | LYS | B | 391 | −9.252 | 23.984 | 28.293 | 1.00 | 113.41 |
| 8179 | CB | LYS | B | 391 | −9.613 | 24.540 | 29.676 | 1.00 | 106.20 |
| 8180 | CG | LYS | B | 391 | −8.414 | 24.996 | 30.504 | 1.00 | 118.63 |
| 8181 | CD | LYS | B | 391 | −8.867 | 25.887 | 31.660 | 1.00 | 119.88 |
| 8182 | CE | LYS | B | 391 | −7.694 | 26.600 | 32.329 | 1.00 | 120.56 |
| 8183 | NZ | LYS | B | 391 | −8.148 | 27.575 | 33.368 | 1.00 | 104.21 |
| 8184 | C | LYS | B | 391 | −8.712 | 22.564 | 28.441 | 1.00 | 111.24 |
| 8185 | O | LYS | B | 391 | −9.456 | 21.583 | 28.383 | 1.00 | 111.32 |
| 8186 | N | GLN | B | 392 | −7.400 | 22.476 | 28.628 | 1.00 | 109.11 |
| 8187 | CA | GLN | B | 392 | −6.715 | 21.205 | 28.812 | 1.00 | 116.69 |
| 8188 | CB | GLN | B | 392 | −5.988 | 20.795 | 27.534 | 1.00 | 111.84 |
| 8189 | CG | GLN | B | 392 | −6.878 | 20.680 | 26.323 | 1.00 | 118.92 |
| 8190 | CD | GLN | B | 392 | −6.083 | 20.443 | 25.065 | 1.00 | 124.54 |
| 8191 | OE1 | GLN | B | 392 | −5.332 | 19.474 | 24.969 | 1.00 | 130.59 |
| 8192 | NE2 | GLN | B | 392 | −6.239 | 21.329 | 24.089 | 1.00 | 120.61 |
| 8193 | C | GLN | B | 392 | −5.697 | 21.398 | 29.927 | 1.00 | 130.16 |
| 8194 | O | GLN | B | 392 | −4.662 | 22.039 | 29.723 | 1.00 | 129.26 |
| 8195 | N | ARG | B | 393 | −5.996 | 20.855 | 31.106 | 1.00 | 137.58 |
| 8196 | CA | ARG | B | 393 | −5.094 | 20.964 | 32.252 | 1.00 | 145.56 |
| 8197 | CB | ARG | B | 393 | −5.662 | 20.188 | 33.446 | 1.00 | 144.55 |
| 8198 | CG | ARG | B | 393 | −6.813 | 19.250 | 33.096 | 1.00 | 148.11 |
| 8199 | CD | ARG | B | 393 | −7.238 | 18.438 | 34.308 | 1.00 | 150.01 |
| 8200 | NE | ARG | B | 393 | −6.146 | 17.606 | 34.803 | 1.00 | 146.01 |
| 8201 | CZ | ARG | B | 393 | −6.231 | 16.818 | 35.867 | 1.00 | 143.21 |
| 8202 | NH1 | ARG | B | 393 | −7.362 | 16.752 | 36.556 | 1.00 | 142.25 |
| 8203 | NH2 | ARG | B | 393 | −5.184 | 16.093 | 36.239 | 1.00 | 148.27 |
| 8204 | C | ARG | B | 393 | −3.703 | 20.437 | 31.885 | 1.00 | 151.36 |
| 8205 | O | ARG | B | 393 | −2.755 | 20.521 | 32.676 | 1.00 | 150.75 |
| 8206 | N | ASN | B | 394 | −3.602 | 19.898 | 30.671 | 1.00 | 152.90 |
| 8207 | CA | ASN | B | 394 | −2.358 | 19.364 | 30.131 | 1.00 | 143.43 |
| 8208 | CB | ASN | B | 394 | −2.641 | 18.641 | 28.812 | 1.00 | 139.82 |
| 8209 | CG | ASN | B | 394 | −1.398 | 18.042 | 28.198 | 1.00 | 150.16 |
| 8210 | OD1 | ASN | B | 394 | −1.369 | 17.734 | 27.006 | 1.00 | 147.59 |
| 8211 | ND2 | ASN | B | 394 | −0.362 | 17.861 | 29.011 | 1.00 | 149.35 |
| 8212 | C | ASN | B | 394 | −1.402 | 20.529 | 29.877 | 1.00 | 140.07 |
| 8213 | O | ASN | B | 394 | −0.262 | 20.338 | 29.457 | 1.00 | 145.19 |
| 8214 | N | GLY | B | 395 | −1.880 | 21.739 | 30.142 | 1.00 | 135.82 |
| 8215 | CA | GLY | B | 395 | −1.071 | 22.921 | 29.919 | 1.00 | 134.57 |
| 8216 | C | GLY | B | 395 | −1.405 | 23.468 | 28.546 | 1.00 | 137.28 |
| 8217 | O | GLY | B | 395 | −0.532 | 23.567 | 27.677 | 1.00 | 124.64 |
| 8218 | N | THR | B | 396 | −2.678 | 23.815 | 28.355 | 1.00 | 137.22 |
| 8219 | CA | THR | B | 396 | −3.159 | 24.341 | 27.081 | 1.00 | 131.77 |
| 8220 | CB | THR | B | 396 | −3.055 | 23.257 | 25.956 | 1.00 | 134.86 |
| 8221 | OG1 | THR | B | 396 | −1.678 | 22.919 | 25.726 | 1.00 | 139.74 |
| 8222 | CG2 | THR | B | 396 | −3.674 | 23.767 | 24.657 | 1.00 | 129.19 |
| 8223 | C | THR | B | 396 | −4.620 | 24.813 | 27.170 | 1.00 | 123.26 |
| 8224 | O | THR | B | 396 | −5.525 | 24.005 | 27.390 | 1.00 | 120.52 |
| 8225 | N | LEU | B | 397 | −4.844 | 26.118 | 27.004 | 1.00 | 124.57 |
| 8226 | CA | LEU | B | 397 | −6.198 | 26.681 | 27.027 | 1.00 | 112.38 |
| 8227 | CB | LEU | B | 397 | −6.295 | 27.870 | 27.989 | 1.00 | 94.46 |
| 8228 | CG | LEU | B | 397 | −7.649 | 28.592 | 27.912 | 1.00 | 97.61 |
| 8229 | CD1 | LEU | B | 397 | −8.777 | 27.608 | 28.214 | 1.00 | 92.88 |
| 8230 | CD2 | LEU | B | 397 | −7.679 | 29.769 | 28.876 | 1.00 | 96.37 |
| 8231 | C | LEU | B | 397 | −6.613 | 27.139 | 25.624 | 1.00 | 105.10 |
| 8232 | O | LEU | B | 397 | −6.540 | 28.324 | 25.296 | 1.00 | 96.44 |
| 8233 | N | THR | B | 398 | −7.043 | 26.190 | 24.801 | 1.00 | 107.97 |
| 8234 | CA | THR | B | 398 | −7.467 | 26.480 | 23.438 | 1.00 | 91.54 |
| 8235 | CB | THR | B | 398 | −7.798 | 25.173 | 22.674 | 1.00 | 98.68 |
| 8236 | OG1 | ThR | B | 398 | −6.585 | 24.486 | 22.345 | 1.00 | 87.29 |
| 8237 | CG2 | THR | B | 398 | −8.571 | 25.470 | 21.405 | 1.00 | 108.62 |
| 8238 | C | THR | B | 398 | −8.689 | 27.393 | 23.408 | 1.00 | 90.23 |
| 8239 | O | THR | B | 398 | −9.639 | 27.222 | 24.174 | 1.00 | 91.46 |
| 8240 | N | VAL | B | 399 | −8.645 | 28.377 | 22.521 | 1.00 | 86.33 |
| 8241 | CA | VAL | B | 399 | −9.743 | 29.320 | 22.350 | 1.00 | 90.49 |
| 8242 | CB | VAL | B | 399 | −9.498 | 30.647 | 23.108 | 1.00 | 94.11 |
| 8243 | CG1 | VAL | B | 399 | −10.694 | 31.575 | 22.918 | 1.00 | 65.34 |
| 8244 | CG2 | VAL | B | 399 | −9.268 | 30.370 | 24.589 | 1.00 | 92.06 |
| 8245 | C | VAL | B | 399 | −9.854 | 29.617 | 20.857 | 1.00 | 94.62 |
| 8246 | O | VAL | B | 399 | −8.960 | 30.229 | 20.263 | 1.00 | 87.44 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8247 | N | THR | B | 400 | −10.945 | 29.164 | 20.251 | 1.00 | 86.75 |
| 8248 | CA | THR | B | 400 | −11.152 | 29.373 | 18.833 | 1.00 | 81.91 |
| 8249 | CB | THR | B | 400 | −11.312 | 28.034 | 18.088 | 1.00 | 86.05 |
| 8250 | OG1 | THR | B | 400 | −12.491 | 27.368 | 18.557 | 1.00 | 68.57 |
| 8251 | CG2 | THR | B | 400 | −10.101 | 27.142 | 18.323 | 1.00 | 76.14 |
| 8252 | C | THR | B | 400 | −12.400 | 30.195 | 18.586 | 1.00 | 81.91 |
| 8253 | O | THR | B | 400 | −13.283 | 30.276 | 19.430 | 1.00 | 68.12 |
| 8254 | N | SER | B | 401 | −12.452 | 30.818 | 17.419 | 1.00 | 83.99 |
| 8255 | CA | SER | B | 401 | −13.602 | 31.604 | 17.025 | 1.00 | 62.25 |
| 8256 | CB | SER | B | 401 | −13.358 | 33.089 | 17.269 | 1.00 | 74.33 |
| 8257 | OG | SER | B | 401 | −14.520 | 33.841 | 16.966 | 1.00 | 81.24 |
| 8258 | C | SER | B | 401 | −13.776 | 31.320 | 15.541 | 1.00 | 72.86 |
| 8259 | O | SER | B | 401 | −12.830 | 31.449 | 14.757 | 1.00 | 51.97 |
| 8260 | N | THR | B | 402 | −14.979 | 30.896 | 15.169 | 1.00 | 67.45 |
| 8261 | CA | THR | B | 402 | −15.267 | 30.572 | 13.786 | 1.00 | 66.68 |
| 8262 | CB | THR | B | 402 | −15.814 | 29.142 | 13.647 | 1.00 | 66.55 |
| 8263 | OG1 | THR | B | 402 | −14.755 | 28.212 | 13.908 | 1.00 | 62.07 |
| 8264 | CG2 | THR | B | 402 | −16.358 | 28.903 | 12.240 | 1.00 | 55.42 |
| 8265 | C | THR | B | 402 | −16.259 | 31.551 | 13.218 | 1.00 | 58.54 |
| 8266 | O | THR | B | 402 | −17.396 | 31.634 | 13.665 | 1.00 | 45.51 |
| 8267 | N | LEU | B | 403 | −15.802 | 32.293 | 12.221 | 1.00 | 61.16 |
| 8268 | CA | LEU | B | 403 | −16.630 | 33.283 | 11.579 | 1.00 | 50.61 |
| 8269 | CB | LEU | B | 403 | −15.847 | 34.589 | 11.418 | 1.00 | 35.75 |
| 8270 | CG | LEU | B | 403 | −16.583 | 35.744 | 10.711 | 1.00 | 79.51 |
| 8271 | CD1 | LEU | B | 403 | −17.714 | 36.248 | 11.612 | 1.00 | 51.35 |
| 8272 | CD2 | LEU | B | 403 | −15.618 | 36.891 | 10.377 | 1.00 | 47.42 |
| 8273 | C | LEU | B | 403 | −17.114 | 32.814 | 10.221 | 1.00 | 52.74 |
| 8274 | O | LEU | B | 403 | −16.307 | 32.462 | 9.366 | 1.00 | 70.32 |
| 8275 | N | PRO | B | 404 | −18.442 | 32.768 | 10.018 | 1.00 | 60.42 |
| 8276 | CD | PRO | B | 404 | −19.464 | 32.829 | 11.072 | 1.00 | 57.94 |
| 8277 | CA | PRO | B | 404 | −19.051 | 32.354 | 8.747 | 1.00 | 53.65 |
| 8278 | CB | PRO | B | 404 | −20.537 | 32.306 | 9.078 | 1.00 | 39.12 |
| 8279 | CG | PRO | B | 404 | −20.540 | 31.940 | 10.507 | 1.00 | 79.06 |
| 8280 | C | PRO | B | 404 | −18.741 | 33.464 | 7.750 | 1.00 | 32.93 |
| 8281 | O | PRO | B | 404 | −18.839 | 34.635 | 8.087 | 1.00 | 42.84 |
| 8282 | N | VAL | B | 405 | −18.361 | 33.106 | 6.536 | 1.00 | 35.23 |
| 8283 | CA | VAL | B | 405 | −18.019 | 34.109 | 5.536 | 1.00 | 38.30 |
| 8284 | CB | VAL | B | 405 | −16.511 | 34.041 | 5.179 | 1.00 | 36.84 |
| 8285 | CG1 | VAL | B | 405 | −16.233 | 34.836 | 3.931 | 1.00 | 74.50 |
| 8286 | CG2 | VAL | B | 405 | −15.675 | 34.577 | 6.331 | 1.00 | 46.26 |
| 8287 | C | VAL | B | 405 | −18.835 | 33.960 | 4.265 | 1.00 | 41.99 |
| 8288 | O | VAL | B | 405 | −19.212 | 32.863 | 3.859 | 1.00 | 50.19 |
| 8289 | N | GLY | B | 406 | −19.111 | 35.086 | 3.637 | 1.00 | 49.58 |
| 8290 | CA | GLY | B | 406 | −19.873 | 35.050 | 2.417 | 1.00 | 42.34 |
| 8291 | C | GLY | B | 406 | −19.043 | 34.389 | 1.351 | 1.00 | 41.31 |
| 8292 | O | GLY | B | 406 | −17.864 | 34.677 | 1.229 | 1.00 | 42.96 |
| 8293 | N | THR | B | 407 | −19.657 | 33.506 | 0.575 | 1.00 | 62.13 |
| 8294 | CA | THR | B | 407 | −18.956 | 32.817 | −0.501 | 1.00 | 64.15 |
| 8295 | CB | THR | B | 407 | −19.907 | 31.841 | −1.226 | 1.00 | 78.25 |
| 8296 | OG1 | THR | B | 407 | −20.449 | 30.907 | −0.284 | 1.00 | 82.50 |
| 8297 | CG2 | THR | B | 407 | −19.170 | 31.077 | −2.293 | 1.00 | 72.82 |
| 8298 | C | THR | B | 407 | −18.385 | 33.821 | −1.513 | 1.00 | 69.20 |
| 8299 | O | THR | B | 407 | −17.177 | 33.842 | −1.783 | 1.00 | 35.03 |
| 8300 | N | ALA | B | 408 | −19.250 | 34.662 | −2.074 | 1.00 | 65.33 |
| 8301 | CA | ALA | B | 408 | −18.788 | 35.642 | −3.048 | 1.00 | 68.18 |
| 8302 | CB | ALA | B | 408 | −19.979 | 36.389 | −3.661 | 1.00 | 71.75 |
| 8303 | C | ALA | B | 408 | −17.786 | 36.630 | −2.430 | 1.00 | 66.35 |
| 8304 | O | ALA | B | 408 | −16.835 | 37.030 | −3.097 | 1.00 | 45.13 |
| 8305 | N | ASP | B | 409 | −17.996 | 37.014 | −1.168 | 1.00 | 61.42 |
| 8306 | CA | ASP | B | 409 | −17.101 | 37.945 | −0.476 | 1.00 | 53.76 |
| 8307 | CB | ASP | B | 409 | −17.568 | 38.176 | 0.969 | 1.00 | 78.99 |
| 8308 | CG | ASP | B | 409 | −18.899 | 38.935 | 1.057 | 1.00 | 91.60 |
| 8309 | OD1 | ASP | B | 409 | −18.971 | 40.101 | 0.608 | 1.00 | 58.40 |
| 8310 | OD2 | ASP | B | 409 | −19.877 | 38.364 | 1.590 | 1.00 | 96.87 |
| 8311 | C | ASP | B | 409 | −15.661 | 37.429 | −0.463 | 1.00 | 60.27 |
| 8312 | O | ASP | B | 409 | −14.742 | 38.108 | −0.932 | 1.00 | 48.30 |
| 8313 | N | TRP | B | 410 | −15.462 | 36.224 | 0.072 | 1.00 | 64.45 |
| 8314 | CA | TRP | B | 410 | −14.125 | 35.644 | 0.129 | 1.00 | 66.04 |
| 8315 | CB | TRP | B | 410 | −14.140 | 34.255 | 0.800 | 1.00 | 38.16 |
| 8316 | CG | TRP | B | 410 | −12.747 | 33.615 | 0.828 | 1.00 | 53.80 |
| 8317 | CD2 | TRP | B | 410 | −11.730 | 33.770 | 1.851 | 1.00 | 27.49 |
| 8318 | CE2 | TRP | B | 410 | −10.576 | 33.077 | 1.406 | 1.00 | 17.06 |
| 8319 | CE3 | TRP | B | 410 | −11.686 | 34.425 | 3.096 | 1.00 | 51.16 |
| 8320 | CD1 | TRP | B | 410 | −12.172 | 32.851 | −0.164 | 1.00 | 11.53 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8321 | NE1 | TRP | B | 410 | −10.871 | 32.530 | 0.180 | 1.00 | 46.46 |
| 8322 | CZ2 | TRP | B | 410 | −9.393 | 33.021 | 2.161 | 1.00 | 16.45 |
| 8323 | CZ3 | TRP | B | 410 | −10.491 | 34.367 | 3.850 | 1.00 | 37.71 |
| 8324 | CH2 | TRP | B | 410 | −9.373 | 33.670 | 3.374 | 1.00 | 39.69 |
| 8325 | C | TRP | B | 410 | −13.541 | 35.521 | −1.272 | 1.00 | 54.19 |
| 8326 | O | TRP | B | 410 | −12.402 | 35.909 | −1.527 | 1.00 | 41.74 |
| 8327 | N | ILE | B | 411 | −14.338 | 34.989 | −2.182 | 1.00 | 49.11 |
| 8328 | CA | ILE | B | 411 | −13.894 | 34.793 | −3.547 | 1.00 | 70.95 |
| 8329 | CB | ILE | B | 411 | −14.986 | 34.056 | −4.347 | 1.00 | 84.29 |
| 8330 | CG2 | ILE | B | 411 | −14.644 | 34.036 | −5.829 | 1.00 | 68.66 |
| 8331 | CG1 | ILE | B | 411 | −15.144 | 32.640 | −3.796 | 1.00 | 53.09 |
| 8332 | CD1 | ILE | B | 411 | −16.129 | 31.813 | −4.548 | 1.00 | 78.55 |
| 8333 | C | ILE | B | 411 | −13.476 | 36.061 | −4.291 | 1.00 | 63.90 |
| 8334 | O | ILE | B | 411 | −12.561 | 36.024 | −5.102 | 1.00 | 64.54 |
| 8335 | N | GLU | B | 412 | −14.125 | 37.187 | −4.018 | 1.00 | 79.47 |
| 8336 | CA | GLU | B | 412 | −13.776 | 38.417 | −4.719 | 1.00 | 56.81 |
| 8337 | CB | GLU | B | 412 | −15.034 | 39.261 | −4.928 | 1.00 | 62.64 |
| 8338 | CG | GLU | B | 412 | −15.836 | 38.754 | −6.135 | 1.00 | 95.39 |
| 8339 | CD | GLU | B | 412 | −17.206 | 39.381 | −6.270 | 1.00 | 106.84 |
| 8340 | OE1 | GLU | B | 412 | −17.299 | 40.620 | −6.182 | 1.00 | 132.58 |
| 8341 | OE2 | GLU | B | 412 | −18.188 | 38.637 | −6.478 | 1.00 | 112.18 |
| 8342 | C | GLU | B | 412 | −12.629 | 39.232 | −4.129 | 1.00 | 43.31 |
| 8343 | O | GLU | B | 412 | −12.275 | 40.288 | −4.642 | 1.00 | 44.55 |
| 8344 | N | GLY | B | 413 | −12.027 | 38.732 | −3.060 | 1.00 | 28.42 |
| 8345 | CA | GLY | B | 413 | −10.889 | 39.428 | −2.497 | 1.00 | 54.05 |
| 8346 | C | GLY | B | 413 | −10.991 | 40.046 | −1.122 | 1.00 | 60.70 |
| 8347 | O | GLY | B | 413 | −10.052 | 40.720 | −0.683 | 1.00 | 50.88 |
| 8348 | N | GLU | B | 414 | −12.096 | 39.829 | −0.424 | 1.00 | 31.55 |
| 8349 | CA | GLU | B | 414 | −12.204 | 40.440 | 0.878 | 1.00 | 34.16 |
| 8350 | CB | GLU | B | 414 | −13.596 | 40.210 | 1.455 | 1.00 | 4.46 |
| 8351 | CG | GLU | B | 414 | −13.834 | 40.722 | 2.876 | 1.00 | 41.64 |
| 8352 | CD | GLU | B | 414 | −13.994 | 42.225 | 2.965 | 1.00 | 53.85 |
| 8353 | OE1 | GLU | B | 414 | −12.967 | 42.935 | 3.024 | 1.00 | 48.31 |
| 8354 | OE2 | GLU | B | 414 | −15.153 | 42.692 | 2.970 | 1.00 | 41.74 |
| 8355 | C | GLU | B | 414 | −11.133 | 39.859 | 1.773 | 1.00 | 22.09 |
| 8356 | O | GLU | B | 414 | −10.689 | 38.751 | 1.557 | 1.00 | 60.15 |
| 8357 | N | THR | B | 415 | −10.708 | 40.626 | 2.765 | 1.00 | 42.79 |
| 8358 | CA | THR | B | 415 | −9.724 | 40.169 | 3.723 | 1.00 | 38.49 |
| 8359 | CB | THR | B | 415 | −8.400 | 40.949 | 3.616 | 1.00 | 24.35 |
| 8360 | OG1 | THR | B | 415 | −7.880 | 41.146 | 4.936 | 1.00 | 48.00 |
| 8361 | CG2 | THR | B | 415 | −8.602 | 42.290 | 2.897 | 1.00 | 72.97 |
| 8362 | C | THR | B | 415 | −10.322 | 40.357 | 5.116 | 1.00 | 45.25 |
| 8363 | O | THR | B | 415 | −10.730 | 41.455 | 5.494 | 1.00 | 30.96 |
| 8364 | N | TYR | B | 416 | −10.391 | 39.270 | 5.871 | 1.00 | 49.50 |
| 8365 | CA | TYR | B | 416 | −10.964 | 39.309 | 7.207 | 1.00 | 35.56 |
| 8366 | CB | TYR | B | 416 | −11.789 | 38.060 | 7.429 | 1.00 | 29.95 |
| 8367 | CG | TYR | B | 416 | −12.920 | 37.946 | 6.429 | 1.00 | 53.85 |
| 8368 | CD1 | TYR | B | 416 | −12.682 | 37.538 | 5.105 | 1.00 | 43.79 |
| 8369 | CE1 | TYR | B | 416 | −13.715 | 37.474 | 4.174 | 1.00 | 45.64 |
| 8370 | CD2 | TYR | B | 416 | −14.224 | 38.288 | 6.796 | 1.00 | 40.55 |
| 8371 | CE2 | TYR | B | 416 | −15.259 | 38.234 | 5.881 | 1.00 | 48.00 |
| 8372 | CZ | TYR | B | 416 | −15.003 | 37.831 | 4.573 | 1.00 | 64.99 |
| 8373 | OH | TYR | B | 416 | −16.042 | 37.828 | 3.671 | 1.00 | 44.34 |
| 8374 | C | TYR | B | 416 | −9.901 | 39.448 | 8.264 | 1.00 | 40.92 |
| 8375 | O | TYR | B | 416 | −8.775 | 39.012 | 8.059 | 1.00 | 55.94 |
| 8376 | N | GLN | B | 417 | −10.257 | 40.072 | 9.386 | 1.00 | 44.11 |
| 8377 | CA | GLN | B | 417 | −9.298 | 40.302 | 10.461 | 1.00 | 48.51 |
| 8378 | CB | GLN | B | 417 | −8.856 | 41.767 | 10.466 | 1.00 | 42.13 |
| 8379 | CG | GLN | B | 417 | −7.820 | 42.090 | 11.553 | 1.00 | 87.17 |
| 8380 | CD | GLN | B | 417 | −7.587 | 43.579 | 11.744 | 1.00 | 87.10 |
| 8381 | OE1 | GLN | B | 417 | −8.481 | 44.311 | 12.168 | 1.00 | 100.92 |
| 8382 | NE2 | GLN | B | 417 | −6.381 | 44.033 | 11.430 | 1.00 | 72.44 |
| 8383 | C | GLN | B | 417 | −9.779 | 39.928 | 11.851 | 1.00 | 39.89 |
| 8384 | O | GLN | B | 417 | −10.916 | 40.167 | 12.206 | 1.00 | 44.16 |
| 8385 | N | CYS | B | 418 | −8.875 | 39.342 | 12.631 | 1.00 | 63.97 |
| 8386 | CA | CYS | B | 418 | −9.145 | 38.913 | 14.010 | 1.00 | 66.27 |
| 8387 | C | CYS | B | 418 | −8.260 | 39.691 | 14.990 | 1.00 | 63.31 |
| 8388 | O | CYS | B | 418 | −7.035 | 39.629 | 14.912 | 1.00 | 72.92 |
| 8389 | CB | CYS | B | 418 | −8.856 | 37.411 | 14.155 | 1.00 | 75.48 |
| 8390 | SG | CYS | B | 418 | −9.059 | 36.715 | 15.829 | 1.00 | 78.40 |
| 8391 | N | ARG | B | 419 | −8.870 | 40.433 | 15.903 | 1.00 | 62.62 |
| 8392 | CA | ARG | B | 419 | −8.091 | 41.189 | 16.870 | 1.00 | 69.65 |
| 8393 | CB | ARG | B | 419 | −8.584 | 42.626 | 16.943 | 1.00 | 77.38 |
| 8394 | CG | ARG | B | 419 | −7.737 | 43.511 | 17.827 | 1.00 | 91.72 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8395 | CD | ARG | B | 419 | −8.059 | 44.978 | 17.596 | 1.00 | 104.25 |
| 8396 | NE | ARG | B | 419 | −7.357 | 45.857 | 18.529 | 1.00 | 120.02 |
| 8397 | CZ | ARG | B | 419 | −7.564 | 45.876 | 19.845 | 1.00 | 116.33 |
| 8398 | NH1 | ARG | B | 419 | −8.457 | 45.061 | 20.399 | 1.00 | 100.82 |
| 8399 | NH2 | ARG | B | 419 | −6.879 | 46.717 | 20.612 | 1.00 | 106.71 |
| 8400 | C | ARG | B | 419 | −8.205 | 40.525 | 18.228 | 1.00 | 76.93 |
| 8401 | O | ARG | B | 419 | −9.308 | 40.349 | 18.749 | 1.00 | 60.56 |
| 8402 | N | VAL | B | 420 | −7.060 | 40.145 | 18.792 | 1.00 | 82.78 |
| 8403 | CA | VAL | B | 420 | −7.030 | 39.470 | 20.088 | 1.00 | 83.97 |
| 8404 | CB | VAL | B | 420 | −6.053 | 38.286 | 20.087 | 1.00 | 71.99 |
| 8405 | CG1 | VAL | B | 420 | −6.225 | 37.484 | 21.369 | 1.00 | 56.24 |
| 8406 | CG2 | VAL | B | 420 | −6.286 | 37.418 | 18.860 | 1.00 | 74.72 |
| 8407 | C | VAL | B | 420 | −6.640 | 40.402 | 21.221 | 1.00 | 78.36 |
| 8408 | O | VAL | B | 420 | −5.647 | 41.113 | 21.138 | 1.00 | 74.15 |
| 8409 | N | THR | B | 421 | −7.436 | 40.386 | 22.282 | 1.00 | 87.84 |
| 8410 | CA | THR | B | 421 | −7.189 | 41.237 | 23.434 | 1.00 | 101.03 |
| 8411 | CB | THR | B | 421 | −8.318 | 42.276 | 23.611 | 1.00 | 101.21 |
| 8412 | OG1 | THR | B | 421 | −8.439 | 43.058 | 22.419 | 1.00 | 104.77 |
| 8413 | CG2 | THR | B | 421 | −8.014 | 43.205 | 24.776 | 1.00 | 102.12 |
| 8414 | C | THR | B | 421 | −7.096 | 40.387 | 24.692 | 1.00 | 103.43 |
| 8415 | O | THR | B | 421 | −7.762 | 39.358 | 24.815 | 1.00 | 102.04 |
| 8416 | N | HIS | B | 422 | −6.258 | 40.824 | 25.623 | 1.00 | 109.50 |
| 8417 | CA | HIS | B | 422 | −6.075 | 40.115 | 26.879 | 1.00 | 120.67 |
| 8418 | CB | HIS | B | 422 | −5.177 | 38.889 | 26.667 | 1.00 | 124.34 |
| 8419 | CG | HIS | B | 422 | −5.093 | 37.983 | 27.858 | 1.00 | 131.39 |
| 8420 | CD2 | HIS | B | 422 | −4.029 | 37.539 | 28.568 | 1.00 | 131.78 |
| 8421 | ND1 | HIS | B | 422 | −6.207 | 37.421 | 28.446 | 1.00 | 138.92 |
| 8422 | CE1 | HIS | B | 422 | −5.832 | 36.672 | 29.468 | 1.00 | 137.60 |
| 8423 | NE2 | HIS | B | 422 | −4.515 | 36.726 | 29.564 | 1.00 | 134.39 |
| 8424 | C | HIS | B | 422 | −5.453 | 41.062 | 27.902 | 1.00 | 122.56 |
| 8425 | O | HIS | B | 422 | −4.661 | 41.939 | 27.551 | 1.00 | 109.28 |
| 8426 | N | PRO | B | 423 | −5.822 | 40.907 | 29.183 | 1.00 | 125.27 |
| 8427 | CD | PRO | B | 423 | −6.874 | 40.010 | 29.700 | 1.00 | 120.50 |
| 8428 | CA | PRO | B | 423 | −5.293 | 41.756 | 30.254 | 1.00 | 128.34 |
| 8429 | CB | PRO | B | 423 | −6.232 | 41.450 | 31.421 | 1.00 | 128.16 |
| 8430 | CG | PRO | B | 423 | −6.601 | 40.011 | 31.179 | 1.00 | 122.79 |
| 8431 | C | PRO | B | 423 | −3.820 | 41.498 | 30.602 | 1.00 | 131.90 |
| 8432 | O | PRO | B | 423 | −3.127 | 42.394 | 31.094 | 1.00 | 140.58 |
| 8433 | N | HIS | B | 424 | −3.344 | 40.282 | 30.339 | 1.00 | 134.04 |
| 8434 | CA | HIS | B | 424 | −1.959 | 39.918 | 30.643 | 1.00 | 134.32 |
| 8435 | CB | HIS | B | 424 | −1.903 | 38.487 | 31.197 | 1.00 | 139.92 |
| 8436 | CG | HIS | B | 424 | −2.785 | 38.265 | 32.391 | 1.00 | 144.66 |
| 8437 | CD2 | HIS | B | 424 | −3.821 | 37.415 | 32.586 | 1.00 | 147.72 |
| 8438 | ND1 | HIS | B | 424 | −2.649 | 38.979 | 33.563 | 1.00 | 140.45 |
| 8439 | CE1 | HIS | B | 424 | −3.565 | 38.579 | 34.428 | 1.00 | 142.19 |
| 8440 | NE2 | HIS | B | 424 | −4.289 | 37.631 | 33.860 | 1.00 | 141.03 |
| 8441 | C | HIS | B | 424 | −1.011 | 40.048 | 29.444 | 1.00 | 134.96 |
| 8442 | O | HIS | B | 424 | −0.079 | 39.253 | 29.291 | 1.00 | 141.47 |
| 8443 | N | LEU | B | 425 | −1.254 | 41.053 | 28.601 | 1.00 | 140.14 |
| 8444 | CA | LEU | B | 425 | −0.426 | 41.318 | 27.422 | 1.00 | 130.47 |
| 8445 | CB | LEU | B | 425 | −0.867 | 40.462 | 26.230 | 1.00 | 130.50 |
| 8446 | CG | LEU | B | 425 | −0.412 | 39.000 | 26.233 | 1.00 | 133.90 |
| 8447 | CD1 | LEU | B | 425 | −0.962 | 38.298 | 25.003 | 1.00 | 132.28 |
| 8448 | CD2 | LEU | B | 425 | 1.111 | 38.925 | 26.251 | 1.00 | 124.99 |
| 8449 | C | LEU | B | 425 | −0.477 | 42.791 | 27.032 | 1.00 | 124.14 |
| 8450 | O | LEU | B | 425 | −1.535 | 43.423 | 27.068 | 1.00 | 117.65 |
| 8451 | N | PRO | B | 426 | 0.675 | 43.351 | 26.637 | 1.00 | 125.26 |
| 8452 | CD | PRO | B | 426 | 1.927 | 42.629 | 26.351 | 1.00 | 126.22 |
| 8453 | CA | PRO | B | 426 | 0.783 | 44.755 | 26.236 | 1.00 | 122.93 |
| 8454 | CB | PRO | B | 426 | 2.260 | 44.893 | 25.885 | 1.00 | 123.31 |
| 8455 | CG | PRO | B | 426 | 2.594 | 43.533 | 25.346 | 1.00 | 117.32 |
| 8456 | C | PRO | B | 426 | −0.124 | 45.097 | 25.066 | 1.00 | 123.61 |
| 8457 | O | PRO | B | 426 | −1.308 | 45.382 | 25.247 | 1.00 | 126.97 |
| 8458 | N | ARG | B | 427 | 0.448 | 45.064 | 23.867 | 1.00 | 121.43 |
| 8459 | CA | ARG | B | 427 | −0.285 | 45.362 | 22.647 | 1.00 | 120.82 |
| 8460 | CB | ARG | B | 427 | 0.699 | 45.696 | 21.519 | 1.00 | 129.63 |
| 8461 | CG | ARG | B | 427 | 0.047 | 46.029 | 20.183 | 1.00 | 143.36 |
| 8462 | CD | ARG | B | 427 | 1.094 | 46.263 | 19.104 | 1.00 | 141.71 |
| 8463 | NE | ARG | B | 427 | 0.494 | 46.448 | 17.786 | 1.00 | 139.02 |
| 8464 | CZ | ARG | B | 427 | 1.190 | 46.660 | 16.674 | 1.00 | 139.83 |
| 8465 | NH1 | ARG | B | 427 | 2.514 | 46.714 | 16.722 | 1.00 | 140.12 |
| 8466 | NH2 | ARG | B | 427 | 0.564 | 46.817 | 15.514 | 1.00 | 137.97 |
| 8467 | C | ARG | B | 427 | −1.145 | 44.163 | 22.255 | 1.00 | 115.53 |
| 8468 | O | ARG | B | 427 | −0.892 | 43.038 | 22.690 | 1.00 | 114.34 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8469 | N | ALA | B | 428 | −2.160 | 44.413 | 21.433 | 1.00 | 110.56 |
| 8470 | CA | ALA | B | 428 | −3.070 | 43.368 | 20.982 | 1.00 | 107.01 |
| 8471 | CB | ALA | B | 428 | −4.434 | 43.975 | 20.659 | 1.00 | 108.60 |
| 8472 | C | ALA | B | 428 | −2.530 | 42.636 | 19.761 | 1.00 | 102.88 |
| 8473 | O | ALA | B | 428 | −1.703 | 43.170 | 19.022 | 1.00 | 104.80 |
| 8474 | N | LEU | B | 429 | −2.999 | 41.409 | 19.556 | 1.00 | 98.47 |
| 8475 | CA | LEU | B | 429 | −2.576 | 40.617 | 18.407 | 1.00 | 105.26 |
| 8476 | CB | LEU | B | 429 | −2.488 | 39.143 | 18.784 | 1.00 | 113.21 |
| 8477 | CG | LEU | B | 429 | −1.358 | 38.770 | 19.735 | 1.00 | 107.61 |
| 8478 | CD1 | LEU | B | 429 | −1.467 | 37.298 | 20.075 | 1.00 | 112.17 |
| 8479 | CD2 | LEU | B | 429 | −0.017 | 39.073 | 19.086 | 1.00 | 98.64 |
| 8480 | C | LEU | B | 429 | −3.543 | 40.781 | 17.237 | 1.00 | 102.29 |
| 8481 | O | LEU | B | 429 | −4.742 | 41.006 | 17.431 | 1.00 | 99.00 |
| 8482 | N | MET | B | 430 | −3.019 | 40.663 | 16.022 | 1.00 | 97.08 |
| 8483 | CA | MET | B | 430 | −3.845 | 40.799 | 14.830 | 1.00 | 92.31 |
| 8484 | CB | MET | B | 430 | −3.769 | 42.235 | 14.305 | 1.00 | 91.61 |
| 8485 | CG | MET | B | 430 | −4.300 | 43.269 | 15.278 | 1.00 | 108.10 |
| 8486 | SD | MET | B | 430 | −3.790 | 44.943 | 14.853 | 1.00 | 128.98 |
| 8487 | CE | MET | B | 430 | −2.316 | 45.140 | 15.883 | 1.00 | 116.18 |
| 8488 | C | MET | B | 430 | −3.420 | 39.837 | 13.736 | 1.00 | 74.13 |
| 8489 | O | MET | B | 430 | −2.237 | 39.649 | 13.488 | 1.00 | 91.73 |
| 8490 | N | ARG | B | 431 | −4.399 | 39.220 | 13.095 | 1.00 | 55.68 |
| 8491 | CA | ARG | B | 431 | −4.144 | 38.307 | 11.995 | 1.00 | 40.78 |
| 8492 | CB | ARG | B | 431 | −4.281 | 36.865 | 12.456 | 1.00 | 63.30 |
| 8493 | CG | ARG | B | 431 | −3.592 | 36.568 | 13.753 | 1.00 | 80.94 |
| 8494 | CD | ARG | B | 431 | −2.100 | 36.734 | 13.626 | 1.00 | 100.14 |
| 8495 | NE | ARG | B | 431 | −1.457 | 36.711 | 14.933 | 1.00 | 97.72 |
| 8496 | CZ | ARG | B | 431 | −0.150 | 36.832 | 15.117 | 1.00 | 99.67 |
| 8497 | NH1 | ARG | B | 431 | 0.652 | 36.982 | 14.070 | 1.00 | 102.08 |
| 8498 | NH2 | ARG | B | 431 | 0.351 | 36.808 | 16.345 | 1.00 | 95.12 |
| 8499 | C | ARG | B | 431 | −5.203 | 38.582 | 10.929 | 1.00 | 59.07 |
| 8500 | O | ARG | B | 431 | −6.346 | 38.899 | 11.255 | 1.00 | 47.62 |
| 8501 | N | SER | B | 432 | −4.825 | 38.466 | 9.663 | 1.00 | 36.27 |
| 8502 | CA | SER | B | 432 | −5.758 | 38.670 | 8.571 | 1.00 | 41.96 |
| 8503 | CB | SER | B | 432 | −5.454 | 39.996 | 7.850 | 1.00 | 51.80 |
| 8504 | OG | SER | B | 432 | −4.182 | 39.999 | 7.230 | 1.00 | 63.04 |
| 8505 | C | SER | B | 432 | −5.647 | 37.493 | 7.604 | 1.00 | 40.32 |
| 8506 | O | SER | B | 432 | −4.685 | 36.750 | 7.666 | 1.00 | 29.96 |
| 8507 | N | THR | B | 433 | −6.635 | 37.311 | 6.728 | 1.00 | 29.14 |
| 8508 | CA | THR | B | 433 | −6.574 | 36.224 | 5.757 | 1.00 | 36.77 |
| 8509 | CB | THR | B | 433 | −7.145 | 34.905 | 6.395 | 1.00 | 61.78 |
| 8510 | OG1 | THR | B | 433 | −7.087 | 33.829 | 5.448 | 1.00 | 55.92 |
| 8511 | CG2 | THR | B | 433 | −8.579 | 35.113 | 6.887 | 1.00 | 37.71 |
| 8512 | C | THR | B | 433 | −7.282 | 36.548 | 4.431 | 1.00 | 45.43 |
| 8513 | O | THR | B | 433 | −8.151 | 37.413 | 4.383 | 1.00 | 52.88 |
| 8514 | N | THR | B | 434 | −6.881 | 35.863 | 3.358 | 1.00 | 46.82 |
| 8515 | CA | THR | B | 434 | −7.486 | 36.021 | 2.029 | 1.00 | 56.79 |
| 8516 | CB | THR | B | 434 | −7.116 | 37.400 | 1.341 | 1.00 | 77.91 |
| 8517 | OG1 | THR | B | 434 | −5.859 | 37.900 | 1.811 | 1.00 | 48.59 |
| 8518 | CG2 | THR | B | 434 | −8.149 | 38.421 | 1.618 | 1.00 | 50.69 |
| 8519 | C | THR | B | 434 | −7.063 | 34.866 | 1.106 | 1.00 | 17.35 |
| 8520 | O | THR | B | 434 | −7.417 | 34.814 | −0.084 | 1.00 | 50.70 |
| 8521 | N | ARG | B | 440 | −2.571 | 29.872 | −10.385 | 1.00 | 25.98 |
| 8522 | CA | ARG | B | 440 | −3.612 | 28.838 | −10.229 | 1.00 | 59.75 |
| 8523 | CB | ARG | B | 440 | −5.017 | 29.411 | −10.483 | 1.00 | 36.20 |
| 8524 | CG | ARG | B | 440 | −5.334 | 30.724 | −9.734 | 1.00 | 66.04 |
| 8525 | CD | ARG | B | 440 | −5.594 | 30.571 | −8.233 | 1.00 | 67.00 |
| 8526 | NE | ARG | B | 440 | −5.573 | 31.869 | −7.551 | 1.00 | 89.01 |
| 8527 | CZ | ARG | B | 440 | −5.959 | 32.087 | −6.294 | 1.00 | 84.68 |
| 8528 | NH1 | ARG | B | 440 | −6.412 | 31.095 | −5.552 | 1.00 | 89.60 |
| 8529 | NH2 | ARG | B | 440 | −5.885 | 33.304 | −5.768 | 1.00 | 92.35 |
| 8530 | C | ARG | B | 440 | −3.362 | 27.681 | −11.195 | 1.00 | 50.11 |
| 8531 | O | ARG | B | 440 | −3.063 | 27.914 | −12.354 | 1.00 | 44.69 |
| 8532 | N | ALA | B | 441 | −3.486 | 26.441 | −10.707 | 1.00 | 53.43 |
| 8533 | CA | ALA | B | 441 | −3.255 | 25.243 | −11.528 | 1.00 | 47.79 |
| 8534 | CB | ALA | B | 441 | −1.769 | 24.940 | −11.591 | 1.00 | 20.64 |
| 8535 | C | ALA | B | 441 | −4.007 | 24.023 | −10.992 | 1.00 | 39.47 |
| 8536 | O | ALA | B | 441 | −3.990 | 23.754 | −9.791 | 1.00 | 49.86 |
| 8537 | N | ALA | B | 442 | −4.643 | 23.284 | −11.898 | 1.00 | 28.89 |
| 8538 | CA | ALA | B | 442 | −5.425 | 22.115 | −11.536 | 1.00 | 39.90 |
| 8539 | CB | ALA | B | 442 | −6.219 | 21.638 | −12.729 | 1.00 | 39.39 |
| 8540 | C | ALA | B | 442 | −4.545 | 20.995 | −11.019 | 1.00 | 42.95 |
| 8541 | O | ALA | B | 442 | −3.379 | 20.920 | −11.363 | 1.00 | 45.36 |
| 8542 | N | PRO | B | 443 | −5.101 | 20.113 | −10.170 | 1.00 | 46.70 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8543 | CD | PRO | B | 443 | −6.346 | 20.290 | −9.405 | 1.00 | 44.95 |
| 8544 | CA | PRO | B | 443 | −4.335 | 19.000 | −9.617 | 1.00 | 45.47 |
| 8545 | CB | PRO | B | 443 | −5.032 | 18.732 | −8.279 | 1.00 | 38.68 |
| 8546 | CG | PRO | B | 443 | −5.905 | 19.921 | −8.044 | 1.00 | 45.03 |
| 8547 | C | PRO | B | 443 | −4.345 | 17.746 | −10.499 | 1.00 | 42.20 |
| 8548 | O | PRO | B | 443 | −5.354 | 17.435 | −11.132 | 1.00 | 38.32 |
| 8549 | N | ALA | B | 444 | −3.211 | 17.046 | −10.534 | 1.00 | 36.55 |
| 8550 | CA | ALA | B | 444 | −3.089 | 15.789 | −11.263 | 1.00 | 27.41 |
| 8551 | CB | ALA | B | 444 | −1.686 | 15.665 | −11.893 | 1.00 | 21.53 |
| 8552 | C | ALA | B | 444 | −3.304 | 14.767 | −10.132 | 1.00 | 30.74 |
| 8553 | O | ALA | B | 444 | −2.687 | 14.885 | −9.075 | 1.00 | 39.28 |
| 8554 | N | VAL | B | 445 | −4.187 | 13.786 | −10.333 | 1.00 | 30.59 |
| 8555 | CA | VAL | B | 445 | −4.498 | 12.821 | −9.270 | 1.00 | 9.16 |
| 8556 | CB | VAL | B | 445 | −5.965 | 13.034 | −8.724 | 1.00 | 36.28 |
| 8557 | CG1 | VAL | B | 445 | −6.357 | 11.947 | −7.697 | 1.00 | 15.65 |
| 8558 | CG2 | VAL | B | 445 | −6.078 | 14.403 | −8.069 | 1.00 | 25.25 |
| 8559 | C | VAL | B | 445 | −4.343 | 11.343 | −9.566 | 1.00 | 32.82 |
| 8560 | O | VAL | B | 445 | −4.825 | 10.849 | −10.581 | 1.00 | 30.58 |
| 8561 | N | TYR | B | 446 | −3.650 | 10.638 | −8.676 | 1.00 | 26.34 |
| 8562 | CA | TYR | B | 446 | −3.524 | 9.214 | −8.854 | 1.00 | 37.62 |
| 8563 | CB | TYR | B | 446 | −2.265 | 8.831 | −9.626 | 1.00 | 50.81 |
| 8564 | CG | TYR | B | 446 | −2.481 | 7.453 | −10.248 | 1.00 | 92.25 |
| 8565 | CD1 | TYR | B | 446 | −3.630 | 7.176 | −11.000 | 1.00 | 92.31 |
| 8566 | CE1 | TYR | B | 446 | −3.859 | 5.901 | −11.532 | 1.00 | 87.11 |
| 8567 | CD2 | TYR | B | 446 | −1.576 | 6.422 | −10.052 | 1.00 | 92.02 |
| 8568 | CE2 | TYR | 3 | 446 | −1.796 | 5.143 | −10.581 | 1.00 | 82.35 |
| 8569 | CZ | TYR | B | 446 | −2.931 | 4.889 | −11.317 | 1.00 | 88.34 |
| 8570 | OH | TYR | B | 446 | −3.113 | 3.621 | −11.835 | 1.00 | 93.85 |
| 8571 | C | TYR | B | 446 | −3.636 | 8.388 | −7.575 | 1.00 | 40.23 |
| 8572 | O | TYR | B | 446 | −3.195 | 8.807 | −6.514 | 1.00 | 30.68 |
| 8573 | N | ALA | B | 447 | −4.226 | 7.203 | −7.712 | 1.00 | 22.14 |
| 8574 | CA | ALA | B | 447 | −4.477 | 6.331 | −6.592 | 1.00 | 25.68 |
| 8575 | CB | ALA | B | 447 | −5.978 | 6.295 | −6.340 | 1.00 | 31.88 |
| 8576 | C | ALA | B | 447 | −3.921 | 4.913 | −6.712 | 1.00 | 33.38 |
| 8577 | O | ALA | B | 447 | −3.966 | 4.300 | −7.763 | 1.00 | 35.35 |
| 8578 | N | PHE | B | 448 | −3.418 | 4.392 | −5.598 | 1.00 | 34.40 |
| 8579 | CA | PHE | B | 448 | −2.842 | 3.063 | −5.590 | 1.00 | 35.53 |
| 8580 | CB | PHE | B | 448 | −1.319 | 3.116 | −5.455 | 1.00 | 44.68 |
| 8581 | CG | PHE | B | 448 | −0.663 | 4.135 | −6.320 | 1.00 | 34.71 |
| 8582 | CD1 | PHE | B | 448 | −0.475 | 5.437 | −5.845 | 1.00 | 29.38 |
| 8583 | CD2 | PHE | B | 448 | −0.221 | 3.805 | −7.604 | 1.00 | 15.74 |
| 8584 | CE1 | PHE | B | 448 | 0.146 | 6.409 | −6.634 | 1.00 | 26.51 |
| 8585 | CE2 | PHE | B | 448 | 0.401 | 4.767 | −8.391 | 1.00 | 40.64 |
| 8586 | CZ | PHE | B | 448 | 0.586 | 6.080 | −7.904 | 1.00 | 18.78 |
| 8587 | C | PHE | B | 448 | −3.344 | 2.187 | −4.473 | 1.00 | 40.88 |
| 8588 | O | PHE | B | 448 | −3.748 | 2.663 | −3.421 | 1.00 | 31.64 |
| 8589 | N | ALA | B | 449 | −3.288 | 0.885 | −4.722 | 1.00 | 25.22 |
| 8590 | CA | ALA | B | 449 | −3.678 | −0.103 | −3.736 | 1.00 | 36.71 |
| 8591 | CB | ALA | B | 449 | −4.818 | −0.945 | −4.256 | 1.00 | 25.81 |
| 8592 | C | ALA | B | 449 | −2.458 | −0.979 | −3.441 | 1.00 | 42.29 |
| 8593 | O | ALA | B | 449 | −1.692 | −1.326 | −4.344 | 1.00 | 45.02 |
| 8594 | N | THR | B | 450 | −2.284 | −1.327 | −2.175 | 1.00 | 44.23 |
| 8595 | CA | THR | B | 450 | −1.162 | −2.150 | −1.757 | 1.00 | 47.24 |
| 8596 | CB | THR | B | 450 | −0.952 | −2.024 | −0.223 | 1.00 | 40.83 |
| 8597 | OG1 | THR | B | 450 | −0.123 | −0.881 | 0.054 | 1.00 | 36.02 |
| 8598 | CG2 | THR | B | 450 | −0.318 | −3.277 | 0.342 | 1.00 | 70.56 |
| 8599 | C | THR | B | 450 | −1.390 | −3.607 | −2.136 | 1.00 | 38.18 |
| 8600 | O | THR | B | 450 | −2.532 | −4.050 | −2.232 | 1.00 | 47.30 |
| 8601 | N | PRO | B | 451 | −0.303 | −4.362 | −2.390 | 1.00 | 61.99 |
| 8602 | CD | PRO | B | 451 | 1.053 | −3.857 | −2.647 | 1.00 | 63.40 |
| 8603 | CA | PRO | B | 451 | −0.392 | −5.779 | −2.757 | 1.00 | 60.32 |
| 8604 | CB | PRO | B | 451 | 0.996 | −6.089 | −3.321 | 1.00 | 60.70 |
| 8605 | CG | PRO | B | 451 | 1.513 | −4.766 | −3.751 | 1.00 | 75.61 |
| 8606 | C | PRO | B | 451 | −0.666 | −6.583 | −1.499 | 1.00 | 57.01 |
| 8607 | O | PRO | B | 451 | −0.606 | −6.024 | −0.413 | 1.00 | 29.65 |
| 8608 | N | GLU | B | 452 | −0.949 | −7.880 | −1.660 | 1.00 | 67.41 |
| 8609 | CA | GLU | B | 452 | −1.227 | −8.815 | −0.554 | 1.00 | 85.51 |
| 8610 | CB | GLU | B | 452 | −1.924 | −8.115 | 0.607 | 1.00 | 99.99 |
| 8611 | CG | GLU | B | 452 | −0.991 | −7.564 | 1.664 | 1.00 | 94.94 |
| 8612 | CD | GLU | B | 452 | −1.593 | −6.347 | 2.370 | 1.00 | 105.28 |
| 8613 | OE1 | GLU | B | 452 | −2.623 | −6.489 | 3.079 | 1.00 | 94.24 |
| 8614 | OE2 | GLU | B | 452 | −1.036 | −5.238 | 2.202 | 1.00 | 81.92 |
| 8615 | C | GLU | B | 452 | −2.102 | −9.989 | −0.996 | 1.00 | 93.88 |
| 8616 | O | GLU | B | 452 | −3.044 | −10.375 | −0.290 | 1.00 | 88.48 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8617 | N | LYS | B | 459 | −5.774 | −4.432 | 7.133 | 1.00 | 64.42 |
| 8618 | CA | LYS | B | 459 | −4.739 | −3.401 | 7.092 | 1.00 | 95.56 |
| 8619 | CB | LYS | B | 459 | −3.600 | −3.793 | 8.044 | 1.00 | 105.96 |
| 8620 | CG | LYS | B | 459 | −3.816 | −3.379 | 9.498 | 1.00 | 100.66 |
| 8621 | CD | LYS | B | 459 | −3.670 | −1.870 | 9.659 | 1.00 | 113.26 |
| 8622 | CE | LYS | B | 459 | −3.727 | −1.452 | 11.121 | 1.00 | 117.95 |
| 8623 | NZ | LYS | B | 459 | −3.405 | −0.001 | 11.303 | 1.00 | 120.02 |
| 8624 | C | LYS | B | 459 | −4.190 | −3.129 | 5.670 | 1.00 | 96.66 |
| 8625 | O | LYS | B | 459 | −3.036 | −2.683 | 5.496 | 1.00 | 72.68 |
| 8626 | N | ARG | B | 460 | −5.037 | −3.393 | 4.669 | 1.00 | 86.44 |
| 8627 | CA | ARG | B | 460 | −4.716 | −3.199 | 3.256 | 1.00 | 65.81 |
| 8628 | CB | ARG | B | 460 | −5.670 | −4.029 | 2.409 | 1.00 | 60.81 |
| 8629 | CG | ARG | B | 460 | −5.471 | −5.543 | 2.637 | 1.00 | 77.44 |
| 8630 | CD | ARG | B | 460 | −5.317 | −5.946 | 4.132 | 1.00 | 57.32 |
| 8631 | NE | ARG | B | 460 | −6.501 | −5.650 | 4.952 | 1.00 | 69.25 |
| 8632 | CZ | ARG | B | 460 | −7.406 | −6.548 | 5.356 | 1.00 | 72.22 |
| 8633 | NH1 | ARG | B | 460 | −7.288 | −7.837 | 5.031 | 1.00 | 77.88 |
| 8634 | NH2 | ARG | B | 460 | −8.448 | −6.155 | 6.079 | 1.00 | 57.40 |
| 8635 | C | ARG | B | 460 | −4.831 | −1.716 | 2.962 | 1.00 | 56.61 |
| 8636 | O | ARG | B | 460 | −5.899 | −1.127 | 3.119 | 1.00 | 46.14 |
| 8637 | N | THR | B | 461 | −3.722 | −1.109 | 2.539 | 1.00 | 39.73 |
| 8638 | CA | THR | B | 461 | −3.720 | 0.328 | 2.331 | 1.00 | 32.33 |
| 8639 | CB | THR | B | 461 | −2.457 | 0.954 | 2.991 | 1.00 | 32.41 |
| 8640 | OG1 | THR | B | 461 | −2.074 | 0.170 | 4.120 | 1.00 | 33.80 |
| 8641 | CG2 | THR | B | 461 | −2.746 | 2.365 | 3.494 | 1.00 | 44.26 |
| 8642 | C | THR | B | 461 | −3.880 | 0.881 | 0.913 | 1.00 | 38.75 |
| 8643 | O | THR | B | 461 | −3.425 | 0.307 | −0.072 | 1.00 | 36.95 |
| 8644 | N | LEU | B | 462 | −4.576 | 2.006 | 0.836 | 1.00 | 24.01 |
| 8645 | CA | LEU | B | 462 | −4.767 | 2.689 | −0.419 | 1.00 | 34.68 |
| 8646 | CB | LEU | B | 462 | −6.250 | 2.909 | −0.707 | 1.00 | 35.64 |
| 8647 | CG | LEU | B | 462 | −7.146 | 1.682 | −0.705 | 1.00 | 42.53 |
| 8648 | CD1 | LEU | B | 462 | −8.578 | 2.131 | −0.831 | 1.00 | 38.48 |
| 8649 | CD2 | LEU | B | 462 | −6.760 | 0.744 | −1.828 | 1.00 | 32.20 |
| 8650 | C | LEU | B | 462 | −4.054 | 4.035 | −0.276 | 1.00 | 32.89 |
| 8651 | O | LEU | B | 462 | −4.112 | 4.691 | 0.759 | 1.00 | 38.96 |
| 8652 | N | ALA | B | 463 | −3.376 | 4.436 | −1.332 | 1.00 | 30.88 |
| 8653 | CA | ALA | B | 463 | −2.656 | 5.664 | −1.314 | 1.00 | 20.81 |
| 8654 | CB | ALA | B | 463 | −1.152 | 5.371 | −1.328 | 1.00 | 38.81 |
| 8655 | C | ALA | B | 463 | −3.044 | 6.510 | −2.504 | 1.00 | 32.64 |
| 8656 | O | ALA | B | 463 | −3.368 | 6.020 | −3.565 | 1.00 | 27.67 |
| 8657 | N | CYS | B | 464 | −2.992 | 7.808 | −2.300 | 1.00 | 34.70 |
| 8658 | CA | CYS | B | 464 | −3.335 | 8.757 | −3.323 | 1.00 | 26.61 |
| 8659 | C | CYS | B | 464 | −2.282 | 9.860 | −3.357 | 1.00 | 35.03 |
| 8660 | O | CYS | B | 464 | −1.918 | 10.431 | −2.327 | 1.00 | 36.12 |
| 8661 | CB | CYS | B | 464 | −4.698 | 9.361 | −3.004 | 1.00 | 44.59 |
| 8662 | SG | CYS | B | 464 | −5.503 | 10.269 | −4.362 | 1.00 | 55.22 |
| 8663 | N | LEU | B | 465 | −1.783 | 10.124 | −4.555 | 1.00 | 29.99 |
| 8664 | CA | LEU | B | 465 | −0.825 | 11.183 | −4.785 | 1.00 | 24.47 |
| 8665 | CB | LEU | B | 465 | 0.346 | 10.689 | −5.644 | 1.00 | 32.93 |
| 8666 | CG | LEU | B | 465 | 1.195 | 11.820 | −6.238 | 1.00 | 27.50 |
| 8667 | CD1 | LEU | B | 465 | 1.785 | 12.677 | −5.122 | 1.00 | 31.46 |
| 8668 | CD2 | LEU | B | 465 | 2.276 | 11.239 | −7.089 | 1.00 | 25.53 |
| 8669 | C | LEU | B | 465 | −1.577 | 12.271 | −5.539 | 1.00 | 30.82 |
| 8670 | O | LEU | B | 465 | −2.205 | 12.009 | −6.554 | 1.00 | 27.11 |
| 8671 | N | ILE | B | 466 | −1.512 | 13.488 | −5.032 | 1.00 | 28.52 |
| 8672 | CA | ILE | B | 466 | −2.197 | 14.619 | −5.645 | 1.00 | 32.53 |
| 8673 | CB | ILE | B | 466 | −3.347 | 15.112 | −4.726 | 1.00 | 56.21 |
| 8674 | CG2 | ILE | B | 466 | −4.171 | 16.202 | −5.432 | 1.00 | 36.76 |
| 8675 | CG1 | ILE | B | 466 | −4.248 | 13.918 | −4.348 | 1.00 | 42.51 |
| 8676 | CD1 | ILE | B | 466 | −4.972 | 14.084 | −3.048 | 1.00 | 33.87 |
| 8677 | C | ILE | B | 466 | −1.152 | 15.692 | −5.822 | 1.00 | 32.62 |
| 8678 | O | ILE | B | 466 | −0.655 | 16.222 | −4.855 | 1.00 | 32.44 |
| 8679 | N | GLN | B | 467 | −0.835 | 16.022 | −7.070 | 1.00 | 31.77 |
| 8680 | CA | GLN | B | 467 | 0.232 | 16.987 | −7.342 | 1.00 | 42.12 |
| 8681 | CB | GLN | B | 467 | 1.507 | 16.199 | −7.611 | 1.00 | 30.12 |
| 8682 | CG | GLN | B | 467 | 1.318 | 15.196 | −8.745 | 1.00 | 18.81 |
| 8683 | CD | GLN | B | 467 | 2.627 | 14.527 | −9.161 | 1.00 | 49.90 |
| 8684 | OE1 | GLN | B | 467 | 3.551 | 14.373 | −8.354 | 1.00 | 29.31 |
| 8685 | NE2 | GLN | B | 467 | 2.705 | 14.108 | −10.415 | 1.00 | 22.36 |
| 8686 | C | GLN | B | 467 | 0.091 | 18.054 | −8.451 | 1.00 | 51.18 |
| 8687 | O | GLN | B | 467 | −0.820 | 18.029 | −9.296 | 1.00 | 32.85 |
| 8688 | N | ASN | B | 468 | 1.054 | 18.978 | −8.428 | 1.00 | 37.54 |
| 8689 | CA | ASN | B | 468 | 1.166 | 20.076 | −9.397 | 1.00 | 41.84 |
| 8690 | CB | ASN | B | 468 | 1.339 | 19.517 | −10.818 | 1.00 | 41.19 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8691 | CG | ASN | B | 468 | 2.518 | 18.576 | −10.934 | 1.00 | 36.60 |
| 8692 | OD1 | ASN | B | 468 | 3.525 | 18.722 | −10.240 | 1.00 | 36.44 |
| 8693 | ND2 | ASN | B | 468 | 2.399 | 17.604 | −11.819 | 1.00 | 39.40 |
| 8694 | C | ASN | B | 468 | 0.000 | 21.043 | −9.388 | 1.00 | 45.74 |
| 8695 | O | ASN | B | 468 | −0.454 | 21.490 | −10.444 | 1.00 | 52.42 |
| 8696 | N | PHE | B | 469 | −0.478 | 21.380 | −8.200 | 1.00 | 32.06 |
| 8697 | CA | PHE | B | 469 | −1.611 | 22.276 | −8.099 | 1.00 | 33.54 |
| 8698 | CB | PHE | B | 469 | −2.783 | 21.570 | −7.390 | 1.00 | 37.54 |
| 8699 | CG | PHE | B | 469 | −2.493 | 21.178 | −5.963 | 1.00 | 22.77 |
| 8700 | CD1 | PHE | B | 469 | −2.530 | 22.119 | −4.932 | 1.00 | 21.74 |
| 8701 | CD2 | PHE | B | 469 | −2.165 | 19.865 | −5.641 | 1.00 | 29.04 |
| 8702 | CE1 | PHE | B | 469 | −2.246 | 21.761 | −3.591 | 1.00 | 17.81 |
| 8703 | CE2 | PHE | B | 469 | −1.875 | 19.501 | −4.300 | 1.00 | 30.76 |
| 8704 | CZ | PHE | B | 469 | −1.921 | 20.461 | −3.282 | 1.00 | 29.23 |
| 8705 | C | PHE | B | 469 | −1.216 | 23.520 | −7.351 | 1.00 | 40.45 |
| 8706 | O | PHE | B | 469 | −0.243 | 23.511 | −6.603 | 1.00 | 36.36 |
| 8707 | N | MET | B | 470 | −1.957 | 24.598 | −7.590 | 1.00 | 46.78 |
| 8708 | CA | MET | B | 470 | −1.732 | 25.861 | −6.894 | 1.00 | 47.27 |
| 8709 | CB | MET | B | 470 | −0.453 | 26.576 | −7.388 | 1.00 | 50.00 |
| 8710 | CG | MET | B | 470 | −0.380 | 26.943 | −8.856 | 1.00 | 73.06 |
| 8711 | SD | MET | B | 470 | 1.312 | 27.479 | −9.251 | 1.00 | 71.67 |
| 8712 | CE | MET | B | 470 | 1.507 | 28.827 | −8.063 | 1.00 | 77.88 |
| 8713 | C | MET | B | 470 | −2.955 | 26.755 | −7.016 | 1.00 | 40.29 |
| 8714 | O | MET | B | 470 | −3.656 | 26.728 | −8.019 | 1.00 | 42.80 |
| 8715 | N | PRO | B | 471 | −3.250 | 27.529 | −5.963 | 1.00 | 39.94 |
| 8716 | CD | PRO | B | 471 | −4.446 | 28.371 | −5.902 | 1.00 | 23.93 |
| 8717 | CA | PRO | B | 471 | −2.509 | 27.605 | −4.693 | 1.00 | 34.53 |
| 8718 | CB | PRO | B | 471 | −3.300 | 28.627 | −3.885 | 1.00 | 42.09 |
| 8719 | CG | PRO | B | 471 | −4.020 | 29.400 | −4.903 | 1.00 | 42.90 |
| 8720 | C | PRO | B | 471 | −2.438 | 26.258 | −3.965 | 1.00 | 44.68 |
| 8721 | O | PRO | B | 471 | −2.910 | 25.240 | −4.468 | 1.00 | 29.77 |
| 8722 | N | GLU | B | 472 | −1.876 | 26.283 | −2.762 | 1.00 | 44.06 |
| 8723 | CA | GLU | B | 472 | −1.723 | 25.088 | −1.953 | 1.00 | 45.92 |
| 8724 | CB | GLU | B | 472 | −0.635 | 25.314 | −0.913 | 1.00 | 39.34 |
| 8725 | CG | GLU | B | 472 | −1.060 | 26.268 | 0.192 | 1.00 | 63.49 |
| 8726 | CD | GLU | B | 472 | −0.042 | 26.359 | 1.303 | 1.00 | 92.72 |
| 8727 | OE1 | GLU | B | 472 | 1.025 | 26.966 | 1.070 | 1.00 | 99.11 |
| 8728 | OE2 | GLU | B | 472 | −0.310 | 25.819 | 2.402 | 1.00 | 100.79 |
| 8729 | C | GLU | B | 472 | −3.003 | 24.605 | −1.246 | 1.00 | 43.87 |
| 8730 | O | GLU | B | 472 | −3.042 | 23.480 | −0.766 | 1.00 | 49.12 |
| 8731 | N | ASP | B | 473 | −4.030 | 25.445 | −1.163 | 1.00 | 39.80 |
| 8732 | CA | ASP | B | 473 | −5.270 | 25.046 | −0.511 | 1.00 | 36.59 |
| 8733 | CB | ASP | B | 473 | −6.253 | 26.214 | −0.477 | 1.00 | 48.94 |
| 8734 | CG | ASP | B | 473 | −5.723 | 27.398 | 0.291 | 1.00 | 73.50 |
| 8735 | OD1 | ASP | B | 473 | −5.271 | 27.211 | 1.431 | 1.00 | 67.93 |
| 8736 | OD2 | ASP | B | 473 | −5.768 | 28.523 | −0.240 | 1.00 | 91.96 |
| 8737 | C | ASP | B | 473 | −5.906 | 23.854 | −1.230 | 1.00 | 26.41 |
| 8738 | O | ASP | B | 473 | −6.108 | 23.876 | −2.437 | 1.00 | 39.55 |
| 8739 | N | ILE | B | 474 | −6.235 | 22.810 | −0.488 | 1.00 | 33.58 |
| 8740 | CA | ILE | B | 474 | −6.836 | 21.638 | −1.109 | 1.00 | 32.31 |
| 8741 | CB | ILE | B | 474 | −5.745 | 20.794 | −1.850 | 1.00 | 27.32 |
| 8742 | CG2 | ILE | B | 474 | −4.883 | 20.036 | −0.844 | 1.00 | 23.17 |
| 8743 | CG1 | ILE | B | 474 | −6.394 | 19.827 | −2.841 | 1.00 | 33.96 |
| 8744 | CD1 | ILE | B | 474 | −5.460 | 19.367 | −3.956 | 1.00 | 27.14 |
| 8745 | C | ILE | B | 474 | −7.591 | 20.762 | −0.105 | 1.00 | 35.21 |
| 8746 | O | ILE | B | 474 | −7.288 | 20.760 | 1.093 | 1.00 | 30.33 |
| 8747 | N | SER | B | 475 | −8.595 | 20.047 | −0.608 | 1.00 | 37.28 |
| 8748 | CA | SER | B | 475 | −9.422 | 19.140 | 0.197 | 1.00 | 29.69 |
| 8749 | CB | SER | B | 475 | −10.869 | 19.632 | 0.261 | 1.00 | 44.39 |
| 8750 | OG | SER | B | 475 | −10.979 | 20.813 | 1.026 | 1.00 | 42.07 |
| 8751 | C | SER | B | 475 | −9.384 | 17.764 | −0.450 | 1.00 | 37.71 |
| 8752 | O | SER | B | 475 | −9.520 | 17.633 | −1.668 | 1.00 | 38.85 |
| 8753 | N | VAL | B | 476 | −9.197 | 16.742 | 0.375 | 1.00 | 30.48 |
| 8754 | CA | VAL | B | 476 | −9.133 | 15.355 | −0.085 | 1.00 | 26.74 |
| 8755 | CB | VAL | B | 476 | −7.760 | 14.714 | 0.236 | 1.00 | 26.55 |
| 8756 | CG1 | VAL | B | 476 | −7.716 | 13.277 | −0.315 | 1.00 | 32.21 |
| 8757 | CG2 | VAL | B | 476 | −6.629 | 15.577 | −0.365 | 1.00 | 4.29 |
| 8758 | C | VAL | B | 476 | −10.205 | 14.493 | 0.550 | 1.00 | 35.53 |
| 8759 | O | VAL | B | 476 | −10.404 | 14.520 | 1.768 | 1.00 | 38.84 |
| 8760 | N | GLN | B | 477 | −10.887 | 13.711 | −0.280 | 1.00 | 39.65 |
| 8761 | CA | GLN | B | 477 | −11.941 | 12.846 | 0.225 | 1.00 | 33.58 |
| 8762 | CB | GLN | B | 477 | −13.320 | 13.428 | −0.079 | 1.00 | 38.27 |
| 8763 | CG | GLN | B | 477 | −13.425 | 14.922 | 0.026 | 1.00 | 53.59 |
| 8764 | CD | GLN | B | 477 | −14.843 | 15.397 | −0.210 | 1.00 | 77.65 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8765 | OE1 | GLN | B | 477 | −15.473 | 15.051 | −1.216 | 1.00 | 61.71 |
| 8766 | NE2 | GLN | B | 477 | −15.359 | 16.191 | 0.719 | 1.00 | 76.62 |
| 8767 | C | GLN | B | 477 | −11.880 | 11.475 | −0.375 | 1.00 | 34.20 |
| 8768 | O | GLN | B | 477 | −11.451 | 11.306 | −1.502 | 1.00 | 29.87 |
| 8769 | N | TRP | B | 478 | −12.324 | 10.496 | 0.403 | 1.00 | 36.77 |
| 8770 | CA | TRP | B | 478 | −12.392 | 9.113 | −0.049 | 1.00 | 27.53 |
| 8771 | CB | TRP | B | 478 | −11.628 | 8.180 | 0.890 | 1.00 | 30.50 |
| 8772 | CG | TRP | B | 478 | −10.124 | 8.288 | 0.778 | 1.00 | 22.05 |
| 8773 | CD2 | TRP | B | 478 | −9.293 | 7.609 | −0.167 | 1.00 | 18.72 |
| 8774 | CE2 | TRP | B | 478 | −7.970 | 8.049 | 0.049 | 1.00 | 23.00 |
| 8775 | CE3 | TRP | B | 478 | −9.538 | 6.669 | −1.186 | 1.00 | 16.17 |
| 8776 | CD1 | TRP | B | 478 | −9.300 | 9.084 | 1.508 | 1.00 | 13.70 |
| 8777 | NE1 | TRP | B | 478 | −8.006 | 8.950 | 1.081 | 1.00 | 32.75 |
| 8778 | CZ2 | TRP | B | 478 | −6.885 | 7.578 | −0.716 | 1.00 | 18.14 |
| 8779 | CZ3 | TRP | B | 478 | −8.461 | 6.202 | −1.946 | 1.00 | 25.16 |
| 8780 | CH2 | TRP | B | 478 | −7.150 | 6.658 | −1.705 | 1.00 | 17.33 |
| 8781 | C | TRP | B | 478 | −13.864 | 8.740 | −0.090 | 1.00 | 35.36 |
| 8782 | O | TRP | B | 478 | −14.651 | 9.149 | 0.768 | 1.00 | 36.83 |
| 8783 | N | LEU | B | 479 | −14.240 | 7.990 | −1.112 | 1.00 | 29.75 |
| 8784 | CA | LEU | B | 479 | −15.624 | 7.582 | −1.284 | 1.00 | 21.72 |
| 8785 | CB | LEU | B | 479 | −16.290 | 8.384 | −2.414 | 1.00 | 48.60 |
| 8786 | CG | LEU | B | 479 | −16.700 | 9.850 | −2.220 | 1.00 | 48.88 |
| 8787 | CD1 | LEU | B | 479 | −15.478 | 10.728 | −2.071 | 1.00 | 52.44 |
| 8788 | CD2 | LEU | B | 479 | −17.526 | 10.294 | −3.423 | 1.00 | 59.47 |
| 8789 | C | LEU | B | 479 | −15.694 | 6.116 | −1.612 | 1.00 | 35.16 |
| 8790 | O | LEU | B | 479 | −14.865 | 5.588 | −2.350 | 1.00 | 31.71 |
| 8791 | N | HIS | B | 480 | −16.685 | 5.453 | −1.041 | 1.00 | 40.68 |
| 8792 | CA | HIS | B | 480 | −16.898 | 4.040 | −1.290 | 1.00 | 41.81 |
| 8793 | CB | HIS | B | 480 | −16.489 | 3.216 | −0.076 | 1.00 | 34.19 |
| 8794 | CG | HIS | B | 480 | −16.584 | 1.741 | −0.292 | 1.00 | 36.94 |
| 8795 | CD2 | HIS | B | 480 | −17.171 | 0.770 | 0.443 | 1.00 | 25.42 |
| 8796 | ND1 | HIS | B | 480 | −16.056 | 1.115 | −1.402 | 1.00 | 44.60 |
| 8797 | CE1 | HIS | B | 480 | −16.320 | −0.176 | −1.346 | 1.00 | 33.98 |
| 8798 | NE2 | HIS | B | 480 | −16.997 | −0.413 | −0.236 | 1.00 | 57.73 |
| 8799 | C | HIS | B | 480 | −18.374 | 3.863 | −1.619 | 1.00 | 57.32 |
| 8800 | O | HIS | B | 480 | −19.233 | 4.349 | −0.894 | 1.00 | 49.11 |
| 8801 | N | ASN | B | 481 | −18.649 | 3.182 | −2.731 | 1.00 | 68.79 |
| 8802 | CA | ASN | B | 481 | −20.007 | 2.957 | −3.224 | 1.00 | 77.89 |
| 8803 | CB | ASN | B | 481 | −20.965 | 2.626 | −2.085 | 1.00 | 65.59 |
| 8804 | CG | ASN | B | 481 | −20.913 | 1.178 | −1.702 | 1.00 | 61.68 |
| 8805 | OD1 | ASN | B | 481 | −21.239 | 0.317 | −2.512 | 1.00 | 58.48 |
| 8806 | ND2 | ASN | B | 481 | −20.491 | 0.894 | −0.471 | 1.00 | 66.59 |
| 8807 | C | ASN | B | 481 | −20.466 | 4.216 | −3.932 | 1.00 | 82.93 |
| 8808 | O | ASN | B | 481 | −20.916 | 4.173 | −5.077 | 1.00 | 89.67 |
| 8809 | N | GLU | B | 482 | −20.320 | 5.338 | −3.241 | 1.00 | 77.03 |
| 8810 | CA | GLU | B | 482 | −20.700 | 6.649 | −3.746 | 1.00 | 79.65 |
| 8811 | CB | GLU | B | 482 | −22.052 | 6.590 | −4.454 | 1.00 | 92.89 |
| 8812 | CG | GLU | B | 482 | −23.103 | 5.695 | −3.780 | 1.00 | 118.58 |
| 8813 | CD | GLU | B | 482 | −23.061 | 5.750 | −2.262 | 1.00 | 127.74 |
| 8814 | OE1 | GLU | B | 482 | −22.106 | 5.201 | −1.668 | 1.00 | 125.30 |
| 8815 | OE2 | GLU | B | 482 | −23.979 | 6.346 | −1.659 | 1.00 | 134.84 |
| 8816 | C | GLU | B | 482 | −20.802 | 7.593 | −2.560 | 1.00 | 66.58 |
| 8817 | O | GLU | B | 482 | −21.098 | 8.776 | −2.696 | 1.00 | 60.48 |
| 8818 | N | VAL | B | 483 | −20.558 | 7.052 | −1.382 | 1.00 | 55.45 |
| 8819 | CA | VAL | B | 483 | −20.631 | 7.834 | −0.170 | 1.00 | 55.89 |
| 8820 | CB | VAL | B | 483 | −21.520 | 7.141 | 0.881 | 1.00 | 47.36 |
| 8821 | CG1 | VAL | B | 483 | −20.963 | 5.770 | 1.209 | 1.00 | 60.28 |
| 8822 | CG2 | VAL | B | 483 | −21.601 | 7.994 | 2.133 | 1.00 | 57.05 |
| 8823 | C | VAL | B | 483 | −19.264 | 8.141 | 0.461 | 1.00 | 51.40 |
| 8824 | O | VAL | B | 483 | −18.393 | 7.284 | 0.591 | 1.00 | 41.85 |
| 8825 | N | GLN | B | 484 | −19.125 | 9.395 | 0.855 | 1.00 | 33.25 |
| 8826 | CA | GLN | B | 484 | −17.949 | 9.933 | 1.483 | 1.00 | 47.57 |
| 8827 | CB | GLN | B | 484 | −18.149 | 11.439 | 1.611 | 1.00 | 41.25 |
| 8828 | CG | GLN | B | 484 | −17.125 | 12.176 | 2.408 | 1.00 | 64.98 |
| 8829 | CD | GLN | B | 484 | −17.341 | 13.664 | 2.309 | 1.00 | 70.10 |
| 8830 | OE1 | GLN | B | 484 | −16.918 | 14.432 | 3.176 | 1.00 | 81.81 |
| 8831 | NE2 | GLN | B | 484 | −18.003 | 14.086 | 1.241 | 1.00 | 76.07 |
| 8832 | C | GLN | B | 484 | −17.707 | 9.292 | 2.846 | 1.00 | 50.60 |
| 8833 | O | GLN | B | 484 | −18.557 | 9.373 | 3.719 | 1.00 | 59.93 |
| 8834 | N | LEU | B | 485 | −16.538 | 8.663 | 3.018 | 1.00 | 52.22 |
| 8835 | CA | LEU | B | 485 | −16.170 | 8.005 | 4.272 | 1.00 | 40.73 |
| 8836 | CB | LEU | B | 485 | −14.963 | 7.110 | 4.058 | 1.00 | 18.82 |
| 8837 | CG | LEU | B | 485 | −15.028 | 6.035 | 2.962 | 1.00 | 52.24 |
| 8838 | CD1 | LEU | B | 485 | −13.749 | 5.246 | 2.929 | 1.00 | 50.04 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8839 | CD2 | LEU | B | 485 | −16.167 | 5.093 | 3.209 | 1.00 | 43.46 |
| 8840 | C | LEU | B | 485 | −15.845 | 9.031 | 5.344 | 1.00 | 48.83 |
| 8841 | O | LEU | B | 485 | −15.514 | 10.180 | 5.038 | 1.00 | 44.23 |
| 8842 | N | PRO | B | 486 | −15.943 | 8.640 | 6.624 | 1.00 | 58.20 |
| 8843 | CD | PRO | B | 486 | −16.247 | 7.302 | 7.151 | 1.00 | 42.43 |
| 8844 | CA | PRO | B | 486 | −15.643 | 9.569 | 7.719 | 1.00 | 46.03 |
| 8845 | CB | PRO | B | 486 | −15.692 | 8.683 | 8.954 | 1.00 | 42.42 |
| 8846 | CG | PRO | B | 486 | −16.640 | 7.619 | 8.567 | 1.00 | 42.18 |
| 8847 | C | PRO | B | 486 | −14.259 | 10.142 | 7.507 | 1.00 | 45.53 |
| 8848 | O | PRO | B | 486 | −13.320 | 9.412 | 7.193 | 1.00 | 44.90 |
| 8849 | N | ASP | B | 487 | −14.125 | 11.448 | 7.679 | 1.00 | 57.98 |
| 8850 | CA | ASP | B | 487 | −12.841 | 12.102 | 7.478 | 1.00 | 62.71 |
| 8851 | CB | ASP | B | 487 | −12.992 | 13.603 | 7.741 | 1.00 | 72.70 |
| 8852 | CG | ASP | B | 487 | −11.910 | 14.428 | 7.065 | 1.00 | 112.21 |
| 8853 | OD1 | ASP | B | 487 | −10.746 | 14.401 | 7.529 | 1.00 | 126.74 |
| 8854 | OD2 | ASP | B | 487 | −12.223 | 15.102 | 6.059 | 1.00 | 117.07 |
| 8855 | C | ASP | B | 487 | −11.723 | 11.494 | 8.348 | 1.00 | 65.20 |
| 8856 | O | ASP | B | 487 | −10.555 | 11.454 | 7.939 | 1.00 | 77.42 |
| 8857 | N | ALA | B | 488 | −12.080 | 10.997 | 9.531 | 1.00 | 55.94 |
| 8858 | CA | ALA | B | 488 | −11.099 | 10.408 | 10.445 | 1.00 | 54.77 |
| 8859 | CB | ALA | B | 488 | −11.685 | 10.316 | 11.843 | 1.00 | 55.36 |
| 8860 | C | ALA | B | 488 | −10.560 | 9.038 | 10.035 | 1.00 | 45.50 |
| 8861 | O | ALA | B | 488 | −9.735 | 8.459 | 10.728 | 1.00 | 53.80 |
| 8862 | N | ARG | B | 489 | −11.022 | 8.524 | 8.908 | 1.00 | 46.13 |
| 8863 | CA | ARG | B | 489 | −10.582 | 7.224 | 8.425 | 1.00 | 48.29 |
| 8864 | CB | ARG | B | 489 | −11.698 | 6.584 | 7.594 | 1.00 | 61.46 |
| 8865 | CG | ARG | B | 489 | −12.659 | 5.729 | 8.395 | 1.00 | 42.13 |
| 8866 | CD | ARG | B | 489 | −12.299 | 4.255 | 8.268 | 1.00 | 16.81 |
| 8867 | NE | ARG | B | 489 | −12.997 | 3.590 | 7.159 | 1.00 | 30.91 |
| 8868 | CZ | ARG | B | 489 | −12.450 | 2.643 | 6.398 | 1.00 | 33.29 |
| 8869 | NH1 | ARG | B | 489 | −11.205 | 2.274 | 6.624 | 1.00 | 68.68 |
| 8870 | NH2 | ARG | B | 489 | −13.148 | 2.025 | 5.456 | 1.00 | 53.22 |
| 8871 | C | ARG | B | 489 | −9.322 | 7.321 | 7.586 | 1.00 | 55.20 |
| 8872 | O | ARG | B | 489 | −8.578 | 6.361 | 7.485 | 1.00 | 56.77 |
| 8873 | N | HIS | B | 490 | −9.088 | 8.481 | 6.978 | 1.00 | 49.46 |
| 8874 | CA | HIS | B | 490 | −7.918 | 8.665 | 6.133 | 1.00 | 34.73 |
| 8875 | CB | HIS | B | 490 | −8.340 | 9.104 | 4.726 | 1.00 | 51.90 |
| 8876 | CG | HIS | B | 490 | −8.802 | 10.525 | 4.645 | 1.00 | 45.37 |
| 8877 | CD2 | HIS | B | 490 | −10.000 | 11.056 | 4.310 | 1.00 | 50.80 |
| 8878 | ND1 | HIS | B | 490 | −7.977 | 11.593 | 4.929 | 1.00 | 53.45 |
| 8879 | CE1 | HIS | B | 490 | −8.648 | 12.720 | 4.777 | 1.00 | 38.03 |
| 8880 | NE2 | HIS | B | 490 | −9.879 | 12.422 | 4.401 | 1.00 | 59.92 |
| 8881 | C | HIS | B | 490 | −6.957 | 9.676 | 6.721 | 1.00 | 37.58 |
| 8882 | O | HIS | B | 490 | −7.318 | 10.460 | 7.588 | 1.00 | 47.28 |
| 8883 | N | SER | B | 491 | −5.722 | 9.653 | 6.244 | 1.00 | 34.76 |
| 8884 | CA | SER | B | 491 | −4.691 | 10.571 | 6.722 | 1.00 | 35.22 |
| 8885 | CB | SER | B | 491 | −3.595 | 9.784 | 7.451 | 1.00 | 28.28 |
| 8886 | OG | SER | B | 491 | −2.771 | 10.655 | 8.186 | 1.00 | 30.69 |
| 8887 | C | SER | B | 491 | −4.095 | 11.328 | 5.533 | 1.00 | 34.73 |
| 8888 | O | SER | B | 491 | −3.716 | 10.721 | 4.528 | 1.00 | 42.78 |
| 8889 | N | THR | B | 492 | −4.010 | 12.648 | 5.655 | 1.00 | 29.20 |
| 8890 | CA | THR | B | 492 | −3.470 | 13.492 | 4.579 | 1.00 | 33.77 |
| 8891 | CB | THR | B | 492 | −4.597 | 14.342 | 3.925 | 1.00 | 27.33 |
| 8892 | OG1 | THR | B | 492 | −5.571 | 13.459 | 3.340 | 1.00 | 51.33 |
| 8893 | CG2 | THR | B | 492 | −4.037 | 15.254 | 2.849 | 1.00 | 32.27 |
| 8894 | C | THR | B | 492 | −2.314 | 14.422 | 4.970 | 1.00 | 26.56 |
| 8895 | O | THR | B | 492 | −2.404 | 15.175 | 5.938 | 1.00 | 34.70 |
| 8896 | N | THR | B | 493 | −1.235 | 14.364 | 4.192 | 1.00 | 31.68 |
| 8897 | CA | THR | B | 493 | −0.019 | 15.176 | 4.420 | 1.00 | 25.35 |
| 8898 | CB | THR | B | 493 | 1.132 | 14.746 | 3.491 | 1.00 | 25.58 |
| 8899 | OG1 | THR | B | 493 | 0.736 | 14.977 | 2.120 | 1.00 | 43.27 |
| 8900 | CG2 | THR | B | 493 | 1.487 | 13.272 | 3.703 | 1.00 | 20.32 |
| 8901 | C | THR | B | 493 | −0.180 | 16.678 | 4.200 | 1.00 | 27.46 |
| 8902 | O | THR | B | 493 | −1.049 | 17.141 | 3.468 | 1.00 | 32.73 |
| 8903 | N | GLN | B | 494 | 0.683 | 17.444 | 4.840 | 1.00 | 39.95 |
| 8904 | CA | GLN | B | 494 | 0.656 | 18.886 | 4.676 | 1.00 | 51.99 |
| 8905 | CB | GLN | B | 494 | 1.534 | 19.555 | 5.736 | 1.00 | 69.23 |
| 8906 | CG | GLN | B | 494 | 1.104 | 19.271 | 7.166 | 1.00 | 91.00 |
| 8907 | CD | GLN | B | 494 | −0.219 | 19.919 | 7.515 | 1.00 | 103.84 |
| 8908 | OE1 | GLN | B | 494 | −0.339 | 21.145 | 7.517 | 1.00 | 111.01 |
| 8909 | NE2 | GLN | B | 494 | −1.222 | 19.098 | 7.811 | 1.00 | 109.11 |
| 8910 | C | GLN | B | 494 | 1.198 | 19.185 | 3.276 | 1.00 | 54.53 |
| 8911 | O | GLN | B | 494 | 2.065 | 18.467 | 2.765 | 1.00 | 45.27 |
| 8912 | N | PRO | B | 495 | 0.677 | 20.235 | 2.627 | 1.00 | 47.92 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8913 | CD | PRO | B | 495 | −0.503 | 21.025 | 3.008 | 1.00 | 55.10 |
| 8914 | CA | PRO | B | 495 | 1.128 | 20.603 | 1.284 | 1.00 | 45.35 |
| 8915 | CB | PRO | B | 495 | 0.292 | 21.827 | 0.971 | 1.00 | 45.26 |
| 8916 | CG | PRO | B | 495 | −0.983 | 21.535 | 1.674 | 1.00 | 36.35 |
| 8917 | C | PRO | B | 495 | 2.618 | 20.898 | 1.243 | 1.00 | 47.91 |
| 8918 | O | PRO | B | 495 | 3.156 | 21.512 | 2.150 | 1.00 | 55.26 |
| 8919 | N | ARG | B | 496 | 3.272 | 20.444 | 0.182 | 1.00 | 51.56 |
| 8920 | CA | ARG | B | 496 | 4.699 | 20.633 | −0.005 | 1.00 | 48.87 |
| 8921 | CB | ARG | B | 496 | 5.442 | 19.351 | 0.335 | 1.00 | 41.93 |
| 8922 | CG | ARG | B | 496 | 5.681 | 19.105 | 1.778 | 1.00 | 39.89 |
| 8923 | CD | ARG | B | 496 | 6.734 | 18.011 | 1.897 | 1.00 | 72.69 |
| 8924 | NE | ARG | B | 496 | 7.398 | 18.007 | 3.198 | 1.00 | 87.96 |
| 8925 | CZ | ARG | B | 496 | 8.657 | 17.628 | 3.378 | 1.00 | 80.43 |
| 8926 | NH1 | ARG | B | 496 | 9.376 | 17.228 | 2.331 | 1.00 | 72.82 |
| 8927 | NH2 | ARG | B | 496 | 9.196 | 17.649 | 4.594 | 1.00 | 80.58 |
| 8928 | C | ARG | B | 496 | 5.004 | 21.005 | −1.459 | 1.00 | 69.83 |
| 8929 | O | ARG | B | 496 | 4.274 | 20.609 | −2.376 | 1.00 | 64.15 |
| 8930 | N | LYS | B | 497 | 6.097 | 21.740 | −1.664 | 1.00 | 62.55 |
| 8931 | CA | LYS | B | 497 | 6.503 | 22.177 | −2.995 | 1.00 | 61.36 |
| 8932 | CB | LYS | B | 497 | 7.532 | 23.294 | −2.880 | 1.00 | 63.31 |
| 8933 | CG | LYS | B | 497 | 7.068 | 24.472 | −2.074 | 1.00 | 75.16 |
| 8934 | CD | LYS | B | 497 | 8.216 | 25.428 | −1.816 | 1.00 | 94.97 |
| 8935 | CE | LYS | B | 497 | 7.790 | 26.565 | −0.903 | 1.00 | 100.50 |
| 8936 | NZ | LYS | B | 497 | 8.914 | 27.501 | −0.638 | 1.00 | 106.15 |
| 8937 | C | LYS | B | 497 | 7.080 | 21.037 | −3.818 | 1.00 | 62.65 |
| 8938 | O | LYS | B | 497 | 7.927 | 20.294 | −3.342 | 1.00 | 60.01 |
| 8939 | N | THR | B | 498 | 6.612 | 20.907 | −5.054 | 1.00 | 66.74 |
| 8940 | CA | THR | B | 498 | 7.076 | 19.859 | −5.949 | 1.00 | 75.71 |
| 8941 | CB | THR | B | 498 | 6.088 | 19.632 | −7.110 | 1.00 | 79.93 |
| 8942 | OG1 | THR | B | 498 | 5.995 | 20.821 | −7.904 | 1.00 | 87.44 |
| 8943 | CG2 | THR | B | 498 | 4.709 | 19.293 | −6.580 | 1.00 | 78.69 |
| 8944 | C | THR | B | 498 | 8.415 | 20.252 | −6.529 | 1.00 | 87.87 |
| 8945 | O | THR | B | 498 | 9.448 | 19.732 | −6.145 | 1.00 | 97.85 |
| 8946 | N | LYS | B | 499 | 8.375 | 21.212 | −7.457 | 1.00 | 97.37 |
| 8947 | CA | LYS | B | 499 | 9.552 | 21.746 | −8.140 | 1.00 | 99.32 |
| 8948 | CB | LYS | B | 499 | 10.381 | 20.624 | −8.777 | 1.00 | 87.56 |
| 8949 | CG | LYS | B | 499 | 11.500 | 20.092 | −7.893 | 1.00 | 98.74 |
| 8950 | CD | LYS | B | 499 | 12.460 | 21.213 | −7.502 | 1.00 | 109.86 |
| 8951 | CE | LYS | B | 499 | 13.593 | 20.721 | −6.610 | 1.00 | 108.37 |
| 8952 | NZ | LYS | B | 499 | 14.530 | 21.835 | −6.242 | 1.00 | 98.10 |
| 8953 | C | LYS | B | 499 | 9.084 | 22.709 | −9.222 | 1.00 | 98.09 |
| 8954 | O | LYS | B | 499 | 9.209 | 22.422 | −10.407 | 1.00 | 91.97 |
| 8955 | N | GLY | B | 500 | 8.526 | 23.842 | −8.802 | 1.00 | 101.54 |
| 8956 | CA | GLY | B | 500 | 8.045 | 24.834 | −9.748 | 1.00 | 101.52 |
| 8957 | C | GLY | B | 500 | 6.563 | 24.736 | −10.092 | 1.00 | 103.58 |
| 8958 | O | GLY | B | 500 | 5.815 | 25.711 | −9.955 | 1.00 | 93.08 |
| 8959 | N | SER | B | 501 | 6.139 | 23.557 | −10.543 | 1.00 | 103.84 |
| 8960 | CA | SER | B | 501 | 4.747 | 23.321 | −10.928 | 1.00 | 103.33 |
| 8961 | CB | SER | B | 501 | 4.576 | 21.881 | −11.424 | 1.00 | 106.06 |
| 8962 | OG | SER | B | 501 | 4.862 | 20.954 | −10.390 | 1.00 | 120.10 |
| 8963 | C | SER | B | 501 | 3.728 | 23.598 | −9.817 | 1.00 | 100.41 |
| 8964 | O | SER | B | 501 | 2.547 | 23.826 | −10.105 | 1.00 | 102.78 |
| 8965 | N | GLY | B | 502 | 4.175 | 23.572 | −8.559 | 1.00 | 84.38 |
| 8966 | CA | GLY | B | 502 | 3.266 | 23.833 | −7.453 | 1.00 | 70.49 |
| 8967 | C | GLY | B | 502 | 3.458 | 22.959 | −6.221 | 1.00 | 58.05 |
| 8968 | O | GLY | B | 502 | 4.565 | 22.814 | −5.720 | 1.00 | 55.66 |
| 8969 | N | PHE | B | 503 | 2.374 | 22.380 | −5.721 | 1.00 | 44.03 |
| 8970 | CA | PHE | B | 503 | 2.453 | 21.533 | −4.549 | 1.00 | 43.53 |
| 8971 | CB | PHE | B | 503 | 1.651 | 22.131 | −3.404 | 1.00 | 29.32 |
| 8972 | CG | PHE | B | 503 | 1.987 | 23.531 | −3.102 | 1.00 | 33.93 |
| 8973 | CD1 | PHE | B | 503 | 1.511 | 24.559 | −3.909 | 1.00 | 42.19 |
| 8974 | CD2 | PHE | B | 503 | 2.765 | 23.848 | −1.994 | 1.00 | 33.28 |
| 8975 | CE1 | PHE | B | 503 | 1.804 | 25.895 | −3.613 | 1.00 | 33.43 |
| 8976 | CE2 | PHE | B | 503 | 3.067 | 25.176 | −1.685 | 1.00 | 52.37 |
| 8977 | CZ | PHE | B | 503 | 2.586 | 26.202 | −2.496 | 1.00 | 26.70 |
| 8978 | C | PHE | B | 503 | 1.943 | 20.117 | −4.770 | 1.00 | 41.75 |
| 8979 | O | PHE | B | 503 | 1.368 | 19.789 | −5.812 | 1.00 | 41.93 |
| 8980 | N | PHE | B | 504 | 2.159 | 19.283 | −3.761 | 1.00 | 32.31 |
| 8981 | CA | PHE | B | 504 | 1.700 | 17.908 | −3.792 | 1.00 | 42.38 |
| 8982 | CB | PHE | B | 504 | 2.796 | 16.960 | −4.308 | 1.00 | 40.15 |
| 8983 | CG | PHE | B | 504 | 3.849 | 16.622 | −3.286 | 1.00 | 52.34 |
| 8984 | CD1 | PHE | B | 504 | 3.631 | 15.616 | −2.347 | 1.00 | 38.49 |
| 8985 | CD2 | PHE | B | 504 | 5.070 | 17.297 | −3.278 | 1.00 | 50.17 |
| 8986 | CE1 | PHE | B | 504 | 4.599 | 15.289 | −1.428 | 1.00 | 38.27 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 8987 | CE2 | PHE | B | 504 | 6.046 | 16.973 | −2.357 | 1.00 | 45.24 |
| 8988 | CZ | PHE | B | 504 | 5.814 | 15.967 | −1.430 | 1.00 | 56.22 |
| 8989 | C | PHE | B | 504 | 1.252 | 17.502 | −2.403 | 1.00 | 35.87 |
| 8990 | O | PHE | B | 504 | 1.659 | 18.064 | −1.391 | 1.00 | 36.52 |
| 8991 | N | VAL | B | 505 | 0.392 | 16.509 | −2.369 | 1.00 | 35.03 |
| 8992 | CA | VAL | B | 505 | −0.139 | 16.016 | −1.129 | 1.00 | 17.36 |
| 8993 | CB | VAL | B | 505 | −1.483 | 16.752 | −0.809 | 1.00 | 27.09 |
| 8994 | CG1 | VAL | B | 505 | −2.624 | 15.784 | −0.716 | 1.00 | 37.31 |
| 8995 | CG2 | VAL | B | 505 | −1.336 | 17.558 | 0.451 | 1.00 | 36.63 |
| 8996 | C | VAL | B | 505 | −0.319 | 14.510 | −1.265 | 1.00 | 30.19 |
| 8997 | O | VAL | B | 505 | −0.548 | 13.989 | −2.350 | 1.00 | 23.28 |
| 8998 | N | PHE | B | 506 | −0.183 | 13.814 | −0.145 | 1.00 | 31.02 |
| 8999 | CA | PHE | B | 506 | −0.343 | 12.364 | −0.139 | 1.00 | 37.55 |
| 9000 | CB | PHE | B | 506 | 0.980 | 11.709 | 0.277 | 1.00 | 28.07 |
| 9001 | CG | PHE | B | 506 | 0.908 | 10.206 | 0.480 | 1.00 | 91.47 |
| 9002 | CD1 | PHE | B | 506 | 0.615 | 9.341 | −0.576 | 1.00 | 90.99 |
| 9003 | CD2 | PHE | B | 506 | 1.258 | 9.646 | 1.721 | 1.00 | 87.32 |
| 9004 | CE1 | PHE | B | 506 | 0.691 | 7.931 | −0.388 | 1.00 | 98.59 |
| 9005 | CE2 | PHE | B | 506 | 1.335 | 8.260 | 1.906 | 1.00 | 30.58 |
| 9006 | CZ | PHE | B | 506 | 1.056 | 7.400 | 0.858 | 1.00 | 54.01 |
| 9007 | C | PHE | B | 506 | −1.448 | 12.043 | 0.826 | 1.00 | 27.33 |
| 9008 | O | PHE | B | 506 | −1.607 | 12.722 | 1.820 | 1.00 | 42.58 |
| 9009 | N | SER | B | 507 | −2.238 | 11.036 | 0.512 | 1.00 | 30.14 |
| 9010 | CA | SER | B | 507 | −3.318 | 10.637 | 1.420 | 1.00 | 35.33 |
| 9011 | CB | SER | B | 507 | −4.682 | 11.160 | 0.933 | 1.00 | 47.15 |
| 9012 | OG | SER | B | 507 | −5.696 | 10.972 | 1.908 | 1.00 | 31.19 |
| 9013 | C | SER | B | 507 | −3.372 | 9.116 | 1.601 | 1.00 | 36.76 |
| 9014 | O | SER | B | 507 | −3.300 | 8.342 | 0.636 | 1.00 | 30.88 |
| 9015 | N | ARG | B | 508 | −3.509 | 8.713 | 2.862 | 1.00 | 30.34 |
| 9016 | CA | ARG | B | 508 | −3.558 | 7.304 | 3.215 | 1.00 | 32.84 |
| 9017 | CB | ARG | B | 508 | −2.473 | 7.027 | 4.253 | 1.00 | 27.28 |
| 9018 | CG | ARG | B | 508 | −2.256 | 5.598 | 4.591 | 1.00 | 20.52 |
| 9019 | CD | ARG | B | 508 | −1.015 | 5.466 | 5.470 | 1.00 | 45.26 |
| 9020 | NE | ARG | B | 508 | −0.918 | 4.134 | 6.046 | 1.00 | 43.61 |
| 9021 | CZ | ARG | B | 508 | −1.646 | 3.739 | 7.070 | 1.00 | 47.65 |
| 9022 | NH1 | ARG | B | 508 | −2.499 | 4.591 | 7.628 | 1.00 | 45.83 |
| 9023 | NH2 | ARG | B | 508 | −1.562 | 2.493 | 7.495 | 1.00 | 53.92 |
| 9024 | C | ARG | B | 508 | −4.908 | 6.866 | 3.744 | 1.00 | 31.70 |
| 9025 | O | ARG | B | 508 | −5.511 | 7.565 | 4.546 | 1.00 | 33.46 |
| 9026 | N | LEU | B | 509 | −5.379 | 5.716 | 3.266 | 1.00 | 31.95 |
| 9027 | CA | LEU | B | 509 | −6.647 | 5.125 | 3.709 | 1.00 | 16.60 |
| 9028 | CB | LEU | B | 509 | −7.743 | 5.390 | 2.701 | 1.00 | 31.46 |
| 9029 | CG | LEU | B | 509 | −9.081 | 4.782 | 3.105 | 1.00 | 25.50 |
| 9030 | CD1 | LEU | B | 509 | −9.675 | 5.619 | 4.235 | 1.00 | 24.67 |
| 9031 | CD2 | LEU | B | 509 | −10.016 | 4.718 | 1.918 | 1.00 | 29.16 |
| 9032 | C | LEU | B | 509 | −6.551 | 3.606 | 3.882 | 1.00 | 37.38 |
| 9033 | O | LEU | B | 509 | −6.408 | 2.878 | 2.881 | 1.00 | 35.37 |
| 9034 | N | GLU | B | 510 | −6.632 | 3.134 | 5.133 | 1.00 | 36.39 |
| 9035 | CA | GLU | B | 510 | −6.605 | 1.689 | 5.405 | 1.00 | 35.09 |
| 9036 | CB | GLU | B | 510 | −6.184 | 1.414 | 6.852 | 1.00 | 56.59 |
| 9037 | CG | GLU | B | 510 | −5.102 | 2.338 | 7.417 | 1.00 | 81.23 |
| 9038 | CD | GLU | B | 510 | −4.655 | 1.934 | 8.819 | 1.00 | 83.19 |
| 9039 | OE1 | GLU | B | 510 | −3.924 | 2.720 | 9.464 | 1.00 | 79.75 |
| 9040 | OE2 | GLU | B | 510 | −5.031 | 0.826 | 9.266 | 1.00 | 82.00 |
| 9041 | C | GLU | B | 510 | −8.024 | 1.139 | 5.185 | 1.00 | 38.02 |
| 9042 | O | GLU | B | 510 | −8.969 | 1.670 | 5.735 | 1.00 | 38.85 |
| 9043 | N | VAL | B | 511 | −8.167 | 0.098 | 4.373 | 1.00 | 29.36 |
| 9044 | CA | VAL | B | 511 | −9.471 | −0.508 | 4.110 | 1.00 | 36.20 |
| 9045 | CB | VAL | B | 511 | −9.863 | −0.350 | 2.601 | 1.00 | 43.10 |
| 9046 | CG1 | VAL | B | 511 | −9.843 | 1.137 | 2.225 | 1.00 | 29.65 |
| 9047 | CG2 | VAL | B | 511 | −8.946 | −1.147 | 1.709 | 1.00 | 18.27 |
| 9048 | C | VAL | B | 511 | −9.535 | −1.985 | 4.551 | 1.00 | 43.66 |
| 9049 | O | VAL | B | 511 | −8.505 | −2.638 | 4.694 | 1.00 | 39.33 |
| 9050 | N | THR | B | 512 | −10.747 | −2.507 | 4.760 | 1.00 | 53.35 |
| 9051 | CA | THR | B | 512 | −10.937 | −3.886 | 5.247 | 1.00 | 48.46 |
| 9052 | CB | THR | B | 512 | −11.818 | −3.912 | 6.502 | 1.00 | 32.17 |
| 9053 | OG1 | THR | B | 512 | −13.146 | −3.526 | 6.152 | 1.00 | 44.19 |
| 9054 | CG2 | THR | B | 512 | −11.285 | −2.961 | 7.562 | 1.00 | 55.53 |
| 9055 | C | THR | B | 512 | −11.523 | −4.927 | 4.297 | 1.00 | 47.14 |
| 9056 | O | THR | B | 512 | −12.347 | −4.614 | 3.449 | 1.00 | 47.97 |
| 9057 | N | ARG | B | 513 | −11.098 | −6.174 | 4.484 | 1.00 | 50.85 |
| 9058 | CA | ARG | B | 513 | −11.531 | −7.308 | 3.684 | 1.00 | 54.47 |
| 9059 | CB | ARG | B | 513 | −11.388 | −8.598 | 4.486 | 1.00 | 71.76 |
| 9060 | CG | ARG | B | 513 | −10.572 | −9.706 | 3.831 | 1.00 | 84.91 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 9061 | CD | ARG | B | 513 | −11.219 | −10.250 | 2.586 | 1.00 | 83.15 |
| 9062 | NE | ARG | B | 513 | −10.281 | −11.074 | 1.825 | 1.00 | 89.03 |
| 9063 | CZ | ARG | B | 513 | −10.516 | −11.538 | 0.600 | 1.00 | 95.30 |
| 9064 | NH1 | ARG | B | 513 | −11.665 | −11.267 | −0.011 | 1.00 | 95.05 |
| 9065 | NH2 | ARG | B | 513 | −9.594 | −12.254 | −0.026 | 1.00 | 90.75 |
| 9066 | C | ARG | B | 513 | −12.962 | −7.180 | 3.235 | 1.00 | 65.02 |
| 9067 | O | ARG | B | 513 | −13.261 | −7.413 | 2.075 | 1.00 | 67.29 |
| 9068 | N | ALA | B | 514 | −13.846 | −6.825 | 4.167 | 1.00 | 66.06 |
| 9069 | CA | ALA | B | 514 | −15.273 | −6.677 | 3.880 | 1.00 | 64.07 |
| 9070 | CB | ALA | B | 514 | −15.940 | −5.862 | 4.966 | 1.00 | 55.50 |
| 9071 | C | ALA | B | 514 | −15.526 | −6.048 | 2.508 | 1.00 | 81.31 |
| 9072 | O | ALA | B | 514 | −15.708 | −6.770 | 1.522 | 1.00 | 83.64 |
| 9073 | N | GLU | B | 515 | −15.532 | −4.717 | 2.436 | 1.00 | 76.15 |
| 9074 | CA | GLU | B | 515 | −15.752 | −4.039 | 1.161 | 1.00 | 57.53 |
| 9075 | CB | GLU | B | 515 | −15.901 | −2.541 | 1.356 | 1.00 | 43.34 |
| 9076 | CG | GLU | B | 515 | −14.706 | −1.867 | 2.011 | 1.00 | 66.45 |
| 9077 | CD | GLU | B | 515 | −14.802 | −1.852 | 3.517 | 1.00 | 74.12 |
| 9078 | OE1 | GLU | B | 515 | −15.120 | −2.925 | 4.070 | 1.00 | 58.82 |
| 9079 | OE2 | GLU | B | 515 | −14.552 | −0.780 | 4.135 | 1.00 | 62.66 |
| 9080 | C | GLU | B | 515 | −14.579 | −4.302 | 0.228 | 1.00 | 62.77 |
| 9081 | O | GLU | B | 515 | −14.721 | −4.222 | −0.988 | 1.00 | 60.33 |
| 9082 | N | TRP | B | 516 | −13.424 | −4.613 | 0.819 | 1.00 | 75.92 |
| 9083 | CA | TRP | B | 516 | −12.176 | −4.928 | 0.099 | 1.00 | 81.49 |
| 9084 | CB | TRP | B | 516 | −11.101 | −5.336 | 1.122 | 1.00 | 90.33 |
| 9085 | CG | TRP | B | 516 | −9.726 | −5.529 | 0.582 | 1.00 | 112.81 |
| 9086 | CD2 | TRP | B | 516 | −8.832 | −6.614 | 0.864 | 1.00 | 120.11 |
| 9087 | CE2 | TRP | B | 516 | −7.627 | −6.357 | 0.163 | 1.00 | 132.93 |
| 9088 | CE3 | TRP | B | 516 | −8.926 | −7.774 | 1.641 | 1.00 | 115.09 |
| 9089 | CD1 | TRP | B | 516 | −9.052 | −4.686 | −0.251 | 1.00 | 124.91 |
| 9090 | NE1 | TRP | B | 516 | −7.791 | −5.174 | −0.509 | 1.00 | 124.42 |
| 9091 | CZ2 | TRP | B | 516 | −6.519 | −7.225 | 0.216 | 1.00 | 128.19 |
| 9092 | CZ3 | TRP | B | 516 | −7.824 | −8.639 | 1.696 | 1.00 | 128.06 |
| 9093 | CH2 | TRP | B | 516 | −6.637 | −8.355 | 0.985 | 1.00 | 126.56 |
| 9094 | C | TRP | B | 516 | −12.438 | −6.078 | −0.877 | 1.00 | 89.10 |
| 9095 | O | TRP | B | 516 | −11.523 | −6.847 | −1.229 | 1.00 | 55.42 |
| 9096 | N | GLU | B | 517 | −13.708 | −6.181 | −1.278 | 1.00 | 81.94 |
| 9097 | CA | GLU | B | 517 | −14.201 | −7.193 | −2.192 | 1.00 | 92.61 |
| 9098 | CB | GLU | B | 517 | −14.990 | −8.251 | −1.410 | 1.00 | 94.48 |
| 9099 | CG | GLU | B | 517 | −14.106 | −9.008 | −0.427 | 1.00 | 108.43 |
| 9100 | CD | GLU | B | 517 | −14.766 | −10.226 | 0.170 | 1.00 | 114.16 |
| 9101 | OE1 | GLU | B | 517 | −15.731 | −10.064 | 0.945 | 1.00 | 118.97 |
| 9102 | OE2 | GLU | B | 517 | −14.314 | −11.348 | −0.136 | 1.00 | 111.26 |
| 9103 | C | GLU | B | 517 | −15.062 | −6.548 | −3.278 | 1.00 | 90.49 |
| 9104 | O | GLU | B | 517 | −15.459 | −7.209 | −4.244 | 1.00 | 86.21 |
| 9105 | N | ALA | B | 518 | −15.337 | −5.254 | −3.103 | 1.00 | 89.60 |
| 9106 | CA | ALA | B | 518 | −16.120 | −4.433 | −4.042 | 1.00 | 82.32 |
| 9107 | CB | ALA | B | 518 | −17.519 | −4.113 | −3.462 | 1.00 | 81.48 |
| 9108 | C | ALA | B | 518 | −15.291 | −3.165 | −4.132 | 1.00 | 76.42 |
| 9109 | O | ALA | B | 518 | −15.726 | −2.096 | −3.702 | 1.00 | 50.18 |
| 9110 | N | LYS | B | 519 | −14.086 | −3.305 | −4.681 | 1.00 | 77.14 |
| 9111 | CA | LYS | B | 519 | −13.144 | −2.193 | −4.772 | 1.00 | 81.74 |
| 9112 | CB | LYS | B | 519 | −11.734 | −2.699 | −5.092 | 1.00 | 82.56 |
| 9113 | CG | LYS | B | 519 | −11.039 | −3.458 | −3.975 | 1.00 | 93.53 |
| 9114 | CD | LYS | B | 519 | −9.516 | −3.309 | −4.103 | 1.00 | 96.48 |
| 9115 | CE | LYS | B | 519 | −8.752 | −4.384 | −3.351 | 1.00 | 85.10 |
| 9116 | NZ | LYS | B | 519 | −7.373 | −4.493 | −3.858 | 1.00 | 73.13 |
| 9117 | C | LYS | B | 519 | −13.177 | −1.090 | −5.748 | 1.00 | 76.33 |
| 9118 | O | LYS | B | 519 | −13.392 | 0.101 | −5.406 | 1.00 | 66.51 |
| 9119 | N | ASP | B | 520 | −13.819 | −1.487 | −6.968 | 1.00 | 63.76 |
| 9120 | CA | ASP | B | 520 | −14.150 | −0.540 | −8.040 | 1.00 | 92.53 |
| 9121 | CB | ASP | B | 520 | −15.116 | −1.202 | −9.035 | 1.00 | 96.04 |
| 9122 | CG | ASP | B | 520 | −14.553 | −2.484 | −9.631 | 1.00 | 106.22 |
| 9123 | OD1 | ASP | B | 520 | −13.600 | −2.401 | −10.435 | 1.00 | 113.17 |
| 9124 | OD2 | ASP | B | 520 | −15.061 | −3.573 | −9.288 | 1.00 | 105.46 |
| 9125 | C | ASP | B | 520 | −14.760 | 0.751 | −7.478 | 1.00 | 88.59 |
| 9126 | O | ASP | B | 520 | −14.842 | 1.791 | −8.167 | 1.00 | 62.29 |
| 9127 | N | GLU | B | 521 | −15.191 | 0.654 | −6.220 | 1.00 | 79.38 |
| 9128 | CA | GLU | B | 521 | −15.788 | 1.758 | −5.496 | 1.00 | 87.01 |
| 9129 | CB | GLU | B | 521 | −17.040 | 1.295 | −4.718 | 1.00 | 91.07 |
| 9130 | CG | GLU | B | 521 | −18.321 | 1.067 | −5.558 | 1.00 | 88.44 |
| 9131 | CD | GLU | B | 521 | −18.525 | −0.390 | −5.995 | 1.00 | 89.73 |
| 9132 | OE1 | GLU | B | 521 | −18.469 | −1.294 | −5.117 | 1.00 | 78.70 |
| 9133 | OE2 | GLU | B | 521 | −18.753 | −0.618 | −7.214 | 1.00 | 74.75 |
| 9134 | C | GLU | B | 521 | −14.807 | 2.429 | −4.538 | 1.00 | 79.92 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 9135 | O | GLU | B | 521 | −15.197 | 2.832 | −3.444 | 1.00 | 102.23 |
| 9136 | N | PHE | B | 522 | −13.538 | 2.532 | −4.918 | 1.00 | 54.15 |
| 9137 | CA | PHE | B | 522 | −12.588 | 3.247 | −4.064 | 1.00 | 50.18 |
| 9138 | CB | PHE | B | 522 | −11.422 | 2.342 | −3.668 | 1.00 | 56.41 |
| 9139 | CG | PHE | B | 522 | −11.751 | 1.436 | −2.518 | 1.00 | 63.63 |
| 9140 | CD1 | PHE | B | 522 | −11.764 | 0.048 | −2.671 | 1.00 | 36.84 |
| 9141 | CD2 | PHE | B | 522 | −12.134 | 1.982 | −1.292 | 1.00 | 49.56 |
| 9142 | CE1 | PHE | B | 522 | −12.163 | −0.769 | −1.624 | 1.00 | 42.57 |
| 9143 | CE2 | PHE | B | 522 | −12.533 | 1.168 | −0.237 | 1.00 | 38.02 |
| 9144 | CZ | PHE | B | 522 | −12.551 | −0.205 | −0.401 | 1.00 | 44.81 |
| 9145 | C | PHE | B | 522 | −12.126 | 4.532 | −4.772 | 1.00 | 45.93 |
| 9146 | O | PHE | B | 522 | −11.314 | 4.528 | −5.684 | 1.00 | 38.00 |
| 9147 | N | ILE | B | 523 | −12.674 | 5.645 | −4.326 | 1.00 | 32.57 |
| 9148 | CA | ILE | B | 523 | −12.386 | 6.921 | −4.938 | 1.00 | 22.82 |
| 9149 | CB | ILE | B | 523 | −13.693 | 7.557 | −5.484 | 1.00 | 42.07 |
| 9150 | CG2 | ILE | B | 523 | −13.424 | 8.982 | −6.002 | 1.00 | 41.49 |
| 9151 | CG1 | ILE | B | 523 | −14.278 | 6.650 | −6.579 | 1.00 | 43.89 |
| 9152 | CD1 | ILE | B | 523 | −15.452 | 7.271 | −7.324 | 1.00 | 32.32 |
| 9153 | C | ILE | B | 523 | −11.685 | 7.987 | −4.125 | 1.00 | 29.98 |
| 9154 | O | ILE | B | 523 | −12.106 | 8.367 | −3.032 | 1.00 | 33.53 |
| 9155 | N | CYS | B | 524 | −10.602 | 8.483 | −4.698 | 1.00 | 37.81 |
| 9156 | CA | CYS | B | 524 | −9.854 | 9.549 | −4.075 | 1.00 | 30.93 |
| 9157 | C | CYS | B | 524 | −10.244 | 10.810 | −4.857 | 1.00 | 35.16 |
| 9158 | O | CYS | B | 524 | −9.981 | 10.933 | −6.050 | 1.00 | 37.85 |
| 9159 | CB | CYS | B | 524 | −8.356 | 9.277 | −4.176 | 1.00 | 32.62 |
| 9160 | SG | CYS | B | 524 | −7.354 | 10.676 | −3.622 | 1.00 | 52.74 |
| 9161 | N | ARG | B | 525 | −10.897 | 11.734 | −4.171 | 1.00 | 30.18 |
| 9162 | CA | ARG | B | 525 | −11.345 | 12.955 | −4.791 | 1.00 | 19.44 |
| 9163 | CB | ARG | B | 525 | −12.858 | 13.021 | −4.725 | 1.00 | 39.03 |
| 9164 | CG | ARG | B | 525 | −13.439 | 14.195 | −5.462 | 1.00 | 51.07 |
| 9165 | CD | ARG | B | 525 | −14.918 | 14.013 | −5.593 | 1.00 | 43.86 |
| 9166 | NE | ARG | B | 525 | −15.603 | 14.339 | −4.356 | 1.00 | 69.23 |
| 9167 | CZ | ARG | B | 525 | −16.863 | 14.008 | −4.108 | 1.00 | 74.74 |
| 9168 | NH1 | ARG | B | 525 | −17.552 | 13.333 | −5.027 | 1.00 | 58.16 |
| 9169 | NH2 | ARG | B | 525 | −17.433 | 14.368 | −2.959 | 1.00 | 69.18 |
| 9170 | C | ARG | B | 525 | −10.763 | 14.198 | −4.148 | 1.00 | 34.37 |
| 9171 | O | ARG | B | 525 | −10.777 | 14.358 | −2.915 | 1.00 | 36.01 |
| 9172 | N | ALA | B | 526 | −10.258 | 15.089 | −4.989 | 1.00 | 27.53 |
| 9173 | CA | ALA | B | 526 | −9.657 | 16.308 | −4.490 | 1.00 | 27.52 |
| 9174 | CB | ALA | B | 526 | −8.249 | 16.467 | −5.057 | 1.00 | 25.01 |
| 9175 | C | ALA | B | 526 | −10.521 | 17.504 | −4.860 | 1.00 | 42.31 |
| 9176 | O | ALA | B | 526 | −11.121 | 17.558 | −5.942 | 1.00 | 39.83 |
| 9177 | N | VAL | B | 527 | −10.597 | 18.453 | −3.939 | 1.00 | 25.88 |
| 9178 | CA | VAL | B | 527 | −11.373 | 19.654 | −4.181 | 1.00 | 37.88 |
| 9179 | CB | VAL | B | 527 | −12.425 | 19.876 | −3.068 | 1.00 | 46.50 |
| 9180 | CG1 | VAL | B | 527 | −13.178 | 21.178 | −3.297 | 1.00 | 42.33 |
| 9181 | CG2 | VAL | B | 527 | −13.407 | 18.719 | −3.071 | 1.00 | 36.73 |
| 9182 | C | VAL | B | 527 | −10.406 | 20.817 | −4.238 | 1.00 | 34.25 |
| 9183 | O | VAL | B | 527 | −9.753 | 21.146 | −3.245 | 1.00 | 38.98 |
| 9184 | N | HIS | B | 528 | −10.309 | 21.425 | −5.416 | 1.00 | 33.02 |
| 9185 | CA | HIS | B | 528 | −9.404 | 22.543 | −5.617 | 1.00 | 34.63 |
| 9186 | CB | HIS | B | 528 | −8.084 | 22.016 | −6.202 | 1.00 | 30.65 |
| 9187 | CG | HIS | B | 528 | −7.001 | 23.042 | −6.267 | 1.00 | 41.55 |
| 9188 | CD2 | HIS | B | 528 | −6.039 | 23.368 | −5.378 | 1.00 | 36.61 |
| 9189 | ND1 | HIS | B | 528 | −6.860 | 23.916 | −7.323 | 1.00 | 27.45 |
| 9190 | CE1 | HIS | B | 528 | −5.855 | 24.734 | −7.082 | 1.00 | 48.29 |
| 9191 | NE2 | HIS | B | 528 | −5.339 | 24.424 | −5.908 | 1.00 | 38.16 |
| 9192 | C | HIS | B | 528 | −9.990 | 23.634 | −6.508 | 1.00 | 37.08 |
| 9193 | O | HIS | B | 528 | −10.643 | 23.353 | −7.517 | 1.00 | 34.41 |
| 9194 | N | GLU | B | 529 | −9.724 | 24.881 | −6.124 | 1.00 | 47.89 |
| 9195 | CA | GLU | B | 529 | −10.191 | 26.072 | −6.843 | 1.00 | 48.06 |
| 9196 | CB | GLU | B | 529 | −9.552 | 27.319 | −6.232 | 1.00 | 41.53 |
| 9197 | CG | GLU | B | 529 | −9.715 | 28.562 | −7.078 | 1.00 | 72.72 |
| 9198 | CD | GLU | B | 529 | −8.968 | 29.734 | −6.503 | 1.00 | 92.33 |
| 9199 | OE1 | GLU | B | 529 | −8.949 | 30.807 | −7.147 | 1.00 | 78.64 |
| 9200 | OE2 | GLU | B | 529 | −8.399 | 29.570 | −5.400 | 1.00 | 85.28 |
| 9201 | C | GLU | B | 529 | −9.938 | 26.091 | −8.357 | 1.00 | 52.06 |
| 9202 | O | GLU | B | 529 | −10.679 | 26.731 | −9.103 | 1.00 | 53.18 |
| 9203 | N | ALA | B | 530 | −8.891 | 25.401 | −8.801 | 1.00 | 52.41 |
| 9204 | CA | ALA | B | 530 | −8.542 | 25.380 | −10.213 | 1.00 | 48.31 |
| 9205 | CB | ALA | B | 530 | −7.049 | 25.593 | −10.355 | 1.00 | 40.40 |
| 9206 | C | ALA | B | 530 | −8.978 | 24.133 | −11.008 | 1.00 | 58.69 |
| 9207 | O | ALA | B | 530 | −8.817 | 24.074 | −12.228 | 1.00 | 51.80 |
| 9208 | N | ALA | B | 531 | −9.545 | 23.139 | −10.336 | 1.00 | 63.92 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 9209 | CA | ALA | B | 531 | −9.975 | 21.937 | −11.033 | 1.00 | 61.35 |
| 9210 | CB | ALA | B | 531 | −10.349 | 20.872 | −10.023 | 1.00 | 49.21 |
| 9211 | C | ALA | B | 531 | −11.146 | 22.211 | −11.975 | 1.00 | 68.86 |
| 9212 | O | ALA | B | 531 | −11.598 | 21.319 | −12.694 | 1.00 | 77.02 |
| 9213 | N | SER | B | 532 | −11.625 | 23.453 | −11.974 | 1.00 | 79.85 |
| 9214 | CA | SER | B | 532 | −12.749 | 23.871 | −12.819 | 1.00 | 95.82 |
| 9215 | CB | SER | B | 532 | −12.663 | 25.380 | −13.107 | 1.00 | 101.37 |
| 9216 | OG | SER | B | 532 | −11.461 | 25.727 | −13.780 | 1.00 | 99.62 |
| 9217 | C | SER | B | 532 | −12.876 | 23.098 | −14.143 | 1.00 | 89.51 |
| 9218 | O | SER | B | 532 | −11.884 | 22.817 | −14.820 | 1.00 | 89.46 |
| 9219 | N | PRO | B | 533 | −14.112 | 22.734 | −14.519 | 1.00 | 90.01 |
| 9220 | CD | PRO | B | 533 | −14.398 | 21.895 | −15.699 | 1.00 | 93.96 |
| 9221 | CA | PRO | B | 533 | −15.346 | 23.011 | −13.776 | 1.00 | 84.11 |
| 9222 | CB | PRO | B | 533 | −16.423 | 22.676 | −14.792 | 1.00 | 84.74 |
| 9223 | CG | PRO | B | 533 | −15.845 | 21.466 | −15.457 | 1.00 | 85.20 |
| 9224 | C | PRO | B | 533 | −15.458 | 22.117 | −12.547 | 1.00 | 83.10 |
| 9225 | O | PRO | B | 533 | −14.510 | 21.422 | −12.188 | 1.00 | 91.90 |
| 9226 | N | SER | B | 534 | −16.627 | 22.136 | −11.918 | 1.00 | 71.70 |
| 9227 | CA | SER | B | 534 | −16.897 | 21.311 | −10.751 | 1.00 | 64.53 |
| 9228 | CB | SER | B | 534 | −16.884 | 19.823 | −11.152 | 1.00 | 61.83 |
| 9229 | OG | SER | B | 534 | −15.633 | 19.420 | −11.702 | 1.00 | 57.63 |
| 9230 | C | SER | B | 534 | −15.962 | 21.529 | −9.566 | 1.00 | 51.23 |
| 9231 | O | SER | B | 534 | −16.318 | 21.225 | −8.430 | 1.00 | 59.10 |
| 9232 | N | GLN | B | 535 | −14.770 | 22.050 | −9.820 | 1.00 | 46.18 |
| 9233 | CA | GLN | B | 535 | −13.784 | 22.275 | −8.757 | 1.00 | 45.54 |
| 9234 | CB | GLN | B | 535 | −14.319 | 23.239 | −7.678 | 1.00 | 45.05 |
| 9235 | CG | GLN | B | 535 | −15.358 | 24.253 | −8.159 | 1.00 | 51.87 |
| 9236 | CD | GLN | B | 535 | −14.891 | 25.066 | −9.351 | 1.00 | 60.56 |
| 9237 | OE1 | GLN | B | 535 | −15.703 | 25.609 | −10.102 | 1.00 | 61.89 |
| 9238 | NE2 | GLN | B | 535 | −13.576 | 25.161 | −9.529 | 1.00 | 73.34 |
| 9239 | C | GLN | B | 535 | −13.347 | 20.965 | −8.089 | 1.00 | 47.83 |
| 9240 | O | GLN | B | 535 | −12.976 | 20.959 | −6.915 | 1.00 | 44.51 |
| 9241 | N | THR | B | 536 | −13.410 | 19.851 | −8.826 | 1.00 | 40.77 |
| 9242 | CA | THR | B | 536 | −12.945 | 18.583 | −8.278 | 1.00 | 47.35 |
| 9243 | CB | THR | B | 536 | −14.082 | 17.782 | −7.623 | 1.00 | 56.31 |
| 9244 | CG1 | THR | B | 536 | −14.959 | 17.294 | −8.635 | 1.00 | 45.94 |
| 9245 | CG2 | THR | B | 536 | −14.867 | 18.656 | −6.640 | 1.00 | 60.08 |
| 9246 | C | THR | B | 536 | −12.280 | 17.675 | −9.303 | 1.00 | 49.91 |
| 9247 | O | THR | B | 536 | −12.540 | 17.766 | −10.493 | 1.00 | 47.82 |
| 9248 | N | VAL | B | 537 | −11.400 | 16.805 | −8.823 | 1.00 | 34.83 |
| 9249 | CA | VAL | B | 537 | −10.733 | 15.827 | −9.670 | 1.00 | 33.53 |
| 9250 | CB | VAL | B | 537 | −9.259 | 16.213 | −9.988 | 1.00 | 44.14 |
| 9251 | CG1 | VAL | B | 537 | −8.819 | 15.525 | −11.288 | 1.00 | 28.85 |
| 9252 | CG2 | VAL | B | 537 | −9.110 | 17.718 | −10.109 | 1.00 | 39.40 |
| 9253 | C | VAL | B | 537 | −10.761 | 14.550 | −8.827 | 1.00 | 30.29 |
| 9254 | O | VAL | B | 537 | −10.721 | 14.609 | −7.604 | 1.00 | 39.98 |
| 9255 | N | GLN | B | 538 | −10.834 | 13.398 | −9.474 | 1.00 | 22.14 |
| 9256 | CA | GLN | B | 538 | −10.887 | 12.166 | −8.736 | 1.00 | 32.27 |
| 9257 | CB | GLN | B | 538 | −12.314 | 11.933 | −8.279 | 1.00 | 34.82 |
| 9258 | CG | GLN | B | 538 | −13.256 | 11.529 | −9.393 | 1.00 | 21.95 |
| 9259 | CD | GLN | B | 538 | −14.673 | 11.312 | −8.888 | 1.00 | 49.45 |
| 9260 | OE1 | GLN | B | 538 | −15.244 | 12.191 | −8.228 | 1.00 | 39.32 |
| 9261 | NE2 | GLN | B | 538 | −15.252 | 10.140 | −9.187 | 1.00 | 15.03 |
| 9262 | C | GLN | B | 538 | −10.411 | 10.968 | −9.527 | 1.00 | 32.35 |
| 9263 | O | GLN | B | 538 | −10.496 | 10.955 | −10.737 | 1.00 | 36.59 |
| 9264 | N | ARG | B | 539 | −9.913 | 9.956 | −8.827 | 1.00 | 32.38 |
| 9265 | CA | ARG | B | 539 | −9.441 | 8.741 | −9.475 | 1.00 | 34.56 |
| 9266 | CB | ARG | B | 539 | −7.917 | 8.724 | −9.563 | 1.00 | 39.29 |
| 9267 | CG | ARG | B | 539 | −7.373 | 7.972 | −10.769 | 1.00 | 63.23 |
| 9268 | CD | ARG | B | 539 | −6.824 | 8.946 | −11.824 | 1.00 | 97.65 |
| 9269 | NE | ARG | B | 539 | −7.800 | 9.957 | −12.245 | 1.00 | 109.11 |
| 9270 | CZ | ARG | B | 539 | −7.539 | 10.941 | −13.107 | 1.00 | 104.95 |
| 9271 | NH1 | ARG | B | 539 | −6.330 | 11.055 | −13.644 | 1.00 | 115.10 |
| 9272 | NH2 | ARG | B | 539 | −8.484 | 11.819 | −13.430 | 1.00 | 97.51 |
| 9273 | C | ARG | B | 539 | −9.940 | 7.563 | −8.666 | 1.00 | 29.63 |
| 9274 | O | ARG | B | 539 | −10.080 | 7.651 | −7.443 | 1.00 | 37.58 |
| 9275 | N | ALA | B | 540 | −10.222 | 6.466 | −9.360 | 1.00 | 26.90 |
| 9276 | CA | ALA | B | 540 | −10.738 | 5.256 | −8.729 | 1.00 | 33.19 |
| 9277 | CB | ALA | B | 540 | −11.870 | 4.719 | −9.517 | 1.00 | 16.83 |
| 9278 | C | ALA | B | 540 | −9.644 | 4.226 | −8.632 | 1.00 | 38.13 |
| 9279 | O | ALA | B | 540 | −8.802 | 4.177 | −9.503 | 1.00 | 36.75 |
| 9280 | N | VAL | B | 541 | −9.655 | 3.426 | −7.565 | 1.00 | 47.16 |
| 9281 | CA | VAL | B | 541 | −8.638 | 2.393 | −7.353 | 1.00 | 45.24 |
| 9282 | CB | VAL | B | 541 | −7.865 | 2.560 | −6.043 | 1.00 | 47.17 |

TABLE III-continued

Atomic coordinates of Crystal 3

| ATOM # | ATOM TYPE | RES | CHN | # | X | Y | Z | OCC | B |
|---|---|---|---|---|---|---|---|---|---|
| 9283 | CG1 | VAL | B | 541 | −6.464 | 2.085 | −6.248 | 1.00 | 32.29 |
| 9284 | CG2 | VAL | B | 541 | −7.917 | 3.980 | −5.554 | 1.00 | 54.14 |
| 9285 | C | VAL | B | 541 | −9.322 | 1.046 | −7.276 | 1.00 | 64.94 |
| 9286 | O | VAL | B | 541 | −10.240 | 0.853 | −6.474 | 1.00 | 36.20 |
| 9287 | N | SER | B | 542 | −8.812 | 0.125 | −8.090 | 1.00 | 77.96 |
| 9288 | CA | SER | B | 542 | −9.333 | −1.225 | −8.264 | 1.00 | 92.36 |
| 9289 | CB | SER | B | 542 | −8.896 | −1.724 | −9.646 | 1.00 | 98.03 |
| 9290 | OG | SER | B | 542 | −7.535 | −1.368 | −9.904 | 1.00 | 89.11 |
| 9291 | C | SER | B | 542 | −8.991 | −2.282 | −7.225 | 1.00 | 92.43 |
| 9292 | O | SER | B | 542 | −8.338 | −2.005 | −6.217 | 1.00 | 71.46 |
| 9293 | N | VAL | B | 543 | −9.444 | −3.505 | −7.520 | 1.00 | 112.53 |
| 9294 | CA | VAL | B | 543 | −9.252 | −4.698 | −6.689 | 1.00 | 112.08 |
| 9295 | CB | VAL | B | 543 | −10.264 | −5.824 | −7.061 | 1.00 | 113.88 |
| 9296 | CG1 | VAL | B | 543 | −9.966 | −7.083 | −6.244 | 1.00 | 111.67 |
| 9297 | CG2 | VAL | B | 543 | −11.698 | −5.358 | −6.808 | 1.00 | 106.63 |
| 9298 | C | VAL | B | 543 | −7.842 | −5.267 | −6.792 | 1.00 | 99.61 |
| 9299 | O | VAL | B | 543 | −7.644 | −6.205 | −7.593 | 1.00 | 89.50 |
| 9300 | OXT | VAL | B | 543 | −6.961 | −4.757 | −6.072 | 1.00 | 87.28 |

As used herein, an atomic coordinate, also referred to herein as a structure coordinate or coordinate, is a mathematical coordinate derived from mathematical equations related to the patterns obtained on diffraction of X-rays by the atoms of a protein or complex crystal. The diffraction data are typically used to calculate an electron density map, which is used to establish the positions of the individual atoms within the unit cell of the crystal. A model that substantially represents the atomic coordinates specified in Table 1, Table 2 or Table 3 of U.S. Patent Publication No. US-2001-0039479-A1 or the atomic coordinates specified in Table I, Table II or Table III includes not only models that literally represent the coordinates but also models representing a coordinate transformation of such atomic coordinates, for example, by changing the spatial orientation of the coordinates.

The present invention also includes a 3-D model that is a modification of a 3-D model that substantially represents the atomic coordinates specified in Table 1, Table 2 or Table 3 of U.S. Patent Publication No. US-2001-0039479-A1 or the atomic coordinates specified in Table I, Table II or Table III. As used herein, a modification, also referred to herein as a model modification, is a model that represents an antibody Fc region that binds to a Fc receptor protein. A model modification includes, but is not limited to: a refinement of the model that substantially represents the atomic coordinates specified in Table 1, Table 2 or Table 3 of U.S. Patent Publication No. US-2001-0039479-A1 or the atomic coordinates specified in Table I, Table II or Table III; a model representing any FcR-binding fragment of an antibody having the atomic coordinates specified in Table 1, Table 2 or Table 3 of U.S. Patent Publication No. US-2001-0039479-A1 or the atomic coordinates specified in Table I, Table II or Table III; a model based on other Fc-Cε3/Cε4 crystals, such as a model based on a crystal disclosed in the Examples; a model produced using homology modeling techniques to, for example, incorporate all or any part of the amino acid sequence of another Fc region into a 3-D model substantially representing the atomic coordinates specified in Table 1, Table 2 or Table 3 of U.S. Patent Publication No. US-2001-0039479-A1 or the atomic coordinates specified in Table I, Table II or Table III or incorporate all or any part of the amino acid sequence of a Fc-Cε3/Cε4 into a 3-D model of another antibody; and a modification representing a Fc region that has an altered function, which preferably can be used to design a mutein with an improved function compared to an unmodified protein. As used herein, the term unmodified protein refers to a protein that has not been intentionally subjected to either random or site-directed (i.e., targeted) mutagenesis. While not being bound by theory, it is believed that the flexibility of the Cε3 and Cε4 chains of the Fc region of IgE which allows the formation of open (receptor-bound) and closed conformations, can also lead to other dynamic conformations, all of which are included in the present invention. Such flexibility is also a target for identification of development of compounds to inhibit binding of IgE to its receptor. In one embodiment, the distance between two Cε3 domains of a Fc region of the present invention ranges from about 10 angstroms to about 25 angstroms. In another embodiment, the distance between two Cε3 domains of a Fc region of the present invention ranges from about 20 angstroms to about 40 angstroms, with a range of from about 20 to about 30 angstroms being preferred.

A model of the present invention can be represented in a variety of forms including, but not limited to, listing the coordinates of all atoms comprising the model, providing a physical 3-D model, imaging the model on a computer screen, providing a picture of said model, and deriving a set of coordinates based of a picture of the model, for example by extracting coordinates from a picture or placing a similar immunoglobulin domain into the 3-D model of a human Fc-Cε3/Cε4$_{222}$ protein having SEQ ID NO:2 or SEQ ID NO:8 and deriving a model of the similar domain. Physical 3-D models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Evans and Sutherland, Salt Lake City, Utah, Biosym Technologies, San Diego, Calif., Tripos, Inc., and Molecular Simulations Inc. The phrase "providing a picture of the model" refers to the ability to generate a "hard copy" of the model. Hard copies include both motion and still pictures. Computer screen images and pictures of the model can be visualized in a number of formats including, but not limited to, electron density maps, ribbon diagrams, space-filling representations, a carbon traces, topology diagrams, lists of interatomic vectors, phi/psi/chi angle representations of the coordinates, and contact maps, examples of some of which are shown in the Figures in U.S. Patent Publication No. US-2001-0039479-A1. Representations of the model can include the entire model or portions thereof. A model can also be represented in a database.

A model of the present invention also defines the space surrounding that model. Such a space can be represented as a mold, or alpha-space, that can be used to predict the shape of a compound that inhibits the binding of a FcR and antibody.

In one embodiment, a model of the present invention identifies the solvent accessability of amino acid residues of the corresponding proteins in the complex. The solvent accessibilities of the amino acids in PhFc-C$\epsilon$3/C$\epsilon$4$_{1\text{-}222}$ are indicated in Table 4 or Table 5 of U.S. Patent Publication No. US-2001-0039479-A1.

In another embodiment, the solvent accessibilities of the amino acids in Crystal 1 of Example 1 are indicated in Table IV.

TABLE IV

IgE-Fc Residue Exposure
Surface plot for Crystal 1:
structure file = C2_easy.mtf
coordinate set = C2_easy.pdb

| segid | resid | resname | residue | mainchain | sidechain |
|---|---|---|---|---|---|
| | | | total accessible area | | |
| A | 336 | VAL | 86.5350 | 62.2875 | 24.2476 |
| A | 337 | SER | 38.1446 | 0.9973 | 37.1472 |
| A | 338 | ALA | 8.0368 | 7.8654 | 0.1714 |
| A | 339 | TYR | 58.5685 | 5.6341 | 52.9344 |
| A | 340 | LEU | 30.2184 | 28.9269 | 1.2915 |
| A | 341 | SER | 60.8470 | 5.3893 | 55.4577 |
| A | 342 | ARG | 91.1293 | 19.8038 | 71.3254 |
| A | 343 | PRO | 11.4784 | 9.6918 | 1.7867 |
| A | 344 | SER | 44.1083 | 7.9488 | 36.1595 |
| A | 345 | PRO | 11.4167 | 0.2220 | 11.1947 |
| A | 346 | PHE | 59.7852 | 0.0000 | 59.7852 |
| A | 347 | ASP | 35.3006 | 0.0000 | 35.3006 |
| A | 348 | LEU | 11.7990 | 1.4247 | 10.3743 |
| A | 349 | PHE | 47.5126 | 15.3482 | 32.1644 |
| A | 350 | ILE | 80.6854 | 21.6013 | 59.0842 |
| A | 351 | ARG | 152.3072 | 29.0413 | 123.2659 |
| A | 352 | LYS | 21.5679 | 15.5636 | 106.0043 |
| A | 353 | SER | 164.7150 | 9.8901 | 54.8249 |
| A | 354 | PRO | 3.0388 | 2.1589 | 0.8799 |
| A | 355 | THR | 46.1823 | 5.0460 | 41.1364 |
| A | 356 | ILE | 2.0304 | 2.0304 | 0.0000 |
| A | 357 | THR | 45.3514 | 2.3949 | 42.9565 |
| A | 358 | CYS | 0.0000 | 0.0000 | 0.0000 |
| A | 359 | LEU | 23.3273 | 0.0012 | 23.3261 |
| A | 360 | VAL | 4.7629 | 0.0063 | 4.7567 |
| A | 361 | VAL | 10.4168 | 2.6890 | 7.7278 |
| A | 362 | ASP | 15.1481 | 0.0025 | 15.1456 |
| A | 363 | GLY | 43.5380 | 43.5380 | 0.0000 |
| A | 364 | ALA | 88.6270 | 23.8594 | 64.7676 |
| A | 365 | PRO | 64.7645 | 24.4713 | 40.2932 |
| A | 366 | SER | 54.0591 | 32.6190 | 21.4400 |
| A | 367 | LYS | 191.6776 | 24.2981 | 167.3794 |
| A | 368 | GLY | 20.5641 | 20.5641 | 0.0000 |
| A | 369 | THR | 127.0332 | 22.0017 | 105.0315 |
| A | 370 | VAL | 16.6581 | 3.0186 | 13.6395 |
| A | 371 | GLN | 102.3597 | 3.2240 | 99.1357 |
| A | 372 | LEU | 23.4307 | 20.7858 | 2.6448 |
| A | 373 | THR | 66.8913 | 5.4396 | 61.4516 |
| A | 374 | TRP | 25.6370 | 15.2770 | 10.3600 |
| A | 375 | SER | 45.3277 | 3.1881 | 42.1396 |
| A | 376 | ARG | 39.9468 | 10.6456 | 29.3012 |
| A | 377 | ALA | 65.7550 | 38.2384 | 27.5166 |

TABLE IV-continued

IgE-Fc Residue Exposure
Surface plot for Crystal 1:
structure file = C2_easy.mtf
coordinate set = C2_easy.pdb

| segid | resid | resname | residue | mainchain | sidechain |
|---|---|---|---|---|---|
| | | | total accessible area | | |
| A | 378 | SER | 64.4776 | 39.9799 | 24.4976 |
| A | 379 | GLY | 66.6713 | 66.6713 | 0.0000 |
| A | 380 | LYS | 123.8931 | 6.8377 | 117.0554 |
| A | 381 | PRO | 113.2876 | 16.6826 | 96.6050 |
| A | 382 | VAL | 57.7242 | 26.3139 | 31.4103 |
| A | 383 | GLN | 104.8662 | 14.9272 | 89.9389 |
| A | 384 | HIS | 67.4639 | 17.9524 | 49.5115 |
| A | 385 | SER | 28.6719 | 7.9482 | 20.7236 |
| A | 386 | THR | 12.9190 | 1.4516 | 11.4673 |
| A | 387 | ARG | 94.4362 | 8.8117 | 85.6246 |
| A | 388 | LYS | 87.8154 | 5.9528 | 81.8626 |
| A | 389 | GLU | 109.5556 | 27.7936 | 81.7620 |
| A | 390 | GLU | 82.2101 | 9.8618 | 72.3484 |
| A | 391 | ALA | 83.6229 | 20.1244 | 63.4985 |
| A | 392 | GLN | 36.2508 | 7.8395 | 28.4113 |
| A | 393 | ALA | 116.6876 | 48.3494 | 68.3381 |
| A | 394 | ASN | 75.9726 | 40.4868 | 35.4858 |
| A | 395 | GLY | 50.0798 | 50.0798 | 0.0000 |
| A | 396 | THR | 10.0444 | 3.0922 | 6.9522 |
| A | 397 | LEU | 54.3873 | 1.0538 | 53.3334 |
| A | 398 | THR | 7.9610 | 0.4051 | 7.5559 |
| A | 399 | VAL | 5.7881 | 0.0000 | 5.7881 |
| A | 400 | THR | 20.0901 | 0.0000 | 20.0901 |
| A | 401 | SER | 6.7002 | 0.0000 | 6.7002 |
| A | 402 | THR | 44.7350 | 1.5639 | 43.1711 |
| A | 403 | LEU | 2.3076 | 0.0026 | 2.3050 |
| A | 404 | PRO | 43.7729 | 3.1090 | 40.6638 |
| A | 405 | VAL | 12.5689 | 12.5005 | 0.0684 |
| A | 406 | GLY | 23.8156 | 23.8156 | 0.0000 |
| A | 407 | THR | 51.2036 | 4.8573 | 46.3464 |
| A | 408 | ARG | 149.7221 | 1.6444 | 148.0777 |
| A | 409 | ASP | 60.0845 | 4.0251 | 56.0594 |
| A | 410 | TRP | 11.0280 | 0.0798 | 10.9482 |
| A | 411 | ILE | 58.0941 | 7.2107 | 50.8834 |
| A | 412 | GLU | 126.6071 | 38.5526 | 88.0545 |
| A | 413 | GLY | 30.8875 | 30.8875 | 0.0000 |
| A | 414 | GLU | 25.6956 | 7.9244 | 17.7711 |
| A | 415 | THR | 37.5586 | 0.0038 | 37.5548 |
| A | 416 | TYR | 8.0826 | 0.0000 | 8.0826 |
| A | 417 | GLN | 65.9093 | 0.5079 | 65.4014 |
| A | 418 | CYS | 0.5124 | 0.5124 | 0.0000 |
| A | 419 | ARG | 115.8342 | 0.0000 | 115.8342 |
| A | 420 | VAL | 6.7478 | 2.6422 | 4.1056 |
| A | 421 | THR | 36.7560 | 0.9676 | 35.7884 |
| A | 422 | HIS | 13.4292 | 0.3284 | 13.1008 |
| A | 423 | PRO | 44.9749 | 19.5832 | 25.3916 |
| A | 424 | HIS | 129.6641 | 33.2319 | 96.4322 |
| A | 425 | LEU | 62.3855 | 5.2096 | 57.1759 |
| A | 426 | PRO | 124.6893 | 35.2881 | 89.4012 |
| A | 427 | ARG | 125.5319 | 17.5603 | 107.9717 |
| A | 428 | ALA | 52.3261 | 15.8853 | 36.4408 |
| A | 429 | LEU | 41.7344 | 6.4739 | 35.2605 |
| A | 430 | MET | 118.0707 | 18.9396 | 99.1312 |
| A | 431 | ARG | 88.7990 | 8.0113 | 80.7877 |
| A | 432 | SER | 71.9343 | 25.1585 | 46.7758 |
| A | 433 | THR | 10.7774 | 7.1170 | 3.6604 |
| A | 434 | THR | 60.1369 | 8.0637 | 52.0732 |
| A | 435 | LYS | 69.8460 | 11.2891 | 58.5570 |
| A | 436 | THR | 55.7860 | 10.2953 | 45.4906 |
| A | 437 | SER | 100.7003 | 20.5314 | 80.1689 |
| A | 438 | GLY | 43.5823 | 43.5823 | 0.0000 |
| A | 439 | PRO | 97.0364 | 11.9934 | 85.0431 |
| A | 440 | ARG | 91.1502 | 33.6586 | 57.4916 |
| A | 441 | ALA | 34.6369 | 6.9627 | 27.6741 |
| A | 442 | ALA | 52.0104 | 16.5535 | 35.4568 |
| A | 443 | PRO | 10.6239 | 10.2238 | 0.4002 |
| A | 444 | GLU | 64.7981 | 5.9673 | 58.8308 |
| A | 445 | VAL | 8.9441 | 8.0725 | 0.8716 |
| A | 446 | TYR | 78.6802 | 0.1667 | 78.5135 |
| A | 447 | ALA | 17.9693 | 17.4932 | 0.4761 |

TABLE IV-continued

IgE-Fc Residue Exposure  
Surface plot for Crystal 1:  
structure file = C2_easy.mtf  
coordinate set = C2_easy.pdb

| segid | resid | resname | residue | mainchain | sidechain |
|---|---|---|---|---|---|
| A | 448 | PHE | 122.9175 | 3.7058 | 119.2117 |
| A | 449 | ALA | 36.1722 | 28.0025 | 8.1697 |
| A | 450 | THR | 63.4896 | 6.3103 | 57.1793 |
| A | 451 | PRO | 111.2250 | 16.5764 | 94.6486 |
| A | 452 | GLU | 85.8461 | 24.7371 | 61.1090 |
| A | 453 | TRP | 199.0121 | 1.9357 | 197.0763 |
| A | 454 | PRO | 113.2244 | 25.2569 | 87.9675 |
| A | 455 | GLY | 88.6507 | 88.6507 | 0.0000 |
| A | 456 | SER | 29.1651 | 5.3069 | 23.8582 |
| A | 457 | ARG | 163.5197 | 3.7596 | 159.7600 |
| A | 458 | ASP | 83.0997 | 8.2671 | 74.8326 |
| A | 459 | LYS | 118.1242 | 5.9209 | 112.2033 |
| A | 460 | ARG | 31.7719 | 6.3640 | 25.4019 |
| A | 461 | THR | 34.9779 | 0.2836 | 34.6943 |
| A | 462 | LEU | 0.0494 | 0.0000 | 0.0494 |
| A | 463 | ALA | 39.2799 | 0.0408 | 39.2391 |
| A | 464 | CYS | 1.0439 | 1.0385 | 0.0054 |
| A | 465 | LEU | 32.1047 | 0.0000 | 32.1047 |
| A | 466 | ILE | 0.4612 | 0.0000 | 0.4612 |
| A | 467 | GLN | 44.6882 | 0.0000 | 44.6882 |
| A | 468 | ASN | 56.1813 | 5.7231 | 50.4583 |
| A | 469 | PHE | 0.0021 | 0.0000 | 0.0021 |
| A | 470 | MET | 41.4446 | 0.0000 | 41.4446 |
| A | 471 | CPR | 14.7328 | 5.0626 | 9.6702 |
| A | 472 | GLU | 73.1646 | 1.3961 | 71.7685 |
| A | 473 | ASP | 52.1007 | 7.1264 | 44.9743 |
| A | 474 | ILE | 34.8155 | 27.6012 | 7.2143 |
| A | 475 | SER | 19.2459 | 6.1445 | 13.1015 |
| A | 476 | VAL | 19.7315 | 15.7090 | 4.0224 |
| A | 477 | GLN | 17.2915 | 0.2891 | 17.0024 |
| A | 478 | TRP | 1.9379 | 1.1122 | 0.8257 |
| A | 479 | LEU | 19.8693 | 1.9468 | 17.9224 |
| A | 480 | HIS | 15.8140 | 1.8126 | 14.0014 |
| A | 481 | ASN | 98.1853 | 33.5336 | 64.6517 |
| A | 482 | ALA | 46.0305 | 34.7746 | 11.2558 |
| A | 483 | VAL | 25.1022 | 3.7550 | 21.3472 |
| A | 484 | GLN | 54.5365 | 4.1718 | 50.3646 |
| A | 485 | LEU | 20.5740 | 4.0960 | 16.4780 |
| A | 486 | PRO | 28.9164 | 4.8856 | 24.0309 |
| A | 487 | ASP | 100.7556 | 10.6010 | 90.1545 |
| A | 488 | ALA | 99.8025 | 39.3163 | 60.4862 |
| A | 489 | ARG | 79.3844 | 11.6796 | 67.7048 |
| A | 490 | HIS | 33.2465 | 17.8850 | 15.3615 |
| A | 491 | SER | 72.7565 | 7.0425 | 65.7140 |
| A | 492 | THR | 51.0975 | 26.9955 | 24.1020 |
| A | 493 | THR | 72.7425 | 11.5456 | 61.1969 |
| A | 494 | GLN | 117.7175 | 4.5973 | 113.1202 |
| A | 495 | PRO | 41.0258 | 12.6664 | 28.3594 |
| A | 496 | ARG | 136.1350 | 3.5511 | 132.5839 |
| A | 497 | LYS | 145.9613 | 22.6305 | 123.3308 |
| A | 498 | THR | 35.1130 | 17.3387 | 17.7743 |
| A | 499 | LYS | 214.0145 | 42.9145 | 171.1000 |
| A | 500 | GLY | 51.8407 | 51.8407 | 0.0000 |
| A | 501 | SER | 92.4451 | 28.0728 | 64.3723 |
| A | 502 | GLY | 2.4603 | 2.4603 | 0.0000 |
| A | 503 | PHE | 32.8295 | 0.0000 | 32.8295 |
| A | 504 | PHE | 56.3738 | 0.0000 | 56.3738 |
| A | 505 | VAL | 2.3735 | 0.0000 | 2.3735 |
| A | 506 | PHE | 100.4969 | 1.0604 | 99.4365 |
| A | 507 | SER | 3.5729 | 2.9946 | 0.5782 |
| A | 508 | ARG | 112.7175 | 1.2515 | 111.4659 |
| A | 509 | LEU | 0.3576 | 0.0000 | 0.3576 |
| A | 510 | GLU | 82.7072 | 4.1867 | 78.5205 |
| A | 511 | VAL | 3.1166 | 2.5543 | 0.5624 |
| A | 512 | THR | 66.0409 | 0.0000 | 66.0409 |
| A | 513 | ARG | 66.0522 | 0.1751 | 65.8772 |
| A | 514 | ALA | 77.0750 | 17.9174 | 59.1576 |
| A | 515 | GLU | 31.6321 | 4.1845 | 27.4476 |
| A | 516 | TRP | 28.5042 | 3.1115 | 25.3927 |
| A | 517 | GLU | 126.1752 | 37.4785 | 88.6967 |
| A | 518 | ALA | 83.3002 | 43.0229 | 40.2773 |
| A | 519 | LYS | 91.2236 | 5.9680 | 85.2556 |
| A | 520 | ASP | 51.5781 | 15.7715 | 35.8066 |
| A | 521 | GLU | 70.3316 | 2.9584 | 67.3731 |
| A | 522 | PHE | 1.4298 | 0.2100 | 1.2198 |
| A | 523 | ILE | 42.5807 | 0.0018 | 42.5789 |
| A | 524 | CYS | 0.3561 | 0.3513 | 0.0047 |
| A | 525 | ARG | 57.9069 | 0.1813 | 57.7255 |
| A | 526 | ALA | 0.2558 | 0.0769 | 0.1789 |
| A | 527 | VAL | 1.9182 | 0.0000 | 1.9182 |
| A | 528 | HIS | 1.3211 | 0.0000 | 1.3211 |
| A | 529 | GLU | 66.6525 | 14.1246 | 52.5279 |
| A | 530 | ALA | 29.2202 | 22.6821 | 6.5381 |
| A | 531 | ALA | 6.7148 | 6.6495 | 0.0653 |
| A | 532 | SER | 68.3360 | 15.7980 | 52.5380 |
| A | 533 | CPR | 68.4113 | 6.4531 | 61.9583 |
| A | 534 | SER | 64.1103 | 18.9721 | 45.1382 |
| A | 535 | GLN | 57.7545 | 0.4563 | 57.2982 |
| A | 536 | THR | 30.2550 | 5.5286 | 24.7263 |
| A | 537 | VAL | 40.0035 | 5.1346 | 34.8689 |
| A | 538 | GLN | 83.1497 | 21.2031 | 61.9466 |
| A | 539 | ARG | 106.3696 | 3.7658 | 102.6038 |
| A | 540 | ALA | 54.9406 | 26.9524 | 27.9882 |
| A | 541 | VAL | 21.3504 | 4.9296 | 16.4208 |
| A | 542 | SER | 47.6548 | 11.1363 | 36.5186 |
| A | 543 | VAL | 6.6168 | 0.4327 | 6.1841 |
| A | 544 | ASN | 188.0680 | 52.9307 | 135.1373 |
| B | 336 | VAL | 118.1033 | 61.0653 | 57.0380 |
| B | 337 | SER | 44.4403 | 6.1183 | 38.3220 |
| B | 338 | ALA | 7.3113 | 7.3113 | 0.0000 |
| B | 339 | TYR | 52.9442 | 5.5634 | 47.3808 |
| B | 340 | LEU | 34.0438 | 30.0676 | 3.9762 |
| B | 341 | SER | 41.2381 | 7.6054 | 33.6327 |
| B | 342 | ARG | 84.4108 | 18.2998 | 66.1110 |
| B | 343 | PRO | 10.2070 | 8.0155 | 2.1914 |
| B | 344 | SER | 49.2854 | 11.0459 | 38.2395 |
| B | 345 | PRO | 10.0028 | 0.5605 | 9.4424 |
| B | 346 | PHE | 37.6651 | 0.0000 | 37.6651 |
| B | 347 | ASP | 31.2803 | 0.0000 | 31.2803 |
| B | 348 | LEU | 11.3151 | 0.9082 | 10.4068 |
| B | 349 | PHE | 46.0219 | 18.7059 | 27.3160 |
| B | 350 | ILE | 52.4521 | 21.1229 | 31.3292 |
| B | 351 | ARG | 73.6219 | 9.9686 | 63.6533 |
| B | 352 | LYS | 125.8663 | 13.1744 | 112.6919 |
| B | 353 | SER | 29.8403 | 8.7316 | 21.1087 |
| B | 354 | PRO | 2.9117 | 2.1758 | 0.7359 |
| B | 355 | THR | 48.1208 | 4.8526 | 43.2683 |
| B | 356 | ILE | 0.3798 | 0.3798 | 0.0000 |
| B | 357 | THR | 40.8906 | 2.4505 | 38.4402 |
| B | 358 | CYS | 0.0000 | 0.0000 | 0.0000 |
| B | 359 | LEU | 14.8413 | 0.0000 | 14.8413 |
| B | 360 | VAL | 4.5547 | 0.4834 | 4.0714 |
| B | 361 | VAL | 16.5162 | 2.5172 | 13.9989 |
| B | 362 | ASP | 25.4930 | 0.0000 | 25.4930 |
| B | 363 | GLY | 53.1439 | 53.1439 | 0.0000 |
| B | 364 | ALA | 76.2389 | 12.4690 | 63.7699 |
| B | 365 | PRO | 47.2249 | 24.0279 | 23.1970 |
| B | 366 | SER | 53.8766 | 26.2418 | 27.6348 |
| B | 367 | LYS | 125.5506 | 31.1216 | 94.4290 |
| B | 368 | GLY | 52.0897 | 52.0897 | 0.0000 |
| B | 369 | THR | 79.8326 | 10.3320 | 69.5005 |
| B | 370 | VAL | 18.4585 | 1.8868 | 16.5717 |
| B | 371 | GLN | 92.5618 | 1.5220 | 91.0398 |
| B | 372 | LEU | 33.0848 | 29.1333 | 3.9515 |
| B | 373 | THR | 74.5806 | 4.2689 | 70.3116 |
| B | 374 | TRP | 22.7390 | 12.1395 | 10.5995 |
| B | 375 | SER | 48.3457 | 3.8975 | 44.4482 |
| B | 376 | ARG | 40.7418 | 14.0881 | 26.6536 |
| B | 377 | ALA | 83.9090 | 46.3041 | 37.6050 |
| B | 378 | SER | 65.2476 | 43.7479 | 21.4996 |

TABLE IV-continued

IgE-Fc Residue Exposure
Surface plot for Crystal 1:
structure file = C2_easy.mtf
coordinate set = C2_easy.pdb

| | | | total accessible area | | |
|---|---|---|---|---|---|
| segid | resid | resname | residue | mainchain | sidechain |
| B | 379 | GLY | 65.9217 | 65.9217 | 0.0000 |
| B | 380 | LYS | 118.5932 | 10.0325 | 108.5607 |
| B | 381 | PRO | 111.8369 | 16.3401 | 95.4968 |
| B | 382 | VAL | 54.3798 | 24.0078 | 30.3720 |
| B | 383 | GLN | 100.3339 | 20.7763 | 79.5576 |
| B | 384 | HIS | 136.8800 | 13.0800 | 123.8000 |
| B | 385 | SER | 37.4059 | 18.0087 | 19.3972 |
| B | 386 | THR | 83.1064 | 5.7222 | 77.3843 |
| B | 387 | ARG | 57.7657 | 17.7260 | 40.0397 |
| B | 388 | LYS | 100.1810 | 2.5659 | 97.6151 |
| B | 389 | GLU | 29.6441 | 7.4115 | 22.2327 |
| B | 390 | GLU | 84.4729 | 2.2760 | 82.1970 |
| B | 391 | LYS | 105.6866 | 30.9712 | 74.7154 |
| B | 392 | GLN | 44.2631 | 8.9945 | 35.2686 |
| B | 393 | ALA | 118.4094 | 49.3139 | 69.0955 |
| B | 394 | ASN | 76.8424 | 38.0877 | 38.7547 |
| B | 395 | GLY | 55.4232 | 55.4232 | 0.0000 |
| B | 396 | THR | 3.5886 | 0.7862 | 2.8024 |
| B | 397 | LEU | 20.1113 | 1.4181 | 18.6932 |
| B | 398 | THR | 6.3498 | 0.3434 | 6.0064 |
| B | 399 | VAL | 2.9517 | 0.1222 | 2.8295 |
| B | 400 | THR | 41.2067 | 1.0386 | 40.1681 |
| B | 401 | SER | 5.2072 | 1.0522 | 4.1551 |
| B | 402 | THR | 45.2623 | 1.6042 | 43.6580 |
| B | 403 | LEU | 1.6908 | 0.0019 | 1.6889 |
| B | 404 | PRO | 44.2621 | 3.1995 | 41.0627 |
| B | 405 | VAL | 13.8644 | 13.2901 | 0.5744 |
| B | 406 | GLY | 31.8143 | 31.8143 | 0.0000 |
| B | 407 | THR | 34.3572 | 3.2514 | 31.1058 |
| B | 408 | ARG | 174.7120 | 5.7016 | 169.0104 |
| B | 409 | ASP | 56.4427 | 5.9401 | 50.5026 |
| B | 410 | TRP | 5.8922 | 0.1525 | 5.7397 |
| B | 411 | ILE | 69.7546 | 15.0483 | 54.7063 |
| B | 412 | GLU | 125.1400 | 38.2965 | 86.8435 |
| B | 413 | GLY | 37.6145 | 37.6145 | 0.0000 |
| B | 414 | GLU | 24.9511 | 8.7064 | 16.2447 |
| B | 415 | THR | 43.9309 | 1.1869 | 42.7440 |
| B | 416 | TYR | 7.1133 | 0.1421 | 6.9712 |
| B | 417 | GLN | 53.3828 | 0.1139 | 53.2689 |
| B | 418 | CYS | 0.0000 | 0.0000 | 0.0000 |
| B | 419 | ARG | 95.5118 | 1.1601 | 94.3517 |
| B | 420 | VAL | 6.8465 | 0.2469 | 6.5996 |
| B | 421 | THR | 62.4202 | 5.5482 | 56.8720 |
| B | 422 | HIS | 41.6207 | 7.7756 | 33.8451 |
| B | 423 | PRO | 107.8765 | 31.7811 | 76.0954 |
| B | 424 | HIS | 137.6765 | 34.5153 | 103.1611 |
| B | 425 | LEU | 123.4505 | 11.0787 | 112.3717 |
| B | 426 | PRO | 115.5164 | 29.7613 | 85.7551 |
| B | 427 | ALA | 61.6441 | 27.2906 | 34.3535 |
| B | 428 | ALA | 45.6437 | 21.1106 | 24.5331 |
| B | 429 | LEU | 39.6151 | 1.9360 | 37.6791 |
| B | 430 | MET | 111.8250 | 21.0626 | 90.7624 |
| B | 431 | ARG | 86.2019 | 6.5973 | 79.6047 |
| B | 432 | SER | 74.5193 | 26.9694 | 47.5500 |
| B | 433 | THR | 12.3643 | 8.0010 | 4.3633 |
| B | 434 | THR | 52.3298 | 6.6360 | 45.6938 |
| B | 435 | LYS | 57.3722 | 13.0414 | 44.3308 |
| B | 436 | THR | 49.3801 | 13.8185 | 35.5616 |
| B | 437 | SER | 113.8087 | 35.0516 | 78.7571 |
| B | 438 | GLY | 32.7348 | 32.7348 | 0.0000 |
| B | 439 | PRO | 102.8905 | 14.1853 | 88.7052 |
| B | 440 | ARG | 136.1764 | 30.8595 | 105.3169 |
| B | 441 | ALA | 40.0822 | 8.2125 | 31.8697 |
| B | 442 | ALA | 50.0155 | 17.2386 | 32.7769 |
| B | 443 | PRO | 9.3878 | 9.3878 | 0.0000 |
| B | 444 | GLU | 65.5398 | 6.9191 | 58.6207 |
| B | 445 | VAL | 4.1673 | 4.0471 | 0.1203 |
| B | 446 | TYR | 92.4889 | 2.2914 | 90.1975 |
| B | 447 | ALA | 18.3891 | 18.2629 | 0.1262 |
| B | 448 | PHE | 122.3988 | 3.1615 | 119.2373 |
| B | 449 | ALA | 36.1136 | 28.2527 | 7.8609 |
| B | 450 | THR | 55.7083 | 4.0753 | 51.6329 |
| B | 451 | PRO | 109.2187 | 13.0992 | 96.1195 |
| B | 452 | ALA | 58.8399 | 24.9853 | 33.8545 |
| B | 453 | TRP | 198.9389 | 4.6705 | 194.2684 |
| B | 454 | PRO | 113.7778 | 31.5414 | 82.2365 |
| B | 455 | GLY | 86.0014 | 86.0014 | 0.0000 |
| B | 456 | SER | 51.9783 | 11.0174 | 40.9609 |
| B | 457 | ARG | 154.2434 | 4.4962 | 149.7473 |
| B | 458 | ASP | 56.2934 | 2.5858 | 53.7077 |
| B | 459 | LYS | 124.6000 | 9.3668 | 115.2332 |
| B | 460 | ARG | 50.9819 | 7.0382 | 43.9437 |
| B | 461 | THR | 36.1395 | 0.1554 | 35.9841 |
| B | 462 | LEU | 0.3513 | 0.0000 | 0.3513 |
| B | 463 | ALA | 36.6294 | 0.0393 | 36.5901 |
| B | 464 | CYS | 0.4165 | 0.4165 | 0.0000 |
| B | 465 | LEU | 30.9358 | 0.0584 | 30.8774 |
| B | 466 | ILE | 0.0178 | 0.0017 | 0.0161 |
| B | 467 | GLN | 44.4411 | 0.0010 | 44.4401 |
| B | 468 | ASN | 53.1302 | 5.7045 | 47.4257 |
| B | 469 | PHE | 0.0000 | 0.0000 | 0.0000 |
| B | 470 | MET | 52.1836 | 0.0024 | 52.1811 |
| B | 471 | CPR | 11.8840 | 1.6934 | 10.1905 |
| B | 472 | GLU | 66.6792 | 2.1603 | 64.5189 |
| B | 473 | ASP | 36.4675 | 8.3774 | 28.0901 |
| B | 474 | ILE | 35.9773 | 26.9877 | 8.9896 |
| B | 475 | SER | 18.6153 | 6.1093 | 12.5060 |
| B | 476 | VAL | 19.8419 | 15.3482 | 4.4937 |
| B | 477 | GLN | 6.3749 | 0.4878 | 5.8871 |
| B | 478 | TRP | 4.3349 | 1.6070 | 2.7280 |
| B | 479 | LEU | 23.2685 | 1.4763 | 21.7923 |
| B | 480 | HIS | 14.4717 | 4.8764 | 9.5952 |
| B | 481 | ASN | 52.7101 | 9.0850 | 43.6252 |
| B | 482 | GLU | 136.3956 | 28.9367 | 107.4589 |
| B | 483 | VAL | 75.2955 | 0.2944 | 75.0010 |
| B | 484 | GLN | 38.2396 | 14.4019 | 23.8377 |
| B | 485 | LEU | 30.6340 | 7.0944 | 23.5396 |
| B | 486 | PRO | 81.0671 | 12.2155 | 68.8516 |
| B | 487 | ASP | 100.1034 | 6.6155 | 93.4879 |
| B | 488 | ALA | 105.0515 | 43.3435 | 61.7080 |
| B | 489 | ARG | 70.2719 | 20.5393 | 49.7326 |
| B | 490 | HIS | 41.0817 | 19.6230 | 21.4586 |
| B | 491 | SER | 68.9723 | 6.0122 | 62.9601 |
| B | 492 | THR | 56.0350 | 29.3525 | 26.6824 |
| B | 493 | THR | 73.5880 | 13.4099 | 60.1782 |
| B | 494 | GLN | 144.0897 | 6.4835 | 137.6062 |
| B | 495 | PRO | 60.6503 | 19.2047 | 41.4456 |
| B | 496 | ARG | 160.6323 | 4.9362 | 155.6961 |
| B | 497 | LYS | 149.8178 | 22.4240 | 127.3938 |
| B | 498 | THR | 29.9271 | 13.9111 | 16.0161 |
| B | 499 | LYS | 203.8692 | 33.6443 | 170.2249 |
| B | 500 | GLY | 67.0397 | 67.0397 | 0.0000 |
| B | 501 | SER | 85.8542 | 13.1628 | 72.6915 |
| B | 502 | GLY | 10.6018 | 10.6018 | 0.0000 |
| B | 503 | PHE | 35.1535 | 0.0000 | 35.1535 |
| B | 504 | PHE | 52.6470 | 0.0045 | 52.6425 |
| B | 505 | VAL | 1.2666 | 0.0000 | 1.2666 |
| B | 506 | PHE | 96.4636 | 1.6721 | 94.7916 |
| B | 507 | SER | 2.1504 | 2.1504 | 0.0000 |
| B | 508 | ARG | 118.9119 | 3.5884 | 115.3235 |
| B | 509 | LEU | 0.8188 | 0.1248 | 0.6940 |
| B | 510 | GLU | 106.9255 | 5.6630 | 101.2625 |
| B | 511 | VAL | 4.9657 | 4.5737 | 0.3921 |
| B | 512 | THR | 32.9693 | 0.0000 | 32.9693 |
| B | 513 | ARG | 67.4033 | 0.0015 | 67.4019 |
| B | 514 | ALA | 73.0099 | 19.1730 | 53.8368 |
| B | 515 | GLU | 38.5565 | 4.6644 | 33.8921 |
| B | 516 | TRP | 26.4513 | 2.5435 | 23.9078 |
| B | 517 | GLU | 120.5848 | 35.8899 | 84.6949 |
| B | 518 | GLN | 118.3129 | 39.2696 | 79.0433 |

TABLE IV-continued

IgE-Fc Residue Exposure
Surface plot for Crystal 1:
structure file = C2_easy.mtf
coordinate set = C2_easy.pdb

| | | | total accessible area | | |
|---|---|---|---|---|---|
| segid | resid | resname | residue | mainchain | sidechain |
| B | 519 | LYS | 68.4606 | 5.0088 | 63.4518 |
| B | 520 | ASP | 45.3206 | 14.3408 | 30.9798 |
| B | 521 | GLU | 81.7370 | 3.8192 | 77.9178 |
| B | 522 | PHE | 1.0228 | 0.1796 | 0.8432 |
| B | 523 | ILE | 42.5544 | 0.0008 | 42.5536 |
| B | 524 | CYS | 0.2555 | 0.1636 | 0.0919 |
| B | 525 | ARG | 40.3384 | 0.0000 | 40.3384 |
| B | 526 | ALA | 0.6568 | 0.5303 | 0.1265 |
| B | 527 | VAL | 0.0459 | 0.0000 | 0.0459 |
| B | 528 | HIS | 0.2391 | 0.0836 | 0.1555 |
| B | 529 | GLU | 43.0331 | 19.6839 | 23.3492 |
| B | 530 | ALA | 25.5689 | 22.0259 | 3.5430 |
| B | 531 | ALA | 3.9877 | 3.5972 | 0.3905 |
| B | 532 | SER | 92.3107 | 23.4483 | 68.8624 |
| B | 533 | CPR | 129.1178 | 26.7487 | 102.3691 |
| B | 534 | SER | 64.6976 | 10.2825 | 54.4151 |
| B | 535 | GLN | 44.9678 | 0.0000 | 44.9678 |
| B | 536 | THR | 39.1974 | 12.1620 | 27.0354 |
| B | 537 | VAL | 32.6656 | 6.2796 | 26.3860 |
| B | 538 | GLN | 83.5925 | 11.3174 | 72.2751 |
| B | 539 | ARG | 116.5750 | 5.4566 | 111.1184 |
| B | 540 | ALA | 50.8640 | 25.3466 | 25.5174 |
| B | 541 | VAL | 23.6494 | 8.1470 | 15.5024 |
| B | 542 | SER | 48.1836 | 12.9024 | 35.2812 |
| B | 543 | VAL | 16.4934 | 12.1301 | 4.3633 |
| B | 544 | ASN | 180.1565 | 47.7001 | 132.4563 |
| E | 336 | VAL | 92.4483 | 56.9193 | 35.5290 |
| E | 337 | SER | 40.7631 | 3.6174 | 37.1457 |
| E | 338 | ALA | 7.5754 | 6.9965 | 0.5788 |
| E | 339 | TYR | 59.5250 | 4.1928 | 55.3322 |
| E | 340 | LEU | 35.5740 | 32.1565 | 3.4176 |
| E | 341 | SER | 41.1811 | 5.6948 | 35.4863 |
| E | 342 | ARG | 85.4987 | 19.1810 | 66.3176 |
| E | 343 | PRO | 12.7604 | 10.5589 | 2.2014 |
| E | 344 | SER | 41.6381 | 7.9259 | 33.7122 |
| E | 345 | PRO | 11.2493 | 0.4002 | 10.8491 |
| E | 346 | PHE | 55.8919 | 0.0000 | 55.8919 |
| E | 347 | ASP | 31.3854 | 0.0000 | 31.3854 |
| E | 348 | LEU | 15.4207 | 2.3001 | 13.1206 |
| E | 349 | PHE | 42.9758 | 8.6156 | 34.3602 |
| E | 350 | ILE | 81.2825 | 17.6452 | 63.6372 |
| E | 351 | ARG | 137.5761 | 30.6293 | 106.9468 |
| E | 352 | LYS | 132.1144 | 19.6936 | 112.4208 |
| E | 353 | SER | 48.7837 | 7.5274 | 41.2563 |
| E | 354 | PRO | 3.1759 | 1.0416 | 2.1344 |
| E | 355 | THR | 45.3624 | 5.9917 | 39.3707 |
| E | 356 | ILE | 0.9000 | 0.9000 | 0.0000 |
| E | 357 | THR | 40.5065 | 2.8039 | 37.7025 |
| E | 358 | CYS | 0.0000 | 0.0000 | 0.0000 |
| E | 359 | LEU | 17.1470 | 0.0000 | 17.1470 |
| E | 360 | VAL | 3.3984 | 0.2434 | 3.1550 |
| E | 361 | VAL | 11.6574 | 2.1610 | 9.4964 |
| E | 362 | ASP | 10.5584 | 0.0000 | 10.5584 |
| E | 363 | GLY | 48.6706 | 48.6706 | 0.0000 |
| E | 364 | ALA | 85.6760 | 20.1428 | 65.5332 |
| E | 365 | PRO | 69.6068 | 25.4494 | 44.1575 |
| E | 366 | SER | 50.1537 | 22.1076 | 28.0461 |
| E | 367 | LYS | 179.4850 | 23.3191 | 156.0859 |
| E | 368 | GLY | 40.5367 | 40.5367 | 0.0000 |
| E | 369 | THR | 91.6952 | 19.5873 | 72.1079 |
| E | 370 | VAL | 11.5837 | 0.6350 | 10.9486 |
| E | 371 | GLN | 90.6578 | 0.2062 | 90.4516 |
| E | 372 | LEU | 28.8003 | 25.9380 | 2.8623 |
| E | 373 | THR | 72.8713 | 4.3762 | 68.4951 |
| E | 374 | TRP | 21.7512 | 14.1919 | 7.5593 |
| E | 375 | SER | 47.5026 | 3.2751 | 44.2276 |
| E | 376 | ARG | 43.4788 | 15.2407 | 28.2381 |
| E | 377 | ALA | 72.9605 | 40.4877 | 32.4727 |
| E | 378 | SER | 47.5887 | 30.9371 | 16.6515 |
| E | 379 | GLY | 54.0807 | 54.0807 | 0.0000 |
| E | 380 | LYS | 121.9015 | 9.7744 | 112.1270 |
| E | 381 | PRO | 85.5523 | 15.3209 | 70.2314 |
| E | 382 | VAL | 53.2165 | 25.0765 | 28.1400 |
| E | 383 | GLN | 99.7412 | 11.5076 | 88.2336 |
| E | 384 | HIS | 158.6358 | 16.5720 | 142.0638 |
| E | 385 | SER | 54.1420 | 30.0194 | 24.1227 |
| E | 386 | THR | 91.1273 | 5.8509 | 85.2764 |
| E | 387 | ARG | 99.0437 | 28.5968 | 70.4469 |
| E | 388 | LYS | 110.8531 | 6.2966 | 104.5565 |
| E | 389 | GLU | 95.9337 | 29.2949 | 66.6388 |
| E | 390 | GLU | 93.4798 | 5.7163 | 87.7634 |
| E | 391 | LYS | 170.3516 | 17.6032 | 152.7483 |
| E | 392 | GLN | 44.2155 | 15.6557 | 28.5598 |
| E | 393 | ALA | 110.0297 | 43.7081 | 66.3216 |
| E | 394 | ASN | 70.0698 | 36.8847 | 33.1851 |
| E | 395 | GLY | 48.9765 | 48.9765 | 0.0000 |
| E | 396 | THR | 4.4758 | 0.4574 | 4.0184 |
| E | 397 | LEU | 37.8150 | 0.1867 | 37.6284 |
| E | 398 | THR | 7.2185 | 0.7704 | 6.4481 |
| E | 399 | VAL | 2.4224 | 0.0239 | 2.3984 |
| E | 400 | THR | 20.0807 | 0.4269 | 19.6538 |
| E | 401 | SER | 5.0281 | 0.0494 | 4.9787 |
| E | 402 | THR | 47.6055 | 0.7841 | 46.8214 |
| E | 403 | LEU | 1.0489 | 0.0000 | 1.0489 |
| E | 404 | PRO | 51.6314 | 2.5220 | 49.1094 |
| E | 405 | VAL | 11.1150 | 10.8181 | 0.2970 |
| E | 406 | GLY | 25.5043 | 25.5043 | 0.0000 |
| E | 407 | THR | 47.0411 | 3.6524 | 43.3886 |
| E | 408 | ARG | 178.3382 | 1.6924 | 176.6458 |
| E | 409 | ASP | 55.0105 | 6.5389 | 48.4716 |
| E | 410 | TRP | 10.6668 | 0.0000 | 10.6668 |
| E | 411 | ILE | 68.6990 | 7.4516 | 61.2474 |
| E | 412 | GLU | 124.0256 | 39.8591 | 84.1665 |
| E | 413 | GLY | 24.8658 | 24.8658 | 0.0000 |
| E | 414 | GLU | 25.1523 | 7.5722 | 17.5801 |
| E | 415 | THR | 7.2875 | 0.5345 | 6.7530 |
| E | 416 | TYR | 5.3741 | 0.4506 | 4.9235 |
| E | 417 | GLN | 62.0296 | 0.6130 | 61.4166 |
| E | 418 | CYS | 0.0002 | 0.0002 | 0.0000 |
| E | 419 | ARG | 102.8398 | 0.8899 | 101.9499 |
| E | 420 | VAL | 5.1622 | 0.4191 | 4.7430 |
| E | 421 | THR | 54.6453 | 0.7996 | 53.8457 |
| E | 422 | HIS | 21.2053 | 7.4685 | 13.7367 |
| E | 423 | PRO | 54.8889 | 32.3395 | 22.5494 |
| E | 424 | HIS | 118.2466 | 42.9979 | 75.2487 |
| E | 425 | LEU | 50.8990 | 22.3652 | 28.5339 |
| E | 426 | PRO | 115.7232 | 23.8066 | 91.9165 |
| E | 427 | ARG | 217.9187 | 23.2029 | 194.7158 |
| E | 428 | ALA | 29.0329 | 19.1131 | 9.9199 |
| E | 429 | LEU | 56.3349 | 2.0770 | 54.2579 |
| E | 430 | MET | 121.7947 | 20.7839 | 101.0108 |
| E | 431 | ARG | 84.7115 | 6.0866 | 78.6249 |
| E | 432 | SER | 74.3609 | 26.7533 | 47.6076 |
| E | 433 | THR | 11.3329 | 6.6590 | 4.6739 |
| E | 434 | THR | 39.7546 | 4.0927 | 35.6619 |
| E | 435 | LYS | 57.3331 | 14.7689 | 42.5642 |
| E | 436 | THR | 50.1961 | 12.2239 | 37.9722 |
| E | 437 | SER | 97.2259 | 30.2784 | 66.9475 |
| E | 438 | GLY | 48.4636 | 48.4636 | 0.0000 |
| E | 439 | PRO | 95.1687 | 15.0071 | 80.1616 |
| E | 440 | ARG | 134.4354 | 30.6746 | 103.7608 |
| E | 441 | ALA | 36.2072 | 8.2328 | 27.9744 |
| E | 442 | ALA | 50.3466 | 16.8889 | 33.4577 |
| E | 443 | PRO | 9.7593 | 8.9974 | 0.7619 |
| E | 444 | GLU | 64.4052 | 5.2774 | 59.1278 |
| E | 445 | VAL | 14.6955 | 13.9522 | 0.7434 |
| E | 446 | TYR | 97.1565 | 1.2900 | 95.8665 |
| E | 447 | ALA | 16.4346 | 16.4346 | 0.0000 |
| E | 448 | PHE | 119.4588 | 3.3867 | 116.0720 |
| E | 449 | ALA | 34.1893 | 27.8246 | 6.3647 |

TABLE IV-continued

IgE-Fc Residue Exposure
Surface plot for Crystal 1:
structure file = C2_easy.mtf
coordinate set = C2_easy.pdb

| segid | resid | resname | residue | mainchain | sidechain |
|---|---|---|---|---|---|
| E | 450 | THR | 62.8056 | 3.4259 | 59.3797 |
| E | 451 | PRO | 99.5793 | 13.5374 | 86.0419 |
| E | 452 | GLU | 103.0379 | 25.4855 | 77.5524 |
| E | 453 | TRP | 191.8190 | 1.7432 | 190.0758 |
| E | 454 | PRO | 124.0582 | 31.0820 | 92.9762 |
| E | 455 | GLY | 88.3799 | 88.3799 | 0.0000 |
| E | 456 | SER | 68.3532 | 6.6052 | 61.7479 |
| E | 457 | ALA | 49.8978 | 7.0310 | 42.8667 |
| E | 458 | ASP | 90.1644 | 3.0872 | 87.0772 |
| E | 459 | LYS | 126.5316 | 10.8761 | 115.6555 |
| E | 460 | ARG | 25.3451 | 7.1252 | 18.2199 |
| E | 461 | THR | 36.0964 | 1.2535 | 34.8429 |
| E | 462 | LEU | 0.3216 | 0.1050 | 0.2166 |
| E | 463 | ALA | 38.1902 | 0.0000 | 38.1902 |
| E | 464 | CYS | 0.6096 | 0.6091 | 0.0005 |
| E | 465 | LEU | 30.0120 | 0.0000 | 30.0120 |
| E | 466 | ILE | 1.1670 | 0.0000 | 1.1670 |
| E | 467 | GLN | 42.6332 | 0.0000 | 42.6332 |
| E | 468 | ASN | 59.4407 | 8.7561 | 50.6846 |
| E | 469 | PHE | 0.0026 | 0.0026 | 0.0000 |
| E | 470 | MET | 31.1167 | 0.0000 | 31.1167 |
| E | 471 | CPR | 22.3931 | 5.0857 | 17.3074 |
| E | 472 | GLU | 75.0844 | 1.6638 | 73.4206 |
| E | 473 | ASP | 42.1782 | 7.5691 | 34.6092 |
| E | 474 | ILE | 33.3636 | 26.8420 | 6.5216 |
| E | 475 | SER | 17.3062 | 5.7456 | 11.5606 |
| E | 476 | VAL | 21.8605 | 16.6454 | 5.2151 |
| E | 477 | GLN | 13.1621 | 0.0000 | 13.1621 |
| E | 478 | TRP | 3.2919 | 1.4331 | 1.8589 |
| E | 479 | LEU | 22.2332 | 2.7674 | 19.4658 |
| E | 480 | HIS | 13.9403 | 1.5058 | 12.4345 |
| E | 481 | ASN | 75.3625 | 11.0035 | 64.3591 |
| E | 482 | GLU | 151.5237 | 26.6074 | 124.9163 |
| E | 483 | VAL | 91.6853 | 4.4231 | 87.2622 |
| E | 484 | GLN | 73.5677 | 16.4720 | 57.0958 |
| E | 485 | LEU | 32.1741 | 9.5614 | 22.6128 |
| E | 486 | PRO | 88.0830 | 11.0178 | 77.0651 |
| E | 487 | ASP | 110.2999 | 9.8419 | 100.4581 |
| E | 488 | ALA | 108.2869 | 45.3537 | 62.9332 |
| E | 489 | ARG | 83.6177 | 21.0491 | 62.5687 |
| E | 490 | HIS | 33.8628 | 17.3684 | 16.4944 |
| E | 491 | SER | 76.4789 | 8.7365 | 67.7424 |
| E | 492 | THR | 51.5563 | 27.1132 | 24.4430 |
| E | 493 | THR | 65.6394 | 13.3548 | 52.2846 |
| E | 494 | GLN | 106.6279 | 3.2644 | 103.3635 |
| E | 495 | PRO | 56.5680 | 24.0375 | 32.5305 |
| E | 496 | ARG | 146.6497 | 5.1470 | 141.5027 |
| E | 497 | LYS | 146.2467 | 21.6286 | 124.6181 |
| E | 498 | THR | 41.7855 | 21.1642 | 20.6213 |
| E | 499 | LYS | 210.2196 | 41.4510 | 168.7686 |
| E | 500 | GLY | 55.1902 | 55.1902 | 0.0000 |
| E | 501 | SER | 89.1767 | 29.8172 | 59.3595 |
| E | 502 | GLY | 2.8614 | 2.8614 | 0.0000 |
| E | 503 | PHE | 33.2073 | 0.0000 | 33.2073 |
| E | 504 | PHE | 49.2929 | 0.1337 | 49.1592 |
| E | 505 | VAL | 3.4432 | 0.0000 | 3.4432 |
| E | 506 | PHE | 97.2276 | 1.0167 | 96.2110 |
| E | 507 | SER | 4.8355 | 3.7461 | 1.0894 |
| E | 508 | ARG | 117.9095 | 3.0500 | 114.8596 |
| E | 509 | LEU | 1.1169 | 0.3737 | 0.7432 |
| E | 510 | GLU | 95.2422 | 5.8712 | 89.3709 |
| E | 511 | VAL | 1.3749 | 1.3749 | 0.0000 |
| E | 512 | THR | 53.2537 | 0.0015 | 53.2522 |
| E | 513 | ARG | 104.2130 | 0.2755 | 103.9375 |
| E | 514 | ALA | 72.8434 | 15.3625 | 57.4809 |
| E | 515 | GLU | 25.3534 | 2.4494 | 22.9040 |
| E | 516 | TRP | 36.3225 | 4.8922 | 31.4302 |
| E | 517 | GLU | 113.1209 | 35.6700 | 77.4509 |
| E | 518 | ALA | 81.8016 | 44.2389 | 37.5627 |
| E | 519 | LYS | 84.0953 | 3.6397 | 80.4556 |
| E | 520 | ASP | 48.4560 | 16.7083 | 31.7477 |
| E | 521 | GLU | 67.7280 | 2.1457 | 65.5823 |
| E | 522 | PHE | 0.8079 | 0.1203 | 0.6876 |
| E | 523 | ILE | 35.8261 | 0.0009 | 35.8252 |
| E | 524 | CYS | 0.0264 | 0.0000 | 0.0264 |
| E | 525 | ARG | 66.9666 | 0.0000 | 66.9666 |
| E | 526 | ALA | 1.1349 | 1.0816 | 0.0533 |
| E | 527 | VAL | 2.4927 | 0.0026 | 2.4901 |
| E | 528 | HIS | 0.6132 | 0.0618 | 0.5514 |
| E | 529 | GLU | 35.3108 | 7.4361 | 27.8747 |
| E | 530 | ALA | 19.4996 | 15.8785 | 3.6211 |
| E | 531 | ALA | 6.3551 | 5.1391 | 1.2160 |
| E | 532 | SER | 89.7404 | 24.1196 | 65.6208 |
| E | 533 | CPR | 131.0337 | 24.2199 | 106.8138 |
| E | 534 | SER | 58.2335 | 15.2551 | 42.9785 |
| E | 535 | GLN | 39.0741 | 0.0012 | 39.0729 |
| E | 536 | THR | 44.3665 | 11.4935 | 32.8730 |
| E | 537 | VAL | 45.0562 | 7.3989 | 37.6573 |
| E | 538 | GLN | 83.8232 | 23.8845 | 59.9386 |
| E | 539 | ARG | 135.4479 | 4.0508 | 131.3971 |
| E | 540 | ALA | 39.4228 | 13.6903 | 25.7325 |
| E | 541 | VAL | 21.7768 | 6.7355 | 15.0412 |
| E | 542 | SER | 56.0048 | 13.9661 | 42.0387 |
| E | 543 | VAL | 10.0301 | 9.1751 | 0.8549 |
| E | 544 | ASN | 159.1980 | 60.8287 | 98.3694 |
| E | 1 | NAG | 184.4551 | 0.0000 | 184.4551 |
| E | 2 | NAG | 128.4129 | 0.0000 | 128.4129 |
| E | 3 | MAN | 115.6757 | 0.0000 | 115.6757 |
| E | 4 | MAN | 205.1619 | 0.0000 | 205.1619 |
| B | 1 | NAG | 178.3897 | 0.0000 | 178.3897 |
| B | 2 | NAG | 127.5007 | 0.0000 | 127.5007 |
| B | 3 | MAN | 67.7419 | 0.0000 | 67.7419 |
| B | 4 | MAN | 232.5164 | 0.0000 | 232.5164 |
| B | 5 | MAN | 216.4935 | 0.0000 | 216.4935 |
| A | 1 | NAG | 169.8799 | 0.0000 | 169.8799 |
| A | 2 | NAG | 135.2116 | 0.0000 | 135.2116 |
| A | 3 | MAN | 172.2505 | 0.0000 | 172.2505 |

In another embodiment, the solvent accessibilities of the amino acids in Crystal 2 in Example 1 are indicated in Table V.

TABLE V

IgE-Fc Residue Exposure

Surface plot for Crystal 2:
structure file = P21_easy.mtf
coordinate set = P21_easy.pdb

| segid | resid | resname | residue | mainchain | sidechain |
|---|---|---|---|---|---|
| C | 336 | VAL | 112.8541 | 52.6241 | 60.2300 |
| C | 337 | SER | 42.2713 | 4.5589 | 37.7124 |
| C | 338 | ALA | 7.8023 | 7.8023 | 0.0000 |
| C | 339 | TYR | 112.7711 | 4.3698 | 108.4013 |
| C | 340 | LEU | 31.1294 | 28.5949 | 2.5345 |
| C | 341 | SER | 55.0470 | 7.5527 | 47.4943 |
| C | 342 | ARG | 79.2168 | 16.3269 | 62.8899 |
| C | 343 | PRO | 7.3357 | 6.1931 | 1.1426 |
| C | 344 | SER | 42.6300 | 8.3383 | 34.2917 |
| C | 345 | PRO | 8.9866 | 0.5681 | 8.4185 |
| C | 346 | PHE | 56.8871 | 0.0000 | 56.8871 |
| C | 347 | ASP | 35.0931 | 0.0000 | 35.0931 |
| C | 348 | LEU | 9.3962 | 1.1821 | 8.2140 |
| C | 349 | PHE | 24.1206 | 7.0516 | 17.0690 |

TABLE V-continued

IgE-Fc Residue Exposure

Surface plot for Crystal 2:
structure file = P21_easy.mtf
coordinate set = P21_easy.pdb

| segid | resid | resname | residue (total accessible area) | mainchain | sidechain |
|---|---|---|---|---|---|
| C | 350 | ILE | 69.6135 | 17.6067 | 52.0067 |
| C | 351 | ARG | 134.6050 | 25.2200 | 109.3850 |
| C | 352 | LYS | 140.6685 | 18.4443 | 122.2242 |
| C | 353 | SER | 45.4412 | 5.7221 | 39.7192 |
| C | 354 | PRO | 2.7223 | 1.5547 | 1.1676 |
| C | 355 | THR | 42.2553 | 4.5034 | 37.7519 |
| C | 356 | ILE | 0.6574 | 0.6574 | 0.0000 |
| C | 357 | THR | 37.6461 | 1.8141 | 35.8320 |
| C | 358 | CYS | 0.0020 | 0.0020 | 0.0000 |
| C | 359 | LEU | 58.5201 | 0.0000 | 58.5201 |
| C | 360 | VAL | 1.1346 | 0.1595 | 0.9751 |
| C | 361 | VAL | 50.6713 | 2.0542 | 48.6171 |
| C | 362 | ASP | 82.9928 | 12.4142 | 70.5787 |
| C | 369 | THR | 141.5566 | 50.9284 | 90.6283 |
| C | 370 | VAL | 15.8914 | 2.5326 | 13.3588 |
| C | 371 | GLN | 91.7927 | 2.5190 | 89.2737 |
| C | 372 | LEU | 27.8925 | 25.3804 | 2.5121 |
| C | 373 | THR | 70.8746 | 4.3030 | 66.5716 |
| C | 374 | TRP | 21.3918 | 14.7891 | 6.6026 |
| C | 375 | SER | 48.4312 | 1.8554 | 46.5759 |
| C | 376 | ARG | 32.2766 | 9.7566 | 22.5200 |
| C | 377 | ALA | 73.8952 | 42.4823 | 31.4128 |
| C | 378 | SER | 63.0220 | 40.8126 | 22.2094 |
| C | 379 | GLY | 68.9906 | 68.9906 | 0.0000 |
| C | 380 | LYS | 112.6465 | 10.4637 | 102.1828 |
| C | 381 | PRO | 112.7478 | 18.3968 | 94.3510 |
| C | 382 | VAL | 50.6805 | 25.4119 | 25.2686 |
| C | 383 | GLN | 106.6811 | 21.4343 | 85.2468 |
| C | 384 | HIS | 150.2916 | 10.9276 | 139.3640 |
| C | 385 | SER | 33.0253 | 11.0106 | 22.0148 |
| C | 386 | THR | 88.2474 | 5.3666 | 82.8808 |
| C | 387 | ARG | 95.5223 | 25.4687 | 70.0537 |
| C | 388 | LYS | 134.0726 | 5.4664 | 128.6062 |
| C | 389 | GLU | 92.9198 | 25.5075 | 67.4123 |
| C | 390 | GLU | 43.1140 | 0.1646 | 42.9495 |
| C | 391 | LYS | 156.5642 | 17.1891 | 139.3751 |
| C | 392 | GLN | 70.0769 | 23.6552 | 46.4218 |
| C | 393 | ARG | 229.3906 | 31.0390 | 198.3516 |
| C | 394 | ASN | 112.3704 | 40.3776 | 71.9928 |
| C | 395 | GLY | 71.4710 | 71.4710 | 0.0000 |
| C | 396 | THR | 40.4121 | 21.0160 | 19.3961 |
| C | 397 | LEU | 66.7416 | 0.3571 | 66.3846 |
| C | 398 | THR | 12.5044 | 0.0000 | 12.5044 |
| C | 399 | VAL | 1.1814 | 0.0000 | 1.1814 |
| C | 400 | THR | 29.9298 | 0.0000 | 29.9298 |
| C | 401 | SER | 2.8209 | 0.0000 | 2.8209 |
| C | 402 | THR | 40.6868 | 1.7292 | 38.9576 |
| C | 403 | LEU | 0.6550 | 0.0000 | 0.6550 |
| C | 404 | PRO | 47.3500 | 2.6577 | 44.6923 |
| C | 405 | VAL | 10.2264 | 10.2233 | 0.0031 |
| C | 406 | GLY | 22.3914 | 22.3914 | 0.0000 |
| C | 407 | THR | 45.2024 | 4.7977 | 40.4046 |
| C | 408 | ALA | 59.4381 | 8.0745 | 51.3636 |
| C | 409 | ASP | 51.9611 | 4.7359 | 47.2252 |
| C | 410 | TRP | 5.7341 | 0.0000 | 5.7341 |
| C | 411 | ILE | 67.6093 | 12.3008 | 55.3085 |
| C | 412 | GLU | 149.5474 | 39.1697 | 110.3777 |
| C | 413 | GLY | 34.6690 | 34.6690 | 0.0000 |
| C | 414 | GLU | 22.2276 | 9.6599 | 12.5677 |
| C | 415 | THR | 41.1079 | 0.3469 | 40.7610 |
| C | 416 | TYR | 5.8170 | 0.0000 | 5.8170 |
| C | 417 | GLN | 72.6769 | 0.1520 | 72.5250 |
| C | 418 | CYS | 0.1111 | 0.1111 | 0.0000 |
| C | 419 | ARG | 107.8529 | 0.0000 | 107.8529 |
| C | 420 | VAL | 1.4478 | 0.0000 | 1.4478 |
| C | 421 | THR | 57.5773 | 0.7775 | 56.7998 |
| C | 422 | ALA | 18.9265 | 9.4738 | 9.4526 |
| C | 423 | PRO | 101.6686 | 32.0584 | 69.6102 |
| C | 424 | ALA | 101.8654 | 41.5174 | 60.3481 |
| C | 425 | LEU | 76.4037 | 30.7426 | 45.6611 |
| C | 426 | PRO | 118.8404 | 34.7714 | 84.0690 |
| C | 427 | ALA | 91.7738 | 41.4738 | 50.3000 |
| C | 428 | ALA | 32.7092 | 22.9925 | 9.7167 |
| C | 429 | LEU | 54.3980 | 0.9841 | 53.4139 |
| C | 430 | MET | 117.3710 | 25.9473 | 91.4237 |
| C | 431 | ARG | 97.1309 | 3.6960 | 93.4349 |
| C | 432 | SER | 70.4707 | 25.6043 | 44.8664 |
| C | 433 | THR | 11.2490 | 6.9444 | 4.3046 |
| C | 434 | THR | 56.1748 | 4.3779 | 51.7968 |
| C | 435 | LYS | 33.8265 | 9.3307 | 24.4958 |
| C | 436 | THR | 46.8301 | 8.6478 | 38.1822 |
| C | 437 | SER | 90.9417 | 21.8578 | 69.0838 |
| C | 438 | GLY | 43.5381 | 43.5381 | 0.0000 |
| C | 439 | PRO | 89.6663 | 11.9590 | 77.7073 |
| C | 440 | ARG | 101.0224 | 28.9572 | 72.0652 |
| C | 441 | ALA | 34.3331 | 8.5479 | 25.7853 |
| C | 442 | ALA | 48.0399 | 13.1635 | 34.8764 |
| C | 443 | PRO | 6.5503 | 6.5503 | 0.0000 |
| C | 444 | GLU | 39.5117 | 5.0302 | 34.4814 |
| C | 445 | VAL | 5.2498 | 4.8195 | 0.4303 |
| C | 446 | TYR | 10.6011 | 1.5178 | 9.0833 |
| C | 447 | ALA | 18.8200 | 18.7101 | 0.1098 |
| C | 448 | PHE | 27.2415 | 3.3934 | 23.8481 |
| C | 449 | ALA | 28.0239 | 20.4138 | 7.6101 |
| C | 450 | THR | 4.4146 | 0.6988 | 3.7158 |
| C | 451 | PRO | 69.7131 | 7.6968 | 62.0163 |
| C | 452 | GLU | 109.3921 | 26.2454 | 83.1467 |
| C | 453 | TRP | 87.6627 | 2.8071 | 84.8556 |
| C | 454 | PRO | 116.0782 | 35.0417 | 81.0365 |
| C | 455 | GLY | 53.8245 | 53.8245 | 0.0000 |
| C | 456 | SER | 60.0495 | 16.2547 | 43.7948 |
| C | 457 | ALA | 34.5055 | 6.8596 | 27.6460 |
| C | 458 | ASP | 88.2274 | 16.3081 | 71.9192 |
| C | 459 | LYS | 70.9165 | 1.6669 | 69.2496 |
| C | 460 | ARG | 50.4082 | 5.5889 | 44.8193 |
| C | 461 | THR | 6.8793 | 0.1574 | 6.7219 |
| C | 462 | LEU | 0.0000 | 0.0000 | 0.0000 |
| C | 463 | ALA | 0.4396 | 0.0433 | 0.3963 |
| C | 464 | CYS | 0.0000 | 0.0000 | 0.0000 |
| C | 465 | LEU | 0.0000 | 0.0000 | 0.0000 |
| C | 466 | ILE | 0.0015 | 0.0000 | 0.0015 |
| C | 467 | GLN | 5.9749 | 0.0004 | 5.9745 |
| C | 468 | ASN | 48.4866 | 4.9562 | 43.5304 |
| C | 469 | PHE | 0.0017 | 0.0000 | 0.0017 |
| C | 470 | MET | 30.1891 | 0.8530 | 29.3361 |
| C | 471 | PRO | 8.8681 | 5.9816 | 2.8865 |
| C | 472 | GLU | 68.1461 | 0.9725 | 67.1736 |
| C | 473 | ASP | 37.6052 | 6.9595 | 30.6457 |
| C | 474 | ILE | 28.1770 | 24.4914 | 3.6857 |
| C | 475 | SER | 17.1341 | 5.2443 | 11.8898 |
| C | 476 | VAL | 18.7312 | 16.5820 | 2.1491 |
| C | 477 | GLN | 9.9513 | 0.0000 | 9.9513 |
| C | 478 | TRP | 0.7914 | 0.4232 | 0.3682 |
| C | 479 | LEU | 3.9375 | 0.4099 | 3.5276 |
| C | 480 | HIS | 13.0911 | 0.2393 | 12.8518 |
| C | 481 | ASN | 74.1912 | 15.8720 | 58.3192 |
| C | 482 | GLU | 119.6062 | 35.7028 | 83.9034 |
| C | 483 | VAL | 84.3959 | 3.4739 | 80.9220 |
| C | 484 | GLN | 68.2132 | 19.2681 | 48.9452 |
| C | 485 | LEU | 19.3213 | 2.6640 | 16.6573 |
| C | 486 | PRO | 84.1332 | 12.0197 | 72.1135 |
| C | 487 | ASP | 97.7132 | 8.9214 | 88.7917 |
| C | 488 | ALA | 102.0463 | 40.5736 | 61.4727 |
| C | 489 | ARG | 83.3985 | 16.2961 | 67.1023 |
| C | 490 | HIS | 33.6126 | 17.6573 | 15.9552 |
| C | 491 | SER | 29.9317 | 6.9558 | 22.9759 |
| C | 492 | THR | 41.4818 | 17.4229 | 24.0589 |
| C | 493 | THR | 10.1067 | 3.9174 | 6.1892 |

TABLE V-continued

IgE-Fc Residue Exposure

Surface plot for Crystal 2:
structure file = P21_easy.mtf
coordinate set = P21_easy.pdb

| segid | resid | resname | residue | mainchain | sidechain |
|---|---|---|---|---|---|
| | | | total accessible area | | |
| C | 494 | GLN | 140.5779 | 8.0984 | 132.4794 |
| C | 495 | PRO | 42.0590 | 16.3432 | 25.7158 |
| C | 496 | ALA | 38.8264 | 7.4488 | 31.3776 |
| C | 497 | LYS | 133.7615 | 13.5762 | 120.1854 |
| C | 498 | THR | 16.0490 | 14.2672 | 1.7818 |
| C | 499 | LYS | 90.8994 | 47.6034 | 43.2960 |
| C | 500 | GLY | 53.3592 | 53.3592 | 0.0000 |
| C | 501 | SER | 72.3024 | 29.1725 | 43.1299 |
| C | 502 | GLY | 1.4441 | 1.4441 | 0.0000 |
| C | 503 | PHE | 28.2734 | 0.0000 | 28.2734 |
| C | 504 | PHE | 5.4650 | 0.0000 | 5.4650 |
| C | 505 | VAL | 0.5332 | 0.0000 | 0.5332 |
| C | 506 | PHE | 0.9926 | 0.2818 | 0.7108 |
| C | 507 | SER | 0.0478 | 0.0478 | 0.0000 |
| C | 508 | ARG | 10.9310 | 2.2742 | 8.6568 |
| C | 509 | LEU | 0.6852 | 0.3180 | 0.3672 |
| C | 510 | GLU | 36.5441 | 4.7199 | 31.8341 |
| C | 511 | VAL | 0.1300 | 0.1300 | 0.0000 |
| C | 512 | THR | 55.9929 | 0.0000 | 55.9929 |
| C | 513 | ARG | 123.0910 | 4.4182 | 118.6727 |
| C | 514 | ALA | 83.3577 | 25.0718 | 58.2858 |
| C | 515 | GLU | 25.4795 | 1.8278 | 23.6517 |
| C | 516 | TRP | 14.6033 | 2.6419 | 11.9615 |
| C | 517 | GLU | 159.8542 | 23.9774 | 135.8768 |
| C | 518 | ALA | 64.4562 | 36.5672 | 27.8890 |
| C | 519 | LYS | 95.5143 | 6.8513 | 88.6630 |
| C | 520 | ASP | 32.7434 | 6.9157 | 25.8276 |
| C | 521 | GLU | 65.4133 | 1.4439 | 63.9694 |
| C | 522 | PHE | 0.1125 | 0.0006 | 0.1119 |
| C | 523 | ILE | 15.2368 | 0.0020 | 15.2349 |
| C | 524 | CYS | 0.0000 | 0.0000 | 0.0000 |
| C | 525 | ARG | 50.1896 | 0.0000 | 50.1896 |
| C | 526 | ALA | 0.0000 | 0.0000 | 0.0000 |
| C | 527 | VAL | 0.4143 | 0.0000 | 0.4143 |
| C | 528 | HIS | 0.3836 | 0.0027 | 0.3809 |
| C | 529 | GLU | 37.2347 | 15.3647 | 21.8700 |
| C | 530 | ALA | 28.2753 | 24.7979 | 3.4773 |
| C | 531 | ALA | 1.0875 | 1.0875 | 0.0000 |
| C | 532 | SER | 90.9238 | 41.8009 | 49.1229 |
| C | 533 | PRO | 94.4894 | 14.0855 | 80.4039 |
| C | 534 | SER | 63.0431 | 14.3303 | 48.7129 |
| C | 535 | GLN | 44.1874 | 0.0044 | 44.1830 |
| C | 536 | THR | 38.7615 | 10.3674 | 28.3942 |
| C | 537 | VAL | 42.2038 | 4.8809 | 37.3228 |
| C | 538 | GLN | 75.9413 | 19.4042 | 56.5371 |
| C | 539 | ARG | 109.6897 | 3.2084 | 106.4813 |
| C | 540 | ALA | 61.4452 | 26.7926 | 34.6526 |
| C | 541 | VAL | 18.2202 | 6.7229 | 11.4973 |
| C | 542 | SER | 47.5281 | 13.5601 | 33.9680 |
| C | 543 | VAL | 5.5312 | 5.1304 | 0.4008 |
| C | 544 | ASN | 163.1237 | 39.3608 | 123.7629 |
| D | 336 | VAL | 111.2250 | 47.3224 | 63.9026 |
| D | 337 | SER | 40.7682 | 6.6913 | 34.0768 |
| D | 338 | ALA | 7.7926 | 7.7926 | 0.0000 |
| D | 339 | TYR | 115.4001 | 4.4228 | 110.9773 |
| D | 340 | LEU | 31.5200 | 29.1015 | 2.4185 |
| D | 341 | SER | 55.6875 | 7.1495 | 48.5380 |
| D | 342 | ARG | 72.9550 | 16.3911 | 56.5639 |
| D | 343 | PRO | 6.9432 | 5.9803 | 0.9629 |
| D | 344 | SER | 42.8700 | 8.2778 | 34.5922 |
| D | 345 | PRO | 7.7442 | 0.6023 | 7.1419 |
| D | 346 | PHE | 58.4026 | 0.0025 | 58.4001 |
| D | 347 | ASP | 32.8126 | 0.0008 | 32.8118 |
| D | 348 | LEU | 13.3456 | 0.6089 | 12.7366 |
| D | 349 | PHE | 38.0382 | 7.2737 | 30.7645 |
| D | 350 | ILE | 83.5579 | 20.5527 | 63.0052 |
| D | 351 | ARG | 131.4936 | 23.4842 | 108.0095 |
| D | 352 | LYS | 124.3088 | 17.9497 | 106.3591 |
| D | 353 | SER | 47.0699 | 5.3437 | 41.7261 |
| D | 354 | PRO | 2.8308 | 1.6899 | 1.1409 |
| D | 355 | THR | 41.8873 | 4.6257 | 37.2616 |
| D | 356 | ILE | 0.5170 | 0.5170 | 0.0000 |
| D | 357 | THR | 37.3100 | 1.7368 | 35.5732 |
| D | 358 | CYS | 0.0000 | 0.0000 | 0.0000 |
| D | 359 | LEU | 58.3354 | 0.0000 | 58.3354 |
| D | 360 | VAL | 1.6065 | 0.0000 | 1.6065 |
| D | 361 | VAL | 51.4461 | 0.1347 | 51.3114 |
| D | 362 | ASP | 107.4640 | 28.1709 | 79.2931 |
| D | 366 | SER | 152.8529 | 89.3206 | 63.5323 |
| D | 367 | ALA | 104.9845 | 42.8934 | 62.0910 |
| D | 368 | GLY | 50.5427 | 50.5427 | 0.0000 |
| D | 369 | THR | 65.9531 | 19.1661 | 46.7870 |
| D | 370 | VAL | 25.5783 | 1.1812 | 24.3971 |
| D | 371 | GLN | 99.4567 | 1.9014 | 97.5553 |
| D | 372 | LEU | 26.0517 | 23.6920 | 2.3598 |
| D | 373 | THR | 73.4198 | 4.8651 | 68.5547 |
| D | 374 | TRP | 19.7751 | 13.0820 | 6.6932 |
| D | 375 | SER | 47.2045 | 1.7240 | 45.4805 |
| D | 376 | ARG | 29.8912 | 9.7857 | 20.1055 |
| D | 377 | ALA | 74.5660 | 39.8485 | 34.7175 |
| D | 378 | SER | 64.6938 | 43.7753 | 20.9185 |
| D | 379 | GLY | 66.6826 | 66.6826 | 0.0000 |
| D | 380 | LYS | 122.0687 | 8.8084 | 113.2603 |
| D | 381 | PRO | 114.5790 | 20.5572 | 94.0218 |
| D | 382 | VAL | 55.6035 | 24.7181 | 30.8854 |
| D | 383 | GLN | 94.3067 | 16.5250 | 77.7817 |
| D | 384 | HIS | 76.7674 | 7.9693 | 68.7981 |
| D | 385 | SER | 34.1123 | 14.7782 | 19.3341 |
| D | 386 | THR | 37.3388 | 1.3701 | 35.9687 |
| D | 387 | ARG | 33.6499 | 0.6355 | 33.0145 |
| D | 388 | LYS | 83.1418 | 2.6056 | 80.5362 |
| D | 389 | GLU | 38.6381 | 1.4723 | 37.1658 |
| D | 390 | GLU | 65.8163 | 3.3336 | 62.4826 |
| D | 391 | ALA | 31.5838 | 1.4562 | 30.1277 |
| D | 392 | GLN | 70.9740 | 4.9315 | 66.0425 |
| D | 393 | ALA | 97.1966 | 31.4383 | 65.7583 |
| D | 394 | ASN | 119.4968 | 40.9939 | 78.5030 |
| D | 395 | GLY | 68.7002 | 68.7002 | 0.0000 |
| D | 396 | ALA | 37.9981 | 27.4930 | 10.5051 |
| D | 397 | LEU | 43.6771 | 1.3181 | 42.3590 |
| D | 398 | THR | 27.2010 | 0.2801 | 26.9209 |
| D | 399 | VAL | 0.7616 | 0.0025 | 0.7590 |
| D | 400 | THR | 31.3592 | 0.6048 | 30.7544 |
| D | 401 | SER | 2.1979 | 0.0157 | 2.1822 |
| D | 402 | THR | 43.5078 | 1.0196 | 42.4882 |
| D | 403 | LEU | 0.4690 | 0.0023 | 0.4667 |
| D | 404 | PRO | 47.2539 | 1.8494 | 45.4046 |
| D | 405 | VAL | 11.6109 | 11.3960 | 0.2149 |
| D | 406 | GLY | 23.9812 | 23.9812 | 0.0000 |
| D | 407 | THR | 41.6538 | 5.4342 | 36.2196 |
| D | 408 | ALA | 57.1547 | 8.7311 | 48.4236 |
| D | 409 | ASP | 57.5656 | 5.4553 | 52.1103 |
| D | 410 | TRP | 8.6432 | 0.0000 | 8.6432 |
| D | 411 | ILE | 94.6994 | 23.2453 | 71.4541 |
| D | 412 | GLU | 141.9111 | 37.1664 | 104.7447 |
| D | 413 | GLY | 35.1505 | 35.1505 | 0.0000 |
| D | 414 | GLU | 23.2947 | 9.8420 | 13.4527 |
| D | 415 | THR | 44.2144 | 0.1500 | 44.0644 |
| D | 416 | TYR | 4.6470 | 0.0000 | 4.6470 |
| D | 417 | GLN | 49.2052 | 0.0000 | 49.2052 |
| D | 418 | CYS | 0.0000 | 0.0000 | 0.0000 |
| D | 419 | ARG | 129.9193 | 0.3950 | 129.5243 |
| D | 420 | VAL | 4.9329 | 2.1420 | 2.7910 |
| D | 421 | THR | 58.0849 | 8.4298 | 49.6551 |
| D | 422 | HIS | 193.0284 | 56.5022 | 136.5263 |
| D | 427 | ALA | 117.6537 | 61.7635 | 55.8901 |
| D | 428 | ALA | 61.9024 | 23.9346 | 37.9678 |
| D | 429 | LEU | 48.4849 | 4.1109 | 44.3740 |

TABLE V-continued

IgE-Fc Residue Exposure

Surface plot for Crystal 2:
structure file = P21_easy.mtf
coordinate set = P21_easy.pdb

| | | | total accessible area | | |
|---|---|---|---|---|---|
| segid | resid | resname | residue | mainchain | sidechain |
| D | 430 | MET | 114.2814 | 27.5387 | 86.7427 |
| D | 431 | ARG | 99.4740 | 2.9602 | 96.5138 |
| D | 432 | SER | 74.4026 | 23.1709 | 51.2317 |
| D | 433 | THR | 11.6812 | 7.8193 | 3.8619 |
| D | 434 | THR | 56.9943 | 4.9554 | 52.0389 |
| D | 435 | ALA | 33.4263 | 12.3418 | 21.0845 |
| D | 436 | THR | 41.6647 | 14.3557 | 27.3090 |
| D | 437 | SER | 94.8862 | 18.6970 | 76.1892 |
| D | 438 | GLY | 45.1763 | 45.1763 | 0.0000 |
| D | 439 | PRO | 99.9234 | 12.3087 | 87.6147 |
| D | 440 | ARG | 112.2731 | 29.1775 | 83.0956 |
| D | 441 | ALA | 35.6958 | 8.4639 | 27.2319 |
| D | 442 | ALA | 50.6936 | 16.3289 | 34.3647 |
| D | 443 | PRO | 3.5784 | 3.5784 | 0.0000 |
| D | 444 | ALA | 3.2095 | 0.0184 | 3.1911 |
| D | 445 | VAL | 0.8930 | 0.5064 | 0.3865 |
| D | 446 | TYR | 11.2395 | 1.8296 | 9.4099 |
| D | 447 | ALA | 17.4133 | 17.4132 | 0.0001 |
| D | 448 | PHE | 26.7733 | 3.1628 | 23.6105 |
| D | 449 | ALA | 16.5251 | 13.9478 | 2.5773 |
| D | 450 | THR | 4.4193 | 0.3524 | 4.0669 |
| D | 451 | PRO | 66.4095 | 3.0850 | 63.3245 |
| D | 452 | GLU | 109.5851 | 25.0296 | 84.5554 |
| D | 453 | ALA | 17.3960 | 5.1673 | 12.2286 |
| D | 454 | PRO | 127.1010 | 30.3584 | 96.7426 |
| D | 455 | GLY | 61.3039 | 61.3039 | 0.0000 |
| D | 456 | ALA | 72.8407 | 19.0223 | 53.8184 |
| D | 457 | ALA | 32.1097 | 28.1062 | 4.0035 |
| D | 458 | ASP | 72.6762 | 5.8468 | 66.8294 |
| D | 459 | LYS | 124.3183 | 11.9131 | 112.4052 |
| D | 460 | ARG | 43.7851 | 6.6214 | 37.1637 |
| D | 461 | THR | 7.0094 | 0.1982 | 6.8113 |
| D | 462 | LEU | 0.0000 | 0.0000 | 0.0000 |
| D | 463 | ALA | 0.3575 | 0.0469 | 0.3106 |
| D | 464 | CYS | 0.0003 | 0.0003 | 0.0000 |
| D | 465 | LEU | 0.0000 | 0.0000 | 0.0000 |
| D | 466 | ILE | 0.0003 | 0.0003 | 0.0000 |
| D | 467 | GLN | 8.5503 | 0.0004 | 8.5499 |
| D | 468 | ASN | 46.7110 | 4.5762 | 42.1348 |
| D | 469 | PHE | 0.0005 | 0.0000 | 0.0005 |
| D | 470 | MET | 30.4058 | 0.0031 | 30.4027 |
| D | 471 | PRO | 6.3052 | 6.0503 | 0.2550 |
| D | 472 | GLU | 68.7222 | 1.9947 | 66.7275 |
| D | 473 | ASP | 34.1180 | 6.0269 | 28.0911 |
| D | 474 | ILE | 28.7680 | 25.4819 | 3.2861 |
| D | 475 | SER | 17.4807 | 5.0142 | 12.4665 |
| D | 476 | VAL | 18.0961 | 16.2615 | 1.8345 |
| D | 477 | GLN | 12.4374 | 0.0000 | 12.4374 |
| D | 478 | TRP | 1.0046 | 0.6794 | 0.3252 |
| D | 479 | LEU | 7.5001 | 1.3376 | 6.1625 |
| D | 480 | HIS | 8.0949 | 0.7508 | 7.3441 |
| D | 481 | ASN | 23.1555 | 8.6422 | 14.5133 |
| D | 482 | GLU | 104.6785 | 22.9582 | 81.7203 |
| D | 483 | VAL | 45.8633 | 7.9795 | 37.8839 |
| D | 484 | GLN | 67.4810 | 18.7606 | 48.7204 |
| D | 485 | LEU | 6.1924 | 2.9937 | 3.1988 |
| D | 486 | PRO | 78.8144 | 12.4082 | 66.4062 |
| D | 487 | ASP | 99.5433 | 8.3638 | 91.1795 |
| D | 488 | ALA | 95.7179 | 32.9480 | 62.7698 |
| D | 489 | ARG | 56.8997 | 0.4441 | 56.4557 |
| D | 490 | HIS | 30.7784 | 14.5106 | 16.2678 |
| D | 491 | SER | 39.9508 | 6.7733 | 33.1775 |
| D | 492 | THR | 51.2575 | 26.8903 | 24.3672 |
| D | 493 | THR | 24.7802 | 12.2497 | 12.5305 |
| D | 494 | GLN | 142.3207 | 2.5655 | 139.7552 |
| D | 495 | PRO | 44.5511 | 19.0716 | 25.4795 |
| D | 496 | ARG | 78.5144 | 5.5247 | 72.9897 |
| D | 497 | LYS | 150.7320 | 21.5729 | 129.1591 |
| D | 498 | THR | 17.7442 | 17.7442 | 0.0000 |
| D | 499 | ALA | 61.3556 | 27.8523 | 33.5033 |
| D | 500 | GLY | 89.8742 | 89.8742 | 0.0000 |
| D | 501 | SER | 60.2735 | 20.1528 | 40.1208 |
| D | 502 | GLY | 6.1948 | 6.1948 | 0.0000 |
| D | 503 | PHE | 28.3581 | 0.0000 | 28.3581 |
| D | 504 | PHE | 1.7159 | 0.0000 | 1.7159 |
| D | 505 | VAL | 0.8449 | 0.0000 | 0.8449 |
| D | 506 | PHE | 1.1162 | 0.2420 | 0.8742 |
| D | 507 | SER | 0.0216 | 0.0216 | 0.0000 |
| D | 508 | ARG | 2.5783 | 0.2732 | 2.3052 |
| D | 509 | LEU | 0.5282 | 0.0000 | 0.5282 |
| D | 510 | GLU | 41.1481 | 4.6648 | 36.4834 |
| D | 511 | VAL | 0.9969 | 0.9969 | 0.0000 |
| D | 512 | THR | 49.7072 | 0.0000 | 49.7072 |
| D | 513 | ARG | 109.0904 | 0.3038 | 108.7866 |
| D | 514 | ALA | 75.2028 | 18.0084 | 57.1944 |
| D | 515 | GLU | 23.8408 | 1.5162 | 22.3246 |
| D | 516 | TRP | 34.7273 | 5.7618 | 28.9656 |
| D | 517 | ALA | 78.0203 | 40.7432 | 37.2771 |
| D | 518 | GLN | 65.9902 | 30.7685 | 35.2217 |
| D | 519 | LYS | 93.9565 | 8.1125 | 85.8439 |
| D | 520 | ASP | 47.3474 | 7.2207 | 40.1267 |
| D | 521 | GLU | 60.6626 | 2.2871 | 58.3755 |
| D | 522 | PHE | 0.1140 | 0.0000 | 0.1140 |
| D | 523 | ILE | 13.0110 | 0.0000 | 13.0110 |
| D | 524 | CYS | 0.0005 | 0.0005 | 0.0000 |
| D | 525 | ARG | 59.4782 | 0.0000 | 59.4782 |
| D | 526 | ALA | 0.0000 | 0.0000 | 0.0000 |
| D | 527 | VAL | 2.3707 | 0.0026 | 2.3682 |
| D | 528 | HIS | 0.2361 | 0.0015 | 0.2347 |
| D | 529 | GLU | 58.4219 | 17.0677 | 41.3542 |
| D | 530 | ALA | 27.7034 | 23.9944 | 3.7090 |
| D | 531 | ALA | 2.3036 | 2.3036 | 0.0000 |
| D | 532 | SER | 81.2022 | 17.6471 | 63.5551 |
| D | 533 | PRO | 103.9903 | 19.3485 | 84.6419 |
| D | 534 | SER | 65.0289 | 14.4434 | 50.5855 |
| D | 535 | GLN | 53.0906 | 0.0000 | 53.0906 |
| D | 536 | THR | 43.4296 | 13.0746 | 30.3550 |
| D | 537 | VAL | 33.6421 | 4.8551 | 28.7870 |
| D | 538 | GLN | 77.8309 | 19.3692 | 58.4618 |
| D | 539 | ARG | 82.5474 | 3.4121 | 79.1353 |
| D | 540 | ALA | 56.4670 | 25.9299 | 30.5372 |
| D | 541 | VAL | 19.2403 | 8.2314 | 11.0089 |
| D | 542 | SER | 34.9715 | 4.1395 | 30.8321 |
| D | 543 | VAL | 16.4696 | 15.9361 | 0.5335 |
| D | 544 | ASN | 147.0919 | 29.2322 | 117.8597 |
| A | 336 | VAL | 76.6072 | 39.1896 | 37.4176 |
| A | 337 | SER | 42.6924 | 7.5146 | 35.1777 |
| A | 338 | ALA | 8.3465 | 8.3465 | 0.0000 |
| A | 339 | TYR | 111.2914 | 4.2153 | 107.0761 |
| A | 340 | LEU | 30.0787 | 28.0434 | 2.0354 |
| A | 341 | SER | 54.8091 | 7.0781 | 47.7310 |
| A | 342 | ARG | 78.9911 | 17.1168 | 61.8743 |
| A | 343 | PRO | 7.3509 | 6.5480 | 0.8029 |
| A | 344 | SER | 40.6869 | 8.3459 | 32.3410 |
| A | 345 | PRO | 8.3705 | 0.0734 | 8.2971 |
| A | 346 | PHE | 48.7704 | 0.0011 | 48.7693 |
| A | 347 | ASP | 33.3427 | 0.0000 | 33.3427 |
| A | 348 | LEU | 13.9258 | 1.8037 | 12.1221 |
| A | 349 | PHE | 35.6445 | 10.7047 | 24.9398 |
| A | 350 | ILE | 69.8836 | 15.2514 | 54.6323 |
| A | 351 | ARG | 138.2507 | 25.6201 | 112.6306 |
| A | 352 | LYS | 131.3378 | 18.2056 | 113.1322 |
| A | 353 | SER | 48.4566 | 5.1580 | 43.2986 |
| A | 354 | PRO | 2.5618 | 1.3816 | 1.1802 |
| A | 355 | THR | 42.3647 | 6.2627 | 36.1021 |
| A | 356 | ILE | 0.1103 | 0.1103 | 0.0000 |
| A | 357 | THR | 37.9718 | 1.6299 | 36.3418 |
| A | 358 | CYS | 0.0000 | 0.0000 | 0.0000 |

TABLE V-continued

IgE-Fc Residue Exposure

Surface plot for Crystal 2:
structure file = P21_easy.mtf
coordinate set = P21_easy.pdb

| | | | total accessible area | | |
|---|---|---|---|---|---|
| segid | resid | resname | residue | mainchain | sidechain |
| A | 359 | LEU | 55.7227 | 0.0000 | 55.7227 |
| A | 360 | VAL | 0.0055 | 0.0021 | 0.0034 |
| A | 361 | VAL | 43.7394 | 0.3986 | 43.3408 |
| A | 362 | ASP | 15.3472 | 0.0000 | 15.3472 |
| A | 363 | LEU | 85.5726 | 3.6926 | 81.8800 |
| A | 364 | ALA | 86.4764 | 21.6785 | 64.7979 |
| A | 365 | PRO | 51.1962 | 30.6743 | 20.5219 |
| A | 366 | SER | 60.5039 | 20.6786 | 39.8253 |
| A | 367 | ALA | 100.5459 | 35.0181 | 65.5278 |
| A | 368 | GLY | 35.5275 | 35.5275 | 0.0000 |
| A | 369 | THR | 75.0414 | 17.5096 | 57.5317 |
| A | 370 | VAL | 15.3882 | 2.8075 | 12.5807 |
| A | 371 | GLN | 88.1966 | 0.8750 | 87.3216 |
| A | 372 | LEU | 26.3884 | 24.3216 | 2.0667 |
| A | 373 | THR | 75.3308 | 4.6477 | 70.6831 |
| A | 374 | TRP | 20.6444 | 13.9201 | 6.7243 |
| A | 375 | SER | 47.8961 | 2.3441 | 45.5520 |
| A | 376 | ARG | 28.2389 | 8.9610 | 19.2779 |
| A | 377 | ALA | 75.7245 | 42.2894 | 33.4351 |
| A | 378 | SER | 61.8040 | 40.0661 | 21.7379 |
| A | 379 | GLY | 67.2754 | 67.2754 | 0.0000 |
| A | 380 | LYS | 119.9490 | 8.2376 | 111.7114 |
| A | 381 | PRO | 114.2758 | 21.0662 | 93.2095 |
| A | 382 | VAL | 53.7889 | 27.2704 | 26.5186 |
| A | 383 | GLN | 105.3871 | 17.4669 | 87.9203 |
| A | 384 | HIS | 89.2326 | 8.1675 | 81.0650 |
| A | 385 | SER | 33.1983 | 10.8329 | 22.3654 |
| A | 386 | THR | 35.4269 | 1.6819 | 33.7449 |
| A | 387 | ARG | 33.0821 | 0.1088 | 32.9733 |
| A | 388 | LYS | 91.1563 | 29.020 | 88.2543 |
| A | 389 | GLU | 40.0844 | 0.9728 | 39.1115 |
| A | 390 | GLU | 77.0441 | 0.4602 | 76.5839 |
| A | 391 | LYS | 98.8923 | 3.3548 | 95.5375 |
| A | 392 | GLN | 66.9259 | 4.4747 | 62.4512 |
| A | 393 | ARG | 209.4349 | 39.3859 | 170.0491 |
| A | 394 | ASN | 119.1244 | 9.9697 | 109.1547 |
| A | 395 | GLY | 57.1251 | 57.1251 | 0.0000 |
| A | 396 | THR | 18.3858 | 0.2614 | 18.1244 |
| A | 397 | LEU | 32.6470 | 0.0001 | 32.6469 |
| A | 398 | THR | 21.7751 | 0.1951 | 21.5800 |
| A | 399 | VAL | 0.0000 | 0.0000 | 0.0000 |
| A | 400 | THR | 29.0428 | 0.0284 | 29.0145 |
| A | 401 | SER | 2.7030 | 0.0000 | 2.7030 |
| A | 402 | THR | 41.9305 | 1.3547 | 40.5857 |
| A | 403 | LEU | 0.5137 | 0.0000 | 0.5137 |
| A | 404 | PRO | 45.3199 | 2.4576 | 42.8623 |
| A | 405 | VAL | 8.0834 | 8.0834 | 0.0000 |
| A | 406 | GLY | 22.8968 | 22.8968 | 0.0000 |
| A | 407 | THR | 46.9681 | 5.4664 | 41.5017 |
| A | 408 | ALA | 58.9598 | 8.1267 | 50.8331 |
| A | 409 | ASP | 57.7033 | 5.7938 | 51.9095 |
| A | 410 | TRP | 5.8188 | 0.0000 | 5.8188 |
| A | 411 | ILE | 65.6252 | 9.6793 | 55.9459 |
| A | 412 | GLU | 148.9299 | 37.9078 | 111.0221 |
| A | 413 | GLY | 38.4757 | 38.4757 | 0.0000 |
| A | 414 | GLU | 21.8144 | 8.4116 | 13.4029 |
| A | 415 | THR | 39.1324 | 0.2085 | 38.9239 |
| A | 416 | TYR | 5.6827 | 0.0000 | 5.6827 |
| A | 417 | GLN | 70.7592 | 0.1417 | 70.6175 |
| A | 418 | CYS | 0.3598 | 0.3598 | 0.0000 |
| A | 419 | ARG | 108.0620 | 0.0129 | 108.0490 |
| A | 420 | VAL | 0.7704 | 0.0015 | 0.7689 |
| A | 421 | THR | 41.0550 | 0.5682 | 40.4867 |
| A | 422 | HIS | 29.5711 | 4.3217 | 25.2494 |
| A | 423 | PRO | 73.1884 | 43.8101 | 29.3782 |
| A | 424 | HIS | 121.9751 | 31.8298 | 90.1453 |
| A | 425 | LEU | 68.5070 | 24.0822 | 44.4248 |
| A | 426 | PRO | 126.6751 | 49.7215 | 76.9536 |
| A | 427 | ALA | 71.6779 | 12.5471 | 59.1308 |
| A | 428 | ALA | 22.4323 | 15.7727 | 6.6596 |
| A | 429 | LEU | 48.4870 | 3.7725 | 44.7144 |
| A | 430 | MET | 115.9633 | 23.2325 | 92.7308 |
| A | 431 | ARG | 94.9043 | 5.0090 | 89.8954 |
| A | 432 | SER | 70.3411 | 26.0240 | 44.3171 |
| A | 433 | THR | 11.0122 | 7.2353 | 3.7768 |
| A | 434 | THR | 59.9456 | 6.3788 | 53.5668 |
| A | 435 | LYS | 72.3218 | 13.5581 | 58.7637 |
| A | 436 | THR | 37.1784 | 10.2818 | 26.8966 |
| A | 437 | SER | 95.8588 | 19.2626 | 76.5962 |
| A | 438 | GLY | 43.4977 | 43.4977 | 0.0000 |
| A | 439 | PRO | 89.8084 | 12.3307 | 77.4777 |
| A | 440 | ARG | 101.3179 | 28.4413 | 72.8767 |
| A | 441 | ALA | 35.5661 | 8.6633 | 26.9027 |
| A | 442 | ALA | 51.2062 | 13.7189 | 37.4873 |
| A | 443 | PRO | 2.0273 | 2.0273 | 0.0000 |
| A | 444 | GLU | 15.7136 | 0.0000 | 15.7136 |
| A | 445 | VAL | 0.0117 | 0.0117 | 0.0000 |
| A | 446 | TYR | 13.9702 | 2.2650 | 11.7052 |
| A | 447 | ALA | 18.6312 | 18.5119 | 0.1193 |
| A | 448 | PHE | 23.6805 | 3.2553 | 20.4253 |
| A | 449 | ALA | 26.4439 | 19.0184 | 7.4255 |
| A | 450 | THR | 5.0246 | 0.8206 | 4.2039 |
| A | 451 | PRO | 77.0283 | 6.4114 | 70.6169 |
| A | 452 | GLU | 83.4586 | 9.5509 | 73.9077 |
| A | 453 | TRP | 104.1789 | 2.2273 | 101.9516 |
| A | 454 | PRO | 82.6259 | 7.9422 | 74.6837 |
| A | 455 | GLY | 78.4922 | 78.4922 | 0.0000 |
| A | 456 | SER | 100.8175 | 18.3535 | 82.4640 |
| A | 457 | ALA | 38.2652 | 36.1930 | 2.0722 |
| A | 458 | ASP | 96.7413 | 5.6723 | 91.0691 |
| A | 459 | LYS | 80.4683 | 9.2090 | 71.2593 |
| A | 460 | ARG | 34.4754 | 4.1101 | 30.3652 |
| A | 461 | THR | 5.9367 | 0.1406 | 5.7961 |
| A | 462 | LEU | 0.0000 | 0.0000 | 0.0000 |
| A | 463 | ALA | 0.5368 | 0.1388 | 0.3980 |
| A | 464 | CYS | 0.0000 | 0.0000 | 0.0000 |
| A | 465 | LEU | 0.0008 | 0.0008 | 0.0000 |
| A | 466 | ILE | 0.0000 | 0.0000 | 0.0000 |
| A | 467 | GLN | 2.9684 | 0.0000 | 2.9684 |
| A | 468 | ASN | 17.7174 | 4.3307 | 13.3867 |
| A | 469 | PHE | 0.0004 | 0.0004 | 0.0000 |
| A | 470 | MET | 46.0256 | 0.7431 | 45.2824 |
| A | 471 | PRO | 7.4359 | 7.1870 | 0.2488 |
| A | 472 | GLU | 71.9977 | 1.3886 | 70.6091 |
| A | 473 | ASP | 36.9672 | 5.3881 | 31.5791 |
| A | 474 | ILE | 30.6045 | 26.0783 | 4.5262 |
| A | 475 | SER | 16.9091 | 4.7440 | 12.1650 |
| A | 476 | VAL | 18.7736 | 16.6656 | 2.1080 |
| A | 477 | GLN | 8.9917 | 0.0000 | 8.9917 |
| A | 478 | TRP | 1.0631 | 0.5195 | 0.5437 |
| A | 479 | LEU | 7.7154 | 0.4549 | 7.2605 |
| A | 480 | HIS | 4.0034 | 0.0445 | 3.9589 |
| A | 481 | ASN | 21.0115 | 12.0230 | 8.9885 |
| A | 482 | GLU | 142.6780 | 29.4288 | 113.2492 |
| A | 483 | VAL | 37.5423 | 1.2993 | 36.2430 |
| A | 484 | GLN | 68.1522 | 20.4717 | 47.6805 |
| A | 485 | LEU | 6.9794 | 3.0193 | 3.9601 |
| A | 486 | PRO | 82.7331 | 12.4725 | 70.2606 |
| A | 487 | ASP | 99.7986 | 8.6821 | 91.1166 |
| A | 488 | ALA | 104.4735 | 41.9673 | 62.5061 |
| A | 489 | ARG | 82.9377 | 15.8430 | 67.0948 |
| A | 490 | HIS | 33.4558 | 17.0279 | 16.4278 |
| A | 491 | SER | 23.2825 | 5.4071 | 17.8753 |
| A | 492 | THR | 36.8192 | 13.1657 | 23.6535 |
| A | 493 | THR | 8.6830 | 4.6160 | 4.0671 |
| A | 494 | GLN | 130.3094 | 2.3750 | 127.9344 |
| A | 495 | PRO | 43.7487 | 18.3604 | 25.3884 |
| A | 496 | ARG | 71.6916 | 5.0872 | 66.6044 |

TABLE V-continued

IgE-Fc Residue Exposure

Surface plot for Crystal 2:
structure file = P21_easy.mtf
coordinate set = P21_easy.pdb

| | | | total accessible area | | |
|---|---|---|---|---|---|
| segid | resid | resname | residue | mainchain | sidechain |
| A | 497 | LYS | 151.8945 | 19.7554 | 132.1391 |
| A | 498 | THR | 24.6476 | 24.6476 | 0.0000 |
| A | 499 | LYS | 76.1423 | 24.1625 | 51.9798 |
| A | 500 | GLY | 91.4516 | 91.4516 | 0.0000 |
| A | 501 | SER | 46.2459 | 15.0049 | 31.2410 |
| A | 502 | GLY | 6.3690 | 6.3690 | 0.0000 |
| A | 503 | PHE | 33.3224 | 0.0000 | 33.3224 |
| A | 504 | PHE | 0.8074 | 0.0000 | 0.8704 |
| A | 505 | VAL | 0.6335 | 0.0000 | 0.6335 |
| A | 506 | PHE | 0.4165 | 0.2013 | 0.2152 |
| A | 507 | SER | 0.0000 | 0.0000 | 0.0000 |
| A | 508 | ARG | 9.4907 | 2.3255 | 7.1652 |
| A | 509 | LEU | 0.7877 | 0.3841 | 0.4037 |
| A | 510 | GLU | 40.6185 | 4.2514 | 36.3671 |
| A | 511 | VAL | 0.0819 | 0.0819 | 0.0000 |
| A | 512 | THR | 61.3338 | 0.0000 | 61.3338 |
| A | 513 | ARG | 103.3052 | 0.2933 | 103.0119 |
| A | 514 | ALA | 69.0538 | 11.8761 | 57.1777 |
| A | 515 | GLU | 17.2121 | 0.0000 | 17.2121 |
| A | 516 | TRP | 14.1456 | 6.6077 | 7.5379 |
| A | 517 | ALA | 74.7229 | 39.2611 | 35.4618 |
| A | 518 | GLN | 87.2179 | 40.9767 | 46.2413 |
| A | 519 | LYS | 97.3059 | 5.2493 | 92.0566 |
| A | 520 | ASP | 34.6246 | 7.1067 | 27.5179 |
| A | 521 | GLU | 70.3476 | 1.1239 | 69.2237 |
| A | 522 | PHE | 0.1366 | 0.0000 | 0.1366 |
| A | 523 | ILE | 16.8598 | 0.0000 | 16.8598 |
| A | 524 | CYS | 0.0037 | 0.0037 | 0.0000 |
| A | 525 | ARG | 58.8644 | 0.0000 | 58.8644 |
| A | 526 | ALA | 0.0000 | 0.0000 | 0.0000 |
| A | 527 | VAL | 0.6353 | 0.0000 | 0.6353 |
| A | 528 | HIS | 0.2062 | 0.0000 | 0.2062 |
| A | 529 | GLU | 43.1069 | 16.5006 | 26.6063 |
| A | 530 | ALA | 27.2584 | 23.6929 | 3.5655 |
| A | 531 | ALA | 0.8980 | 0.8961 | 0.0019 |
| A | 532 | SER | 86.4772 | 30.4416 | 56.0356 |
| A | 533 | PRO | 97.1843 | 13.6870 | 83.4973 |
| A | 534 | SER | 62.8102 | 14.1796 | 48.6306 |
| A | 535 | GLN | 43.8839 | 0.0000 | 43.8839 |
| A | 536 | THR | 38.9212 | 12.8596 | 26.0615 |
| A | 537 | VAL | 34.2723 | 4.8129 | 29.4595 |
| A | 538 | GLN | 75.3088 | 17.9396 | 57.3692 |
| A | 539 | ARG | 101.0729 | 3.0273 | 98.0456 |
| A | 540 | ALA | 55.2678 | 26.5109 | 28.7569 |
| A | 541 | VAL | 18.7418 | 6.3646 | 12.3772 |
| A | 542 | SER | 41.8695 | 10.0734 | 31.7960 |
| A | 543 | VAL | 1.2333 | 1.2333 | 0.0000 |
| A | 544 | ASN | 133.7411 | 42.8003 | 90.9409 |
| A | 545 | PRO | 85.4255 | 34.9689 | 50.4565 |
| B | 336 | VAL | 102.9314 | 52.6626 | 50.2688 |
| B | 337 | SER | 42.7456 | 7.5274 | 35.2182 |
| B | 338 | ALA | 4.3539 | 4.0843 | 0.2696 |
| B | 339 | TYR | 115.9563 | 2.4708 | 113.4855 |
| B | 340 | LEU | 30.8566 | 29.0230 | 1.8337 |
| B | 341 | SER | 52.2327 | 6.7779 | 45.4547 |
| B | 342 | ARG | 87.6319 | 16.7636 | 70.8683 |
| B | 343 | PRO | 7.8935 | 6.7713 | 1.1222 |
| B | 344 | SER | 45.6170 | 9.0314 | 36.5856 |
| B | 345 | PRO | 12.1704 | 0.4957 | 11.6747 |
| B | 346 | PHE | 52.3686 | 0.0000 | 52.3686 |
| B | 347 | ASP | 29.8201 | 0.0019 | 29.8182 |
| B | 348 | LEU | 13.7579 | 1.4360 | 12.3219 |
| B | 349 | PHE | 38.9855 | 13.2575 | 25.7280 |
| B | 350 | ILE | 74.5322 | 20.6151 | 53.9171 |
| B | 351 | ARG | 138.8679 | 24.3229 | 114.5450 |
| B | 352 | LYS | 135.7997 | 18.4977 | 117.3020 |
| B | 353 | SER | 51.7723 | 4.6525 | 47.1199 |
| B | 354 | PRO | 2.9569 | 1.3241 | 1.6327 |
| B | 355 | THR | 41.9668 | 5.0097 | 36.9571 |
| B | 356 | ILE | 0.7579 | 0.7579 | 0.0000 |
| B | 357 | THR | 39.5537 | 1.9652 | 37.5885 |
| B | 358 | CYS | 0.0000 | 0.0000 | 0.0000 |
| B | 359 | LEU | 59.5214 | 0.0000 | 59.5214 |
| B | 360 | VAL | 0.3008 | 0.0000 | 0.3008 |
| B | 361 | VAL | 55.6992 | 5.2145 | 50.4847 |
| B | 362 | ASP | 23.7006 | 0.8691 | 22.8316 |
| B | 363 | LEU | 172.3477 | 76.9271 | 95.4206 |
| B | 369 | THR | 159.9325 | 69.9437 | 89.9887 |
| B | 370 | VAL | 22.5382 | 7.2895 | 15.2487 |
| B | 371 | GLN | 90.2277 | 1.5536 | 88.6742 |
| B | 372 | LEU | 26.6677 | 23.5802 | 3.0875 |
| B | 373 | THR | 68.5172 | 3.8769 | 64.6403 |
| B | 374 | TRP | 20.8045 | 14.6978 | 6.1066 |
| B | 375 | SER | 48.7446 | 1.8295 | 46.9150 |
| B | 376 | ARG | 30.9388 | 10.2980 | 20.6408 |
| B | 377 | ALA | 73.0403 | 40.7021 | 32.3382 |
| B | 378 | SER | 61.8941 | 42.0236 | 19.8705 |
| B | 379 | GLY | 67.1330 | 67.1330 | 0.0000 |
| B | 380 | LYS | 120.6183 | 7.8609 | 112.7574 |
| B | 381 | PRO | 112.0724 | 20.0034 | 92.0690 |
| B | 382 | VAL | 53.8831 | 26.9959 | 26.8872 |
| B | 383 | GLN | 107.4407 | 15.8760 | 91.5647 |
| B | 384 | HIS | 172.0046 | 9.4535 | 162.5511 |
| B | 385 | SER | 52.0964 | 31.6203 | 20.4761 |
| B | 386 | THR | 88.5184 | 4.0969 | 84.4215 |
| B | 387 | ARG | 101.7495 | 27.1031 | 74.6464 |
| B | 388 | LYS | 123.0346 | 2.9619 | 120.0727 |
| B | 389 | GLU | 101.5218 | 32.1410 | 69.3808 |
| B | 390 | GLU | 91.4529 | 3.1735 | 88.2794 |
| B | 391 | LYS | 163.6679 | 28.9916 | 134.6763 |
| B | 392 | GLN | 71.3563 | 8.3807 | 62.9756 |
| B | 393 | ARG | 229.6861 | 26.4482 | 203.2379 |
| B | 394 | ASN | 132.5852 | 36.0595 | 96.5257 |
| B | 395 | GLY | 57.4036 | 57.4036 | 0.0000 |
| B | 396 | THR | 18.4934 | 0.8836 | 17.6099 |
| B | 397 | LEU | 31.7338 | 0.0000 | 31.7338 |
| B | 398 | THR | 22.7946 | 0.0004 | 22.7942 |
| B | 399 | VAL | 0.0000 | 0.0000 | 0.0000 |
| B | 400 | THR | 29.0670 | 0.4915 | 28.5755 |
| B | 401 | SER | 3.2735 | 0.0180 | 3.2555 |
| B | 402 | THR | 42.6909 | 1.1269 | 41.5640 |
| B | 403 | LEU | 0.4645 | 0.0000 | 0.4645 |
| B | 404 | PRO | 48.5964 | 2.4350 | 46.1613 |
| B | 405 | VAL | 10.5911 | 10.5911 | 0.0000 |
| B | 406 | GLY | 23.4236 | 23.4236 | 0.0000 |
| B | 407 | THR | 43.7708 | 5.4029 | 38.3679 |
| B | 408 | ALA | 57.6440 | 7.6006 | 50.0434 |
| B | 409 | ASP | 59.2277 | 5.9258 | 53.3019 |
| B | 410 | TRP | 8.3075 | 0.0023 | 8.3052 |
| B | 411 | ILE | 72.7996 | 4.4446 | 68.3551 |
| B | 412 | GLU | 142.5567 | 34.3947 | 108.1620 |
| B | 413 | GLY | 25.6299 | 25.6299 | 0.0000 |
| B | 414 | GLU | 21.9683 | 9.3013 | 12.6670 |
| B | 415 | THR | 43.0611 | 0.2058 | 42.8552 |
| B | 416 | TYR | 5.8725 | 0.0000 | 5.8725 |
| B | 417 | GLN | 37.5047 | 0.2322 | 37.2725 |
| B | 418 | CYS | 0.0000 | 0.0000 | 0.0000 |
| B | 419 | ARG | 98.7506 | 0.0105 | 98.7402 |
| B | 420 | VAL | 8.7594 | 2.6721 | 6.0873 |
| B | 421 | THR | 74.3083 | 24.8059 | 49.5024 |
| B | 424 | HIS | 183.5944 | 40.8567 | 142.7378 |
| B | 425 | LEU | 131.5581 | 67.4467 | 64.1114 |
| B | 427 | ALA | 90.6654 | 30.0621 | 60.6033 |
| B | 428 | ALA | 55.5794 | 24.2546 | 31.3247 |
| B | 429 | LEU | 56.5726 | 3.7892 | 52.7834 |
| B | 430 | MET | 100.1155 | 28.0906 | 72.0249 |
| B | 431 | ARG | 105.2256 | 1.8627 | 103.3629 |
| B | 432 | SER | 73.9499 | 24.5706 | 49.3793 |

TABLE V-continued

IgE-Fc Residue Exposure

Surface plot for Crystal 2:
structure file = P21_easy.mtf
coordinate set = P21_easy.pdb

| | | | total accessible area | | |
|---|---|---|---|---|---|
| segid | resid | resname | residue | mainchain | sidechain |
| B | 433 | THR | 11.9933 | 8.6061 | 3.3872 |
| B | 434 | THR | 52.2865 | 5.5509 | 46.7356 |
| B | 435 | LYS | 77.5112 | 10.1269 | 67.3844 |
| B | 436 | THR | 40.7857 | 9.7639 | 31.0219 |
| B | 437 | SER | 97.7155 | 19.1715 | 78.5440 |
| B | 438 | GLY | 44.1036 | 44.1036 | 0.0000 |
| B | 439 | PRO | 89.3647 | 12.4103 | 76.9544 |
| B | 440 | ARG | 102.0583 | 28.0384 | 74.0198 |
| B | 441 | ALA | 36.4647 | 8.1592 | 28.3055 |
| B | 442 | ALA | 52.6920 | 16.1153 | 36.5767 |
| B | 443 | PRO | 2.7465 | 2.7465 | 0.0000 |
| B | 444 | ALA | 6.0005 | 0.0008 | 5.9996 |
| B | 445 | VAL | 0.9759 | 0.6038 | 0.3721 |
| B | 446 | TYR | 10.6883 | 1.7839 | 8.9044 |
| B | 447 | ALA | 18.6367 | 18.4619 | 0.1748 |
| B | 448 | PHE | 25.9268 | 3.2310 | 22.6958 |
| B | 449 | ALA | 27.9133 | 20.2300 | 7.6834 |
| B | 450 | THR | 4.9101 | 0.1700 | 4.7401 |
| B | 451 | PRO | 80.8189 | 3.2156 | 77.7033 |
| B | 452 | GLU | 84.1341 | 22.8506 | 61.2836 |
| B | 453 | TRP | 55.4455 | 3.2699 | 52.1756 |
| B | 454 | PRO | 105.2485 | 19.1970 | 86.0514 |
| B | 455 | GLY | 67.0432 | 67.0432 | 0.0000 |
| B | 456 | SER | 54.5384 | 31.8148 | 22.7236 |
| B | 457 | ARG | 156.0198 | 6.9033 | 149.1165 |
| B | 458 | ASP | 51.2485 | 14.5009 | 36.7476 |
| B | 459 | LYS | 105.5385 | 9.3376 | 96.2009 |
| B | 460 | ARG | 47.7929 | 5.9953 | 41.7976 |
| B | 461 | THR | 7.0269 | 0.2108 | 6.8162 |
| B | 462 | LEU | 0.0000 | 0.0000 | 0.0000 |
| B | 463 | ALA | 0.3885 | 0.0769 | 0.3116 |
| B | 464 | CYS | 0.0000 | 0.0000 | 0.0000 |
| B | 465 | LEU | 0.0000 | 0.0000 | 0.0000 |
| B | 466 | ILE | 0.0000 | 0.0000 | 0.0000 |
| B | 467 | GLN | 8.2681 | 0.0000 | 8.2681 |
| B | 468 | ASN | 50.2133 | 4.5942 | 45.6191 |
| B | 469 | PHE | 0.0036 | 0.0018 | 0.0018 |
| B | 470 | MET | 47.2929 | 0.0419 | 47.2510 |
| B | 471 | PRO | 5.8318 | 4.7300 | 1.1018 |
| B | 472 | GLU | 68.3927 | 1.5384 | 66.8542 |
| B | 473 | ASP | 38.9865 | 6.8005 | 32.1859 |
| B | 474 | ILE | 26.3311 | 22.6056 | 3.7256 |
| B | 475 | SER | 11.9252 | 5.0600 | 6.8652 |
| B | 476 | VAL | 17.8401 | 15.7173 | 2.1227 |
| B | 477 | GLN | 4.1484 | 0.0120 | 4.1364 |
| B | 478 | TRP | 0.9926 | 0.3334 | 0.6592 |
| B | 479 | LEU | 16.5726 | 1.3116 | 15.2610 |
| B | 480 | HIS | 19.0243 | 3.5169 | 15.5074 |
| B | 481 | ASN | 73.9828 | 2.1174 | 71.8654 |
| B | 482 | GLU | 147.5595 | 42.2183 | 105.3412 |
| B | 483 | VAL | 118.3522 | 5.1640 | 113.1882 |
| B | 484 | GLN | 61.1666 | 20.1458 | 41.0208 |
| B | 485 | LEU | 23.2130 | 3.3304 | 19.8827 |
| B | 486 | PRO | 88.0033 | 12.8429 | 75.1604 |
| B | 487 | ASP | 90.4370 | 8.2128 | 82.2242 |
| B | 488 | ALA | 102.6214 | 42.1276 | 60.4938 |
| B | 489 | ARG | 80.4665 | 16.1978 | 64.2687 |
| B | 490 | HIS | 33.4724 | 16.9573 | 16.5151 |
| B | 491 | SER | 27.7598 | 5.5150 | 22.2448 |
| B | 492 | THR | 36.8430 | 13.1440 | 23.6989 |
| B | 493 | THR | 6.4874 | 4.0771 | 2.4104 |
| B | 494 | GLN | 127.7951 | 2.1400 | 125.6552 |
| B | 495 | PRO | 43.9933 | 18.8931 | 25.1002 |
| B | 496 | ARG | 77.0911 | 5.7973 | 71.2938 |
| B | 497 | LYS | 66.7264 | 9.2063 | 57.5201 |
| B | 498 | THR | 14.7952 | 14.6498 | 0.1454 |
| B | 499 | LYS | 176.1240 | 27.1598 | 148.9641 |
| B | 500 | GLY | 73.9536 | 73.9536 | 0.0000 |
| B | 501 | SER | 56.8991 | 12.9714 | 43.9278 |
| B | 502 | GLY | 0.0020 | 0.0020 | 0.0000 |
| B | 503 | PHE | 29.0814 | 0.0000 | 29.0814 |
| B | 504 | PHE | 0.5056 | 0.0000 | 0.5056 |
| B | 505 | VAL | 0.6639 | 0.0000 | 0.6639 |
| B | 506 | PHE | 0.3195 | 0.0614 | 0.2581 |
| B | 507 | SER | 0.0000 | 0.0000 | 0.0000 |
| B | 508 | ARG | 10.3608 | 2.0544 | 8.3064 |
| B | 509 | LEU | 0.8699 | 0.4038 | 0.4661 |
| B | 510 | GLU | 36.7167 | 4.5500 | 32.1667 |
| B | 511 | VAL | 0.3987 | 0.3987 | 0.0000 |
| B | 512 | THR | 56.2089 | 0.0000 | 56.2089 |
| B | 513 | ARG | 122.4227 | 1.8035 | 120.6193 |
| B | 514 | ALA | 77.6893 | 18.5063 | 59.1830 |
| B | 515 | GLU | 24.1431 | 1.8537 | 22.2894 |
| B | 516 | TRP | 21.5800 | 3.1040 | 18.4761 |
| B | 517 | ALA | 80.4076 | 32.0273 | 48.3803 |
| B | 518 | GLN | 136.7340 | 40.3669 | 96.3671 |
| B | 519 | LYS | 85.6622 | 2.4749 | 83.1874 |
| B | 520 | ASP | 39.6850 | 5.3508 | 34.3341 |
| B | 521 | GLU | 77.5958 | 2.0790 | 75.5168 |
| B | 522 | PHE | 0.1810 | 0.0000 | 0.1810 |
| B | 523 | ILE | 36.4083 | 0.0000 | 36.4083 |
| B | 524 | CYS | 0.0000 | 0.0000 | 0.0000 |
| B | 525 | ARG | 56.0549 | 0.0030 | 56.0520 |
| B | 526 | ALA | 0.0000 | 0.0000 | 0.0000 |
| B | 527 | VAL | 0.0000 | 0.0000 | 0.0000 |
| B | 528 | HIS | 0.2581 | 0.1623 | 0.0958 |
| B | 529 | GLU | 63.2584 | 17.7586 | 45.4998 |
| B | 530 | ALA | 27.0098 | 23.3410 | 3.6688 |
| B | 531 | ALA | 1.3232 | 1.3232 | 0.0000 |
| B | 532 | SER | 91.4553 | 16.2370 | 75.2183 |
| B | 533 | PRO | 101.7150 | 10.5333 | 91.1817 |
| B | 534 | SER | 71.5510 | 19.8232 | 51.7278 |
| B | 535 | GLN | 56.2268 | 0.0000 | 56.2268 |
| B | 536 | THR | 40.7351 | 12.0499 | 28.6852 |
| B | 537 | VAL | 39.6441 | 5.0384 | 34.6057 |
| B | 538 | GLN | 79.9484 | 19.4485 | 60.4999 |
| B | 539 | ARG | 92.7878 | 3.2641 | 89.5237 |
| B | 540 | ALA | 57.6947 | 26.5860 | 31.1086 |
| B | 541 | VAL | 18.5867 | 6.2550 | 12.3317 |
| B | 542 | SER | 47.8288 | 14.5909 | 33.2379 |
| B | 543 | VAL | 1.3729 | 0.8522 | 0.5207 |
| B | 544 | ASN | 167.5363 | 45.6777 | 121.8586 |

In another embodiment, the solvent accessibilities of the amino acids in Crystal 3 in Example 1 are indicated in Table VI.

TABLE VI

IgE-Fc Residue Exposure
>>>> Surface plot for Crystal 3:
>>>> structure file = P21_BIG_easy.mtf
>>>> coordinate set = P21_BIG_easy.pdb

| | | | total accessible area | | |
|---|---|---|---|---|---|
| segid | resid | resname | residue | mainchain | sidechain |
| C | 336 | VAL | 93.2742 | 50.6494 | 42.6248 |
| C | 337 | SER | 42.4787 | 3.3532 | 39.1254 |
| C | 338 | ALA | 10.0938 | 10.0938 | 0.0000 |
| C | 339 | TYR | 137.0270 | 5.5075 | 131.5195 |
| C | 340 | LEU | 31.0749 | 28.3193 | 2.7557 |
| C | 341 | SER | 57.7555 | 6.7204 | 51.0351 |
| C | 342 | ARG | 104.2513 | 17.4860 | 86.7653 |
| C | 343 | PRO | 9.1318 | 7.8358 | 1.2960 |

TABLE VI-continued

IgE-Fc Residue Exposure
>>>> Surface plot for Crystal 3:
>>>> structure file = P21_BIG_easy.mtf
>>>> coordinate set = P21_BIG_easy.pdb

| | | | total accessible area | | |
|---|---|---|---|---|---|
| segid | resid | resname | residue | mainchain | sidechain |
| C | 344 | SER | 41.8775 | 7.4636 | 34.4139 |
| C | 345 | PRO | 10.9549 | 1.1234 | 9.8316 |
| C | 346 | PHE | 47.2664 | 0.0000 | 47.2664 |
| C | 347 | ASP | 35.1754 | 0.0000 | 35.1754 |
| C | 348 | LEU | 10.8723 | 1.1923 | 9.6800 |
| C | 349 | PHE | 35.4149 | 8.0386 | 27.3763 |
| C | 350 | ILE | 74.1415 | 24.7111 | 49.4304 |
| C | 351 | ARG | 142.4024 | 17.4580 | 124.9444 |
| C | 352 | LYS | 137.4225 | 19.0602 | 118.3623 |
| C | 353 | SER | 35.9313 | 10.4723 | 25.4590 |
| C | 354 | PRO | 2.2277 | 1.8099 | 0.4178 |
| C | 355 | THR | 41.8000 | 4.7330 | 37.0670 |
| C | 356 | ILE | 0.4759 | 0.4759 | 0.0000 |
| C | 357 | THR | 39.4993 | 2.4208 | 37.0785 |
| C | 358 | CYS | 0.0000 | 0.0000 | 0.0000 |
| C | 359 | LEU | 53.6796 | 0.0017 | 53.6778 |
| C | 360 | VAL | 9.1151 | 0.0073 | 9.1078 |
| C | 361 | VAL | 38.0435 | 0.7715 | 37.2720 |
| C | 362 | ASP | 20.0077 | 0.0000 | 20.0077 |
| C | 363 | LEU | 118.3887 | 13.0042 | 105.3845 |
| C | 364 | ALA | 70.7626 | 9.2997 | 61.4629 |
| C | 365 | PRO | 45.8442 | 24.3833 | 21.4609 |
| C | 366 | SER | 45.5956 | 16.1602 | 29.4353 |
| C | 367 | LYS | 182.6042 | 16.6884 | 165.9158 |
| C | 368 | GLY | 41.3173 | 41.3173 | 0.0000 |
| C | 369 | THR | 116.3251 | 12.2614 | 104.0638 |
| C | 370 | VAL | 22.6541 | 5.0378 | 17.6163 |
| C | 371 | ASN | 79.6774 | 2.2323 | 77.4451 |
| C | 372 | LEU | 25.4548 | 22.1823 | 3.2725 |
| C | 373 | THR | 70.8754 | 4.7661 | 66.1093 |
| C | 374 | TRP | 16.2334 | 12.7312 | 3.5022 |
| C | 375 | SER | 41.3674 | 3.0782 | 38.2892 |
| C | 376 | ARG | 36.0093 | 13.1422 | 22.8671 |
| C | 377 | ALA | 73.7104 | 41.7104 | 31.3959 |
| C | 378 | SER | 66.0379 | 43.5228 | 22.5151 |
| C | 379 | GLY | 64.5074 | 64.5074 | 0.0000 |
| C | 380 | LYS | 117.6860 | 9.9244 | 107.7616 |
| C | 381 | PRO | 110.3885 | 12.4724 | 97.9161 |
| C | 382 | VAL | 49.5740 | 21.7378 | 27.8361 |
| C | 383 | ASN | 82.4694 | 12.6045 | 69.8649 |
| C | 384 | HIS | 166.7747 | 12.6430 | 154.1317 |
| C | 385 | SER | 54.3239 | 27.0266 | 27.2973 |
| C | 386 | THR | 60.4776 | 4.1216 | 56.3560 |
| C | 387 | ARG | 95.1837 | 25.4827 | 69.7010 |
| C | 388 | LYS | 107.4088 | 8.0349 | 99.3739 |
| C | 389 | GLU | 103.4659 | 34.1024 | 69.3635 |
| C | 390 | GLU | 112.2932 | 5.2169 | 107.0763 |
| C | 391 | LYS | 123.4569 | 26.5999 | 96.8570 |
| C | 392 | GLN | 69.9627 | 5.9827 | 63.9800 |
| C | 393 | ARG | 238.1610 | 38.3541 | 199.8068 |
| C | 394 | ASN | 126.0943 | 29.3421 | 96.7522 |
| C | 395 | GLY | 25.9257 | 25.9257 | 0.0000 |
| C | 396 | THR | 26.5787 | 0.0000 | 26.5787 |
| C | 397 | LEU | 27.4752 | 0.7815 | 26.6937 |
| C | 398 | THR | 21.3868 | 0.0000 | 21.3868 |
| C | 399 | VAL | 3.6584 | 0.0000 | 3.6584 |
| C | 400 | THR | 24.7551 | 0.0000 | 24.7551 |
| C | 401 | SER | 3.6821 | 0.0000 | 3.6821 |
| C | 402 | THR | 28.1164 | 0.3838 | 27.7325 |
| C | 403 | LEU | 0.5866 | 0.0000 | 0.5866 |
| C | 404 | PRO | 49.7650 | 2.4140 | 47.3511 |
| C | 405 | VAL | 12.1320 | 12.1320 | 0.0000 |
| C | 406 | GLY | 28.1240 | 28.1240 | 0.0000 |
| C | 407 | THR | 45.4795 | 4.5765 | 40.9030 |
| C | 408 | ALA | 59.9647 | 6.8943 | 53.0704 |
| C | 409 | ASP | 52.0157 | 4.5262 | 47.4895 |
| C | 410 | TRP | 23.0007 | 4.9687 | 18.0320 |
| C | 411 | ILE | 96.1330 | 28.4278 | 67.7052 |
| C | 412 | GLU | 152.1086 | 39.7287 | 112.3799 |
| C | 413 | GLY | 49.5983 | 49.5983 | 0.0000 |
| C | 414 | GLU | 20.3921 | 6.4546 | 13.9374 |
| C | 415 | THR | 42.7631 | 0.3478 | 42.4152 |
| C | 416 | TYR | 5.9063 | 0.0000 | 5.9063 |
| C | 417 | GLN | 57.6284 | 0.0181 | 57.6103 |
| C | 418 | CYS | 0.0007 | 0.0000 | 0.0007 |
| C | 419 | ARG | 96.6880 | 0.1631 | 96.5250 |
| C | 420 | VAL | 7.4753 | 1.8817 | 5.5936 |
| C | 421 | THR | 47.6164 | 2.0582 | 45.5581 |
| C | 422 | HIS | 24.5099 | 10.8352 | 13.6747 |
| C | 423 | PRO | 88.3451 | 41.4740 | 46.8711 |
| C | 424 | HIS | 105.7207 | 27.0309 | 78.6897 |
| C | 425 | LEU | 62.9442 | 15.1491 | 47.7951 |
| C | 426 | PRO | 133.7924 | 43.7657 | 90.0267 |
| C | 427 | ARG | 178.5783 | 18.3361 | 160.2422 |
| C | 428 | ALA | 21.2732 | 11.9560 | 9.3172 |
| C | 429 | LEU | 46.0840 | 1.1453 | 44.9386 |
| C | 430 | MET | 78.1467 | 19.4257 | 58.7210 |
| C | 431 | ARG | 86.3409 | 8.1275 | 78.2134 |
| C | 432 | SER | 76.2207 | 24.6560 | 51.5647 |
| C | 433 | THR | 11.7456 | 7.8255 | 3.9200 |
| C | 434 | THR | 88.2309 | 39.7849 | 48.4460 |
| C | 440 | ARG | 173.7465 | 53.5605 | 120.1860 |
| C | 441 | ALA | 31.2332 | 7.0059 | 24.2273 |
| C | 442 | ALA | 35.0522 | 16.2284 | 18.8238 |
| C | 443 | PRO | 4.5675 | 4.5675 | 0.0000 |
| C | 444 | ALA | 50.5074 | 9.8683 | 40.6391 |
| C | 445 | VAL | 7.7539 | 7.7530 | 0.0009 |
| C | 446 | TYR | 65.1640 | 0.2631 | 64.9009 |
| C | 447 | ALA | 4.2134 | 4.2134 | 0.0000 |
| C | 448 | PHE | 16.8614 | 3.3112 | 13.5502 |
| C | 449 | ALA | 26.9000 | 15.5851 | 11.3149 |
| C | 450 | THR | 24.1243 | 11.2592 | 12.8652 |
| C | 451 | PRO | 65.3543 | 15.3586 | 49.9957 |
| C | 452 | GLU | 141.0356 | 85.6877 | 55.3479 |
| C | 459 | LYS | 94.9750 | 18.3732 | 76.6018 |
| C | 460 | ARG | 44.0133 | 0.0328 | 43.9805 |
| C | 461 | THR | 2.2899 | 2.1119 | 0.1780 |
| C | 462 | LEU | 2.6374 | 0.0000 | 2.6374 |
| C | 463 | ALA | 1.5179 | 0.1033 | 1.4146 |
| C | 464 | CYS | 0.0899 | 0.0899 | 0.0000 |
| C | 465 | LEU | 3.8724 | 0.7836 | 3.0889 |
| C | 466 | ILE | 0.0019 | 0.0000 | 0.0019 |
| C | 467 | GLN | 11.2029 | 0.0000 | 11.2029 |
| C | 468 | ASN | 33.9292 | 3.7877 | 30.1415 |
| C | 469 | PHE | 0.0000 | 0.0000 | 0.0000 |
| C | 470 | MET | 77.3647 | 0.0441 | 77.3205 |
| C | 471 | PRO | 39.3284 | 4.1927 | 35.1357 |
| C | 472 | GLU | 72.4320 | 1.3655 | 71.0665 |
| C | 473 | ASP | 50.5518 | 6.9933 | 43.5586 |
| C | 474 | ILE | 28.0735 | 23.4028 | 4.6707 |
| C | 475 | SER | 14.7692 | 5.7185 | 9.0507 |
| C | 476 | VAL | 13.7680 | 10.7915 | 2.9765 |
| C | 477 | GLN | 10.4653 | 1.9946 | 8.4707 |
| C | 478 | TRP | 1.9543 | 1.3489 | 0.6054 |
| C | 479 | LEU | 15.4353 | 1.1077 | 14.3276 |
| C | 480 | HIS | 18.0149 | 0.4669 | 17.5479 |
| C | 481 | ASN | 75.5504 | 6.5082 | 69.0422 |
| C | 482 | GLU | 102.1004 | 27.7007 | 74.3997 |
| C | 483 | VAL | 77.0701 | 3.0254 | 74.0447 |
| C | 484 | GLN | 77.5177 | 17.5837 | 59.9340 |
| C | 485 | LEU | 26.6360 | 6.6283 | 20.0077 |
| C | 486 | PRO | 88.4632 | 12.8282 | 75.6350 |
| C | 487 | ASP | 104.4215 | 8.8138 | 95.6078 |
| C | 488 | ALA | 94.3136 | 32.3680 | 61.9455 |
| C | 489 | ARG | 84.0690 | 17.5345 | 66.5345 |
| C | 490 | HIS | 28.5595 | 14.8669 | 13.6926 |
| C | 491 | SER | 28.5244 | 6.0028 | 22.5216 |
| C | 492 | THR | 36.1265 | 13.7054 | 22.4210 |
| C | 493 | THR | 16.5690 | 5.8181 | 10.7510 |
| C | 494 | GLN | 127.3073 | 4.7523 | 122.5550 |

TABLE VI-continued

IgE-Fc Residue Exposure
>>>> Surface plot for Crystal 3:
>>>> structure file = P21_BIG_easy.mtf
>>>> coordinate set = P21_BIG_easy.pdb

| segid | resid | resname | residue | mainchain | sidechain |
|---|---|---|---|---|---|
| C | 495 | PRO | 46.2301 | 19.2857 | 26.9444 |
| C | 496 | ARG | 90.0612 | 4.4085 | 85.6527 |
| C | 497 | LYS | 157.3700 | 17.0659 | 140.3041 |
| C | 498 | THR | 8.7143 | 8.7116 | 0.0027 |
| C | 499 | LYS | 147.8789 | 22.3458 | 125.5331 |
| C | 500 | GLY | 76.1456 | 76.1456 | 0.0000 |
| C | 501 | SER | 38.4968 | 17.1124 | 21.3844 |
| C | 502 | GLY | 8.6727 | 8.6727 | 0.0000 |
| C | 503 | PHE | 39.3847 | 0.0000 | 39.3847 |
| C | 504 | PHE | 2.7110 | 0.0000 | 2.7110 |
| C | 505 | VAL | 0.9095 | 0.0000 | 0.9095 |
| C | 506 | PHE | 1.8932 | 0.0000 | 1.8932 |
| C | 507 | SER | 0.0015 | 0.0015 | 0.0000 |
| C | 508 | ARG | 7.5987 | 1.5837 | 6.0151 |
| C | 509 | LEU | 0.3344 | 0.0386 | 0.2959 |
| C | 510 | GLU | 26.0848 | 2.2021 | 23.8828 |
| C | 511 | VAL | 0.7758 | 0.7230 | 0.0528 |
| C | 512 | THR | 68.1046 | 0.0000 | 68.1046 |
| C | 513 | ARG | 126.5725 | 0.1729 | 126.3996 |
| C | 514 | ALA | 68.3454 | 23.3983 | 44.9471 |
| C | 515 | GLU | 39.5090 | 8.4560 | 31.0530 |
| C | 516 | TRP | 42.2735 | 5.4396 | 36.8340 |
| C | 517 | GLU | 117.1124 | 35.7175 | 81.3949 |
| C | 518 | ALA | 44.2894 | 6.5670 | 37.7224 |
| C | 519 | LYS | 9.4660 | 0.0004 | 9.4656 |
| C | 520 | ASP | 88.2292 | 6.9644 | 81.2648 |
| C | 521 | GLU | 39.6999 | 3.4845 | 36.2154 |
| C | 522 | PHE | 0.8042 | 0.0000 | 0.8042 |
| C | 523 | ILE | 29.3892 | 0.0000 | 29.3892 |
| C | 524 | CYS | 0.0020 | 0.0000 | 0.0020 |
| C | 525 | ARG | 39.3954 | 0.0000 | 39.3954 |
| C | 526 | ALA | 0.0000 | 0.0000 | 0.0000 |
| C | 527 | VAL | 0.1407 | 0.0000 | 0.1407 |
| C | 528 | HIS | 0.7894 | 0.0000 | 0.7894 |
| C | 529 | GLU | 76.2471 | 10.8300 | 65.4171 |
| C | 530 | ALA | 17.1710 | 9.7310 | 7.4400 |
| C | 531 | ALA | 12.1120 | 12.1120 | 0.0000 |
| C | 532 | SER | 26.8802 | 5.9574 | 20.9228 |
| C | 533 | PRO | 35.5296 | 3.9947 | 31.5349 |
| C | 534 | SER | 28.7562 | 25.6015 | 3.1547 |
| C | 535 | GLN | 37.6185 | 0.0000 | 37.6185 |
| C | 536 | THR | 16.2725 | 9.9042 | 6.3683 |
| C | 537 | VAL | 31.3396 | 4.2146 | 27.1250 |
| C | 538 | GLN | 26.7059 | 11.0219 | 15.6840 |
| C | 539 | ARG | 80.5289 | 4.0336 | 76.4952 |
| C | 540 | ALA | 44.9983 | 21.4836 | 23.5147 |
| C | 541 | VAL | 9.9594 | 2.6164 | 7.3430 |
| C | 542 | SER | 72.4057 | 2.6000 | 69.8057 |
| C | 543 | VAL | 118.7146 | 35.4103 | 83.3043 |
| D | 336 | VAL | 92.5263 | 49.9479 | 42.5784 |
| D | 337 | SER | 42.0291 | 3.5113 | 38.5178 |
| D | 338 | ALA | 10.6947 | 10.6947 | 0.0000 |
| D | 339 | TYR | 135.6000 | 5.1942 | 130.4058 |
| D | 340 | LEU | 33.0395 | 29.7915 | 3.2480 |
| D | 341 | SER | 56.4933 | 5.7017 | 50.7915 |
| D | 342 | ARG | 107.3974 | 16.9443 | 90.4530 |
| D | 343 | PRO | 8.5262 | 7.4149 | 1.1114 |
| D | 344 | SER | 40.6891 | 8.1281 | 32.5610 |
| D | 345 | PRO | 10.0945 | 0.3238 | 9.7708 |
| D | 346 | PHE | 45.2694 | 0.0000 | 45.2694 |
| D | 347 | ASP | 30.7798 | 0.0000 | 30.7798 |
| D | 348 | LEU | 15.1456 | 1.8359 | 13.3096 |
| D | 349 | PHE | 43.3433 | 11.9301 | 31.4132 |
| D | 350 | ILE | 70.7585 | 16.6943 | 54.0642 |
| D | 351 | ARG | 130.2066 | 26.0839 | 104.1227 |
| D | 352 | LYS | 133.0467 | 19.1352 | 113.9114 |
| D | 353 | SER | 50.0282 | 9.4575 | 40.5707 |
| D | 354 | PRO | 2.4304 | 1.9923 | 0.4381 |
| D | 355 | THR | 39.1474 | 3.7790 | 35.3683 |
| D | 356 | ILE | 0.4544 | 0.4521 | 0.0023 |
| D | 357 | THR | 40.1661 | 1.9497 | 38.2164 |
| D | 358 | CYS | 0.0000 | 0.0000 | 0.0000 |
| D | 359 | LEU | 53.1029 | 0.0000 | 53.1029 |
| D | 360 | VAL | 9.5196 | 0.0809 | 9.4387 |
| D | 361 | VAL | 37.8728 | 1.0111 | 36.8617 |
| D | 362 | ASP | 20.2157 | 0.0000 | 20.2157 |
| D | 363 | LEU | 120.7616 | 13.2661 | 107.4955 |
| D | 364 | ALA | 69.6622 | 8.3472 | 61.3150 |
| D | 365 | PRO | 50.3021 | 24.1512 | 26.1509 |
| D | 366 | SER | 46.8579 | 16.6839 | 30.1740 |
| D | 367 | LYS | 185.3419 | 17.0725 | 168.2694 |
| D | 368 | GLY | 39.7110 | 39.7110 | 0.0000 |
| D | 369 | THR | 118.7491 | 13.7177 | 105.0314 |
| D | 370 | VAL | 23.3628 | 4.8739 | 18.4889 |
| D | 371 | ASN | 79.7539 | 2.4833 | 77.2706 |
| D | 372 | LEU | 25.5630 | 22.3192 | 3.2438 |
| D | 373 | THR | 70.8725 | 4.3878 | 66.4847 |
| D | 374 | TRP | 16.8505 | 12.7662 | 4.0843 |
| D | 375 | SER | 40.4787 | 3.0245 | 37.4542 |
| D | 376 | ARG | 37.1881 | 13.8068 | 23.3813 |
| D | 377 | ALA | 75.3768 | 42.2404 | 33.1364 |
| D | 378 | SER | 65.4297 | 42.5303 | 22.8994 |
| D | 379 | GLY | 63.8020 | 63.8020 | 0.0000 |
| D | 380 | LYS | 118.5378 | 9.8832 | 108.6546 |
| D | 381 | PRO | 109.2168 | 12.2885 | 96.9283 |
| D | 382 | VAL | 52.2558 | 21.0651 | 31.1907 |
| D | 383 | ASN | 80.5544 | 11.7990 | 68.7554 |
| D | 384 | HIS | 168.7016 | 12.3573 | 156.3444 |
| D | 385 | SER | 54.2863 | 27.2166 | 27.0697 |
| D | 386 | THR | 62.5480 | 3.6854 | 58.8626 |
| D | 387 | ARG | 92.3524 | 24.4723 | 67.8800 |
| D | 388 | LYS | 109.4481 | 8.9694 | 100.4787 |
| D | 389 | GLU | 103.2487 | 33.2911 | 69.9576 |
| D | 390 | GLU | 112.6685 | 5.4559 | 107.2126 |
| D | 391 | LYS | 130.8061 | 27.2903 | 103.5158 |
| D | 392 | GLN | 70.8209 | 5.8119 | 65.0089 |
| D | 393 | ARG | 236.8265 | 38.9520 | 197.8746 |
| D | 394 | ASN | 128.3642 | 31.8587 | 96.5055 |
| D | 395 | GLY | 25.5957 | 25.5957 | 0.0000 |
| D | 396 | THR | 25.7985 | 0.0000 | 25.7985 |
| D | 397 | LEU | 27.4468 | 0.8627 | 26.5842 |
| D | 398 | THR | 20.8737 | 0.0000 | 20.8737 |
| D | 399 | VAL | 4.1735 | 0.0000 | 4.1735 |
| D | 400 | THR | 23.2103 | 0.0000 | 23.2103 |
| D | 401 | SER | 3.6578 | 0.0000 | 3.6578 |
| D | 402 | THR | 28.5474 | 0.4567 | 28.0907 |
| D | 403 | LEU | 0.5958 | 0.0000 | 0.5958 |
| D | 404 | PRO | 48.0669 | 2.1389 | 45.9280 |
| D | 405 | VAL | 10.6080 | 10.6080 | 0.0000 |
| D | 406 | GLY | 28.6932 | 28.6932 | 0.0000 |
| D | 407 | THR | 45.0537 | 5.2256 | 39.8282 |
| D | 408 | ALA | 59.3358 | 6.6052 | 52.7306 |
| D | 409 | ASP | 51.4092 | 6.3452 | 45.0640 |
| D | 410 | TRP | 21.1030 | 4.8859 | 16.2171 |
| D | 411 | ILE | 104.8482 | 28.9555 | 75.8926 |
| D | 412 | GLU | 151.0674 | 39.8137 | 111.2536 |
| D | 413 | GLY | 49.6224 | 49.6224 | 0.0000 |
| D | 414 | GLU | 20.7041 | 7.0785 | 13.6256 |
| D | 415 | THR | 41.8677 | 0.2655 | 41.6022 |
| D | 416 | TYR | 5.4766 | 0.0010 | 5.4755 |
| D | 417 | GLN | 60.1368 | 0.0476 | 60.0892 |
| D | 418 | CYS | 0.0000 | 0.0000 | 0.0000 |
| D | 419 | ARG | 97.9568 | 0.0035 | 97.9534 |
| D | 420 | VAL | 8.3203 | 2.6217 | 5.6986 |
| D | 421 | THR | 46.3207 | 1.9018 | 44.4189 |
| D | 422 | HIS | 26.4185 | 12.6661 | 13.7524 |
| D | 423 | PRO | 88.7915 | 41.6431 | 47.1484 |
| D | 424 | HIS | 104.0793 | 26.7882 | 77.2911 |
| D | 425 | LEU | 65.5955 | 15.6469 | 49.9486 |
| D | 426 | PRO | 132.6612 | 43.3990 | 89.2621 |

TABLE VI-continued

IgE-Fc Residue Exposure
>>>> Surface plot for Crystal 3:
>>>> structure file = P21_BIG_easy.mtf
>>>> coordinate set = P21_BIG_easy.pdb

| | | | total accessible area | | |
|---|---|---|---|---|---|
| segid | resid | resname | residue | mainchain | sidechain |
| D | 427 | ARG | 178.3938 | 19.3527 | 159.0410 |
| D | 428 | ALA | 20.8257 | 11.3100 | 9.5156 |
| D | 429 | LEU | 47.0080 | 0.9466 | 46.0614 |
| D | 430 | MET | 79.0413 | 19.7218 | 59.3195 |
| D | 431 | ARG | 82.8257 | 7.6716 | 75.1541 |
| D | 432 | SER | 75.5677 | 24.8308 | 50.7369 |
| D | 433 | THR | 12.0115 | 8.1066 | 3.9049 |
| D | 434 | THR | 86.3949 | 38.5674 | 47.8275 |
| D | 440 | ARG | 170.4409 | 52.6284 | 117.8125 |
| D | 441 | ALA | 32.3299 | 7.3019 | 25.0279 |
| D | 442 | ALA | 39.8574 | 15.6697 | 24.1876 |
| D | 443 | PRO | 4.7528 | 4.7466 | 0.0062 |
| D | 444 | ALA | 48.4088 | 10.1000 | 38.3087 |
| D | 445 | VAL | 8.2434 | 8.2433 | 0.0001 |
| D | 446 | TYR | 67.5723 | 0.1698 | 67.4024 |
| D | 447 | ALA | 4.3216 | 4.3216 | 0.0000 |
| D | 448 | PHE | 17.6010 | 3.3558 | 14.2452 |
| D | 449 | ALA | 26.8923 | 15.3675 | 11.5248 |
| D | 450 | THR | 24.1372 | 11.0401 | 13.0971 |
| D | 451 | PRO | 65.2230 | 15.0767 | 50.1463 |
| D | 452 | GLU | 140.9019 | 83.3766 | 57.5253 |
| D | 459 | LYS | 94.5766 | 18.6538 | 75.9228 |
| D | 460 | ARG | 45.3395 | 0.1346 | 45.2049 |
| D | 461 | THR | 2.3392 | 2.1642 | 0.1750 |
| D | 462 | LEU | 2.5473 | 0.1231 | 2.4242 |
| D | 463 | ALA | 1.5352 | 0.1343 | 1.4009 |
| D | 464 | CYS | 0.0475 | 0.0475 | 0.0000 |
| D | 465 | LEU | 3.1119 | 0.7011 | 2.4108 |
| D | 466 | ILE | 0.0023 | 0.0000 | 0.0023 |
| D | 467 | GLN | 11.3638 | 0.0000 | 11.3638 |
| D | 468 | ASN | 33.6562 | 3.9756 | 29.6806 |
| D | 469 | PHE | 0.0000 | 0.0000 | 0.0000 |
| D | 470 | MET | 75.0996 | 0.0050 | 75.0946 |
| D | 471 | PRO | 39.2680 | 4.0216 | 35.2463 |
| D | 472 | GLU | 74.1461 | 1.1796 | 72.9665 |
| D | 473 | ASP | 51.2558 | 6.3412 | 44.9146 |
| D | 474 | ILE | 32.0468 | 27.6347 | 4.4121 |
| D | 475 | SER | 16.9489 | 5.6714 | 11.2776 |
| D | 476 | VAL | 13.6975 | 11.0459 | 2.6516 |
| D | 477 | GLN | 11.4867 | 2.1876 | 9.2991 |
| D | 478 | TRP | 1.8893 | 1.2327 | 0.6566 |
| D | 479 | LEU | 15.4913 | 1.1212 | 14.3701 |
| D | 480 | HIS | 17.8676 | 0.3986 | 17.4690 |
| D | 481 | ASN | 78.4892 | 10.0091 | 68.4801 |
| D | 482 | GLU | 113.0589 | 27.8682 | 85.1908 |
| D | 483 | VAL | 78.7102 | 3.3084 | 75.4018 |
| D | 484 | GLN | 78.9205 | 17.8747 | 61.0458 |
| D | 485 | LEU | 27.5038 | 6.5974 | 20.9064 |
| D | 486 | PRO | 86.6423 | 12.6772 | 73.9651 |
| D | 487 | ASP | 104.7231 | 8.7564 | 95.9667 |
| D | 488 | ALA | 92.3860 | 31.9831 | 60.4029 |
| D | 489 | ARG | 82.1330 | 16.6044 | 65.6286 |
| D | 490 | HIS | 28.7064 | 15.4682 | 13.2383 |
| D | 491 | SER | 25.4428 | 5.8144 | 19.6284 |
| D | 492 | THR | 36.9343 | 13.8189 | 23.1153 |
| D | 493 | THR | 17.7046 | 6.0207 | 11.6839 |
| D | 494 | GLN | 126.9962 | 4.7088 | 122.2875 |
| D | 495 | PRO | 47.0570 | 19.7301 | 27.3268 |
| D | 496 | ARG | 89.4788 | 4.3988 | 85.0800 |
| D | 497 | LYS | 157.4444 | 17.1115 | 140.3328 |
| D | 498 | THR | 9.9055 | 9.9052 | 0.0004 |
| D | 499 | LYS | 146.6389 | 22.1823 | 124.4566 |
| D | 500 | GLY | 74.2945 | 74.2945 | 0.0000 |
| D | 501 | SER | 42.1000 | 20.1221 | 21.9779 |
| D | 502 | GLY | 8.6451 | 8.6451 | 0.0000 |
| D | 503 | PHE | 38.0057 | 0.0000 | 38.0057 |
| D | 504 | PHE | 3.8606 | 0.0000 | 3.8606 |
| D | 505 | VAL | 0.9477 | 0.0000 | 0.9477 |
| D | 506 | PHE | 2.1090 | 0.0000 | 2.1090 |
| D | 507 | SER | 0.0000 | 0.0000 | 0.0000 |
| D | 508 | ARG | 6.8857 | 1.0029 | 5.8828 |
| D | 509 | LEU | 0.4268 | 0.0077 | 0.4190 |
| D | 510 | GLU | 26.4790 | 2.3820 | 24.0970 |
| D | 511 | VAL | 0.9722 | 0.7676 | 0.2046 |
| D | 512 | THR | 64.5773 | 0.0000 | 64.5773 |
| D | 513 | ARG | 131.4165 | 0.1277 | 131.2889 |
| D | 514 | ALA | 67.9404 | 22.5694 | 45.3710 |
| D | 515 | GLU | 40.2531 | 8.6299 | 31.6232 |
| D | 516 | TRP | 43.4407 | 5.4015 | 38.0393 |
| D | 517 | GLU | 117.7518 | 34.6753 | 83.0764 |
| D | 518 | ALA | 43.7688 | 6.9304 | 36.8384 |
| D | 519 | LYS | 9.2251 | 0.0000 | 9.2251 |
| D | 520 | ASP | 69.9166 | 9.5560 | 60.3606 |
| D | 521 | GLU | 39.0952 | 3.6256 | 35.4697 |
| D | 522 | PHE | 0.7623 | 0.0015 | 0.7608 |
| D | 523 | ILE | 36.5855 | 0.0000 | 36.5855 |
| D | 524 | CYS | 0.0000 | 0.0000 | 0.0000 |
| D | 525 | ARG | 46.6531 | 0.0000 | 46.6531 |
| D | 526 | ALA | 0.0217 | 0.0217 | 0.0000 |
| D | 527 | VAL | 0.3616 | 0.0013 | 0.3603 |
| D | 528 | HIS | 0.4971 | 0.0000 | 0.4971 |
| D | 529 | GLU | 74.1352 | 10.5626 | 63.5727 |
| D | 530 | ALA | 10.3703 | 5.8154 | 4.5549 |
| D | 531 | ALA | 11.8751 | 11.8751 | 0.0000 |
| D | 532 | SER | 25.3685 | 5.6789 | 19.6896 |
| D | 533 | PRO | 37.3384 | 4.3587 | 32.9797 |
| D | 534 | SER | 32.7470 | 25.6020 | 7.1450 |
| D | 535 | GLN | 38.8328 | 0.0000 | 38.8328 |
| D | 536 | THR | 17.5122 | 9.7259 | 7.7863 |
| D | 537 | VAL | 32.4636 | 3.9748 | 27.4889 |
| D | 538 | GLN | 27.2599 | 10.4851 | 16.7748 |
| D | 539 | ARG | 83.8512 | 4.2894 | 79.5618 |
| D | 540 | ALA | 48.0983 | 21.4510 | 26.6473 |
| D | 541 | VAL | 9.6759 | 2.5504 | 7.1255 |
| D | 542 | SER | 73.1779 | 3.4281 | 69.7498 |
| D | 543 | VAL | 108.4150 | 36.6096 | 71.8054 |
| E | 336 | VAL | 89.5775 | 48.5529 | 41.0246 |
| E | 337 | SER | 41.5476 | 3.3201 | 38.2275 |
| E | 338 | ALA | 10.1696 | 10.1696 | 0.0000 |
| E | 339 | TYR | 137.3830 | 5.3968 | 131.9861 |
| E | 340 | LEU | 30.5493 | 27.6971 | 2.8523 |
| E | 341 | SER | 55.3413 | 7.0280 | 48.3134 |
| E | 342 | ARG | 112.9876 | 19.6572 | 93.3305 |
| E | 343 | PRO | 12.4042 | 10.8233 | 1.5808 |
| E | 344 | SER | 39.7658 | 2.2401 | 37.5256 |
| E | 345 | PRO | 10.5311 | 0.0000 | 10.5311 |
| E | 346 | PHE | 65.7091 | 0.0000 | 65.7091 |
| E | 347 | ASP | 27.6850 | 0.0000 | 27.6850 |
| E | 348 | LEU | 19.2065 | 3.2370 | 15.9695 |
| E | 349 | PHE | 52.0299 | 18.497 | 33.9802 |
| E | 350 | ILE | 65.3731 | 13.0202 | 52.3529 |
| E | 351 | ARG | 148.5087 | 26.2556 | 122.2531 |
| E | 352 | LYS | 135.0376 | 18.4815 | 116.5562 |
| E | 353 | SER | 55.3443 | 14.7253 | 40.6190 |
| E | 354 | PRO | 1.9975 | 1.8043 | 0.1931 |
| E | 355 | THR | 45.9913 | 5.4874 | 40.5039 |
| E | 356 | ILE | 0.4708 | 0.4708 | 0.0000 |
| E | 357 | THR | 40.7313 | 2.1856 | 38.5457 |
| E | 358 | CYS | 0.0000 | 0.0000 | 0.0000 |
| E | 359 | LEU | 53.1940 | 0.0000 | 53.1940 |
| E | 360 | VAL | 9.2606 | 0.0000 | 9.2606 |
| E | 361 | VAL | 38.3245 | 1.0419 | 37.2826 |
| E | 362 | ASP | 20.0274 | 0.0000 | 20.0274 |
| E | 363 | LEU | 122.9983 | 12.6133 | 110.3850 |
| E | 364 | ALA | 69.0694 | 8.7750 | 60.2944 |
| E | 365 | PRO | 26.3664 | 6.3005 | 20.0660 |
| E | 366 | SER | 26.9535 | 8.9539 | 17.9997 |
| E | 367 | LYS | 104.1536 | 14.9794 | 89.1742 |
| E | 368 | GLY | 39.1795 | 39.1795 | 0.0000 |
| E | 369 | THR | 115.8751 | 12.5380 | 103.3371 |

TABLE VI-continued

IgE-Fc Residue Exposure
>>>> Surface plot for Crystal 3:
>>>> structure file = P21_BIG_easy.mtf
>>>> coordinate set = P21_BIG_easy.pdb total accessible area

| segid | resid | resname | residue | mainchain | sidechain |
|-------|-------|---------|---------|-----------|-----------|
| E | 370 | VAL | 23.9806 | 5.0318 | 18.9488 |
| E | 371 | ASN | 78.2555 | 2.4060 | 75.8495 |
| E | 372 | LEU | 25.0596 | 21.6854 | 3.3741 |
| E | 373 | THR | 71.7591 | 5.6662 | 66.0929 |
| E | 374 | TRP | 16.5382 | 12.8735 | 3.6647 |
| E | 375 | SER | 40.3082 | 3.2328 | 37.0753 |
| E | 376 | ARG | 36.5186 | 13.3645 | 23.1541 |
| E | 377 | ALA | 74.7151 | 42.6504 | 32.0647 |
| E | 378 | SER | 67.5323 | 46.0662 | 21.4661 |
| E | 379 | GLY | 63.5502 | 63.5502 | 0.0000 |
| E | 380 | LYS | 118.3851 | 8.4752 | 109.9099 |
| E | 381 | PRO | 109.4925 | 11.9628 | 97.5297 |
| E | 382 | VAL | 47.7825 | 20.1560 | 27.6265 |
| E | 383 | ASN | 82.5854 | 10.9846 | 71.6007 |
| E | 384 | HIS | 166.6147 | 12.0105 | 154.6043 |
| E | 385 | SER | 55.9917 | 27.7266 | 28.2651 |
| E | 386 | THR | 55.9465 | 3.9831 | 51.9635 |
| E | 387 | ARG | 94.6444 | 24.1672 | 70.4771 |
| E | 388 | LYS | 110.3506 | 9.5156 | 100.8350 |
| E | 389 | GLU | 101.0052 | 32.2000 | 68.8052 |
| E | 390 | GLU | 111.6129 | 5.7306 | 105.8823 |
| E | 391 | LYS | 127.9670 | 27.4732 | 100.4938 |
| E | 392 | GLN | 67.9671 | 5.6794 | 62.2876 |
| E | 393 | ARG | 196.4996 | 35.0290 | 161.4705 |
| E | 394 | ASN | 129.1265 | 31.2531 | 97.8734 |
| E | 395 | GLY | 25.1905 | 25.1905 | 0.0000 |
| E | 396 | THR | 23.8202 | 0.0000 | 23.8202 |
| E | 397 | LEU | 27.0089 | 0.5844 | 26.4244 |
| E | 398 | THR | 20.7027 | 0.0000 | 20.7027 |
| E | 399 | VAL | 3.8998 | 0.0000 | 3.8998 |
| E | 400 | THR | 23.5256 | 0.0016 | 23.5240 |
| E | 401 | SER | 3.8291 | 0.0107 | 3.8184 |
| E | 402 | THR | 30.3125 | 0.4203 | 29.8922 |
| E | 403 | LEU | 0.4251 | 0.0000 | 0.4251 |
| E | 404 | PRO | 51.1815 | 2.4787 | 48.7028 |
| E | 405 | VAL | 11.2119 | 11.2119 | 0.0000 |
| E | 406 | GLY | 28.5445 | 28.5445 | 0.0000 |
| E | 407 | THR | 49.7554 | 4.7993 | 44.9561 |
| E | 408 | ALA | 60.6211 | 6.8825 | 53.7385 |
| E | 409 | ASP | 52.1499 | 5.9878 | 46.1621 |
| E | 410 | TRP | 21.8170 | 4.8345 | 16.9826 |
| E | 411 | ILE | 94.7959 | 28.8702 | 65.9257 |
| E | 412 | GLU | 147.7531 | 39.2294 | 108.5236 |
| E | 413 | GLY | 50.5019 | 50.5019 | 0.0000 |
| E | 414 | GLU | 21.7125 | 7.3761 | 14.3364 |
| E | 415 | THR | 41.8217 | 0.2863 | 41.5355 |
| E | 416 | TYR | 6.0034 | 0.0010 | 6.0024 |
| E | 417 | GLN | 60.1623 | 0.0156 | 60.1467 |
| E | 418 | CYS | 0.0005 | 0.0005 | 0.0000 |
| E | 419 | ARG | 98.2318 | 0.0079 | 98.2239 |
| E | 420 | VAL | 8.2564 | 2.2291 | 6.0274 |
| E | 421 | THR | 45.6679 | 2.1028 | 43.5651 |
| E | 422 | HIS | 27.3717 | 12.9684 | 14.4033 |
| E | 423 | PRO | 86.7455 | 39.5612 | 47.1843 |
| E | 424 | HIS | 102.4911 | 27.5260 | 74.9651 |
| E | 425 | LEU | 65.5777 | 15.7778 | 49.7998 |
| E | 426 | PRO | 128.7517 | 41.7297 | 87.0220 |
| E | 427 | ARG | 178.5206 | 18.2226 | 160.2980 |
| E | 428 | ALA | 19.2377 | 11.6556 | 7.5821 |
| E | 429 | LEU | 47.2674 | 1.3976 | 45.8698 |
| E | 430 | MET | 80.4663 | 20.4818 | 59.9845 |
| E | 431 | ARG | 83.1696 | 7.4778 | 75.6917 |
| E | 432 | SER | 76.1420 | 25.4921 | 50.6500 |
| E | 433 | THR | 11.0244 | 7.4448 | 3.5797 |
| E | 434 | THR | 88.5142 | 41.5494 | 46.9648 |
| E | 440 | ARG | 174.2127 | 54.0769 | 120.1358 |
| E | 441 | ALA | 30.8105 | 7.0099 | 23.8006 |
| E | 442 | ALA | 53.2295 | 15.2574 | 37.9720 |
| E | 443 | PRO | 6.7855 | 6.7855 | 0.0000 |
| E | 444 | ALA | 51.4961 | 10.5208 | 40.9752 |
| E | 445 | VAL | 8.4253 | 8.4253 | 0.0000 |
| E | 446 | TYR | 67.3601 | 0.1780 | 67.1821 |
| E | 447 | ALA | 4.1887 | 4.1887 | 0.0000 |
| E | 448 | PHE | 16.3097 | 3.0472 | 13.2626 |
| E | 449 | ALA | 26.0450 | 13.9143 | 12.1306 |
| E | 450 | THR | 25.6764 | 10.4415 | 15.2349 |
| E | 451 | PRO | 65.5237 | 14.5160 | 51.0077 |
| E | 452 | GLU | 142.9446 | 85.1490 | 57.7956 |
| E | 459 | LYS | 105.6838 | 20.9279 | 84.7559 |
| E | 460 | ARG | 44.7754 | 0.0902 | 44.6852 |
| E | 461 | THR | 2.2598 | 2.0205 | 0.2393 |
| E | 462 | LEU | 2.8041 | 0.0110 | 2.7931 |
| E | 463 | ALA | 1.2869 | 0.1165 | 1.1704 |
| E | 464 | CYS | 0.1546 | 0.1546 | 0.0000 |
| E | 465 | LEU | 3.2471 | 0.5573 | 2.6898 |
| E | 466 | ILE | 0.0000 | 0.0000 | 0.0000 |
| E | 467 | GLN | 13.3994 | 0.0015 | 13.3979 |
| E | 468 | ASN | 36.5841 | 3.8989 | 32.6852 |
| E | 469 | PHE | 0.0000 | 0.0000 | 0.0000 |
| E | 470 | MET | 74.9871 | 0.0010 | 74.9861 |
| E | 471 | PRO | 39.9887 | 4.0078 | 35.9809 |
| E | 472 | GLU | 67.3856 | 0.8478 | 66.5378 |
| E | 473 | ASP | 57.5237 | 6.7851 | 50.7386 |
| E | 474 | ILE | 28.1214 | 24.2166 | 3.9049 |
| E | 475 | SER | 14.0129 | 5.2524 | 8.7604 |
| E | 476 | VAL | 12.3825 | 5.9685 | 2.4140 |
| E | 477 | GLN | 10.0685 | 1.6500 | 8.4185 |
| E | 478 | TRP | 2.0693 | 1.5459 | 0.5234 |
| E | 479 | LEU | 14.4006 | 0.9057 | 13.4949 |
| E | 480 | HIS | 17.5355 | 0.1696 | 17.3659 |
| E | 481 | ASN | 92.8634 | 25.0133 | 67.8501 |
| E | 482 | GLU | 125.4189 | 29.6566 | 95.7623 |
| E | 483 | VAL | 76.5897 | 3.0249 | 73.5648 |
| E | 484 | GLN | 77.7176 | 16.9029 | 60.8148 |
| E | 485 | LEU | 27.5816 | 6.9826 | 20.5990 |
| E | 486 | PRO | 88.0801 | 13.0976 | 74.9824 |
| E | 487 | ASP | 104.9131 | 9.1069 | 95.8063 |
| E | 488 | ALA | 84.1468 | 24.1910 | 59.9557 |
| E | 489 | ARG | 84.9968 | 17.5138 | 67.4830 |
| E | 490 | HIS | 28.1531 | 14.8453 | 13.3078 |
| E | 491 | SER | 20.4498 | 3.9378 | 16.5120 |
| E | 492 | THR | 31.2884 | 9.1001 | 22.1884 |
| E | 493 | THR | 8.5416 | 4.3474 | 4.1942 |
| E | 494 | GLN | 122.3714 | 4.8834 | 117.4880 |
| E | 495 | PRO | 46.3315 | 19.8347 | 26.4968 |
| E | 496 | ARG | 74.7011 | 4.1944 | 70.5067 |
| E | 497 | LYS | 158.5411 | 13.2042 | 145.3368 |
| E | 498 | THR | 10.0998 | 10.0998 | 0.0000 |
| E | 499 | LYS | 148.4467 | 23.9195 | 124.5272 |
| E | 500 | GLY | 77.1479 | 77.1479 | 0.0000 |
| E | 501 | SER | 41.2082 | 20.4404 | 20.7678 |
| E | 502 | GLY | 8.3578 | 8.3578 | 0.0000 |
| E | 503 | PHE | 37.9840 | 0.0000 | 37.9840 |
| E | 504 | PHE | 0.5211 | 0.0000 | 0.5211 |
| E | 505 | VAL | 0.8406 | 0.0000 | 0.8406 |
| E | 506 | PHE | 1.1519 | 0.0064 | 1.1455 |
| E | 507 | SER | 0.0000 | 0.0000 | 0.0000 |
| E | 508 | ARG | 6.0117 | 1.3727 | 4.6390 |
| E | 509 | LEU | 0.4503 | 0.1502 | 0.3001 |
| E | 510 | GLU | 26.6986 | 2.2927 | 24.4059 |
| E | 511 | VAL | 1.0252 | 0.9450 | 0.0803 |
| E | 512 | THR | 68.6505 | 0.0000 | 68.6505 |
| E | 513 | ARG | 128.3597 | 0.1249 | 128.2348 |
| E | 514 | ALA | 70.7675 | 23.4429 | 47.3246 |
| E | 515 | GLU | 41.9160 | 8.5772 | 33.3388 |
| E | 516 | TRP | 41.7209 | 5.4488 | 36.2721 |
| E | 517 | GLU | 117.1962 | 34.7928 | 82.4034 |
| E | 518 | ALA | 44.0651 | 6.3858 | 37.6793 |
| E | 519 | LYS | 9.2649 | 0.0000 | 9.2649 |
| E | 520 | ASP | 106.3773 | 19.5346 | 86.8426 |

TABLE VI-continued

IgE-Fc Residue Exposure
>>>> Surface plot for Crystal 3:
>>>> structure file = P21_BIG_easy.mtf
>>>> coordinate set = P21_BIG_easy.pdb

| segid | resid | resname | residue | mainchain | sidechain |
|---|---|---|---|---|---|
| E | 521 | GLU | 58.6379 | 3.8520 | 54.7859 |
| E | 522 | PHE | 0.9156 | 0.0000 | 0.9156 |
| E | 523 | ILE | 37.0969 | 0.0000 | 37.0969 |
| E | 524 | CYS | 0.0000 | 0.0000 | 0.0000 |
| E | 525 | ARG | 54.2656 | 0.0000 | 54.2656 |
| E | 526 | ALA | 0.0000 | 0.0000 | 0.0000 |
| E | 527 | VAL | 1.8180 | 0.0000 | 1.8180 |
| E | 528 | HIS | 0.6659 | 0.0000 | 0.6659 |
| E | 529 | GLU | 70.0508 | 11.6763 | 58.3745 |
| E | 530 | ALA | 19.8678 | 13.4023 | 6.4655 |
| E | 531 | ALA | 12.8303 | 12.8303 | 0.0000 |
| E | 532 | SER | 71.8931 | 22.0724 | 49.8207 |
| E | 533 | PRO | 111.9141 | 5.3032 | 106.6109 |
| E | 534 | SER | 74.9184 | 29.1331 | 45.7853 |
| E | 535 | GLN | 50.1411 | 0.0000 | 50.1411 |
| E | 536 | THR | 38.1321 | 12.8025 | 25.3296 |
| E | 537 | VAL | 31.0375 | 4.2760 | 26.7615 |
| E | 538 | GLN | 74.9445 | 12.0658 | 62.8788 |
| E | 539 | ARG | 96.8419 | 4.3390 | 92.5029 |
| E | 540 | ALA | 59.2739 | 20.5601 | 38.7138 |
| E | 541 | VAL | 9.0334 | 2.5995 | 6.4339 |
| E | 542 | SER | 70.4902 | 2.9925 | 67.4976 |
| E | 543 | VAL | 117.6865 | 36.3136 | 81.3729 |
| F | 336 | VAL | 92.0772 | 49.0083 | 43.0689 |
| F | 337 | SER | 42.5384 | 3.6385 | 38.9000 |
| F | 338 | ALA | 11.5989 | 11.5989 | 0.0000 |
| F | 339 | TYR | 131.9209 | 5.3409 | 126.5800 |
| F | 340 | LEU | 31.2423 | 28.1429 | 3.0994 |
| F | 341 | SER | 53.7333 | 7.0106 | 46.7227 |
| F | 342 | ARG | 106.3428 | 19.9853 | 86.3576 |
| F | 343 | PRO | 8.7474 | 7.5945 | 1.1529 |
| F | 344 | SER | 40.9491 | 7.2393 | 33.7098 |
| F | 345 | PRO | 9.1859 | 0.3550 | 8.8309 |
| F | 346 | PHE | 49.4223 | 0.0000 | 49.4223 |
| F | 347 | ASP | 36.1746 | 0.0000 | 36.1746 |
| F | 348 | LEU | 11.9989 | 0.9440 | 11.0550 |
| F | 349 | PHE | 27.5999 | 11.6347 | 15.9652 |
| F | 350 | ILE | 58.7925 | 9.4898 | 49.3026 |
| F | 351 | ARG | 143.4226 | 32.9625 | 110.4600 |
| F | 352 | LYS | 120.7405 | 14.0797 | 106.6608 |
| F | 353 | SER | 59.1314 | 9.5252 | 49.6062 |
| F | 354 | PRO | 2.2832 | 1.8868 | 0.3964 |
| F | 355 | THR | 48.1841 | 5.7324 | 42.4516 |
| F | 356 | ILE | 0.2801 | 0.2791 | 0.0010 |
| F | 357 | THR | 38.6843 | 1.8153 | 36.8690 |
| F | 358 | CYS | 0.0000 | 0.0000 | 0.0000 |
| F | 359 | LEU | 53.8415 | 0.0000 | 53.8415 |
| F | 360 | VAL | 9.6396 | 0.1089 | 9.5306 |
| F | 361 | VAL | 34.6960 | 1.0430 | 33.6530 |
| F | 362 | ASP | 20.0866 | 0.0000 | 20.0866 |
| F | 363 | LEU | 124.7270 | 13.4305 | 111.2965 |
| F | 364 | ALA | 67.2924 | 9.0078 | 58.2846 |
| F | 365 | PRO | 52.5182 | 26.8886 | 25.6297 |
| F | 366 | SER | 46.6742 | 16.3001 | 30.3741 |
| F | 367 | LYS | 184.3637 | 16.6251 | 167.7386 |
| F | 368 | GLY | 39.1117 | 39.1117 | 0.0000 |
| F | 369 | THR | 116.7167 | 12.5954 | 104.1213 |
| F | 370 | VAL | 23.1827 | 4.6100 | 18.5727 |
| F | 371 | ASN | 78.9886 | 2.5037 | 76.4849 |
| F | 372 | LEU | 24.7902 | 21.3892 | 3.4010 |
| F | 373 | THR | 71.2828 | 5.5272 | 65.7556 |
| F | 374 | TRP | 15.6160 | 11.9994 | 3.6166 |
| F | 375 | SER | 37.4894 | 3.2859 | 34.2036 |
| F | 376 | ARG | 36.1957 | 14.0218 | 22.1739 |
| F | 377 | ALA | 33.4050 | 17.2556 | 16.1494 |
| F | 378 | SER | 35.7664 | 20.9105 | 14.8559 |
| F | 379 | GLY | 63.6141 | 63.6141 | 0.0000 |
| F | 380 | LYS | 110.7480 | 11.7806 | 98.9674 |
| F | 381 | PRO | 107.3841 | 11.3160 | 96.0681 |
| F | 382 | VAL | 48.0877 | 21.0726 | 27.0151 |
| F | 383 | ASN | 80.4601 | 11.5462 | 68.9139 |
| F | 384 | HIS | 165.3400 | 11.7604 | 153.5796 |
| F | 385 | SER | 55.0442 | 27.5043 | 27.5399 |
| F | 386 | THR | 57.0671 | 3.8136 | 53.2535 |
| F | 387 | ARG | 96.0759 | 25.5893 | 70.4866 |
| F | 388 | LYS | 107.9006 | 9.4504 | 98.4502 |
| F | 389 | GLU | 103.8123 | 35.6498 | 68.1625 |
| F | 390 | GLU | 111.9709 | 5.7065 | 106.2645 |
| F | 391 | LYS | 125.9925 | 27.1701 | 98.8224 |
| F | 392 | GLN | 70.2379 | 5.6649 | 64.5730 |
| F | 393 | ARG | 234.5298 | 40.5797 | 193.9501 |
| F | 394 | ASN | 127.5024 | 31.7704 | 95.7319 |
| F | 395 | GLY | 26.1876 | 26.1876 | 0.0000 |
| F | 396 | THR | 26.1301 | 0.0008 | 26.1293 |
| F | 397 | LEU | 27.2589 | 0.3886 | 26.8703 |
| F | 398 | THR | 20.8578 | 0.0000 | 20.8578 |
| F | 399 | VAL | 3.6920 | 0.0000 | 3.6920 |
| F | 400 | THR | 23.9737 | 0.0000 | 23.9737 |
| F | 401 | SER | 3.1534 | 0.0022 | 3.1512 |
| F | 402 | THR | 26.1934 | 0.1968 | 25.9966 |
| F | 403 | LEU | 0.5235 | 0.0000 | 0.5235 |
| F | 404 | PRO | 50.2773 | 1.6036 | 48.6736 |
| F | 405 | VAL | 11.7817 | 11.7817 | 0.0000 |
| F | 406 | GLY | 27.8103 | 27.8103 | 0.0000 |
| F | 407 | THR | 38.0322 | 4.4937 | 33.5385 |
| F | 408 | ALA | 59.8575 | 5.5729 | 54.2846 |
| F | 409 | ASP | 51.1661 | 5.1854 | 45.9807 |
| F | 410 | TRP | 22.6276 | 5.2286 | 17.3990 |
| F | 411 | ILE | 41.3387 | 17.9206 | 23.4181 |
| F | 412 | GLU | 99.5650 | 8.1318 | 91.4332 |
| F | 413 | GLY | 17.0574 | 17.0574 | 0.0000 |
| F | 414 | GLU | 21.1629 | 7.6144 | 13.5485 |
| F | 415 | THR | 23.0750 | 0.2864 | 22.7886 |
| F | 416 | TYR | 5.1008 | 0.0000 | 5.1008 |
| F | 417 | GLN | 61.3692 | 0.0000 | 61.3692 |
| F | 418 | CYS | 0.0019 | 0.0000 | 0.0019 |
| F | 419 | ARG | 95.2294 | 0.0021 | 95.2273 |
| F | 420 | VAL | 9.2952 | 2.2664 | 7.0288 |
| F | 421 | THR | 46.2222 | 2.2353 | 43.9870 |
| F | 422 | HIS | 27.1300 | 12.3976 | 14.7324 |
| F | 423 | PRO | 78.6822 | 34.7386 | 43.9436 |
| F | 424 | HIS | 105.8901 | 27.3927 | 78.4975 |
| F | 425 | LEU | 68.2164 | 15.6858 | 52.5305 |
| F | 426 | PRO | 131.4806 | 43.5597 | 87.9208 |
| F | 427 | ARG | 173.8656 | 19.7371 | 154.1285 |
| F | 428 | ALA | 20.9333 | 11.7443 | 9.1890 |
| F | 429 | LEU | 47.4288 | 1.1392 | 46.2897 |
| F | 430 | MET | 76.6222 | 20.2827 | 56.3395 |
| F | 431 | ARG | 81.8252 | 6.8896 | 74.9356 |
| F | 432 | SER | 77.3298 | 24.0736 | 53.2562 |
| F | 433 | THR | 11.0164 | 7.7629 | 3.2534 |
| F | 434 | THR | 81.9400 | 37.6618 | 44.2782 |
| F | 440 | ARG | 130.6955 | 53.4609 | 77.2346 |
| F | 441 | ALA | 31.3844 | 6.8060 | 24.5784 |
| F | 442 | ALA | 53.2295 | 15.4995 | 37.7300 |
| F | 443 | PRO | 9.2249 | 9.2249 | 0.0000 |
| F | 444 | ALA | 51.4567 | 10.3422 | 41.1145 |
| F | 445 | VAL | 7.8949 | 7.8942 | 0.0008 |
| F | 446 | TYR | 66.4996 | 0.1530 | 66.3466 |
| F | 447 | ALA | 4.2012 | 4.2012 | 0.0000 |
| F | 448 | PHE | 18.0607 | 3.1559 | 14.9047 |
| F | 449 | ALA | 28.7521 | 17.7591 | 10.9930 |
| F | 450 | THR | 27.4502 | 10.2474 | 17.2028 |
| F | 451 | PRO | 68.6882 | 15.4534 | 53.2347 |
| F | 452 | GLU | 144.6770 | 86.0302 | 58.6468 |
| F | 459 | LYS | 111.4093 | 22.7011 | 88.7082 |
| F | 460 | ARG | 45.9760 | 0.0219 | 45.9541 |
| F | 461 | THR | 2.4701 | 2.0884 | 0.3817 |
| F | 462 | LEU | 2.9224 | 0.0000 | 2.9224 |
| F | 463 | ALA | 1.4540 | 0.0000 | 1.4540 |

TABLE VI-continued

IgE-Fc Residue Exposure
>>>> Surface plot for Crystal 3:
>>>> structure file = P21_BIG_easy.mtf
>>>> coordinate set = P21_BIG_easy.pdb

| segid | resid | resname | residue | mainchain | sidechain |
|---|---|---|---|---|---|
| F | 464 | CYS | 0.0515 | 0.0515 | 0.0000 |
| F | 465 | LEU | 3.7060 | 0.7133 | 2.9927 |
| F | 466 | ILE | 0.0029 | 0.0000 | 0.0029 |
| F | 467 | GLN | 14.1203 | 0.0018 | 14.1186 |
| F | 468 | ASN | 34.4780 | 3.8430 | 30.6350 |
| F | 469 | PHE | 0.0036 | 0.0020 | 0.0016 |
| F | 470 | MET | 75.6234 | 0.1495 | 75.4739 |
| F | 471 | PRO | 34.2396 | 4.5759 | 29.6637 |
| F | 472 | GLU | 75.6667 | 1.2296 | 74.4371 |
| F | 473 | ASP | 47.5468 | 6.689 | 40.8478 |
| F | 474 | ILE | 30.8305 | 26.0225 | 4.8080 |
| F | 475 | SER | 14.7870 | 5.4986 | 9.2885 |
| F | 476 | VAL | 13.5519 | 10.8057 | 2.7462 |
| F | 477 | GLN | 9.5681 | 2.1337 | 7.4344 |
| F | 478 | TRP | 2.0262 | 1.3205 | 0.7056 |
| F | 479 | LEU | 15.2163 | 1.0654 | 14.1509 |
| F | 480 | HIS | 17.3914 | 0.2171 | 17.1743 |
| F | 481 | ASN | 93.2921 | 24.7430 | 68.5492 |
| F | 482 | GLU | 124.4508 | 29.0972 | 95.3536 |
| F | 483 | VAL | 77.4347 | 3.3392 | 74.0955 |
| F | 484 | GLN | 78.0256 | 17.9715 | 60.0541 |
| F | 485 | LEU | 27.1705 | 6.5829 | 20.5876 |
| F | 486 | PRO | 87.9988 | 12.7290 | 75.2698 |
| F | 487 | ASP | 105.1732 | 8.535 | 96.5897 |
| F | 488 | ALA | 84.2531 | 24.7208 | 59.5323 |
| F | 489 | ARG | 81.8967 | 17.5452 | 64.3515 |
| F | 490 | HIS | 28.8253 | 15.0674 | 13.7578 |
| F | 491 | SER | 22.4322 | 3.9319 | 18.5004 |
| F | 492 | THR | 31.6925 | 9.1646 | 22.5279 |
| F | 493 | THR | 8.5098 | 4.6794 | 3.8304 |
| F | 494 | GLN | 119.6025 | 4.3149 | 115.2876 |
| F | 495 | PRO | 45.5667 | 19.8265 | 26.7402 |
| F | 496 | ARG | 68.4768 | 4.2366 | 64.2402 |
| F | 497 | LYS | 158.8854 | 12.7997 | 146.0857 |
| F | 498 | THR | 8.9551 | 8.9551 | 0.0000 |
| F | 499 | LYS | 144.3457 | 24.0615 | 120.2842 |
| F | 500 | GLY | 74.8488 | 74.8488 | 0.0000 |
| F | 501 | SER | 40.1061 | 20.0780 | 20.0281 |
| F | 502 | GLY | 8.5558 | 8.5558 | 0.0000 |
| F | 503 | PHE | 38.3723 | 0.0002 | 38.3722 |
| F | 504 | PHE | 0.3533 | 0.0000 | 0.3533 |
| F | 505 | VAL | 1.0870 | 0.0000 | 1.0870 |
| F | 506 | PHE | 1.0285 | 0.0055 | 1.0231 |
| F | 507 | SER | 0.0025 | 0.0025 | 0.0000 |
| F | 508 | ARG | 6.2110 | 1.2998 | 4.9112 |
| F | 509 | LEU | 0.4287 | 0.1390 | 0.2897 |
| F | 510 | GLU | 28.0172 | 2.0606 | 25.9565 |
| F | 511 | VAL | 0.8137 | 0.7099 | 0.1038 |
| F | 512 | THR | 68.6246 | 0.0000 | 68.6246 |
| F | 513 | ARG | 127.2185 | 0.0000 | 127.2185 |
| F | 514 | ALA | 70.9437 | 22.7657 | 48.1780 |
| F | 515 | GLU | 40.8713 | 8.5832 | 32.2881 |
| F | 516 | TRP | 41.7845 | 5.5052 | 36.2793 |
| F | 517 | GLU | 117.7463 | 35.6411 | 82.1052 |
| F | 518 | ALA | 43.5753 | 6.7932 | 36.7822 |
| F | 519 | LYS | 9.1842 | 0.0000 | 9.1842 |
| F | 520 | ASP | 105.7149 | 19.1491 | 86.5658 |
| F | 521 | GLU | 59.2866 | 3.6025 | 55.6841 |
| F | 522 | PHE | 0.5992 | 0.0000 | 0.5992 |
| F | 523 | ILE | 37.5654 | 0.0000 | 37.5654 |
| F | 524 | CYS | 0.0027 | 0.0027 | 0.0000 |
| F | 525 | ARG | 43.5875 | 0.0000 | 43.5875 |
| F | 526 | ALA | 0.0000 | 0.0000 | 0.0000 |
| F | 527 | VAL | 0.0271 | 0.0000 | 0.0271 |
| F | 528 | HIS | 0.6233 | 0.0000 | 0.6233 |
| F | 529 | GLU | 65.4774 | 1.6960 | 63.7814 |
| F | 530 | ALA | 20.1403 | 13.6010 | 6.5393 |
| F | 531 | ALA | 12.5001 | 12.4986 | 0.0015 |
| F | 532 | SER | 40.9179 | 22.4642 | 18.4538 |
| F | 533 | PRO | 107.9778 | 3.6460 | 104.3318 |
| F | 534 | SER | 74.1400 | 29.1252 | 45.0148 |
| F | 535 | GLN | 17.8579 | 0.0000 | 17.8579 |
| F | 536 | THR | 33.0660 | 12.3750 | 20.6911 |
| F | 537 | VAL | 32.7533 | 4.3270 | 28.4263 |
| F | 538 | GLN | 76.4306 | 11.2941 | 65.1365 |
| F | 539 | ARG | 94.9317 | 4.0484 | 90.8833 |
| F | 540 | ALA | 59.6591 | 20.8897 | 38.7694 |
| F | 541 | VAL | 9.2314 | 2.2520 | 6.9794 |
| F | 542 | SER | 74.0065 | 3.1237 | 70.8828 |
| F | 543 | VAL | 120.0746 | 36.0772 | 83.9974 |
| A | 336 | VAL | 89.5878 | 46.5948 | 42.9930 |
| A | 337 | SER | 41.0859 | 3.4423 | 37.6436 |
| A | 338 | ALA | 10.4261 | 10.4261 | 0.0000 |
| A | 339 | TYR | 131.9640 | 5.1528 | 126.8113 |
| A | 340 | LEU | 31.2709 | 27.9615 | 3.3093 |
| A | 341 | SER | 57.1006 | 7.2467 | 49.8539 |
| A | 342 | ARG | 99.2473 | 17.9886 | 81.2587 |
| A | 343 | PRO | 7.5525 | 6.2367 | 1.3158 |
| A | 344 | SER | 43.6139 | 10.9600 | 32.6539 |
| A | 345 | PRO | 6.9402 | 0.0000 | 6.9402 |
| A | 346 | PHE | 55.9178 | 0.0002 | 55.9176 |
| A | 347 | ASP | 37.2781 | 0.0000 | 37.2781 |
| A | 348 | LEU | 11.5426 | 1.6233 | 9.9193 |
| A | 349 | PHE | 24.0950 | 13.1826 | 10.9124 |
| A | 350 | ILE | 57.8108 | 13.8850 | 43.9258 |
| A | 351 | ARG | 143.5474 | 17.7597 | 125.7877 |
| A | 352 | LYS | 132.0019 | 16.2001 | 115.8018 |
| A | 353 | SER | 49.0945 | 9.3832 | 39.7113 |
| A | 354 | PRO | 2.4728 | 2.0314 | 0.4414 |
| A | 355 | THR | 43.8734 | 5.6483 | 38.2251 |
| A | 356 | ILE | 0.6293 | 0.6288 | 0.0005 |
| A | 357 | THR | 38.1335 | 1.7244 | 36.4091 |
| A | 358 | CYS | 0.0000 | 0.0000 | 0.0000 |
| A | 359 | LEU | 54.0319 | 0.0000 | 54.0319 |
| A | 360 | VAL | 9.1084 | 0.0621 | 9.0463 |
| A | 361 | VAL | 34.8981 | 0.6950 | 34.2031 |
| A | 362 | ASP | 20.4988 | 0.0000 | 20.4988 |
| A | 363 | LEU | 125.2853 | 13.5564 | 111.7289 |
| A | 364 | ALA | 67.4520 | 9.1820 | 58.2700 |
| A | 365 | PRO | 51.9757 | 26.2136 | 25.7621 |
| A | 366 | SER | 46.4876 | 15.8550 | 30.6326 |
| A | 367 | LYS | 183.0731 | 16.2541 | 166.8190 |
| A | 368 | GLY | 41.3568 | 41.3568 | 0.0000 |
| A | 369 | THR | 116.1629 | 12.6004 | 103.5625 |
| A | 370 | VAL | 23.1334 | 4.2695 | 18.8640 |
| A | 371 | ASN | 77.5204 | 2.2047 | 75.3157 |
| A | 372 | LEU | 24.9936 | 21.8879 | 3.1057 |
| A | 373 | THR | 72.2209 | 4.9896 | 67.2314 |
| A | 374 | TRP | 15.7079 | 12.6533 | 3.0546 |
| A | 375 | SER | 39.7704 | 3.2386 | 36.5318 |
| A | 376 | ARG | 36.8158 | 15.0724 | 21.7433 |
| A | 377 | ALA | 40.1167 | 20.2361 | 19.8806 |
| A | 378 | SER | 45.3645 | 29.3496 | 16.0149 |
| A | 379 | GLY | 63.4442 | 63.4442 | 0.0000 |
| A | 380 | LYS | 109.4127 | 9.7822 | 99.6305 |
| A | 381 | PRO | 108.8876 | 13.1800 | 95.7076 |
| A | 382 | VAL | 50.1689 | 21.8934 | 28.2755 |
| A | 383 | ASN | 79.8194 | 11.7917 | 68.0277 |
| A | 384 | HIS | 173.7204 | 14.2987 | 159.4217 |
| A | 385 | SER | 54.6841 | 28.5396 | 26.1445 |
| A | 386 | THR | 60.2042 | 3.6661 | 56.5380 |
| A | 387 | ARG | 97.5588 | 26.0913 | 71.4675 |
| A | 388 | LYS | 104.7149 | 8.6638 | 96.0510 |
| A | 389 | GLU | 102.6751 | 35.6854 | 66.9897 |
| A | 390 | GLU | 113.0360 | 5.9249 | 107.1111 |
| A | 391 | LYS | 128.4432 | 26.1504 | 102.2928 |
| A | 392 | GLN | 68.5233 | 5.8822 | 62.6411 |
| A | 393 | ARG | 237.7998 | 40.8021 | 196.9977 |
| A | 394 | ASN | 126.6907 | 31.9001 | 94.7906 |
| A | 395 | GLY | 26.3987 | 26.3987 | 0.0000 |

TABLE VI-continued

IgE-Fc Residue Exposure
>>>> Surface plot for Crystal 3:
>>>> structure file = P21_BIG_easy.mtf
>>>> coordinate set = P21_BIG_easy.pdb

| segid | resid | resname | residue | mainchain | sidechain |
|---|---|---|---|---|---|
| A | 396 | THR | 26.9067 | 0.0000 | 26.9067 |
| A | 397 | LEU | 26.9976 | 0.3608 | 26.6368 |
| A | 398 | THR | 20.4677 | 0.0000 | 20.4677 |
| A | 399 | VAL | 3.5853 | 0.0000 | 3.5853 |
| A | 400 | THR | 21.6681 | 0.0000 | 21.6681 |
| A | 401 | SER | 4.2053 | 0.0007 | 4.2045 |
| A | 402 | THR | 27.9735 | 0.5350 | 27.4384 |
| A | 403 | LEU | 0.4041 | 0.0015 | 0.4026 |
| A | 404 | PRO | 49.9858 | 2.3878 | 47.5980 |
| A | 405 | VAL | 10.8447 | 10.8447 | 0.0000 |
| A | 406 | GLY | 27.8051 | 27.8051 | 0.0000 |
| A | 407 | THR | 40.0821 | 4.5341 | 35.5481 |
| A | 408 | ALA | 59.2368 | 6.1068 | 53.1300 |
| A | 409 | ASP | 52.3240 | 6.5354 | 45.7886 |
| A | 410 | TRP | 21.5446 | 4.7199 | 16.8247 |
| A | 411 | ILE | 42.0121 | 18.1738 | 23.8383 |
| A | 412 | GLU | 104.0035 | 9.3671 | 94.6364 |
| A | 413 | GLY | 22.2660 | 22.2660 | 0.0000 |
| A | 414 | GLU | 22.3386 | 8.0537 | 14.2848 |
| A | 415 | THR | 31.2476 | 0.4610 | 30.7866 |
| A | 416 | TYR | 5.6624 | 0.0000 | 5.6624 |
| A | 417 | GLN | 59.4850 | 0.0503 | 59.4347 |
| A | 418 | CYS | 0.0025 | 0.0013 | 0.0012 |
| A | 419 | ARG | 98.8049 | 0.0655 | 98.7394 |
| A | 420 | VAL | 8.4783 | 2.2559 | 6.2224 |
| A | 421 | THR | 20.9732 | 2.0907 | 18.8824 |
| A | 422 | HIS | 17.8740 | 4.1146 | 13.7595 |
| A | 423 | PRO | 80.3177 | 34.4066 | 45.9110 |
| A | 424 | HIS | 105.9053 | 27.3775 | 78.5278 |
| A | 425 | LEU | 58.4627 | 8.0291 | 50.4336 |
| A | 426 | PRO | 78.7154 | 4.4658 | 74.2496 |
| A | 427 | ARG | 151.6270 | 12.3658 | 139.2612 |
| A | 428 | ALA | 16.8268 | 11.0410 | 5.7858 |
| A | 429 | LEU | 45.3907 | 1.1255 | 44.2652 |
| A | 430 | MET | 80.6988 | 19.5540 | 61.1447 |
| A | 431 | ARG | 87.4890 | 6.7058 | 80.7832 |
| A | 432 | SER | 77.1358 | 25.6800 | 51.4558 |
| A | 433 | THR | 10.9724 | 7.7377 | 3.2347 |
| A | 434 | THR | 81.6568 | 34.7850 | 46.8719 |
| A | 440 | ARG | 137.1148 | 54.5557 | 82.5591 |
| A | 441 | ALA | 30.8275 | 7.1093 | 23.7182 |
| A | 442 | ALA | 53.9578 | 16.1557 | 37.8021 |
| A | 443 | PRO | 9.3815 | 9.3815 | 0.0000 |
| A | 444 | ALA | 50.8107 | 11.0863 | 39.7243 |
| A | 445 | VAL | 8.5599 | 8.5582 | 0.0016 |
| A | 446 | TYR | 65.2563 | 0.1978 | 65.0585 |
| A | 447 | ALA | 4.5637 | 4.5637 | 0.0000 |
| A | 448 | PHE | 15.0247 | 3.2706 | 11.7541 |
| A | 449 | ALA | 27.0610 | 15.6793 | 11.3817 |
| A | 450 | THR | 26.4582 | 11.9391 | 14.5191 |
| A | 451 | PRO | 65.5743 | 14.8611 | 50.7132 |
| A | 452 | GLU | 144.6123 | 85.1575 | 59.4548 |
| A | 459 | LYS | 102.2028 | 20.5218 | 81.6810 |
| A | 460 | ARG | 46.2655 | 0.1225 | 46.1430 |
| A | 461 | THR | 2.0768 | 1.8554 | 0.2214 |
| A | 462 | LEU | 2.5150 | 0.0000 | 2.5150 |
| A | 463 | ALA | 0.7585 | 0.0742 | 0.6842 |
| A | 464 | CYS | 0.0434 | 0.0434 | 0.0000 |
| A | 465 | LEU | 3.3935 | 0.5969 | 2.7966 |
| A | 466 | ILE | 0.0017 | 0.0000 | 0.0017 |
| A | 467 | GLN | 12.8841 | 0.0032 | 12.8809 |
| A | 468 | ASN | 33.7439 | 3.6431 | 30.1007 |
| A | 469 | PHE | 0.0000 | 0.0000 | 0.0000 |
| A | 470 | MET | 74.8338 | 0.0000 | 74.8338 |
| A | 471 | PRO | 29.7467 | 4.5112 | 25.2354 |
| A | 472 | GLU | 78.0451 | 1.6359 | 76.4092 |
| A | 473 | ASP | 46.6665 | 6.4317 | 40.2348 |
| A | 474 | ILE | 31.7072 | 26.8323 | 4.8749 |
| A | 475 | SER | 15.3749 | 5.6015 | 9.7734 |
| A | 476 | VAL | 13.4279 | 10.6834 | 2.7445 |
| A | 477 | GLN | 9.0332 | 1.9848 | 7.0485 |
| A | 478 | TRP | 2.0722 | 1.3923 | 0.6799 |
| A | 479 | LEU | 14.9164 | 0.9177 | 13.9987 |
| A | 480 | HIS | 17.6760 | 0.2604 | 17.4156 |
| A | 481 | ASN | 94.3415 | 25.0348 | 69.3068 |
| A | 482 | GLU | 125.5214 | 29.3303 | 96.1912 |
| A | 483 | VAL | 79.5163 | 3.5863 | 75.9300 |
| A | 484 | GLN | 74.6960 | 17.9639 | 56.7321 |
| A | 485 | LEU | 27.4475 | 6.9174 | 20.5301 |
| A | 486 | PRO | 86.6057 | 13.1341 | 73.4716 |
| A | 487 | ASP | 102.2932 | 8.8801 | 93.4131 |
| A | 488 | ALA | 86.3173 | 26.1194 | 60.1979 |
| A | 489 | ARG | 82.4231 | 18.1873 | 64.2359 |
| A | 490 | HIS | 28.6084 | 14.5665 | 14.0418 |
| A | 491 | SER | 24.3293 | 4.5210 | 19.8083 |
| A | 492 | THR | 33.5945 | 10.9005 | 22.6940 |
| A | 493 | THR | 10.5478 | 4.6641 | 5.8837 |
| A | 494 | GLN | 123.1011 | 4.7646 | 118.3366 |
| A | 495 | PRO | 47.1775 | 20.2540 | 26.9235 |
| A | 496 | ARG | 75.6274 | 4.4246 | 71.2028 |
| A | 497 | LYS | 160.8063 | 14.1992 | 146.6071 |
| A | 498 | THR | 10.8060 | 10.8060 | 0.0000 |
| A | 499 | LYS | 147.6809 | 23.4142 | 124.2667 |
| A | 500 | GLY | 77.8409 | 77.8409 | 0.0000 |
| A | 501 | SER | 39.5714 | 19.6808 | 19.8906 |
| A | 502 | GLY | 8.3633 | 8.3633 | 0.0000 |
| A | 503 | PHE | 37.9300 | 0.0000 | 37.9300 |
| A | 504 | PHE | 0.8397 | 0.0006 | 0.8391 |
| A | 505 | VAL | 1.0199 | 0.0000 | 1.0199 |
| A | 506 | PHE | 0.9377 | 0.0378 | 0.8999 |
| A | 507 | SER | 0.0000 | 0.0000 | 0.0000 |
| A | 508 | ARG | 6.1138 | 1.2700 | 4.8438 |
| A | 509 | LEU | 0.5287 | 0.1710 | 0.3576 |
| A | 510 | GLU | 26.5509 | 2.6704 | 23.8805 |
| A | 511 | VAL | 0.8972 | 0.8076 | 0.0896 |
| A | 512 | THR | 68.6189 | 0.0000 | 68.6189 |
| A | 513 | ARG | 126.3199 | 0.3513 | 125.9685 |
| A | 514 | ALA | 72.1192 | 24.7398 | 47.3793 |
| A | 515 | GLU | 40.6759 | 8.0623 | 32.6136 |
| A | 516 | TRP | 42.1764 | 5.4667 | 36.7097 |
| A | 517 | GLU | 113.1267 | 33.7774 | 79.3493 |
| A | 518 | ALA | 45.1228 | 6.7523 | 38.3705 |
| A | 519 | LYS | 9.4248 | 0.0000 | 9.4248 |
| A | 520 | ASP | 103.3793 | 19.0326 | 84.3467 |
| A | 521 | GLU | 59.0603 | 3.8149 | 55.2453 |
| A | 522 | PHE | 0.7294 | 0.0000 | 0.7294 |
| A | 523 | ILE | 36.1749 | 0.0000 | 36.1749 |
| A | 524 | CYS | 0.0000 | 0.0000 | 0.0000 |
| A | 525 | ARG | 43.0860 | 0.0000 | 43.0860 |
| A | 526 | ALA | 0.0000 | 0.0000 | 0.0000 |
| A | 527 | VAL | 0.0009 | 0.0000 | 0.0009 |
| A | 528 | HIS | 0.8481 | 0.0000 | 0.8481 |
| A | 529 | GLU | 67.0803 | 2.5476 | 64.5326 |
| A | 530 | ALA | 19.7646 | 13.2084 | 6.5562 |
| A | 531 | ALA | 11.8550 | 11.8550 | 0.0000 |
| A | 532 | SER | 37.0225 | 22.3848 | 14.6378 |
| A | 533 | PRO | 105.6202 | 1.6341 | 103.9861 |
| A | 534 | SER | 73.2842 | 28.9087 | 44.3755 |
| A | 535 | GLN | 15.9287 | 0.0024 | 15.9263 |
| A | 536 | THR | 33.2806 | 12.5191 | 20.7614 |
| A | 537 | VAL | 32.4350 | 4.7058 | 27.7292 |
| A | 538 | GLN | 75.9237 | 12.1175 | 63.8062 |
| A | 539 | ARG | 94.4850 | 4.0897 | 90.3954 |
| A | 540 | ALA | 58.9141 | 22.4623 | 36.4518 |
| A | 541 | VAL | 9.4999 | 2.3554 | 7.1444 |
| A | 542 | SER | 72.9540 | 2.8577 | 70.0963 |
| A | 543 | VAL | 120.3752 | 36.8198 | 83.5555 |
| B | 336 | VAL | 94.0761 | 49.8966 | 44.1794 |
| B | 337 | SER | 42.0050 | 3.2352 | 38.7698 |
| B | 338 | ALA | 10.4941 | 10.4941 | 0.0000 |

TABLE VI-continued

IgE-Fc Residue Exposure
>>>> Surface plot for Crystal 3:
>>>> structure file = P21_BIG_easy.mtf
>>>> coordinate set = P21_BIG_easy.pdb

| | | | total accessible area | | |
|---|---|---|---|---|---|
| segid | resid | resname | residue | mainchain | sidechain |
| B | 339 | TYR | 136.5372 | 5.1200 | 131.4173 |
| B | 340 | LEU | 30.3281 | 27.7130 | 2.6151 |
| B | 341 | SER | 56.7878 | 7.5202 | 49.2676 |
| B | 342 | ARG | 98.0880 | 17.8439 | 80.2441 |
| B | 343 | PRO | 8.6324 | 7.3826 | 1.2498 |
| B | 344 | SER | 41.9949 | 8.0502 | 33.9446 |
| B | 345 | PRO | 8.7840 | 0.5623 | 8.2217 |
| B | 346 | PHE | 54.6782 | 0.0000 | 54.6782 |
| B | 347 | ASP | 32.6928 | 0.0022 | 32.6906 |
| B | 348 | LEU | 14.8926 | 1.1178 | 13.7748 |
| B | 349 | PHE | 39.9704 | 10.4255 | 29.5448 |
| B | 350 | ILE | 73.8619 | 21.9211 | 51.9407 |
| B | 351 | ARG | 147.3887 | 26.4137 | 120.9751 |
| B | 352 | LYS | 135.7416 | 13.6787 | 122.0629 |
| B | 353 | SER | 61.2658 | 9.1613 | 52.1044 |
| B | 354 | PRO | 2.5939 | 2.1299 | 0.4639 |
| B | 355 | THR | 42.7428 | 4.7400 | 38.0028 |
| B | 356 | ILE | 0.5514 | 0.5514 | 0.0000 |
| B | 357 | THR | 40.3271 | 1.9728 | 38.3542 |
| B | 358 | CYS | 0.0001 | 0.0000 | 0.0001 |
| B | 359 | LEU | 54.9866 | 0.0000 | 54.9866 |
| B | 360 | VAL | 7.6979 | 0.0000 | 7.6979 |
| B | 361 | VAL | 38.3830 | 0.9751 | 37.4079 |
| B | 362 | ASP | 20.1195 | 0.0000 | 20.1195 |
| B | 363 | LEU | 123.8794 | 13.1026 | 110.7767 |
| B | 364 | ALA | 68.0883 | 8.3308 | 59.7575 |
| B | 365 | PRO | 51.1372 | 26.4772 | 24.6601 |
| B | 366 | SER | 46.0645 | 15.7449 | 30.3196 |
| B | 367 | LYS | 175.7613 | 17.0268 | 158.7345 |
| B | 368 | GLY | 40.2741 | 40.2741 | 0.0000 |
| B | 369 | THR | 116.4286 | 12.3087 | 104.1199 |
| B | 370 | VAL | 22.6851 | 4.9095 | 17.7756 |
| B | 371 | ASN | 78.4885 | 2.3986 | 76.0898 |
| B | 372 | LEU | 24.9856 | 22.0727 | 2.9130 |
| B | 373 | THR | 74.3952 | 4.8477 | 69.5475 |
| B | 374 | TRP | 17.2787 | 13.4167 | 3.8621 |
| B | 375 | SER | 40.6442 | 2.9067 | 37.7376 |
| B | 376 | ARG | 37.1391 | 14.6843 | 22.4548 |
| B | 377 | ALA | 75.7209 | 44.2220 | 31.4989 |
| B | 378 | SER | 66.9922 | 45.9070 | 21.0852 |
| B | 379 | GLY | 64.7560 | 64.7560 | 0.0000 |
| B | 380 | LYS | 119.6208 | 9.5358 | 110.0849 |
| B | 381 | PRO | 106.2747 | 11.0642 | 95.2105 |
| B | 382 | VAL | 48.3386 | 20.9550 | 27.3835 |
| B | 383 | ASN | 83.0881 | 12.8457 | 70.2423 |
| B | 384 | HIS | 170.6799 | 11.9946 | 158.6853 |
| B | 385 | SER | 52.6162 | 26.0625 | 26.5537 |
| B | 386 | THR | 60.9428 | 3.2430 | 57.6998 |
| B | 387 | ARG | 97.2044 | 26.5188 | 70.6856 |
| B | 388 | LYS | 107.8917 | 8.2856 | 99.6061 |
| B | 389 | GLU | 100.8905 | 34.4469 | 66.4436 |
| B | 390 | GLU | 112.4192 | 5.5458 | 106.8734 |
| B | 391 | LYS | 127.1799 | 27.5948 | 99.5851 |
| B | 392 | GLN | 69.3230 | 5.7324 | 63.5906 |
| B | 393 | ARG | 230.0171 | 40.6982 | 189.3189 |
| B | 394 | ASN | 128.6791 | 32.0249 | 96.6542 |
| B | 395 | GLY | 24.4431 | 24.4431 | 0.0000 |
| B | 396 | THR | 25.5405 | 0.0000 | 25.5405 |
| B | 397 | LEU | 27.1060 | 0.6674 | 26.4386 |
| B | 398 | THR | 20.5985 | 0.0015 | 20.5970 |
| B | 399 | VAL | 3.5042 | 0.0000 | 3.5042 |
| B | 400 | THR | 23.6661 | 0.0000 | 23.6661 |
| B | 401 | SER | 3.7622 | 0.0000 | 3.7622 |
| B | 402 | THR | 27.7013 | 0.5216 | 27.1797 |
| B | 403 | LEU | 0.4650 | 0.0000 | 0.4650 |
| B | 404 | PRO | 50.8792 | 2.4469 | 48.4324 |
| B | 405 | VAL | 11.4217 | 11.4207 | 0.0010 |
| B | 406 | GLY | 29.0436 | 29.0436 | 0.0000 |
| B | 407 | THR | 43.0556 | 4.1821 | 38.8734 |
| B | 408 | ALA | 61.4297 | 6.8248 | 54.6049 |
| B | 409 | ASP | 55.3480 | 6.3286 | 49.0194 |
| B | 410 | TRP | 22.6758 | 5.0163 | 17.6595 |
| B | 411 | ILE | 92.9296 | 28.1330 | 64.7966 |
| B | 412 | GLU | 152.7922 | 38.3551 | 114.4372 |
| B | 413 | GLY | 48.6396 | 48.6396 | 0.0000 |
| B | 414 | GLU | 21.8918 | 7.5759 | 14.3159 |
| B | 415 | THR | 42.0078 | 0.2223 | 41.7856 |
| B | 416 | TYR | 5.5797 | 0.0000 | 5.5797 |
| B | 417 | GLN | 60.9693 | 0.0000 | 60.9693 |
| B | 418 | CYS | 0.0000 | 0.0000 | 0.0000 |
| B | 419 | ARG | 99.3469 | 0.0171 | 99.3298 |
| B | 420 | VAL | 8.2836 | 2.1863 | 6.0973 |
| B | 421 | THR | 44.9190 | 1.9459 | 42.9731 |
| B | 422 | HIS | 26.0502 | 12.4704 | 13.5798 |
| B | 423 | PRO | 87.2876 | 39.8069 | 47.4806 |
| B | 424 | HIS | 105.3668 | 27.1986 | 78.1682 |
| B | 425 | LEU | 66.9696 | 16.1712 | 50.7984 |
| B | 426 | PRO | 130.9478 | 44.9208 | 86.0270 |
| B | 427 | ARG | 178.5795 | 17.8897 | 160.6898 |
| B | 428 | ALA | 20.5710 | 11.7815 | 8.7895 |
| B | 429 | LEU | 45.6696 | 1.1565 | 44.5131 |
| B | 430 | MET | 79.0738 | 19.1545 | 59.9193 |
| B | 431 | ARG | 84.7514 | 7.5867 | 77.1648 |
| B | 432 | SER | 75.7537 | 23.7187 | 52.0351 |
| B | 433 | THR | 11.5776 | 8.0075 | 3.5701 |
| B | 434 | THR | 90.7088 | 42.8306 | 47.8781 |
| B | 440 | ARG | 174.6324 | 54.1971 | 120.4352 |
| B | 441 | ALA | 31.7872 | 7.2521 | 24.5352 |
| B | 442 | ALA | 54.1588 | 15.3292 | 38.8296 |
| B | 443 | PRO | 8.9092 | 8.9092 | 0.0000 |
| B | 444 | ALA | 51.5892 | 11.4500 | 40.1392 |
| B | 445 | VAL | 7.6589 | 7.6589 | 0.0000 |
| B | 446 | TYR | 66.9839 | 0.2109 | 66.7730 |
| B | 447 | ALA | 4.1767 | 4.1767 | 0.0000 |
| B | 448 | PHE | 17.6291 | 3.0962 | 14.5329 |
| B | 449 | ALA | 25.4344 | 15.5042 | 9.9303 |
| B | 450 | THR | 27.0878 | 10.8774 | 16.2104 |
| B | 451 | PRO | 65.4887 | 15.0567 | 50.4320 |
| B | 452 | GLU | 143.9717 | 84.9314 | 59.0403 |
| B | 459 | LYS | 103.0908 | 20.8278 | 82.2630 |
| B | 460 | ARG | 47.0337 | 0.0000 | 47.0337 |
| B | 461 | THR | 2.2905 | 2.1839 | 0.1066 |
| B | 462 | LEU | 2.6891 | 0.0000 | 2.6891 |
| B | 463 | ALA | 0.9506 | 0.0217 | 0.9289 |
| B | 464 | CYS | 0.0792 | 0.0792 | 0.0000 |
| B | 465 | LEU | 3.0710 | 0.5753 | 2.4957 |
| B | 466 | ILE | 0.0000 | 0.0000 | 0.0000 |
| B | 467 | GLN | 12.7692 | 0.0000 | 12.7692 |
| B | 468 | ASN | 33.8649 | 4.4567 | 29.4083 |
| B | 469 | PHE | 0.0054 | 0.0022 | 0.0032 |
| B | 470 | MET | 74.8306 | 0.0243 | 74.8063 |
| B | 471 | PRO | 39.3649 | 4.3033 | 35.0616 |
| B | 472 | GLU | 69.4348 | 0.8078 | 68.6270 |
| B | 473 | ASP | 48.3670 | 6.8665 | 41.5005 |
| B | 474 | ILE | 29.7325 | 25.4238 | 4.3087 |
| B | 475 | SER | 12.0014 | 4.0010 | 8.0004 |
| B | 476 | VAL | 13.4892 | 10.8369 | 2.6523 |
| B | 477 | GLN | 11.3814 | 1.9418 | 9.4396 |
| B | 478 | TRP | 1.5124 | 0.8684 | 0.6440 |
| B | 479 | LEU | 13.6857 | 0.9802 | 12.7055 |
| B | 480 | HIS | 17.3895 | 0.1658 | 17.2237 |
| B | 481 | ASN | 93.6719 | 25.1285 | 68.5434 |
| B | 482 | GLU | 125.6713 | 29.6418 | 96.0295 |
| B | 483 | VAL | 79.4087 | 3.3215 | 76.0872 |
| B | 484 | GLN | 78.1896 | 17.5637 | 60.6259 |
| B | 485 | LEU | 27.8300 | 7.0753 | 20.7547 |
| B | 486 | PRO | 87.6683 | 13.0267 | 74.6416 |
| B | 487 | ASP | 106.0327 | 8.9586 | 97.0742 |
| B | 488 | ALA | 88.6451 | 26.1062 | 62.5389 |
| B | 489 | ARG | 85.0155 | 17.5300 | 67.4855 |

TABLE VI-continued

IgE-Fc Residue Exposure
>>>> Surface plot for Crystal 3:
>>>> structure file = P21_BIG_easy.mtf
>>>> coordinate set = P21_BIG_easy.pdb

| segid | resid | resname | total accessible area residue | mainchain | sidechain |
|---|---|---|---|---|---|
| B | 490 | HIS | 28.9263 | 15.2503 | 13.6760 |
| B | 491 | SER | 22.8732 | 4.5357 | 18.3375 |
| B | 492 | THR | 33.3185 | 10.4185 | 22.8999 |
| B | 493 | THR | 9.8008 | 4.4290 | 5.3718 |
| B | 494 | GLN | 122.1816 | 4.4854 | 117.6962 |
| B | 495 | PRO | 45.9100 | 19.1505 | 26.7595 |
| B | 496 | ARG | 77.4821 | 4.6438 | 72.8383 |
| B | 497 | LYS | 156.9060 | 13.7662 | 143.1398 |
| B | 498 | THR | 10.5284 | 10.5284 | 0.0000 |
| B | 499 | LYS | 141.8348 | 21.1031 | 120.7317 |
| B | 500 | GLY | 76.9514 | 76.9514 | 0.0000 |
| B | 501 | SER | 37.5657 | 19.4374 | 18.1283 |
| B | 502 | GLY | 8.5572 | 8.5572 | 0.0000 |
| B | 503 | PHE | 38.7960 | 0.0000 | 38.7960 |
| B | 504 | PHE | 0.8833 | 0.0000 | 0.8833 |
| B | 505 | VAL | 1.0566 | 0.0000 | 1.0566 |
| B | 506 | PHE | 1.1032 | 0.0075 | 1.0957 |
| B | 507 | SER | 0.0000 | 0.0000 | 0.0000 |
| B | 508 | ARG | 6.2707 | 1.3763 | 4.8944 |
| B | 509 | LEU | 0.4075 | 0.1302 | 0.2774 |
| B | 510 | GLU | 26.9288 | 1.9346 | 24.9942 |
| B | 511 | VAL | 0.7112 | 0.5731 | 0.1381 |
| B | 512 | THR | 68.8463 | 0.0000 | 68.8463 |
| B | 513 | ARG | 126.9518 | 0.1391 | 126.8127 |
| B | 514 | ALA | 71.8963 | 24.0304 | 47.8659 |
| B | 515 | GLU | 41.8017 | 8.6065 | 33.1952 |
| B | 516 | TRP | 43.0303 | 5.5354 | 37.4949 |
| B | 517 | GLU | 115.1456 | 34.7904 | 80.3553 |
| B | 518 | ALA | 44.2655 | 6.4136 | 37.8519 |
| B | 519 | LYS | 9.5012 | 0.0021 | 9.5081 |
| B | 520 | ASP | 107.0301 | 19.9959 | 87.0341 |
| B | 521 | GLU | 57.9270 | 3.7465 | 54.1805 |
| B | 522 | PHE | 0.6518 | 0.0000 | 0.6518 |
| B | 523 | ILE | 37.2788 | 0.0000 | 37.2788 |
| B | 524 | CYS | 0.0000 | 0.0000 | 0.0000 |
| B | 525 | ARG | 48.3983 | 0.0019 | 48.3965 |
| B | 526 | ALA | 0.0000 | 0.0000 | 0.0000 |
| B | 527 | VAL | 0.4592 | 0.0013 | 0.4579 |
| B | 528 | HIS | 0.5688 | 0.0000 | 0.5688 |
| B | 529 | GLU | 73.0282 | 10.6039 | 62.4243 |
| B | 530 | ALA | 19.5162 | 13.0527 | 6.4635 |
| B | 531 | ALA | 11.9582 | 11.9582 | 0.0000 |
| B | 532 | SER | 72.6143 | 22.6389 | 49.9754 |
| B | 533 | PRO | 110.6703 | 5.5908 | 105.0795 |
| B | 534 | SER | 73.0953 | 28.2636 | 44.8317 |
| B | 535 | GLN | 42.4382 | 0.0000 | 42.4382 |
| B | 536 | THR | 35.5345 | 12.1649 | 23.3696 |
| B | 537 | VAL | 34.0768 | 4.7706 | 29.3062 |
| B | 538 | GLN | 71.8790 | 10.8341 | 61.0450 |
| B | 539 | ARG | 95.9551 | 4.2539 | 91.7012 |
| B | 540 | ALA | 58.1624 | 20.4943 | 37.6680 |
| B | 541 | VAL | 8.8788 | 2.4114 | 6.4673 |
| B | 542 | SER | 72.8072 | 2.5036 | 70.3035 |
| B | 543 | VAL | 118.6025 | 36.4280 | 82.1745 |

Residues that are solvent accessible are important as they represent amino acids that are on the external surface of the protein and, as such, may be involved in binding of FcR to an antibody and be useful in designing proteins with an enhanced binding activity or in identifying compounds that inhibit such binding. In addition, solvent accessible residues can represent targets for modification to produce a Fc region of an antibody with improved function. Such analysis also identifies residues in the interior, or core, of the proteins in the complex. Such residues can also be targeted to produce proteins with improved functions, such as enhanced stability.

A model of the present invention also provides additional information that is not available from other sources. For example, a model can identify the crystal contacts between crystals and predict the location of the FcR binding domain, including those amino acids that actually form contacts with a FcR. Particularly important regions of the model representing the coordinates of Table 1, Table 2 or Table 3 of U.S. Patent Publication No. US-2001-0039479-A1 or the atomic coordinates specified in Table I, Table II or Table m include, but are not limited to the interdomain groove (i.e., space, gap) between the two Cε3/Cε4-containing chains of the IgE antibody Fe region, the hinge between the Cε3 and Cε4 domains of the Fe region, and a loop involved in FcεRIα protein binding, such as the linker between Cε2 and Cε3, the BC loop of Cε3, the DE loop of Cε3, and the FG loop of Cε3. These sites are described in more detail in the Examples in U.S. Patent Publication No. US-2001-0039479-A1 and represent sites to target for drug design and mutein production.

A model of the present invention can also represent a complex that includes a Fc domain of an antibody that binds to a FcεRIα protein with an affinity that is at least equivalent to the affinity of a human IgE antibody Fc-Cε3/Cε4 region for the extracellular domain of any of the following FcεRIα proteins: a human FcεRIα protein, a canine FcεRIα protein, a feline FcεRIα protein, an equine FcεRIα protein, a murine FcεRIα protein and a rat FcεRIα protein. Such a model can represent a FceRI-binding domain of a human, canine, feline, equine, murine or rat Fc region. Such a model can also represent a Fc region with altered substrate specificity, preferably designed based on a model of the present invention.

The present invention includes a model that represents a Fc domain that binds to a Fc receptor of its respective class. Also included is a model that represents a Fe region of an antibody designed to bind to a Fc receptor of a class other than the class to which the protein naturally binds. Such classes include IgA, IgD, IgE, IgG, and IgM. Such a model of the present invention can be produced, for example, by incorporating all or any part of the amino acid sequence of the other antibody into a 3-D model substantially representing the coordinates in Table 1, Table 2 or Table 3 of U.S. Patent Publication No. US-2001-0039479-A 1 or the atomic coordinates specified in Table I, Table II or Table III. Such an embodiment includes any model that specifically incorporates any Ig domains that are placed in an orientation (packing interfaces and bend angles) that is based on the structure predicted by the coordinates in Table 1, Table 2 or Table 3 of U.S. Patent Publication No. US-2001-0039479-A1 or the atomic coordinates specified in Table I, Table II or Table III or a similar structure such that the distance between the two antibody-binding domains (i.e., Cε3 for IgE) ranges from about 10 angstroms to about 25 angstroms or from about 20 angstroms to about 40 angstroms. As such, both open and closed conformations of Fc regions are included in the present invention. In one embodiment, a model of the present invention is a 3-D model of a FcεRIα binding domain other than a human FcεRIα binding domain. Such proteins and models thereof can be designed by homology modeling.

A preferred modified model of the present invention is a model that has a 3-D structure comprising atomic coordinates that have a root mean square deviation of protein backbone atoms of less than 10 angstrom when superimposed, using backbone atoms, on the 3-D model substantially represented by the atomic coordinates specified in Table 1, Table 2 or Table 3 of U.S. Patent Publication No.

US-2001-0039479-A1 or the atomic coordinates specified in Table I, Table II or Table III. It is within the abilities of one skilled in the art to determine an optimal root mean square deviation based on the average deviation of the models disclosed herein. Preferably such a model has a 3-D structure comprising atomic coordinates that have a root mean square deviation of protein backbone atoms of less than 8 angstroms, preferably less than 7 angstroms, preferably less than 6 angstroms, preferably less than 5 angstroms, preferably less than 4 angstroms, preferably less than 3 angstroms, preferably less than 2 angstroms, and preferably less than 1 angstroms, when superimposed, using backbone atoms, on the 3-D model substantially represented by the atomic coordinates specified in Table 1, Table 2 or Table 3 of U.S. Patent Publication No. US-2001--0039479-A1 or the atomic coordinates specified in Table I, Table II or Table III. In this embodiment, such a model represents a Fc region binding to a FcR. The backbone atoms are those atoms that form the backbone, or 3-D folding pattern, of the model. As such, backbone atoms are the base residues of amino acids, i.e., nitrogen, carbon, the alpha carbon and oxygen. Also preferred is a model modification that includes a Fc region having an amino acid sequence that shares at least about 30%, preferably at least about 40%, more preferably at least about 45%, more preferably at least about 50%, more preferably at least about 60% and even more preferably at least about 80% amino acid sequence homology, with a Fc-Cε3/Cε4 region of a human IgE antibody, as determined using the program ALIGN with default parameters, optimal global alignment of two sequences with no short-cuts. A preferred model of the present invention represents a FcεRIα-binding domain, i.e., a region that binds to a FcεRIα protein.

One embodiment of the present invention is a 3-D model of a human Fc-Cε3/Cε4 region produced by a method that includes the steps of: (a) crystallizing a human Fc-CεCε3/Cε4 region, such as, but not limited to a protein having amino acid sequence SEQ ID NO:2 or amino acid sequence SEQ ID NO:8; (b) collecting X-ray diffraction data from the crystallized protein; and (c) determining the model from the X-ray diffraction data, preferably in combination with an amino acid sequence of the protein. A complex for crystal formation can be produced using a variety of techniques well known to those skilled in the art. As disclosed herein) a human Fc-Cε3/Cε4 region to be crystallized is preferably produced in recombinant insect cells transformed with a gene encoding such a region, such as a baculovirus genetically engineered to produce the respective protein.

The purity of the Fc-Cε3/Cε4 region must be sufficient to permit the production of crystals that can be analyzed by X-ray crystallography to a resolution that permits determination of a 3-D model of the protein. Preferably the resolution is at least about 4.5 angstroms (i.e., 4.4 angstroms or better), more preferably at least about 4 angstroms, more preferably at least about 3.5 angstroms, more preferably at least about 3.25 angstroms, more preferably at least about 3 angstroms, more preferably at least about 2.5 angstroms, more preferably at least about 2.3 angstroms, more preferably at least about 2 angstroms and even more preferably at least about 1.5 angstroms. Methods to obtain such purity levels are well known to those skilled in the art.

As disclosed herein, a preferred method to crystallize a Fc-Cε3/Cε4 region is by vapor distillation. Particularly preferred methods are disclosed in the Examples. It should be appreciated that the present invention also includes other methods known to those skilled in the art by which such a complex can be crystallized.

3-D models of some proteins have been determined; see, for example, Blundell et al., *Protein Crystallography*, Academic Press, London, 1976. However, as discussed herein, elucidation of the crystal structure of a Fc-Cε3/Cε4 region of a human IgE was difficult. In one embodiment, crystal structure determination includes obtaining high-resolution data using synchrotron radiation. Such data can be collected, for example, at the Stanford Synchrotron Source Laboratory, Palo Alto, Calif., or the Advanced Photon Source at Argonne National Laboratories, Argonne, Ill. Additional locations to collect such data include, but are not limited to, Brookhaven, N.Y., and Japan. In one embodiment, diffraction data from native and heavy-atom treated crystals provide an initial image of the protein structure which is refined into an electron density map. Details regarding data collection and interpretation are provided in the Examples section.

One embodiment of the present invention is a method to produce a 3-D model of a Fc region that includes positioning amino acid representations (i.e., representing amino acids) of the protein at substantially the coordinates listed in Table 1, Table 2 or Table 3 of U.S. Patent Publication No. US-2001-0039479-A1 or the atomic coordinates specified in Table I, Table II or Table III. That is, knowledge of the coordinates of the complex permits one skilled in the art to produce a model of the protein using those coordinates. Such a model, or any model which is essentially represented by a simple coordinate transformation of the coordinates specified in Table 1, Table 2 or Table 3 of U.S. Patent Publication No. US-2001-0039479-A1 or the atomic coordinates specified in Table I, Table II or Table III, can be represented in a variety of methods as heretofore disclosed and is included in the present invention.

In another embodiment, a model of the present invention can be refined to obtain an improved model, which is an example of a model modification, also referred to as a modified model. Refining methods can include, but are not limited to, further data collection and analysis; data collection from frozen crystals; introduction of solvent molecules to the structure; clarification of secondary structure; and analyses of crystallized complexes between a FcR and an antibody or inhibitory compound or of crystallized FcRs or antibodies alone. An additional model refinement method includes analyzing a 3-D model to predict amino acid residues that if replaced are likely to yield proteins with at least one improved function, effecting at least one such replacement, determining whether the activity of the modified protein agrees with the prediction, and refining the model as necessary. Methods to determine whether the modification agrees with prediction include producing the modified protein and performing assays with that modified protein to determine if the protein does indeed exhibit the improved function(s), such as desired activity, stability and solubility properties. Assays to measure such functions are well known in the art; examples of several such assays are disclosed herein.

Another embodiment of the present invention is a modified 3-D model that represents an antibody other than human IgE as represented by the coordinates in Table 1, Table 2 or Table 3 of U.S. Patent Publication No. US-2001-0039479-A1 or the atomic coordinates specified in Table I, Table II or Table III. Preferably the amino acid sequence of the protein (s) to be modeled is known. In such a case, the modified model an be produced using the technique of homology modeling, preferably by incorporating (e.g., grafting, overlaying or replacing) all or any portion of the amino acid sequence of the other antibody into the 3-D model representing the coordinates of Table 1, Table 2 or Table 3 of U.S.

Patent Publication No. US-20014039479-A1 or the atomic coordinates specified in Table I, Table II or Table III to produce the modified model. General techniques for homology modeling, also referred to as molecular replacement, have been disclosed in, for example, Greer, 1990, *Proteins: Structure, Function, and Genetics* 7, 317–334; Havel et al., 1991, *J. Mol. Biol.* 217, 1–7; Schiffer et al., 1990, *Proteins: Structure; Function, and Genetics* 8, 3043; and Lattman, 1985, *Methods Enzymol* 115, 55–77. However, such technology has not been applied to Fc regions of IgE antibodies since, until the present invention, no 3-D model of any Fc region of IgE was available. Thus, the present invention now allows the solving of the structures of a number of other natural and mutated forms of antibodies.

In one embodiment, a model of a Fc region, such as, but not limited to a Fc-C$\epsilon$3/C$\epsilon$4 region, is produced by extracting the 3-D coordinates from a published figure or building a 3-D model with atoms from other domains wherein FcR-binding domains of the antibody are oriented as predicted for a human Fc-C$\epsilon$3/C$\epsilon$4 protein. For example, a model of the present invention can be produced by orienting two known FcR-binding domains into a bent confirmation such that the distance between the domains ranges from about 10 to about 25 angstroms or from about 20 to about 40 angstroms. In another example, a model can be produced by orienting the hinge between two Ig domains in a manner similar to that specified by the coordinates in Table 1, Table 2 or Table 3 of U.S. Patent Publication No. US-2001-0039479-A1 or the atomic coordinates specified in Table I, Table II or Table III. Such a model is referred to as a model in which the hinge between two Ig domains, e.g., between C$\epsilon$3 and C$\epsilon$4 are oriented in a manner as specified by the structural coordinates listed in Table 1, Table 2 or Table 3 of U.S. Patent Publication No. US-2001-0039479-A1 or the atomic coordinates specified in Table I, Table II or Table III. This model can then be used in further molecular replacement methods. Such methods can include the steps of (a) orienting the model by three rotations; and (b) translating the model in one to three directions to produce additional model modifications.

Suitable antibodies for which a 3-D model can be determined using homology modeling include any mammalian antibody such as a protein that binds to a FcR for IgE, IgG, IgM, IgA or IgD antibodies. Preferred antibodies that bind to FcRs include human, canine, feline, equine, murine and rat antibodies. The present invention also includes the use of other Ig domains to produce models of the present invention.

One embodiment of the present invention is a 3-D model of a Fe region of an antibody in which the protein has an improved function compared to an unmodified protein as well as a method to produce such a modified model. Such an improved function includes, but is not limited to, enhanced activity, enhanced stability and enhanced solubility. Such a modified model can be produced by replacing at least one amino acid based on information derived from analyzing the 3-D model representing the coordinates in Table 1, Table 2 or Table 3 of U.S. Patent Publication No. US-2001-0039479-A1 or the atomic coordinates specified in Table I, Table II or Table III, such -that the replacement leads to a protein with an improved function. As used herein, a replacement refers to an (i.e., one or more) amino acid substitution, insertion, deletion, inversion and/or derivatization (e.g., acetylation, glycosylation, phosphorylation, PEG modification, biotinylation, and covalent attachment of other ligands or other compounds to the protein. In one embodiment, synthetic chemical methods are used to produce either a fragment or the entire protein to, for example, introduce non-natural amino acids or other chemical compounds into the structure of a Fc region. For example, based on a structure of the present invention, one can design synthetic peptides or larger proteins that could be linked to produce an intact protein with FcR binding activity, the structure allowing one to design the start and stop points for these peptides, e.g., at surface accessible loops. In accordance with the present invention, an amino acid that is substituted or inserted can be a natural amino acid or an unnatural amino acid, including a derivitized amino acid. Methods to identify regions in the protein that, if changed, yield a protein with an improved function are disclosed below.

The present invention includes use of a 3-D model of the present invention to identify a compound that inhibits binding between a FcR and an antibody. The advantages of using a 3-D model to identify inhibitory compounds are multi-fold in that the model depicts the site at which a Fc region of an antibody binds to its FcR, i.e., the antibody-binding domain, also referred to as the antibody binding site, and the FcR-binding domain, also referred to as the FcR binding site. The antibody binding site and the FcR binding site together form an FcR:antibody interaction site. As such, a large number of potential inhibitory compounds can be initially analyzed without having to perform in vitro or in vivo laboratory studies. As used herein, methods to identify inhibitory compounds include, but are not limited to, designing inhibitory compounds based on the 3-D model of a Fc region, probing such a 3-D model with compounds that are potential inhibitors in order to identify those compounds that are actually inhibitory of the binding of an antibody to its FcR, screening a compound data base using such a 3-D model to identify compounds that inhibit such binding, and combinations thereof. Methods to use 3-D models to design, probe for, or screen for suitable inhibitory compounds are known to those skilled in the art. In particular, there are a number of computer programs that enable such methods. See, for example, PCT Publication No.

WO 95/35367, by Wilson et al., published Dec. 28, 1995, which is incorporated by reference herein in its entirety.

An inhibitory compound can be any natural or synthetic compound that inhibits the binding of an antibody to a FcR. Examples include, but are not limited to, inorganic compounds, oligonucleotides, proteins, peptides, antibodies, antibody fragments, mimetics of peptides or antibodies (such as, mimetics of antibody or receptor binding sites), and other organic compounds. Compounds can inhibit binding in either a competitive or non-competitive manner and can either interact at the binding site or allosterically. An inhibitory compound should be capable of physically and structurally associating with a FcR and/or an antibody such that the compound can inhibit binding between the two entitites. As such, an inhibitory compound is preferably small and is of a structure that effectively prevents or disrupts binding. Inhibitory compounds can be identified in one or multiple steps. For example, a compound initially identified that inhibits binding between an antibody and FcR to some extent can be used as a lead to design, probe or screen for a compound with improved characteristics, such as greater efficacy, safety, solubility, etc. A preferred inhibitory compound is a compound that is efficacious when administered to an animal in an amount that results in a serum concentration of from about 1 nanomolar (nM) to 100 micromolar (uM), with a concentration of from about 10 nM to 10 uM being more preferred.

One embodiment of the present invention is a method to identify a compound that inhibits the binding between an IgE antibody and a FcεRIα protein. Such a method includes the step of using a 3-D model substantially representing the atomic coordinates specified in Table 1, Table 2 or Table 3 of U.S. Patent Publication No. US-2001-0039479-A1 or the atomic coordinates specified in Table I, Table II or Table III to identify such a compound. Included in the present invention are inhibitory compounds that interact directly with the IgE binding domain or the receptor binding domain of the IgE antibody as well as compounds that interact indirectly with such structures. Preferably a compound interacts with at least one of the following regions: a FcεRIα binding domain, an interdomain groove between the two Cε3/Cε4 domains of the antibody Fc region, a hinge between Cε3 and Cε4 domains of the antibody Fc region, and a region of a Cε3 or Cε4 domain, the relative position of which changes by greater than 1 angstrom between closed and receptor-bound Fc-Cε3/Cε4 conformations. It is to be noted that many residues in the Cε3 domains are significantly closer to the Cε4 domains in the closed form of the IgE as compared to the open form. While not being bound by theory, it is believed that molecules that could interact with Cε3 residues and Cε4 residues at the same time but only in the closed form of the IgE, would be potential inhibitors. Regions to target include a set of residues in the two domains whose relative distances change significantly (i.e., by more than 1 angstrom) in comparison of the receptor-bound and closed IgE conformations. Preferably the distance between the two Cε3 domains of the closed conformation of the Fc-Cε3/Cε4 region ranges from about 10 to about 25 angstroms, more preferably from about 10 and 15 angstroms, and even more preferably about 13 angstroms. In a preferred embodiment, an inhibitory compound reacts with at least one of the following regions: a linker between Cε2 and Cε3 (amino acids 4, 7, 8, 9, 10 and 11 of SEQ ID NO:2 or SEQ ID NO:8); a BC loop of Cε3 (amino acids 37, 38 and 39 of SEQ ID NO:2; a DE loop of Cε3 (amino acids 68, 69, and 70 of SEQ ID NO:2 or SEQ ID NO:8); a FG loop of Cε3 (amino acids 99, 100, 101 and 102 of SEQ ID NO:2 or SEQ ID NO:8); a loop or strand defining (i.e., abutting, forming) the interdomain groove; a AB helix of Cε3 (amino acid 20, 21, 22, 23 and 24 of SEQ ID NO:2 or SEQ ID NO:8) which is thought to regulate the full conformational flexibility of the IgE-Fc region; and a region lying above said AB helix of Cε3, i.e., the region constituting the hinge and including amino acids 17, 18 and 19 (after strand A), amino acids 29, 30 and 31 (after strand B), and amino acids 109, 110 and 111 (after strand G) of SEQ ID NO:2 or SEQ ID NO:8. Particularly preferred amino acids with which to have an inhibitory compound interact include: (a) a residue at position 4, 7, 8, 9, 10, 11, 17, 18, 19, 20, 21, 22, 23, 24, 29, 30, 31, 37, 38, 39, 68, 69, 70, 99, 100, 101, 102, 109, 110, or 111 of SEQ ID NO:2 or SEQ ID NO:8; and (b) a surface residue within about 10 angstroms of any of said residues of (a). Even more preferred residues include: (a) a residue at position 4, 7, 8, 9, 10, 11, 37, 38, 39, 68, 69, 70, 99, 100, 101, or 102 of SEQ ID NO:2 or SEQ ID NO:8; (b) a residue in a region of a Cε3 or Cε4 domain, the relative position of which changes by greater than 1 angstrom between closed and receptor-bound Fc-Cε3/Cε4 conformations; and (c) a surface residue within about 10 angstroms of any of said residues of (a) or (b). Also preferred are additional residues identified in the Examples as being in at least one of the above cited regions. One preferred embodiment is a compound that inhibits the ability of an IgE antibody to convert from a closed conformation into a receptor-bound or open conformation. It is to be noted that the ability to identify such key regions and residues is only possible in view of a model of the present invention. In one embodiment, an inhibitory compound of the present invention is a peptide corresponding to at least a portion of any of the identified regions or a derivative thereof, such as a peptide mimetic or other compound that mimics that peptide.

One embodiment of a method to identify a compound that inhibits the binding between an IgE antibody and a FcεRIα protein includes the steps of: (a) generating a model substantially representing the atomic coordinates listed in Table 1, Table 2 or Table 3 of U.S. Patent Publication No. US-2001-0039479-A1 or the atomic coordinates specified in Table I, Table II or Table III or of the binding domains thereof, on a computer screen; (b) generating the spacial structure of a compound to be tested; and (c) testing to determine if the compound interacts with said FcR binding domain, wherein such an interaction indicates that the compound is capable of inhibiting the binding of an IgE antibody to a FcεRIα protein. In a preferred embodiment, step (a) includes the step of identifying one or more amino acid(s) in the FcR binding domain of the model that interact directly with the FcR. Preferably a compound to be tested will interact directly with one or more of those amino acid(s). Preferred amino acids with which an inhibitory compound should interact are disclosed herein.

The present invention also includes inhibitory compounds isolated in accordance with the methods disclosed herein. Methods to produce such compounds in quantities sufficient for use, for example, as protective agents (e.g., preventatives or therapeutics) are known to those skilled in the art. It should also be appreciated that it is within the scope of the present invention to expand the use of models of the present invention to produce models of any suitable Fc regions (i.e., model modifications) and to identify compounds that inhibit the binding of antibodies to such Fc regions.

A preferred inhibitory compound of the present invention, or lead that can be used to produce a more efficacious inhibitory compound, is a saturated tetracyclic hydrocarbon perhydrocyclopentanophenanthrene or a derivative thereof. Such a compound can include a structure having the following formula:

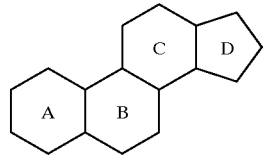

It is to be understood that such a compound can have any number of "R" groups, even though they are not indicated in the formula Examples of saturated tetracyclic hydrocarbon perhydrocyclopentanophenanthrenes include, but are not limited to, isoprenoids, terpenes, bile acids, detergents (such as CHAPS and CHAPSO) cholestanes, cholic acids, cholesterols, androgens, estrogens, and other steroids. A preferred inhibitory compound, or compound to use as a lead to design a more efficacious compound is 3-[3-(cholamidopropyl) dimethylammonio]-1-propane-sulfonate (CHAPS) or a compound having a similar ring structure. The interaction of CHAPS with amino acids in the FcεRIα protein and Fc-Cε3/Cε4 region is described in further detail in Ser. No. 60/189,853, ibid.

In one embodiment, an inhibitory compound of the present invention is a bivalent, or other multivalent, compound that interacts with the two Cε3/Cε4 domains with high affinity or a compound that is sufficiently large to bind the interdomain groove, such as, but not limited to, macromolecules such as in vitro selected peptides, peptoids, nucleic acids, similar molecules, mimetopes thereof.

The present invention also includes use of a 3-D model of the present invention to rationally design and construct modified forms of Fc regions of antibodies, and particularly of IgE antibodies, that have one or more improved functions, such as, but not limited to, increased activity, increased stability and increased solubility compared to an unmodified Fc region of an IgE antibody. Muteins of the present invention include full-length proteins as well as fragments (i.e., truncated versions) of such proteins.

One embodiment of the present invention is a Fc region that comprises a mutein that binds to a Fc binding domain of a FcR. Such a mutein has an improved function compared to a protein comprising SEQ ID NO:2. Examples of such an improved function include, but are not limited to, increased stability, increased affinity for an FcR, altered substrate specificity, and increased solubility. Such a mutein can be produced by a method that includes the steps of: (a) analyzing a 3-D model substantially representing the atomic coordinates specified in Table 1, Table 2 or Table 3 of U.S. Patent Publication No. US-2001-0039479-A1 or the atomic coordinates specified in Table I, Table II or Table III to identify at least one amino acid of the protein represented by the model which if replaced by a specified amino acid would effect the improved function of the protein; and (b) replacing the identified amino acid(s) to produce a mutein having the improved function. Knowledge of the coordinates allows one to target specific residues, e.g. in the hydrophobic core or on the surface, to generate an accessible set of variants that can then be selected for a particular property, e.g. high stability, high affinity, altered substrate specificity, or other desirable properties (i.e., improved functions). Without the coordinates, one would have to analyze an extraordinarily large number of variants, e.g., on the order of . $10^{11}$ possibilities. The structure, in contrast, allows one to pick the most relevant residues for selecting a desired property by, for example, phage display or other methods. In a preferred embodiment, replacement of one or more amino acids does not substantially disrupt the 3-D structure of the protein; i.e., the modified protein, or mutein, is still capable of binding to the FcR. A preferred mutein is a Fc domain of an IgE antibody that binds to a FcεRIα protein, although the invention also covers muteins binding to other classes of FcRs.

In one embodiment, a mutein of the present invention has increased stability compared to its unmodified counterpart. As used herein, increased stability refers to the ability of a mutein to be more resistant, for example, to higher or lower temperature, to more acidic or basic pH, to higher or lower salt concentrations, to oxidation and/or reduction, to deamidation, to other forms of chemical degradation and to proteolytic degradation compared to an unmodified Fc region. Increased stability can also refer to the ability of a mutein of the present invention to be stable for a longer period of time either during storage (i.e., to have a longer shelf life) or during use (i.e., to have a longer half-life under reaction conditions) than does an unmodified protein. Muteins of the present invention can also exhibit a decreased entropy of unfolding, thereby stabilizing the proteins. Increased stability can be measured using a variety of methods known to those skilled in the art; examples include, but are not limited to, determination of melting temperature, thermal denaturation, pressure denaturation, enthalpy of unfolding, free energy of the protein, or stability in the presence of a chaotropic agents such as urea, guanidinium chloride, guanidinium thiocyanate, etc. A preferred mutein of the present invention has a melting temperature substantially higher than that of an unmodified Fc region. Preferably the melting temperature of a mutein is at least about 1° C. higher, and more preferably at least about 10° C. higher than the melting temperature of the corresponding unmodified protein. Also preferred is a mutein having binding activity over a pH range that is at least about 1 pH unit higher and/or lower than the active pH range of the corresponding unmodified protein.

Another embodiment of the present invention is a mutein that exhibits increased affinity for a FcR compared to its unmodified counterpart. As used herein, a mutein having increased affinity is a Fc region that exhibits a higher affinity constant ($K_A$) or lower dissociation constant ($K_D$) than its unmodified counterpart. Such a higher affinity constant can be achieved by increasing the association rate ($k_a$) between the mutein and the FcR and/or decreasing the dissociation rate ($k_d$) between the mutein and the FcR. A preferred mutein of the present invention has a $K_A$ for a FcR of at least about $3 \times 10^9$ liters/mole ($M^{-1}$), which is equivalent to a $K_D$ of less than or equal to about $3.3 \times 10^{-10}$ moles/liter (M). More preferred is a mutein having a $K_A$ for a FcR of at least about $2 \times 10^{10}$ $M^{-1}$, and even more preferably of at least about $1 \times 10^{11}$ $M^{-1}$. Also preferred is a mutein having a $k_a$ for a FcR of at least about $1 \times 10^5$ liters/mole-second as well as a mutein having a $k_d$ for a FcR of less than or equal to $3 \times 10^{-5}$/second. More preferred is a mutein having a $k_a$ for a FcR of at least about $3 \times 10^5$ liters/mole-second, and even more preferably of $1 \times 10^6$ liters/mole-second. Also preferred are muteins having a $k_d$ for a FcR of less than or equal to $1 \times 10^{-5}$/second or even more preferably less than or equal to $3 \times 10^{-4}$ second. A preferred FcR is FcεRIα. Methods to measure such binding constants is well known to those skilled in the art; see, for example, Cook et al., 1997, ibid., which reports the following values for the binding of human FcεRIα protein to human IgE: $k_{a1}$ of 3.5 ($\pm 0.9$)$\times 10^5$ $M^{-1}s^{-1}$; $k_{a2}$ of 8.6 ($\pm +3.5$)$\times 10^4$ $M^{-1}s^{-1}$; $k_{d1}$ of 1.2 ($\pm 0.1$)$\times 10^{-2}$ $s^{-1}$; $k_{d2}$ of 3.2 ($\pm 0.8$)$\times 10^{-5}$ $s^{-1}$; $K_{A1}$ of $2.0 \times 10^7$ $M^{-1}$; $K_{A2}$ of $2.9 \times 10^9$ $M^{-1}$.

Another embodiment of the present invention is a mutein that exhibits altered substrate specificity compared to its unmodified counterpart. A mutein exhibiting altered substrate specificity is a mutein that binds with increased affinity to a FcR for an to antibody class or antibody species of a different type than that normally bound by its unmodified counterpart. In one embodiment, a mutein of a human Fc-Cε3/Cε4 region with altered substrate specificity is a Fc region that binds with increased affinity to a receptor that binds to an IgE antibody of another mammal, such as, but not limited to, a canine, feline, equine, murine, or rat IgE antibody. In another embodiment, a mutein of a is human Fc-Cε3/Cε4 region with altered substrate specificity is a Fc region that binds with increased affinity to a Fc receptor for an antibody of another class, such as IgG, IgM, IgA, or IgD, with IgG being preferred. Such a mutein can also show altered species substrate specificity. Methods to determine whether a mutein exhibits altered substrate specificity are well known to those skilled in the art.

Yet another embodiment of the present invention is a mutein that exhibits increased solubility compared to its unmodified counterpart. Such a protein is less likely to form aggregates. Methods to determine whether a mutein exhibits increased solubility are well known to those skilled in the art.

As disclosed herein, the 3-D model substantially representing the coordinates in Table 1, Table 2 or Table 3 of U.S. Patent Publication No. US-2001-0039479-A1 or the atomic coordinates specified in Table I, Table II or Table III is advantageous in determining strategies for producing muteins having an improved function, e.g., for identifying targets to modify in order to obtain muteins having improved functions. Examples of targets include, but are not limited to, those regions of the Fc-Cε3/Cε4 region that directly or indirectly interact with a FcεRIα protein.

In accordance with the present invention, a mutein having an improved function can be produced by a method that includes replacing at least one amino acid based on information derived from analyzing a 3-D model of the present invention to produce the mutein having the improved function. Knowledge of the structure of the human Fc-Cε3/Cε4 region, for example, permits the rational design and construction of modified forms of the protein by permitting the prediction and production of substitutions, insertions, deletions, inversions and/or derivatizations that effect an improved function. That is, analysis of 3-D models of the present invention provide information as to which amino acid residues are important and, as such, which amino acids can be changed without harming the protein. In making amino acid replacements, it is preferred to use amino acid replacements that have similar numbers of atoms and that allow conservation of salt bridges, hydrophobic interactions and hydrogen bonds unless the goal is to purposefully change such interactions. The 3-D structure of the human Fc-Cε3/Cε4 region suggests that large deletions may not be desirable, particularly due to the relation between the various domains of the protein and the observation that most of the structure is well ordered in the crystal.

It is to be appreciated that although one amino acid replacement capable of improving the function of a protein can substantially improve that function, more than one amino acid replacement can result in cumulative changes depending on the number and location of the replacements. For example, although one amino acid replacement capable of substantially increasing the stability of a protein can increase the melting temperature of that modified protein by about 1° C., about 5 to about 6 replacements may increase the melting temperature of the resultant protein by about 10° C.

In accordance with the present invention, the 3-D model of the Fc region has been analyzed, using techniques known to those skilled in the art, to determine the 10 accessibility of the amino acids represented within the model to solvent. Such information is provided in, for example, Table 4 or Table 5 of U.S. Patent Publication No. US-2001-0039479-A1, and also in Table IV, Table V or Table VI.

A number of methods can be used to produce muteins of the present invention. One method includes the steps of: (a) analyzing a 3-D model substantially representing the coordinates specified in Table 1, Table 2 or Table 3 of U.S. Patent Publication No. US-2001-0039479-A1 or the atomic coordinates specified in Table I, Table II or Table III to identify at least one amino acid of the modeled protein which if replaced by a specified amino acid would effect an improved function; and (b) replacing the identified amino acid(s) to produce a mutein having that improved function. In one embodiment, a method to produce a mutein includes the steps of (a) comparing a key region of a model of a human Fc-Cε3/Cε4 region with the amino acid sequence of a Fc region having an improved function compared to the unmodified Fc-Cε3/Cε4 region in order to identify at least one amino acid segment of the Fc region with the improved function that if incorporated into the Fc-Cε3/Cε4 region represented by the model would give the Fe-Cε3/Cε4 region the improved function; and (b) incorporating the segment into the Fc-Cε3/Cε4 region, thereby providing a mutein with the improved function. In another embodiment, a method to produce a protein includes the steps of: (a) using a model representing a human Fc-Cε3/Cε4 region to identify a 3-D arrangement of residues that can be randomized by mutagenesis to allow the construction of a library of molecules from which a improved function can be selected; and (b) identifying at least one member of the mutagenized library having the improved function. In one example, a mutein is produced by a method that includes the steps of: (a) effecting random mutagenesis of nucleic acid molecules encoding a target of a Fc-Cε3/Cε4 region as identified by analyzing a model of that protein, such as an FcR binding domain; (b) cloning such mutagenized nucleic acid molecules into a phage display library, wherein said phage display library expresses the target; and (c) identifying at least one member of the library that expresses a target with an improved function, such as an FcR binding domain exhibiting increased affinity for an FcR. As stated above, the model allows the use of this technique in a straightforward manner that could not be accomplished in the absence of the model. It is to be also noted that these methods can also be used with other models of the present invention to produce muteins of the present invention.

The present invention includes a number of methods, based on analysis of a 3-D model of the present invention, to replace (i.e., add, delete, substitute, invert, derivatize) at least one amino acid residue in the protein represented by the model in order to produce a mutein of the present invention. Such methods include, but are not limited to: (a) replacing at least one amino acid in at least one non-constrained loop; (b) joining an amino-terminal amino acid residue to a carboxyl-terminal amino acid residue; (c) replacing at least one amino acid site with an amino acid suitable for derivatization; (d) replacing at least one pair of amino acids of the protein with a cysteine pair to enable the formation of a disulfide bond that stabilizes the protein; (e) replacing at least one amino acid in the FcεRIα binding domain in order to increase the affinity between an IgE Fc region and the corresponding FcR; (f) replacing at least one amino acid of the protein with an amino acid such that the replacement decreases the entropy of unfolding of the protein; (g) replacing at least one asparagine or glutamine of the protein with an amino acid that is less susceptible to deamidation than is the amino acid to be replaced; (h) replacing at least one methionine, histidine or tryptophan with an amino acid that is less susceptible to an oxidation or reduction reaction than is the amino acid to be replaced; (i) replacing at least one arginine of the protein with an amino acid that is less susceptible to dicarbonyl compound modification than is the amino acid to be replaced; (j) replacing at least one amino acid of the protein susceptible to reaction with a reducing sugar sufficient to reduce protein function with an amino acid less susceptible to that reaction; (k) replacing at least one amino acid of the protein with an amino acid capable of increasing the stability of the inner core of the protein; (l) replacing at least one amino acid of the protein with at least one N-linked glycosylation site; (m) replacing at least one N-linked glycosylation site of the protein with at least one amino acid that does not comprise an N-linked glycosylation site; and (n) replacing at least one amino acid of the protein with an amino acid that reduces aggregation of the protein. Muteins of the present invention can be produced using methods and rationales similar to those disclosed in PCT WO 00/26246, ibid.; such methods, which are incorporated herein by reference in their entirety, can be applied to Fc-Cε3/Cε4 muteins of the present invention.

Amino acid replacements can be carried out using recombinant DNA techniques known to those skilled in the art, including site-directed mutagenesis (e.g., oligonucleotide mutagenesis, random mutagenesis, polymerase chain reaction (PCR)-aided mutagenesis, gapped-circle site-directed mutagenesis) or chemical synthetic methods of a nucleic acid molecule encoding the desired protein, such as, but not limited to a human FcεRIα protein, followed by expression of the mutated gene in a suitable expression system, preferably an insect, mammalian, bacterial, yeast, insect, or so mammalian expression system. See, for example, Sambrook et al., ibid.

It is to be appreciated that muteins of the present invention can include amino acids which are not modified because they would negatively impact the function of the protein. Such amino acids can be identified using a 3-D model of the present invention.

It should also be appreciated that it is within the scope of the present invention to expand the use of models of the present invention to produce models of and make modifications to any suitable FcRs or other Ig domain-containing proteins to produce muteins having a desired function.

Antibody muteins have a variety of uses, including but not limited to, diagnostic and therapeutic uses. For example, muteins could be used to image cells that express an antibody receptor protein, such as NMR-specific labeling for in vivo imaging to detect, for example, mast cell cancers, asthma, and other pathologies, or to treat cancers that express an antibody receptor protein using, for example, radioimmune therapy of derivatized IgE. Muteins could also be used for monitoring FcR expression in atopic individuals (e.g. with a tag for one-step FACS analysis) or for monitoring IgE in atopic individuals. Muteins could also be used as inhibitors or as toxin-IgE-Fc fusion proteins to target FcR-expressing cells to kill them (e.g. in mast cell tumors or severe allergy). Also muteins that affect the low affinity affinity IgE-receptor (FceRII) binding but not FceRI binding could be designed or selected.

The present invention also includes nucleic acid molecules that encode muteins of the present invention as well as recombinant molecules and recombinant cells that include such nucleic acid molecules. Methods to produce such proteins are also disclosed herein.

The present invention also includes the following novel structures as identified by a 3-D model of the present invention. Preferred structures exhibiting direct interaction between IgE and FcεRIα include a FcεRIα binding domain, an interdomain groove between the two Cε3Cε4 domains of said antibody Fc region, a hinge between Cε3 and Cε4 domains of said antibody Fc region, and a region of a Cε3 or Cε4 domain, the relative position of which changes by greater than 1 angstrom between closed and receptor-bound Fc-Cε3/Cε4 conformations. Preferred compositions include a linker between Cε2 and Cε3, a BC loop of Cε3, a DE loop of Cε3, and a FG loop of Cε3, a loop or strand defining the interdomain groove, a AB helix of Cε3 and, a region lying above said AB helix of Cε3. The present invention also includes nucleic acid molecules to encode such compositions.

The present invention also includes an isolated Fc-Cε3/Cε4 protein selected from the group consisting of: (a) a protein consisting of SEQ ID NO:2; (b) a protein consisting of SEQ ID NO:8; and (c) an isolated protein that is structurally homologous to a protein of (a) or (b), wherein said protein of (c) binds to a FcεRIα protein. Also included in the present invention is such a protein produced in insect cells. In one embodiment the Fc-Cε3Cε4 protein a human Fc-Cε3/Cε4 protein, a canine Fc-Cε3/Cε4 protein, a feline Fc-Cε3Cε4 protein, an equine Fc-Cε3/Cε4 protein, a murine Fc-Cε3/Cε4 protein, or a rat Fc-Cε3/Cε4 protein. The present invention also includes nucleic acid molecules that encode such proteins, as well as recombinant molecules, recombinant cells and recombinant viruses that include such nucleic acid molecules. Also included are methods to produce such proteins using such nucleic acid molecules, recombinant molecules, recombinant viruses and recombinant cells.

The present invention also includes isolated nucleic acid molecules encoding proteins of the present invention, including, but not limited to, unmodified proteins, novel structures within such proteins, and muteins. As used herein, an isolated nucleic acid molecule encoding a protein is a nucleic acid molecule that has been removed from its natural milieu. As such, "isolated" does not reflect the extent to which the nucleic acid molecule has been purified. An isolated nucleic acid molecule can be DNA, RNA, or derivatives of either DNA or RNA.

A nucleic acid molecule encoding a mutein of the present invention can be produced by mutation of parental protein genes (e.g., unmodified or previously modified protein-encoding genes, or portions thereof) using recombinant DNA techniques heretofore disclosed or by chemical synthesis. Resultant mutein nucleic acid molecules can be amplified using recombinant DNA techniques known to those skilled in the art, such as PCR amplification or cloning (see, for example, Sambrook et al., ibid.), or by chemical synthesis. A mutein can also be produced by chemical modification of a protein expressed by a nucleic acid molecule encoding an unmodified protein or mutein-encoding gene.

Proteins of the present invention can be produced in a variety of ways, including production and recovery of recombinant proteins and chemical synthesis. In one embodiment, a protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a host cell can be accomplished by any method by which a nucleic acid molecule can be inserted into a cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of a host cell in such a manner that their ability to be expressed is retained.

Suitable host cells to transform include any cell that can be transformed. Host cells can be either untransformed cells or cells that are already transformed with at least one nucleic acid molecule. Host cells of the present invention can be endogenously (i.e., naturally) capable of producing a protein of the present invention, but such cells are not preferred. Host cells of the present invention can be any cell that when transformed with a nucleic acid molecule of the present invention are capable of producing a protein of the present invention, including bacterial, yeast, other fungal, insect, animal, and plant cells. Preferred host cells include bacterial, yeast, insect and mammalian cells, and more preferred host cells include *Escherichia, Bacillus, Saccharomyces, Pichia,*

*Trichoplusia, Spodoptera* and mammalian cells. Particularly preferred host cells are *Trichoplusia ni* cells and *Spodoptera frugiperda* cells with T. ni cells being particularly preferred.

A recombinant cell is preferably produced by transforming a host cell with a recombinant molecule comprising a nucleic acid molecule of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell, of replicating within the host cell, and of effecting expression of a specified nucleic acid molecule. Expression vectors can be either prokaryotic or eukaryotic, and are typically viruses or plasmids. Expression vectors of the present invention include any vectors that function (i.e., direct gene is expression) in recombinant cells of the present invention, including in bacterial, yeast, other fungal, insect, animal, and plant cells. Preferred expression vectors of the present invention can direct gene expression in bacterial, yeast, insect and mammalian cells.

Nucleic acid molecules of the present invention can be operatively linked to expression vectors containing regulatory control sequences such as promoters, operators, repressors, enhancers, termination sequences, origins of replication, and other regulatory control sequences that are compatible with the host cell and that control the expression of the nucleic acid molecules. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing nucleic acid molecules encoding such a protein.

In accordance with the present invention, recombinant cells can be used to produce proteins by culturing such cells under conditions effective to produce such a protein, and recovering the protein. Effective conditions to produce a protein include, but are not limited to, appropriate media, bioreactor, temperature, pH and oxygen conditions that permit protein production. An appropriate medium refers to any medium in which a cell of the present invention, when cultured, is capable of producing the protein. An effective medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant proteins may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

The present invention also includes isolated (i.e., removed from their natural milieu) antibodies that selectively bind to a Fc region of the present invention. As used herein, the term "selectively binds to" refers to the ability of antibodies of the present invention to preferentially bind to an Fc region of the present invention. Binding can be measured using a variety of methods standard in the art including enzyme immunoassays (e.g., ELISA), immunoblot assays, etc.; see, for example, Sambrook et al., ibid. Isolated antibodies of the present invention can include antibodies in a bodily fluid (such as, but not limited to, serum), or antibodies that have been purified to varying degrees. Antibodies of the present invention can be polyclonal or monoclonal. Functional equivalents of such antibodies, such as antibody fragments and genetically-engineered antibodies (including single chain antibodies or chimeric antibodies that can bind to more than one epitope) are also included in the present invention. Antibodies can be produced using methods known to those skilled in the art. A preferred method to produce antibodies of the present invention includes (a) administering to an animal an effective amount of a protein of the present invention to produce the antibodies and (b) recovering the antibodies. In another method, antibodies of the present invention are produced recombinantly using techniques as heretofore disclosed to produce proteins of the present invention. Antibodies raised against defined proteins can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. Examples of such uses are disclosed in WO 98/27208, ibid., see, for example, page 24; such uses are incorporated by reference herein in their entireties.

A Fc region of the present invention can include chimeric molecules comprising at least a portion of a Fc region that binds to an antibody and a second molecule that enables the chimeric molecule to be bound to a substrate in such a manner that the antibody receptor portion binds to the antibody in at least as effective a manner as a Fc region that is not bound to a substrate. An example of a suitable second molecule includes a portion of an immunoglobulin molecule or another ligand that has a suitable binding partner that can be immobilized on a substrate, e.g., biotin and avidin, or a metal-binding protein and a metal (e.g., His), or a sugar-binding protein and a sugar (e.g., maltose).

The present invention includes uses of Fc regions, antibodies thereto, and inhibitory compounds of the present invention for the diagnosis and treatment of allergy and the regulation of other immune responses in an animal.

One embodiment is a therapeutic composition comprising at least one of the following therapeutic compounds: an inhibitory compound of the present invention, a mutein of the present invention, or an antibody of the present invention. Also included is a method to protect an animal from allergy or other abnormal immune responses. Such a method includes the step of administering a therapeutic composition of the present invention to the animal. As used herein, the ability of a therapeutic composition of the present invention to protect an animal from allergy or other abnormal immune responses refers to the ability of that composition to, for example, treat, ameliorate or prevent allergy or other abnormal immune responses. General characteristics of therapeutic compositions and methods to produce and use such therapeutic compositions are disclosed, for example, in WO 98127208, ibid., see, for example, page 3947; such compositions and methods are incorporated by reference herein in their entireties. It is to be noted that although the compositions and methods disclosed in WO 98/27208, ibid., relate to feline FcεRIα proteins, they are also applicable to therapeutic compositions of the present invention. Therapeutic compositions of the present invention are advantageous because they can be derived from analysis of 3-D models of the present invention and have improved functions, such as efficacy and safety.

Another embodiment is a diagnostic reagent comprising a mutein of the present invention. As used herein, a diagnostic reagent is a composition that includes a mutein that is used to detect allergy or other abnormal immune responses in an animal. Also included in the present invention are methods, including in vivo methods and in vitro methods, to (a) detect allergy or other abnormal immune response, or susceptibility thereto, in an animal, comprising use of a diagnostic reagent comprising a mutein of the present invention and (b) to enhance the performance of an IgE or FcR binding assay, said method comprising incorporating into the assay a mutein of the present invention. General characteristics of diagnostic reagents and methods to produce and use such diagnostic reagents are disclosed, for example, in WO 98/27208, ibid., see, for example, page 2–39; such reagents and methods are incorporated by reference herein in their entireties. It is to be noted that although the reagents and methods disclosed in WO 98/27208, ibid., relate to feline FcεRIα proteins, they are also applicable to diagnostic reagents, kits and detection methods of the present invention. Muteins of the present invention are advantageous in such applications because of their enhanced affinity for antibodies, altered specificity, enhanced solubility and/or enhanced stability, enabling for example use in otherwise adverse conditions and longer shelf-life.

EXAMPLES

The following examples are provided for the purposes of illustration and are not intended to limit the scope of the invention.

Example 1

This Example describes the production and analysis of crystals of a glycosylation mutant of the Cε3/Cε4 domain of human IgE.

A. Construction of a IgE Fc-Cε3/Cε4 CHO mutant

A new mutant IgE-Fc protein was created in which the sequence of the glycosylation sites in the IgE Fc-region Cε3/Cε4 domain protein were altered in order to prevent glycosylation at these sites. The CHO mutant was created using polymerase chain reaction (PCR) mutagenesis as follows:

Using a gene encoding the IgE Cε3/Cε4 domains of IgE (SEQ ID NO:1) as a template, a 5' gene fragment and a 3' gene fragment were created in two separate PCR reactions. The 5' gene fragment was synthesized using the primers HIGEFC1b and N371Q. The primer HIGEFC1 b, which has the sequence 5' TAGGGCTACGTAGATTCCAAC-CCGAGAGG 3', (represented by SEQ ID NO:3) contains a SnaB I restriction site and encodes an a portion of the Fc protein having an N-terminal sequence (following restriction digest with Sna BI) of VDSNPR with D corresponding to D330 of the mature sequence. The primer N371Q, which has the sequence 5' ACTGGCTCGAGACCAGGTCAGCT-GCACGGTCCCCTTGCTGGGT 3' (represented by SEQ ID NO:4), introduces unique Xho I and Pvu II sites and contains the mutation which changes the asparagine at position 371 to a glutamine. The 3' gene fragment was synthesized using primers N383Q and HIGEFC2B. Primer N383Q, which has the sequence 5' CCTGGTCTCGAGC-CAGTGGGAAGCCTGTGCAACACTCCAC-CAGAAAGGAGGAG 3' (represented by SEQ ID NO:5), introduces a uniqe Xho I restriction site and contains the mutation that changes the asparagine at position 383 to a glutamine. Primer HIGEFC2B, which has the sequence 5' TCTAGGCAGCGGCCGCTTATCATTTAC-CGGGATTTACAG 3' (represented by SEQ ID NO:6), terminates the Fc sequence at Lys 547 and contains a Not I restriction site. The 5' and 3' gene fragments were generated using standard PCR conditions, gel purified and then digested with the restriction enzymes SnaB I and Xho I (5' fragment) or Not I and Xho I (3' fragment). The digested fragments were then ligated together at their Xho sites to yield the full length gene encoding the Cε3/Cε4 domains containing the glycosylation site mutations (represented by SEQ ID NO:7). Translation of the newly constructed gene results in a protein (represented by SEQ ID NO:8) lacking glycosylation recognition sites at positions 371 and 383.

For expression in insect cells, the newly constructed gene for the carbohydrate mutant was amplified using primers IgECABac and HIGEF2b. The primer IgECAbac, which has the sequence 5' TAGGGCGGATCCCTGTGCAGATTC-GAACCCGAGAGGGGTGAGCG 3' (represented by SEQ ID NO:9), contains a BamH I site for cloning the gene behind a signal sequence in the expression vector pAcGP67A (Catalog Number 221220P, Becton Dickinson Pharmingen, Franklin Lakes, N.J.). The encoded sequence of the N-terminus of the mature (signal sequence cleaved) protein is ADPCAD with C corresponding to C328 of the mature IgE. Following amplification, the gene was digested with BamH I and Not I, gel purified and ligated into the pAcGP67A vector.

B. Expression, purification and crystallization of the CHO mutant proteins

The IgE-Fc CHO mutant protein was expressed, purified to homogeneity and crystallized. The expression, purification, crystallization, characterization and data collection and refinement of the mutant protein was performed as described in Example 1 and Example 2 of U.S. Patent Publication No. US-2001-0039479-A. Three new crystals were generated and data obtained from these crystals are shown in Table VII.

TABLE VII

Data for the CHO mutant IgE Protein Crystals

| | Space Group | a | b | c | β | Mol/asym | Resolution |
|---|---|---|---|---|---|---|---|
| Crystal 1 | C2 | 158 | 108 | 50 | 102 | 1.5 | 2.3 Å |
| Crystal 2 | P2$_1$ | 66 | 99 | 77 | 97 | 2.0 | 2.45 Å |
| Crystal 3 | P2$_1$ (Big) | 48 | 104 | 150 | 96 | 3.0 | 2.8 Å |

The structural coordinates obtained from Crystal 1 are listed in Table I and data collection and refinement statistics are shown below in Table VIII.

Statistics based on m10_bi50CHO_m25_bi5_m35_P+EBA.pdb

TABLE VIII

Data Collection and Refinement

| | C2 (f5) (pH 4.6) |
|---|---|
| Data Collection Statistics | |
| Source | APS DND 5-ID |
| Wavelength (Å) | 1.008 |
| Resolution (Å) | 30.0–2.30 (2.38–2.30)$^\dagger$ |
| Completeness | 98.8% (89.8%)$^\dagger$ |
| Unique reflections (Total) | 36,675 (139,507) |
| Average redundancy | 3.8 (3.7)$^\dagger$ |
| $<I/\sigma_I>$ | 15.4 (2.4)$^\dagger$ |
| R$_{merge}$ | 6.2% (41.3%)$^\dagger$ |
| Refinement | |
| No. of Reflections (free) | 36,675 (1,866) |
| R$_{work}$/R$_{free}$ | 27.4/29.3 |
| Atoms (Total) | 5059 |
| Protein Atoms | 4909 |
| Water Molecules | 0 |
| Carbohydrate Atoms | 150 |
| Average B factor Protein | *59.6 Å$^2$ |
| RMS Deviations from Ideality | |
| Bond angles | 1.33° |
| Bond lengths | 0.008 Å |
| Ramachandran (ϕ,ψ) | |
| Favored | 86.5% |
| Allowed | 12.2% |
| Generous | 0.9% |
| Disallowed | 0.4% |

$^\dagger$Values for the highest resolution shell are shown in parentheses
R$_{merge}$ = Σ|I$_1$ − <I>|/Σ|I|, where I$_i$ is the intensity of an individual reflection and <I> is the average intensity of that reflection.

TABLE VIII-continued

Data Collection and Refinement

| | C2 (f5) (pH 4.6) |
|---|---|

R$_{work/free}$ = Σ||F$_p$| − |F$_c$||/Σ|F$_p$|, where F$_c$ is the calculated and F$_p$ is the observed structure factor amplitude.
R$_{work}$ and R$_{free}$ were calculated using the working set and test set reflections, respectively.
Cell a = 158.8 b = 108.5 c = 50.4 β = 102° [**These are Denzo ave (not scalepack) refined]
Refinement values based on m10_bi50CHO_m25_bi5_m35_p+EBA.pdb
Total # residues = 627
1.5 dimers/asu (=1.5 Fc molecules/asu)

The structural coordinates obtained from Crystal 2 are listed in Table II and data collection and refinement statistics are shown below in Table IX.

Statistics based on min300_c31.pdb

TABLE IX

Data Collection and Refinement

| | P2$_1$ (f8) (pH 4.6) |
|---|---|
| Data Collection Statistics | |
| Source | APS DND 5-ID |
| Wavelength (Å) | 1.000 |
| Resolution (Å) | 30.0–2.45 (2.54–2.45)$^\dagger$ |
| Completeness | 98.2% (82.3%)$^\dagger$ |
| Unique reflections (Total) | 36,017 (128,258) |
| Average redundancy | 3.63 (2.3)$^\dagger$ |
| $<I/\sigma_I>$ | 22.2 (3.35)$^\dagger$ |
| R$_{merge}$ | 5.9% (24.1%)$^\dagger$ |
| Refinement | |
| No. of Reflections (free) | 34,123 (1,824) |
| R$_{work}$/R$_{free}$ | 29.3/31.2 |
| Atoms (Total) | 6,345 |
| Protein Atoms | 6,345 |
| Water Molecules | 0 |
| Carbohydrate Atoms | 0 |
| Average B factor Protein | 48.3 Å$^2$ |
| RMS Deviations from Ideality | |
| Bond angles | 3.06° |
| Bond lengths | 0.03 Å |
| Ramachandran (ϕ,ψ) | |
| Favored | 85.7% |
| Allowed | 11.2% |
| Generous | 1.8% |
| Disallowed | 1.3% |

$^\dagger$Values for the highest resolution shell are shown in parentheses
R$_{merge}$ = Σ|I$_1$ − <I>|/Σ|I|, where I$_i$ is the intensity of an individual reflection and <I> is the average intensity of that reflection.
R$_{work/free}$ = Σ||F$_p$| − |F$_c$||/Σ|F$_p$|, where F$_c$ is the calculated and F$_p$ is the observed structure factor amplitude.
R$_{work}$ and R$_{free}$ were calculated using the working set and test set reflections, respectively.
Cell a = 65.7 b = 99.6 c = 77.9 β = 97.1°
Refinement values based on min300_c31.pdb
Total # residues = 816
2 dimers/asu (=2 Fc molecules/asu)

The structural coordinates obtained from Crystal 3 are listed in Table III and data collection and refinement statistics are shown below in Table X.

Statistics based on m200_bi14v3_bg10_bd8_m250_BE_new.pdb

TABLE X

Data Collection and Refinement

| | P2₁ "BIG" (f7) (pH 4.6) |
|---|---|
| Data Collection Statistics | |
| Source | APS DND 5-ID |
| Wavelength (Å) | 1.000 |
| Resolution (Å) | 30.0–2.80 (2.90–2.80)[†] |
| Completeness | 98.9% (100%)[†] |
| Unique reflections (Total) | 36,906 (139,248) |
| Average redundancy | 3.8 (3.8)[†] |
| $<I/\sigma_1>$ | 16.7 (4.9)[†] |
| $R_{merge}$ | 7.3% (54.1%)[†] |
| Refinement | |
| No. of Reflections (free) | 35,046 (1,860) |
| $R_{work}/R_{free}$ | 31.3/36.0 |
| Atoms (Total) | 9,300 |
| Protein Atoms | 9,300 |
| Water Molecules | 0 |
| Carbohydrate Atoms | 0 |
| Average B factor Protein | 72.3 Å² |
| RMS Deviations from Ideality | |
| Bond angles | 1.41° |
| Bond lengths | 0.009 Å |
| Ramachandran (φ,ψ) | |
| Favored | 82.9% |
| Allowed | 13.9% |
| Generous | 2.5% |
| Disallowed | 0.6% |

[†]Values for the highest resolution shell are shown in parentheses
$R_{merge} = \Sigma|I_1 - <I>|/\Sigma|I|$, where $I_i$ is the intensity of an individual reflection and $<I>$ is the average intensity of that reflection.
$R_{work/free} = \Sigma||F_p| - |F_c||/\Sigma|F_p|$, where $F_c$ is the calculated and $F_p$ is the observed structure factor amplitude.
$R_{work}$ and $R_{free}$ were calculated using the working set and test set reflections, respectively.
Cell a = 48.9 b = 104.9 c = 150.0 β = 96.2°
Refinement values based on m165__bi15v2___bg10_bd28_m250_BE_new.pdb
Total # residues = 1,182
3 dimers/asu (=3 Fc molecule/asu)

C. Description of the Ige Fc-region Cε3/Cε4 domain mutant protein structure

The new crystal forms reveal additional information on the IgE-Fc conformational change, showing that the C3 domains can adopt a variety of intermediate conformations between the open and closed forms. Interestingly, the C3 domains that are in the closed conformation are generally more similar and therefore probably more restricted in their conformational flexibility. In contrast, those C3 domains that are closer to the open conformation adopt a wider variety of side-side conformations, suggesting that there are fewer restrictions on the movements of the domains in the open configuration. These differences may have an impact on drug design and binding to the different forms and could be important for docking experiments.

Analysis of the conformational ensemble revealed by the determination of these additional crystal forms of the IgE-Fc suggest how dynamic motions within the IgE-Fc may be coupled to receptor binding and dissociation. For example, conformational changes of the IgE-Fc are likely important to the microscopic steps in association and release from the receptor Binding Sites 1 and 2. In addition, analysis of the conformational ensemble suggests how interactions with the IgE Cε2 domain could be involved in restricting such conformational flexibility and influence the rates of binding and dissociation from the receptor. The range of motions and conformational arrangements of the Cε3 domains observed in these multiple crystal forms establish a set of preferred arrangements which restrict possible models and approaches to blocking IgE binding to its receptor and to stimulating dissociation from the bound state.

While the various embodiments of the present invention have been described in detail, it is apparent that modifications and adaptations of those embodiments will occur to those skilled in the art. It is to be expressly understood, however, that such modifications are adaptations are within the scope of the present invention, as set forth in the following claims.

---

What is claimed is:

1. A method to identify a compound that inhibits the binding between an IgE antibody and a FcεRIα protein said method comprising:
   (a) using a three dimensional model of a Fe-Cε3/Cε4 region of a human IgE antibody to identify a test compound;
   (b) obtaining said test compound; and
   (c) determining if said test compound interacts with said IgE antibody, wherein such interaction indicates the compound is capable of inhibiting the binding of an IgE antibody to a FcεRIα protein.

2. The method of claim 1, wherein said IgE antibody model is substantially represented by the atomic coordinates, listed in Table 1, Table 2 or Table 3 of U.S. Patent Publication No. US-2001-0039479-A1 or by the atomic coordinates listed in table I, Table II or Table III.

3. The method of claim 1, wherein said IgE antibody model is represented by the atomic coordinates defining the relative position of protein backbone atoms having a root mean square deviation less than 10 angstroms from the human IgE protein Cε3 or Cε4 domain atoms defined by the atomic coordinates represented in Table 1, Table 2 or table 3 of U.S. Patent Publication No. US-2001-0039479-A1 or by the atomic coordinates listed in Table I, Table II or Table III.

4. The method of claim 1, wherein said IgE antibody model is represented by atomic coordinates defining, the relative position of backbone atoms form a protein having an amino acid sequence at least 80% homologous with SEQ ID NO:2.

5. The method of claim 1, wherein said IgE antibody model is represented by at least a portion or the atomic coordinates listed in Table 1, Table 2 or Table 3 of U.S. Patent Publication No. U.S. 2001-0039479-A1 or by at least a portion of the atomic coordinates listed in Table I, Table II or Table III.

6. The method of claim 1, wherein said IgE antibody model is represented by atomic coordinates comprising the atomic coordinates listed in Table 1, Table 2 or Table 3 of U.S. Patent Publication No. US-2001-0039479-A1 or by atomic coordinates comprising the atomic coordinates listed in Table I, Table II or Table III.

7. The method of claim 1, wherein said IgE antibody model is obtained by the steps of:
   (i) obtaining a protein crystal comprising at least the Cε3 or at least the Cε4 domain from the Fe region of the human IgE protein;
   (ii) producing diffraction x-ray diffraction data from said protein crystal; and
   (iii) transforming said diffraction data into atomic coordinates defining the relative position of atoms in said protein comprising at least the Cε3 or at least Cε4 domain from the Fe region of the human IgE protein.

8. The method of claim 7, wherein said protein crystal belongs to the space group P42$_1$2 with unit cell dimensions of a equals about 105° A., b equals about 105° A and c equals about 47° A.

9. The method of claim 8, wherein said protein crystal is produced using the hanging drop method or the vapor diffusion method and crystallization is preformed using a precipitant comprising about 33% polyethylene glycol 4000 and about 25 mM sodium acetate at a pH of about 4.6.

10. A method to identify a compound that inhibits the binding between an IgE antibody and a FcεRIα protein, said method comprising the steps of:
  (a) obtaining the three-dimensional model of a Fe-Cε3/Cε4 region of a human IgE antibody;
  (b) generating the spatial structure of a test compound; and
  (c) determining if said test compound model interacts with said IgE antibody model, wherein such interaction indicates the compound is capable of inhibiting the binding of an IgE antibody to a Fe-Cε3/Cε4 protein;
  (d) obtaining said test compound; and
  (e) testing said compound in a IgE antibody/FcεRIα protein binding assay to determine if said test compound inhibits the binding of IgE to FcεRIα protein.

11. A method to design a compound that inhibits the binding between an IgE antibody and a FcεRIα protein, said method comprising the steps of:
  (a) obtaining a three dimensional model of a Fe-Cε3/Cε4 region of a human IgE protein; and
  (b) using computer means to generate a model representing the spatial structure of a compound that interacts with said IgE protein model, wherein such interaction indicates the compound is capable of inhibiting the binding of an IgE antibody to a FcεRIα protein;
  (c) obtaining said compound; and
  (d) testing said compound in a IgE antibody/FcεRIα protein binding assay to determine if said compound inhibits the binding of IgE to FcεRIα protein.

* * * * *